US012503452B2

(12) United States Patent
Looper et al.

(10) Patent No.: US 12,503,452 B2
(45) Date of Patent: Dec. 23, 2025

(54) ANTIMICROBIAL COMPOUNDS AND METHODS

(71) Applicants: Curza Global, LLC, Salt Lake City, UT (US); The University of Utah Research Foundation, Salt Lake City, UT (US)

(72) Inventors: Ryan E. Looper, Salt Lake City, UT (US); Paul Sebahar, Sandy, UT (US); Hariprasada R. Kanna Reddy, Salt Lake City, UT (US); Travis J. Haussener, Salt Lake City, UT (US); Charles A. Testa, North Salt Lake, UT (US); BenIsaac C. Tresco, Salt Lake City, UT (US); Seth Grant, West Jordan, UT (US); Carmela Napolitano, Verona (IT); Fabio Maria Sabbatini, Verona (IT)

(73) Assignees: Curza Global, LLC, Salt Lake City, UT (US); The University of Utah Research Foundation, Salt Lake City, UT (US)

( * ) Notice: Subject to any disclaimer, the term of this patent is extended or adjusted under 35 U.S.C. 154(b) by 776 days.

(21) Appl. No.: 17/423,432

(22) PCT Filed: Jan. 15, 2020

(86) PCT No.: PCT/US2020/013733

§ 371 (c)(1),
(2) Date: Jul. 15, 2021

(87) PCT Pub. No.: WO2020/150385

PCT Pub. Date: Jul. 23, 2020

(65) Prior Publication Data

US 2023/0159491 A1 May 25, 2023

Related U.S. Application Data

(60) Provisional application No. 62/793,216, filed on Jan. 16, 2019.

(51) Int. Cl.

| | |
|---|---|
| ***C07D 401/10*** | (2006.01) |
| ***A61P 31/04*** | (2006.01) |
| ***C07D 239/36*** | (2006.01) |
| ***C07D 401/12*** | (2006.01) |
| ***C07D 401/14*** | (2006.01) |
| ***C07D 403/10*** | (2006.01) |
| ***C07D 403/12*** | (2006.01) |
| ***C07D 413/14*** | (2006.01) |
| ***C07D 471/04*** | (2006.01) |
| ***C07D 487/04*** | (2006.01) |
| ***C07D 487/08*** | (2006.01) |
| ***C07D 498/18*** | (2006.01) |

(52) U.S. Cl.

CPC ............ *C07D 401/10* (2013.01); *A61P 31/04* (2018.01); *C07D 239/36* (2013.01); *C07D 401/12* (2013.01); *C07D 401/14* (2013.01); *C07D 403/10* (2013.01); *C07D 403/12* (2013.01); *C07D 413/14* (2013.01); *C07D 471/04* (2013.01); *C07D 487/04* (2013.01); *C07D 487/08* (2013.01); *C07D 498/18* (2013.01)

(58) Field of Classification Search

None

See application file for complete search history.

(56) References Cited

U.S. PATENT DOCUMENTS

| | | | | |
|---|---|---|---|---|
| 2013/0090326 | A1 | 4/2013 | Duffy et al. | |
| 2018/0065966 | A1 | 3/2018 | Bhattacharjee et al. | |
| 2023/0072397 | A1 * | 3/2023 | Looper ................ | C07D 471/04 |
| 2023/0159491 | A1 | 5/2023 | Looper et al. | |
| 2023/0278987 | A1 * | 9/2023 | Sebahar ............... | C07D 403/12 514/217.06 |
| 2025/0084041 | A1 * | 3/2025 | Sebahar ............... | C07D 239/47 |

FOREIGN PATENT DOCUMENTS

| | | | |
|---|---|---|---|
| WO | 2011047319 | A2 | 4/2011 |
| WO | 2011047323 | A3 | 8/2011 |
| WO | 2012173689 | A2 | 12/2012 |
| WO | 2015035421 | A1 | 3/2015 |
| WO | 2016145417 | A1 | 9/2016 |
| WO | 2017193016 | A1 | 11/2017 |
| WO | 2017193017 | A1 | 11/2017 |
| WO | 2017193023 | A1 | 11/2017 |
| WO | 2015035426 | A1 | 3/2018 |
| WO | 2018236692 | A1 | 12/2018 |
| WO | 2019013789 | A1 | 1/2019 |

(Continued)

OTHER PUBLICATIONS

International Search Report for PCT/US2020/013733 mailed Apr. 21, 2020.

(Continued)

*Primary Examiner* — Jeffrey S Lundgren

*Assistant Examiner* — Anthony Joseph Seitz

(74) *Attorney, Agent, or Firm* — Honigman LLP; Heidi M. Berven

(57) ABSTRACT

The invention is directed to compounds that are active as antibacterial agents. The invention compounds are active against gram-positive and gram-negative bacteria and can be used to treat infections caused by gram-positive and gram-negative bacteria. Also disclosed are processes and intermediates for making the compounds.

30 Claims, No Drawings

(56) References Cited

FOREIGN PATENT DOCUMENTS

| | | | | | |
|---|---|---|---|---|---|
| WO | 2019164880 | A1 | | 8/2019 | |
| WO | 2020150385 | A1 | | 7/2020 | |
| WO | WO-2020150372 | A1 | * | 7/2020 | ............. A61P 31/04 |

OTHER PUBLICATIONS

Yamada, et al. "Synthesis of Novel Iso-4'-thionucleosides Using the Mitsunobu Reaction", The Journal of Organic Chemistry, 1998, pp. 6891-6899.

International Search Report for PCT/US2020/013717 dated Apr. 21, 2020.

International Search Report for PCT/US2020/060185 dated Mar. 21, 2021.

International Search Report for PCT/US2022/082474 dated Apr. 26, 2023.

* cited by examiner

ANTIMICROBIAL COMPOUNDS AND METHODS

CROSS-REFERENCE TO RELATED APPLICATIONS

This application is a United States National Phase filing of PCT/US2020/013733, filed Jan. 15, 2020, which claims the benefit of priority to U.S. Provisional Application No. 62/793,216, filed Jan. 16, 2019, the entire contents of which are incorporated herein by reference.

This invention was made with government support under grant AI127724 awarded by the National Institutes of Health. The government has certain rights in this invention.

FIELD OF THE INVENTION

The present disclosure relates to compounds that are active as antibacterial agents. The present disclosure also relates to methods of treating bacterial infections with the present compounds.

BACKGROUND OF THE INVENTION

Antibacterial resistance is a worldwide problem. Both gram-positive and gram-negative bacteria are increasingly becoming resistant to antibiotics.

Gram-positive bacteria such as methicillin resistant *Staphylococcus aureus* (MRSA) are resistant to most antibiotics that are related to penicillin. MRSA strains are commonly involved in infections acquired in health care facilities and can cause infections in greater communities.

Gram-negative bacteria are believed to be more resistant to antibiotics than Gram-positive bacteria, because of the impermeability of their cell walls. According to the National Institutes of Health (NIH), Gram-negative bacteria can cause many types of infections and are spread to humans in a variety of ways. Several species, including *Escherichia coli*, are common causes of foodborne disease. *Vibrio cholerae*, the bacteria responsible for cholera, is a waterborne pathogen. Gram-negative bacteria can also cause respiratory infections, such as certain types of pneumonia, and sexually transmitted diseases, including gonorrhea. *Yersinia pestis*, the Gram-negative bacterium responsible for plague, is transmitted to people through the bite of an infected insect or handling an infected animal. See www.niaid.nih.gov/research/gram-negative-bacteria (last visited Jan. 7, 2020).

Certain types of Gram-negative bacteria have become increasingly resistant to available antibiotic drugs. Some strains are now resistant to many, most, or all available treatments resulting in increased illness and death from bacterial infections and contributing to escalating healthcare costs. Examples of Gram-negative bacteria that have demonstrated drug resistance include: *E. coli*, which causes the majority of urinary tract infections; *Acinetobacter baumanii*, which causes disease mainly in healthcare settings; *Pseudomonas aeruginosa*, which causes bloodstream infections and pneumonia in hospitalized patients and is a common cause of pneumonia in patients with cystic fibrosis; *Klebsiella pneumoniae*, which causes many types of healthcare-associated infections, including pneumonia, urinary tract infections, and bloodstream infections; and *Neisseria gonorrhoeae*, which causes the sexually transmitted disease gonorrhea and is the second most commonly reported infectious disease in the United States.

As a result, new drugs to combat Gram-positive and Gram-negative bacterial infections are needed.

SUMMARY OF THE INVENTION

These and other needs are met by the present invention which provides in one aspect a compound of formula I:

I

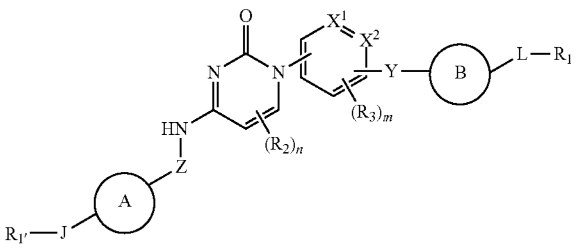

or a pharmaceutically acceptable salt thereof, wherein:

Z is (C═O), (C═S), (C═$NR_z$), (S═O), or $SO_2$; wherein $R_z$ is H, $C_1$-$C_6$ alkyl, or CN;

ring A is a monocyclic heterocycloalkylene or bicyclic heterocycloalkylene, wherein the monocyclic heterocycloalkylene or bicyclic heterocycloalkylene are optionally substituted with up to three substituents independently selected from the group consisting of $C_1$-$C_6$ alkyl, $C_1$-$C_6$ alkoxy, $C_1$-$C_6$ hydroxyalkyl, halo, CN, $C_1$-$C_6$ haloalkyl, phenyl, OH, $NH_2$, NH($C_1$-$C_6$ alkyl), N($C_1$-$C_6$ alkyl)$_2$, COOH, COO($C_1$-$C_6$ alkyl), —$CONH_2$, and oxo;

J is absent or is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to three substituents independently selected from the group consisting of halo, $C_1$-$C_6$ alkyl, $C_1$-$C_6$ alkoxy, $C_1$-$C_6$ haloalkyl, $NH_2$, CN, and OH; wherein at each occurrence of $C_1$-$C_6$ alkylene, up to two methylene units of the $C_1$-$C_6$ alkylene may independently and optionally be replaced with O, S, $SO_2$, C═O, or

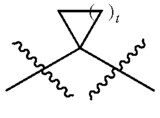 ;

wherein t is 1, 2, 3, or 4;

$X^1$ and $X^2$ are each independently C—H or N;

Y is a linear $C_1$-$C_8$ alkylene, $C_2$-$C_8$ alkenylene, or $C_2$-$C_8$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), N—($C_{3-8}$ cycloalkyl), NH(C═O), N—($C_{1-6}$ alkyl) (C═O), (C═O), or

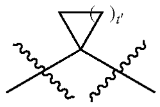
;

wherein t' is 1, 2, 3, or 4;

ring B is a monocyclic cycloalkylene or monocyclic heterocycloalkylene, either of which is optionally substituted with up to three substituents independently selected from the group consisting of $C_1$-$C_6$ alkyl, $C_1$-$C_6$ alkoxy, halo, CN, $NH_2$, $C_1$-$C_6$ haloalkyl, OH, COOH, COO($C_1$-$C_6$ alkyl), $CONH_2$, and $C_1$-$C_6$ hydroxyalkyl;

L is absent, or is a $C_1$-$C_6$ alkylene, wherein up to two methylene units of the $C_1$-$C_6$ alkylene may independently be replaced with O, NH, (C═O), NH(C═O), N—($C_{1-6}$ alkyl)(C═O), (C═NH), NH(C═N), or N—($C_{1-6}$ alkyl);

$R_1$ is H, halo, $C_1$-$C_6$ haloalkyl, $NR_{x'}R_{y'}$, or monocyclic heterocycloalkyl optionally substituted with $NH_2$, NH($C_1$-$C_6$ alkyl), N($C_1$-$C_6$ alkyl)$_2$, wherein $R_{x'}$ and $R_{y'}$ are each independently H, $C_1$-$C_6$ alkyl, $C_3$-$C_8$ cycloalkyl, or an amino protecting group, wherein the $C_1$-$C_6$ alkyl and $C_3$-$C_8$ cycloalkyl are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$CONH_2$, and oxo; or $R_1$ is NH(C═O)—($C_1$-$C_6$) alkyl, or NH—(C═NH)—$NH_2$, either of which may be optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, COO($C_1$-$C_6$ alkyl), $CONH_2$, and oxo;

$R_{1'}$ is H or $NR_xR_y$, wherein $R_x$ and $R_y$ are each independently H, $C_1$-$C_6$ alkyl, $C_1$-$C_6$ alkyl-$SO_3$, CO($C_1$-$C_6$ alkyl), CO—($C_1$-$C_6$ alkylene)-$NH_2$, or an amino protecting group;

$R_2$ and $R_3$ are each independently selected from the group consisting of $C_1$-$C_6$ alkyl, halo, CN, OH, $NH_2$, O($C_1$-$C_6$ haloalkyl), NH($C_1$-$C_6$ alkyl), N($C_1$-$C_6$ alkyl)$_2$, —COO($C_1$-$C_6$ alkyl), —$CONH_2$, $C_1$-$C_6$ haloalkyl, $C_1$-$C_6$ alkoxy, and $C_1$-$C_6$ haloalkoxy; and m and n are each independently 0, 1, 2, or 3.

In another aspect, the invention provides methods of using compounds of formula I or a pharmaceutically acceptable salt thereof for the treatment of bacterial infections.

In another aspect, the invention provides pharmaceutical compositions comprising a compound of formula I or a pharmaceutically acceptable salt thereof and a pharmaceutically acceptable carrier.

In a further aspect, the invention provides processes for making compounds of formula I or a pharmaceutically acceptable salt thereof, as well as compound intermediates used in the processes, as depicted in the synthetic schemes.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety, including U.S. Pat. Publ. No. 2013/0090326. In case of conflict, the present specification, including these definitions, will control.

The terms "a," "an," and "the" as used herein not only include aspects with one member, but also include aspects with more than one member.

The term "about" as used herein means "approximately" and is used to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

As used herein, a wavy line drawn on a structure can be used to show the attachment point of the structure, such as

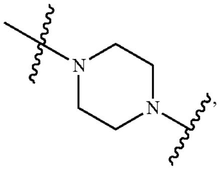 [SMILES: *N1CCN(*)CC1]
, wherein "∿" indicates points of attachment.

The term "acyl" as used herein includes an alkanoyl, aroyl, heterocycloyl, or heteroaroyl group as defined herein. Examples of acyl groups include, but are not limited to, acetyl, benzoyl, and nicotinoyl.

The term "alkanoyl" as used herein includes an alkyl-C(O)— group wherein the alkyl group is as defined herein. Examples of alkanoyl groups include, but are not limited to, acetyl and propanoyl.

The term "agent" as used herein includes a compound or mixture of compounds that, when added to a composition, tend to produce a particular effect on the composition's properties. For example, a composition comprising a thickening agent is likely to be more viscous than an otherwise identical comparative composition that lacks the thickening agent.

The term "alkyl" as used herein includes an aliphatic hydrocarbon chain that may be straight chain or branched. The chain may contain an indicated number of carbon atoms: For example, $C_1$-$C_{10}$ indicates that the group may have from 1 to 10 (inclusive) carbon atoms in it. If not otherwise indicated, an alkyl group contains from 1 to about 20 carbon atoms. In some aspects, alkyl groups have 1 to about 10 carbon atoms. In some aspects, alkyl groups ("lower alkyl") have 1 to 8, 1 to 6, or 1 to 3 carbon atoms in the chain. Examples may include, but are not limited to, methyl, ethyl, propyl, isopropyl (iPr), 1-butyl, 2-butyl, isobutyl (iBu), tert-butyl, pentyl, 2-methylbutyl, 1,1-dimethylpropyl, hexyl, heptyl, octyl, nonyl, decyl, docecyl, cyclopentyl, or cyclohexyl.

An alkyl group can be unsubstituted or optionally substituted. When optionally substituted, one or more hydrogen atoms of the alkyl group (e.g., from 1 to 4, from 1 to 2, or 1) may be replaced with a moiety independently selected from the group consisting of fluoro, hydroxy, alkoxy, amino, alkylamino, acylamino, thio, and alkylthio. In some aspects, the alkyl group is unsubstituted or not optionally substituted.

"Alkylene" as used herein includes an alkyl group that is substituted at two points. An example is methylene ($—CH_2—$), propylene ($—CH_2CH_2CH_2—$), and the like.

The term "alkenyl" as used herein includes a straight or branched chain hydrocarbon containing at least one carbon-carbon double bond. The chain may contain an indicated number of carbon atoms. For example, "$C_1$-$C_{12}$ alkenyl" indicates that the group may have from 1 to 12 (inclusive) carbon atoms and at least one carbon-carbon double bond. When the indicated number of carbon atoms is 1, then the $C_i$ alkenyl is double bonded to a carbon (i.e., a carbon equivalent to an oxo group). In certain aspects, the chain includes 1 to 12, about 2 to 15, about 2 to 12, about 2 to 8, or about 2 to 6 carbon atoms. An alkenyl group can be preferably one stereoisomer (i.e., cis- or, alternatively, trans-). Examples of an alkenyl group may include, but are not limited to, ethenyl (i.e., vinyl), allyl, propenyl, butenyl, crotyl, pentenyl, hexenyl, heptenyl, octenyl, nonenyl, decenyl, dodecenyl, cyclopentenyl, cyclohexenyl, 2-isopentenyl, allenyl, butadienyl, pentadienyl, 3-(1,4-pentadienyl), and hexadienyl.

An alkenyl group can be unsubstituted or optionally substituted. When optionally substituted, one or more hydrogen atoms of the alkenyl group (e.g., from 1 to 4, from 1 to 2, or 1) may be replaced with a moiety independently selected from the group consisting of fluoro, hydroxy, alkoxy, amino, alkylamino, acylamino, thio, and alkylthio, with the proviso that no hydrogen atom substituent on the carbon-carbon double bond is replaced by a hydroxy, amino, or thio group. In some aspects, the alkenyl group is unsubstituted or not optionally substituted.

"Alkenylene" as used herein includes an alkenyl group that is substituted at two points. An example is but-2-enylene ($—CH_2CH{=}CHCH_2—$) and the like.

The term "alkynyl" as used herein includes a straight, branched, or cyclic hydrocarbon containing at least one carbon-carbon triple bond. Examples may include, but are not limited to, ethynyl, propargyl, propynyl, butynyl, pentynyl, hexynyl, heptynyl, octynyl, nonynyl, decynyl, or decynyl.

An alkynyl group can be unsubstituted or optionally substituted. When optionally substituted, one or more hydrogen atoms of the alkynyl group (e.g., from 1 to 4, from 1 to 2, or 1) may be replaced with a moiety independently selected from the group consisting of fluoro, hydroxy, alkoxy, amino, alkylamino, acylamino, thio, and alkylthio, with the proviso that no sp-hybridized hydrogen atom substituent is replaced by a hydroxy, amino, or thio group. In some aspects, the alkynyl group is unsubstituted or not optionally substituted.

"Alkynylene" as used herein includes an alkynyl group that is substituted at two points. An example is 2-butynylene ($—CH_2CCCH_2—$) and the like.

The term "alkoxy" as used herein includes a straight or branched chain saturated or unsaturated hydrocarbon containing at least one oxygen atom in an ether group (e.g., EtO—).

The chain may contain an indicated number of carbon atoms. For example, "$C_1$-$C_{12}$ alkoxy" indicates that the group may have from 1 to 12 (inclusive) carbon atoms and at least one oxygen atom. Examples of a $C_1$-$C_{12}$ alkoxy group include, but are not limited to, methoxy, ethoxy, isopropoxy, butoxy, n-pentoxy, isopentoxy, neopentoxy, and hexoxy.

An alkoxy group can be unsubstituted or optionally substituted. When optionally substituted, one or more hydrogen atoms of the alkoxy group (e.g., from 1 to 4, from 1 to 2, or 1) may be replaced with a moiety independently selected from the group consisting of fluoro, hydroxy, alkoxy, amino, alkylamino, acylamino, thio, and alkylthio, with the proviso that no hydrogen atom alpha to the ether oxygen is replaced by a hydroxy, amino, or thio group. In some aspects, the alkoxy group is unsubstituted or not optionally substituted.

The term "aryl" as used herein includes cyclic aromatic carbon ring systems containing from 6 to 18 carbons. Examples of an aryl group include, but are not limited to, phenyl, naphthyl, anthracenyl, tetracenyl, biphenyl and phenanthrenyl.

The term "cycloalkyl" as used herein includes non-aromatic saturated monocyclic or multicyclic ring system that may contain an indicated number of carbon atoms. For example, $C_3$-$C_{12}$ indicates that the group may have from 3 to 12 (inclusive) carbon atoms in it. If not otherwise indicated, a cycloalkyl group includes about 3 to about 20 carbon atoms. In some aspects, cyclo alkyl groups have 3 to about 12 carbon atoms in the group. In some aspects, cycloalkyl groups have 3 to about 7 carbon atoms in the group. Examples may include, but are not limited to, cyclopropyl, cyclobutyl, cyclopentyl, cyclohexyl, 4,4-dimethylcyclohexyl, and cycloheptyl. The term "cycloalkyl" also includes multicyclic rings such as a bicyclic cycloalkyl, or a tricyclic cycloalkyl which may be in a fused, bridged, or spiro orientation.

The term "cycloalkylene" as used herein includes a cycloalkyl group that is substituted at two points.

The terms "disorder" and "disease" are used herein interchangeably for a condition in a subject. A disorder is a disturbance or derangement that affects the normal function of the body of a subject. A disease is a pathological condition of an organ, a body part, or a system resulting from various causes, such as infection, genetic defect, or environmental stress that is characterized by an identifiable group of symptoms. A disorder or disease can refer to a biofilm-related disorder or disorder caused by a planktonic bacterial phenotype that is characterized by a disease-related growth of bacteria.

The term "effective amount" or "effective dose" as used herein includes an amount sufficient to achieve the desired result and accordingly will depend on the ingredient and its desired result. Nonetheless, once the desired effect is identified, determining the effective amount is within the skill of a person skilled in the art.

As used herein, "fluoroalkyl" includes an alkyl group wherein the alkyl group includes one or more fluoro-substituents. Examples include, but are not limited to, trifluoromethyl.

As used herein, "geminal" substitution includes two or more substituents that are directly attached to the same atom. An example is 3,3-dimethyl substitution on a cyclohexyl or spirocyclohexyl ring.

As used herein, "halo" or "halogen" includes fluoro, chloro, bromo, and iodo.

As used herein, "heterocycloalkyl" includes a non-aromatic saturated ring of about 3 to about 12 ring atoms (e.g., 5 to about 10 ring atoms, 3 to about 8 ring atoms, or 3 to about 6 ring atoms), in which one or more of the atoms in the ring system is an element or elements other than carbon, e.g., nitrogen, oxygen or sulfur. A heterocycloalkyl group optionally comprises at least one $sp^2$-hybridized atom (e.g., a ring incorporating a carbonyl, endocyclic olefin, or exocyclic olefin). In some embodiments, a nitrogen or sulfur atom of the heterocycloalkyl is optionally oxidized to the corresponding N-oxide, S-oxide or S,S-dioxide. The monocyclic heterocycle means a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycloalkyl include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyridazin-3(2H)-onyl, pyridin-2(1H)-onyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "heterocycloalkylene" as used herein includes a heterocycloalkyl group that is substituted at two points.

The term "heterocycloalkyl" also includes multicyclic rings such as a bicyclic heterocycle, or a tricyclic heterocycle which may be in a fused, bridged, or spiro orientation. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, 3-azabicyclo[3.1.0]hexane, 3-azabicyclo[4.1.0]heptane, 3-azabicyclo[3.2.0]heptane, (3aR,6aS)-hexahydro-1H-2$\lambda_2$-cyclopenta[c]pyrrole, (3aR,7aS)-octahydro-2$\lambda_2$-isoindole.

Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms.

A heterocycloalkyl group can be unsubstituted or optionally substituted. When optionally substituted, one or more hydrogen atoms of the group (e.g., from 1 to 4, from 1 to 2, or 1) may be replaced with a moiety independently selected from the group consisting of fluoro, hydroxy, alkoxy, amino, alkylamino, acylamino, thio, and alkylthio. In some aspects, a substituted heterocycyl group can incorporate an exo- or endocyclic alkene (e.g., cyclohex-2-en-1-yl). In some aspects, the heterocycloalkyl group is unsubstituted or not optionally substituted.

The monocyclic, bicyclic, and tricyclic heterocycles are connected to the parent molecular moiety through any carbon atom or any nitrogen atom contained within the rings, and can be unsubstituted or substituted.

As used herein, the term "hydrophilic moiety" or "hydrophilic group" includes a moiety or a functional group that has a strong affinity to water. Examples may include, but are not limited to, a charged moiety, such as a cationic moiety or an anionic moiety, or a polar uncharged moiety, such as an alkoxy group or an amine group.

As used herein, the term "hydroxyalkyl" includes an alkyl group where at least one hydrogen substituent has been replaced with an alcohol (—OH) group. In certain aspects, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

When any two substituent groups or any two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be an alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different).

"Amino protecting group" is a protecting group that is suitable for preventing undesired reactions at an amino nitrogen. Representative amino-protecting groups include, but are not limited to, formyl; acyl groups, for example alkanoyl groups, such as acetyl and trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; and the like.

"Hydroxyl protecting group" is a protecting group that is suitable for preventing undesired reactions at a hydroxyl oxygen. Representative hydroxy-protecting groups include, but are not limited to, acyl groups, for example alkanoyl groups, such as acetyl; arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, orotic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

As used herein, "or" should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

As used herein, "spiro bicyclic cycloalkyl" includes a cycloalkyl in which geminal substituents on a carbon atom are replaced to join in forming a 1,1-substituted ring. For example, but without limitation, for a —C(R')($R^2$)— group that was part of a longer carbon chain, if $R^1$ and $R^2$ joined to form a cyclopropyl ring incorporating the carbon to which $R^1$ and $R^2$ were bonded, this would be a spiro bicyclic cycloalkyl group (i.e., spirocyclopropyl).

The term "spiro bicyclic cycloalkylene" as used herein includes a spiro bicyclic cycloalkyl group that is substituted at two points.

As used herein, "spiro bicyclic heterocycloalkyl" includes a heterocycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a pyrrolidine ring incorporating the carbon to which $R^1$ and $R^2$ were bonded, this would be a spiro bicyclic heterocycloalkyl group.

The term "spiro bicyclic heterocycloalkylene" as used herein includes a spiro bicyclic heterocycloalkyl group that is substituted at two points.

Some compounds disclosed herein are characterized by the presence of amino functional groups. One of ordinary skill would therefore understand that compounds can be isolated as salts wherein the amino functional group nitrogen is quarternized.

As used herein, the term "treat," "treating," or "treatment" includes administering or applying a composition (e.g., a composition described herein) in an amount, manner (e.g., schedule of administration), and mode (e.g., route of administration) that is effective to improve a disorder or a symptom thereof, or to retard, or to slow the progression of a disorder or a symptom thereof. Such improvements can include, but are not limited to, alleviation or amelioration of one or more symptoms or conditions, diminishment of the extent of a disease, stabilizing (i.e., not worsening) the state of disease, delaying or slowing of disease progression, amelioration or palliation of the disease state, diminishment of the reoccurrence of disease, and remission, whether partial or total and whether detectable or undetectable.

Embodiments

Compounds

In a first aspect, the disclosure provides a compound of Formula I:

I

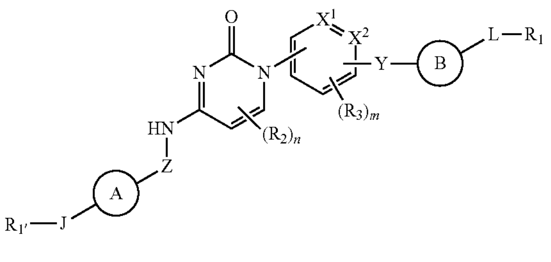

or a pharmaceutically acceptable salt thereof, wherein:

Z is (C═O), (C═S), (C═$NR_z$), (S═O), or $SO_2$; wherein $R_z$ is H, $C_1$-$C_6$ alkyl, or CN;

ring A is a monocyclic heterocycloalkylene or bicyclic heterocycloalkylene, wherein the monocyclic heterocycloalkylene or bicyclic heterocycloalkylene are optionally substituted with up to three substituents independently selected from the group consisting of $C_1$-$C_6$ alkyl, $C_1$-$C_6$ alkoxy, $C_1$-$C_6$ hydroxyalkyl, halo, CN, $C_1$-$C_6$ haloalkyl, phenyl, OH, $NH_2$, NH($C_1$-$C_6$ alkyl), N($C_1$-$C_6$ alkyl)$_2$, COOH, COO($C_1$-$C_6$ alkyl), —$CONH_2$, and oxo;

J is absent or is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to three substituents independently selected from the group consisting of halo, $C_1$-$C_6$ alkyl, $C_1$-$C_6$ alkoxy, $C_1$-$C_6$ haloalkyl, $NH_2$, CN, and OH; wherein at each occurrence of $C_1$-$C_6$ alkylene, up to two methylene units of the $C_1$-$C_6$ alkylene may independently and optionally be replaced with O, S, $SO_2$, C═O, or

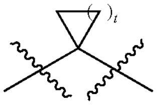
;

wherein t is 1, 2, 3, or 4;

$X^1$ and $X^2$ are each independently C—H or N;

Y is a linear $C_1$-$C_8$ alkylene, $C_2$-$C_8$ alkenylene, or $C_2$-$C_8$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), N—($C_{3-8}$ cycloalkyl), NH(C═O), N—($C_{1-6}$ alkyl) (C═O), (C═O), or

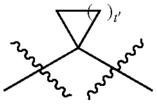
;

wherein t' is 1, 2, 3, or 4;

ring B is a monocyclic cycloalkylene or monocyclic heterocycloalkylene, either of which is optionally substituted with up to three substituents independently selected from the group consisting of $C_1$-$C_6$ alkyl, $C_1$-$C_6$ alkoxy, halo, CN, $NH_2$, $C_1$-$C_6$ haloalkyl, OH, COOH, COO($C_1$-$C_6$ alkyl), $CONH_2$, and $C_1$-$C_6$ hydroxyalkyl;

L is absent, or is a $C_1$-$C_6$ alkylene, wherein up to two methylene units of the $C_1$-$C_6$ alkylene may independently be replaced with O, NH, (C═O), NH(C═O), N—($C_{1-6}$ alkyl)(C═O), (C═NH), NH(C═N), or N—($C_{1-6}$ alkyl);

$R_1$ is H, halo, $C_1$-$C_6$ haloalkyl, $NR_{x'}R_{y'}$, or monocyclic heterocycloalkyl optionally substituted with $NH_2$, NH($C_1$-$C_6$ alkyl), N($C_1$-$C_6$ alkyl)$_2$, wherein $R_{x'}$ and $R_{y'}$ are each independently H, $C_1$-$C_6$ alkyl, $C_3$-$C_8$ cycloalkyl, or an amino protecting group, wherein the $C_1$-$C_6$ alkyl and $C_3$-$C_8$ cycloalkyl are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$CONH_2$, and oxo; or $R_1$ is NH(C═O)—($C_1$-$C_6$) alkyl, or NH—(C═NH)—$NH_2$, either of which may be optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, COO($C_1$-$C_6$ alkyl), $CONH_2$, and oxo;

$R_{1'}$ is H or $NR_xR_y$, wherein $R_x$ and $R_y$ are each independently H, $C_1$-$C_6$ alkyl, $C_1$-$C_6$ alkyl-$SO_3$, CO($C_1$-$C_6$ alkyl), CO—($C_1$-$C_6$ alkylene)-$NH_2$, or an amino protecting group;

$R_2$ and $R_3$ are each independently selected from the group consisting of $C_1$-$C_6$ alkyl, halo, CN, OH, $NH_2$, O($C_1$-$C_6$ haloalkyl), NH($C_1$-$C_6$ alkyl), N($C_1$-$C_6$ alkyl)$_2$, —COO($C_1$-$C_6$ alkyl), —$CONH_2$, $C_1$-$C_6$ haloalkyl, $C_1$-$C_6$ alkoxy, and $C_1$-$C_6$ haloalkoxy; and m and n are each independently 0, 1, 2, or 3.

In one embodiment of a compound of formula I or a pharmaceutically acceptable salt thereof, Z is (C═S), (C═$NR_z$), S═O, or $SO_2$, wherein $R_z$ is H, $C_1$-$C_6$ alkyl, or CN.

In another embodiment of a compound of formula I or a pharmaceutically acceptable salt thereof, Z is C═NH, C═N ($C_1$-$C_6$ alkyl), or C═N—CN.

In another embodiment of a compound of formula I or a pharmaceutically acceptable salt thereof, Z is —(C═O)—.

In another embodiment of a compound of formula I or a pharmaceutically acceptable salt thereof, ring A is a 4 to 8 membered monocyclic heterocycloalkylene or a 6 to 12 membered bicyclic heterocycloalkylene, wherein the monocyclic heterocycloalkylene and bicyclic heterocycloalkylene are optionally substituted with up to three substituents independently selected from the group consisting of $C_1$-$C_6$ alkyl, $C_1$-$C_6$ alkoxy, $C_1$-$C_6$ hydroxyalkyl, halo, $C_1$-$C_6$ haloalkyl, phenyl, OH, $NH_2$, COOH, COO($C_1$-$C_6$ alkyl), and $CONH_2$.

In another embodiment, ring A is a 4 to 7 membered monocyclic heterocycloalkylene optionally substituted with up to three substituents selected from the group consisting of halo, $C_1$-$C_6$ alkyl, $C_1$-$C_6$ hydroxyalkyl, phenyl, COOH, and COO($C_1$-$C_6$ alkyl). In another embodiment, ring A is a 4 to 7 membered monocyclic heterocycloalkylene optionally substituted with up to two substituents independently selected from the group consisting of halo, $C_1$-$C_6$ alkyl, $C_1$-$C_6$ hydroxyalkyl, phenyl, COOH, and COO($C_1$-$C_6$ alkyl), wherein the monocyclic heterocycloalkylene contains up to two heteroatoms selected from nitrogen and oxygen. In another embodiment, ring A contains two nitrogen atoms. In another embodiment, ring A is a 6 membered monocyclic heterocycloalkylene optionally substituted with halo, $C_1$-$C_6$ alkyl, $C_1$-$C_6$ hydroxyalkyl, phenyl, COOH, or COO($C_1$-$C_6$ alkyl), wherein the monocyclic heterocycloalkylene contains two nitrogen atoms.

In another embodiment, ring A is a 6 to 12 membered bicyclic heterocycloalkylene optionally substituted with up to three substituents selected from the group consisting of $C_1$-$C_6$ alkyl, $C_1$-$C_6$ alkoxy, $C_1$-$C_6$ hydroxyalkyl, halo, $C_1$-$C_6$ haloalkyl, phenyl, OH, $NH_2$, COOH, COO($C_1$-$C_6$ alkyl), and —$CONH_2$. In another embodiment, ring A is a 6 to 11 membered bicyclic heterocycloalkylene optionally substituted with up to three substituents selected from the group consisting of $C_1$-$C_6$ alkyl, $C_1$-$C_6$ alkoxy, $C_1$-$C_6$ hydroxyalkyl, halo, $C_1$-$C_6$ haloalkyl, phenyl, OH, $NH_2$, COOH, COO ($C_1$-$C_6$ alkyl), and —$CONH_2$, wherein the bicyclic heterocycloalkylene contains up to three heteroatoms selected from nitrogen and oxygen. In another embodiment, ring A is a 6 to 10 membered bicyclic heterocycloalkylene contains up to three heteroatoms selected from nitrogen and oxygen. In another embodiment, ring A is a 6 to 10 membered fused, spiro, or bridged bicyclic heterocycloalkylene containing up to three heteroatoms selected from nitrogen and oxygen.

In another embodiment of a compound of formula I or a pharmaceutically acceptable salt thereof, ring A is selected from any of the moieties provided in Table 1:

TABLE 1

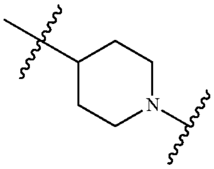,
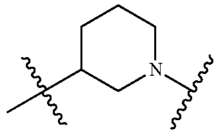,
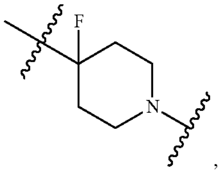,
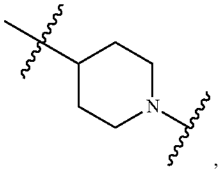,
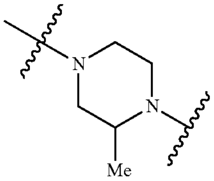,
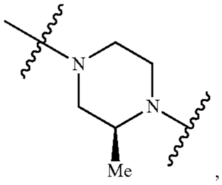,
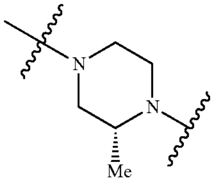,
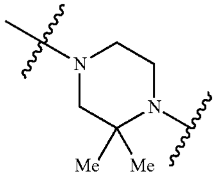,
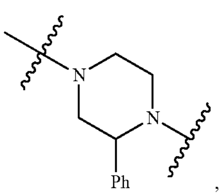,
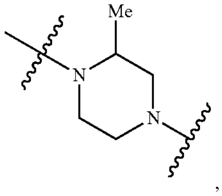,
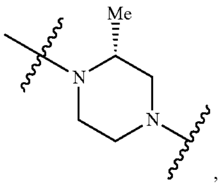,
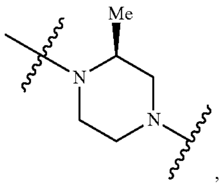, TABLE 1-continued

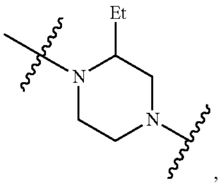,
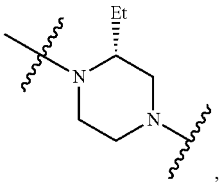,
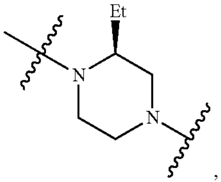,
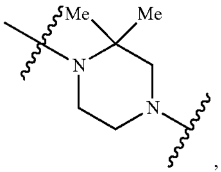,
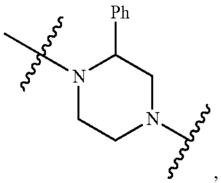,
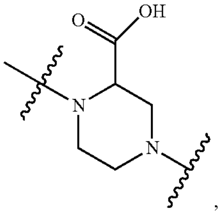,
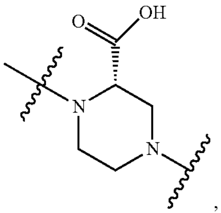,
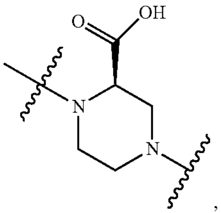,
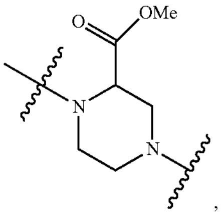,
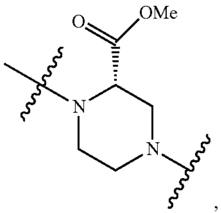,
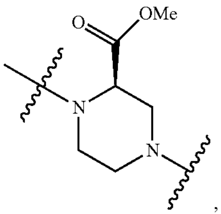,
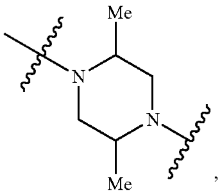,
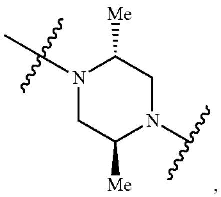,
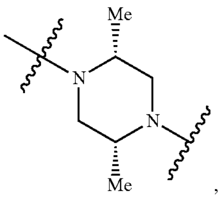, TABLE 1-continued
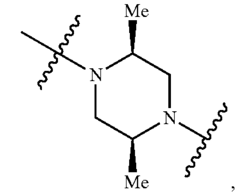
,
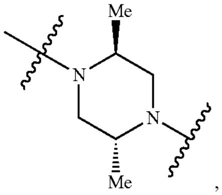
,
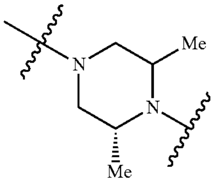
,
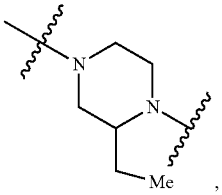
,
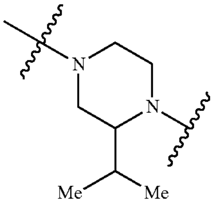
,
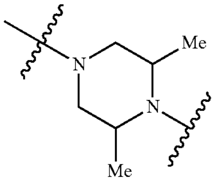
,
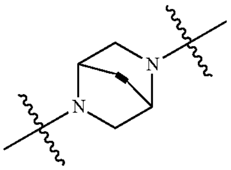
,
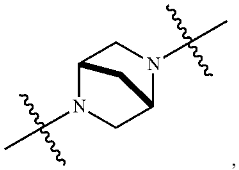
,
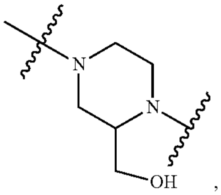
,
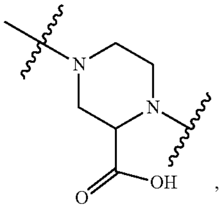
,
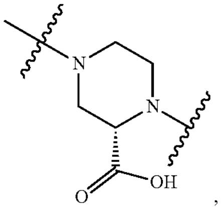
,
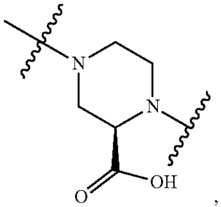
,
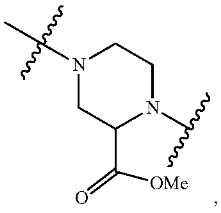
,
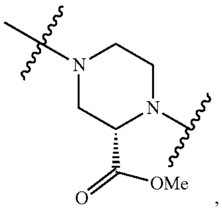
,
TABLE 1-continued
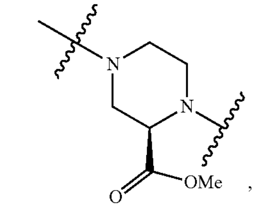
,
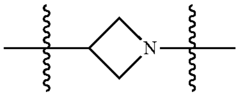
,
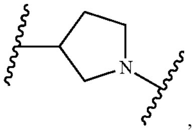
,
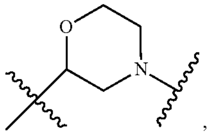
,
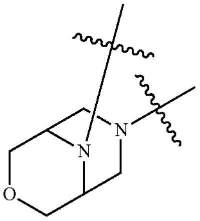
,
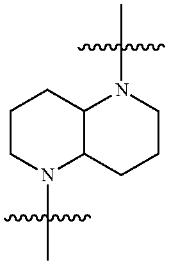
,
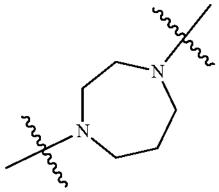
,
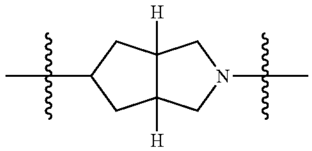
,
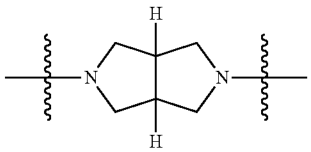
,
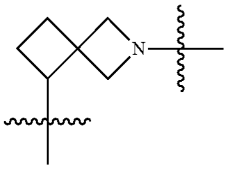
,
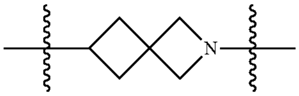
,
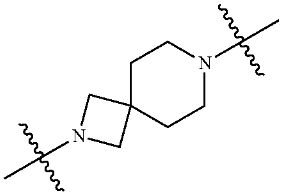
, and
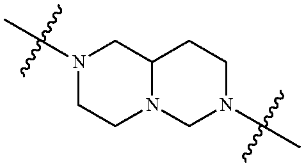
.
In another embodiment of a compound of formula I or a pharmaceutically acceptable salt thereof, J is absent.

In another embodiment of a compound of formula I or a pharmaceutically acceptable salt thereof, J is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to two substituents independently selected from halo, $C_1$-$C_6$ alkyl, $C_1$-$C_6$ alkoxy, $C_1$-$C_6$ haloalkyl, $NH_2$, CN, or OH; wherein at each occurrence of $C_1$-$C_6$ alkylene, one or two methylene units of the $C_1$-$C_6$ alkylene may independently and optionally be replaced with (C═O) or

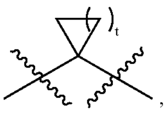, wherein t is 1, 2, or 3.

In another embodiment, J is $C_1$-$C_6$ alkylene, $C_1$-$C_6$ alkylene-heterocycloalkylene or $C_1$-$C_6$ alkylene-cycloalkylene, wherein one methylene unit of the $C_1$-$C_6$ alkylene may be replaced with (C═O). In another embodiment, J is $C_1$-$C_6$ alkylene, wherein one methylene unit of the $C_1$-$C_6$ alkylene may be replaced with (C═O). In another embodiment, J is (C═O)-heterocycloalkylene, wherein the heterocycloalkylene is a 5 or 6 membered nitrogen containing heterocycloalkylene optionally substituted with up to two $C_1$-$C_6$ alkyl. In another embodiment, J is (C═O)—($C_3$-$C_6$ cycloalkylene).

In another embodiment, J is $C_1$-$C_6$ alkylene optionally substituted with halo, $C_1$-$C_6$ haloalkyl, or OH, wherein one methylene unit of the $C_1$-$C_6$ alkylene may be replaced with (C═O). In another embodiment, J is $C_1$-$C_6$ alkylene, wherein one methylene unit of the $C_1$-$C_6$ alkylene may be replaced with (C═O), and another methylene unit of the $C_1$-$C_6$ alkylene may be replaced by

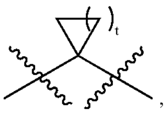, wherein t is 1, 2, 3, or 4. In another embodiment, t is 1 or 2.

In another embodiment, J is a $C_1$-$C_6$ alkylene optionally substituted with $CF_3$ or OH, wherein one methylene unit of the optionally substituted $C_1$-$C_6$ alkylene may be replaced with —(C═O)—.

In another embodiment of a compound of formula I or a pharmaceutically acceptable salt thereof, J is selected from any of the moieties provided in Table 2:

TABLE 2

$—CH_2—$, 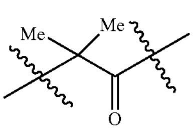, 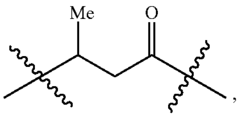,

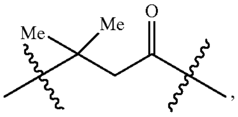, 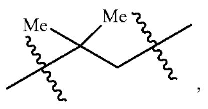,

TABLE 2-continued

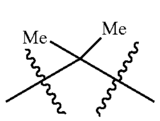 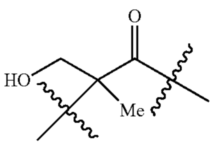,

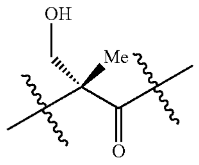, 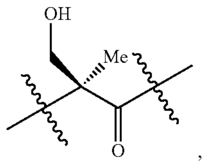,

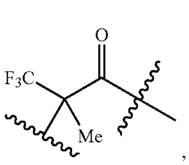, 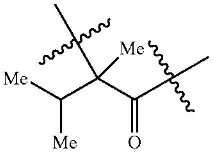,

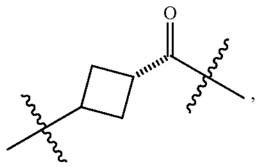, 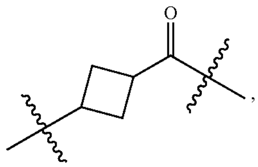,

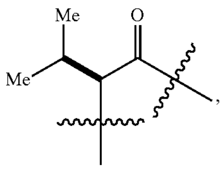, 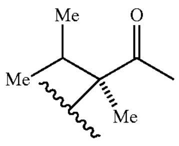,

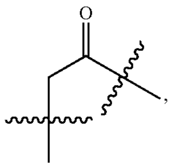, 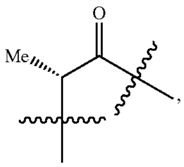,

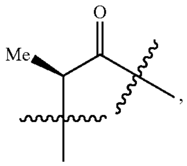, 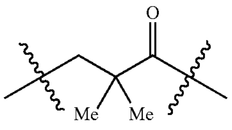,

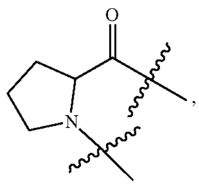, 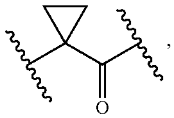,

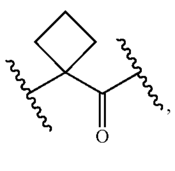, 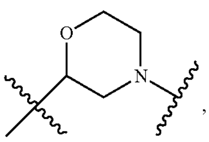,

TABLE 2-continued

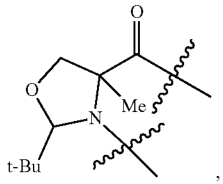
, 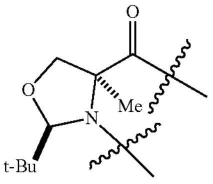
, and

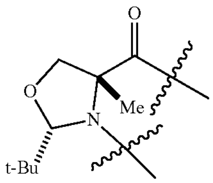
.

In another embodiment of a compound of formula I or a pharmaceutically acceptable salt thereof, $R_{1'}$ is H or $NR_xR_y$, wherein $R_x$ and $R_y$ are each independently H, $C_1$-$C_6$ alkyl, $C_1$-$C_6$ alkyl-$SO_3$, CO($C_1$-$C_6$ alkyl), or CO—($C_1$-$C_6$ alkylene)-$NH_2$. In another embodiment, $R_{1'}$ is H, $NH_2$, NH($C_1$-$C_6$ alkyl), NH($C_1$-$C_6$ alkyl)$_2$, NH—CO($C_1$-$C_6$ alkyl), or NH—CO—($C_1$-$C_6$ alkylene)-$NH_2$. In another embodiment, $R_{1'}$ is H, $NH_2$, or NH($C_1$-$C_6$ alkyl). In another embodiment, $R_{1'}$ is H or $NH_2$. In another embodiment, $R_{1'}$ is H. In another embodiment, $R_{1'}$ is $NH_2$.

$R_{1'}$ is H or $NR_xR_y$, wherein $R_x$ and $R_y$ are each independently H, $C_1$-$C_6$ alkyl, $C_1$-$C_6$ alkyl-$SO_3$, CO($C_1$-$C_6$ alkyl), CO—($C_1$-$C_6$ alkylene)-$NH_2$, or an amino protecting group.

In another embodiment of a compound of formula I or a pharmaceutically acceptable salt thereof, Z is (C═O); ring A is a 4 to 7 membered monocyclic heterocycloalkylene optionally substituted with up to two substituents independently selected from the group consisting of halo, $C_1$-$C_6$ alkyl, $C_1$-$C_6$ hydroxyalkyl, phenyl, COOH, and COO($C_1$-$C_6$ alkyl), wherein the monocyclic heterocycloalkylene contains up to two heteroatoms selected from nitrogen or oxygen; J is $C_1$-$C_6$ alkylene, $C_1$-$C_6$ alkylene-heterocycloalkylene or $C_1$-$C_6$ alkylene-cycloalkylene, any of which may be optionally substituted with up to two substituents independently selected from halo, $C_1$-$C_6$ alkyl, $C_1$-$C_6$ alkoxy, $C_1$-$C_6$ haloalkyl, $NH_2$, CN, or OH; wherein at each occurrence of $C_1$-$C_6$ alkylene, one or two methylene units of the $C_1$-$C_6$ alkylene may independently and optionally be replaced with C═O or

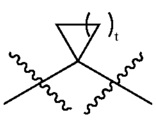
, wherein t is 1, 2, or 3; and $R_{1'}$ is H, $NH_2$, or NH($C_1$-$C_6$ alkyl). In another embodiment, Z is (C═O); ring A is selected from any of the moieties provided in Table 1; J is selected from any of the moieties provided in Table 2; and $R_{1'}$ is H, $NH_2$, or NH($C_1$-$C_6$ alkyl).

In another embodiment of a compound of formula I or a pharmaceutically acceptable salt thereof,

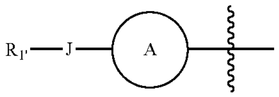

is selected from any of the moieties provided in Table 3:

TABLE 3

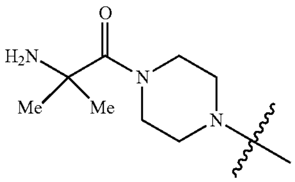
,

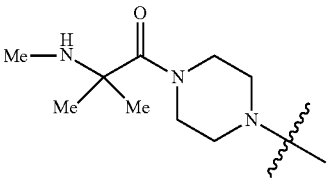
,

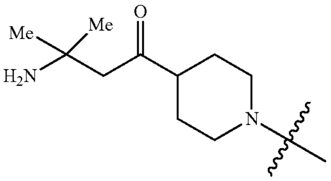
,

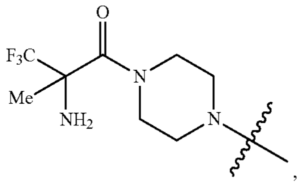 [SMILES: *N1CCN(C(=O)C(C)(N)C(F)(F)F)CC1]
,

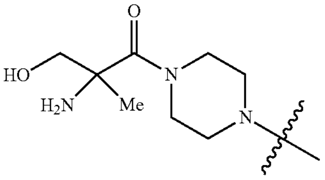
,

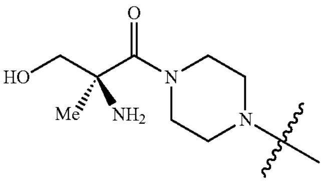
,

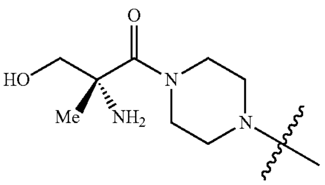
,

TABLE 3-continued
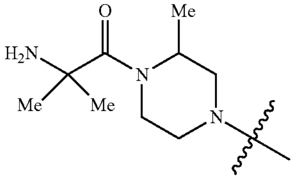,
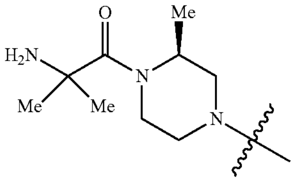,
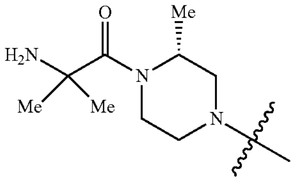,
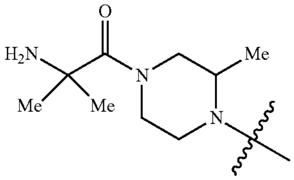,
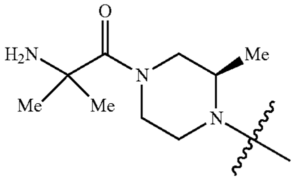,
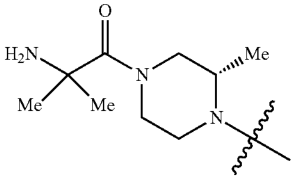,
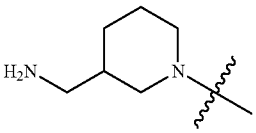, 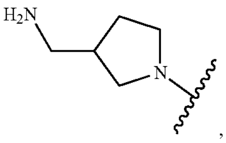,
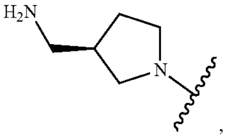, 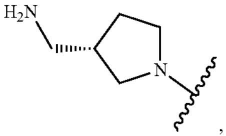,
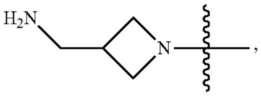, 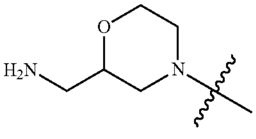,
TABLE 3-continued
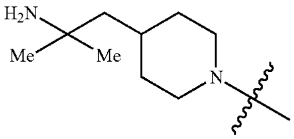,
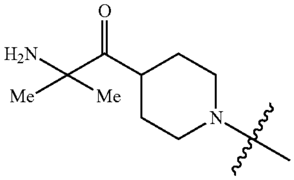,
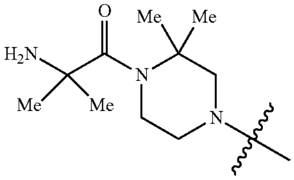,
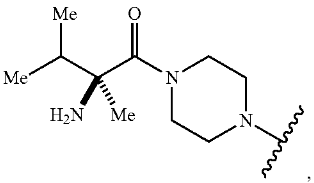 [SMILES: *N1CCN(C(=O)[C@@](C)(N)C(C)C)CC1],
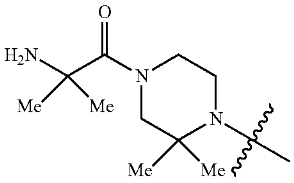,
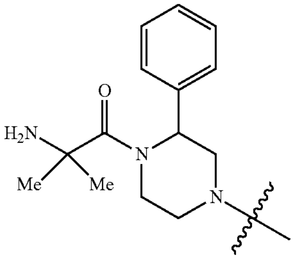,
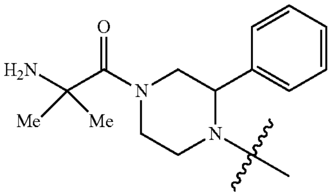,
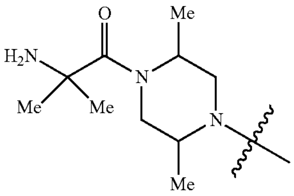, TABLE 3-continued
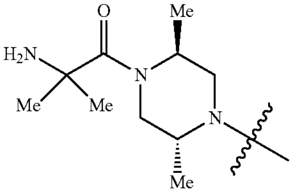
,
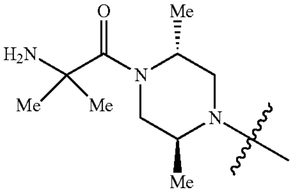
,
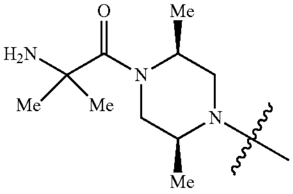 [SMILES: *N1C[C@H](C)N(C(=O)C(C)(C)N)C[C@@H]1C]
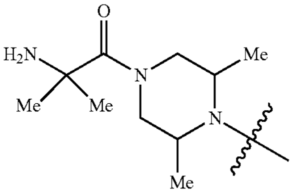
,
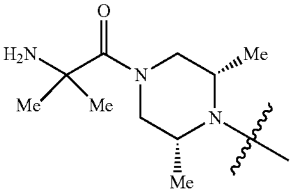
,
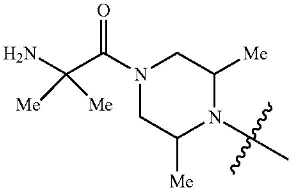
,
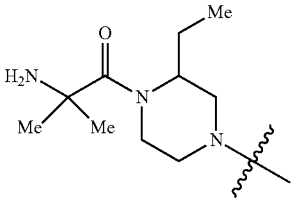
,
TABLE 3-continued
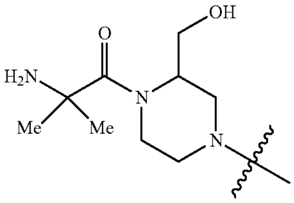
,
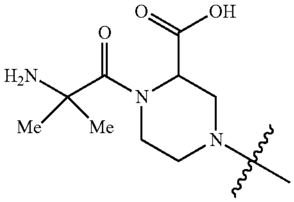
,
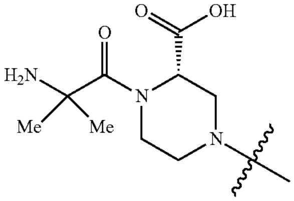
,
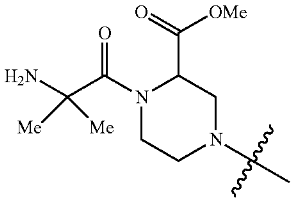
,
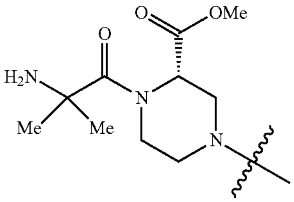
,
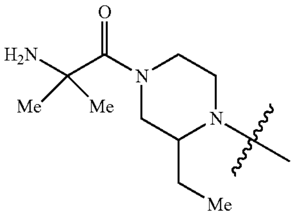
,
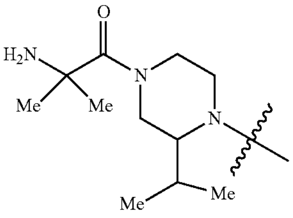
, TABLE 3-continued
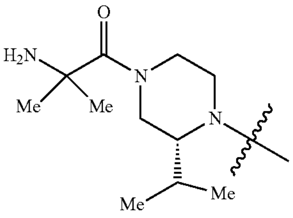
,
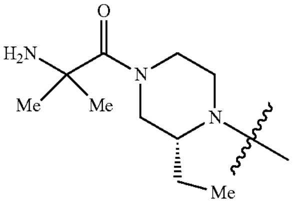
,
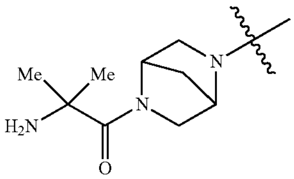
,
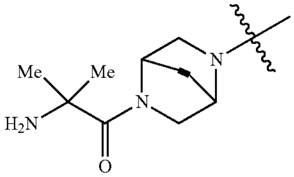
,
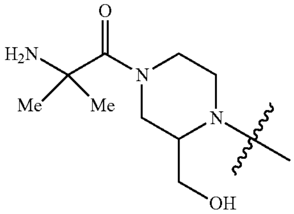
,
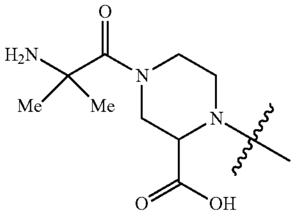
,
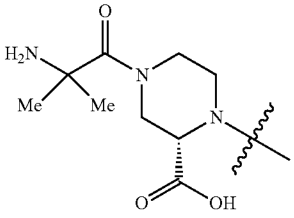
,
TABLE 3-continued
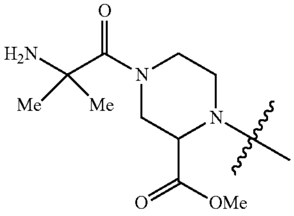
,
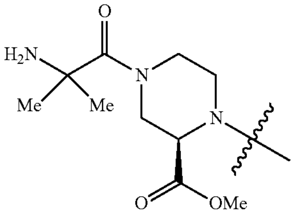
,
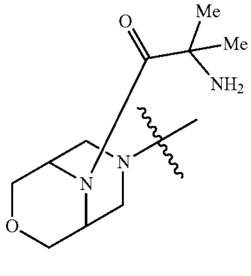
,
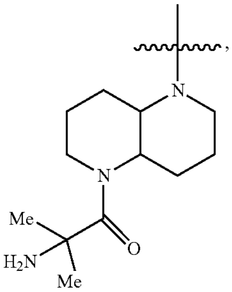 [SMILES: *N1CCCC2C1CCCN2C(=O)C(C)(C)N]
,
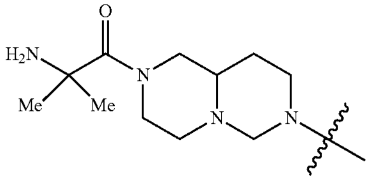
,
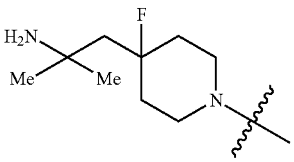
,
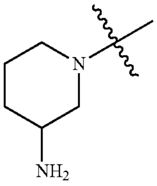
,
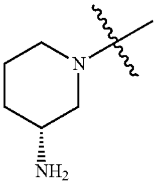
,
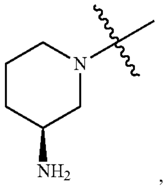
, TABLE 3-continued
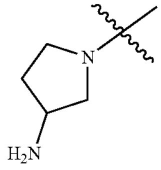 , 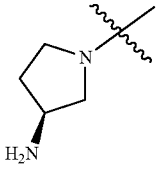 , 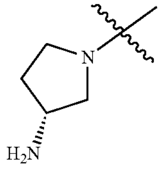 ,
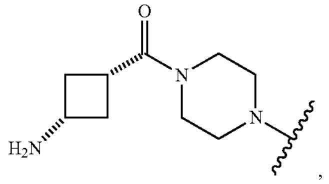 ,
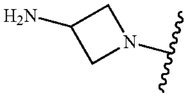 , 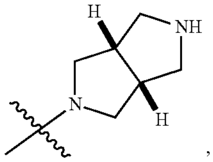 ,
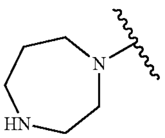 , 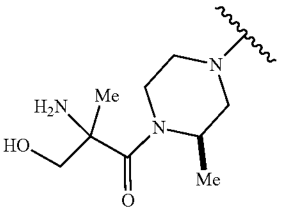 ,
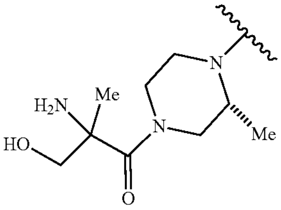 ,
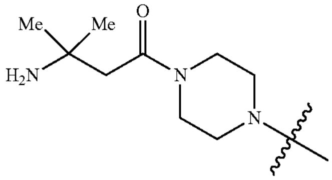 ,
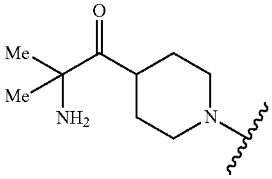 , 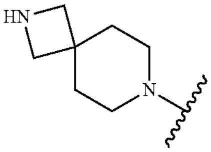 ,
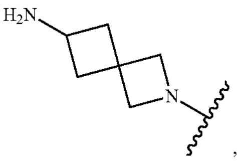 , 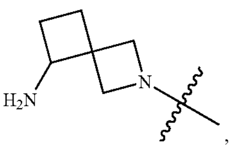 ,
TABLE 3-continued
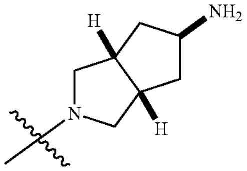 , 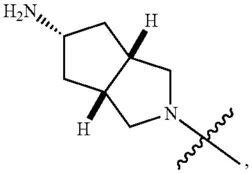 ,
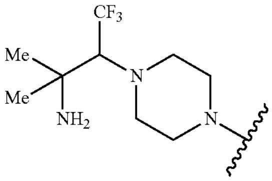 ,
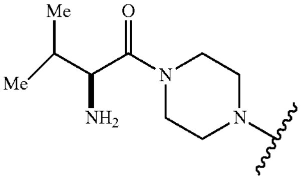 ,
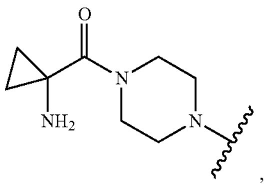 , 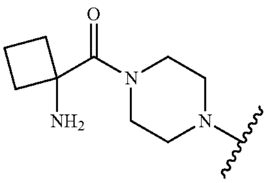 ,
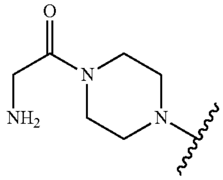 , 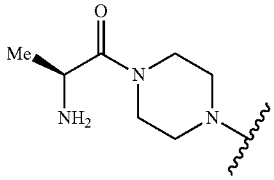 ,
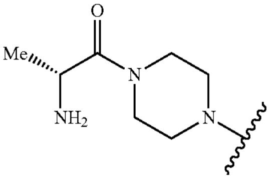 , 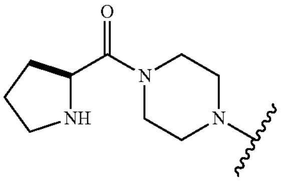 ,
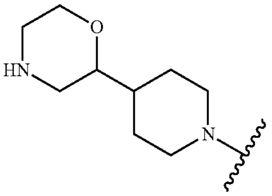 , 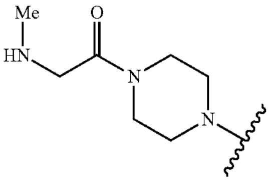 ,
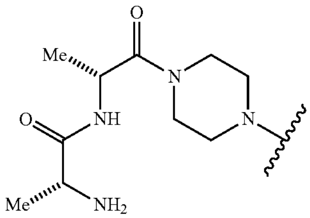 , TABLE 3-continued

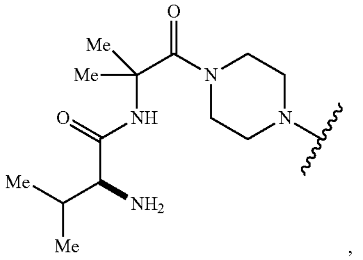 [SMILES: *N1CCN(C(=O)C(C)(C)NC(=O)[C@@H](N)C(C)C)CC1]

,

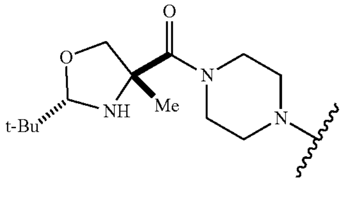

, and

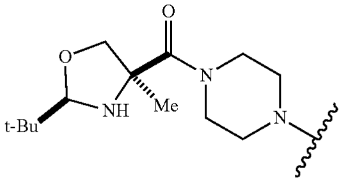

.

In another embodiment of a compound of formula I or a pharmaceutically acceptable salt thereof,

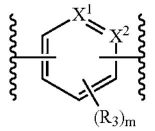

is

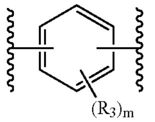

or

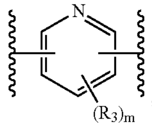

, wherein each $R_3$ is independently selected from $C_1$-$C_6$ alkyl, halo, CN, OH, $NH_2$, $NH(C_1$-$C_6$ alkyl), $O(C_1$-$C_6$ haloalkyl), $N(C_1$-$C_6$ alkyl$)_2$, $COO(C_1$-$C_6$ alkyl), $CONH_2$, $C_1$-$C_6$ haloalkyl, or $C_1$-$C_6$ alkoxy, wherein m is 0, 1, 2, or 3. In another embodiment, each $R_3$ is independently selected from the group consisting of $C_1$-$C_6$ alkyl, $C_1$-$C_6$ alkoxy, halo, $O(C_1$-$C_6$ haloalkyl), and $C_1$-$C_6$ haloalkyl, wherein m is 0, 1 or 2.

In another embodiment,

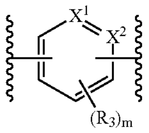

is

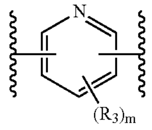

,

In another embodiment,

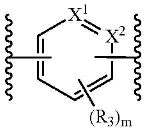

is

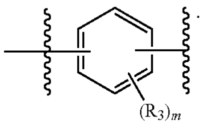

.

In another embodiment,

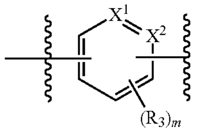

is

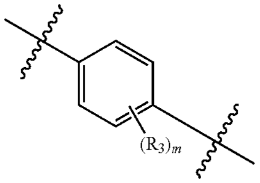

or

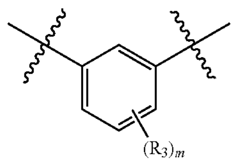

, wherein each $R_3$ is independently selected from the group consisting of $C_1$-$C_6$ alkyl, $C_1$-$C_6$ alkoxy, halo, $O(C_1$-$C_6$ haloalkyl), and $C_1$-$C_6$ haloalkyl, wherein m is 0, 1 or 2.

In another embodiment,

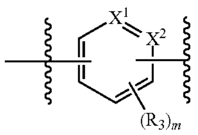

is

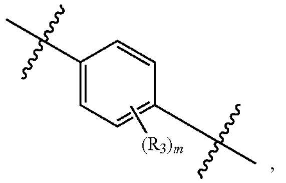

wherein each $R_3$ is independently $C_1$-$C_6$ alkyl, $C_1$-$C_6$ alkoxy, halo, O($C_1$-$C_6$ haloalkyl), and $C_1$-$C_6$ haloalkyl, wherein m is 0, 1, or 2.

In another embodiment,

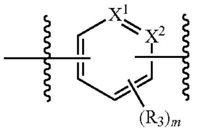

is selected from the group consisting of

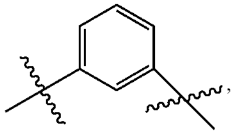

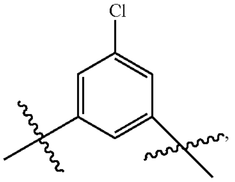

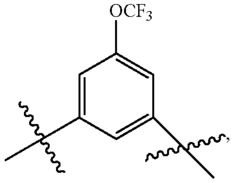

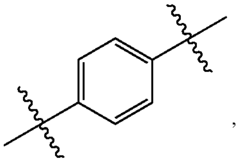

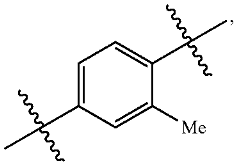

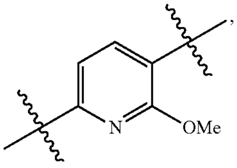

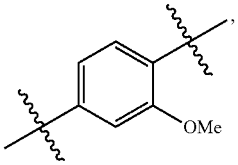

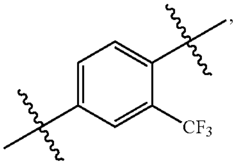

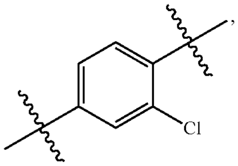

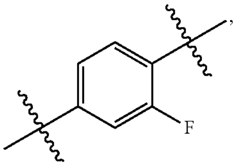

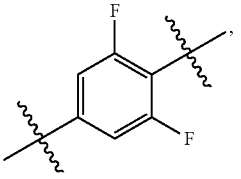

, and

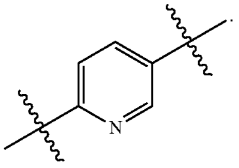

In one embodiment of a compound of formula I or a pharmaceutically acceptable salt thereof, Y is a linear $C_1$-$C_8$ alkylene optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, wherein up to two methylene units of the $C_1$-$C_8$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-$C_{3-8}$ cycloalkyl), N—($C_{3-8}$ cycloalkyl), NH(C═O), N—($C_{1-6}$ alkyl) (C═O), (C═O), or

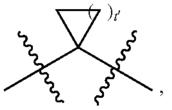

wherein t' is 1 or 2.

In another embodiment, Y is a linear $C_1$-$C_6$ alkylene optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, wherein up to two methylene units of the $C_1$-$C_8$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-$C_{3-8}$ cycloalkyl), N—($C_{3-8}$ cycloalkyl), NH(C═O), N—($C_{1-6}$ alkyl) (C═O), (C═O), or

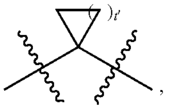

wherein t' is 1 or 2.

In another embodiment, Y is a linear $C_1$-$C_4$ alkylene optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, wherein up to two methylene units of the $C_1$-$C_8$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-$C_3$ cycloalkyl), N—($C_3$ cycloalkyl), NH(C═O), N—($C_{1-6}$ alkyl) (C═O), (C═O), or

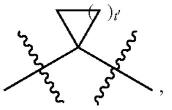

wherein t' is 1 or 2.

In another embodiment, Y is $CR_iR_{ii}$, wherein $R_i$ and $R_{ii}$ are each independently H, OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy. In another embodiment, $R_i$ and $R_{ii}$ are each independently H, $C_1$-$C_6$ alkyl, COO($C_1$-$C_6$ alkyl), or COOH. In another embodiment, $CR_iR_{ii}$ is $CH_2$, CH($C_1$-$C_6$ alkyl), C($C_1$-$C_6$ alkyl)$_2$, CHCOO($C_1$-$C_6$ alkyl) and CHCOOH. In another embodiment, $CR_iR_{ii}$ is $CH_2$, CH($CH_3$), CH(COOEt), or CH(COOH). In another embodiment, $CR_iR_{ii}$ is $CH_2$.

In another embodiment, Y is —C($R_iR_j$)—C($R_{i'}R_{j'}$)—, wherein $R_i$, $R_j$, $R_{i'}$, $R_{j'}$ are each independently H or $C_1$-$C_6$ alkyl, wherein C($R_iR_j$) and C($R_{i'}R_{j'}$) are each independently and optionally replaced with NH, N—($C_{1-6}$ alkyl), N—($C_1$-

$C_6$ hydroxyalkyl), N—($C_1$-$C_6$ haloalkyl), N—($C_{1-6}$ alkylene-$C_{3-8}$ cycloalkyl), N—($C_{3-8}$ cycloalkyl),

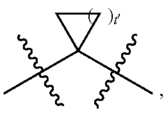

or (C═O), wherein t' is 1 or 2.

In another embodiment, Y is C—($R_iR_j$)—C($R_{i'}R_{j'}$)—, which is selected from the group consisting of

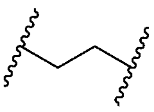 , 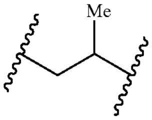 , 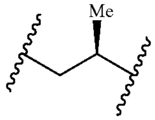 , 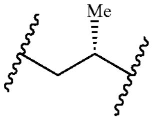 , 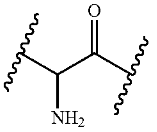 , 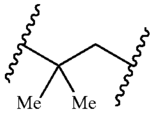 ,

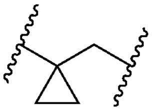 ,

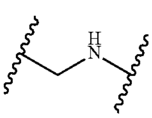 , 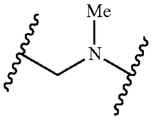 , 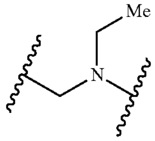 , 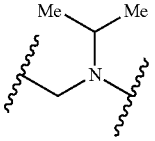 , 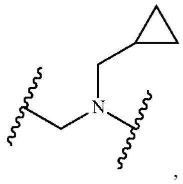 , 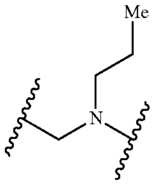 ,

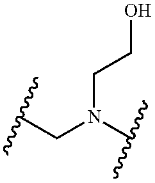 , 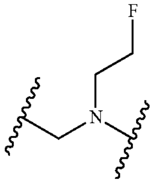 , 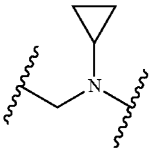 , 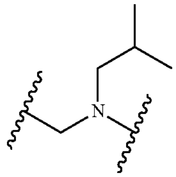 , and 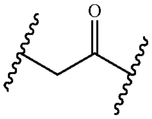 ,

-continued

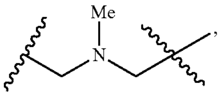

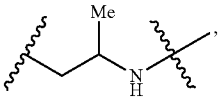

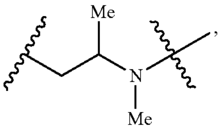

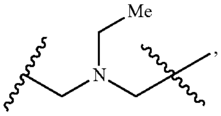

In another embodiment, Y is a linear $C_3$ alkylene, $C_3$ alkenylene, or $C_3$ alkynylene, any of which are optionally substituted with OH, $NH_2$, halo, $C_1$-$C_6$ alkyl, or $C_1$-$C_6$ alkoxy, and wherein one or two carbon atoms of the $C_3$ alkylene, $C_3$ alkenylene, or $C_3$ alkynylene is replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-$C_{3-8}$ cycloalkyl), NH(C═O)—, N—($C_{1-6}$ alkyl)(C═O)—, or (C═O). In another embodiment, Y is a linear $C_3$ alkylene optionally substituted with $NH_2$ or $C_1$-$C_6$ alkyl, wherein up to two one methylene units of the linear $C_3$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-$C_{3-8}$ cycloalkyl), or (C═O).

In another embodiment, Y is the optionally substituted and replaced linear $C_3$ alkylene, which is selected from the group consisting of

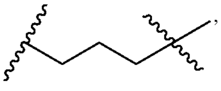

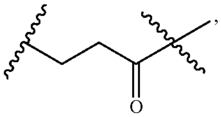

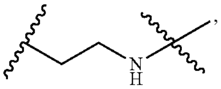

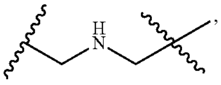

-continued

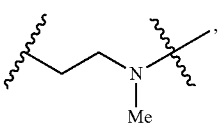

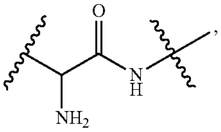

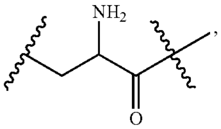

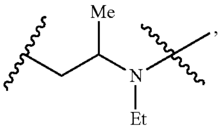

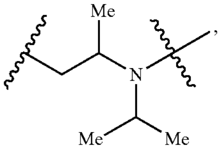

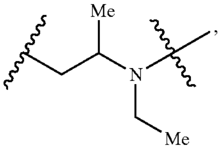

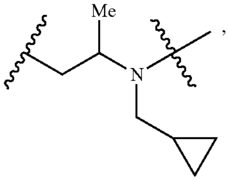

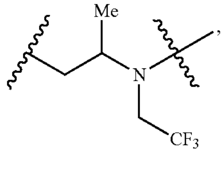

-continued

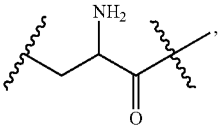,
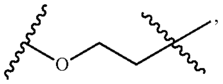,

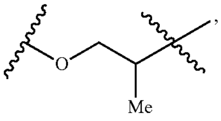,
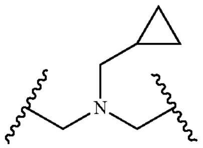,

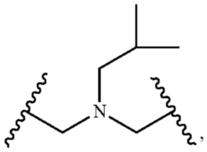,
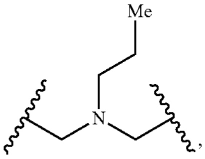,

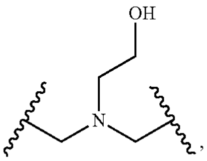, and
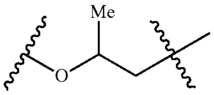.

In another embodiment, Y is a linear $C_4$ alkylene, $C_4$ alkenylene, or $C_4$ alkynylene, any of which are optionally substituted with OH, $NH_2$, halo, $C_1$-$C_6$ alkyl, or $C_1$-$C_6$ alkoxy, and wherein one or two carbon atoms of the $C_4$ alkylene, $C_4$ alkenylene, or $C_4$ alkynylene is replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O)—, N—($C_{1-6}$ alkyl)(C═O)—, or (C═O). In another embodiment, Y is a linear $C_4$ alkylene optionally substituted with $NH_2$ or $C_1$-$C_6$ alkyl, wherein up to two one methylene units of the linear $C_3$ alkylene are optionally and independently replaced by O, NH, N—($C_1$-$C_6$ alkyl), or (C═O).

In another embodiment, Y is the optionally substituted and replaced linear $C_4$ alkylene, which is selected from the group consisting of

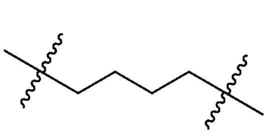,
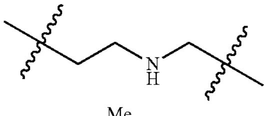,
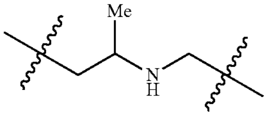,

-continued

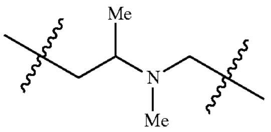,
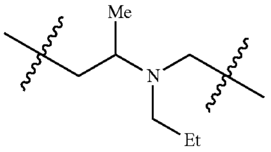,
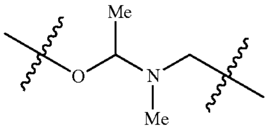,
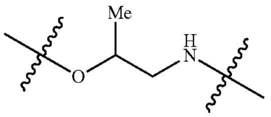,
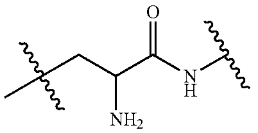 and
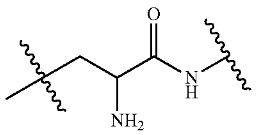.

In another embodiment, Y is selected from any of the moieties provided in Table 4:

TABLE 4

$CH_2$, $CH(CH_3)$, CH(COOEt), CH(COOH),

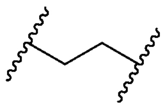, 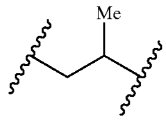, 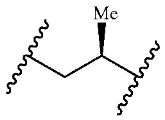,
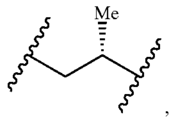, 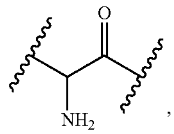, 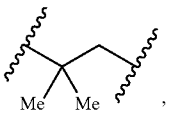,
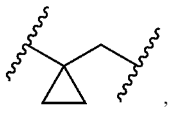, 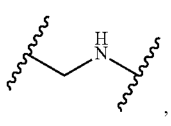, 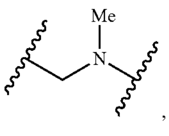,
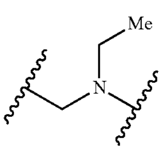, 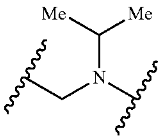, 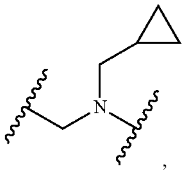, TABLE 4-continued
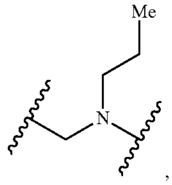, 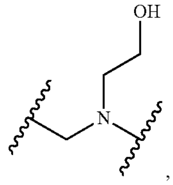, 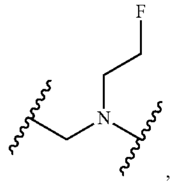,
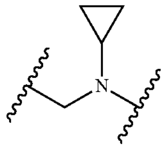, 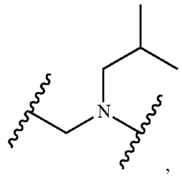, 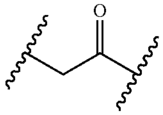,
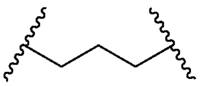, 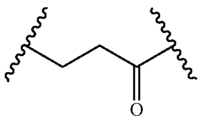,
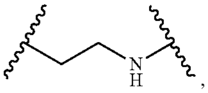, 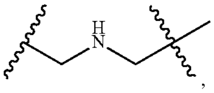,
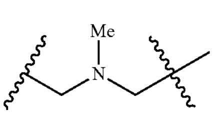, 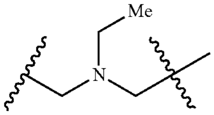,
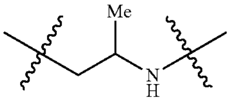, 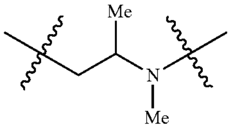,
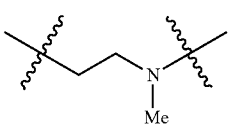, 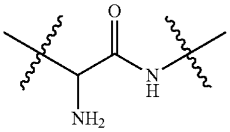,
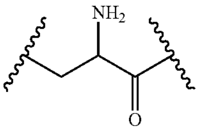, 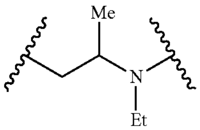,
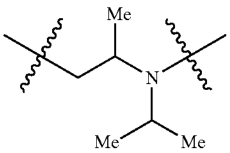, 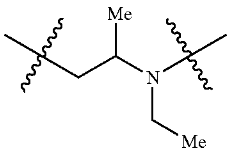,
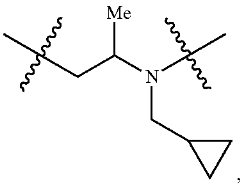, 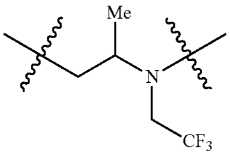,
TABLE 4-continued
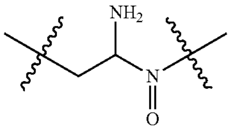, 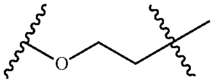,
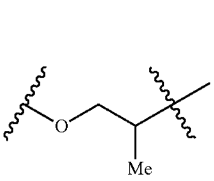, 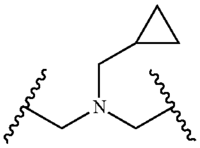,
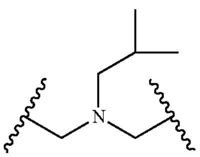, 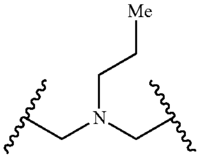,
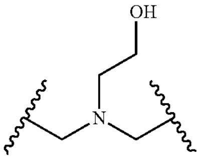, 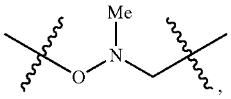,
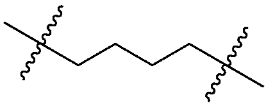, 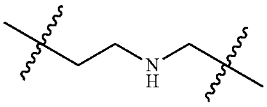,
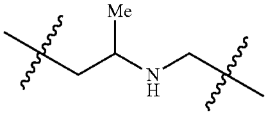, 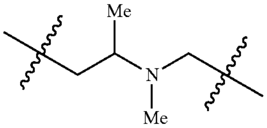,
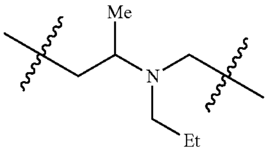, 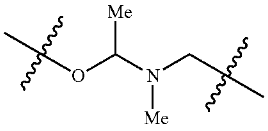,
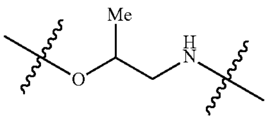,
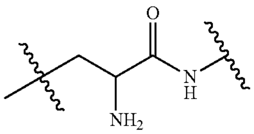 and 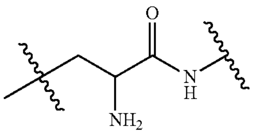.

In another embodiment of a compound of formula I or a pharmaceutically acceptable salt thereof,
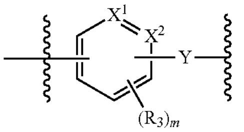
is selected from the group consisting of
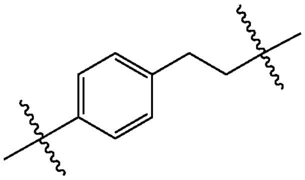
,
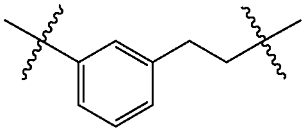
,
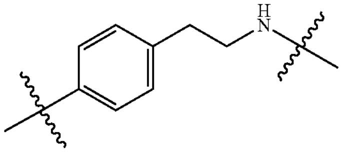
,
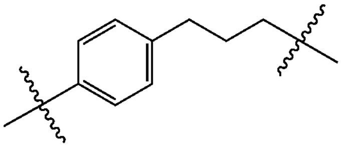
,
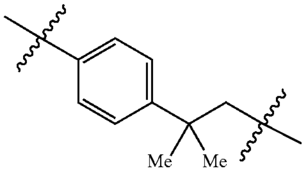
,
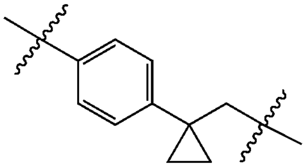
,
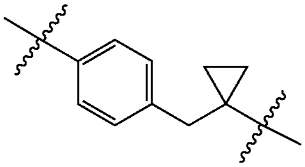
,
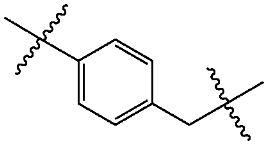
,
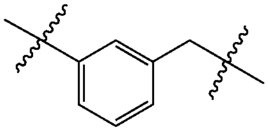
,
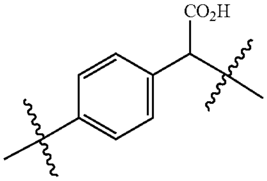
,
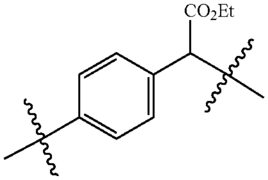
,
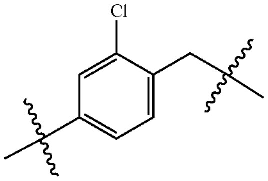
,
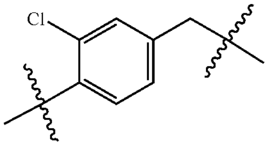
,
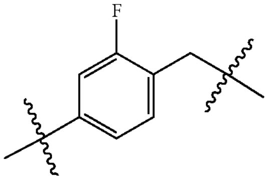
,
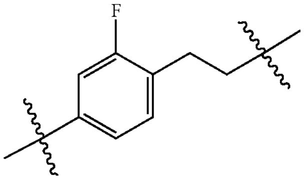
,
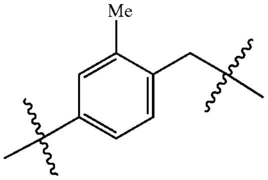
,
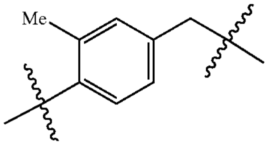
,
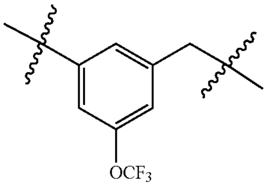
,
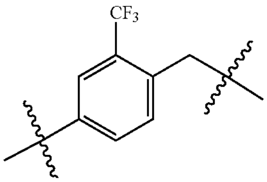
, -continued
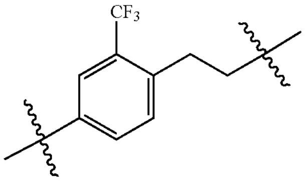 , 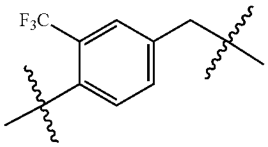 , 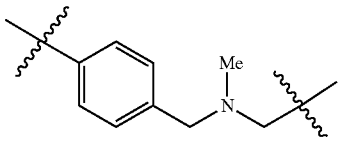 ,
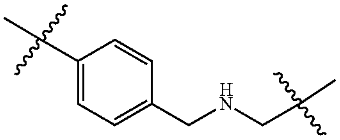 , 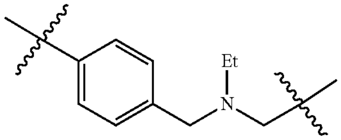 , 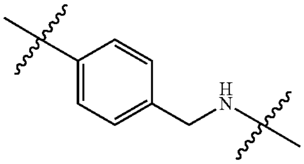 ,
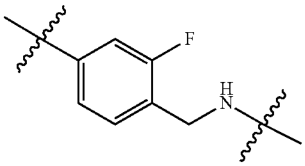 , 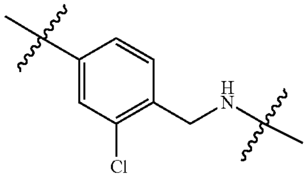 , 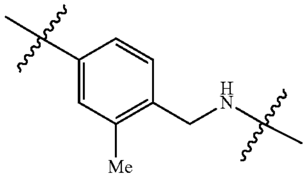 ,
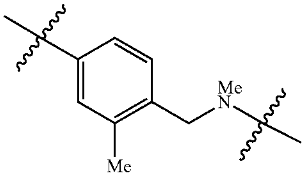 , 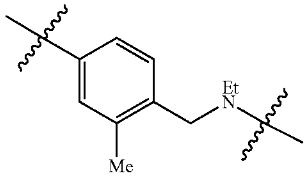 , 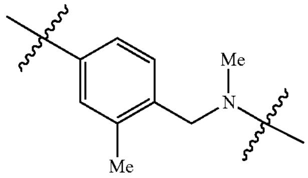 ,
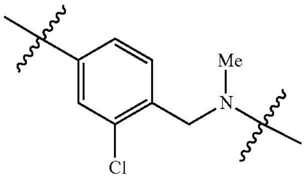 , 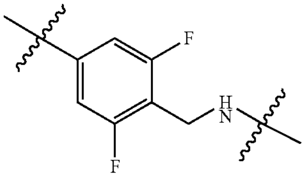 , 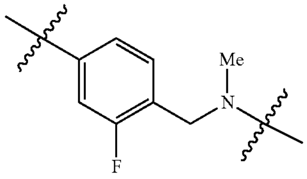 ,
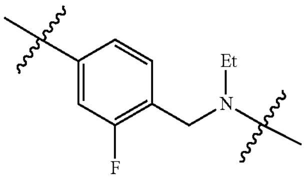 , 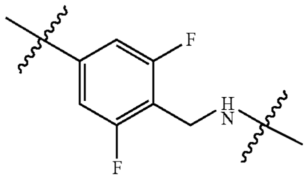 , 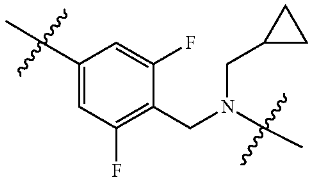 ,
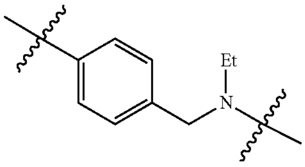 , 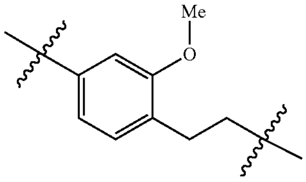 , 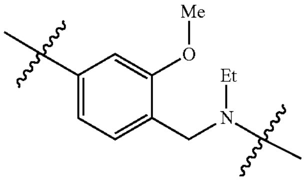 ,
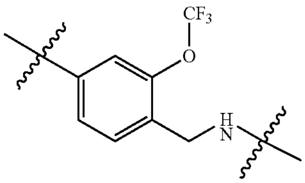 , 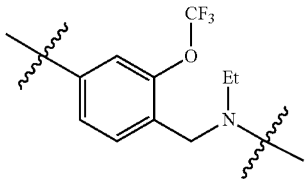 , 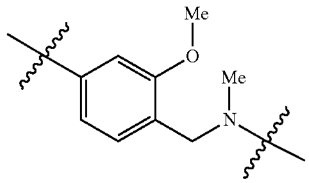 ,
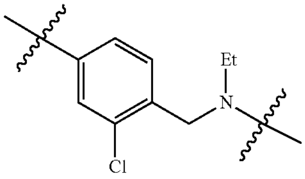 , 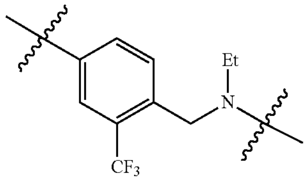 , 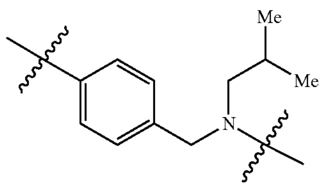 , -continued
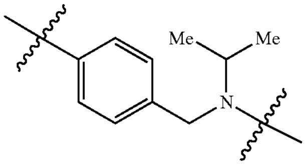
,
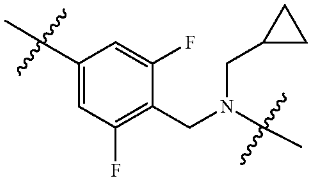
,
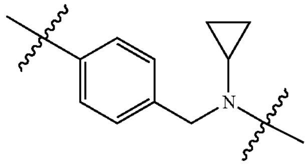
,
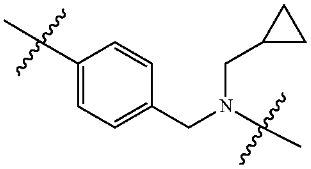
,
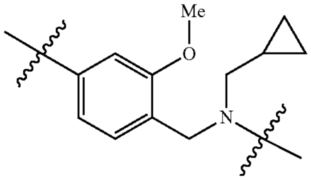
,
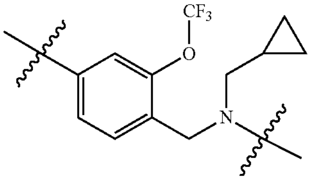
,
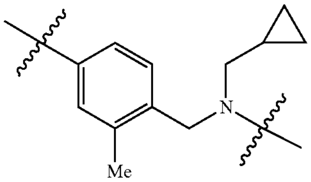
,
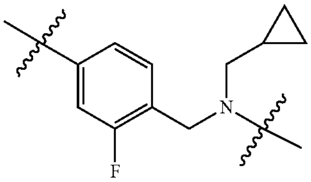
,
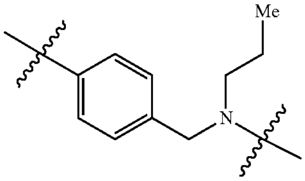
,
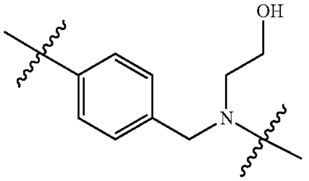
,
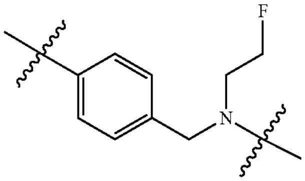
,
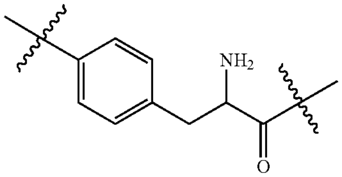
,
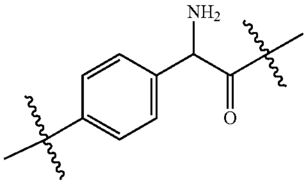
,
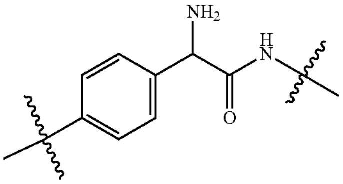
,
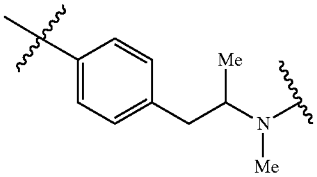
,
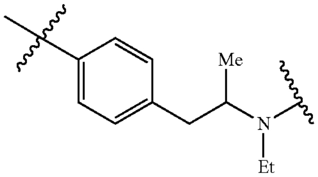
,
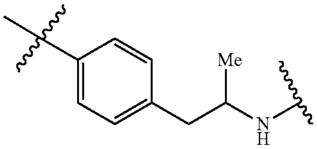
,
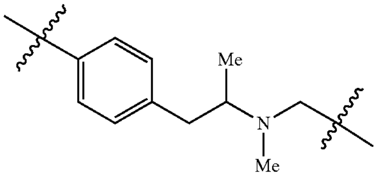
,
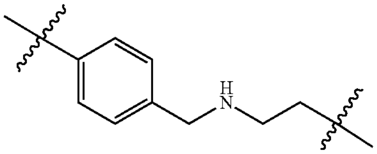
,
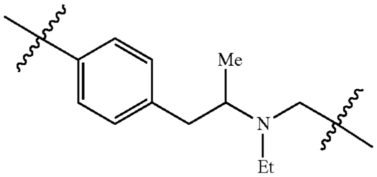
,
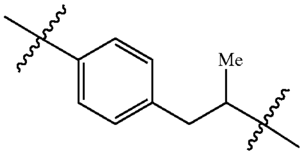
,
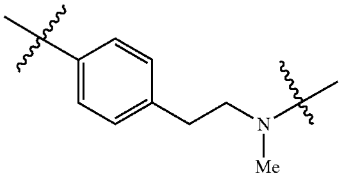
,
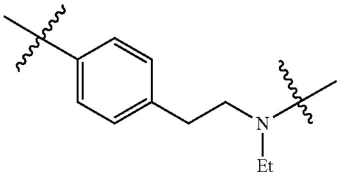
,
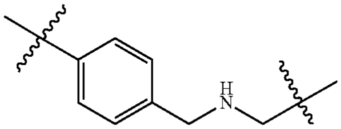
,
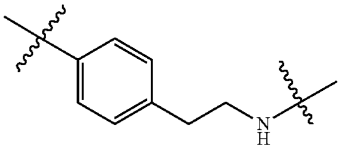
,
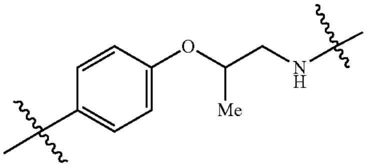
, -continued

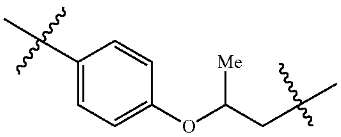,
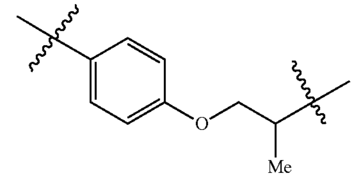,
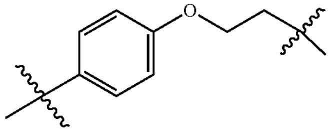,
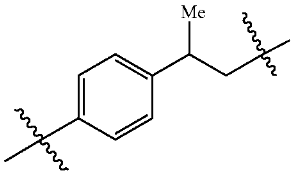,
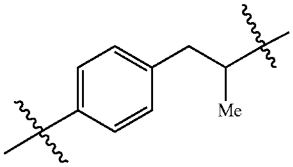,
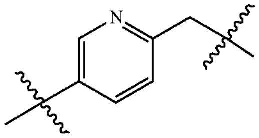, and
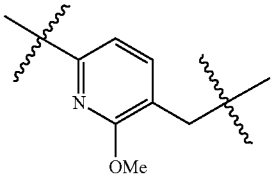.

In another embodiment of a compound of formula I or a pharmaceutically acceptable salt thereof, ring B is a 4-7 membered monocyclic cycloalkylene or 4-7 membered monocyclic heterocycloalkylene, either of which is optionally substituted with up to three substituents selected from the group consisting of $C_1$-$C_6$ alkyl, $C_1$-$C_6$ alkoxy, halo, $NH_2$, $C_1$-$C_6$ haloalkyl, OH, COO($C_1$-$C_6$ alkyl), COOH, and $C_1$-$C_6$ hydroxyalkyl.

In another embodiment, ring B is a 4-6 membered monocyclic cycloalkylene optionally substituted with up to two substituents selected from the group consisting of $C_1$-$C_6$ alkyl, $C_1$-$C_6$ alkoxy, halo, $NH_2$, $C_1$-$C_6$ haloalkyl, OH, COO ($C_1$-$C_6$ alkyl), COOH, and $C_1$-$C_6$ hydroxyalkyl. In another embodiment, ring B is a 4-6 membered monocyclic cycloalkylene.

In another embodiment, ring B is a 4-7 membered monocyclic heterocycloalkylene optionally substituted with up to two substituents selected from the group consisting of $C_1$-$C_6$ alkyl, $C_1$-$C_6$ alkoxy, halo, $NH_2$, $C_1$-$C_6$ haloalkyl, OH, COO ($C_1$-$C_6$ alkyl), COOH, and $C_1$-$C_6$ hydroxyalkyl, wherein the monocyclic heterocycloalkylene contains up to two heteroatoms selected from nitrogen and oxygen. In another embodiment, ring B is a 5 or 6 membered monocyclic heterocycloalkylene optionally substituted with up to two substituents selected from the group consisting of $C_1$-$C_6$ alkyl, $C_1$-$C_6$ alkoxy, halo, $NH_2$, $C_1$-$C_6$ haloalkyl, OH, COO ($C_1$-$C_6$ alkyl), COOH, and $C_1$-$C_6$ hydroxyalkyl, wherein the monocyclic heterocycloalkylene contains up to two heteroatoms selected from nitrogen and oxygen.

In another embodiment, ring B is selected from any of the moieties provided in Table 5:

TABLE 5

| | |
|---|---|
| 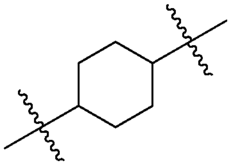, | 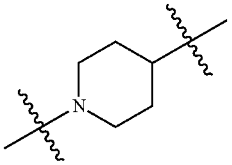, |

TABLE 5-continued

| | |
|---|---|
| 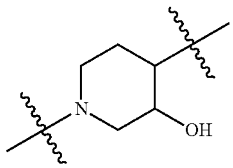, | 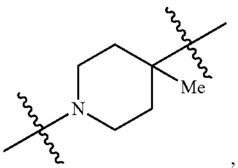, |
| 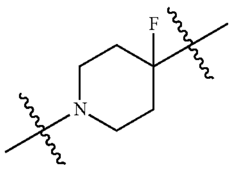, | 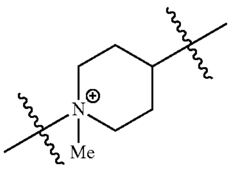, |
| 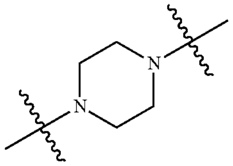, | 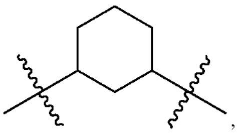, |
| 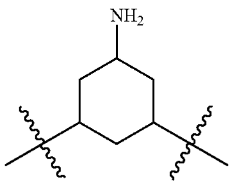, | 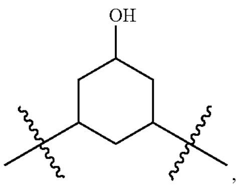, |
| 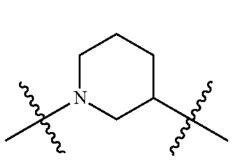, | 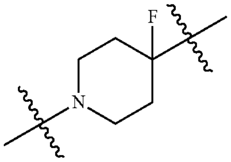, |

TABLE 5-continued

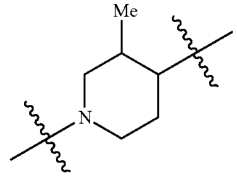, 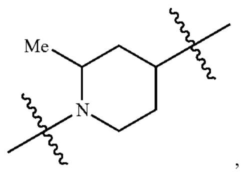,

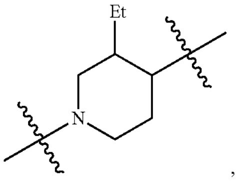, 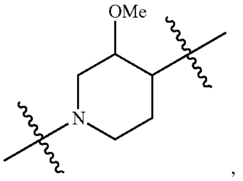,

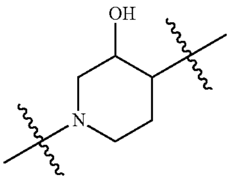, 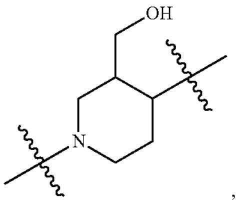,

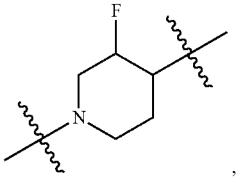, 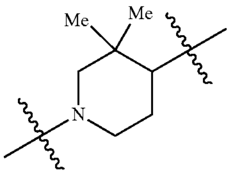,

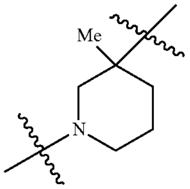 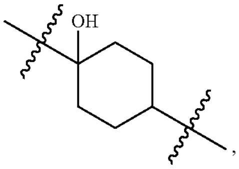,

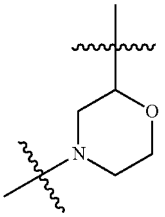, 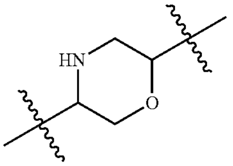,

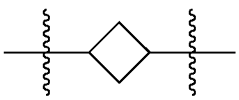, 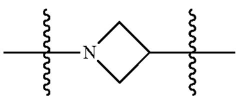,

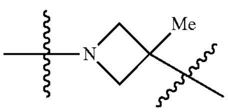, 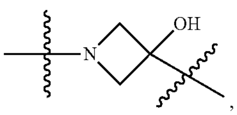,

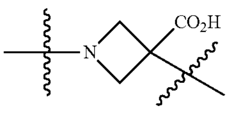, 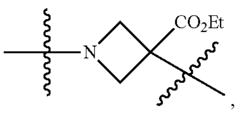,

TABLE 5-continued

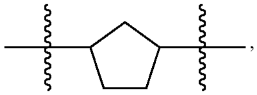, 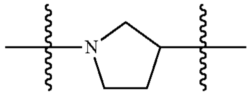,

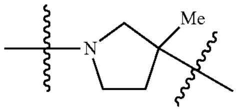, 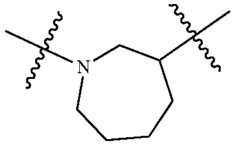,

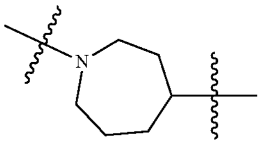, 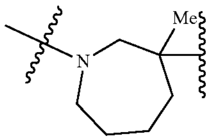,

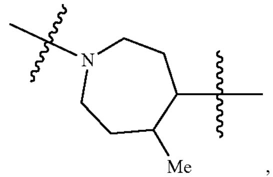, 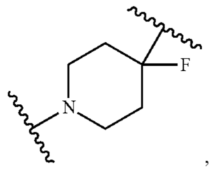,

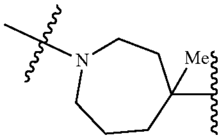, and 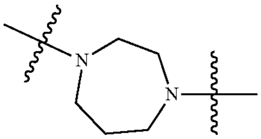.

In another embodiment of a compound of formula I or a pharmaceutically acceptable salt thereof, L is absent.

In another embodiment of a compound of formula I or a pharmaceutically acceptable salt thereof, L is a linear or branched $C_1$-$C_6$ alkylene optionally substituted with $C_1$-$C_6$ alkoxy, halo, CN, OH, $NH_2$, COO($C_1$-$C_6$ alkyl), or $CONH_2$, wherein up to two methylene units of the $C_1$-$C_6$ alkylene are optionally and independently replaced with O, NH, (C═O), NH(C═O), N—($C_{1-6}$ alkyl)(C═O), (C═NH), NH(C═N), or N—($C_{1-6}$ alkyl). In another embodiment, L is a linear or branched $C_1$-$C_6$ alkylene, wherein up to two methylene units of the $C_1$-$C_6$ alkylene are optionally and independently replaced with O, NH, (C═O), NH(C═O), N—($C_{1-6}$ alkyl) (C═O), (C═NH), NH(C═N), or N—($C_{1-6}$ alkyl).

In another embodiment, L is a linear or branched $C_1$-$C_4$ alkylene, wherein up to two methylene units of the $C_1$-$C_4$ alkylene are optionally and independently replaced with NH, (C═O), NH(C═O), (C═NH), NH(C═N), or N—($C_{1-6}$ alkyl). In another embodiment, L is a linear or branched $C_1$-$C_4$ alkylene optionally substituted with OH or $NH_2$, wherein one methylene unit of the $C_1$-$C_4$ alkylene may be replaced with (C═O). In another embodiment, L is $C_1$-$C_4$ alkylene.

In another embodiment, L is absent or is $CH_2$, $CH_2CH_2$, $C(Me)_2$, CH(Me), CH(Et), (C═NH),

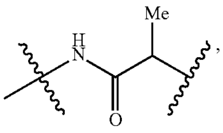, 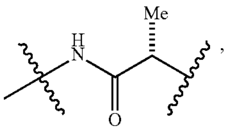, or

-continued

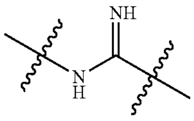

, or

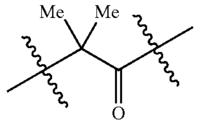

.

In another embodiment, L is absent or is $CH_2$.

In another embodiment of a compound of formula I or a pharmaceutically acceptable salt thereof, $R_1$ is H, halo, $C_1$-$C_6$ haloalkyl, $NR_{x'}R_{y'}$, or monocyclic heterocycloalkyl optionally substituted with $NH_2$, $NH(C_1$-$C_6$ alkyl), $N(C_1$-$C_6$ alkyl$)_2$, wherein $R_{x'}$ and $R_{y'}$ are each independently H, $C_1$-$C_6$ alkyl, $C_3$-$C_8$ cycloalkyl, or an amino protecting group. In another embodiment, $R_1$ is H, $NH_2$, $NH(C_1$-$C_6$ alkyl), $NH(C_1$-$C_6$ alkyl$)_2$, $NH(C_3$-$C_6$ cycloalkyl), $CF_3$, or 4 to 6 membered monocyclic heterocycloalkyl optionally substituted with $NH_2$. In another embodiment, $R_1$ is H or $NH_2$. In another embodiment, $R_1$ is H. In another embodiment, $R_1$ is $NH_2$.

In another embodiment, $R_1$ is NH(C═O)—($C_1$-$C_6$) alkyl, or NH—(C═NH)—$NH_2$, either of which may be optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, $NH(C_1$-$C_6$ alkyl), $N(C_1$-$C_6$ alkyl$)_2$, $COO(C_1$-$C_6$ alkyl), $CONH_2$, and oxo. In another embodiment, $R_1$ is NH(C═O)—($C_1$-$C_6$) alkyl, or NH—(C═NH)—$NH_2$.

In another embodiment of a compound of formula I or a pharmaceutically acceptable salt thereof, Y is any one of the moieties provided in Table 4; ring B is any one of the moieties provided in Table 5; L is a linear or branched $C_1$-$C_4$ alkylene, wherein up to two methylene units of the $C_1$-$C_4$ alkylene are optionally and independently replaced with NH, (C═O), NH(C═O), (C═NH), NH(C═N), or N—($C_{1-6}$ alkyl); and $R_1$ is H, $NH_2$, or $NH(C_1$-$C_6$ alkyl). In another embodiment, Y is any one of the moieties provided in Table 4; ring B is any one of the moieties provided in Table 5; L is absent or is $C_1$-$C_4$ alkylene; and $R_1$ is H or $NH_2$.

In another embodiment of a compound of formula I or a pharmaceutically acceptable salt thereof,

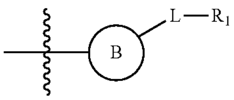

is selected from any of moieties provided in Table 6:

TABLE 6

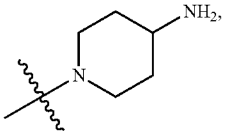
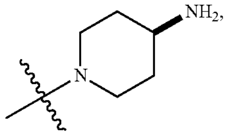
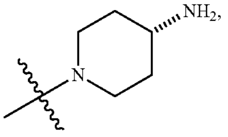
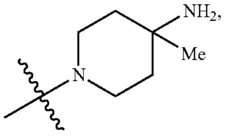

TABLE 6-continued

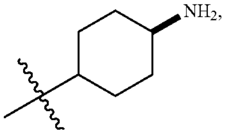
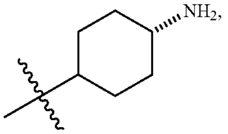
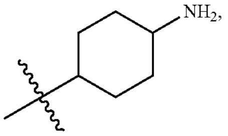
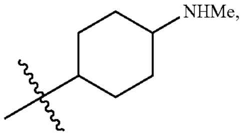
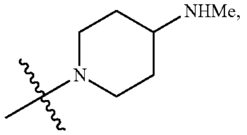
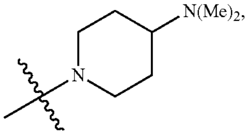
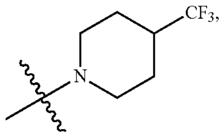
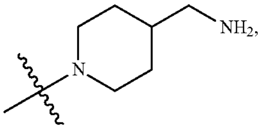
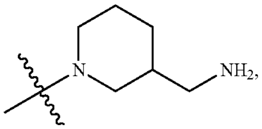
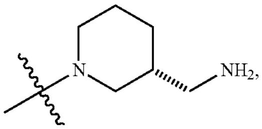
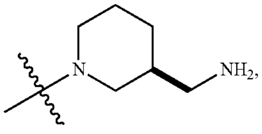
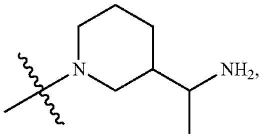
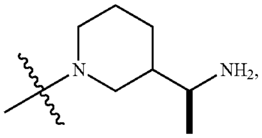
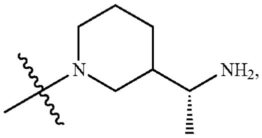
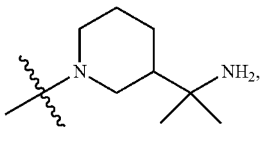
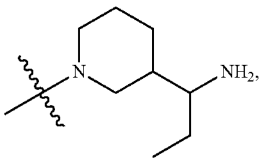
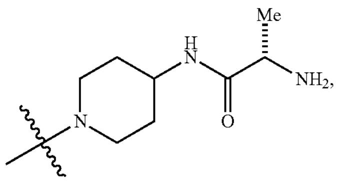 [SMILES: *N1CCC(NC(=O)[C@H](C)N)CC1]
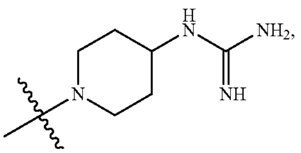
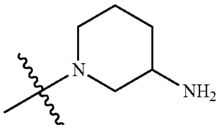

, .

TABLE 6-continued
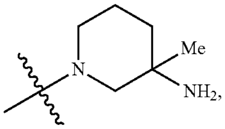 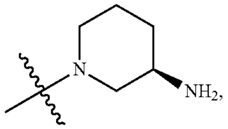
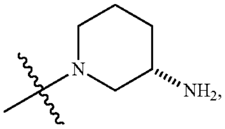 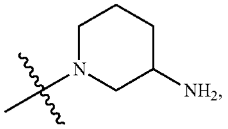
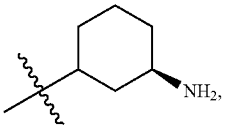 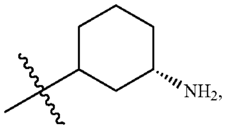
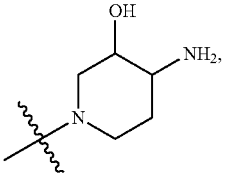 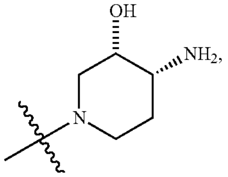
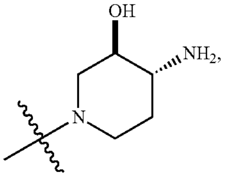 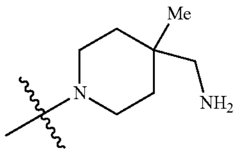 ,
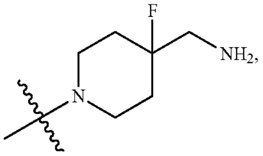 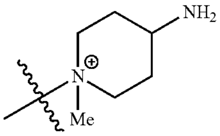 ,
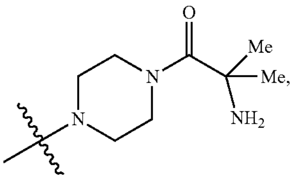 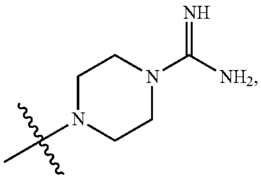
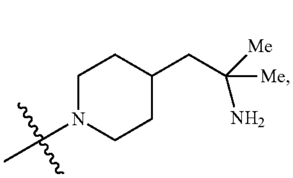 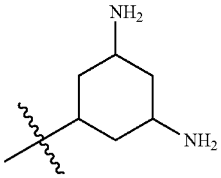 ,
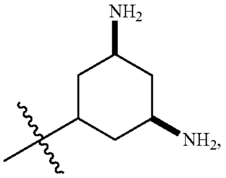 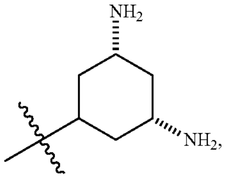
TABLE 6-continued
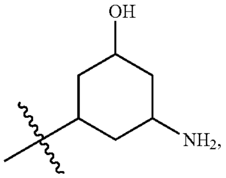 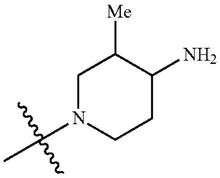 ,
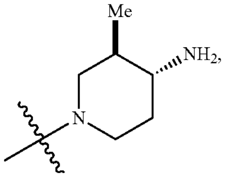 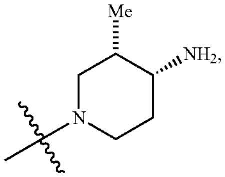
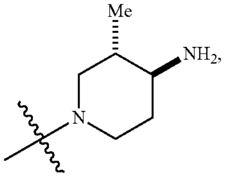 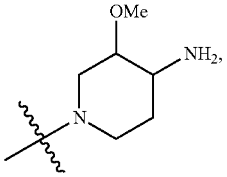
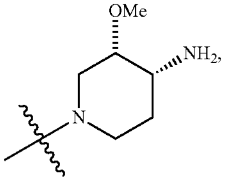 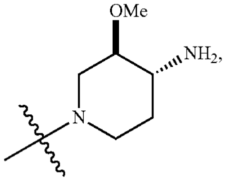
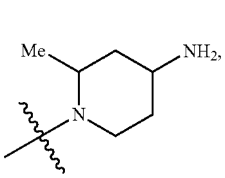 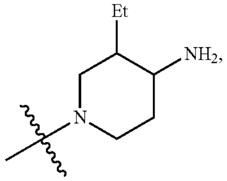
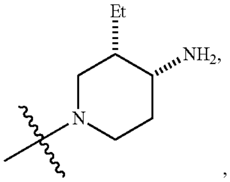 , 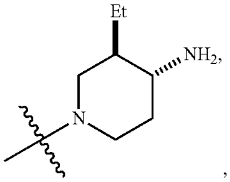 ,
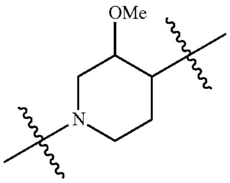 , 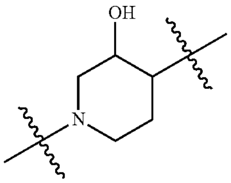 , ,
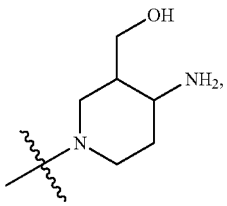 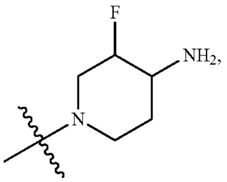

TABLE 6-continued
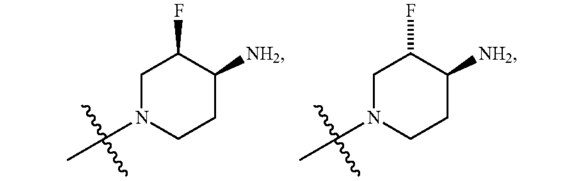 [SMILES: *N1CC[C@H](N)[C@H](F)C1 ; *N1CC[C@H](N)[C@@H](F)C1]
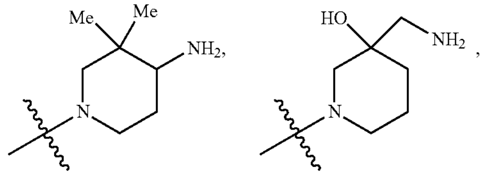 [SMILES: *N1CCC(N)C(C)(C)C1 ; *N1CCCC(O)(CN)C1]
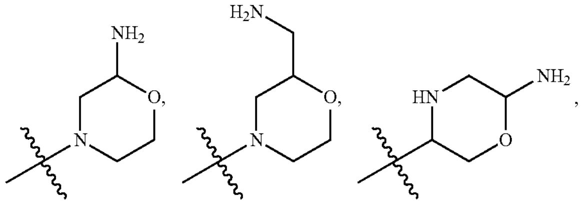 [SMILES: *N1CCOC(N)C1 ; *N1CCOC(CN)C1 ; *C1COC(N)CN1]
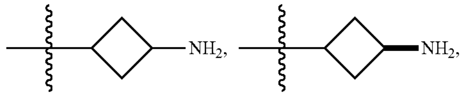
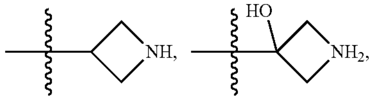
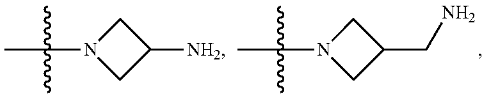
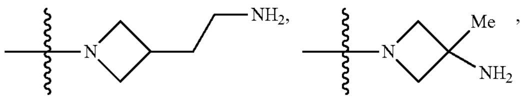 [SMILES: *N1CC(CCN)C1 ; *N1CC(C)(N)C1]
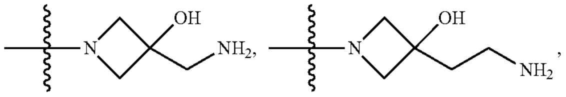 [SMILES: *N1CC(O)(CN)C1 ; *N1CC(O)(CCN)C1]
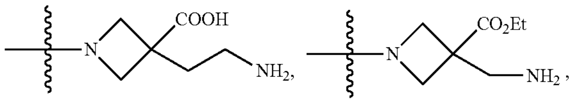 [SMILES: *N1CC(CCN)(C(=O)O)C1 ; *N1CC(CN)(C(=O)OCC)C1]
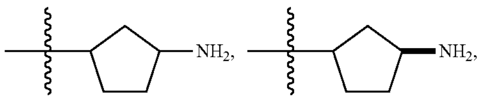
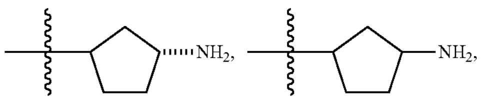
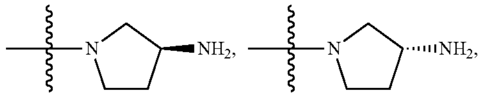 [SMILES: *N1CC[C@H](N)C1 ; *N1CC[C@@H](N)C1]
TABLE 6-continued
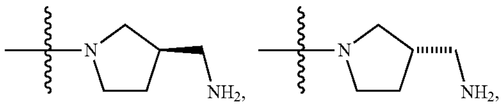
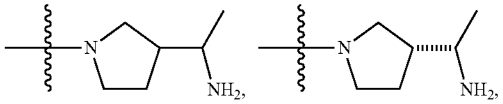
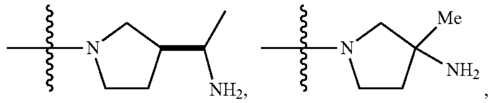
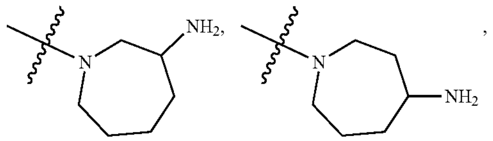 [SMILES: *N1CCCCC(N)C1 ; *N1CCCC(N)CC1]
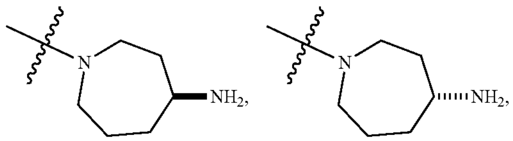 [SMILES: *N1CCC[C@H](N)CC1 ; *N1CCC[C@@H](N)CC1]
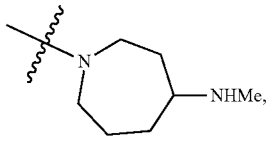 [SMILES: *N1CCCC(NC)CC1]
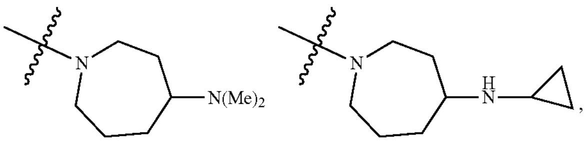
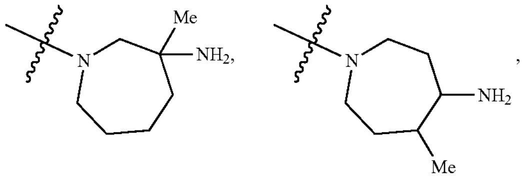 [SMILES: *N1CCCCC(C)(N)C1 ; *N1CCC(C)C(N)CC1]
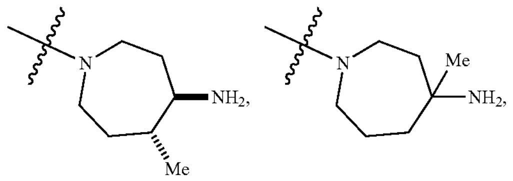 [SMILES: *N1CC[C@@H](C)[C@H](N)CC1 ; *N1CCCC(C)(N)CC1]
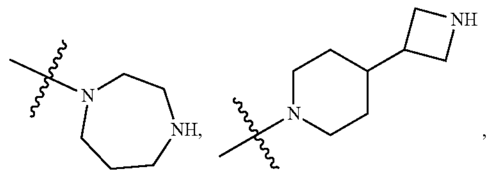 [SMILES: *N1CCCNCC1 ; *N1CCC(C2CNC2)CC1]

TABLE 6-continued

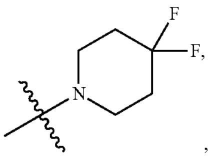

,

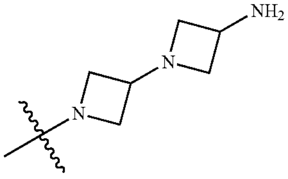

, and

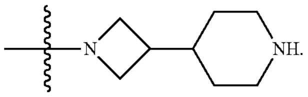 [SMILES: *N1CC(C2CCNCC2)C1]

In another embodiment of a compound of formula I or a pharmaceutically acceptable salt thereof, each $R_2$ and $R_3$ is independently selected from the group consisting of $C_1$-$C_6$ alkyl, halo, $C_1$-$C_6$ haloalkyl, O($C_1$-$C_6$ haloalkyl), and $C_1$-$C_6$ alkoxy, and m and n are each independently 0, 1, or 2. In another embodiment, each $R_3$ is $C_1$-$C_6$ alkyl, halo, $C_1$-$C_6$ haloalkyl, O($C_1$-$C_6$ haloalkyl), or $C_1$-$C_6$ alkoxy, m is 0, 1, or 2.

In another embodiment of a compound of formula I or a pharmaceutically acceptable salt thereof, n is 0, m is 0, 1 or 2, and each $R_3$ is independently selected from the group consisting $CH_3$, Cl, F, $OCH_3$, $OCF_3$, and $CF_3$.

In another embodiment, the compound of formula I is a compound of formula I-1.

I-1

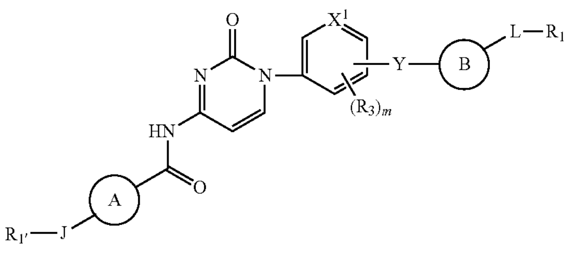

or a pharmaceutically acceptable salt thereof, wherein ring A, ring B, J, L, Y, $R_1$, $R_{1'}$, $R_3$, $X^1$, and m are the same as defined herein.

In another embodiment, the compound of formula I or I-1 is a compound of formula I-2:

I-2

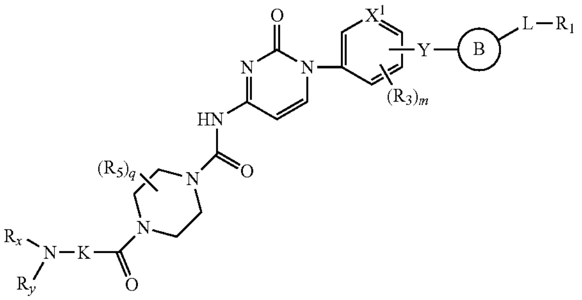

or a pharmaceutically acceptable salt thereof, wherein ring B, L, Y, $R_1$, $R_3$, $R_x$, $R_y$, $X^1$, and m are the same as defined herein; K is $C_1$-$C_5$ alkylene, 4 to 7 membered heterocycloalkylene, or 4 to 6 membered cycloalkylene, any of which may be optionally substituted with up to two substituents independently selected from halo, $C_1$-$C_6$ alkyl, $C_1$-$C_6$ alkoxy, $C_1$-$C_6$ haloalkyl, $NH_2$, CN, or OH, wherein one methylene unit of the $C_1$-$C_5$ alkylene is optionally replaced with

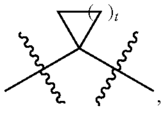

, wherein t is 1, 2, 3, or 4; each $R_5$ is independently $C_1$-$C_6$ alkyl, $C_1$-$C_6$ alkoxy, $C_1$-$C_6$ hydroxyalkyl, halo, CN, $C_1$-$C_6$ haloalkyl, phenyl, OH, $NH_2$, NH($C_1$-$C_6$ alkyl), N($C_1$-$C_6$ alkyl)$_2$, COOH, COO($C_1$-$C_6$ alkyl), $CONH_2$, or oxo; $R_x$ and $R_y$ are each independently H, $C_1$-$C_6$ alkyl, $C_1$-$C_6$ alkyl-$SO_3$, CO($C_1$-$C_6$ alkyl), CO—($C_1$-$C_6$ alkylene)-$NH_2$; and q is 0, 1, 2, or 3.

In another embodiment of a compound of formula I-2 or a pharmaceutically acceptable salt thereof, K is $C_1$-$C_5$ alkylene optionally substituted with $C_1$-$C_6$ haloalkyl, $NH_2$, or OH, wherein one methylene unit of the $C_1$-$C_8$ alkylene is optionally replaced with

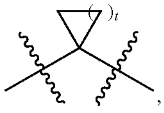

, wherein t is 1 or 2; each $R_5$ is independently halo, $C_1$-$C_6$ alkyl, $C_1$-$C_6$ hydroxyalkyl, phenyl, COOH, and COO($C_1$-$C_6$ alkyl); and q is 0, 1, or 2.

In another embodiment, the compound of formula I, I-1, or I-2 is a compound of formula I-3:

I-3

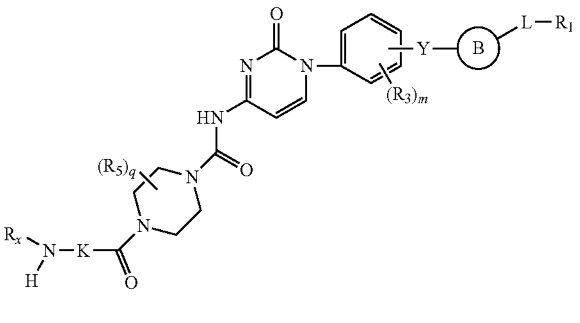

or a pharmaceutically acceptable salt thereof, wherein ring B, L, Y, K, $R_1$, $R_3$, $R_5$, $R_x$, q, and m are the same as defined herein.

In another embodiment of a compound of formula I-3 or a pharmaceutically acceptable salt thereof, K is $C_1$-$C_4$ alkylene optionally substituted with halo, $C_1$-$C_6$ alkoxy, $C_1$-$C_6$ haloalkyl, or OH; each $R_5$ is independently $C_1$-$C_6$ alkyl, $C_1$-$C_6$ alkoxy, halo, $C_1$-$C_6$ haloalkyl, phenyl, OH, $NH_2$, COOH, or COO($C_1$-$C_6$ alkyl); and q is 0, 1, or 2.

In another embodiment, the compound of formula I, I-1, 1-2, or 1-3 is a compound of formula I-4:

I-4

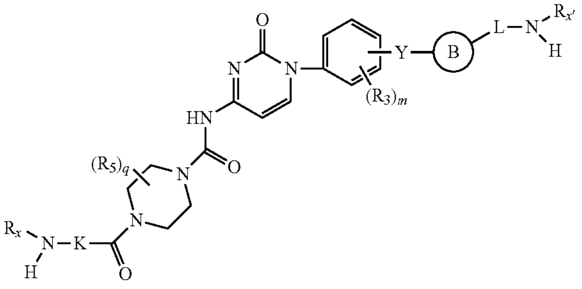

or a pharmaceutically acceptable salt thereof, wherein ring B, L, Y, K, $R_x$, $R_{x'}$, $R_3$, $R_5$, q, and m are the same as defined herein.

In another embodiment of a compound of formula I-4 or a pharmaceutically acceptable salt thereof, Y is a linear $C_1$-$C_4$ alkylene optionally substituted with $C_1$-$C_6$ alkyl, COOH, COO($C_1$-$C_6$ alkyl), or $NH_2$, and wherein up to two methylene units of the $C_1$-$C_4$ alkylene are optionally and independently replaced by (C═O), O, NH, N—($C_1$-$C_6$ alkyl), N—($C_1$-$C_6$ hydroxyalkyl), N—($C_1$-$C_6$ haloalkyl), N—($C_{1-6}$ alkylene-$C_{3-6}$ cycloalkyl), N—($C_{3-8}$ cycloalkyl), or

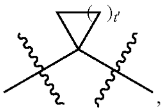

wherein t' is 1 or 2; each $R_3$ is independently $C_1$-$C_6$ alkyl, halo, $C_1$-$C_6$ haloalkyl, O($C_1$-$C_6$ haloalkyl), or $C_1$-$C_6$ alkoxy; m is 0, 1, or 2; and $R_x$ and $R_{x'}$ are each independently H or $C_1$-$C_6$ alkyl.

In another embodiment, the compound of formula I, I-1, I-2, I-3, or I-4 is a compound of formula I-5:

I-5

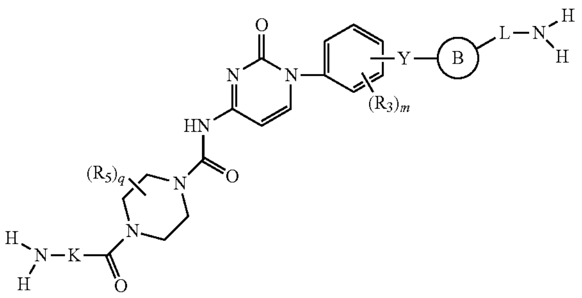

or a pharmaceutically acceptable salt thereof, wherein ring B, L, Y, K, $R_3$, $R_5$, q, and m are the same as defined herein.

In another aspect, the disclosure provides a compound of Formula II:

II

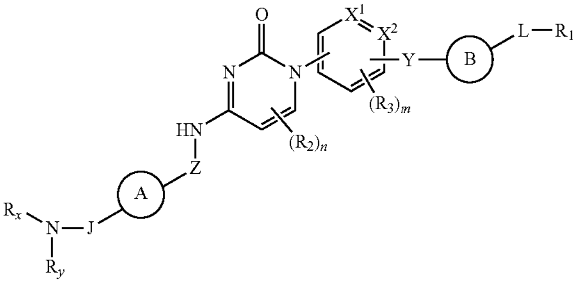

or a pharmaceutically acceptable salt thereof, wherein:

Z is —(C═O)—;

ring A is a monocyclic heterocycloalkylene or bicyclic heterocycloalkylene, wherein the monocyclic heterocycloalkylene or bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$COONH_2$, and oxo;

J is $C_1$-$C_6$ alkylene optionally substituted with halo, hydroxy, or alkoxy, wherein one or two carbons of the $C_1$-$C_6$ alkylene may optionally be replaced with O, S, $SO_2$, or C═O;

$R_x$ and $R_y$ are each independently H, $C_1$-$C_6$ alkyl, or a protecting group;

$X^1$ and $X^2$ are each independently C—H or N;

Y is a linear $C_1$-$C_8$ alkylene, $C_2$-$C_8$ alkenylene, or $C_2$-$C_8$ alkynylene, any of which are optionally substituted with OH, $NH_2$, halo, $C_1$-$C_6$ alkyl, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O);

ring B is a monocyclic cycloalkylene or moncyclic heterocycloalkylene which is optionally substituted with up to three substituents selected from the group consisting of $C_1$-$C_6$ alkyl, $C_1$-$C_6$ alkoxy, halo, CN, $C_1$-$C_6$ haloalkyl, OH, —COO($C_1$-$C_6$ alkyl), —$COONH_2$, and $C_1$-$C_6$ hydroxyalkyl;

L is absent, or is a $C_1$-$C_6$ alkylene, wherein up to two carbon atoms of the $C_1$-$C_6$ alkylene may be replaced with O, NH, (C═O), NH(C═O), N—($C_{1-6}$ alkyl) (C═O), (C═NH), NH(C═N), or N—($C_{1-6}$ alkyl);

$R_1$ is H, halo, haloalkyl, $NR_{x'}R_{y'}$, wherein $R_{x'}$ and $R_{y'}$ are each independently H, $C_1$-$C_6$ alkyl which may be optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$COONH_2$, and oxo, or a or a protecting group; NH(C═O)—($C_1$-$C_6$) alkyl, or NH—(C═N)—$NH_2$; which may be optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$COONH_2$, and oxo;

$R_2$ and $R_3$ are each independently selected from the group consisting of $C_1$-$C_6$ alkyl, halo, CN, OH, $NH_2$, NH($C_1$-

$C_6$ alkyl), $N(C_1$-$C_6$ alkyl$)_2$, —COO($C_1$-$C_6$ alkyl), —$COONH_2$, $C_1$-$C_6$ haloalkyl, $C_1$-$C_6$ alkoxy, and $C_1$-$C_6$ haloalkoxy; and m and n are each independently 0, 1, 2, or 3.

In another embodiment of a compound of formula I or II or a pharmaceutically acceptable salt thereof, Z is —(C═O)—.

In another embodiment of a compound of formula I or II or a pharmaceutically acceptable salt thereof, ring A is a monocyclic heterocycloalkylene or bicyclic heterocycloalkyene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a monocyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a bicyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a monocyclic heterocycloalkylene or bicyclic heterocycloalkyene, wherein the monocyclic heterocycloalkylene and bicyclic heterocycloalkylene are selected from the group consisting of

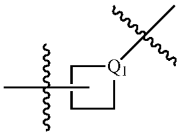,
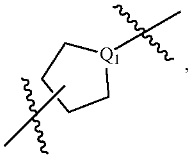,
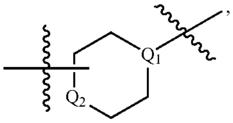,
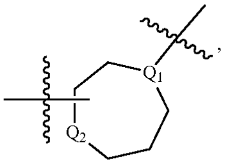,
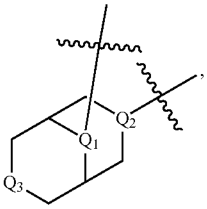,
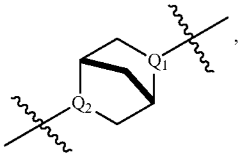,
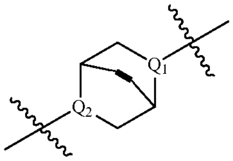,
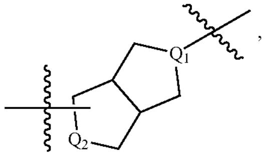,
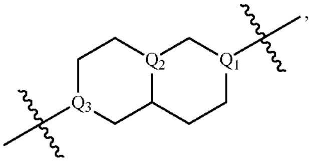, and -continued

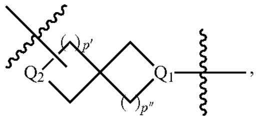, wherein $Q_1$ is N, and $Q_2$ and $Q_3$ are each independently selected from the group consisting of C, N, S, or O, and wherein the monocyclic heterocycloalkylene and bicyclic heterocycloalkylene may be optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, —$CO_2H$, —$CO_2Me$, —$CO_2Et$, and oxo.

In another embodiment, ring A is selected from the group consisting of

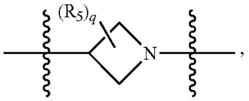,
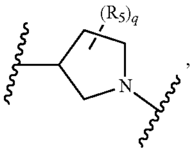,
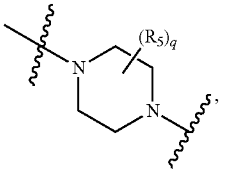,
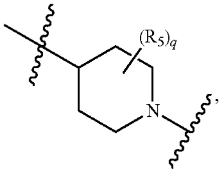,
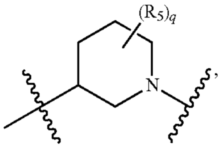,
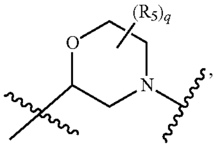,
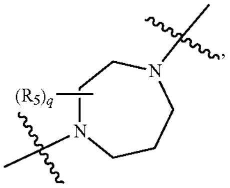,
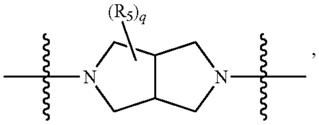,
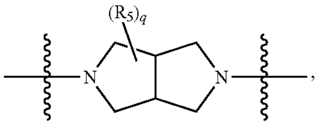,
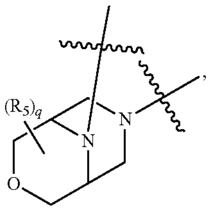,
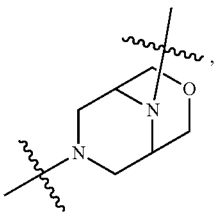,
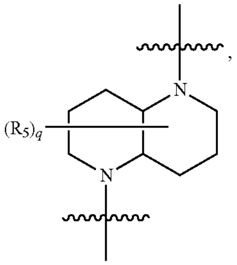

-continued
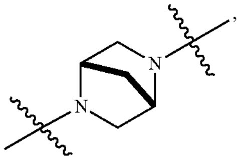,
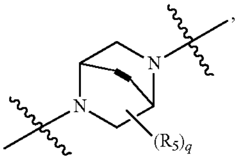,
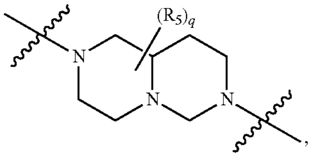,
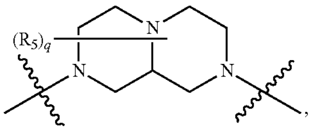,
-continued
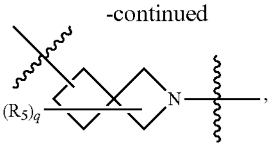, and
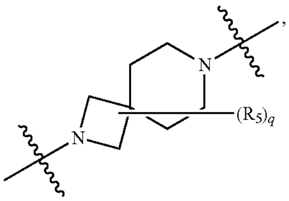,
wherein each $R_5$ is independently selected from the group consisting of H, $C_1$-$C_6$ alkyl, $C_1$-$C_6$ alkoxy, halo, CN, $C_1$-$C_6$ haloalkyl, phenyl, OH, $NH_2$, and oxo, wherein q is 1, 2, or 3.
In another embodiment, ring A is selected from the group consisting of
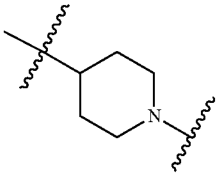, 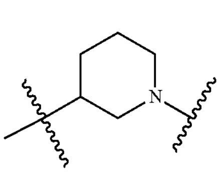, 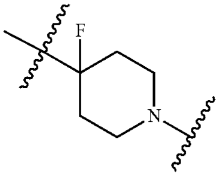, 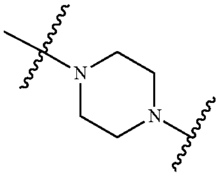,
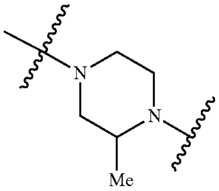, 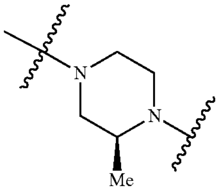, 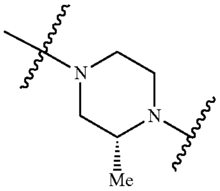,
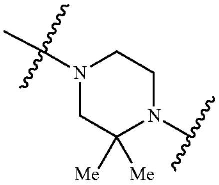, 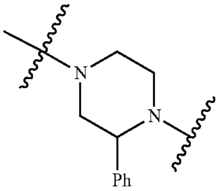, 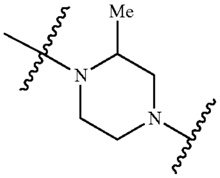, 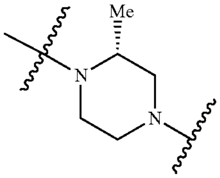,
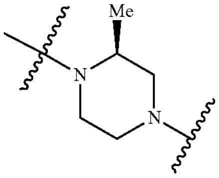, 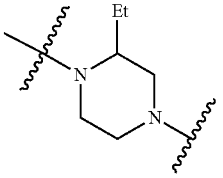, 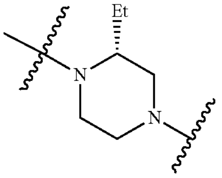, 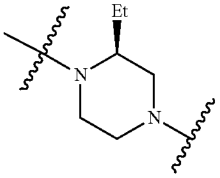,
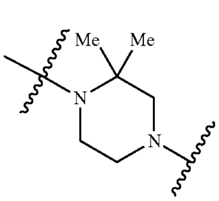, 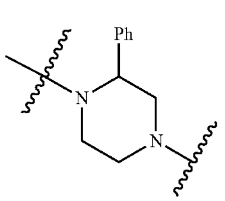, 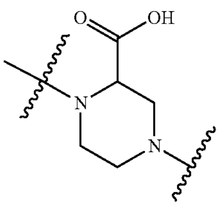, 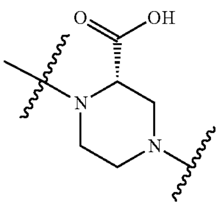, -continued
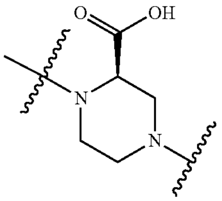 , 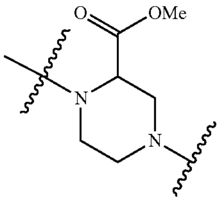 , 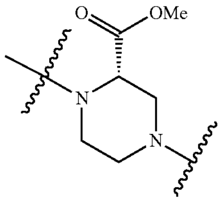 , 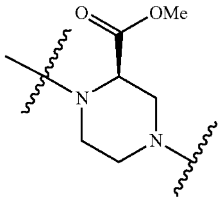 ,
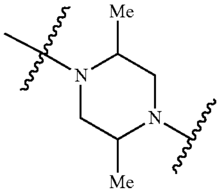 , 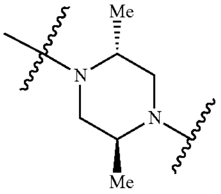 , 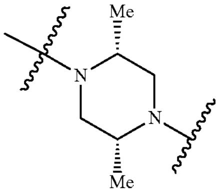 , 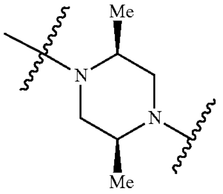 ,
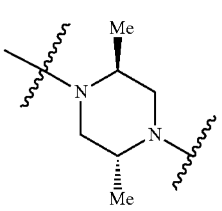 , 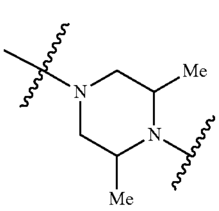 , 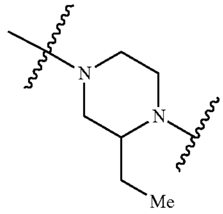 , 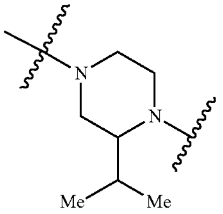 ,
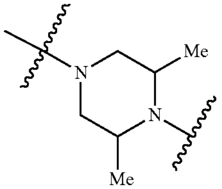 , 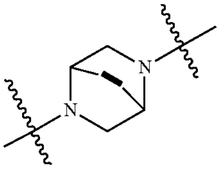 , 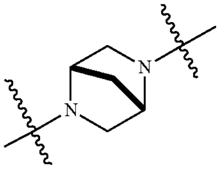 , 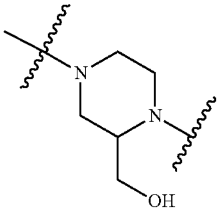 ,
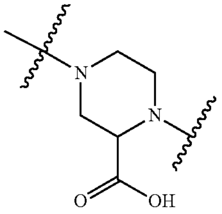 , 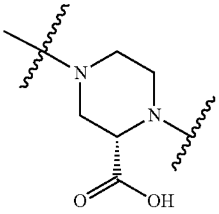 , 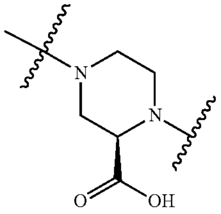 , 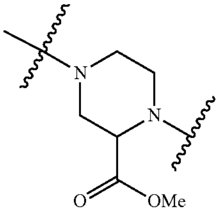 ,
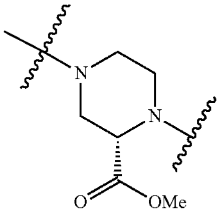 , 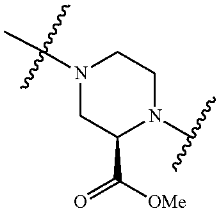 , 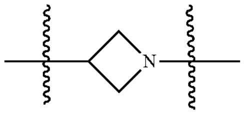 , 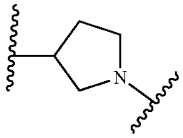 ,
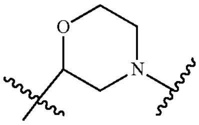 , 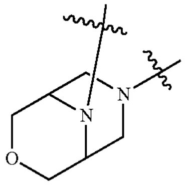 , 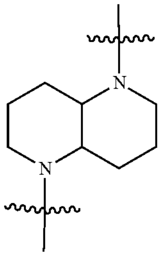 , 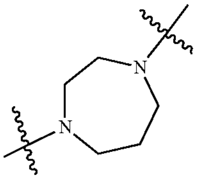 ,
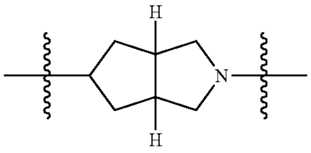 , 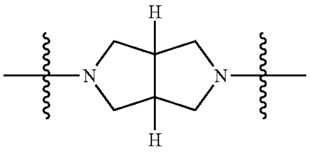 , 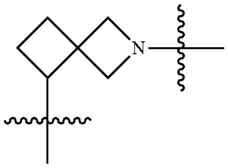 , -continued

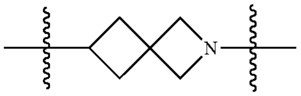
,
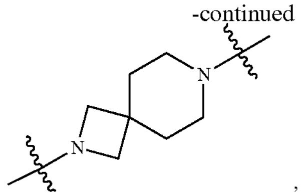
, and
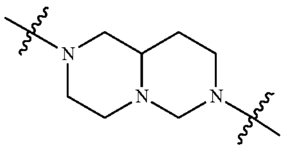
.

In another embodiment of a compound of formula I or II or a pharmaceutically acceptable salt thereof, one of the $C_1$-$C_6$ alkylene carbons of J is —(C═O)—.

In another embodiment, J is optionally substituted with —OH.

In another embodiment, J is selected from the group consisting of $CH_2$,

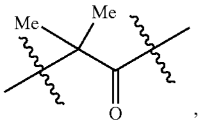
,
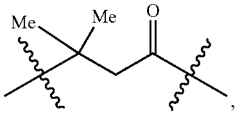
,
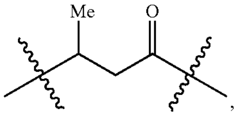
,
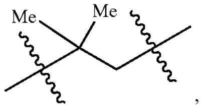
,
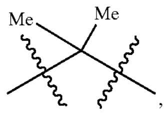
,
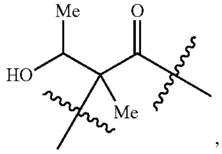
, and
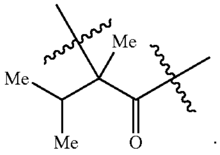
.

In another embodiment, J is selected from the group consisting of $CH_2$,

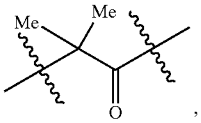
,
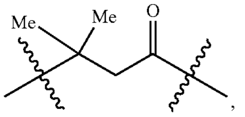
,
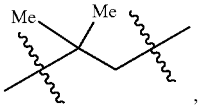
,
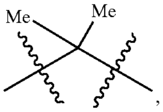
, and
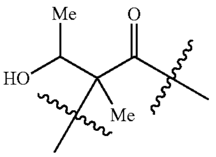
.

In another embodiment, J is selected from the group consisting of $CH_2$,

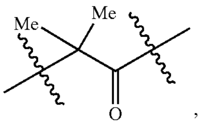
,
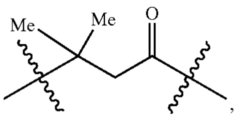
, and
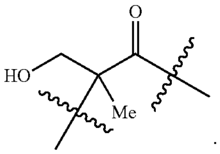
.

In another embodiment, J is

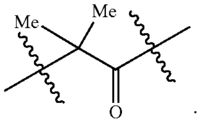 [SMILES: *C(=O)C(*)(C)C]
.

In another embodiment of a compound of formula I or II or a pharmaceutically acceptable salt thereof, $NR_xR_y$ is selected from the group consisting of $NH_2$, NHMe, NHEt, NHPG, $N(Me)_2$, and $N(Et)_2$.

In another embodiment of a compound of formula I or II or a pharmaceutically acceptable salt thereof, ($R_x$ $R_y$)NJ is selected from the group consisting of $H_2N$—$CH_2$—,

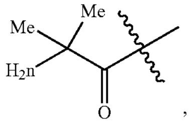
,
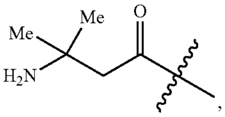
,
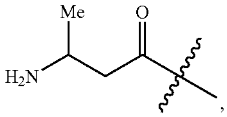
,
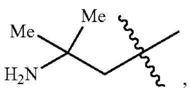
,
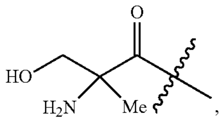
,
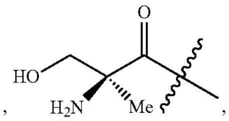
,
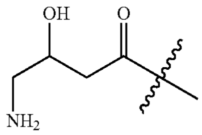
and
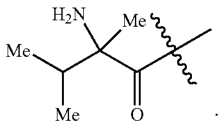
.

In another embodiment of a compound of formula I or II or a pharmaceutically acceptable salt thereof, ($R_x$ $R_y$)NJ is selected from the group consisting of $H_2N$—$CH_2$—,

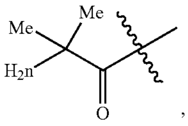 , 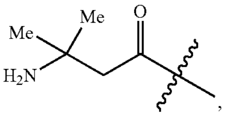 ,
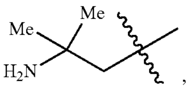 , 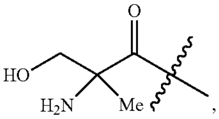 , and
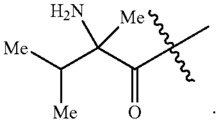 .
In another embodiment of a compound of formula I or II or a pharmaceutically acceptable salt thereof, ($R_x$ $R_y$)NJ is selected from the group consisting of $H_2N—CH_2—$,
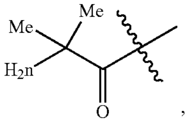 , 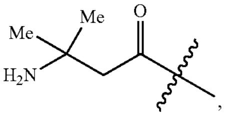 ,
-continued
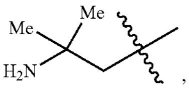 , and 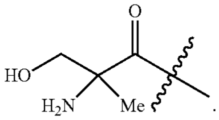 .
In another embodiment of a compound of formula I or II or a pharmaceutically acceptable salt thereof,
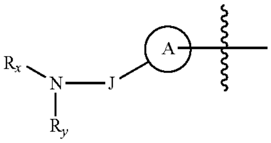
is selected from the group consisting of
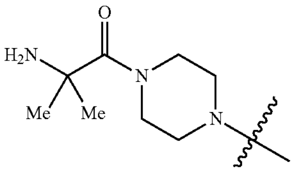 , 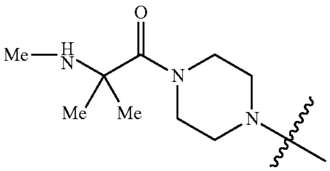 , 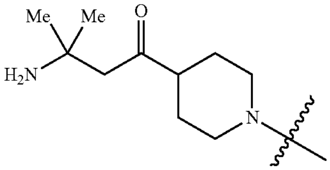 ,
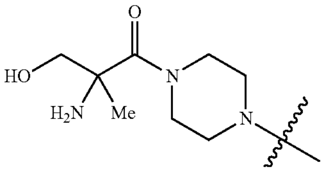 , 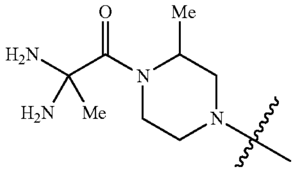 , 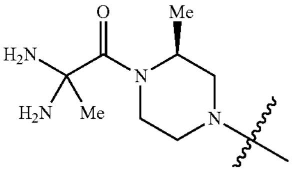 ,
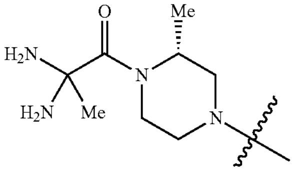 , 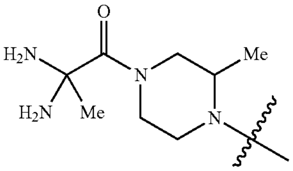 , 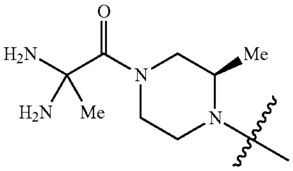 ,
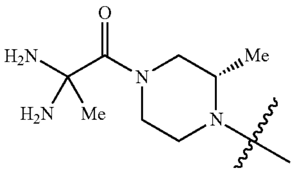 , 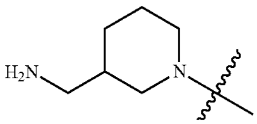 , 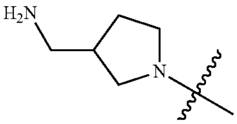 ,
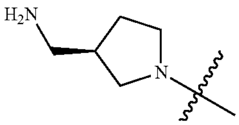 , 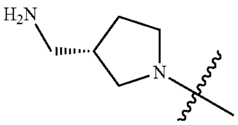 , 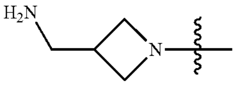 ,
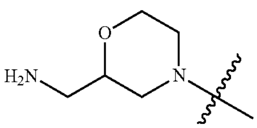 , 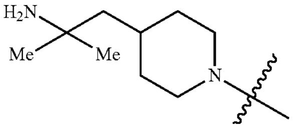 , 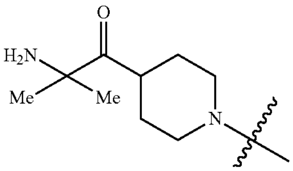 , -continued
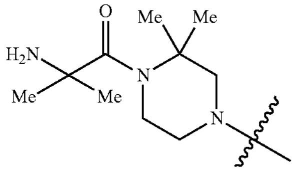,
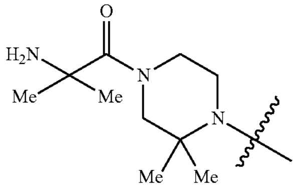,
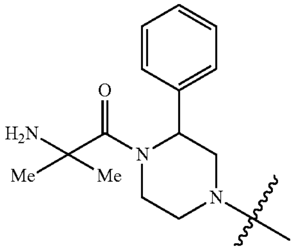,
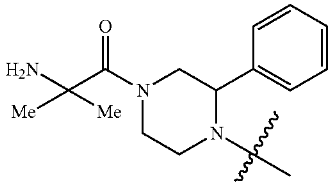,
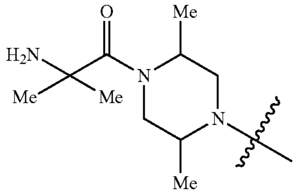,
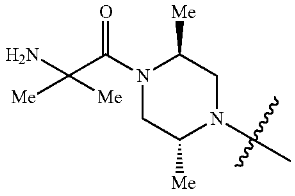,
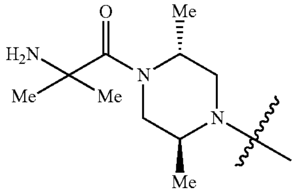,
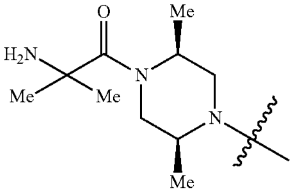,
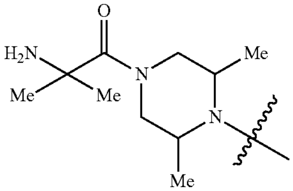,
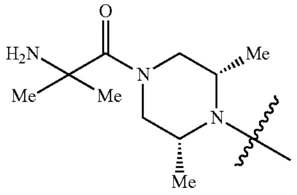,
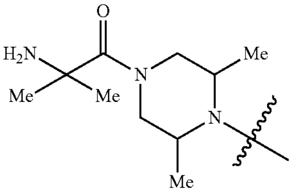,
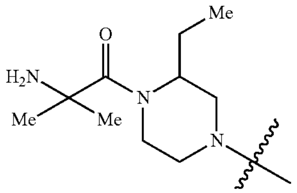,
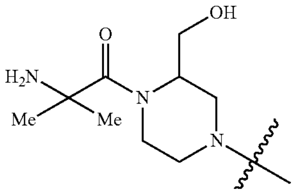,
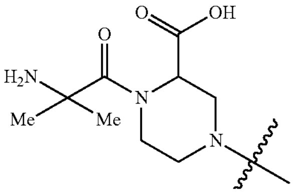,
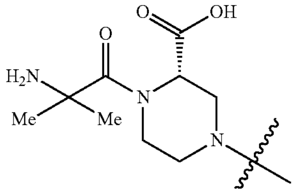,
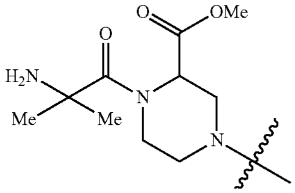,
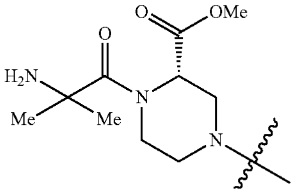,
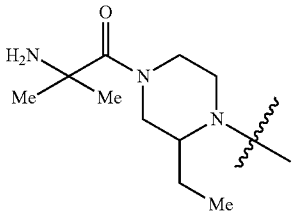,
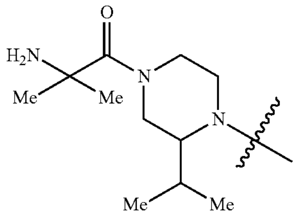,
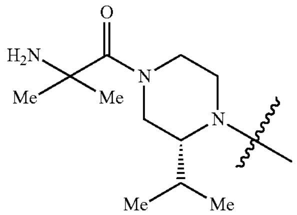,
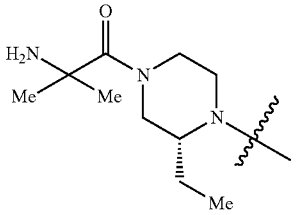,
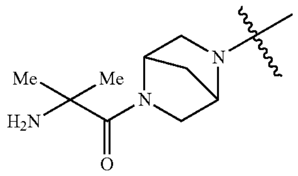,
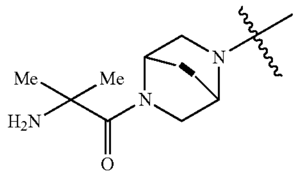, -continued

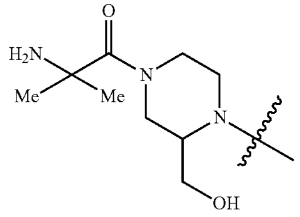
,
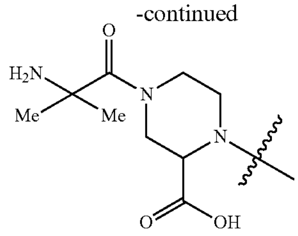
,
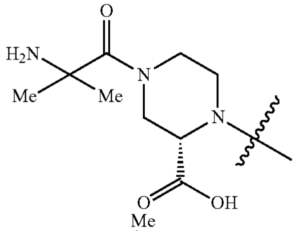
,
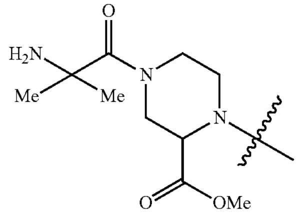
,
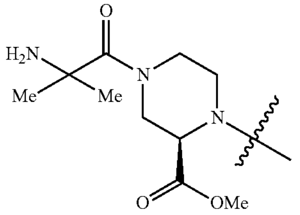
,
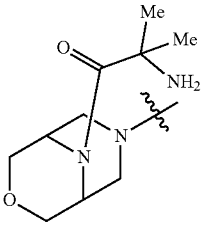
,
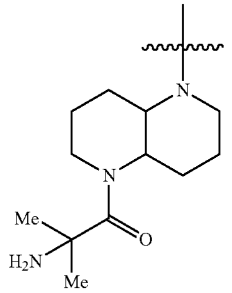
,
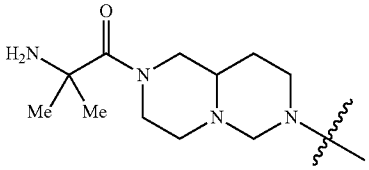
, and
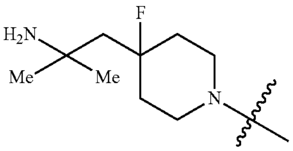
.

In another embodiment of a compound of formula I or II or a pharmaceutically acceptable salt thereof,

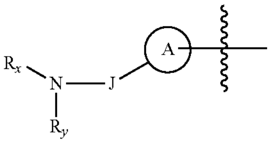

is selected from the group consisting of

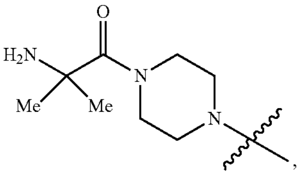
,
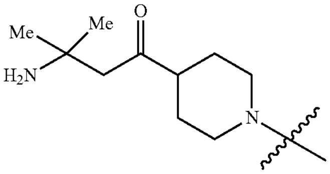
, and
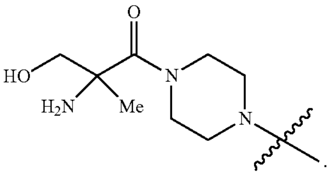
.

In another embodiment of a compound of formula I or II or a pharmaceutically acceptable salt thereof,

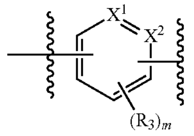

is

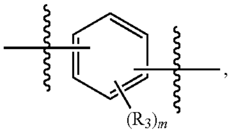
,
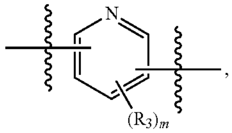
, or
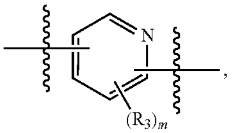
, wherein each $R_4$ is independently selected from the group consisting of $C_1$-$C_6$ alkyl, halo, $C_1$-$C_6$ haloalkyl, wherein m is 0, 1, or 2.

In another embodiment,

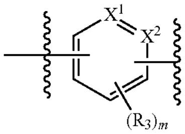

is

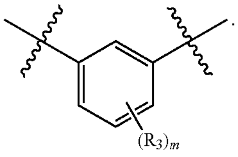

.

In another embodiment,

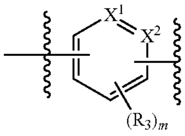

is

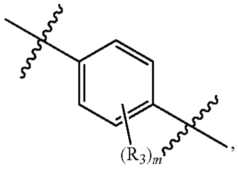

, wherein each $R_3$ is independently selected from the group consisting of $C_1$-$C_6$ alkyl, halo, $C_1$-$C_6$ haloalkyl, wherein m is 0, 1, or 2.

In another embodiment,

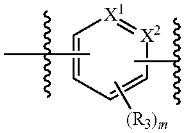

is selected from any of the moieties provided in Table 7:

TABLE 7

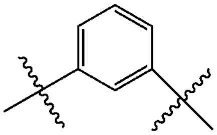

,

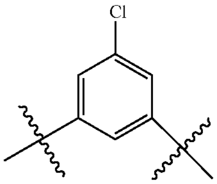

,

TABLE 7-continued

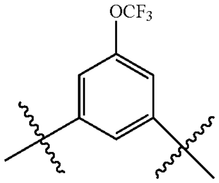

,

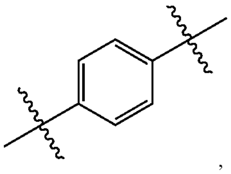

,

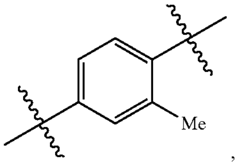

,

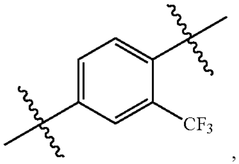

,

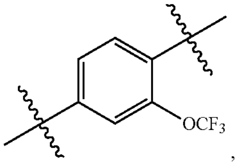

,

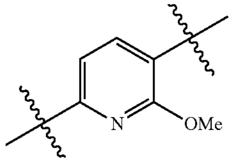

,,

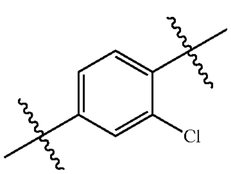

,

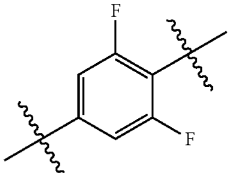

,

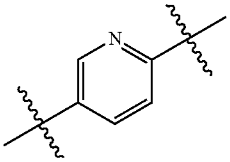

, and

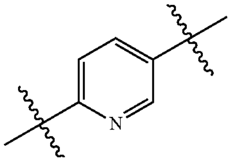

.

In another embodiment,

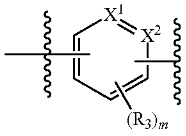

is

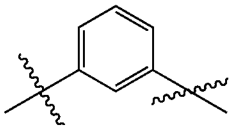

or

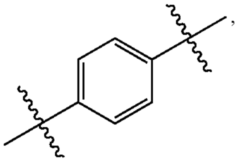

,

In another embodiment of a compound of formula I or II or a pharmaceutically acceptable salt thereof, Y is $Y_1$ and $Y_1$ is —$C(R_iR_j)$—, wherein $R_i$, and $R_{i'}$ are each independently H or $C_1$-$C_6$ alkyl which may be optionally substituted with halo, or hydroxy, wherein $C(R_iR_j)$ or $C(R_{i'}R_{j'})$ may be replaced with NH, N—($C_{1-6}$ alkyl), or (C═O).

In another embodiment of a compound of formula I or II or a pharmaceutically acceptable salt thereof, Y is $Y_1$, and $Y_1$ is $CR_iR_{ii}$, which is selected from the group consisting of $CH_2$, $CH(C_1\text{-}C_6$ alkyl), $C(C_1\text{-}C_6$ alkyl$)_2$, CH—COO($C_1$-$C_6$ alkyl) and CHCOOH.

In another embodiment of a compound of formula I or II or a pharmaceutically acceptable salt thereof $Y_1$ is selected from the group consisting of $CH_2$, $CH(CH_3)$, CH(COOEt) and CH(COOH).

In another embodiment of a compound of formula I or II or a pharmaceutically acceptable salt thereof, Y is $Y_2$, and $Y_2$ is —$C(R_iR_j)$—$C(R_{i'}R_{j'})$—, wherein $R_{i'}$, $R_j$, $R_{i'}$, $R_{j'}$ are each independently H or $C_1$-$C_6$ alkyl optionally substituted with OH or halo, and wherein $C(R_iR_j)$ or $C(R_{i'}R_{j'})$ may be replaced with NH, N—($C_{1-6}$ alkyl), or (C═O).

In another embodiment of a compound of formula I or II or a pharmaceutically acceptable salt thereof, $Y_2$ is selected from the group consisting of

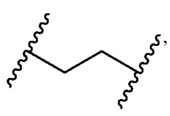, 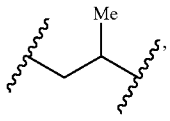, 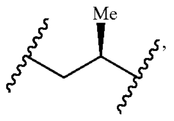,

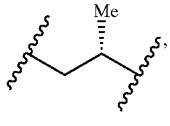, 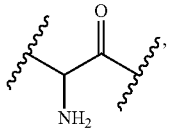, 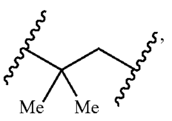,

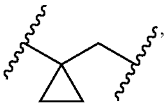, 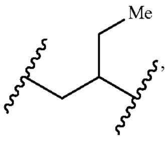,

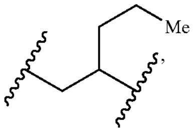, 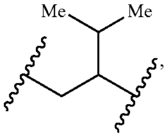,

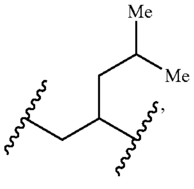, 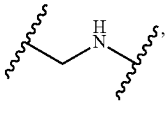, 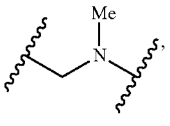,

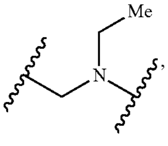, 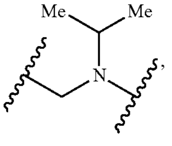,

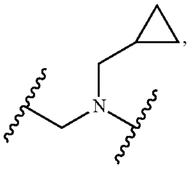, 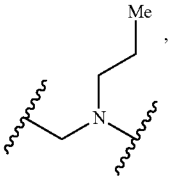, 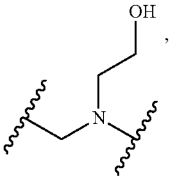,

-continued

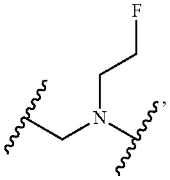, and 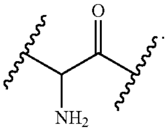.

In another embodiment, Y is $Y_3$, and $Y_3$ is a linear $C_3$ alkylene, $C_3$ alkenylene, or $C_3$ alkynylene, any of which are optionally substituted with OH, $NH_2$, halo, $C_1$-$C_6$ alkyl, or $C_1$-$C_6$ alkoxy, and wherein one or two carbon atoms of the $C_3$ alkylene, $C_3$ alkenylene, or $C_3$ alkynylene is replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), —NH(C═O)—, —N—($C_{1-6}$ alkyl)(C═O)—, —O(C═O)—, or —(C═O).

In another embodiment, $Y_3$ is $C_3$ alkylene, or $C_3$ alkenylene, either of which is optionally substituted with OH, $NH_2$, halo, $C_1$-$C_6$ alkyl, or $C_1$-$C_6$ alkoxy, and wherein one or two carbon atoms of the $C_3$ alkylene, $C_3$ alkenylene, is replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), —NH(C═O)—, —N—($C_{1-6}$ alkyl)(C═O)—, —O(C═O)—, or —(C═O)—.

In another embodiment, $Y_3$ is selected from the group consisting of

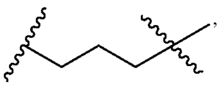, 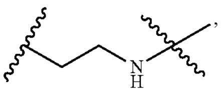,

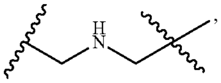, 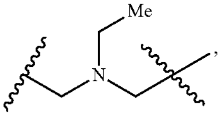,

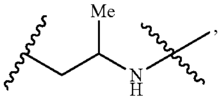, 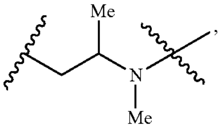,

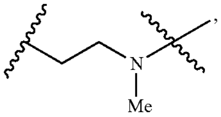, 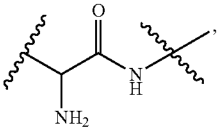,

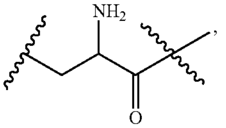, 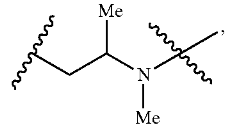,

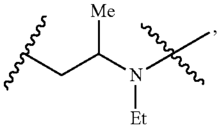, 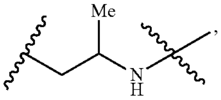,

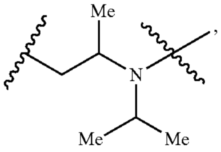, 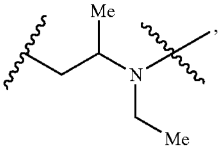,

-continued

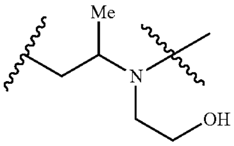,
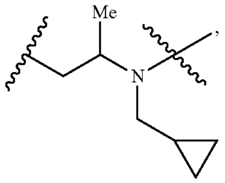,
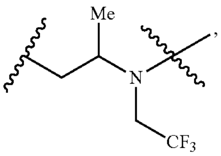,
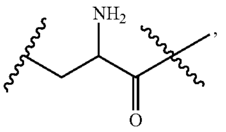,
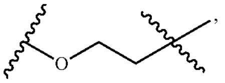,
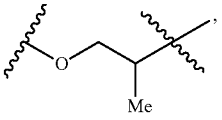, and
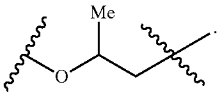.

In another embodiment, $Y_3$ is selected from the group consisting of

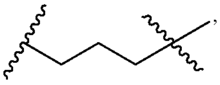,
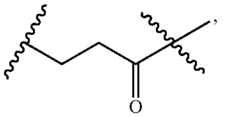,
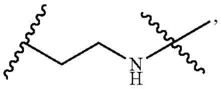,
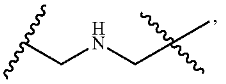,
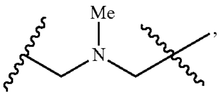,
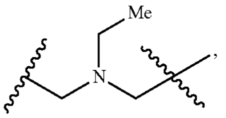,
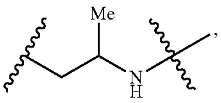,
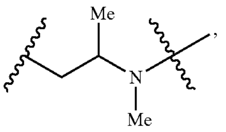,
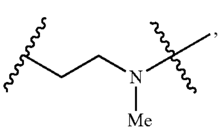,
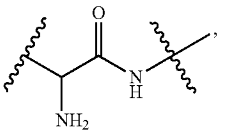,
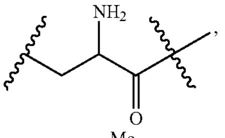,
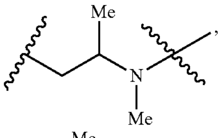,
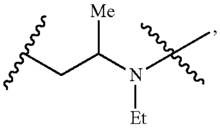,
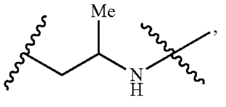,
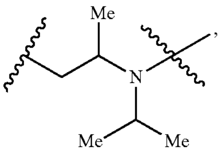,
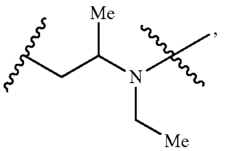, -continued

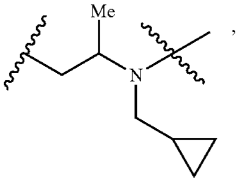,
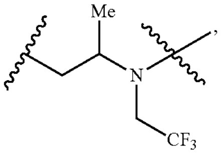,
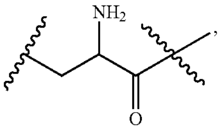,
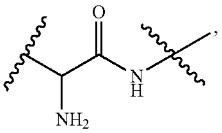,
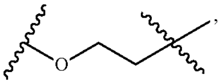,
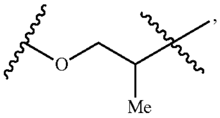, and
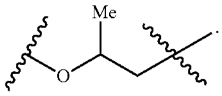.

In another embodiment, Y is $Y_4$, and $Y_4$ is a linear $C_4$ alkylene, $C_4$ alkenylene, or $C_4$ alkynylene, any of which are optionally substituted with OH, $NH_2$, halo, $C_1$-$C_6$ alkyl, or $C_1$-$C_6$ alkoxy, and wherein one or two carbon atoms of the $C_4$ alkylene, $C_4$ alkenylene, or $C_4$ alkynylene is replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), —NH(C═O)—, —N—($C_{1-6}$ alkyl)(C═O)—, —O(C═O)—, or —(C═O)—.

In another embodiment, $Y_4$ is $C_4$ alkylene, or $C_4$ alkenylene, either of which is optionally substituted with OH, $NH_2$, halo, $C_1$-$C_6$ alkyl, or $C_1$-$C_6$ alkoxy, and wherein one or two carbon atoms of the $C_3$-$C_5$ alkylene, $C_3$-$C_5$ alkenylene is replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), —NH(C═O)—, —N—($C_{1-6}$ alkyl)(C═O)—, —O(C═O)—, or —(C═O)—.

In another embodiment, $Y_4$ is selected from the group consisting of

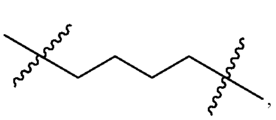,
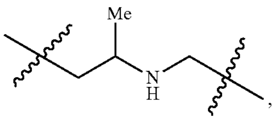,
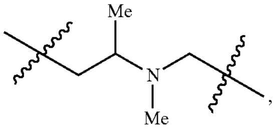,
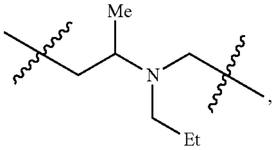,
and
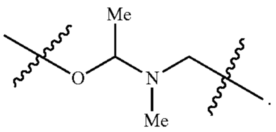.

In another embodiment of a compound of formula I or II or a pharmaceutically acceptable salt thereof,
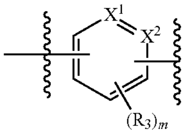
is selected from any of the moieties provided in Table 7; and Y is selected from any of the moieties provided in Table 8:
TABLE 8
$CH_2$, $CH(CH_3)$ $CH(COOEt)$, $CH(COOH)$,
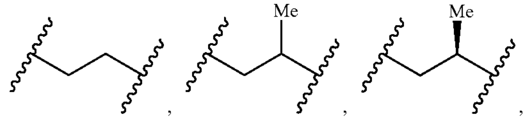 , , ,
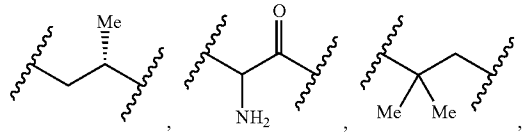 [SMILES: *C[C@@H](*)C ; *C(=O)C(*)N ; *CC(*)(C)C] , , ,
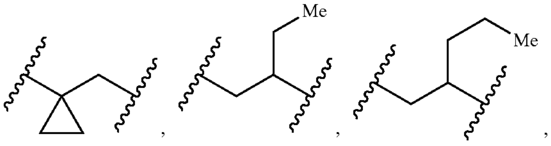 [SMILES: *CC1(*)CC1 ; *CC(*)CC ; *CC(*)CCC] , , ,
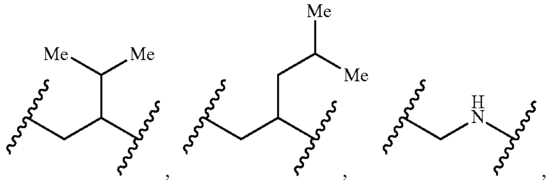 , , ,
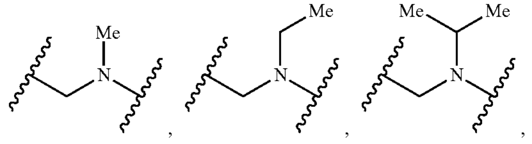 [SMILES: *CN(*)C ; *CN(*)CC ; *CN(*)C(C)C] , , ,
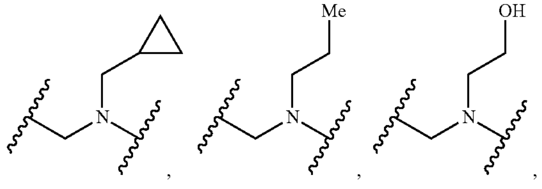 [SMILES: *CN(*)CC1CC1 ; *CN(*)CCC ; *CN(*)CCO] , , ,
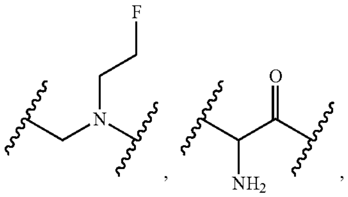 [SMILES: *CN(*)CCF ; *C(=O)C(*)N] , ,
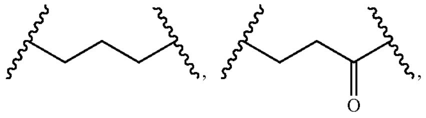 [SMILES: *CCC* ; *CCC(*)=O] , ,
TABLE 8-continued
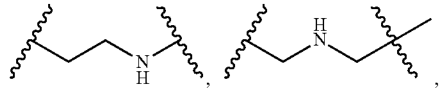 [SMILES: *CCN* ; *CNC*] , ,
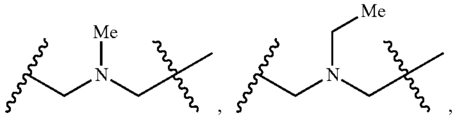 [SMILES: *CN(C)C* ; *CN(C*)CC] , ,
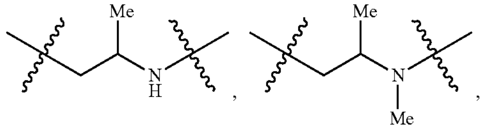 [SMILES: *CC(C)N* ; *CC(C)N(*)C] , ,
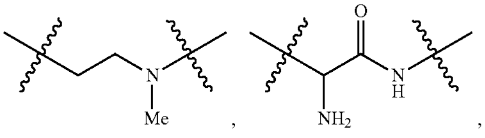 [SMILES: *CCN(*)C ; *NC(=O)C(*)N] , ,
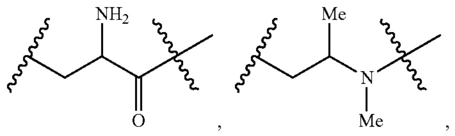 [SMILES: *CC(N)C(*)=O ; *CC(C)N(*)C] , ,
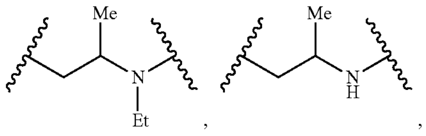 [SMILES: *CC(C)N(*)CC ; *CC(C)N*] , ,
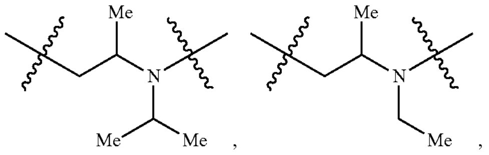 [SMILES: *CC(C)N(*)C(C)C ; *CC(C)N(*)CC] , ,
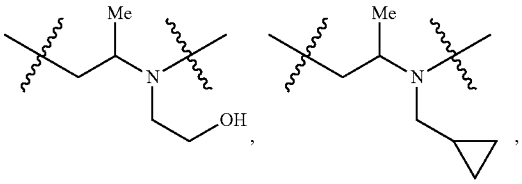 [SMILES: *CC(C)N(*)CCO ; *CC(C)N(*)CC1CC1] , ,
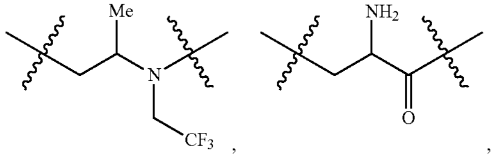 [SMILES: *CC(C)N(*)CC(F)(F)F ; *CC(N)C(*)=O] , ,
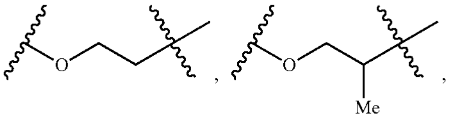 [SMILES: *CCO* ; *OCC(*)C] , ,
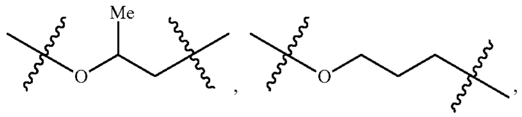 [SMILES: *CC(C)O* ; *CCCO*] , , TABLE 8-continued
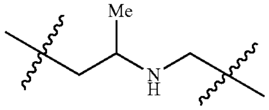,
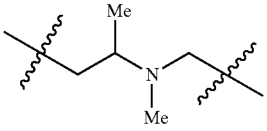,
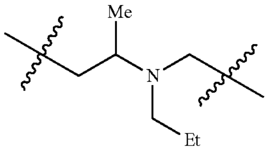, and
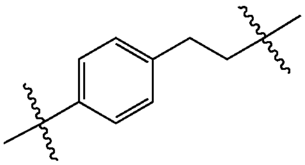,
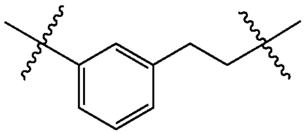,
TABLE 8-continued
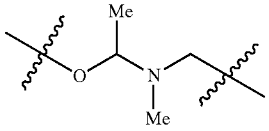.
In another embodiment of a compound of formula I or II or a pharmaceutically acceptable salt thereof,
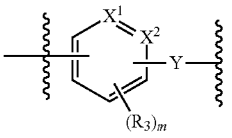
is selected from the group consisting of
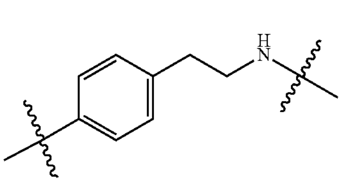,
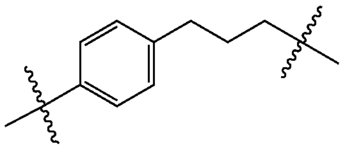,
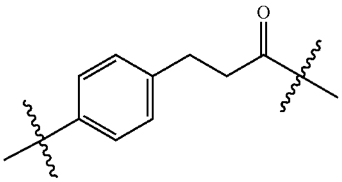,
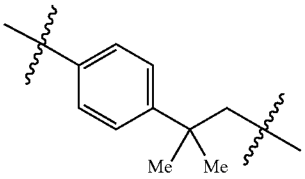,
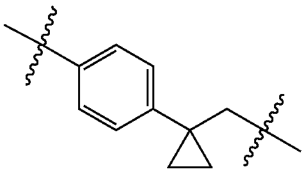,
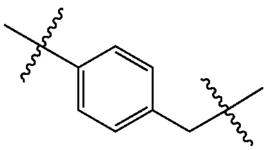,
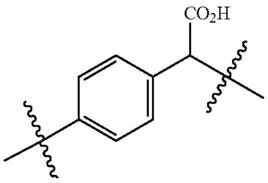,
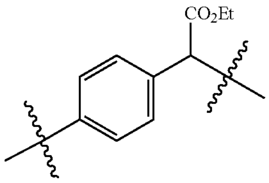,
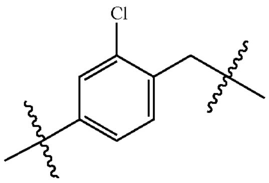,
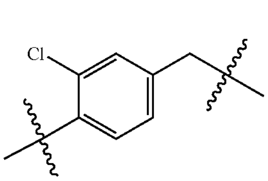,
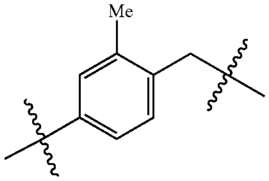,
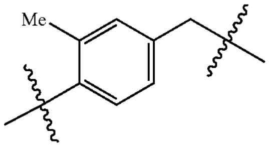, -continued
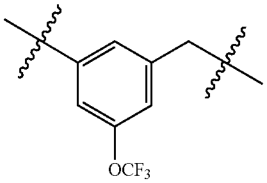
,
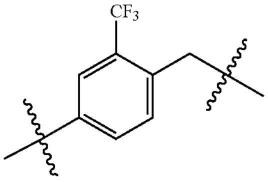
,
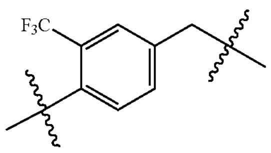
,
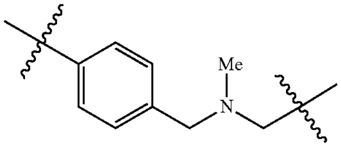
,
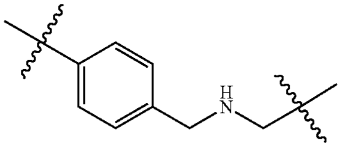
,
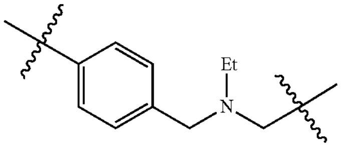
,
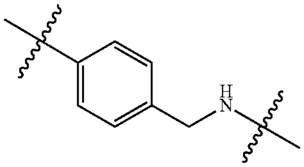
,
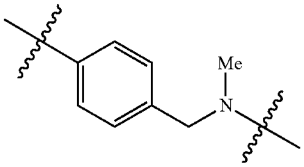
,
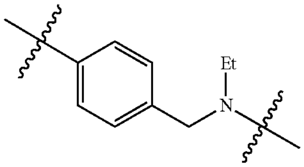
,
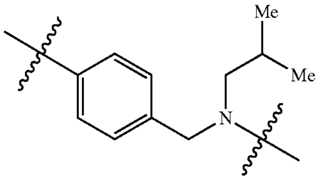
,
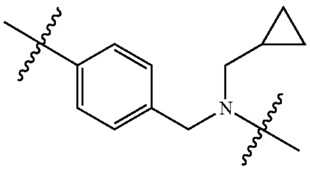
,
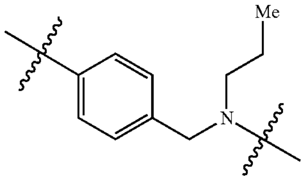
,
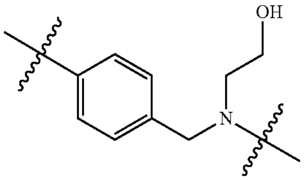
,
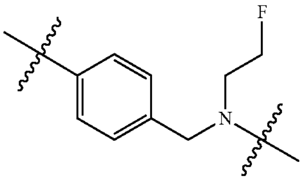
,
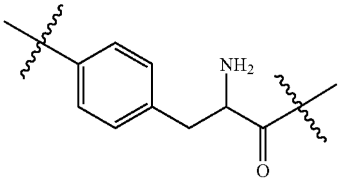
,
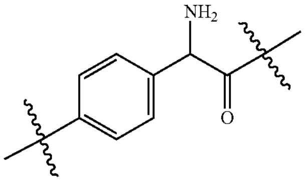
,
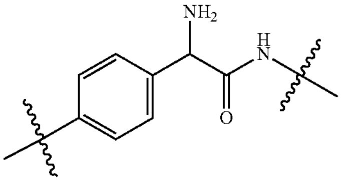
,
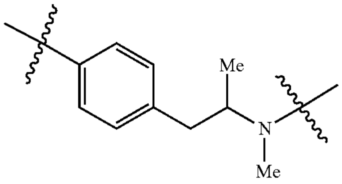
,
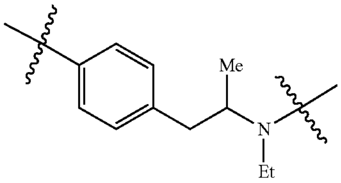
,
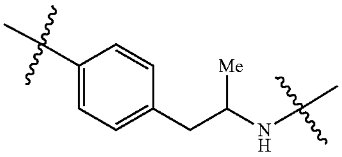
,
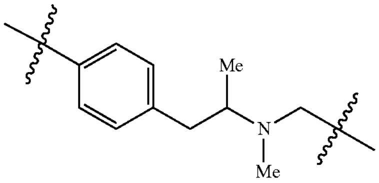
,
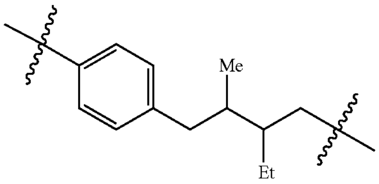
,
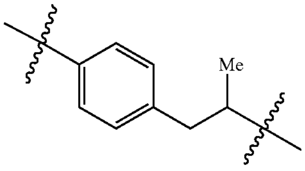
,
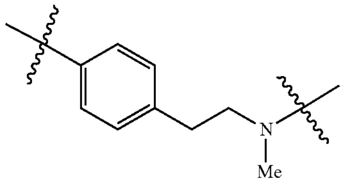
,
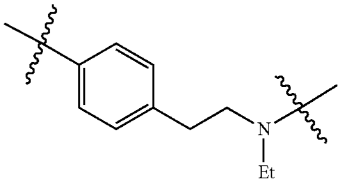
,
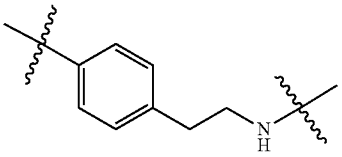
,
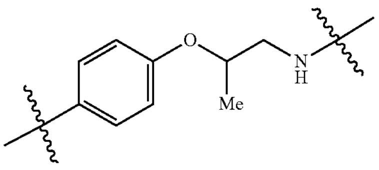
, -continued

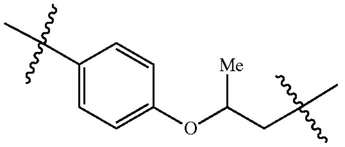,
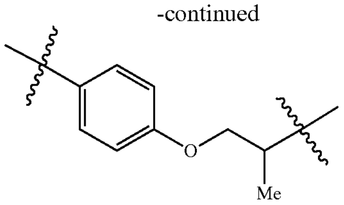,
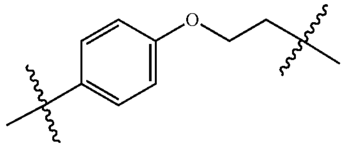,
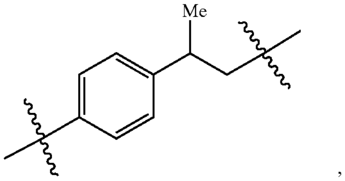,
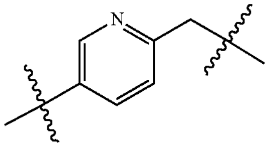, and
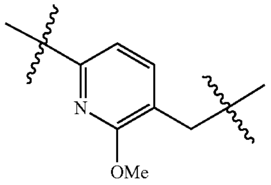.

In another embodiment of a compound of formula I or II or a pharmaceutically acceptable salt thereof, ring B is a 4-7 membered monocyclic cycloalkylene or 4-7 membered monocyclic heterocycloalkylene, either of which is optionally substituted with up to three substituents selected from the group consisting of $C_1$-$C_6$ alkyl, $C_1$-$C_6$ alkoxy, halo, CN, $C_1$-$C_6$ haloalkyl, OH, —COO($C_1$-$C_6$ alkyl), —$COONH_2$, and $C_1$-$C_6$ hydroxyalkyl.

In another embodiment of a compound of formula I or II or a pharmaceutically acceptable salt thereof, ring B is selected from the group consisting of

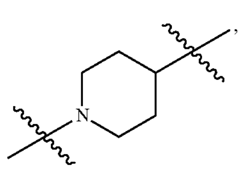,
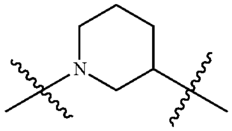,
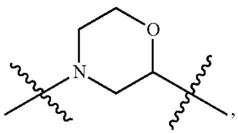,
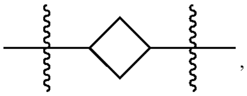,
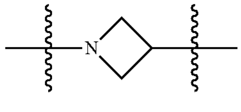,
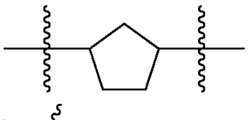,
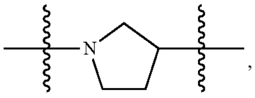,
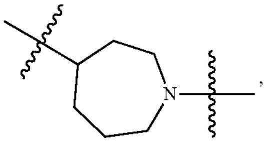,
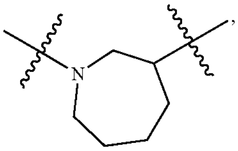, and
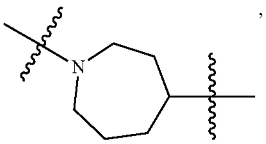, any of which is optionally substituted with up to three substituents selected from the group consisting of $C_1$-$C_6$ alkyl, $C_1$-$C_6$ alkoxy, halo, CN, $C_1$-$C_6$ haloalkyl, OH, —COO ($C_1$-$C_6$ alkyl), —$COONH_2$, and $C_1$-$C_6$ hydroxyalkyl.

In another embodiment of a compound of formula I or II or a pharmaceutically acceptable salt thereof, ring B is selected from any of the moieties provided in Table 9:

TABLE 9

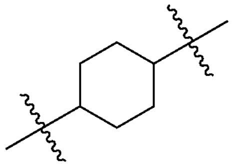,
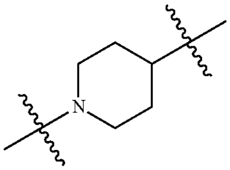,
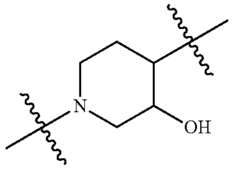,
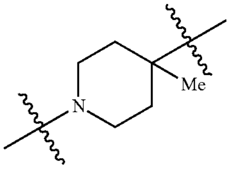,
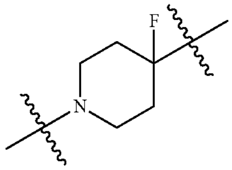,
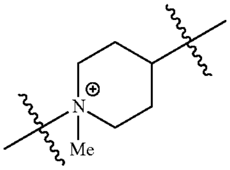,
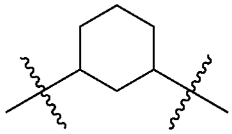,
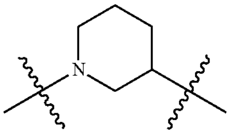,
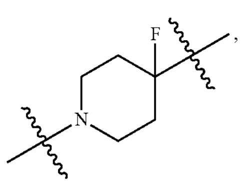,
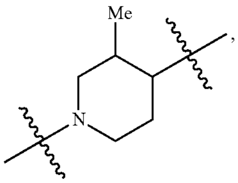,
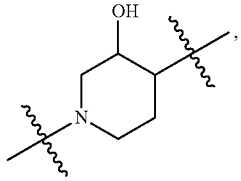,
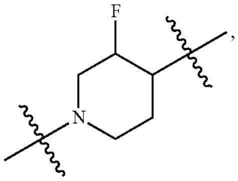, TABLE 9-continued

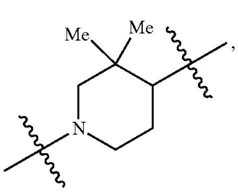, 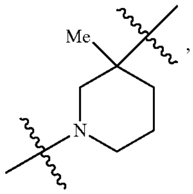,

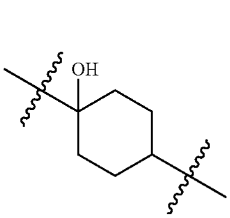, 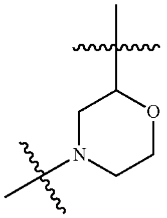,

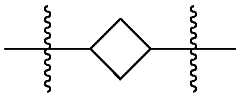, 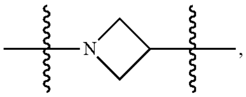,

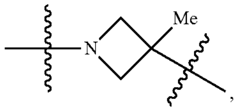, 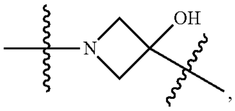,

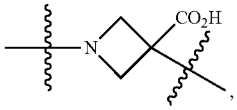, 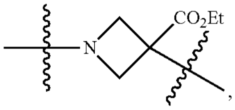,

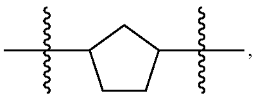, 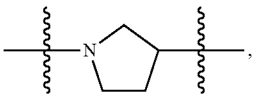,

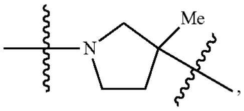, 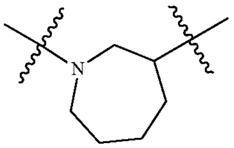,

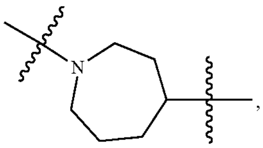, 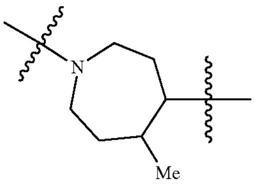,

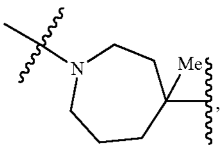, and 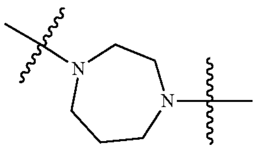.

In another embodiment of a compound of formula I or II or a pharmaceutically acceptable salt thereof, L is absent.

In another embodiment, L is a linear or branched $C_1$-$C_6$ alkylene, wherein up to two carbon atoms of the $C_1$-$C_6$ alkylene may be replaced with O, NH, (C═O), NH(C═O), N—($C_{1-6}$ alkyl)(C═O), (C═NH), NH(C═N), or N—($C_{1-6}$ alkyl)

In another embodiment, L is —$CH_2$—.

In another embodiment, L is —CH(Me)-.

In another embodiment, L is —CH(Et)-.

In another embodiment, L is C═O.

In another embodiment of a compound of formula I or II or a pharmaceutically acceptable salt thereof, $R_1$ is H, fluoro, $NH_2$, NH($C_1$-$C_6$ alkyl) NH($C_3$-$C_6$ cycloalkyl), or a protecting group.

In another embodiment of a compound of formula I or II or a pharmaceutically acceptable salt thereof, $R_1$ is H, F, $CF_3$, H, $NH_2$, $NHCH_3$, NH-cyclopropyl, NH(C═O)—$C_1$-$C_6$ alkyl-$NH_2$, or NH(C═N)$NH_2$.

In another embodiment, $R_1$ is H or $NH_2$.

In another embodiment of a compound of formula I or II or a pharmaceutically acceptable salt thereof,

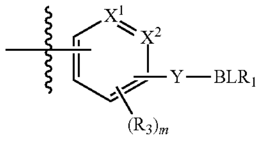

is selected from the group consisting of:

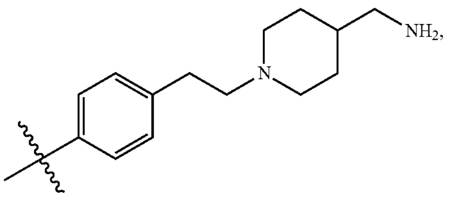

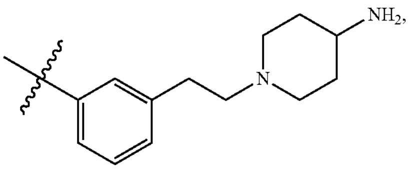

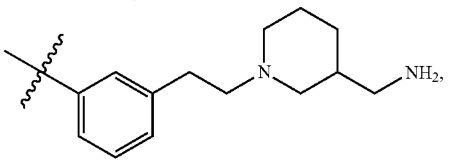

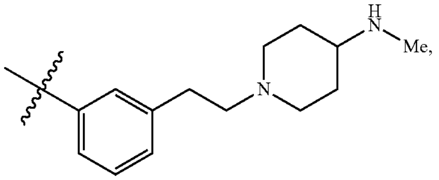

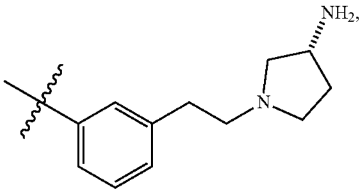

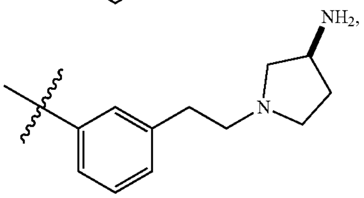

-continued
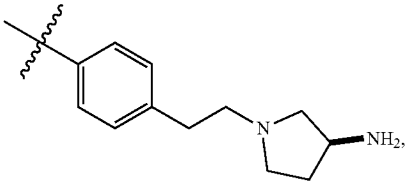
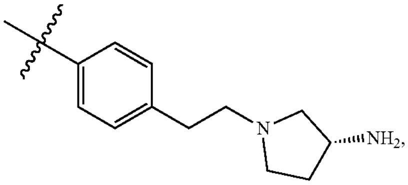
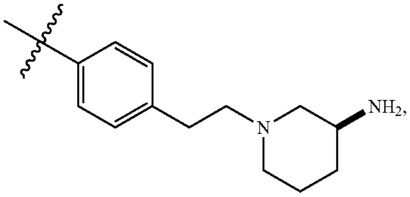
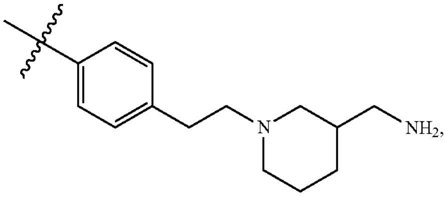
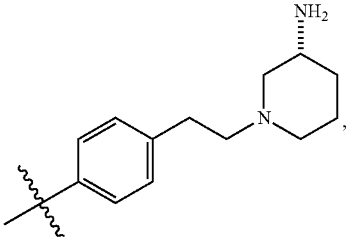
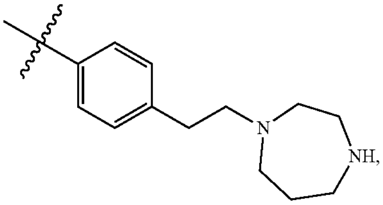
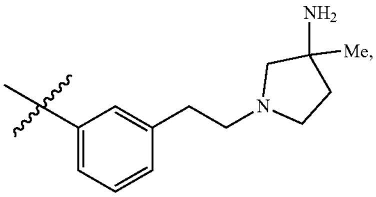
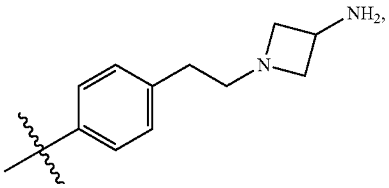
-continued
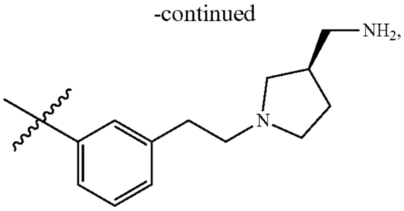
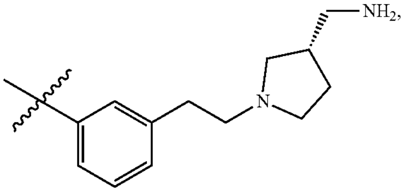
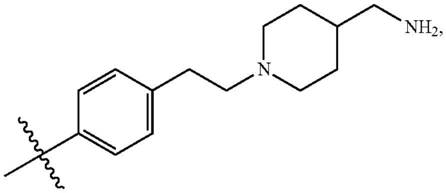
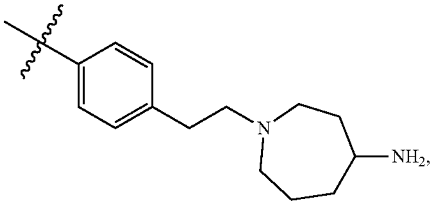
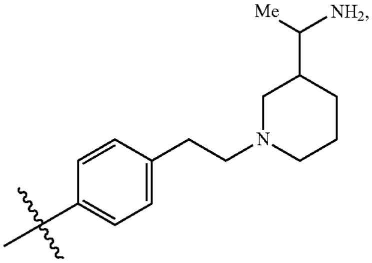
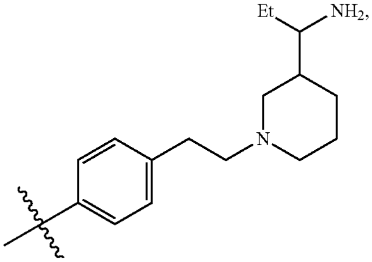
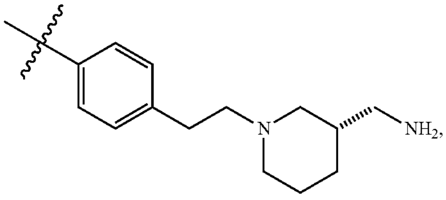
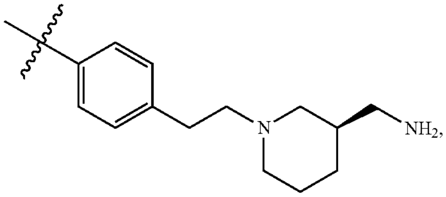

-continued
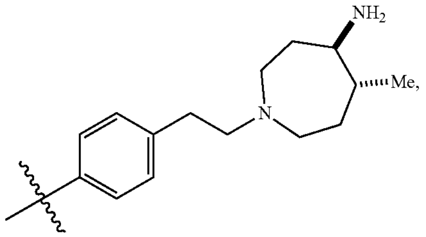
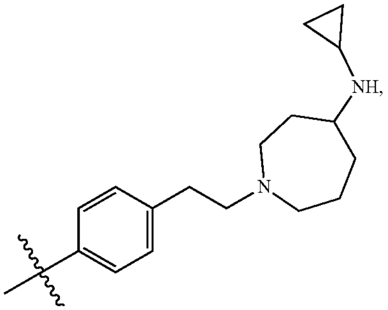
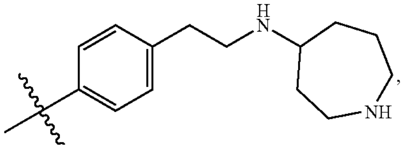
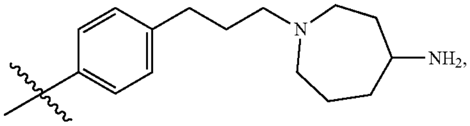
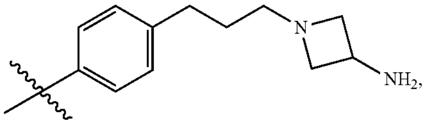
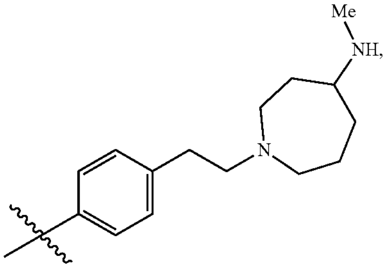
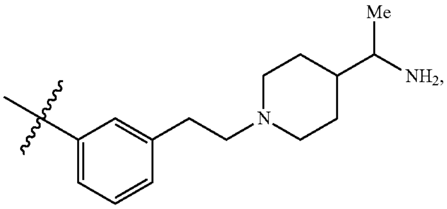
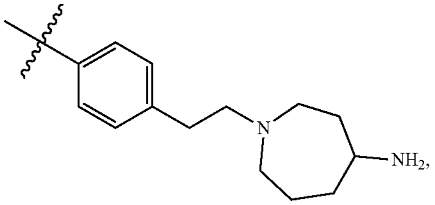
-continued
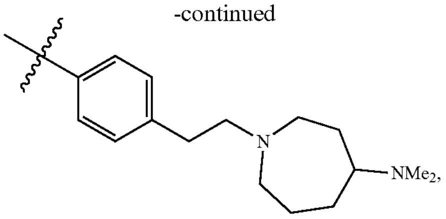
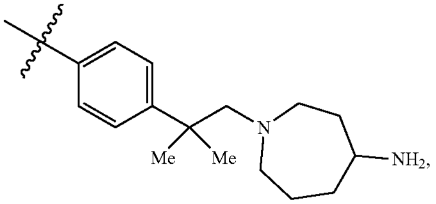
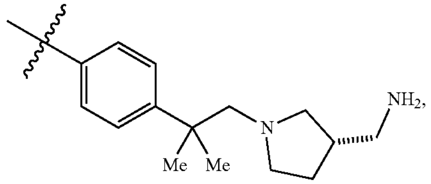
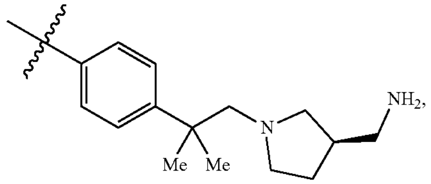
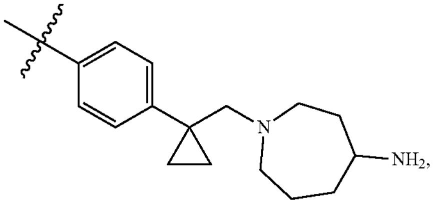
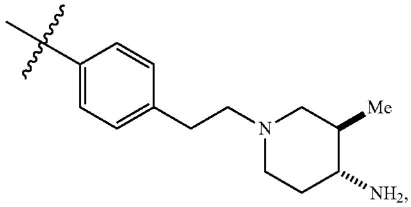
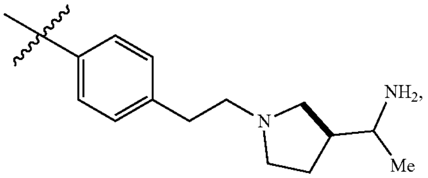
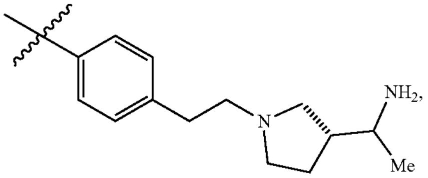
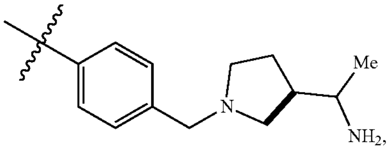

-continued
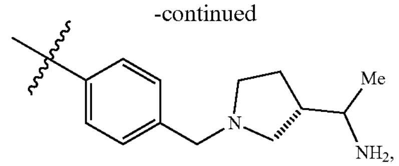
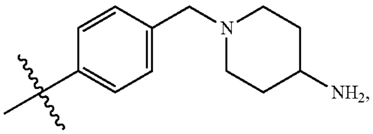
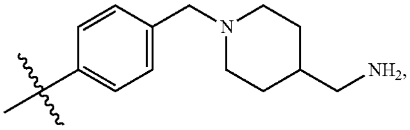
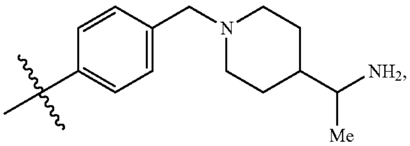
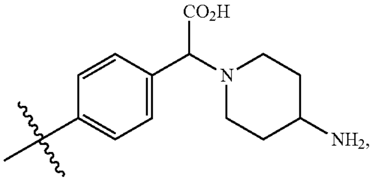
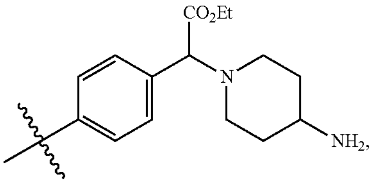
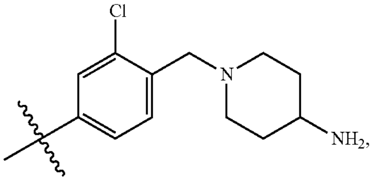
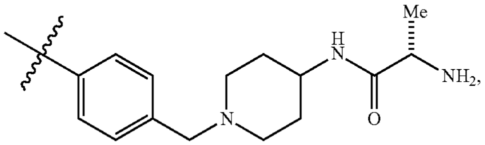
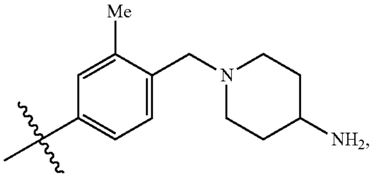
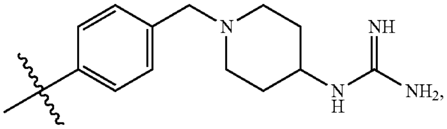
-continued
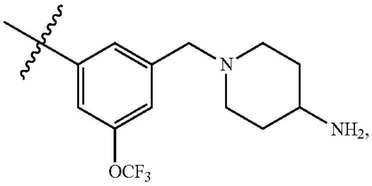
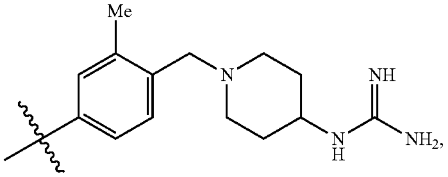
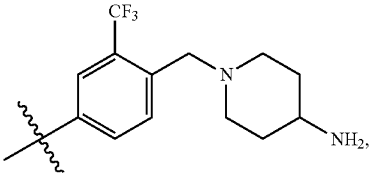
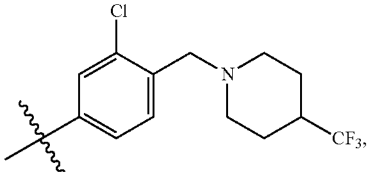
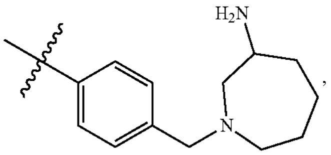
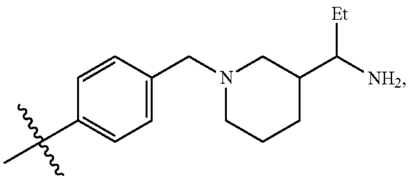
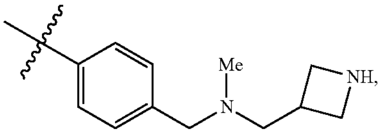
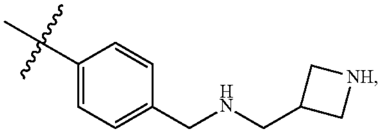
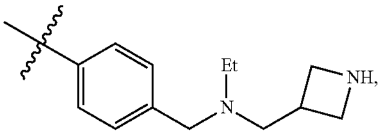
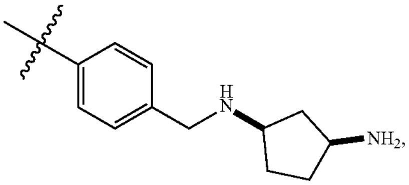

-continued
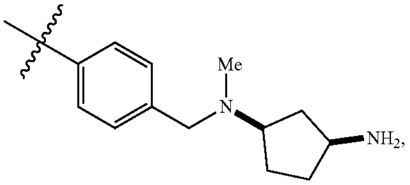
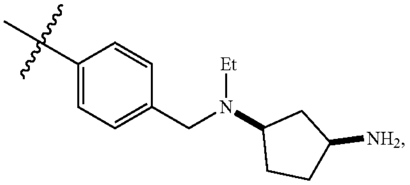
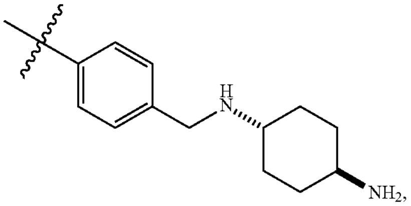
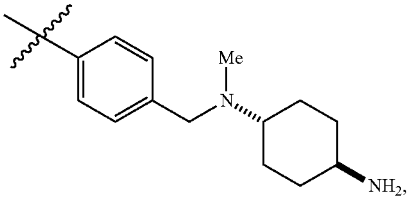
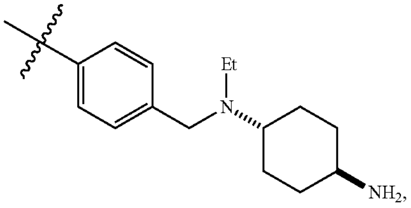
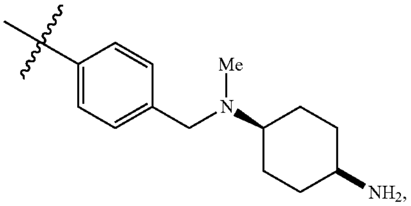
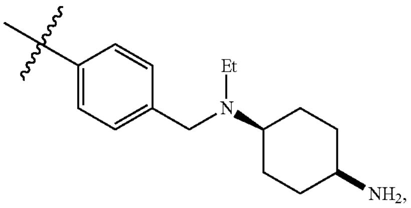
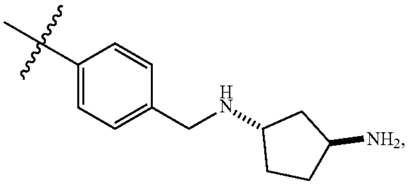
-continued
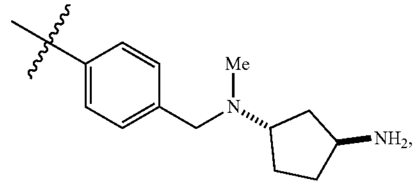
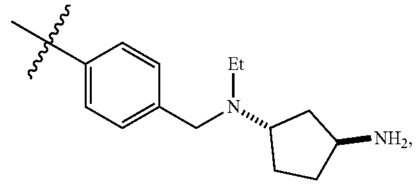
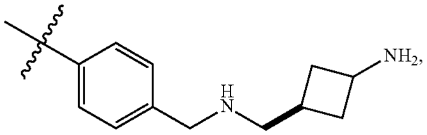
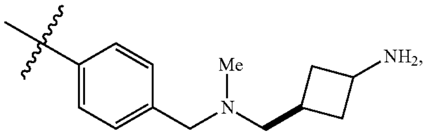
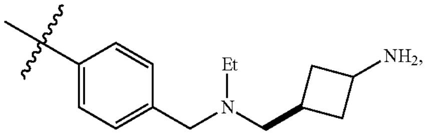
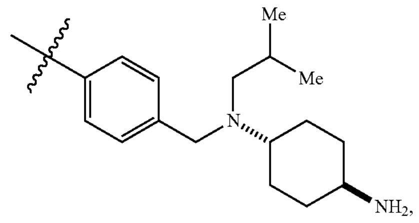
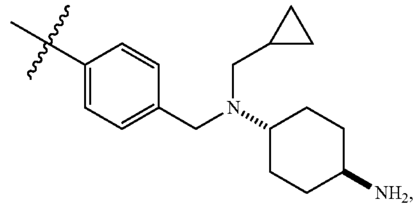
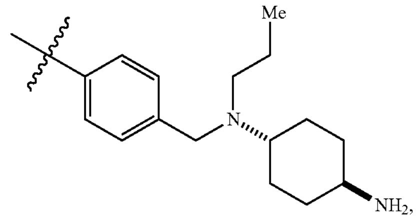
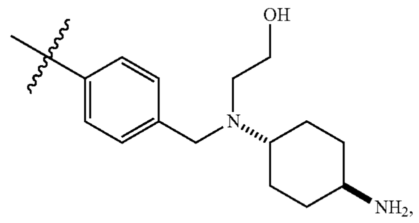

-continued
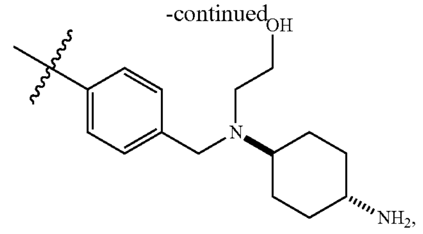
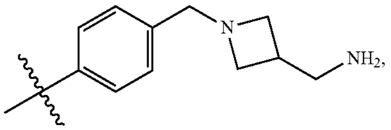
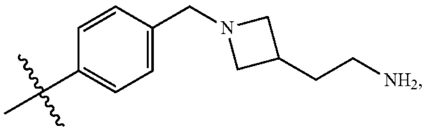
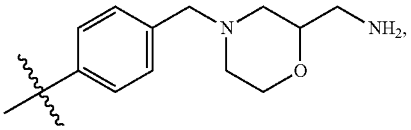
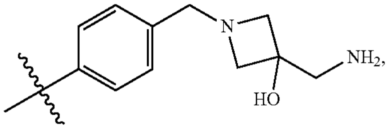
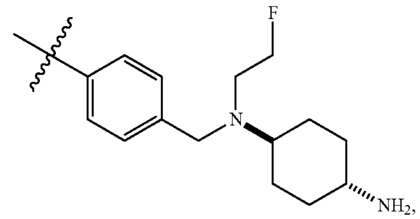
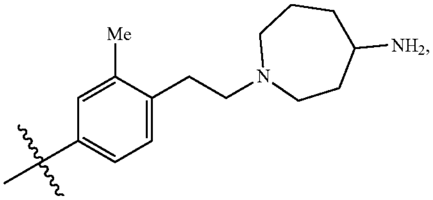
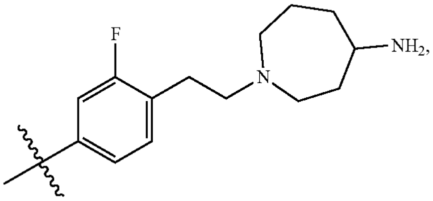
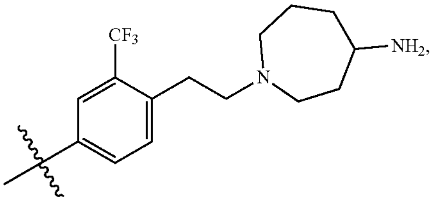
-continued
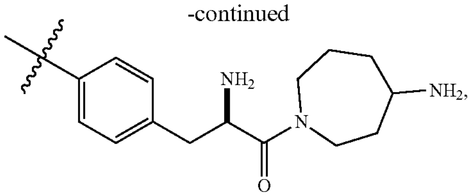
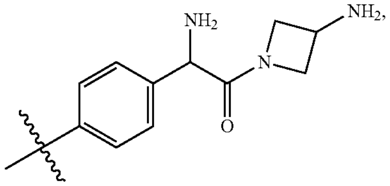
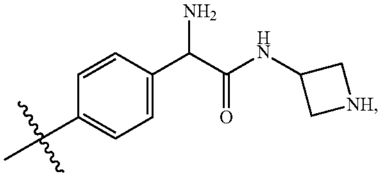
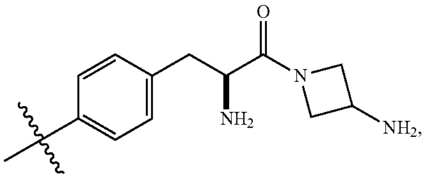
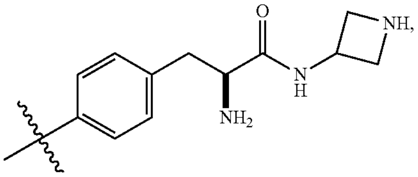
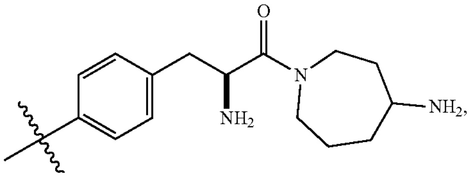
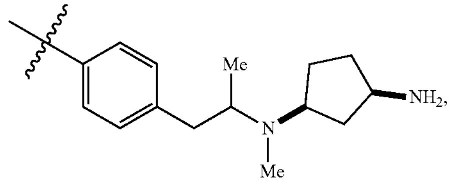
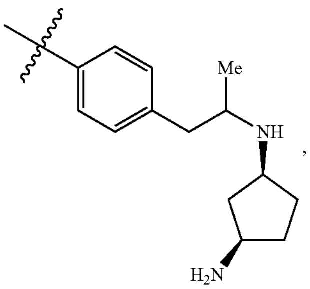

-continued
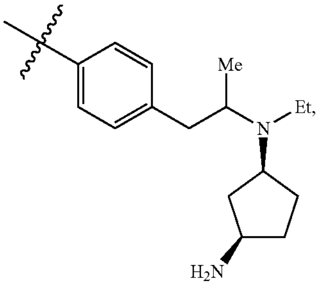
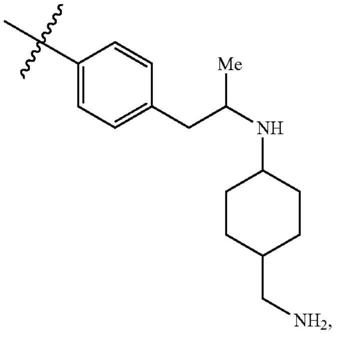
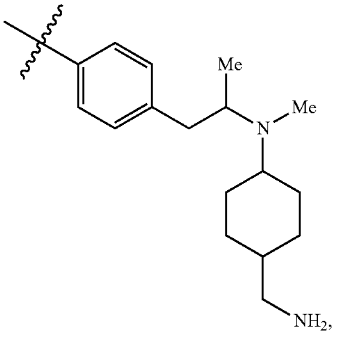
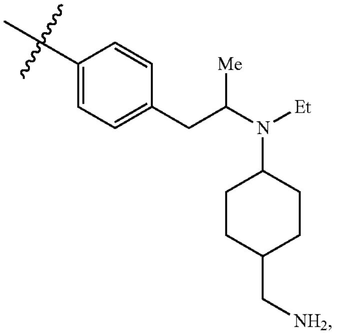
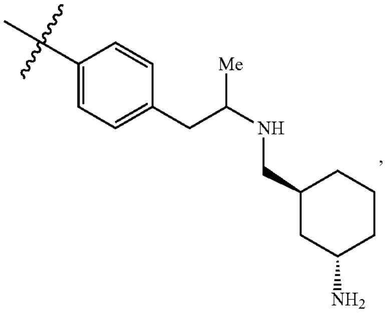
,
-continued
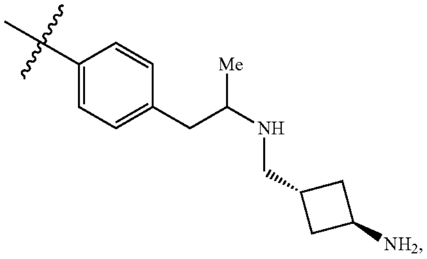
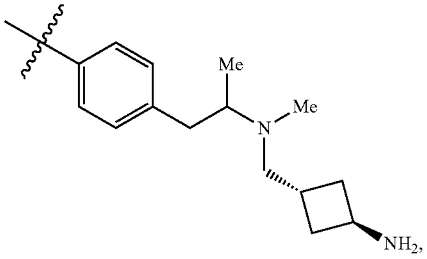
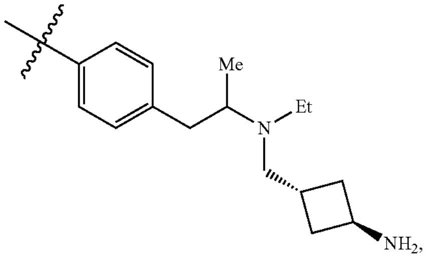
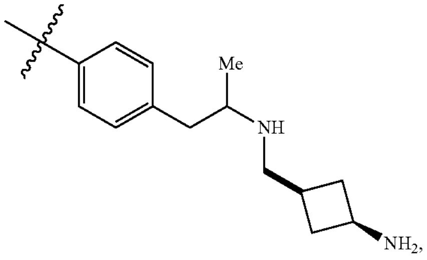
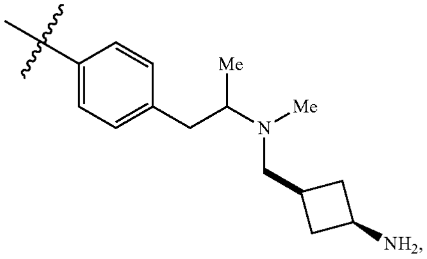
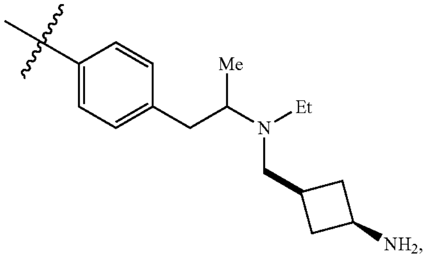

-continued
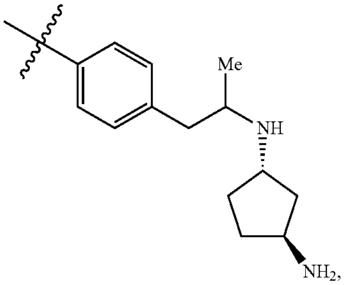
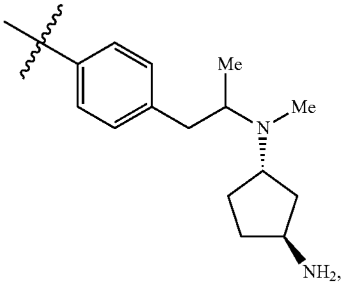
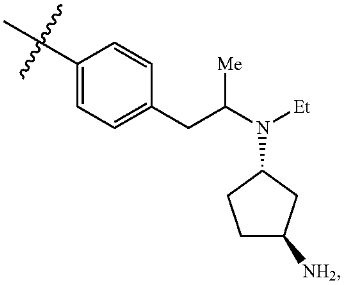
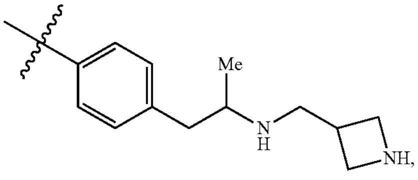
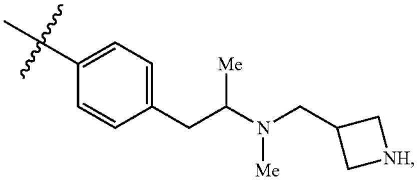
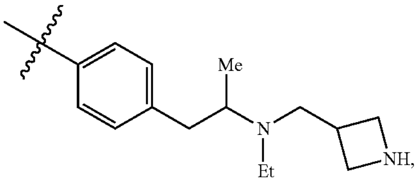
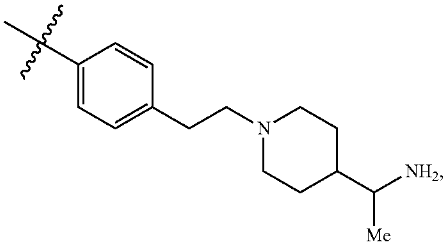
-continued
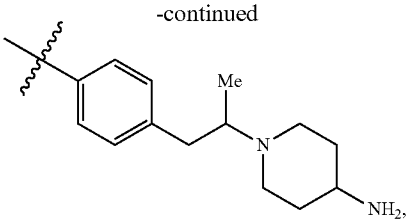
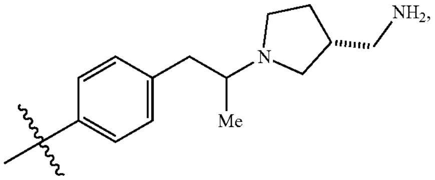
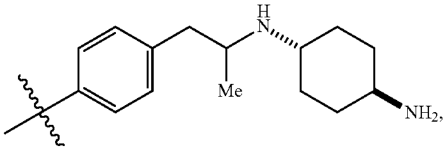
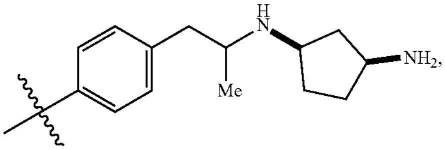
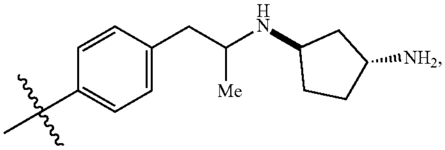
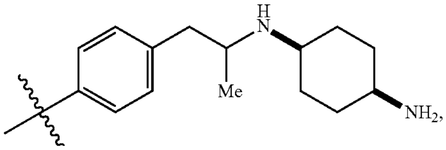
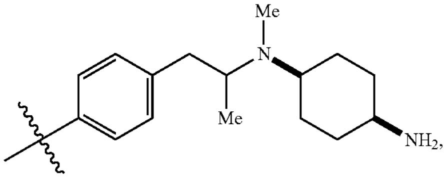
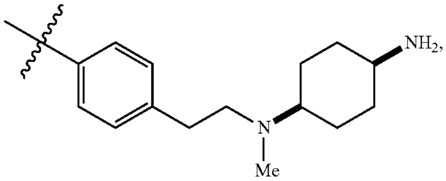
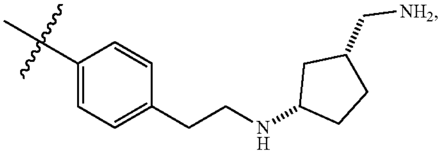
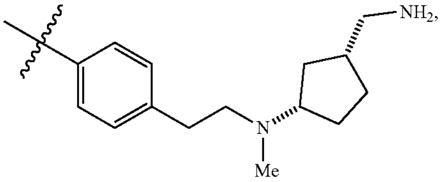

-continued
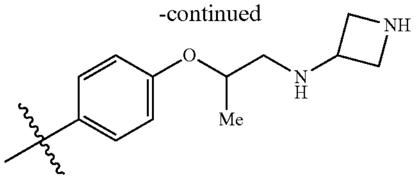
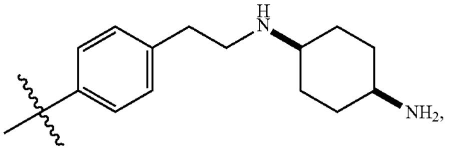
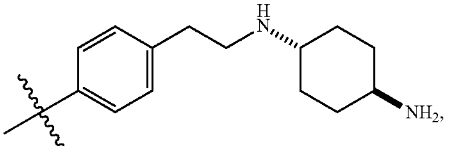
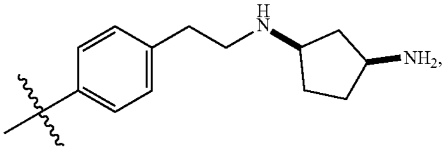
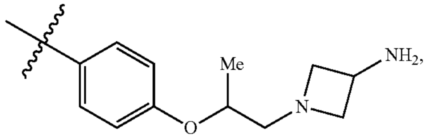
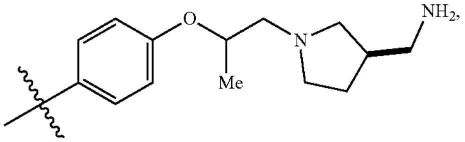
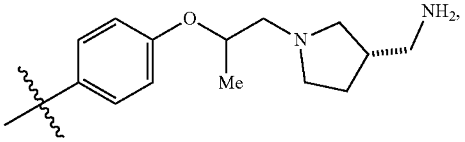
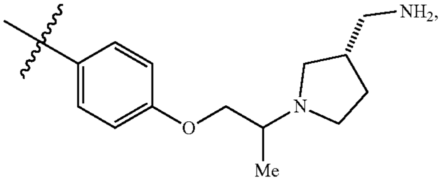
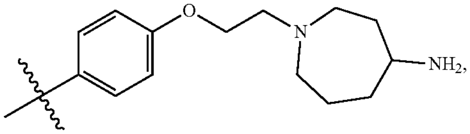
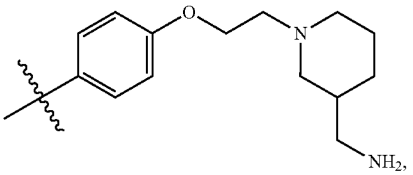
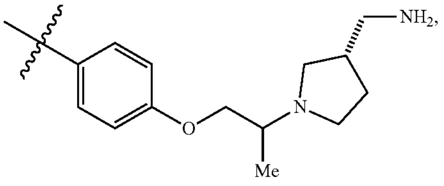
-continued
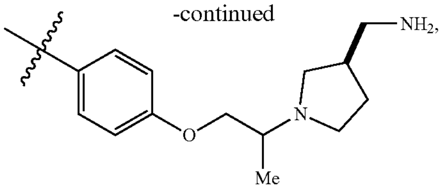
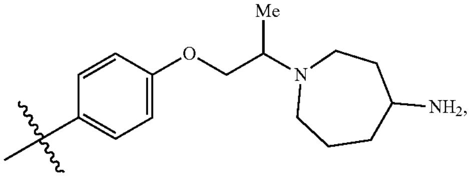
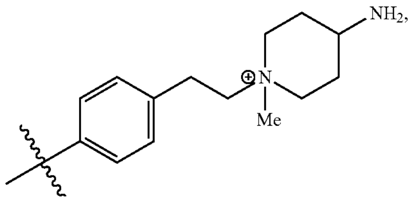
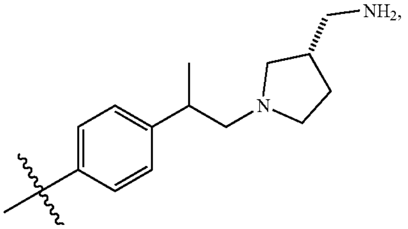
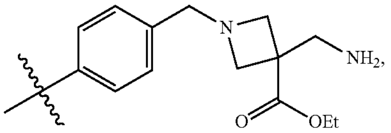
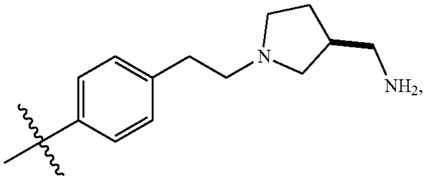
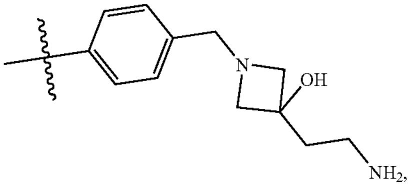
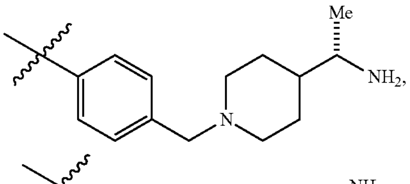
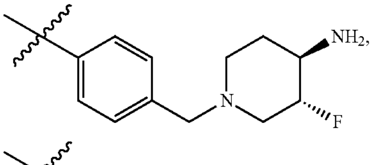
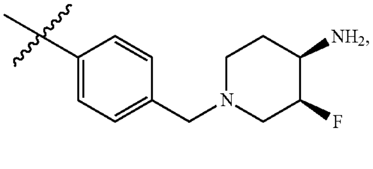

-continued
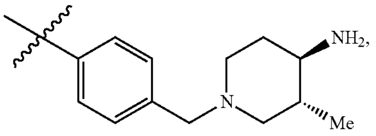
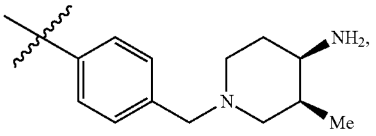
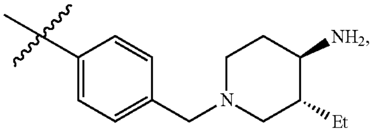
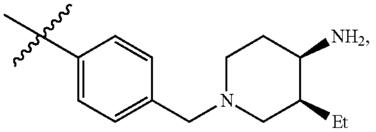
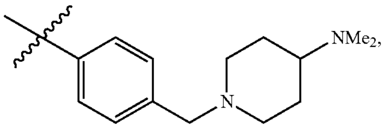
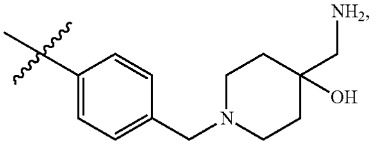
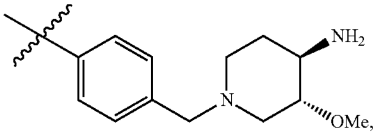
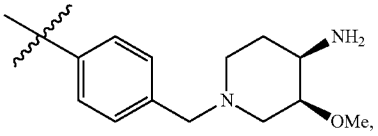
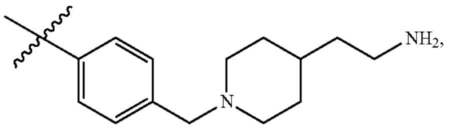
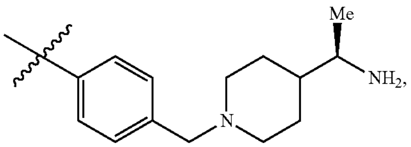
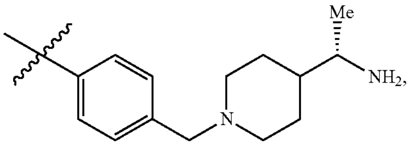
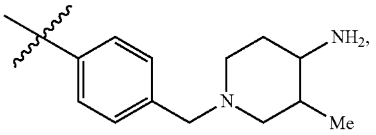
-continued
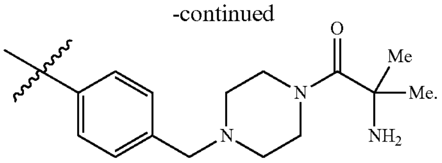
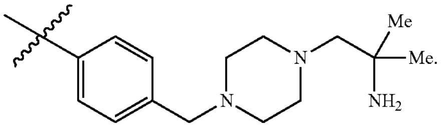
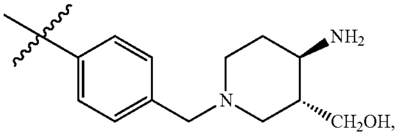
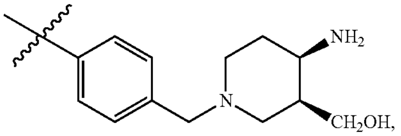
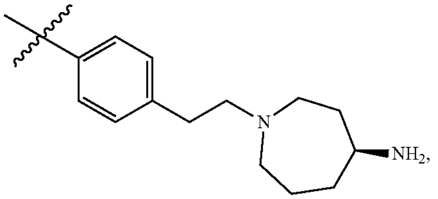
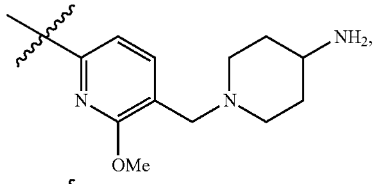
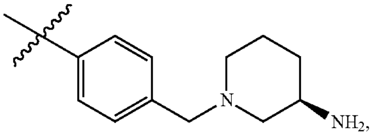
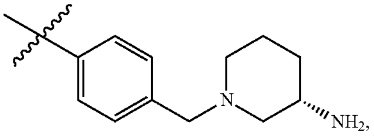
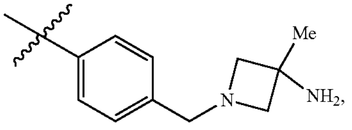
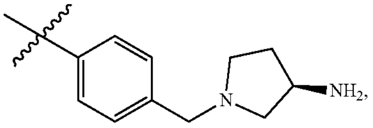
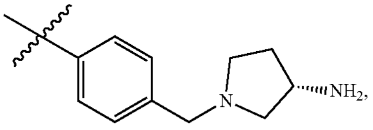
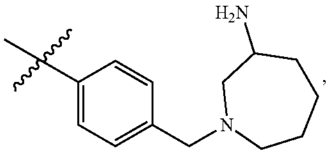

-continued

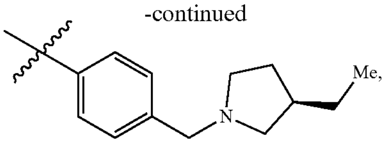

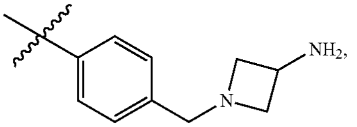

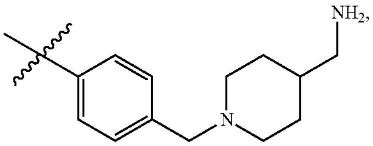

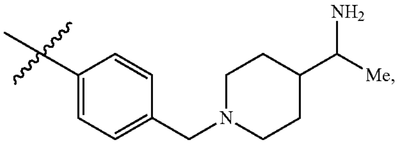

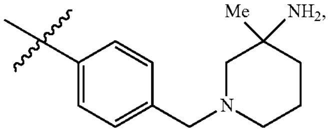

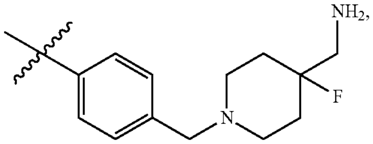

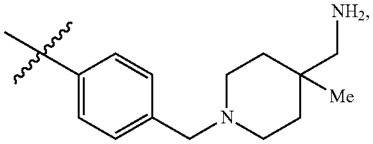

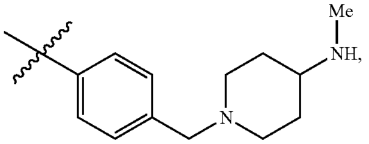

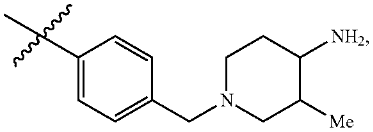

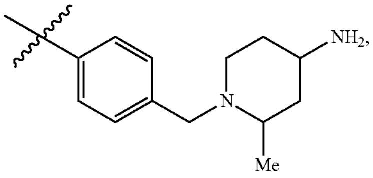

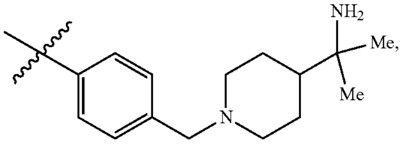

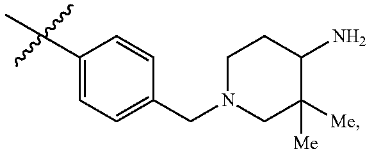

and

-continued

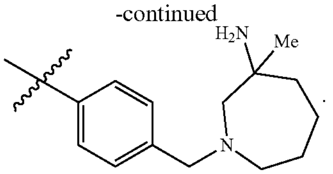

In another embodiment of a compound of formula I or II or a pharmaceutically acceptable salt thereof, $R_2$ and $R_3$ are each independently selected from the group consisting of $C_1$-$C_6$ alkyl, halo, $C_1$-$C_6$ haloalkyl, and $C_1$-$C_6$ alkoxy and m and n are each independently 0, 1, or 2.

In another embodiment, $R_2$ and $R_3$ are each independently selected from the group consisting of $CH_3$, Cl, F, $OCH_3$, $CH_3$, and $CF_3$, and m and n are each independently 0 or 1.

In another embodiment, the compound of formula I or II is a compound of formula IIA-1:

IIA-1

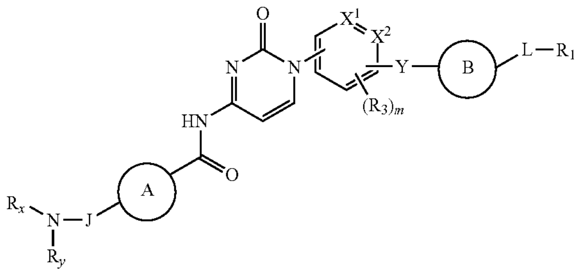

or a pharmaceutically acceptable salt thereof, wherein the variables are described herein.

In another embodiment, the compound of formula I or II is a compound of formula IIA-2:

IIA-2

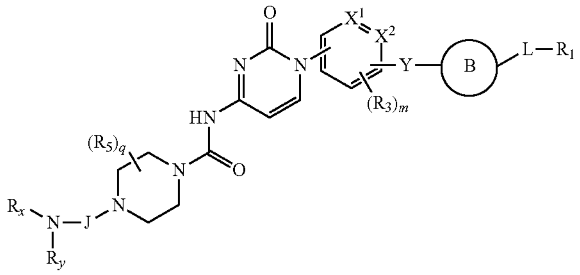

or a pharmaceutically acceptable salt thereof, wherein the variables are described herein; $R_5$ is selected from the group consisting of H, $C_1$-$C_6$ alkyl, $C_1$-$C_6$ alkoxy, halo, CN, $C_1$-$C_6$ haloalkyl, phenyl, OH, $NH_2$, and oxo; and q is 0, 1, 2, or 3.

In another embodiment, the compound of formula I or II is a compound of formula IIA-3:

IIA-3

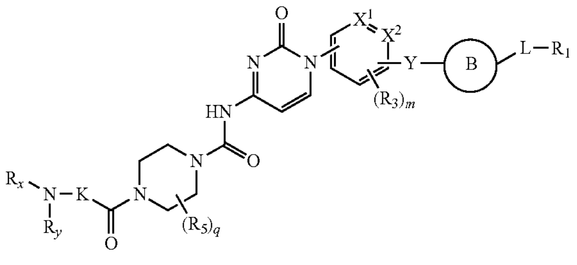

or a pharmaceutically acceptable salt thereof, wherein the variables are described herein. In another embodiment, K is $C_1$-$C_4$ alkylene optionally substituted with hydroxy or alkoxy.

In another embodiment, the compound of formula I or II is a compound of formula IIA-4:

IIA-4

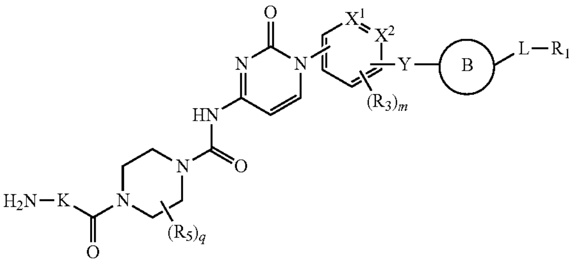

or a pharmaceutically acceptable salt thereof, wherein the variables are described herein.

In another embodiment, the compound of formula I or II is a compound of formula IIA-4a or IIA-4b:

IIa-4a

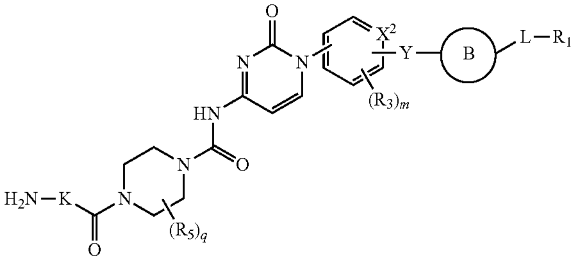

IIa-4b

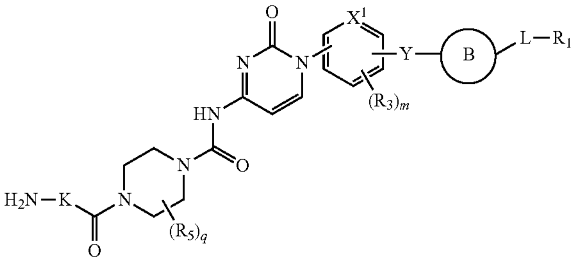

or a pharmaceutically acceptable salt thereof, wherein the variables are described herein.

In another embodiment, the compound of formula I or II is a compound of formula IIA-5:

IIa-5

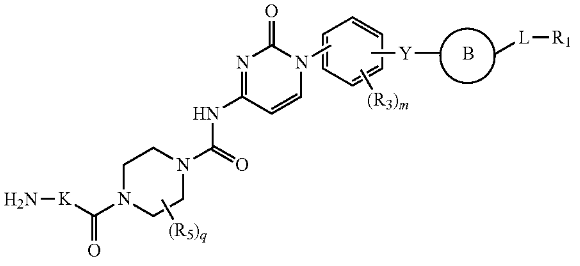

or a pharmaceutically acceptable salt thereof, wherein the variables are described herein. In another embodiment, $R_3$ is selected from the group consisting of $C_1$-$C_6$ alkyl, halo, $C_1$-$C_6$ haloalkyl, and $C_1$-$C_6$ alkoxy; m is 0, 1, or 2.

In another embodiment, the compound of formula I or II is a compound of formula IIA-6:

IIA-6

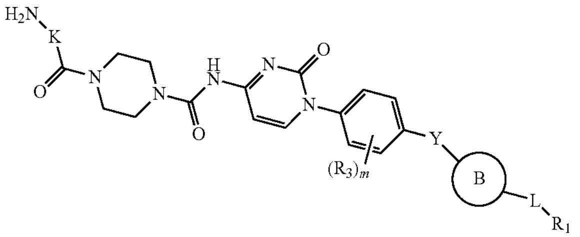

or a pharmaceutically acceptable salt thereof.

In another embodiment, the compound of formula I or II is a compound of formula IIA-7:

IIA-7

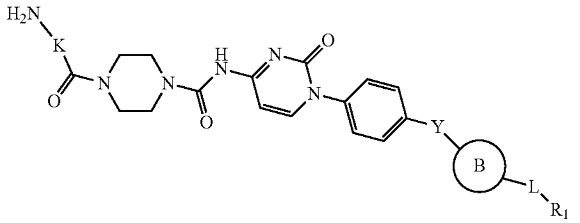

or a pharmaceutically acceptable salt thereof.

In another embodiment, the compound of formula I or II is a compound of formula IIA-8a of IIA-8b:

IIA-8

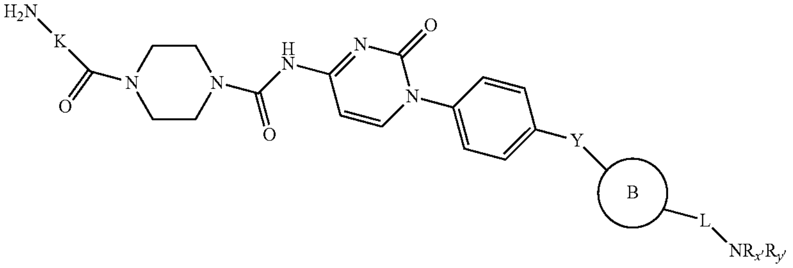

IIA-8b

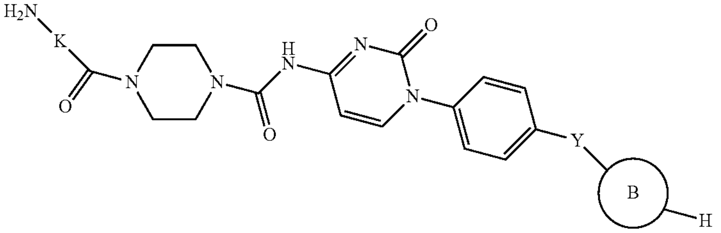

or a pharmaceutically acceptable salt thereof.

In another embodiment, the compound of formula I or II is a compound of formula IIA-9:

IIA-9

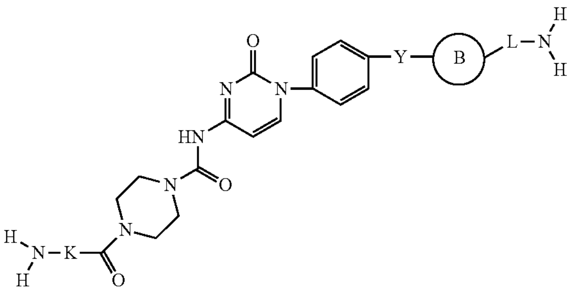

or a pharmaceutically acceptable salt thereof.

In embodiment of a compound of formula IIA-9 or a pharmaceutically acceptable salt thereof, ring B is selected from any of the moieties provided in Table 9.

In another embodiment of a compound of formula IIA-3 through IIA-9 or a pharmaceutically acceptable salt thereof, K is selected from the group consisting of

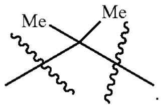

,

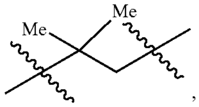

, and

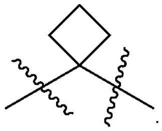

.

In another embodiment of compounds IIA-1 through IIA-9, Y is selected from any of the moieties provided in Table 8.

In another embodiment, the compound of formula I or II is a compound of formula IIA-10:

IIA-10

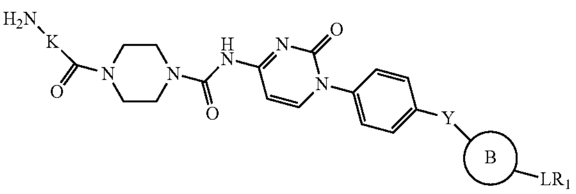

or a pharmaceutically acceptable salt thereof.

In another embodiment,

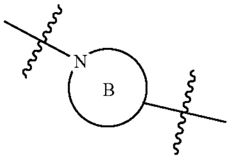

is selected from the group consisting of

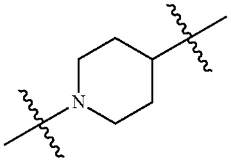

,

-continued
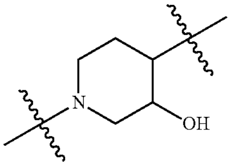,
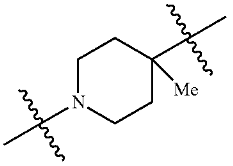,
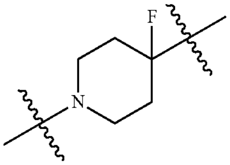,
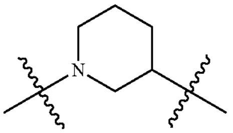,
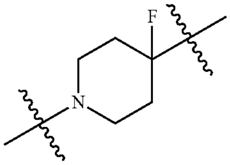,
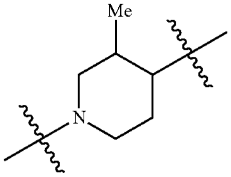,
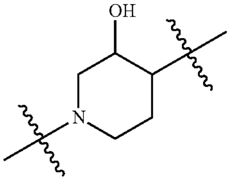,
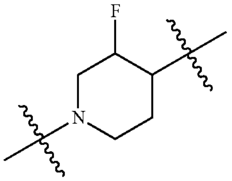,
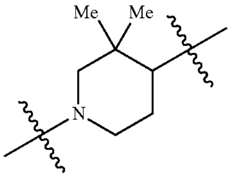,
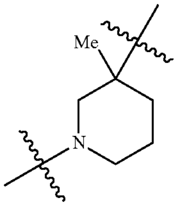
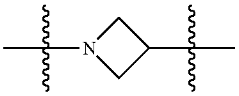,
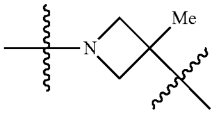,
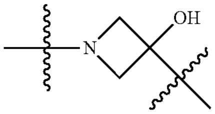,
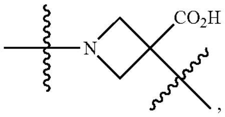,
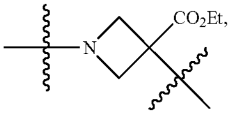
-continued
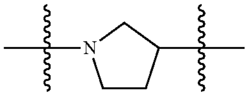,
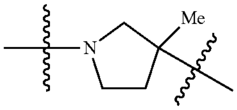,
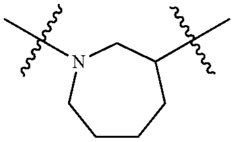,
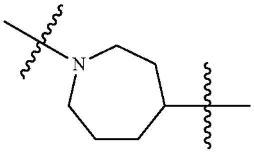, and
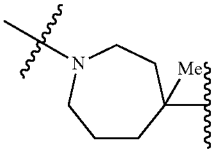.
In another embodiment, the compound of formula I or II is a compound of formula IIA-11:
IIA-11
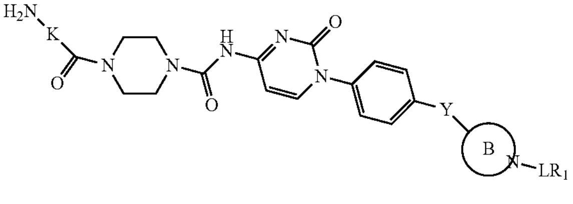
or a pharmaceutically acceptable salt thereof.
In another embodiment,
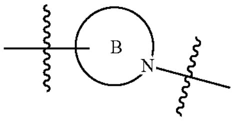
is
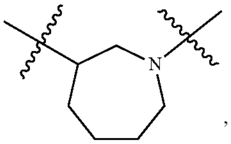,
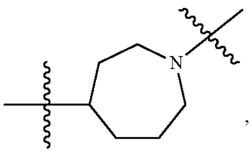,
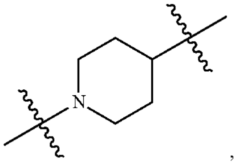,
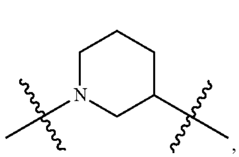, -continued

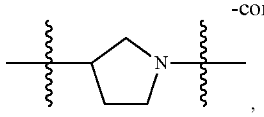

, or

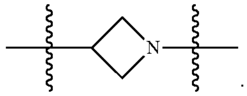

.

In another embodiment, the compound of formula I or II is a compound of formula IIA-12:

IIA-12

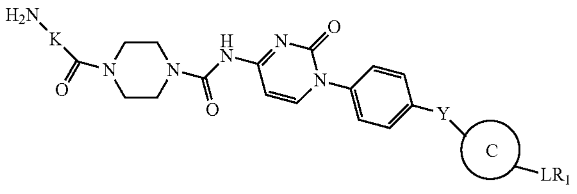

or a pharmaceutically acceptable salt thereof wherein ring C is an optionally substituted $C_3$-$C_7$ cycloalkylene.

In another embodiment,

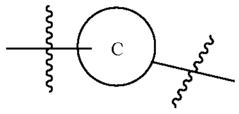

is selected from the group consisting of

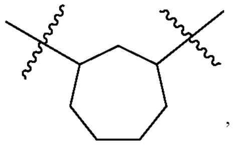

,

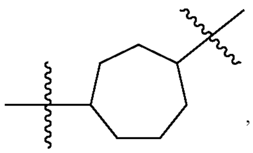

,

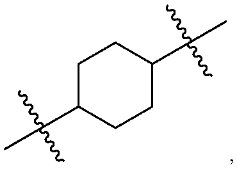

,

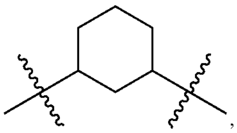

,

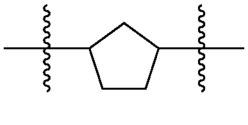

, and

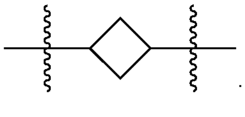

.

In another aspect, the disclosure provides a compound of formula III:

III

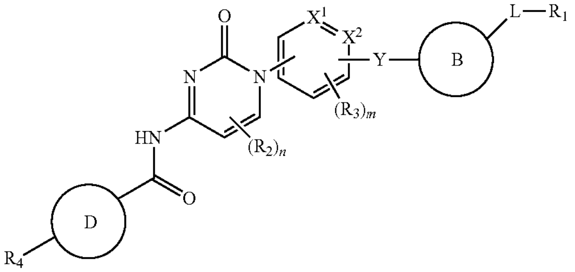

or a pharmaceutically acceptable salt thereof, wherein:

$R_1$, $R_2$, $R_3$, $X^1$, $X^2$, Y, ring B, L, m, and n are as defined herein;

ring D is a monocyclic heterocycloalkylene or bicyclic heterocycloalkylene, wherein the bicyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, $NH(C_1$-$C_6$ alkyl), $N(C_1$-$C_6$ alkyl$)_2$, —COO($C_1$-$C_6$ alkyl), —$COONH_2$, and oxo; and $R_4$ is H or $NR_{x''}R_{y''}$, wherein $R_{x''}$ and $R_{y''}$ are each independently H or $C_1$-$C_6$ alkyl.

In one embodiment, the compound of formula III is a compound of formula IIIA:

IIIA

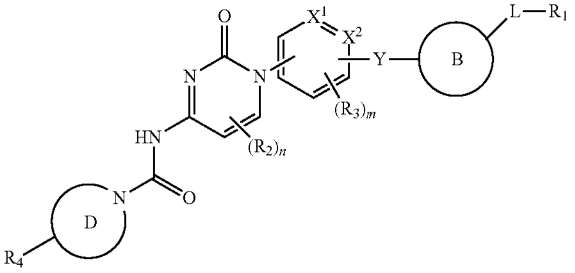

or a pharmaceutically acceptable salt thereof.

In another embodiment, ring D is selected from the group consisting of

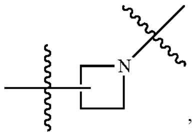

,

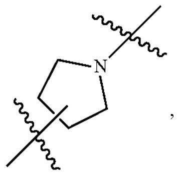

,

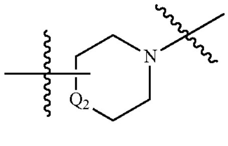

,

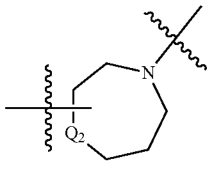

,

-continued

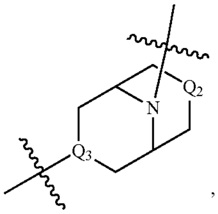

,

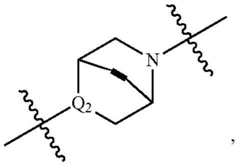

,

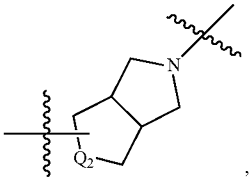

,

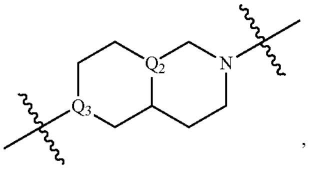

, and

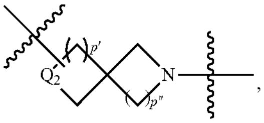

, wherein p' and p" are each independently 0, 1, 2, 3, 4, or 5; wherein $Q_1$ is N, and $Q_2$ and $Q_3$ are independently selected from the group consisting of C, N, S, or O, and wherein the monocyclic heterocycloalkylene and bicyclic heterocycloalkylene may be optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, —$CO_2H$, —$CO_2Me$, —$CO_2Et$, and oxo.

In another embodiment, ring D is selected from the group consisting of

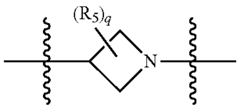

,

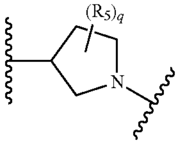

,

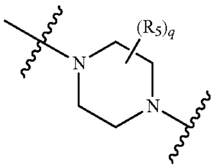

,

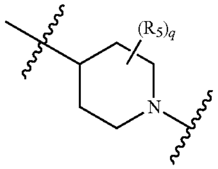

,

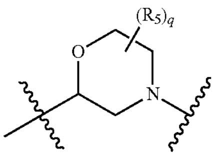

,

-continued

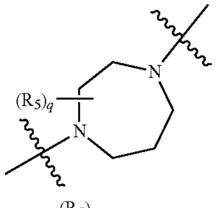

,

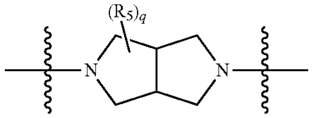

,

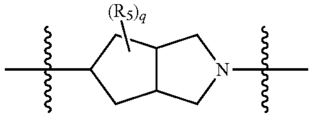

,

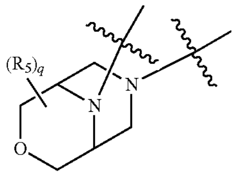

,

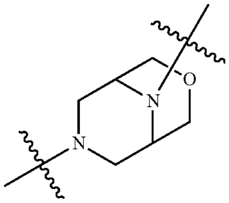

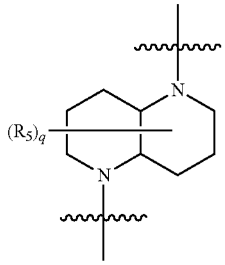

,

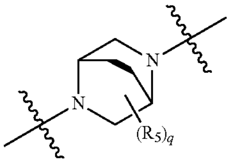

,

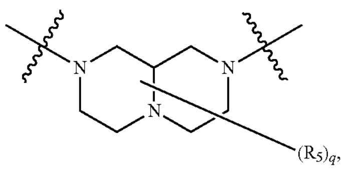

,

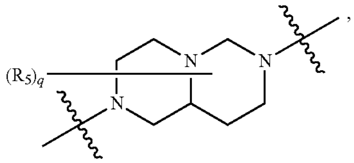

,

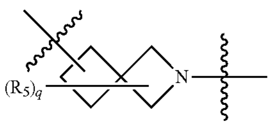

, and

-continued
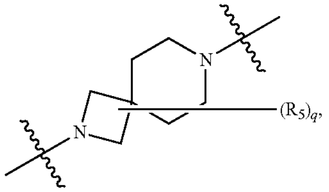
wherein each $R_5$ is independently selected from the group consisting of H, $C_1$-$C_6$ alkyl, $C_1$-$C_6$ alkoxy, halo, CN, $C_1$-$C_6$ haloalkyl, phenyl, OH, $NH_2$, and oxo, wherein q is 1, 2, or 3.
In another embodiment, ring D is selected from the group consisting of
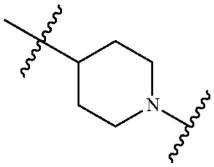,
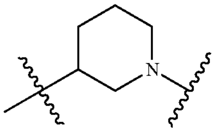,
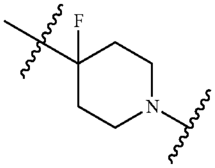,
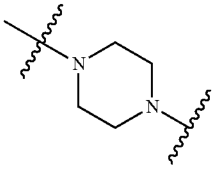,
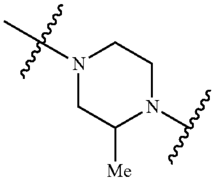,
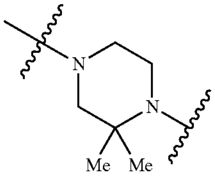,
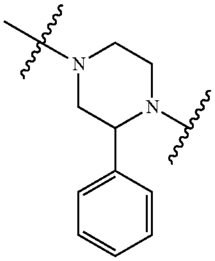,
-continued
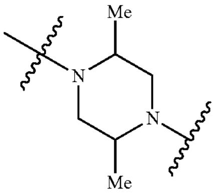,
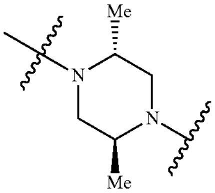,
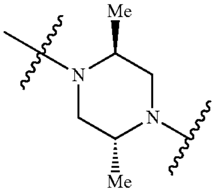,
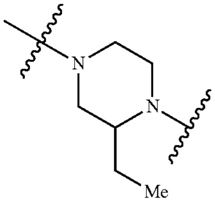,
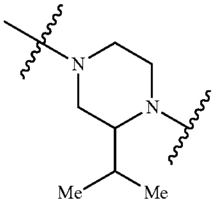,
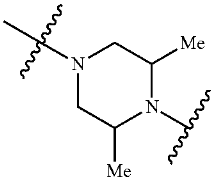,
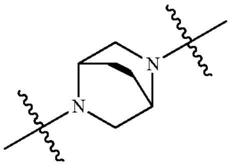,
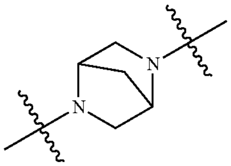,
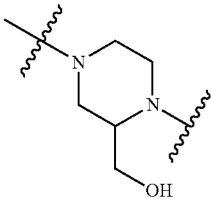, -continued
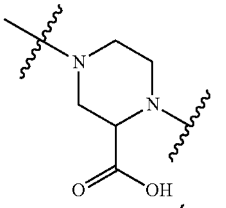
,
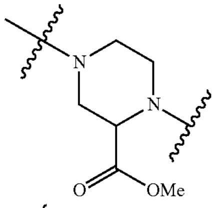
,
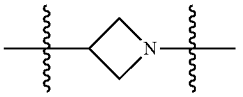
,
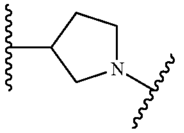
,
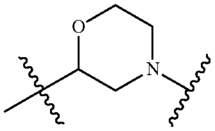
,
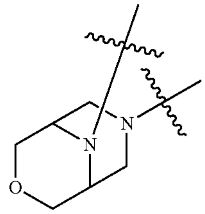
,
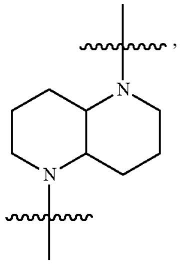
,
-continued
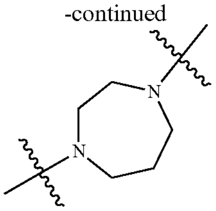
,
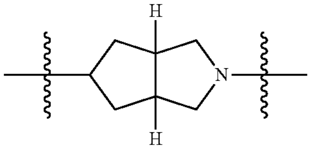
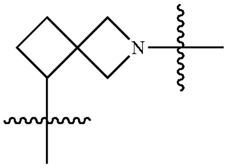
,
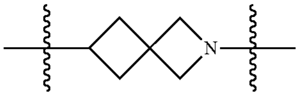
,
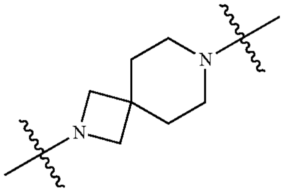
, and
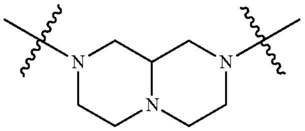
.
In another aspect, the disclosure provides a compound or a pharmaceutically acceptable salt thereof which is depicted in Table 10. In Table 10, free base and salt structures of the compounds of the invention are depicted.
TABLE 10
| Compounds of Formula I | |
|---|---|
| No. | Salt Structure |
| 1 | 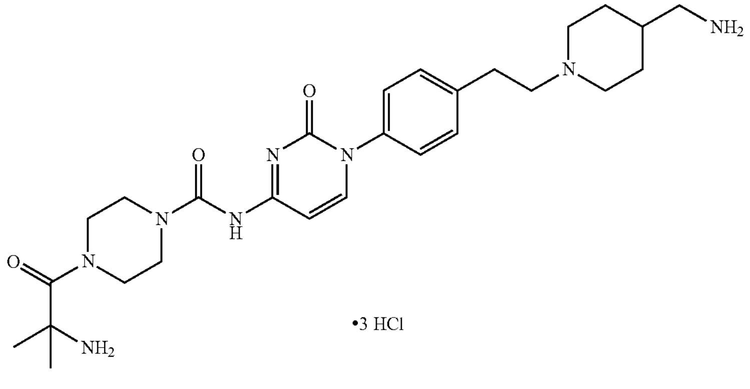 [SMILES: CC(C)(N)C(=O)N1CCN(C(=O)Nc2ccn(-c3ccc(CCN4CCC(CN)CC4)cc3)c(=O)n2)CC1] •3 HCl |

TABLE 10-continued
| Compounds of Formula I | |
|---|---|
| 2 | 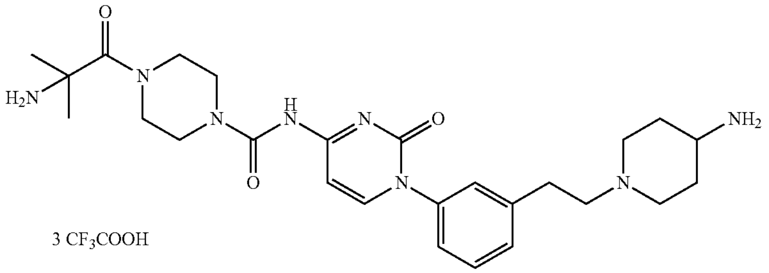 [SMILES: CC(C)(N)C(=O)N1CCN(C(=O)Nc2ccn(-c3cccc(CCN4CCC(N)CC4)c3)c(=O)n2)CC1] 3 $CF_3COOH$ |
| 3 | 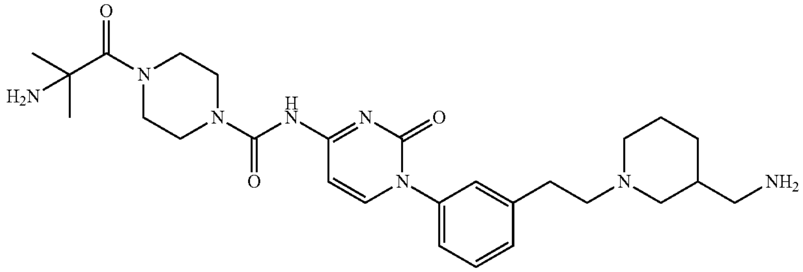 3 $CF_3COOH$ |
| 4 | 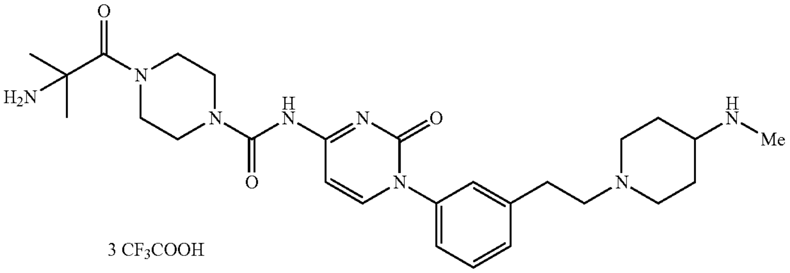 [SMILES: CNC1CCN(CCc2cccc(-n3ccc(NC(=O)N4CCN(C(=O)C(C)(C)N)CC4)nc3=O)c2)CC1] 3 $CF_3COOH$ |
| 5 | 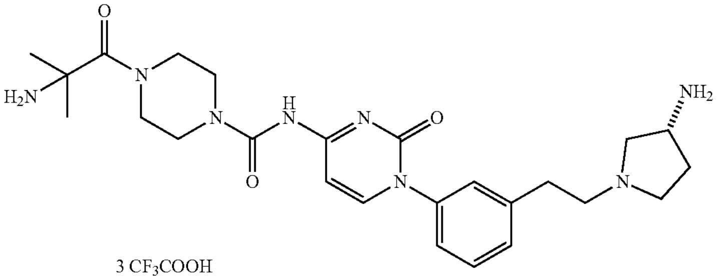 [SMILES: CC(C)(N)C(=O)N1CCN(C(=O)Nc2ccn(-c3cccc(CCN4CC[C@@H](N)C4)c3)c(=O)n2)CC1] 3 $CF_3COOH$ |
| 6 | 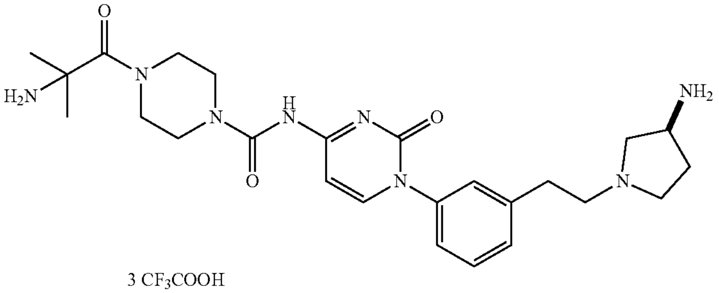 [SMILES: CC(C)(N)C(=O)N1CCN(C(=O)Nc2ccn(-c3cccc(CCN4CC[C@H](N)C4)c3)c(=O)n2)CC1] 3 $CF_3COOH$ |

TABLE 10-continued
| Compounds of Formula I |
|---|
| 7 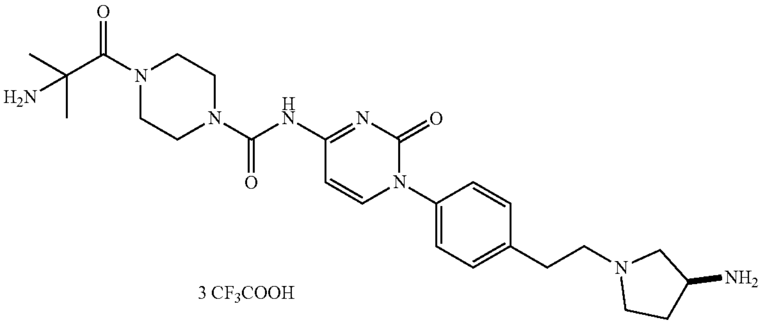 [SMILES: CC(C)(N)C(=O)N1CCN(C(=O)Nc2ccn(-c3ccc(CCN4CC[C@H](N)C4)cc3)c(=O)n2)CC1] 3 $CF_3COOH$ |
| 8 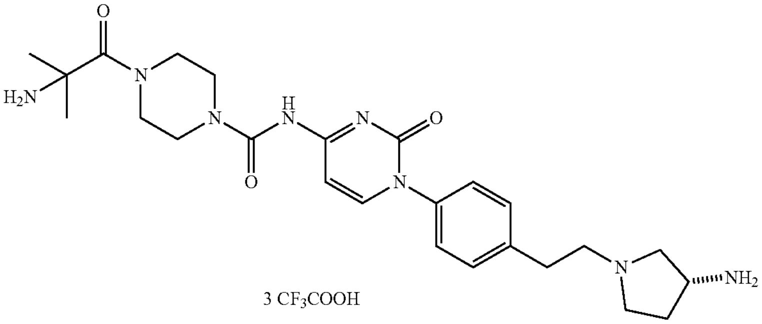 [SMILES: CC(C)(N)C(=O)N1CCN(C(=O)Nc2ccn(-c3ccc(CCN4CC[C@@H](N)C4)cc3)c(=O)n2)CC1] 3 $CF_3COOH$ |
| 9 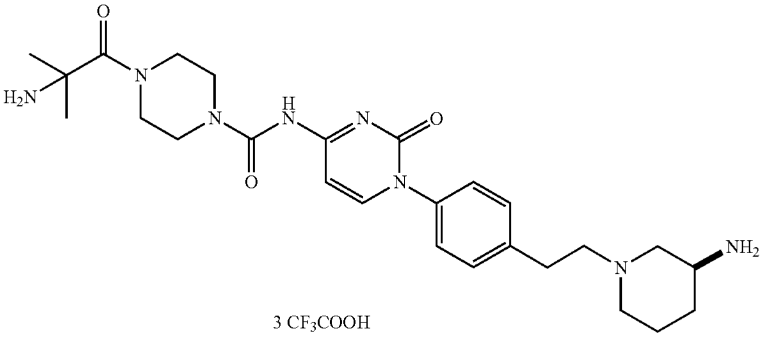 [SMILES: CC(C)(N)C(=O)N1CCN(C(=O)Nc2ccn(-c3ccc(CCN4CCC[C@H](N)C4)cc3)c(=O)n2)CC1] 3 $CF_3COOH$ |
| 10 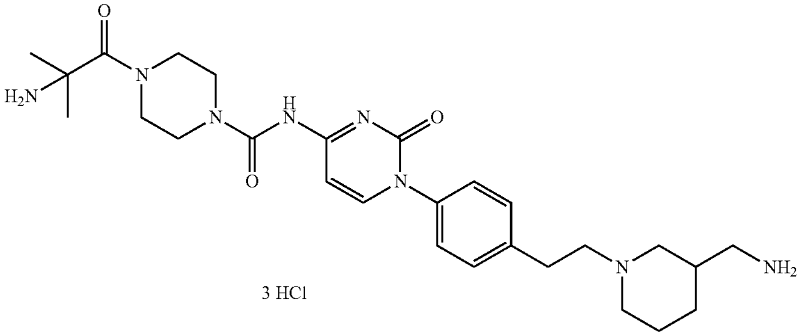 [SMILES: CC(C)(N)C(=O)N1CCN(C(=O)Nc2ccn(-c3ccc(CCN4CCCC(CN)C4)cc3)c(=O)n2)CC1] 3 HCl |

TABLE 10-continued
| Compounds of Formula I | |
|---|---|
| 11 | 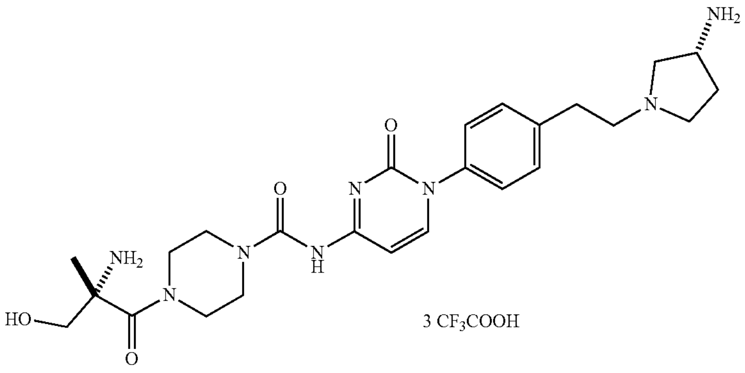 [SMILES: C[C@](N)(CO)C(=O)N1CCN(C(=O)Nc2ccn(-c3ccc(CCN4CC[C@@H](N)C4)cc3)c(=O)n2)CC1] 3 $CF_3COOH$ |
| 12 | 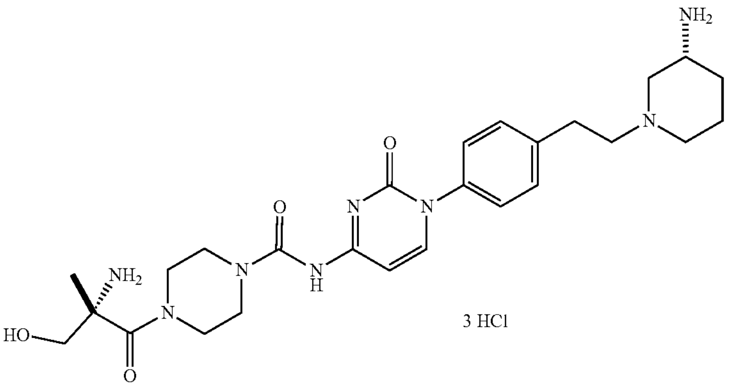 [SMILES: C[C@](N)(CO)C(=O)N1CCN(C(=O)Nc2ccn(-c3ccc(CCN4CCC[C@@H](N)C4)cc3)c(=O)n2)CC1] 3 HCl |
| 13 | 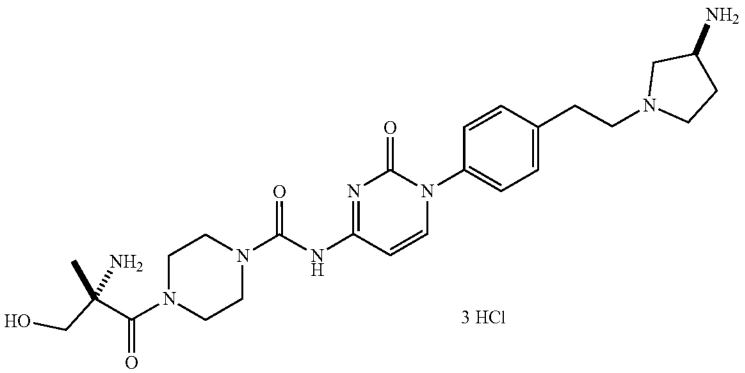 [SMILES: C[C@](N)(CO)C(=O)N1CCN(C(=O)Nc2ccn(-c3ccc(CCN4CC[C@H](N)C4)cc3)c(=O)n2)CC1] 3 HCl |
| 14 | 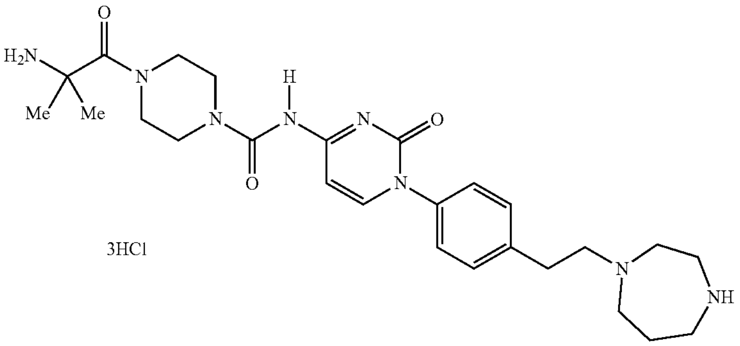 [SMILES: CC(C)(N)C(=O)N1CCN(C(=O)Nc2ccn(-c3ccc(CCN4CCCNCC4)cc3)c(=O)n2)CC1] 3HCl |

TABLE 10-continued
| Compounds of Formula I | |
|---|---|
| 15 | 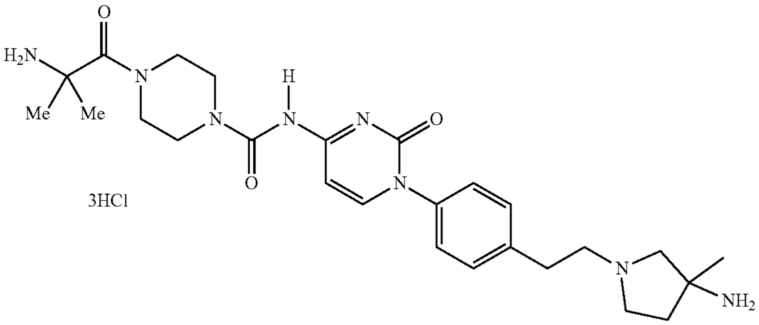 [SMILES: CC1(N)CCN(CCc2ccc(-n3ccc(NC(=O)N4CCN(C(=O)C(C)(C)N)CC4)nc3=O)cc2)C1] 3HCl |
| 16 | 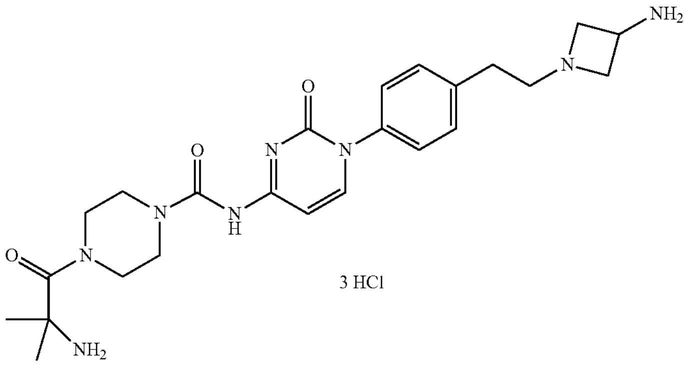 [SMILES: CC(C)(N)C(=O)N1CCN(C(=O)Nc2ccn(-c3ccc(CCN4CC(N)C4)cc3)c(=O)n2)CC1] 3 HCl |
| 17 | 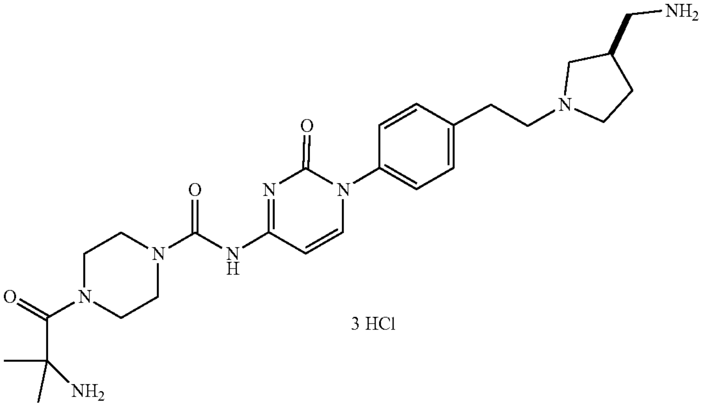 [SMILES: CC(C)(N)C(=O)N1CCN(C(=O)Nc2ccn(-c3ccc(CCN4CC[C@H](CN)C4)cc3)c(=O)n2)CC1] 3 HCl |
| 18 | 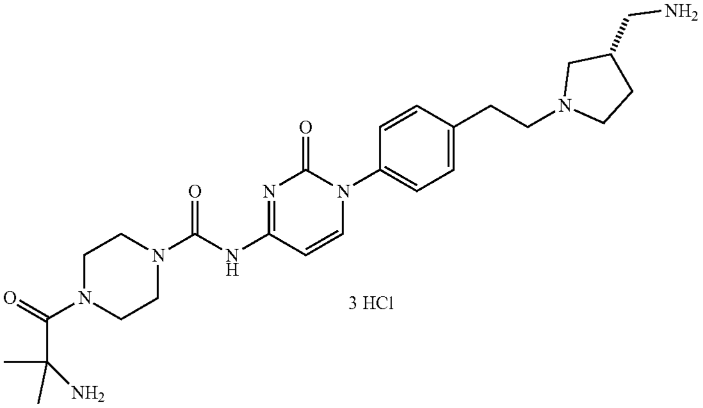 [SMILES: CC(C)(N)C(=O)N1CCN(C(=O)Nc2ccn(-c3ccc(CCN4CC[C@@H](CN)C4)cc3)c(=O)n2)CC1] 3 HCl |

TABLE 10-continued
| Compounds of Formula I |
| --- |
21
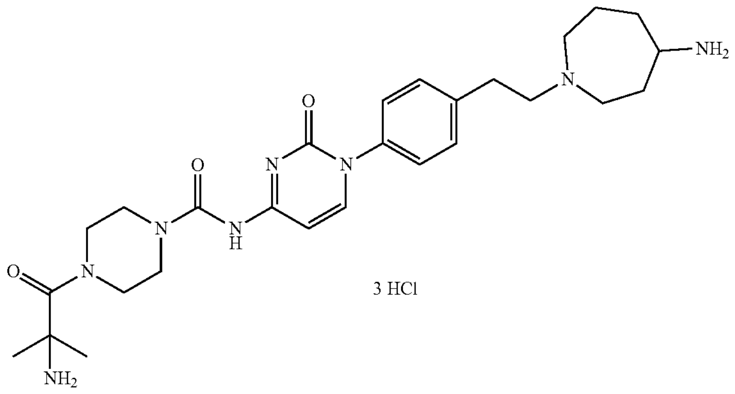 [SMILES: CC(C)(N)C(=O)N1CCN(C(=O)Nc2ccn(-c3ccc(CCN4CCCC(N)CC4)cc3)c(=O)n2)CC1]
3 HCl
22
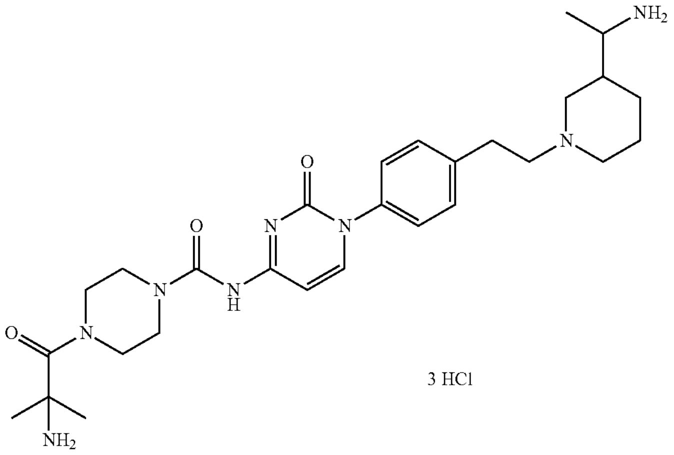 [SMILES: CC(N)C1CCCN(CCc2ccc(-n3ccc(NC(=O)N4CCN(C(=O)C(C)(C)N)CC4)nc3=O)cc2)C1]
3 HCl
23
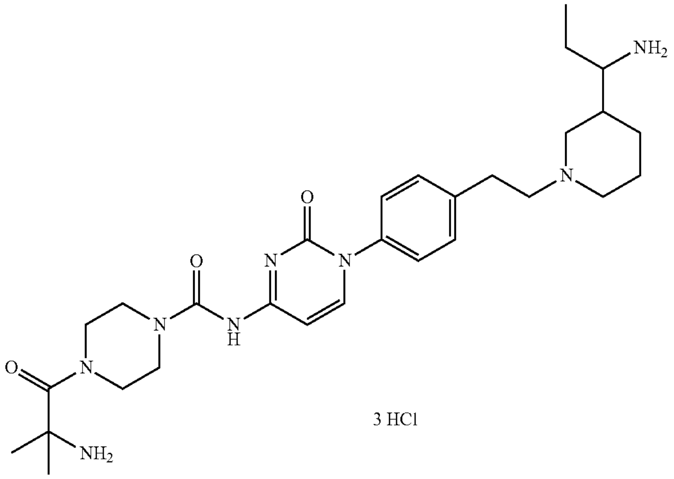 [SMILES: CCC(N)C1CCCN(CCc2ccc(-n3ccc(NC(=O)N4CCN(C(=O)C(C)(C)N)CC4)nc3=O)cc2)C1]
3 HCl
24
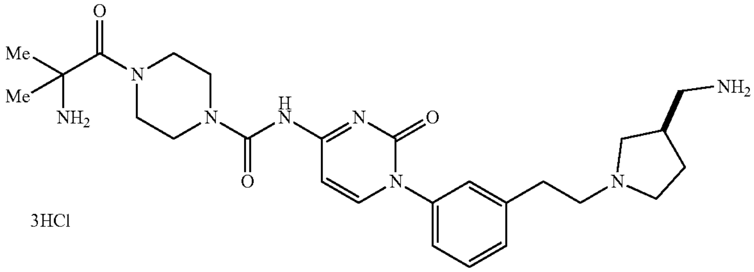 [SMILES: CC(C)(N)C(=O)N1CCN(C(=O)Nc2ccn(-c3cccc(CCN4CC[C@H](CN)C4)c3)c(=O)n2)CC1]
3HCl TABLE 10-continued
| Compounds of Formula I |
|---|
| 25 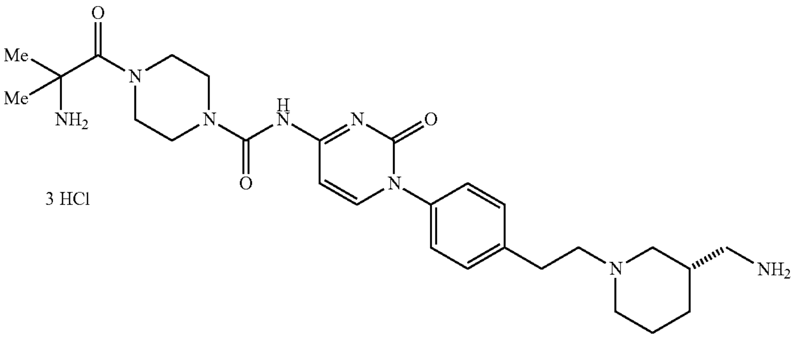 [SMILES: CC(C)(N)C(=O)N1CCN(C(=O)Nc2ccn(-c3ccc(CCN4CCC[C@@H](CN)C4)cc3)c(=O)n2)CC1] 3 HCl |
| 26 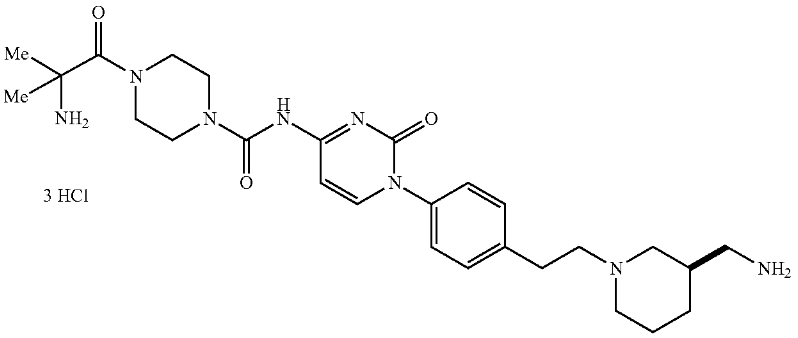 [SMILES: CC(C)(N)C(=O)N1CCN(C(=O)Nc2ccn(-c3ccc(CCN4CCC[C@H](CN)C4)cc3)c(=O)n2)CC1] 3 HCl |
| 27 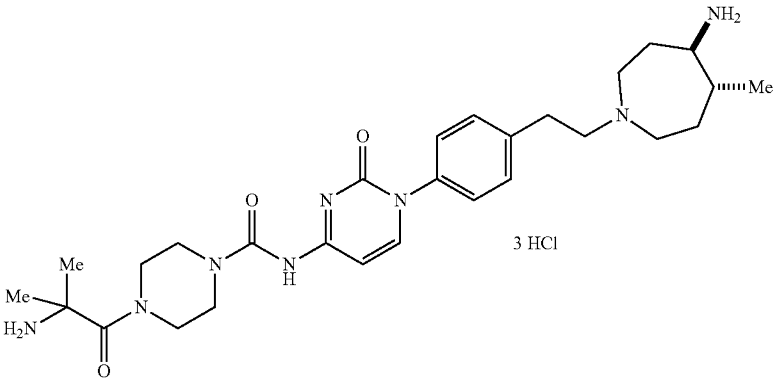 [SMILES: C[C@@H]1CCN(CCc2ccc(-n3ccc(NC(=O)N4CCN(C(=O)C(C)(C)N)CC4)nc3=O)cc2)CC[C@H]1N] 3 HCl |
| 28 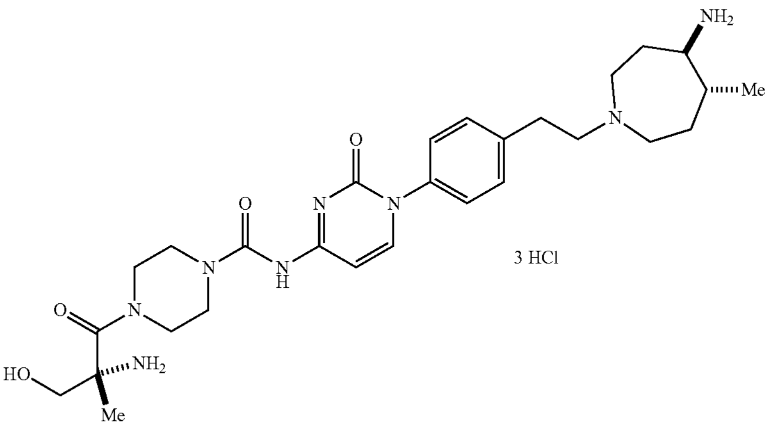 [SMILES: C[C@@H]1CCN(CCc2ccc(-n3ccc(NC(=O)N4CCN(C(=O)[C@](C)(N)CO)CC4)nc3=O)cc2)CC[C@H]1N] 3 HCl |

TABLE 10-continued
| Compounds of Formula I | |
|---|---|
| 29 | 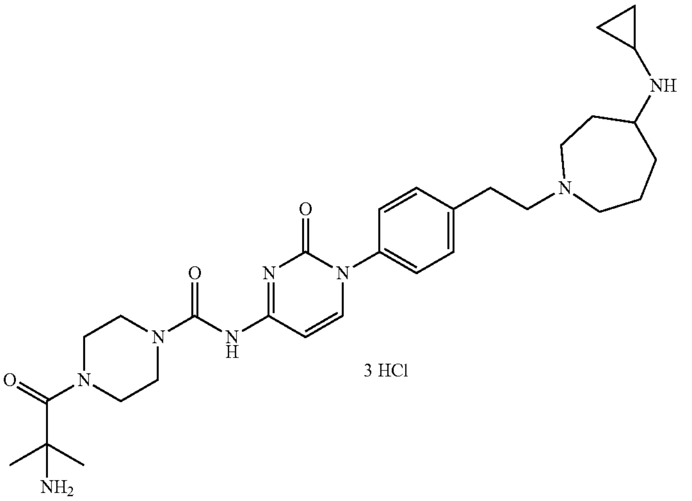 [SMILES: CC(C)(N)C(=O)N1CCN(C(=O)Nc2ccn(-c3ccc(CCN4CCCC(NC5CC5)CC4)cc3)c(=O)n2)CC1] 3 HCl |
| 30 | 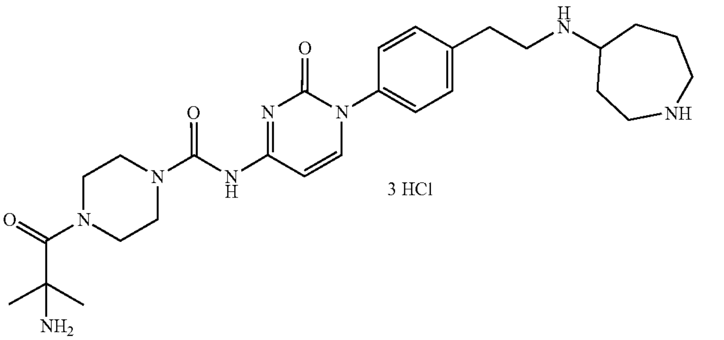 [SMILES: CC(C)(N)C(=O)N1CCN(C(=O)Nc2ccn(-c3ccc(CCNC4CCCNCC4)cc3)c(=O)n2)CC1] 3 HCl |
| 31 | 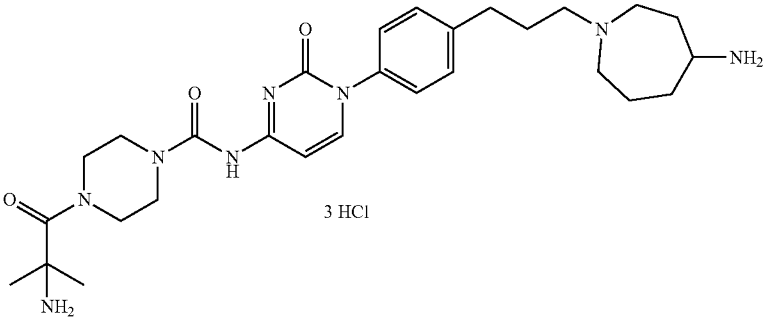 [SMILES: CC(C)(N)C(=O)N1CCN(C(=O)Nc2ccn(-c3ccc(CCCN4CCCC(N)CC4)cc3)c(=O)n2)CC1] 3 HCl |
| 32 | 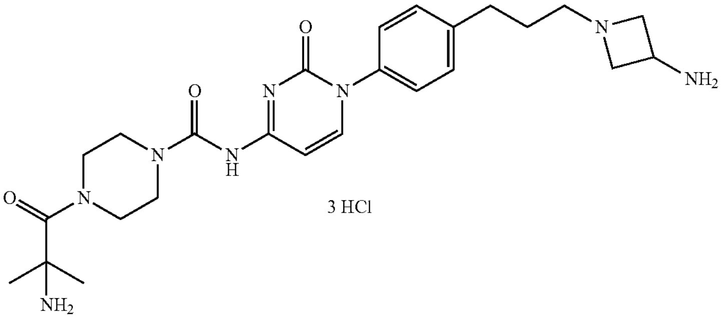 [SMILES: CC(C)(N)C(=O)N1CCN(C(=O)Nc2ccn(-c3ccc(CCCN4CC(N)C4)cc3)c(=O)n2)CC1] 3 HCl |

TABLE 10-continued
Compounds of Formula I
33
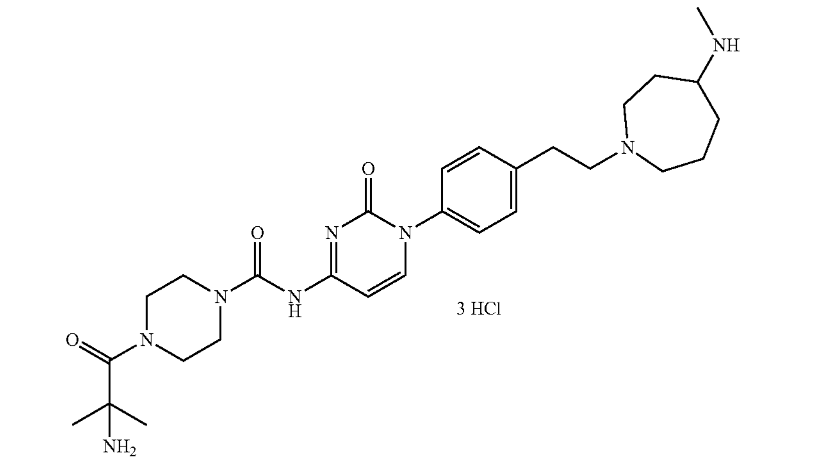 [SMILES: CNC1CCCN(CCc2ccc(-n3ccc(NC(=O)N4CCN(C(=O)C(C)(C)N)CC4)nc3=O)cc2)CC1]
34
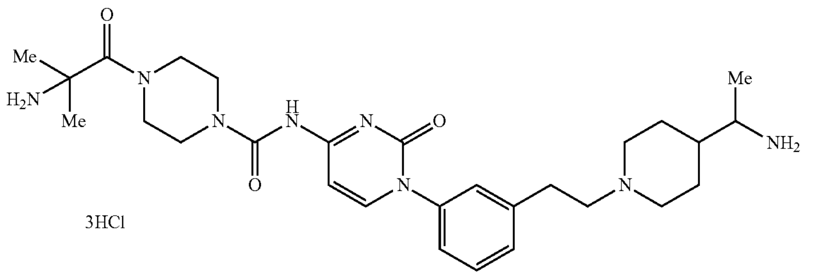 [SMILES: CC(N)C1CCN(CCc2cccc(-n3ccc(NC(=O)N4CCN(C(=O)C(C)(C)N)CC4)nc3=O)c2)CC1]
35
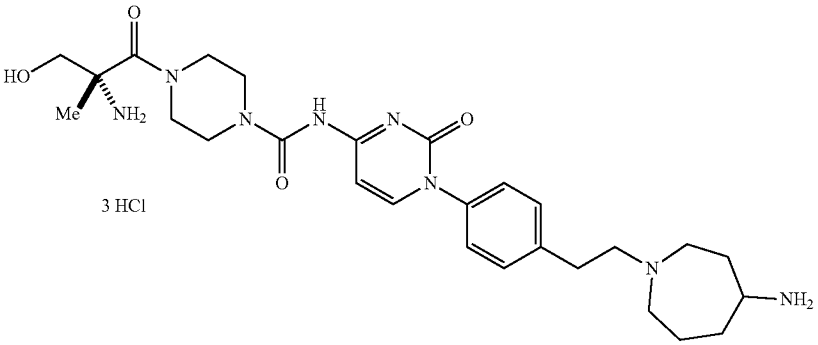 [SMILES: C[C@@](N)(CO)C(=O)N1CCN(C(=O)Nc2ccn(-c3ccc(CCN4CCCC(N)CC4)cc3)c(=O)n2)CC1]
36
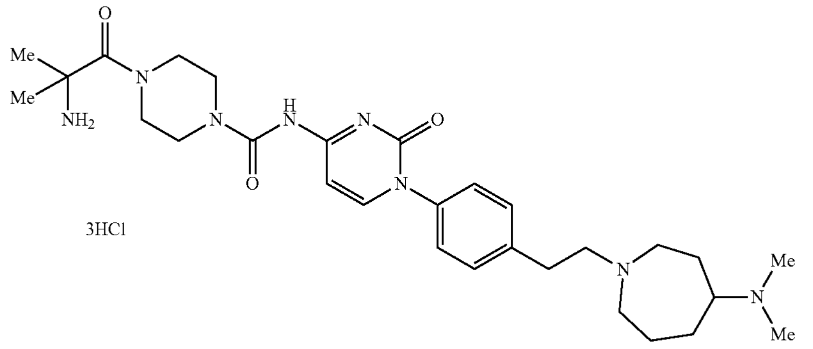 [SMILES: CN(C)C1CCCN(CCc2ccc(-n3ccc(NC(=O)N4CCN(C(=O)C(C)(C)N)CC4)nc3=O)cc2)CC1]

TABLE 10-continued
| Compounds of Formula I |
|---|
| 37 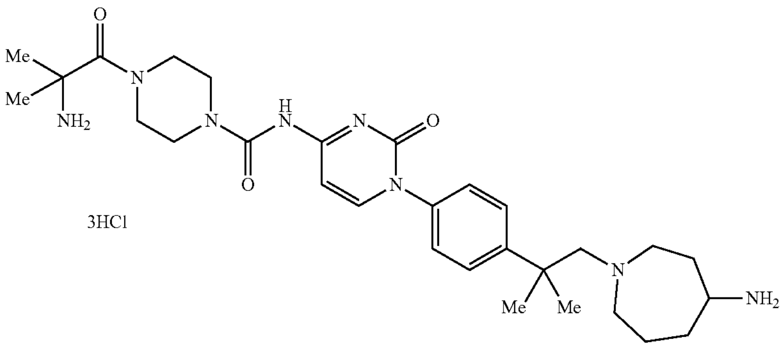 [SMILES: CC(C)(N)C(=O)N1CCN(C(=O)Nc2ccn(-c3ccc(C(C)(C)CN4CCCC(N)CC4)cc3)c(=O)n2)CC1] 3HCl |
| 38 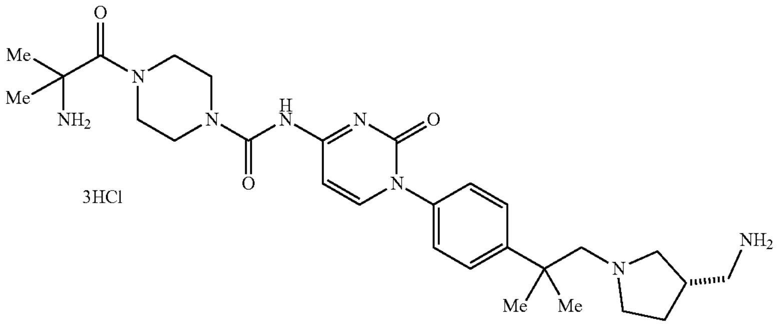 [SMILES: CC(C)(N)C(=O)N1CCN(C(=O)Nc2ccn(-c3ccc(C(C)(C)CN4CC[C@@H](CN)C4)cc3)c(=O)n2)CC1] 3HCl |
| 39 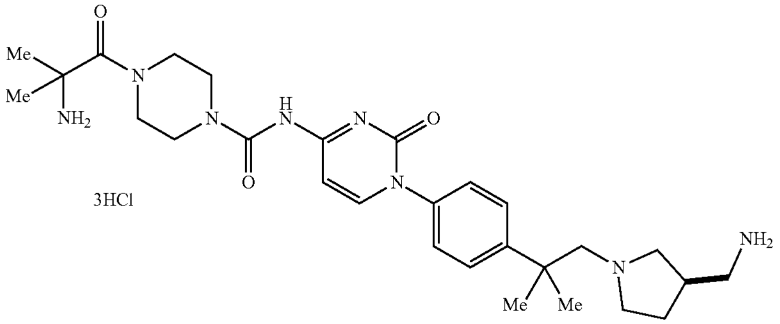 [SMILES: CC(C)(N)C(=O)N1CCN(C(=O)Nc2ccn(-c3ccc(C(C)(C)CN4CC[C@H](CN)C4)cc3)c(=O)n2)CC1] 3HCl |
| 40 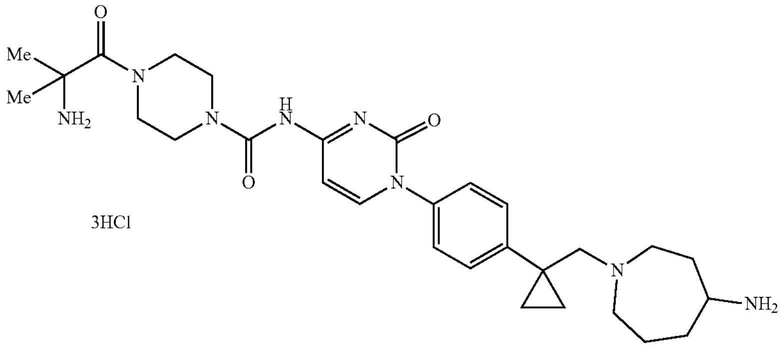 [SMILES: CC(C)(N)C(=O)N1CCN(C(=O)Nc2ccn(-c3ccc(C4(CN5CCCC(N)CC5)CC4)cc3)c(=O)n2)CC1] 3HCl |

TABLE 10-continued
| Compounds of Formula I | |
|---|---|
| 41 | 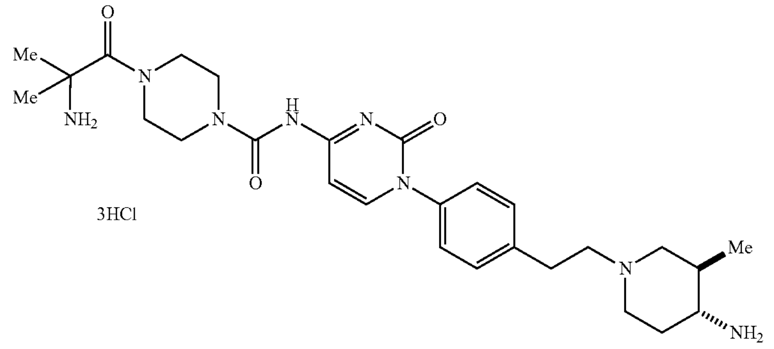 [SMILES: C[C@@H]1CN(CCc2ccc(-n3ccc(NC(=O)N4CCN(C(=O)C(C)(C)N)CC4)nc3=O)cc2)CC[C@H]1N] |
| 42 | 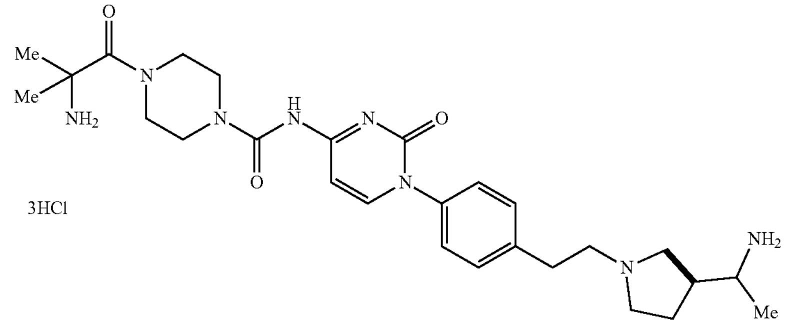 [SMILES: CC(N)[C@H]1CCN(CCc2ccc(-n3ccc(NC(=O)N4CCN(C(=O)C(C)(C)N)CC4)nc3=O)cc2)C1] |
| 43 | 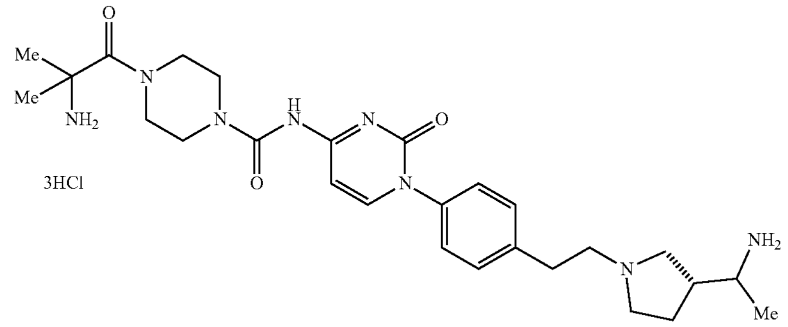 [SMILES: CC(N)[C@@H]1CCN(CCc2ccc(-n3ccc(NC(=O)N4CCN(C(=O)C(C)(C)N)CC4)nc3=O)cc2)C1] |
| 44 | 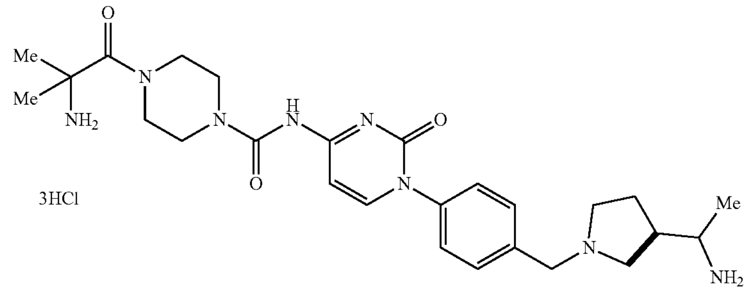 [SMILES: CC(N)[C@@H]1CCN(Cc2ccc(-n3ccc(NC(=O)N4CCN(C(=O)C(C)(C)N)CC4)nc3=O)cc2)C1] |
| 45 | 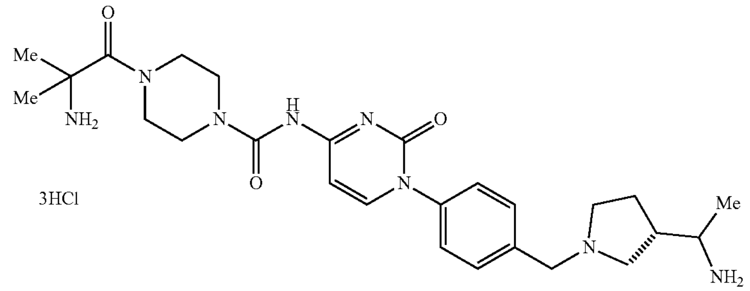 [SMILES: CC(N)[C@H]1CCN(Cc2ccc(-n3ccc(NC(=O)N4CCN(C(=O)C(C)(C)N)CC4)nc3=O)cc2)C1] |

TABLE 10-continued
Compounds of Formula I
46
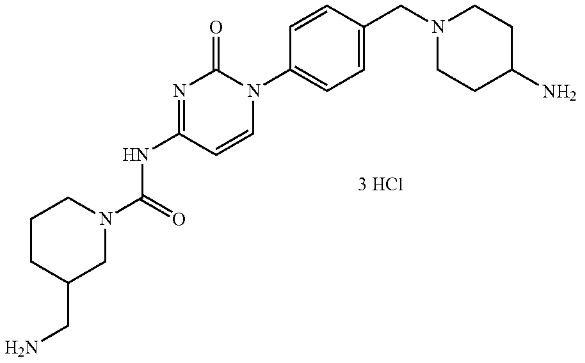 [SMILES: NCC1CCCN(C(=O)Nc2ccn(-c3ccc(CN4CCC(N)CC4)cc3)c(=O)n2)C1]
3 HCl
47
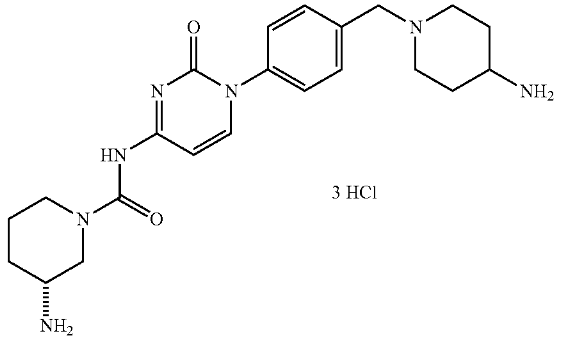 [SMILES: NC1CCN(Cc2ccc(-n3ccc(NC(=O)N4CCC[C@@H](N)C4)nc3=O)cc2)CC1]
3 HCl
48
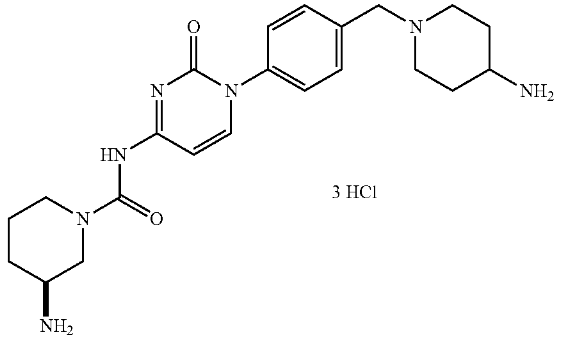 [SMILES: NC1CCN(Cc2ccc(-n3ccc(NC(=O)N4CCC[C@H](N)C4)nc3=O)cc2)CC1]
3 HCl
49
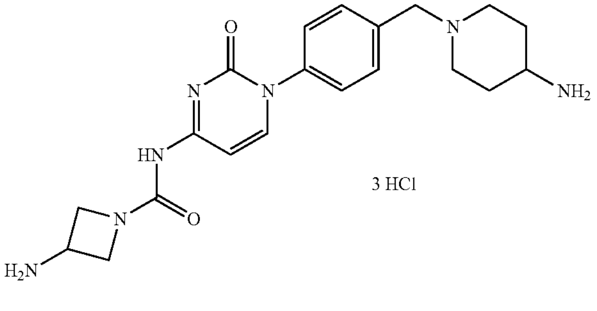 [SMILES: NC1CCN(Cc2ccc(-n3ccc(NC(=O)N4CC(N)C4)nc3=O)cc2)CC1]
3 HCl TABLE 10-continued
| Compounds of Formula I |
|---|
50
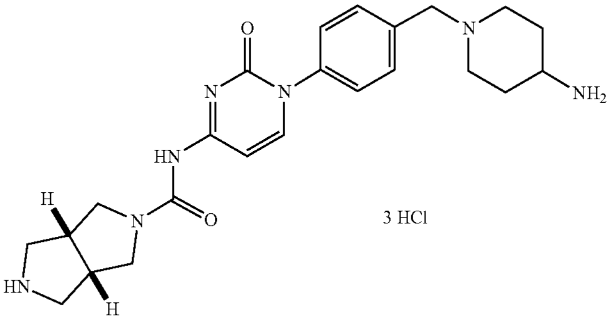 [SMILES: NC1CCN(Cc2ccc(-n3ccc(NC(=O)N4C[C@H]5CNC[C@H]5C4)nc3=O)cc2)CC1]
3 HCl
51
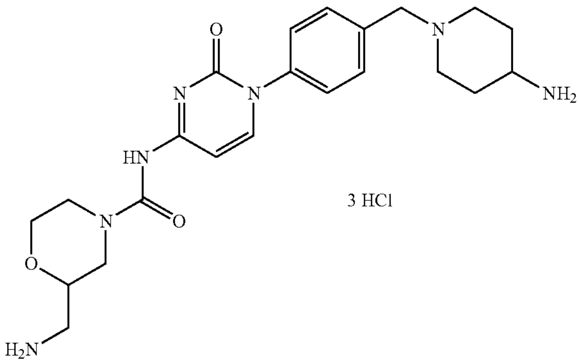 [SMILES: NCC1CN(C(=O)Nc2ccn(-c3ccc(CN4CCC(N)CC4)cc3)c(=O)n2)CCO1]
3 HCl
52
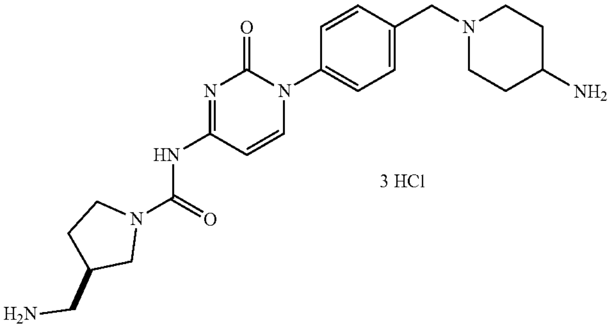 [SMILES: NC[C@H]1CCN(C(=O)Nc2ccn(-c3ccc(CN4CCC(N)CC4)cc3)c(=O)n2)C1]
3 HCl
53
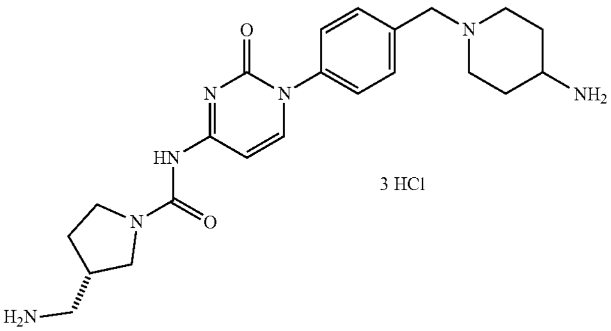 [SMILES: NC[C@@H]1CCN(C(=O)Nc2ccn(-c3ccc(CN4CCC(N)CC4)cc3)c(=O)n2)C1]
3 HCl TABLE 10-continued
| Compounds of Formula I | |
|---|---|
| 54 | 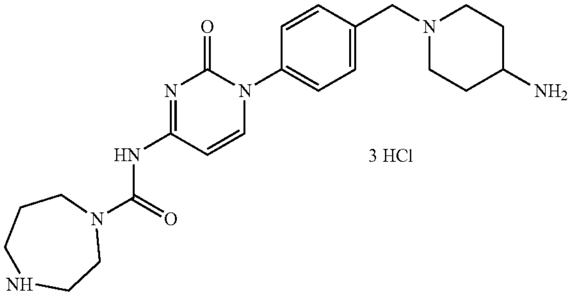 [SMILES: NC1CCN(Cc2ccc(-n3ccc(NC(=O)N4CCCNCC4)nc3=O)cc2)CC1] 3 HCl |
| 55 | 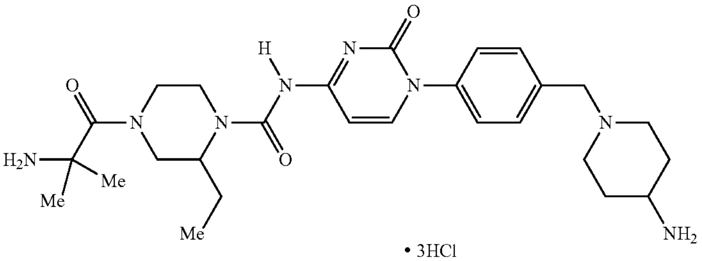 [SMILES: CCC1CN(C(=O)C(C)(C)N)CCN1C(=O)Nc1ccn(-c2ccc(CN3CCC(N)CC3)cc2)c(=O)n1] • 3HCl |
| 56 | 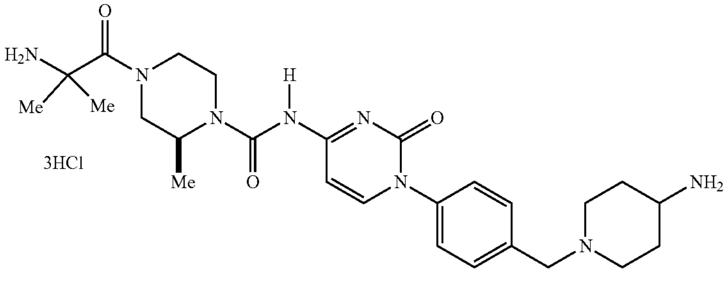 [SMILES: C[C@H]1CN(C(=O)C(C)(C)N)CCN1C(=O)Nc1ccn(-c2ccc(CN3CCC(N)CC3)cc2)c(=O)n1] 3HCl |
| 57 | 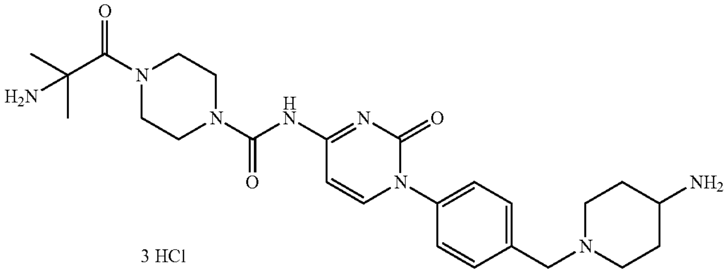 [SMILES: CC(C)(N)C(=O)N1CCN(C(=O)Nc2ccn(-c3ccc(CN4CCC(N)CC4)cc3)c(=O)n2)CC1] 3 HCl |
| 58 | 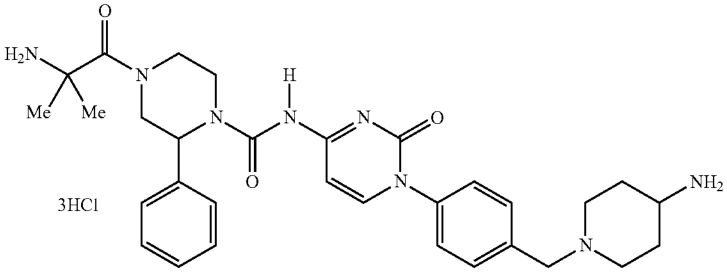 [SMILES: CC(C)(N)C(=O)N1CCN(C(=O)Nc2ccn(-c3ccc(CN4CCC(N)CC4)cc3)c(=O)n2)C(c2ccccc2)C1] 3HCl |

TABLE 10-continued
| Compounds of Formula I |
| --- |
59
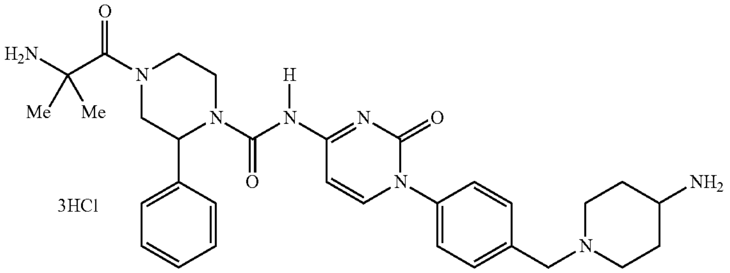 [SMILES: CC(C)(N)C(=O)N1CCN(C(=O)Nc2ccn(-c3ccc(CN4CCC(N)CC4)cc3)c(=O)n2)C(c2ccccc2)C1]
3HCl
60
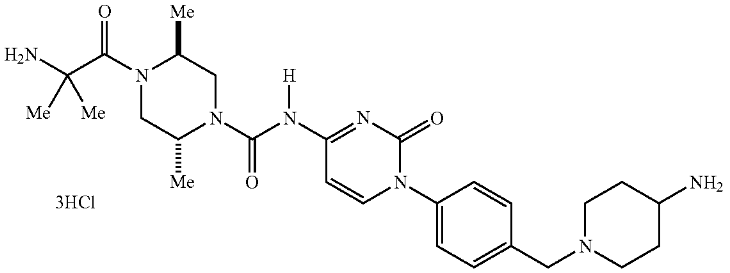 [SMILES: C[C@@H]1CN(C(=O)C(C)(C)N)[C@@H](C)CN1C(=O)Nc1ccn(-c2ccc(CN3CCC(N)CC3)cc2)c(=O)n1]
3HCl
61
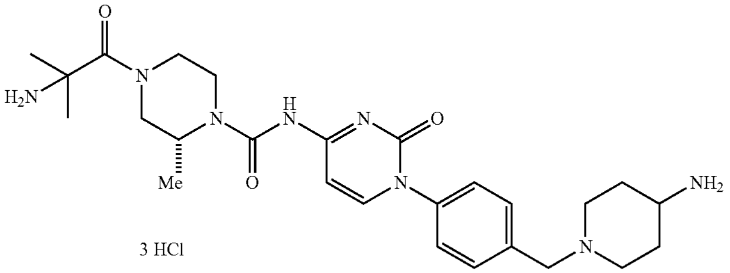 [SMILES: C[C@@H]1CN(C(=O)C(C)(C)N)CCN1C(=O)Nc1ccn(-c2ccc(CN3CCC(N)CC3)cc2)c(=O)n1]
3 HCl
62
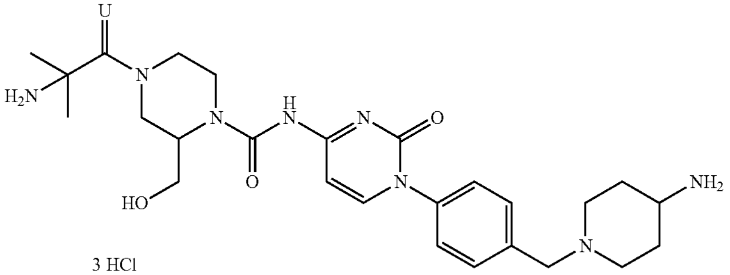
3 HCl
63
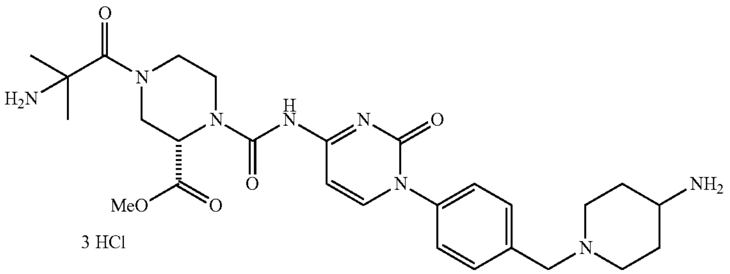
3 HCl TABLE 10-continued
| Compounds of Formula I | |
|---|---|
| 64 | 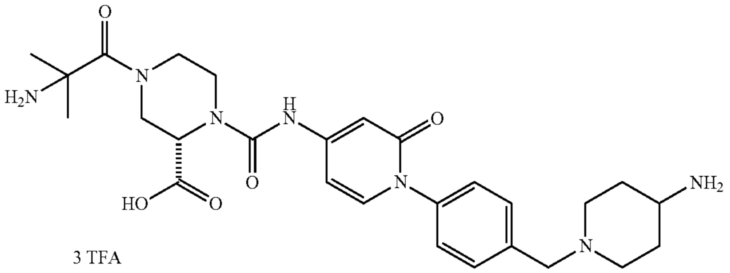 [SMILES: CC(C)(N)C(=O)N1CCN(C(=O)Nc2ccn(-c3ccc(CN4CCC(N)CC4)cc3)c(=O)c2)[C@H](C(=O)O)C1] 3 TFA |
| 65 | 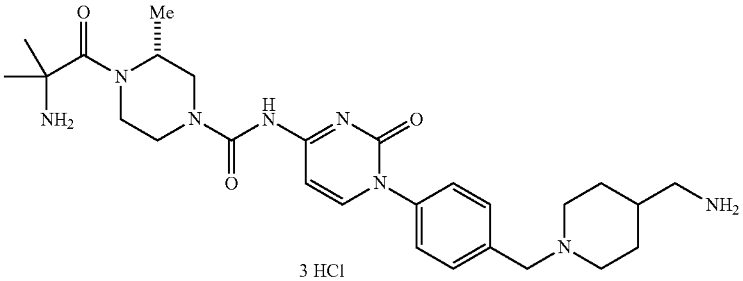 [SMILES: C[C@@H]1CN(C(=O)Nc2ccn(-c3ccc(CN4CCC(CN)CC4)cc3)c(=O)n2)CCN1C(=O)C(C)(C)N] 3 HCl |
| 66 | 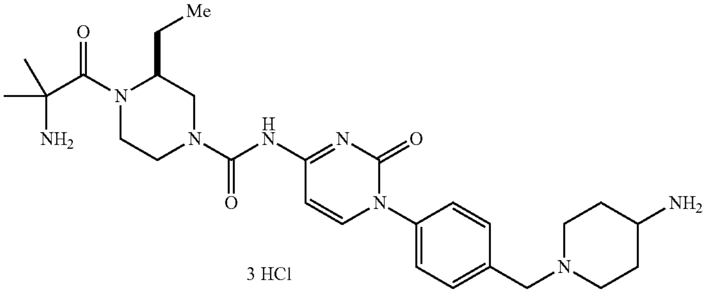 [SMILES: CC[C@H]1CN(C(=O)Nc2ccn(-c3ccc(CN4CCC(N)CC4)cc3)c(=O)n2)CCN1C(=O)C(C)(C)N] 3 HCl |
| 67 | 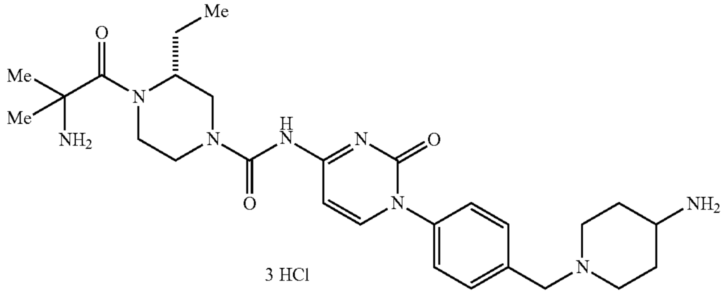 [SMILES: CC[C@@H]1CN(C(=O)Nc2ccn(-c3ccc(CN4CCC(N)CC4)cc3)c(=O)n2)CCN1C(=O)C(C)(C)N] 3 HCl |
| 68 | 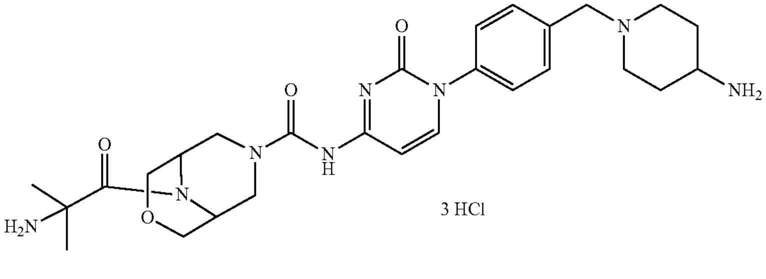 [SMILES: CC(C)(N)C(=O)N1C2COCC1CN(C(=O)Nc1ccn(-c3ccc(CN4CCC(N)CC4)cc3)c(=O)n1)C2] 3 HCl |

TABLE 10-continued
| Compounds of Formula I |
|---|
| 69 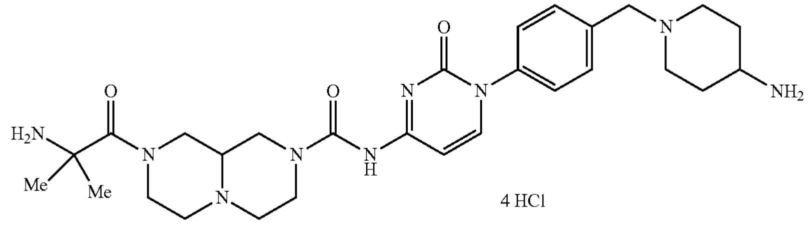 [SMILES: CC(C)(N)C(=O)N1CCN2CCN(C(=O)Nc3ccn(-c4ccc(CN5CCC(N)CC5)cc4)c(=O)n3)CC2C1] 4 HCl |
| 70 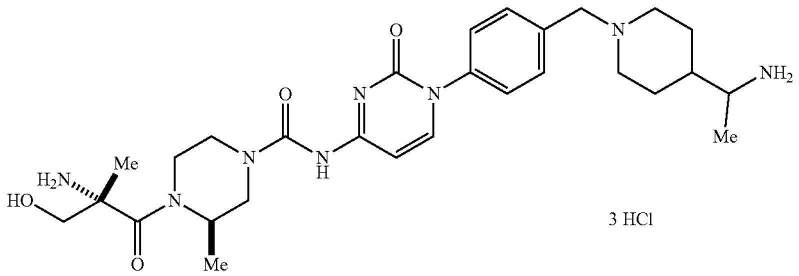 [SMILES: CC(N)C1CCN(Cc2ccc(-n3ccc(NC(=O)N4CCN(C(=O)[C@@](C)(N)CO)[C@H](C)C4)nc3=O)cc2)CC1] 3 HCl |
| 71 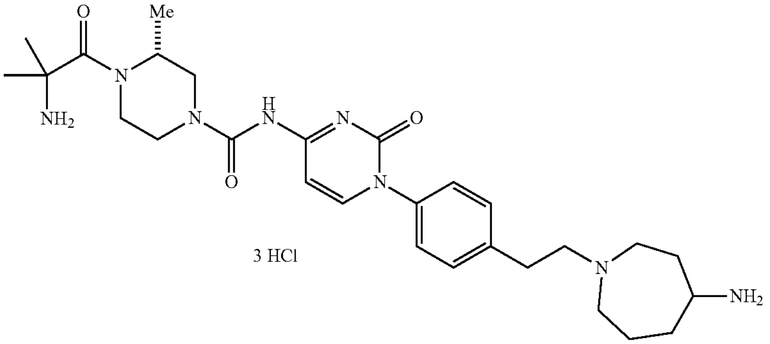 [SMILES: C[C@@H]1CN(C(=O)Nc2ccn(-c3ccc(CCN4CCCC(N)CC4)cc3)c(=O)n2)CCN1C(=O)C(C)(C)N] 3 HCl |
| 72 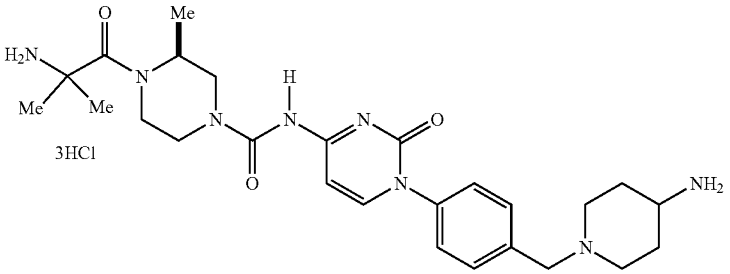 [SMILES: C[C@H]1CN(C(=O)Nc2ccn(-c3ccc(CN4CCC(N)CC4)cc3)c(=O)n2)CCN1C(=O)C(C)(C)N] 3HCl |
| 73 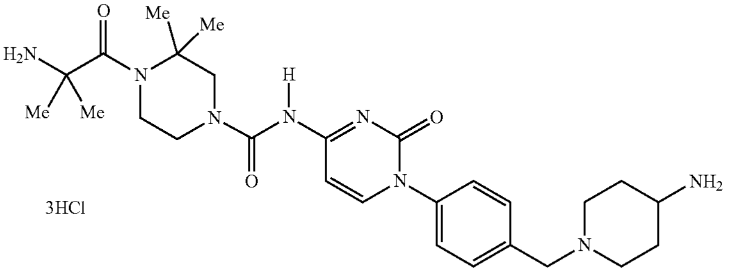 [SMILES: CC(C)(N)C(=O)N1CCN(C(=O)Nc2ccn(-c3ccc(CN4CCC(N)CC4)cc3)c(=O)n2)CC1(C)C] 3HCl |

TABLE 10-continued
| Compounds of Formula I | |
|---|---|
| 74 | 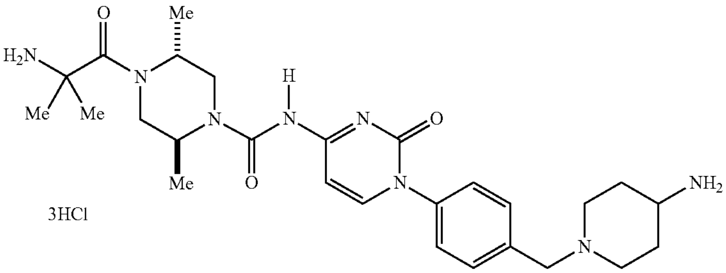 [SMILES: C[C@@H]1CN(C(=O)Nc2ccn(-c3ccc(CN4CCC(N)CC4)cc3)c(=O)n2)[C@@H](C)CN1C(=O)C(C)(C)N] 3HCl |
| 75 | 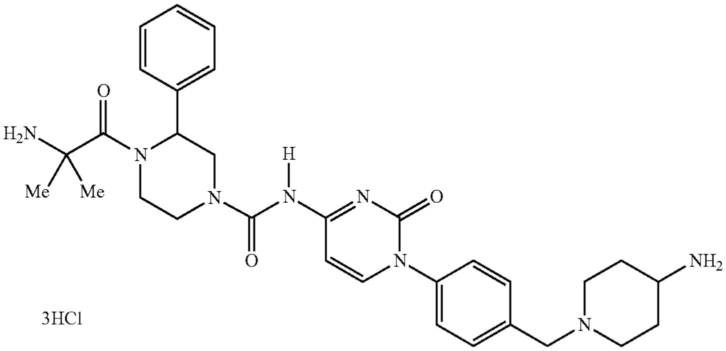 [SMILES: CC(C)(N)C(=O)N1CCN(C(=O)Nc2ccn(-c3ccc(CN4CCC(N)CC4)cc3)c(=O)n2)CC1c1ccccc1] 3HCl |
| 76 | 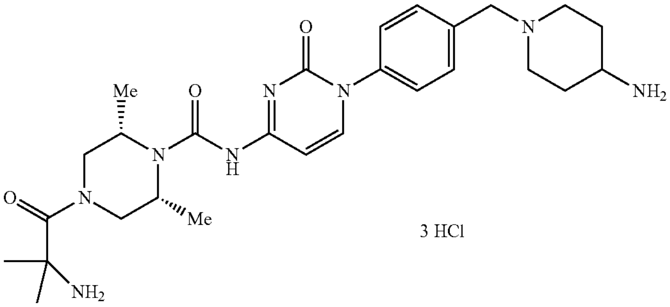 [SMILES: C[C@@H]1CN(C(=O)C(C)(C)N)C[C@H](C)N1C(=O)Nc1ccn(-c2ccc(CN3CCC(N)CC3)cc2)c(=O)n1] 3 HCl |
| 77 | 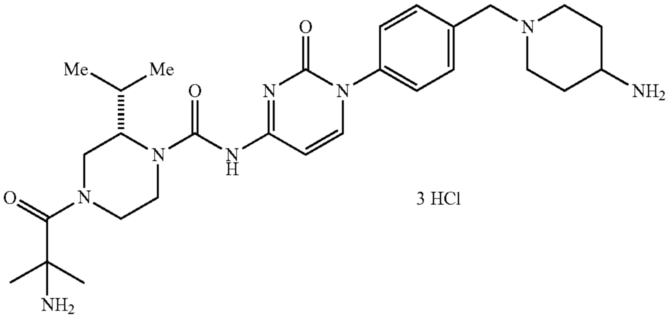 [SMILES: CC(C)[C@H]1CN(C(=O)C(C)(C)N)CCN1C(=O)Nc1ccn(-c2ccc(CN3CCC(N)CC3)cc2)c(=O)n1] 3 HCl |
| 78 | 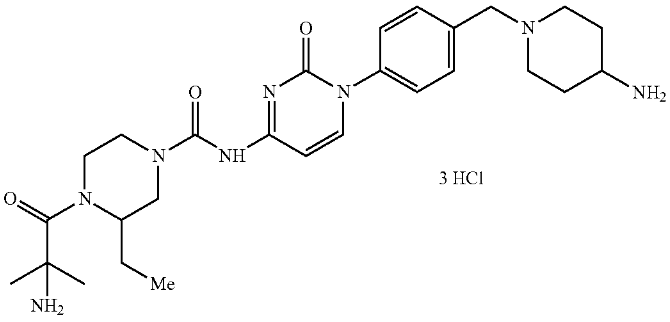 [SMILES: CCC1CN(C(=O)Nc2ccn(-c3ccc(CN4CCC(N)CC4)cc3)c(=O)n2)CCN1C(=O)C(C)(C)N] 3 HCl |

TABLE 10-continued
| Compounds of Formula I |
|---|
| 79 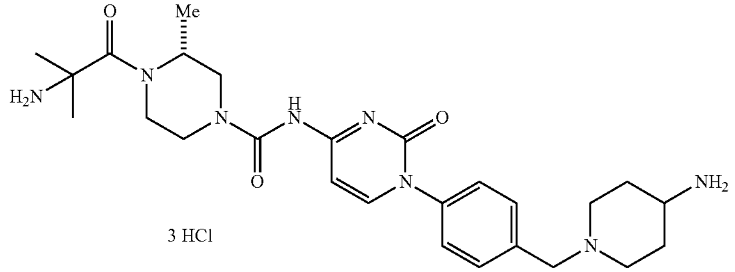 [SMILES: C[C@@H]1CN(C(=O)Nc2ccn(-c3ccc(CN4CCC(N)CC4)cc3)c(=O)n2)CCN1C(=O)C(C)(C)N] 3 HCl |
| 80 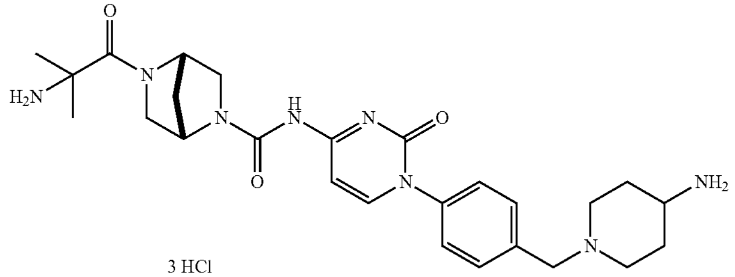 3 HCl |
| 81 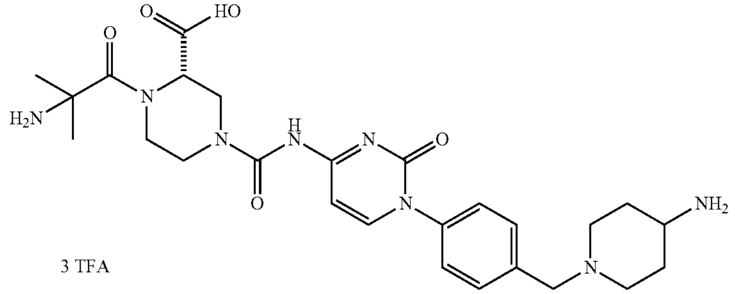 [SMILES: CC(C)(N)C(=O)N1CCN(C(=O)Nc2ccn(-c3ccc(CN4CCC(N)CC4)cc3)c(=O)n2)C[C@H]1C(=O)O] 3 TFA |
| 82 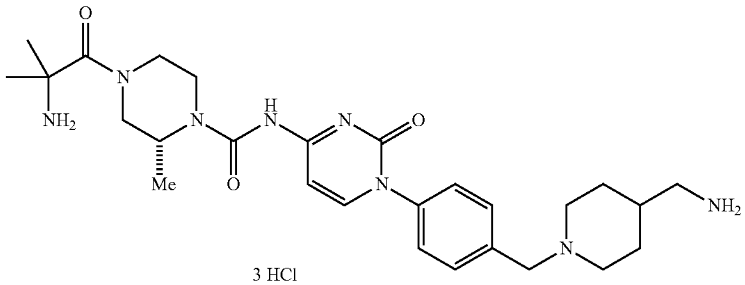 [SMILES: C[C@@H]1CN(C(=O)C(C)(C)N)CCN1C(=O)Nc1ccn(-c2ccc(CN3CCC(CN)CC3)cc2)c(=O)n1] 3 HCl |
| 83 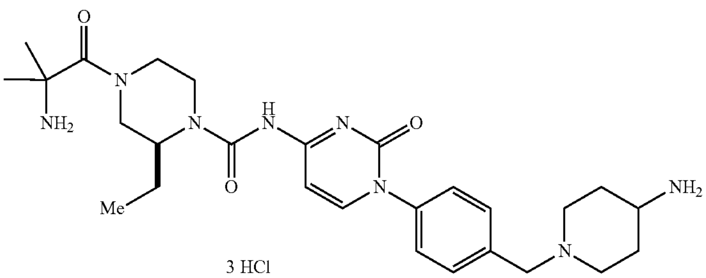 [SMILES: CC[C@H]1CN(C(=O)C(C)(C)N)CCN1C(=O)Nc1ccn(-c2ccc(CN3CCC(N)CC3)cc2)c(=O)n1] 3 HCl |

TABLE 10-continued
| Compounds of Formula I | |
|---|---|
| 84 | 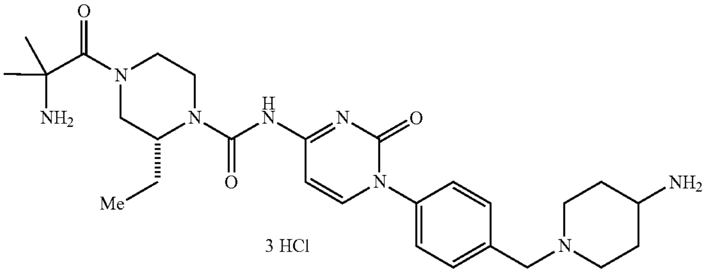 [SMILES: CC[C@@H]1CN(C(=O)C(C)(C)N)CCN1C(=O)Nc1ccn(-c2ccc(CN3CCC(N)CC3)cc2)c(=O)n1] 3 HCl |
| 85 | 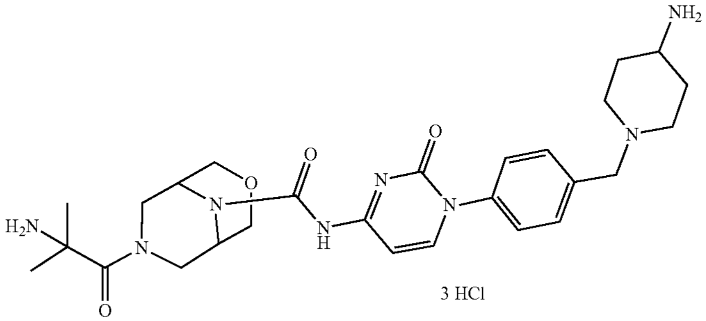 [SMILES: CC(C)(N)C(=O)N1CC2COCC(C1)N2C(=O)Nc1ccn(-c2ccc(CN3CCC(N)CC3)cc2)c(=O)n1] 3 HCl |
| 86 | 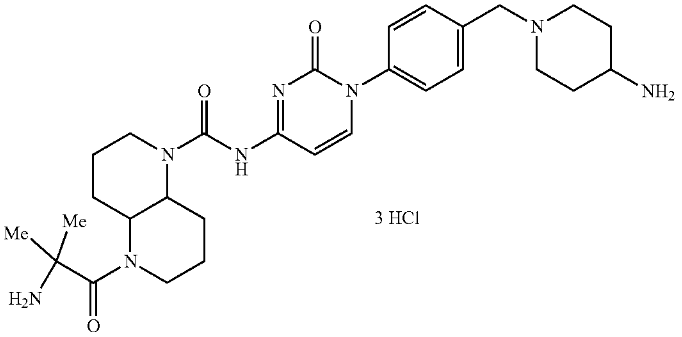 [SMILES: CC(C)(N)C(=O)N1CCCC2C1CCCN2C(=O)Nc1ccn(-c2ccc(CN3CCC(N)CC3)cc2)c(=O)n1] 3 HCl |
| 87 | 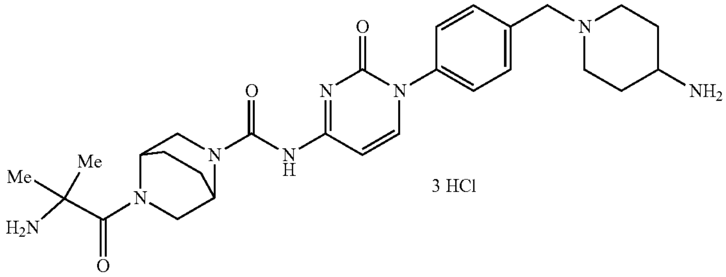 [SMILES: CC(C)(N)C(=O)N1CC2CCC1CN2C(=O)Nc1ccn(-c2ccc(CN3CCC(N)CC3)cc2)c(=O)n1] 3 HCl |
| 88 | 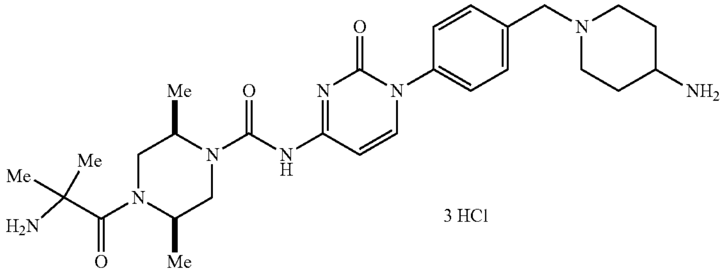 [SMILES: C[C@@H]1CN(C(=O)C(C)(C)N)[C@H](C)CN1C(=O)Nc1ccn(-c2ccc(CN3CCC(N)CC3)cc2)c(=O)n1] 3 HCl |

TABLE 10-continued
Compounds of Formula I
89
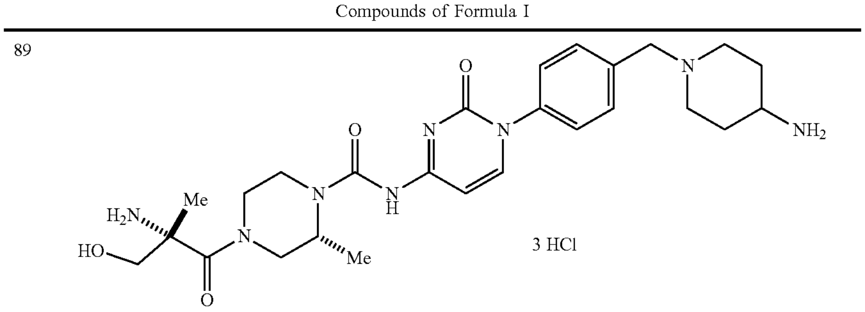
3 HCl
90
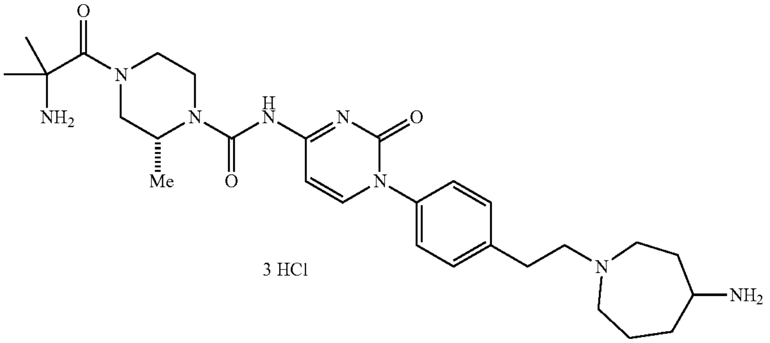 [SMILES: C[C@@H]1CN(C(=O)C(C)(C)N)CCN1C(=O)Nc1ccn(-c2ccc(CCN3CCCC(N)CC3)cc2)c(=O)n1]
3 HCl
91
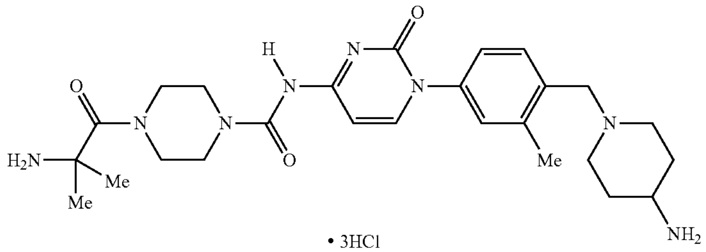
• 3HCl
92
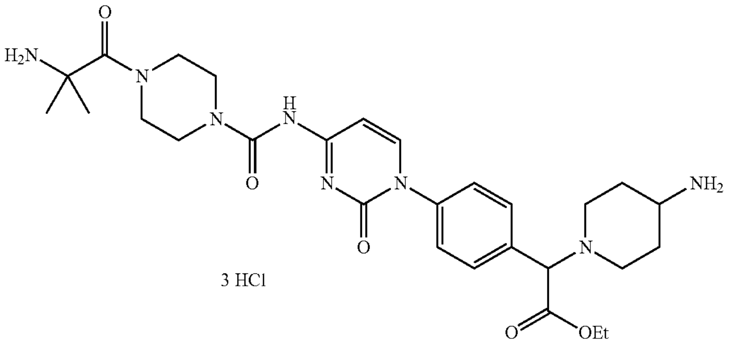 [SMILES: CCOC(=O)C(c1ccc(-n2ccc(NC(=O)N3CCN(C(=O)C(C)(C)N)CC3)nc2=O)cc1)N1CCC(N)CC1]
3 HCl
93
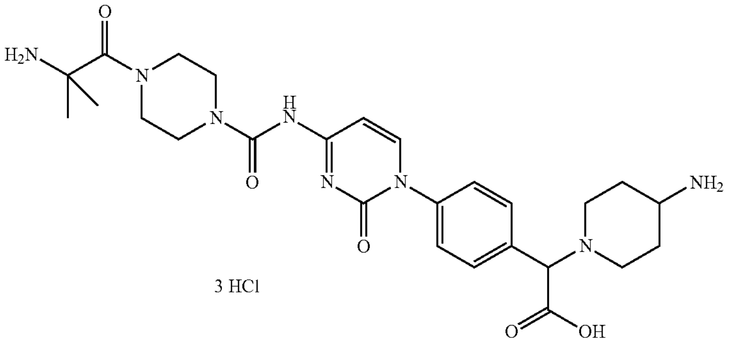 [SMILES: CC(C)(N)C(=O)N1CCN(C(=O)Nc2ccn(-c3ccc(C(C(=O)O)N4CCC(N)CC4)cc3)c(=O)n2)CC1]
3 HCl TABLE 10-continued
| Compounds of Formula I | |
|---|---|
| 94 | 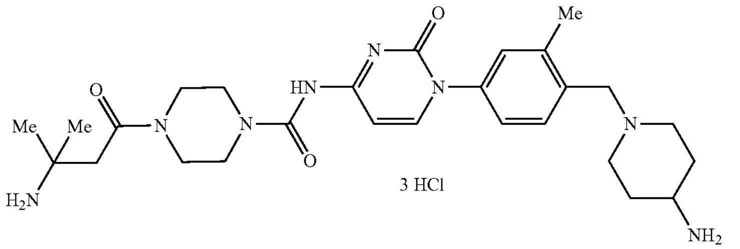 [SMILES: Cc1cc(-n2ccc(NC(=O)N3CCN(C(=O)CC(C)(C)N)CC3)nc2=O)ccc1CN1CCC(N)CC1] 3 HCl |
| 95 | 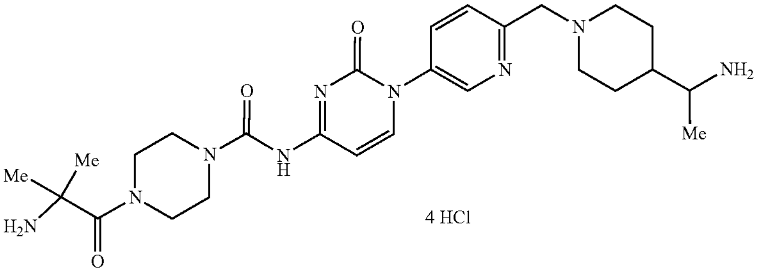 [SMILES: CC(N)C1CCN(Cc2ccc(-n3ccc(NC(=O)N4CCN(C(=O)C(C)(C)N)CC4)nc3=O)cn2)CC1] 4 HCl |
| 96 | 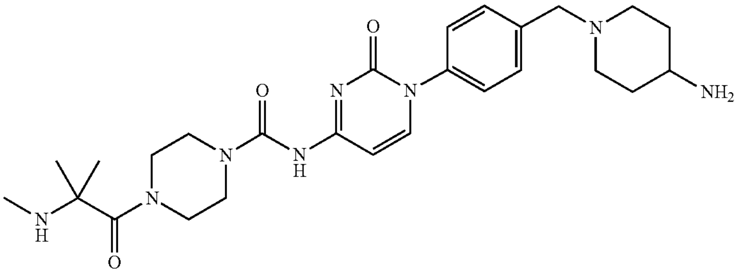 [SMILES: CNC(C)(C)C(=O)N1CCN(C(=O)Nc2ccn(-c3ccc(CN4CCC(N)CC4)cc3)c(=O)n2)CC1] |
| 97 | 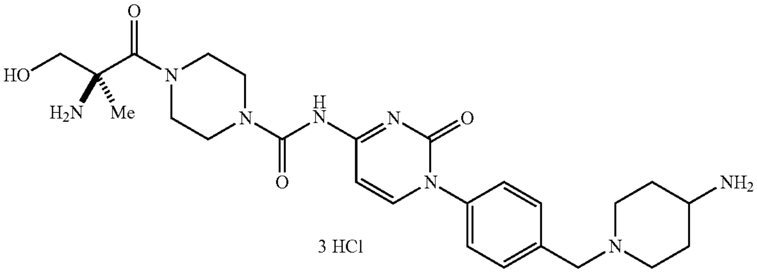 3 HCl |
| 98 | 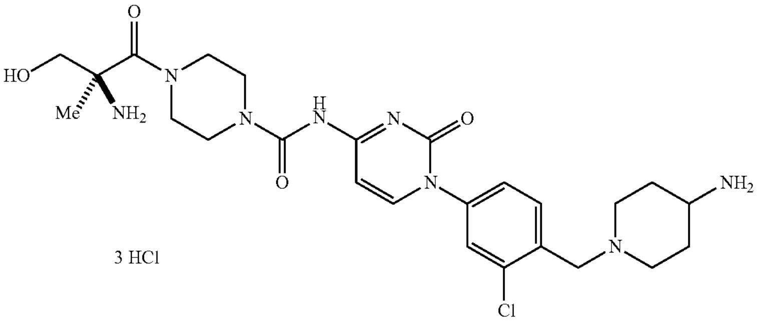 3 HCl |

TABLE 10-continued
| Compounds of Formula I | |
|---|---|
| 99 | 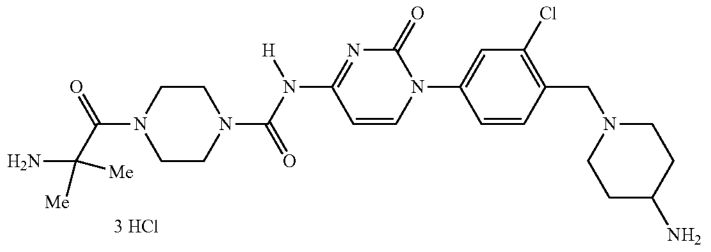 [SMILES: CC(C)(N)C(=O)N1CCN(C(=O)Nc2ccn(-c3ccc(CN4CCC(N)CC4)c(Cl)c3)c(=O)n2)CC1] |
| 100 | 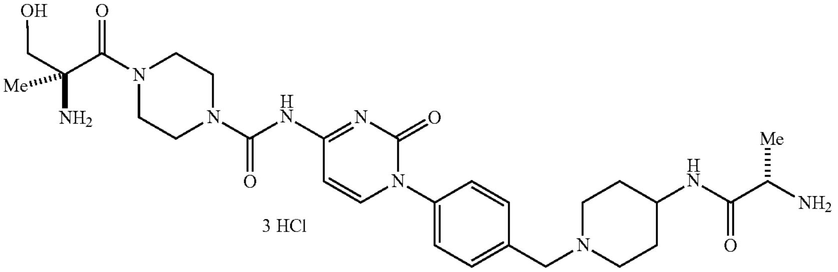 [SMILES: C[C@H](N)C(=O)NC1CCN(Cc2ccc(-n3ccc(NC(=O)N4CCN(C(=O)[C@@](C)(N)CO)CC4)nc3=O)cc2)CC1] |
| 101 | 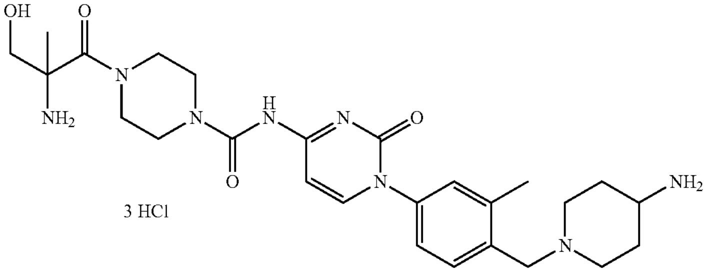 [SMILES: Cc1cc(-n2ccc(NC(=O)N3CCN(C(=O)C(C)(N)CO)CC3)nc2=O)ccc1CN1CCC(N)CC1] |
| 102 | 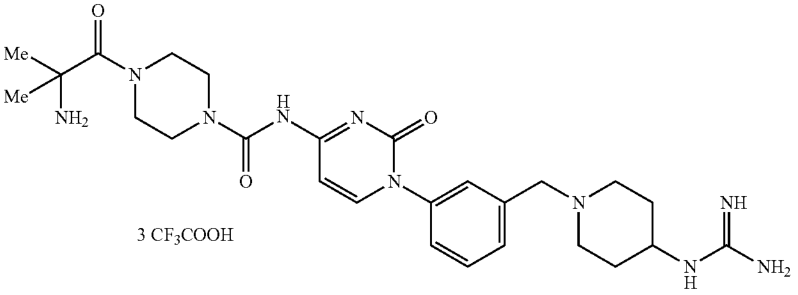 [SMILES: CC(C)(N)C(=O)N1CCN(C(=O)Nc2ccn(-c3cccc(CN4CCC(NC(=N)N)CC4)c3)c(=O)n2)CC1] |
| 103 | 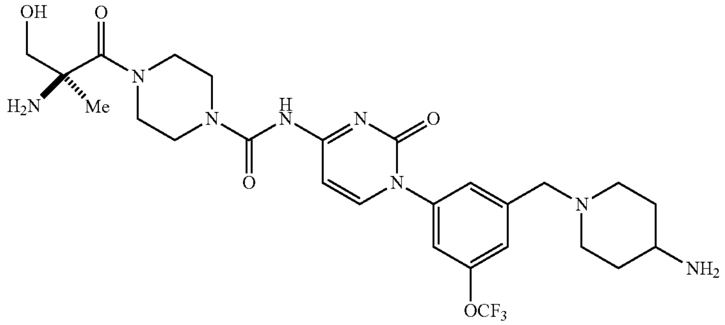 [SMILES: C[C@](N)(CO)C(=O)N1CCN(C(=O)Nc2ccn(-c3cc(CN4CCC(N)CC4)cc(OC(F)(F)F)c3)c(=O)n2)CC1] |

TABLE 10-continued
| Compounds of Formula I |
|---|
104
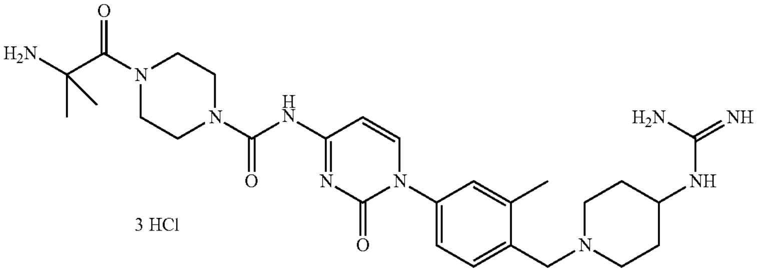 [SMILES: Cc1cc(-n2ccc(NC(=O)N3CCN(C(=O)C(C)(C)N)CC3)nc2=O)ccc1CN1CCC(NC(=N)N)CC1]
3 HCl
105
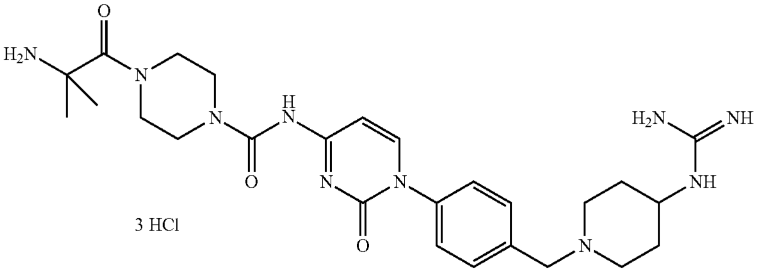 [SMILES: CC(C)(N)C(=O)N1CCN(C(=O)Nc2ccn(-c3ccc(CN4CCC(NC(=N)N)CC4)cc3)c(=O)n2)CC1]
3 HCl
106
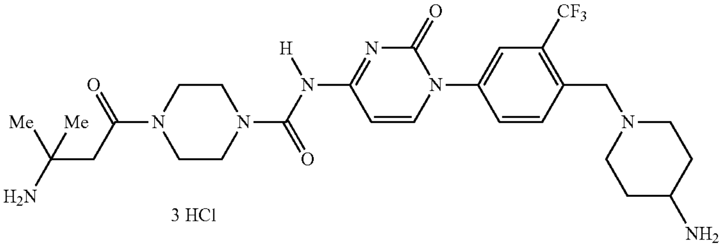
3 HCl
107
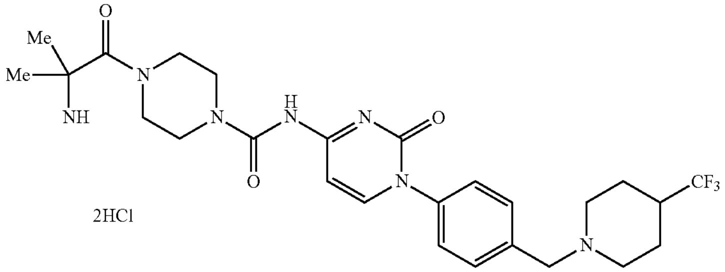 [SMILES: CC(C)(N)C(=O)N1CCN(C(=O)Nc2ccn(-c3ccc(CN4CCC(C(F)(F)F)CC4)cc3)c(=O)n2)CC1]
2HCl
108
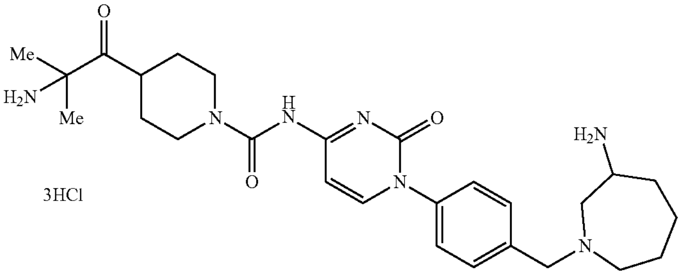 [SMILES: CC(C)(N)C(=O)C1CCN(C(=O)Nc2ccn(-c3ccc(CN4CCCCC(N)C4)cc3)c(=O)n2)CC1]
3HCl TABLE 10-continued
| Compounds of Formula I |
|---|
| 109 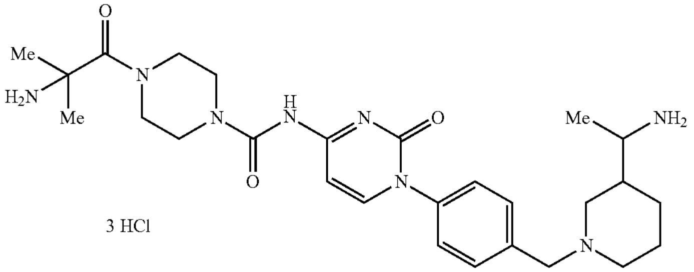 [SMILES: CC(N)C1CCCN(Cc2ccc(-n3ccc(NC(=O)N4CCN(C(=O)C(C)(C)N)CC4)nc3=O)cc2)C1] 3 HCl |
| 110 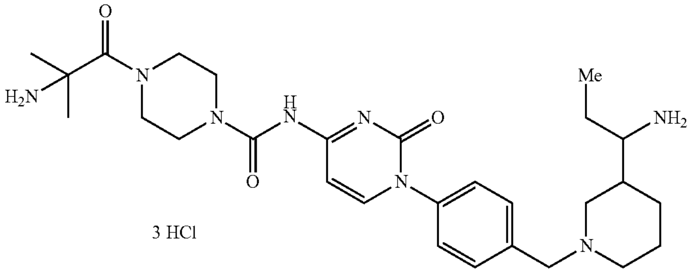 [SMILES: CCC(N)C1CCCN(Cc2ccc(-n3ccc(NC(=O)N4CCN(C(=O)C(C)(C)N)CC4)nc3=O)cc2)C1] 3 HCl |
| 111 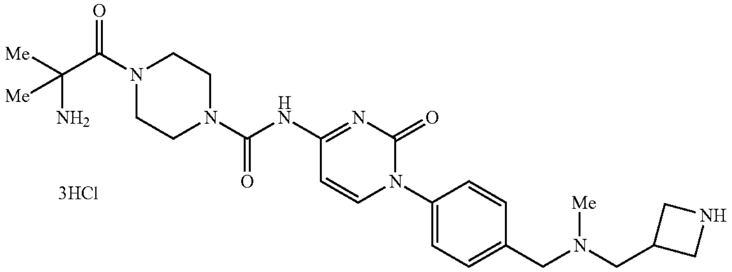 [SMILES: CN(Cc1ccc(-n2ccc(NC(=O)N3CCN(C(=O)C(C)(C)N)CC3)nc2=O)cc1)CC1CNC1] 3HCl |
| 112 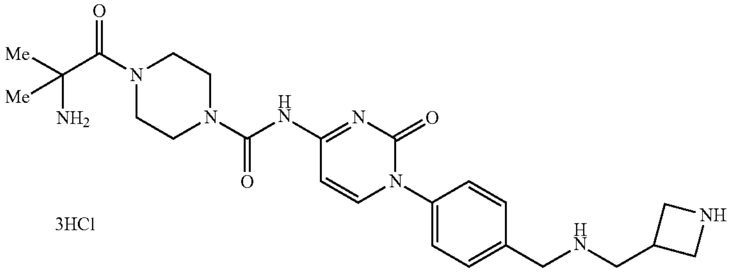 [SMILES: CC(C)(N)C(=O)N1CCN(C(=O)Nc2ccn(-c3ccc(CNCC4CNC4)cc3)c(=O)n2)CC1] 3HCl |
| 114 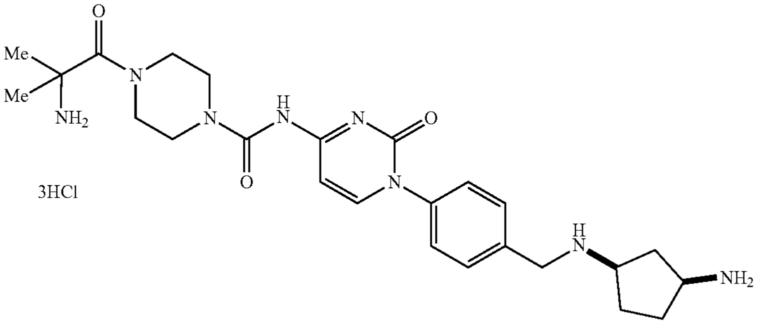 [SMILES: CC(C)(N)C(=O)N1CCN(C(=O)Nc2ccn(-c3ccc(CN[C@@H]4CC[C@H](N)C4)cc3)c(=O)n2)CC1] 3HCl |

TABLE 10-continued
| Compounds of Formula I |
|---|
| 115 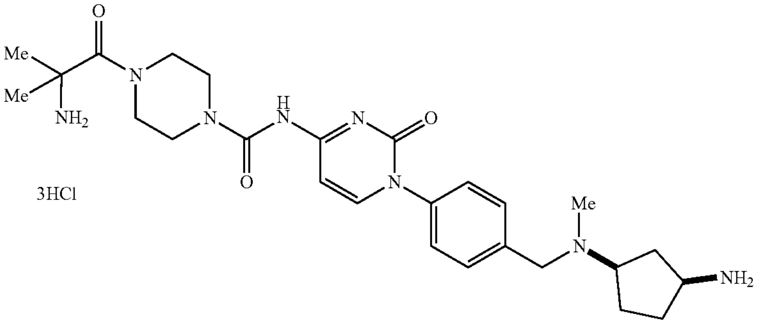 [SMILES: CN(Cc1ccc(-n2ccc(NC(=O)N3CCN(C(=O)C(C)(C)N)CC3)nc2=O)cc1)[C@@H]1CC[C@H](N)C1] |
| 116 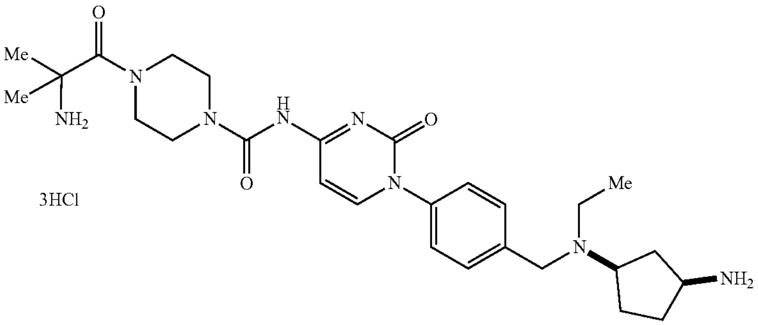 [SMILES: CCN(Cc1ccc(-n2ccc(NC(=O)N3CCN(C(=O)C(C)(C)N)CC3)nc2=O)cc1)[C@@H]1CC[C@H](N)C1] |
| 117 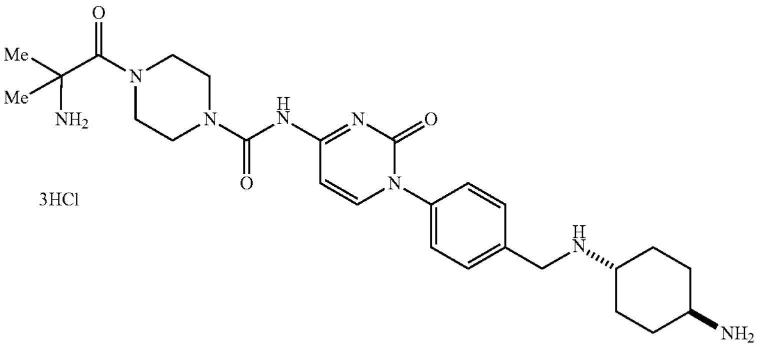 [SMILES: CC(C)(N)C(=O)N1CCN(C(=O)Nc2ccn(-c3ccc(CN[C@H]4CC[C@H](N)CC4)cc3)c(=O)n2)CC1] |
| 118 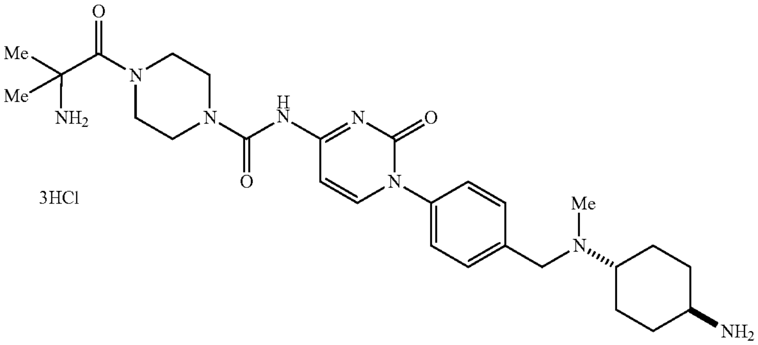 [SMILES: CN(Cc1ccc(-n2ccc(NC(=O)N3CCN(C(=O)C(C)(C)N)CC3)nc2=O)cc1)[C@H]1CC[C@H](N)CC1] |

TABLE 10-continued
| Compounds of Formula I |
| --- |
119
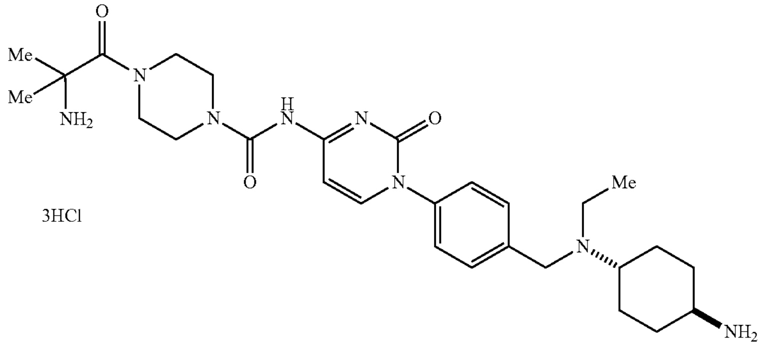 [SMILES: CCN(Cc1ccc(-n2ccc(NC(=O)N3CCN(C(=O)C(C)(C)N)CC3)nc2=O)cc1)[C@H]1CC[C@H](N)CC1]
3HCl
120
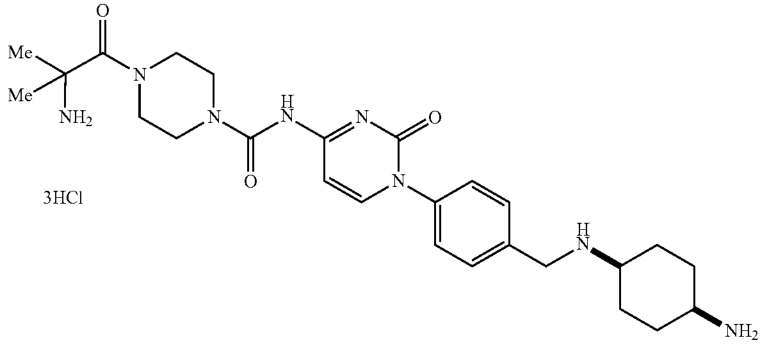 [SMILES: CC(C)(N)C(=O)N1CCN(C(=O)Nc2ccn(-c3ccc(CN[C@H]4CC[C@@H](N)CC4)cc3)c(=O)n2)CC1]
3HCl
121
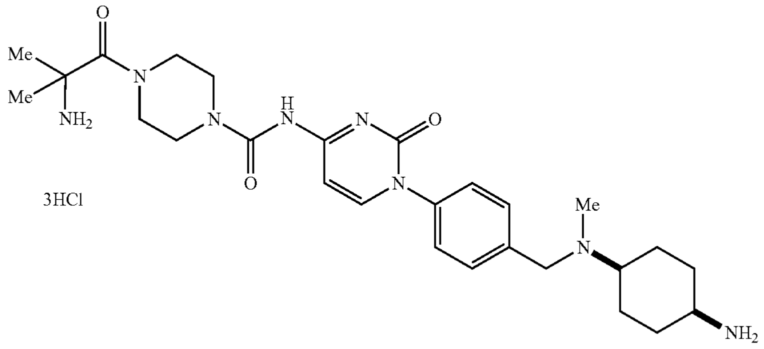 [SMILES: CN(Cc1ccc(-n2ccc(NC(=O)N3CCN(C(=O)C(C)(C)N)CC3)nc2=O)cc1)[C@H]1CC[C@@H](N)CC1]
3HCl
122
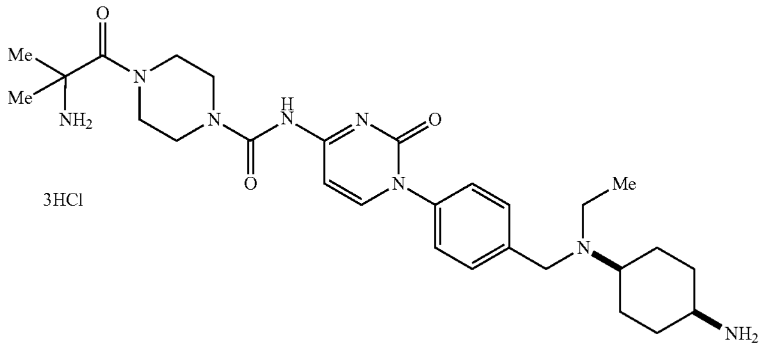 [SMILES: CCN(Cc1ccc(-n2ccc(NC(=O)N3CCN(C(=O)C(C)(C)N)CC3)nc2=O)cc1)[C@H]1CC[C@@H](N)CC1]
3HCl TABLE 10-continued
| Compounds of Formula I |
|---|
| 123 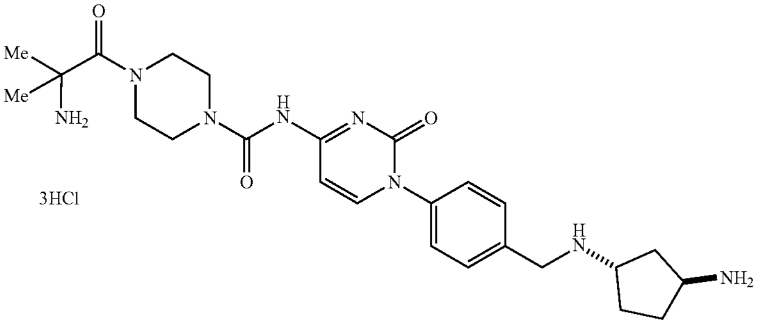 [SMILES: CC(C)(N)C(=O)N1CCN(C(=O)Nc2ccn(-c3ccc(CN[C@H]4CC[C@H](N)C4)cc3)c(=O)n2)CC1] 3HCl |
| 124 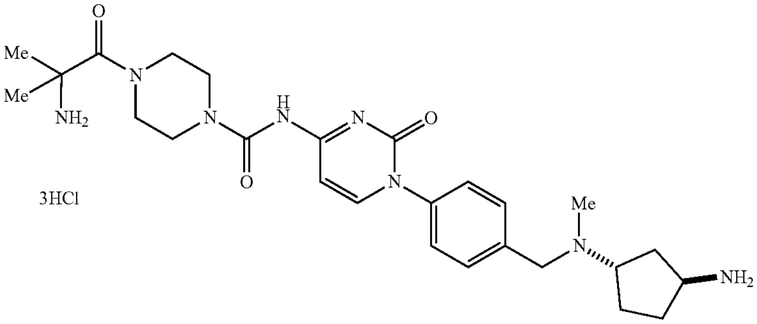 [SMILES: CN(Cc1ccc(-n2ccc(NC(=O)N3CCN(C(=O)C(C)(C)N)CC3)nc2=O)cc1)[C@H]1CC[C@H](N)C1] 3HCl |
| 125 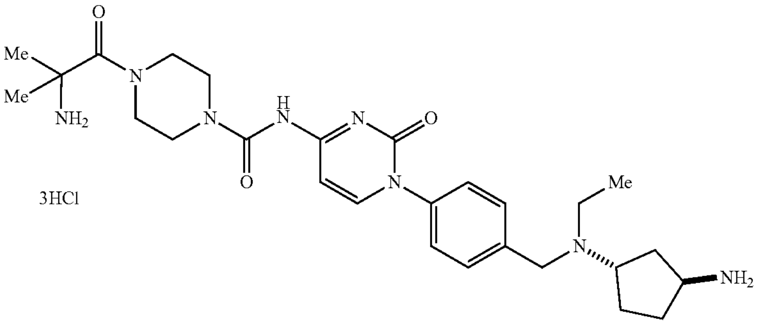 [SMILES: CCN(Cc1ccc(-n2ccc(NC(=O)N3CCN(C(=O)C(C)(C)N)CC3)nc2=O)cc1)[C@H]1CC[C@H](N)C1] 3HCl |
| 126 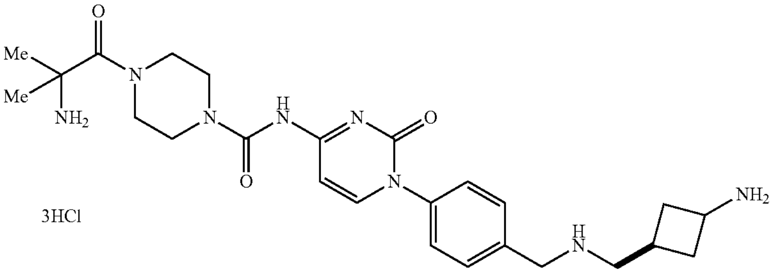 3HCl |
| 127 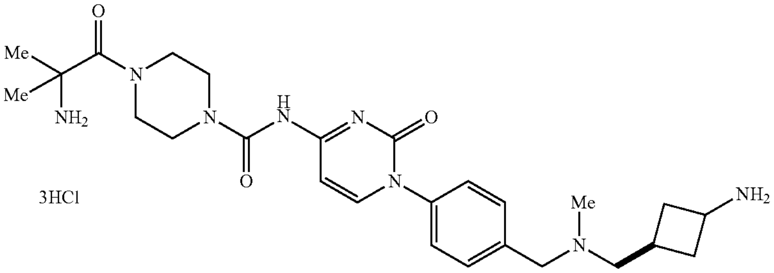 3HCl |

TABLE 10-continued
| Compounds of Formula I |
| --- |
128
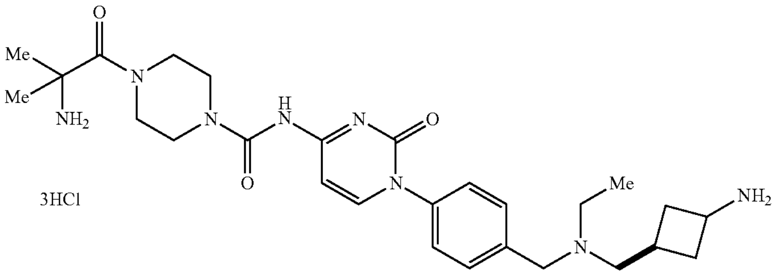
3HCl
129
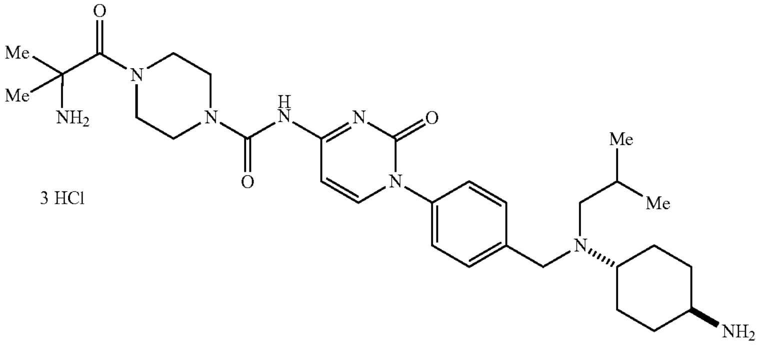 [SMILES: CC(C)CN(Cc1ccc(-n2ccc(NC(=O)N3CCN(C(=O)C(C)(C)N)CC3)nc2=O)cc1)[C@H]1CC[C@H](N)CC1]
3 HCl
130
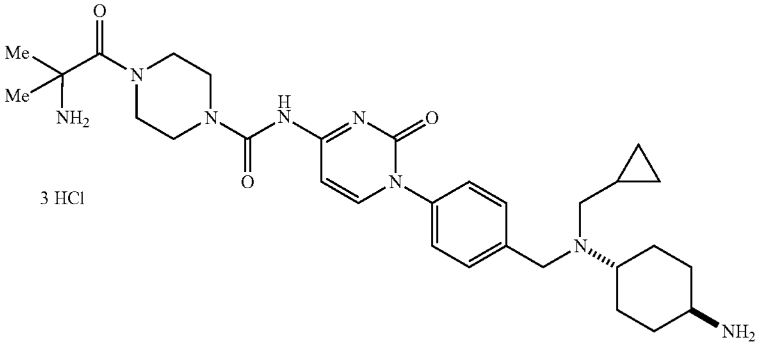 [SMILES: CC(C)(N)C(=O)N1CCN(C(=O)Nc2ccn(-c3ccc(CN(CC4CC4)[C@H]4CC[C@H](N)CC4)cc3)c(=O)n2)CC1]
3 HCl
131
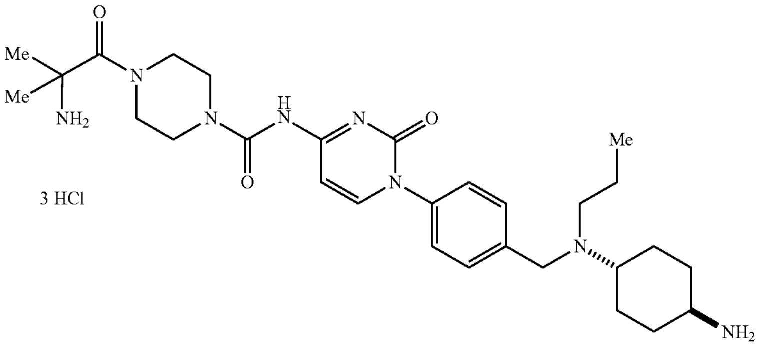 [SMILES: CCCN(Cc1ccc(-n2ccc(NC(=O)N3CCN(C(=O)C(C)(C)N)CC3)nc2=O)cc1)[C@H]1CC[C@H](N)CC1]
3 HCl TABLE 10-continued
| Compounds of Formula I |
|---|
| 132 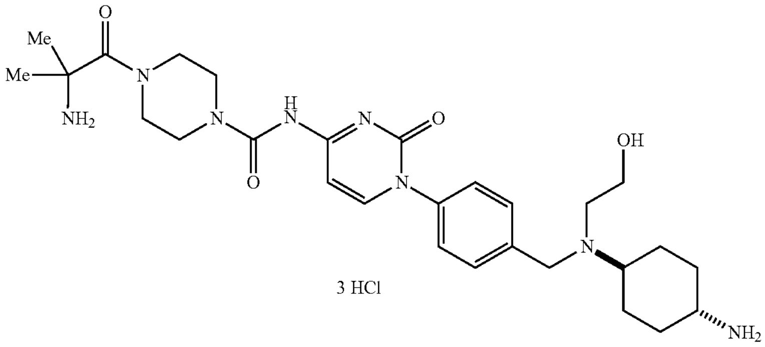 [SMILES: CC(C)(N)C(=O)N1CCN(C(=O)Nc2ccn(-c3ccc(CN(CCO)[C@H]4CC[C@H](N)CC4)cc3)c(=O)n2)CC1] 3 HCl |
| 133 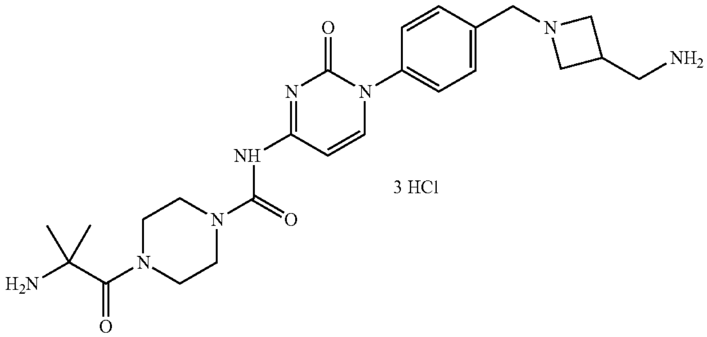 [SMILES: CC(C)(N)C(=O)N1CCN(C(=O)Nc2ccn(-c3ccc(CN4CC(CN)C4)cc3)c(=O)n2)CC1] 3 HCl |
| 134 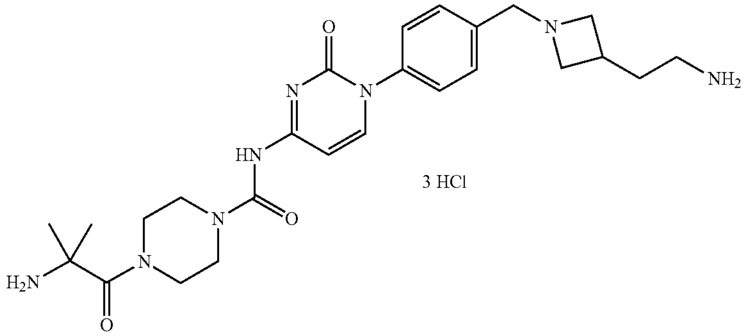 [SMILES: CC(C)(N)C(=O)N1CCN(C(=O)Nc2ccn(-c3ccc(CN4CC(CCN)C4)cc3)c(=O)n2)CC1] 3 HCl |
| 135 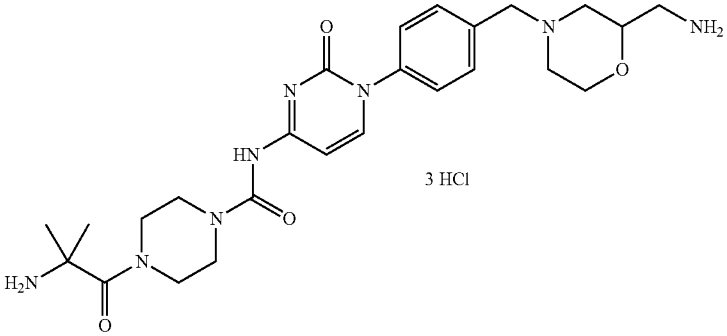 [SMILES: CC(C)(N)C(=O)N1CCN(C(=O)Nc2ccn(-c3ccc(CN4CCOC(CN)C4)cc3)c(=O)n2)CC1] 3 HCl |

TABLE 10-continued
| Compounds of Formula I |
|---|
| 136 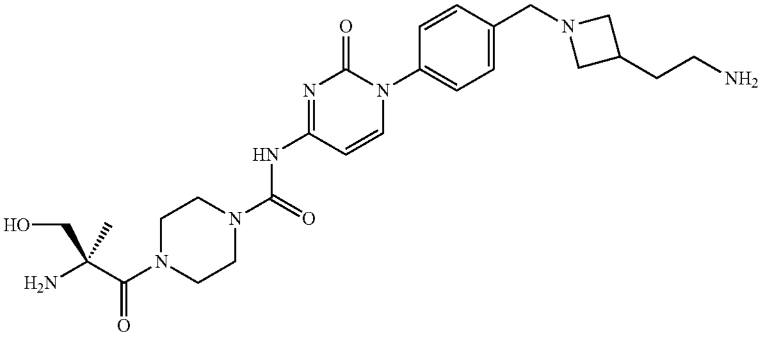 [SMILES: C[C@](N)(CO)C(=O)N1CCN(C(=O)Nc2ccn(-c3ccc(CN4CC(CCN)C4)cc3)c(=O)n2)CC1] |
| 137 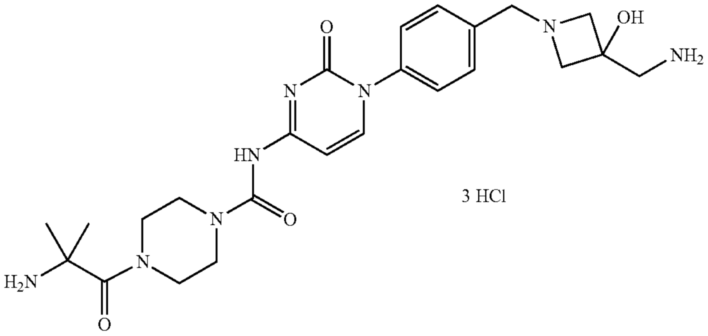 [SMILES: CC(C)(N)C(=O)N1CCN(C(=O)Nc2ccn(-c3ccc(CN4CC(O)(CN)C4)cc3)c(=O)n2)CC1] 3 HCl |
| 138 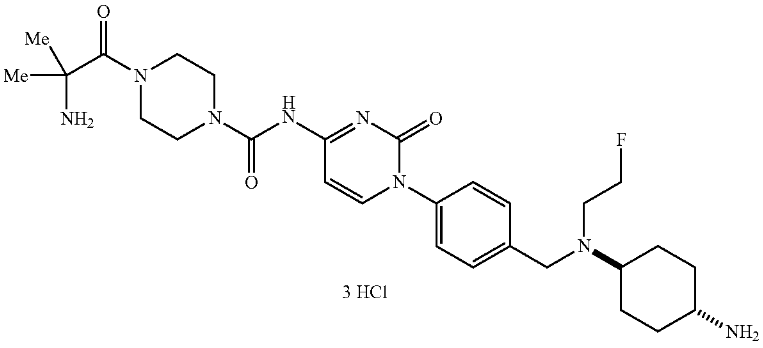 [SMILES: CC(C)(N)C(=O)N1CCN(C(=O)Nc2ccn(-c3ccc(CN(CCF)[C@H]4CC[C@H](N)CC4)cc3)c(=O)n2)CC1] 3 HCl |
| 139 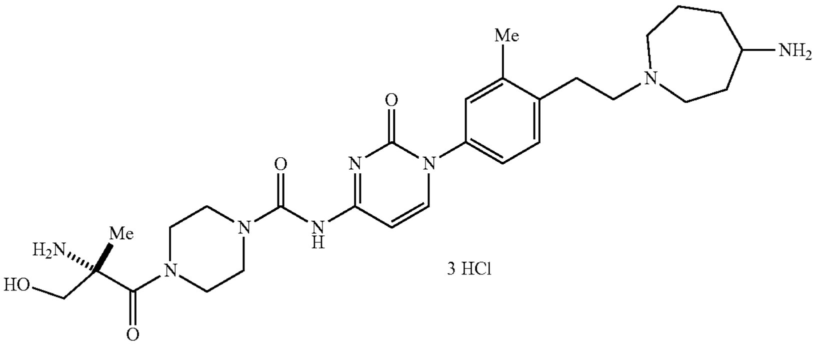 [SMILES: Cc1cc(-n2ccc(NC(=O)N3CCN(C(=O)[C@@](C)(N)CO)CC3)nc2=O)ccc1CCN1CCCC(N)CC1] 3 HCl |

TABLE 10-continued
| Compounds of Formula I |
| --- |
| 140 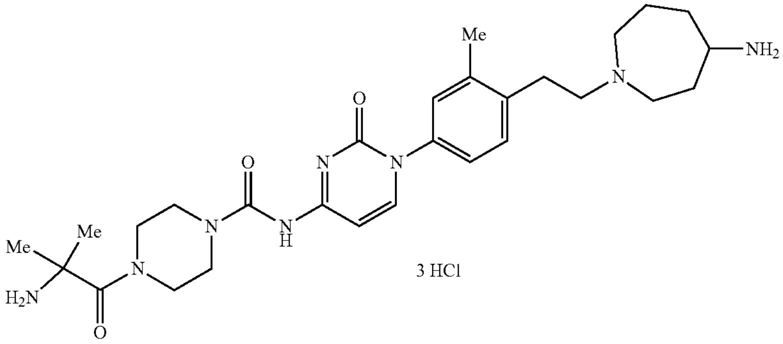 [SMILES: Cc1cc(-n2ccc(NC(=O)N3CCN(C(=O)C(C)(C)N)CC3)nc2=O)ccc1CCN1CCCC(N)CC1] 3 HCl |
| 141 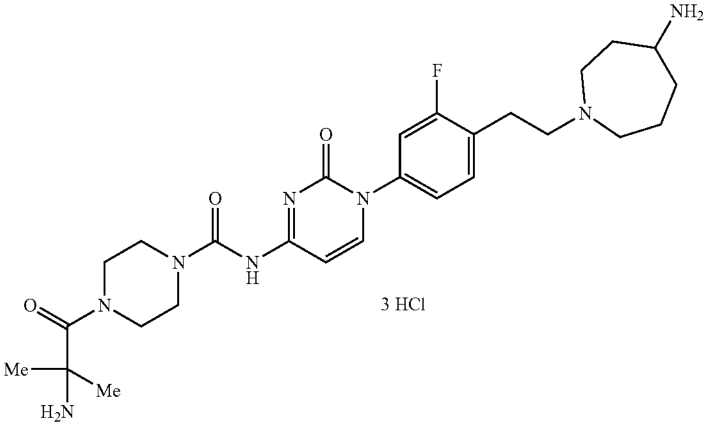 [SMILES: CC(C)(N)C(=O)N1CCN(C(=O)Nc2ccn(-c3ccc(CCN4CCCC(N)CC4)c(F)c3)c(=O)n2)CC1] 3 HCl |
| 142 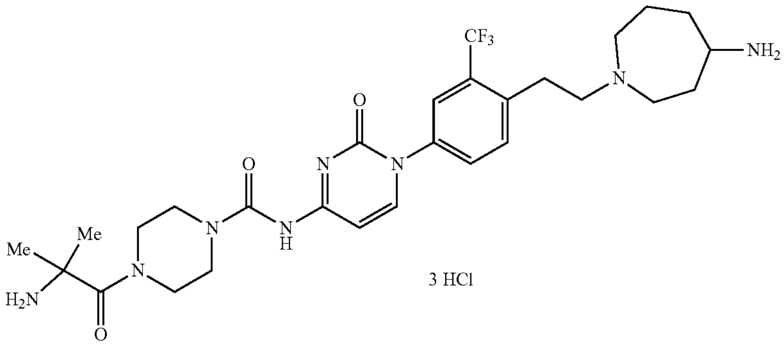 [SMILES: CC(C)(N)C(=O)N1CCN(C(=O)Nc2ccn(-c3ccc(CCN4CCCC(N)CC4)c(C(F)(F)F)c3)c(=O)n2)CC1] 3 HCl |
| 143 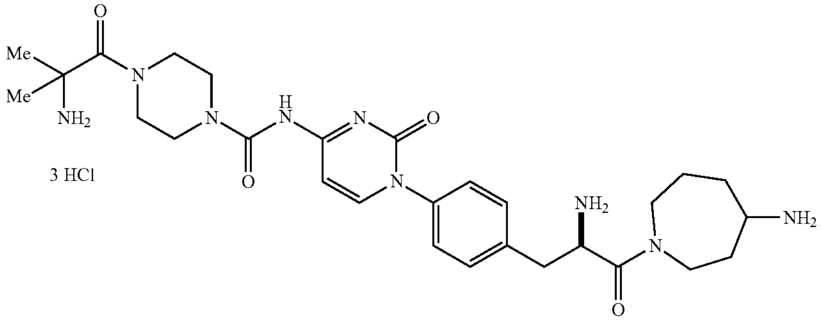 [SMILES: CC(C)(N)C(=O)N1CCN(C(=O)Nc2ccn(-c3ccc(C[C@@H](N)C(=O)N4CCCC(N)CC4)cc3)c(=O)n2)CC1] 3 HCl |

TABLE 10-continued
| Compounds of Formula I |
|---|
| 144 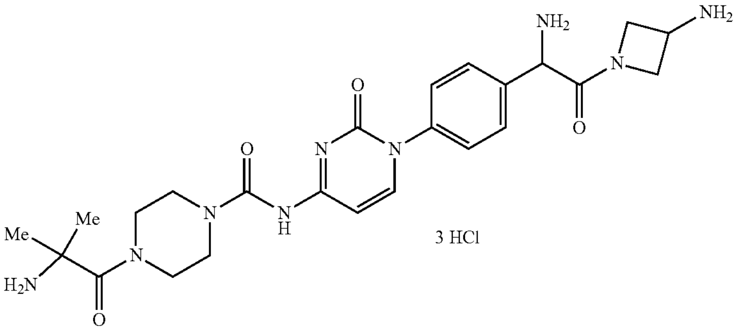 [SMILES: CC(C)(N)C(=O)N1CCN(C(=O)Nc2ccn(-c3ccc(C(N)C(=O)N4CC(N)C4)cc3)c(=O)n2)CC1] 3 HCl |
| 145 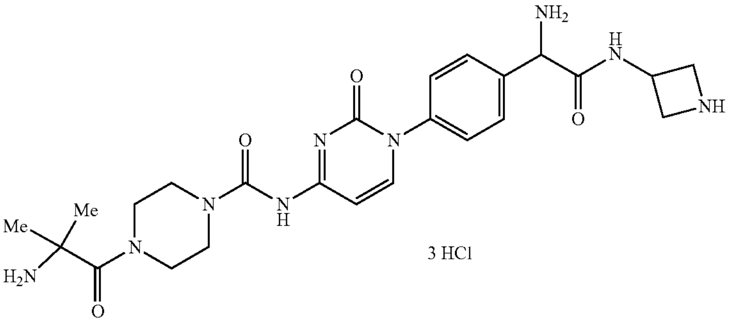 [SMILES: CC(C)(N)C(=O)N1CCN(C(=O)Nc2ccn(-c3ccc(C(N)C(=O)NC4CNC4)cc3)c(=O)n2)CC1] 3 HCl |
| 146 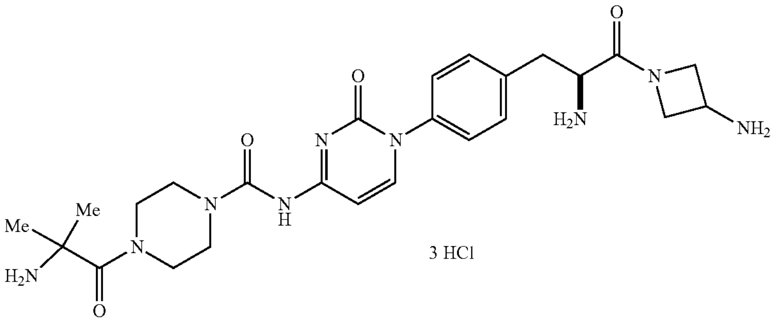 [SMILES: CC(C)(N)C(=O)N1CCN(C(=O)Nc2ccn(-c3ccc(C[C@H](N)C(=O)N4CC(N)C4)cc3)c(=O)n2)CC1] 3 HCl |
| 147 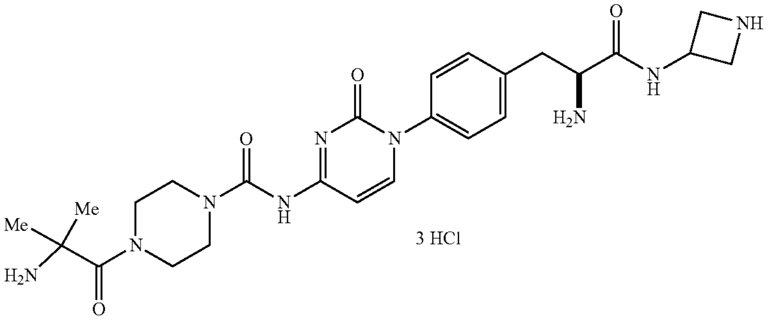 [SMILES: CC(C)(N)C(=O)N1CCN(C(=O)Nc2ccn(-c3ccc(C[C@H](N)C(=O)NC4CNC4)cc3)c(=O)n2)CC1] 3 HCl |

TABLE 10-continued
| Compounds of Formula I |
|---|
| 148 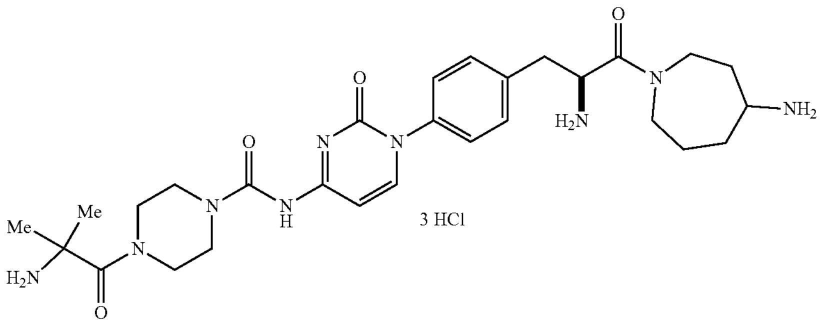 [SMILES: CC(C)(N)C(=O)N1CCN(C(=O)Nc2ccn(-c3ccc(C[C@H](N)C(=O)N4CCCC(N)CC4)cc3)c(=O)n2)CC1] |
| 149 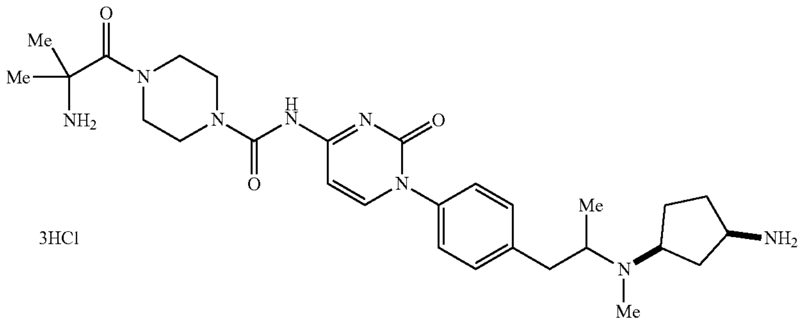 [SMILES: CC(Cc1ccc(-n2ccc(NC(=O)N3CCN(C(=O)C(C)(C)N)CC3)nc2=O)cc1)N(C)[C@H]1CC[C@@H](N)C1] |
| 150 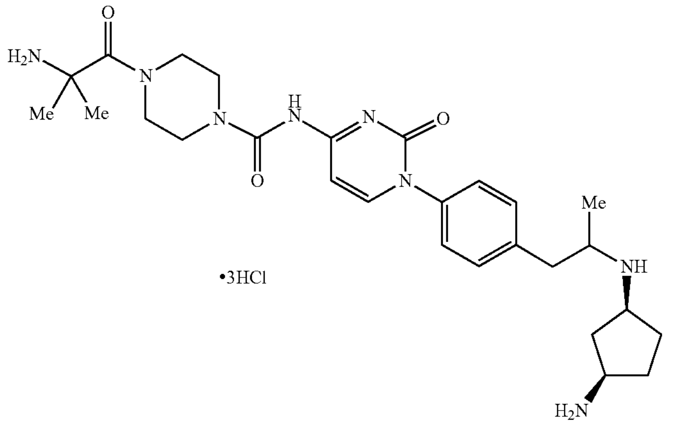 [SMILES: CC(Cc1ccc(-n2ccc(NC(=O)N3CCN(C(=O)C(C)(C)N)CC3)nc2=O)cc1)N[C@H]1CC[C@@H](N)C1] |
| 151 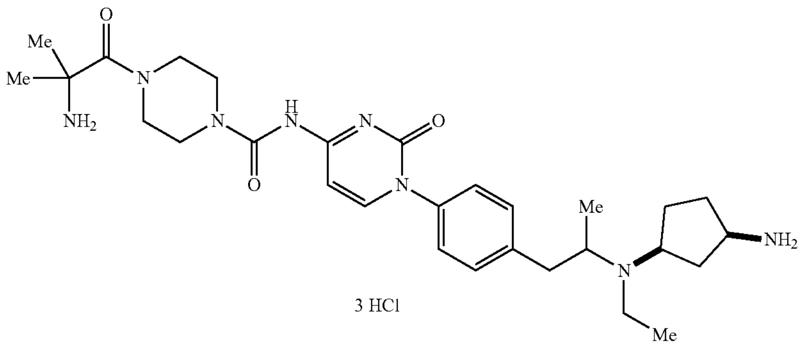 [SMILES: CCN(C(C)Cc1ccc(-n2ccc(NC(=O)N3CCN(C(=O)C(C)(C)N)CC3)nc2=O)cc1)[C@H]1CC[C@@H](N)C1] |

TABLE 10-continued
| Compounds of Formula I |
|---|
| 152 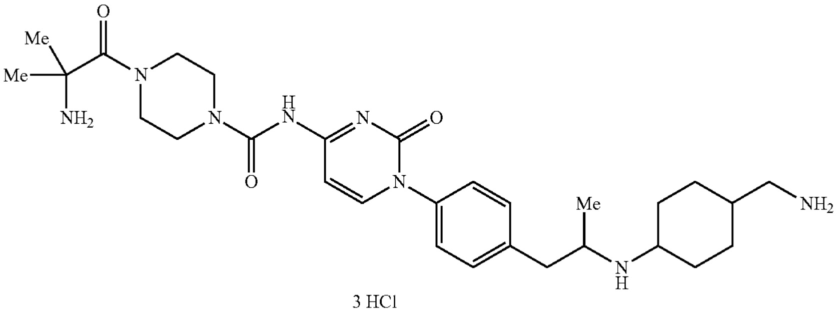 [SMILES: CC(Cc1ccc(-n2ccc(NC(=O)N3CCN(C(=O)C(C)(C)N)CC3)nc2=O)cc1)NC1CCC(CN)CC1] 3 HCl |
| 153 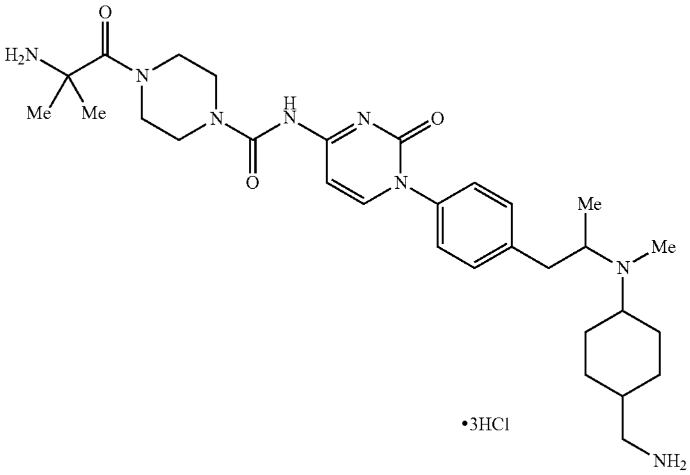 [SMILES: CC(Cc1ccc(-n2ccc(NC(=O)N3CCN(C(=O)C(C)(C)N)CC3)nc2=O)cc1)N(C)C1CCC(CN)CC1] •3HCl |
| 154 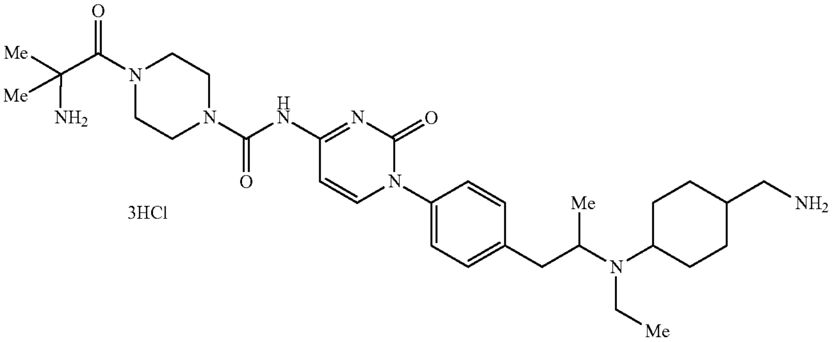 [SMILES: CCN(C(C)Cc1ccc(-n2ccc(NC(=O)N3CCN(C(=O)C(C)(C)N)CC3)nc2=O)cc1)C1CCC(CN)CC1] 3HCl |
| 155 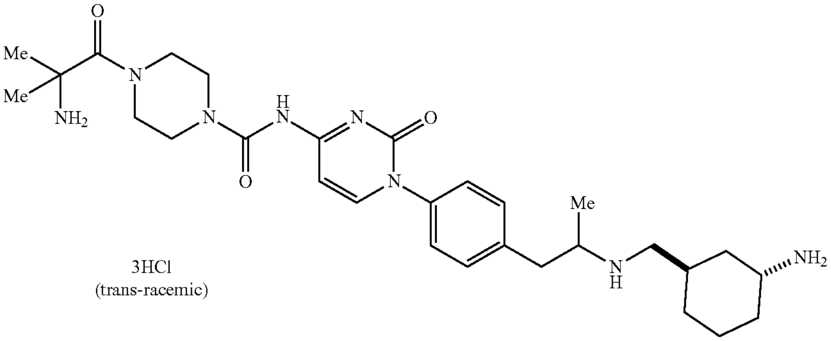 [SMILES: CC(Cc1ccc(-n2ccc(NC(=O)N3CCN(C(=O)C(C)(C)N)CC3)nc2=O)cc1)NC[C@@H]1CCC[C@@H](N)C1] 3HCl (trans-racemic) |

TABLE 10-continued
Compounds of Formula I
156
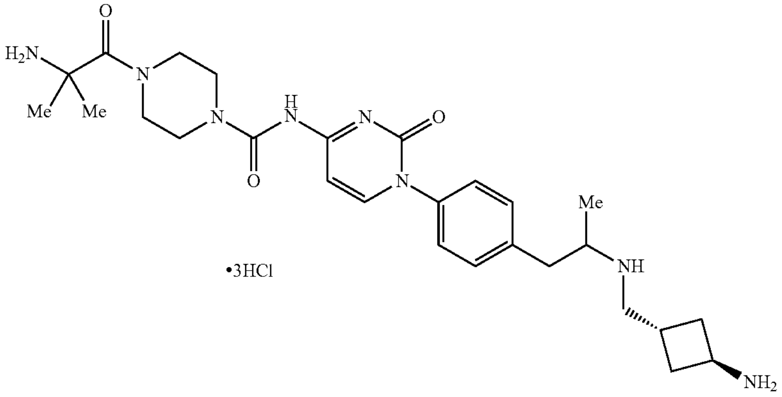 [SMILES: CC(Cc1ccc(-n2ccc(NC(=O)N3CCN(C(=O)C(C)(C)N)CC3)nc2=O)cc1)NC[C@H]1C[C@H](N)C1]
•3HCl
157
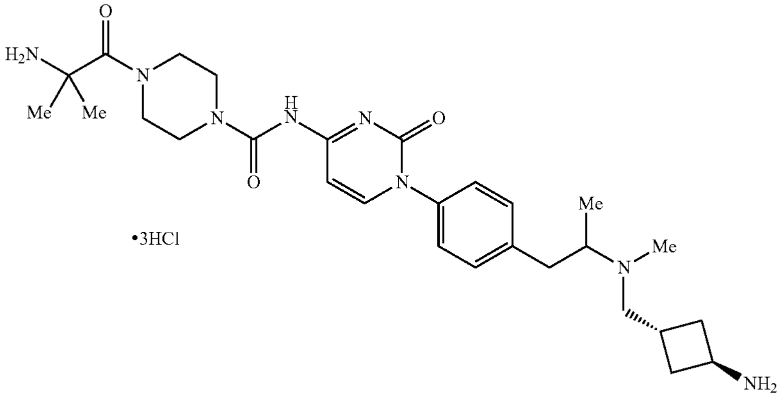 [SMILES: CC(Cc1ccc(-n2ccc(NC(=O)N3CCN(C(=O)C(C)(C)N)CC3)nc2=O)cc1)N(C)C[C@H]1C[C@H](N)C1]
•3HCl
158
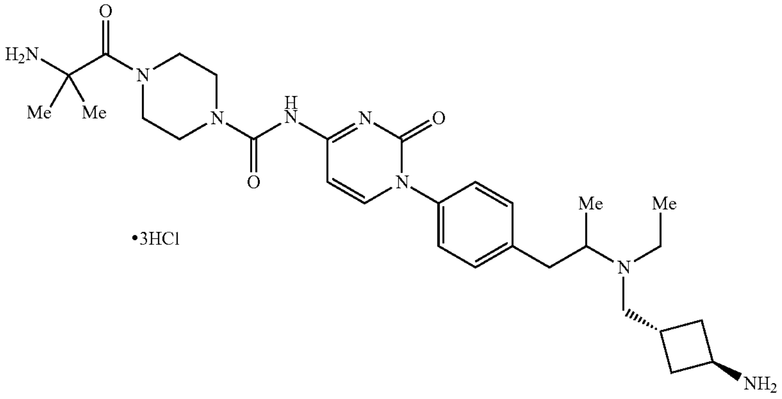 [SMILES: CCN(C[C@H]1C[C@H](N)C1)C(C)Cc1ccc(-n2ccc(NC(=O)N3CCN(C(=O)C(C)(C)N)CC3)nc2=O)cc1]
•3HCl
159
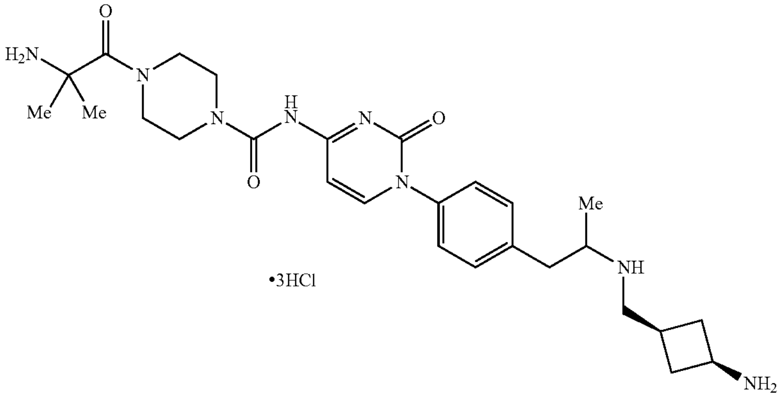 [SMILES: CC(Cc1ccc(-n2ccc(NC(=O)N3CCN(C(=O)C(C)(C)N)CC3)nc2=O)cc1)NC[C@H]1C[C@@H](N)C1]
•3HCl TABLE 10-continued
| Compounds of Formula I |
| --- |
| 160 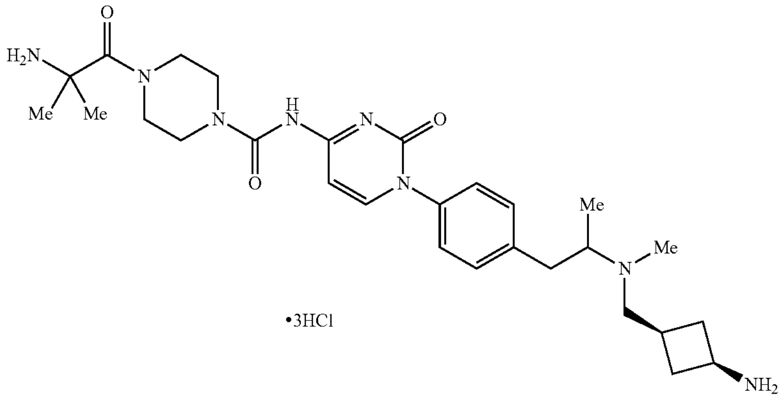 [SMILES: CC(Cc1ccc(-n2ccc(NC(=O)N3CCN(C(=O)C(C)(C)N)CC3)nc2=O)cc1)N(C)C[C@H]1C[C@@H](N)C1] •3HCl |
| 161 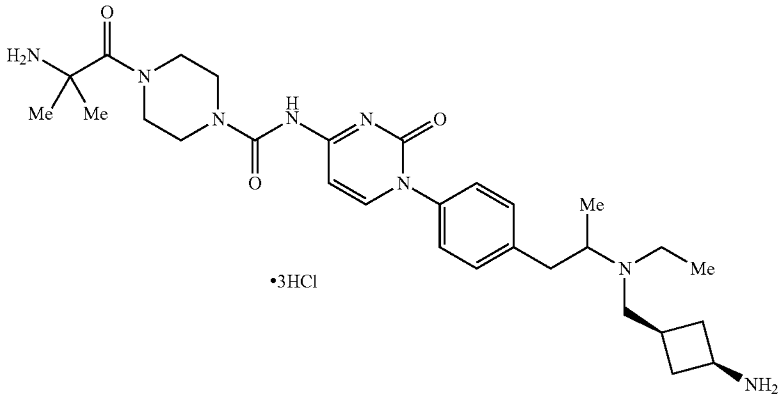 [SMILES: CCN(C[C@H]1C[C@@H](N)C1)C(C)Cc1ccc(-n2ccc(NC(=O)N3CCN(C(=O)C(C)(C)N)CC3)nc2=O)cc1] •3HCl |
| 162 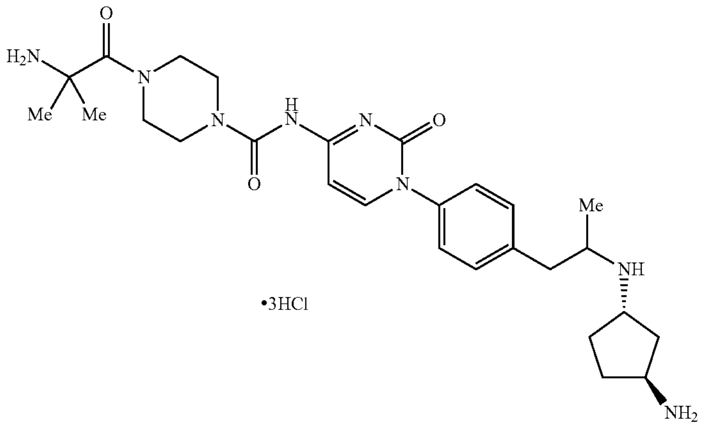 [SMILES: CC(Cc1ccc(-n2ccc(NC(=O)N3CCN(C(=O)C(C)(C)N)CC3)nc2=O)cc1)N[C@H]1CC[C@H](N)C1] •3HCl |

TABLE 10-continued
| Compounds of Formula I |
|---|
163
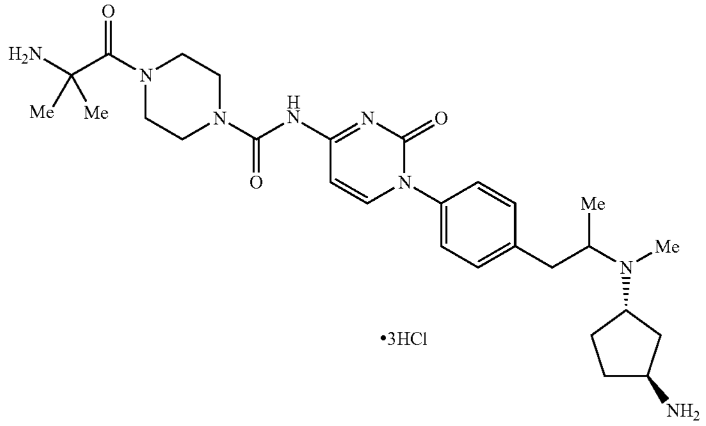 [SMILES: CC(Cc1ccc(-n2ccc(NC(=O)N3CCN(C(=O)C(C)(C)N)CC3)nc2=O)cc1)N(C)[C@H]1CC[C@H](N)C1]
•3HCl
164
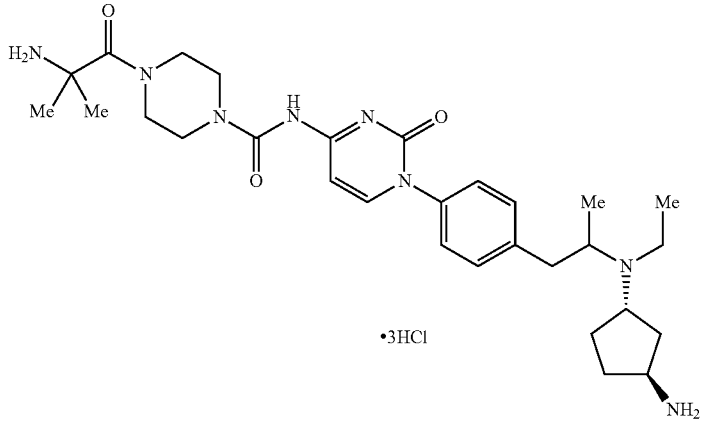 [SMILES: CCN(C(C)Cc1ccc(-n2ccc(NC(=O)N3CCN(C(=O)C(C)(C)N)CC3)nc2=O)cc1)[C@H]1CC[C@H](N)C1]
•3HCl
165
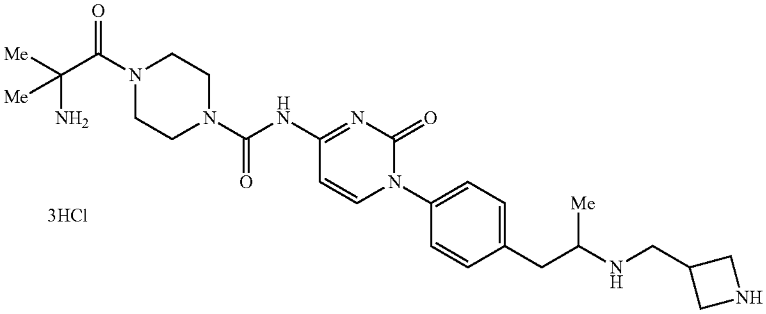 [SMILES: CC(Cc1ccc(-n2ccc(NC(=O)N3CCN(C(=O)C(C)(C)N)CC3)nc2=O)cc1)NCC1CNC1]
3HCl
166
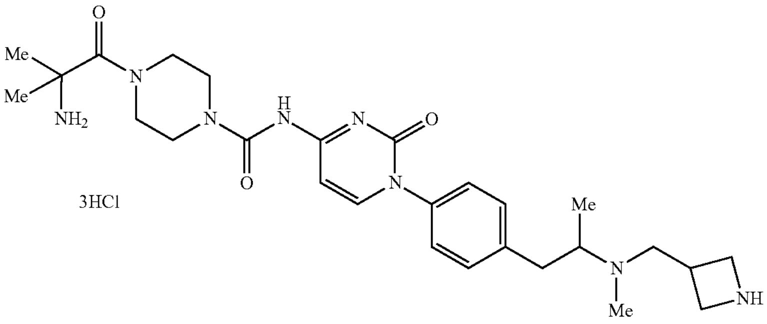 [SMILES: CC(Cc1ccc(-n2ccc(NC(=O)N3CCN(C(=O)C(C)(C)N)CC3)nc2=O)cc1)N(C)CC1CNC1]
3HCl TABLE 10-continued
| Compounds of Formula I |
| --- |
167
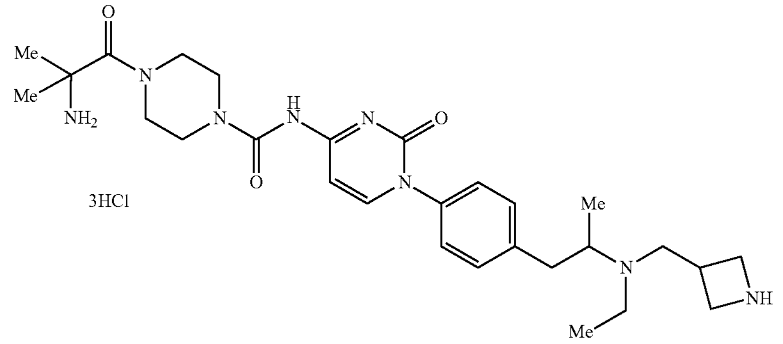 [SMILES: CCN(CC1CNC1)C(C)Cc1ccc(-n2ccc(NC(=O)N3CCN(C(=O)C(C)(C)N)CC3)nc2=O)cc1]
3HCl
168
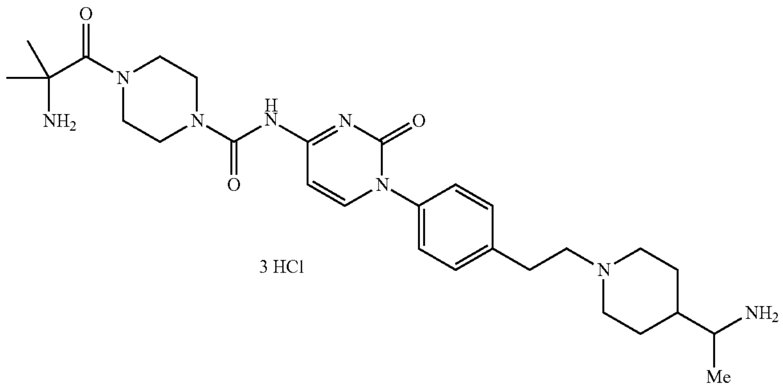 [SMILES: CC(N)C1CCN(CCc2ccc(-n3ccc(NC(=O)N4CCN(C(=O)C(C)(C)N)CC4)nc3=O)cc2)CC1]
3 HCl
169
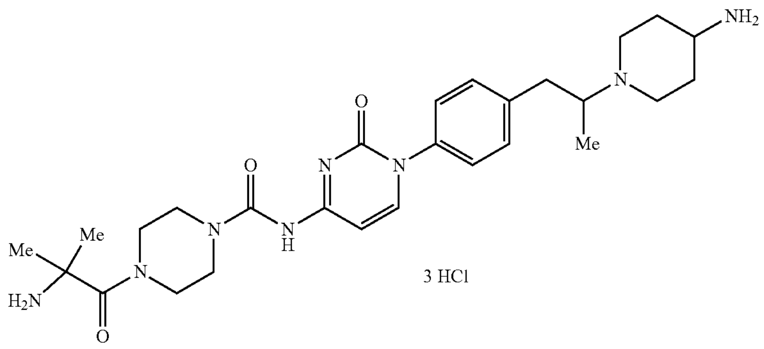 [SMILES: CC(Cc1ccc(-n2ccc(NC(=O)N3CCN(C(=O)C(C)(C)N)CC3)nc2=O)cc1)N1CCC(N)CC1]
3 HCl
170
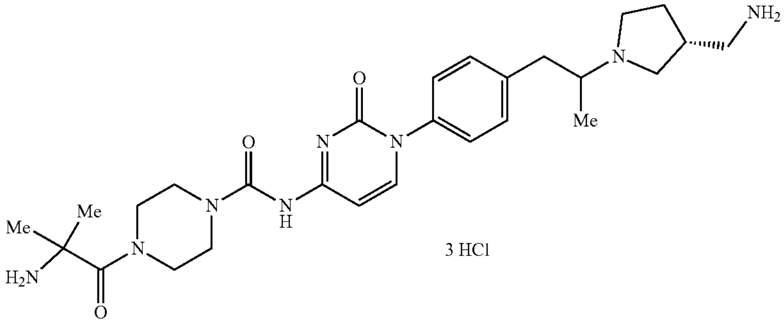 [SMILES: CC(Cc1ccc(-n2ccc(NC(=O)N3CCN(C(=O)C(C)(C)N)CC3)nc2=O)cc1)N1CC[C@H](CN)C1]
3 HCl TABLE 10-continued
| Compounds of Formula I | |
|---|---|
| 171 | 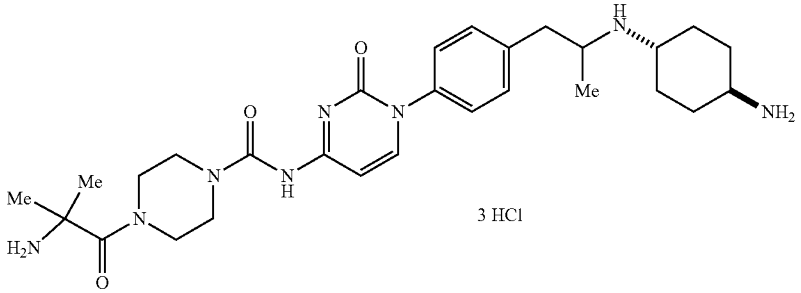 [SMILES: CC(Cc1ccc(-n2ccc(NC(=O)N3CCN(C(=O)C(C)(C)N)CC3)nc2=O)cc1)N[C@H]1CC[C@H](N)CC1] 3 HCl |
| 172 | 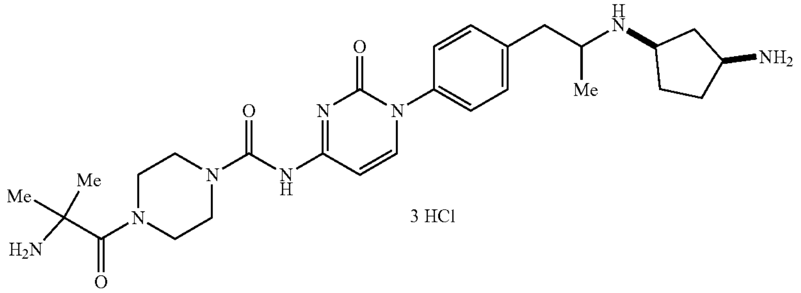 [SMILES: CC(Cc1ccc(-n2ccc(NC(=O)N3CCN(C(=O)C(C)(C)N)CC3)nc2=O)cc1)N[C@@H]1CC[C@H](N)C1] 3 HCl |
| 173 | 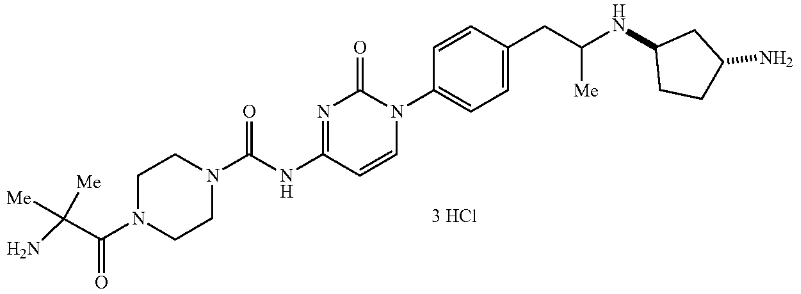 [SMILES: CC(Cc1ccc(-n2ccc(NC(=O)N3CCN(C(=O)C(C)(C)N)CC3)nc2=O)cc1)N[C@@H]1CC[C@@H](N)C1] 3 HCl |
| 174 | 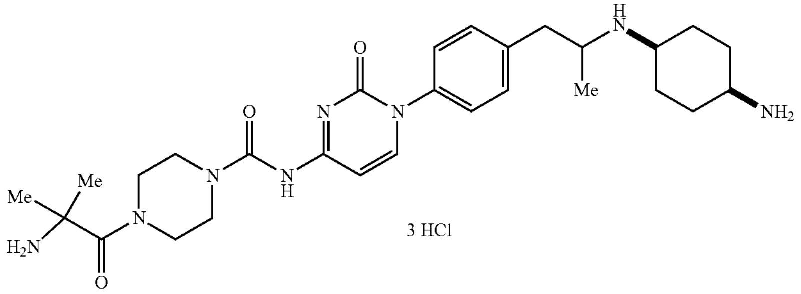 [SMILES: CC(Cc1ccc(-n2ccc(NC(=O)N3CCN(C(=O)C(C)(C)N)CC3)nc2=O)cc1)N[C@H]1CC[C@@H](N)CC1] 3 HCl |
| 175 | 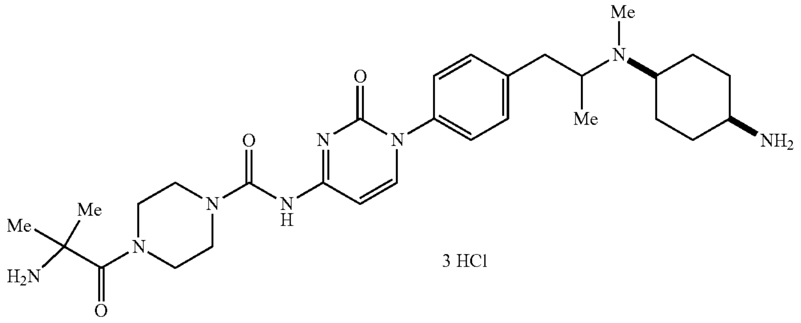 [SMILES: CC(Cc1ccc(-n2ccc(NC(=O)N3CCN(C(=O)C(C)(C)N)CC3)nc2=O)cc1)N(C)[C@H]1CC[C@@H](N)CC1] 3 HCl |

TABLE 10-continued
| Compounds of Formula I |
|---|
| 176 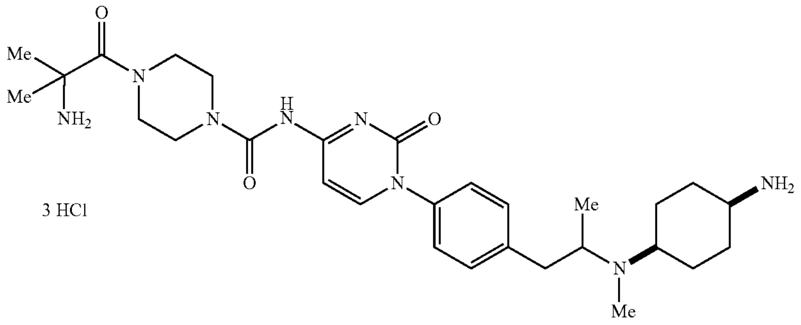 [SMILES: CC(Cc1ccc(-n2ccc(NC(=O)N3CCN(C(=O)C(C)(C)N)CC3)nc2=O)cc1)N(C)[C@H]1CC[C@@H](N)CC1] |
| 177 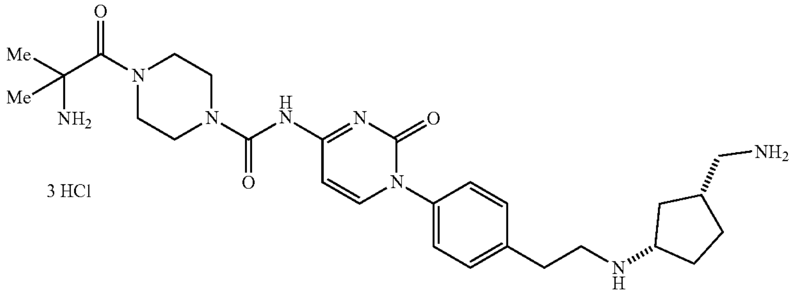 [SMILES: CC(C)(N)C(=O)N1CCN(C(=O)Nc2ccn(-c3ccc(CCN[C@H]4CC[C@@H](CN)C4)cc3)c(=O)n2)CC1] |
| 178 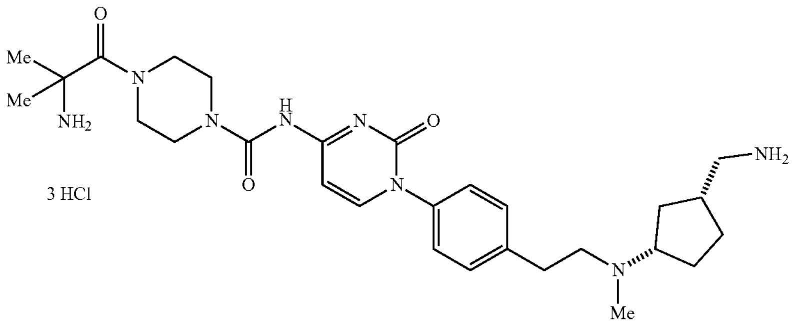 [SMILES: CN(CCc1ccc(-n2ccc(NC(=O)N3CCN(C(=O)C(C)(C)N)CC3)nc2=O)cc1)[C@H]1CC[C@@H](CN)C1] |
| 179 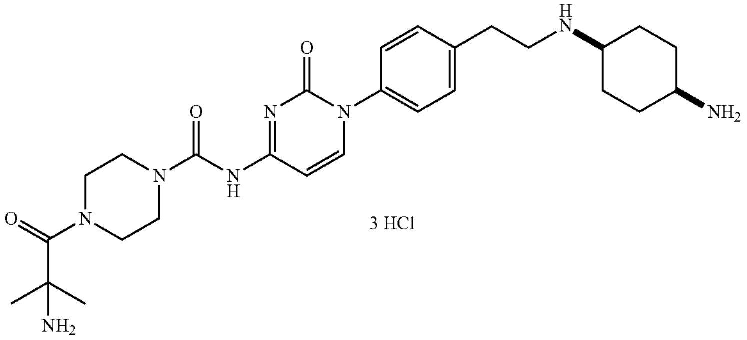 [SMILES: CC(C)(N)C(=O)N1CCN(C(=O)Nc2ccn(-c3ccc(CCN[C@H]4CC[C@@H](N)CC4)cc3)c(=O)n2)CC1] |

TABLE 10-continued
Compounds of Formula I
180
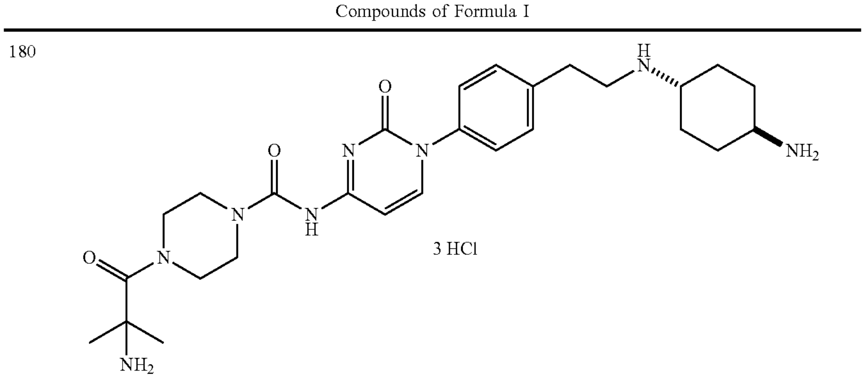
3 HCl
181
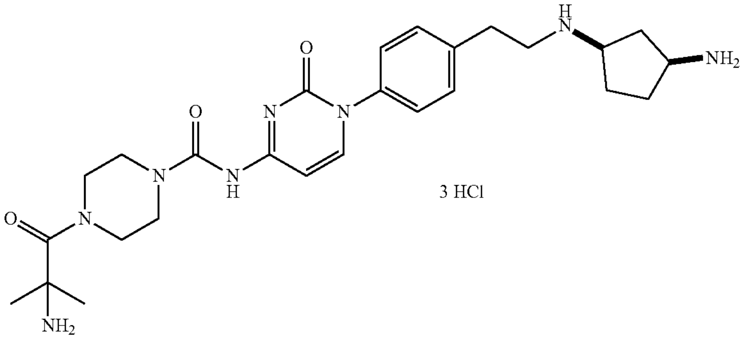 [SMILES: CC(C)(N)C(=O)N1CCN(C(=O)Nc2ccn(-c3ccc(CCN[C@@H]4CC[C@H](N)C4)cc3)c(=O)n2)CC1]
3 HCl
182
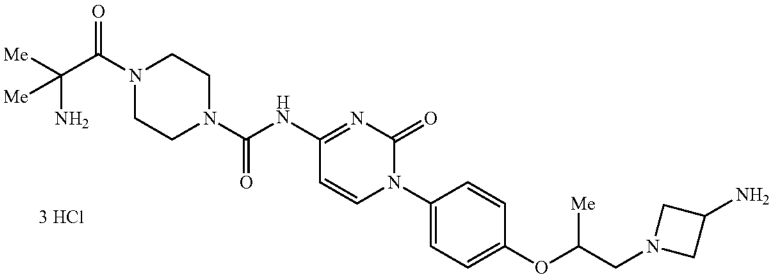 [SMILES: CC(CN1CC(N)C1)Oc1ccc(-n2ccc(NC(=O)N3CCN(C(=O)C(C)(C)N)CC3)nc2=O)cc1]
3 HCl
183
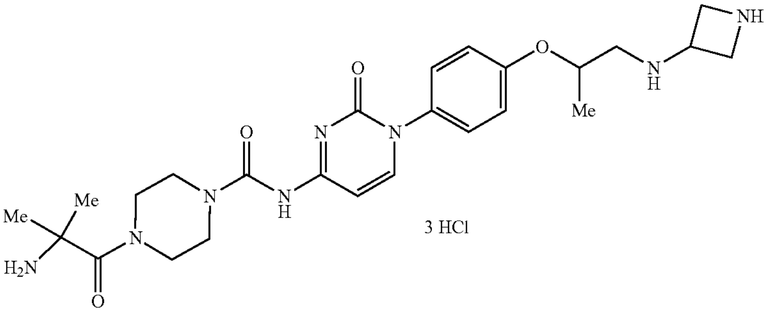 [SMILES: CC(CNC1CNC1)Oc1ccc(-n2ccc(NC(=O)N3CCN(C(=O)C(C)(C)N)CC3)nc2=O)cc1]
3 HCl
184
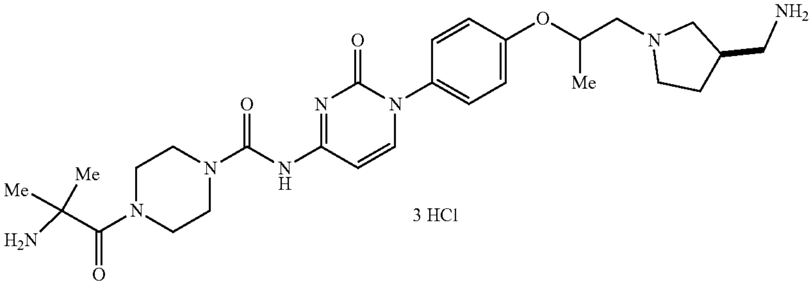 [SMILES: CC(CN1CC[C@H](CN)C1)Oc1ccc(-n2ccc(NC(=O)N3CCN(C(=O)C(C)(C)N)CC3)nc2=O)cc1]
3 HCl TABLE 10-continued
| Compounds of Formula I | |
|---|---|
| 185 | 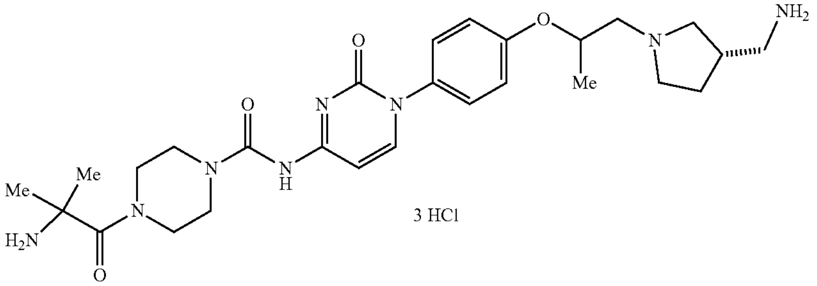 [SMILES: CC(CN1CC[C@@H](CN)C1)Oc1ccc(-n2ccc(NC(=O)N3CCN(C(=O)C(C)(C)N)CC3)nc2=O)cc1] 3 HCl |
| 186 | 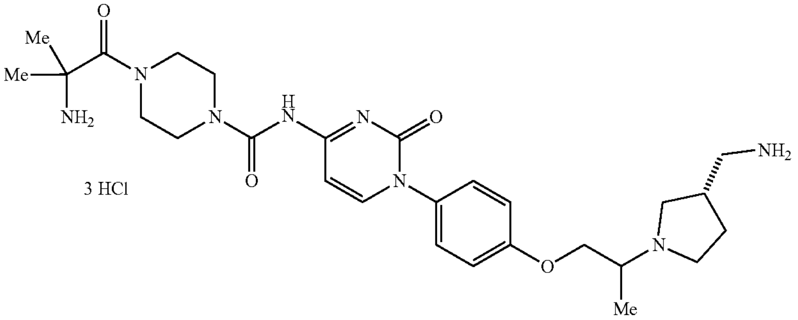 [SMILES: CC(COc1ccc(-n2ccc(NC(=O)N3CCN(C(=O)C(C)(C)N)CC3)nc2=O)cc1)N1CC[C@@H](CN)C1] 3 HCl |
| 187 | 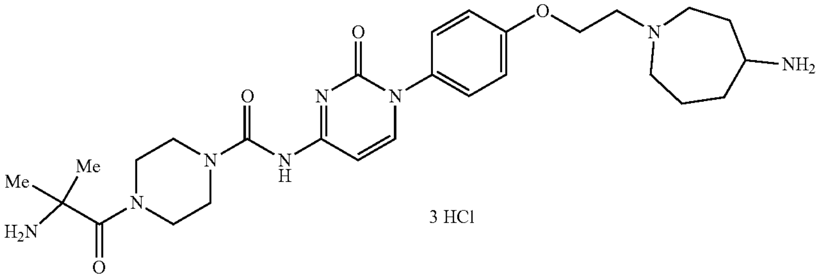 [SMILES: CC(C)(N)C(=O)N1CCN(C(=O)Nc2ccn(-c3ccc(OCCN4CCCC(N)CC4)cc3)c(=O)n2)CC1] 3 HCl |
| 188 | 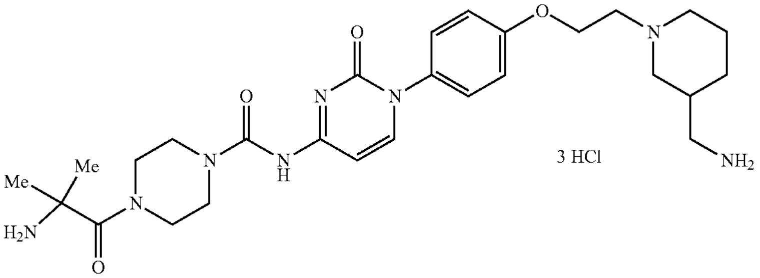 [SMILES: CC(C)(N)C(=O)N1CCN(C(=O)Nc2ccn(-c3ccc(OCCN4CCCC(CN)C4)cc3)c(=O)n2)CC1] 3 HCl |
| 190 | 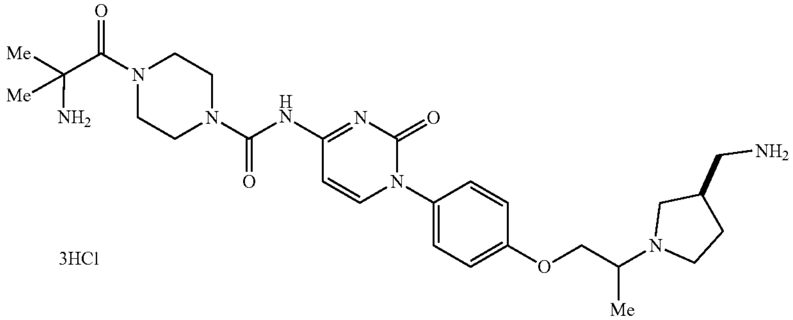 [SMILES: CC(COc1ccc(-n2ccc(NC(=O)N3CCN(C(=O)C(C)(C)N)CC3)nc2=O)cc1)N1CC[C@H](CN)C1] 3HCl |

TABLE 10-continued
| Compounds of Formula I | |
|---|---|
| 191 | 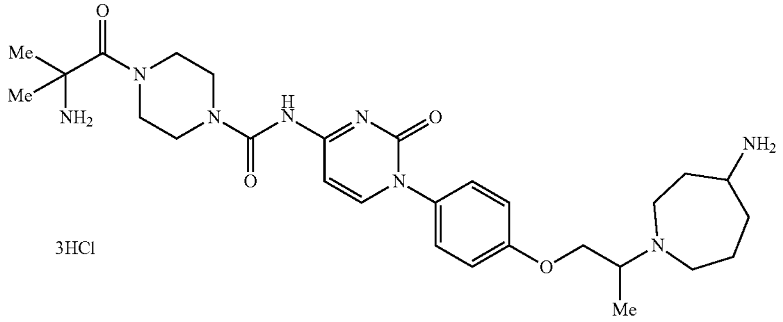 [SMILES: CC(COc1ccc(-n2ccc(NC(=O)N3CCN(C(=O)C(C)(C)N)CC3)nc2=O)cc1)N1CCCC(N)CC1] 3HCl |
| 192 | 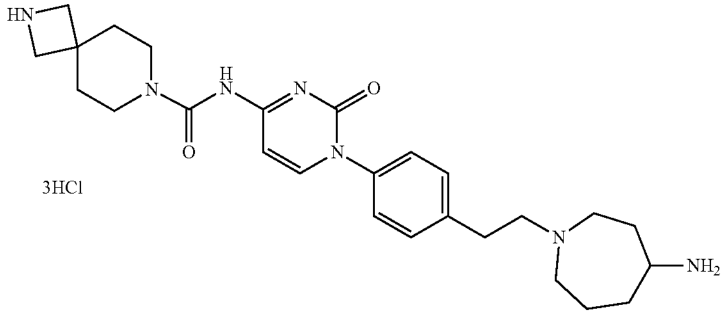 [SMILES: NC1CCCN(CCc2ccc(-n3ccc(NC(=O)N4CCC5(CC4)CNC5)nc3=O)cc2)CC1] 3HCl |
| 193 | 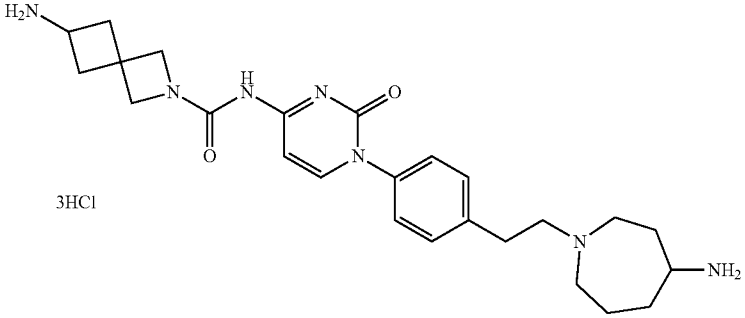 [SMILES: NC1CCCN(CCc2ccc(-n3ccc(NC(=O)N4CC5(CC(N)C5)C4)nc3=O)cc2)CC1] 3HCl |
| 194 | 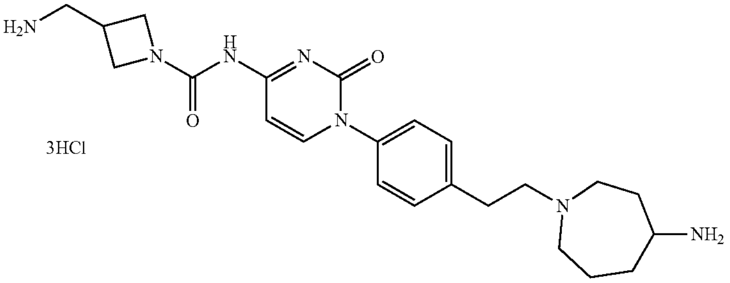 [SMILES: NCC1CN(C(=O)Nc2ccn(-c3ccc(CCN4CCCC(N)CC4)cc3)c(=O)n2)C1] 3HCl |
| 195 | 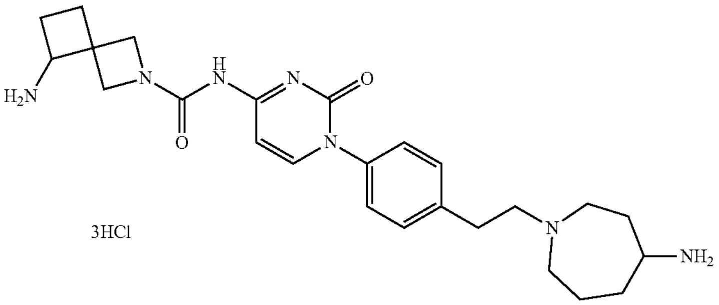 [SMILES: NC1CCCN(CCc2ccc(-n3ccc(NC(=O)N4CC5(CCC5N)C4)nc3=O)cc2)CC1] 3HCl |

TABLE 10-continued
| Compounds of Formula I |
|---|
| 196 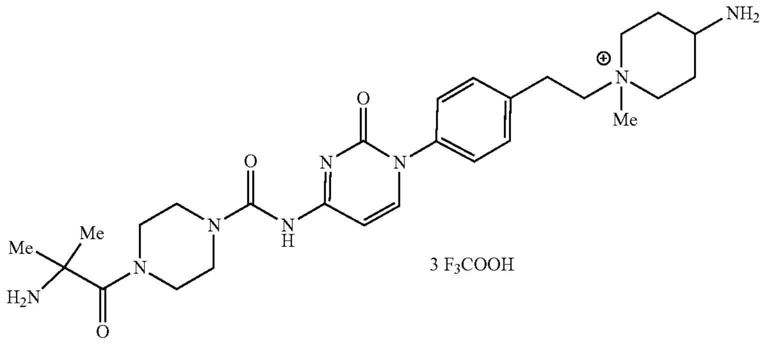 [SMILES: CC(C)(N)C(=O)N1CCN(C(=O)Nc2ccn(-c3ccc(CC[N+]4(C)CCC(N)CC4)cc3)c(=O)n2)CC1] 3 $F_3COOH$ |
| 197 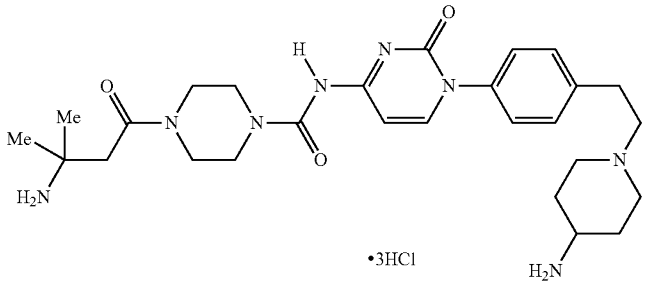 •3HCl |
| 198 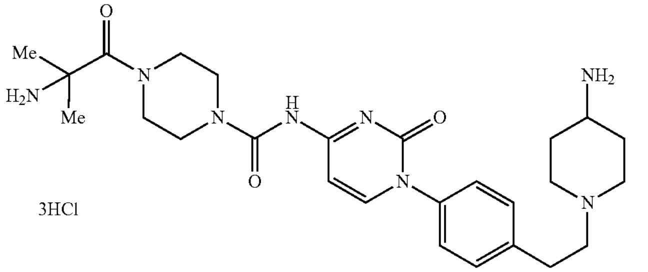 [SMILES: CC(C)(N)C(=O)N1CCN(C(=O)Nc2ccn(-c3ccc(CCN4CCC(N)CC4)cc3)c(=O)n2)CC1] 3HCl |
| 199 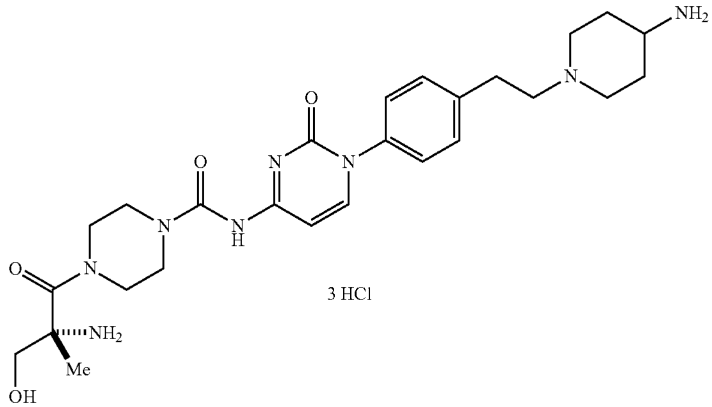 [SMILES: C[C@@](N)(CO)C(=O)N1CCN(C(=O)Nc2ccn(-c3ccc(CCN4CCC(N)CC4)cc3)c(=O)n2)CC1] 3 HCl |

TABLE 10-continued
| Compounds of Formula I | |
|---|---|
| 200 | 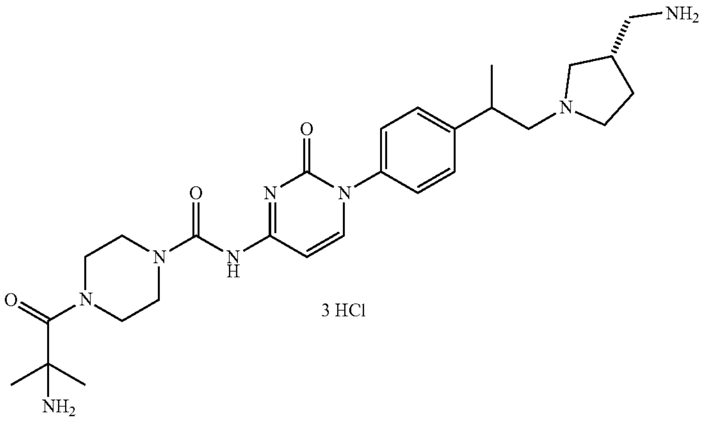 [SMILES: CC(CN1CC[C@@H](CN)C1)c1ccc(-n2ccc(NC(=O)N3CCN(C(=O)C(C)(C)N)CC3)nc2=O)cc1] 3 HCl |
| 201 | 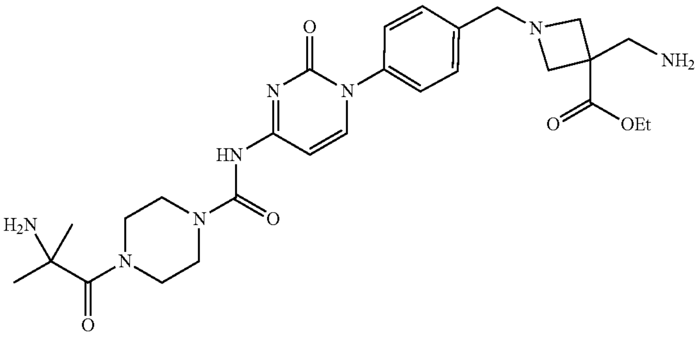 [SMILES: CCOC(=O)C1(CN)CN(Cc2ccc(-n3ccc(NC(=O)N4CCN(C(=O)C(C)(C)N)CC4)nc3=O)cc2)C1] |
| 204 | 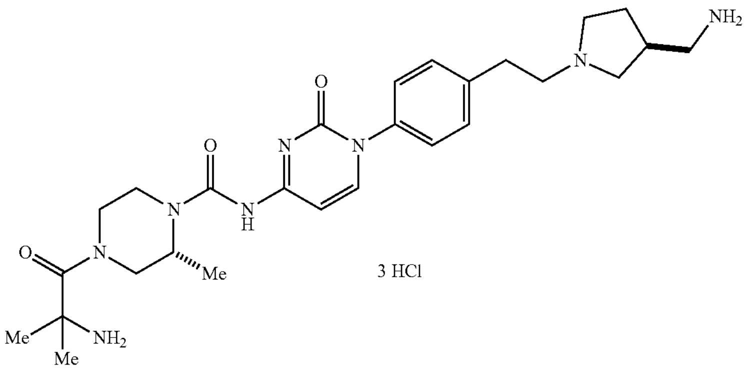 [SMILES: C[C@@H]1CN(C(=O)C(C)(C)N)CCN1C(=O)Nc1ccn(-c2ccc(CCN3CC[C@@H](CN)C3)cc2)c(=O)n1] 3 HCl |
| 205 | 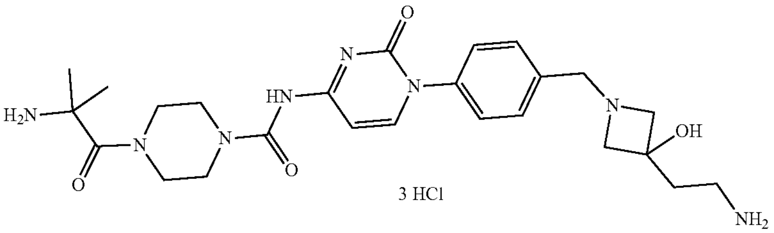 [SMILES: CC(C)(N)C(=O)N1CCN(C(=O)Nc2ccn(-c3ccc(CN4CC(O)(CCN)C4)cc3)c(=O)n2)CC1] 3 HCl |

TABLE 10-continued
Compounds of Formula I
206
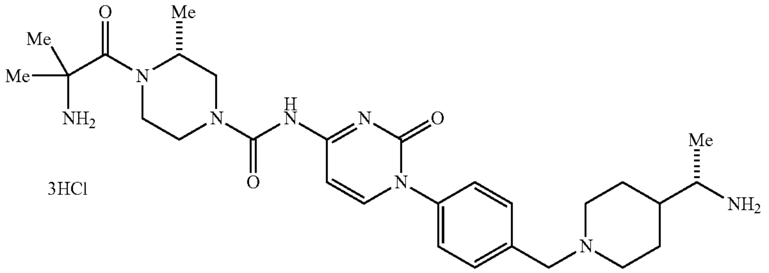 [SMILES: C[C@H](N)C1CCN(Cc2ccc(-n3ccc(NC(=O)N4CCN(C(=O)C(C)(C)N)[C@H](C)C4)nc3=O)cc2)CC1]
207
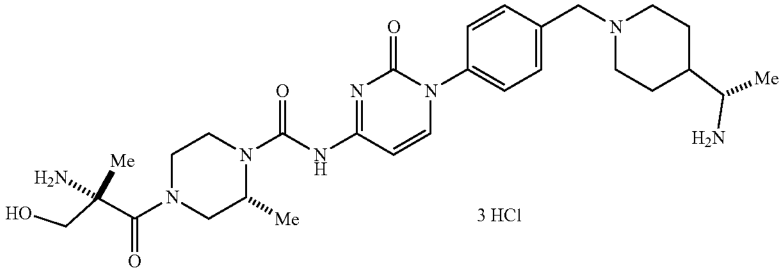 [SMILES: C[C@H](N)C1CCN(Cc2ccc(-n3ccc(NC(=O)N4CCN(C(=O)[C@@](C)(N)CO)C[C@H]4C)nc3=O)cc2)CC1]
208
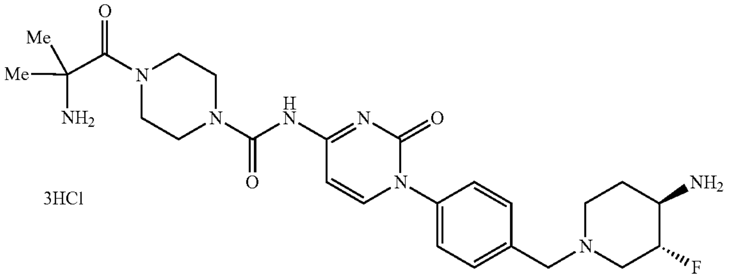 [SMILES: CC(C)(N)C(=O)N1CCN(C(=O)Nc2ccn(-c3ccc(CN4CC[C@@H](N)[C@H](F)C4)cc3)c(=O)n2)CC1]
209
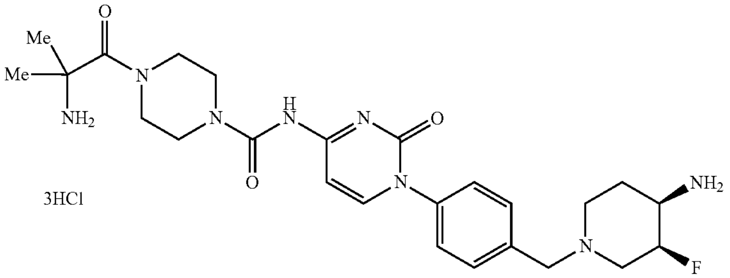 [SMILES: CC(C)(N)C(=O)N1CCN(C(=O)Nc2ccn(-c3ccc(CN4CC[C@@H](N)[C@@H](F)C4)cc3)c(=O)n2)CC1]
210
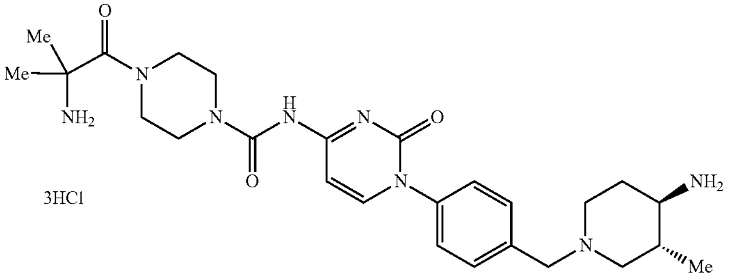 [SMILES: C[C@@H]1CN(Cc2ccc(-n3ccc(NC(=O)N4CCN(C(=O)C(C)(C)N)CC4)nc3=O)cc2)CC[C@H]1N]

TABLE 10-continued
| Compounds of Formula I | |
|---|---|
| 211 | 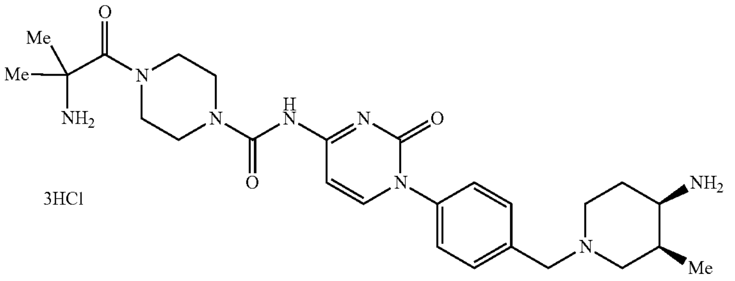 [SMILES: C[C@H]1CN(Cc2ccc(-n3ccc(NC(=O)N4CCN(C(=O)C(C)(C)N)CC4)nc3=O)cc2)CC[C@H]1N] 3HCl |
| 212 | 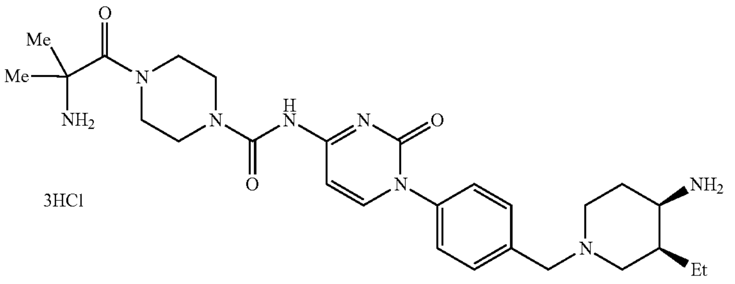 [SMILES: CC[C@H]1CN(Cc2ccc(-n3ccc(NC(=O)N4CCN(C(=O)C(C)(C)N)CC4)nc3=O)cc2)CC[C@H]1N] 3HCl |
| 213 | 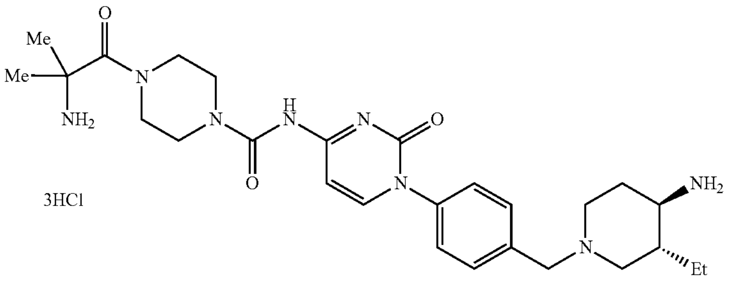 3HCl |
| 214 | 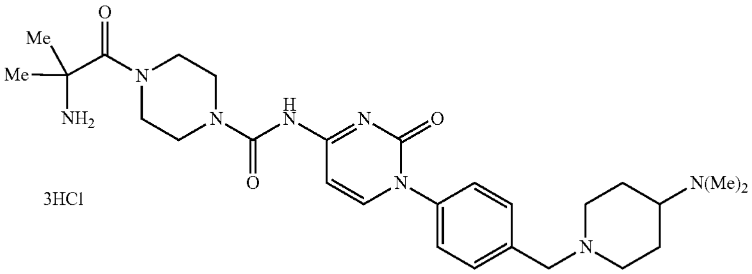 3HCl |
| 215 | 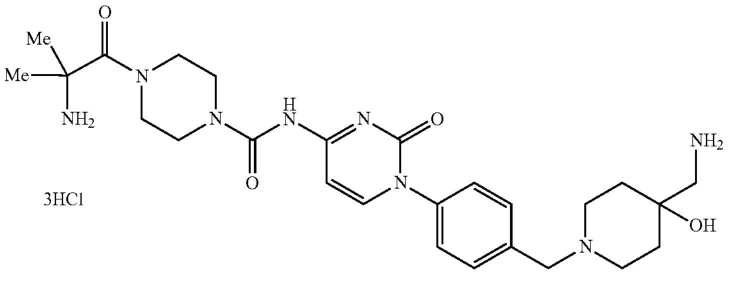 [SMILES: CC(C)(N)C(=O)N1CCN(C(=O)Nc2ccn(-c3ccc(CN4CCC(O)(CN)CC4)cc3)c(=O)n2)CC1] 3HCl |

TABLE 10-continued
| Compounds of Formula I |
|---|
| 216 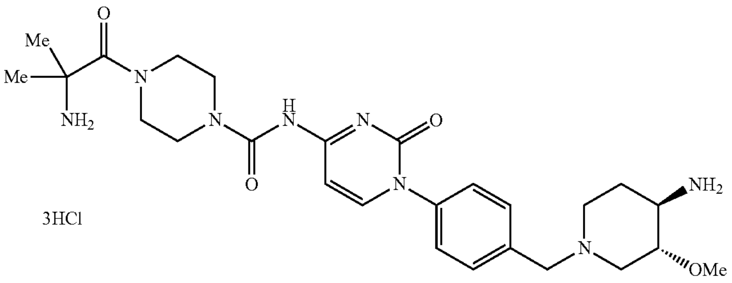 [SMILES: CO[C@@H]1CN(Cc2ccc(-n3ccc(NC(=O)N4CCN(C(=O)C(C)(C)N)CC4)nc3=O)cc2)CC[C@H]1N] 3HCl |
| 217 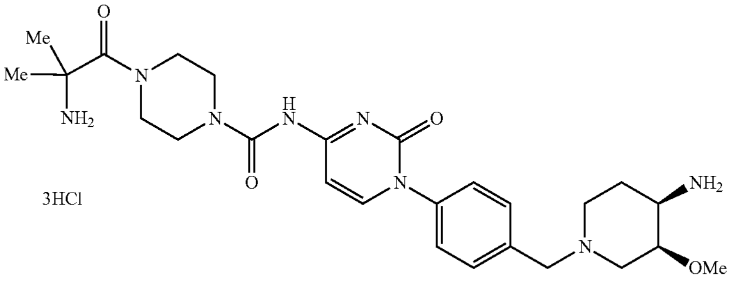 [SMILES: CO[C@H]1CN(Cc2ccc(-n3ccc(NC(=O)N4CCN(C(=O)C(C)(C)N)CC4)nc3=O)cc2)CC[C@H]1N] 3HCl |
| 218 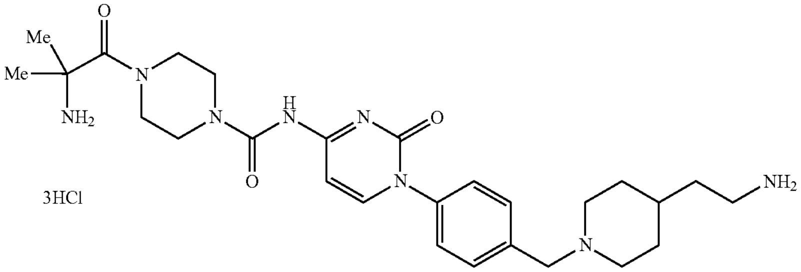 [SMILES: CC(C)(N)C(=O)N1CCN(C(=O)Nc2ccn(-c3ccc(CN4CCC(CCN)CC4)cc3)c(=O)n2)CC1] 3HCl |
| 219 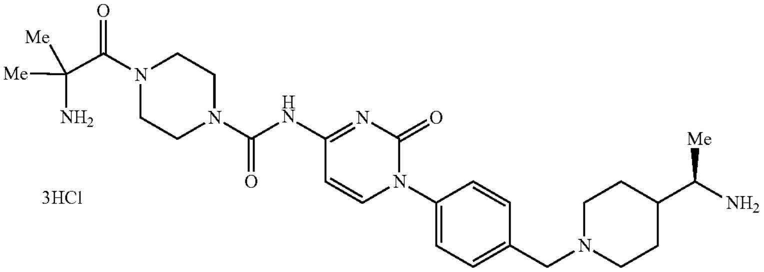 [SMILES: C[C@@H](N)C1CCN(Cc2ccc(-n3ccc(NC(=O)N4CCN(C(=O)C(C)(C)N)CC4)nc3=O)cc2)CC1] 3HCl |
| 220 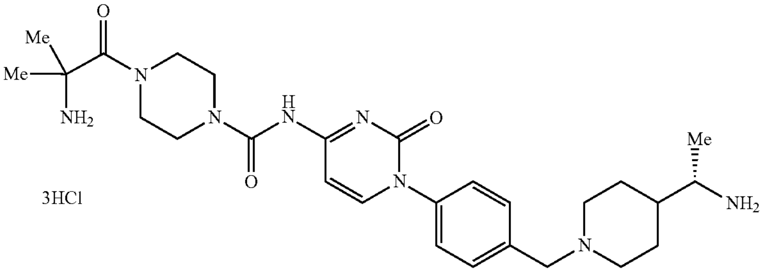 [SMILES: C[C@H](N)C1CCN(Cc2ccc(-n3ccc(NC(=O)N4CCN(C(=O)C(C)(C)N)CC4)nc3=O)cc2)CC1] 3HCl |

TABLE 10-continued
| Compounds of Formula I |
| --- |
| 221 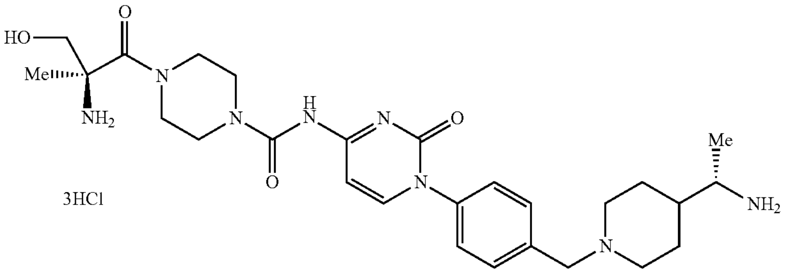 [SMILES: C[C@H](N)C1CCN(Cc2ccc(-n3ccc(NC(=O)N4CCN(C(=O)[C@@](C)(N)CO)CC4)nc3=O)cc2)CC1] 3HCl |
| 222 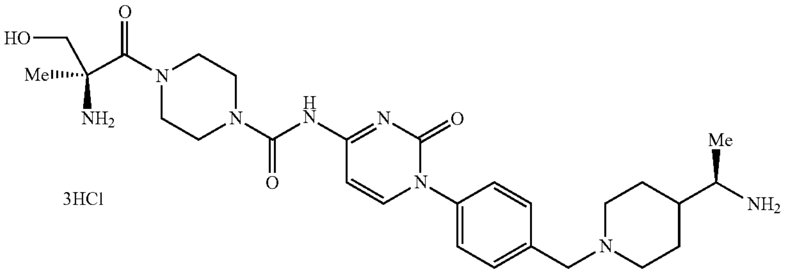 [SMILES: C[C@@H](N)C1CCN(Cc2ccc(-n3ccc(NC(=O)N4CCN(C(=O)[C@@](C)(N)CO)CC4)nc3=O)cc2)CC1] 3HCl |
| 223 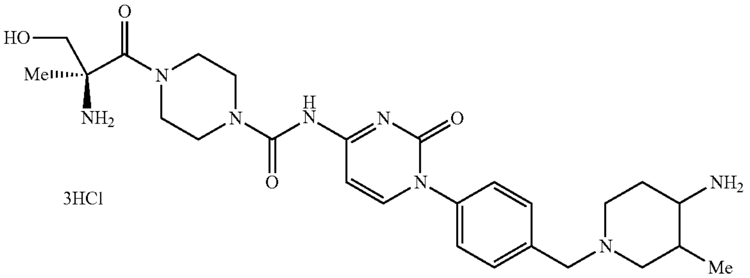 [SMILES: CC1CN(Cc2ccc(-n3ccc(NC(=O)N4CCN(C(=O)[C@@](C)(N)CO)CC4)nc3=O)cc2)CCC1N] 3HCl |
| 224 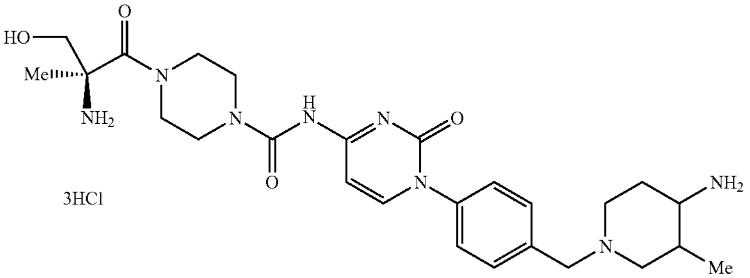 [SMILES: CC1CN(Cc2ccc(-n3ccc(NC(=O)N4CCN(C(=O)[C@@](C)(N)CO)CC4)nc3=O)cc2)CCC1N] 3HCl |
| 225 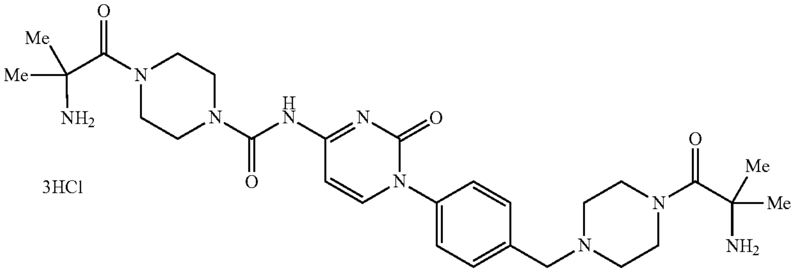 [SMILES: CC(C)(N)C(=O)N1CCN(Cc2ccc(-n3ccc(NC(=O)N4CCN(C(=O)C(C)(C)N)CC4)nc3=O)cc2)CC1] 3HCl |

TABLE 10-continued
| Compounds of Formula I |
| --- |
| 226 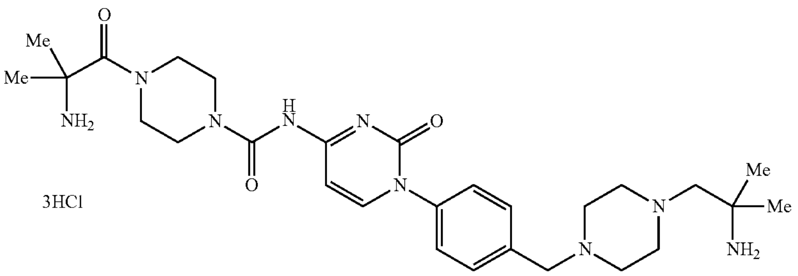 [SMILES: CC(C)(N)CN1CCN(Cc2ccc(-n3ccc(NC(=O)N4CCN(C(=O)C(C)(C)N)CC4)nc3=O)cc2)CC1] 3HCl |
| 227 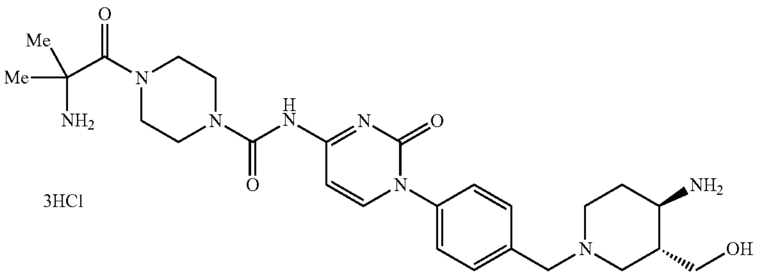 [SMILES: CC(C)(N)C(=O)N1CCN(C(=O)Nc2ccn(-c3ccc(CN4CC[C@@H](N)[C@H](CO)C4)cc3)c(=O)n2)CC1] 3HCl |
| 230 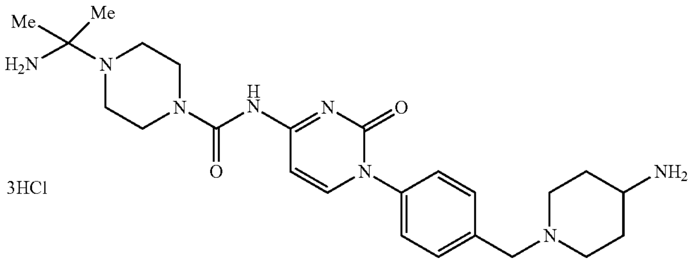 [SMILES: CC(C)(N)N1CCN(C(=O)Nc2ccn(-c3ccc(CN4CCC(N)CC4)cc3)c(=O)n2)CC1] 3HCl |
| 231 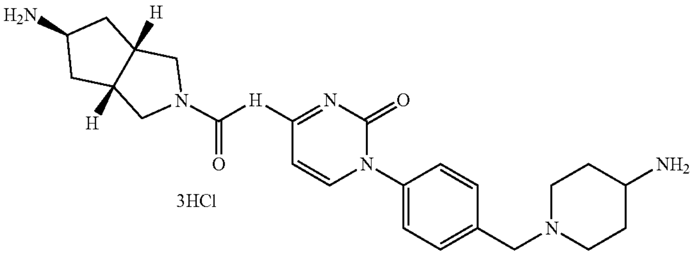 3HCl |
| 233 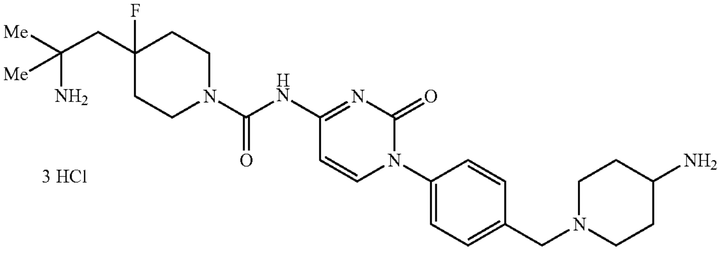 [SMILES: CC(C)(N)CC1(F)CCN(C(=O)Nc2ccn(-c3ccc(CN4CCC(N)CC4)cc3)c(=O)n2)CC1] 3 HCl |

TABLE 10-continued
| Compounds of Formula I |
|---|
| 234 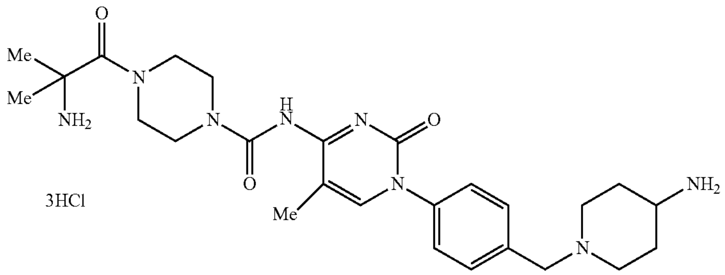 [SMILES: Cc1cn(-c2ccc(CN3CCC(N)CC3)cc2)c(=O)nc1NC(=O)N1CCN(C(=O)C(C)(C)N)CC1] 3HCl |
| 235 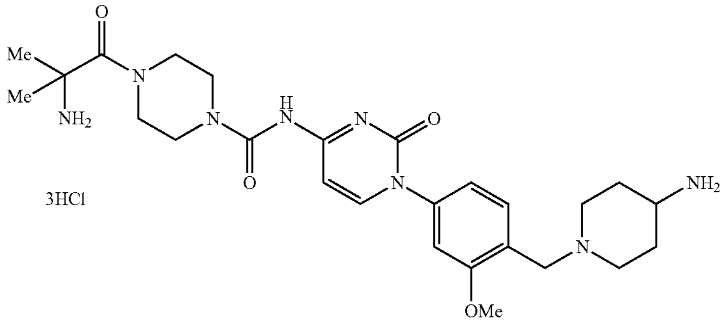 [SMILES: COc1cc(-n2ccc(NC(=O)N3CCN(C(=O)C(C)(C)N)CC3)nc2=O)ccc1CN1CCC(N)CC1] 3HCl |
| 236 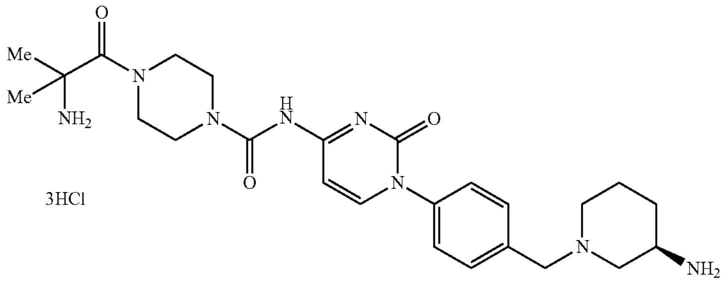 [SMILES: CC(C)(N)C(=O)N1CCN(C(=O)Nc2ccn(-c3ccc(CN4CCC[C@@H](N)C4)cc3)c(=O)n2)CC1] 3HCl |
| 237 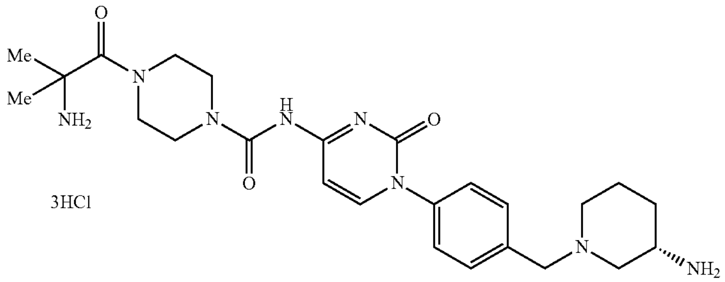 [SMILES: CC(C)(N)C(=O)N1CCN(C(=O)Nc2ccn(-c3ccc(CN4CCC[C@H](N)C4)cc3)c(=O)n2)CC1] 3HCl |
| 238 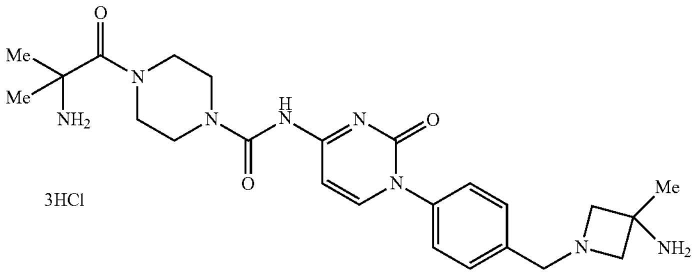 [SMILES: CC1(N)CN(Cc2ccc(-n3ccc(NC(=O)N4CCN(C(=O)C(C)(C)N)CC4)nc3=O)cc2)C1] 3HCl |

TABLE 10-continued
| Compounds of Formula I | |
|---|---|
| 239 | 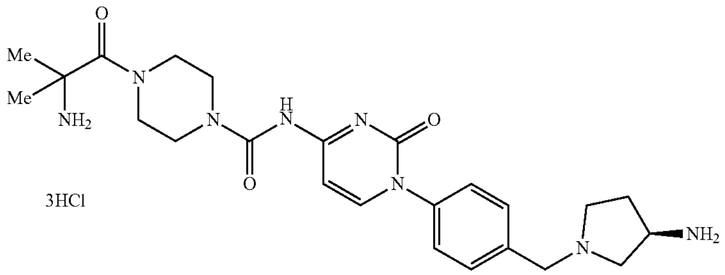 [SMILES: CC(C)(N)C(=O)N1CCN(C(=O)Nc2ccn(-c3ccc(CN4CC[C@@H](N)C4)cc3)c(=O)n2)CC1] |
| 240 | 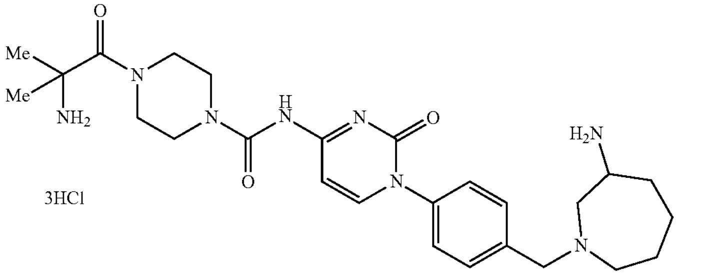 [SMILES: CC(C)(N)C(=O)N1CCN(C(=O)Nc2ccn(-c3ccc(CN4CCCCC(N)C4)cc3)c(=O)n2)CC1] |
| 241 | 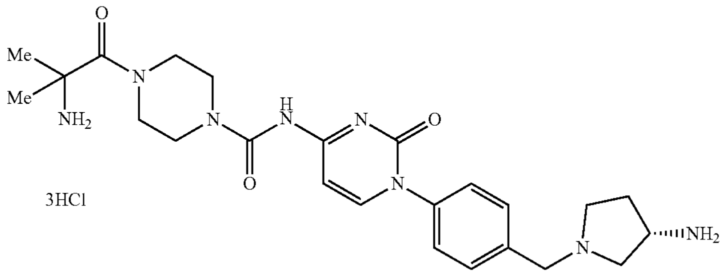 [SMILES: CC(C)(N)C(=O)N1CCN(C(=O)Nc2ccn(-c3ccc(CN4CC[C@H](N)C4)cc3)c(=O)n2)CC1] |
| 242 | 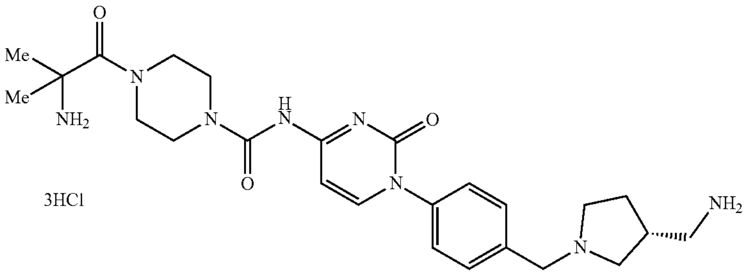 [SMILES: CC(C)(N)C(=O)N1CCN(C(=O)Nc2ccn(-c3ccc(CN4CC[C@H](CN)C4)cc3)c(=O)n2)CC1] |
| 243 | 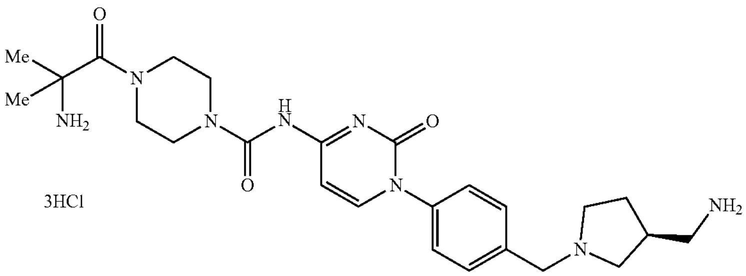 [SMILES: CC(C)(N)C(=O)N1CCN(C(=O)Nc2ccn(-c3ccc(CN4CC[C@@H](CN)C4)cc3)c(=O)n2)CC1] |

TABLE 10-continued
| Compounds of Formula I |
|---|
| 244 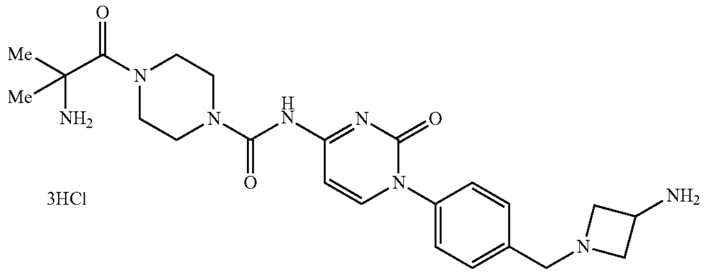 [SMILES: CC(C)(N)C(=O)N1CCN(C(=O)Nc2ccn(-c3ccc(CN4CC(N)C4)cc3)c(=O)n2)CC1] 3HCl |
| 245 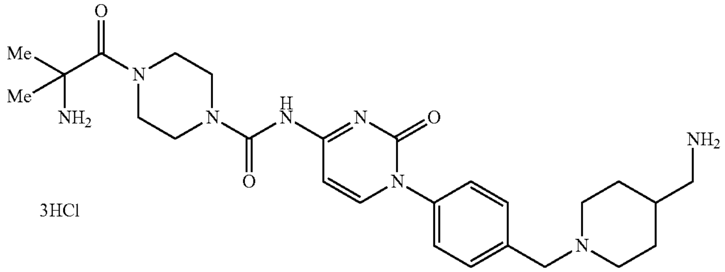 [SMILES: CC(C)(N)C(=O)N1CCN(C(=O)Nc2ccn(-c3ccc(CN4CCC(CN)CC4)cc3)c(=O)n2)CC1] 3HCl |
| 246 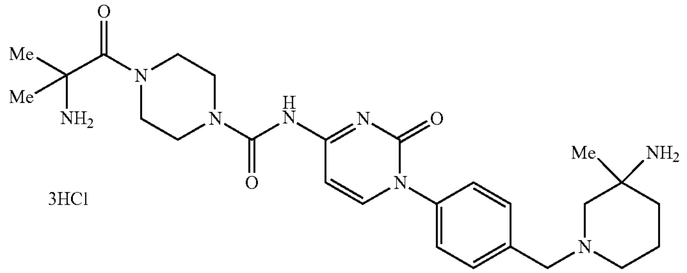 [SMILES: CC1(N)CCCN(Cc2ccc(-n3ccc(NC(=O)N4CCN(C(=O)C(C)(C)N)CC4)nc3=O)cc2)C1] 3HCl |
| 247 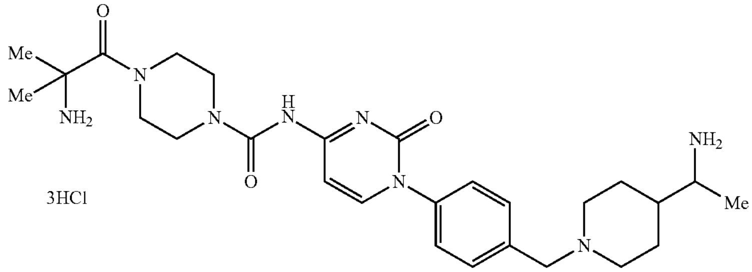 [SMILES: CC(N)C1CCN(Cc2ccc(-n3ccc(NC(=O)N4CCN(C(=O)C(C)(C)N)CC4)nc3=O)cc2)CC1] 3HCl |
| 248 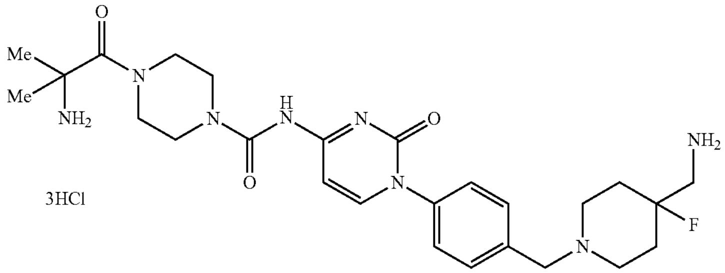 [SMILES: CC(C)(N)C(=O)N1CCN(C(=O)Nc2ccn(-c3ccc(CN4CCC(F)(CN)CC4)cc3)c(=O)n2)CC1] 3HCl |

TABLE 10-continued
| Compounds of Formula I | |
|---|---|
| 249 | 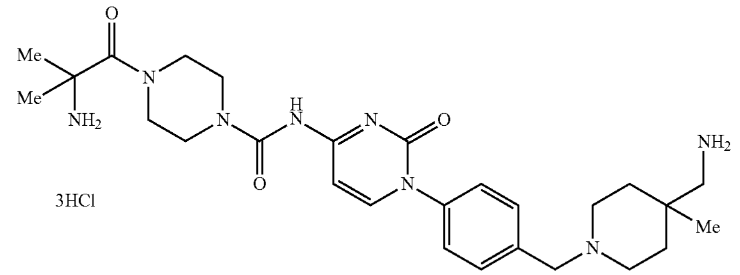 [SMILES: CC1(CN)CCN(Cc2ccc(-n3ccc(NC(=O)N4CCN(C(=O)C(C)(C)N)CC4)nc3=O)cc2)CC1] |
| 250 | 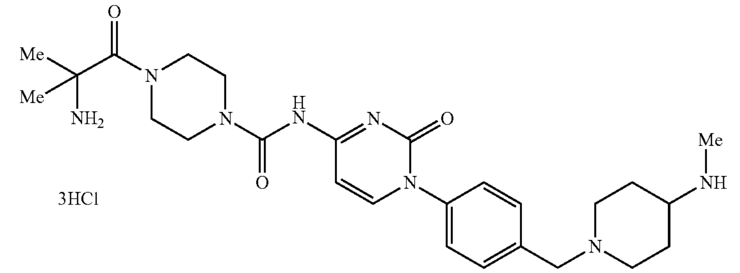 [SMILES: CNC1CCN(Cc2ccc(-n3ccc(NC(=O)N4CCN(C(=O)C(C)(C)N)CC4)nc3=O)cc2)CC1] |
| 251 | 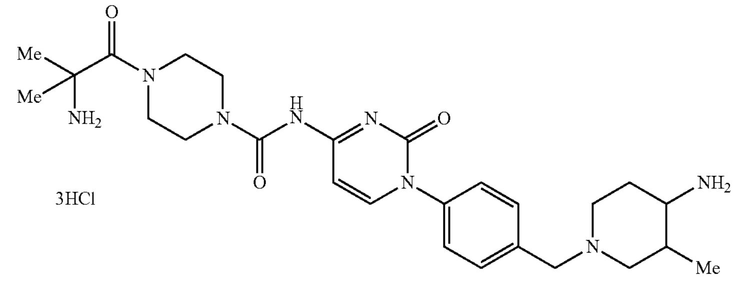 [SMILES: CC1CN(Cc2ccc(-n3ccc(NC(=O)N4CCN(C(=O)C(C)(C)N)CC4)nc3=O)cc2)CCC1N] |
| 252 | 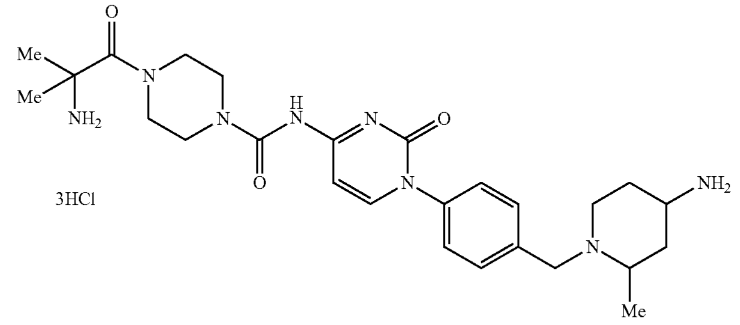 [SMILES: CC1CC(N)CCN1Cc1ccc(-n2ccc(NC(=O)N3CCN(C(=O)C(C)(C)N)CC3)nc2=O)cc1] |
| 253 | 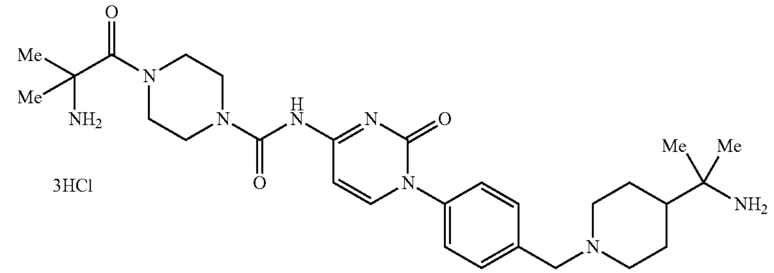 [SMILES: CC(C)(N)C(=O)N1CCN(C(=O)Nc2ccn(-c3ccc(CN4CCC(C(C)(C)N)CC4)cc3)c(=O)n2)CC1] |

TABLE 10-continued
| Compounds of Formula I | |
|---|---|
| 254 | 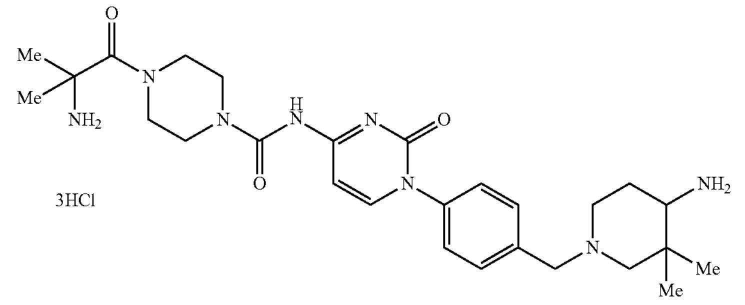 [SMILES: CC(C)(N)C(=O)N1CCN(C(=O)Nc2ccn(-c3ccc(CN4CCC(N)C(C)(C)C4)cc3)c(=O)n2)CC1] |
| 255 | 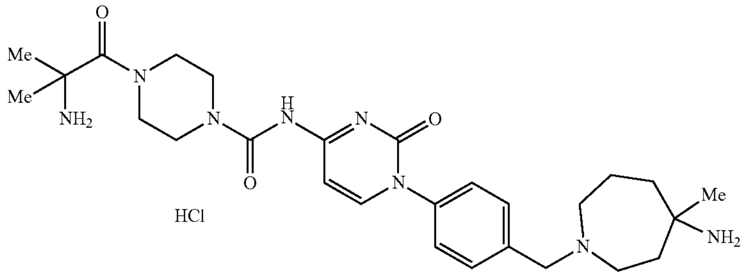 [SMILES: CC1(N)CCCN(Cc2ccc(-n3ccc(NC(=O)N4CCN(C(=O)C(C)(C)N)CC4)nc3=O)cc2)CC1 ; Cl] |
| 265 | 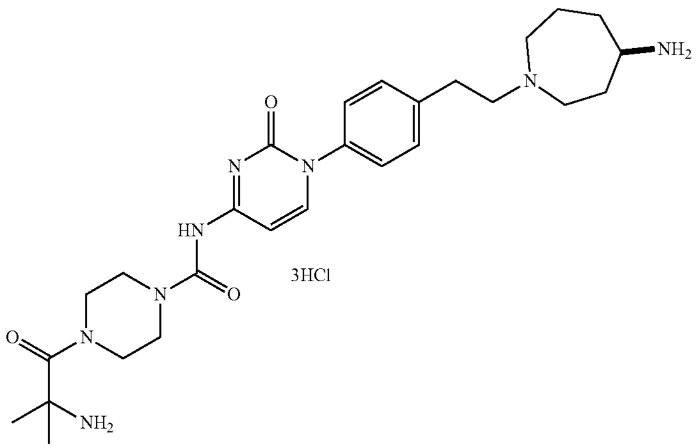 [SMILES: CC(C)(N)C(=O)N1CCN(C(=O)Nc2ccn(-c3ccc(CCN4CCC[C@@H](N)CC4)cc3)c(=O)n2)CC1] |
| 266 | 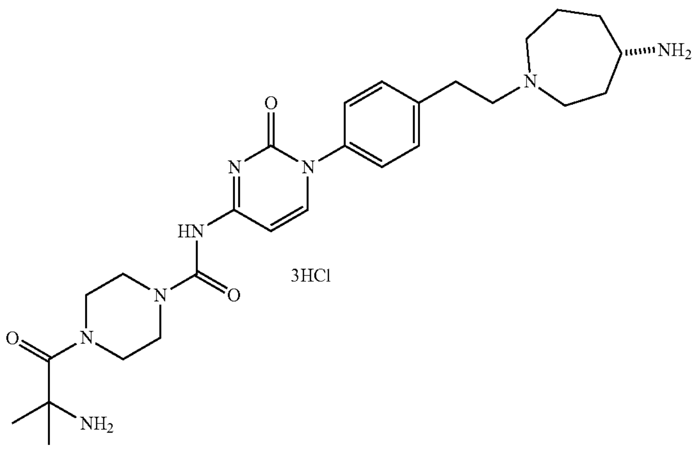 [SMILES: CC(C)(N)C(=O)N1CCN(C(=O)Nc2ccn(-c3ccc(CCN4CCC[C@H](N)CC4)cc3)c(=O)n2)CC1] |

TABLE 10-continued
| Compounds of Formula I |
|---|
| 267 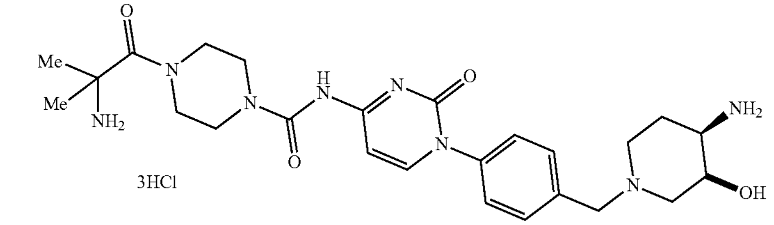 3HCl |
| 268 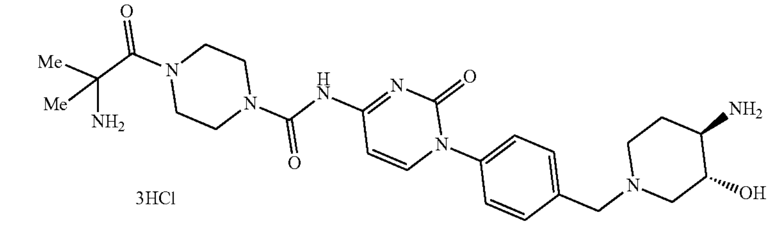 [SMILES: CC(C)(N)C(=O)N1CCN(C(=O)Nc2ccn(-c3ccc(CN4CC[C@@H](N)[C@H](O)C4)cc3)c(=O)n2)CC1] 3HCl |
| 269 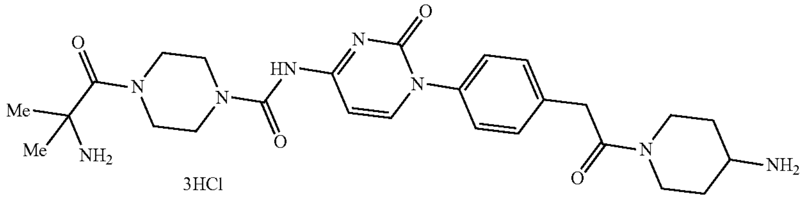 [SMILES: CC(C)(N)C(=O)N1CCN(C(=O)Nc2ccn(-c3ccc(CC(=O)N4CCC(N)CC4)cc3)c(=O)n2)CC1] 3HCl |
| No. | Free Base Structure |
|---|---|
| 1 | 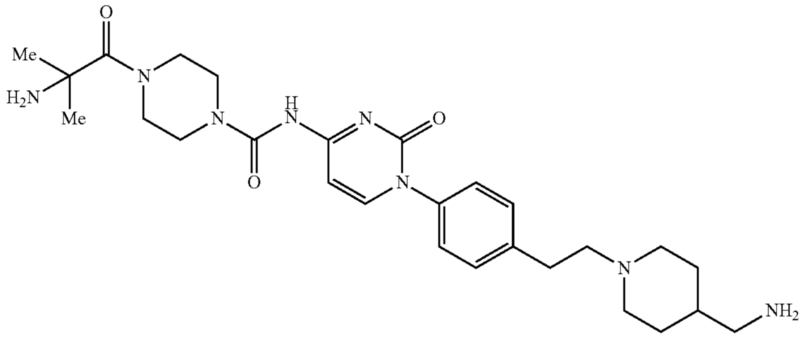 [SMILES: CC(C)(N)C(=O)N1CCN(C(=O)Nc2ccn(-c3ccc(CCN4CCC(CN)CC4)cc3)c(=O)n2)CC1] |
| 2 | 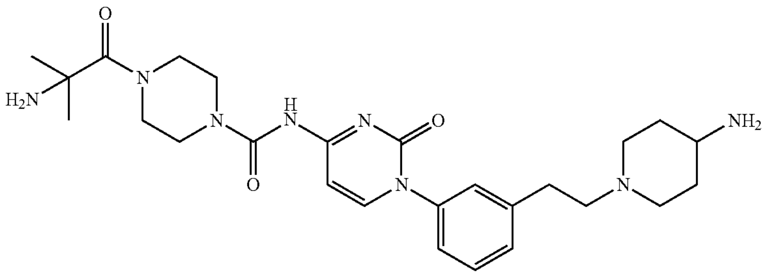 [SMILES: CC(C)(N)C(=O)N1CCN(C(=O)Nc2ccn(-c3cccc(CCN4CCC(N)CC4)c3)c(=O)n2)CC1] |

TABLE 10-continued
| Compounds of Formula I |
|---|
| 3 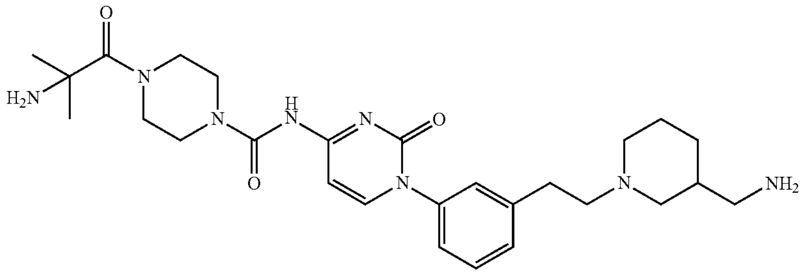 [SMILES: CC(C)(N)C(=O)N1CCN(C(=O)Nc2ccn(-c3cccc(CCN4CCCC(CN)C4)c3)c(=O)n2)CC1] |
| 4 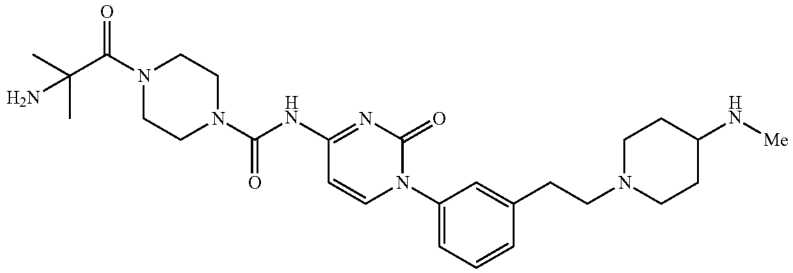 [SMILES: CNC1CCN(CCc2cccc(-n3ccc(NC(=O)N4CCN(C(=O)C(C)(C)N)CC4)nc3=O)c2)CC1] |
| 5 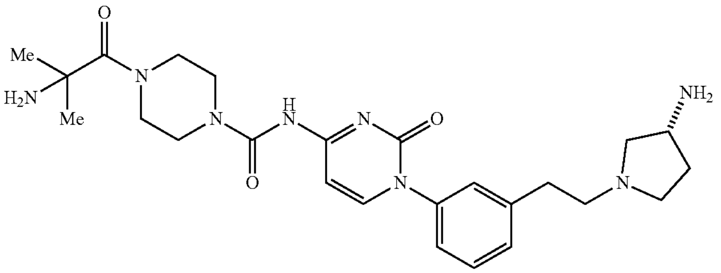 [SMILES: CC(C)(N)C(=O)N1CCN(C(=O)Nc2ccn(-c3cccc(CCN4CC[C@@H](N)C4)c3)c(=O)n2)CC1] |
| 6 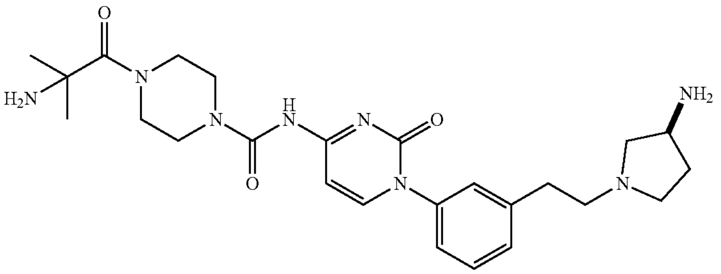 [SMILES: CC(C)(N)C(=O)N1CCN(C(=O)Nc2ccn(-c3cccc(CCN4CC[C@H](N)C4)c3)c(=O)n2)CC1] |
| 7 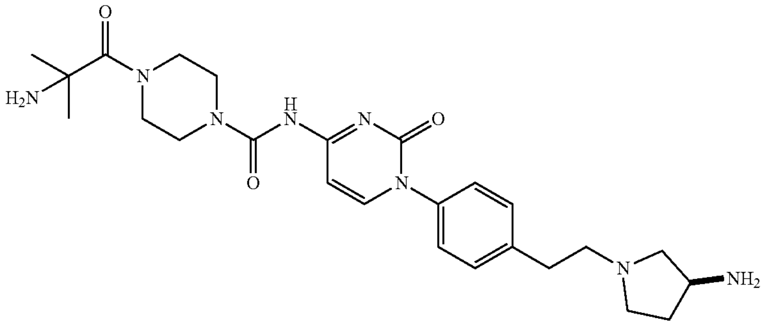 [SMILES: CC(C)(N)C(=O)N1CCN(C(=O)Nc2ccn(-c3ccc(CCN4CC[C@H](N)C4)cc3)c(=O)n2)CC1] |

TABLE 10-continued
| Compounds of Formula I |
|---|
| 8 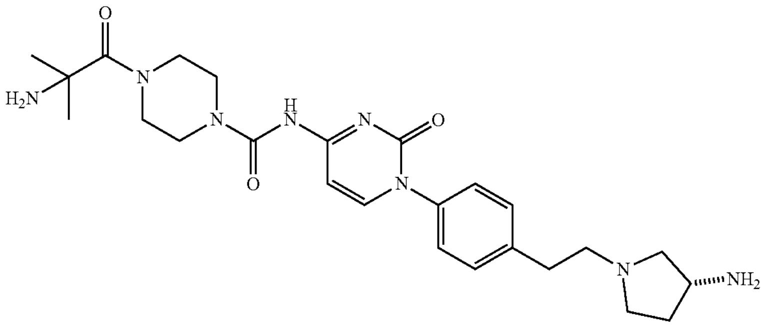 [SMILES: CC(C)(N)C(=O)N1CCN(C(=O)Nc2ccn(-c3ccc(CCN4CC[C@@H](N)C4)cc3)c(=O)n2)CC1] |
| 9 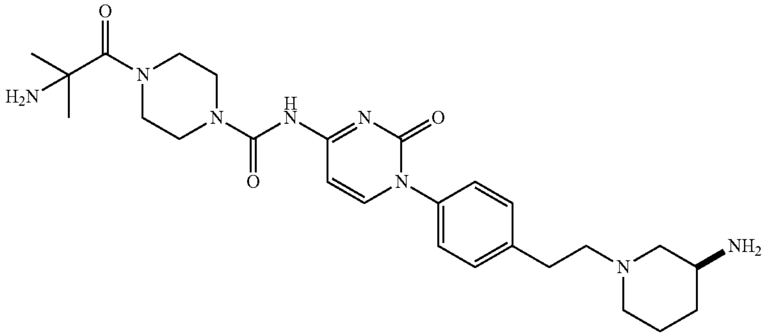 [SMILES: CC(C)(N)C(=O)N1CCN(C(=O)Nc2ccn(-c3ccc(CCN4CCC[C@H](N)C4)cc3)c(=O)n2)CC1] |
| 10 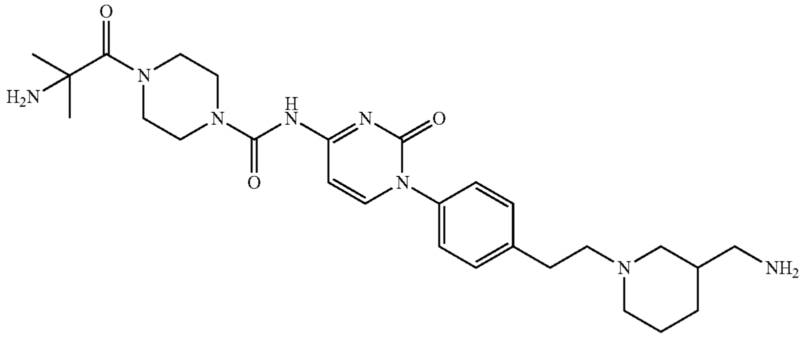 [SMILES: CC(C)(N)C(=O)N1CCN(C(=O)Nc2ccn(-c3ccc(CCN4CCCC(CN)C4)cc3)c(=O)n2)CC1] |
| 11 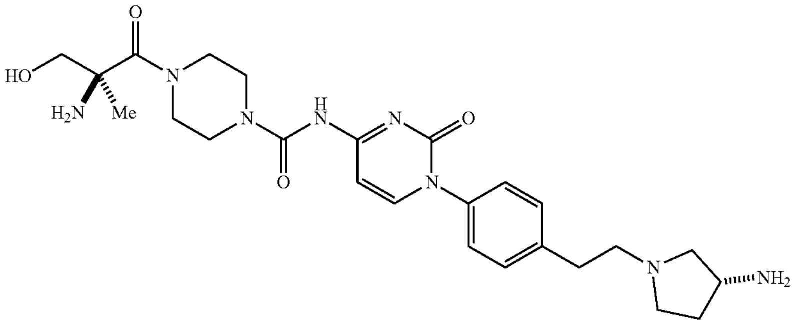 [SMILES: C[C@](N)(CO)C(=O)N1CCN(C(=O)Nc2ccn(-c3ccc(CCN4CC[C@@H](N)C4)cc3)c(=O)n2)CC1] |

TABLE 10-continued
| Compounds of Formula I |
|---|
| 12 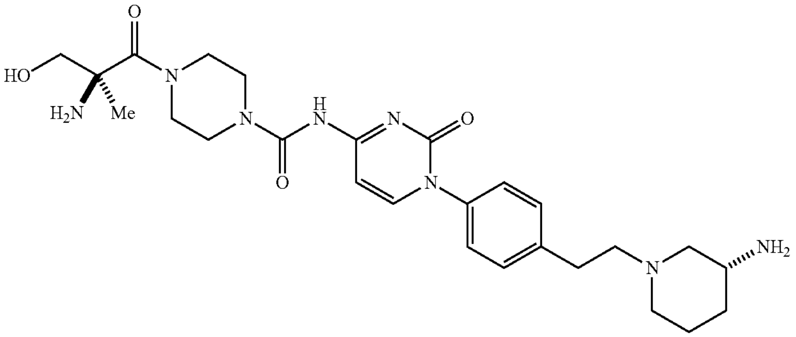 [SMILES: C[C@](N)(CO)C(=O)N1CCN(C(=O)Nc2ccn(-c3ccc(CCN4CCC[C@@H](N)C4)cc3)c(=O)n2)CC1] |
| 13 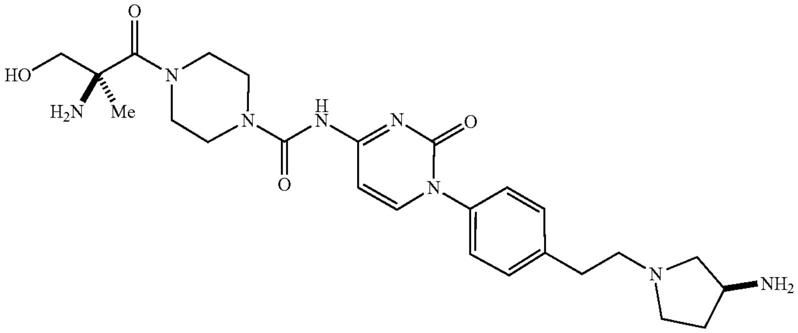 [SMILES: C[C@](N)(CO)C(=O)N1CCN(C(=O)Nc2ccn(-c3ccc(CCN4CC[C@H](N)C4)cc3)c(=O)n2)CC1] |
| 14 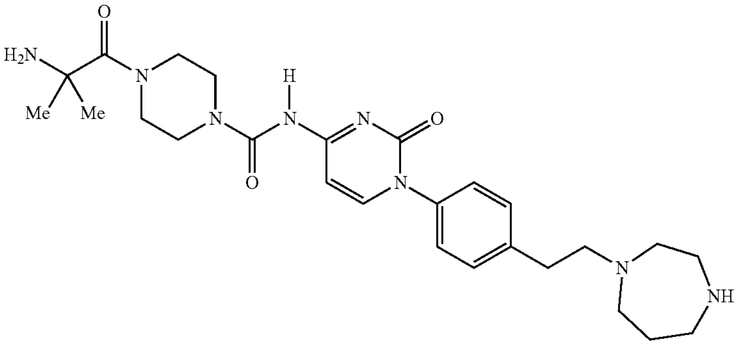 [SMILES: CC(C)(N)C(=O)N1CCN(C(=O)Nc2ccn(-c3ccc(CCN4CCCNCC4)cc3)c(=O)n2)CC1] |
| 15 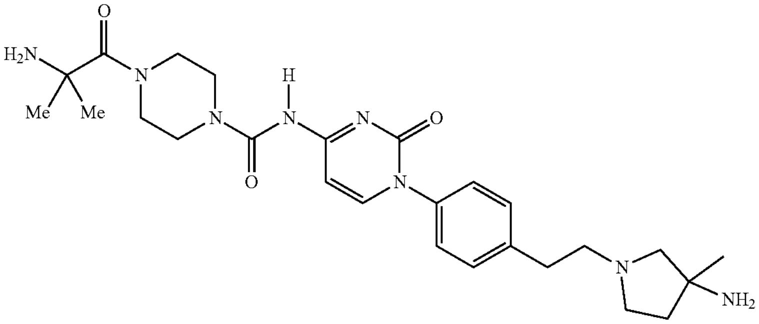 [SMILES: CC1(N)CCN(CCc2ccc(-n3ccc(NC(=O)N4CCN(C(=O)C(C)(C)N)CC4)nc3=O)cc2)C1] |

TABLE 10-continued
| Compounds of Formula I |
|---|
| 16 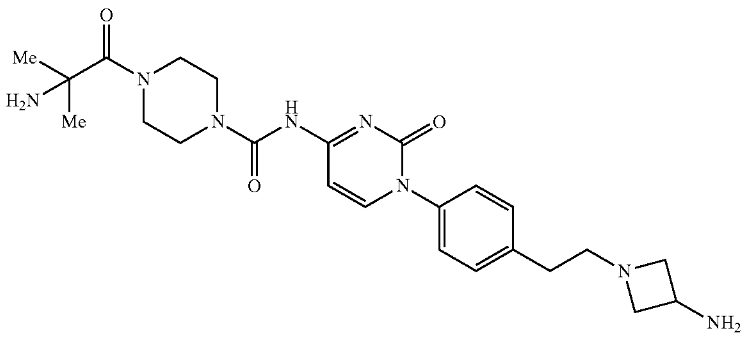 [SMILES: CC(C)(N)C(=O)N1CCN(C(=O)Nc2ccn(-c3ccc(CCN4CC(N)C4)cc3)c(=O)n2)CC1] |
| 17 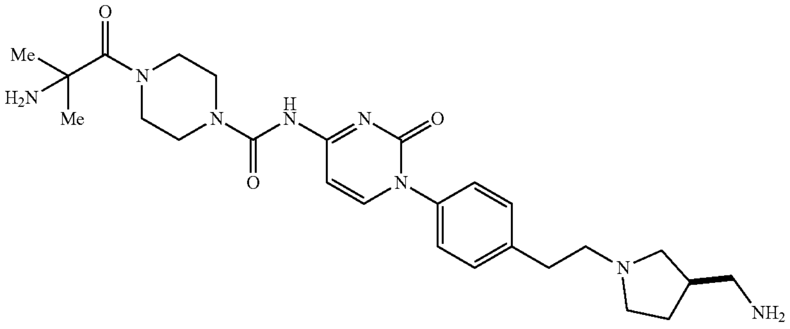 |
| 18 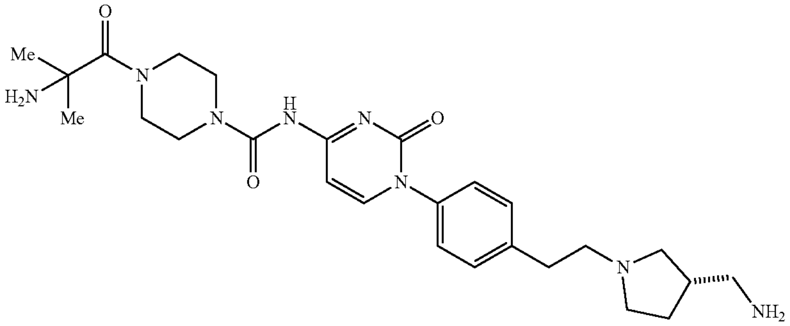 [SMILES: CC(C)(N)C(=O)N1CCN(C(=O)Nc2ccn(-c3ccc(CCN4CC[C@@H](CN)C4)cc3)c(=O)n2)CC1] |
| 21 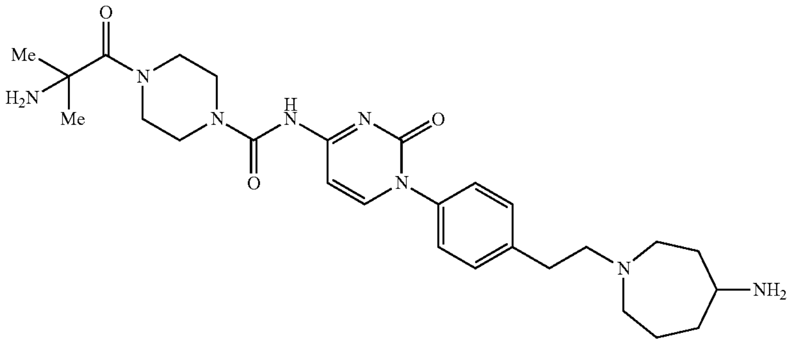 [SMILES: CC(C)(N)C(=O)N1CCN(C(=O)Nc2ccn(-c3ccc(CCN4CCCC(N)CC4)cc3)c(=O)n2)CC1] |

TABLE 10-continued
| Compounds of Formula I |
|---|
| 22 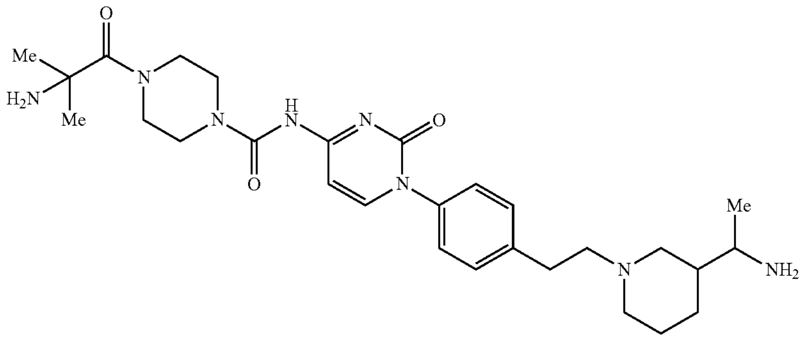 [SMILES: CC(N)C1CCCN(CCc2ccc(-n3ccc(NC(=O)N4CCN(C(=O)C(C)(C)N)CC4)nc3=O)cc2)C1] |
| 23 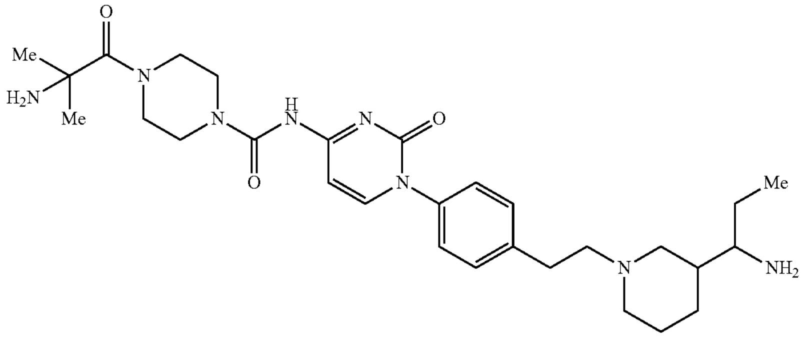 [SMILES: CCC(N)C1CCCN(CCc2ccc(-n3ccc(NC(=O)N4CCN(C(=O)C(C)(C)N)CC4)nc3=O)cc2)C1] |
| 24 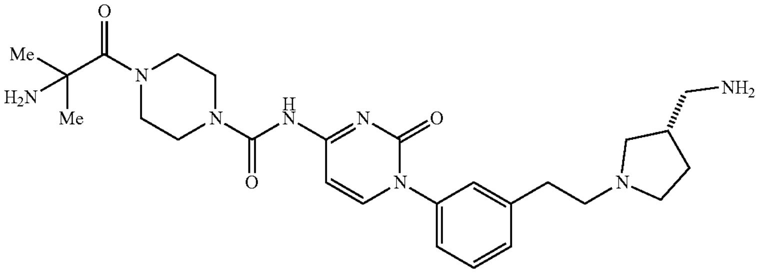 [SMILES: CC(C)(N)C(=O)N1CCN(C(=O)Nc2ccn(-c3cccc(CCN4CC[C@@H](CN)C4)c3)c(=O)n2)CC1] |
| 25 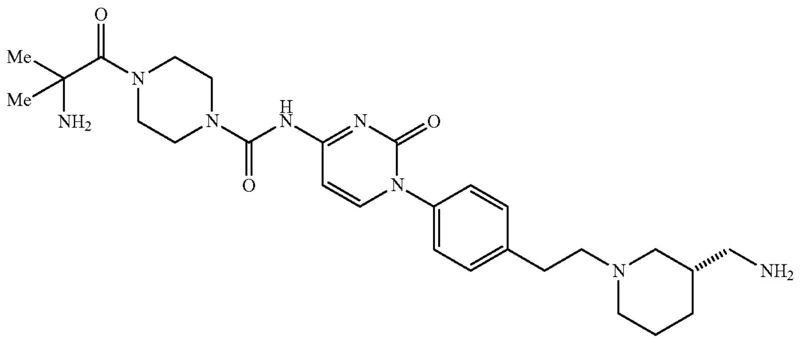 [SMILES: CC(C)(N)C(=O)N1CCN(C(=O)Nc2ccn(-c3ccc(CCN4CCC[C@@H](CN)C4)cc3)c(=O)n2)CC1] |

TABLE 10-continued
| Compounds of Formula I |
|---|
26
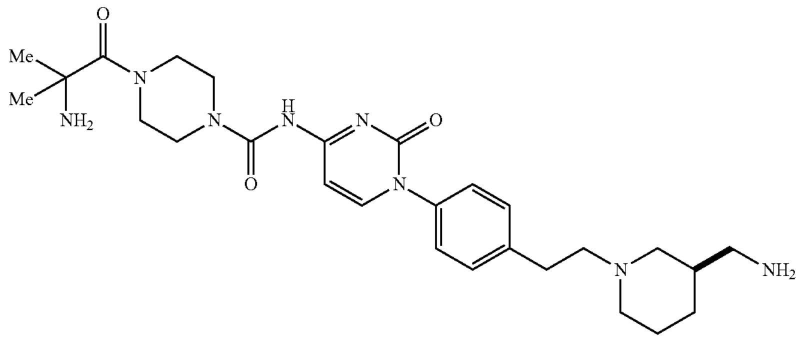 [SMILES: CC(C)(N)C(=O)N1CCN(C(=O)Nc2ccn(-c3ccc(CCN4CCC[C@H](CN)C4)cc3)c(=O)n2)CC1]
27
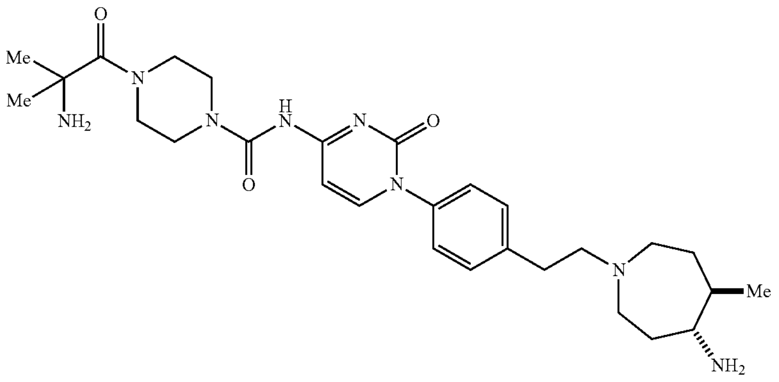 [SMILES: C[C@@H]1CCN(CCc2ccc(-n3ccc(NC(=O)N4CCN(C(=O)C(C)(C)N)CC4)nc3=O)cc2)CC[C@H]1N]
28
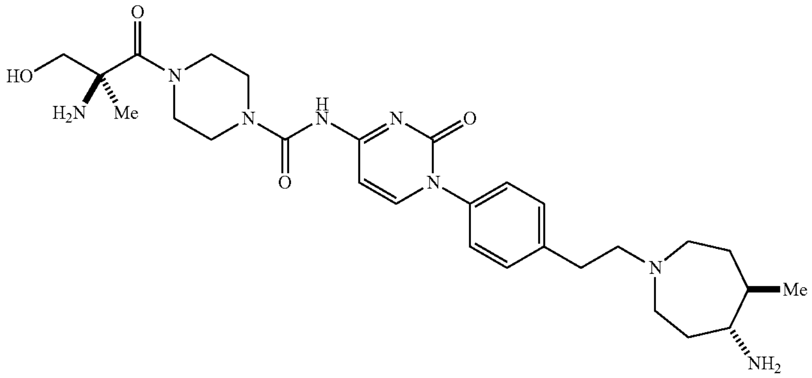 [SMILES: C[C@@H]1CCN(CCc2ccc(-n3ccc(NC(=O)N4CCN(C(=O)[C@@](C)(N)CO)CC4)nc3=O)cc2)CC[C@H]1N]
29
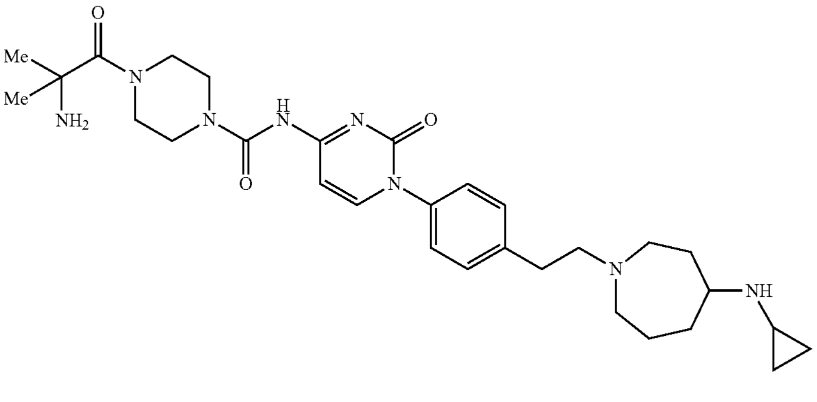 [SMILES: CC(C)(N)C(=O)N1CCN(C(=O)Nc2ccn(-c3ccc(CCN4CCCC(NC5CC5)CC4)cc3)c(=O)n2)CC1]

TABLE 10-continued
| Compounds of Formula I | |
|---|---|
| 30 | 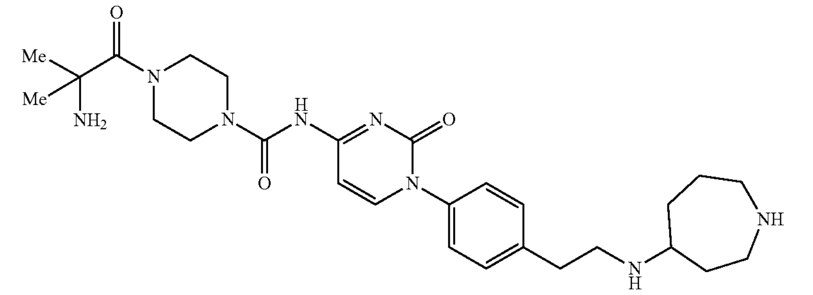 [SMILES: CC(C)(N)C(=O)N1CCN(C(=O)Nc2ccn(-c3ccc(CCNC4CCCNCC4)cc3)c(=O)n2)CC1] |
| 31 | 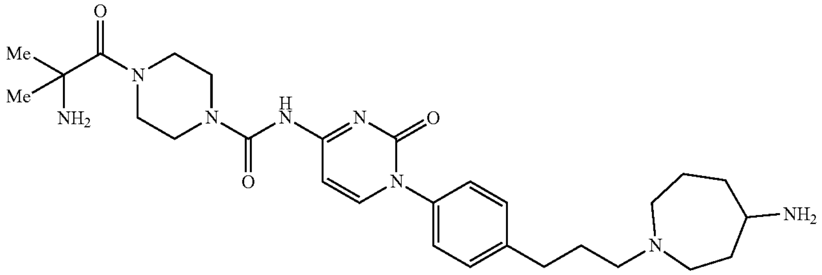 [SMILES: CC(C)(N)C(=O)N1CCN(C(=O)Nc2ccn(-c3ccc(CCCN4CCCC(N)CC4)cc3)c(=O)n2)CC1] |
| 32 | 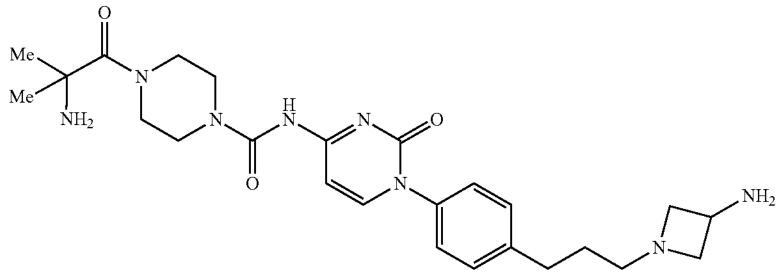 [SMILES: CC(C)(N)C(=O)N1CCN(C(=O)Nc2ccn(-c3ccc(CCCN4CC(N)C4)cc3)c(=O)n2)CC1] |
| 33 | 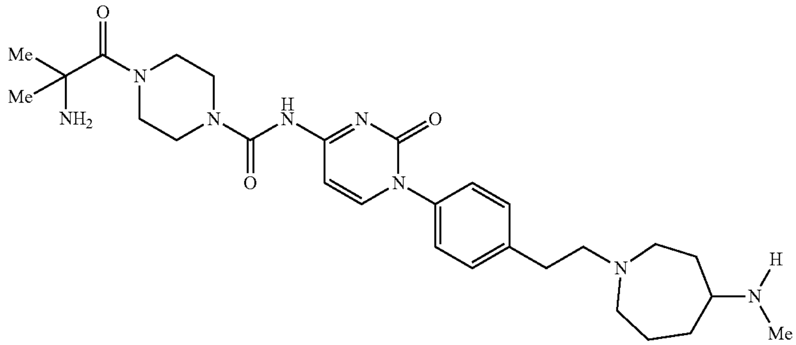 [SMILES: CNC1CCCN(CCc2ccc(-n3ccc(NC(=O)N4CCN(C(=O)C(C)(C)N)CC4)nc3=O)cc2)CC1] |
| 34 | 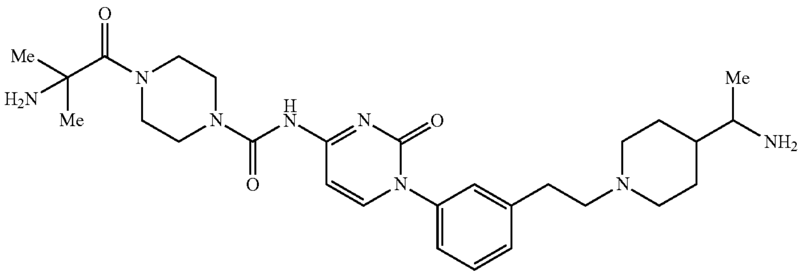 [SMILES: CC(N)C1CCN(CCc2cccc(-n3ccc(NC(=O)N4CCN(C(=O)C(C)(C)N)CC4)nc3=O)c2)CC1] |

TABLE 10-continued
| Compounds of Formula I |
| --- |
| 35 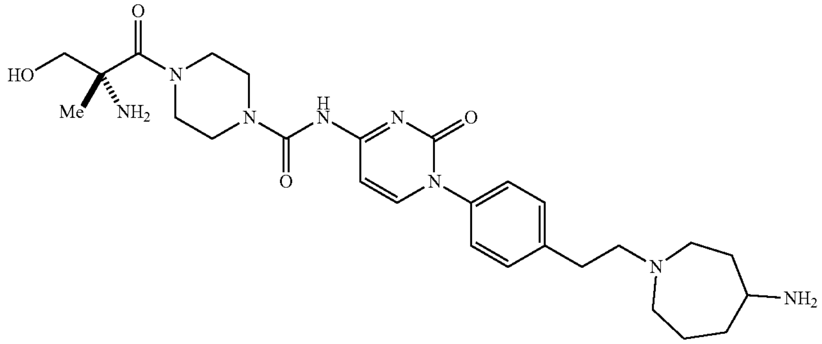 |
| 36 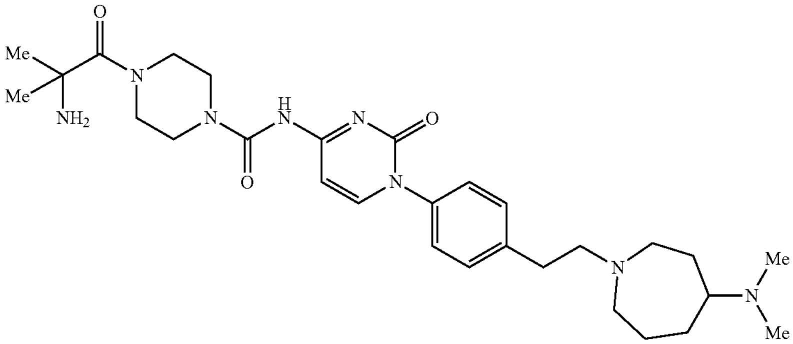 |
| 37 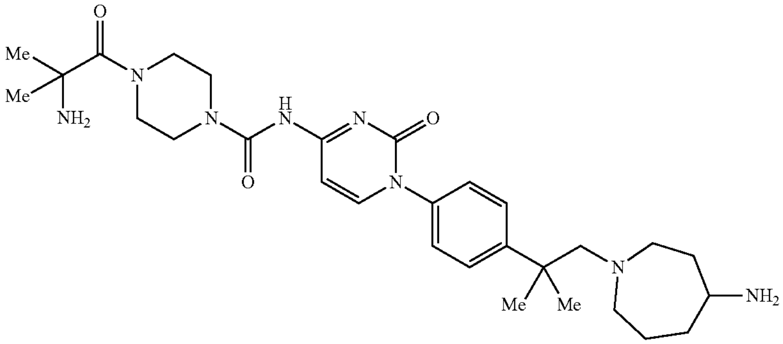 [SMILES: CC(C)(N)C(=O)N1CCN(C(=O)Nc2ccn(-c3ccc(C(C)(C)CN4CCCC(N)CC4)cc3)c(=O)n2)CC1] |
| 38 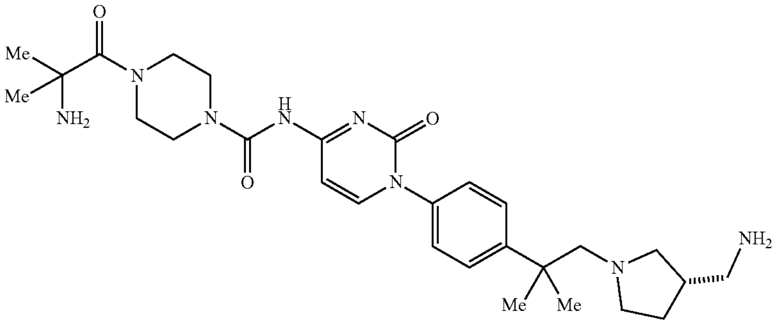 [SMILES: CC(C)(N)C(=O)N1CCN(C(=O)Nc2ccn(-c3ccc(C(C)(C)CN4CC[C@@H](CN)C4)cc3)c(=O)n2)CC1] |

TABLE 10-continued
| Compounds of Formula I | |
| --- | --- |
| 39 | 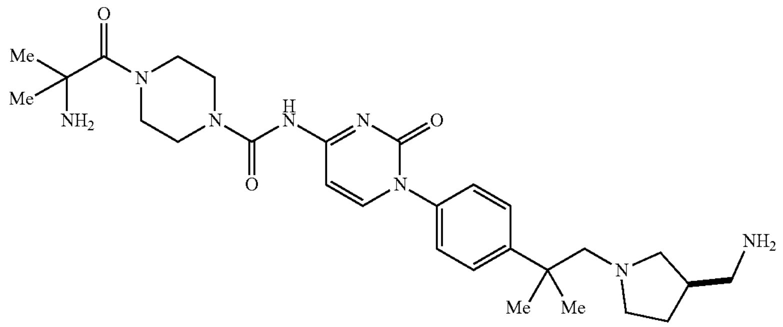 [SMILES: CC(C)(N)C(=O)N1CCN(C(=O)Nc2ccn(-c3ccc(C(C)(C)CN4CC[C@H](CN)C4)cc3)c(=O)n2)CC1] |
| 40 | 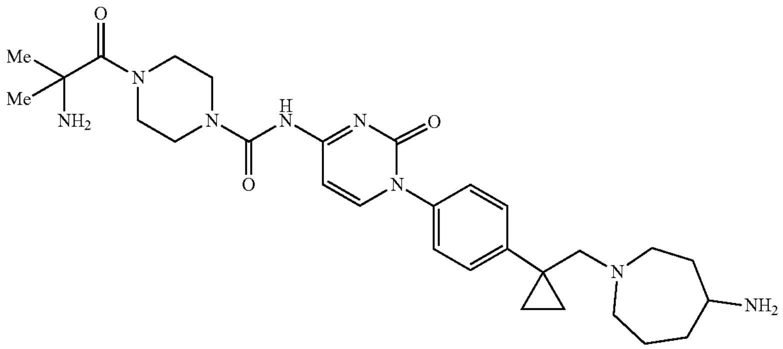 [SMILES: CC(C)(N)C(=O)N1CCN(C(=O)Nc2ccn(-c3ccc(C4(CN5CCCC(N)CC5)CC4)cc3)c(=O)n2)CC1] |
| 41 | 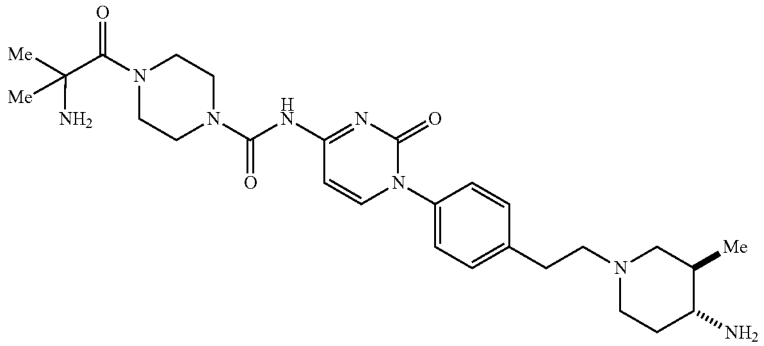 [SMILES: C[C@@H]1CN(CCc2ccc(-n3ccc(NC(=O)N4CCN(C(=O)C(C)(C)N)CC4)nc3=O)cc2)CC[C@H]1N] |
| 42 | 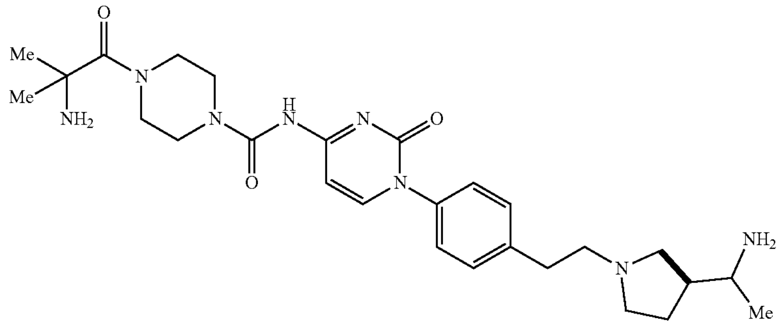 [SMILES: CC(N)[C@H]1CCN(CCc2ccc(-n3ccc(NC(=O)N4CCN(C(=O)C(C)(C)N)CC4)nc3=O)cc2)C1] |

TABLE 10-continued
| Compounds of Formula I | |
|---|---|
| 43 | 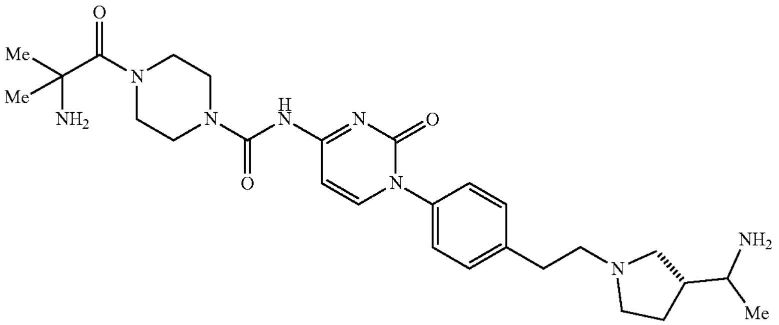 [SMILES: CC(N)[C@@H]1CCN(CCc2ccc(-n3ccc(NC(=O)N4CCN(C(=O)C(C)(C)N)CC4)nc3=O)cc2)C1] |
| 44 | 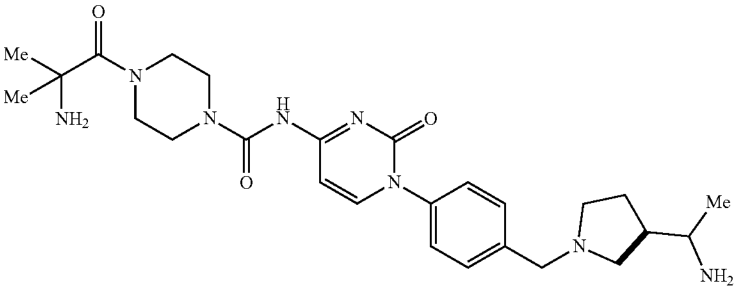 [SMILES: CC(N)[C@@H]1CCN(Cc2ccc(-n3ccc(NC(=O)N4CCN(C(=O)C(C)(C)N)CC4)nc3=O)cc2)C1] |
| 45 | 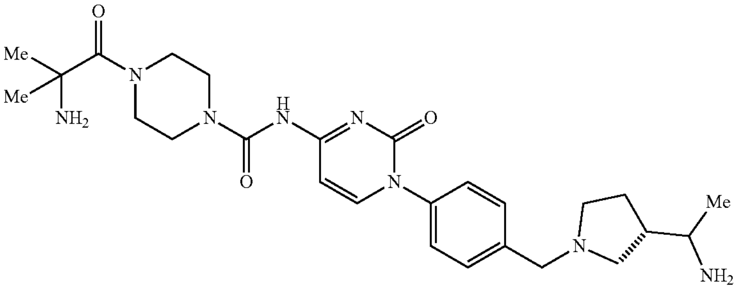 [SMILES: CC(N)[C@H]1CCN(Cc2ccc(-n3ccc(NC(=O)N4CCN(C(=O)C(C)(C)N)CC4)nc3=O)cc2)C1] |
| 46 | 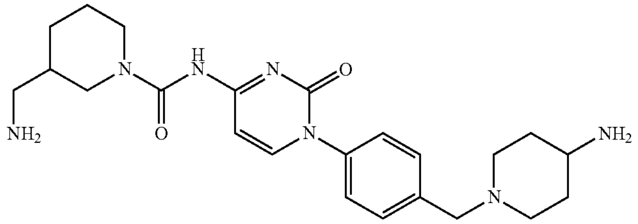 [SMILES: NCC1CCCN(C(=O)Nc2ccn(-c3ccc(CN4CCC(N)CC4)cc3)c(=O)n2)C1] |
| 47 | 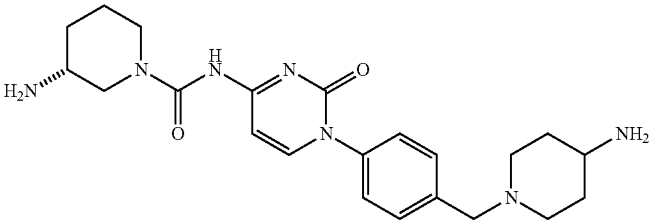 [SMILES: NC1CCN(Cc2ccc(-n3ccc(NC(=O)N4CCC[C@@H](N)C4)nc3=O)cc2)CC1] |

TABLE 10-continued
| Compounds of Formula I | |
|---|---|
| 48 | 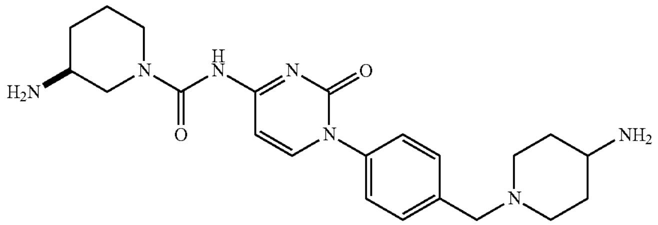 [SMILES: NC1CCN(Cc2ccc(-n3ccc(NC(=O)N4CCC[C@H](N)C4)nc3=O)cc2)CC1] |
| 49 | 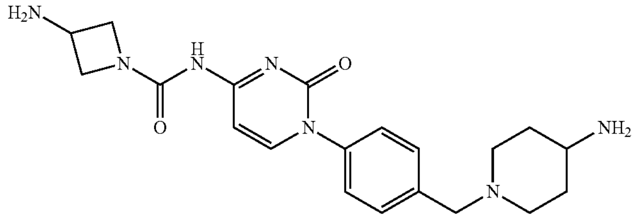 [SMILES: NC1CCN(Cc2ccc(-n3ccc(NC(=O)N4CC(N)C4)nc3=O)cc2)CC1] |
| 50 | 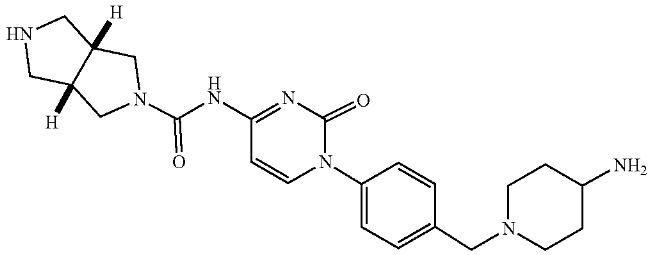 [SMILES: NC1CCN(Cc2ccc(-n3ccc(NC(=O)N4C[C@H]5CNC[C@H]5C4)nc3=O)cc2)CC1] |
| 51 | 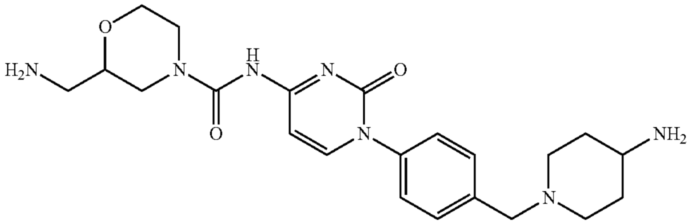 [SMILES: NCC1CN(C(=O)Nc2ccn(-c3ccc(CN4CCC(N)CC4)cc3)c(=O)n2)CCO1] |
| 52 | 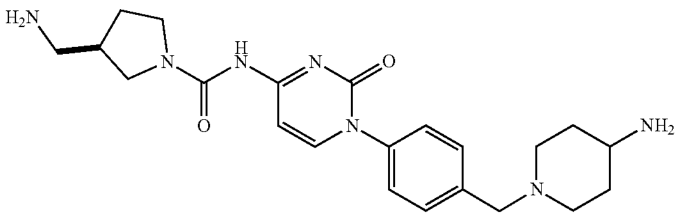 [SMILES: NC[C@H]1CCN(C(=O)Nc2ccn(-c3ccc(CN4CCC(N)CC4)cc3)c(=O)n2)C1] |
| 53 | 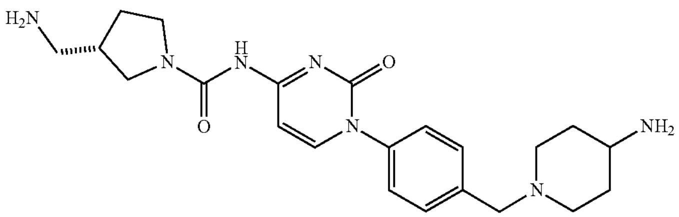 [SMILES: NC[C@@H]1CCN(C(=O)Nc2ccn(-c3ccc(CN4CCC(N)CC4)cc3)c(=O)n2)C1] |

TABLE 10-continued
| Compounds of Formula I | |
|---|---|
| 54 | 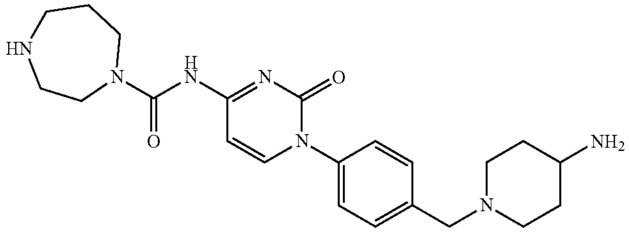 [SMILES: NC1CCN(Cc2ccc(-n3ccc(NC(=O)N4CCCNCC4)nc3=O)cc2)CC1] |
| 55 | 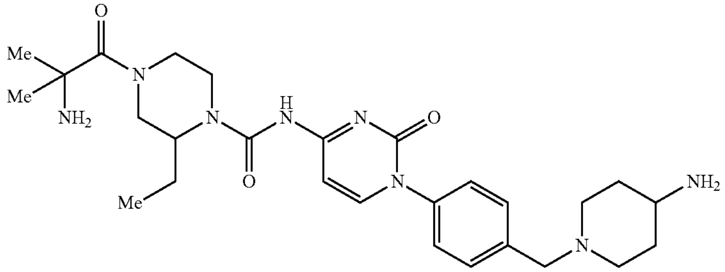 [SMILES: CCC1CN(C(=O)C(C)(C)N)CCN1C(=O)Nc1ccn(-c2ccc(CN3CCC(N)CC3)cc2)c(=O)n1] |
| 56 | 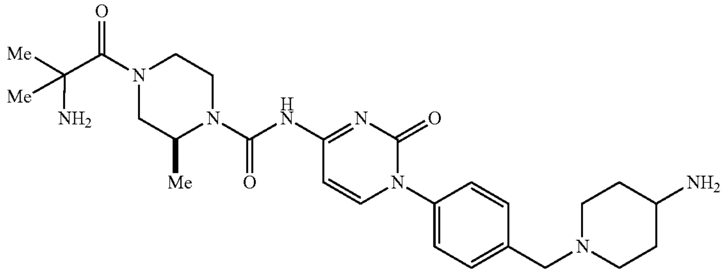 [SMILES: C[C@H]1CN(C(=O)C(C)(C)N)CCN1C(=O)Nc1ccn(-c2ccc(CN3CCC(N)CC3)cc2)c(=O)n1] |
| 57 | 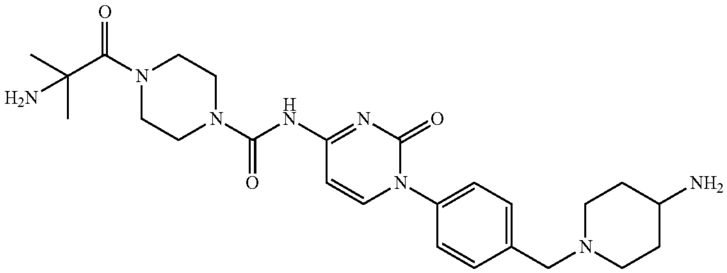 [SMILES: CC(C)(N)C(=O)N1CCN(C(=O)Nc2ccn(-c3ccc(CN4CCC(N)CC4)cc3)c(=O)n2)CC1] |
| 58 | 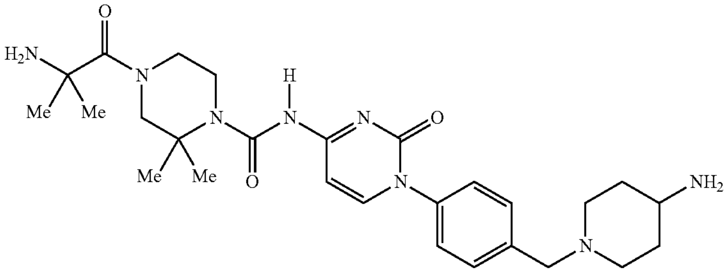 [SMILES: CC(C)(N)C(=O)N1CCN(C(=O)Nc2ccn(-c3ccc(CN4CCC(N)CC4)cc3)c(=O)n2)C(C)(C)C1] |

TABLE 10-continued
| Compounds of Formula I | |
|---|---|
| 59 | 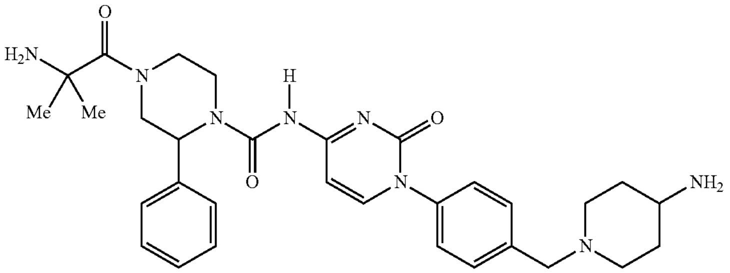 [SMILES: CC(C)(N)C(=O)N1CCN(C(=O)Nc2ccn(-c3ccc(CN4CCC(N)CC4)cc3)c(=O)n2)C(c2ccccc2)C1] |
| 60 | 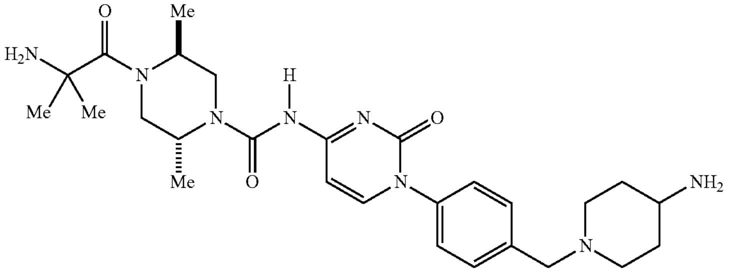 [SMILES: C[C@@H]1CN(C(=O)C(C)(C)N)[C@@H](C)CN1C(=O)Nc1ccn(-c2ccc(CN3CCC(N)CC3)cc2)c(=O)n1] |
| 61 | 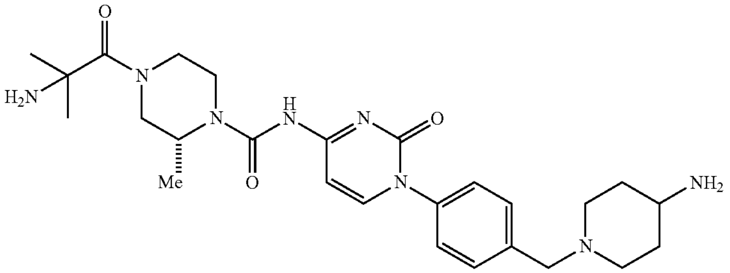 [SMILES: C[C@@H]1CN(C(=O)C(C)(C)N)CCN1C(=O)Nc1ccn(-c2ccc(CN3CCC(N)CC3)cc2)c(=O)n1] |
| 62 | 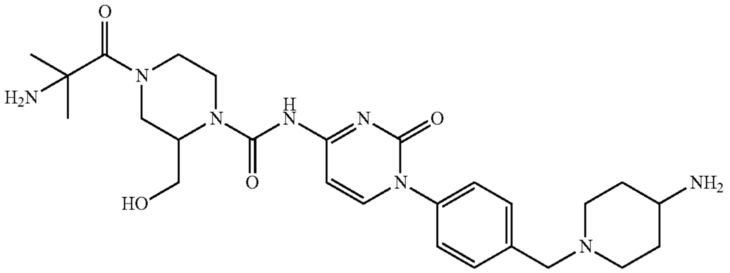 [SMILES: CC(C)(N)C(=O)N1CCN(C(=O)Nc2ccn(-c3ccc(CN4CCC(N)CC4)cc3)c(=O)n2)C(CO)C1] |
| 63 | 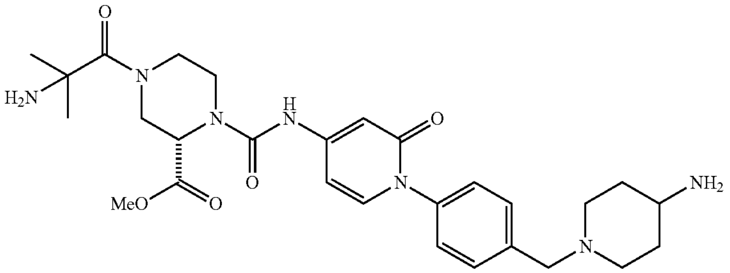 [SMILES: COC(=O)[C@@H]1CN(C(=O)C(C)(C)N)CCN1C(=O)Nc1ccn(-c2ccc(CN3CCC(N)CC3)cc2)c(=O)c1] |

TABLE 10-continued
| Compounds of Formula I | |
|---|---|
| 64 | 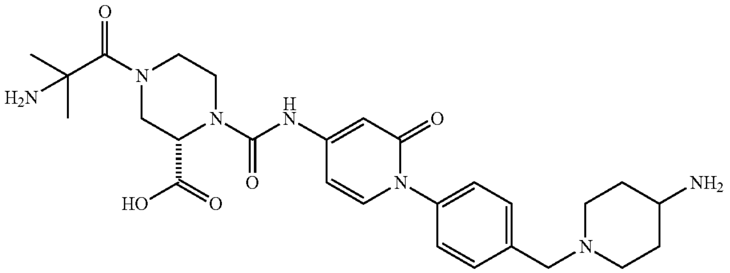 [SMILES: CC(C)(N)C(=O)N1CCN(C(=O)Nc2ccn(-c3ccc(CN4CCC(N)CC4)cc3)c(=O)c2)[C@H](C(=O)O)C1] |
| 65 | 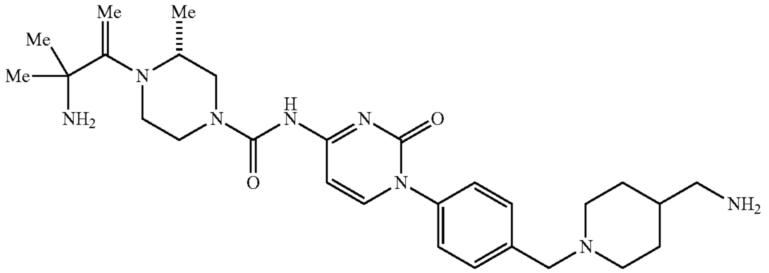 |
| 66 | 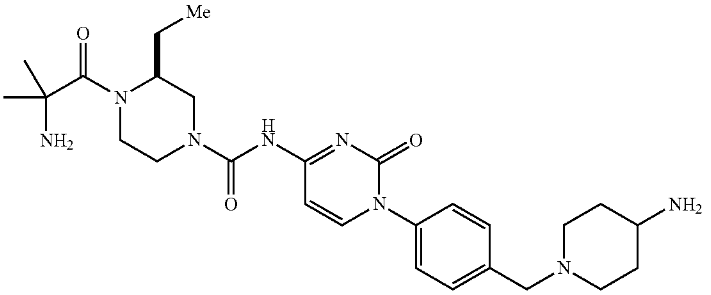 [SMILES: CC[C@H]1CN(C(=O)Nc2ccn(-c3ccc(CN4CCC(N)CC4)cc3)c(=O)n2)CCN1C(=O)C(C)(C)N] |
| 67 | 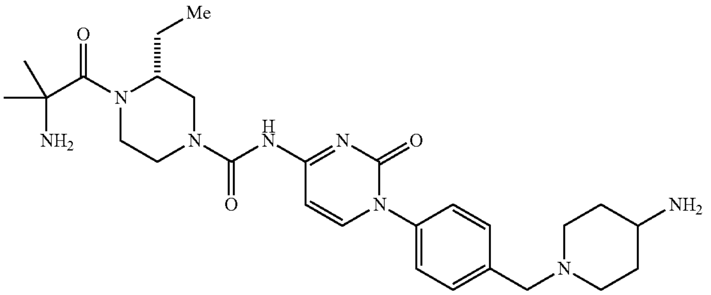 [SMILES: CC[C@@H]1CN(C(=O)Nc2ccn(-c3ccc(CN4CCC(N)CC4)cc3)c(=O)n2)CCN1C(=O)C(C)(C)N] |
| 68 | 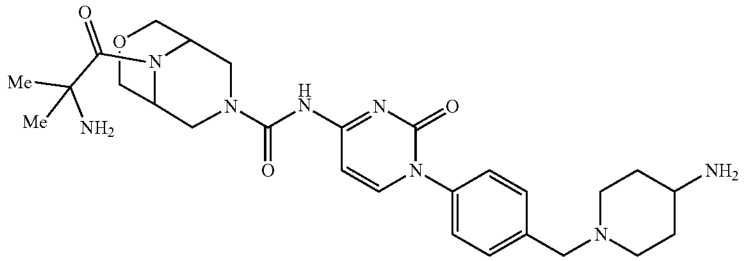 [SMILES: CC(C)(N)C(=O)N1C2COCC1CN(C(=O)Nc1ccn(-c3ccc(CN4CCC(N)CC4)cc3)c(=O)n1)C2] |

TABLE 10-continued
| Compounds of Formula I | |
|---|---|
| 69 | 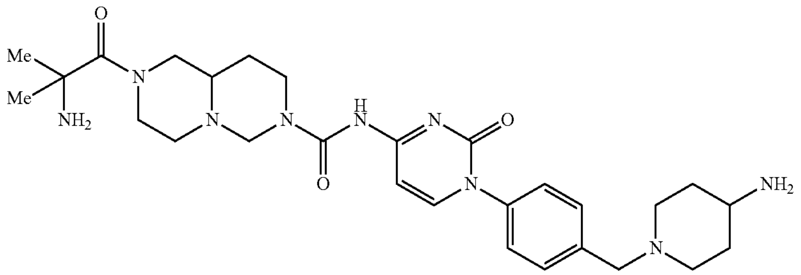 [SMILES: CC(C)(N)C(=O)N1CCN2CN(C(=O)Nc3ccn(-c4ccc(CN5CCC(N)CC5)cc4)c(=O)n3)CCC2C1] |
| 70 | 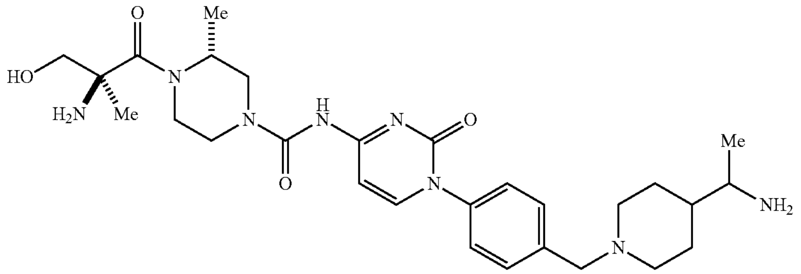 [SMILES: CC(N)C1CCN(Cc2ccc(-n3ccc(NC(=O)N4CCN(C(=O)[C@@](C)(N)CO)[C@H](C)C4)nc3=O)cc2)CC1] |
| 71 | 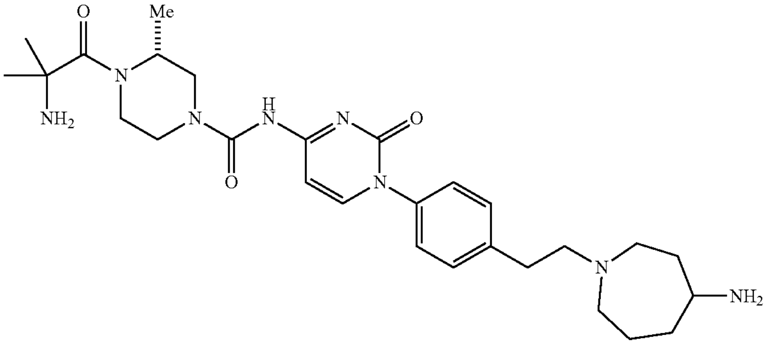 [SMILES: C[C@@H]1CN(C(=O)Nc2ccn(-c3ccc(CCN4CCCC(N)CC4)cc3)c(=O)n2)CCN1C(=O)C(C)(C)N] |
| 72 | 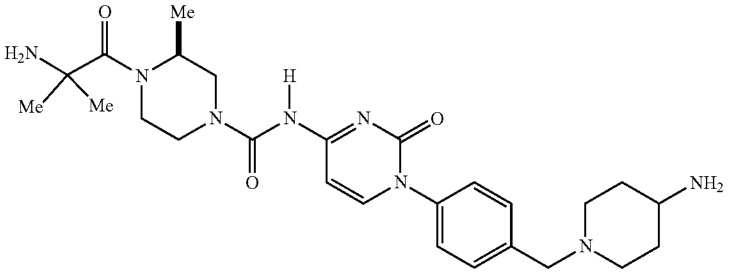 [SMILES: C[C@H]1CN(C(=O)Nc2ccn(-c3ccc(CN4CCC(N)CC4)cc3)c(=O)n2)CCN1C(=O)C(C)(C)N] |
| 73 | 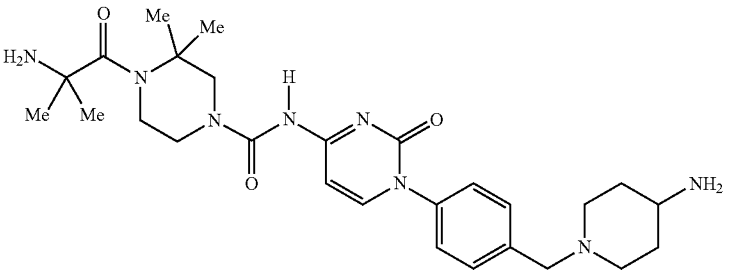 [SMILES: CC(C)(N)C(=O)N1CCN(C(=O)Nc2ccn(-c3ccc(CN4CCC(N)CC4)cc3)c(=O)n2)CC1(C)C] |

TABLE 10-continued
| Compounds of Formula I | |
|---|---|
| 74 | 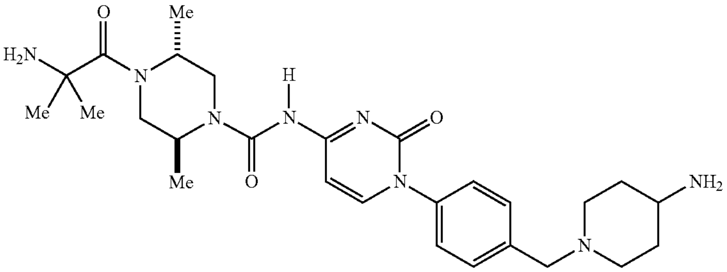 [SMILES: C[C@@H]1CN(C(=O)Nc2ccn(-c3ccc(CN4CCC(N)CC4)cc3)c(=O)n2)[C@@H](C)CN1C(=O)C(C)(C)N] |
| 75 | 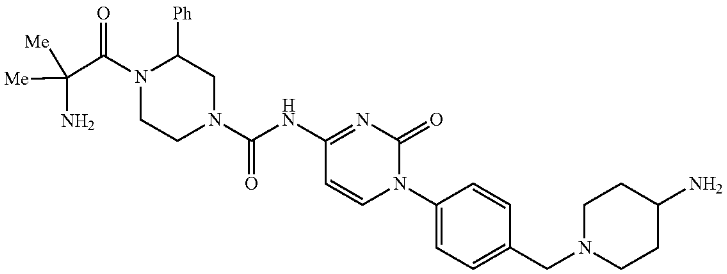 [SMILES: CC(C)(N)C(=O)N1CCN(C(=O)Nc2ccn(-c3ccc(CN4CCC(N)CC4)cc3)c(=O)n2)CC1c1ccccc1] |
| 76 | 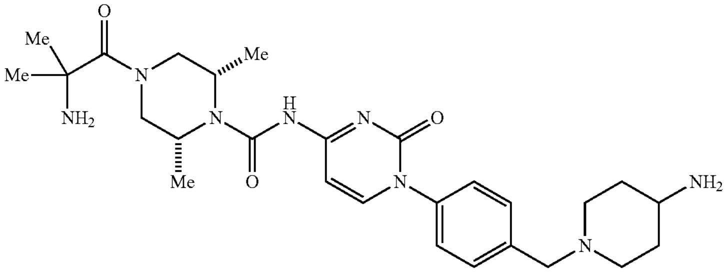 [SMILES: C[C@@H]1CN(C(=O)C(C)(C)N)C[C@H](C)N1C(=O)Nc1ccn(-c2ccc(CN3CCC(N)CC3)cc2)c(=O)n1] |
| 77 | 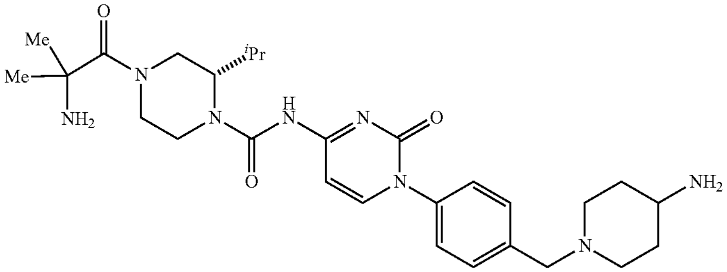 [SMILES: CC(C)[C@H]1CN(C(=O)C(C)(C)N)CCN1C(=O)Nc1ccn(-c2ccc(CN3CCC(N)CC3)cc2)c(=O)n1] |
| 78 | 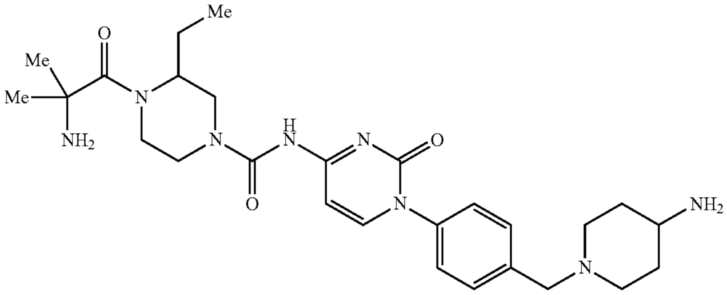 [SMILES: CCC1CN(C(=O)Nc2ccn(-c3ccc(CN4CCC(N)CC4)cc3)c(=O)n2)CCN1C(=O)C(C)(C)N] |

TABLE 10-continued
| Compounds of Formula I | |
|---|---|
| 79 | 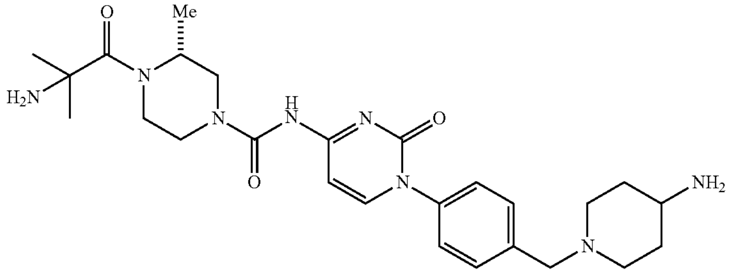 [SMILES: C[C@@H]1CN(C(=O)Nc2ccn(-c3ccc(CN4CCC(N)CC4)cc3)c(=O)n2)CCN1C(=O)C(C)(C)N] |
| 80 | 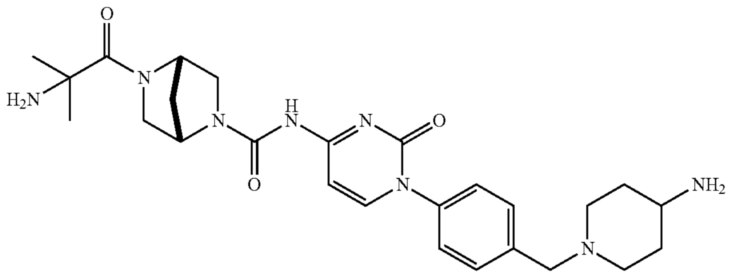 |
| 81 | 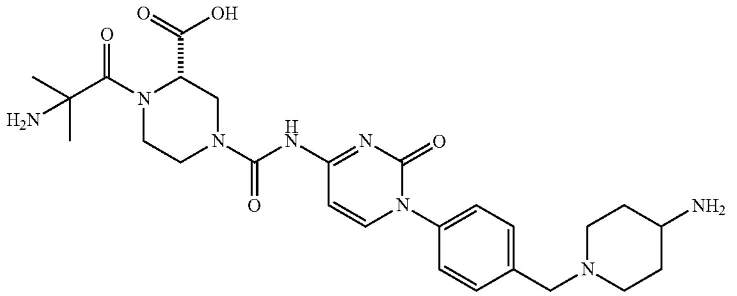 [SMILES: CC(C)(N)C(=O)N1CCN(C(=O)Nc2ccn(-c3ccc(CN4CCC(N)CC4)cc3)c(=O)n2)C[C@H]1C(=O)O] |
| 82 | 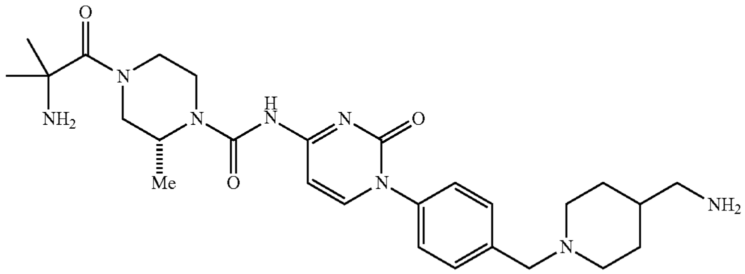 [SMILES: C[C@@H]1CN(C(=O)C(C)(C)N)CCN1C(=O)Nc1ccn(-c2ccc(CN3CCC(CN)CC3)cc2)c(=O)n1] |
| 83 | 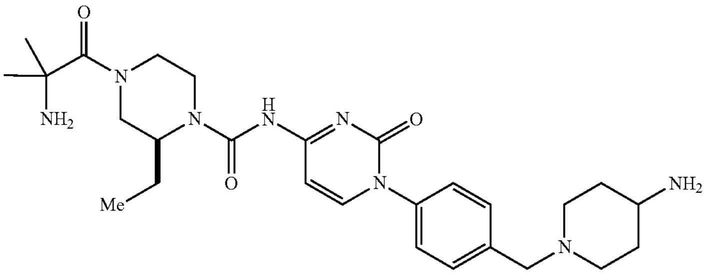 [SMILES: CC[C@H]1CN(C(=O)C(C)(C)N)CCN1C(=O)Nc1ccn(-c2ccc(CN3CCC(N)CC3)cc2)c(=O)n1] |

TABLE 10-continued
| Compounds of Formula I |
|---|
| 84 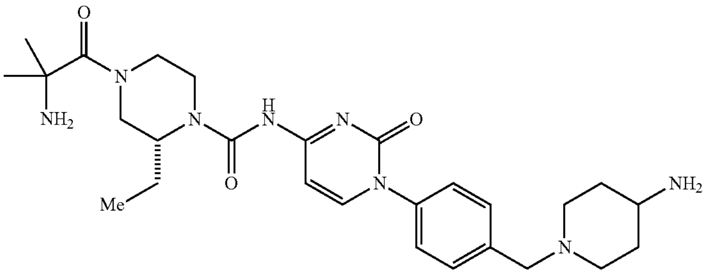 [SMILES: CC[C@@H]1CN(C(=O)C(C)(C)N)CCN1C(=O)Nc1ccn(-c2ccc(CN3CCC(N)CC3)cc2)c(=O)n1] |
| 85 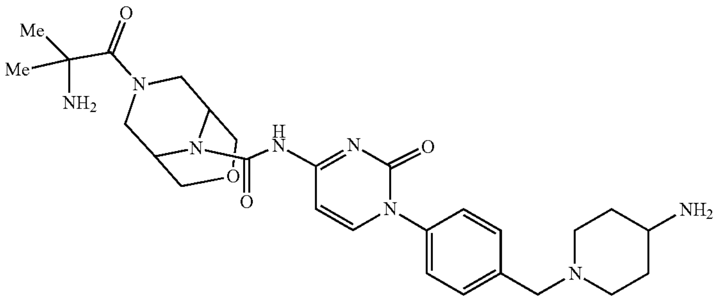 |
| 86 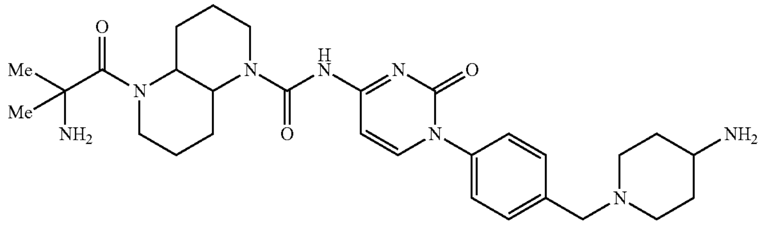 [SMILES: CC(C)(N)C(=O)N1CCCC2C1CCCN2C(=O)Nc1ccn(-c2ccc(CN3CCC(N)CC3)cc2)c(=O)n1] |
| 87 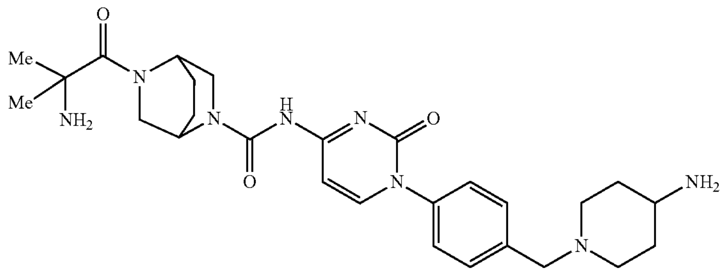 [SMILES: CC(C)(N)C(=O)N1CC2CCC1CN2C(=O)Nc1ccn(-c2ccc(CN3CCC(N)CC3)cc2)c(=O)n1] |
| 88 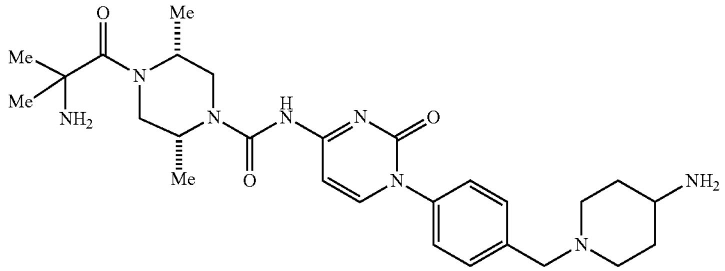 [SMILES: C[C@@H]1CN(C(=O)C(C)(C)N)[C@H](C)CN1C(=O)Nc1ccn(-c2ccc(CN3CCC(N)CC3)cc2)c(=O)n1] |

TABLE 10-continued
| Compounds of Formula I | |
|---|---|
| 89 | 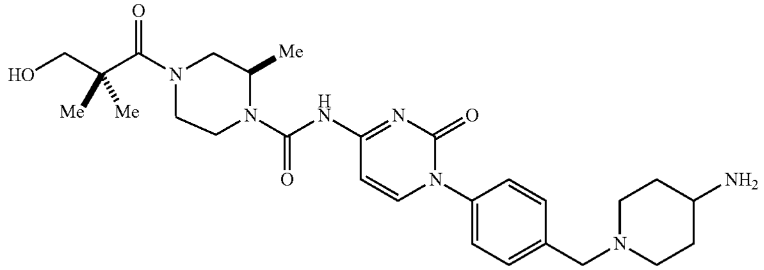 |
| 90 | 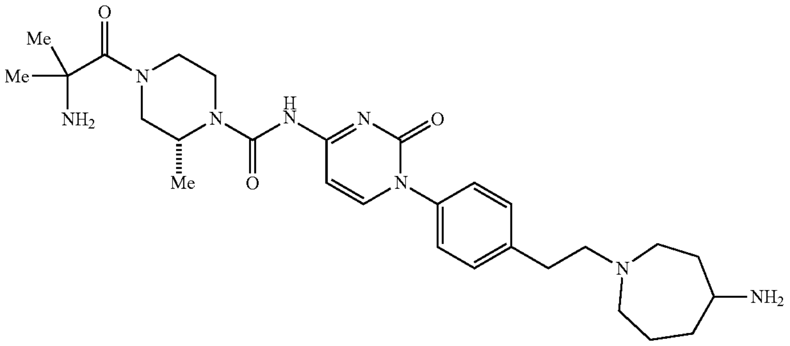 [SMILES: C[C@@H]1CN(C(=O)C(C)(C)N)CCN1C(=O)Nc1ccn(-c2ccc(CCN3CCCC(N)CC3)cc2)c(=O)n1] |
| 91 | 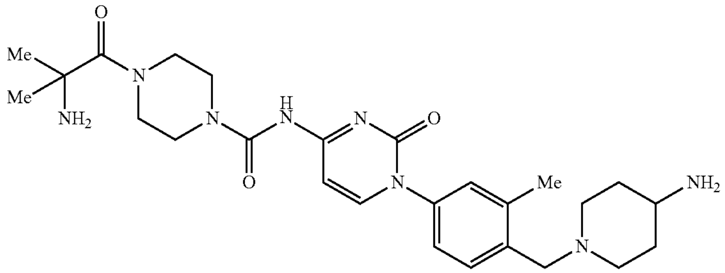 [SMILES: Cc1cc(-n2ccc(NC(=O)N3CCN(C(=O)C(C)(C)N)CC3)nc2=O)ccc1CN1CCC(N)CC1] |
| 92 | 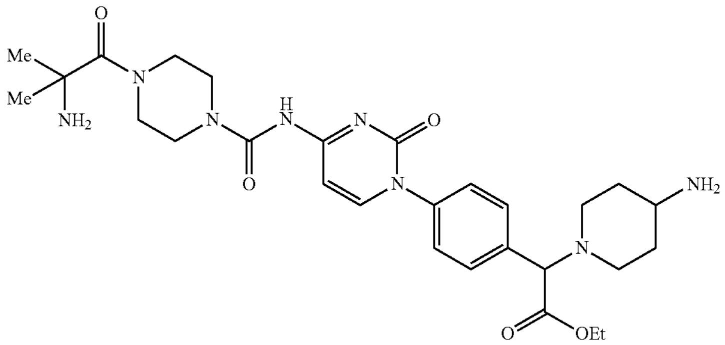 [SMILES: CCOC(=O)C(c1ccc(-n2ccc(NC(=O)N3CCN(C(=O)C(C)(C)N)CC3)nc2=O)cc1)N1CCC(N)CC1] |
| 93 | 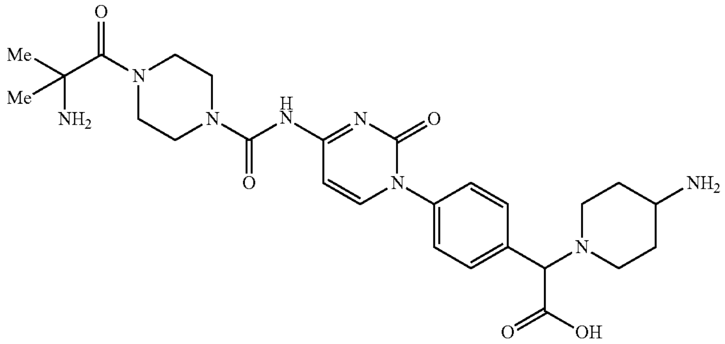 [SMILES: CC(C)(N)C(=O)N1CCN(C(=O)Nc2ccn(-c3ccc(C(C(=O)O)N4CCC(N)CC4)cc3)c(=O)n2)CC1] |

TABLE 10-continued
| Compounds of Formula I |
| --- |
94 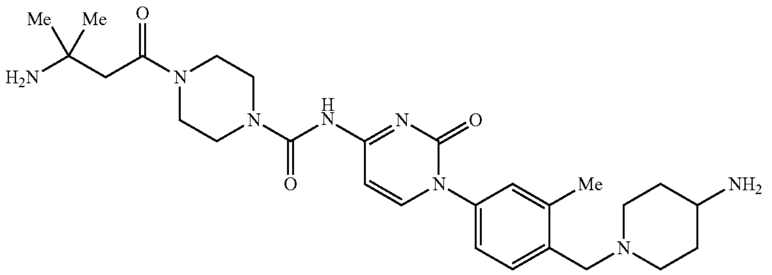
95 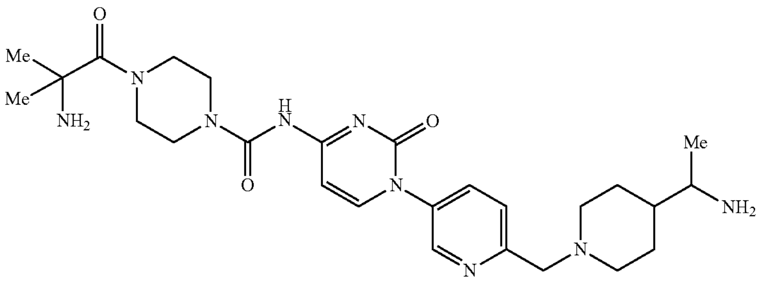 [SMILES: CC(N)C1CCN(Cc2ccc(-n3ccc(NC(=O)N4CCN(C(=O)C(C)(C)N)CC4)nc3=O)cn2)CC1]
96 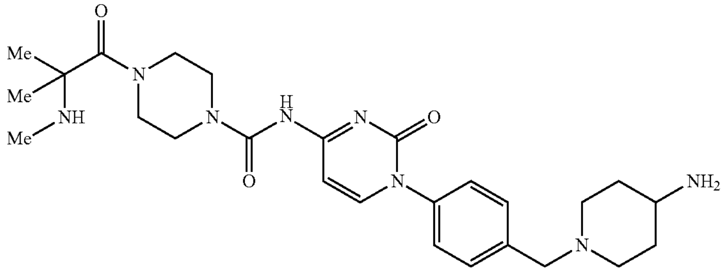 [SMILES: CNC(C)(C)C(=O)N1CCN(C(=O)Nc2ccn(-c3ccc(CN4CCC(N)CC4)cc3)c(=O)n2)CC1]
97 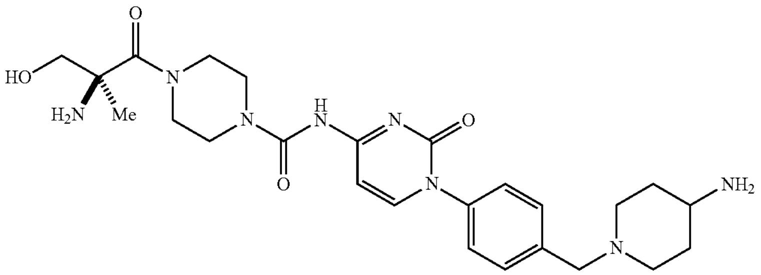 [SMILES: C[C@](N)(CO)C(=O)N1CCN(C(=O)Nc2ccn(-c3ccc(CN4CCC(N)CC4)cc3)c(=O)n2)CC1]
98 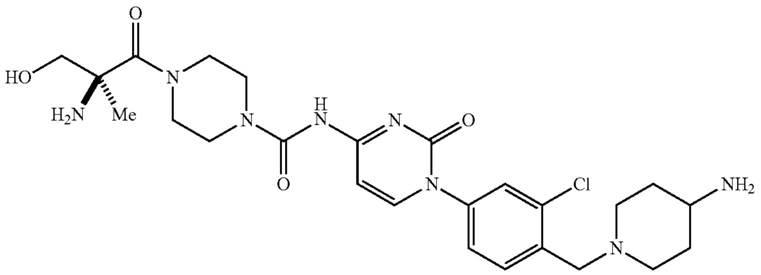 [SMILES: C[C@](N)(CO)C(=O)N1CCN(C(=O)Nc2ccn(-c3ccc(CN4CCC(N)CC4)c(Cl)c3)c(=O)n2)CC1]

TABLE 10-continued
| Compounds of Formula I | |
|---|---|
| 99 | 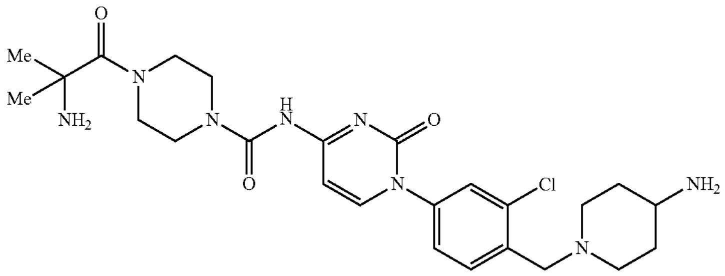 [SMILES: CC(C)(N)C(=O)N1CCN(C(=O)Nc2ccn(-c3ccc(CN4CCC(N)CC4)c(Cl)c3)c(=O)n2)CC1] |
| 100 | 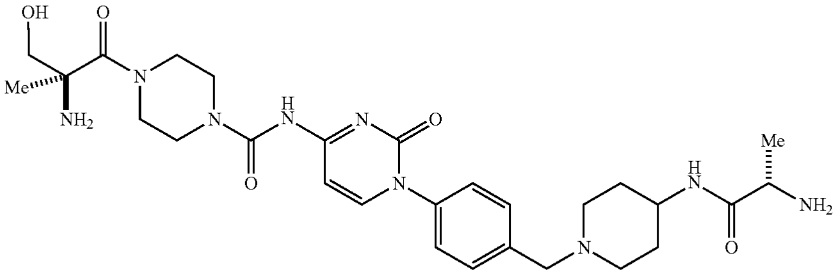 [SMILES: C[C@H](N)C(=O)NC1CCN(Cc2ccc(-n3ccc(NC(=O)N4CCN(C(=O)[C@@](C)(N)CO)CC4)nc3=O)cc2)CC1] |
| 101 | 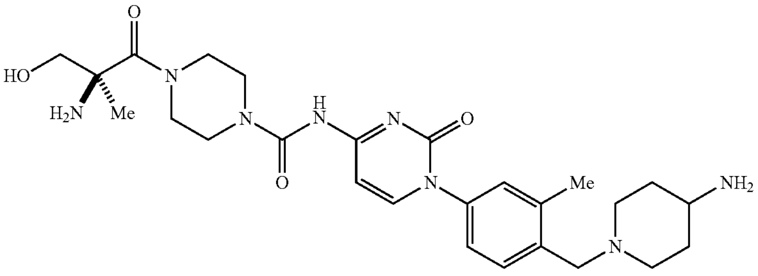 |
| 102 | 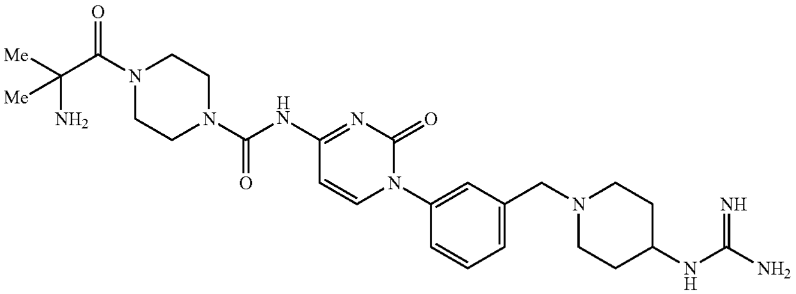 [SMILES: CC(C)(N)C(=O)N1CCN(C(=O)Nc2ccn(-c3cccc(CN4CCC(NC(=N)N)CC4)c3)c(=O)n2)CC1] |
| 103 | 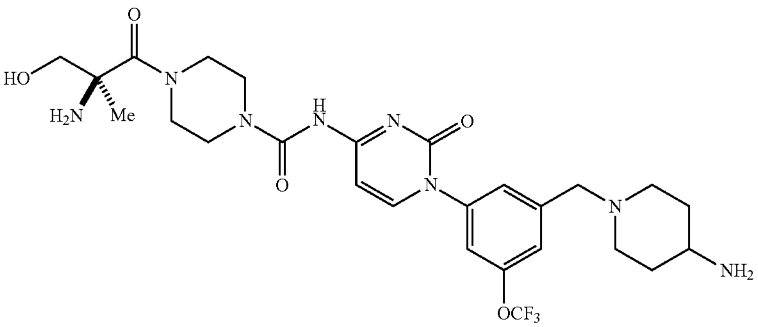 |

TABLE 10-continued
| Compounds of Formula I |
| --- |
104
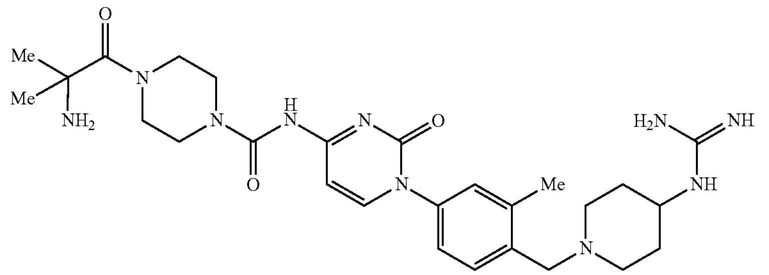 [SMILES: Cc1cc(-n2ccc(NC(=O)N3CCN(C(=O)C(C)(C)N)CC3)nc2=O)ccc1CN1CCC(NC(=N)N)CC1]
105
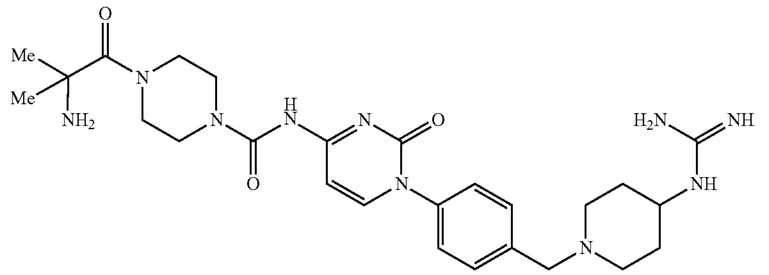 [SMILES: CC(C)(N)C(=O)N1CCN(C(=O)Nc2ccn(-c3ccc(CN4CCC(NC(=N)N)CC4)cc3)c(=O)n2)CC1]
106
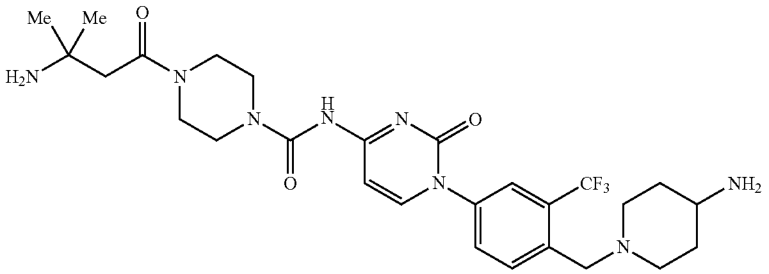 [SMILES: CC(C)(N)CC(=O)N1CCN(C(=O)Nc2ccn(-c3ccc(CN4CCC(N)CC4)c(C(F)(F)F)c3)c(=O)n2)CC1]
107
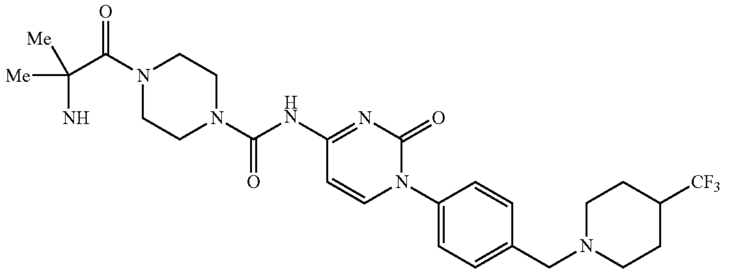 [SMILES: CC(C)(N)C(=O)N1CCN(C(=O)Nc2ccn(-c3ccc(CN4CCC(C(F)(F)F)CC4)cc3)c(=O)n2)CC1]
108
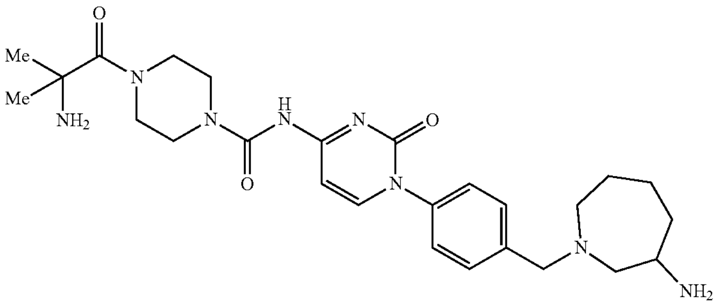 [SMILES: CC(C)(N)C(=O)N1CCN(C(=O)Nc2ccn(-c3ccc(CN4CCCCC(N)C4)cc3)c(=O)n2)CC1]

TABLE 10-continued
| Compounds of Formula I | |
|---|---|
| 109 | 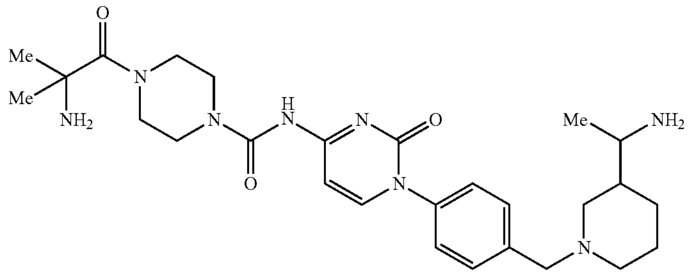 [SMILES: CC(N)C1CCCN(Cc2ccc(-n3ccc(NC(=O)N4CCN(C(=O)C(C)(C)N)CC4)nc3=O)cc2)C1] |
| 110 | 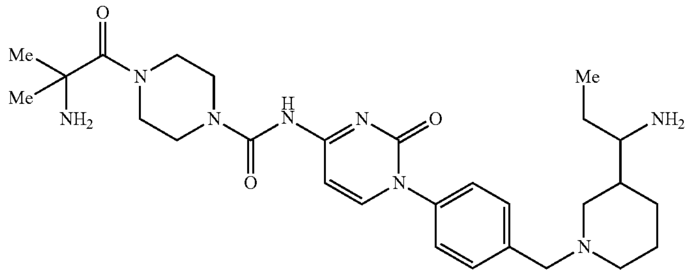 [SMILES: CCC(N)C1CCCN(Cc2ccc(-n3ccc(NC(=O)N4CCN(C(=O)C(C)(C)N)CC4)nc3=O)cc2)C1] |
| 111 | 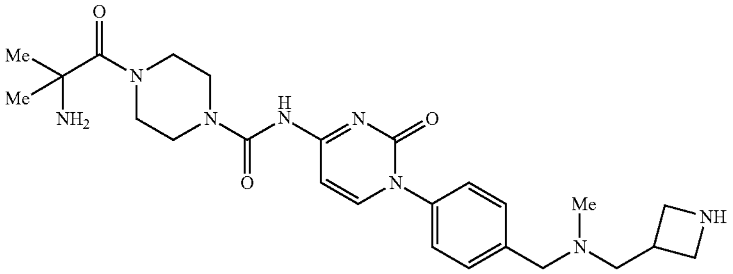 [SMILES: CN(Cc1ccc(-n2ccc(NC(=O)N3CCN(C(=O)C(C)(C)N)CC3)nc2=O)cc1)CC1CNC1] |
| 112 | 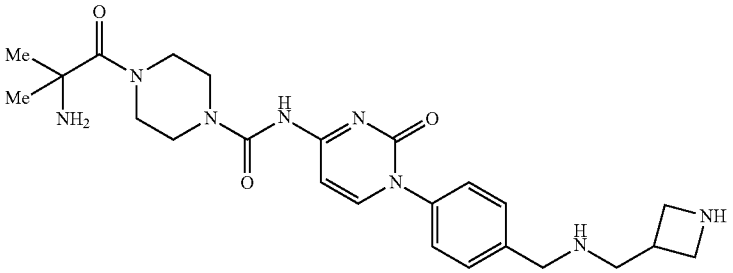 [SMILES: CC(C)(N)C(=O)N1CCN(C(=O)Nc2ccn(-c3ccc(CNCC4CNC4)cc3)c(=O)n2)CC1] |
| 114 | 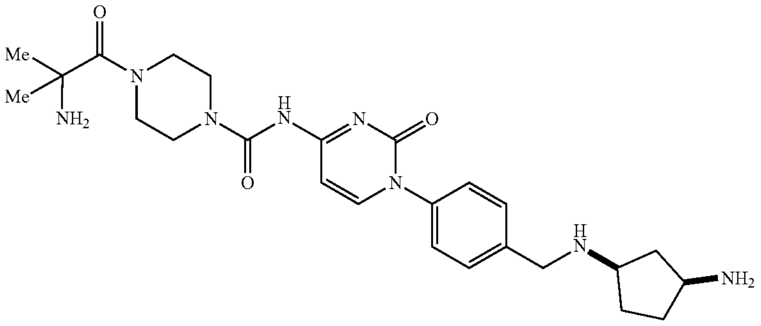 |

TABLE 10-continued
| Compounds of Formula I |
|---|
115
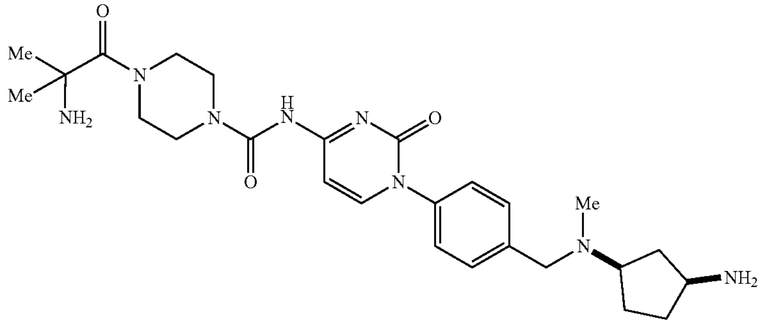
116
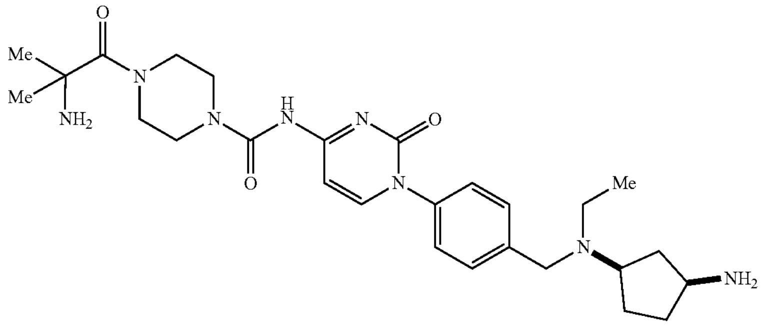
117
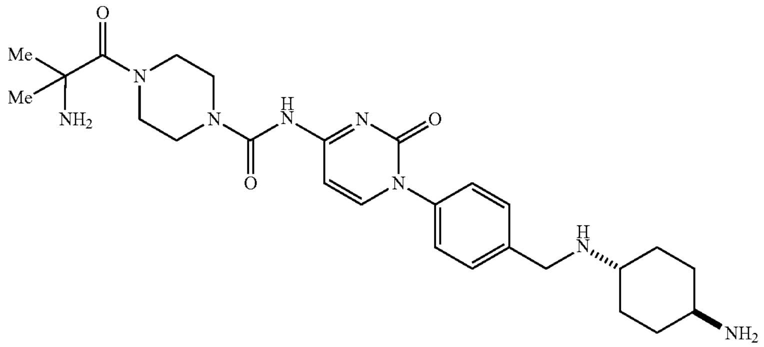
118
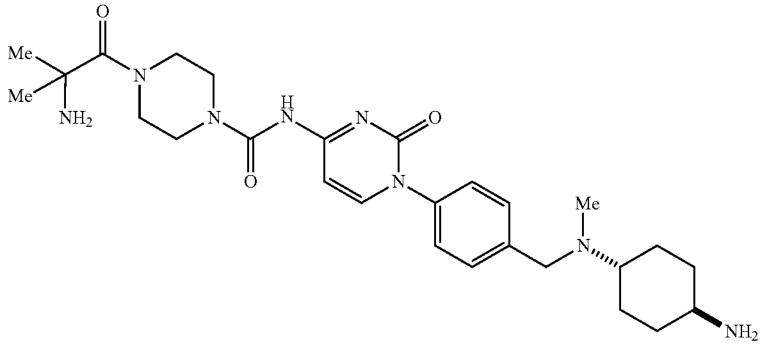

TABLE 10-continued
| Compounds of Formula I |
|---|
119
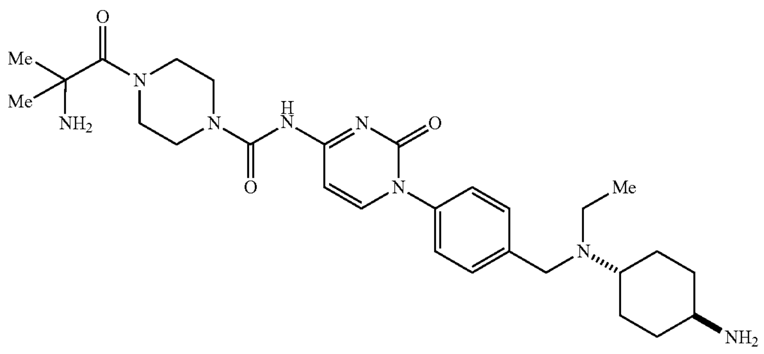
120
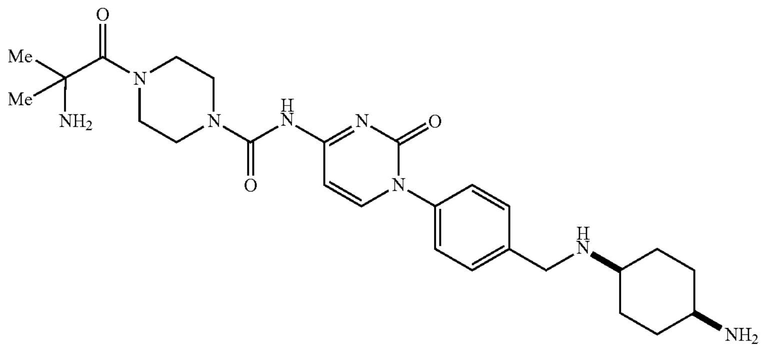 [SMILES: CC(C)(N)C(=O)N1CCN(C(=O)Nc2ccn(-c3ccc(CN[C@H]4CC[C@@H](N)CC4)cc3)c(=O)n2)CC1]
121
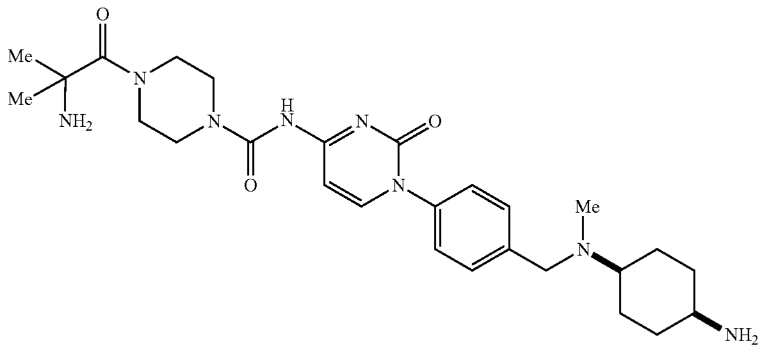 [SMILES: CN(Cc1ccc(-n2ccc(NC(=O)N3CCN(C(=O)C(C)(C)N)CC3)nc2=O)cc1)[C@H]1CC[C@@H](N)CC1]
122
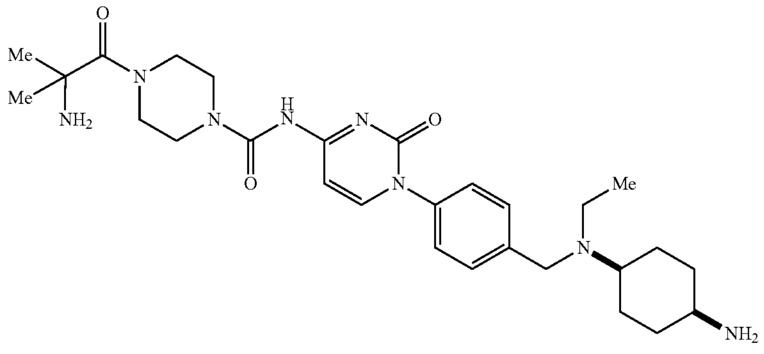 [SMILES: CCN(Cc1ccc(-n2ccc(NC(=O)N3CCN(C(=O)C(C)(C)N)CC3)nc2=O)cc1)[C@H]1CC[C@@H](N)CC1]

TABLE 10-continued
| Compounds of Formula I | |
|---|---|
| 123 | 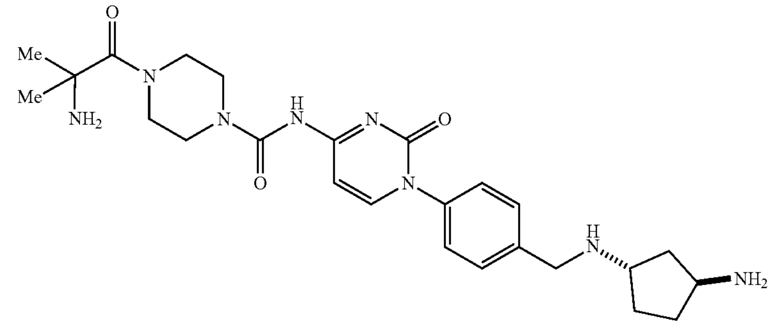 [SMILES: CC(C)(N)C(=O)N1CCN(C(=O)Nc2ccn(-c3ccc(CN[C@H]4CC[C@H](N)C4)cc3)c(=O)n2)CC1] |
| 124 | 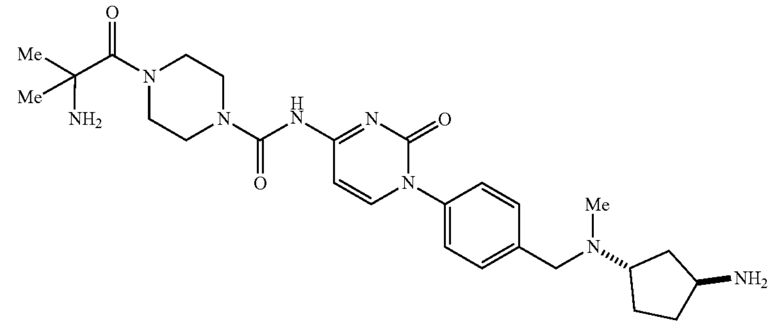 [SMILES: CN(Cc1ccc(-n2ccc(NC(=O)N3CCN(C(=O)C(C)(C)N)CC3)nc2=O)cc1)[C@H]1CC[C@H](N)C1] |
| 125 | 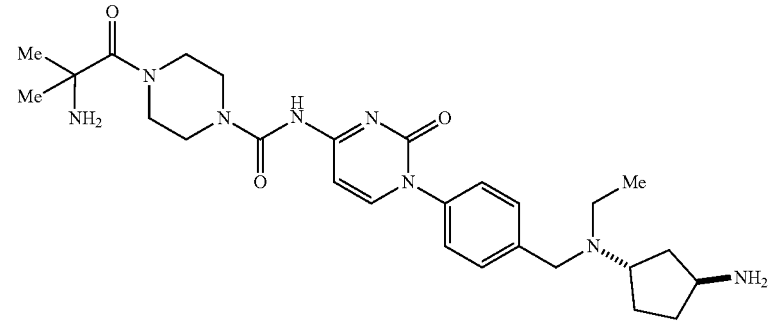 [SMILES: CCN(Cc1ccc(-n2ccc(NC(=O)N3CCN(C(=O)C(C)(C)N)CC3)nc2=O)cc1)[C@H]1CC[C@H](N)C1] |
| 126 | 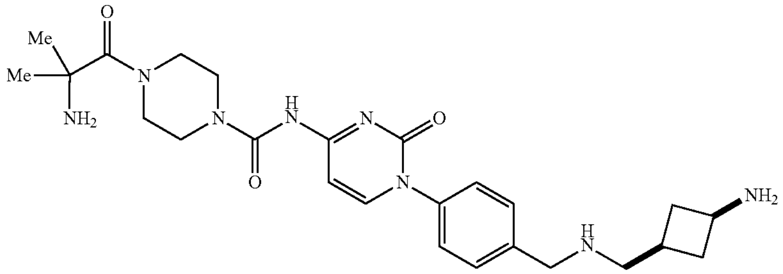 |
| 127 | 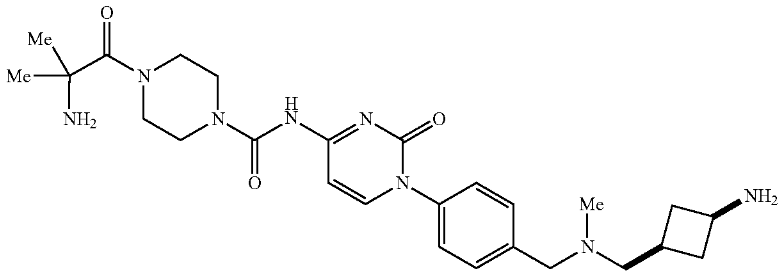 |

TABLE 10-continued
| Compounds of Formula I |
|---|
| 128 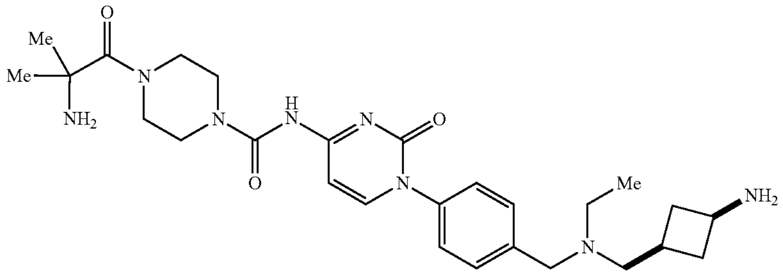 |
| 129 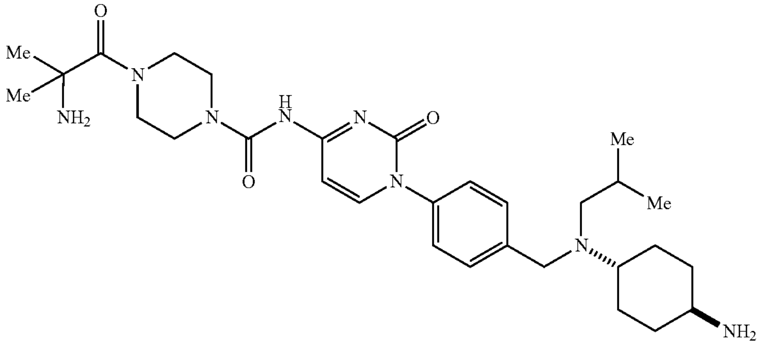 [SMILES: CC(C)CN(Cc1ccc(-n2ccc(NC(=O)N3CCN(C(=O)C(C)(C)N)CC3)nc2=O)cc1)[C@H]1CC[C@H](N)CC1] |
| 130 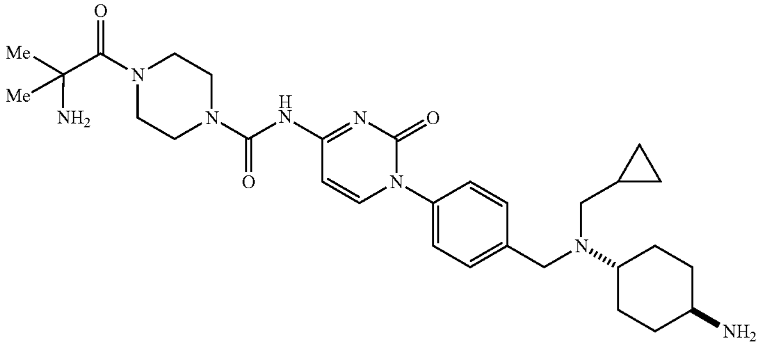 [SMILES: CC(C)(N)C(=O)N1CCN(C(=O)Nc2ccn(-c3ccc(CN(CC4CC4)[C@H]4CC[C@H](N)CC4)cc3)c(=O)n2)CC1] |
| 131 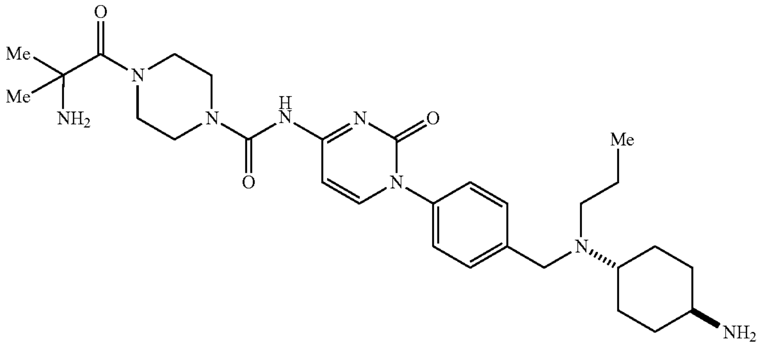 [SMILES: CCCN(Cc1ccc(-n2ccc(NC(=O)N3CCN(C(=O)C(C)(C)N)CC3)nc2=O)cc1)[C@H]1CC[C@H](N)CC1] |

TABLE 10-continued
| Compounds of Formula I | |
|---|---|
| 132 | 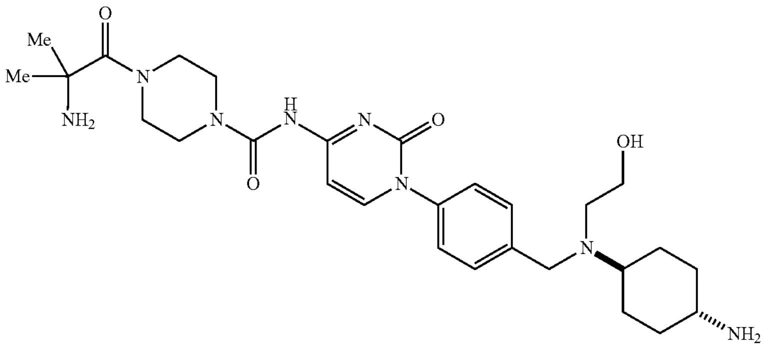 [SMILES: CC(C)(N)C(=O)N1CCN(C(=O)Nc2ccn(-c3ccc(CN(CCO)[C@H]4CC[C@H](N)CC4)cc3)c(=O)n2)CC1] |
| 133 | 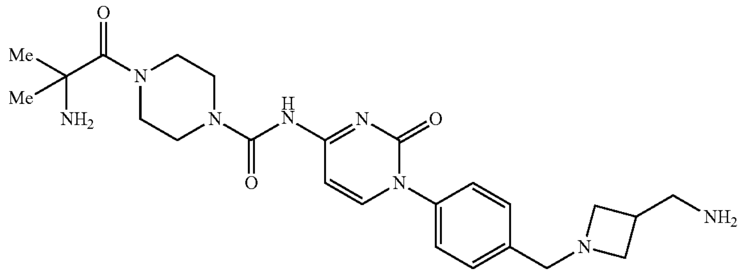 [SMILES: CC(C)(N)C(=O)N1CCN(C(=O)Nc2ccn(-c3ccc(CN4CC(CN)C4)cc3)c(=O)n2)CC1] |
| 134 | 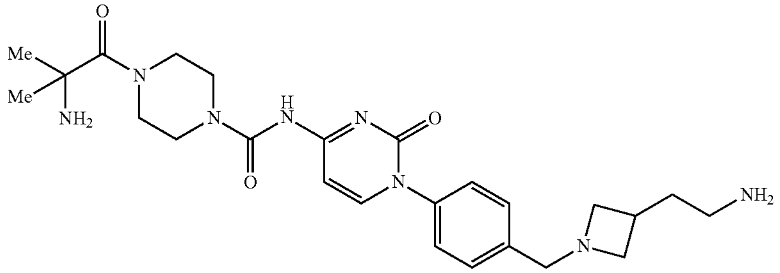 [SMILES: CC(C)(N)C(=O)N1CCN(C(=O)Nc2ccn(-c3ccc(CN4CC(CCN)C4)cc3)c(=O)n2)CC1] |
| 135 | 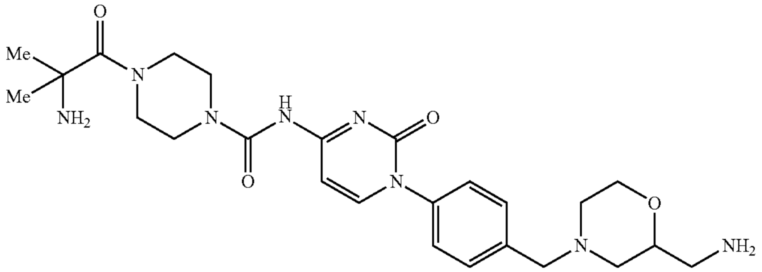 [SMILES: CC(C)(N)C(=O)N1CCN(C(=O)Nc2ccn(-c3ccc(CN4CCOC(CN)C4)cc3)c(=O)n2)CC1] |
| 136 | 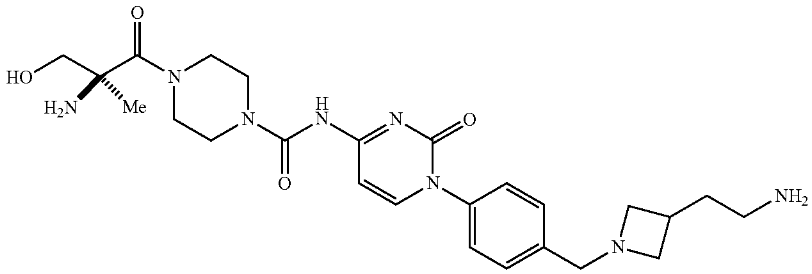 [SMILES: C[C@](N)(CO)C(=O)N1CCN(C(=O)Nc2ccn(-c3ccc(CN4CC(CCN)C4)cc3)c(=O)n2)CC1] |

TABLE 10-continued
| Compounds of Formula I |
|---|
| 137 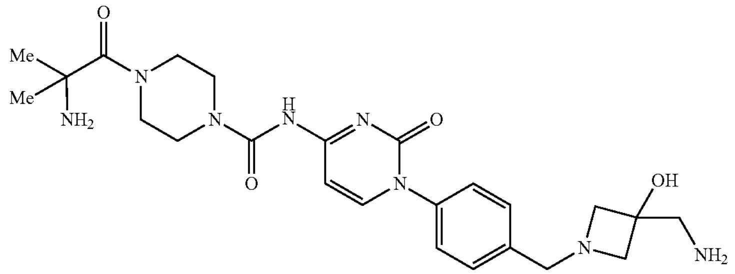 [SMILES: CC(C)(N)C(=O)N1CCN(C(=O)Nc2ccn(-c3ccc(CN4CC(O)(CN)C4)cc3)c(=O)n2)CC1] |
| 138 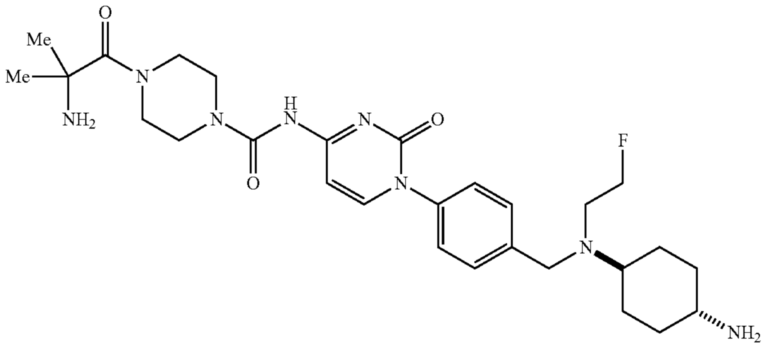 |
| 139 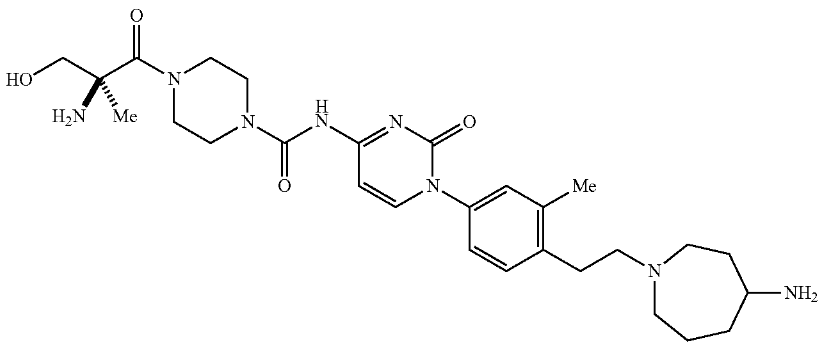 [SMILES: Cc1cc(-n2ccc(NC(=O)N3CCN(C(=O)[C@@](C)(N)CO)CC3)nc2=O)ccc1CCN1CCCC(N)CC1] |
| 140 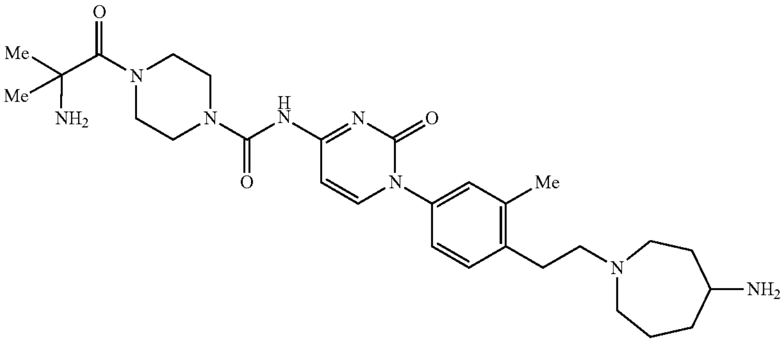 |

TABLE 10-continued
| Compounds of Formula I |
|---|
141
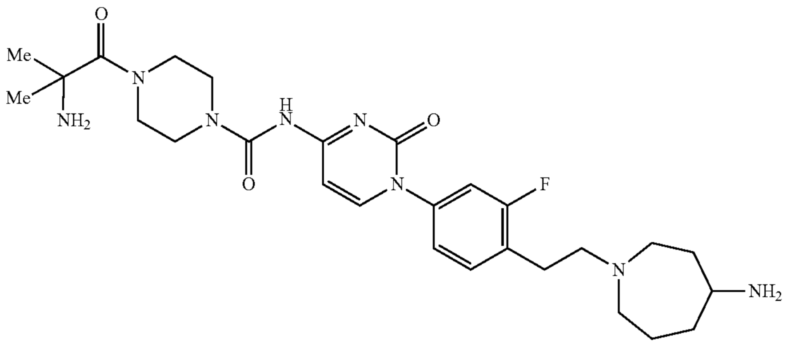 [SMILES: CC(C)(N)C(=O)N1CCN(C(=O)Nc2ccn(-c3ccc(CCN4CCCC(N)CC4)c(F)c3)c(=O)n2)CC1]
142
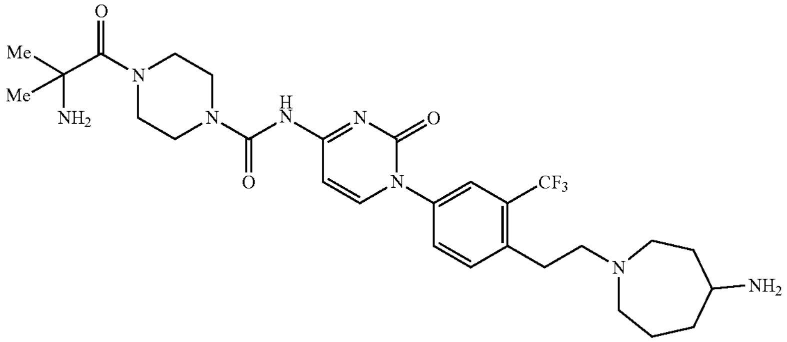 [SMILES: CC(C)(N)C(=O)N1CCN(C(=O)Nc2ccn(-c3ccc(CCN4CCCC(N)CC4)c(C(F)(F)F)c3)c(=O)n2)CC1]
143
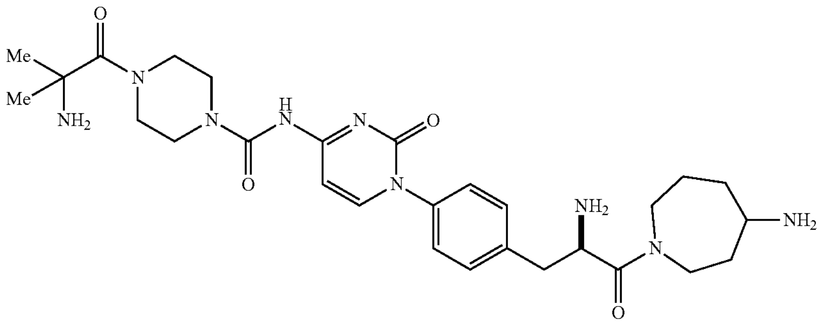 [SMILES: CC(C)(N)C(=O)N1CCN(C(=O)Nc2ccn(-c3ccc(C[C@@H](N)C(=O)N4CCCC(N)CC4)cc3)c(=O)n2)CC1]
144
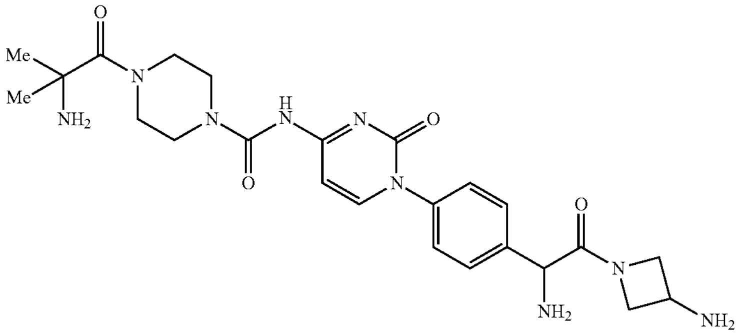 [SMILES: CC(C)(N)C(=O)N1CCN(C(=O)Nc2ccn(-c3ccc(C(N)C(=O)N4CC(N)C4)cc3)c(=O)n2)CC1]

TABLE 10-continued
Compounds of Formula I
145
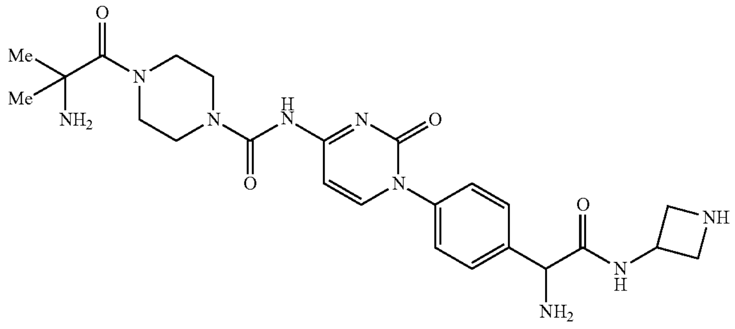 [SMILES: CC(C)(N)C(=O)N1CCN(C(=O)Nc2ccn(-c3ccc(C(N)C(=O)NC4CNC4)cc3)c(=O)n2)CC1]
146
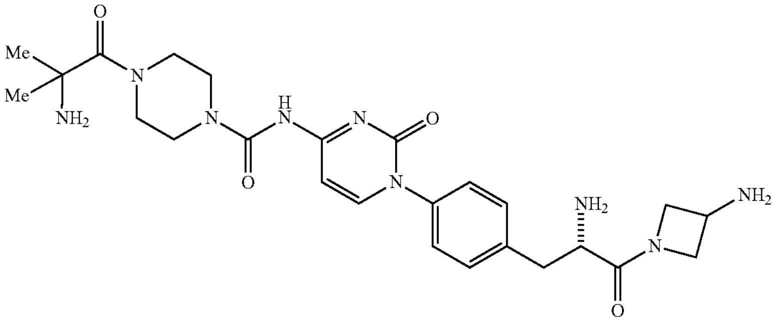 [SMILES: CC(C)(N)C(=O)N1CCN(C(=O)Nc2ccn(-c3ccc(C[C@H](N)C(=O)N4CC(N)C4)cc3)c(=O)n2)CC1]
147
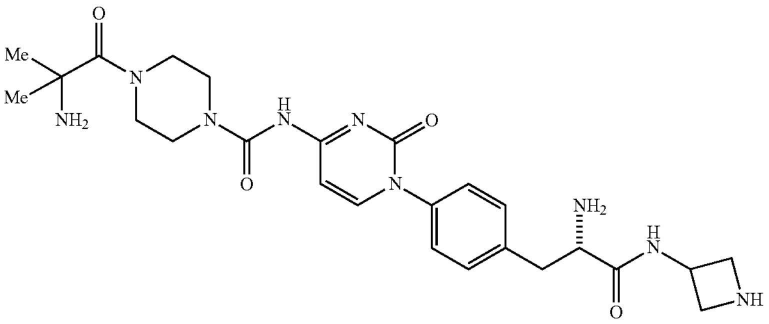 [SMILES: CC(C)(N)C(=O)N1CCN(C(=O)Nc2ccn(-c3ccc(C[C@H](N)C(=O)NC4CNC4)cc3)c(=O)n2)CC1]
148
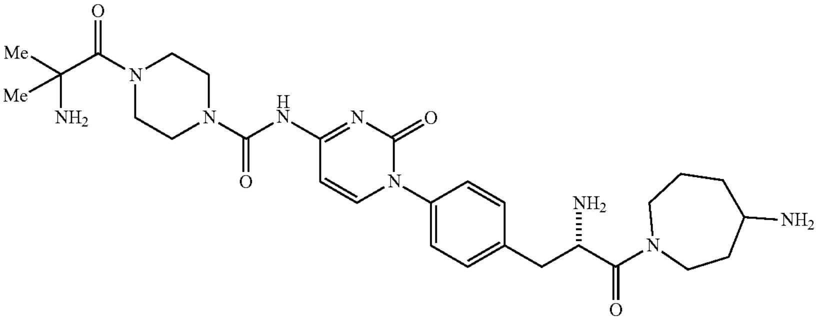 [SMILES: CC(C)(N)C(=O)N1CCN(C(=O)Nc2ccn(-c3ccc(C[C@H](N)C(=O)N4CCCC(N)CC4)cc3)c(=O)n2)CC1]

TABLE 10-continued
Compounds of Formula I
149
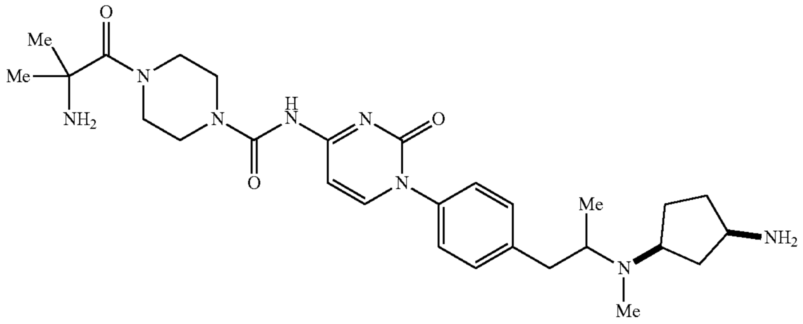 [SMILES: CC(Cc1ccc(-n2ccc(NC(=O)N3CCN(C(=O)C(C)(C)N)CC3)nc2=O)cc1)N(C)[C@H]1CC[C@@H](N)C1]
150
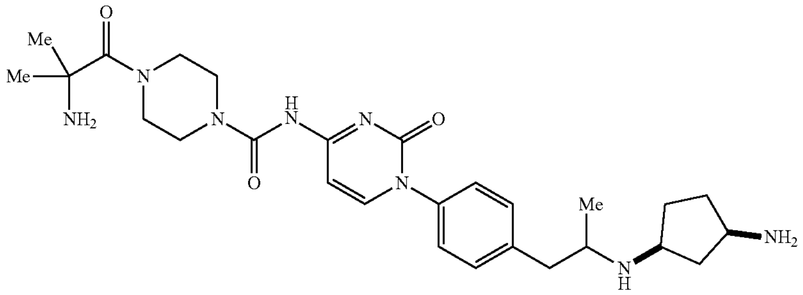 [SMILES: CC(Cc1ccc(-n2ccc(NC(=O)N3CCN(C(=O)C(C)(C)N)CC3)nc2=O)cc1)N[C@H]1CC[C@@H](N)C1]
151
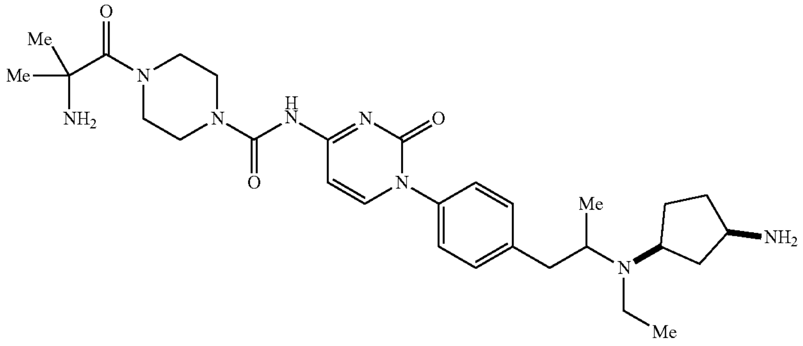 [SMILES: CCN(C(C)Cc1ccc(-n2ccc(NC(=O)N3CCN(C(=O)C(C)(C)N)CC3)nc2=O)cc1)[C@H]1CC[C@@H](N)C1]
152
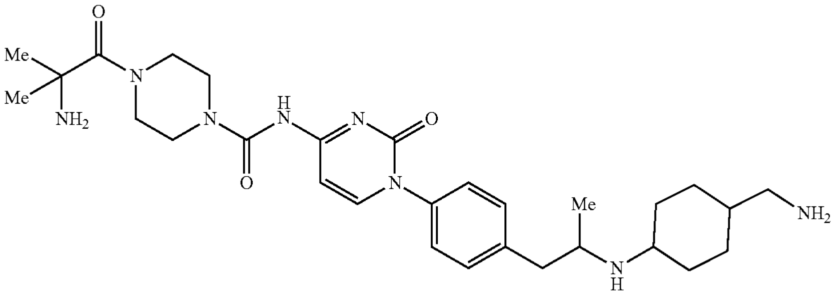 [SMILES: CC(Cc1ccc(-n2ccc(NC(=O)N3CCN(C(=O)C(C)(C)N)CC3)nc2=O)cc1)NC1CCC(CN)CC1]
153
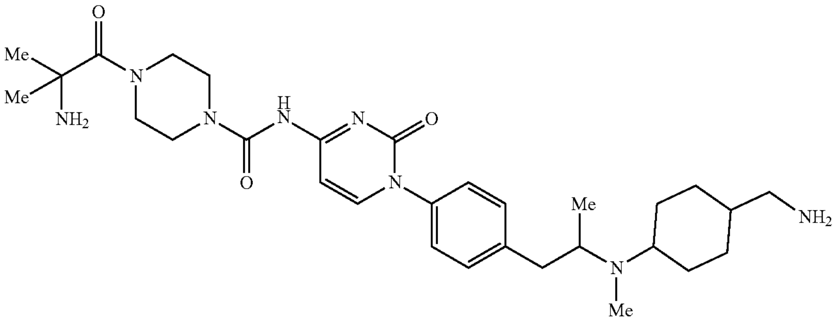 [SMILES: CC(Cc1ccc(-n2ccc(NC(=O)N3CCN(C(=O)C(C)(C)N)CC3)nc2=O)cc1)N(C)C1CCC(CN)CC1]

TABLE 10-continued
| Compounds of Formula I |
|---|
154
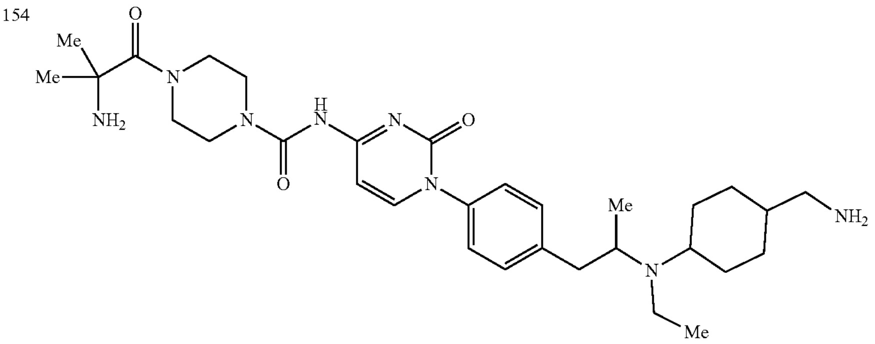
155
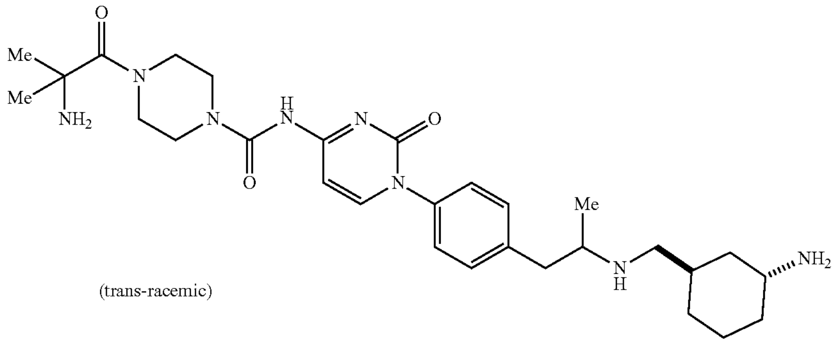 [SMILES: CC(Cc1ccc(-n2ccc(NC(=O)N3CCN(C(=O)C(C)(C)N)CC3)nc2=O)cc1)NC[C@@H]1CCC[C@@H](N)C1]
156
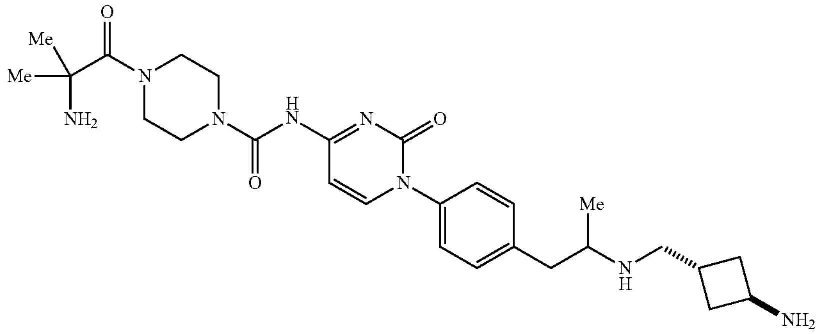 [SMILES: CC(Cc1ccc(-n2ccc(NC(=O)N3CCN(C(=O)C(C)(C)N)CC3)nc2=O)cc1)NC[C@H]1C[C@H](N)C1]
157
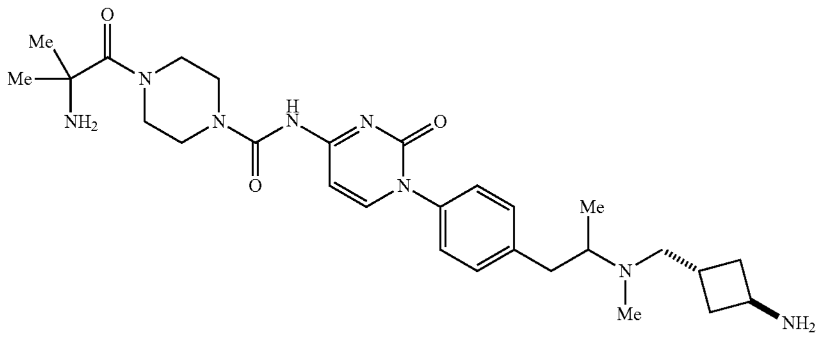 [SMILES: CC(Cc1ccc(-n2ccc(NC(=O)N3CCN(C(=O)C(C)(C)N)CC3)nc2=O)cc1)N(C)C[C@H]1C[C@H](N)C1]

TABLE 10-continued
| Compounds of Formula I |
| --- |
158 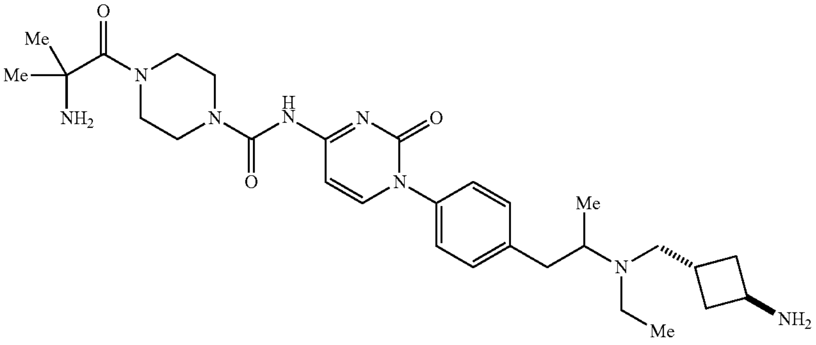
159 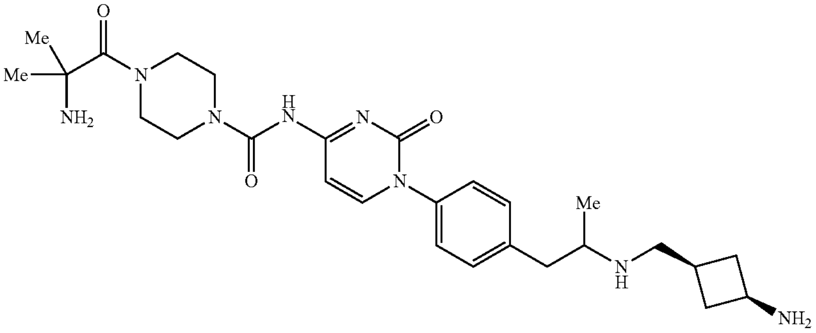 [SMILES: CC(Cc1ccc(-n2ccc(NC(=O)N3CCN(C(=O)C(C)(C)N)CC3)nc2=O)cc1)NC[C@H]1C[C@@H](N)C1]
160 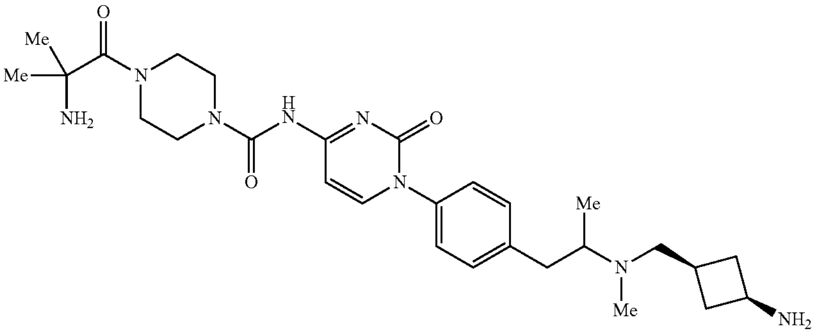 [SMILES: CC(Cc1ccc(-n2ccc(NC(=O)N3CCN(C(=O)C(C)(C)N)CC3)nc2=O)cc1)N(C)C[C@H]1C[C@@H](N)C1]
161 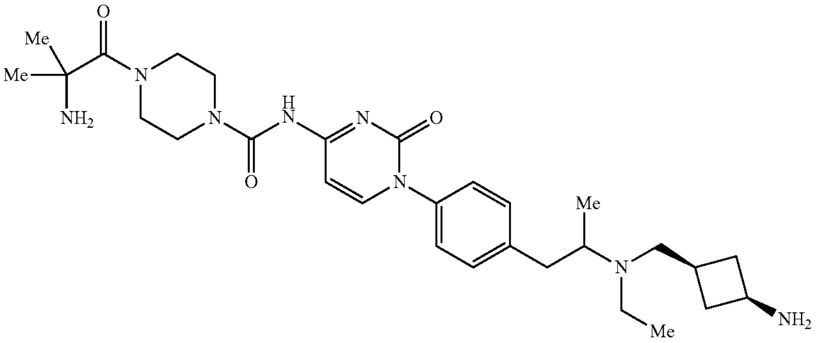 [SMILES: CCN(C[C@H]1C[C@@H](N)C1)C(C)Cc1ccc(-n2ccc(NC(=O)N3CCN(C(=O)C(C)(C)N)CC3)nc2=O)cc1]

TABLE 10-continued
| Compounds of Formula I |
| --- |
| 162 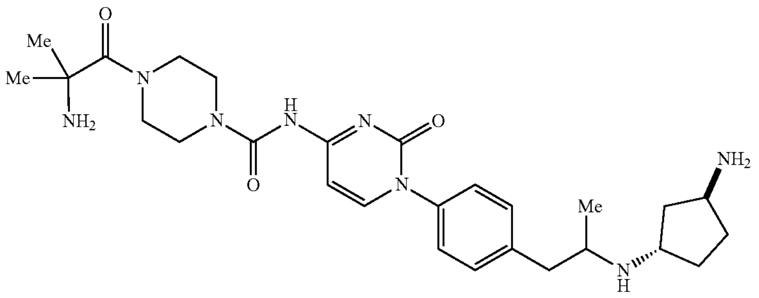 [SMILES: CC(Cc1ccc(-n2ccc(NC(=O)N3CCN(C(=O)C(C)(C)N)CC3)nc2=O)cc1)N[C@H]1CC[C@H](N)C1] |
| 163 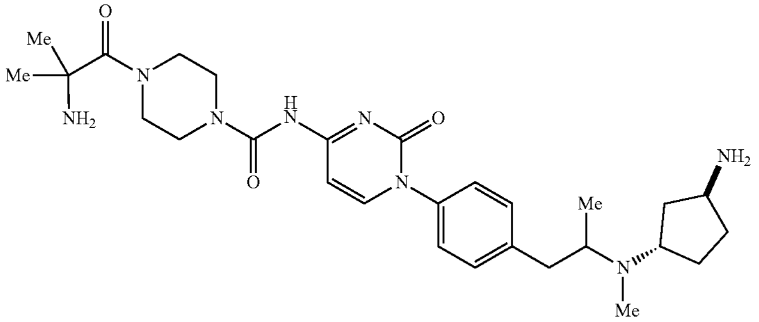 [SMILES: CC(Cc1ccc(-n2ccc(NC(=O)N3CCN(C(=O)C(C)(C)N)CC3)nc2=O)cc1)N(C)[C@H]1CC[C@H](N)C1] |
| 164 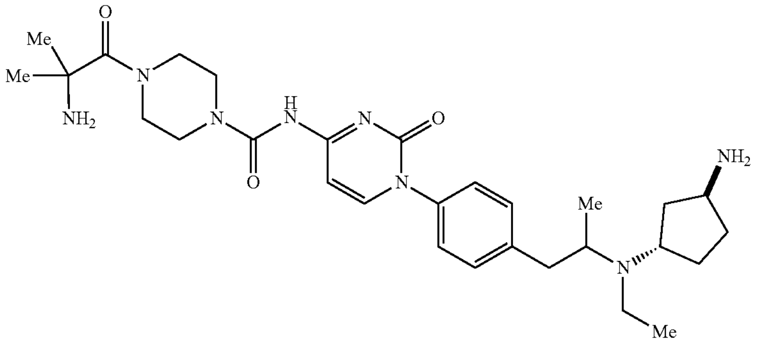 [SMILES: CCN(C(C)Cc1ccc(-n2ccc(NC(=O)N3CCN(C(=O)C(C)(C)N)CC3)nc2=O)cc1)[C@H]1CC[C@H](N)C1] |
| 165 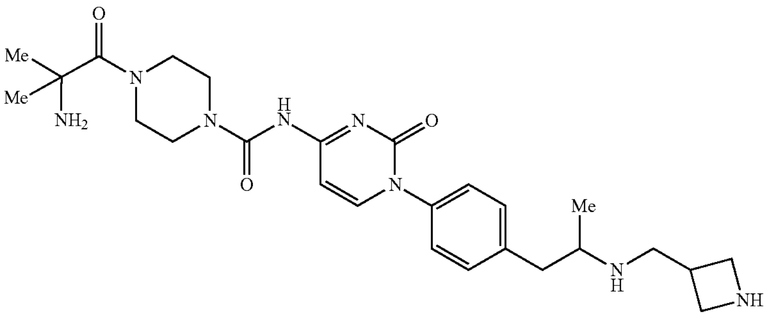 [SMILES: CC(Cc1ccc(-n2ccc(NC(=O)N3CCN(C(=O)C(C)(C)N)CC3)nc2=O)cc1)NCC1CNC1] |

TABLE 10-continued
| Compounds of Formula I |
|---|
| 166 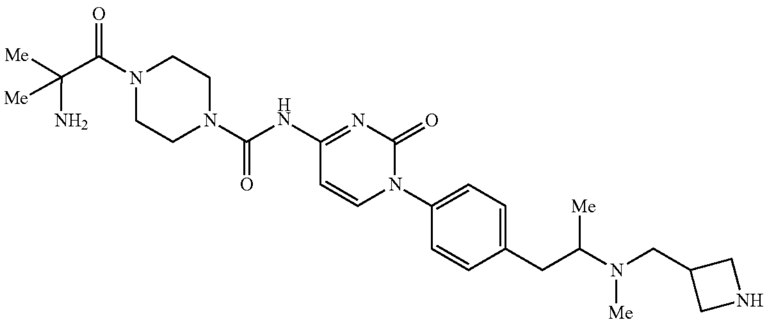 [SMILES: CC(Cc1ccc(-n2ccc(NC(=O)N3CCN(C(=O)C(C)(C)N)CC3)nc2=O)cc1)N(C)CC1CNC1] |
| 167 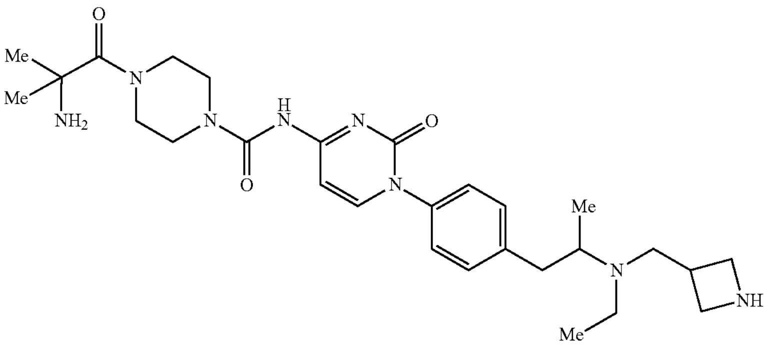 [SMILES: CCN(CC1CNC1)C(C)Cc1ccc(-n2ccc(NC(=O)N3CCN(C(=O)C(C)(C)N)CC3)nc2=O)cc1] |
| 168 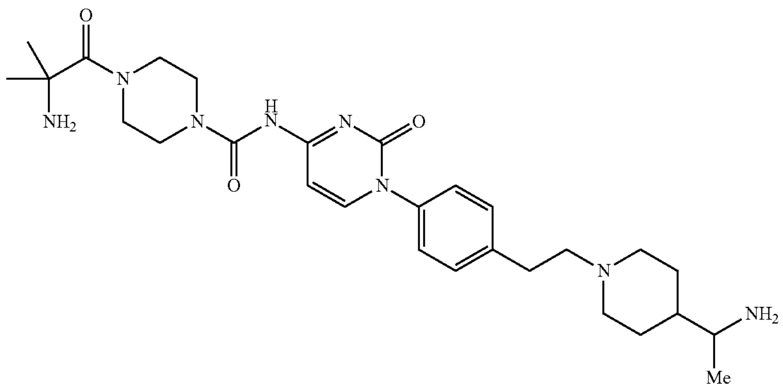 [SMILES: CC(N)C1CCN(CCc2ccc(-n3ccc(NC(=O)N4CCN(C(=O)C(C)(C)N)CC4)nc3=O)cc2)CC1] |
| 169 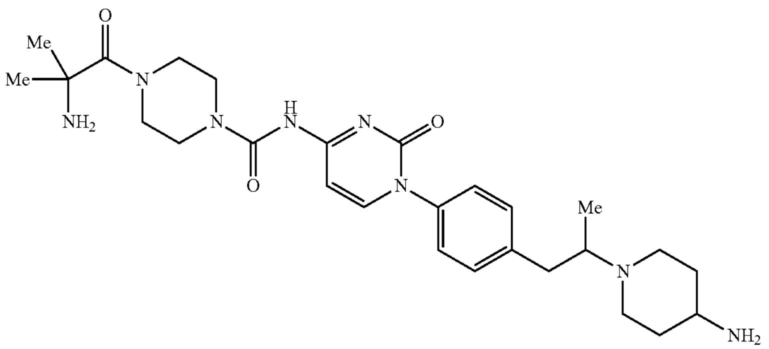 [SMILES: CC(Cc1ccc(-n2ccc(NC(=O)N3CCN(C(=O)C(C)(C)N)CC3)nc2=O)cc1)N1CCC(N)CC1] |

TABLE 10-continued
| Compounds of Formula I | |
|---|---|
| 170 | 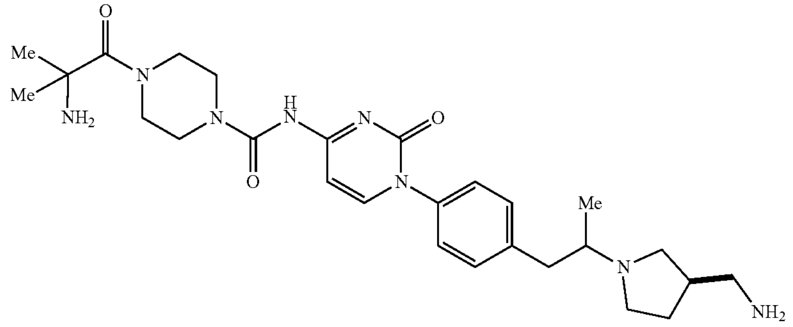 [SMILES: CC(Cc1ccc(-n2ccc(NC(=O)N3CCN(C(=O)C(C)(C)N)CC3)nc2=O)cc1)N1CC[C@H](CN)C1] |
| 171 | 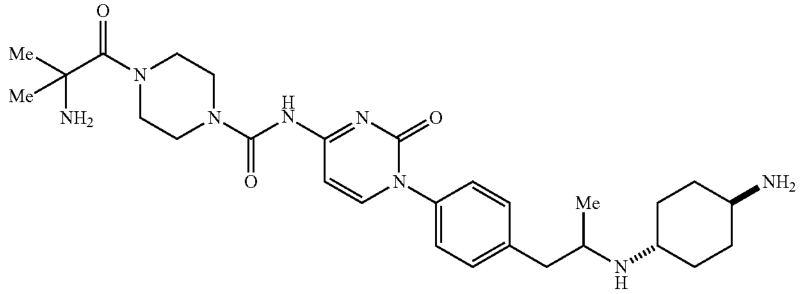 [SMILES: CC(Cc1ccc(-n2ccc(NC(=O)N3CCN(C(=O)C(C)(C)N)CC3)nc2=O)cc1)N[C@H]1CC[C@H](N)CC1] |
| 172 | 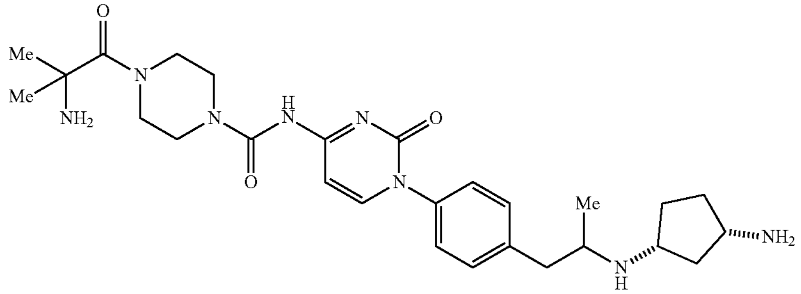 [SMILES: CC(Cc1ccc(-n2ccc(NC(=O)N3CCN(C(=O)C(C)(C)N)CC3)nc2=O)cc1)N[C@@H]1CC[C@H](N)C1] |
| 173 | 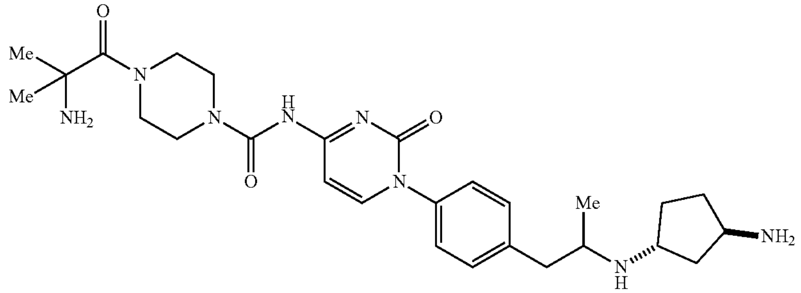 [SMILES: CC(Cc1ccc(-n2ccc(NC(=O)N3CCN(C(=O)C(C)(C)N)CC3)nc2=O)cc1)N[C@@H]1CC[C@@H](N)C1] |
| 174 | 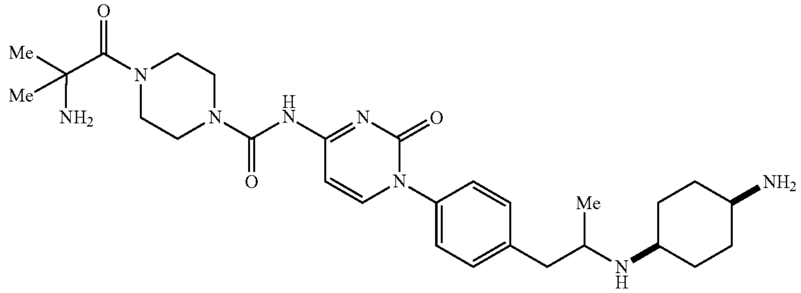 [SMILES: CC(Cc1ccc(-n2ccc(NC(=O)N3CCN(C(=O)C(C)(C)N)CC3)nc2=O)cc1)N[C@H]1CC[C@@H](N)CC1] |

TABLE 10-continued
| Compounds of Formula I |
|---|
175
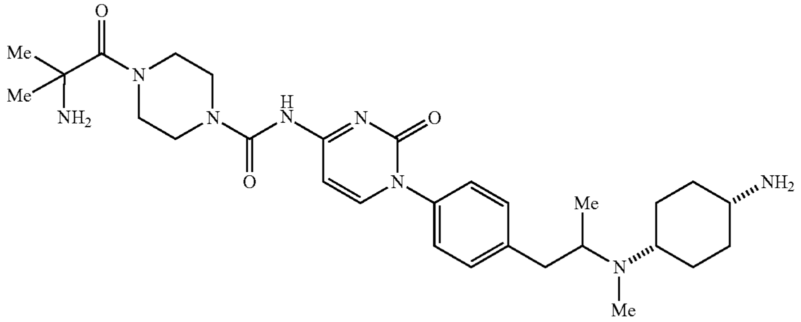 [SMILES: CC(Cc1ccc(-n2ccc(NC(=O)N3CCN(C(=O)C(C)(C)N)CC3)nc2=O)cc1)N(C)[C@H]1CC[C@@H](N)CC1]
176
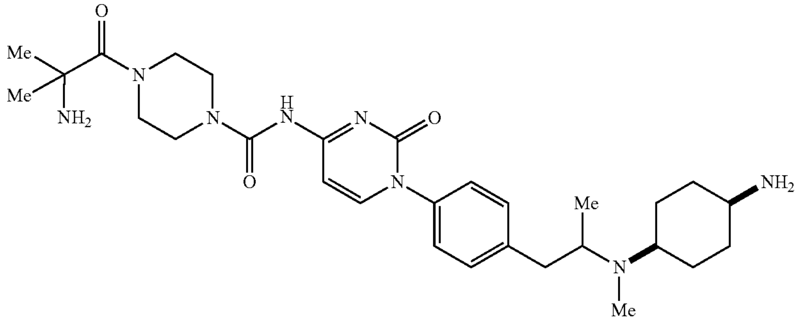 [SMILES: CC(Cc1ccc(-n2ccc(NC(=O)N3CCN(C(=O)C(C)(C)N)CC3)nc2=O)cc1)N(C)[C@H]1CC[C@@H](N)CC1]
177
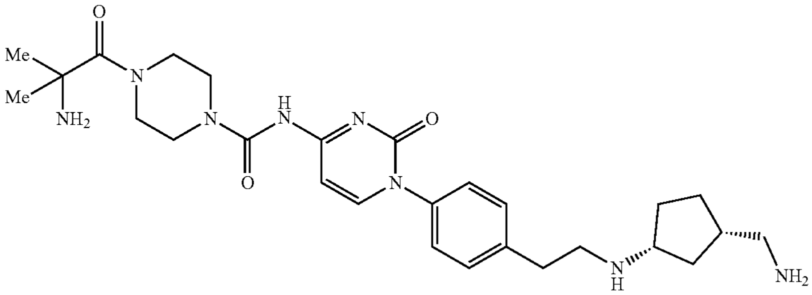 [SMILES: CC(C)(N)C(=O)N1CCN(C(=O)Nc2ccn(-c3ccc(CCN[C@@H]4CC[C@H](CN)C4)cc3)c(=O)n2)CC1]
178
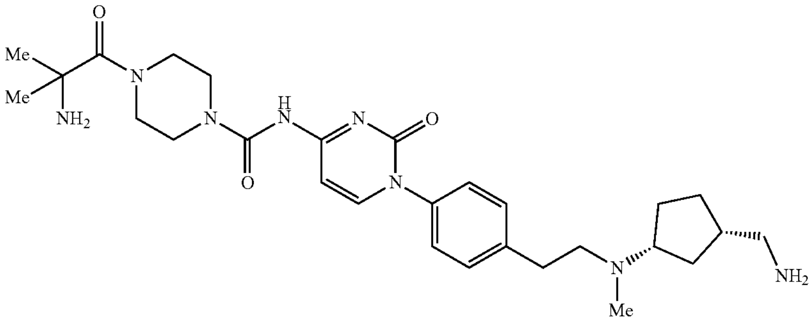 [SMILES: CN(CCc1ccc(-n2ccc(NC(=O)N3CCN(C(=O)C(C)(C)N)CC3)nc2=O)cc1)[C@@H]1CC[C@H](CN)C1]
179
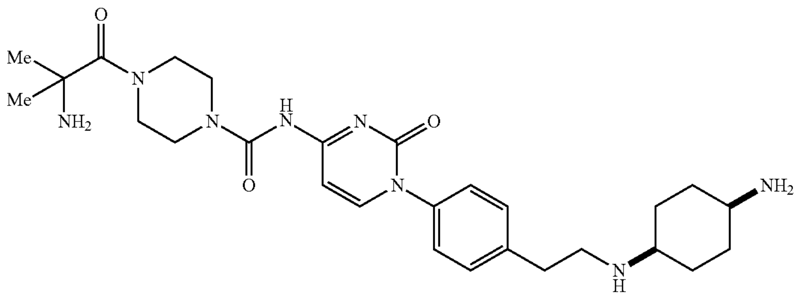 [SMILES: CC(C)(N)C(=O)N1CCN(C(=O)Nc2ccn(-c3ccc(CCN[C@H]4CC[C@@H](N)CC4)cc3)c(=O)n2)CC1]

TABLE 10-continued
| Compounds of Formula I |
|---|
180
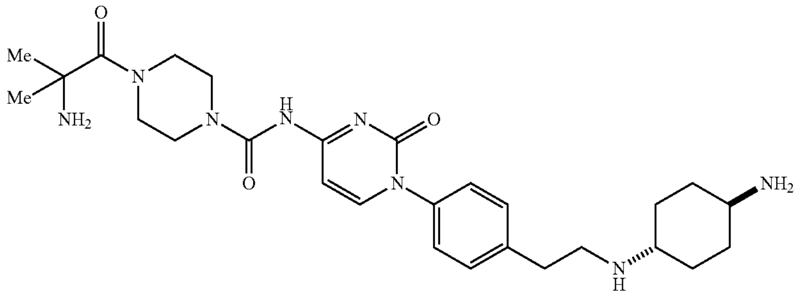 [SMILES: CC(C)(N)C(=O)N1CCN(C(=O)Nc2ccn(-c3ccc(CCN[C@H]4CC[C@H](N)CC4)cc3)c(=O)n2)CC1]
181
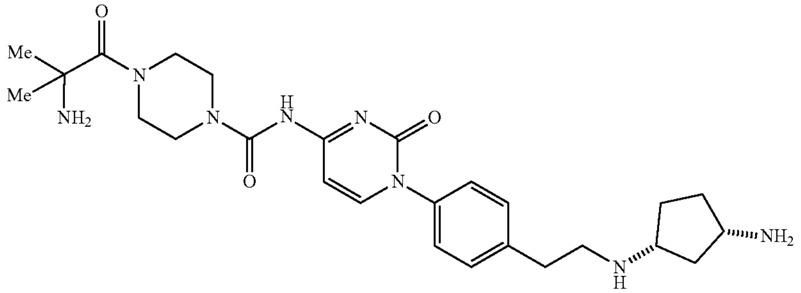 [SMILES: CC(C)(N)C(=O)N1CCN(C(=O)Nc2ccn(-c3ccc(CCN[C@@H]4CC[C@H](N)C4)cc3)c(=O)n2)CC1]
182
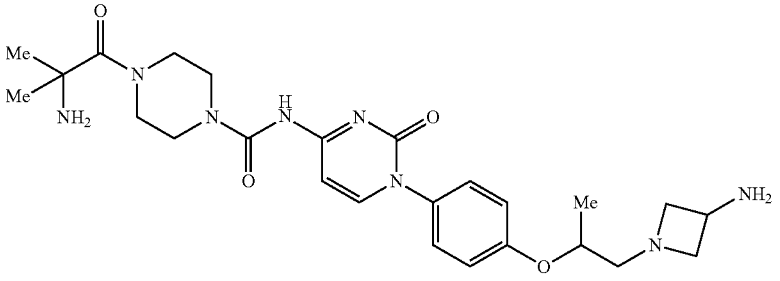 [SMILES: CC(CN1CC(N)C1)Oc1ccc(-n2ccc(NC(=O)N3CCN(C(=O)C(C)(C)N)CC3)nc2=O)cc1]
183
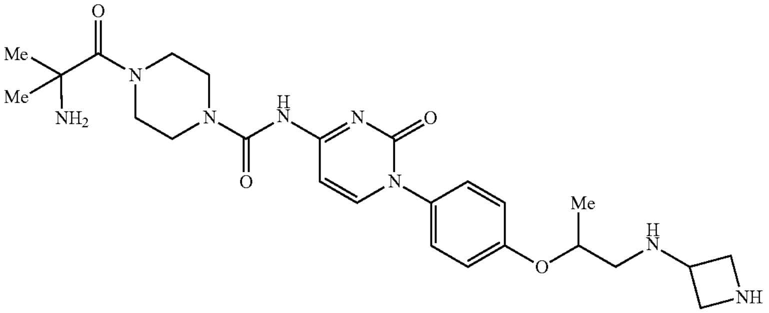 [SMILES: CC(CNC1CNC1)Oc1ccc(-n2ccc(NC(=O)N3CCN(C(=O)C(C)(C)N)CC3)nc2=O)cc1]
184
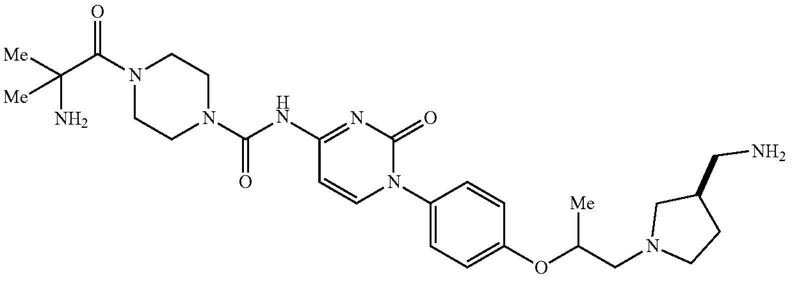 [SMILES: CC(CN1CC[C@H](CN)C1)Oc1ccc(-n2ccc(NC(=O)N3CCN(C(=O)C(C)(C)N)CC3)nc2=O)cc1]

TABLE 10-continued
| Compounds of Formula I | |
|---|---|
| 185 | 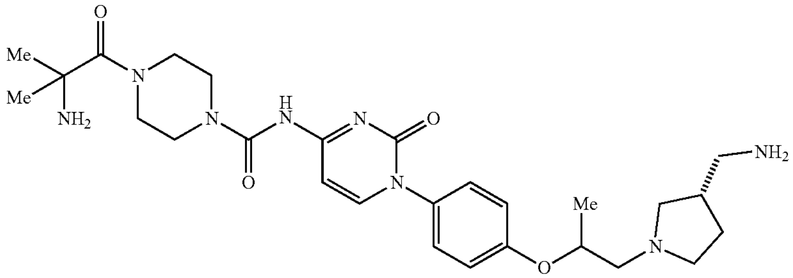 [SMILES: CC(CN1CC[C@@H](CN)C1)Oc1ccc(-n2ccc(NC(=O)N3CCN(C(=O)C(C)(C)N)CC3)nc2=O)cc1] |
| 186 | 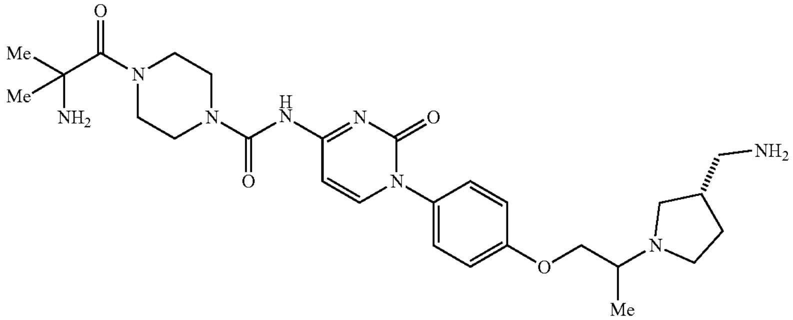 [SMILES: CC(COc1ccc(-n2ccc(NC(=O)N3CCN(C(=O)C(C)(C)N)CC3)nc2=O)cc1)N1CC[C@@H](CN)C1] |
| 187 | 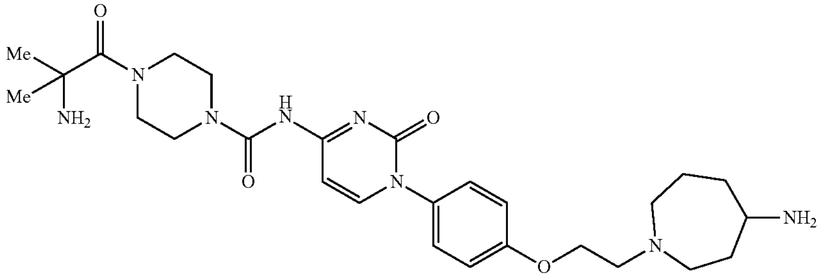 [SMILES: CC(C)(N)C(=O)N1CCN(C(=O)Nc2ccn(-c3ccc(OCCN4CCCC(N)CC4)cc3)c(=O)n2)CC1] |
| 188 | 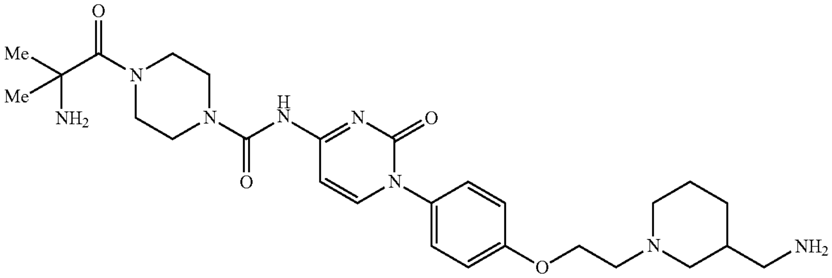 [SMILES: CC(C)(N)C(=O)N1CCN(C(=O)Nc2ccn(-c3ccc(OCCN4CCCC(CN)C4)cc3)c(=O)n2)CC1] |
| 190 | 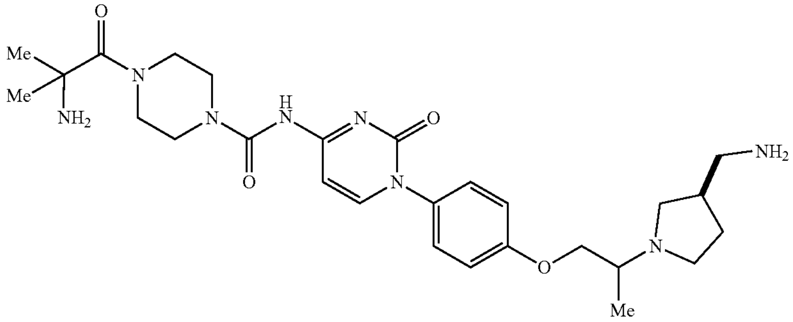 [SMILES: CC(COc1ccc(-n2ccc(NC(=O)N3CCN(C(=O)C(C)(C)N)CC3)nc2=O)cc1)N1CC[C@H](CN)C1] |

TABLE 10-continued
| Compounds of Formula I | |
|---|---|
| 191 | 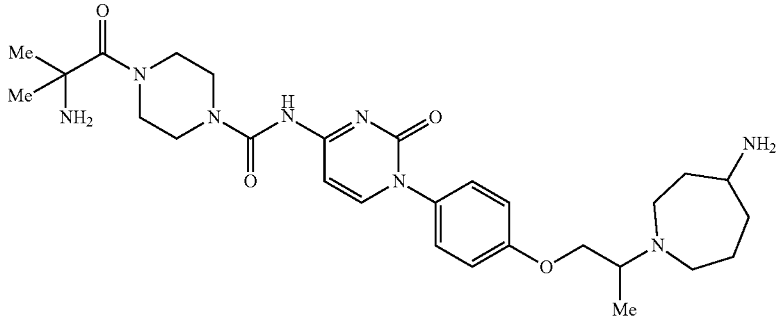 [SMILES: CC(COc1ccc(-n2ccc(NC(=O)N3CCN(C(=O)C(C)(C)N)CC3)nc2=O)cc1)N1CCCC(N)CC1] |
| 192 | 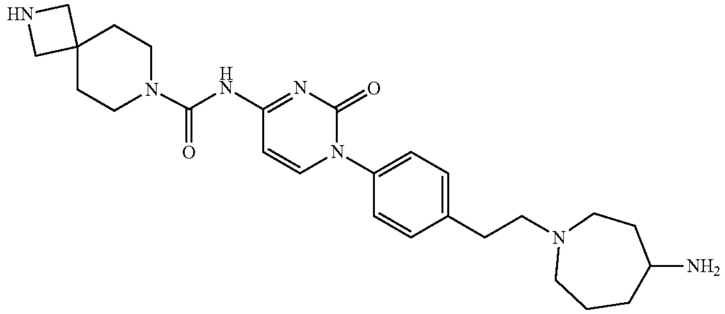 [SMILES: NC1CCCN(CCc2ccc(-n3ccc(NC(=O)N4CCC5(CC4)CNC5)nc3=O)cc2)CC1] |
| 193 | 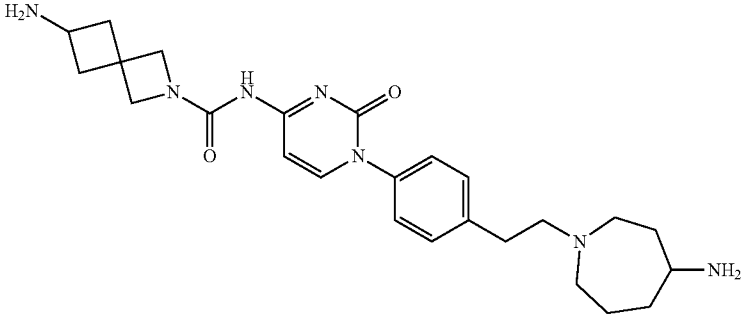 [SMILES: NC1CCCN(CCc2ccc(-n3ccc(NC(=O)N4CC5(CC(N)C5)C4)nc3=O)cc2)CC1] |
| 194 | 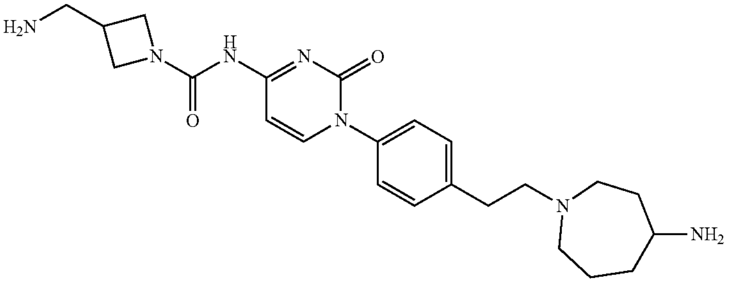 [SMILES: NCC1CN(C(=O)Nc2ccn(-c3ccc(CCN4CCCC(N)CC4)cc3)c(=O)n2)C1] |
| 195 | 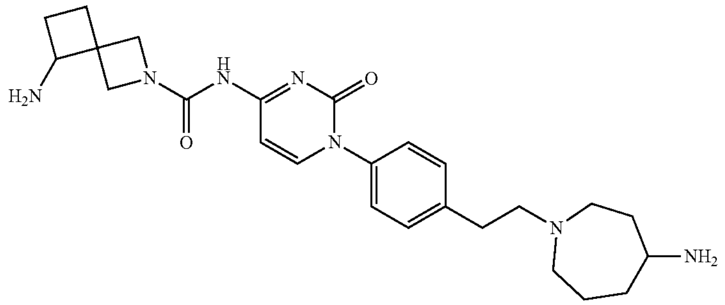 [SMILES: NC1CCCN(CCc2ccc(-n3ccc(NC(=O)N4CC5(CCC5N)C4)nc3=O)cc2)CC1] |

TABLE 10-continued
| Compounds of Formula I |
|---|
196
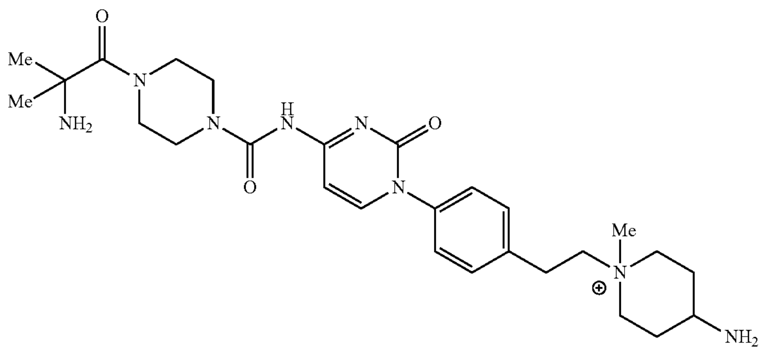 [SMILES: CC(C)(N)C(=O)N1CCN(C(=O)Nc2ccn(-c3ccc(CC[N+]4(C)CCC(N)CC4)cc3)c(=O)n2)CC1]
197
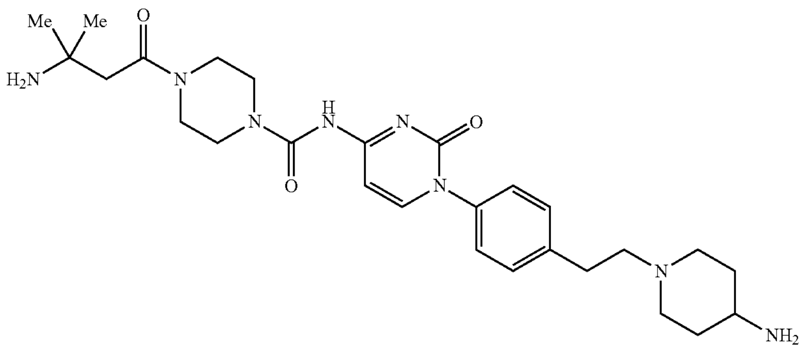 [SMILES: CC(C)(N)CC(=O)N1CCN(C(=O)Nc2ccn(-c3ccc(CCN4CCC(N)CC4)cc3)c(=O)n2)CC1]
198
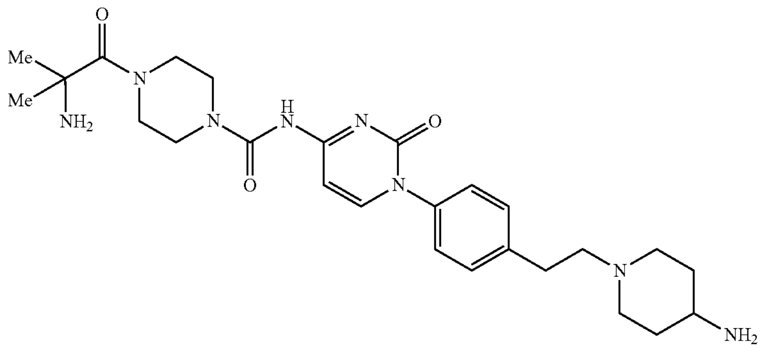 [SMILES: CC(C)(N)C(=O)N1CCN(C(=O)Nc2ccn(-c3ccc(CCN4CCC(N)CC4)cc3)c(=O)n2)CC1]
199
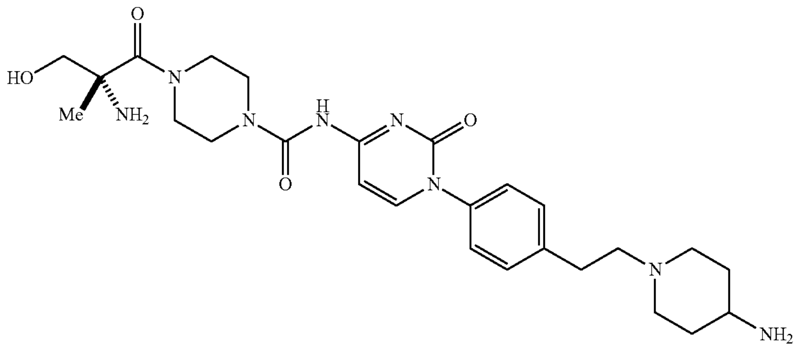

TABLE 10-continued
| Compounds of Formula I | |
|---|---|
| 200 | 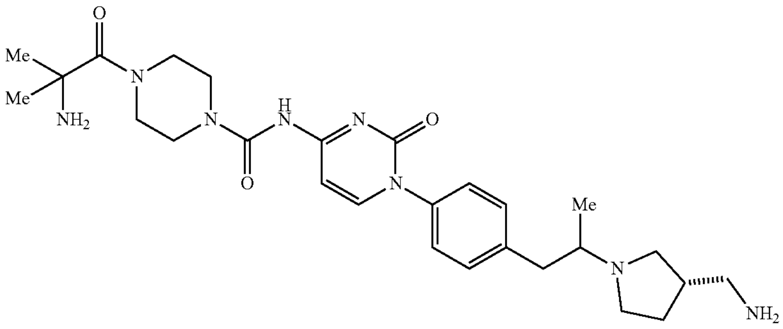 [SMILES: CC(Cc1ccc(-n2ccc(NC(=O)N3CCN(C(=O)C(C)(C)N)CC3)nc2=O)cc1)N1CC[C@@H](CN)C1] |
| 201 | 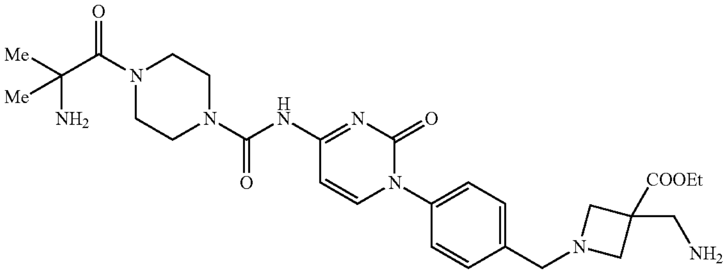 [SMILES: CCOC(=O)C1(CN)CN(Cc2ccc(-n3ccc(NC(=O)N4CCN(C(=O)C(C)(C)N)CC4)nc3=O)cc2)C1] |
| 204 | 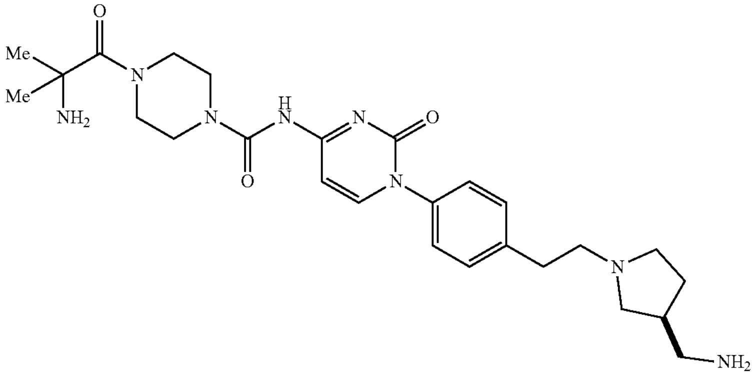 [SMILES: CC(C)(N)C(=O)N1CCN(C(=O)Nc2ccn(-c3ccc(CCN4CC[C@@H](CN)C4)cc3)c(=O)n2)CC1] |
| 205 | 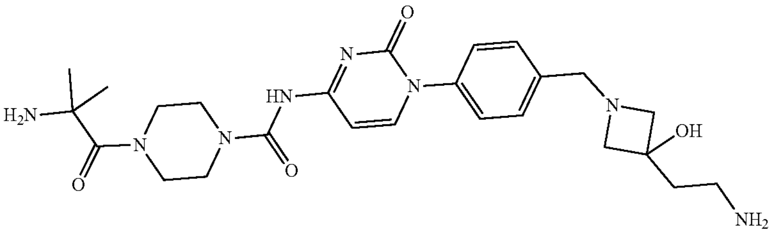 [SMILES: CC(C)(N)C(=O)N1CCN(C(=O)Nc2ccn(-c3ccc(CN4CC(O)(CCN)C4)cc3)c(=O)n2)CC1] |
| 206 | 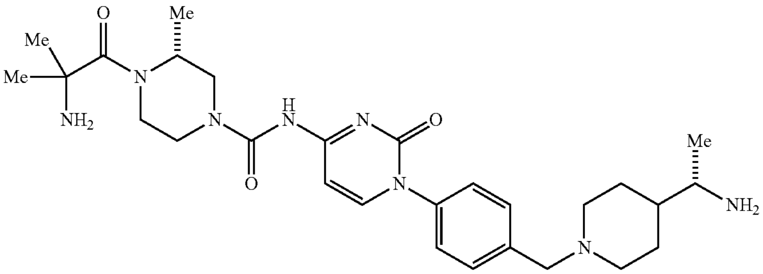 [SMILES: C[C@H](N)C1CCN(Cc2ccc(-n3ccc(NC(=O)N4CCN(C(=O)C(C)(C)N)[C@H](C)C4)nc3=O)cc2)CC1] |

TABLE 10-continued
| Compounds of Formula I |
|---|
| 207 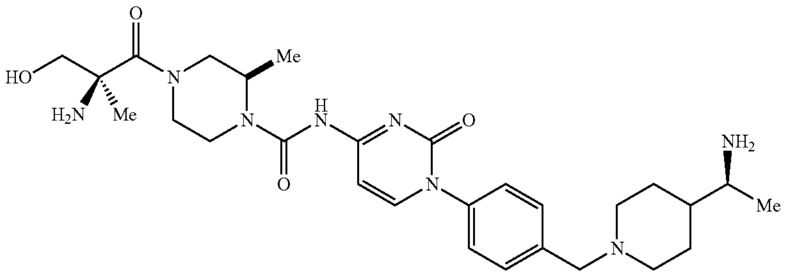 [SMILES: C[C@H](N)C1CCN(Cc2ccc(-n3ccc(NC(=O)N4CCN(C(=O)[C@@](C)(N)CO)C[C@H]4C)nc3=O)cc2)CC1] |
| 208 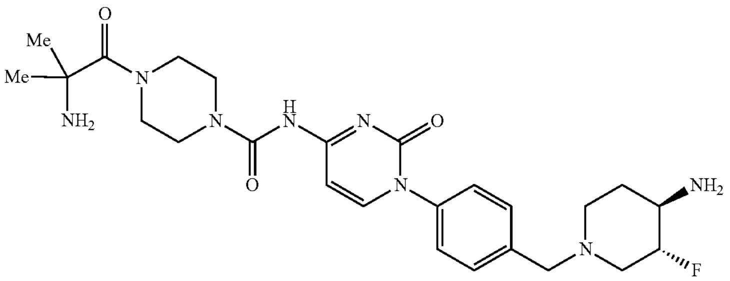 [SMILES: CC(C)(N)C(=O)N1CCN(C(=O)Nc2ccn(-c3ccc(CN4CC[C@@H](N)[C@H](F)C4)cc3)c(=O)n2)CC1] |
| 209 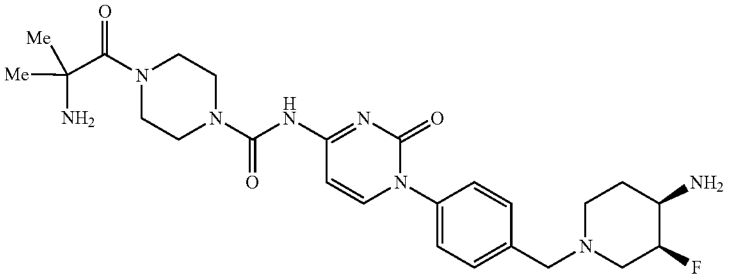 [SMILES: CC(C)(N)C(=O)N1CCN(C(=O)Nc2ccn(-c3ccc(CN4CC[C@@H](N)[C@@H](F)C4)cc3)c(=O)n2)CC1] |
| 210 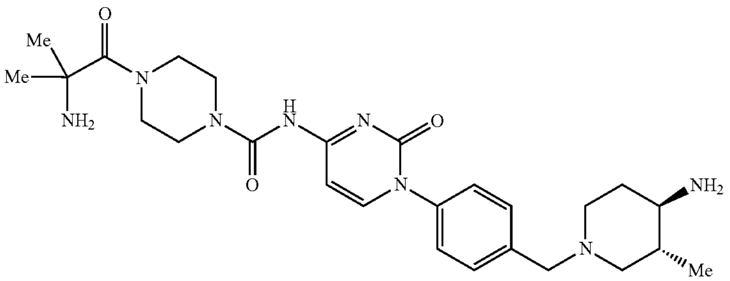 [SMILES: C[C@@H]1CN(Cc2ccc(-n3ccc(NC(=O)N4CCN(C(=O)C(C)(C)N)CC4)nc3=O)cc2)CC[C@H]1N] |
| 211 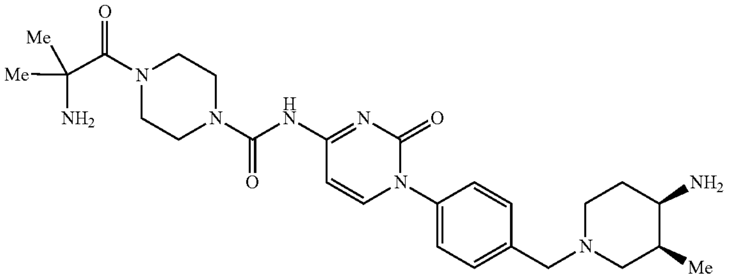 [SMILES: C[C@H]1CN(Cc2ccc(-n3ccc(NC(=O)N4CCN(C(=O)C(C)(C)N)CC4)nc3=O)cc2)CC[C@H]1N] |

TABLE 10-continued
| Compounds of Formula I | |
|---|---|
| 212 | 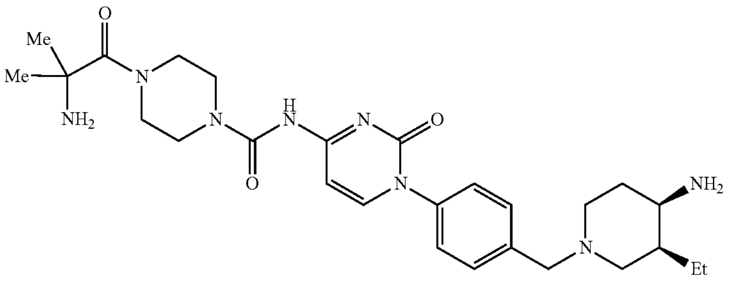 [SMILES: CC[C@H]1CN(Cc2ccc(-n3ccc(NC(=O)N4CCN(C(=O)C(C)(C)N)CC4)nc3=O)cc2)CC[C@H]1N] |
| 213 | 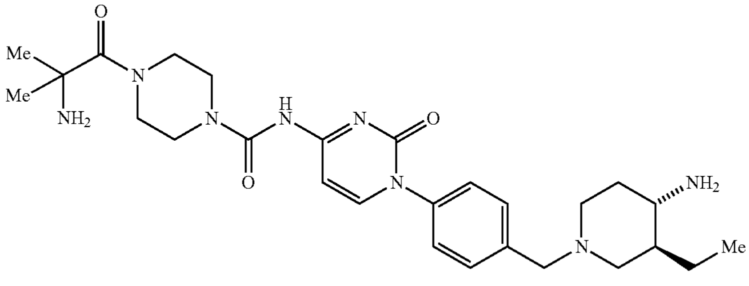 [SMILES: CC[C@H]1CN(Cc2ccc(-n3ccc(NC(=O)N4CCN(C(=O)C(C)(C)N)CC4)nc3=O)cc2)CC[C@@H]1N] |
| 214 | 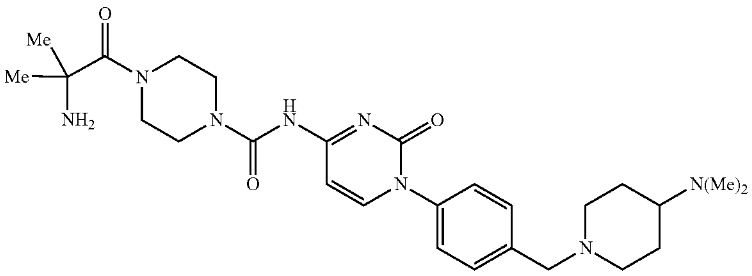 |
| 215 | 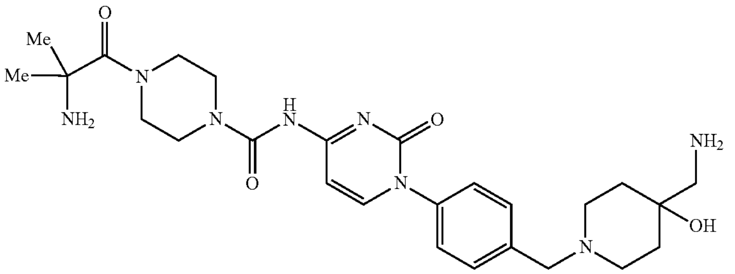 [SMILES: CC(C)(N)C(=O)N1CCN(C(=O)Nc2ccn(-c3ccc(CN4CCC(O)(CN)CC4)cc3)c(=O)n2)CC1] |
| 216 | 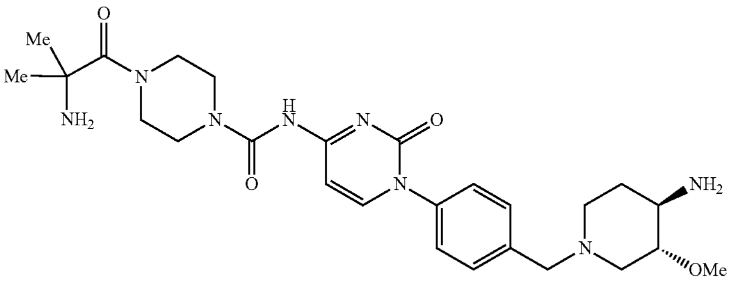 [SMILES: CO[C@@H]1CN(Cc2ccc(-n3ccc(NC(=O)N4CCN(C(=O)C(C)(C)N)CC4)nc3=O)cc2)CC[C@H]1N] |

TABLE 10-continued
| Compounds of Formula I |
|---|
217
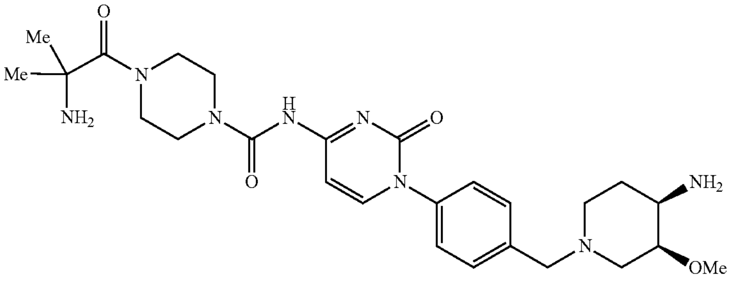 [SMILES: CO[C@H]1CN(Cc2ccc(-n3ccc(NC(=O)N4CCN(C(=O)C(C)(C)N)CC4)nc3=O)cc2)CC[C@H]1N]
218
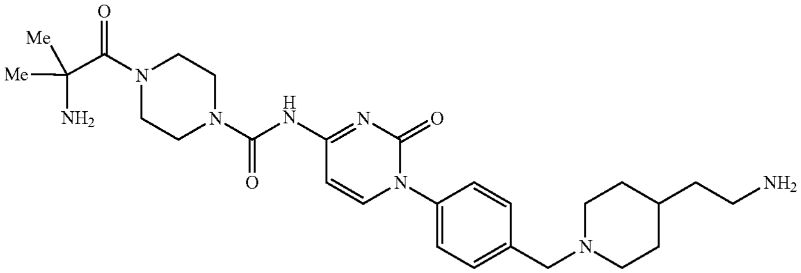 [SMILES: CC(C)(N)C(=O)N1CCN(C(=O)Nc2ccn(-c3ccc(CN4CCC(CCN)CC4)cc3)c(=O)n2)CC1]
219
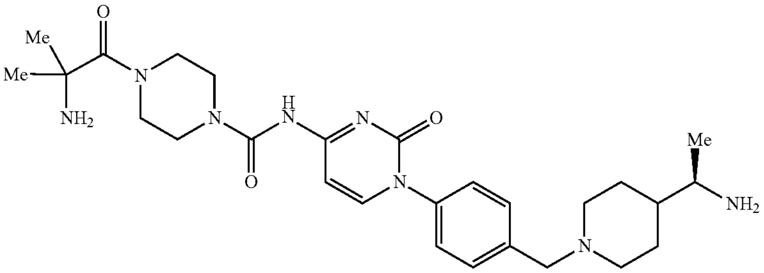 [SMILES: C[C@@H](N)C1CCN(Cc2ccc(-n3ccc(NC(=O)N4CCN(C(=O)C(C)(C)N)CC4)nc3=O)cc2)CC1]
220
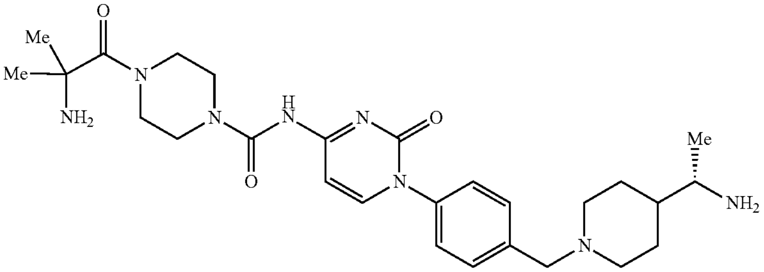 [SMILES: C[C@H](N)C1CCN(Cc2ccc(-n3ccc(NC(=O)N4CCN(C(=O)C(C)(C)N)CC4)nc3=O)cc2)CC1]
221
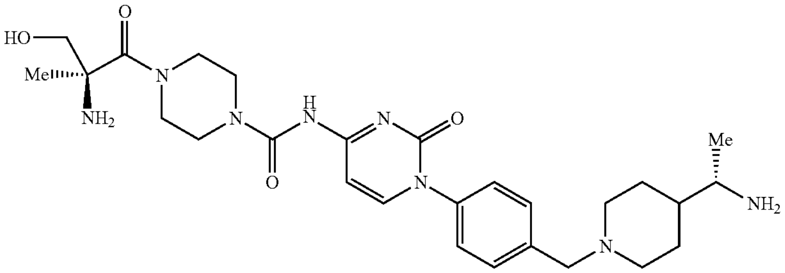 [SMILES: C[C@H](N)C1CCN(Cc2ccc(-n3ccc(NC(=O)N4CCN(C(=O)[C@@](C)(N)CO)CC4)nc3=O)cc2)CC1]

TABLE 10-continued
| Compounds of Formula I |
|---|
222
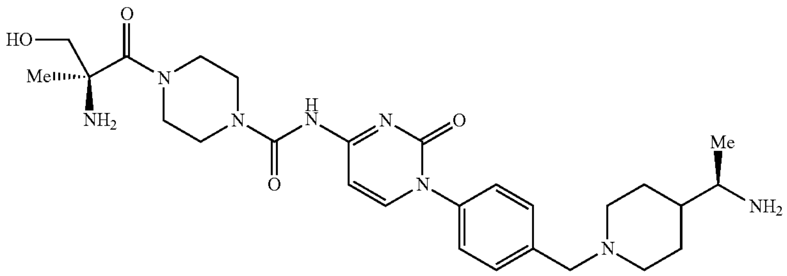 [SMILES: C[C@@H](N)C1CCN(Cc2ccc(-n3ccc(NC(=O)N4CCN(C(=O)[C@@](C)(N)CO)CC4)nc3=O)cc2)CC1]
223
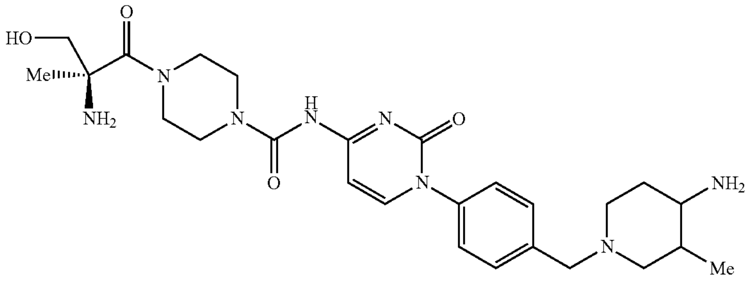 [SMILES: CC1CN(Cc2ccc(-n3ccc(NC(=O)N4CCN(C(=O)[C@@](C)(N)CO)CC4)nc3=O)cc2)CCC1N]
224
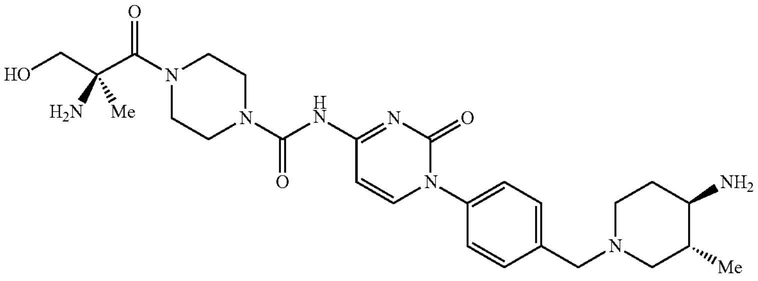 [SMILES: C[C@@H]1CN(Cc2ccc(-n3ccc(NC(=O)N4CCN(C(=O)[C@@](C)(N)CO)CC4)nc3=O)cc2)CC[C@H]1N]
225
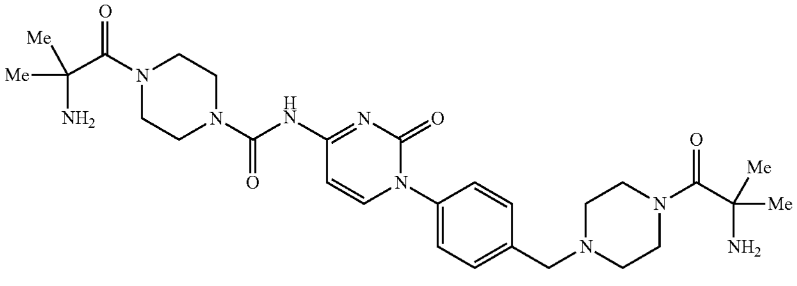 [SMILES: CC(C)(N)C(=O)N1CCN(Cc2ccc(-n3ccc(NC(=O)N4CCN(C(=O)C(C)(C)N)CC4)nc3=O)cc2)CC1]
226
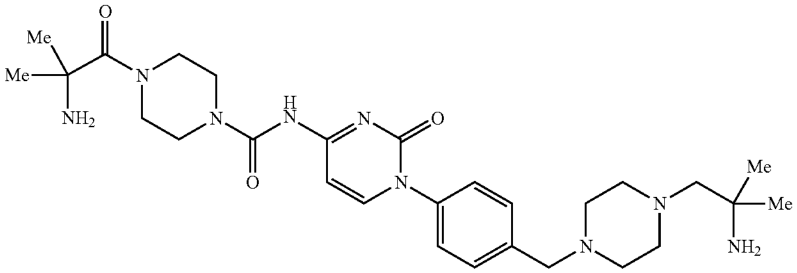 [SMILES: CC(C)(N)CN1CCN(Cc2ccc(-n3ccc(NC(=O)N4CCN(C(=O)C(C)(C)N)CC4)nc3=O)cc2)CC1]

TABLE 10-continued
Compounds of Formula I
227
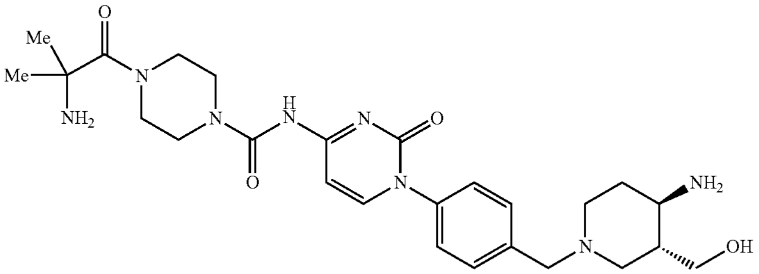 [SMILES: CC(C)(N)C(=O)N1CCN(C(=O)Nc2ccn(-c3ccc(CN4CC[C@@H](N)[C@H](CO)C4)cc3)c(=O)n2)CC1]
230
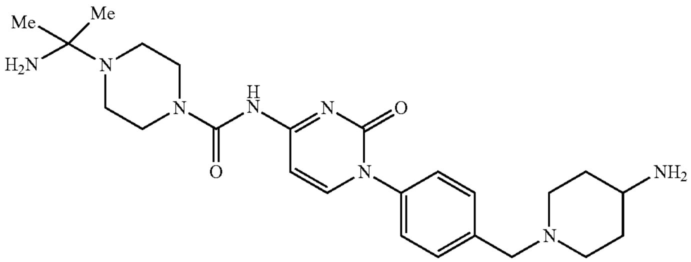
231
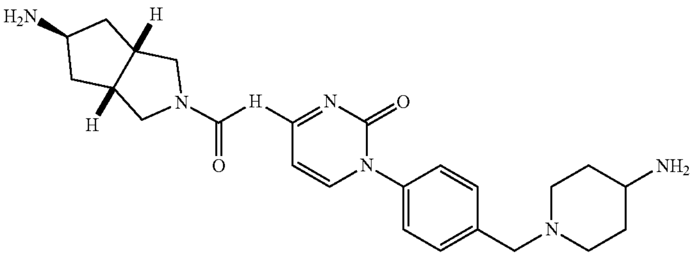
233
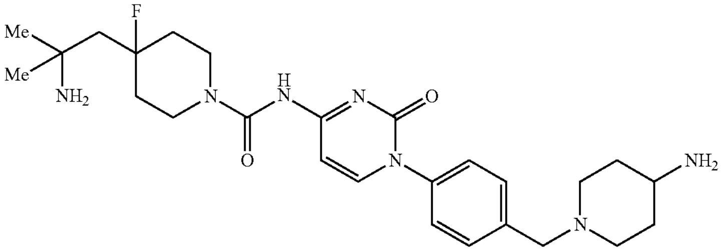 [SMILES: CC(C)(N)CC1(F)CCN(C(=O)Nc2ccn(-c3ccc(CN4CCC(N)CC4)cc3)c(=O)n2)CC1]
234
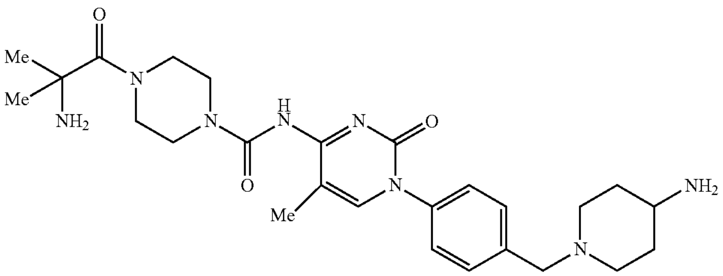 [SMILES: Cc1cn(-c2ccc(CN3CCC(N)CC3)cc2)c(=O)nc1NC(=O)N1CCN(C(=O)C(C)(C)N)CC1]

TABLE 10-continued
| Compounds of Formula I | |
|---|---|
| 235 | 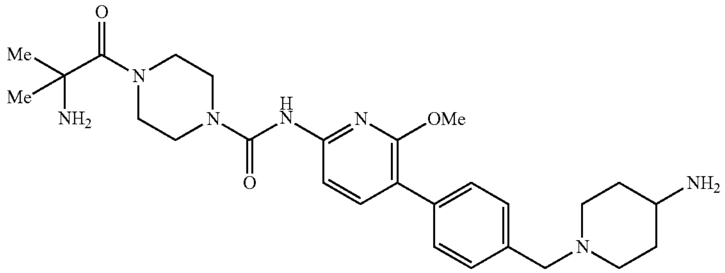 [SMILES: COc1nc(NC(=O)N2CCN(C(=O)C(C)(C)N)CC2)ccc1-c1ccc(CN2CCC(N)CC2)cc1] |
| 236 | 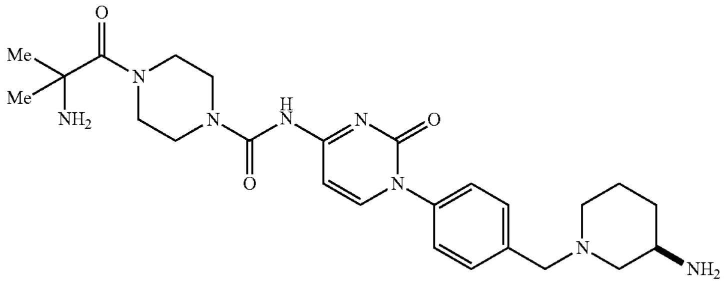 [SMILES: CC(C)(N)C(=O)N1CCN(C(=O)Nc2ccn(-c3ccc(CN4CCC[C@@H](N)C4)cc3)c(=O)n2)CC1] |
| 237 | 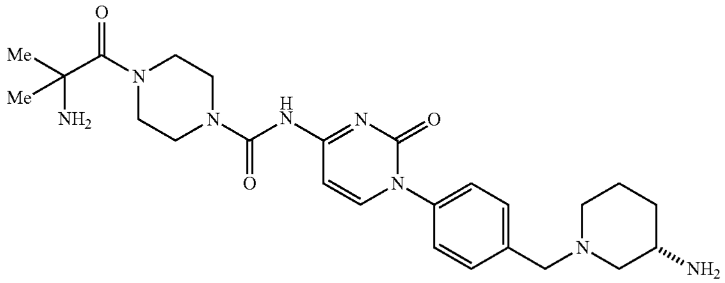 [SMILES: CC(C)(N)C(=O)N1CCN(C(=O)Nc2ccn(-c3ccc(CN4CCC[C@H](N)C4)cc3)c(=O)n2)CC1] |
| 238 | 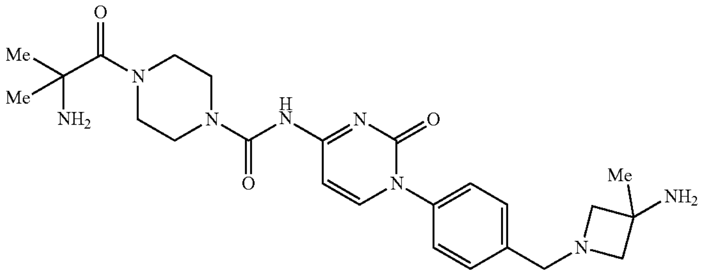 [SMILES: CC1(N)CN(Cc2ccc(-n3ccc(NC(=O)N4CCN(C(=O)C(C)(C)N)CC4)nc3=O)cc2)C1] |
| 239 | 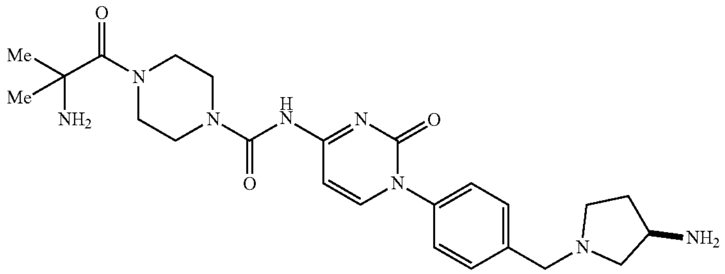 [SMILES: CC(C)(N)C(=O)N1CCN(C(=O)Nc2ccn(-c3ccc(CN4CC[C@@H](N)C4)cc3)c(=O)n2)CC1] |

TABLE 10-continued
| Compounds of Formula I | |
|---|---|
| 240 | 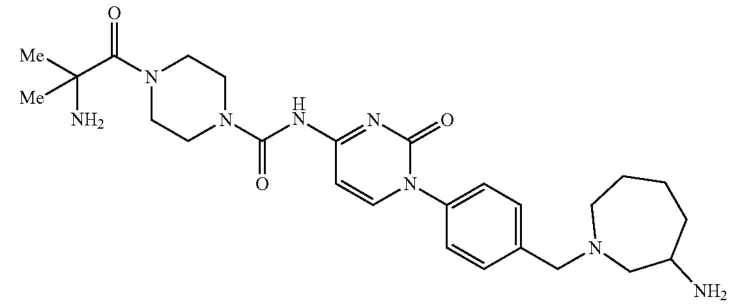 [SMILES: CC(C)(N)C(=O)N1CCN(C(=O)Nc2ccn(-c3ccc(CN4CCCCC(N)C4)cc3)c(=O)n2)CC1] |
| 241 | 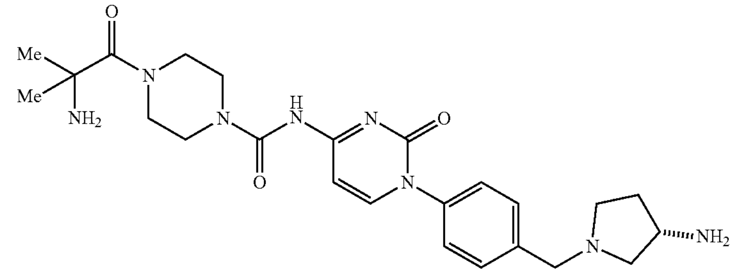 [SMILES: CC(C)(N)C(=O)N1CCN(C(=O)Nc2ccn(-c3ccc(CN4CC[C@H](N)C4)cc3)c(=O)n2)CC1] |
| 242 | 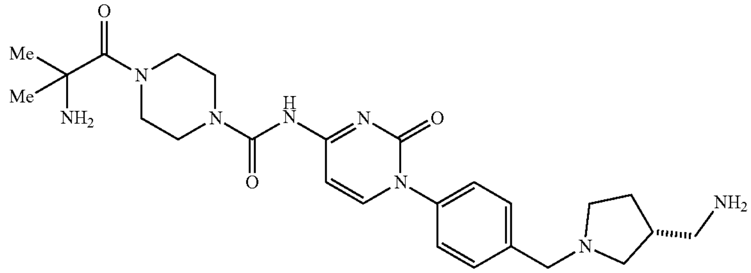 [SMILES: CC(C)(N)C(=O)N1CCN(C(=O)Nc2ccn(-c3ccc(CN4CC[C@H](CN)C4)cc3)c(=O)n2)CC1] |
| 243 | 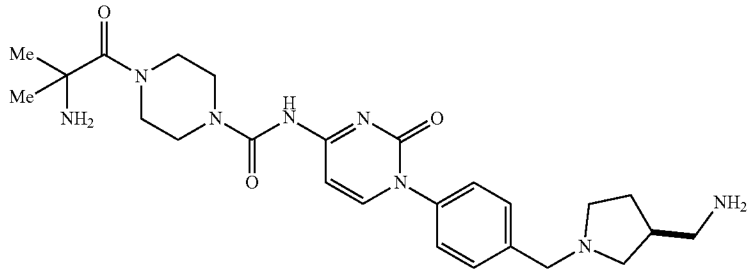 [SMILES: CC(C)(N)C(=O)N1CCN(C(=O)Nc2ccn(-c3ccc(CN4CC[C@@H](CN)C4)cc3)c(=O)n2)CC1] |
| 244 | 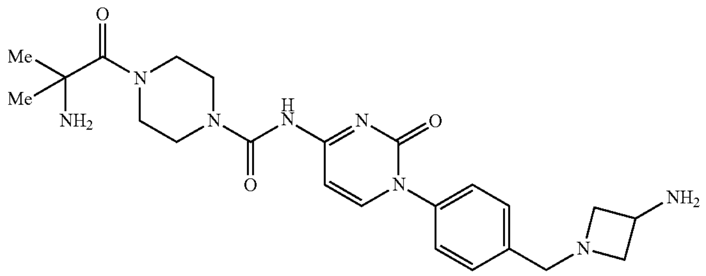 [SMILES: CC(C)(N)C(=O)N1CCN(C(=O)Nc2ccn(-c3ccc(CN4CC(N)C4)cc3)c(=O)n2)CC1] |

TABLE 10-continued
Compounds of Formula I
245
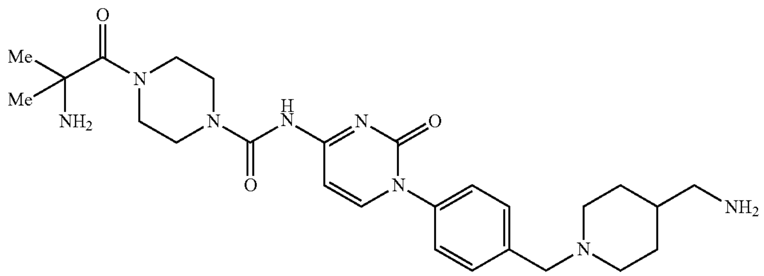 [SMILES: CC(C)(N)C(=O)N1CCN(C(=O)Nc2ccn(-c3ccc(CN4CCC(CN)CC4)cc3)c(=O)n2)CC1]
246
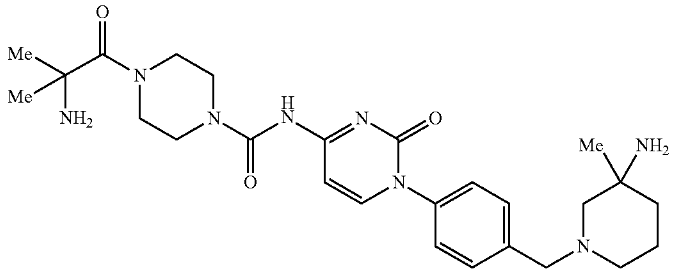 [SMILES: CC1(N)CCCN(Cc2ccc(-n3ccc(NC(=O)N4CCN(C(=O)C(C)(C)N)CC4)nc3=O)cc2)C1]
247
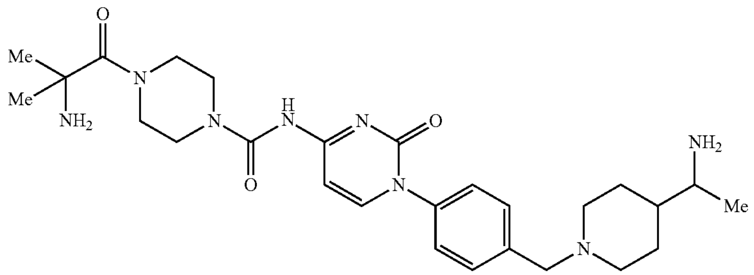 [SMILES: CC(N)C1CCN(Cc2ccc(-n3ccc(NC(=O)N4CCN(C(=O)C(C)(C)N)CC4)nc3=O)cc2)CC1]
248
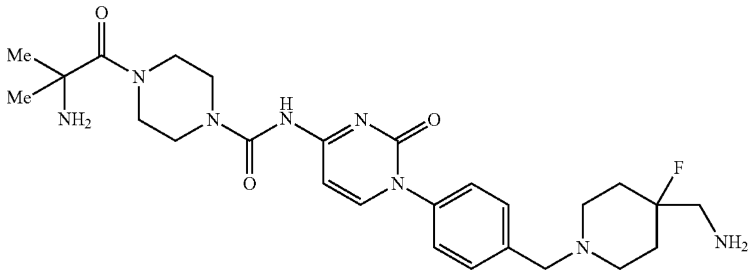 [SMILES: CC(C)(N)C(=O)N1CCN(C(=O)Nc2ccn(-c3ccc(CN4CCC(F)(CN)CC4)cc3)c(=O)n2)CC1]
249
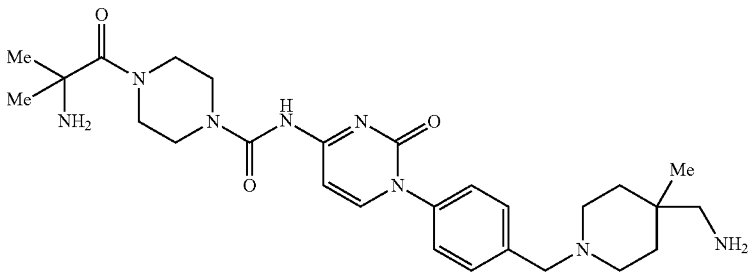 [SMILES: CC1(CN)CCN(Cc2ccc(-n3ccc(NC(=O)N4CCN(C(=O)C(C)(C)N)CC4)nc3=O)cc2)CC1]

TABLE 10-continued
Compounds of Formula I
250
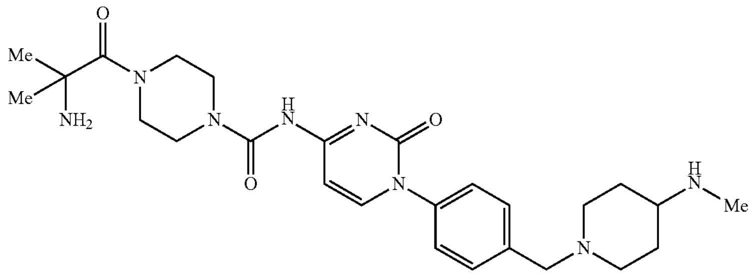 [SMILES: CNC1CCN(Cc2ccc(-n3ccc(NC(=O)N4CCN(C(=O)C(C)(C)N)CC4)nc3=O)cc2)CC1]
251
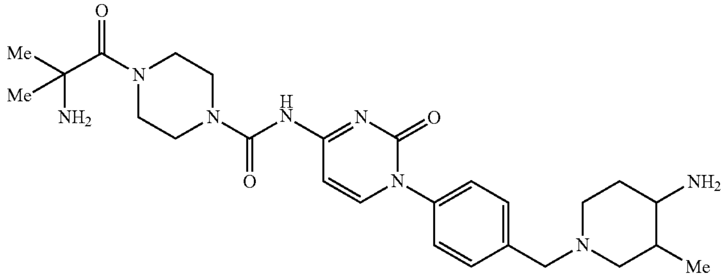 [SMILES: CC1CN(Cc2ccc(-n3ccc(NC(=O)N4CCN(C(=O)C(C)(C)N)CC4)nc3=O)cc2)CCC1N]
252
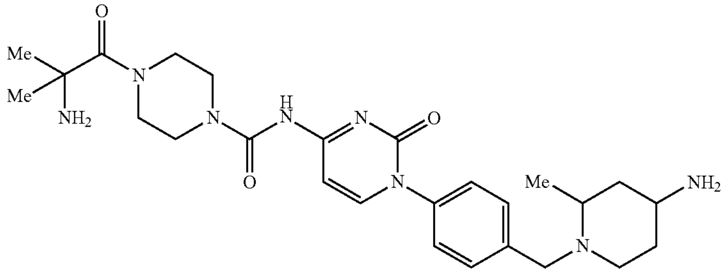 [SMILES: CC1CC(N)CCN1Cc1ccc(-n2ccc(NC(=O)N3CCN(C(=O)C(C)(C)N)CC3)nc2=O)cc1]
253
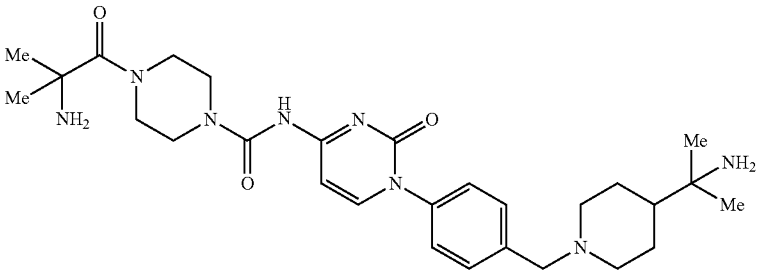 [SMILES: CC(C)(N)C(=O)N1CCN(C(=O)Nc2ccn(-c3ccc(CN4CCC(C(C)(C)N)CC4)cc3)c(=O)n2)CC1]
254
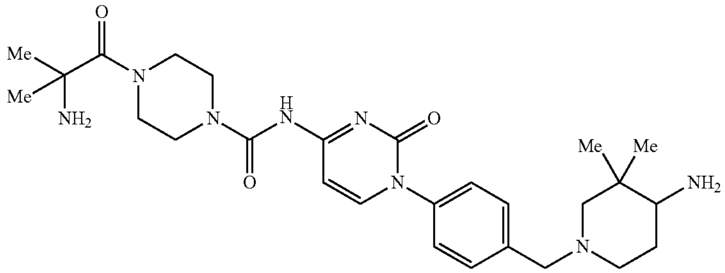 [SMILES: CC(C)(N)C(=O)N1CCN(C(=O)Nc2ccn(-c3ccc(CN4CCC(N)C(C)(C)C4)cc3)c(=O)n2)CC1]

TABLE 10-continued
| Compounds of Formula I |
|---|
| 255 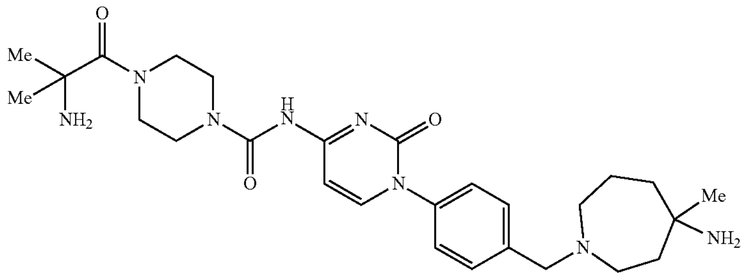 [SMILES: CC1(N)CCCN(Cc2ccc(-n3ccc(NC(=O)N4CCN(C(=O)C(C)(C)N)CC4)nc3=O)cc2)CC1] |
| 265 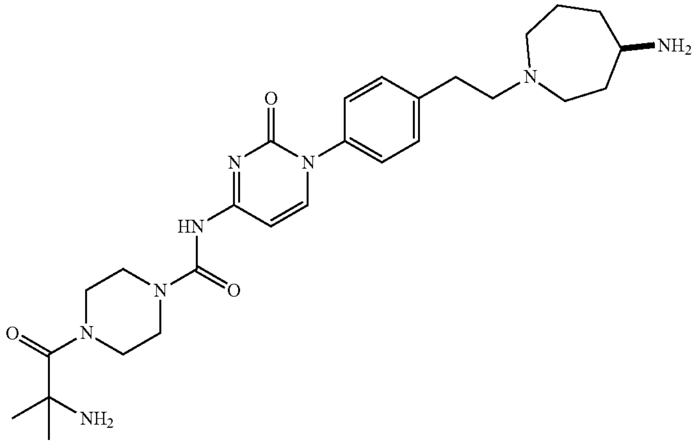 [SMILES: CC(C)(N)C(=O)N1CCN(C(=O)Nc2ccn(-c3ccc(CCN4CCC[C@@H](N)CC4)cc3)c(=O)n2)CC1] |
| 266 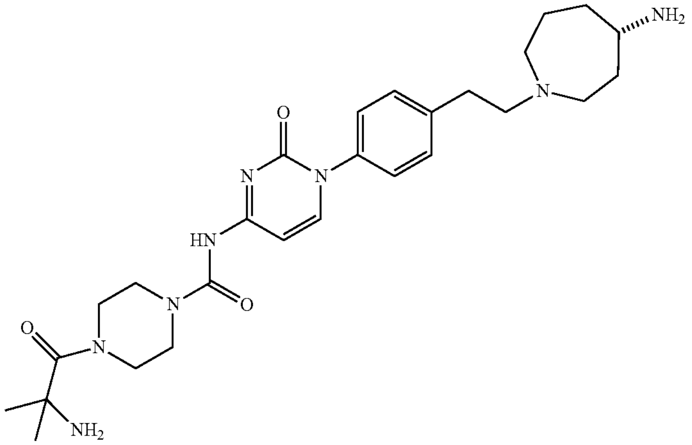 [SMILES: CC(C)(N)C(=O)N1CCN(C(=O)Nc2ccn(-c3ccc(CCN4CCC[C@H](N)CC4)cc3)c(=O)n2)CC1] |
| 267 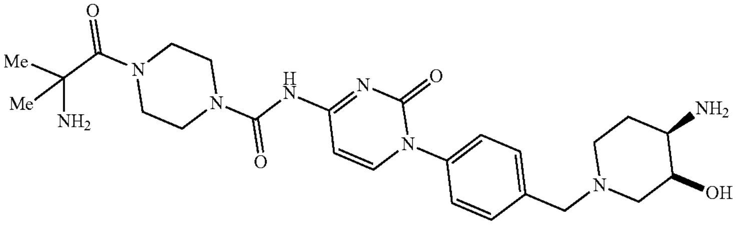 |

TABLE 10-continued
| Compounds of Formula I | |
|---|---|
| 268 | 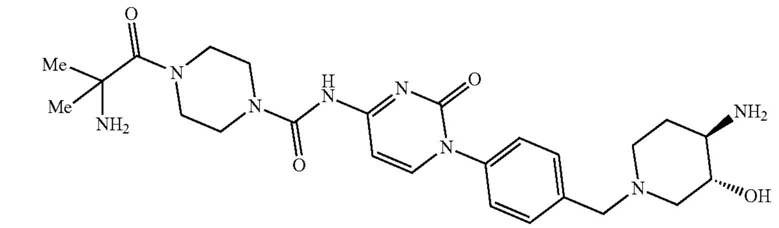 [SMILES: CC(C)(N)C(=O)N1CCN(C(=O)Nc2ccn(-c3ccc(CN4CC[C@@H](N)[C@H](O)C4)cc3)c(=O)n2)CC1] |
| 269 | 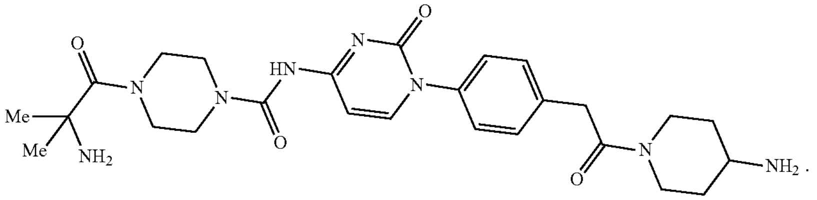 [SMILES: CC(C)(N)C(=O)N1CCN(C(=O)Nc2ccn(-c3ccc(CC(=O)N4CCC(N)CC4)cc3)c(=O)n2)CC1] |
In another aspect, the disclosure provides a compound or a pharmaceutically acceptable salt thereof which is depicted in Table 11. In Table 11, free base and salt structures of the compounds of the invention are depicted TABLE 11
| Compounds of Formula I Continued | | |
|---|---|---|
| No. | Salt Structure | Free Base Structure |
| 270 | 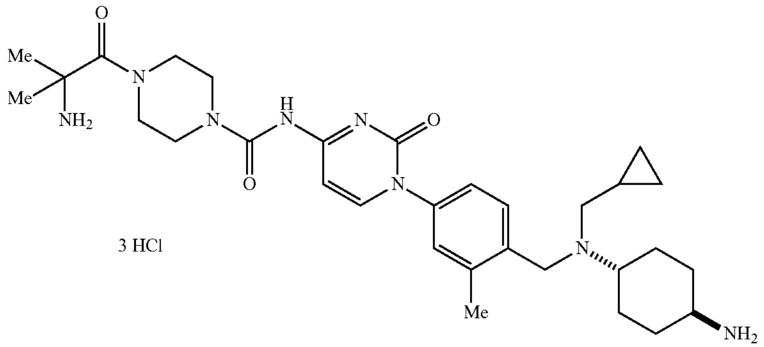 3 HCl | 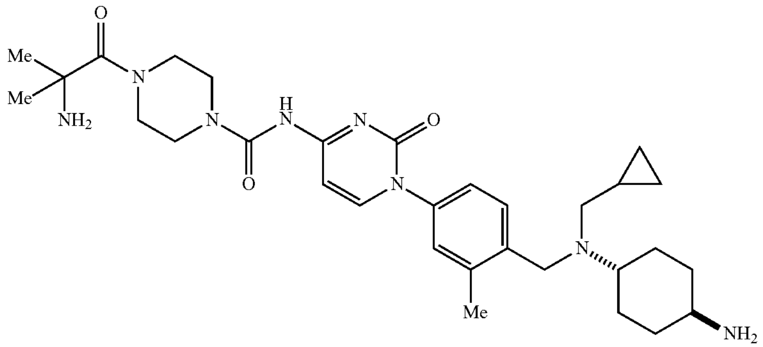 |
| 271 | 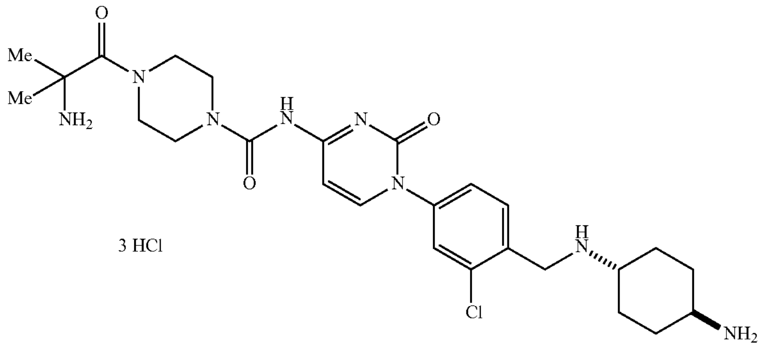 3 HCl | 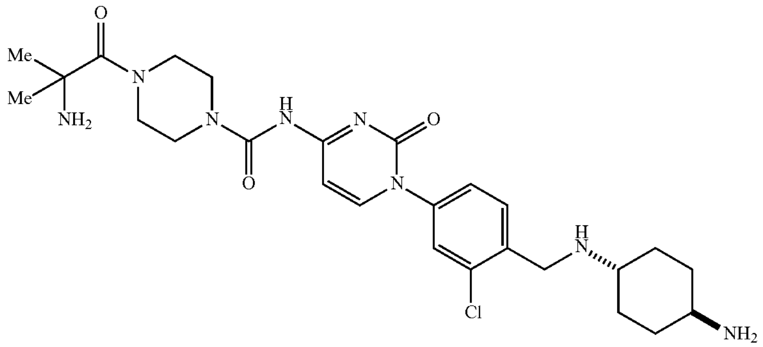 |

TABLE 11-continued
| Compounds of Formula I Continued | | |
|---|---|---|
| No. | Salt Structure | Free Base Structure |
| 272 | 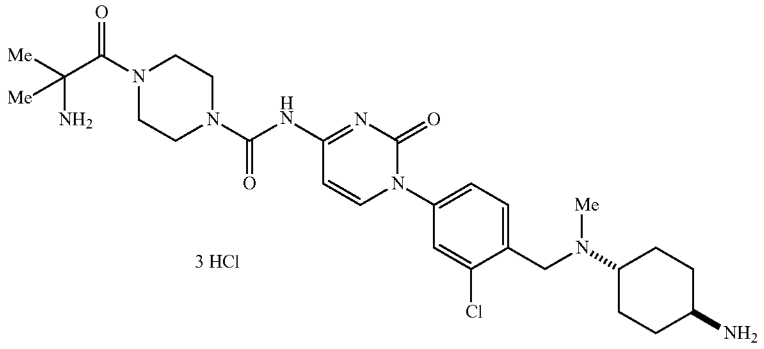 3 HCl | 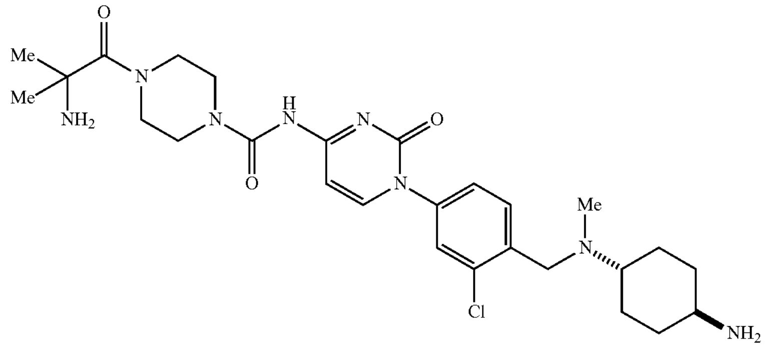 |
| 273 | 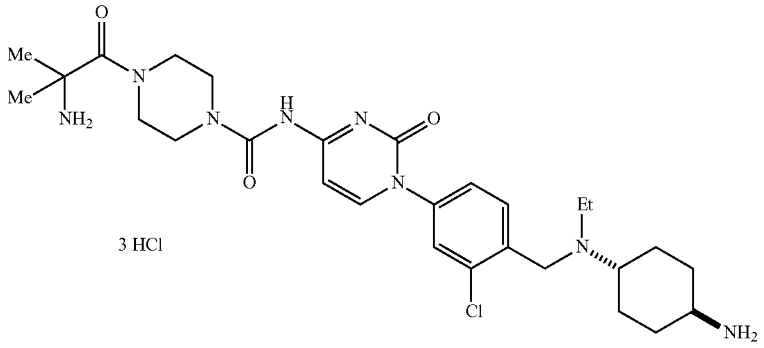 3 HCl | 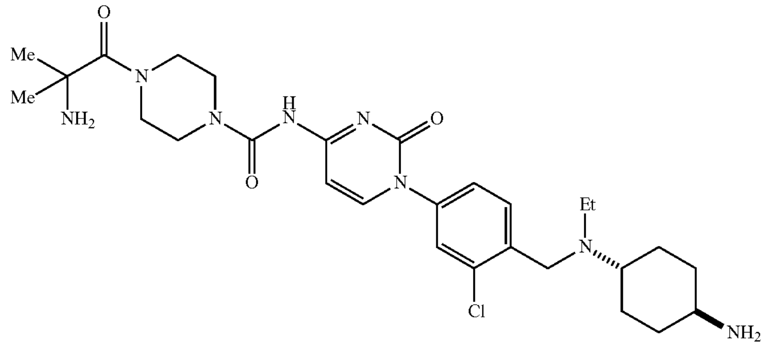 |

TABLE 11-continued
| Compounds of Formula I Continued | | |
|---|---|---|
| No. | Salt Structure | Free Base Structure |
| 274 | 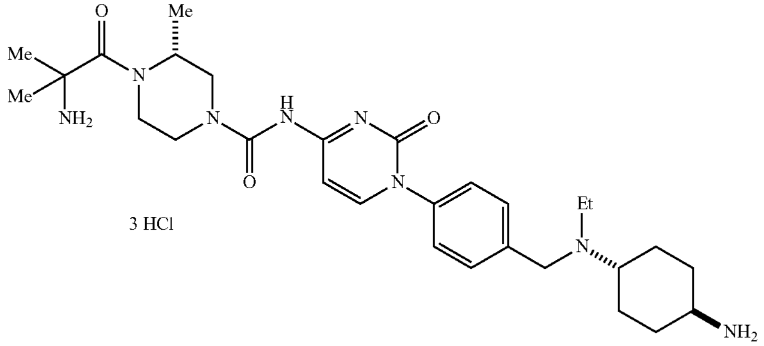 3 HCl | 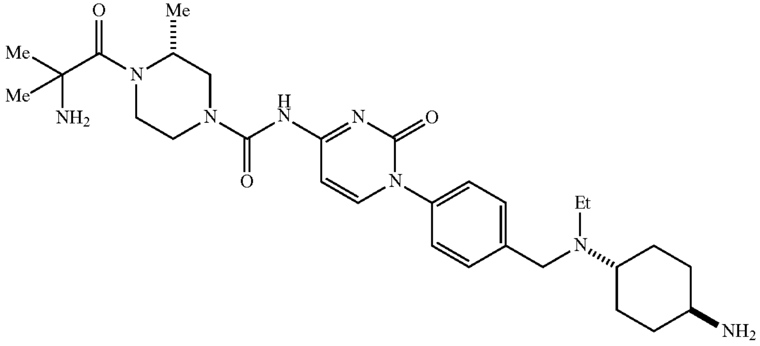 |
| 275 | 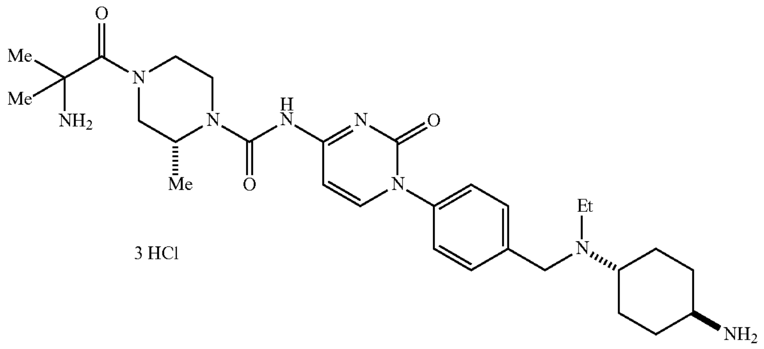 3 HCl | 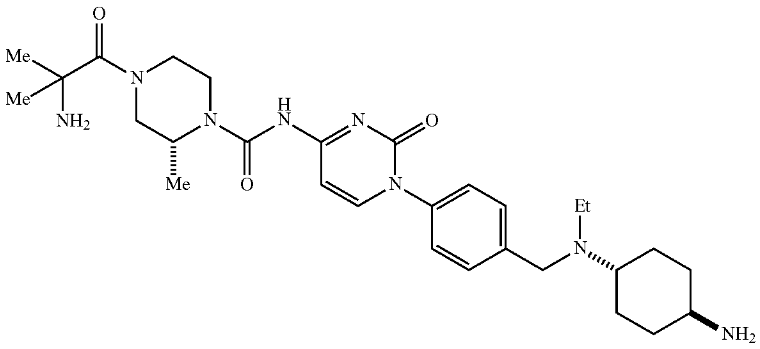 |

TABLE 11-continued
| Compounds of Formula I Continued | | |
|---|---|---|
| No. | Salt Structure | Free Base Structure |
| 276 | 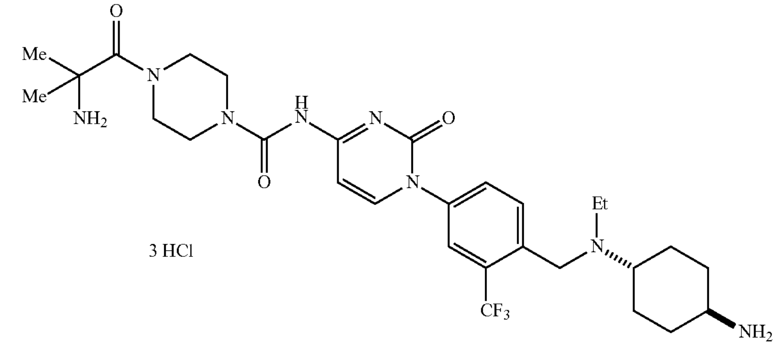 3 HCl | 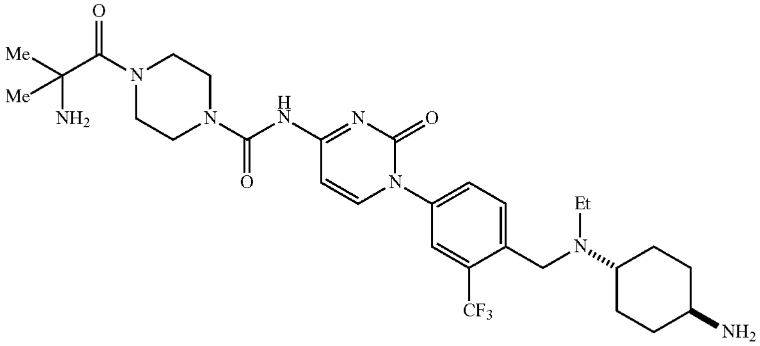 |
| 277 | 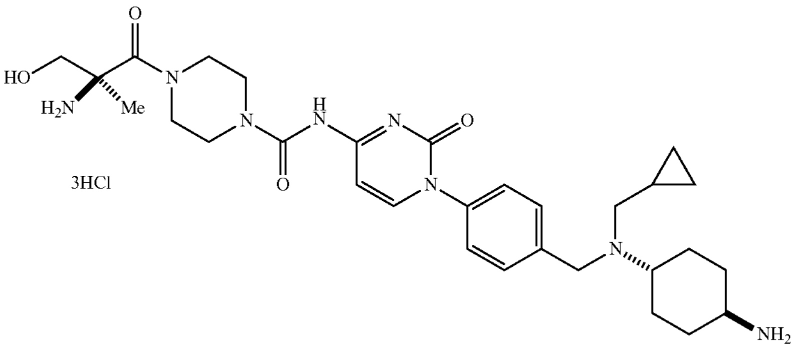 3HCl | 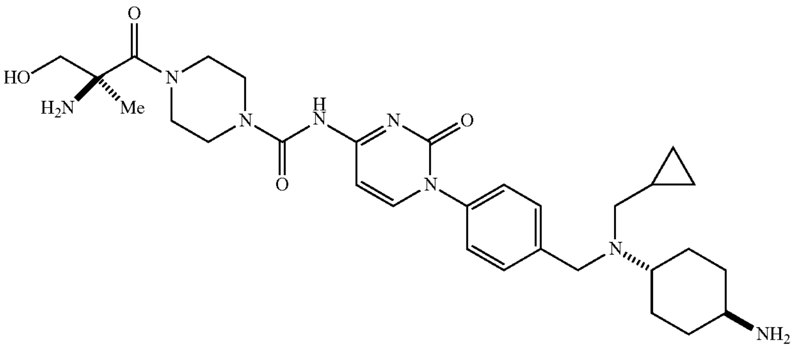 |

TABLE 11-continued
| Compounds of Formula I Continued | | |
|---|---|---|
| No. | Salt Structure | Free Base Structure |
| 278 | 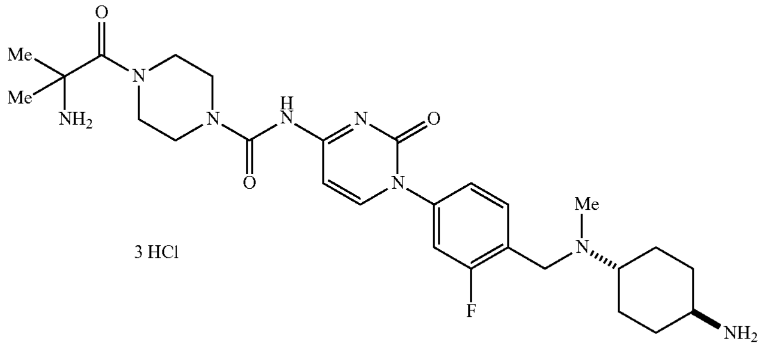 3 HCl | 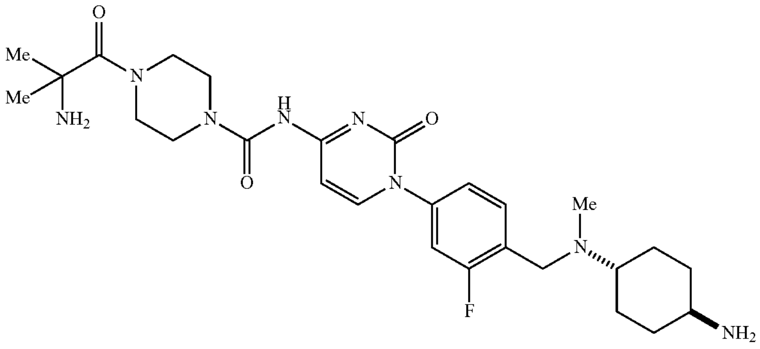 |
| 279 | 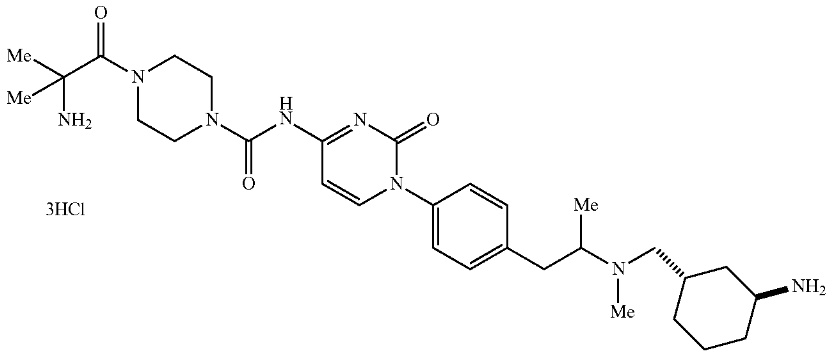 [SMILES: CC(Cc1ccc(-n2ccc(NC(=O)N3CCN(C(=O)C(C)(C)N)CC3)nc2=O)cc1)N(C)C[C@H]1CCC[C@H](N)C1] 3HCl | 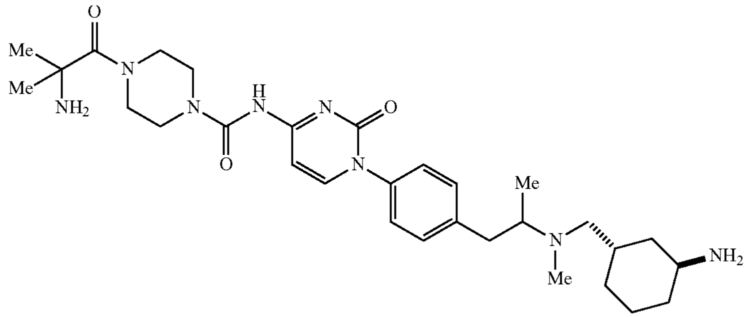 [SMILES: CC(Cc1ccc(-n2ccc(NC(=O)N3CCN(C(=O)C(C)(C)N)CC3)nc2=O)cc1)N(C)C[C@H]1CCC[C@H](N)C1] |

TABLE 11-continued
| Compounds of Formula I Continued | | |
|---|---|---|
| No. | Salt Structure | Free Base Structure |
| 280 | 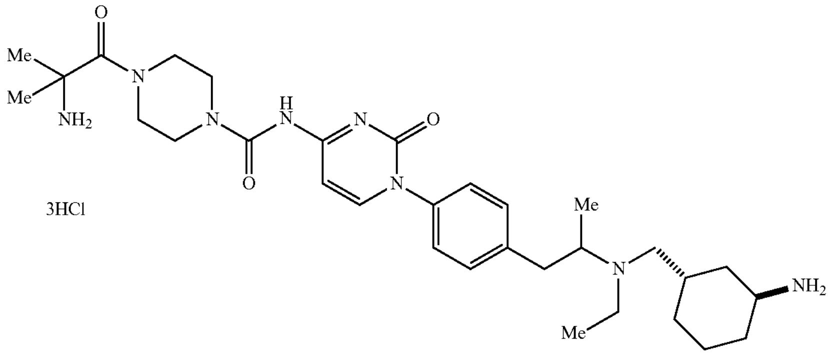 [SMILES: CCN(C[C@H]1CCC[C@H](N)C1)C(C)Cc1ccc(-n2ccc(NC(=O)N3CCN(C(=O)C(C)(C)N)CC3)nc2=O)cc1] 3HCl | 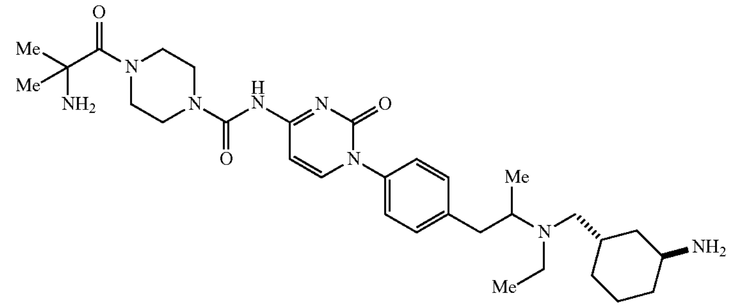 [SMILES: CCN(C[C@H]1CCC[C@H](N)C1)C(C)Cc1ccc(-n2ccc(NC(=O)N3CCN(C(=O)C(C)(C)N)CC3)nc2=O)cc1] |
| 281 | 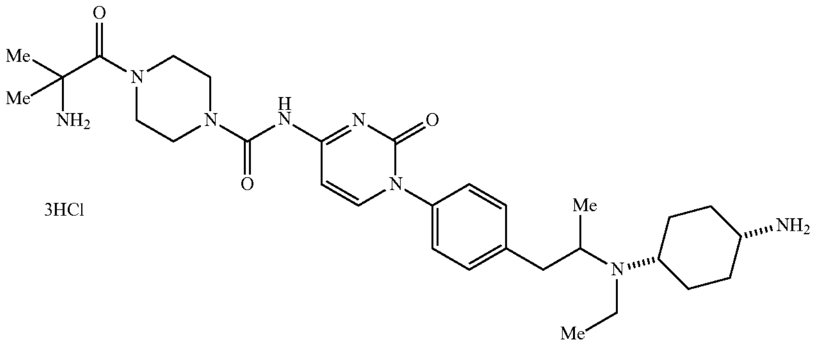 3HCl | 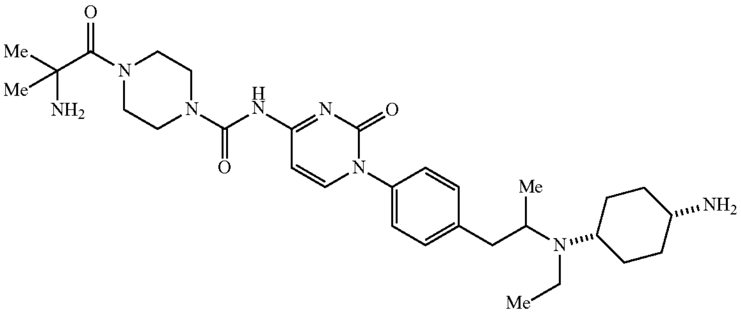 |

TABLE 11-continued
| Compounds of Formula I Continued | | |
|---|---|---|
| No. | Salt Structure | Free Base Structure |
| 282 | 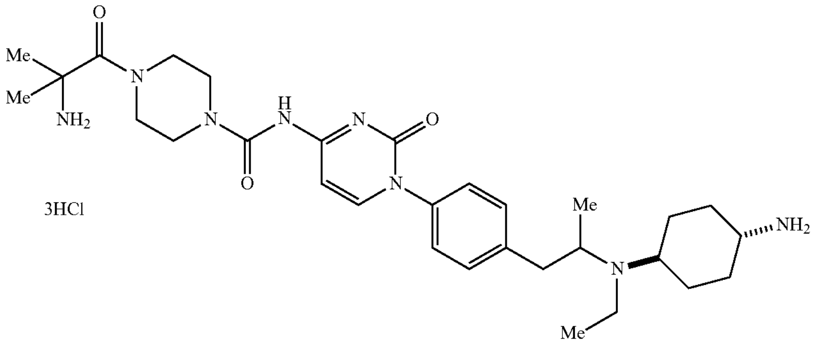 3HCl | 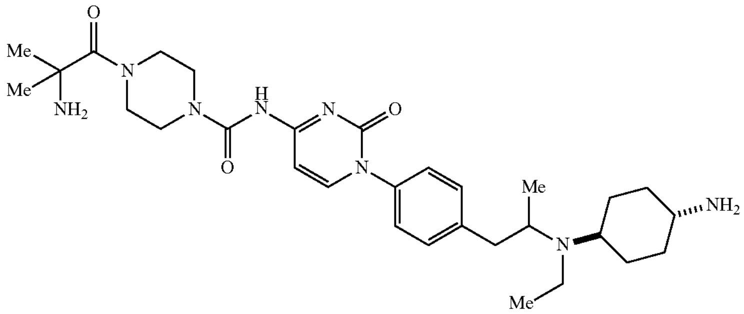 |
| 283 | 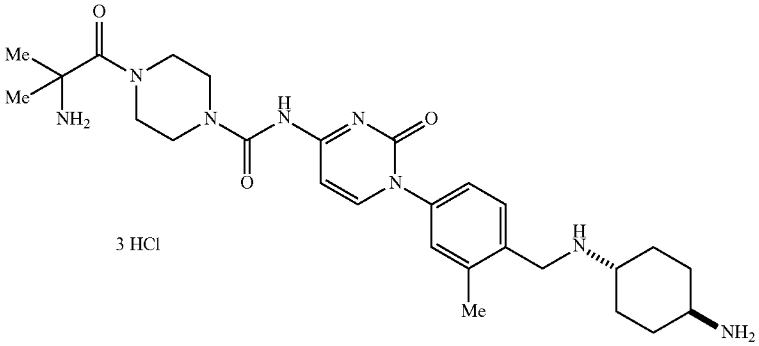 3 HCl | 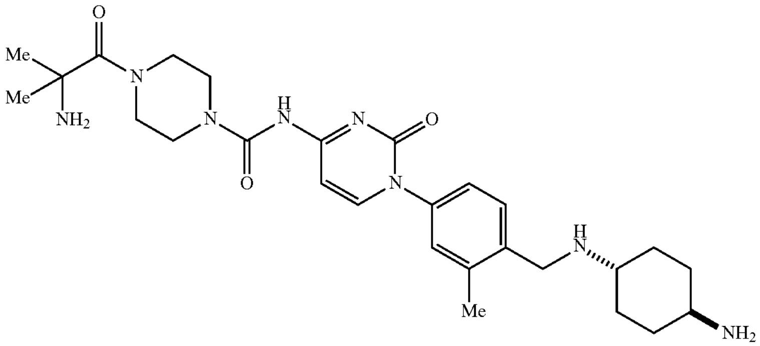 |

TABLE 11-continued
| Compounds of Formula I Continued | | |
|---|---|---|
| No. | Salt Structure | Free Base Structure |
| 284 | 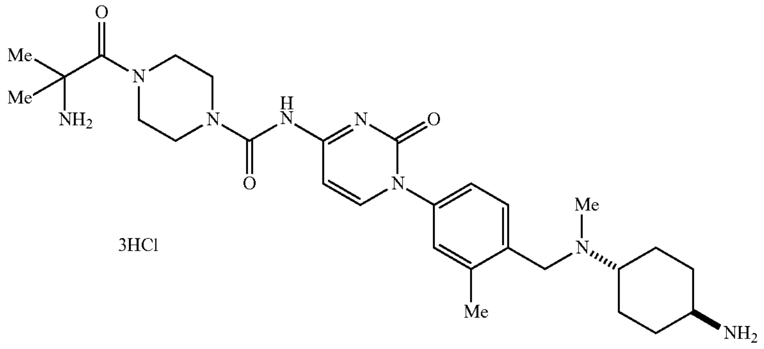 3HCl | 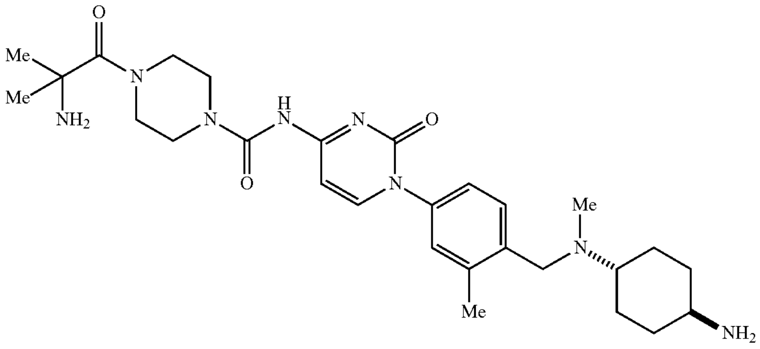 |
| 285 | 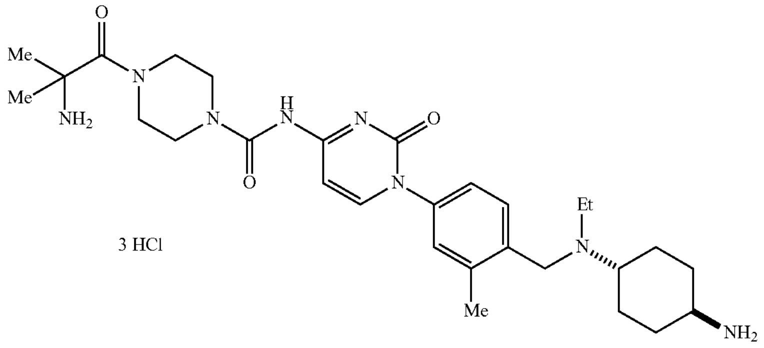 3 HCl | 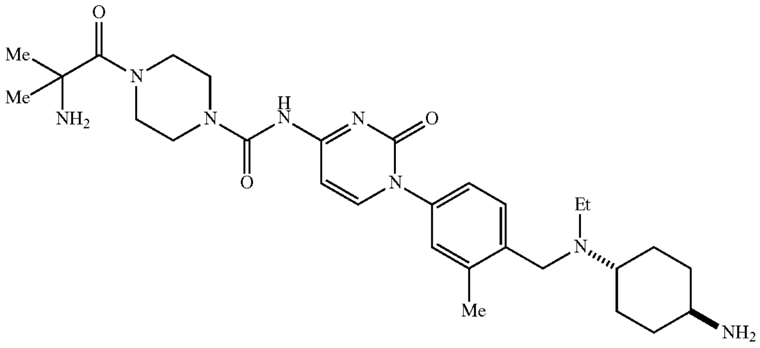 |

TABLE 11-continued
| Compounds of Formula I Continued | | |
|---|---|---|
| No. | Salt Structure | Free Base Structure |
| 286 | 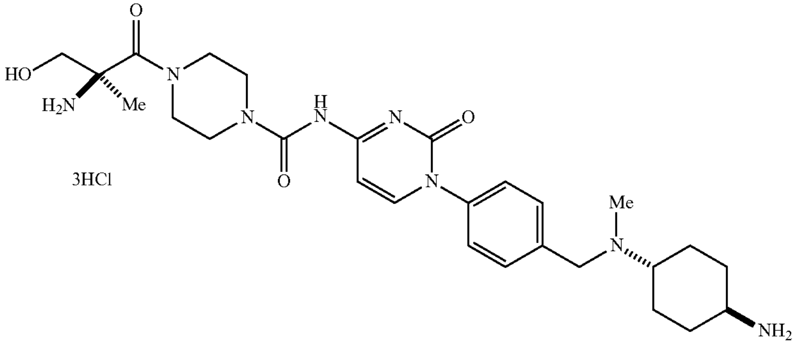 3HCl | 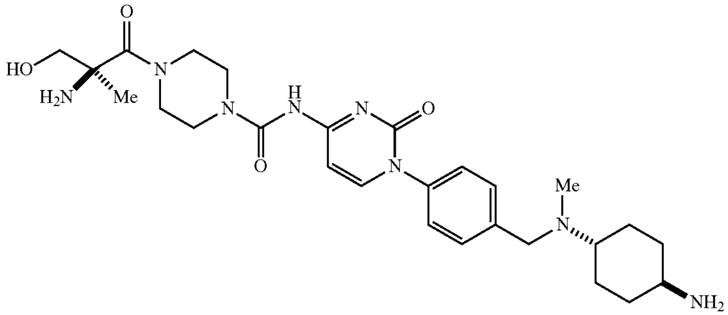 |
| 287 | 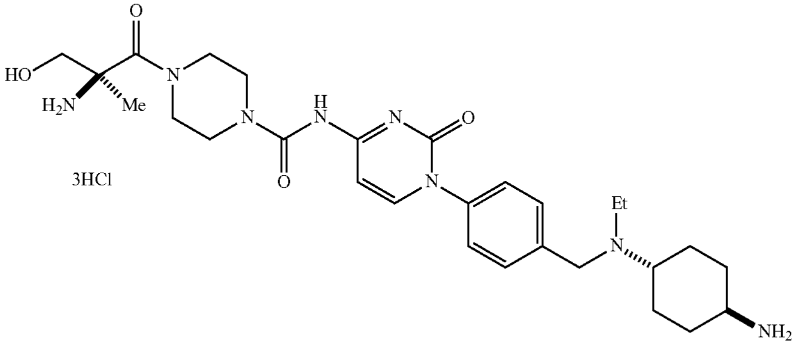 3HCl | 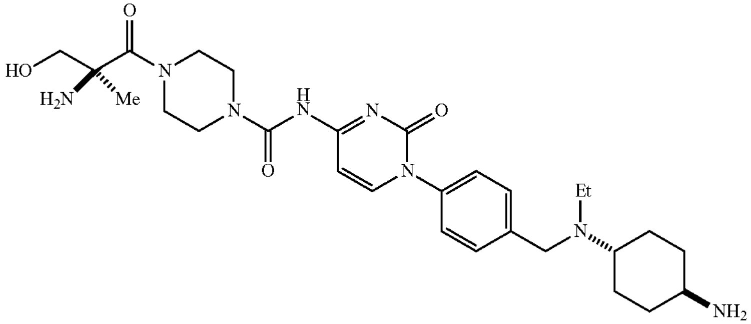 |

TABLE 11-continued
| Compounds of Formula I Continued | | |
|---|---|---|
| No. | Salt Structure | Free Base Structure |
| 288 | 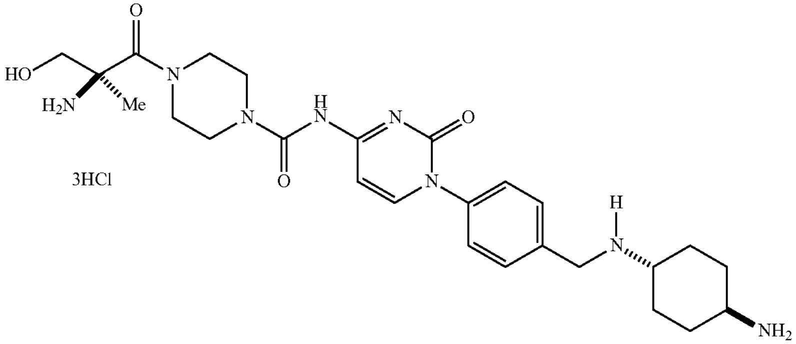 3HCl | 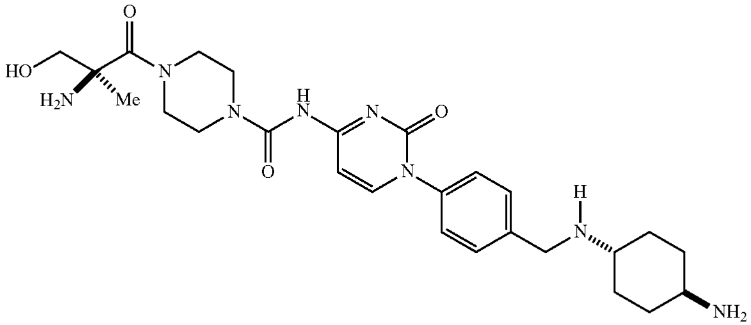 |
| 289 | 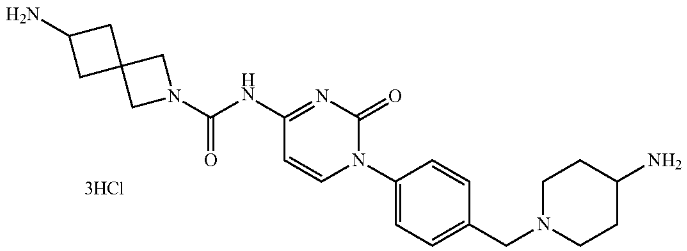 [SMILES: NC1CCN(Cc2ccc(-n3ccc(NC(=O)N4CC5(CC(N)C5)C4)nc3=O)cc2)CC1] 3HCl | 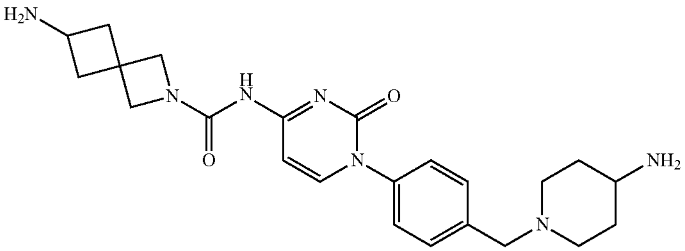 [SMILES: NC1CCN(Cc2ccc(-n3ccc(NC(=O)N4CC5(CC(N)C5)C4)nc3=O)cc2)CC1] |
| 290 | 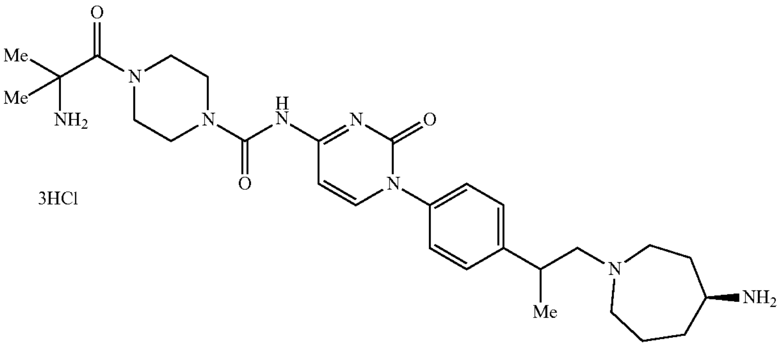 [SMILES: CC(CN1CCC[C@H](N)CC1)c1ccc(-n2ccc(NC(=O)N3CCN(C(=O)C(C)(C)N)CC3)nc2=O)cc1] 3HCl | 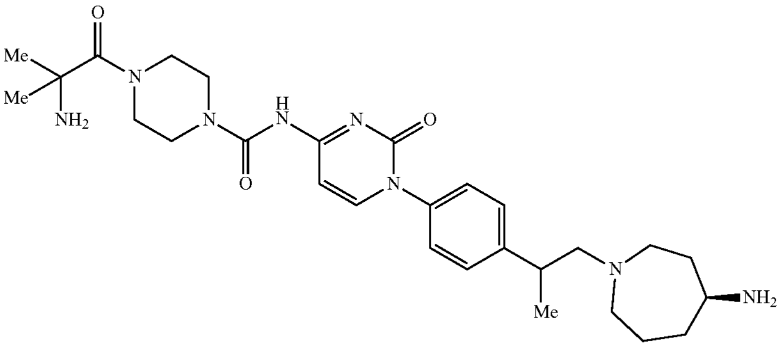 [SMILES: CC(CN1CCC[C@H](N)CC1)c1ccc(-n2ccc(NC(=O)N3CCN(C(=O)C(C)(C)N)CC3)nc2=O)cc1] |

TABLE 11-continued
| Compounds of Formula I Continued | | |
|---|---|---|
| No. | Salt Structure | Free Base Structure |
| 291 | 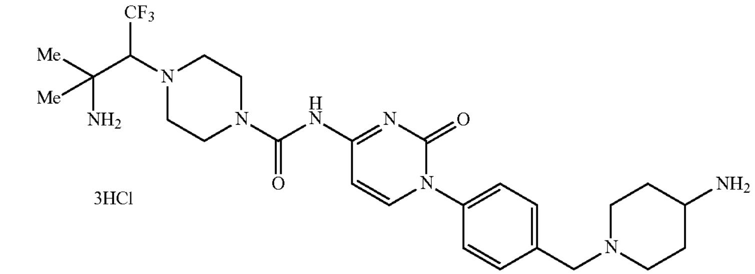 [SMILES: CC(C)(N)C(N1CCN(C(=O)Nc2ccn(-c3ccc(CN4CCC(N)CC4)cc3)c(=O)n2)CC1)C(F)(F)F] 3HCl | 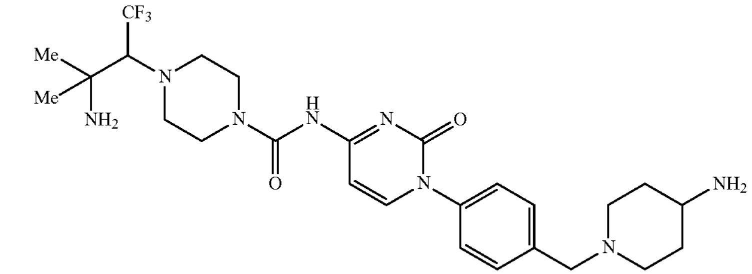 [SMILES: CC(C)(N)C(N1CCN(C(=O)Nc2ccn(-c3ccc(CN4CCC(N)CC4)cc3)c(=O)n2)CC1)C(F)(F)F] |
| 292 | 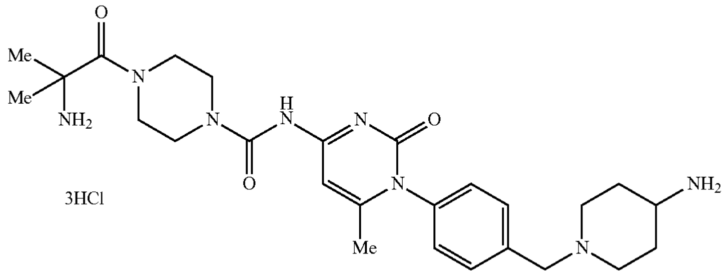 [SMILES: Cc1cc(NC(=O)N2CCN(C(=O)C(C)(C)N)CC2)nc(=O)n1-c1ccc(CN2CCC(N)CC2)cc1] 3HCl | 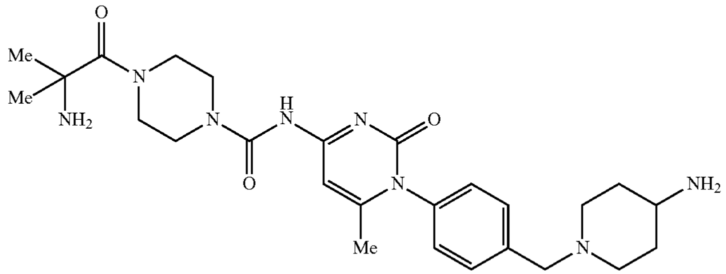 [SMILES: Cc1cc(NC(=O)N2CCN(C(=O)C(C)(C)N)CC2)nc(=O)n1-c1ccc(CN2CCC(N)CC2)cc1] |
| 293 | 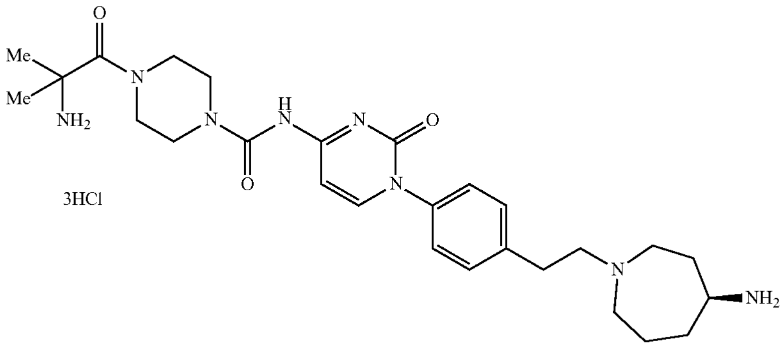 [SMILES: CC(C)(N)C(=O)N1CCN(C(=O)Nc2ccn(-c3ccc(CCN4CCC[C@H](N)CC4)cc3)c(=O)n2)CC1] 3HCl | 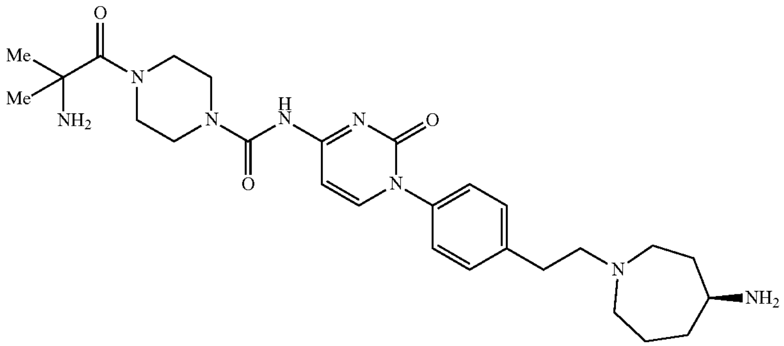 [SMILES: CC(C)(N)C(=O)N1CCN(C(=O)Nc2ccn(-c3ccc(CCN4CCC[C@H](N)CC4)cc3)c(=O)n2)CC1] |

TABLE 11-continued
| Compounds of Formula I Continued | | |
|---|---|---|
| No. | Salt Structure | Free Base Structure |
| 294 | 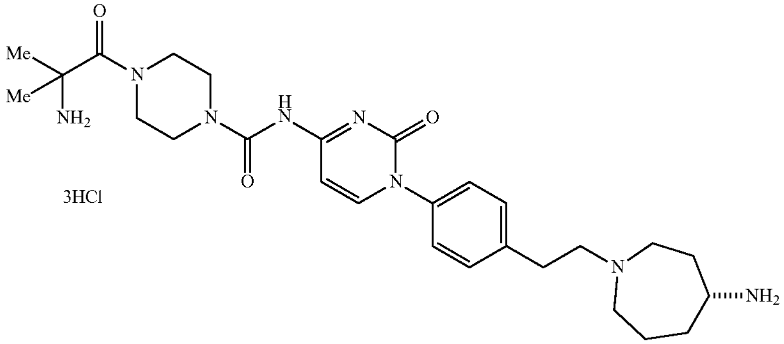 [SMILES: CC(C)(N)C(=O)N1CCN(C(=O)Nc2ccn(-c3ccc(CCN4CCC[C@@H](N)CC4)cc3)c(=O)n2)CC1] 3HCl | 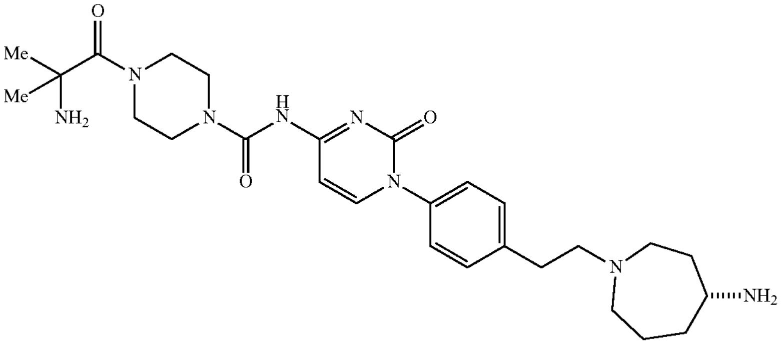 [SMILES: CC(C)(N)C(=O)N1CCN(C(=O)Nc2ccn(-c3ccc(CCN4CCC[C@@H](N)CC4)cc3)c(=O)n2)CC1] |
| 295 | 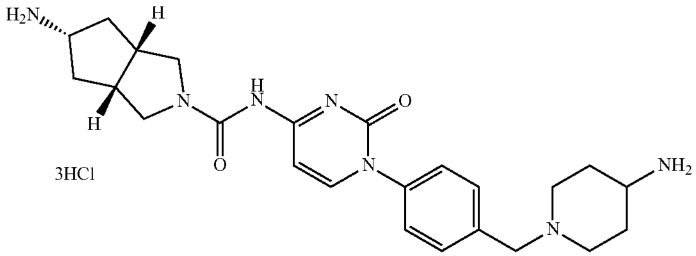 [SMILES: NC1CCN(Cc2ccc(-n3ccc(NC(=O)N4C[C@H]5C[C@@H](N)C[C@H]5C4)nc3=O)cc2)CC1] 3HCl | 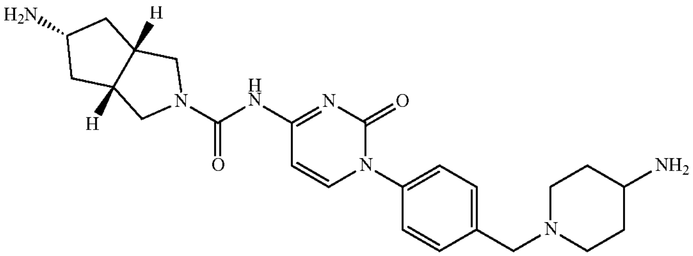 [SMILES: NC1CCN(Cc2ccc(-n3ccc(NC(=O)N4C[C@H]5C[C@@H](N)C[C@H]5C4)nc3=O)cc2)CC1] |
| 296 | 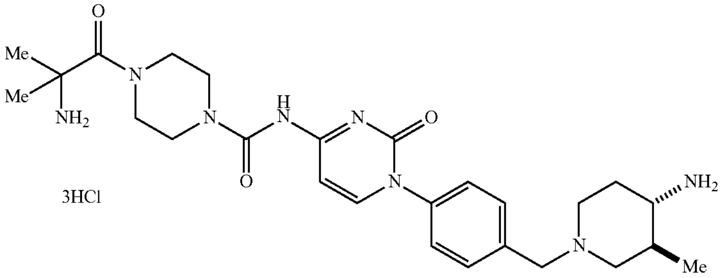 [SMILES: C[C@H]1CN(Cc2ccc(-n3ccc(NC(=O)N4CCN(C(=O)C(C)(C)N)CC4)nc3=O)cc2)CC[C@@H]1N] 3HCl | 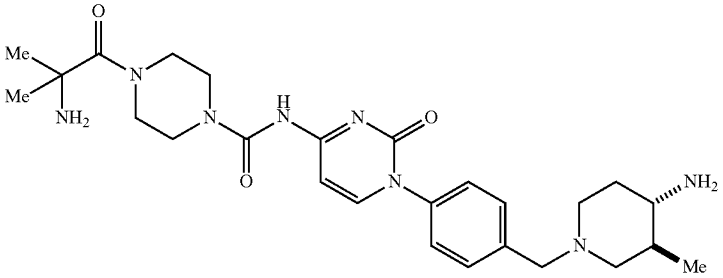 [SMILES: C[C@H]1CN(Cc2ccc(-n3ccc(NC(=O)N4CCN(C(=O)C(C)(C)N)CC4)nc3=O)cc2)CC[C@@H]1N] |

TABLE 11-continued
| Compounds of Formula I Continued | | |
|---|---|---|
| No. | Salt Structure | Free Base Structure |
| 297 | 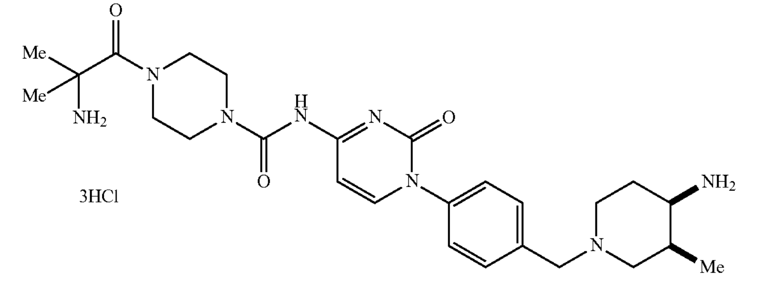 [SMILES: C[C@H]1CN(Cc2ccc(-n3ccc(NC(=O)N4CCN(C(=O)C(C)(C)N)CC4)nc3=O)cc2)CC[C@H]1N] 3HCl | 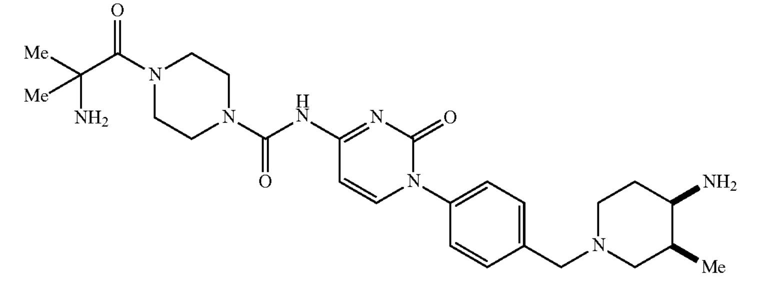 [SMILES: C[C@H]1CN(Cc2ccc(-n3ccc(NC(=O)N4CCN(C(=O)C(C)(C)N)CC4)nc3=O)cc2)CC[C@H]1N] |
| 298 | 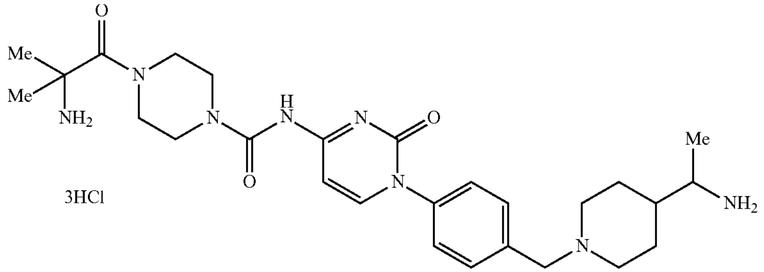 3HCl Enantiomer 1 | 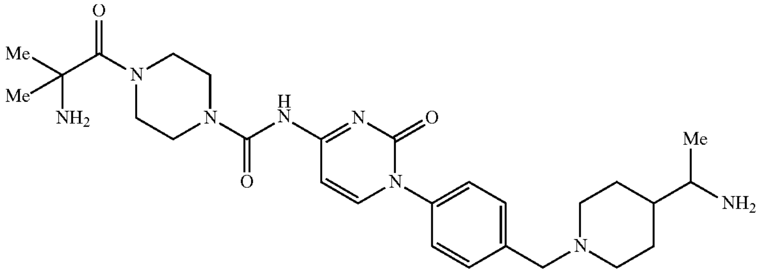 Enantiomer 1 |
| 299 | 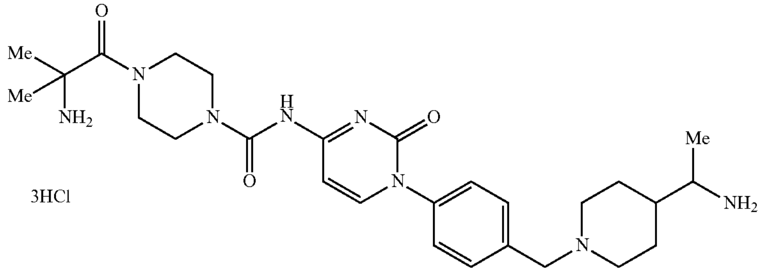 3HCl Enantiomer 2 | 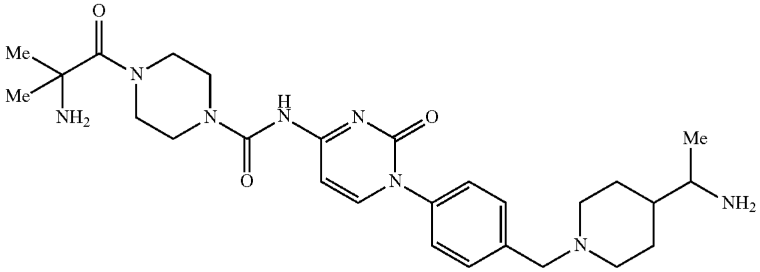 Enantiomer 2 |

TABLE 11-continued
| Compounds of Formula I Continued | | |
|---|---|---|
| No. | Salt Structure | Free Base Structure |
| 300 | 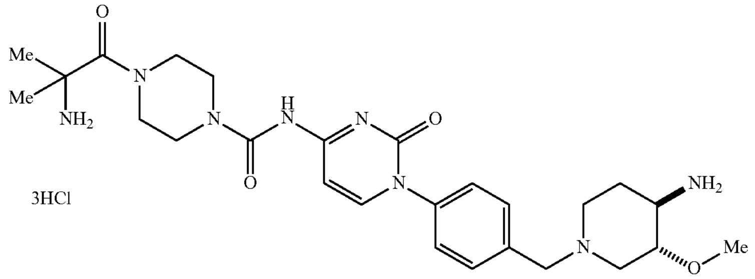 [SMILES: CO[C@@H]1CN(Cc2ccc(-n3ccc(NC(=O)N4CCN(C(=O)C(C)(C)N)CC4)nc3=O)cc2)CC[C@H]1N] 3HCl | 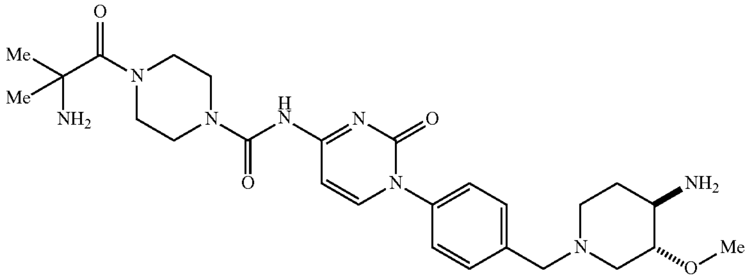 [SMILES: CO[C@@H]1CN(Cc2ccc(-n3ccc(NC(=O)N4CCN(C(=O)C(C)(C)N)CC4)nc3=O)cc2)CC[C@H]1N] |
| 301 | 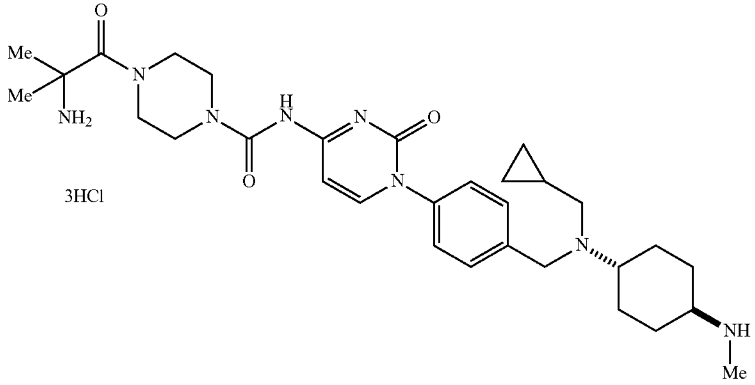 3HCl | 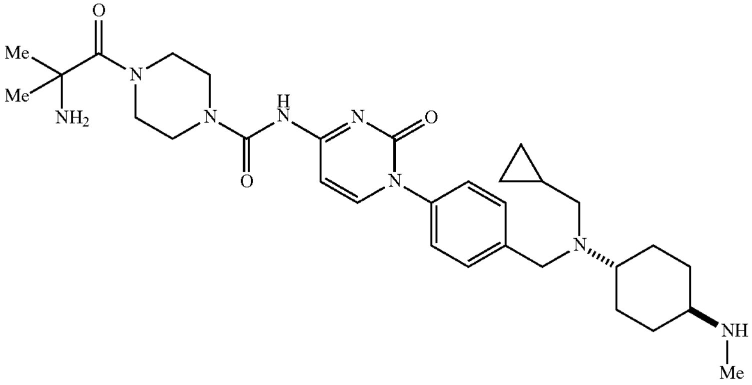 |
| 302 | 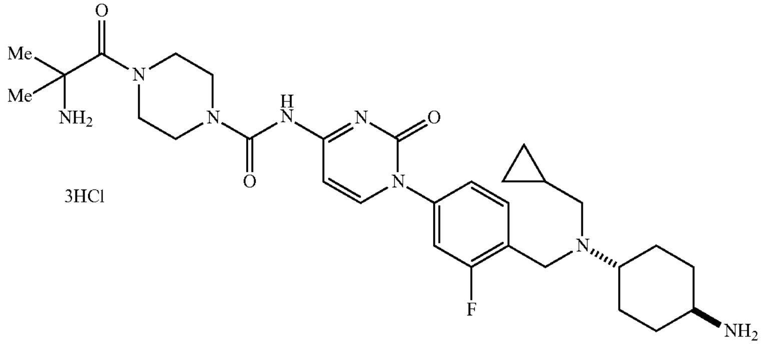 3HCl | 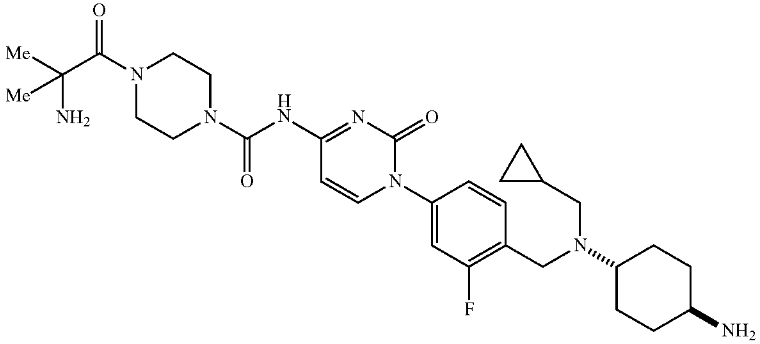 |

TABLE 11-continued
| Compounds of Formula I Continued | | |
|---|---|---|
| No. | Salt Structure | Free Base Structure |
| 303 | 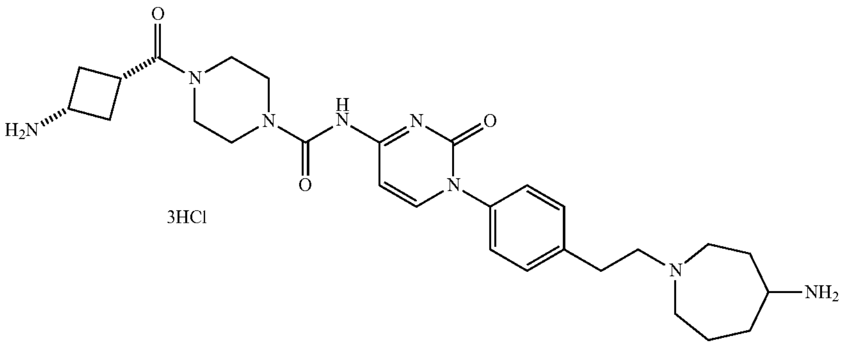 3HCl | 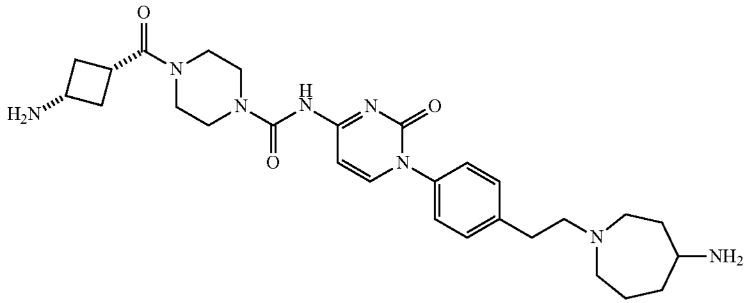 |
| 304 | 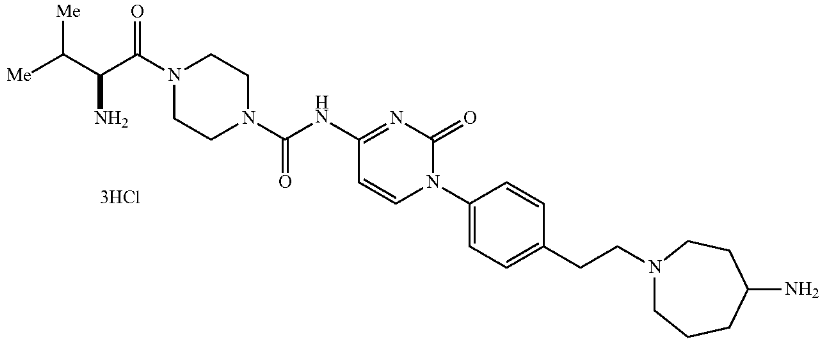 [SMILES: CC(C)[C@H](N)C(=O)N1CCN(C(=O)Nc2ccn(-c3ccc(CCN4CCCC(N)CC4)cc3)c(=O)n2)CC1] 3HCl | 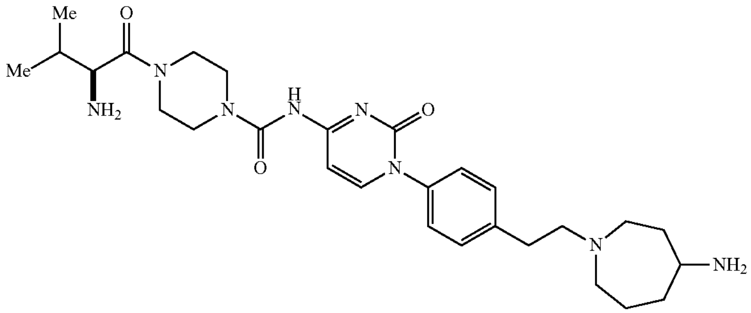 [SMILES: CC(C)[C@H](N)C(=O)N1CCN(C(=O)Nc2ccn(-c3ccc(CCN4CCCC(N)CC4)cc3)c(=O)n2)CC1] |

TABLE 11-continued
| Compounds of Formula I Continued | | |
|---|---|---|
| No. | Salt Structure | Free Base Structure |
| 305 | 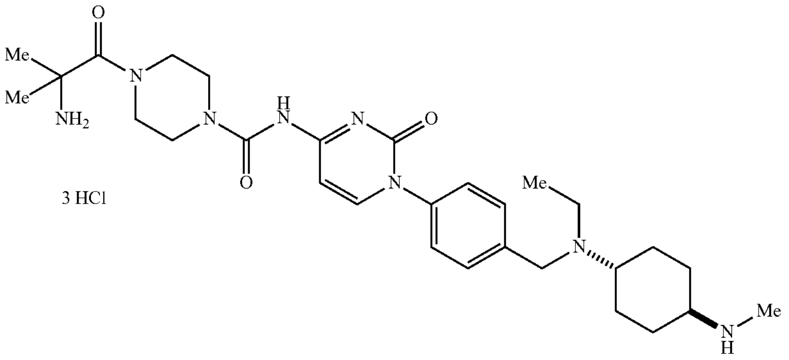 3 HCl | 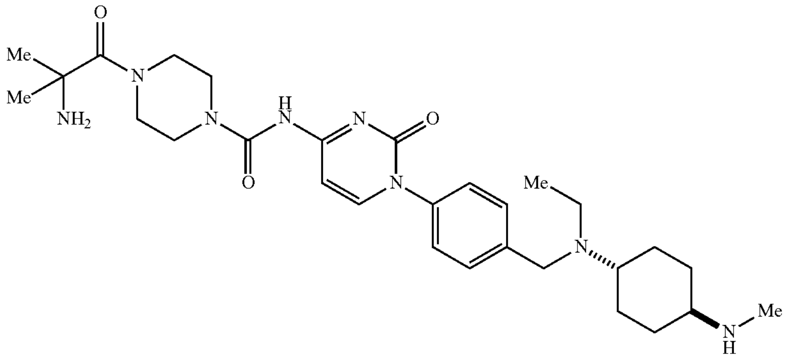 |
| 306 | 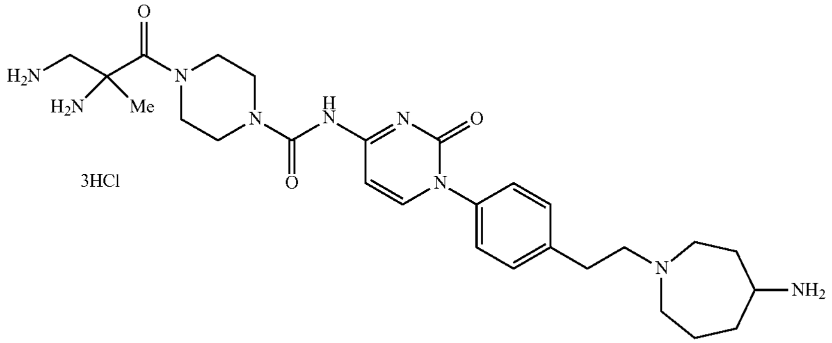 [SMILES: CC(N)(CN)C(=O)N1CCN(C(=O)Nc2ccn(-c3ccc(CCN4CCCC(N)CC4)cc3)c(=O)n2)CC1] 3HCl | 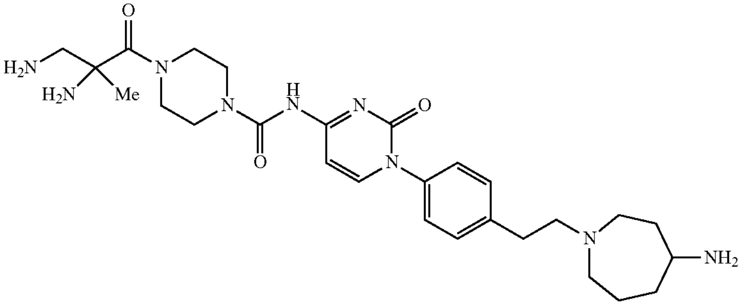 [SMILES: CC(N)(CN)C(=O)N1CCN(C(=O)Nc2ccn(-c3ccc(CCN4CCCC(N)CC4)cc3)c(=O)n2)CC1] |

TABLE 11-continued
| Compounds of Formula I Continued | | |
|---|---|---|
| No. | Salt Structure | Free Base Structure |
| 307 | 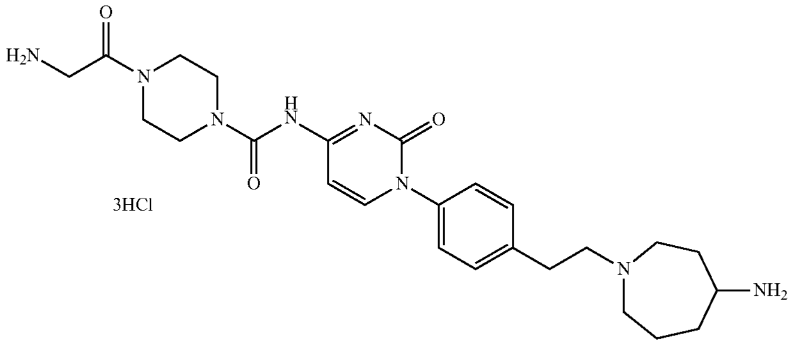 [SMILES: NCC(=O)N1CCN(C(=O)Nc2ccn(-c3ccc(CCN4CCCC(N)CC4)cc3)c(=O)n2)CC1] 3HCl | 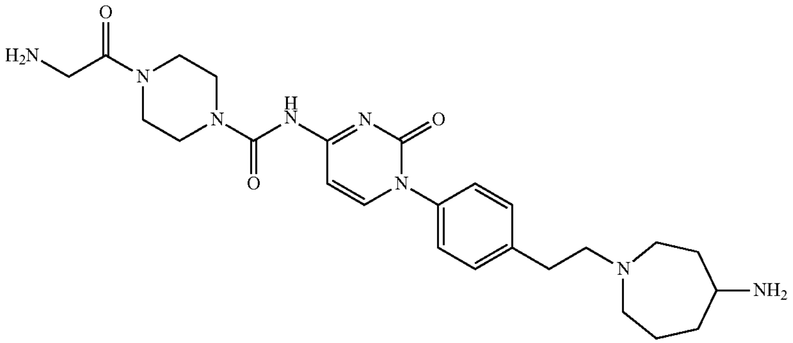 [SMILES: NCC(=O)N1CCN(C(=O)Nc2ccn(-c3ccc(CCN4CCCC(N)CC4)cc3)c(=O)n2)CC1] |
| 308 | 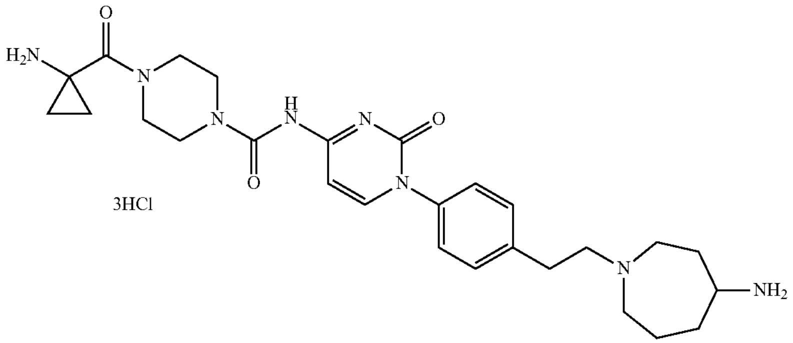 [SMILES: NC1CCCN(CCc2ccc(-n3ccc(NC(=O)N4CCN(C(=O)C5(N)CC5)CC4)nc3=O)cc2)CC1] 3HCl | 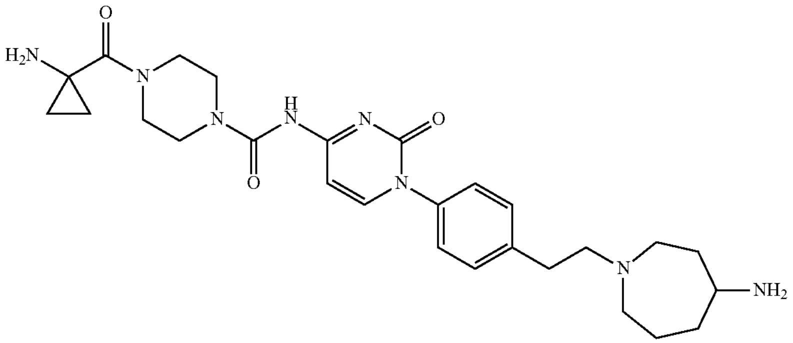 [SMILES: NC1CCCN(CCc2ccc(-n3ccc(NC(=O)N4CCN(C(=O)C5(N)CC5)CC4)nc3=O)cc2)CC1] |
| 309 | 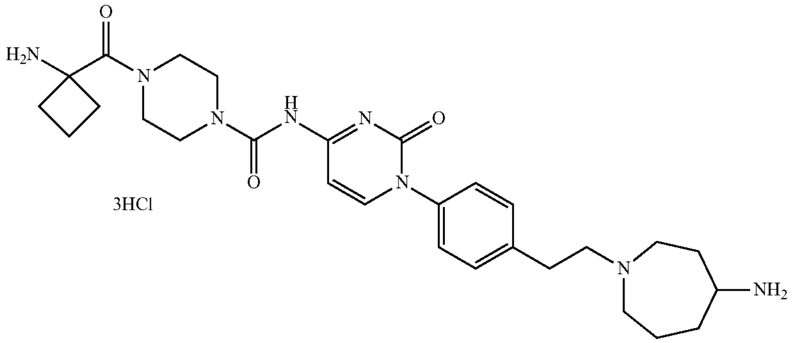 [SMILES: NC1CCCN(CCc2ccc(-n3ccc(NC(=O)N4CCN(C(=O)C5(N)CCC5)CC4)nc3=O)cc2)CC1] 3HCl | 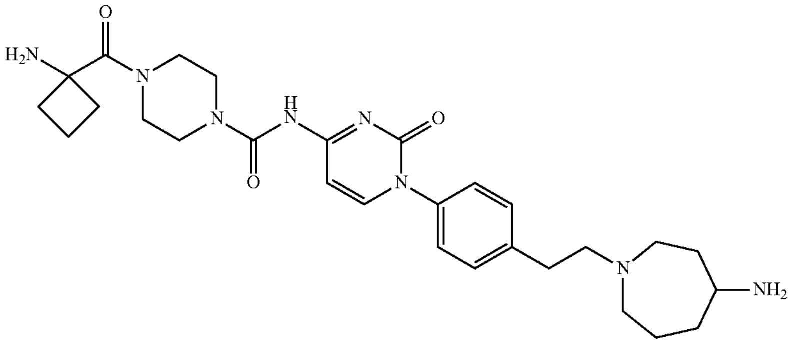 [SMILES: NC1CCCN(CCc2ccc(-n3ccc(NC(=O)N4CCN(C(=O)C5(N)CCC5)CC4)nc3=O)cc2)CC1] |

TABLE 11-continued
| Compounds of Formula I Continued | | |
|---|---|---|
| No. | Salt Structure | Free Base Structure |
| 310 | 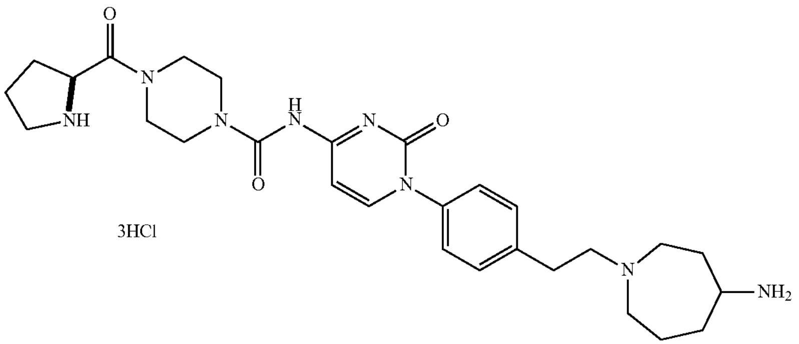 3HCl | 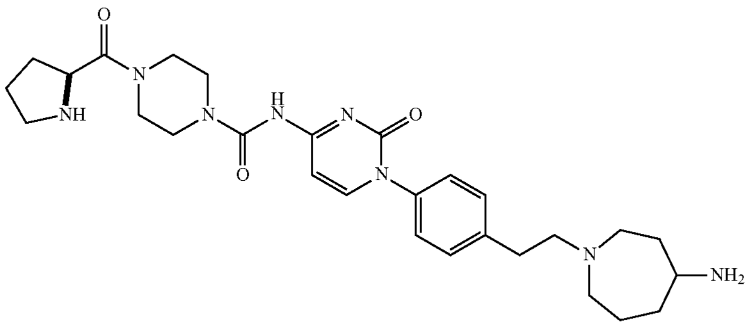 |
| 311 | 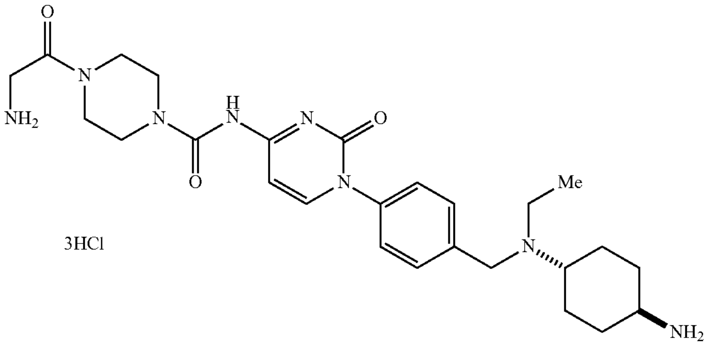 3HCl | 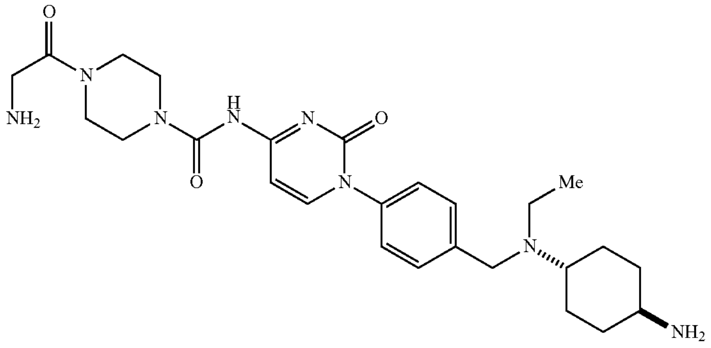 |

TABLE 11-continued
| Compounds of Formula I Continued | | |
|---|---|---|
| No. | Salt Structure | Free Base Structure |
| 312 | 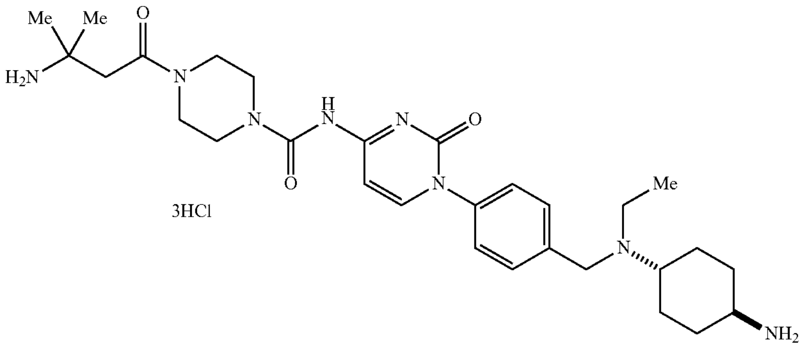 3HCl | 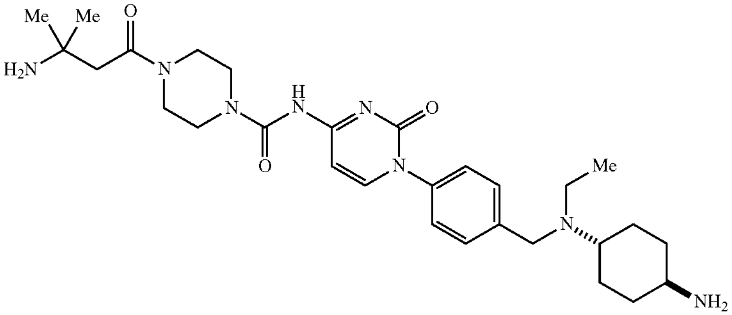 |
| 313 | 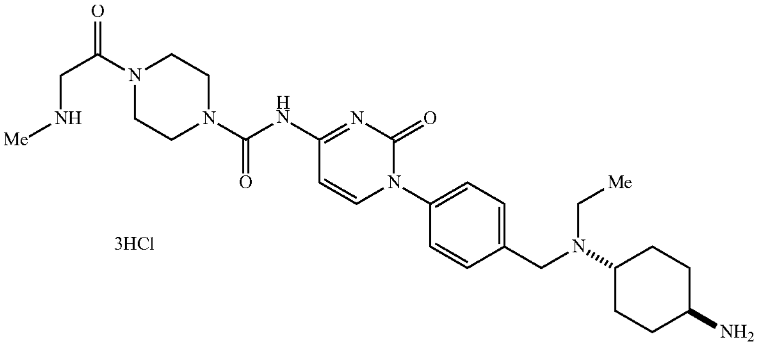 3HCl | 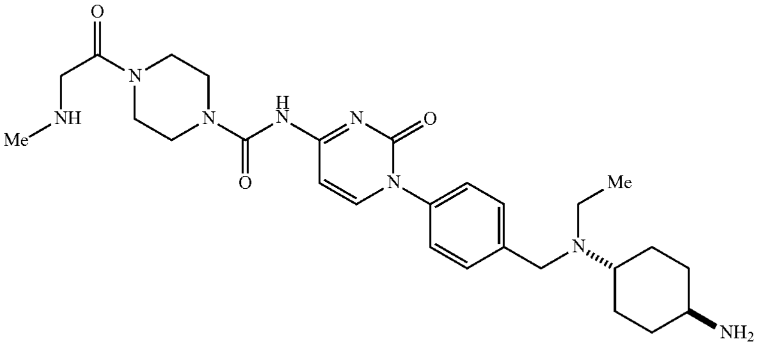 |

TABLE 11-continued
| Compounds of Formula I Continued | | |
|---|---|---|
| No. | Salt Structure | Free Base Structure |
| 314 | 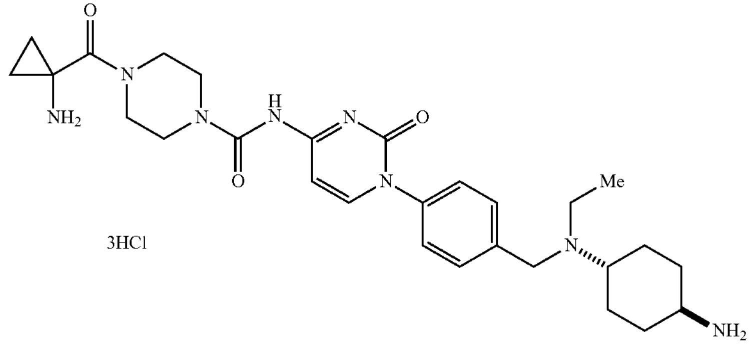 3HCl | 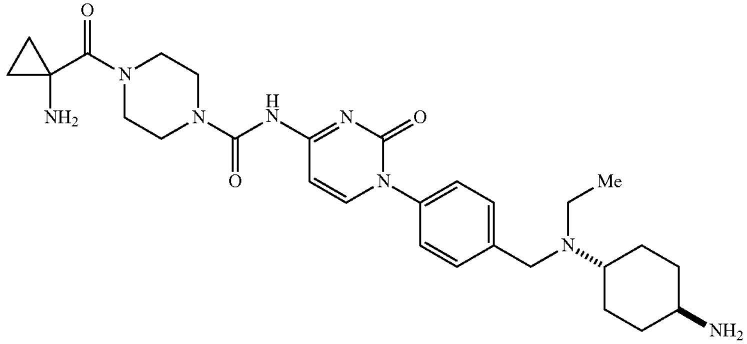 |
| 315 | 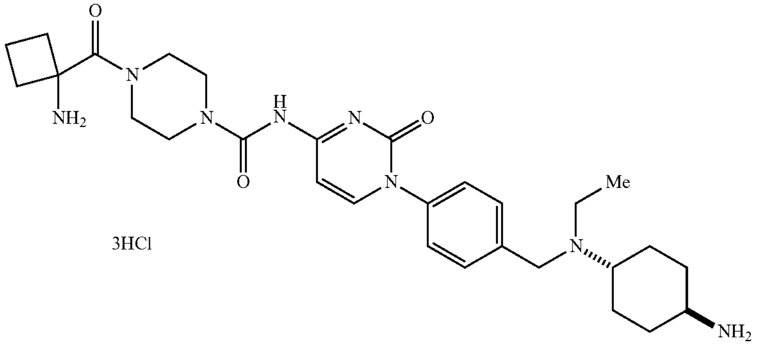 3HCl | 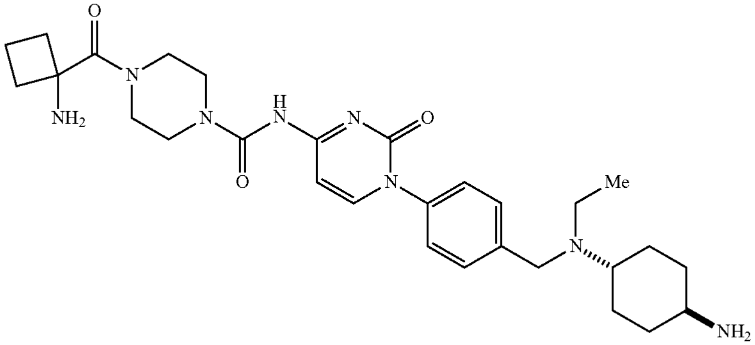 |

TABLE 11-continued
| Compounds of Formula I Continued | | |
|---|---|---|
| No. | Salt Structure | Free Base Structure |
| 316 | 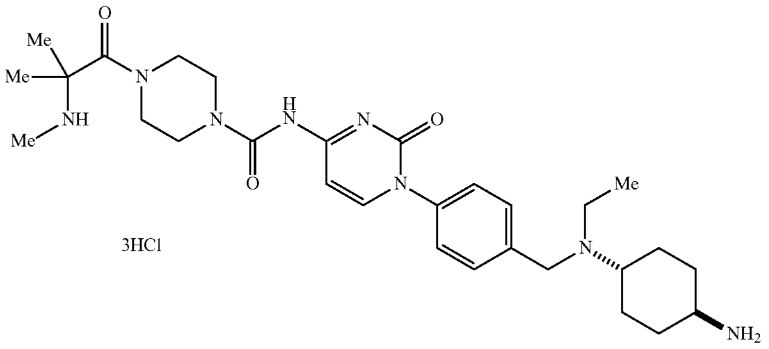 3HCl | 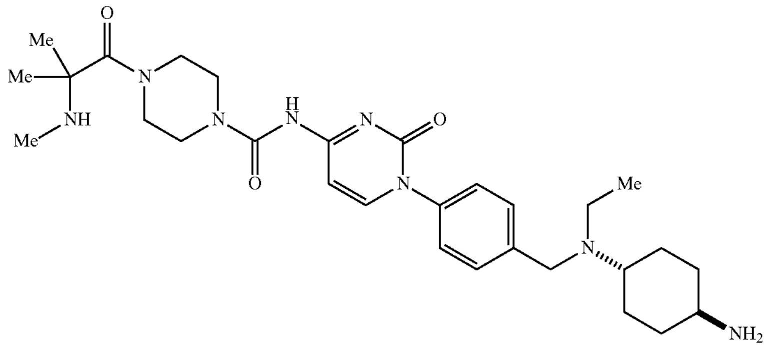 |
| 317 | 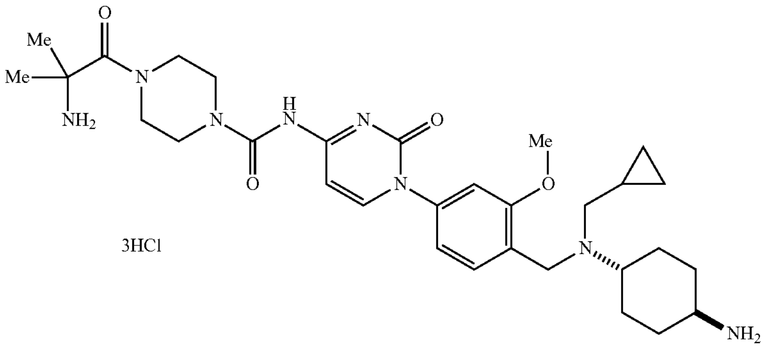 3HCl | 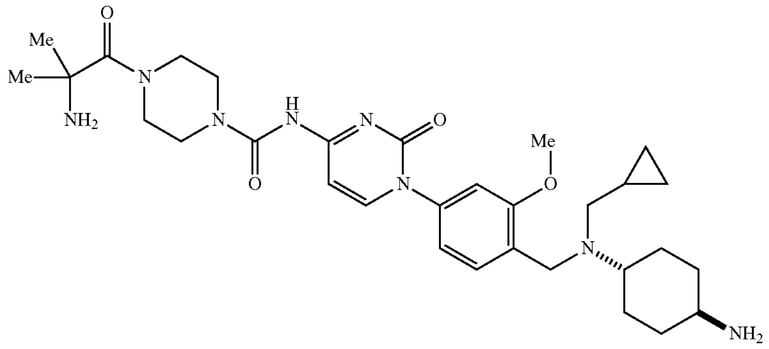 |

TABLE 11-continued
| Compounds of Formula I Continued | | |
|---|---|---|
| No. | Salt Structure | Free Base Structure |
| 318 | 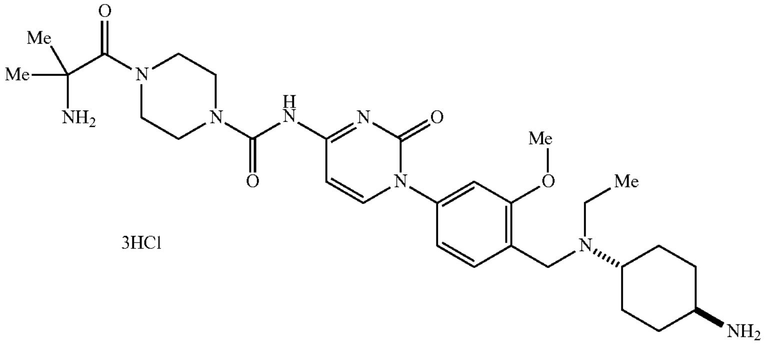 3HCl | 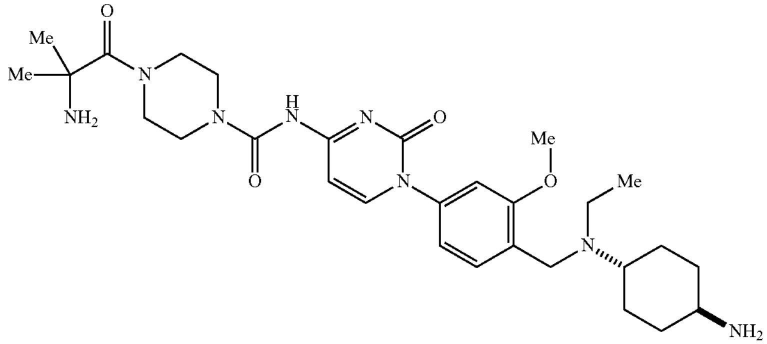 |
| 319 | 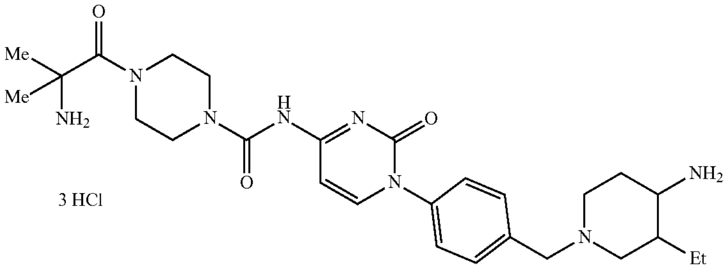 [SMILES: CCC1CN(Cc2ccc(-n3ccc(NC(=O)N4CCN(C(=O)C(C)(C)N)CC4)nc3=O)cc2)CCC1N] 3 HCl | 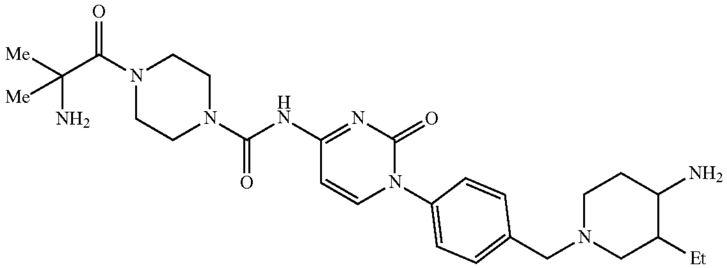 [SMILES: CCC1CN(Cc2ccc(-n3ccc(NC(=O)N4CCN(C(=O)C(C)(C)N)CC4)nc3=O)cc2)CCC1N] |
| 320 | 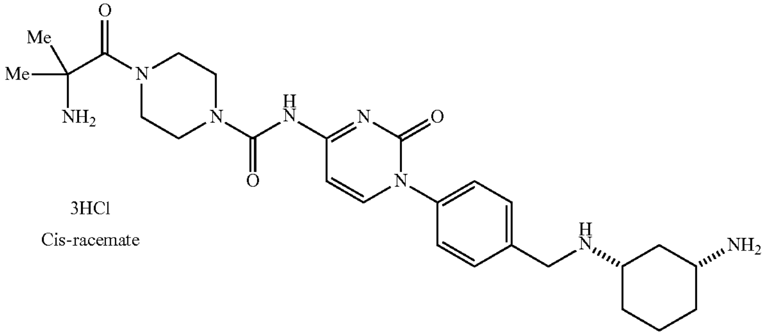 3HCl Cis-racemate | 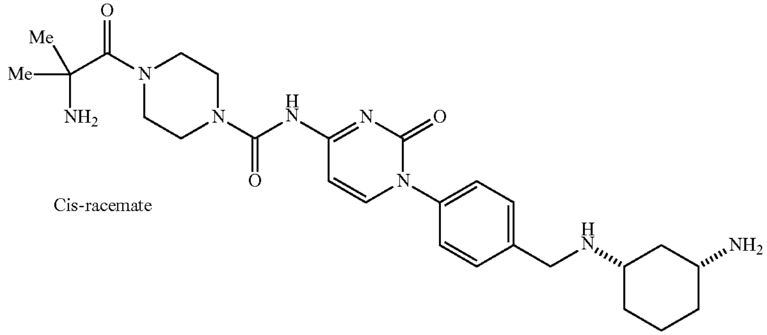 Cis-racemate |

TABLE 11-continued
Compounds of Formula I Continued
| No. | Salt Structure | Free Base Structure |
| --- | --- | --- |
| 321 | 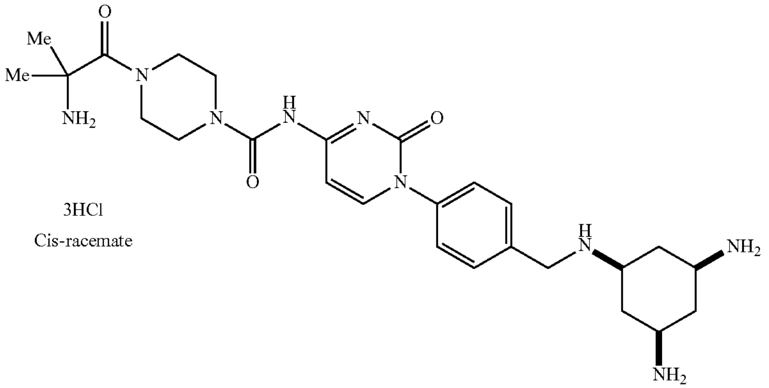 3HCl Cis-racemate | 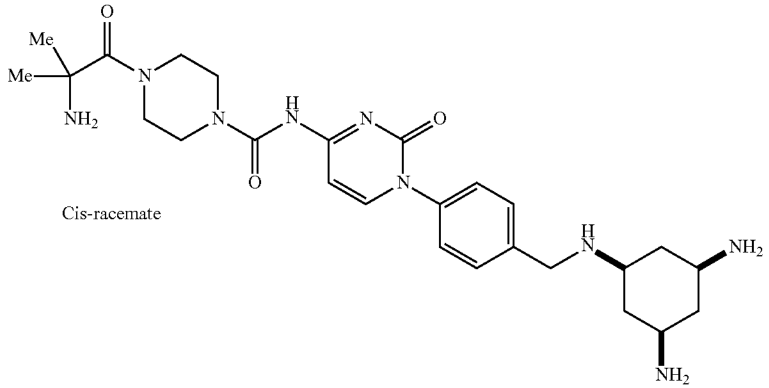 Cis-racemate |
| 322 | 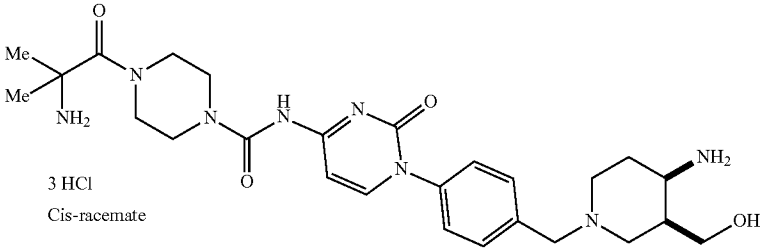 3 HCl Cis-racemate | 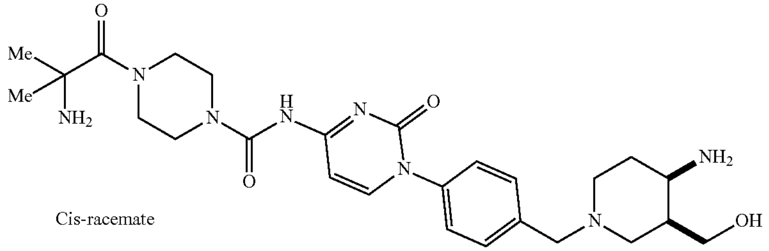 Cis-racemate |
| 323 | 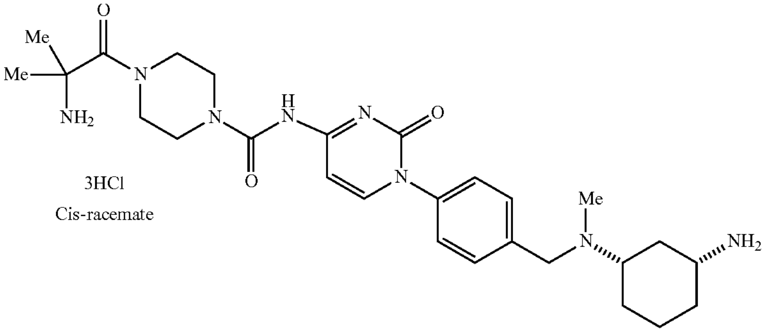 3HCl Cis-racemate | 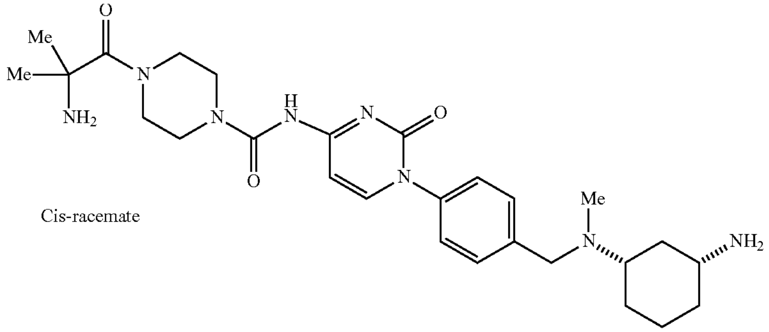 Cis-racemate |

TABLE 11-continued
| Compounds of Formula I Continued | | |
|---|---|---|
| No. | Salt Structure | Free Base Structure |
| 324 | 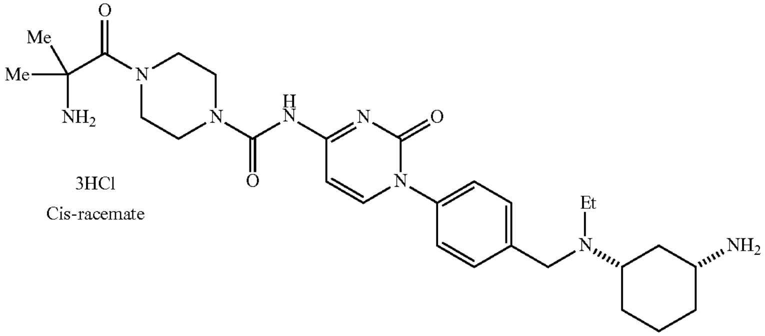 3HCl Cis-racemate | 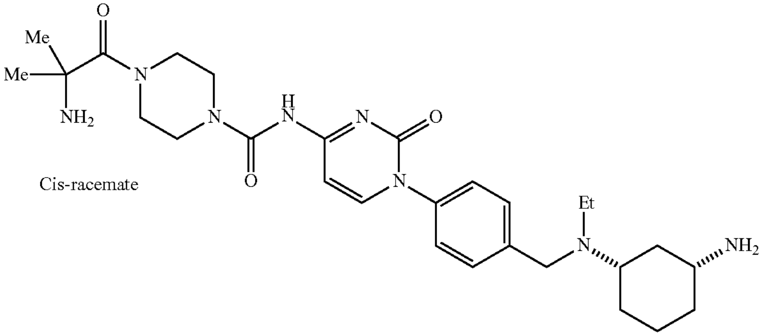 Cis-racemate |
| 325 | 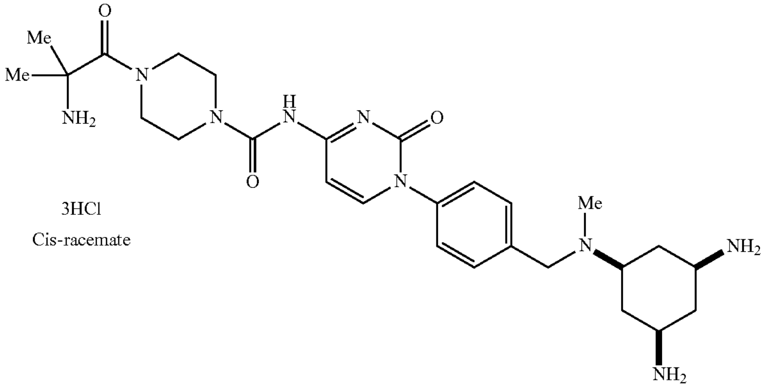 3HCl Cis-racemate | 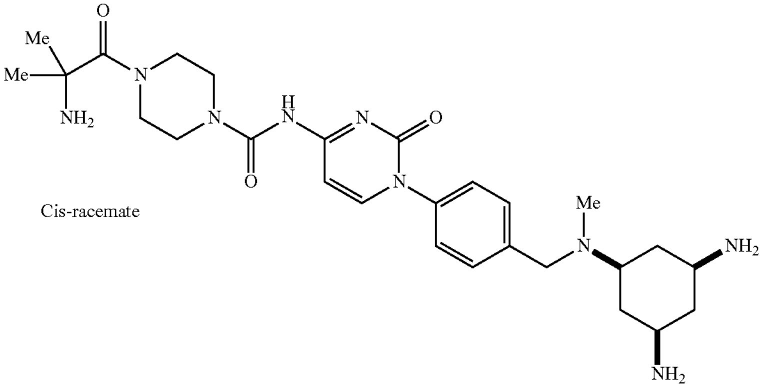 Cis-racemate |

TABLE 11-continued
| Compounds of Formula I Continued | | |
|---|---|---|
| No. | Salt Structure | Free Base Structure |
| 326 | 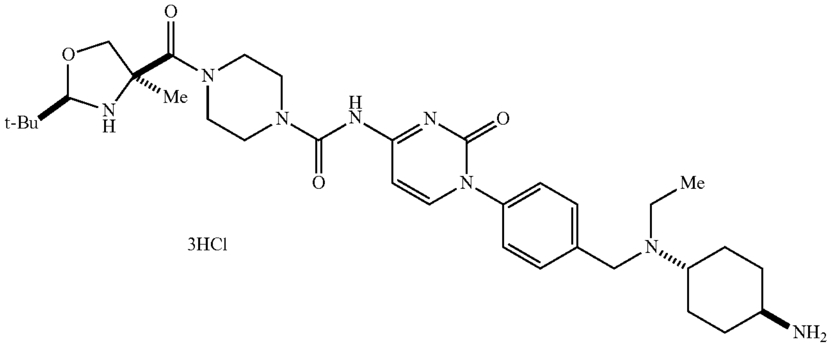 3HCl | 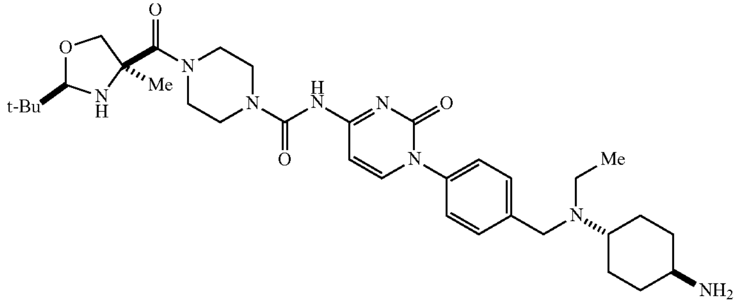 |
| 327 | 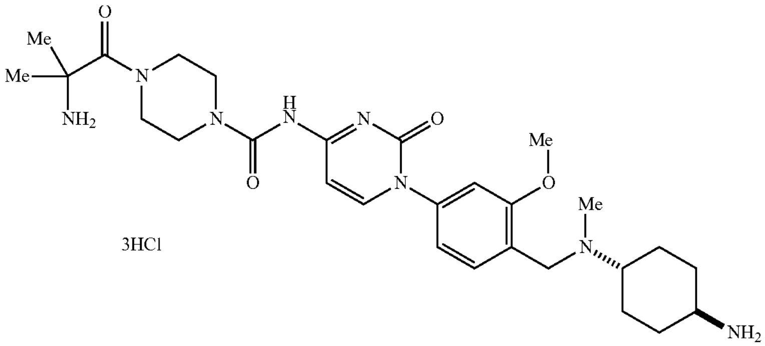 3HCl | 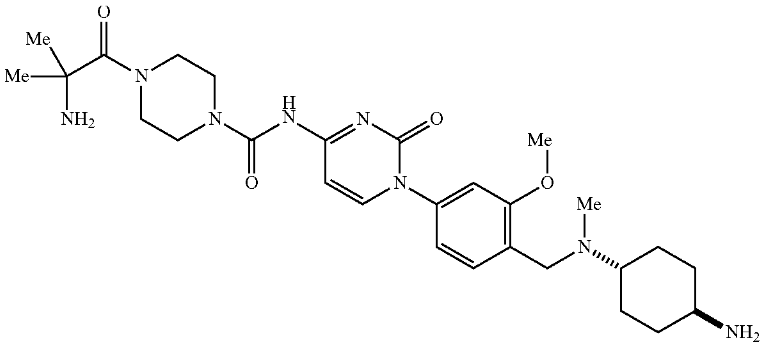 |

TABLE 11-continued
| Compounds of Formula I Continued | | |
|---|---|---|
| No. | Salt Structure | Free Base Structure |
| 328 | 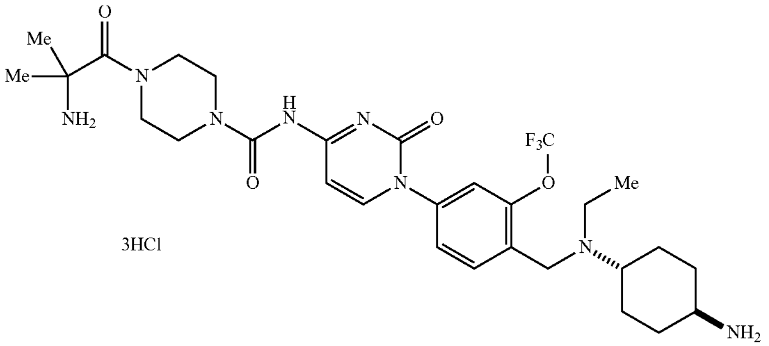 3HCl | 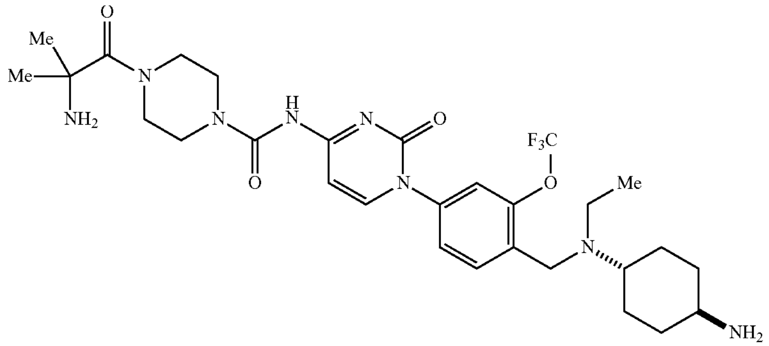 |
| 329 | 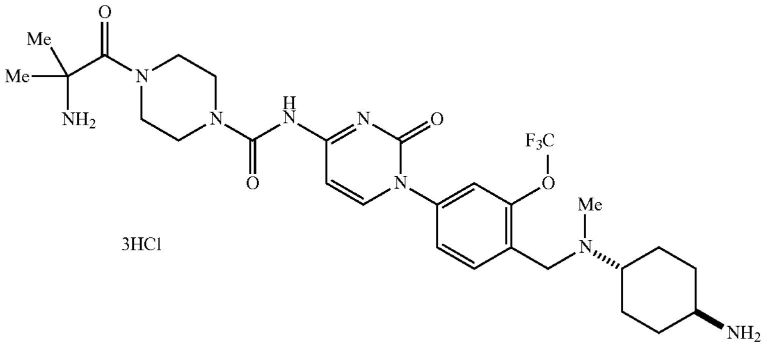 3HCl | 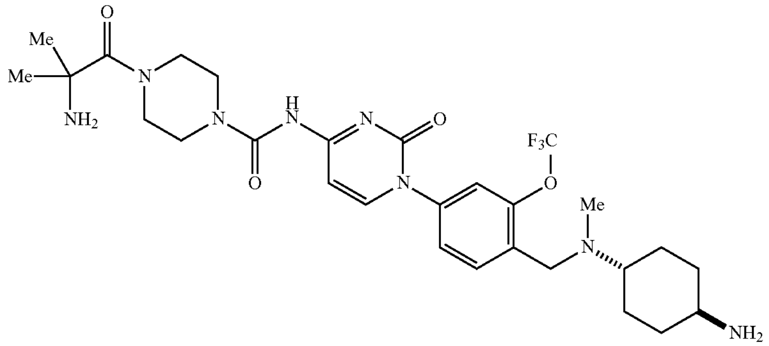 |

TABLE 11-continued
| Compounds of Formula I Continued | | |
|---|---|---|
| No. | Salt Structure | Free Base Structure |
| 330 | 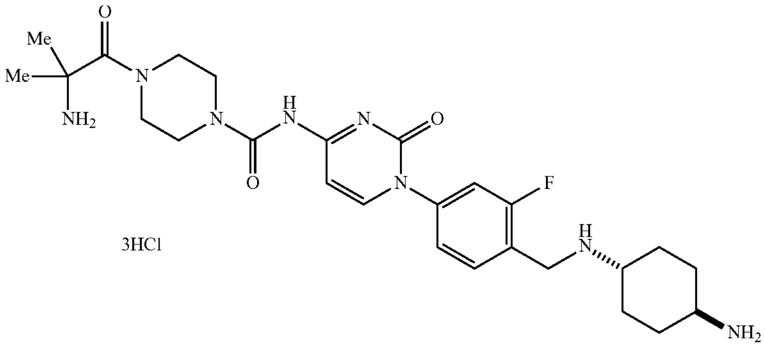 3HCl | 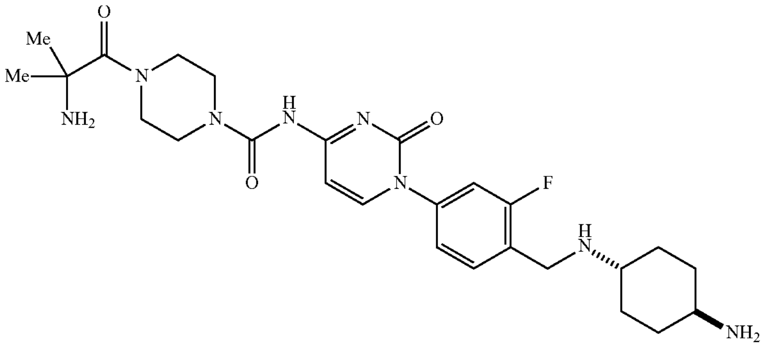 |
| 331 | 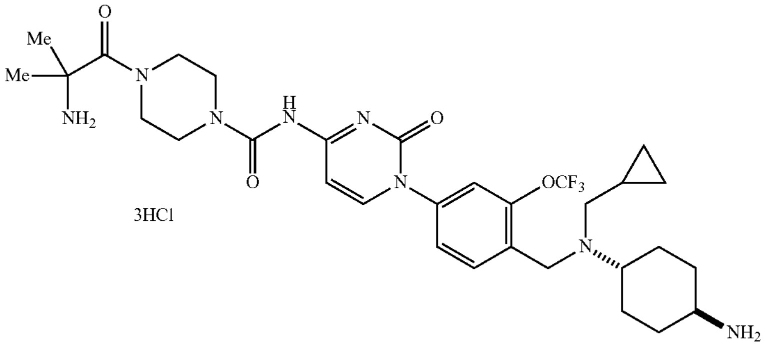 3HCl | 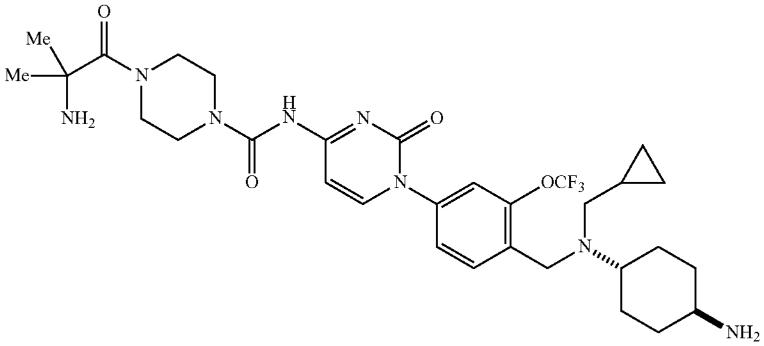 |

TABLE 11-continued
| Compounds of Formula I Continued | | |
|---|---|---|
| No. | Salt Structure | Free Base Structure |
| 332 | 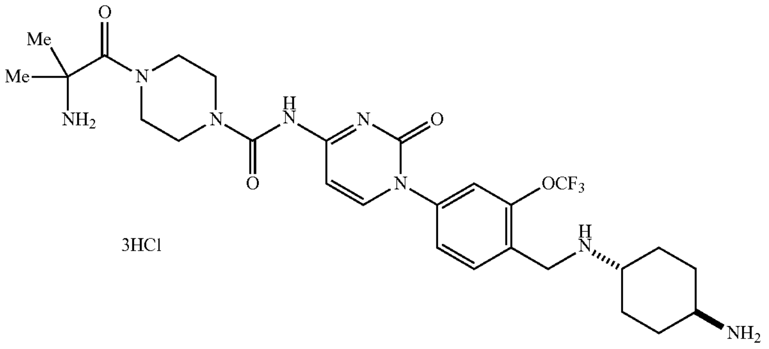 3HCl | 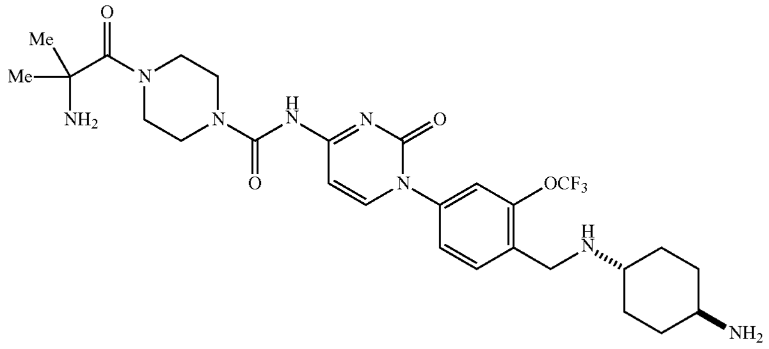 |
| 333 | 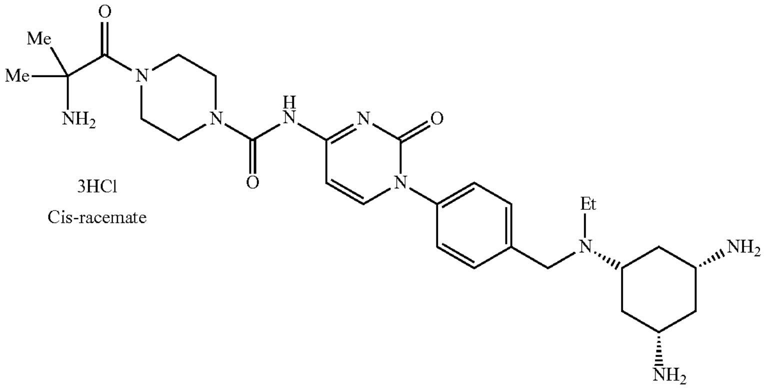 3HCl Cis-racemate | 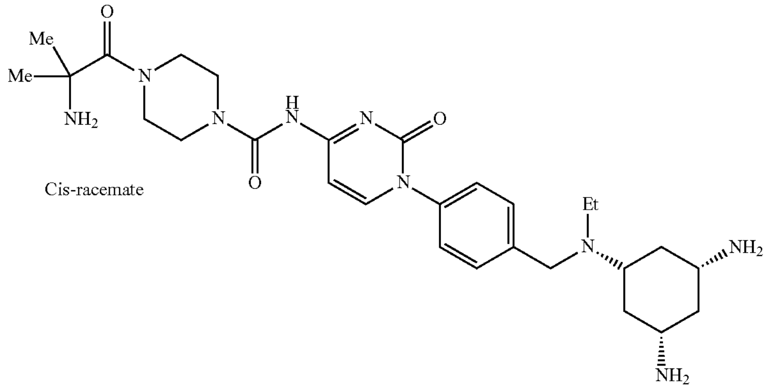 Cis-racemate |
| 334 | 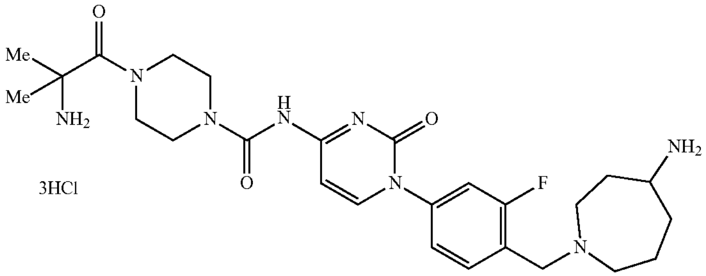 [SMILES: CC(C)(N)C(=O)N1CCN(C(=O)Nc2ccn(-c3ccc(CN4CCCC(N)CC4)c(F)c3)c(=O)n2)CC1] 3HCl | 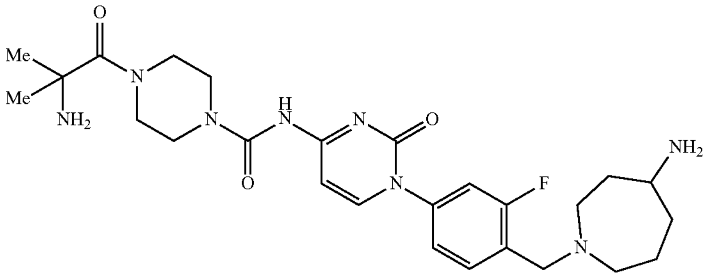 [SMILES: CC(C)(N)C(=O)N1CCN(C(=O)Nc2ccn(-c3ccc(CN4CCCC(N)CC4)c(F)c3)c(=O)n2)CC1] |

TABLE 11-continued
Compounds of Formula I Continued
| No. | Salt Structure | Free Base Structure |
|---|---|---|
| 335 | 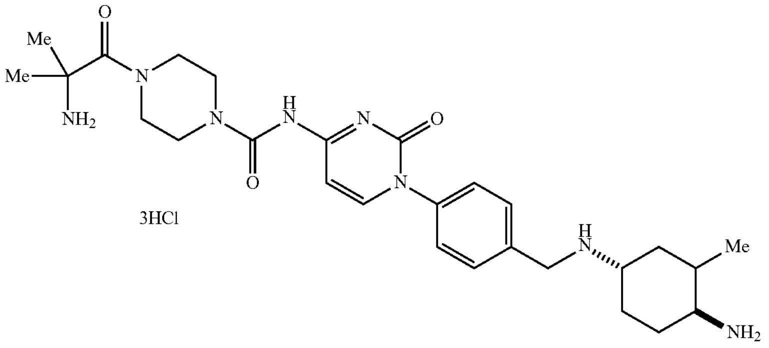 3HCl | 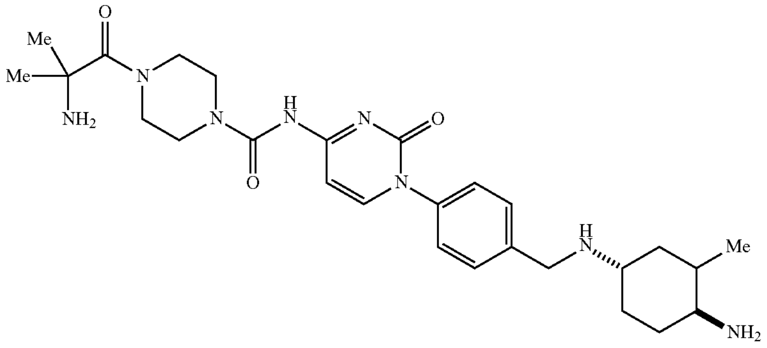 |
| 336 | 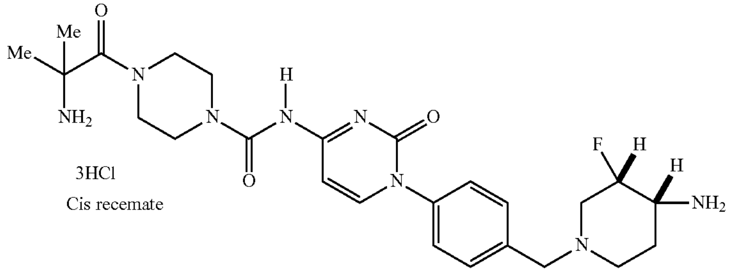 [SMILES: CC(C)(N)C(=O)N1CCN(C(=O)Nc2ccn(-c3ccc(CN4CC[C@@H](N)[C@@H](F)C4)cc3)c(=O)n2)CC1] 3HCl Cis recemate | 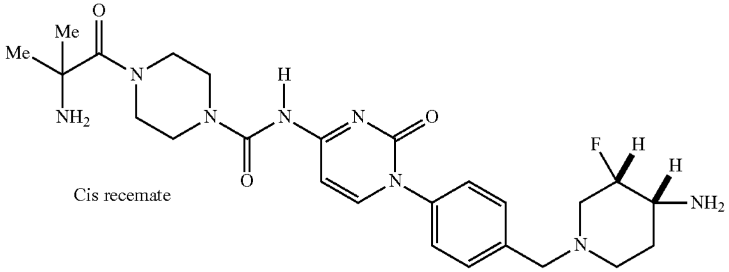 [SMILES: CC(C)(N)C(=O)N1CCN(C(=O)Nc2ccn(-c3ccc(CN4CC[C@@H](N)[C@@H](F)C4)cc3)c(=O)n2)CC1] Cis recemate |

TABLE 11-continued
| Compounds of Formula I Continued | | |
|---|---|---|
| No. | Salt Structure | Free Base Structure |
| 337 | 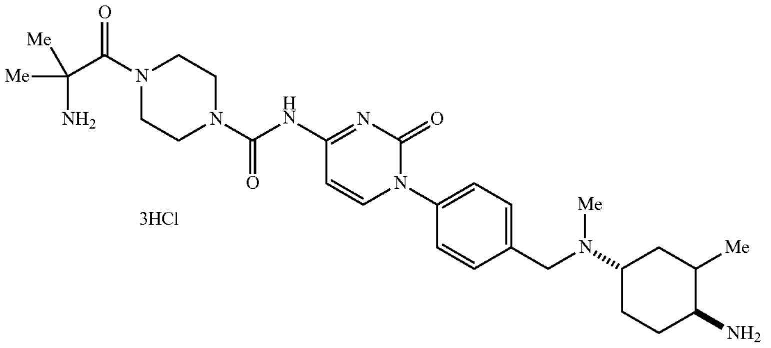 3HCl | 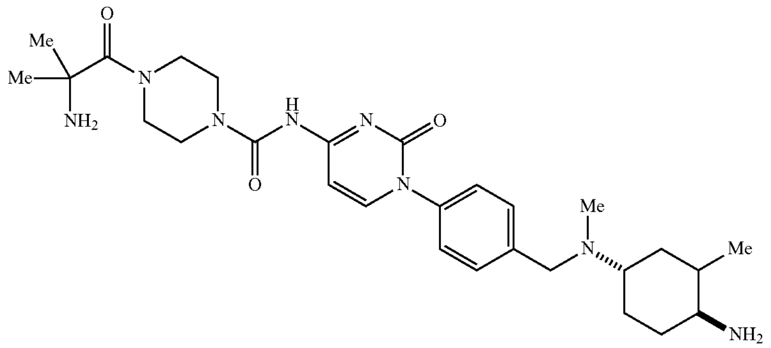 Mixture of Diastereomers |
| 338 | 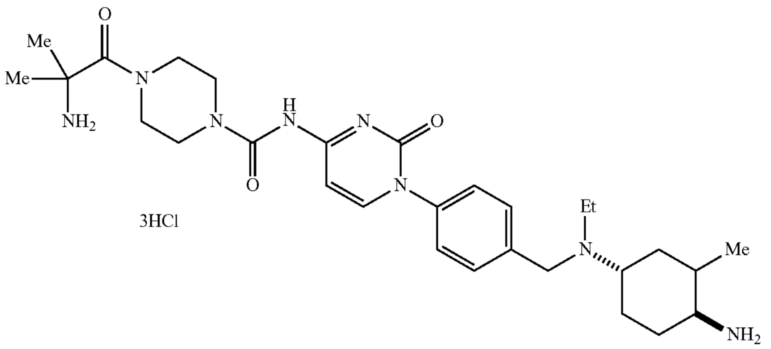 3HCl | 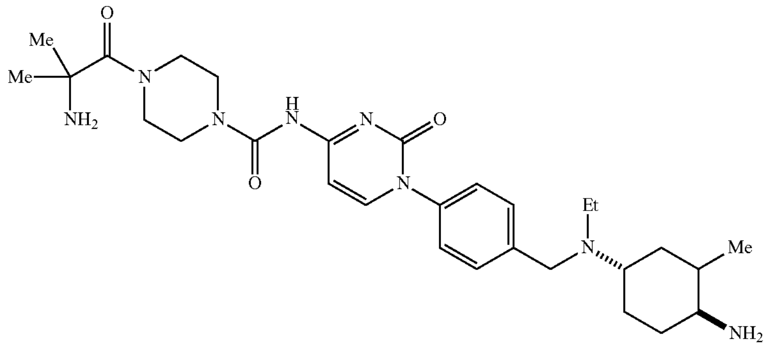 |

TABLE 11-continued
| Compounds of Formula I Continued | | |
|---|---|---|
| No. | Salt Structure | Free Base Structure |
| 339 | 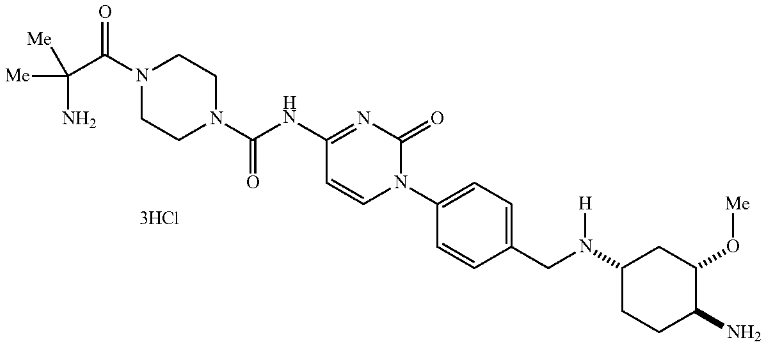 3HCl | 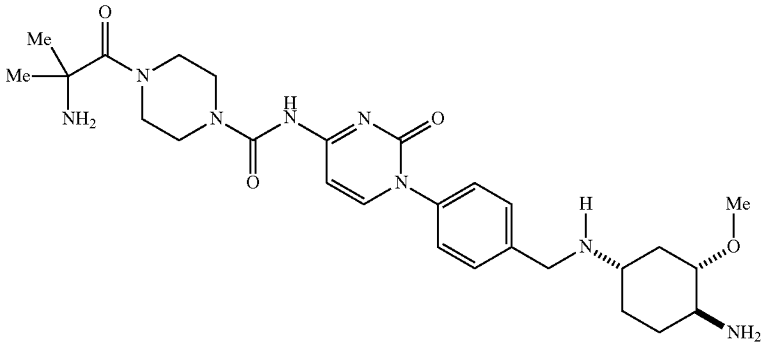 |
| 340 | 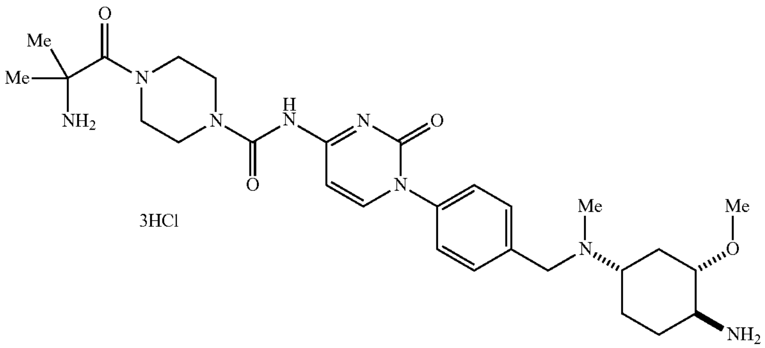 3HCl | 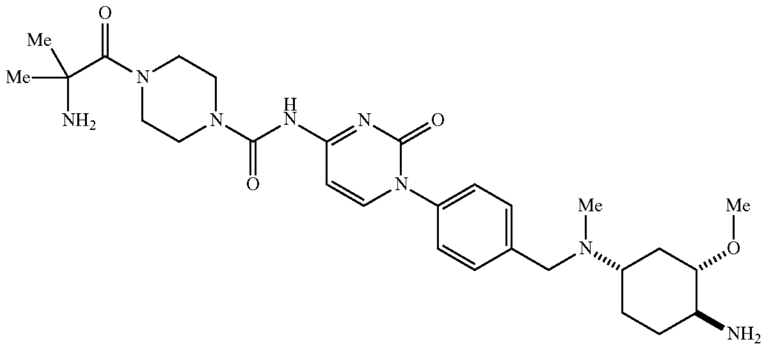 |

TABLE 11-continued
| Compounds of Formula I Continued | | |
|---|---|---|
| No. | Salt Structure | Free Base Structure |
| 341 | 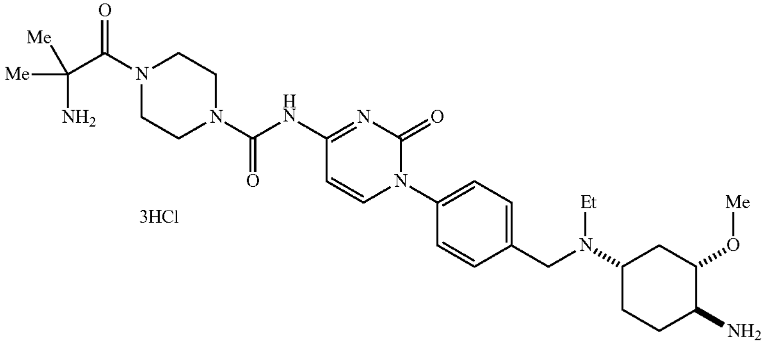 3HCl | 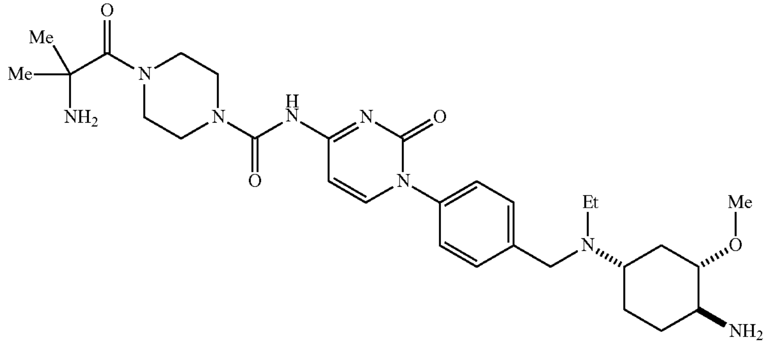 |
| 342 | 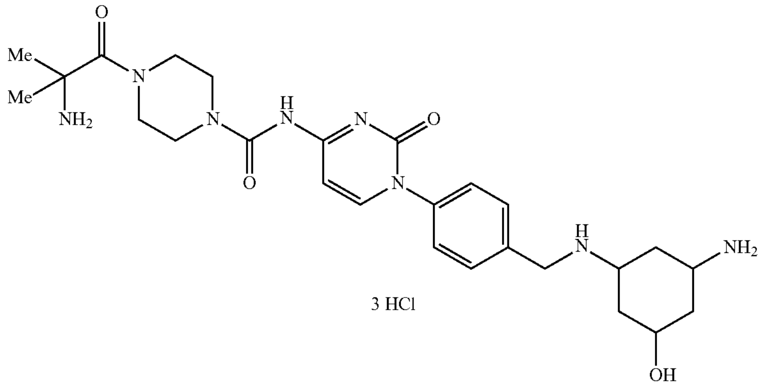 [SMILES: CC(C)(N)C(=O)N1CCN(C(=O)Nc2ccn(-c3ccc(CNC4CC(N)CC(O)C4)cc3)c(=O)n2)CC1] 3 HCl | 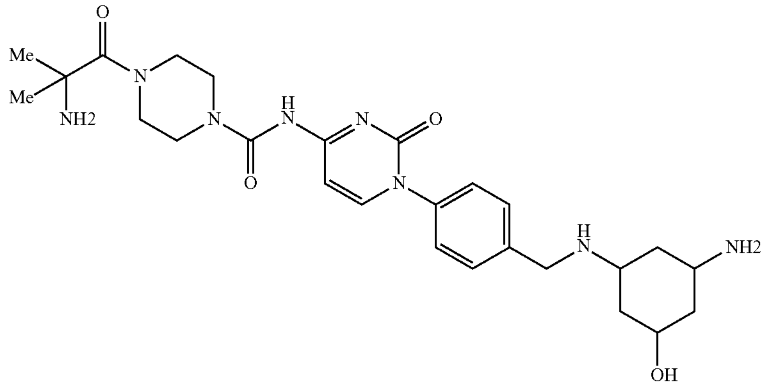 [SMILES: CC(C)(N)C(=O)N1CCN(C(=O)Nc2ccn(-c3ccc(CNC4CC(N)CC(O)C4)cc3)c(=O)n2)CC1] |

TABLE 11-continued
| Compounds of Formula I Continued | | |
|---|---|---|
| No. | Salt Structure | Free Base Structure |
| 343 | 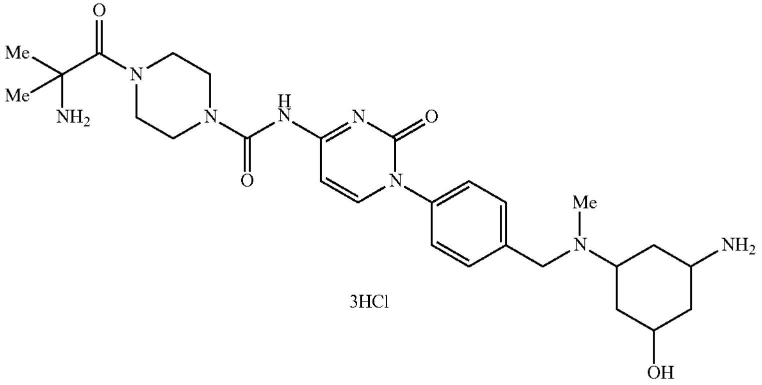 [SMILES: CN(Cc1ccc(-n2ccc(NC(=O)N3CCN(C(=O)C(C)(C)N)CC3)nc2=O)cc1)C1CC(N)CC(O)C1] 3HCl | 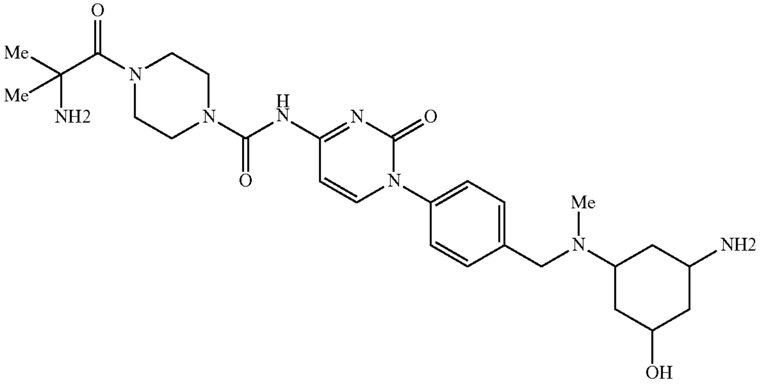 [SMILES: CN(Cc1ccc(-n2ccc(NC(=O)N3CCN(C(=O)C(C)(C)N)CC3)nc2=O)cc1)C1CC(N)CC(O)C1] |
| 344 | 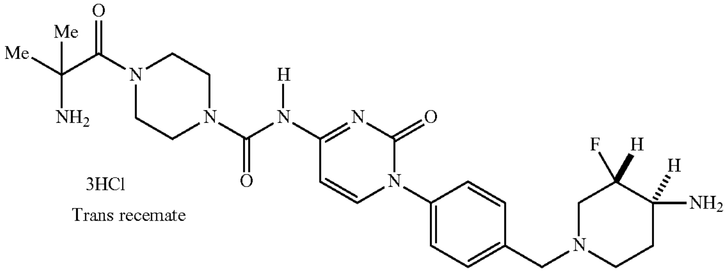 [SMILES: CC(C)(N)C(=O)N1CCN(C(=O)Nc2ccn(-c3ccc(CN4CC[C@H](N)[C@@H](F)C4)cc3)c(=O)n2)CC1] 3HCl Trans recemate | 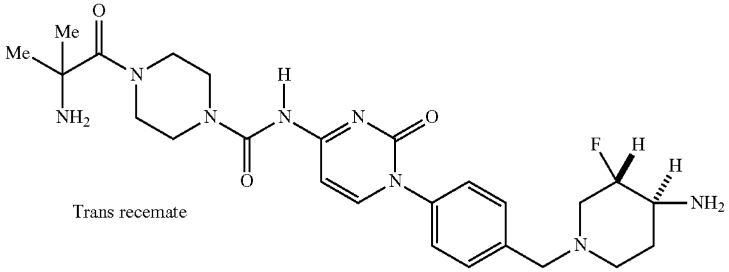 [SMILES: CC(C)(N)C(=O)N1CCN(C(=O)Nc2ccn(-c3ccc(CN4CC[C@H](N)[C@@H](F)C4)cc3)c(=O)n2)CC1] Trans recemate |
| 345 | 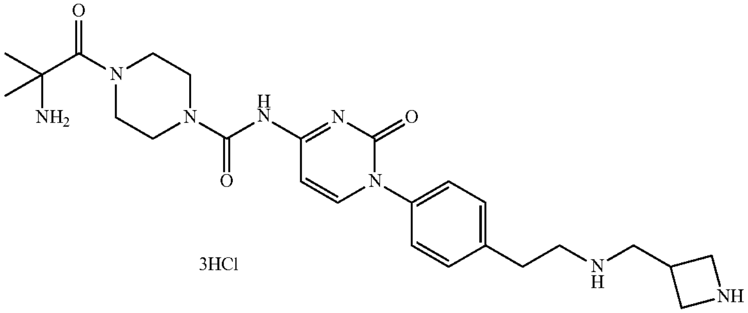 [SMILES: CC(C)(N)C(=O)N1CCN(C(=O)Nc2ccn(-c3ccc(CCNCC4CNC4)cc3)c(=O)n2)CC1] 3HCl | 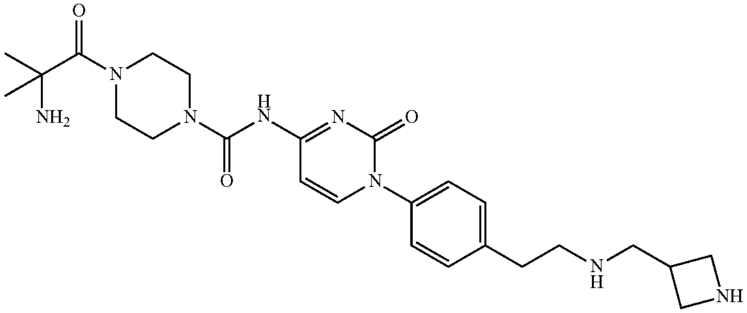 [SMILES: CC(C)(N)C(=O)N1CCN(C(=O)Nc2ccn(-c3ccc(CCNCC4CNC4)cc3)c(=O)n2)CC1] |

TABLE 11-continued
| Compounds of Formula I Continued | | |
|---|---|---|
| No. | Salt Structure | Free Base Structure |
| 346 | 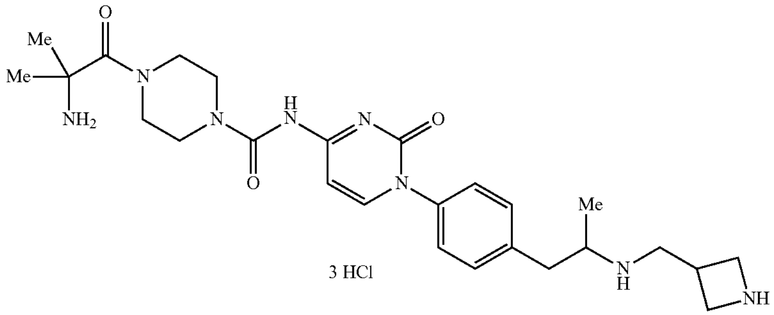 [SMILES: CC(Cc1ccc(-n2ccc(NC(=O)N3CCN(C(=O)C(C)(C)N)CC3)nc2=O)cc1)NCC1CNC1] 3 HCl | 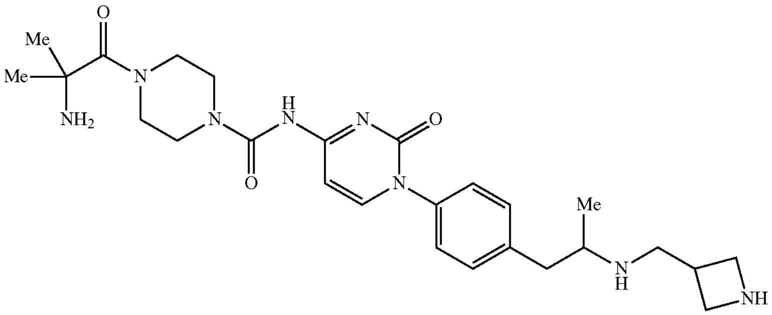 [SMILES: CC(Cc1ccc(-n2ccc(NC(=O)N3CCN(C(=O)C(C)(C)N)CC3)nc2=O)cc1)NCC1CNC1] |
| 347 | 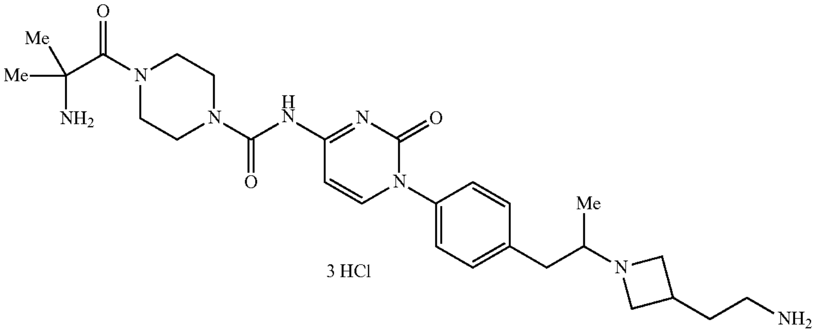 [SMILES: CC(Cc1ccc(-n2ccc(NC(=O)N3CCN(C(=O)C(C)(C)N)CC3)nc2=O)cc1)N1CC(CCN)C1] 3 HCl | 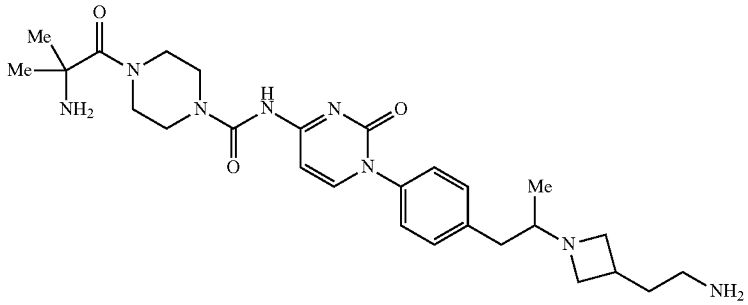 [SMILES: CC(Cc1ccc(-n2ccc(NC(=O)N3CCN(C(=O)C(C)(C)N)CC3)nc2=O)cc1)N1CC(CCN)C1] |
| 348 | 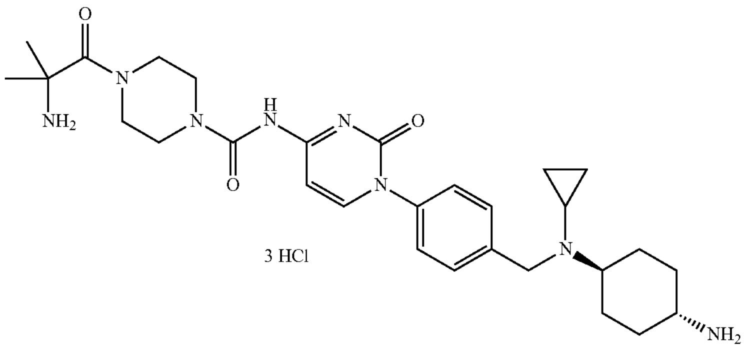 [SMILES: CC(C)(N)C(=O)N1CCN(C(=O)Nc2ccn(-c3ccc(CN(C4CC4)[C@H]4CC[C@H](N)CC4)cc3)c(=O)n2)CC1] 3 HCl | 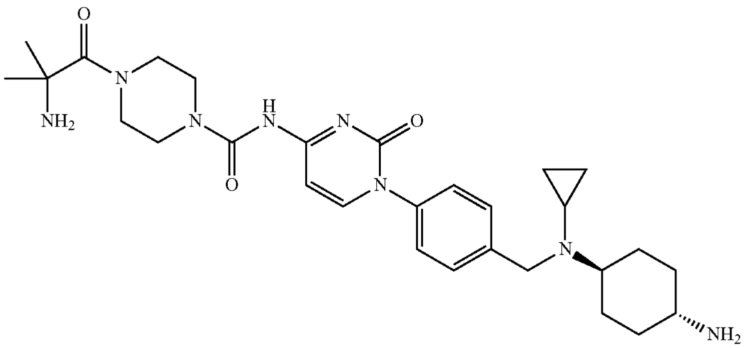 [SMILES: CC(C)(N)C(=O)N1CCN(C(=O)Nc2ccn(-c3ccc(CN(C4CC4)[C@H]4CC[C@H](N)CC4)cc3)c(=O)n2)CC1] |

TABLE 11-continued
| Compounds of Formula I Continued | | |
|---|---|---|
| No. | Salt Structure | Free Base Structure |
| 349 | 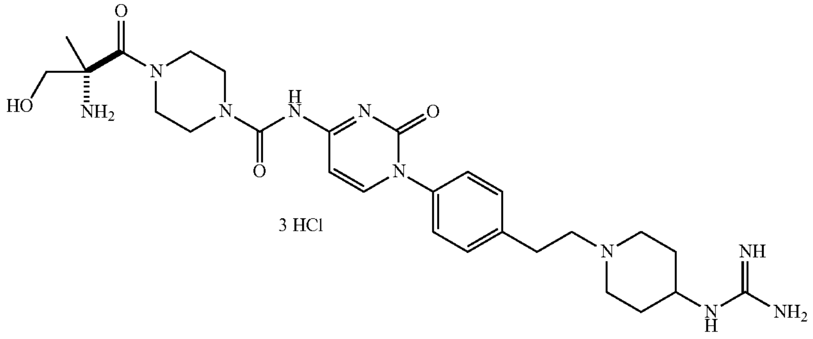 3 HCl | 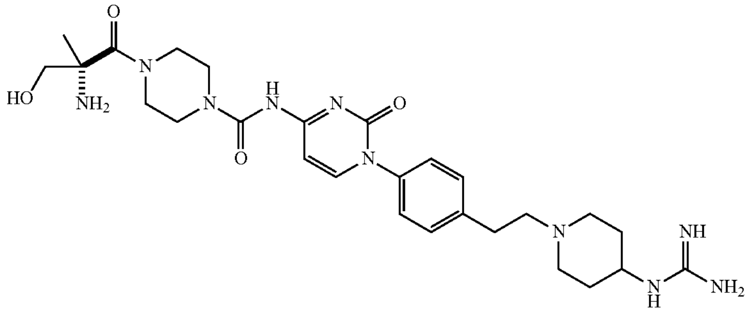 |
| 350 | 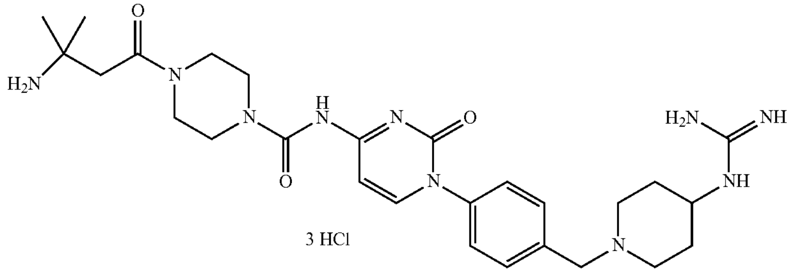 [SMILES: CC(C)(N)CC(=O)N1CCN(C(=O)Nc2ccn(-c3ccc(CN4CCC(NC(=N)N)CC4)cc3)c(=O)n2)CC1] 3 HCl | 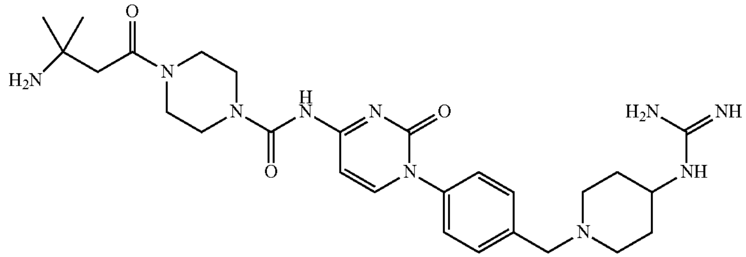 [SMILES: CC(C)(N)CC(=O)N1CCN(C(=O)Nc2ccn(-c3ccc(CN4CCC(NC(=N)N)CC4)cc3)c(=O)n2)CC1] |
| 351 | 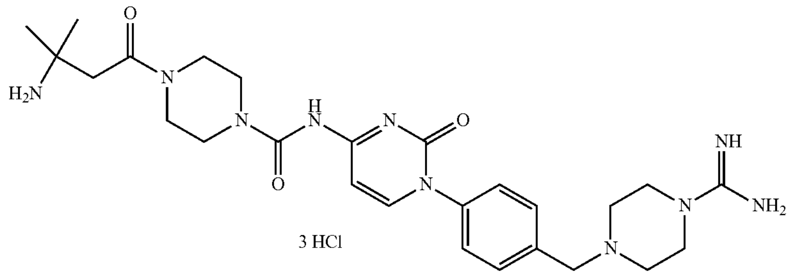 [SMILES: CC(C)(N)CC(=O)N1CCN(C(=O)Nc2ccn(-c3ccc(CN4CCN(C(=N)N)CC4)cc3)c(=O)n2)CC1] 3 HCl | 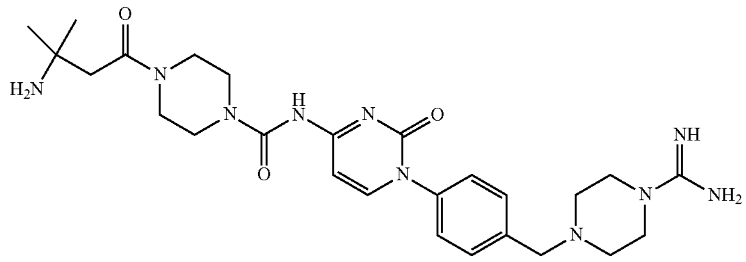 [SMILES: CC(C)(N)CC(=O)N1CCN(C(=O)Nc2ccn(-c3ccc(CN4CCN(C(=N)N)CC4)cc3)c(=O)n2)CC1] |

TABLE 11-continued
| Compounds of Formula I Continued | | |
|---|---|---|
| No. | Salt Structure | Free Base Structure |
| 352 | 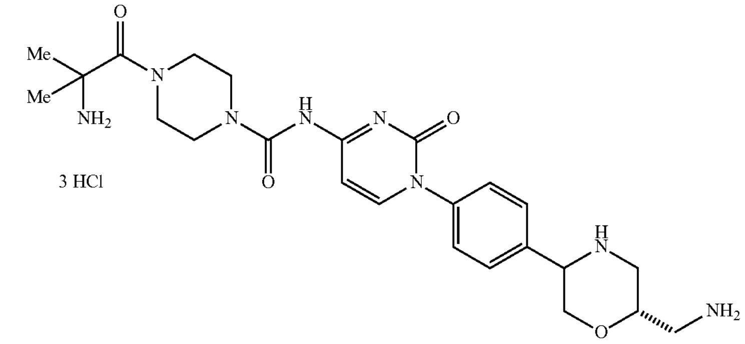 [SMILES: CC(C)(N)C(=O)N1CCN(C(=O)Nc2ccn(-c3ccc(C4CO[C@@H](CN)CN4)cc3)c(=O)n2)CC1] 3 HCl | 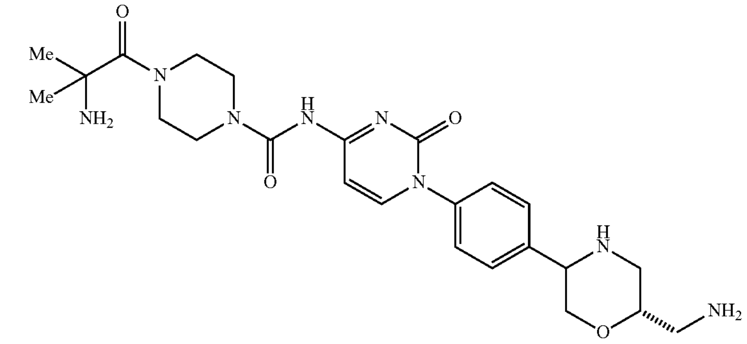 [SMILES: CC(C)(N)C(=O)N1CCN(C(=O)Nc2ccn(-c3ccc(C4CO[C@@H](CN)CN4)cc3)c(=O)n2)CC1] |
| 353 | 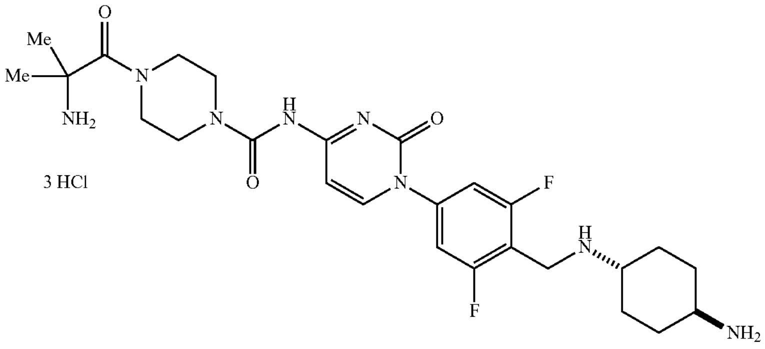 3 HCl | 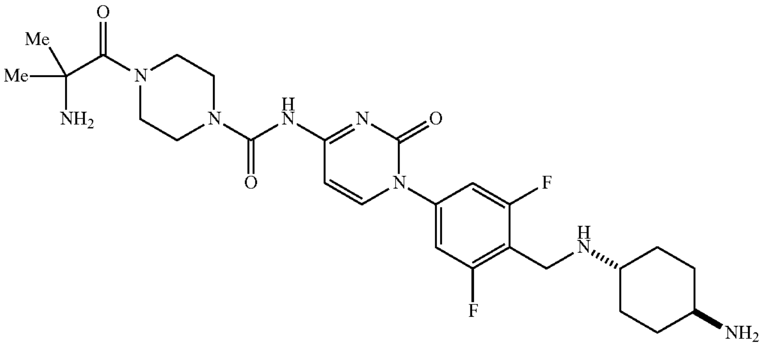 |

TABLE 11-continued
| Compounds of Formula I Continued | | |
|---|---|---|
| No. | Salt Structure | Free Base Structure |
| 354 | 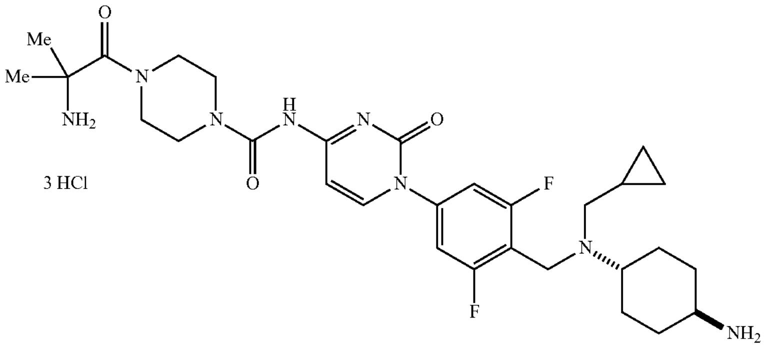 3 HCl | 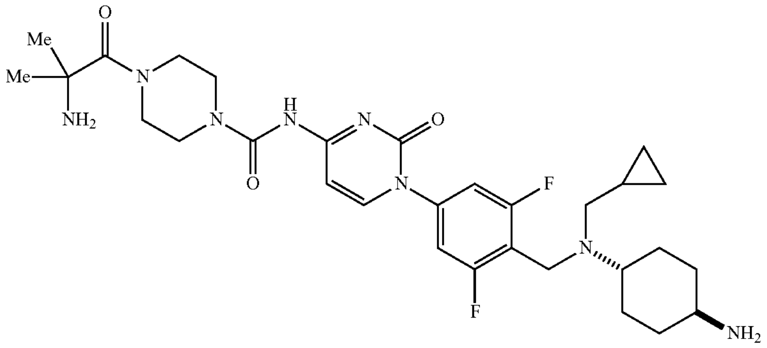 |
| 355 | 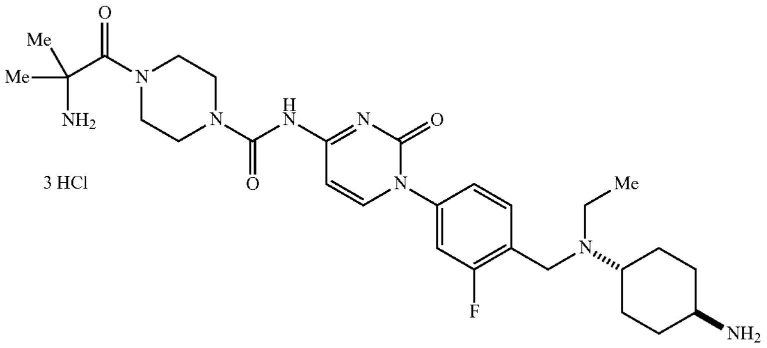 3 HCl | 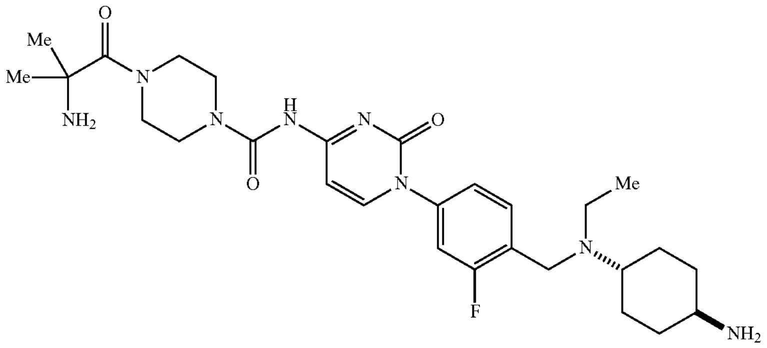 |

TABLE 11-continued
| Compounds of Formula I Continued | | |
|---|---|---|
| No. | Salt Structure | Free Base Structure |
| 356 | 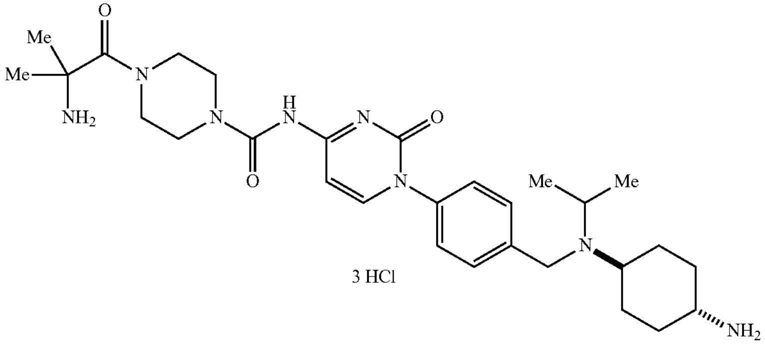 3 HCl | 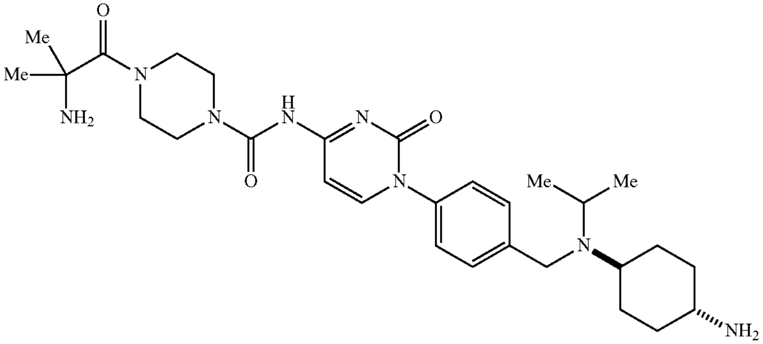 |
| 357 | 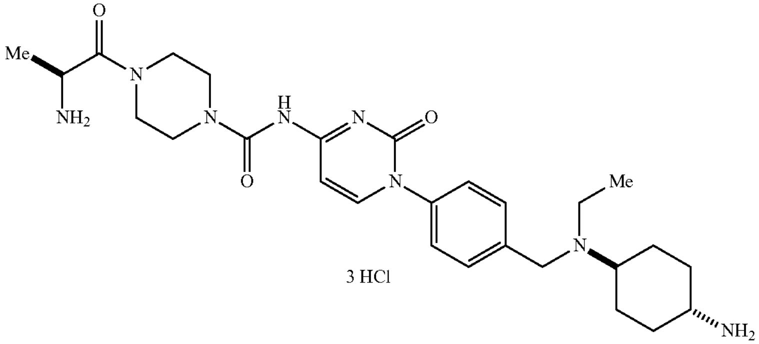 3 HCl | 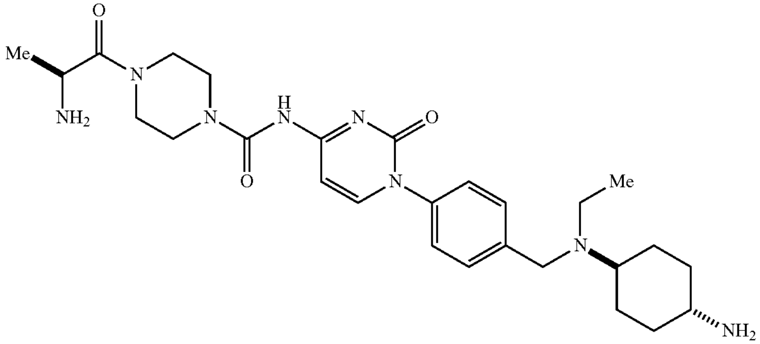 |

TABLE 11-continued
| Compounds of Formula I Continued | | |
|---|---|---|
| No. | Salt Structure | Free Base Structure |
| 358 | 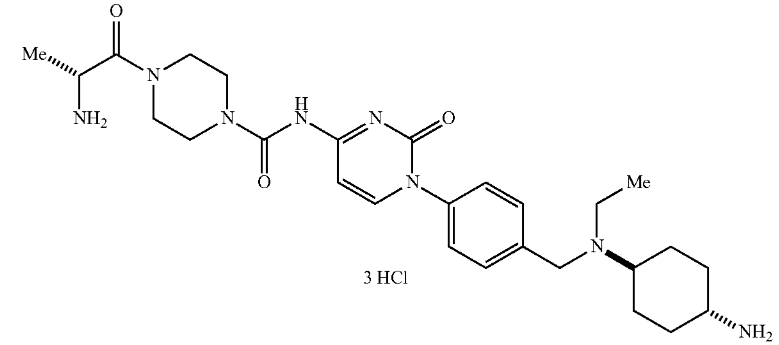 3 HCl | 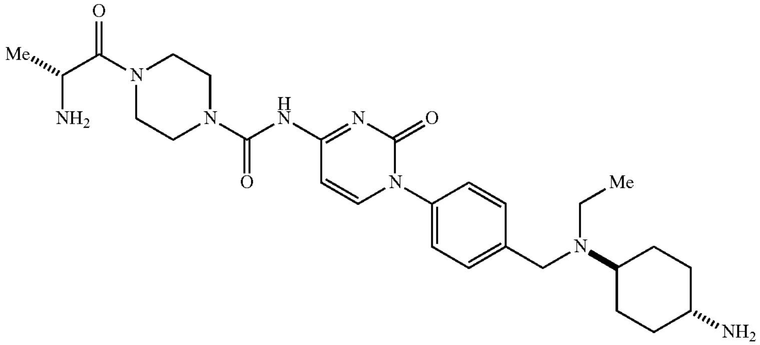 |
| 359 | 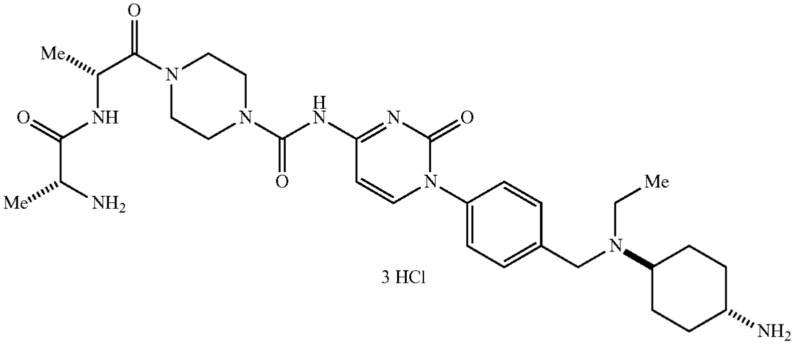 3 HCl | 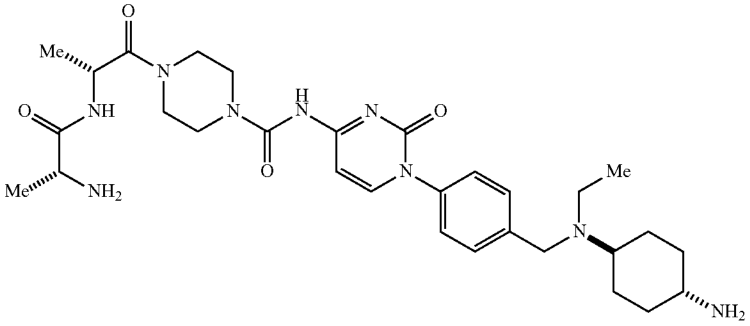 |
| 360 | 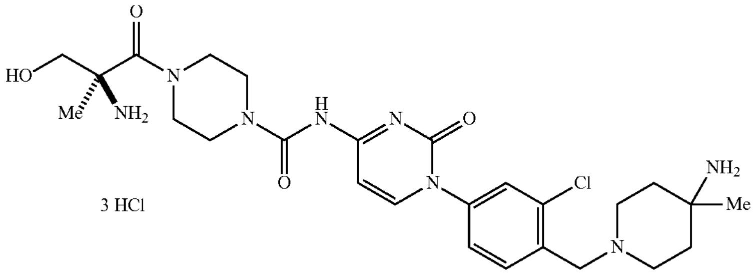 [SMILES: CC1(N)CCN(Cc2ccc(-n3ccc(NC(=O)N4CCN(C(=O)[C@@](C)(N)CO)CC4)nc3=O)cc2Cl)CC1] 3 HCl | 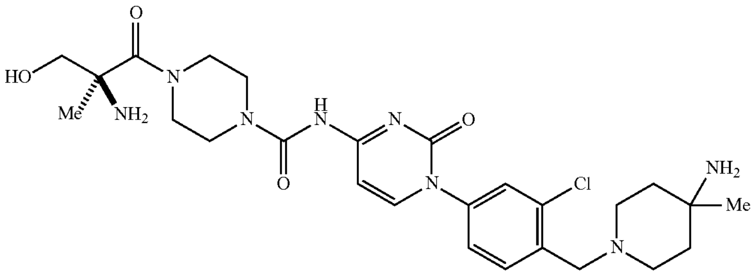 [SMILES: CC1(N)CCN(Cc2ccc(-n3ccc(NC(=O)N4CCN(C(=O)[C@@](C)(N)CO)CC4)nc3=O)cc2Cl)CC1] |

TABLE 11-continued
| Compounds of Formula I Continued | | |
|---|---|---|
| No. | Salt Structure | Free Base Structure |
| 361 | 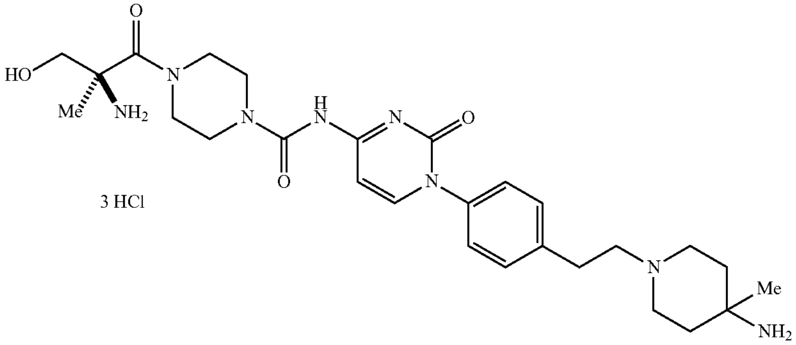 [SMILES: CC1(N)CCN(CCc2ccc(-n3ccc(NC(=O)N4CCN(C(=O)[C@@](C)(N)CO)CC4)nc3=O)cc2)CC1] 3 HCl | 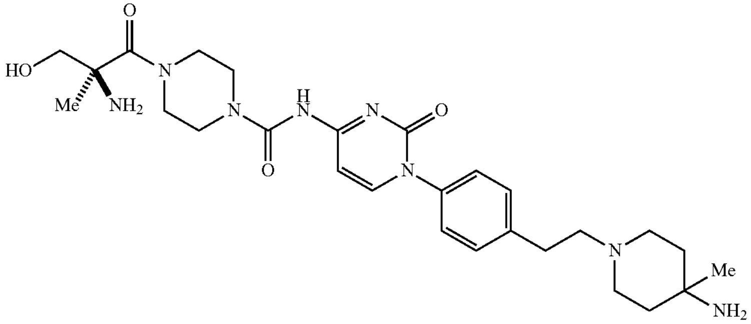 [SMILES: CC1(N)CCN(CCc2ccc(-n3ccc(NC(=O)N4CCN(C(=O)[C@@](C)(N)CO)CC4)nc3=O)cc2)CC1] |
| 362 | 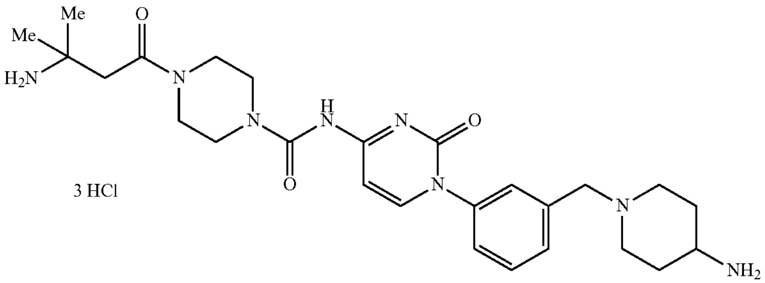 [SMILES: CC(C)(N)CC(=O)N1CCN(C(=O)Nc2ccn(-c3cccc(CN4CCC(N)CC4)c3)c(=O)n2)CC1] 3 HCl | 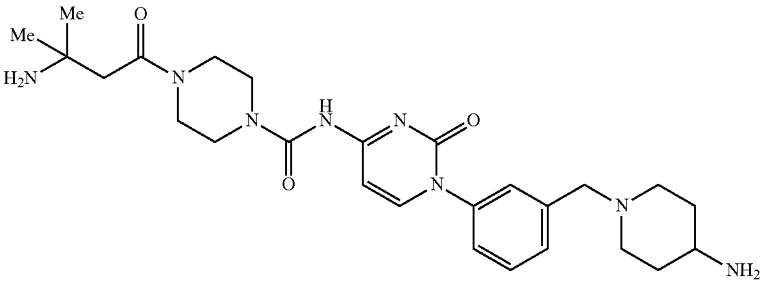 [SMILES: CC(C)(N)CC(=O)N1CCN(C(=O)Nc2ccn(-c3cccc(CN4CCC(N)CC4)c3)c(=O)n2)CC1] |
| 363 | 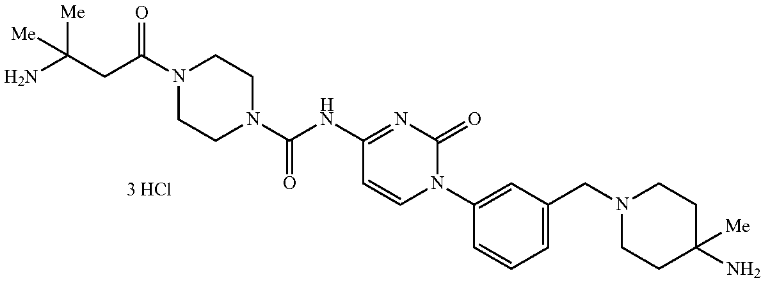 [SMILES: CC(C)(N)CC(=O)N1CCN(C(=O)Nc2ccn(-c3cccc(CN4CCC(C)(N)CC4)c3)c(=O)n2)CC1] 3 HCl | 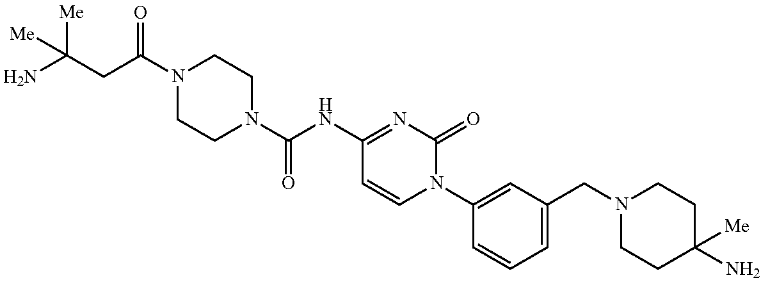 [SMILES: CC(C)(N)CC(=O)N1CCN(C(=O)Nc2ccn(-c3cccc(CN4CCC(C)(N)CC4)c3)c(=O)n2)CC1] |

TABLE 11-continued
| Compounds of Formula I Continued | | |
|---|---|---|
| No. | Salt Structure | Free Base Structure |
| 364 | 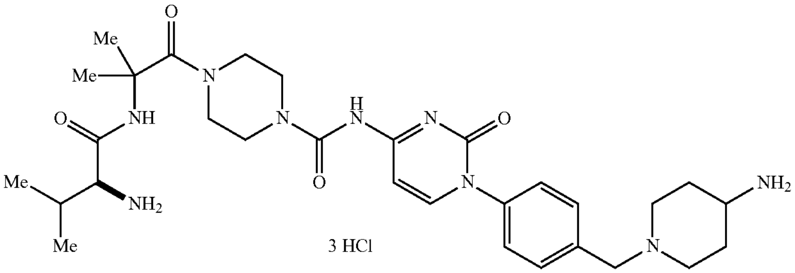 [SMILES: CC(C)[C@H](N)C(=O)NC(C)(C)C(=O)N1CCN(C(=O)Nc2ccn(-c3ccc(CN4CCC(N)CC4)cc3)c(=O)n2)CC1] 3 HCl | 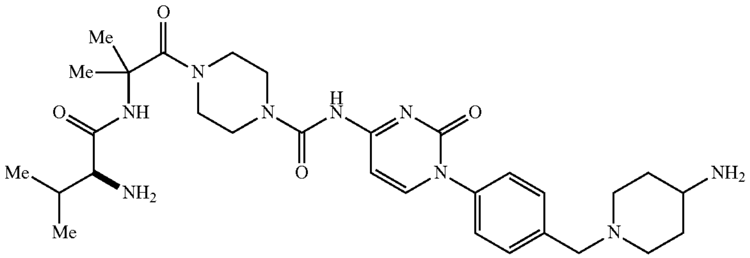 [SMILES: CC(C)[C@H](N)C(=O)NC(C)(C)C(=O)N1CCN(C(=O)Nc2ccn(-c3ccc(CN4CCC(N)CC4)cc3)c(=O)n2)CC1] |
| 365 | 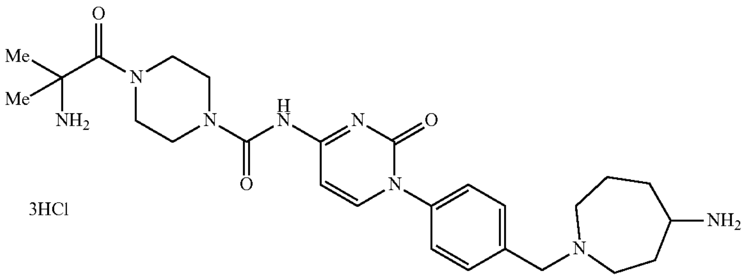 [SMILES: CC(C)(N)C(=O)N1CCN(C(=O)Nc2ccn(-c3ccc(CN4CCCC(N)CC4)cc3)c(=O)n2)CC1] 3HCl | 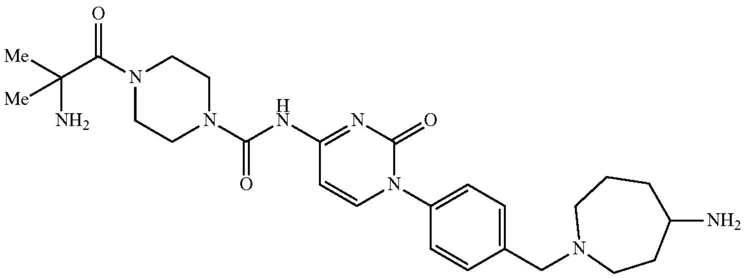 [SMILES: CC(C)(N)C(=O)N1CCN(C(=O)Nc2ccn(-c3ccc(CN4CCCC(N)CC4)cc3)c(=O)n2)CC1] |
| 366 | 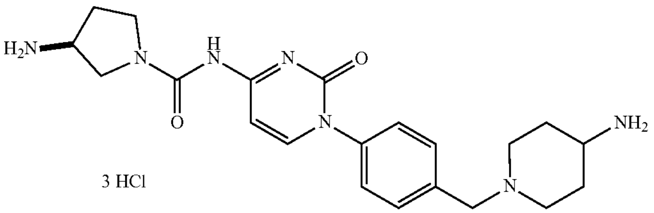 [SMILES: NC1CCN(Cc2ccc(-n3ccc(NC(=O)N4CC[C@H](N)C4)nc3=O)cc2)CC1] 3 HCl | 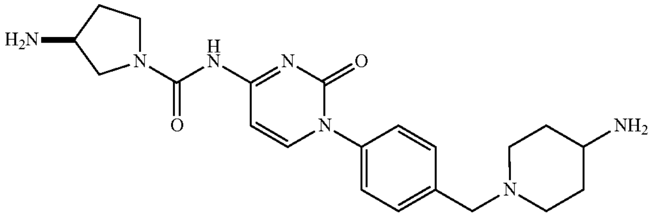 [SMILES: NC1CCN(Cc2ccc(-n3ccc(NC(=O)N4CC[C@H](N)C4)nc3=O)cc2)CC1] |
| 367 | 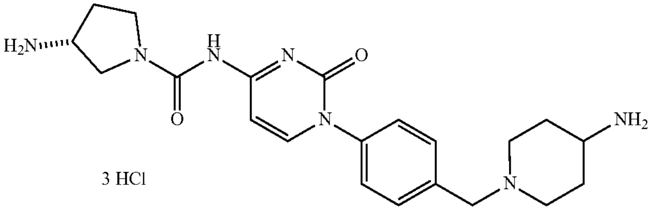 [SMILES: NC1CCN(Cc2ccc(-n3ccc(NC(=O)N4CC[C@@H](N)C4)nc3=O)cc2)CC1] 3 HCl | 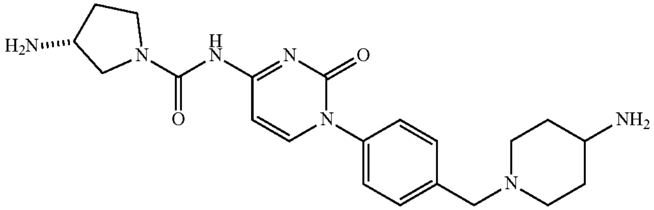 [SMILES: NC1CCN(Cc2ccc(-n3ccc(NC(=O)N4CC[C@@H](N)C4)nc3=O)cc2)CC1] |

TABLE 11-continued
| Compounds of Formula I Continued | | |
|---|---|---|
| No. | Salt Structure | Free Base Structure |
| 368 | 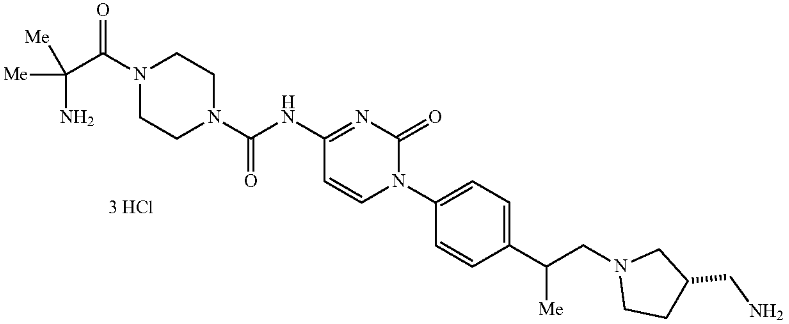 3 HCl | 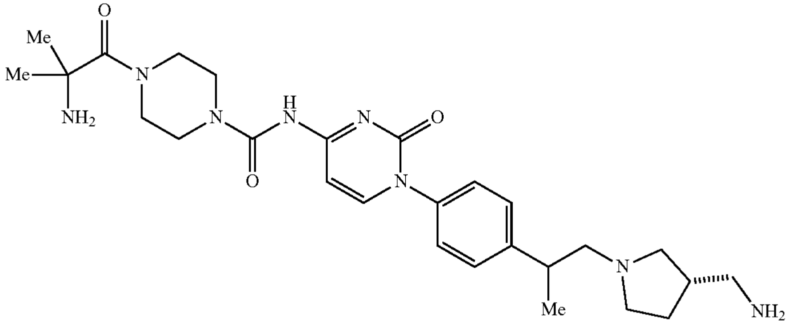 [SMILES: CC(CN1CC[C@@H](CN)C1)c1ccc(-n2ccc(NC(=O)N3CCN(C(=O)C(C)(C)N)CC3)nc2=O)cc1] |
| 369 | 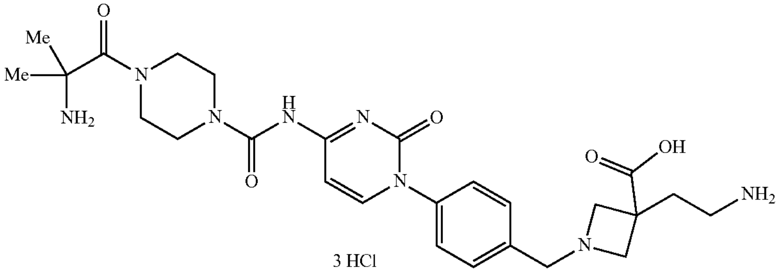 [SMILES: CC(C)(N)C(=O)N1CCN(C(=O)Nc2ccn(-c3ccc(CN4CC(CCN)(C(=O)O)C4)cc3)c(=O)n2)CC1] 3 HCl | 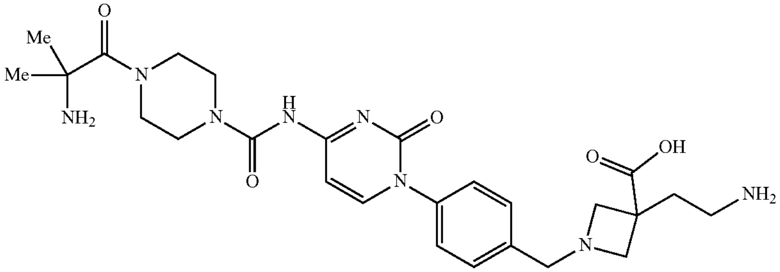 [SMILES: CC(C)(N)C(=O)N1CCN(C(=O)Nc2ccn(-c3ccc(CN4CC(CCN)(C(=O)O)C4)cc3)c(=O)n2)CC1] |
| 370 | 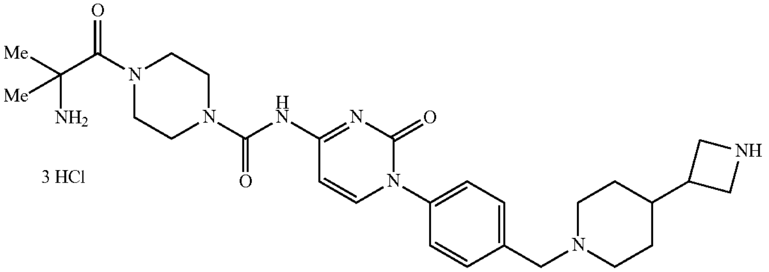 [SMILES: CC(C)(N)C(=O)N1CCN(C(=O)Nc2ccn(-c3ccc(CN4CCC(C5CNC5)CC4)cc3)c(=O)n2)CC1] 3 HCl | 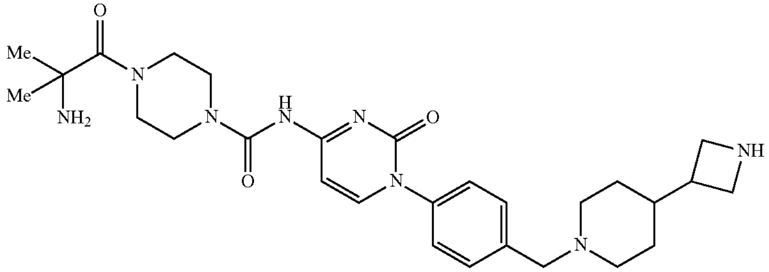 [SMILES: CC(C)(N)C(=O)N1CCN(C(=O)Nc2ccn(-c3ccc(CN4CCC(C5CNC5)CC4)cc3)c(=O)n2)CC1] |

TABLE 11-continued
| Compounds of Formula I Continued | | |
|---|---|---|
| No. | Salt Structure | Free Base Structure |
| 371 | 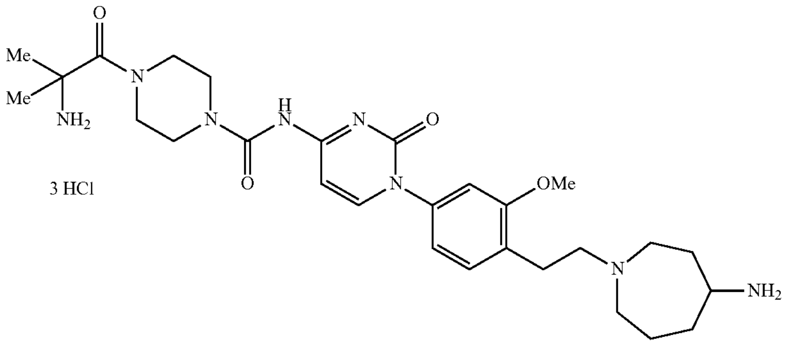 [SMILES: COc1cc(-n2ccc(NC(=O)N3CCN(C(=O)C(C)(C)N)CC3)nc2=O)ccc1CCN1CCCC(N)CC1] 3 HCl | 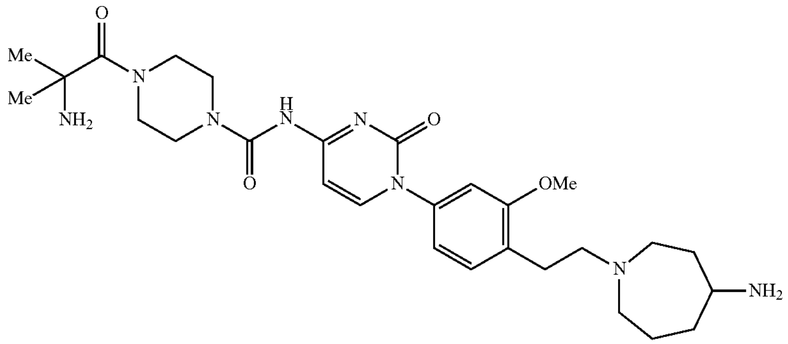 [SMILES: COc1cc(-n2ccc(NC(=O)N3CCN(C(=O)C(C)(C)N)CC3)nc2=O)ccc1CCN1CCCC(N)CC1] |
| 372 | 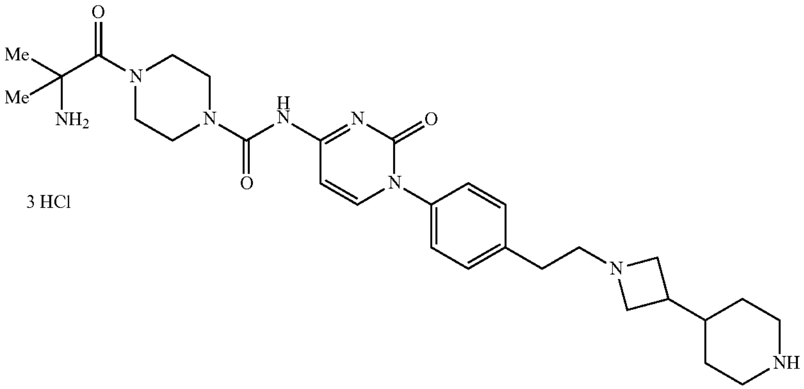 [SMILES: CC(C)(N)C(=O)N1CCN(C(=O)Nc2ccn(-c3ccc(CCN4CC(C5CCNCC5)C4)cc3)c(=O)n2)CC1] 3 HCl | 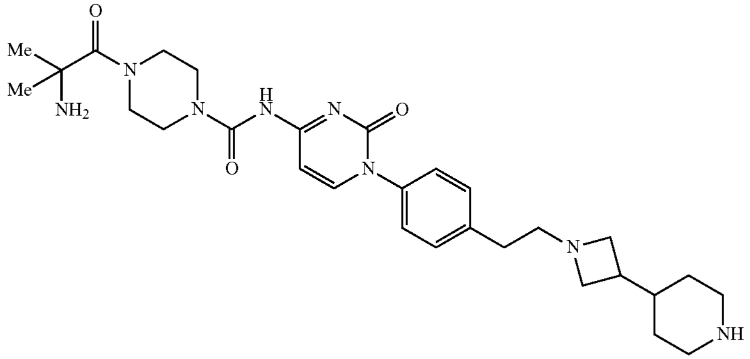 [SMILES: CC(C)(N)C(=O)N1CCN(C(=O)Nc2ccn(-c3ccc(CCN4CC(C5CCNCC5)C4)cc3)c(=O)n2)CC1] |

TABLE 11-continued
| Compounds of Formula I Continued | | |
|---|---|---|
| No. | Salt Structure | Free Base Structure |
| 373 | 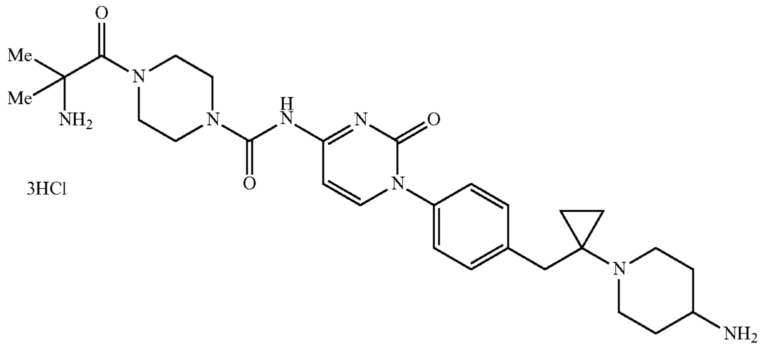 [SMILES: CC(C)(N)C(=O)N1CCN(C(=O)Nc2ccn(-c3ccc(CC4(N5CCC(N)CC5)CC4)cc3)c(=O)n2)CC1] 3HCl | 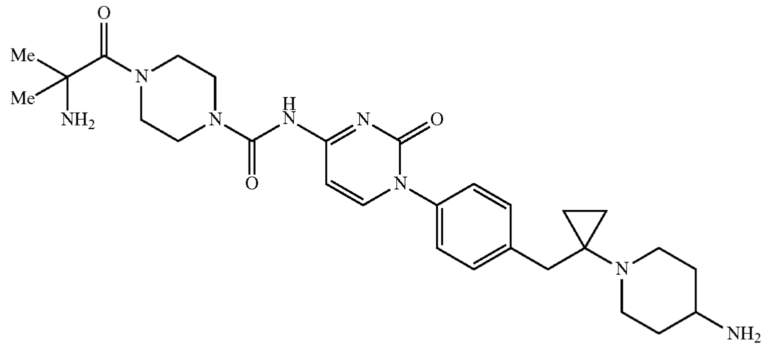 [SMILES: CC(C)(N)C(=O)N1CCN(C(=O)Nc2ccn(-c3ccc(CC4(N5CCC(N)CC5)CC4)cc3)c(=O)n2)CC1] |
| 374 | 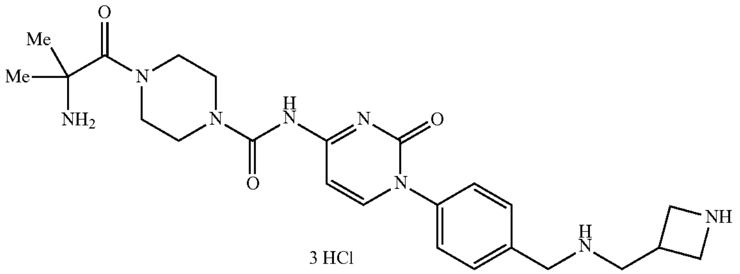 [SMILES: CC(C)(N)C(=O)N1CCN(C(=O)Nc2ccn(-c3ccc(CNCC4CNC4)cc3)c(=O)n2)CC1] 3 HCl | 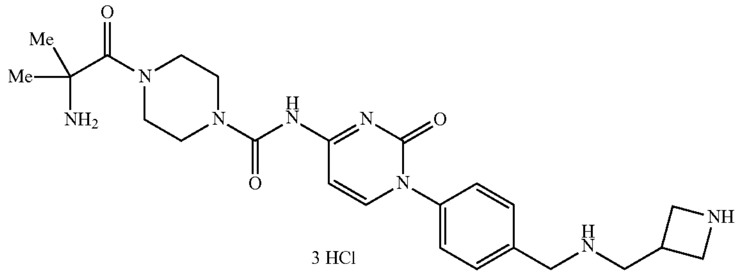 [SMILES: CC(C)(N)C(=O)N1CCN(C(=O)Nc2ccn(-c3ccc(CNCC4CNC4)cc3)c(=O)n2)CC1] 3 HCl |
| 375 | 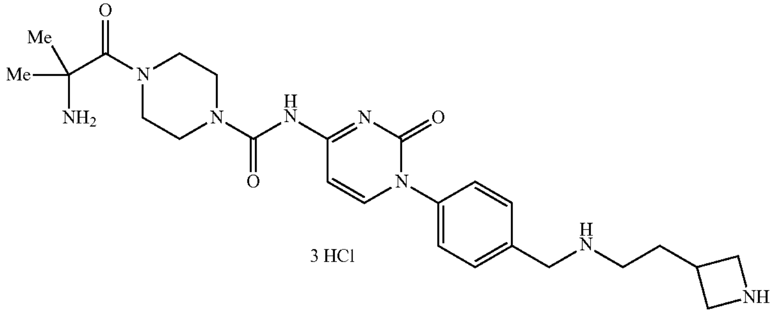 [SMILES: CC(C)(N)C(=O)N1CCN(C(=O)Nc2ccn(-c3ccc(CNCCC4CNC4)cc3)c(=O)n2)CC1] 3 HCl | 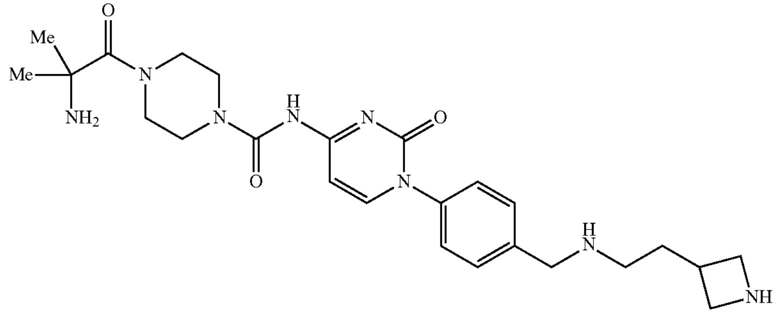 [SMILES: CC(C)(N)C(=O)N1CCN(C(=O)Nc2ccn(-c3ccc(CNCCC4CNC4)cc3)c(=O)n2)CC1] |

TABLE 11-continued
| Compounds of Formula I Continued | | |
|---|---|---|
| No. | Salt Structure | Free Base Structure |
| 376 | 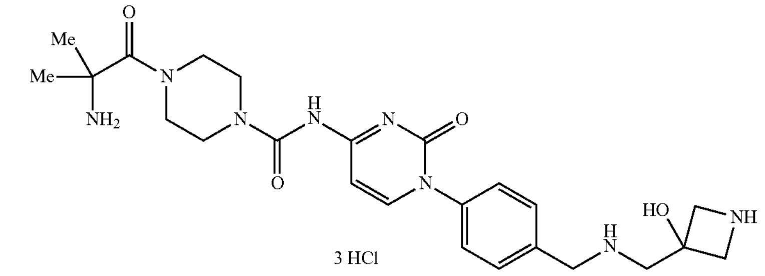 [SMILES: CC(C)(N)C(=O)N1CCN(C(=O)Nc2ccn(-c3ccc(CNCC4(O)CNC4)cc3)c(=O)n2)CC1] 3 HCl | 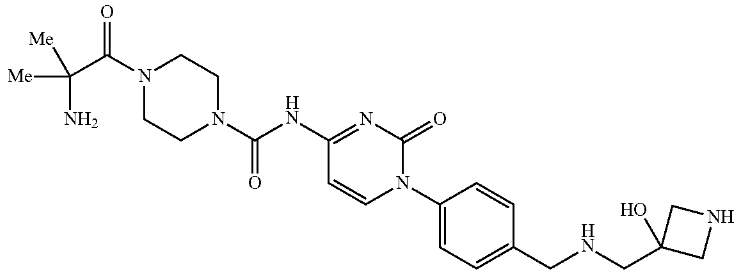 [SMILES: CC(C)(N)C(=O)N1CCN(C(=O)Nc2ccn(-c3ccc(CNCC4(O)CNC4)cc3)c(=O)n2)CC1] |
| 377 | 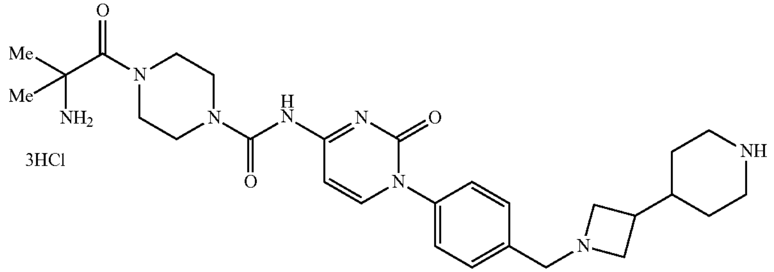 [SMILES: CC(C)(N)C(=O)N1CCN(C(=O)Nc2ccn(-c3ccc(CN4CC(C5CCNCC5)C4)cc3)c(=O)n2)CC1] 3HCl | 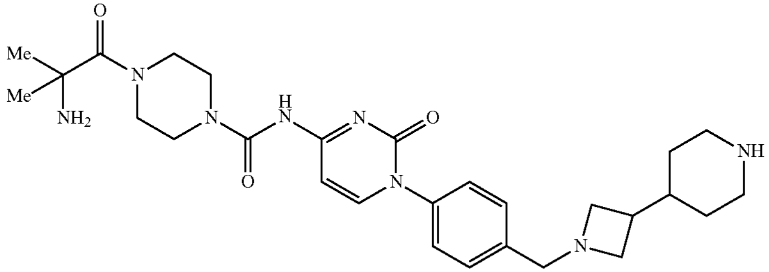 [SMILES: CC(C)(N)C(=O)N1CCN(C(=O)Nc2ccn(-c3ccc(CN4CC(C5CCNCC5)C4)cc3)c(=O)n2)CC1] |
| 378 | 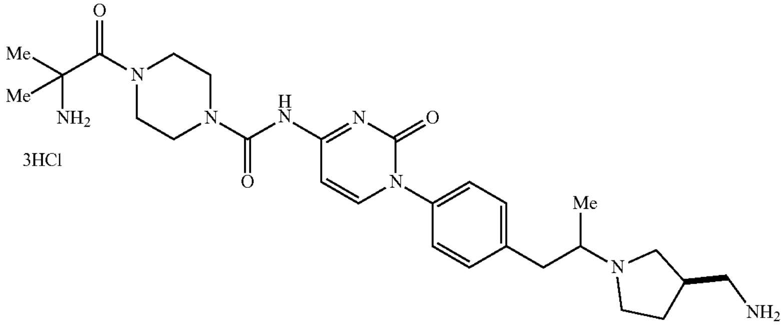 [SMILES: CC(Cc1ccc(-n2ccc(NC(=O)N3CCN(C(=O)C(C)(C)N)CC3)nc2=O)cc1)N1CC[C@H](CN)C1] 3HCl | 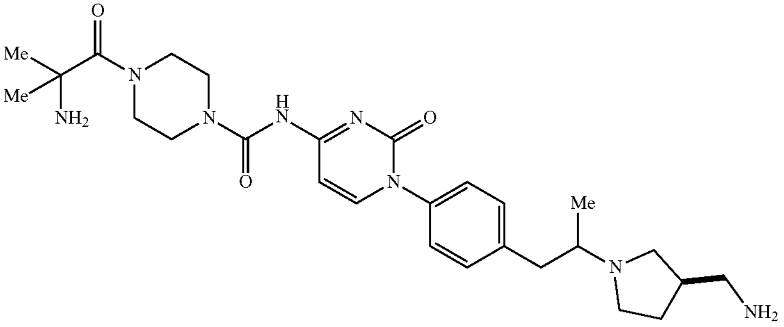 |

TABLE 11-continued
| Compounds of Formula I Continued | | |
|---|---|---|
| No. | Salt Structure | Free Base Structure |
| 379 | 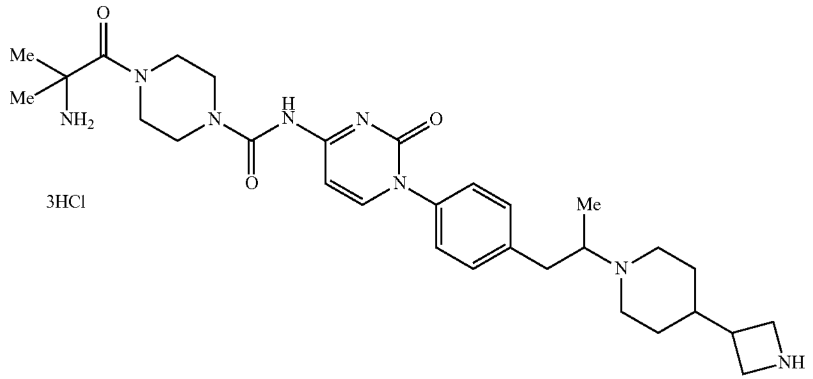 [SMILES: CC(Cc1ccc(-n2ccc(NC(=O)N3CCN(C(=O)C(C)(C)N)CC3)nc2=O)cc1)N1CCC(C2CNC2)CC1] 3HCl | 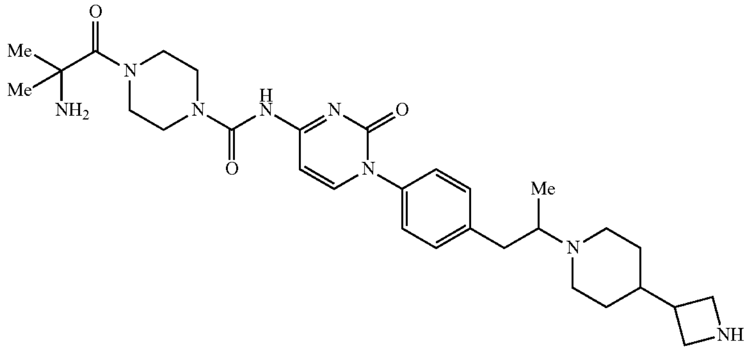 [SMILES: CC(Cc1ccc(-n2ccc(NC(=O)N3CCN(C(=O)C(C)(C)N)CC3)nc2=O)cc1)N1CCC(C2CNC2)CC1] |
| 380 | 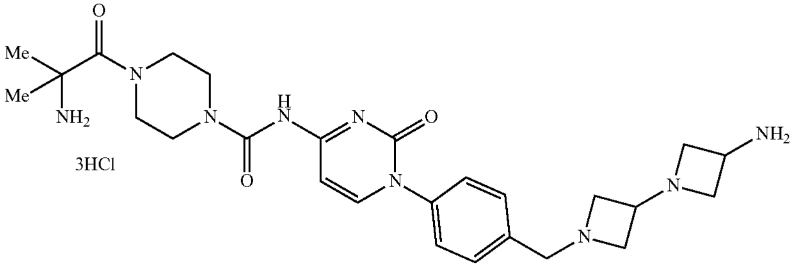 [SMILES: CC(C)(N)C(=O)N1CCN(C(=O)Nc2ccn(-c3ccc(CN4CC(N5CC(N)C5)C4)cc3)c(=O)n2)CC1] 3HCl | 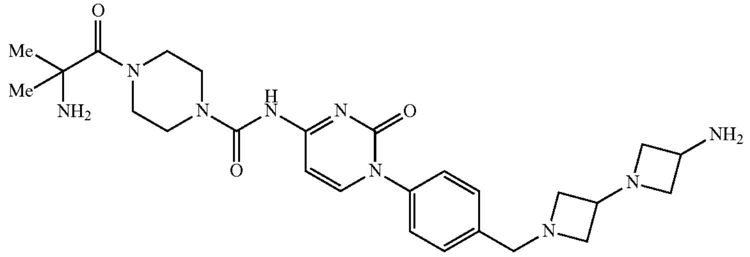 [SMILES: CC(C)(N)C(=O)N1CCN(C(=O)Nc2ccn(-c3ccc(CN4CC(N5CC(N)C5)C4)cc3)c(=O)n2)CC1] |
| 381 | 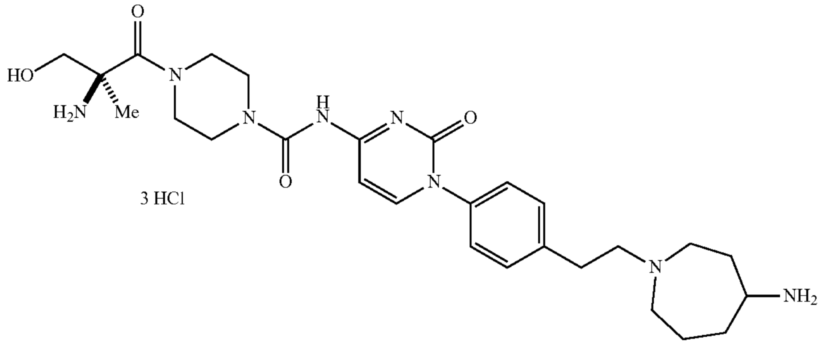 [SMILES: C[C@](N)(CO)C(=O)N1CCN(C(=O)Nc2ccn(-c3ccc(CCN4CCCC(N)CC4)cc3)c(=O)n2)CC1] 3 HCl | 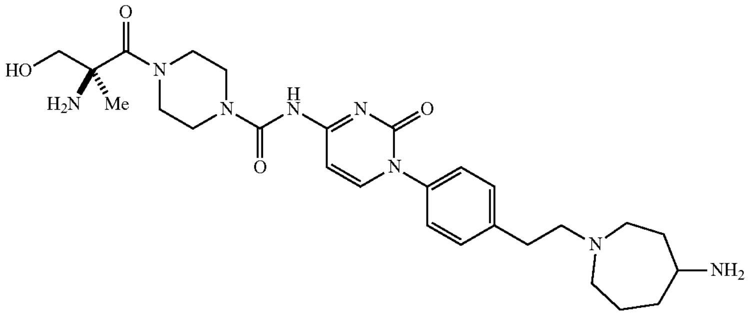 [SMILES: C[C@](N)(CO)C(=O)N1CCN(C(=O)Nc2ccn(-c3ccc(CCN4CCCC(N)CC4)cc3)c(=O)n2)CC1] |

TABLE 11-continued
| Compounds of Formula I Continued | | |
|---|---|---|
| No. | Salt Structure | Free Base Structure |
| 382 | 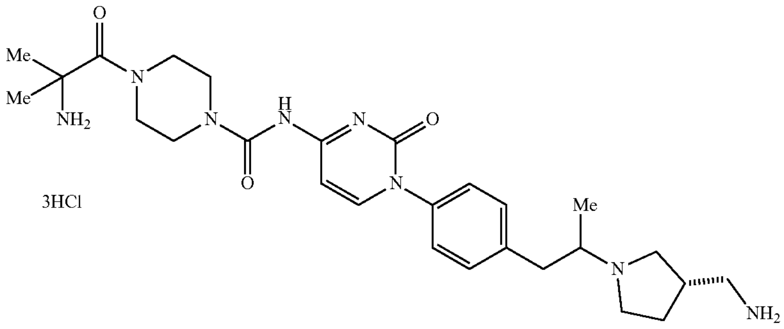 [SMILES: CC(Cc1ccc(-n2ccc(NC(=O)N3CCN(C(=O)C(C)(C)N)CC3)nc2=O)cc1)N1CC[C@@H](CN)C1] 3HCl | 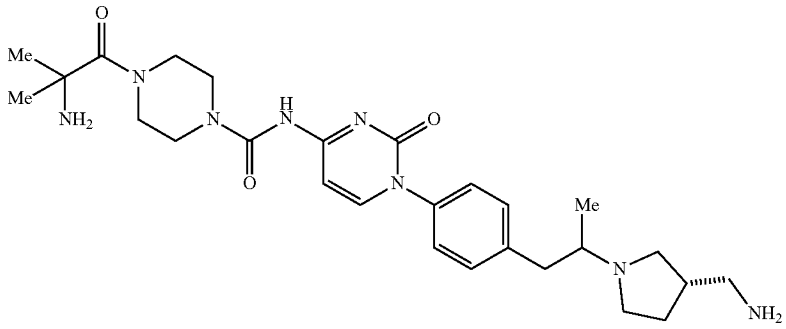 [SMILES: CC(Cc1ccc(-n2ccc(NC(=O)N3CCN(C(=O)C(C)(C)N)CC3)nc2=O)cc1)N1CC[C@@H](CN)C1] |
| 383 | 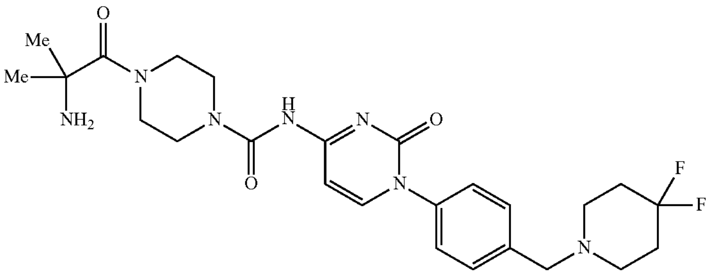 2 HCl | 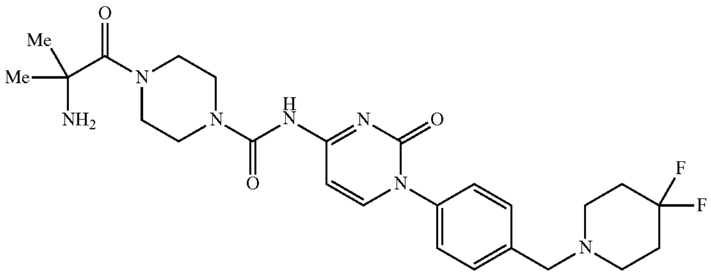 [SMILES: CC(C)(N)C(=O)N1CCN(C(=O)Nc2ccn(-c3ccc(CN4CCC(F)(F)CC4)cc3)c(=O)n2)CC1] |

TABLE 11-continued
| Compounds of Formula I Continued | | |
|---|---|---|
| No. | Salt Structure | Free Base Structure |
| 384 | 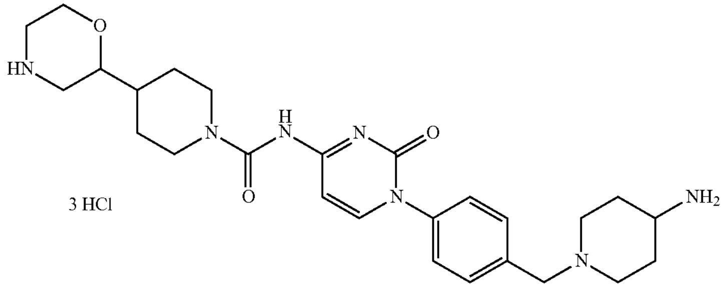 [SMILES: NC1CCN(Cc2ccc(-n3ccc(NC(=O)N4CCC(C5CNCCO5)CC4)nc3=O)cc2)CC1] 3 HCl | 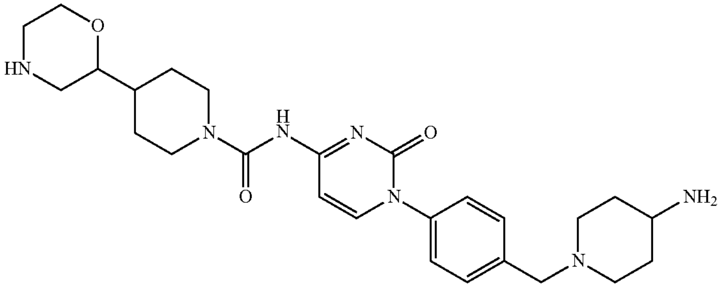 [SMILES: NC1CCN(Cc2ccc(-n3ccc(NC(=O)N4CCC(C5CNCCO5)CC4)nc3=O)cc2)CC1] |
| 385 | 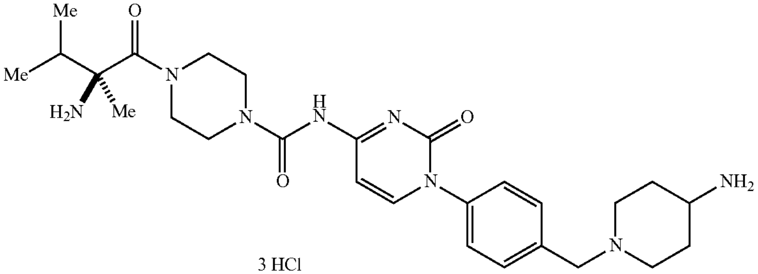 [SMILES: CC(C)[C@](C)(N)C(=O)N1CCN(C(=O)Nc2ccn(-c3ccc(CN4CCC(N)CC4)cc3)c(=O)n2)CC1] 3 HCl | 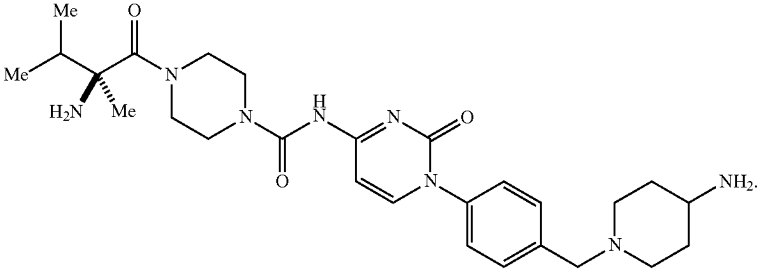 [SMILES: CC(C)[C@](C)(N)C(=O)N1CCN(C(=O)Nc2ccn(-c3ccc(CN4CCC(N)CC4)cc3)c(=O)n2)CC1] |

In another embodiment, the compound of formula I or a pharmaceutically acceptable salt thereof is selected from the compounds listed in any one of Table 10 and Table 11.

In another embodiment, the compound of formula II or III or a pharmaceutically acceptable salt thereof is selected from the compounds listed in Table 10.

In another aspect, the disclosure provides a compound of formula IV:

IV

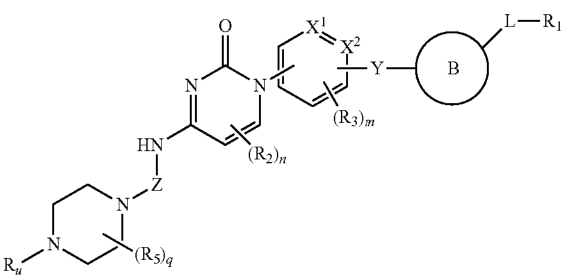

or a pharmaceutically acceptable salt thereof, wherein the variables have the definitions as defined herein and Ru is H or an amino protecting group.

In another embodiment, the compound of formula IV is selected from the compounds as depicted in Table 12 below.

TABLE 12

| Compounds of Formula IV |
| --- |
| Structure |
| 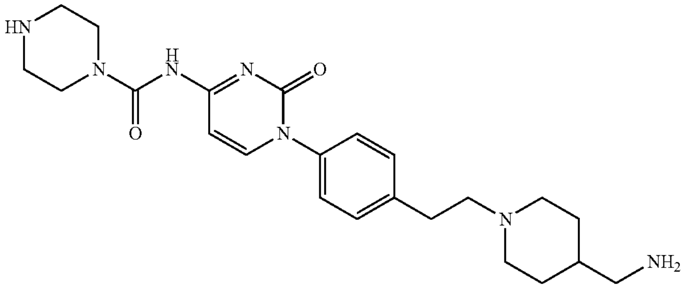 [SMILES: NCC1CCN(CCc2ccc(-n3ccc(NC(=O)N4CCNCC4)nc3=O)cc2)CC1] |
| 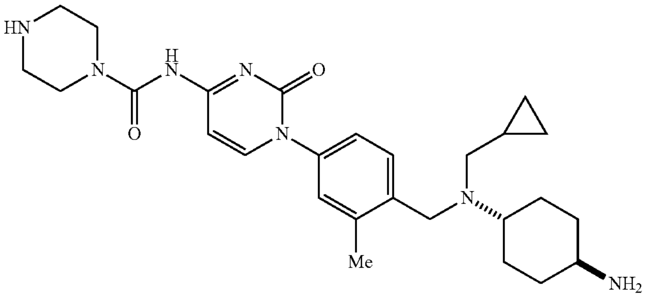 [SMILES: Cc1cc(-n2ccc(NC(=O)N3CCNCC3)nc2=O)ccc1CN(CC1CC1)[C@H]1CC[C@H](N)CC1] |
| 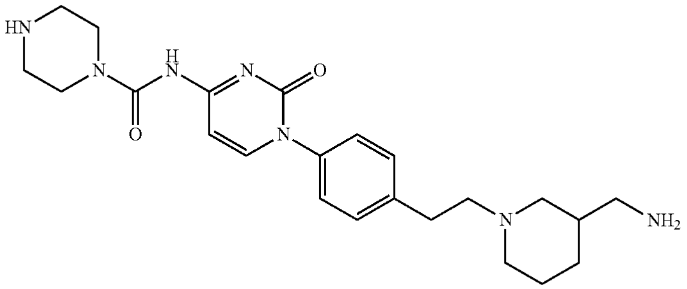 [SMILES: NCC1CCCN(CCc2ccc(-n3ccc(NC(=O)N4CCNCC4)nc3=O)cc2)C1] |

TABLE 12-continued
| Compounds of Formula IV |
|---|
| Structure |
| 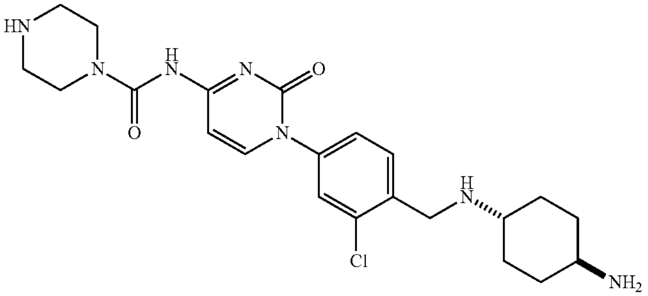 [SMILES: N[C@H]1CC[C@H](NCc2ccc(-n3ccc(NC(=O)N4CCNCC4)nc3=O)cc2Cl)CC1] |
| 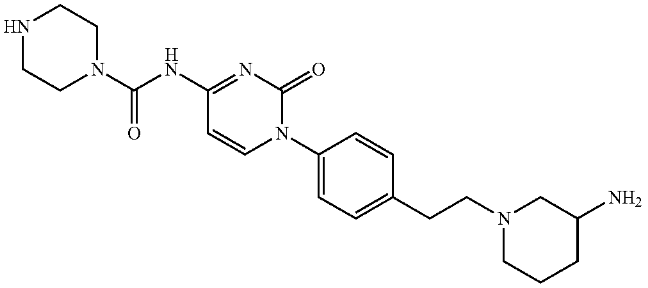 [SMILES: NC1CCCN(CCc2ccc(-n3ccc(NC(=O)N4CCNCC4)nc3=O)cc2)C1] |
| 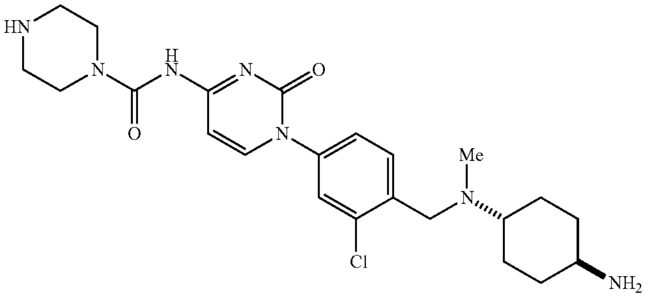 |
| 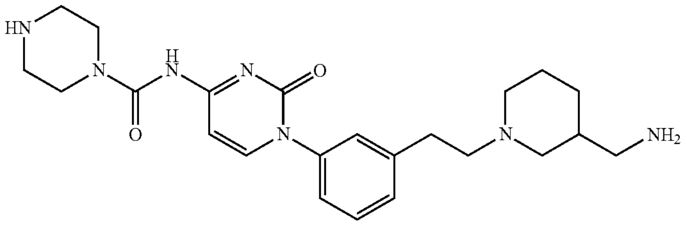 [SMILES: NCC1CCCN(CCc2cccc(-n3ccc(NC(=O)N4CCNCC4)nc3=O)c2)C1] |
| 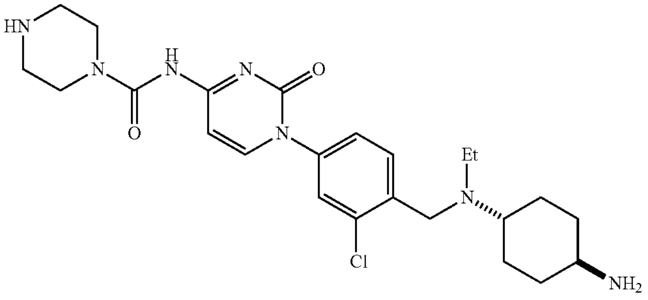 [SMILES: CCN(Cc1ccc(-n2ccc(NC(=O)N3CCNCC3)nc2=O)cc1Cl)[C@H]1CC[C@H](N)CC1] |

TABLE 12-continued
| Compounds of Formula IV |
|---|
| Structure |
| 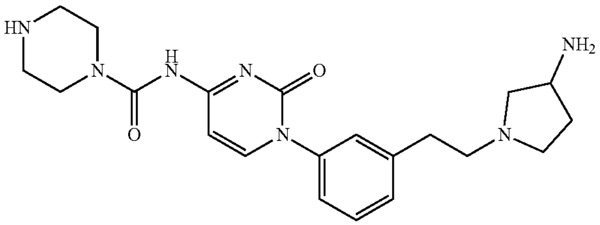 [SMILES: NC1CCN(CCc2cccc(-n3ccc(NC(=O)N4CCNCC4)nc3=O)c2)C1] |
| 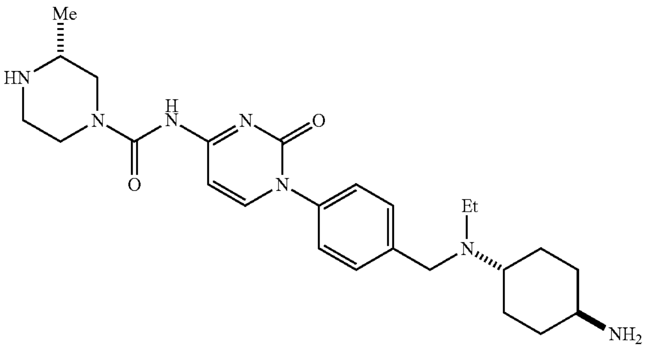 [SMILES: CCN(Cc1ccc(-n2ccc(NC(=O)N3CCN[C@H](C)C3)nc2=O)cc1)[C@H]1CC[C@H](N)CC1] |
| 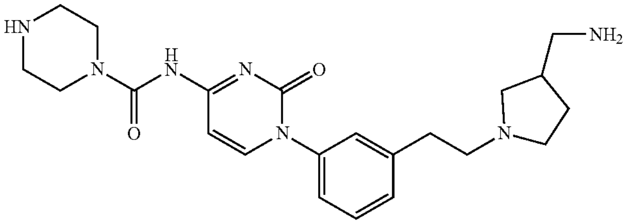 [SMILES: NCC1CCN(CCc2cccc(-n3ccc(NC(=O)N4CCNCC4)nc3=O)c2)C1] |
| 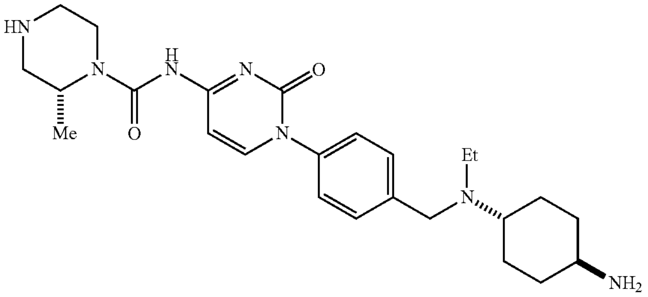 |
| 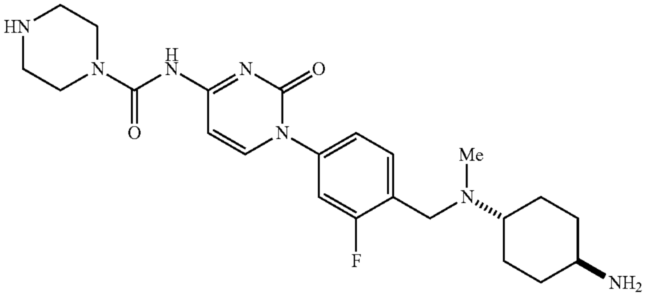 |

TABLE 12-continued
| Compounds of Formula IV |
| --- |
| Structure |
| 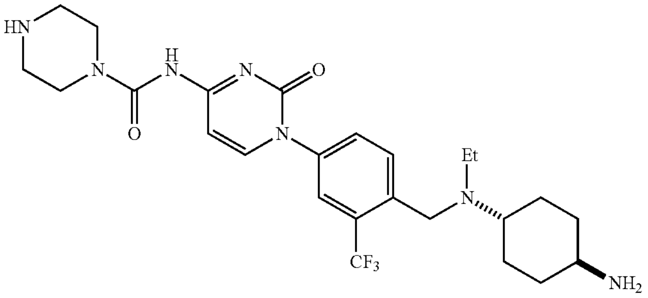 |
| 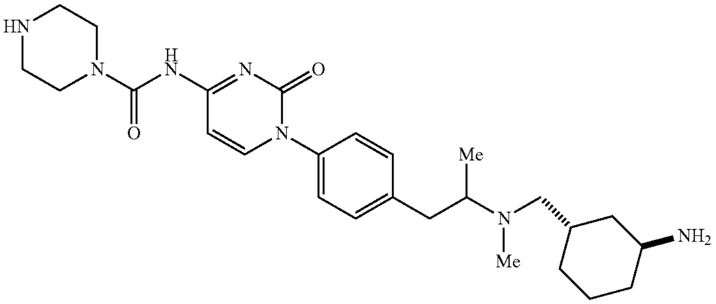 [SMILES: CC(Cc1ccc(-n2ccc(NC(=O)N3CCNCC3)nc2=O)cc1)N(C)C[C@H]1CCC[C@H](N)C1] |
| 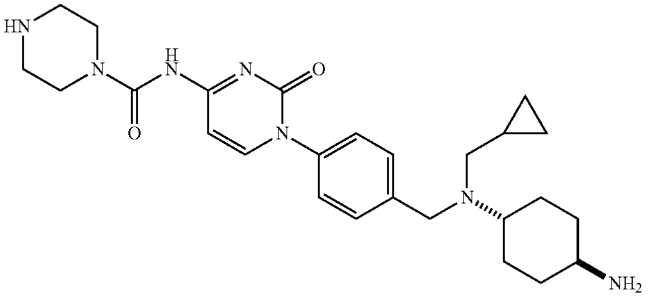 [SMILES: N[C@H]1CC[C@H](N(Cc2ccc(-n3ccc(NC(=O)N4CCNCC4)nc3=O)cc2)CC2CC2)CC1] |
| 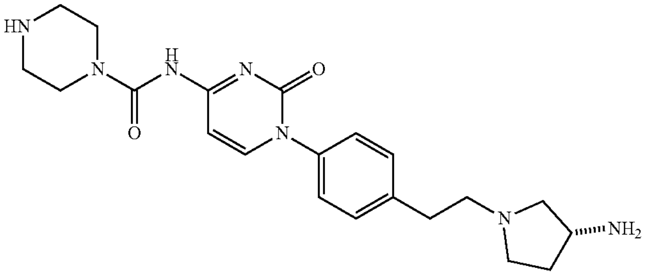 [SMILES: N[C@@H]1CCN(CCc2ccc(-n3ccc(NC(=O)N4CCNCC4)nc3=O)cc2)C1] |
| 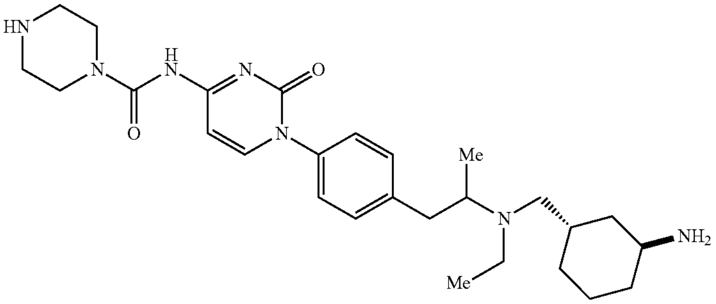 [SMILES: CCN(C[C@H]1CCC[C@H](N)C1)C(C)Cc1ccc(-n2ccc(NC(=O)N3CCNCC3)nc2=O)cc1] |

TABLE 12-continued
| Compounds of Formula IV |
| --- |
| Structure |
| 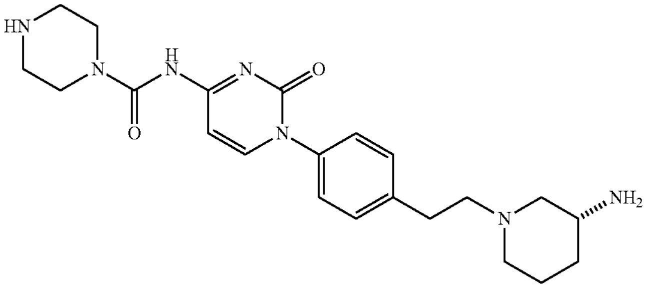 |
| 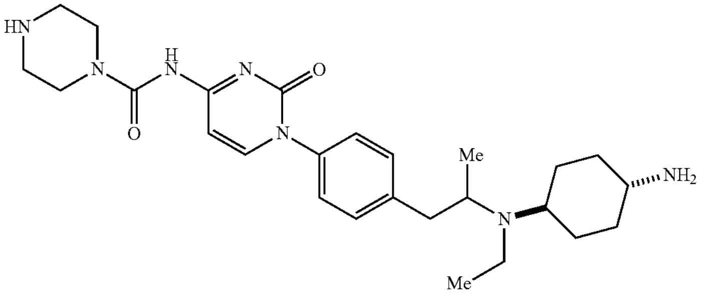 [SMILES: CCN(C(C)Cc1ccc(-n2ccc(NC(=O)N3CCNCC3)nc2=O)cc1)[C@H]1CC[C@H](N)CC1] |
| 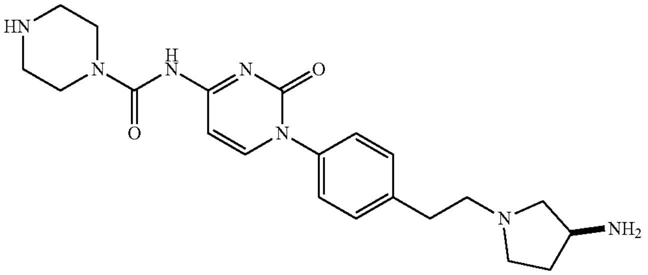 [SMILES: N[C@H]1CCN(CCc2ccc(-n3ccc(NC(=O)N4CCNCC4)nc3=O)cc2)C1] |
| 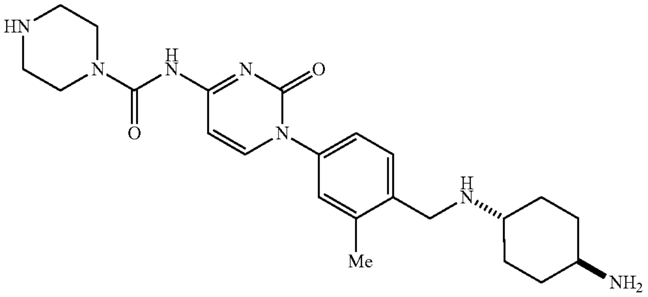 |
| 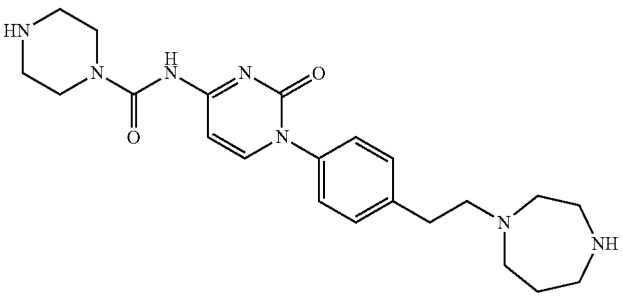 [SMILES: O=C(Nc1ccn(-c2ccc(CCN3CCCNCC3)cc2)c(=O)n1)N1CCNCC1] |

TABLE 12-continued
| Compounds of Formula IV |
| --- |
| Structure |
| 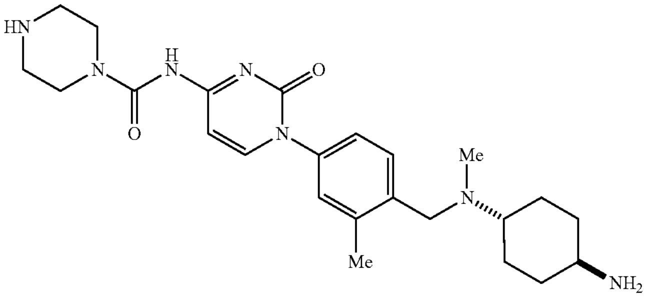 |
| 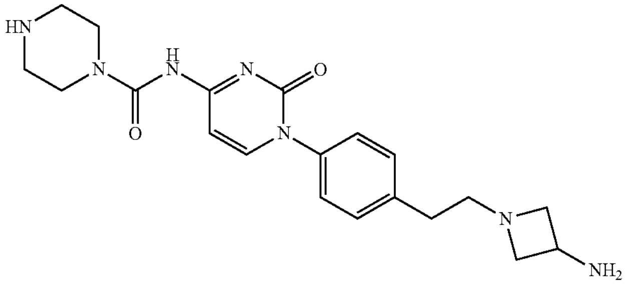 [SMILES: NC1CN(CCc2ccc(-n3ccc(NC(=O)N4CCNCC4)nc3=O)cc2)C1] |
| 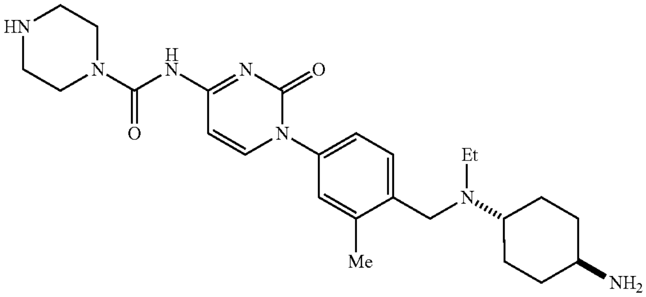 |
| 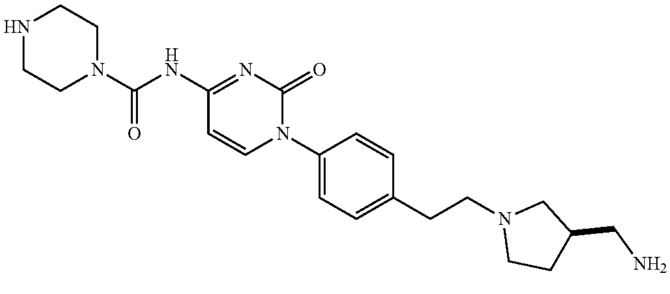 [SMILES: NC[C@H]1CCN(CCc2ccc(-n3ccc(NC(=O)N4CCNCC4)nc3=O)cc2)C1] |
| 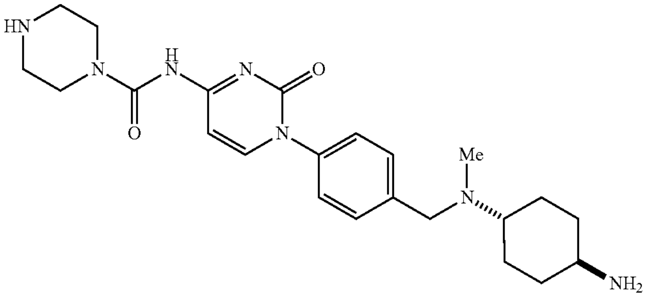 |

TABLE 12-continued
| Compounds of Formula IV |
| --- |
| Structure |
| 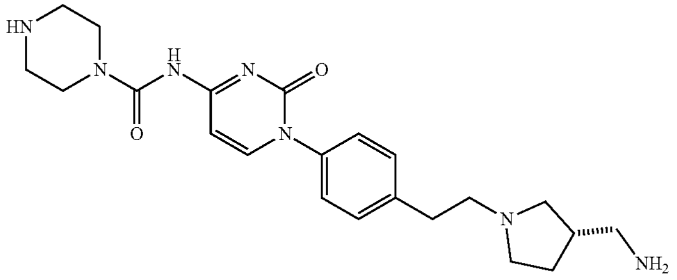 [SMILES: NC[C@@H]1CCN(CCc2ccc(-n3ccc(NC(=O)N4CCNCC4)nc3=O)cc2)C1] |
| 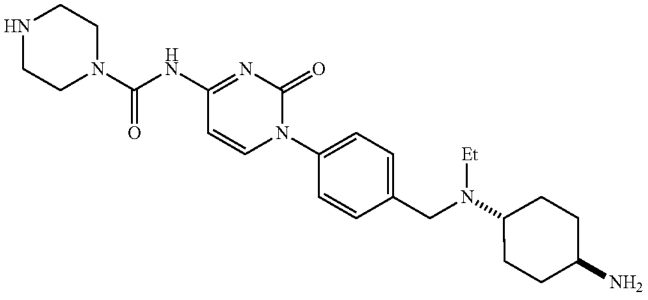 |
| 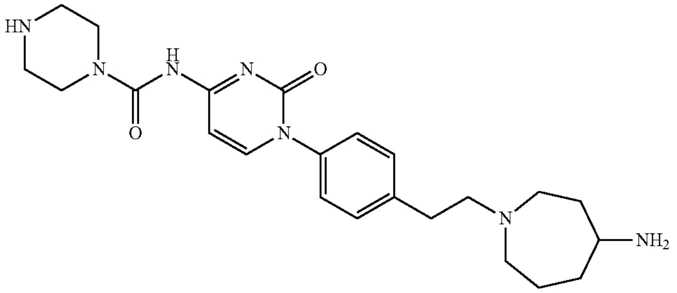 [SMILES: NC1CCCN(CCc2ccc(-n3ccc(NC(=O)N4CCNCC4)nc3=O)cc2)CC1] |
| 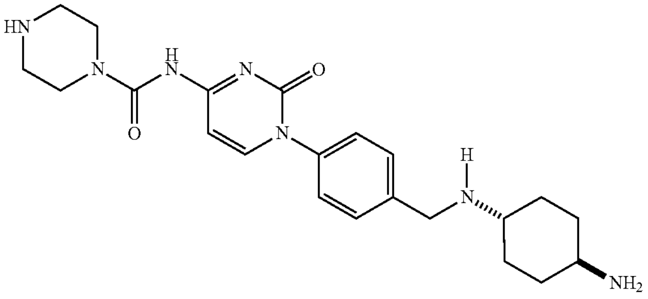 |
| 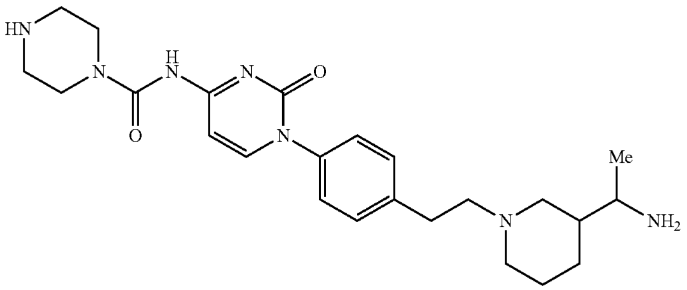 [SMILES: CC(N)C1CCCN(CCc2ccc(-n3ccc(NC(=O)N4CCNCC4)nc3=O)cc2)C1] |

TABLE 12-continued
| Compounds of Formula IV |
| --- |
| Structure |
| 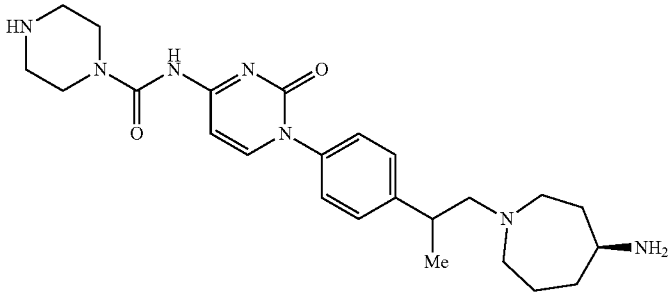 [SMILES: CC(CN1CCC[C@H](N)CC1)c1ccc(-n2ccc(NC(=O)N3CCNCC3)nc2=O)cc1] |
| 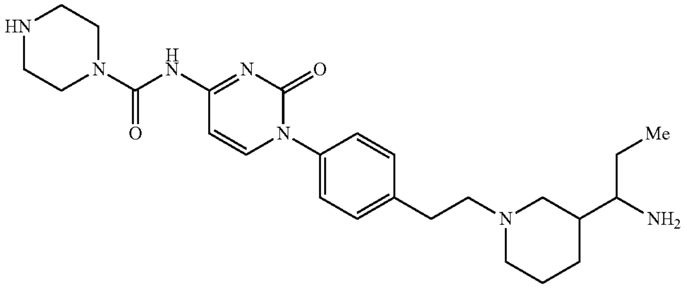 [SMILES: CCC(N)C1CCCN(CCc2ccc(-n3ccc(NC(=O)N4CCNCC4)nc3=O)cc2)C1] |
| 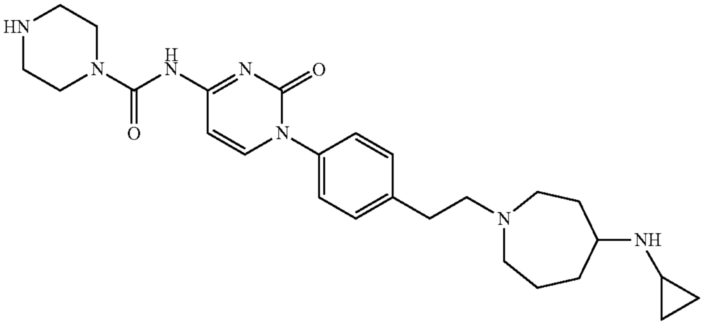 [SMILES: O=C(Nc1ccn(-c2ccc(CCN3CCCC(NC4CC4)CC3)cc2)c(=O)n1)N1CCNCC1] |
| 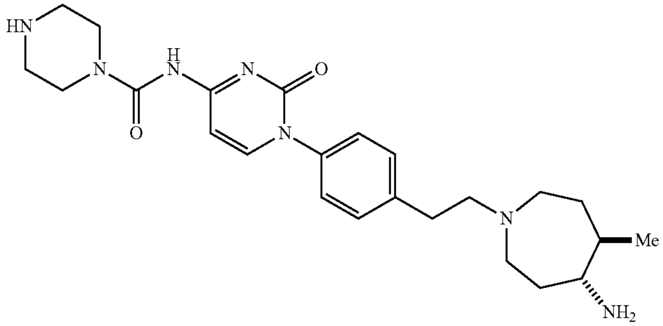 [SMILES: C[C@@H]1CCN(CCc2ccc(-n3ccc(NC(=O)N4CCNCC4)nc3=O)cc2)CC[C@H]1N] |
| 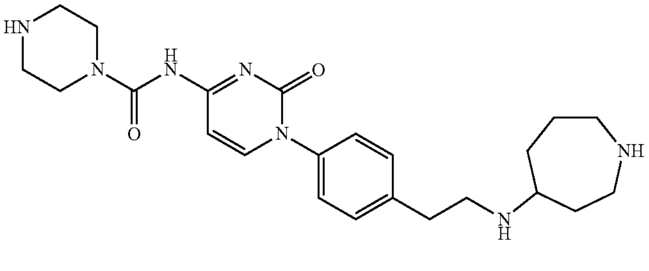 [SMILES: O=C(Nc1ccn(-c2ccc(CCNC3CCCNCC3)cc2)c(=O)n1)N1CCNCC1] |

TABLE 12-continued
| Compounds of Formula IV |
| --- |
| Structure |
| 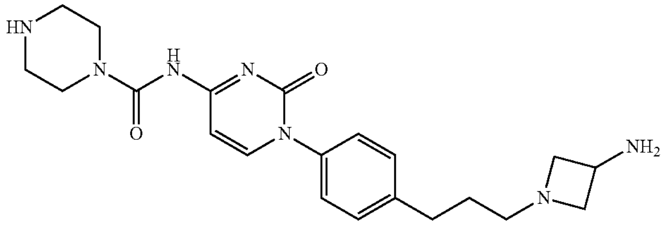 [SMILES: NC1CN(CCCc2ccc(-n3ccc(NC(=O)N4CCNCC4)nc3=O)cc2)C1] |
| 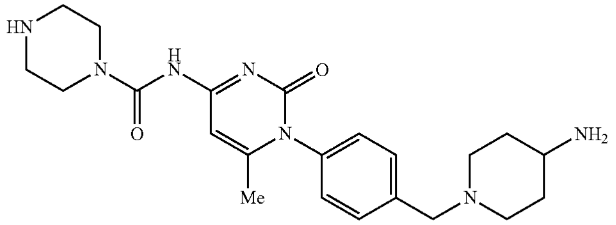 [SMILES: Cc1cc(NC(=O)N2CCNCC2)nc(=O)n1-c1ccc(CN2CCC(N)CC2)cc1] |
| 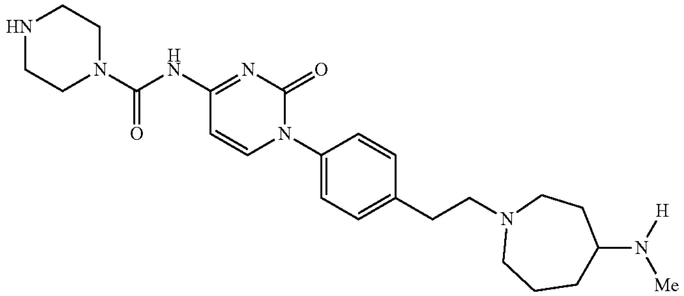 [SMILES: CNC1CCCN(CCc2ccc(-n3ccc(NC(=O)N4CCNCC4)nc3=O)cc2)CC1] |
| 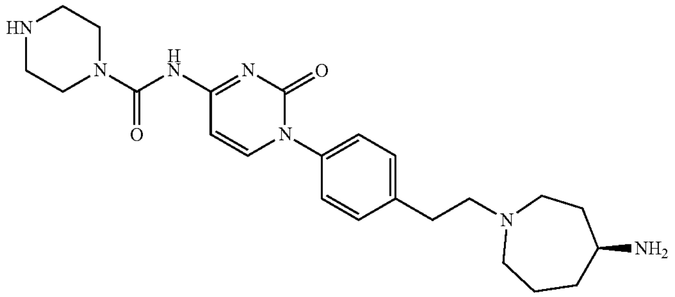 [SMILES: N[C@H]1CCCN(CCc2ccc(-n3ccc(NC(=O)N4CCNCC4)nc3=O)cc2)CC1] |
| 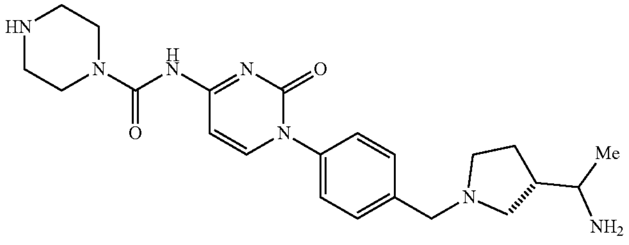 [SMILES: CC(N)[C@H]1CCN(Cc2ccc(-n3ccc(NC(=O)N4CCNCC4)nc3=O)cc2)C1] |

TABLE 12-continued
| Compounds of Formula IV |
|---|
| Structure |
| 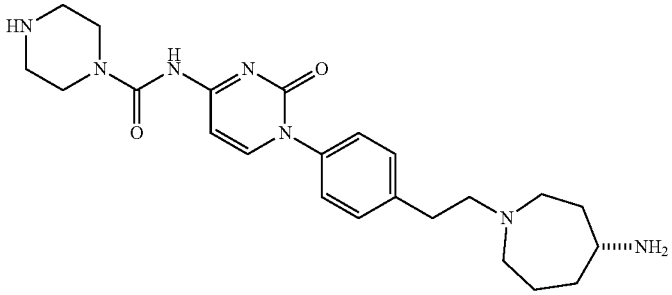 [SMILES: N[C@@H]1CCCN(CCc2ccc(-n3ccc(NC(=O)N4CCNCC4)nc3=O)cc2)CC1] |
| 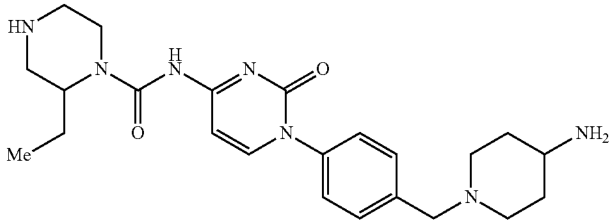 [SMILES: CCC1CNCCN1C(=O)Nc1ccn(-c2ccc(CN3CCC(N)CC3)cc2)c(=O)n1] |
| 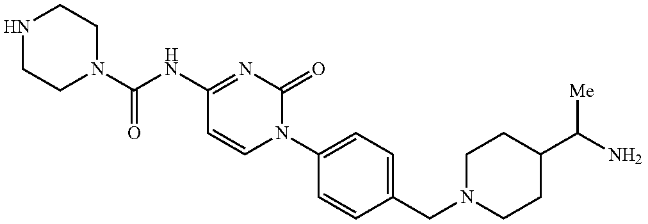 [SMILES: CC(N)C1CCN(Cc2ccc(-n3ccc(NC(=O)N4CCNCC4)nc3=O)cc2)CC1] |
| 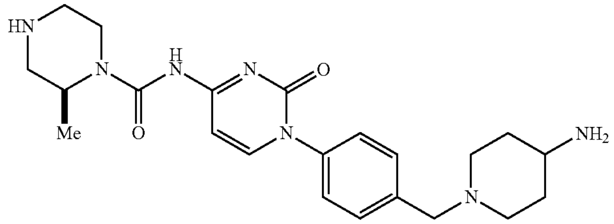 [SMILES: C[C@H]1CNCCN1C(=O)Nc1ccn(-c2ccc(CN3CCC(N)CC3)cc2)c(=O)n1] |
| 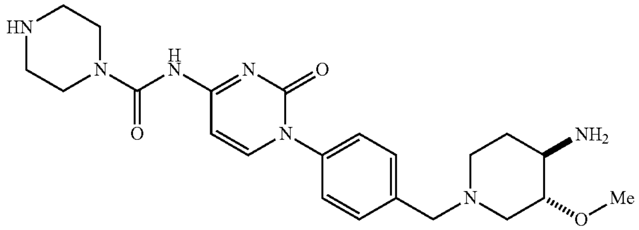 [SMILES: CO[C@@H]1CN(Cc2ccc(-n3ccc(NC(=O)N4CCNCC4)nc3=O)cc2)CC[C@H]1N] |
| 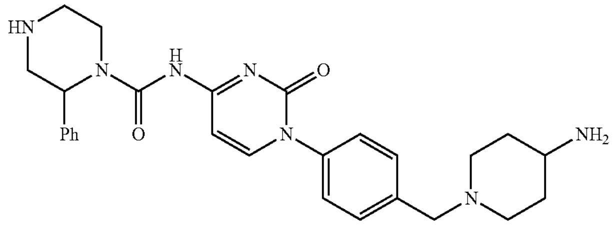 [SMILES: NC1CCN(Cc2ccc(-n3ccc(NC(=O)N4CCNCC4c4ccccc4)nc3=O)cc2)CC1] |

TABLE 12-continued
| Compounds of Formula IV |
|---|
| Structure |
| 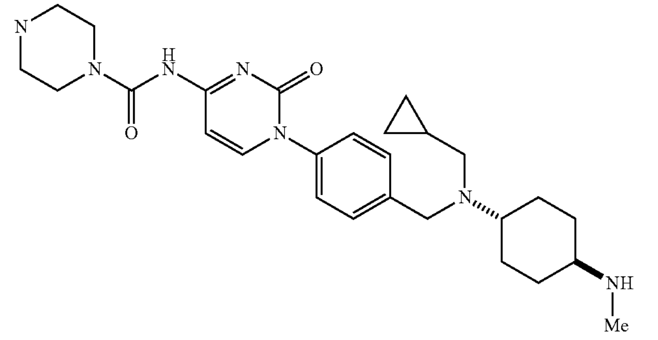 |
| 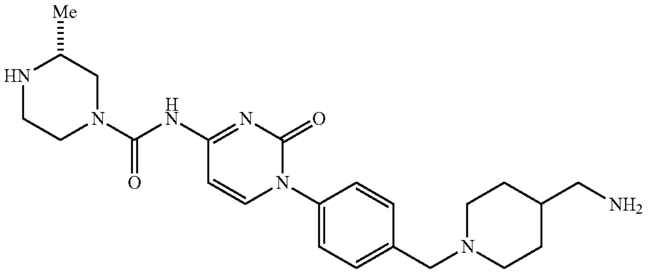 [SMILES: C[C@@H]1CN(C(=O)Nc2ccn(-c3ccc(CN4CCC(CN)CC4)cc3)c(=O)n2)CCN1] |
| 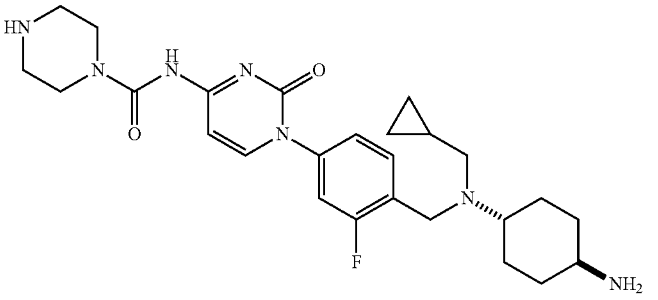 [SMILES: N[C@H]1CC[C@H](N(Cc2ccc(-n3ccc(NC(=O)N4CCNCC4)nc3=O)cc2F)CC2CC2)CC1] |
| 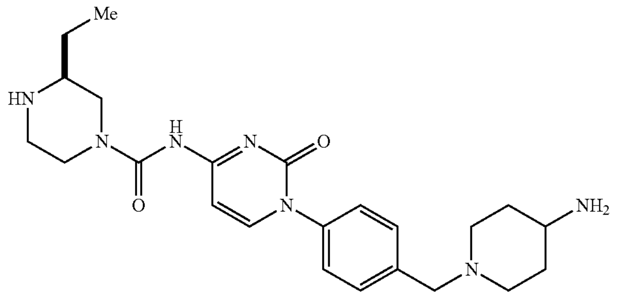 [SMILES: CC[C@H]1CN(C(=O)Nc2ccn(-c3ccc(CN4CCC(N)CC4)cc3)c(=O)n2)CCN1] |
| 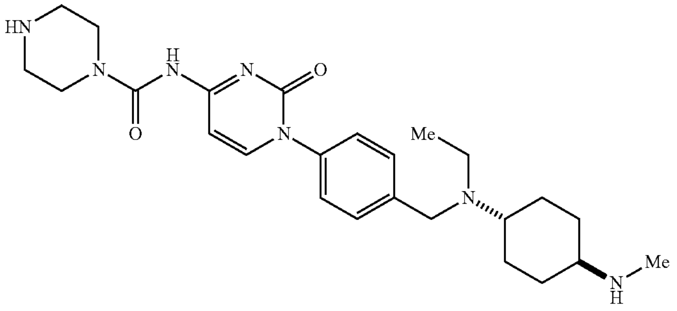 [SMILES: CCN(Cc1ccc(-n2ccc(NC(=O)N3CCNCC3)nc2=O)cc1)[C@H]1CC[C@H](NC)CC1] |

TABLE 12-continued
| Compounds of Formula IV |
| --- |
| Structure |
| 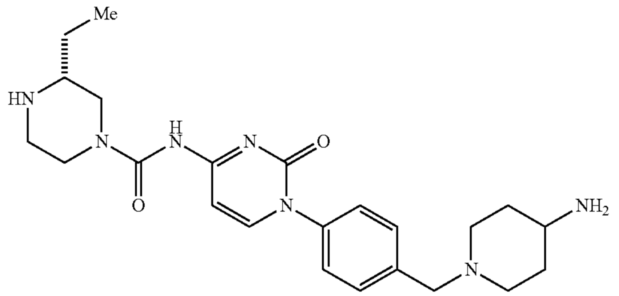 [SMILES: CC[C@@H]1CN(C(=O)Nc2ccn(-c3ccc(CN4CCC(N)CC4)cc3)c(=O)n2)CCN1] |
| 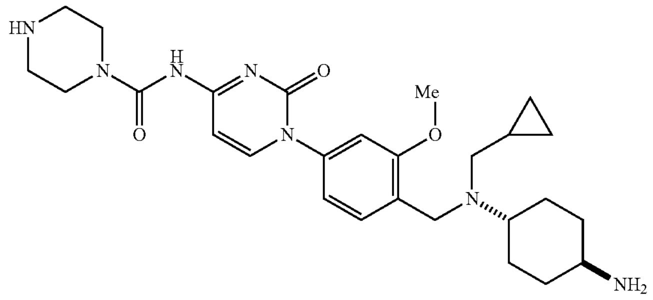 [SMILES: COc1cc(-n2ccc(NC(=O)N3CCNCC3)nc2=O)ccc1CN(CC1CC1)[C@H]1CC[C@H](N)CC1] |
| 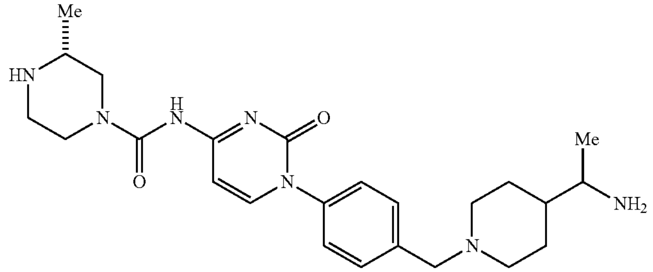 [SMILES: CC(N)C1CCN(Cc2ccc(-n3ccc(NC(=O)N4CCN[C@H](C)C4)nc3=O)cc2)CC1] |
| 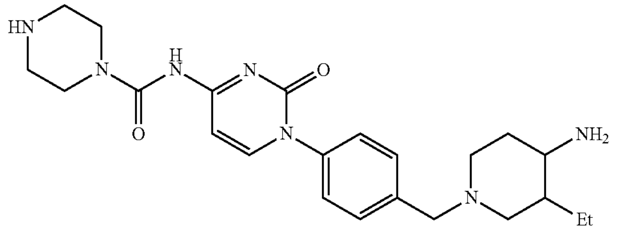 [SMILES: CCC1CN(Cc2ccc(-n3ccc(NC(=O)N4CCNCC4)nc3=O)cc2)CCC1N] |
| 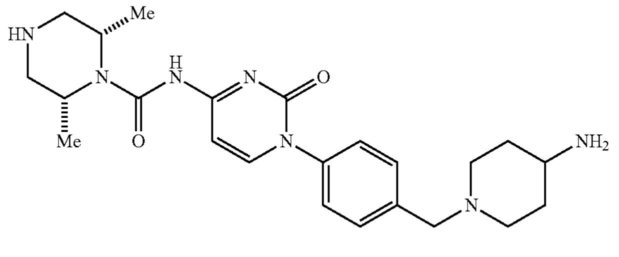 [SMILES: C[C@@H]1CNC[C@H](C)N1C(=O)Nc1ccn(-c2ccc(CN3CCC(N)CC3)cc2)c(=O)n1] |

TABLE 12-continued
| Compounds of Formula IV |
| --- |
| Structure |
| 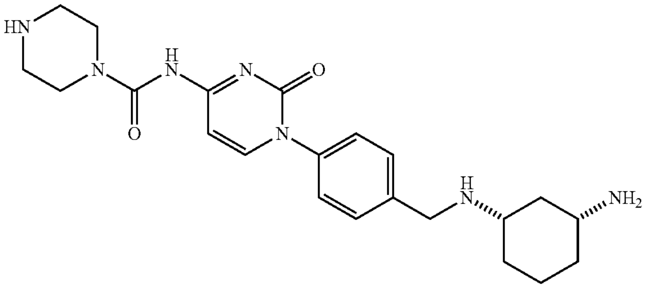 [SMILES: N[C@@H]1CCC[C@H](NCc2ccc(-n3ccc(NC(=O)N4CCNCC4)nc3=O)cc2)C1] |
| 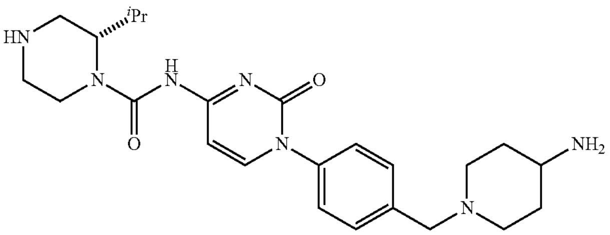 [SMILES: CC(C)[C@H]1CNCCN1C(=O)Nc1ccn(-c2ccc(CN3CCC(N)CC3)cc2)c(=O)n1] |
| 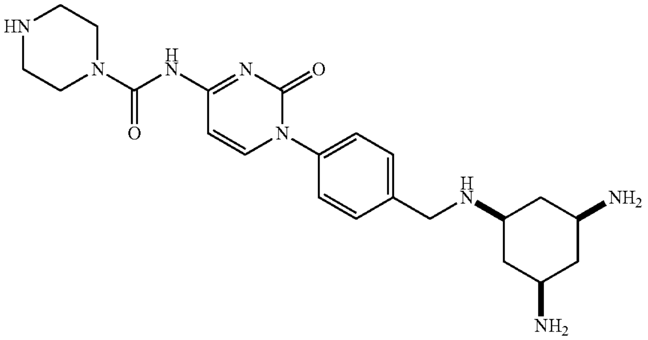 |
| 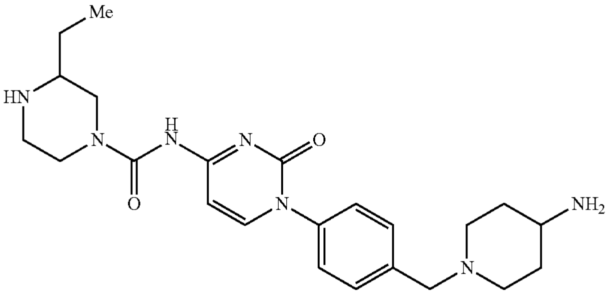 |
| 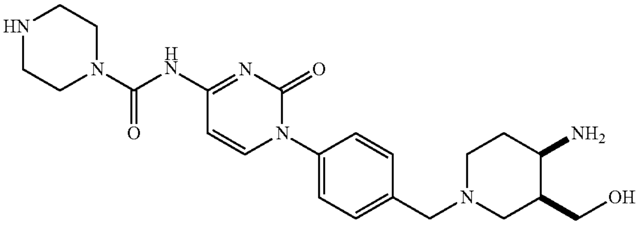 [SMILES: N[C@@H]1CCN(Cc2ccc(-n3ccc(NC(=O)N4CCNCC4)nc3=O)cc2)C[C@@H]1CO] |

TABLE 12-continued
| Compounds of Formula IV |
| --- |
| Structure |
| 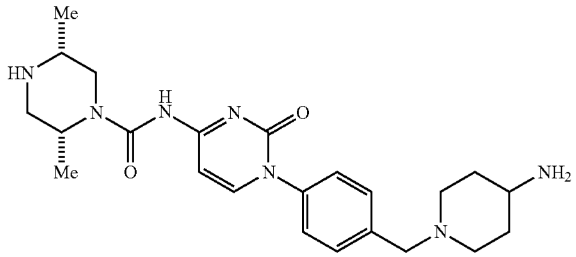 [SMILES: C[C@@H]1CN(C(=O)Nc2ccn(-c3ccc(CN4CCC(N)CC4)cc3)c(=O)n2)[C@H](C)CN1] |
| 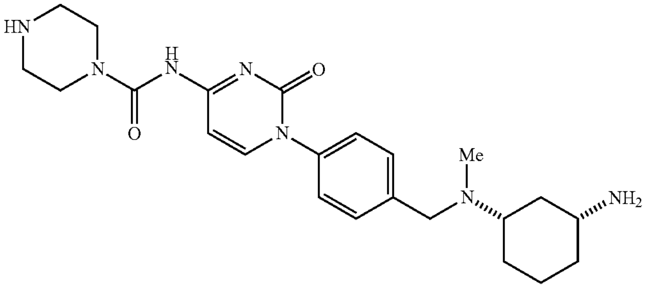 [SMILES: CN(Cc1ccc(-n2ccc(NC(=O)N3CCNCC3)nc2=O)cc1)[C@H]1CCC[C@@H](N)C1] |
| 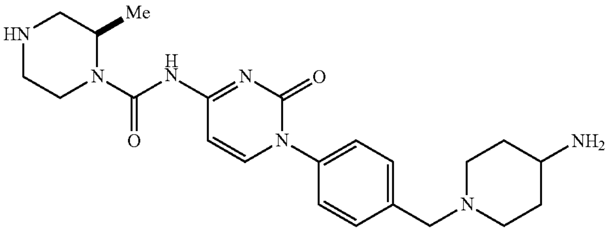 [SMILES: C[C@@H]1CNCCN1C(=O)Nc1ccn(-c2ccc(CN3CCC(N)CC3)cc2)c(=O)n1] |
| 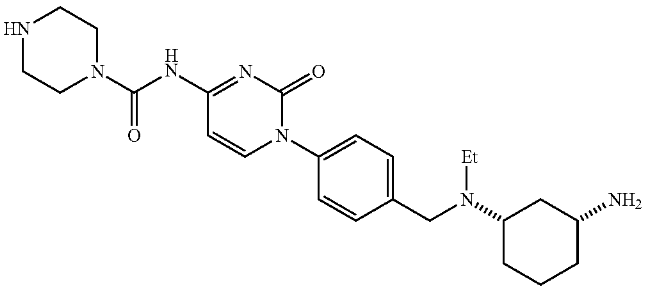 [SMILES: CCN(Cc1ccc(-n2ccc(NC(=O)N3CCNCC3)nc2=O)cc1)[C@H]1CCC[C@@H](N)C1] |
| 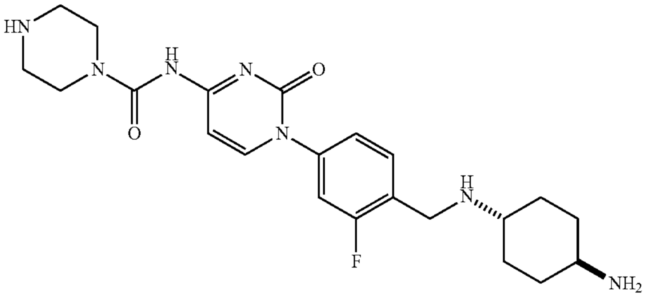 [SMILES: N[C@H]1CC[C@H](NCc2ccc(-n3ccc(NC(=O)N4CCNCC4)nc3=O)cc2F)CC1] |

TABLE 12-continued
| Compounds of Formula IV |
|---|
| Structure |
| 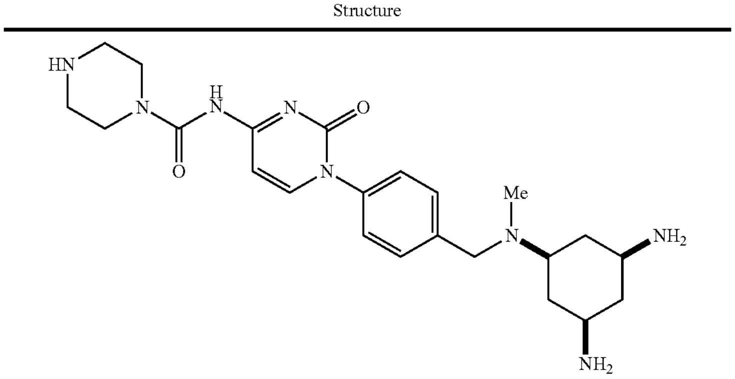 |
| 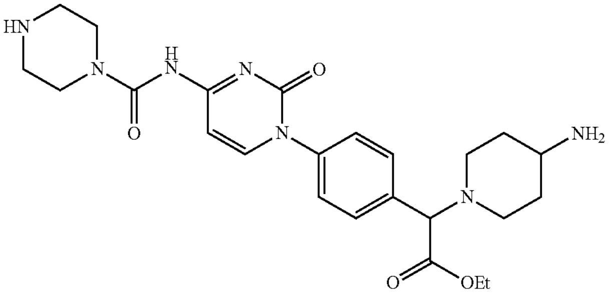 [SMILES: CCOC(=O)C(c1ccc(-n2ccc(NC(=O)N3CCNCC3)nc2=O)cc1)N1CCC(N)CC1] |
| 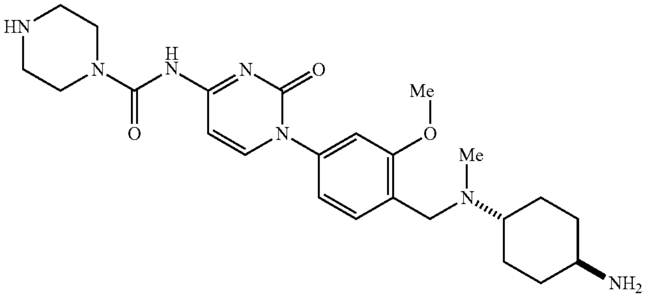 [SMILES: COc1cc(-n2ccc(NC(=O)N3CCNCC3)nc2=O)ccc1CN(C)[C@H]1CC[C@H](N)CC1] |
| 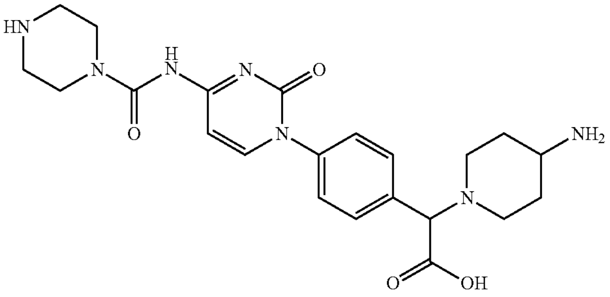 [SMILES: NC1CCN(C(C(=O)O)c2ccc(-n3ccc(NC(=O)N4CCNCC4)nc3=O)cc2)CC1] |
| 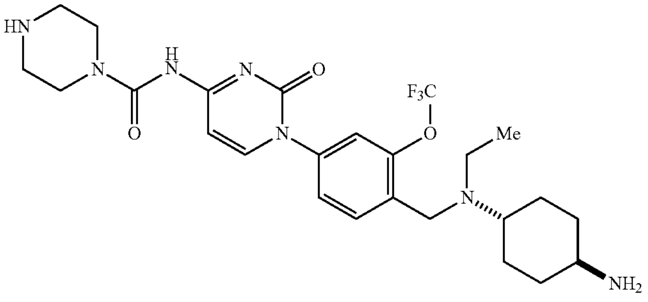 [SMILES: CCN(Cc1ccc(-n2ccc(NC(=O)N3CCNCC3)nc2=O)cc1OC(F)(F)F)[C@H]1CC[C@H](N)CC1] |

TABLE 12-continued
| Compounds of Formula IV |
| --- |
| Structure |
| 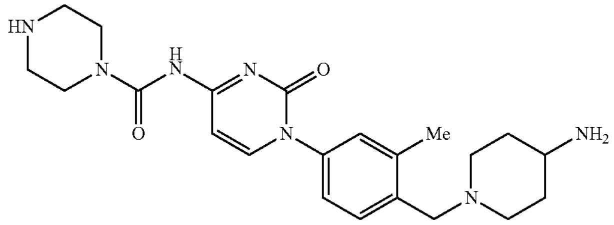 [SMILES: Cc1cc(-n2ccc(NC(=O)N3CCNCC3)nc2=O)ccc1CN1CCC(N)CC1] |
| 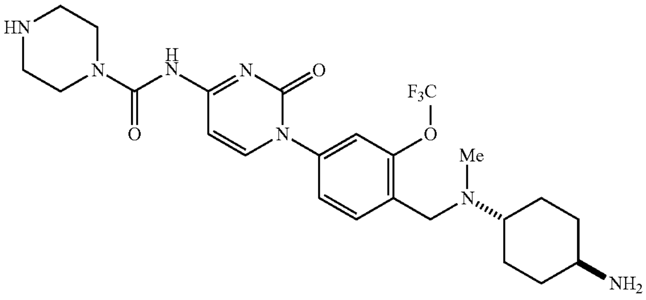 [SMILES: CN(Cc1ccc(-n2ccc(NC(=O)N3CCNCC3)nc2=O)cc1OC(F)(F)F)[C@H]1CC[C@H](N)CC1] |
| 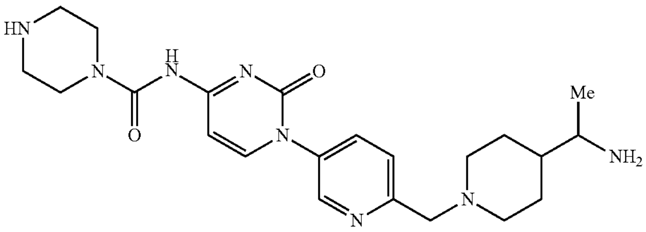 [SMILES: CC(N)C1CCN(Cc2ccc(-n3ccc(NC(=O)N4CCNCC4)nc3=O)cn2)CC1] |
| 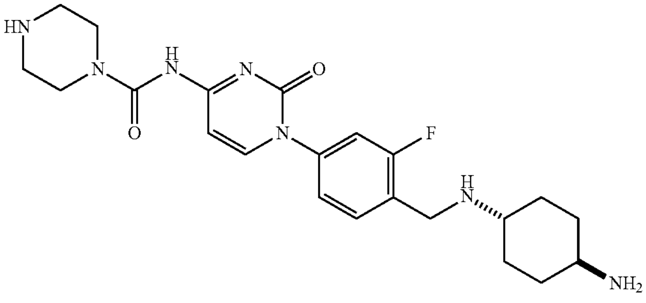 [SMILES: N[C@H]1CC[C@H](NCc2ccc(-n3ccc(NC(=O)N4CCNCC4)nc3=O)cc2F)CC1] |
| 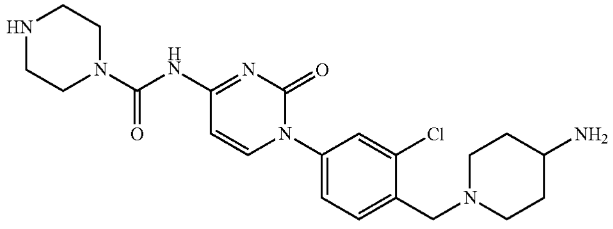 [SMILES: NC1CCN(Cc2ccc(-n3ccc(NC(=O)N4CCNCC4)nc3=O)cc2Cl)CC1] |

TABLE 12-continued
| Compounds of Formula IV |
|---|
| Structure |
| 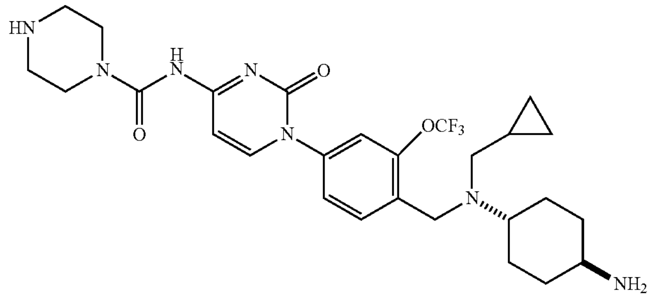 [SMILES: N[C@H]1CC[C@H](N(Cc2ccc(-n3ccc(NC(=O)N4CCNCC4)nc3=O)cc2OC(F)(F)F)CC2CC2)CC1] |
| 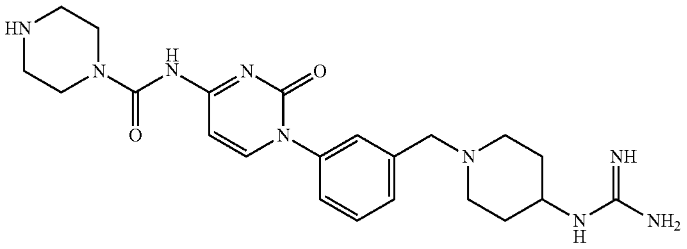 [SMILES: N=C(N)NC1CCN(Cc2cccc(-n3ccc(NC(=O)N4CCNCC4)nc3=O)c2)CC1] |
| 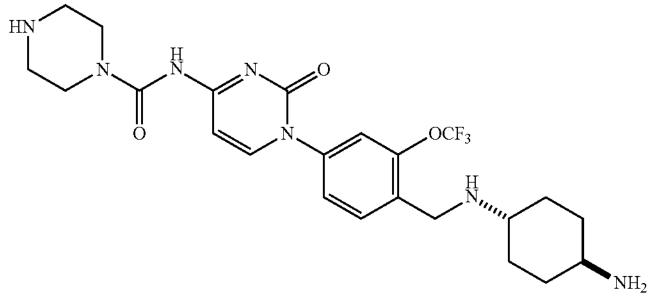 [SMILES: N[C@H]1CC[C@H](NCc2ccc(-n3ccc(NC(=O)N4CCNCC4)nc3=O)cc2OC(F)(F)F)CC1] |
| 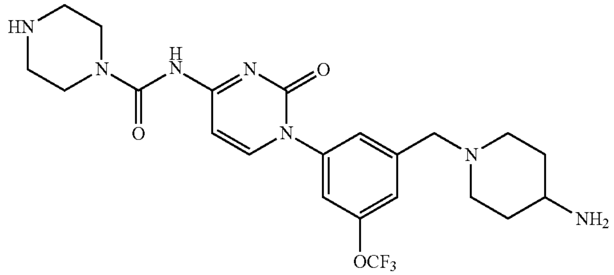 [SMILES: NC1CCN(Cc2cc(OC(F)(F)F)cc(-n3ccc(NC(=O)N4CCNCC4)nc3=O)c2)CC1] |
| 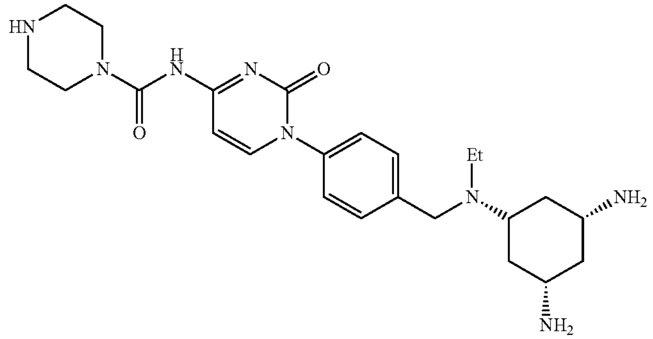 |

TABLE 12-continued
| Compounds of Formula IV |
| --- |
| Structure |
| 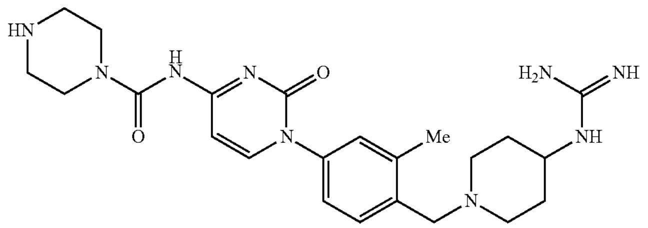 [SMILES: Cc1cc(-n2ccc(NC(=O)N3CCNCC3)nc2=O)ccc1CN1CCC(NC(=N)N)CC1] |
| 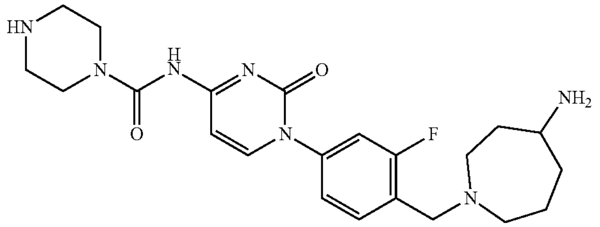 [SMILES: NC1CCCN(Cc2ccc(-n3ccc(NC(=O)N4CCNCC4)nc3=O)cc2F)CC1] |
| 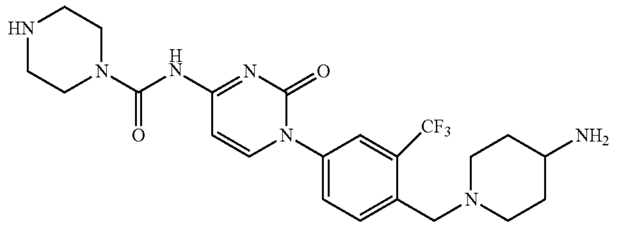 [SMILES: NC1CCN(Cc2ccc(-n3ccc(NC(=O)N4CCNCC4)nc3=O)cc2C(F)(F)F)CC1] |
| 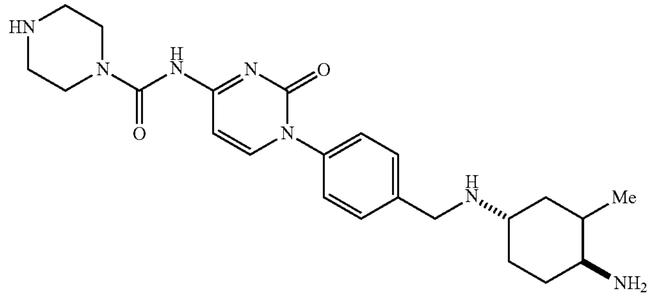 |
| 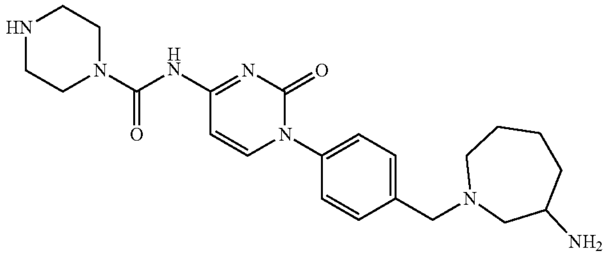 [SMILES: NC1CCCCN(Cc2ccc(-n3ccc(NC(=O)N4CCNCC4)nc3=O)cc2)C1] |
| 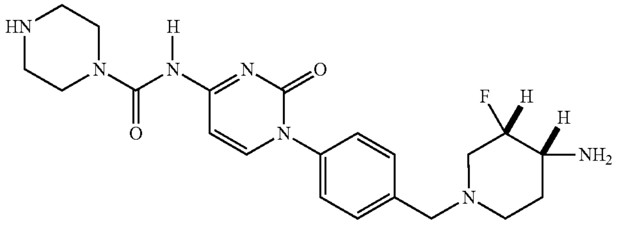 [SMILES: N[C@@H]1CCN(Cc2ccc(-n3ccc(NC(=O)N4CCNCC4)nc3=O)cc2)C[C@@H]1F] |

TABLE 12-continued
| Compounds of Formula IV |
|---|
| Structure |
| 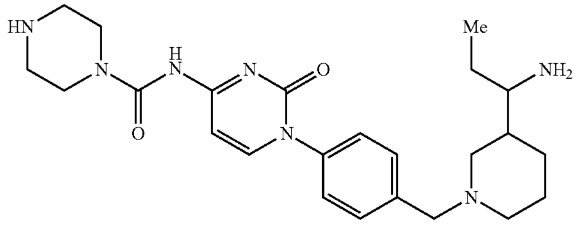 [SMILES: CCC(N)C1CCCN(Cc2ccc(-n3ccc(NC(=O)N4CCNCC4)nc3=O)cc2)C1] |
| 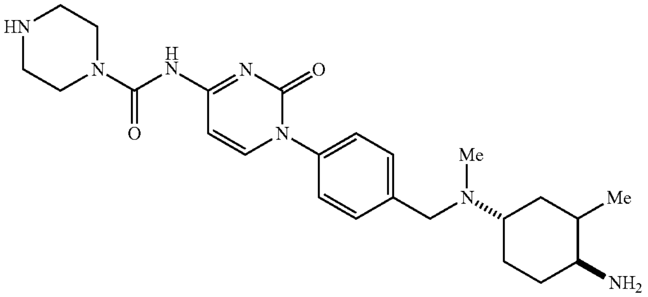 |
| 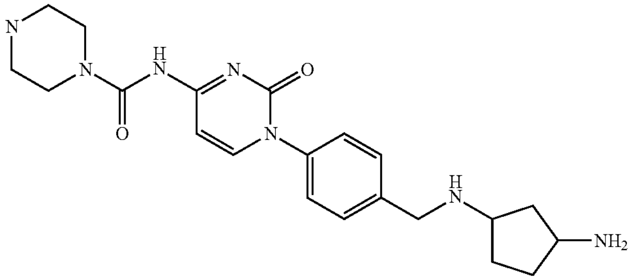 [SMILES: NC1CCC(NCc2ccc(-n3ccc(NC(=O)N4CCNCC4)nc3=O)cc2)C1] |
| 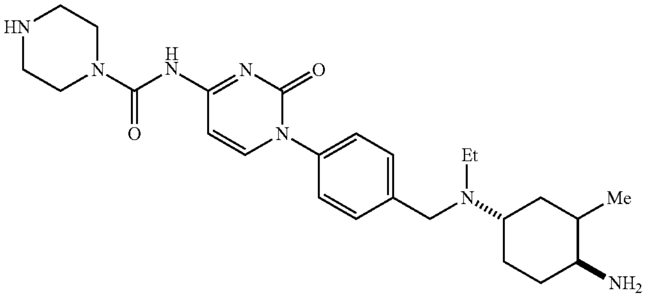 |
| 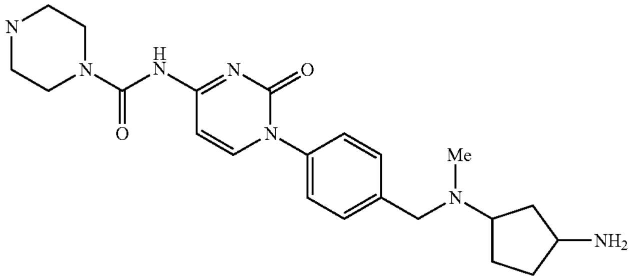 [SMILES: CN(Cc1ccc(-n2ccc(NC(=O)N3CCNCC3)nc2=O)cc1)C1CCC(N)C1] |

TABLE 12-continued
| Compounds of Formula IV |
|---|
| Structure |
| 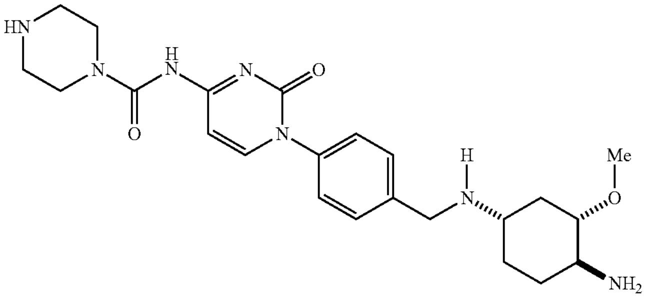 |
| 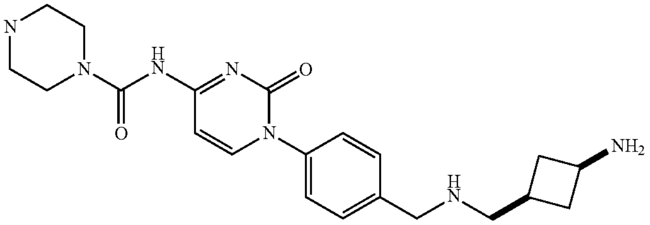 |
| 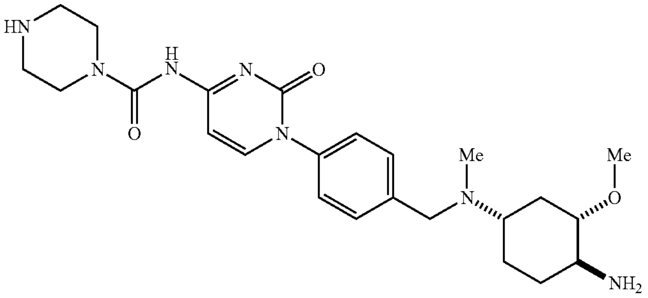 |
| 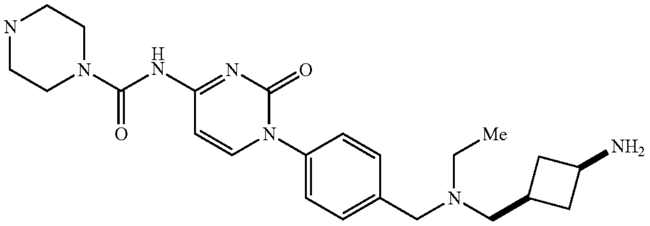 |
| 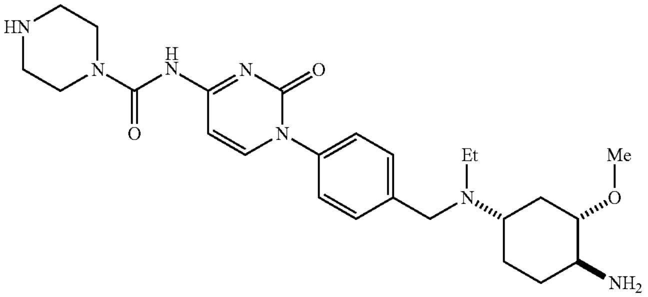 |

TABLE 12-continued
| Compounds of Formula IV |
| --- |
| Structure |
| 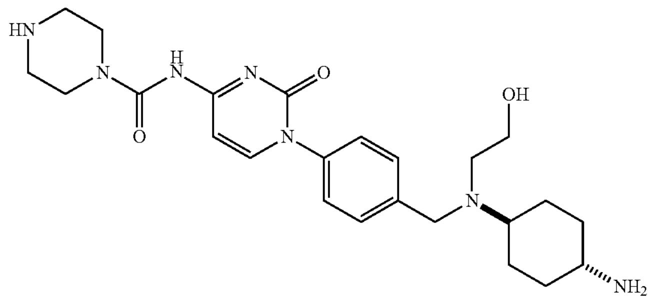 |
| 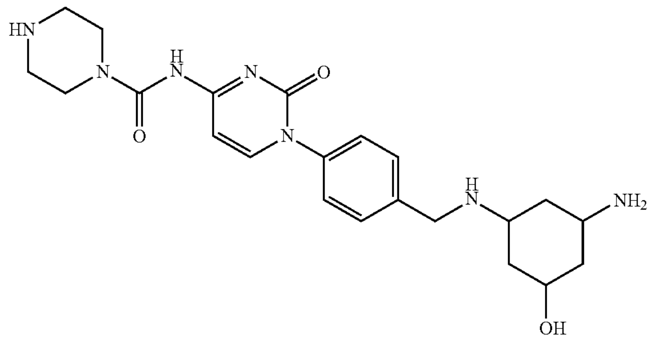 [SMILES: NC1CC(O)CC(NCc2ccc(-n3ccc(NC(=O)N4CCNCC4)nc3=O)cc2)C1] |
| 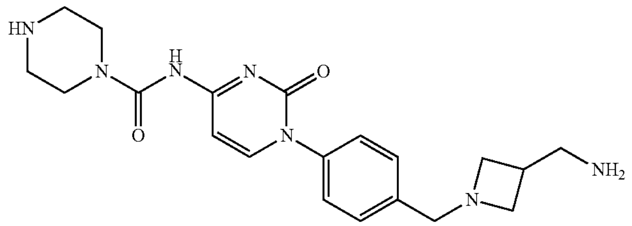 [SMILES: NCC1CN(Cc2ccc(-n3ccc(NC(=O)N4CCNCC4)nc3=O)cc2)C1] |
| 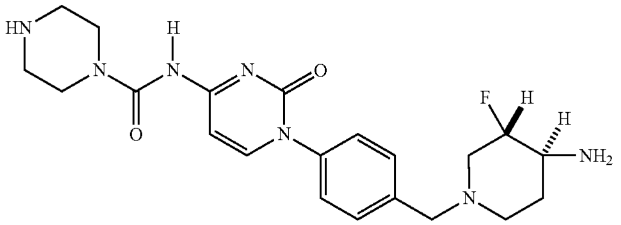 [SMILES: N[C@H]1CCN(Cc2ccc(-n3ccc(NC(=O)N4CCNCC4)nc3=O)cc2)C[C@@H]1F] |
| 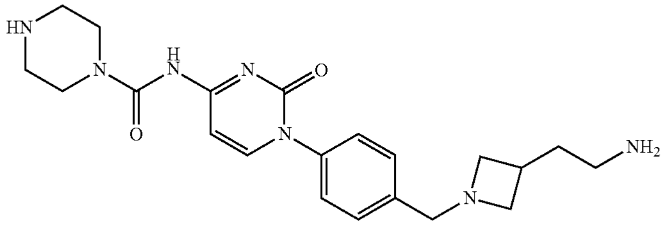 [SMILES: NCCC1CN(Cc2ccc(-n3ccc(NC(=O)N4CCNCC4)nc3=O)cc2)C1] |

TABLE 12-continued
| Compounds of Formula IV |
| --- |
| Structure |
| 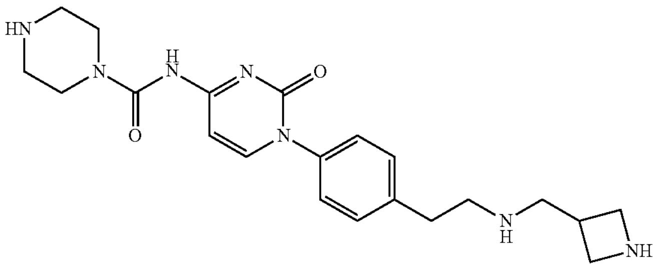 [SMILES: O=C(Nc1ccn(-c2ccc(CCNCC3CNC3)cc2)c(=O)n1)N1CCNCC1] |
| 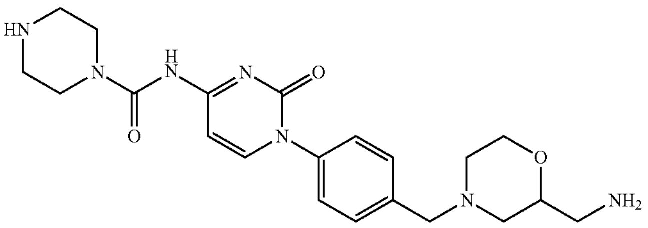 [SMILES: NCC1CN(Cc2ccc(-n3ccc(NC(=O)N4CCNCC4)nc3=O)cc2)CCO1] |
| 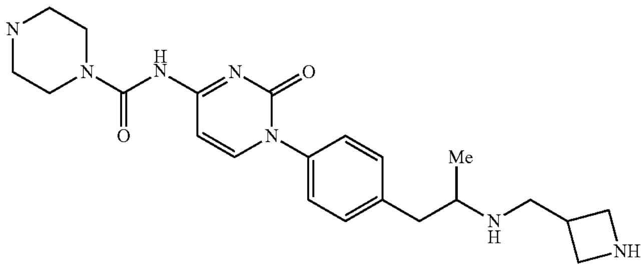 [SMILES: CC(Cc1ccc(-n2ccc(NC(=O)N3CCNCC3)nc2=O)cc1)NCC1CNC1] |
| 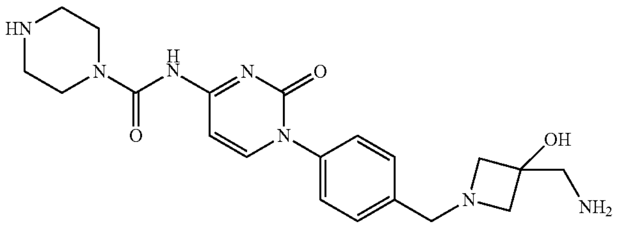 [SMILES: NCC1(O)CN(Cc2ccc(-n3ccc(NC(=O)N4CCNCC4)nc3=O)cc2)C1] |
| 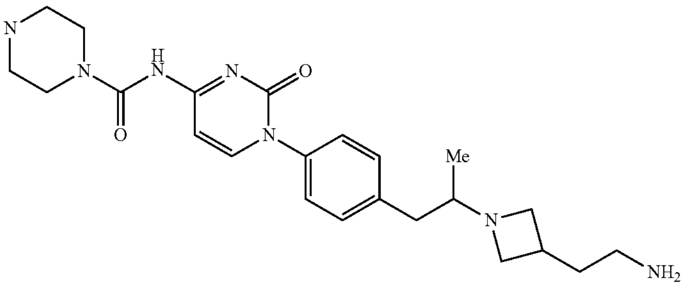 [SMILES: CC(Cc1ccc(-n2ccc(NC(=O)N3CCNCC3)nc2=O)cc1)N1CC(CCN)C1] |

TABLE 12-continued
| Compounds of Formula IV |
| --- |
| Structure |
| 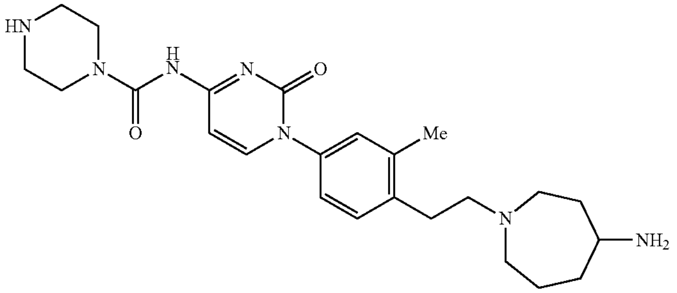 [SMILES: Cc1cc(-n2ccc(NC(=O)N3CCNCC3)nc2=O)ccc1CCN1CCCC(N)CC1] |
| 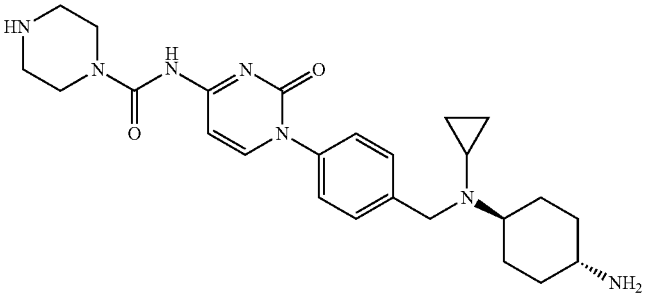 [SMILES: N[C@H]1CC[C@H](N(Cc2ccc(-n3ccc(NC(=O)N4CCNCC4)nc3=O)cc2)C2CC2)CC1] |
| 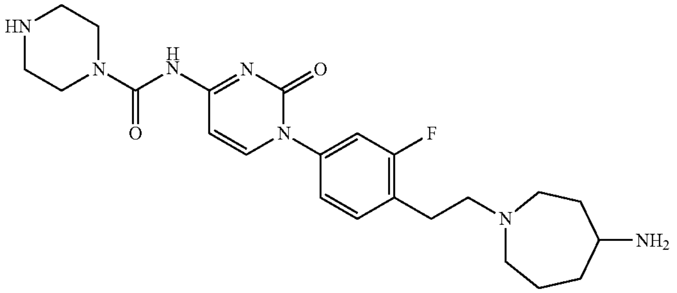 [SMILES: NC1CCCN(CCc2ccc(-n3ccc(NC(=O)N4CCNCC4)nc3=O)cc2F)CC1] |
| 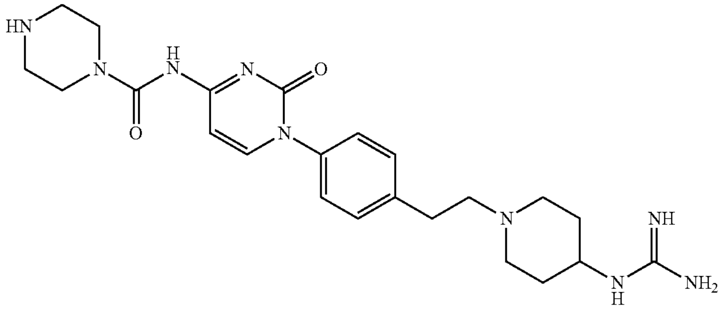 [SMILES: N=C(N)NC1CCN(CCc2ccc(-n3ccc(NC(=O)N4CCNCC4)nc3=O)cc2)CC1] |
| 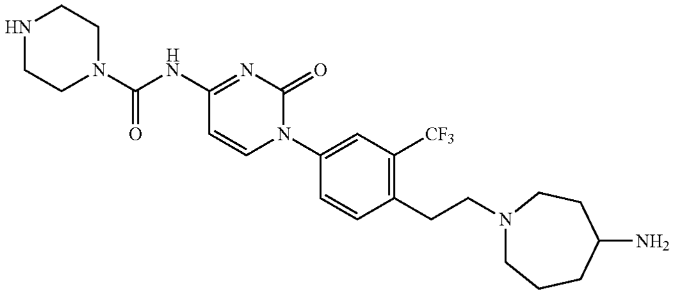 [SMILES: NC1CCCN(CCc2ccc(-n3ccc(NC(=O)N4CCNCC4)nc3=O)cc2C(F)(F)F)CC1] |

TABLE 12-continued
| Compounds of Formula IV |
|---|
| Structure |
| 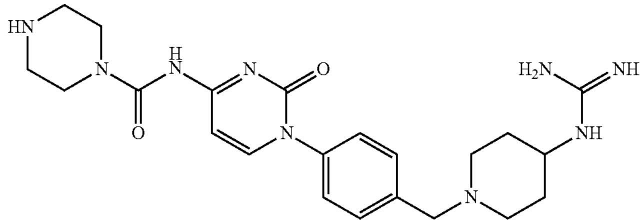 [SMILES: N=C(N)NC1CCN(Cc2ccc(-n3ccc(NC(=O)N4CCNCC4)nc3=O)cc2)CC1] |
| 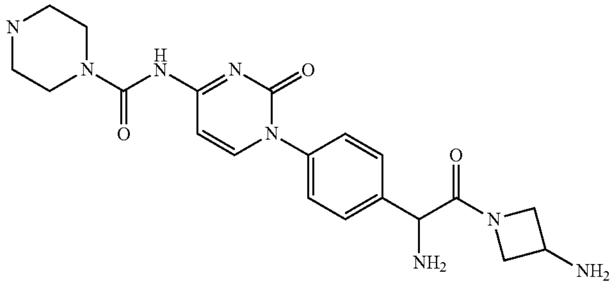 [SMILES: NC1CN(C(=O)C(N)c2ccc(-n3ccc(NC(=O)N4CCNCC4)nc3=O)cc2)C1] |
| 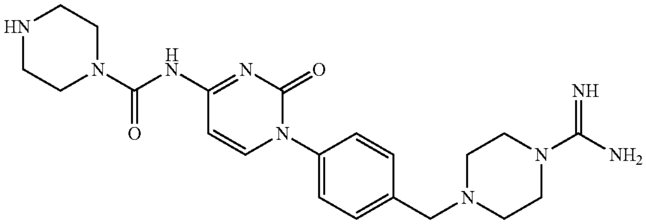 [SMILES: N=C(N)N1CCN(Cc2ccc(-n3ccc(NC(=O)N4CCNCC4)nc3=O)cc2)CC1] |
| 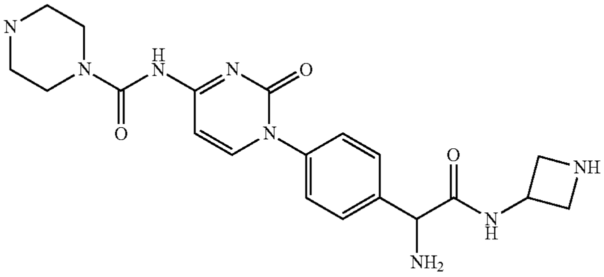 [SMILES: NC(C(=O)NC1CNC1)c1ccc(-n2ccc(NC(=O)N3CCNCC3)nc2=O)cc1] |
| 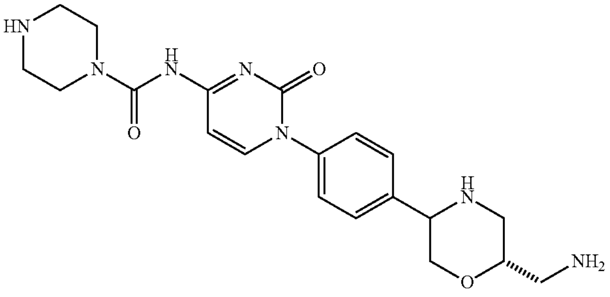 [SMILES: NC[C@H]1CNC(c2ccc(-n3ccc(NC(=O)N4CCNCC4)nc3=O)cc2)CO1] |

TABLE 12-continued
| Compounds of Formula IV |
|---|
| Structure |
| 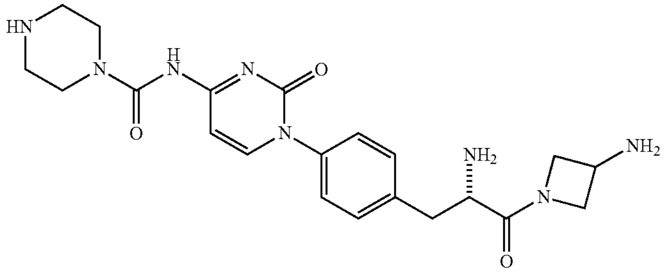 [SMILES: NC1CN(C(=O)[C@@H](N)Cc2ccc(-n3ccc(NC(=O)N4CCNCC4)nc3=O)cc2)C1] |
| 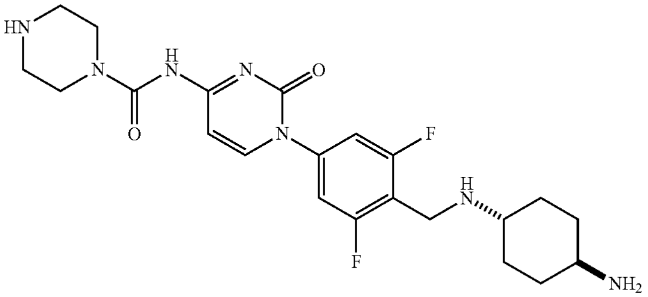 |
| 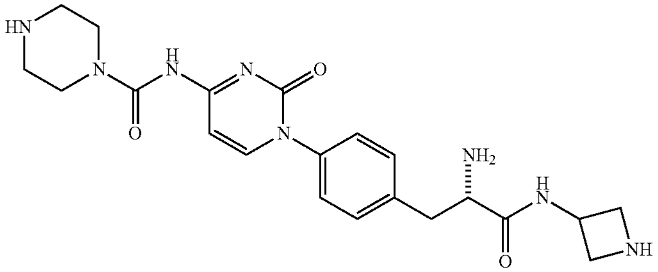 [SMILES: N[C@@H](Cc1ccc(-n2ccc(NC(=O)N3CCNCC3)nc2=O)cc1)C(=O)NC1CNC1] |
| 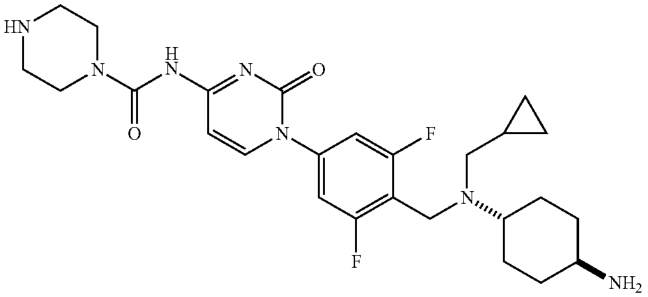 |
| 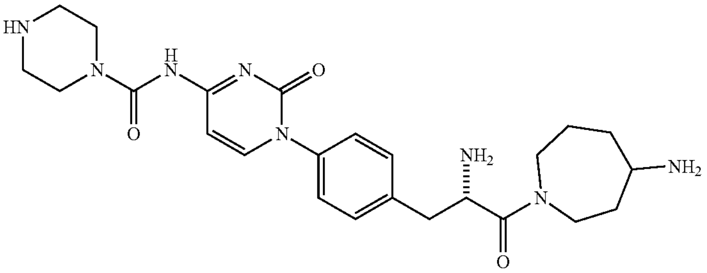 [SMILES: NC1CCCN(C(=O)[C@@H](N)Cc2ccc(-n3ccc(NC(=O)N4CCNCC4)nc3=O)cc2)CC1] |

TABLE 12-continued
| Compounds of Formula IV |
| --- |
| Structure |
| 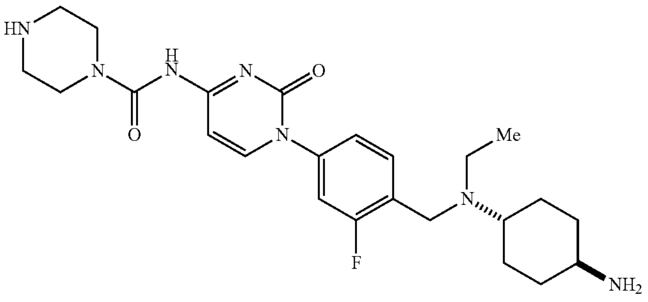 |
| 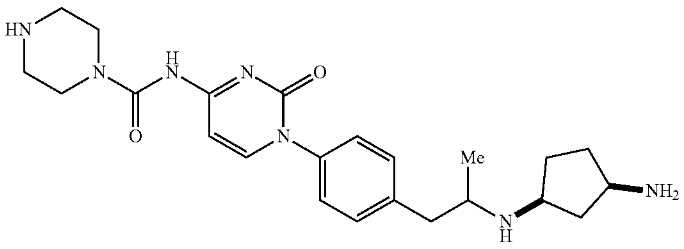 |
| 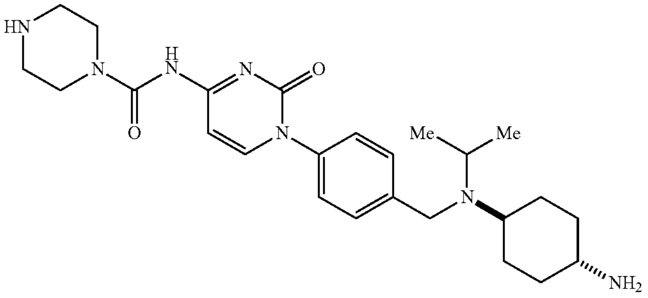 |
| 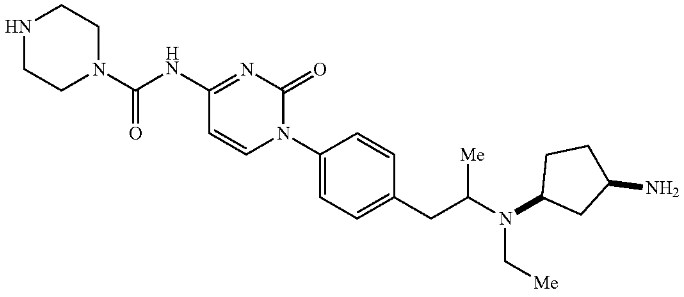 |
| 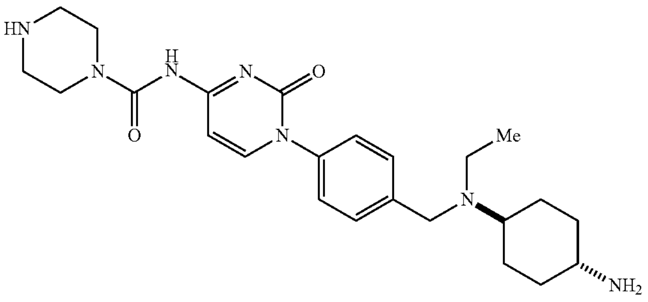 |

TABLE 12-continued
| Compounds of Formula IV |
| --- |
| Structure |
| 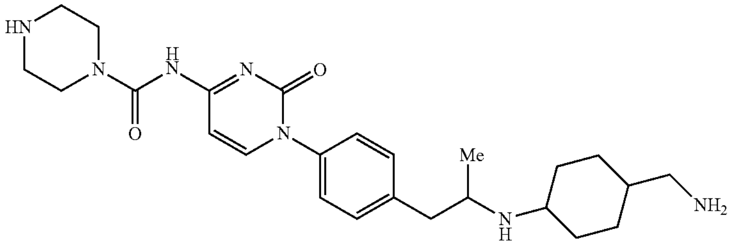 [SMILES: CC(Cc1ccc(-n2ccc(NC(=O)N3CCNCC3)nc2=O)cc1)NC1CCC(CN)CC1] |
| 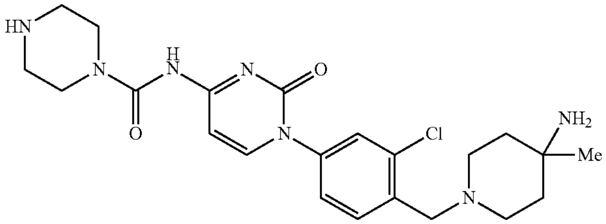 [SMILES: CC1(N)CCN(Cc2ccc(-n3ccc(NC(=O)N4CCNCC4)nc3=O)cc2Cl)CC1] |
| 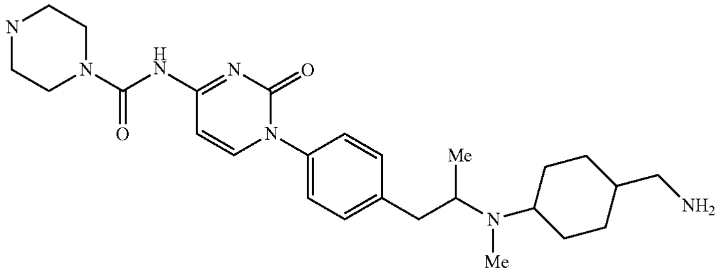 [SMILES: CC(Cc1ccc(-n2ccc(NC(=O)N3CCNCC3)nc2=O)cc1)N(C)C1CCC(CN)CC1] |
| 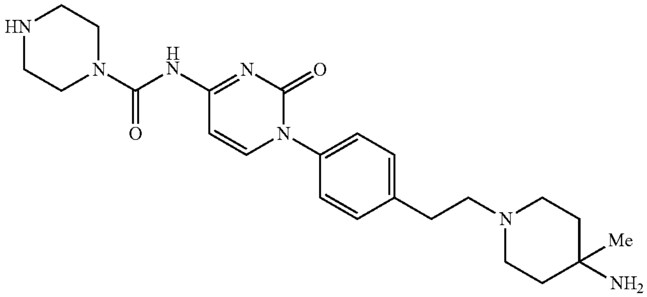 [SMILES: CC1(N)CCN(CCc2ccc(-n3ccc(NC(=O)N4CCNCC4)nc3=O)cc2)CC1] |
| 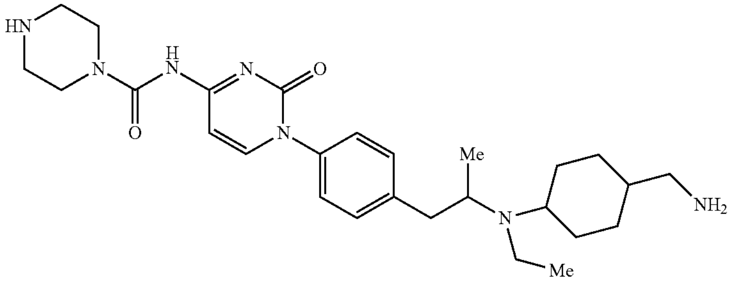 [SMILES: CCN(C(C)Cc1ccc(-n2ccc(NC(=O)N3CCNCC3)nc2=O)cc1)C1CCC(CN)CC1] |

TABLE 12-continued
| Compounds of Formula IV |
| --- |
| Structure |
| 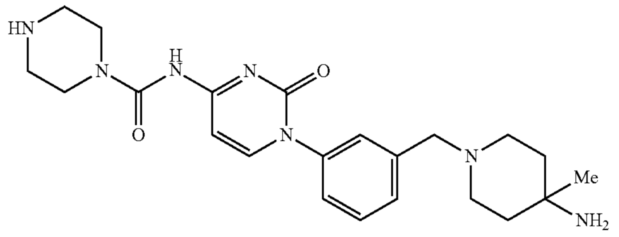 [SMILES: CC1(N)CCN(Cc2cccc(-n3ccc(NC(=O)N4CCNCC4)nc3=O)c2)CC1] |
| 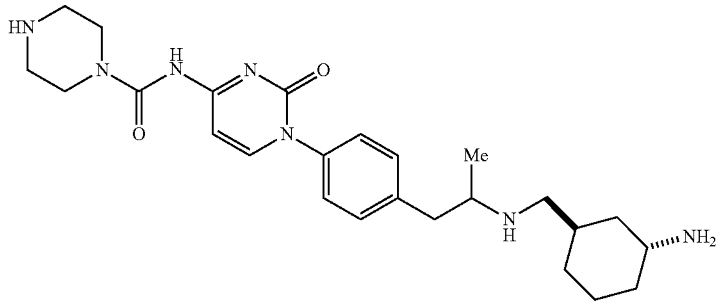 |
| 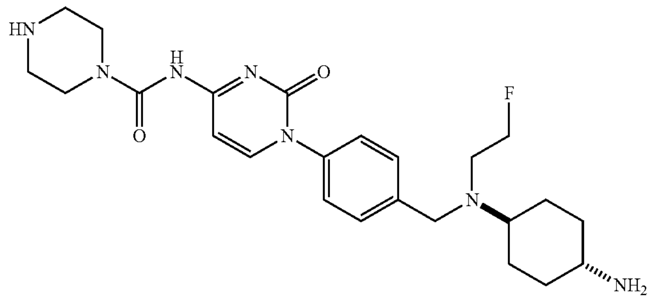 [SMILES: N[C@H]1CC[C@H](N(CCF)Cc2ccc(-n3ccc(NC(=O)N4CCNCC4)nc3=O)cc2)CC1] |
| 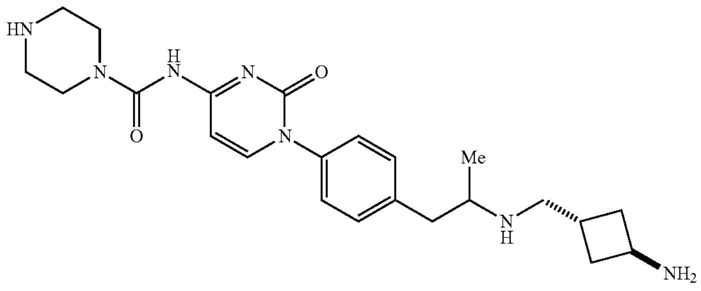 [SMILES: CC(Cc1ccc(-n2ccc(NC(=O)N3CCNCC3)nc2=O)cc1)NC[C@H]1C[C@H](N)C1] |
| 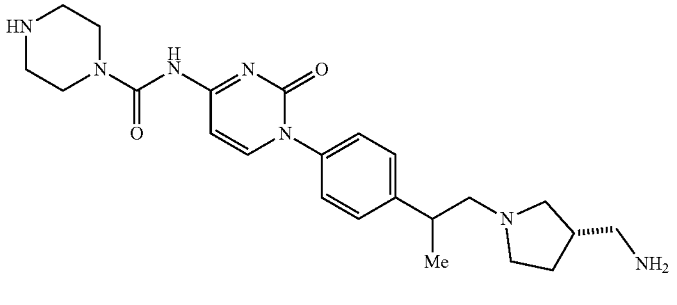 [SMILES: CC(CN1CC[C@@H](CN)C1)c1ccc(-n2ccc(NC(=O)N3CCNCC3)nc2=O)cc1] |

TABLE 12-continued
| Compounds of Formula IV |
|---|
| Structure |
| 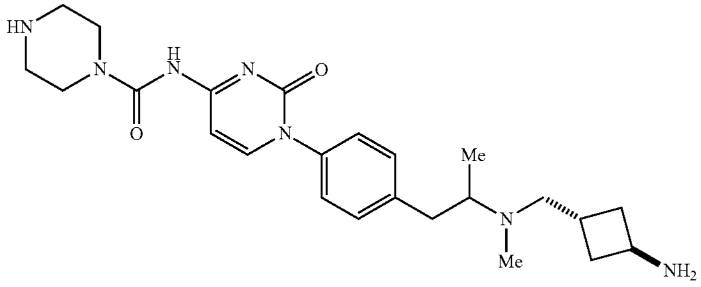 [SMILES: CC(Cc1ccc(-n2ccc(NC(=O)N3CCNCC3)nc2=O)cc1)N(C)C[C@H]1C[C@H](N)C1] |
| 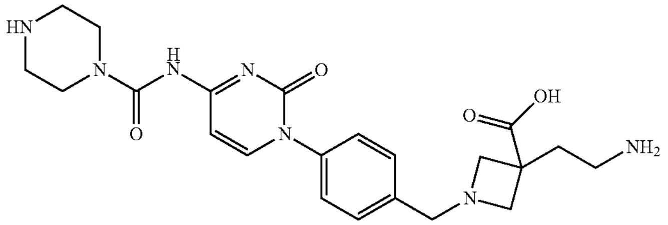 [SMILES: NCCC1(C(=O)O)CN(Cc2ccc(-n3ccc(NC(=O)N4CCNCC4)nc3=O)cc2)C1] |
| 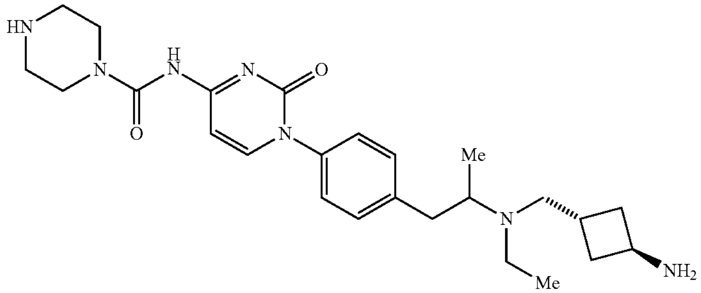 [SMILES: CCN(C[C@H]1C[C@H](N)C1)C(C)Cc1ccc(-n2ccc(NC(=O)N3CCNCC3)nc2=O)cc1] |
| 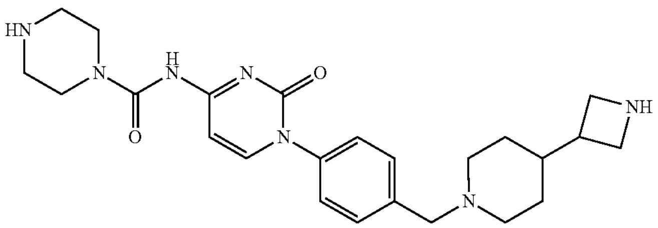 [SMILES: O=C(Nc1ccn(-c2ccc(CN3CCC(C4CNC4)CC3)cc2)c(=O)n1)N1CCNCC1] |
| 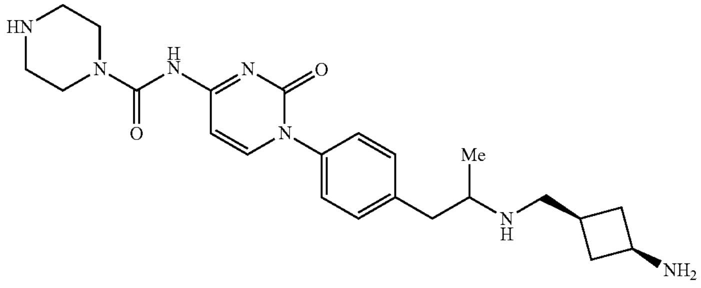 [SMILES: CC(Cc1ccc(-n2ccc(NC(=O)N3CCNCC3)nc2=O)cc1)NC[C@H]1C[C@@H](N)C1] |

TABLE 12-continued
| Compounds of Formula IV |
| --- |
| Structure |
| 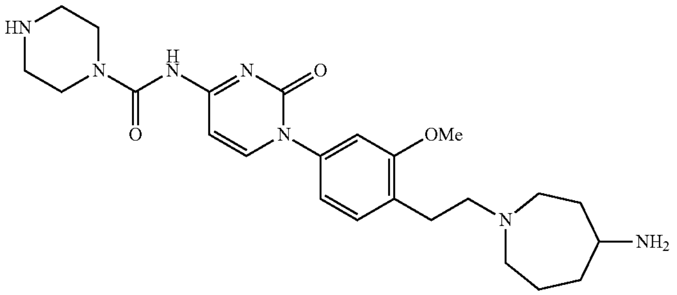 [SMILES: COc1cc(-n2ccc(NC(=O)N3CCNCC3)nc2=O)ccc1CCN1CCCC(N)CC1] |
| 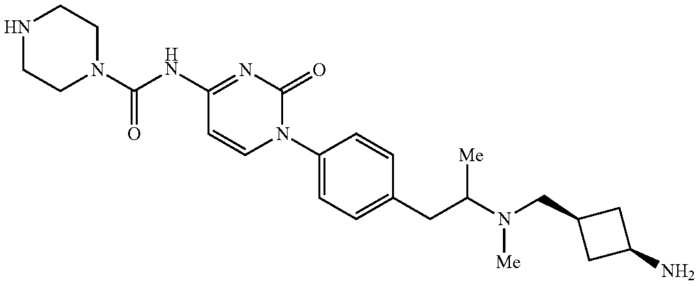 [SMILES: CC(Cc1ccc(-n2ccc(NC(=O)N3CCNCC3)nc2=O)cc1)N(C)C[C@H]1C[C@@H](N)C1] |
| 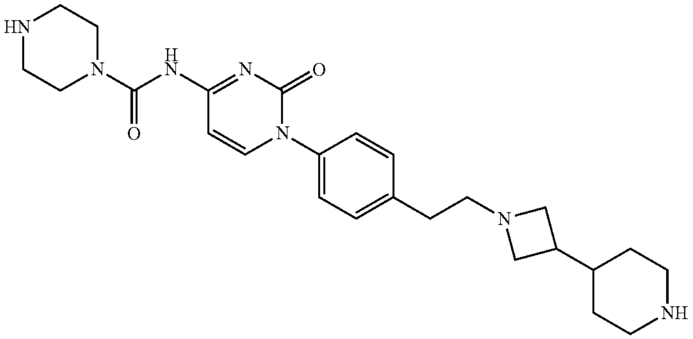 [SMILES: O=C(Nc1ccn(-c2ccc(CCN3CC(C4CCNCC4)C3)cc2)c(=O)n1)N1CCNCC1] |
| 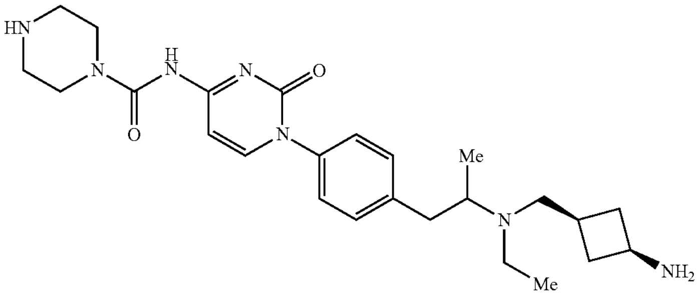 [SMILES: CCN(C[C@H]1C[C@@H](N)C1)C(C)Cc1ccc(-n2ccc(NC(=O)N3CCNCC3)nc2=O)cc1] |
| 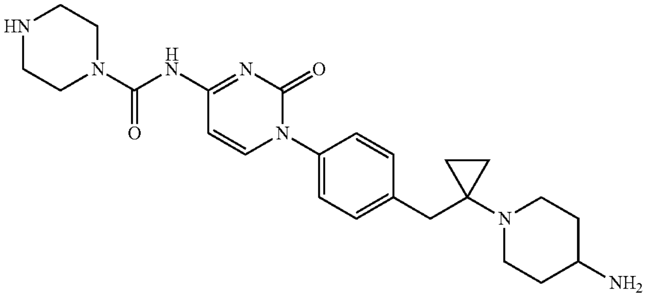 [SMILES: NC1CCN(C2(Cc3ccc(-n4ccc(NC(=O)N5CCNCC5)nc4=O)cc3)CC2)CC1] |

TABLE 12-continued
| Compounds of Formula IV |
| --- |
| Structure |
| 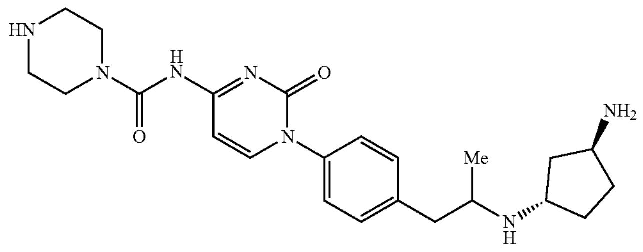 [SMILES: CC(Cc1ccc(-n2ccc(NC(=O)N3CCNCC3)nc2=O)cc1)N[C@H]1CC[C@H](N)C1] |
| 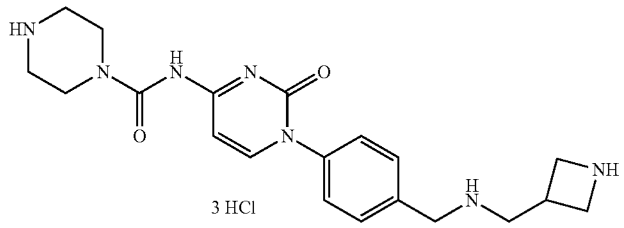 [SMILES: O=C(Nc1ccn(-c2ccc(CNCC3CNC3)cc2)c(=O)n1)N1CCNCC1] 3 HCl |
| 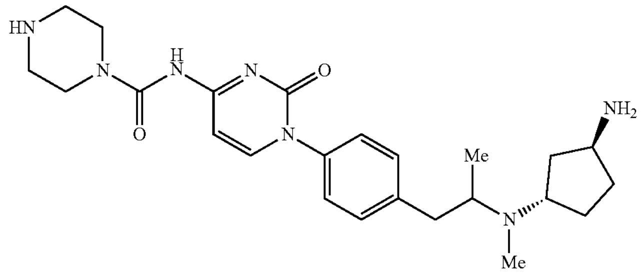 [SMILES: CC(Cc1ccc(-n2ccc(NC(=O)N3CCNCC3)nc2=O)cc1)N(C)[C@H]1CC[C@H](N)C1] |
| 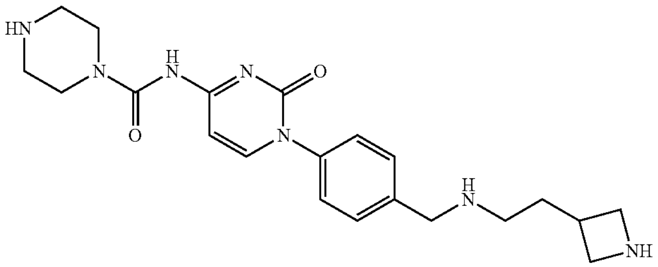 [SMILES: O=C(Nc1ccn(-c2ccc(CNCCC3CNC3)cc2)c(=O)n1)N1CCNCC1] |
| 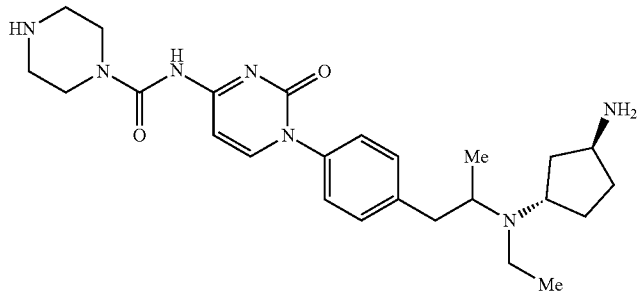 [SMILES: CCN(C(C)Cc1ccc(-n2ccc(NC(=O)N3CCNCC3)nc2=O)cc1)[C@H]1CC[C@H](N)C1] |

TABLE 12-continued
| Compounds of Formula IV |
| --- |
| Structure |
| 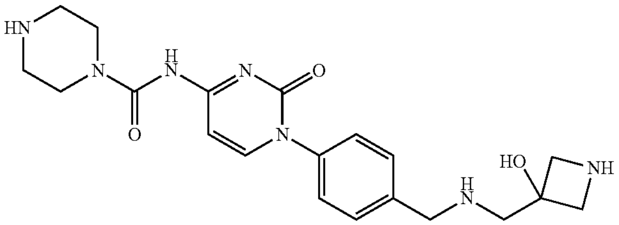 [SMILES: O=C(Nc1ccn(-c2ccc(CNCC3(O)CNC3)cc2)c(=O)n1)N1CCNCC1] |
| 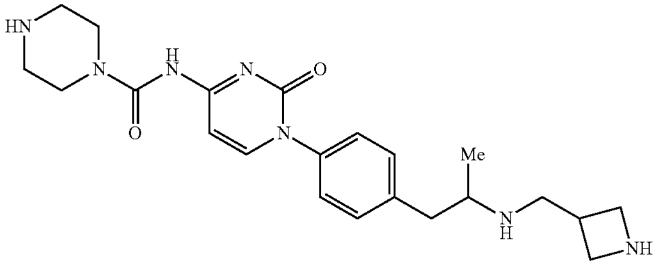 [SMILES: CC(Cc1ccc(-n2ccc(NC(=O)N3CCNCC3)nc2=O)cc1)NCC1CNC1] |
| 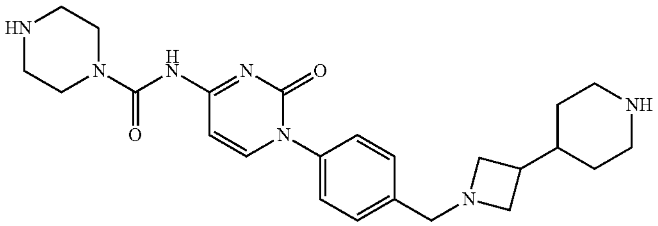 [SMILES: O=C(Nc1ccn(-c2ccc(CN3CC(C4CCNCC4)C3)cc2)c(=O)n1)N1CCNCC1] |
| 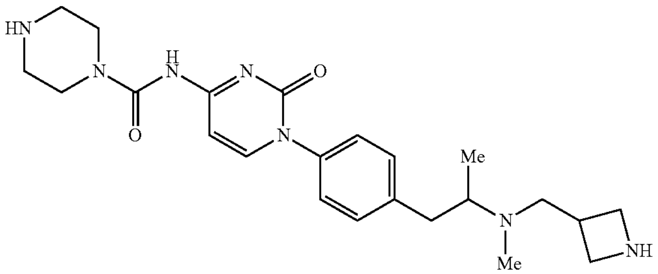 |
| 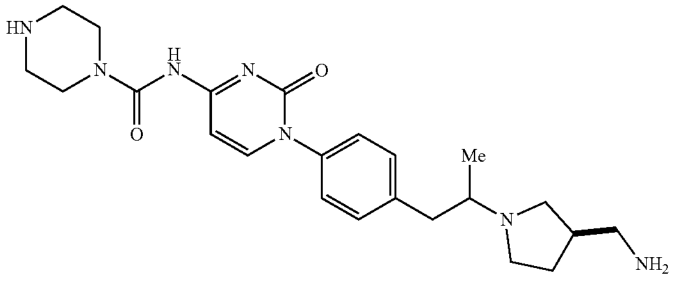 [SMILES: CC(Cc1ccc(-n2ccc(NC(=O)N3CCNCC3)nc2=O)cc1)N1CC[C@H](CN)C1] |

TABLE 12-continued
| Compounds of Formula IV |
| --- |
| Structure |
| 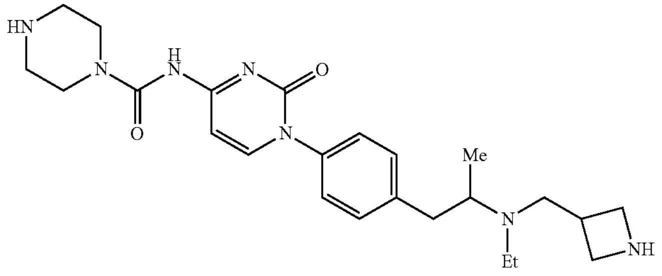 [SMILES: CCN(CC1CNC1)C(C)Cc1ccc(-n2ccc(NC(=O)N3CCNCC3)nc2=O)cc1] |
| 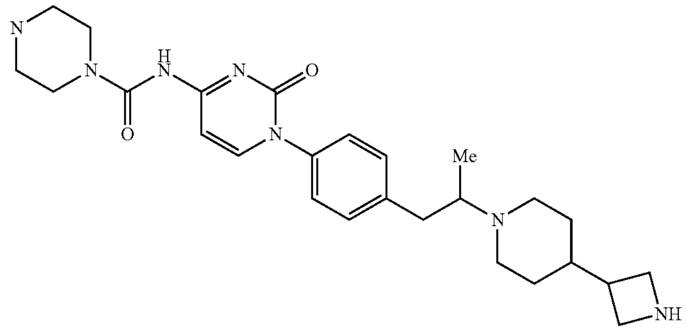 |
| 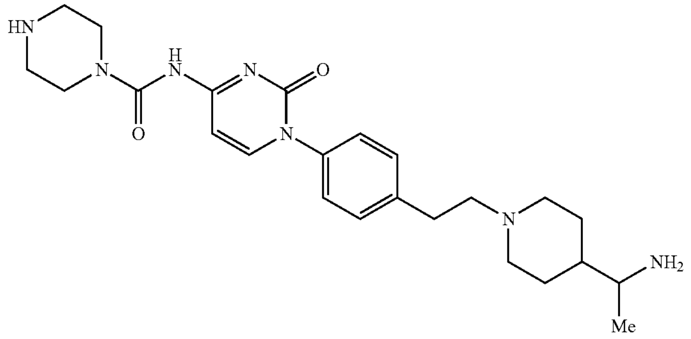 [SMILES: CC(N)C1CCN(CCc2ccc(-n3ccc(NC(=O)N4CCNCC4)nc3=O)cc2)CC1] |
| 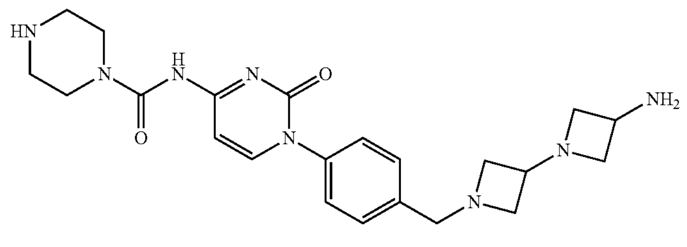 [SMILES: NC1CN(C2CN(Cc3ccc(-n4ccc(NC(=O)N5CCNCC5)nc4=O)cc3)C2)C1] |
| 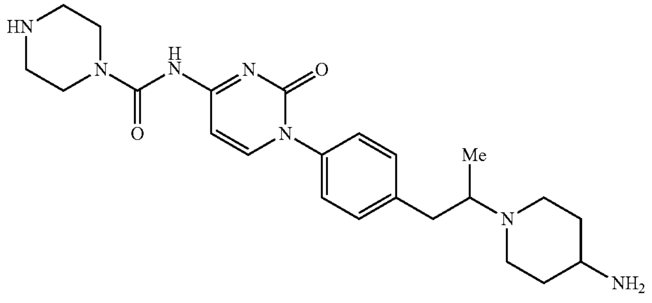 [SMILES: CC(Cc1ccc(-n2ccc(NC(=O)N3CCNCC3)nc2=O)cc1)N1CCC(N)CC1] |

TABLE 12-continued
| Compounds of Formula IV |
|---|
| Structure |
| 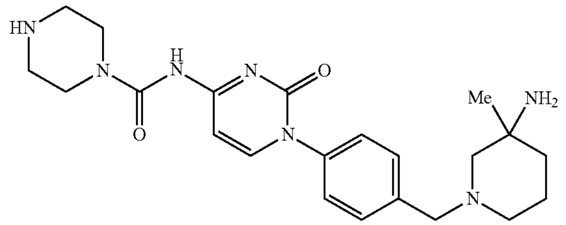 [SMILES: CC1(N)CCCN(Cc2ccc(-n3ccc(NC(=O)N4CCNCC4)nc3=O)cc2)C1] |
| 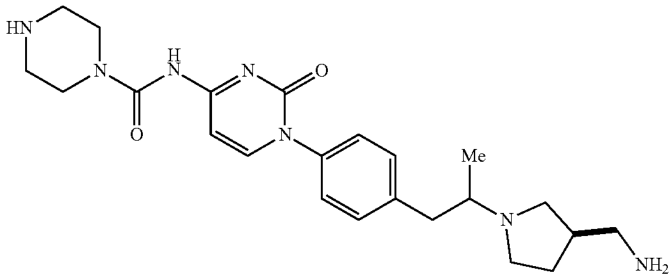 [SMILES: CC(Cc1ccc(-n2ccc(NC(=O)N3CCNCC3)nc2=O)cc1)N1CC[C@H](CN)C1] |
| 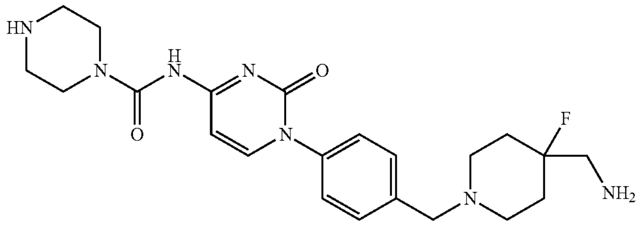 [SMILES: NCC1(F)CCN(Cc2ccc(-n3ccc(NC(=O)N4CCNCC4)nc3=O)cc2)CC1] |
| 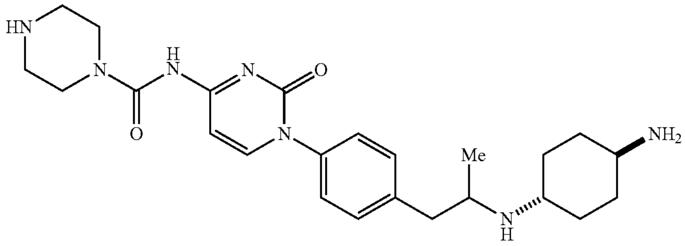 |
| 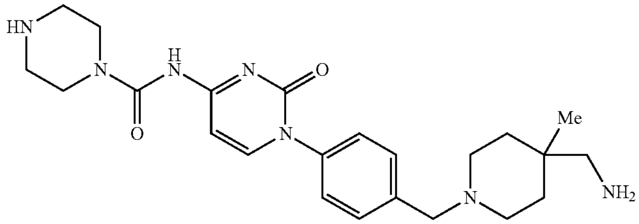 [SMILES: CC1(CN)CCN(Cc2ccc(-n3ccc(NC(=O)N4CCNCC4)nc3=O)cc2)CC1] |
| 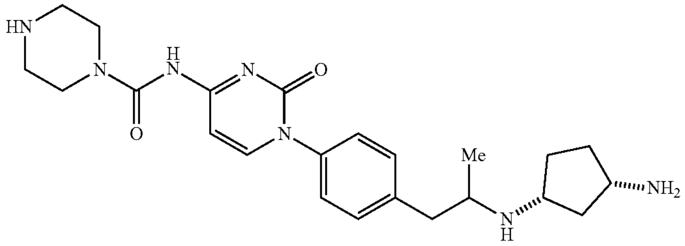 |

TABLE 12-continued
| Compounds of Formula IV |
| --- |
| Structure |
| 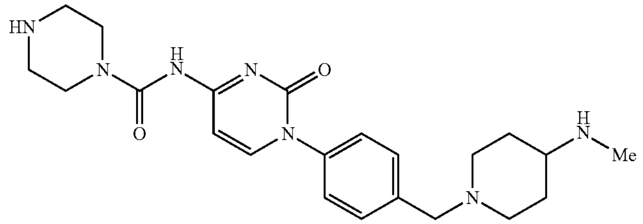 [SMILES: CNC1CCN(Cc2ccc(-n3ccc(NC(=O)N4CCNCC4)nc3=O)cc2)CC1] |
| 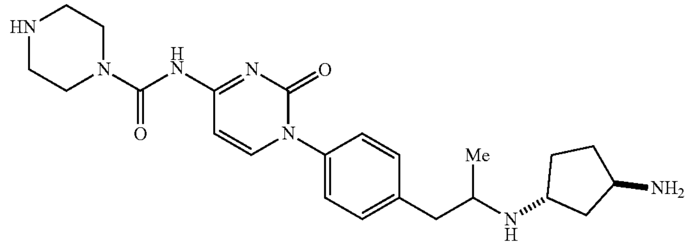 |
| 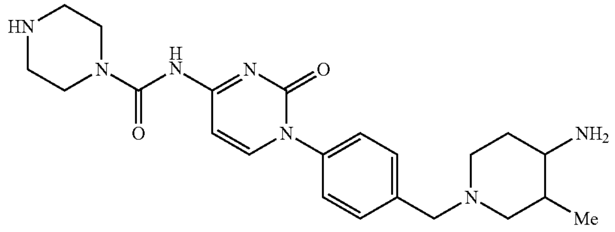 [SMILES: CC1CN(Cc2ccc(-n3ccc(NC(=O)N4CCNCC4)nc3=O)cc2)CCC1N] |
| 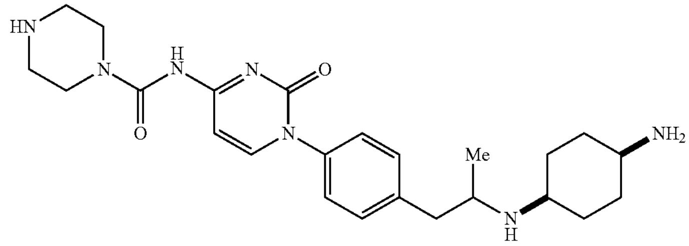 |
| 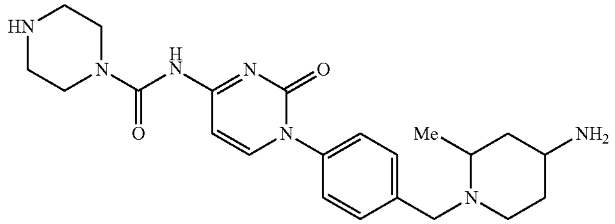 [SMILES: CC1CC(N)CCN1Cc1ccc(-n2ccc(NC(=O)N3CCNCC3)nc2=O)cc1] |
| 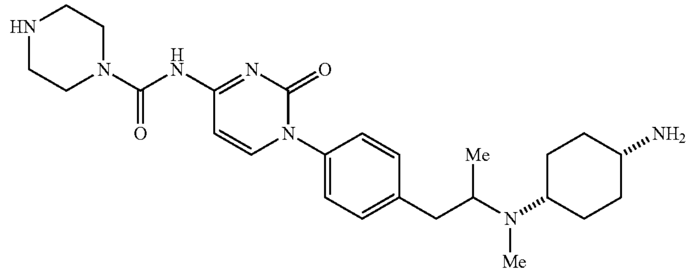 |

TABLE 12-continued
| Compounds of Formula IV |
| --- |
| Structure |
| 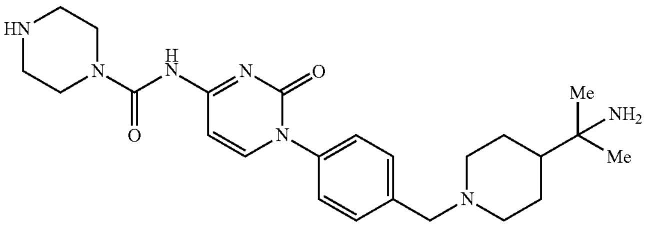 [SMILES: CC(C)(N)C1CCN(Cc2ccc(-n3ccc(NC(=O)N4CCNCC4)nc3=O)cc2)CC1] |
| 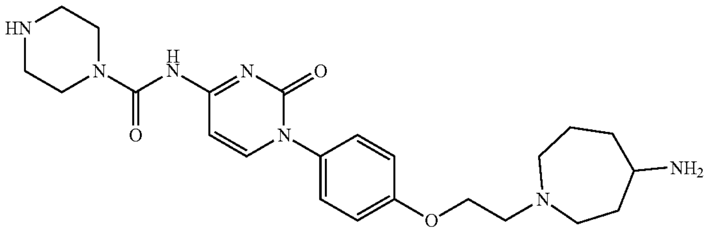 [SMILES: NC1CCCN(CCOc2ccc(-n3ccc(NC(=O)N4CCNCC4)nc3=O)cc2)CC1] |
| 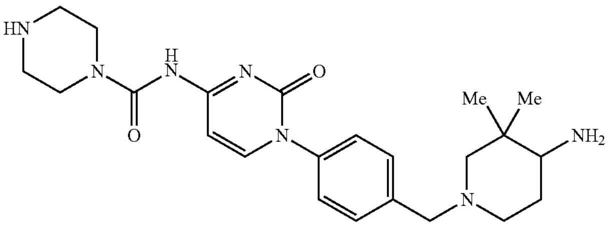 [SMILES: CC1(C)CN(Cc2ccc(-n3ccc(NC(=O)N4CCNCC4)nc3=O)cc2)CCC1N] |
| 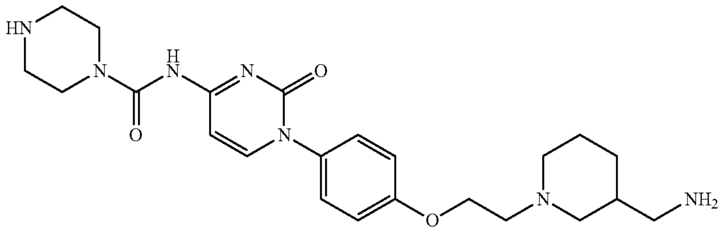 [SMILES: NCC1CCCN(CCOc2ccc(-n3ccc(NC(=O)N4CCNCC4)nc3=O)cc2)C1] |
| 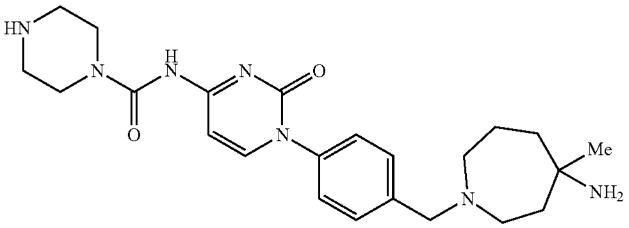 [SMILES: CC1(N)CCCN(Cc2ccc(-n3ccc(NC(=O)N4CCNCC4)nc3=O)cc2)CC1] |
| 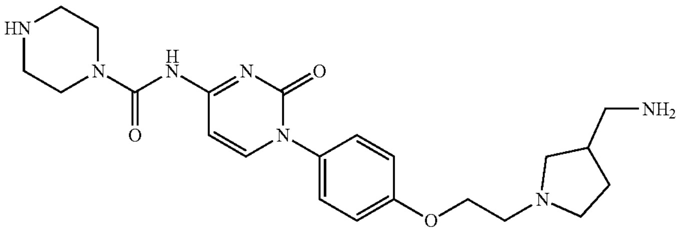 [SMILES: NCC1CCN(CCOc2ccc(-n3ccc(NC(=O)N4CCNCC4)nc3=O)cc2)C1] |

TABLE 12-continued
| Compounds of Formula IV |
|---|
| Structure |
| 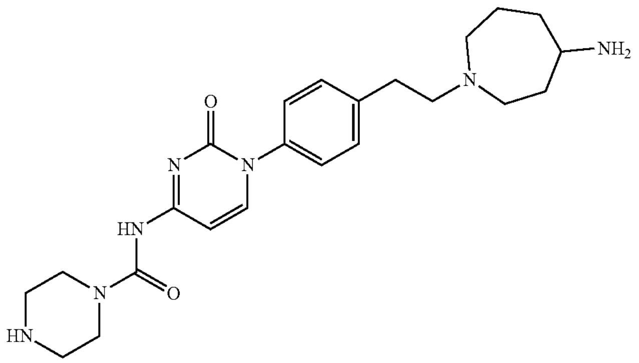 [SMILES: NC1CCCN(CCc2ccc(-n3ccc(NC(=O)N4CCNCC4)nc3=O)cc2)CC1] |
| 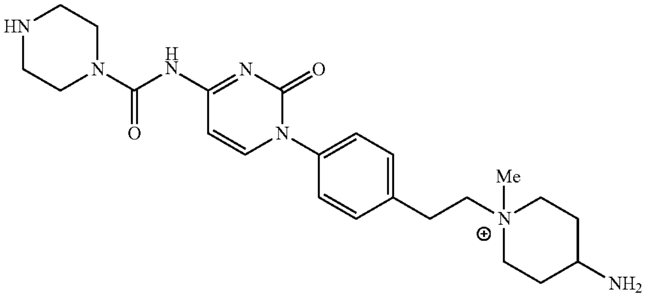 [SMILES: C[N+]1(CCc2ccc(-n3ccc(NC(=O)N4CCNCC4)nc3=O)cc2)CCC(N)CC1] |
| 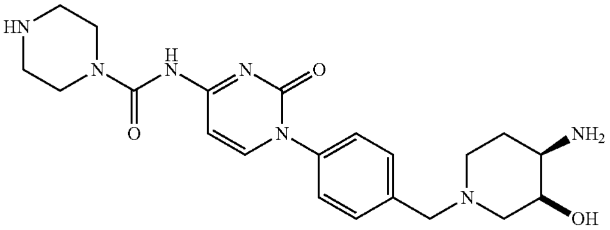 [SMILES: N[C@@H]1CCN(Cc2ccc(-n3ccc(NC(=O)N4CCNCC4)nc3=O)cc2)C[C@@H]1O] |
| 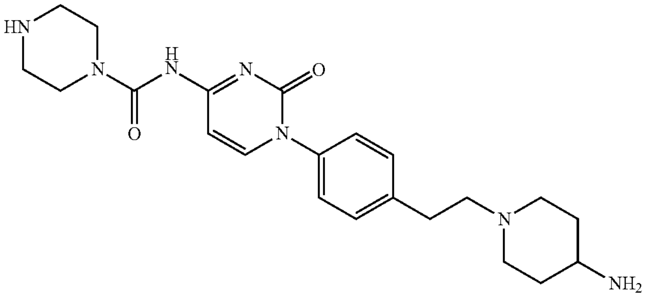 [SMILES: NC1CCN(CCc2ccc(-n3ccc(NC(=O)N4CCNCC4)nc3=O)cc2)CC1] |
| 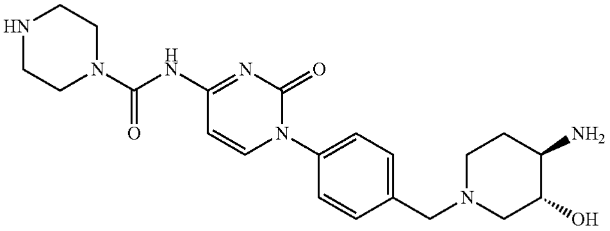 [SMILES: N[C@@H]1CCN(Cc2ccc(-n3ccc(NC(=O)N4CCNCC4)nc3=O)cc2)C[C@H]1O] |

TABLE 12-continued
| Compounds of Formula IV |
| --- |
| Structure |
| 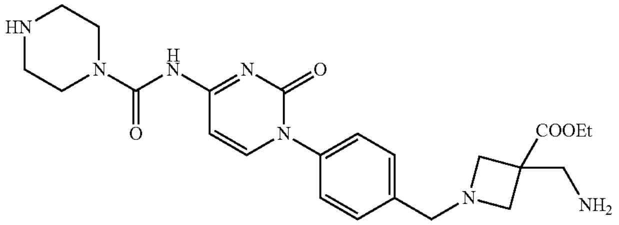 [SMILES: CCOC(=O)C1(CN)CN(Cc2ccc(-n3ccc(NC(=O)N4CCNCC4)nc3=O)cc2)C1] |
| 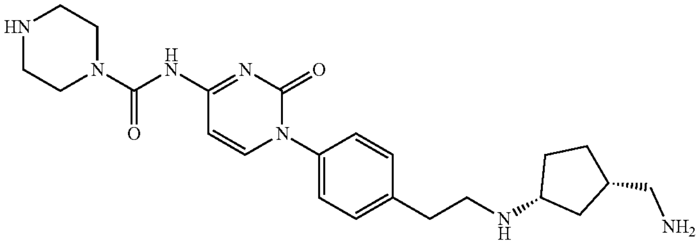 [SMILES: NC[C@H]1CC[C@@H](NCCc2ccc(-n3ccc(NC(=O)N4CCNCC4)nc3=O)cc2)C1] |
| 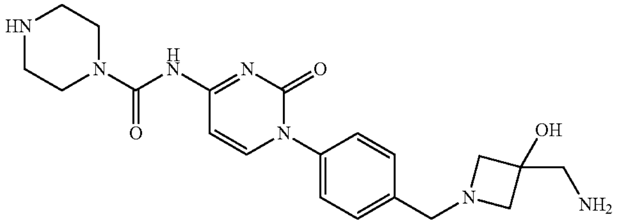 [SMILES: NCC1(O)CN(Cc2ccc(-n3ccc(NC(=O)N4CCNCC4)nc3=O)cc2)C1] |
| 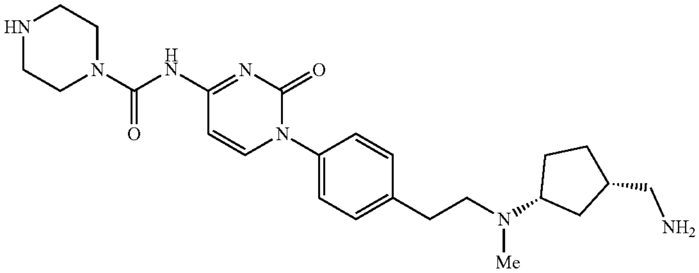 [SMILES: CN(CCc1ccc(-n2ccc(NC(=O)N3CCNCC3)nc2=O)cc1)[C@@H]1CC[C@H](CN)C1] |
| 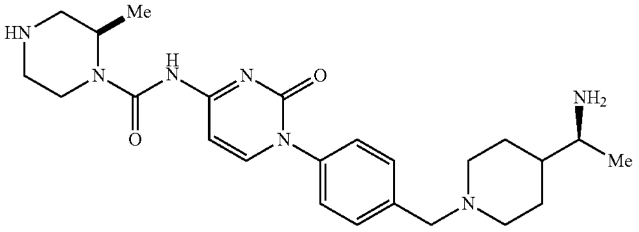 [SMILES: C[C@H](N)C1CCN(Cc2ccc(-n3ccc(NC(=O)N4CCNC[C@H]4C)nc3=O)cc2)CC1] |
| 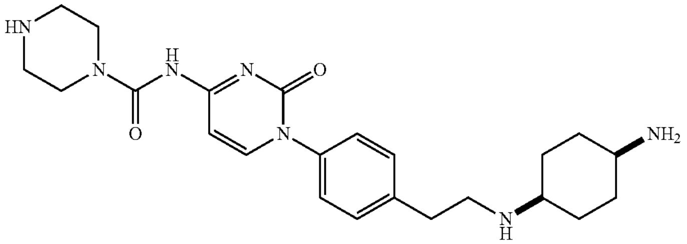 |

TABLE 12-continued
| Compounds of Formula IV |
|---|
| Structure |
| 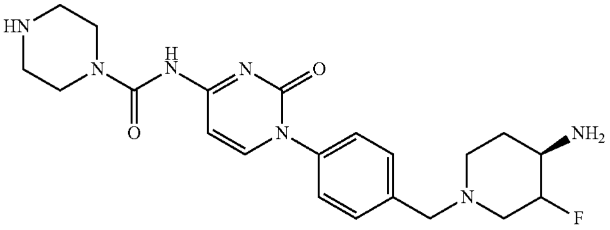 [SMILES: N[C@@H]1CCN(Cc2ccc(-n3ccc(NC(=O)N4CCNCC4)nc3=O)cc2)CC1F] |
| 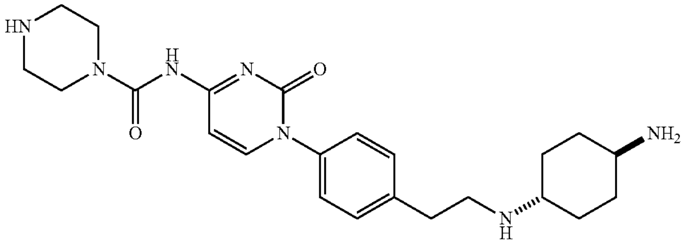 [SMILES: N[C@H]1CC[C@H](NCCc2ccc(-n3ccc(NC(=O)N4CCNCC4)nc3=O)cc2)CC1] |
| 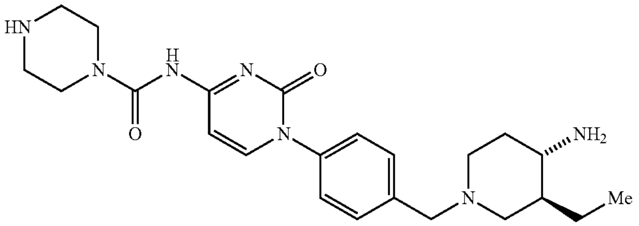 [SMILES: CC[C@H]1CN(Cc2ccc(-n3ccc(NC(=O)N4CCNCC4)nc3=O)cc2)CC[C@@H]1N] |
| 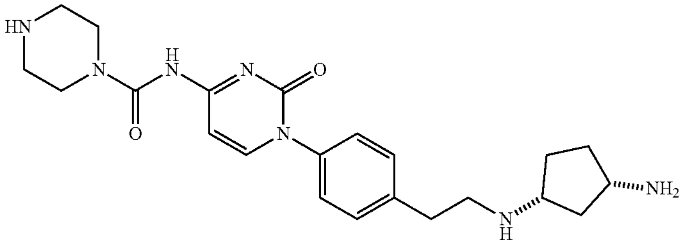 [SMILES: N[C@H]1CC[C@@H](NCCc2ccc(-n3ccc(NC(=O)N4CCNCC4)nc3=O)cc2)C1] |
| 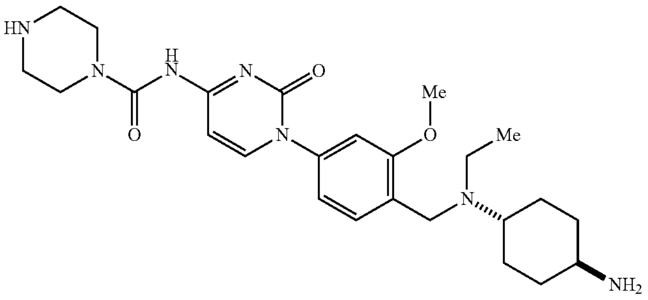 [SMILES: CCN(Cc1ccc(-n2ccc(NC(=O)N3CCNCC3)nc2=O)cc1OC)[C@H]1CC[C@H](N)CC1] |
| 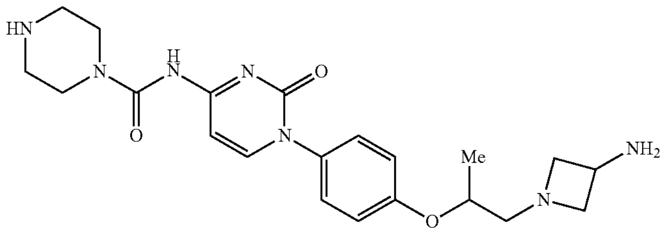 [SMILES: CC(CN1CC(N)C1)Oc1ccc(-n2ccc(NC(=O)N3CCNCC3)nc2=O)cc1] |

TABLE 12-continued
| Compounds of Formula IV |
| --- |
| Structure |
| 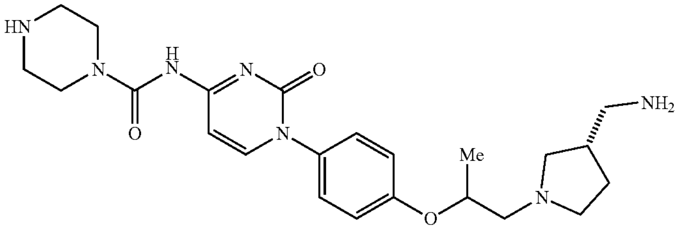 [SMILES: CC(CN1CC[C@@H](CN)C1)Oc1ccc(-n2ccc(NC(=O)N3CCNCC3)nc2=O)cc1] |
| 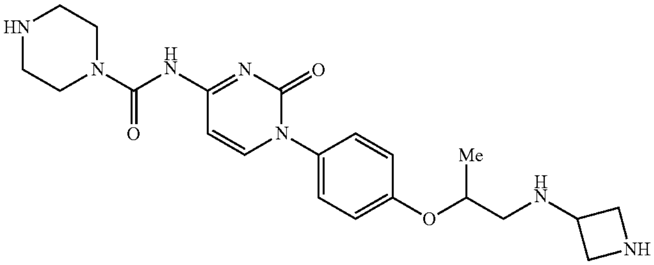 [SMILES: CC(CNC1CNC1)Oc1ccc(-n2ccc(NC(=O)N3CCNCC3)nc2=O)cc1] |
| 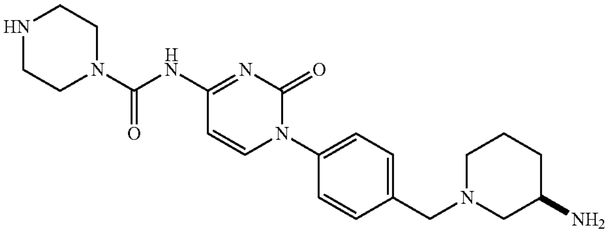 [SMILES: N[C@@H]1CCCN(Cc2ccc(-n3ccc(NC(=O)N4CCNCC4)nc3=O)cc2)C1] |
| 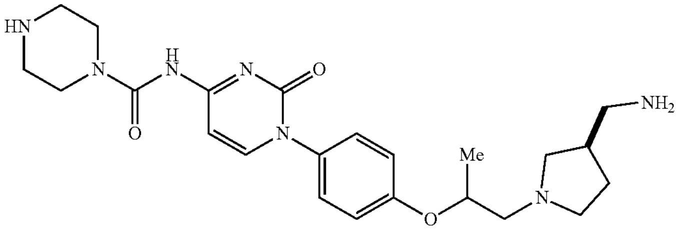 [SMILES: CC(CN1CC[C@H](CN)C1)Oc1ccc(-n2ccc(NC(=O)N3CCNCC3)nc2=O)cc1] |
| 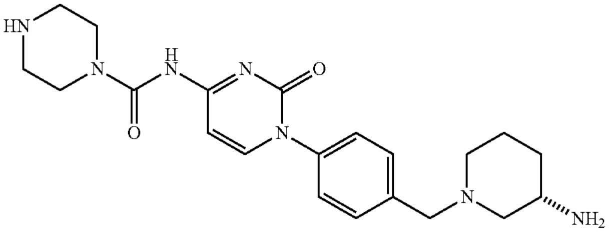 [SMILES: N[C@H]1CCCN(Cc2ccc(-n3ccc(NC(=O)N4CCNCC4)nc3=O)cc2)C1] |
| 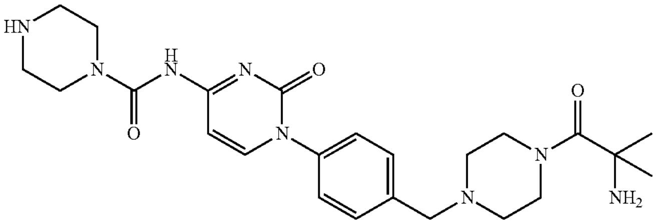 [SMILES: CC(C)(N)C(=O)N1CCN(Cc2ccc(-n3ccc(NC(=O)N4CCNCC4)nc3=O)cc2)CC1] |

TABLE 12-continued
| Compounds of Formula IV |
| --- |
| Structure |
| 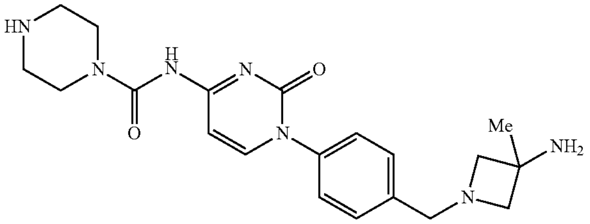 [SMILES: CC1(N)CN(Cc2ccc(-n3ccc(NC(=O)N4CCNCC4)nc3=O)cc2)C1] |
| 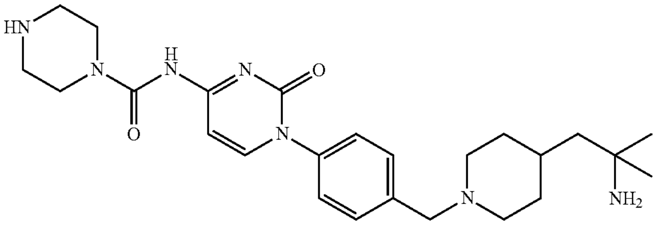 [SMILES: CC(C)(N)CC1CCN(Cc2ccc(-n3ccc(NC(=O)N4CCNCC4)nc3=O)cc2)CC1] |
| 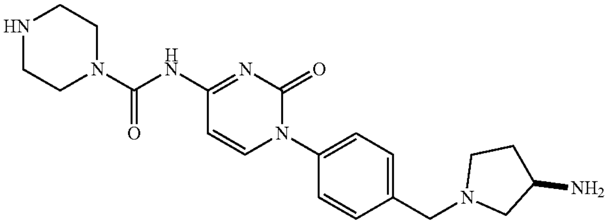 [SMILES: N[C@@H]1CCN(Cc2ccc(-n3ccc(NC(=O)N4CCNCC4)nc3=O)cc2)C1] |
| 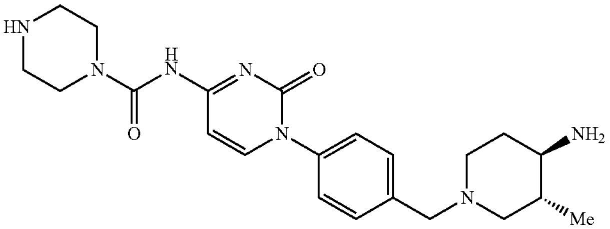 [SMILES: C[C@@H]1CN(Cc2ccc(-n3ccc(NC(=O)N4CCNCC4)nc3=O)cc2)CC[C@H]1N] |
| 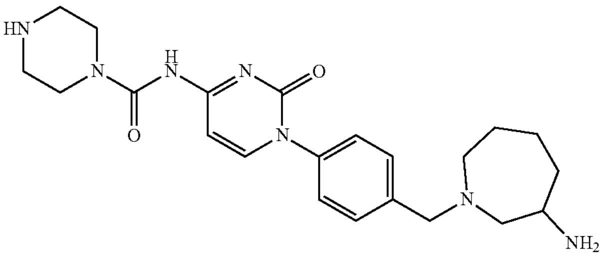 [SMILES: NC1CCCCN(Cc2ccc(-n3ccc(NC(=O)N4CCNCC4)nc3=O)cc2)C1] |
| 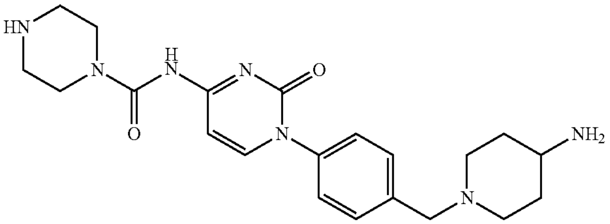 [SMILES: NC1CCN(Cc2ccc(-n3ccc(NC(=O)N4CCNCC4)nc3=O)cc2)CC1] |

TABLE 12-continued

| Compounds of Formula IV |
| --- |
| Structure |
| 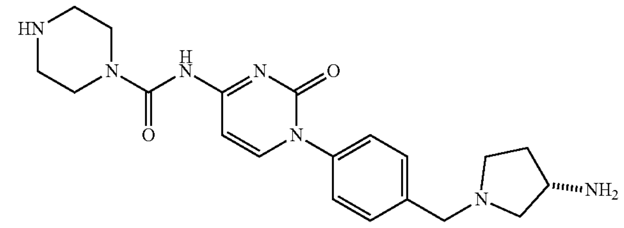 [SMILES: N[C@H]1CCN(Cc2ccc(-n3ccc(NC(=O)N4CCNCC4)nc3=O)cc2)C1] |
| 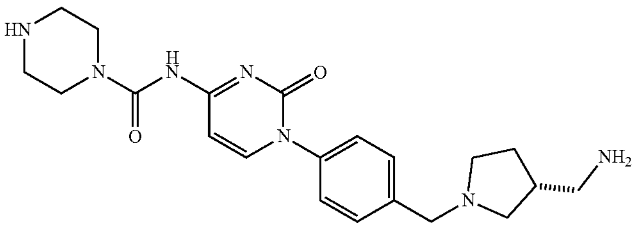 [SMILES: NC[C@H]1CCN(Cc2ccc(-n3ccc(NC(=O)N4CCNCC4)nc3=O)cc2)C1] |
| 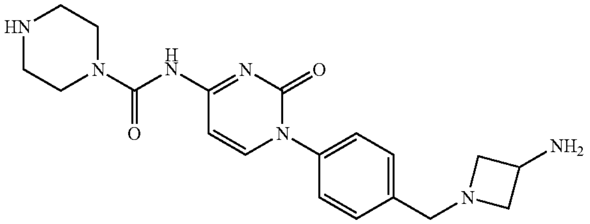 [SMILES: NC1CN(Cc2ccc(-n3ccc(NC(=O)N4CCNCC4)nc3=O)cc2)C1] |
| 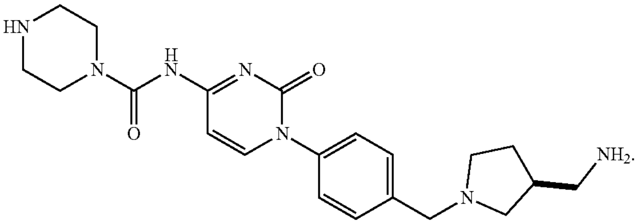 [SMILES: NC[C@@H]1CCN(Cc2ccc(-n3ccc(NC(=O)N4CCNCC4)nc3=O)cc2)C1] |

In another aspect, the disclosure provides a compound of formula V:

V

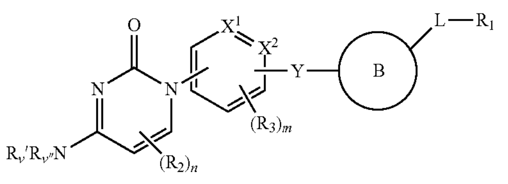

or a pharmaceutically acceptable salt thereof, wherein the variables have the definitions herein, and one of $R_{v'}$ and $R_{v''}$ is H and the other of $R_{v'}$ and $R_{v''}$ is H or an amino protecting group.

In another embodiment, the compound of formula V is a compound of formula VI:

VI

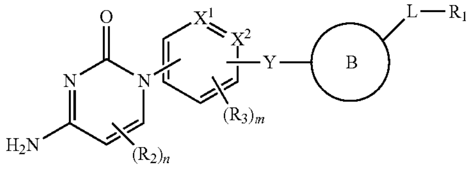

or a pharmaceutically acceptable salt thereof, wherein the variables have the definitions as disclosed herein.

In another embodiment, the compound of formula V or VI is selected from the compounds as depicted in Table 13 below.

TABLE 13
Compounds of Formula VI
Structure
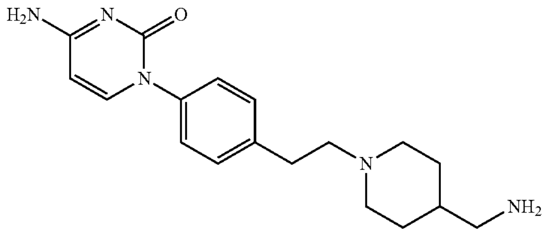 [SMILES: NCC1CCN(CCc2ccc(-n3ccc(N)nc3=O)cc2)CC1]
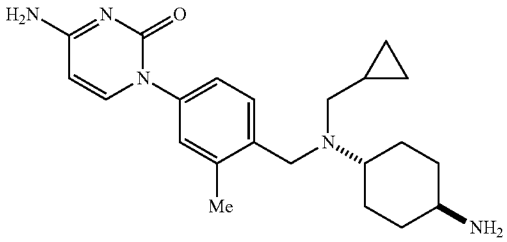 [SMILES: Cc1cc(-n2ccc(N)nc2=O)ccc1CN(CC1CC1)[C@H]1CC[C@H](N)CC1]
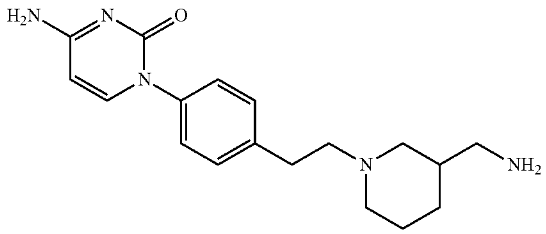 [SMILES: NCC1CCCN(CCc2ccc(-n3ccc(N)nc3=O)cc2)C1]
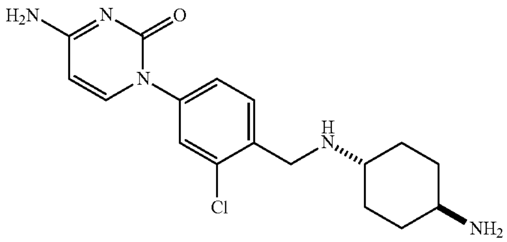
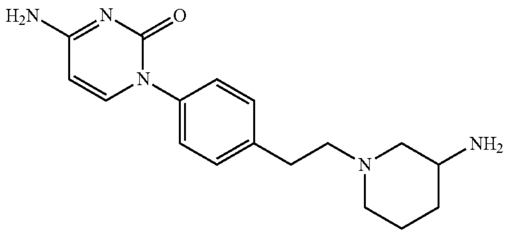
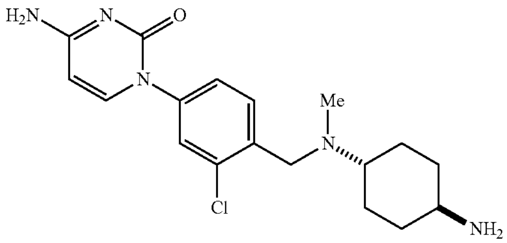 [SMILES: CN(Cc1ccc(-n2ccc(N)nc2=O)cc1Cl)[C@H]1CC[C@H](N)CC1]
TABLE 13-continued
Compounds of Formula VI
Structure
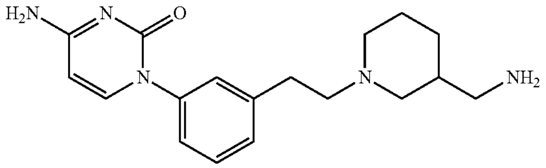 [SMILES: NCC1CCCN(CCc2cccc(-n3ccc(N)nc3=O)c2)C1]
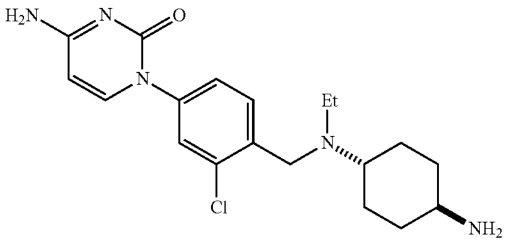
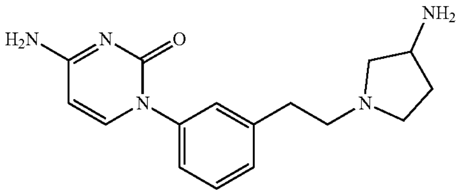 [SMILES: Nc1ccn(-c2cccc(CCN3CCC(N)C3)c2)c(=O)n1]
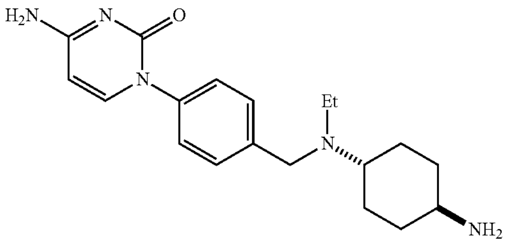
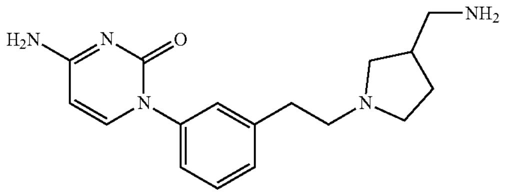 [SMILES: NCC1CCN(CCc2cccc(-n3ccc(N)nc3=O)c2)C1]
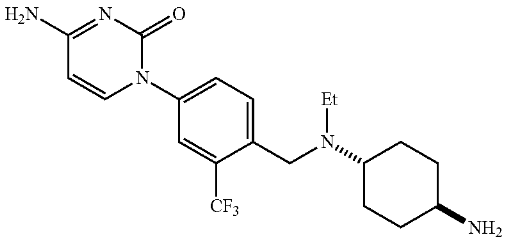 [SMILES: CCN(Cc1ccc(-n2ccc(N)nc2=O)cc1C(F)(F)F)[C@H]1CC[C@H](N)CC1]
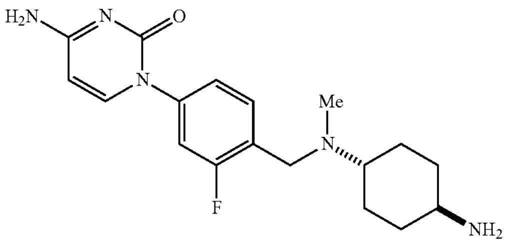

TABLE 13-continued
| Compounds of Formula VI |
| --- |
| Structure |
| 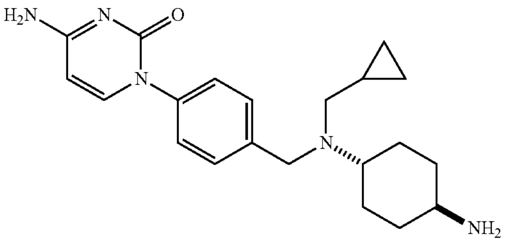 [SMILES: Nc1ccn(-c2ccc(CN(CC3CC3)[C@H]3CC[C@H](N)CC3)cc2)c(=O)n1] |
| 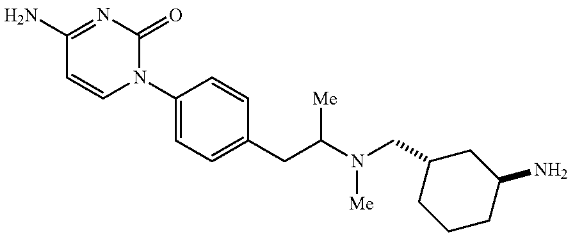 |
| 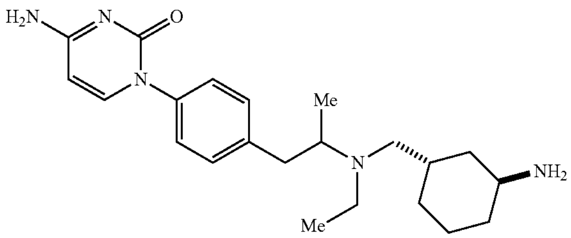 |
| 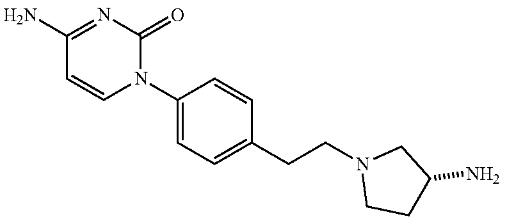 [SMILES: Nc1ccn(-c2ccc(CCN3CC[C@@H](N)C3)cc2)c(=O)n1] |
| 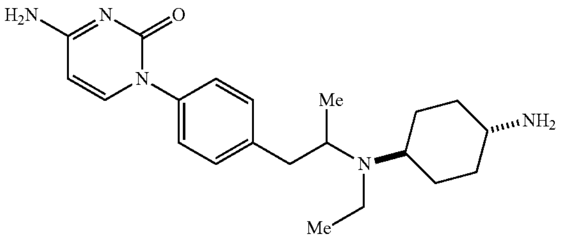 |
| 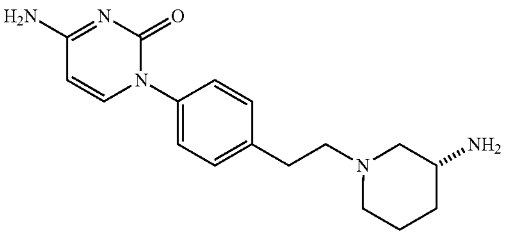 [SMILES: Nc1ccn(-c2ccc(CCN3CCC[C@@H](N)C3)cc2)c(=O)n1] |
TABLE 13-continued
| Compounds of Formula VI |
| --- |
| Structure |
| 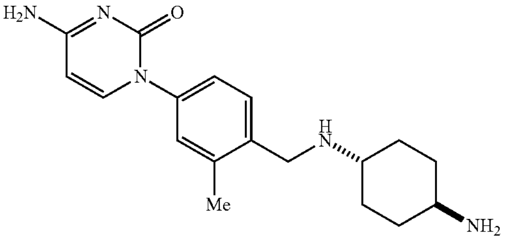 [SMILES: Cc1cc(-n2ccc(N)nc2=O)ccc1CN[C@H]1CC[C@H](N)CC1] |
| 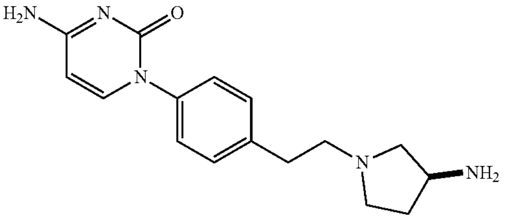 [SMILES: Nc1ccn(-c2ccc(CCN3CC[C@H](N)C3)cc2)c(=O)n1] |
| 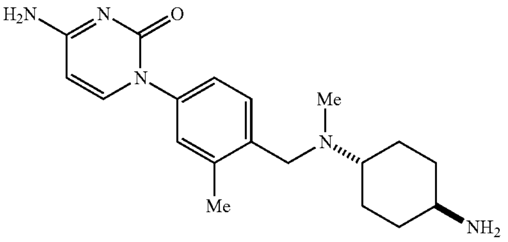 [SMILES: Cc1cc(-n2ccc(N)nc2=O)ccc1CN(C)[C@H]1CC[C@H](N)CC1] |
| 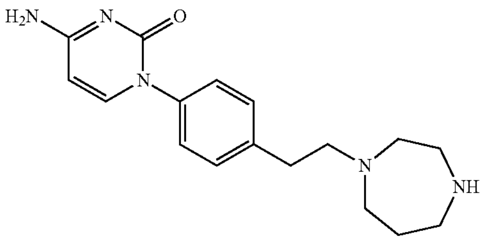 [SMILES: Nc1ccn(-c2ccc(CCN3CCCNCC3)cc2)c(=O)n1] |
| 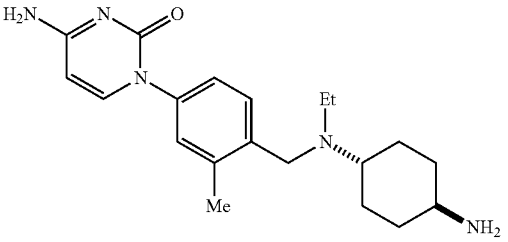 [SMILES: CCN(Cc1ccc(-n2ccc(N)nc2=O)cc1C)[C@H]1CC[C@H](N)CC1] |
| 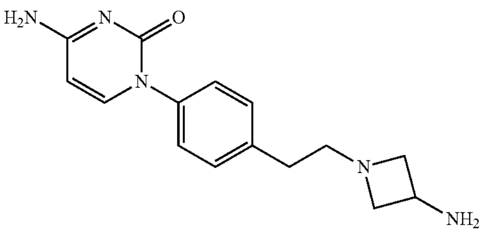 [SMILES: Nc1ccn(-c2ccc(CCN3CC(N)C3)cc2)c(=O)n1] |

TABLE 13-continued
| Compounds of Formula VI |
|---|
| Structure |
| 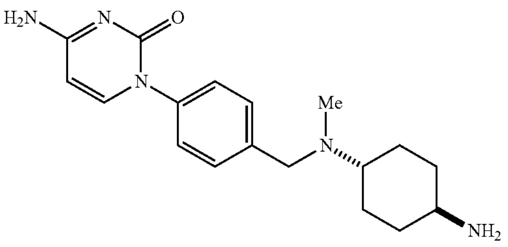 [SMILES: CN(Cc1ccc(-n2ccc(N)nc2=O)cc1)[C@H]1CC[C@H](N)CC1] |
| 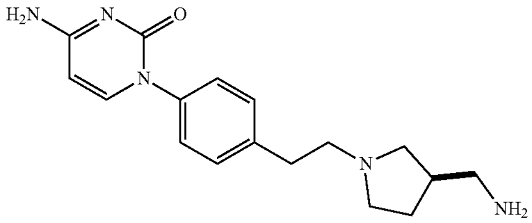 [SMILES: NC[C@H]1CCN(CCc2ccc(-n3ccc(N)nc3=O)cc2)C1] |
| 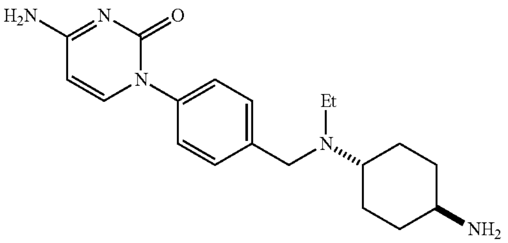 [SMILES: CCN(Cc1ccc(-n2ccc(N)nc2=O)cc1)[C@H]1CC[C@H](N)CC1] |
| 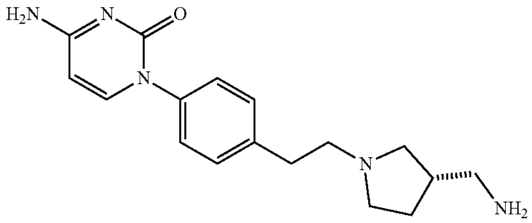 [SMILES: NC[C@@H]1CCN(CCc2ccc(-n3ccc(N)nc3=O)cc2)C1] |
| 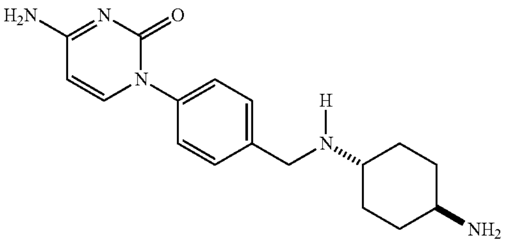 [SMILES: Nc1ccn(-c2ccc(CN[C@H]3CC[C@H](N)CC3)cc2)c(=O)n1] |
| 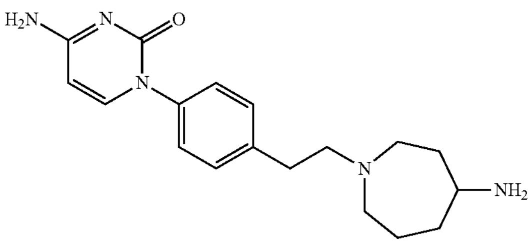 [SMILES: Nc1ccn(-c2ccc(CCN3CCCC(N)CC3)cc2)c(=O)n1] |
TABLE 13-continued
| Compounds of Formula VI |
|---|
| Structure |
| 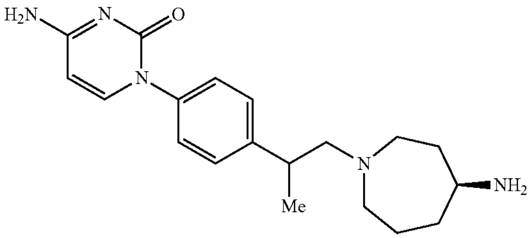 [SMILES: CC(CN1CCC[C@H](N)CC1)c1ccc(-n2ccc(N)nc2=O)cc1] |
| 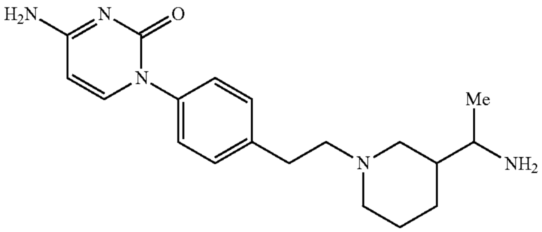 [SMILES: CC(N)C1CCCN(CCc2ccc(-n3ccc(N)nc3=O)cc2)C1] |
| 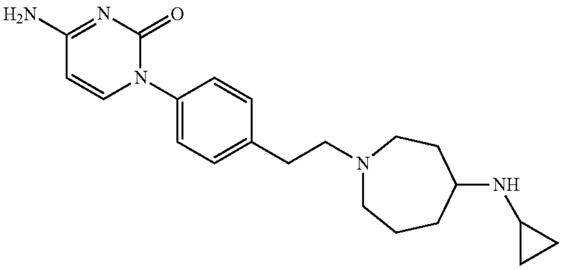 [SMILES: Nc1ccn(-c2ccc(CCN3CCCC(NC4CC4)CC3)cc2)c(=O)n1] |
| 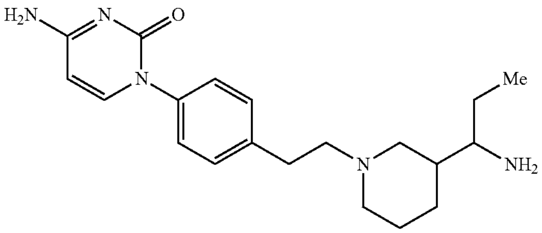 [SMILES: CCC(N)C1CCCN(CCc2ccc(-n3ccc(N)nc3=O)cc2)C1] |
| 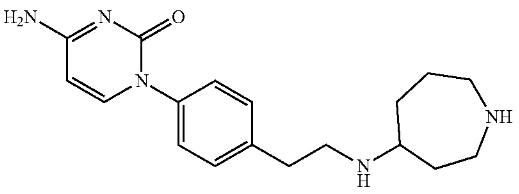 [SMILES: Nc1ccn(-c2ccc(CCNC3CCCNCC3)cc2)c(=O)n1] |
| 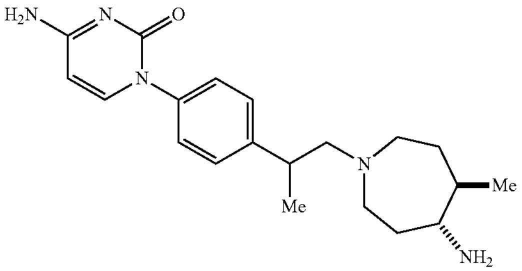 [SMILES: CC(CN1CC[C@@H](C)[C@H](N)CC1)c1ccc(-n2ccc(N)nc2=O)cc1] |

TABLE 13-continued
| Compounds of Formula VI |
| --- |
| Structure |
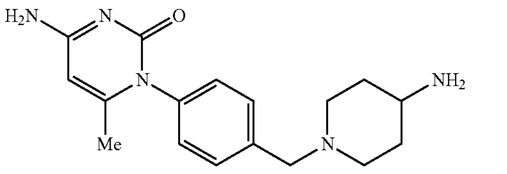 [SMILES: Cc1cc(N)nc(=O)n1-c1ccc(CN2CCC(N)CC2)cc1]
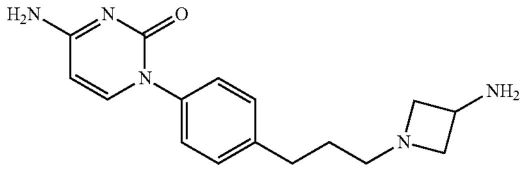 [SMILES: Nc1ccn(-c2ccc(CCCN3CC(N)C3)cc2)c(=O)n1]
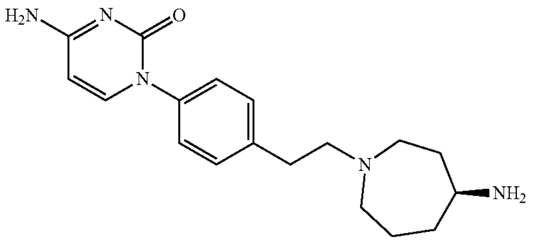 [SMILES: Nc1ccn(-c2ccc(CCN3CCC[C@H](N)CC3)cc2)c(=O)n1]
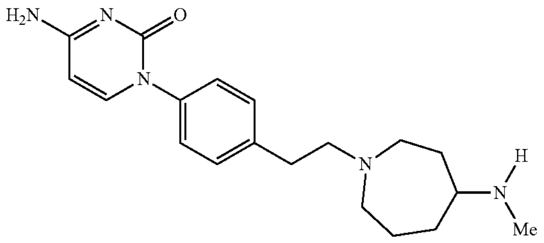 [SMILES: CNC1CCCN(CCc2ccc(-n3ccc(N)nc3=O)cc2)CC1]
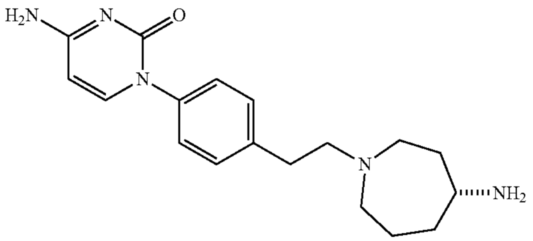 [SMILES: Nc1ccn(-c2ccc(CCN3CCC[C@@H](N)CC3)cc2)c(=O)n1]
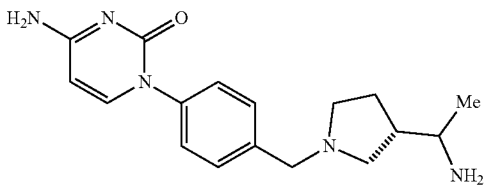
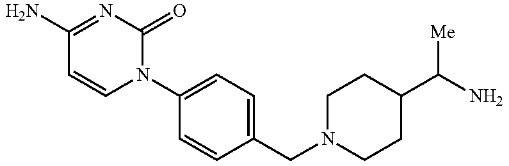 [SMILES: CC(N)C1CCN(Cc2ccc(-n3ccc(N)nc3=O)cc2)CC1]
TABLE 13-continued
| Compounds of Formula VI |
| --- |
| Structure |
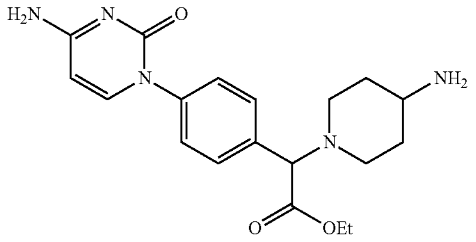
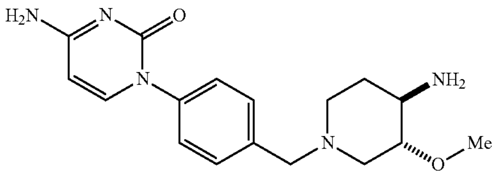 [SMILES: CO[C@@H]1CN(Cc2ccc(-n3ccc(N)nc3=O)cc2)CC[C@H]1N]
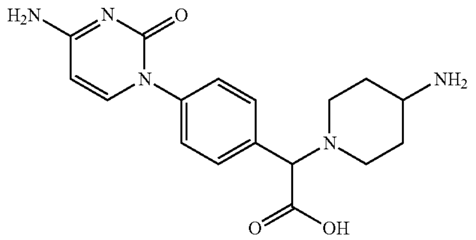 [SMILES: Nc1ccn(-c2ccc(C(C(=O)O)N3CCC(N)CC3)cc2)c(=O)n1]
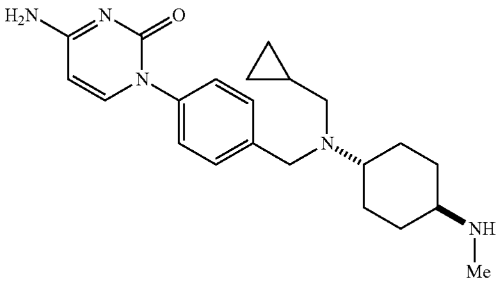
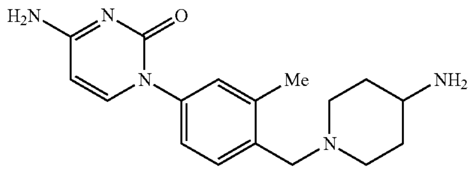 [SMILES: Cc1cc(-n2ccc(N)nc2=O)ccc1CN1CCC(N)CC1]
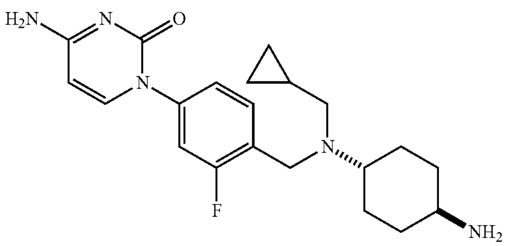
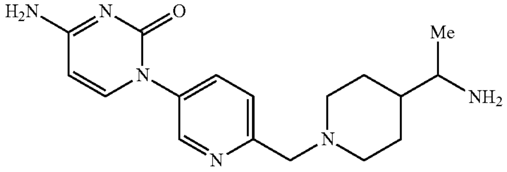 [SMILES: CC(N)C1CCN(Cc2ccc(-n3ccc(N)nc3=O)cn2)CC1]

TABLE 13-continued
| Compounds of Formula VI |
| --- |
| Structure |
| 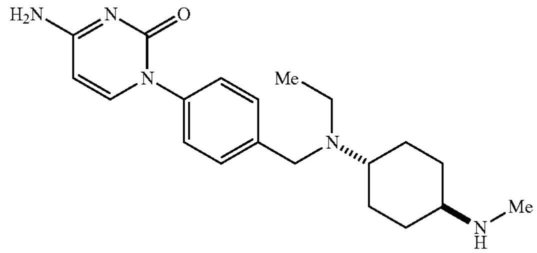 |
| 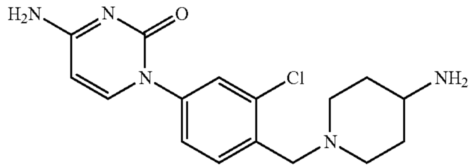 [SMILES: Nc1ccn(-c2ccc(CN3CCC(N)CC3)c(Cl)c2)c(=O)n1] |
| 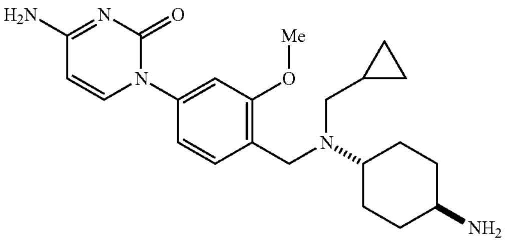 |
| 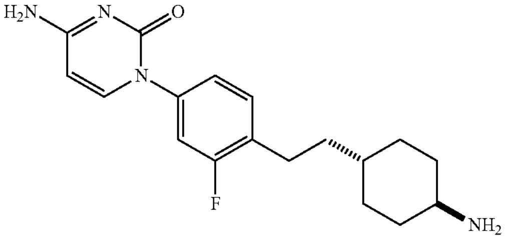 |
| 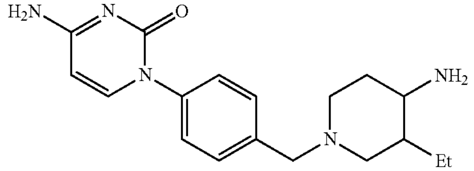 [SMILES: CCC1CN(Cc2ccc(-n3ccc(N)nc3=O)cc2)CCC1N] |
| 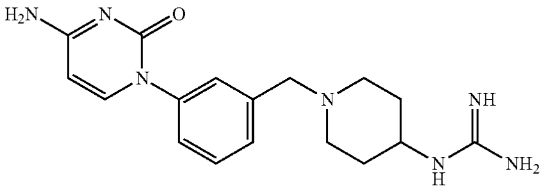 [SMILES: N=C(N)NC1CCN(Cc2cccc(-n3ccc(N)nc3=O)c2)CC1] |
| 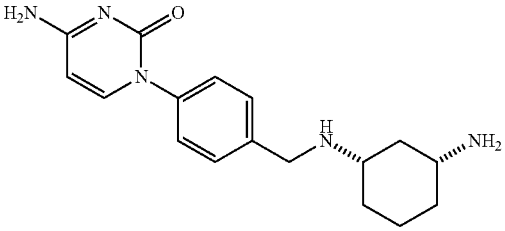 [SMILES: Nc1ccn(-c2ccc(CN[C@H]3CCC[C@@H](N)C3)cc2)c(=O)n1] |
TABLE 13-continued
| Compounds of Formula VI |
| --- |
| Structure |
| 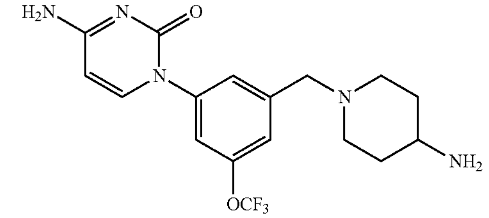 [SMILES: Nc1ccn(-c2cc(CN3CCC(N)CC3)cc(OC(F)(F)F)c2)c(=O)n1] |
| 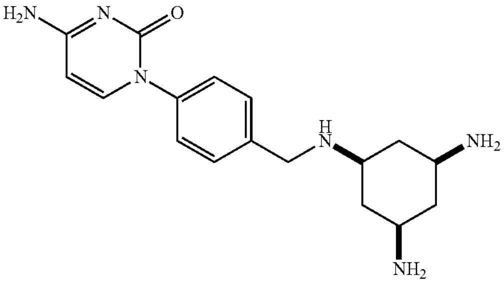 [SMILES: Nc1ccn(-c2ccc(CN[C@@H]3C[C@H](N)C[C@H](N)C3)cc2)c(=O)n1] |
| 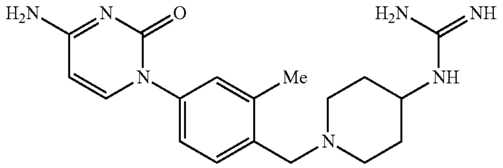 [SMILES: Cc1cc(-n2ccc(N)nc2=O)ccc1CN1CCC(NC(=N)N)CC1] |
| 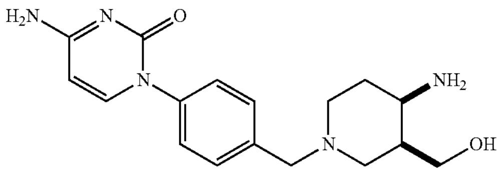 [SMILES: Nc1ccn(-c2ccc(CN3CC[C@@H](N)[C@@H](CO)C3)cc2)c(=O)n1] |
| 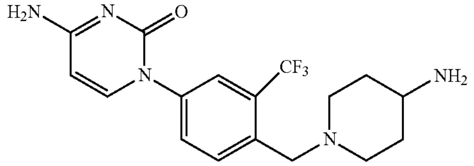 [SMILES: Nc1ccn(-c2ccc(CN3CCC(N)CC3)c(C(F)(F)F)c2)c(=O)n1] |
| 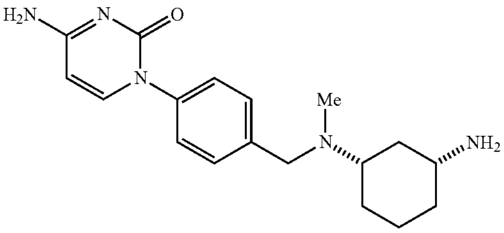 [SMILES: CN(Cc1ccc(-n2ccc(N)nc2=O)cc1)[C@H]1CCC[C@@H](N)C1] |
| 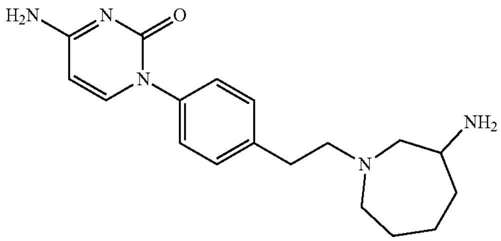 [SMILES: Nc1ccn(-c2ccc(CCN3CCCCC(N)C3)cc2)c(=O)n1] |

TABLE 13-continued
| Compounds of Formula VI |
| --- |
| Structure |
| 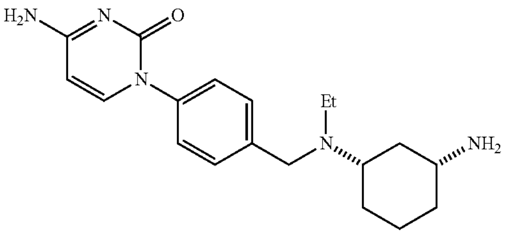 [SMILES: CCN(Cc1ccc(-n2ccc(N)nc2=O)cc1)[C@H]1CCC[C@@H](N)C1] |
| 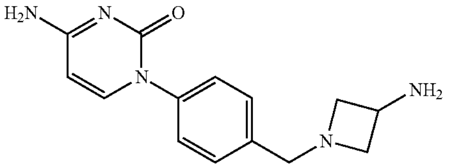 [SMILES: Nc1ccn(-c2ccc(CN3CC(N)C3)cc2)c(=O)n1] |
| 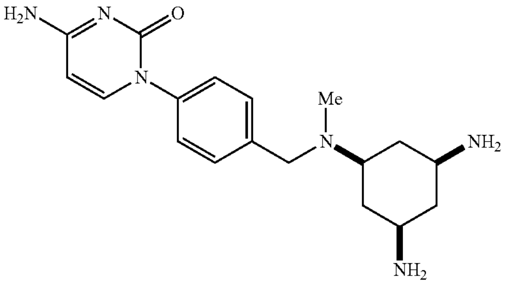 [SMILES: CN(Cc1ccc(-n2ccc(N)nc2=O)cc1)[C@@H]1C[C@H](N)C[C@H](N)C1] |
| 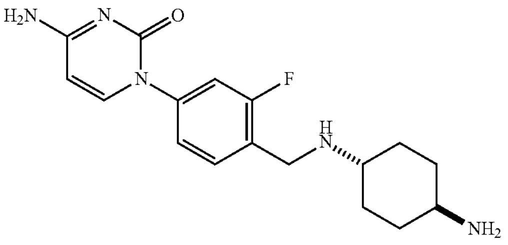 [SMILES: Nc1ccn(-c2ccc(CN[C@H]3CC[C@H](N)CC3)c(F)c2)c(=O)n1] |
| 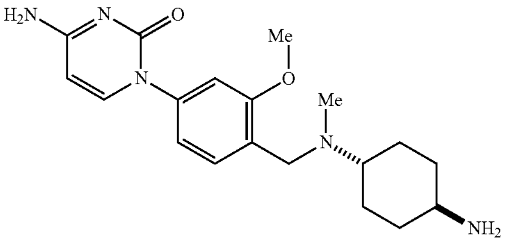 |
| 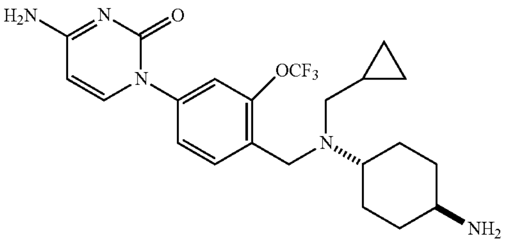 [SMILES: Nc1ccn(-c2ccc(CN(CC3CC3)[C@H]3CC[C@H](N)CC3)c(OC(F)(F)F)c2)c(=O)n1] |
TABLE 13-continued
| Compounds of Formula VI |
| --- |
| Structure |
| 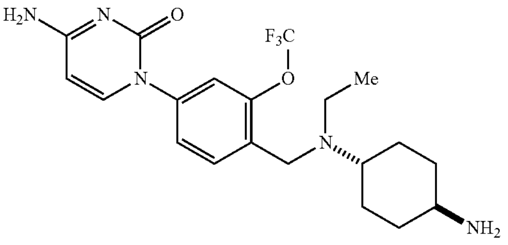 [SMILES: CCN(Cc1ccc(-n2ccc(N)nc2=O)cc1OC(F)(F)F)[C@H]1CC[C@H](N)CC1] |
| 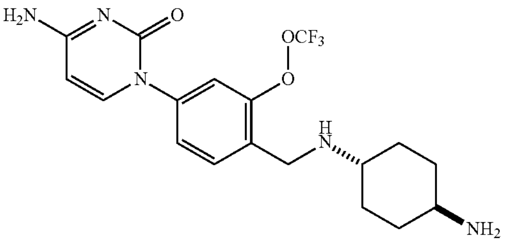 [SMILES: Nc1ccn(-c2ccc(CN[C@H]3CC[C@H](N)CC3)c(OOC(F)(F)F)c2)c(=O)n1] |
| 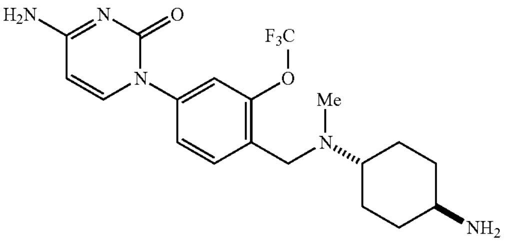 |
| 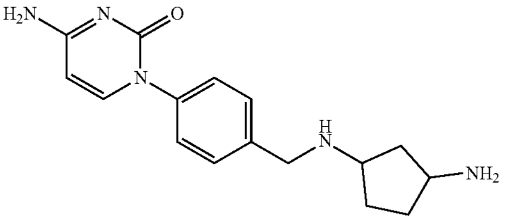 [SMILES: Nc1ccn(-c2ccc(CNC3CCC(N)C3)cc2)c(=O)n1] |
| 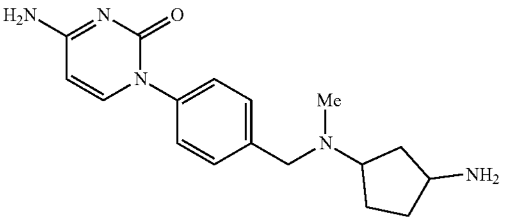 [SMILES: CN(Cc1ccc(-n2ccc(N)nc2=O)cc1)C1CCC(N)C1] |
| 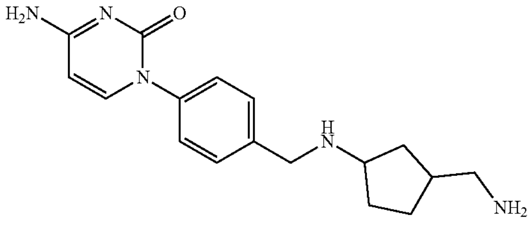 [SMILES: NCC1CCC(NCc2ccc(-n3ccc(N)nc3=O)cc2)C1] |

TABLE 13-continued
Compounds of Formula VI
Structure
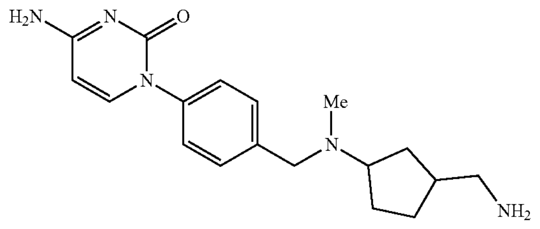
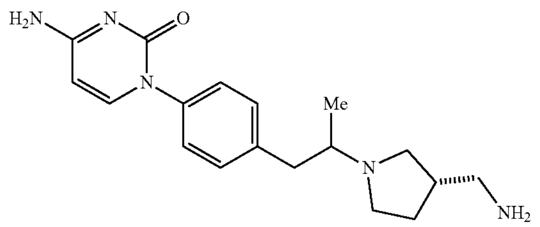
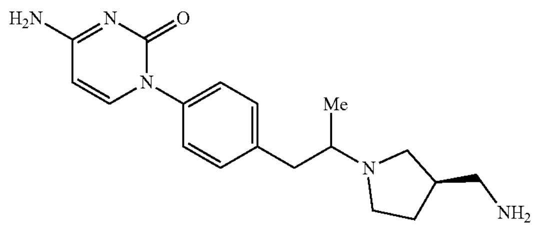 [SMILES: CC(Cc1ccc(-n2ccc(N)nc2=O)cc1)N1CC[C@H](CN)C1]
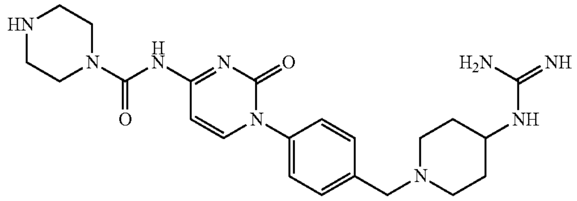 [SMILES: N=C(N)NC1CCN(Cc2ccc(-n3ccc(NC(=O)N4CCNCC4)nc3=O)cc2)CC1]
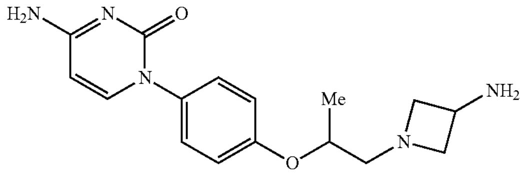 [SMILES: CC(CN1CC(N)C1)Oc1ccc(-n2ccc(N)nc2=O)cc1]
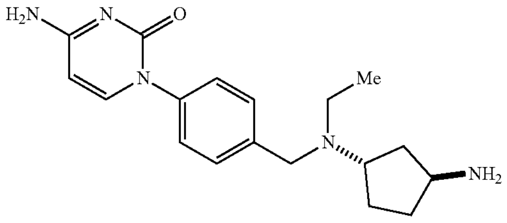
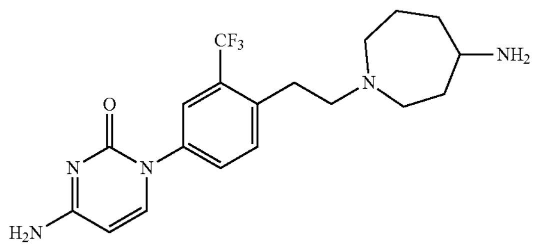 [SMILES: Nc1ccn(-c2ccc(CCN3CCCC(N)CC3)c(C(F)(F)F)c2)c(=O)n1]
TABLE 13-continued
Compounds of Formula VI
Structure
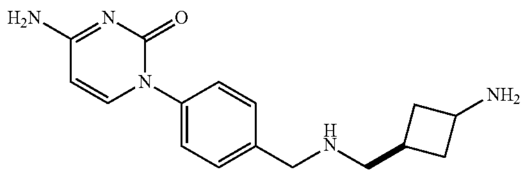
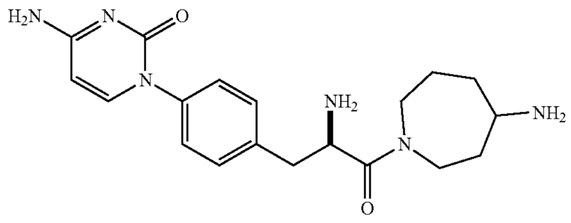
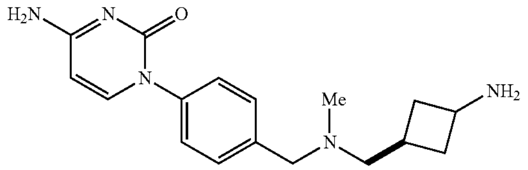
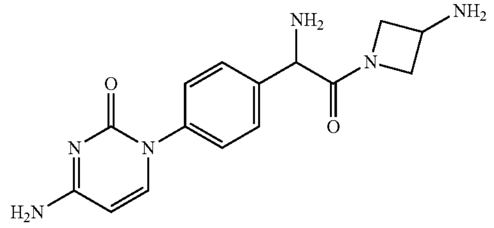 [SMILES: Nc1ccn(-c2ccc(C(N)C(=O)N3CC(N)C3)cc2)c(=O)n1]
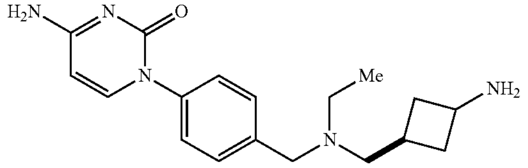
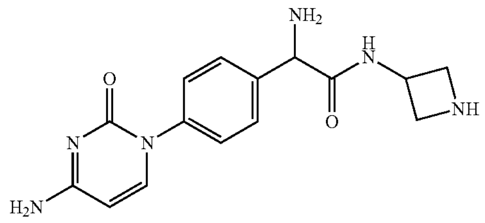 [SMILES: Nc1ccn(-c2ccc(C(N)C(=O)NC3CNC3)cc2)c(=O)n1]
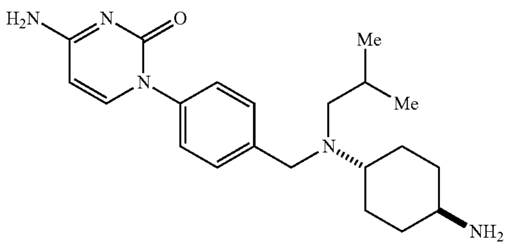 [SMILES: CC(C)CN(Cc1ccc(-n2ccc(N)nc2=O)cc1)[C@H]1CC[C@H](N)CC1]

TABLE 13-continued
| Compounds of Formula VI |
| --- |
| Structure |
| 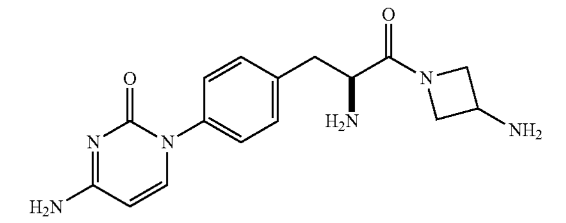 [SMILES: Nc1ccn(-c2ccc(C[C@H](N)C(=O)N3CC(N)C3)cc2)c(=O)n1] |
| 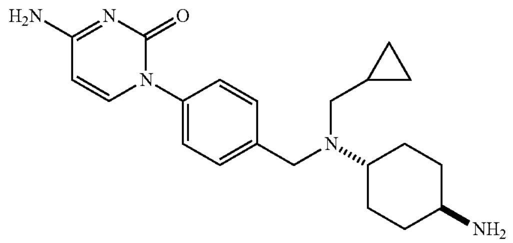 [SMILES: Nc1ccn(-c2ccc(CN(CC3CC3)[C@H]3CC[C@H](N)CC3)cc2)c(=O)n1] |
| 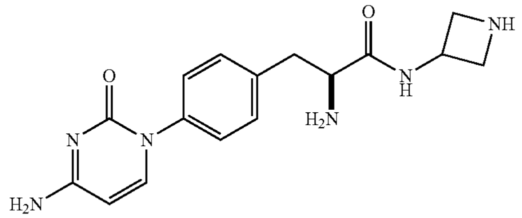 [SMILES: Nc1ccn(-c2ccc(C[C@H](N)C(=O)NC3CNC3)cc2)c(=O)n1] |
| 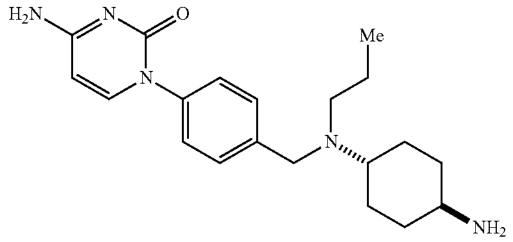 [SMILES: CCCN(Cc1ccc(-n2ccc(N)nc2=O)cc1)[C@H]1CC[C@H](N)CC1] |
| 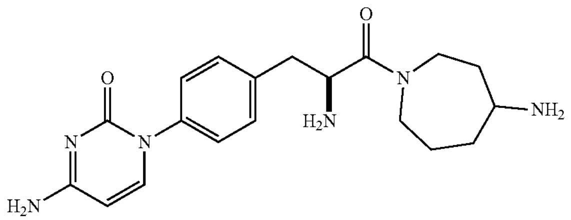 [SMILES: Nc1ccn(-c2ccc(C[C@H](N)C(=O)N3CCCC(N)CC3)cc2)c(=O)n1] |
| 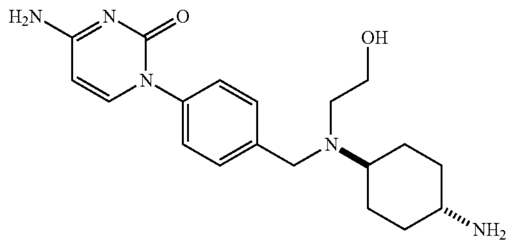 [SMILES: Nc1ccn(-c2ccc(CN(CCO)[C@H]3CC[C@H](N)CC3)cc2)c(=O)n1] |
TABLE 13-continued
| Compounds of Formula VI |
| --- |
| Structure |
| 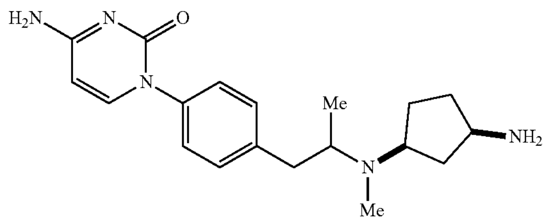 |
| 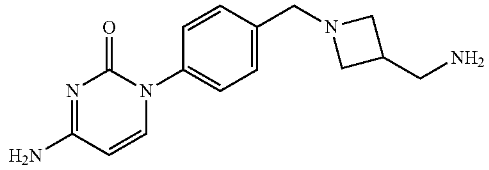 [SMILES: NCC1CN(Cc2ccc(-n3ccc(N)nc3=O)cc2)C1] |
| 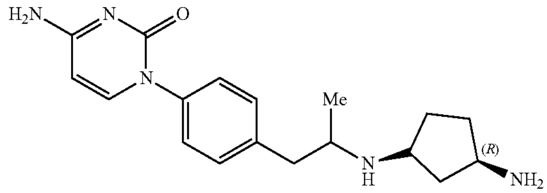 |
| 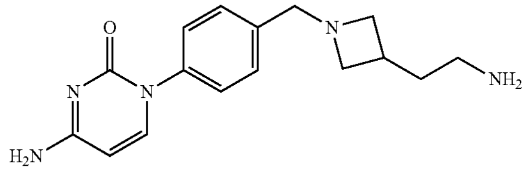 [SMILES: NCCC1CN(Cc2ccc(-n3ccc(N)nc3=O)cc2)C1] |
| 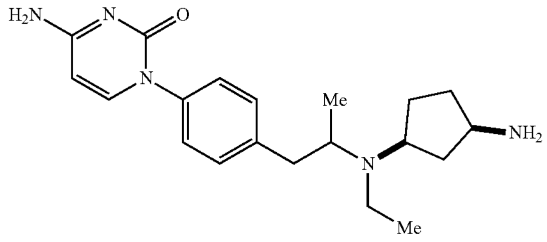 |
| 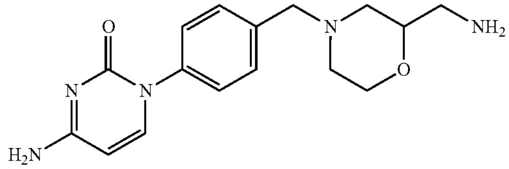 [SMILES: NCC1CN(Cc2ccc(-n3ccc(N)nc3=O)cc2)CCO1] |
| 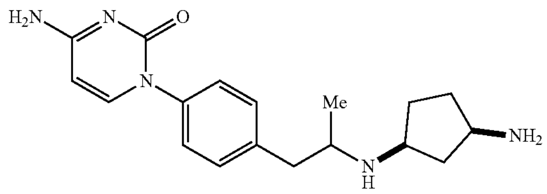 |

TABLE 13-continued
| Compounds of Formula VI |
| --- |
| Structure |
| 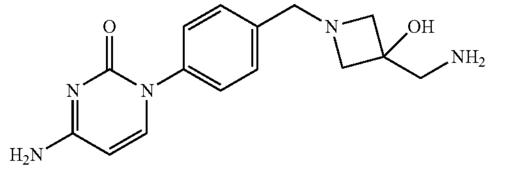 [SMILES: NCC1(O)CN(Cc2ccc(-n3ccc(N)nc3=O)cc2)C1] |
| 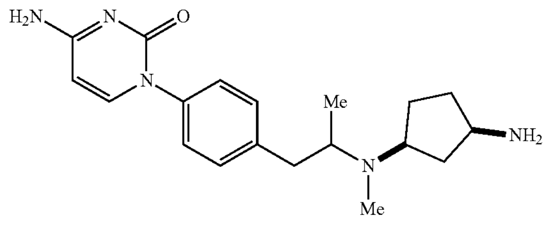 |
| 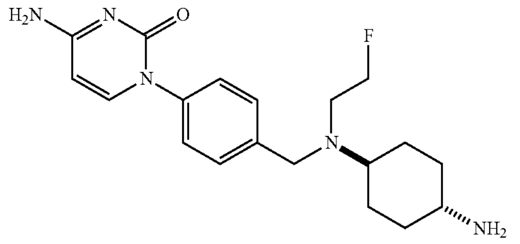 [SMILES: Nc1ccn(-c2ccc(CN(CCF)[C@H]3CC[C@H](N)CC3)cc2)c(=O)n1] |
| 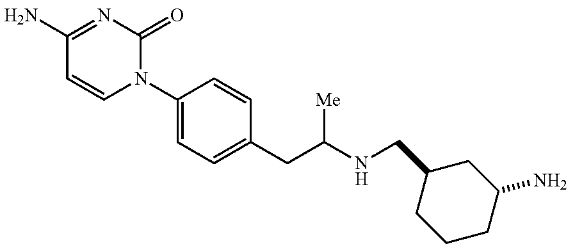 |
| 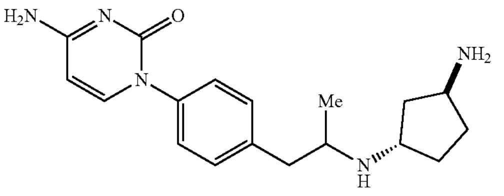 [SMILES: CC(Cc1ccc(-n2ccc(N)nc2=O)cc1)N[C@H]1CC[C@H](N)C1] |
| 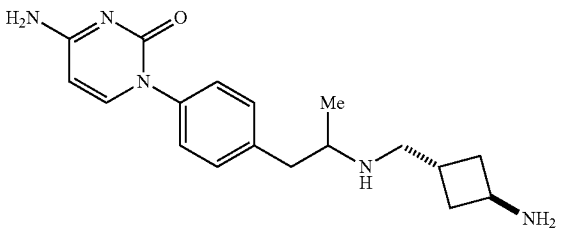 |
| 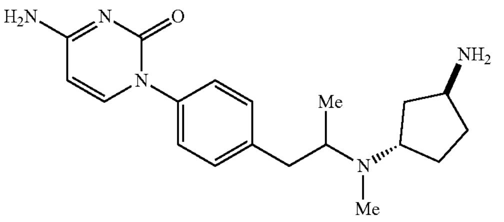 [SMILES: CC(Cc1ccc(-n2ccc(N)nc2=O)cc1)N(C)[C@H]1CC[C@H](N)C1] |
TABLE 13-continued
| Compounds of Formula VI |
| --- |
| Structure |
| 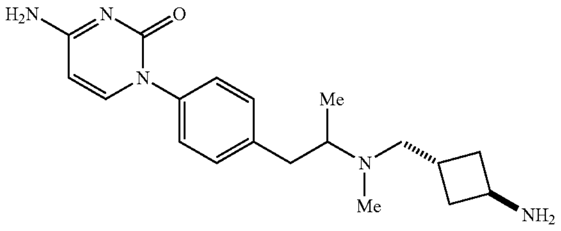 |
| 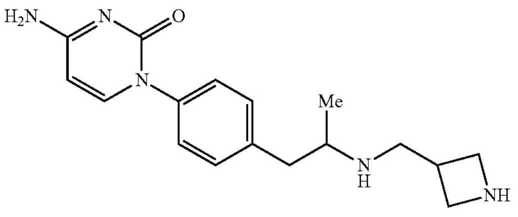 [SMILES: CC(Cc1ccc(-n2ccc(N)nc2=O)cc1)NCC1CNC1] |
| 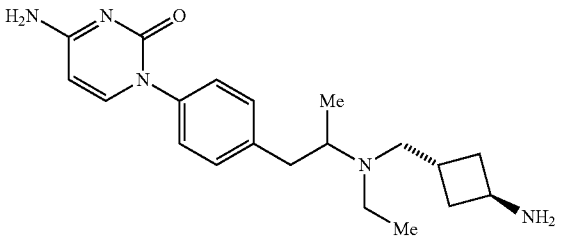 |
| 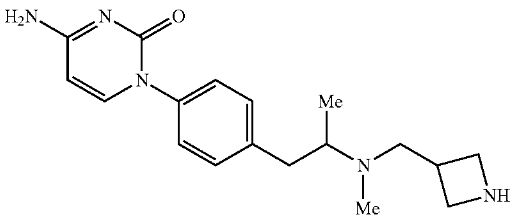 [SMILES: CC(Cc1ccc(-n2ccc(N)nc2=O)cc1)N(C)CC1CNC1] |
| 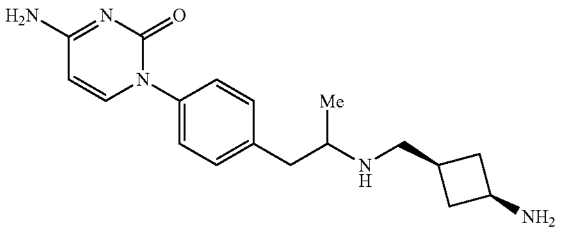 [SMILES: CC(Cc1ccc(-n2ccc(N)nc2=O)cc1)NC[C@H]1C[C@@H](N)C1] |
| 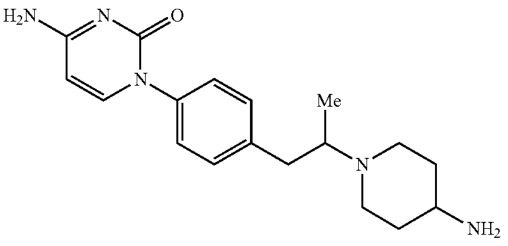 [SMILES: CC(Cc1ccc(-n2ccc(N)nc2=O)cc1)N1CCC(N)CC1] |

TABLE 13-continued
| Compounds of Formula VI Structure |
|---|
| 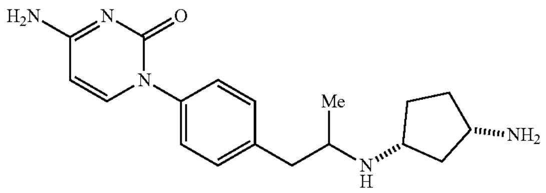 |
| 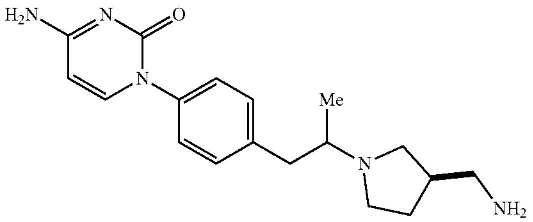 [SMILES: CC(Cc1ccc(-n2ccc(N)nc2=O)cc1)N1CC[C@H](CN)C1] |
| 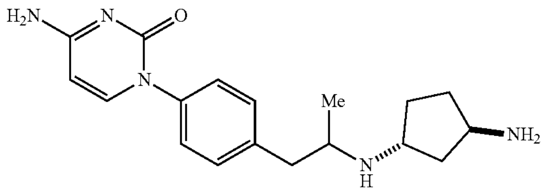 |
| 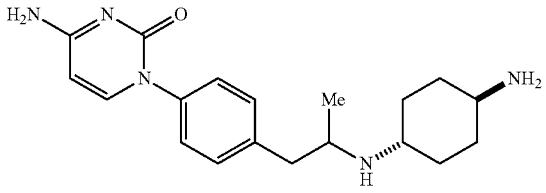 |
| 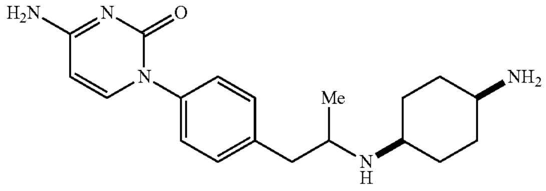 |
| 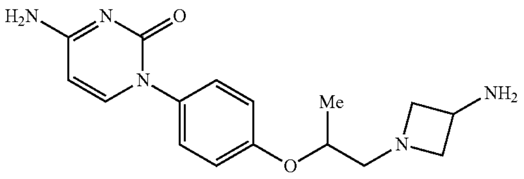 [SMILES: CC(CN1CC(N)C1)Oc1ccc(-n2ccc(N)nc2=O)cc1] |
| 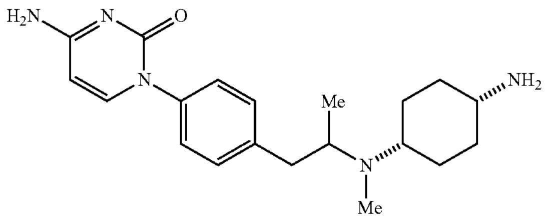 |
TABLE 13-continued
| Compounds of Formula VI Structure |
|---|
| 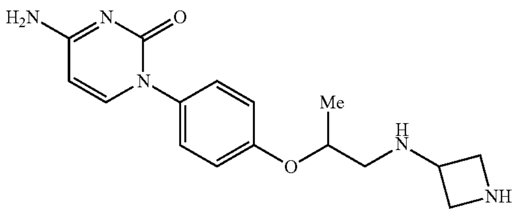 [SMILES: CC(CNC1CNC1)Oc1ccc(-n2ccc(N)nc2=O)cc1] |
| 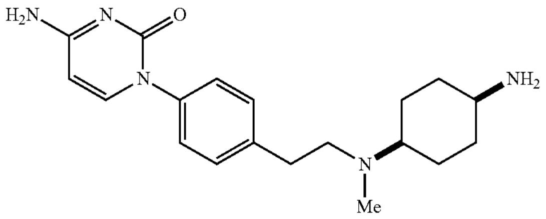 |
| 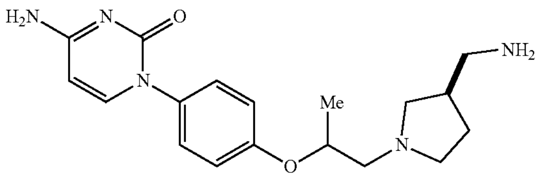 [SMILES: CC(CN1CC[C@H](CN)C1)Oc1ccc(-n2ccc(N)nc2=O)cc1] |
| 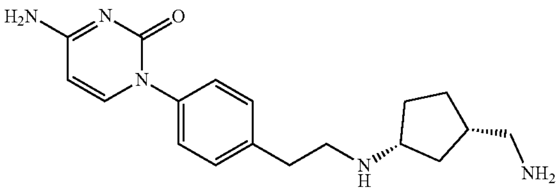 [SMILES: NC[C@H]1CC[C@@H](NCCc2ccc(-n3ccc(N)nc3=O)cc2)C1] |
| 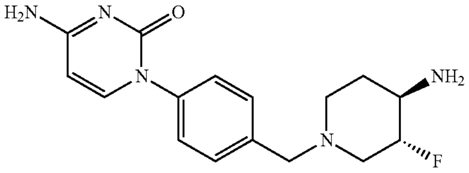 [SMILES: Nc1ccn(-c2ccc(CN3CC[C@@H](N)[C@H](F)C3)cc2)c(=O)n1] |
| 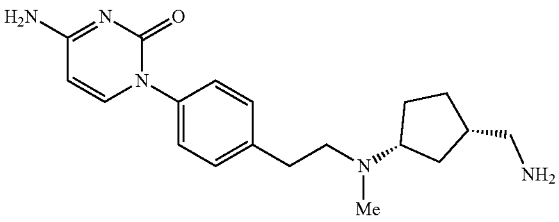 [SMILES: CN(CCc1ccc(-n2ccc(N)nc2=O)cc1)[C@@H]1CC[C@H](CN)C1] |
| 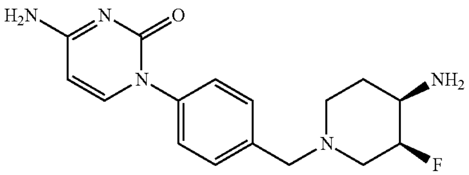 [SMILES: Nc1ccn(-c2ccc(CN3CC[C@@H](N)[C@@H](F)C3)cc2)c(=O)n1] |

TABLE 13-continued
| Compounds of Formula VI |
| --- |
| Structure |
| 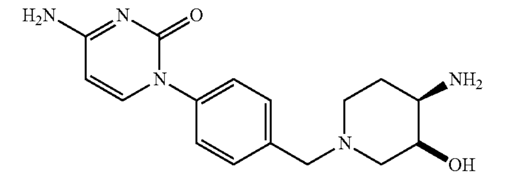 [SMILES: Nc1ccn(-c2ccc(CN3CC[C@@H](N)[C@@H](O)C3)cc2)c(=O)n1] |
| 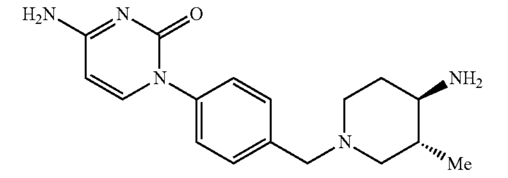 [SMILES: C[C@@H]1CN(Cc2ccc(-n3ccc(N)nc3=O)cc2)CC[C@H]1N] |
| 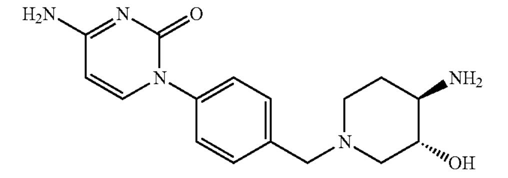 [SMILES: Nc1ccn(-c2ccc(CN3CC[C@@H](N)[C@H](O)C3)cc2)c(=O)n1] |
| 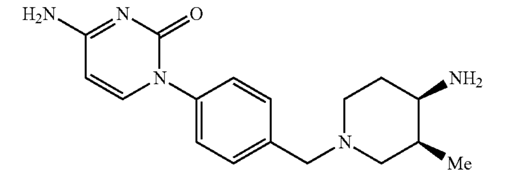 [SMILES: C[C@H]1CN(Cc2ccc(-n3ccc(N)nc3=O)cc2)CC[C@H]1N] |
| 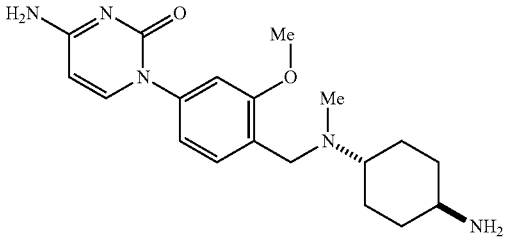 [SMILES: COc1cc(-n2ccc(N)nc2=O)ccc1CN(C)[C@H]1CC[C@H](N)CC1] |
| 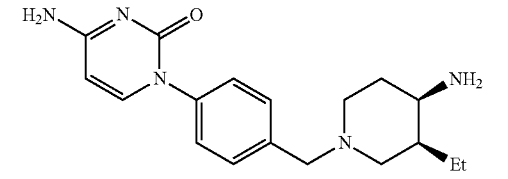 [SMILES: CC[C@H]1CN(Cc2ccc(-n3ccc(N)nc3=O)cc2)CC[C@H]1N] |
| 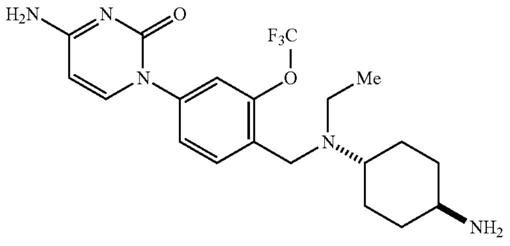 [SMILES: CCN(Cc1ccc(-n2ccc(N)nc2=O)cc1OC(F)(F)F)[C@H]1CC[C@H](N)CC1] |
TABLE 13-continued
| Compounds of Formula VI |
| --- |
| Structure |
| 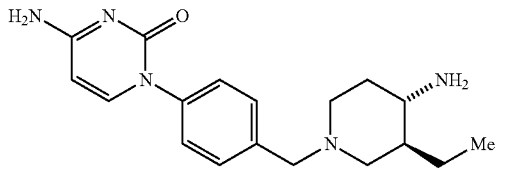 [SMILES: CC[C@H]1CN(Cc2ccc(-n3ccc(N)nc3=O)cc2)CC[C@@H]1N] |
| 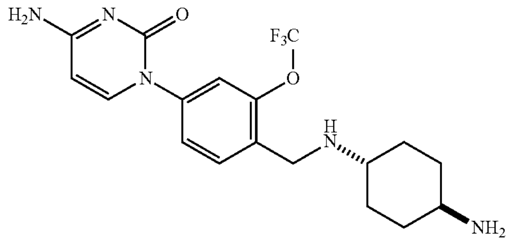 [SMILES: Nc1ccn(-c2ccc(CN[C@H]3CC[C@H](N)CC3)c(OC(F)(F)F)c2)c(=O)n1] |
| 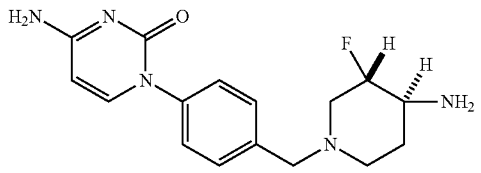 [SMILES: Nc1ccn(-c2ccc(CN3CC[C@H](N)[C@@H](F)C3)cc2)c(=O)n1] |
| 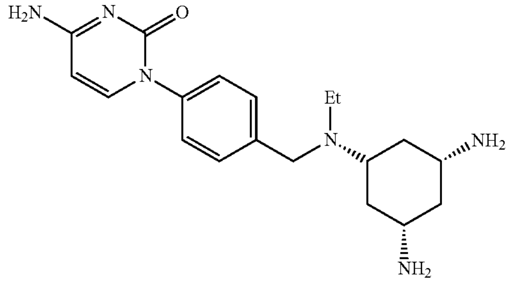 |
| 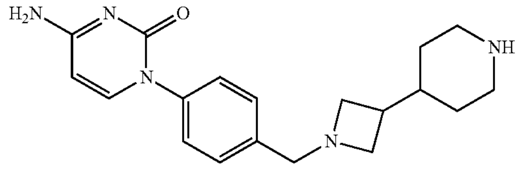 [SMILES: Nc1ccn(-c2ccc(CN3CC(C4CCNCC4)C3)cc2)c(=O)n1] |
| 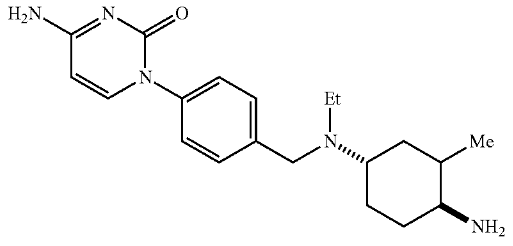 [SMILES: CCN(Cc1ccc(-n2ccc(N)nc2=O)cc1)[C@H]1CC[C@H](N)C(C)C1] |
| 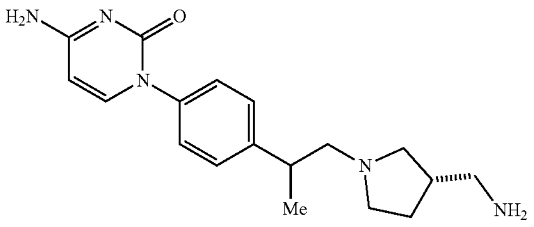 [SMILES: CC(CN1CC[C@@H](CN)C1)c1ccc(-n2ccc(N)nc2=O)cc1] |

TABLE 13-continued

| Compounds of Formula VI Structure |
|---|
| 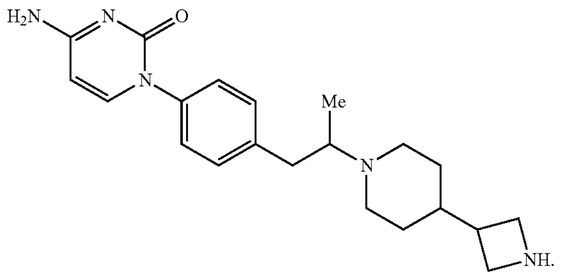 [SMILES: CC(Cc1ccc(-n2ccc(N)nc2=O)cc1)N1CCC(C2CNC2)CC1] |

In another aspect, the disclosure provides a compound formula F:

E

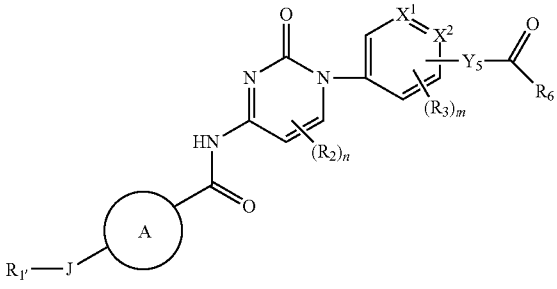

or a pharmaceutically acceptable salt thereof wherein ring A, ring B, J, $X^1$, $X^2$, $R_{1'}$, $R_2$, $R_3$, $R_6$, m, and n have the same definitions in the preceding paragraphs; $Y_5$ is a bond or is a linear $C_1$-$C_7$ alkylene, $C_2$-$C_7$ alkenylene, or $C_2$-$C_7$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, wherein up to two carbon atoms of the $C_2$-$C_7$ alkylene, $C_2$-$C_7$alkenylene, or $C_2$-$C_7$ alkynylene may be independently replaced by O, (C═O), or

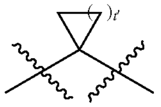

wherein t' is 1, 2, 3, or 4; and $R_6$ is H or $C_1$-$C_6$ alkyl.

In another embodiment of the compound of formula E or a pharmaceutically acceptable salt, $Y_5$ is a bond or is a linear $C_1$-$C_3$ alkylene optionally substituted with OH, $NH_2$, halo, $C_1$-$C_6$ alkyl, or $C_1$-$C_6$ alkoxy.

In an embodiment, the compound of formula E or pharmaceutically acceptable salt thereof is selected from the compounds as depicted in Table 14 below.

TABLE 14

| Compound of formula E |
|---|
| 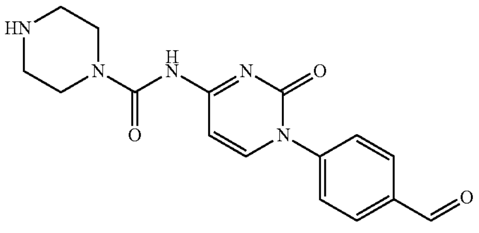 [SMILES: O=Cc1ccc(-n2ccc(NC(=O)N3CCNCC3)nc2=O)cc1] |
| 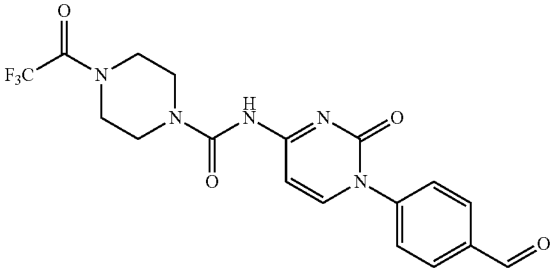 |

TABLE 14-continued
| Compound of formula E |
| --- |
| 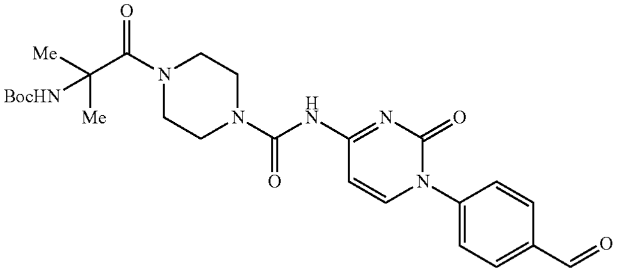 [SMILES: CC(C)(C)OC(=O)NC(C)(C)C(=O)N1CCN(C(=O)Nc2ccn(-c3ccc(C=O)cc3)c(=O)n2)CC1] |
| 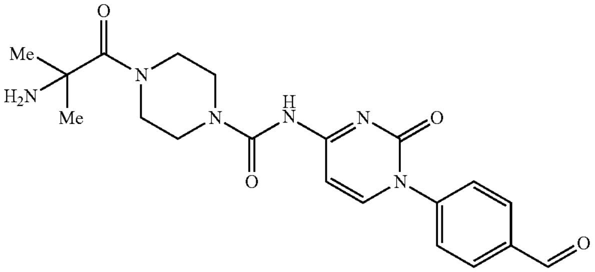 [SMILES: CC(C)(N)C(=O)N1CCN(C(=O)Nc2ccn(-c3ccc(C=O)cc3)c(=O)n2)CC1] |
| 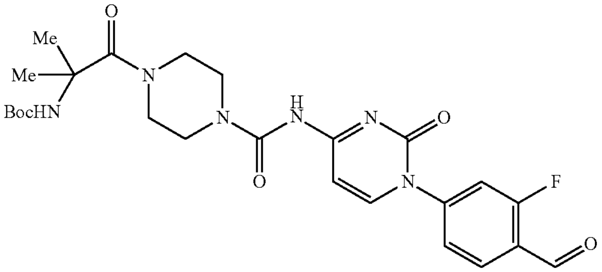 [SMILES: CC(C)(C)OC(=O)NC(C)(C)C(=O)N1CCN(C(=O)Nc2ccn(-c3ccc(C=O)c(F)c3)c(=O)n2)CC1] |
| 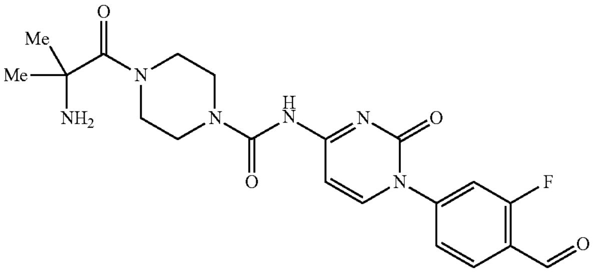 [SMILES: CC(C)(N)C(=O)N1CCN(C(=O)Nc2ccn(-c3ccc(C=O)c(F)c3)c(=O)n2)CC1] |
| 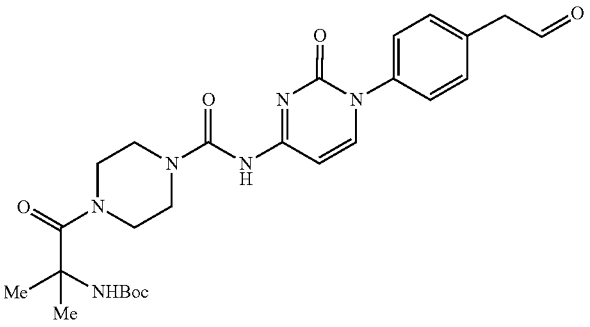 [SMILES: CC(C)(C)OC(=O)NC(C)(C)C(=O)N1CCN(C(=O)Nc2ccn(-c3ccc(CC=O)cc3)c(=O)n2)CC1] |

TABLE 14-continued
| Compound of formula E |
| --- |
| 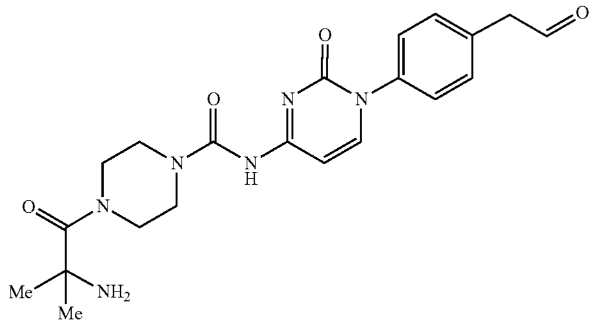 [SMILES: CC(C)(N)C(=O)N1CCN(C(=O)Nc2ccn(-c3ccc(CC=O)cc3)c(=O)n2)CC1] |
| 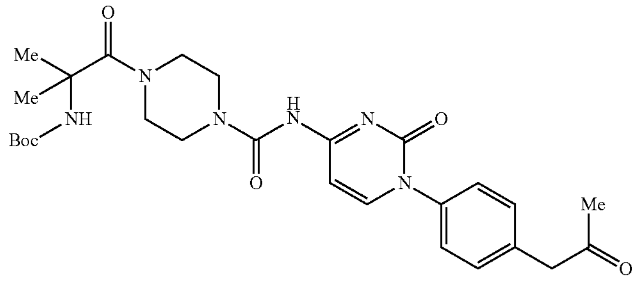 [SMILES: CC(=O)Cc1ccc(-n2ccc(NC(=O)N3CCN(C(=O)C(C)(C)NC(=O)OC(C)(C)C)CC3)nc2=O)cc1] |
| 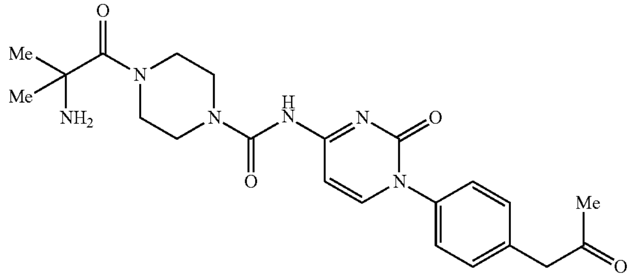 [SMILES: CC(=O)Cc1ccc(-n2ccc(NC(=O)N3CCN(C(=O)C(C)(C)N)CC3)nc2=O)cc1] |
| 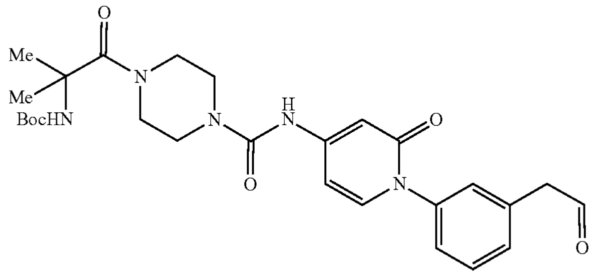 [SMILES: CC(C)(C)OC(=O)NC(C)(C)C(=O)N1CCN(C(=O)Nc2ccn(-c3cccc(CC=O)c3)c(=O)c2)CC1] |
| 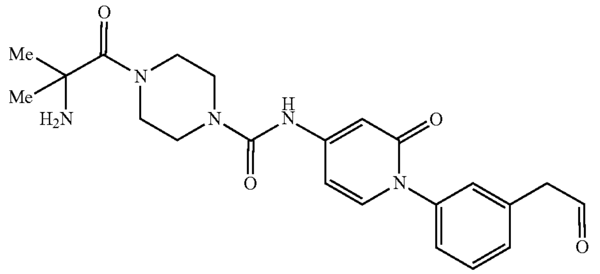 [SMILES: CC(C)(N)C(=O)N1CCN(C(=O)Nc2ccn(-c3cccc(CC=O)c3)c(=O)c2)CC1] |

TABLE 14-continued
| Compound of formula E |
| --- |
| 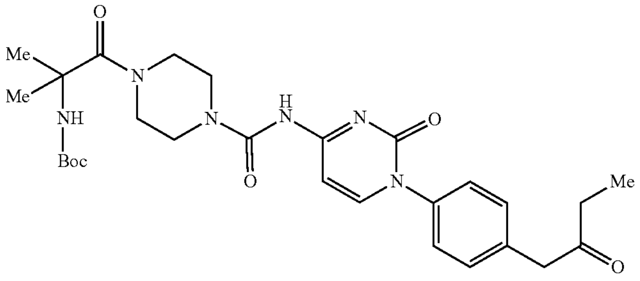 [SMILES: CCC(=O)Cc1ccc(-n2ccc(NC(=O)N3CCN(C(=O)C(C)(C)NC(=O)OC(C)(C)C)CC3)nc2=O)cc1] |
| 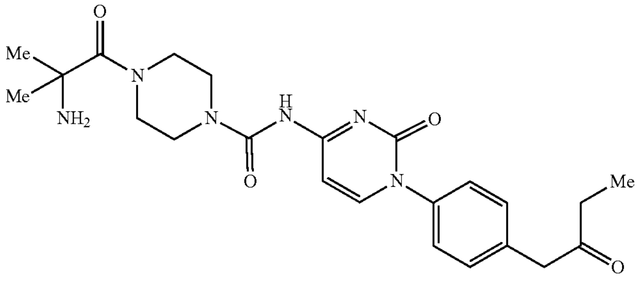 [SMILES: CCC(=O)Cc1ccc(-n2ccc(NC(=O)N3CCN(C(=O)C(C)(C)N)CC3)nc2=O)cc1] |
| 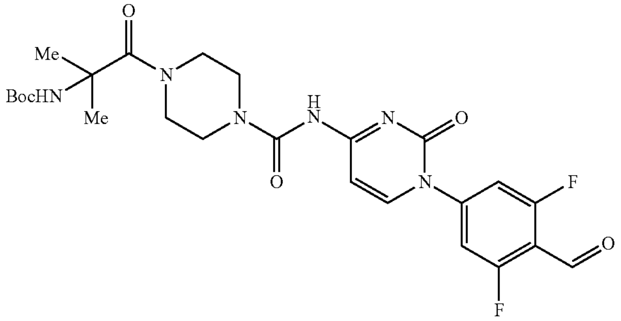 [SMILES: CC(C)(C)OC(=O)NC(C)(C)C(=O)N1CCN(C(=O)Nc2ccn(-c3cc(F)c(C=O)c(F)c3)c(=O)n2)CC1] |
| 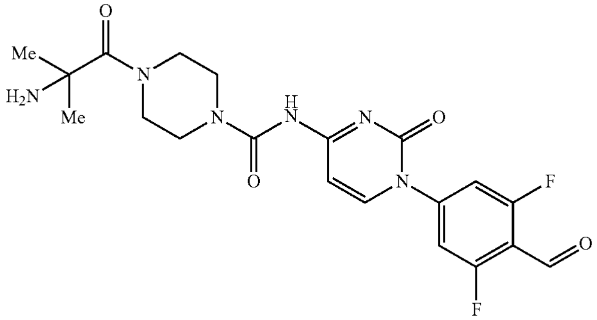 [SMILES: CC(C)(N)C(=O)N1CCN(C(=O)Nc2ccn(-c3cc(F)c(C=O)c(F)c3)c(=O)n2)CC1] |
| 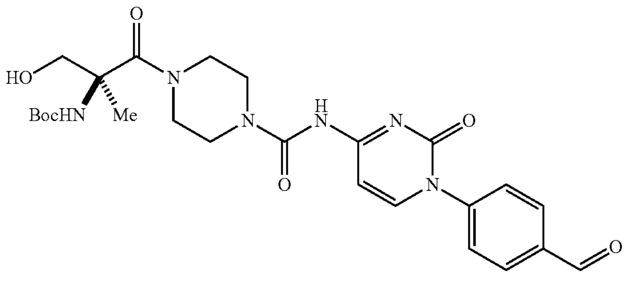 [SMILES: CC(C)(C)OC(=O)N[C@@](C)(CO)C(=O)N1CCN(C(=O)Nc2ccn(-c3ccc(C=O)cc3)c(=O)n2)CC1] |

TABLE 14-continued
| Compound of formula E |
|---|
| 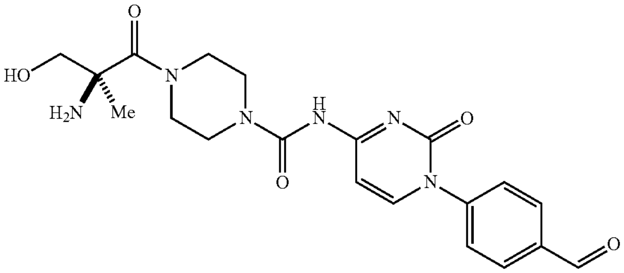 [SMILES: C[C@](N)(CO)C(=O)N1CCN(C(=O)Nc2ccn(-c3ccc(C=O)cc3)c(=O)n2)CC1] |
| 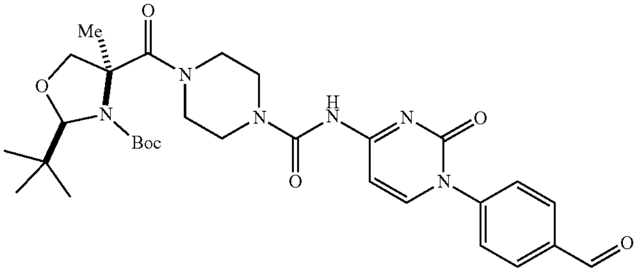 [SMILES: CC(C)(C)OC(=O)N1[C@@H](C(C)(C)C)OC[C@]1(C)C(=O)N1CCN(C(=O)Nc2ccn(-c3ccc(C=O)cc3)c(=O)n2)CC1] |
| 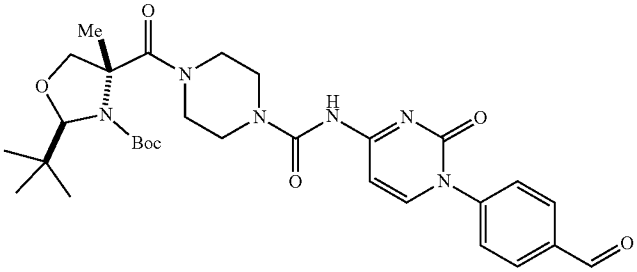 [SMILES: CC(C)(C)OC(=O)N1[C@@H](C(C)(C)C)OC[C@@]1(C)C(=O)N1CCN(C(=O)Nc2ccn(-c3ccc(C=O)cc3)c(=O)n2)CC1] |
| 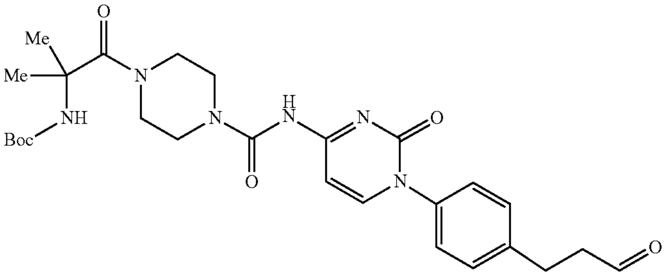 [SMILES: CC(C)(C)OC(=O)NC(C)(C)C(=O)N1CCN(C(=O)Nc2ccn(-c3ccc(CCC=O)cc3)c(=O)n2)CC1] |
| 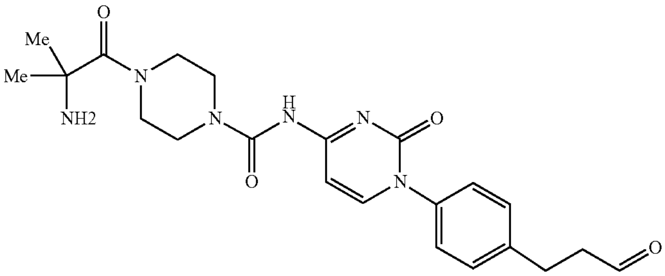 [SMILES: CC(C)(N)C(=O)N1CCN(C(=O)Nc2ccn(-c3ccc(CCC=O)cc3)c(=O)n2)CC1] |

TABLE 14-continued

| Compound of formula E |
|---|
| 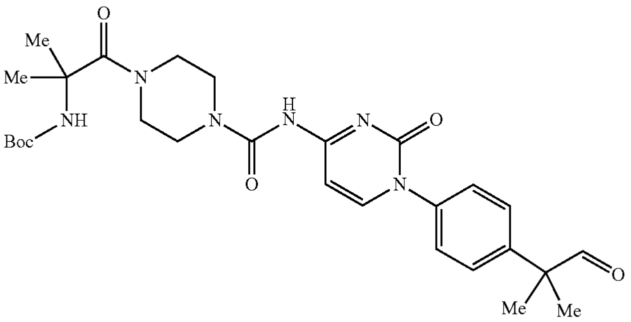 [SMILES: CC(C)(C)OC(=O)NC(C)(C)C(=O)N1CCN(C(=O)Nc2ccn(-c3ccc(C(C)(C)C=O)cc3)c(=O)n2)CC1] |
| 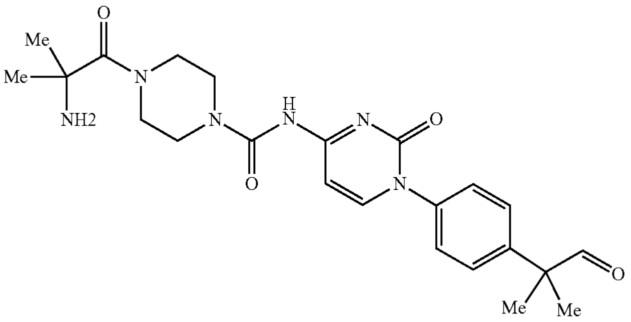 [SMILES: CC(C)(N)C(=O)N1CCN(C(=O)Nc2ccn(-c3ccc(C(C)(C)C=O)cc3)c(=O)n2)CC1] |
| 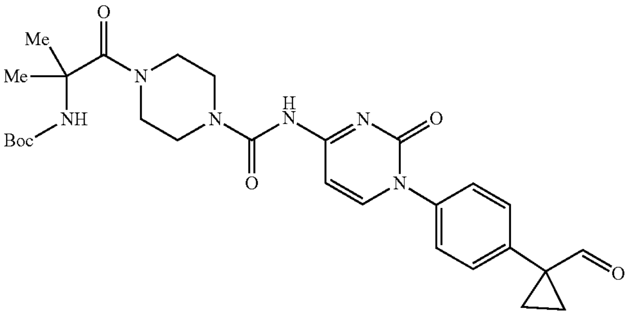 [SMILES: CC(C)(C)OC(=O)NC(C)(C)C(=O)N1CCN(C(=O)Nc2ccn(-c3ccc(C4(C=O)CC4)cc3)c(=O)n2)CC1] |
| 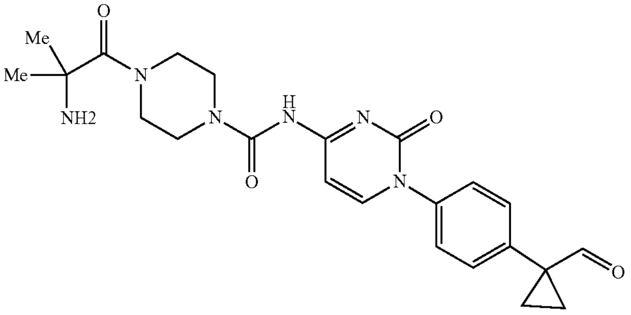 [SMILES: CC(C)(N)C(=O)N1CCN(C(=O)Nc2ccn(-c3ccc(C4(C=O)CC4)cc3)c(=O)n2)CC1] |

Pharmaceutical Compositions and Administration

The present invention provides pharmaceutical compositions comprising a compound of the present invention and a pharmaceutically acceptable excipient. In certain embodiments, the compound of the present invention is provided in an effective amount in the pharmaceutical composition. In certain embodiments, the effective amount is a therapeutically effective amount. In certain embodiments, the effective amount is a prophylactically effective amount.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof: malic acid and salts and hydrates thereof: phosphoric acid and salts and hydrates thereof: and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

To practice the method of this invention, the above-described compound or its pharmaceutical composition can be administered orally, parenterally, by inhalation spray, topically, rectally, nasally, buccally, vaginally, rectally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Additional therapeutically active agents include antibiotic agents, e.g., antibiotics useful for treating tuberculosis. Exemplary antibiotics include, but are not limited to, isoniazid, rifampin, pyrazinamide, ethambutol, and streptomycin.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Uses and Methods of Treatment

In another aspect, the invention provides a method of treating a bacterial infection in a patient in need of such treatment, comprising administering an effective amount of a compound of formula I or a pharmaceutically acceptable salt thereof or a composition comprising a compound of formula I or a pharmaceutically acceptable salt thereof. In certain embodiments, the effective amount is a therapeutically effective amount. In certain other embodiments, the effective amount is a prophylactically effective amount.

In some embodiments, the compounds of the invention can be active against a wide range of both Gram-positive and Gram-negative organisms. In these and other embodiments, the compounds of the invention can be used to treat infections and to inhibit microbial growth. Thus, the compounds of the invention can be used to treat humans and animals having a broad spectrum of bacterial infections such as impetigo, pneumonia, bronchitis, pharyngitis, endocarditis, urinary tract infections, diabetes foot ulcers, gastro-intestinal infections and bacteremia. These bacterial infections could be caused by any of the following bacteria—*Staphylococcus aureus*, coagulase negative staphylococci, methicillin-resistant *Staphylococcus aureus*, methicillin-resistant coagulase negative staphylococci, enterococci, beta-haemolytic streptococci, *viridans* group of streptococci, *Bacillus* mycobacterial infections due to multi-drug resistant *M. tuberculosis* and other atypical mycobacteria such as *M. intracellulare* and *M. avium*, as well as newly emerging Gram-negative pathogens such as *Chryseobacterium meningosepticum, Chryseobacterium indologense* and other Gram-negative pathogens such as *E. coli, Klebsiella, Proteus, Serratia, Citrobacter, Pseudomonas, Burkholderia, Brucella, Yersinia, Francisella, Coxiella, Chlamydia, Salmonella, Rickettsia, Shigella* and *Campylobacter.*

In one embodiment, the bacterial infection is tuberculosis. In certain embodiments, the tuberculosis infection is a *Mycobacterium tuberculosis* infection. In certain embodiments, the tuberculosis infection is multi-drug-resistant tuberculosis (MDR-TB) infection, e.g., resistant to first-line TB drugs rifampicin and/or isoniazid. In certain embodiments, the tuberculosis infection is extensively-drug-resistant tuberculosis (XDR-TB) infection, e.g., also resistant to three or more of the six classes of second-line drugs (see, e.g., Centers for Disease Control and Prevention (CDC) (2006). "Emergence of *Mycobacterium tuberculosis* with extensive resistance to second-line drugs worldwide, 2000-2004". MMWR Morb Mortal Wkly Rep 55 (11): 301-5).

Processes

In some aspects, the compounds and intermediates of the present disclosure can be prepared according to General Synthetic Schemes G-1 and G-2 below. In the general schemes, variables such as ring A, ring B, J, L, $X^1$, $X^2$, Y, $R_1$, $R_{1'}$, $R_2$, $R_3$, $R_6$, m, and n have the same definitions in the preceding paragraphs; $Y_5$ is a bond or is a linear $C_1$-$C_7$ alkylene, $C_2$-$C_7$ alkenylene, or $C_2$-$C_7$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, (C═O), or

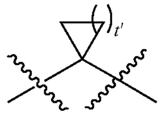

, wherein t' is 1, 2, 3, or 4; $R_6$ is H or $C_1$-$C_6$ alkyl; X is halo; and P is a hydroxyl protecting group.

General Synthetic Scheme G-1

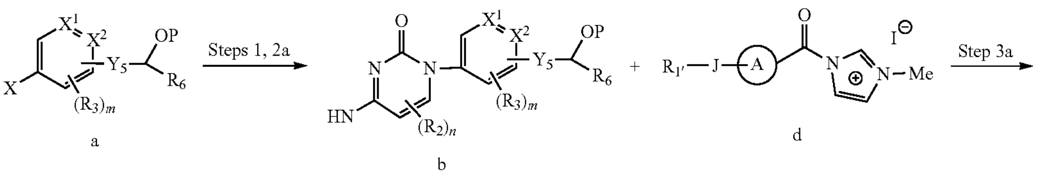

a b d

+

-continued
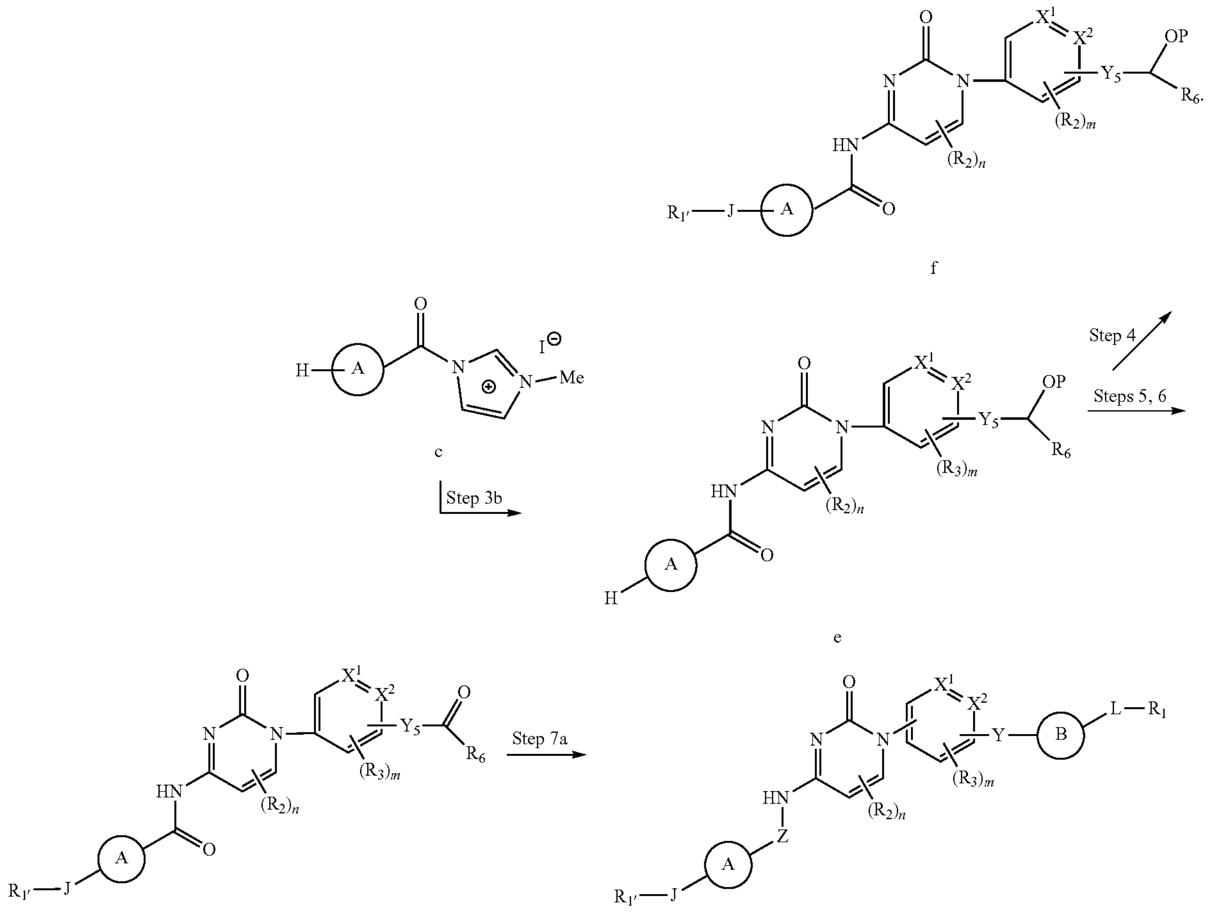
f
c
e
E
I
General Synthetic Scheme G-2
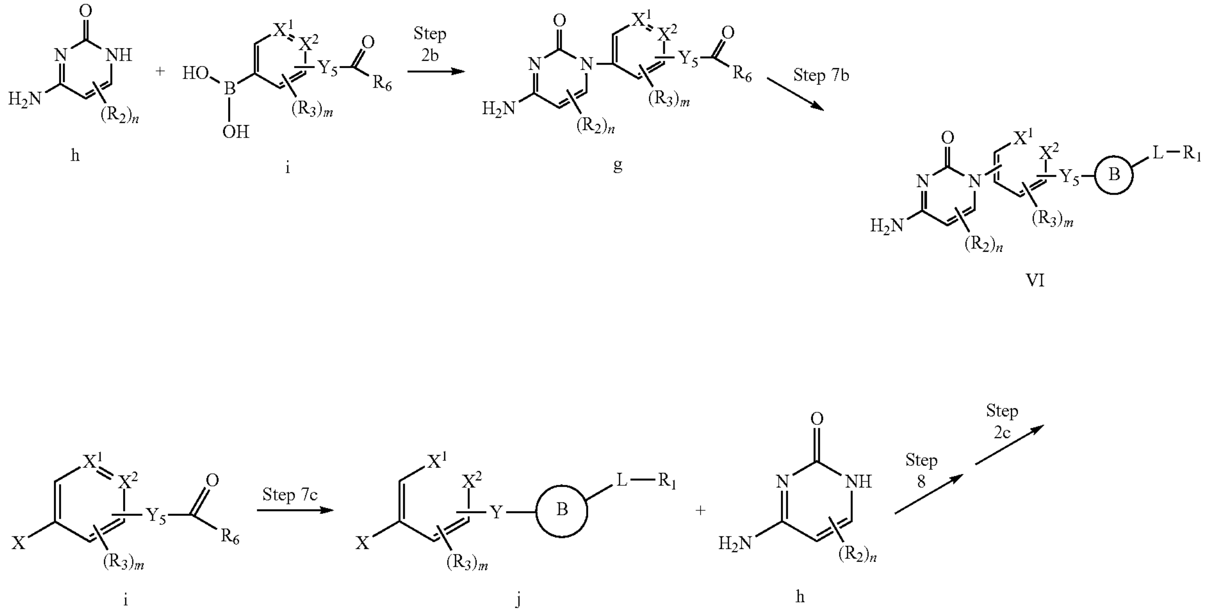
h
i
g
VI
i
j
h -continued

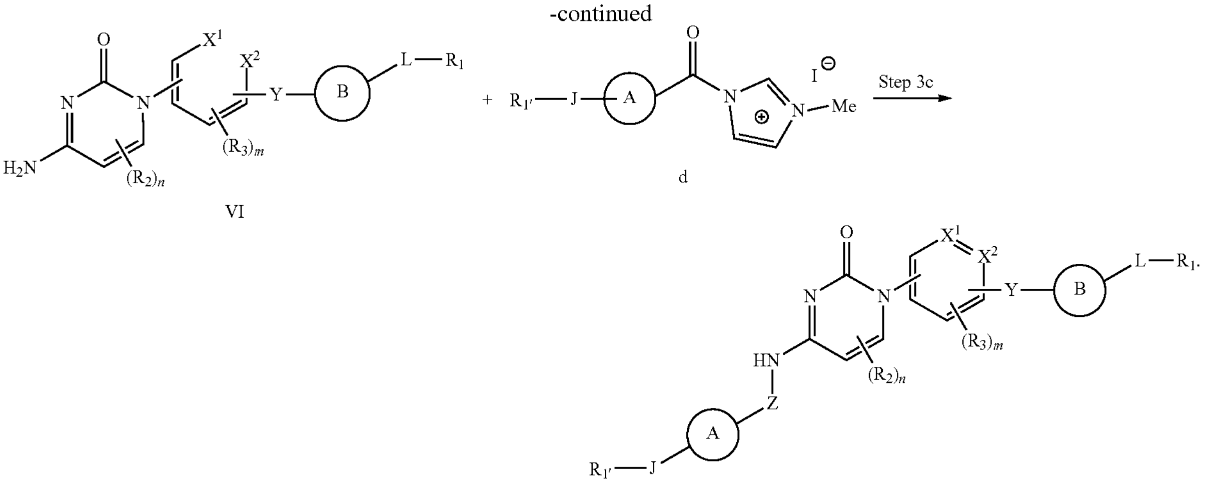

VI d

I

In step 1 of General Synthetic Scheme G-1, the protected alcohol (a) is reacted with a borate such as triisopropyl borate in the presence of a base such as butyl lithium to afford a boronate.

In steps 2a, 2b, and 2c of General Synthetic Schemes G-1 and G-2, the boronate or boric acid is cross-coupled with cytosine in the presence of a base such as a tertiary amine and a copper reagent such as a copper (II) reagent to afford the compound of formula (b), (g), or (VI).

In steps 3a, 3b, and 3c of General Synthetic Schemes G-1 and G-2, the compound of formula (b) or (VI) and the iodide (c) or (d) undergo an amide coupling to yield the intermediate (e) or (f), or the compound of formula I. In a typical procedure, 1.1 to 2.0 molar equivalents of the compound of formula (b) or (VI) are combined with 1 molar equivalent of the iodide (c) or (d) in a suitable solvent, such as a polar aprotic solvent. Polar aprotic solvents include solvents such as dichloromethane, dimethylformamide, acetonitrile, and the like. The mixture in the polar aprotic solvent are then allowed to undergo reaction at a temperature of from about 0° C. to 100° C. for a sufficient time. Typically, the temperature is from about 25° C. to 95° C. or from about 50° C. to 95° C. and the reaction time is from about 1 to 24 hours and more typically 2 to 20 hours or from about 5 to 18 hours.

In step 4 of General Synthetic Scheme G-1, the compound of formula (e) may conduct a further coupling to afford the compound of formula (f).

In steps 5 and 6 of General Synthetic Scheme G-1, the compound of formula (f) is deprotected to yield a free alcohol and then oxidized to a ketone, a compound of formula E.

In steps 7a, 7b and 7c of General Synthetic Scheme G-1 and G-2, the compound of formula E (or i, or g) is reacted with an amine under a reductive amination condition to afford the compound of formula I (or j, or VI). The reductive amination can be performed in the presence of a reducing agent and a suitable solvent. A suitable solvent includes protic solvents or aprotic solvents. Protic solvents include but is not limited to water and alcohols such as methanol, ethanol, propanol, and the like. Aprotic solvents include but is not limited to solvents such as dichloromethane, dimethylformamide, acetonitrile, and the like. The suitable solvent may also be a combination of two or three solvents. The reducing agent includes but is not limited to a borohydride reagent or a metal hydride reagent. Non-limiting examples are lithium borohydride, sodium borohydride, sodium cyanoborohydride and Sodium triacetoxyborohydride.

In step 8 of General Synthetic Scheme G-2, the compound of formula (j) is reacted with a boron agent such as bis (pinacolato)diboron ($B_2pin_2$) to form a pinacol boronic ester of compound (j) in the presence of a phosphine ligand such as [1,1'-Bis(diphenylphosphino)ferrocene]dichloropalladium ($Pd(dppf)Cl_2$), a base, and a suitable solvent. The base includes but is not limited to sodium bicarbonate, sodium carbonate, potassium carbonate, sodium acetate, potassium acetate, and cesium carbonate. The suitable solvent can be an aprotic solvent such as dioxane, dichloromethane, dimethylformamide, acetonitrile, and the like. In a typical procedure, 1.0 molar equivalents of a compound of formula (j) are combined with 1 to 2.0 molar equivalent of the boron agent together with the base, the phosphine ligand in a suitable solvent such as dioxane. The mixture is then allowed to undergo reaction at a temperature of from about 0° C. to 150° C. for a sufficient time. Typically, the temperature is from about 25° C. to 130° C. or from about 50° C. to 125° C. and the reaction time is from about 1 to 24 hours and more typically 2 to 24 hours or from about 10 to 24 hours.

In one aspect, the disclosure provides a process for preparing a compound of formula I-2:

I-2

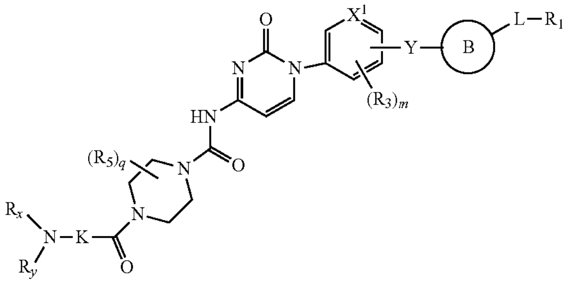

or a pharmaceutically acceptable salt thereof, the process comprising:

coupling a compound of formula A with a compound of formula B to provide a compound of formula I-2:

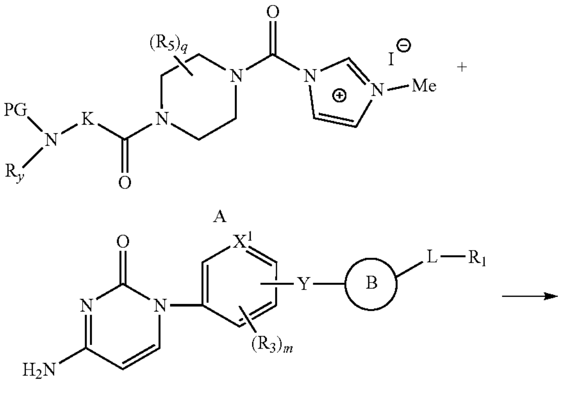

A

B

I-2 wherein ring B, K, L, Y, $R_1$, $R_x$, $R_y$, $R_5$, $X^1$, m, and q are as defined herein, and wherein PG is an amino protecting group.

Processes and conditions for performing the amide coupling of a compound of formula A to a compound of formula B are as in the general synthetic schemes Steps 3a, 3b, and 3c.

In one embodiment, the process further comprises the step of removing the amino protecting group PG.

In another embodiment, the compound of formula B is selected from the compounds as depicted in Table 13.

In another aspect, the disclosure provides a process for preparing a compound of formula I-6:

I-6

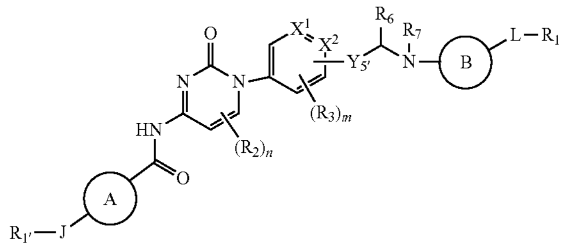

or a pharmaceutically acceptable salt thereof, the process comprising:

combining a compound of formula C with a compound of formula D under a reductive amination condition to provide a compound of formula I-6:

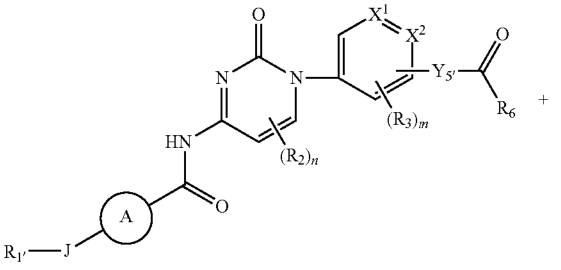

C

-continued

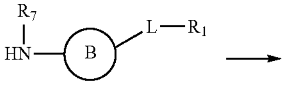

I-6,

D wherein ring A, ring B, J, L, $R_1$, $R_{1'}$, $R_2$, $R_3$, $X^1$, $X^2$, m, and n are as defined herein;

$Y_{5'}$ is a bond or is a linear $C_1$-$C_6$ alkylene, $C_2$-$C_6$ alkenylene, or $C_2$-$C_6$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, (C═O), or

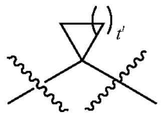

wherein t' is 1, 2, 3, or 4;

$R_6$ is H or $C_1$-$C_6$ alkyl; and $R_7$ is H, $C_1$-$C_6$ alkyl, $C_1$-$C_6$ hydroxyalkyl, $C_1$-$C_6$ haloalkyl, or $C_1$-$C_6$ alkylene-$C_3$-$C_8$ cycloalkyl.

In another embodiment, $Y_{5'}$ is a bond or is a linear $C_1$-$C_4$ alkylene optionally substituted optionally substituted with OH, $NH_2$, halo, $C_1$-$C_6$ alkyl, or $C_1$-$C_6$ alkoxy.

In another embodiment, the compound of formula C is selected from the compounds as depicted in Table 14.

In another aspect, the disclosure provides processes for preparing a compound of formula I-7:

I-7

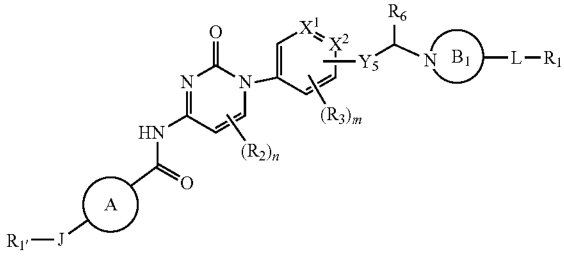

or a pharmaceutically acceptable salt thereof, the process comprising:

combining a compound of formula E with a compound of formula F under a reductive amination condition to provide a compound of formula I-7

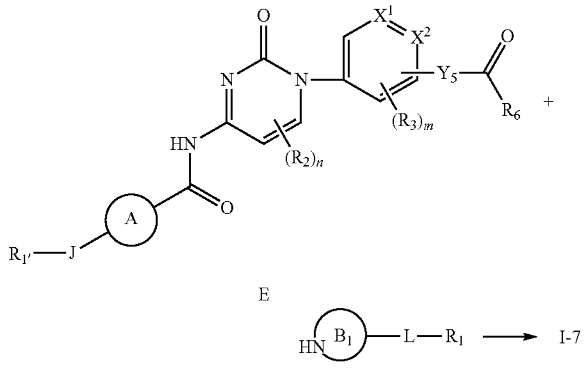

E

F

I-7 wherein ring A, J, L, $R_1$, $R_{1'}$, $R_2$, $R_3$, $X^1$, $X^2$, m, and n are as defined herein;

ring $B_1$ is a nitrogen containing bicyclic heterocycloalkylene optionally substituted with up to three substituents independently selected from the group consisting of $C_1$-$C_6$ alkyl, $C_1$-$C_6$ alkoxy, halo, CN, $C_1$-$C_6$ haloalkyl, OH, COO($C_1$-$C_6$ alkyl), $CONH_2$, and $C_1$-$C_6$ hydroxyalkyl;

$Y_5$ is a bond or is a linear $C_1$-$C_7$ alkylene, $C_2$-$C_7$ alkenylene, or $C_2$-$C_7$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, (C═O), or

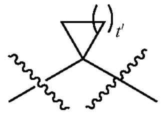

wherein t' is 1, 2, 3, or 4; and $R_6$ is H or $C_1$-$C_6$ alkyl.

In another embodiment, $Y_5$ is a bond or is a linear $C_1$-$C_7$ alkylene optionally substituted with OH, $NH_2$, halo, $C_1$-$C_6$ alkyl, or $C_1$-$C_6$ alkoxy.

The reductive amination between a compound of formula C and a compound of formula D or between a compound of formula E and a compound of formula F are as in general synthetic schemes Steps 7a and 7b. In a typical procedure, 1.1 to 2.0 molar equivalents of the compound of formula D (or F) are combined with 1 molar equivalent of a compound of formula C (or E) and 1.0 to 2.0 molar equivalents of the reducing agent in a suitable solvent. The mixture are then allowed to undergo reaction at a temperature of from about 0° C. to 100° C. for a sufficient time. Typically, the temperature is from about 10° C. to 95° C., or from about 10° C. to 50° C., or at room temperature, and the reaction time is from about 1 to 24 hours and more typically 2 to 20 hours or from about 5 to 18 hours. Work-up and purification as needed provides the compound of formula I-6 or I-7.

In another embodiment, the compound of formula E is selected from the compounds listed in Table 14.

Compound Preparation

The preparation of starting materials that are commercially available, described in the literature, or readily obtainable by those skilled in the art is not described. It will be appreciated by the skilled person that where it is stated that compounds were prepared analogously to earlier examples or intermediates, the reaction time, number of equivalents of reagents, and temperature, can be modified for each specific reaction and that it may be necessary or desirable to employ different work-up or purification techniques. Where reactions are carried out using microwave irradiation, the microwave oven used was either a Biotage Initiator or in CEM Discover System Model 908005. The actual power supplied varies during the reaction in order to maintain a constant temperature.

General Methods

All reactions requiring anhydrous conditions were conducted in flame-dried glassware under a positive pressure of either nitrogen or argon. Commercially available reagents were used as received; otherwise, materials were purified according to *Purification of Laboratory Chemicals*. Dichloromethane ($CH_2Cl_2$), N,N'-dimethylformamide (DMF), toluene and tetrahydrofuran (THF) were degassed with nitrogen and passed through a solvent purification system (Innovative Technologies Pure Solv). Dry 1,4-dioxane was purchased from Acros Organics in an Acros Seal™ bottle. Triethylamine ($Et_3N$) N,N-diisopropylethylamine (DIPEA were distilled from $CaH_2$ immediately prior to use, stored over 4 Å molecular sieves or distilled over 4 Å molecular sieves prior to usage. Microwave reactions were done in CEM Discover System Model 908005. Reactions were monitored by TLC and visualized by a dual short wave/long wave UV lamp and/or stained with ethanolic solutions of either $KMnO_4$, 12-phosphomolybdic acid or other commonly used stains. Flash chromatography was performed on Merck silica gel Kieselgel 60 (230-400 mesh) from EM Science with the indicated HPLC grade solvent or an automated medium pressure column chromatography system (Teledyne ISCO CombiFlash RF75 or CombiFlash Rf+). Reverse phase HPLC was conducted on a Waters HPLC Semi Prep 150B system with Sunfire C18 Prep Column or Atlantis T3 Prep Column with isocratic or gradient conditions with $H_2O$ (0.1% TFA) and 10% $H_2O$:90 $CH_3CN$ (0.1% TFA) as eluents Melting points were determined using Mel-Temp® Capillary Melting Point Apparatus. Infrared spectra were obtained using Nicolet 380-FT IR spectrometer fitted with a Smart Orbit sample system. Optical rotations were obtained at ambient temperature on a Perkin Elmer Model 343 polarimeter (Na D line) using a microcell with a 1 decimeter path length. Mass spectra determined by LCMS were collected on Thermo Scientific™ UltiMate™ 3000 UHPLC with electrochemical detector with a fluorescence detector monitored at either 214 or 254 nm, or a Waters Aquity UPLC H-Class Series with photodiode array detector and QDa mass detector. $^1$H NMR spectra were recorded at 500 MHz, 400 MHz, and 300 MHz, and $^{13}$C at 125 MHz. Proton resonances were reported relative to the deuterated solvent peak: 7.27 ppm for $CDCl_3$, 3.31 ppm (center line signal) for $CD_3OD$, 2.50 for D6-DMSO and 4.79 for $D_2O$ using the following format: chemical shift (δ (ppm)) [multiplicity (s=singlet, br s=broad singlet, d=doublet, t=triplet, q=quartet, m=multiplet)]. Carbon resonances were reported as chemical shifts (6) in parts per million, relative to the center line signal of the respective solvent peak: 77.23 ppm for $CDCl_3$ and 49.15 ppm for $CD_3OD$. Commercially available chemicals are purchased from vendors including Sigma-Aldrich, Acros, Enamine, TCI America, Combi- Blocks, Alfa-Aesar, Angene, Ark Pharma, PharmaBlock, Strem Chemicals, Frontier Scientific, and AstaTech, Inc.

Liquid Chromatography-Mass Spectrometry Methods

Liquid Chromatography-Mass Spectrometry Method A

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, C18 column (50×2.1 mm, 1.7 μm particle size), column temperature 40° C., mobile phase: A—water+0.1% HCOOH/B—$CH_3CN$+0.1% HCOOH, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method B

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ BEH, C18 column (50×2.1 mm, 1.7 μm particle size), column temperature 40° C., mobile phase: A—0.1% v/v aqueous (aq) ammonia solution pH 10/B—$CH_3CN$, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method C

LC/MS-ES (+/−): analyses performed using an AQUITY with PDA detector and QDA Performance, C18 column (50×2.1 mm, 1.6 μm particle size), column temperature 35° C., mobile phase: A—0.1% Formic acid in Milli Q water (pH=2.70)/B—0.1% Formic acid in water:Acetonitrile (10:90), flow rate: 0.8-1.0 mL/min, runtime=4.0 min, gradient: t=0 min 3% B, t=2.7 min 98% B, t=3.0 min 100% B, t=3.51 min 3% B, stop time 4.0 min.

Liquid Chromatography-Mass Spectrometry Method D

LC/MS-ES (+/−): analyses performed using AQUITY H-Class with PDA detector and QDA, C18 column (50×2.1 mm, 1.6 μm particle size), column temperature 35° C., mobile phase: A—0.1% Formic acid in Milli Q water (pH=2.70)/B—0.1% Formic acid in water:Acetonitrile (10:90), flow rate: 0.8-1.0 mL/min, runtime=4.0 min, gradient: t=0 min 3% B, t=2.7 min 98% B, t=3.0 min 100% B, t=3.51 min 3% B, stop time 4.0 min.

Liquid Chromatography-Mass Spectrometry Method E

LC/MS-ES (+/−): analyses performed using AQUITY H-Class with PDA detector and QDA, C18 column (50×2.1 mm, 1.6 μm particle size), column temperature 35° C., mobile phase: A 0.1% Formic acid in water (pH=2.70)/B 0.1% Formic acid in water:Acetonitrile (10:90), runtime=9.0 min, gradient: t=0 min 1% B, t=2.5 min 50% B, t=4.5 min 97.5% B, t=6.5 min 1% B, stop time 9.0 min.

Liquid Chromatography-Mass Spectrometry Method F

LC/MS-ES (+/−): analyses performed using Agilent Infinity II G6125C LCMS, C18 column (50×4.6 mm, 3.5 μm particle size), column temperature 35° C., mobile phase: A 5 mM Ammonium Bicarbonate in Milli-Qwater (pH=7.35)/B—Methanol, runtime=7.0 min, gradient: t=0 min 8% B, t=3.0 min 70% B, t=3.7 min 95% B, t=4.2 min 100% B, t=5.21 min 8% B, stop time 7.0 min.

Liquid Chromatography-Mass Spectrometry Method G

LC/MS-ES (+/−): analyses performed using Waters Alliance 2690 and 996 PDA detector with Micromass ZQ, C18 column (150×4.6 mm, 3.5 μm particle size), column temperature 35° C., mobile phase: A—5 mM Ammonium Acetate+0.1% FA in Water/B—Methanol, runtime=17.0 min, gradient: t=0 min 10% B, t=7.0 min 90% B, t=9.0 min 100% B, t=14.01 min 10% B, stop time 17.0 min.

Liquid Chromatography-Mass Spectrometry Method H

LC/MS-ES (+/−): analyses performed using AQUITY with PDA detector and QDA Performance, C18 column (50×2.1 mm, 1.6 μm particle size), column temperature 35° C., mobile phase: A—0.1% Formic acid inMilli Q water (pH=2.70)/B—0.1% Formic acid in water:Acetonitrile (10:90), flow rate: 0.9 mL/min, runtime=3.0 min, gradient: t=0 min 5% B, t=1.8 min 98% B, t=2.0 min 100% B, t=2.51 min 5% B, stop time 17.0 min.

Analytical Methods $^1$H Nuclear magnetic resonance (NMR) spectroscopy was carried out using one of the following instruments: a Bruker Avance 400 instrument equipped with probe DUAL 400 MHz Si, a Bruker Avance 400 instrument equipped with probe 6 Si 400 MHz 5 mm $^1$H-$^{13}$C ID, a Bruker Avance III 400 instrument with nanobay equipped with probe Broadband BBFO 5 mm direct, a 400 MHz Agilent Direct Drive instrument with ID AUTO-X PFG probe, all operating at 400 MHz, or an Agilent VNMRS500 Direct Drive instrument equipped with a 5 mm Triple Resonance $^1$H{$^{13}$C/$^{15}$N} cryoprobe operating at 500 MHz. The spectra were acquired in the stated solvent at around room temperature unless otherwise stated. In all cases, NMR data were consistent with the proposed structures. Characteristic chemical shifts (δ (ppm)) are given in parts-per-million using conventional abbreviations for designation of major peaks: e.g. s, singlet; d, doublet; t, triplet; q, quartet; dd, doublet of doublets; dt, doublet of triplets; br, broad.

Thin layer chromatography (TLC) refers to silica gel TLC using silica gel F254 (Merck) plates. Column chromatography was performed using an automatic column chromatography (Biotage SP1 or Isolera) system over Biotage silica gel cartridges (KP-Sil or KP-NH) or in the case of reverse phase chromatography over Biotage C18 cartridges (KP-C18).

Prep HPLC were performed on Shimadzu LC-20AP, Waters 2545 and Agilent 1260 infinity. Purity was determined on Waters Alliance e2695-PDA detector 2998 and Agilent 1260 Infinity-II. (Mobile phase: 0.05% HCl in Water/Methanol in gradient elution method).

TABLE 15

Abbreviations and Names of Reagents

| Abbreviations/ Acronyms | Full Name/Description |
|---|---|
| AcOH | Acetic acid |
| aq. | Aqueous |
| $CH_3CN$ | Acetonitrile |
| $B_2pin_2$ | Bis(pinacolato)diboron |
| $Boc_2O$ | Di-tert-butyl dicarbonate |
| $BH_3$•$SMe_2$ | Borane dimethyl sulfide complex |
| i-BuMgBr | Isobutyl magnesium bromide |
| n-BuLi | n-Butyllithium |
| B(O—iPr)$_3$• | Triisopropyl borate |
| CBzCl | Benzyl chloroformate |
| CDI | 1,1'-Carbonyldiimidazole |
| DAST | Diethylaminosulfur trifluoride |
| DCE | 1,2-Dichloethane |
| DCM | Dichloromethane |

TABLE 15-continued

| Abbreviations and Names of Reagents | |
|---|---|
| Abbreviations/ Acronyms | Full Name/Description |
| DIAD | Diisopropyl azodicarboxylate |
| DIPEA | N,N-Diisopropylethylamine |
| DMAP | N,N-dimethylaminopyridine |
| DMF | N,N'-dimethylformamide |
| DMP | Dess-Martin periodinane |
| DMSO | Dimethylsulfoxide |
| EDCI | 1-Ethyl-3-(3-dimethylaminopropyl)carbodiimide |
| DPPA | Diphenylphosphoryl azide |
| $Et_2O$ | Diethyl ether |
| $Et_3N$ | Triethylamine |
| EtOAc | Ethyl acetate |
| EtOH | Ethanol |
| EtMgBr | Ethylmagnesium bromide |
| HATU | Hexafluorophosphate azabenzotriazole tetramethyl uronium |
| HPLC | High performance liquid chromatography |
| KHMDS | Potassium bis(trimethylsilyl)amide |
| LCMS | Liquid chromatography mass spectrometry |
| LDA | Lithium diisopropylamide |
| $Li(ALH)_4$ | Lithium aluminum hydride |
| $LiAlH(Ot-Bu)_3$ | Lithium tri-tert-butoxyaluminum hydride |
| LHMDS | Lithium bis(trimethylsilyl)amide |
| MeOH | Methanol |
| MeI | Methyl Iodide |
| min. | minutes |
| NMR | Nuclear magnetic resonance |
| rt | Room temperature |
| $NaBH_4$ | Sodium borohydride |
| $NaBH(Oac)_3$ | Sodium triacetoxyborohydride |
| NaOAc | Sodium acetate |
| $NaBH_3CN$ | Sodium cyanoborohydride |
| PCC | Pyridinium chlorochromate |
| $Pd(dba)_2$ | Bis(dibenzylideneacetone)palladium |
| $Pd(dppf)Cl_2$ | [1,1'-Bis(diphenylphosphino)ferrocene]dichloropalladium |
| $PPh_3$ | Triphenylphosphine |
| i-PrBr | 2-Bromopropane |
| Sat. | Saturated |
| TBAF | Tetrabutlyammonium fluoride |
| TBSCl/TBDMSCl | t-butyldimethylsilyl chloride |
| $Ti(O—iPr)_4$ | Titanium isopropoxide |
| TEA | Triethylamine |
| TFA | Trifluoroacetic acid |
| TFAA | Trifluoroacetic anhydride |
| THF | Tetrahydrofuran |
| TMEDA | N,N,N',N'-Tetramethylethylenediamine |
| TMSCN | Trimethylsilyl cyanide |
| TsOH | p-Toluenesulfonic acid |

Intermediate Synthesis

Intermediate 1

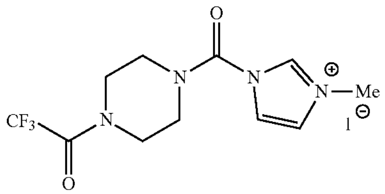 [SMILES: C[n+]1ccn(C(=O)N2CCN(C(=O)C(F)(F)F)CC2)c1]

3-Methyl-1-(4-(2,2,2-trifluoroacetylpiperazine-1-carbonyl)-1H-imidazol-3-ium iodide Scheme I-1

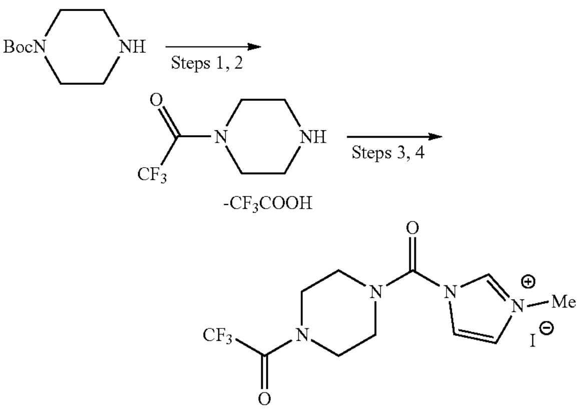

Reagents: 1) TFAA, $CH_2Cl_2$, 0° C. to rt, 16 h 2) TFA, $CH_2Cl_2$, rt, 1.5 h 3) CDI, $CH_2Cl_2$, 16 h 4) MeI, $CH_3CN$, rt, 16 h.

Step 1: tert-butyl 4-(2,2,2-trifluoroacetyl)piperazine-1-carboxylate

A solution of tert-butyl piperazine-1-carboxylate (20 g, 107 mmol) in dry $CH_2Cl_2$ (100 mL) was cooled to 0° C. under a nitrogen atmosphere. Trifluoroacetic anhydride (15.0 ml, 107 mmol) was added dropwise over 10 min. The reaction was allowed to warm to rt and stirred for 16 h. The reaction mixture was diluted with $CH_2Cl_2$ (1 L), and quenched with saturated $NaHCO_3$ solution (1 L). The organic layer was separated, dried over $Na_2SO_4$, filtered, and concentrated under reduced pressure to afford the title compound (29.1 g, 96%) as a pale orange solid.

Step 2: 2,2,2-trifluoro-1-(piperazin-1-yl)ethan-1-one triflouroacetate salt

To a solution of trifluoroacetic acid in $CH_2Cl_2$ (50 mL, 1:1) was added tert-butyl 4-(2,2,2-trifluoroacetyl) piperazine-1-carboxylate (29.1 g, 103 mmol). The reaction was left to stir at rt for 1.5 h. The solvent and trifluoroacetic acid were removed under reduced pressure. The crude reaction mixture was triturated with diethyl ether to yield a solid precipitate. The solid was filtered and washed with diethyl ether to yield the title compound (29.5 g, 97%) as a white solid.

Step 3: 1-(4-(1H-imidazole-1-carbonyl)piperazin-1-yl)-2,2,2-trifluoroethan-1-one To a round bottom flask containing 2,2,2-trifluoro-1-(piperazin-1-yl)ethan-1-one trifluoroacetate salt (26.0 g, 88 mmol) was added 1,1'-carbonyldiimidazole (17.1 g, 105 mmol) and dry $CH_2Cl_2$ (100 mL) to yield a suspension. This suspension was stirred at rt for 16 h. The solvent was subsequently removed under reduced pressure and the crude reaction mixture was purified by flash chromatography to afford the title compound (18 g, 76%) as a white solid.

3-methyl-1-(4-(2,2,2-trifluoroacetylpiperazine-1-carbonyl)-1H-imidazol-3-ium iodide To a round bottom flask containing a solution of 1-(4-(1H-imidazole-1-carbonyl)piperazin-1-yl)-2,2,2-trifluoroethan-1-one (10.8 g, 39.1 mmol) in dry MeCN (80 mL) was added iodomethane (15.0 mL, 235 mmol). The reaction stirred for 24 h at rt. The solvent and excess iodomethane were removed under reduced pressure to yield the title compound (27.6 g, 98%) as a light yellow solid.

Intermediate 2

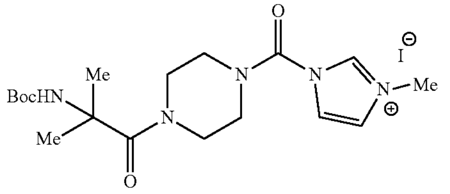 [SMILES: C[n+]1ccn(C(=O)N2CCN(C(=O)C(C)(C)NC(=O)OC(C)(C)C)CC2)c1 ; [I-]]

1-(4-(2-((tert-Butoxycarbonyl)amino)-2-methylpropanoyl)piperazine-1-carbonyl)-3-methyl-1H-imidazol-3-ium iodide Scheme I-2

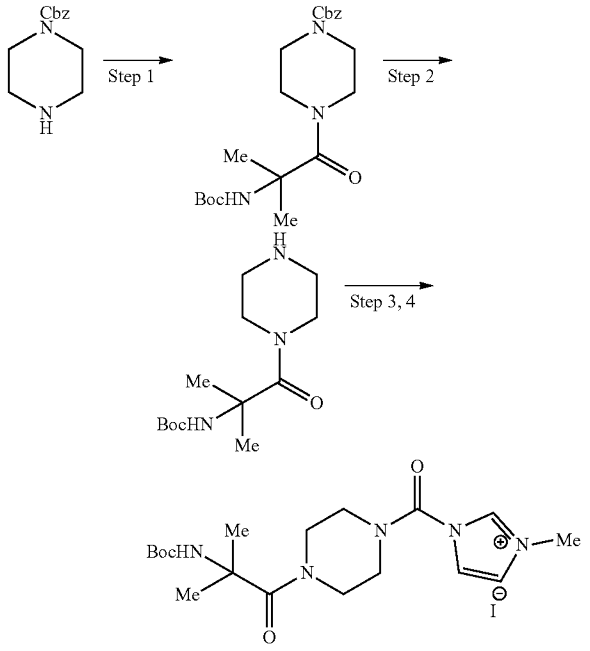

Reagents: 1) Boc-AIB, HATU, DIPEA, DMF, rt, 16 h 2) 10% Pd/C, MeOH, rt, 16 h 3) CDI, DCM, rt, 16 h 4) MeI, $CH_3CN$, rt, 16 h.

Step 1: benzyl 4-(2-((tert-butoxycarbonyl) amino)-2-methylpropanoyl) piperazine-1-carboxylate To a stirred solution of 2-((tert-butoxycarbonyl) amino)-2-methylpropanoic acid (35.5 g, 174.8 mmol) in DMF (350 mL) were added DIPEA (51.24 g, 397.2 mmol) and HATU (90.62 g, 238.3 mmol) at 0° C. The reaction mixture was stirred at 0° C. for 45 min. Benzyl piperazine-1-carboxylate (35 g, 158.9 mmol) was added into the reaction mixture at 0° C. and stirred at rt for 16 h. The resulting reaction mixture was poured into $H_2O$ (1.5 L) and extracted with EtOAc (3x700 mL) and the combined organics were dried over $Na_2SO_4$, filtered, and concentrated under reduced pressure.

The resulting crude material was purified by flash chromatography (20-30% EtOAc:Hex) to afford the title compound (36.0 g, 55%) as an off-white solid LCMS [M+H] 406.

Step 2: tert-butyl (2-methyl-1-oxo-1(piperazin-1-yl) propan-2-yl)carbamate

To a stirred solution of benzyl 4-(2-((tert-butoxycarbonyl) amino)-2-methylpropanoyl) piperazine-1-carboxylate (35.0 g, 86.4 mmol) in MeOH (500 mL) was added 10% Pd/C (3.5 g). The reaction mixture was stirred under a hydrogen atmosphere at rt for 16 h. The resulting reaction mixture was filtered through Celite® and washed with MeOH (1500 mL). The resulting filtrate was concentrated under reduced pressure and dried to afford the title compound (25.0 g, Quant.) as a viscous oil. LCMS [M+H] 272.

Step 3: tert-butyl (1-(4-1H-imidazole-1-carbonyl) piperazin-1-yl)-2-methyl-1-oxopropan-2-yl) carbamate To a stirred solution of tert-butyl (2-methyl-1-oxo-1(piperazin-1-yl) propan-2-yl) carbamate (25.0 g, 92.2 mmol) in $CH_2Cl_2$ (300 mL) was added CDI (17.78 g, 109.7 mmol) at rt. The reaction mixture was stirred at rt for 16 h. The reaction mixture was concentrated under reduced pressure. The resulting crude material was purified by column chromatography (4-5% MeOH in $CH_2Cl_2$) to afford the title compound (30.0 g, 89%) as an off-white solid. $^1H$ NMR (DMSO-$d_6$, 400 MHz) δ 8.04 (s, 1H), 7.48 (s, 1H), 7.36 (s, 1H), 7.03 (s, 1H), 3.65-3.52 (m, 4H), 3.51-3.40 (m, 4H), 1.38 (s, 6H), 1.30 (s, 9H). LCMS [M+H] 366.3.

Step 4: 1-(4-(2-((tert-butoxycarbonyl) amino)-2-methylpropanoyl) piperazine-1-carbonyl)-3-methyl-1H-imidazol-3-ium iodide To a stirred solution of t-butyl (1-(4-1H-imidazole-1-carbonyl)piperazin-1-yl)-2-methyl-1-oxopropan-2-yl)carbamate (20.0 g, 54.8 mmol) in $CH_3CN$ (250 mL) was added Mel (46.66 g, 20.8 mL, 328.7 mmol) at 0° C. The reaction mixture was stirred at rt for 16 h. The reaction mixture was concentrated under reduced pressure to afford the title compound (30.0 g, quantitative) as a pale yellow solid. $^1H$ NMR (DMSO-$d_6$, 400 MHz) δ 9.57 9 s, 1H), 8.05 (s, 1H), 7.87 (t, 1H), 7.40 (s, 1H), 3.93 (s, 3H), 3.78-3.65 (m, 4H), 3.59-3.45 (m, 4H), 1.40 (s, 6H), 1.32 (S, 9H). LCMS [M+H] 380.2 (-iodide).

Intermediate 3

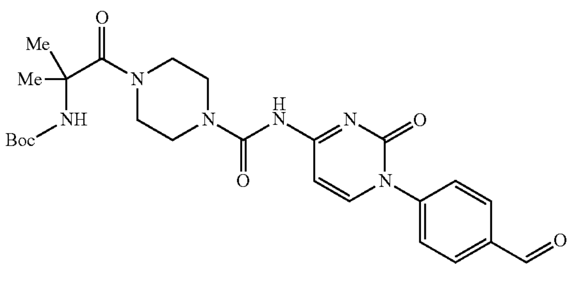 [SMILES: CC(C)(C)OC(=O)NC(C)(C)C(=O)N1CCN(C(=O)Nc2ccn(-c3ccc(C=O)cc3)c(=O)n2)CC1]

tert-Butyl N-[1-(4-{[1-(4-formyl-phenyl)-2-oxo-1,2-dihydropyrimidin-4-yl]carbamoyl}piperazin-1-yl)-2-methyl-1-oxopropan-2-yl]carbamate Scheme I-3

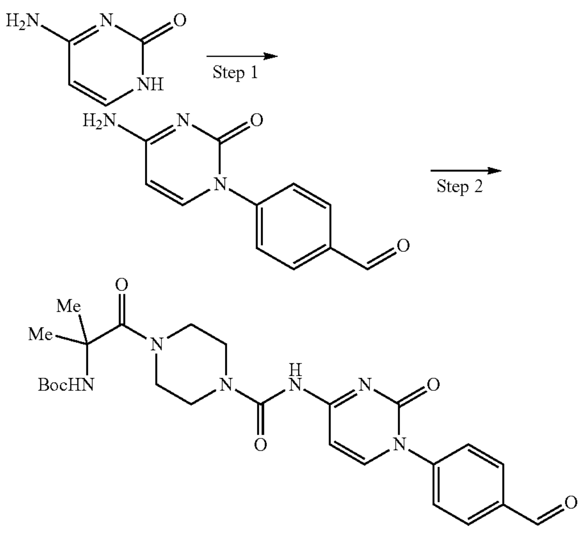

Reagents: 1) 4-formylphenylboronic acid, TMEDA, $Cu(OAc)_2 \cdot H_2O$, 2) 1-(4-(2-((tert-butoxycarbonyl)amino)-2-methylpropanoyl)piperazine-1-carbonyl)-3-methyl-1H-imidazol-3-ium iodide, $CH_3CN$, 78° C., 22 h.

Step 1: 4-(4-amino-2-oxopyrimidin-1(2H)-yl)benzaldehyde

Copper (II) acetate monohydrate (18.0 g, 90.2 mmol) and TMEDA (16.2 mL, 108 mmol) were added to a mixture of cytosine (10.0 g, 90.1 mmol) and (4-formylphenyl)boronic acid (13.5 g, 90.2 mmol) in MeOH (400 mL) and $H_2O$ (100 mL), and the mixture was stirred at rt open to the air for 6 days. It was concentrated to remove the MeOH, ice and water were added (ca. 1 L total), and the precipitate was collected by vacuum filtration to afford the title compound (8.84 g, 41.1 mmol) as a white solid. $^1H$ NMR (500 MHz, DMSO-$d_6$) δ 10.04 (s, 1H), 7.98 (d, 2H), 7.71 (d, 1H), 7.61 (d, 2H), 7.46-7.27 (m, 2H), 5.85 (d, 1H).

tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate A mixture of 4-(4-amino-2-oxopyrimidin-1(2H)-yl)benzaldehyde (1.0 g, 4.67 mmol) and 1-(4-(2-((tert-butoxycarbonyl)amino)-2-methylpropanoyl)piperazine-1-carbonyl)-3-methyl-1H-imidazol-3-ium iodide (3.57 g, 5.62 mmol) in $CH_3CN$ (35 mL) was stirred at reflux for 22 h. The reaction mixture was cooled, diluted with EtOAc (250 mL), washed with sat. aq. $NaHCO_3$ (2×200 mL) and brine (200 mL), dried over $Na_2SO_4$, decanted, and concentrated under reduced pressure. The residue was purified by flash chromatography (hexanes/EtOAc/MeOH) to afford the title compound. $^1H$ NMR (400 MHz, $CDCl_3$) δ 13.01 (br. s., 1H), 10.07 (s, 1H), 8.01 (d, 2H), 7.58 (d, 2H), 7.31 (d, 1H), 5.90 (d, 1H), 4.95-4.72 (m, 1H), 3.95-3.57 (m, 8H), 1.52 (s, 6H), 1.44 (s, 9H). LCMS [M+H] 513.1.

Intermediate 4

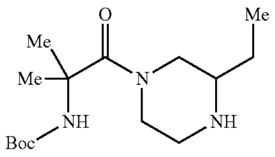 [SMILES: CCC1CN(C(=O)C(C)(C)NC(=O)OC(C)(C)C)CCN1]

tert-Butyl (1-(3-ethylpiperazin-1-yl)-2-methyl-1-oxopropan-2-yl)carbamate

Scheme I-4

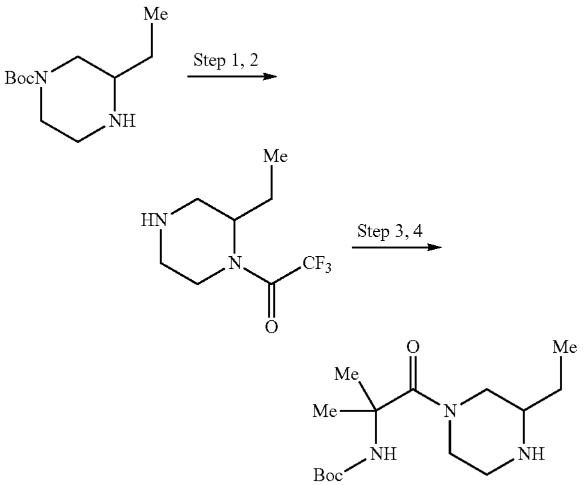

Reagents: 1) TFAA, $Et_3N$, $CH_2Cl_2$, 0° C., 16 h 2) TFA, 1.5 h 3) 2-((tert-butoxycarbonyl)amino)-2-methylpropanoic acid, HATU, DIPEA, $CH_2Cl_2$, 16 h 4) LiOH, THF:$H_2O$, 2 h.

Step 1: tert-butyl 3-ethyl-4-(2,2,2-trifluoroacetyl)piperazine-1-carboxylate A solution of tert-butyl 3-ethylpiperazine-1-carboxylate (500 mg, 2.4 mmol) in dry $CH_2Cl_2$ (15 mL) and $NEt_3$ (0.39 mL, 2.8 mmol) was cooled to 0° C. Trifluoroacetic anhydride (0.34 mL, 2.4 mmol) was added dropwise over 10 min. The reaction was warmed to rt and stirred for 16 h. The reaction mixture was diluted with $CH_2Cl_2$ (50 mL) and quenched with sat. $NaHCO_3$ (75 mL). The organic layer was dried over $Na_2SO_4$ and concentrated under reduced pressure to afford the title compound.

Step 2: 1-(2-ethylpiperazin-1-yl)-2,2,2-trifluoroethan-1-one triflouroacetate salt tert-Butyl 3-ethyl-4-(2,2,2-trifluoroacetyl)piperazine-1-carboxylate (700 mg, 2.2 mmol) was dissolved in a 1:1 solution of trifluoroacetic acid and $CH_2Cl_2$ (20 mL). The reaction was stirred at rt for 1.5 h. The reaction mixture was concentrated under reduced pressure. The crude reaction mixture was triturated with diethyl ether to yield a solid precipitate, which was collected by filtration and washed with diethyl ether to yield the title compound.

Step 3: tert-butyl (1-(3-ethyl-4-(2,2,2-trifluoroacetyl)piperazin-1-yl)-2-methyl-1-oxopropan-2-yl)carbamate To a suspension of 2-((tert-butoxycarbonyl)amino)-2-methylpropanoic acid (144 mg, 0.71 mmol) and HATU (270 mg, 0.71 mmol) in $CH_2Cl_2$, was added DIPEA (0.31 ml, 1.8 mmol). The suspension was stirred for 10 min. and 1-(2-ethylpiperazin-1-yl)-2,2,2-trifluoroethan-1-one trifluoroacetate salt (250 mg, 0.71 mmol) was added. The solution was stirred at rt for 16 h. The reaction mixture was diluted with $CH_2Cl_2$ (75 mL) and washed with $H_2O$. The organic layer was concentrated under reduced pressure and purified by flash chromatography (EtOAc:Hex) to afford the title compound.

Step 4: tert-butyl (1-(3-ethylpiperazin-1-yl)-2-methyl-1-oxopropan-2-yl) carbamate tert-Butyl (1-(3-ethyl-4-(2,2,2-trifluoroacetyl)piperazin-1-yl)-2-methyl-1-oxopropan-2-yl)carbamate (132 mg, 0.31 mmol) and $LiOH \cdot H_2O$ (139 mg, 3.1 mmol) were suspended in $THF:H_2O$ (1:1) and stirred at rt for 2 h. The solvent was removed under reduced pressure, diluted with $H_2O$ (50 mL), and extracted with $CHCl_3$ (3×50 mL). The organic layers were dried over $Na_2SO_4$ and concentrated under reduced pressure to afford the title compound.

Intermediate 5

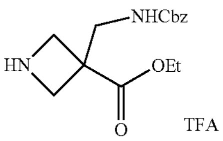 [SMILES: CCOC(=O)C1(CNC(=O)OCc2ccccc2)CNC1]

ethyl 3-((((benzyloxy)carbonyl)amino)methyl)azetidine-3-carboxylate trifluoroacetate salt Scheme I-5

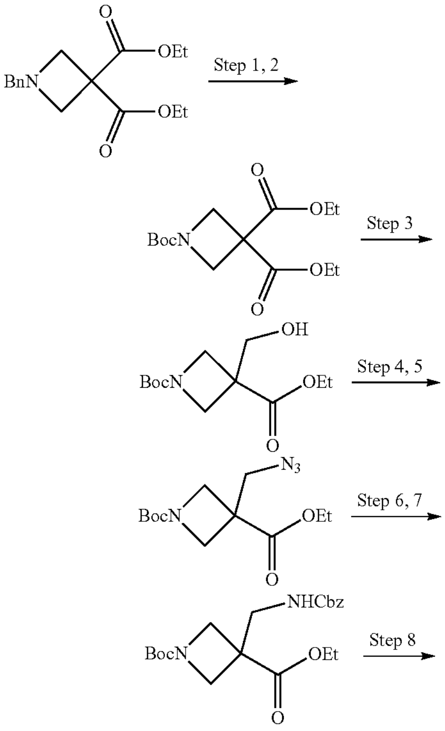

-continued

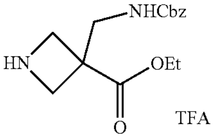

Reagents: 1) $H_2$, $Pd(OH)_2/C$, 4.0 M HCl in dioxane, EtOH, rt, 6 d 2) $Boc_2O$, sat. aq. $NaHCO_3$, dioxane, rt, 24 h 3) $LiAlH(Ot\text{-}Bu)_3$, THF, 0° C. to rt, 24 h 4) MsCl, $Et_3N$, $CH_2Cl_2$, 0° C. to rt, 24 h 5) $NaN_3$, DMF, 50° C., 24 h 6) $H_2$, Pd/C, EtOH, rt, 24 h 7) CbzCl, sat. aq. $NaHCO_3$, dioxane, rt, 4 d 8) TFA, $CH_2Cl_2$, rt, 1.5 h.

Step 1: diethyl azetidine-3,3-dicarboxylate hydrochloride

A mixture of diethyl 1-benzylazetidine-3,3-dicarboxylate (prepared according to *Syn Commun.* 2003, 33, 3347) (830 mg, 2.85 mmol), 4.0 MHCl in dioxane (0.78 mL, 3.12 mmol), and 20 w/w % $Pd(OH)_2/C$ (173 mg) in EtOH (25 mL) was stirred under an atmosphere of $H_2$ for 6 days. The reaction mixture filtered through a pad of Celite® and rinsed with MeOH. The filtrate was concentrated to afford the title compound.

Step 2: 1-(tert-butyl) 3,3-diethyl azetidine-1,3,3-tricarboxylate

A mixture of diethyl azetidine-3,3-dicarboxylate hydrochloride (756 mg, 2.85 mmol) and $Boc_2O$ (0.82 mL, 4.00 mmol) in dioxane (12 mL) and sat. aq. $NaHCO_3$ was stirred at rt for 24 h. The reaction mixture was diluted with sat. aq. $NaHCO_3$(100 mL) and extracted with EtOAc (2×75 mL). The extracts were washed with brine (75 mL), dried over $Na_2SO_4$, filtered and concentrated in vacuo. The residue was purified by flash chromatography (Hexanes/EtOAc) to afford the title compound. $^1H$ NMR (500 MHz, $CDCl_3$) δ 4.22-4.31 (m, 8H), 1.44 (s, 9H), 1.28 (t, 6H).

Step 3: 1-(tert-butyl) 3-ethyl 3-(hydroxymethyl)azetidine-1,3-dicarboxylate $LiAlH(Ot\text{-}Bu)_3$ in THF (1.0M, 4.4 mL) was added dropwise to a solution of 1-(tert-butyl) 3,3-diethyl azetidine-1,3,3-tricarboxylate (604 mg, 2.01 mmol) in dry THF (20 mL) at 0° C. under $N_2$. The mixture was warmed to rt and stirred for 24 h. The reaction mixture was diluted with EtOAc (100 mL), washed with 1 M HCl (2×50 mL) and brine (50 mL), dried over $Na_2SO_4$, filtered and concentrated in vacuo. The residue was purified by flash chromatography (Hexanes/EtOAc) to afford the title compound.

Step 4: 1-(tert-butyl) 3-ethyl 3-(((methylsulfonyl)oxy)methyl)azetidine-1,3-dicarboxylate MsCl (0.16 mL, 2.07 mmol) was added dropwise to a solution of 1-(tert-butyl) 3-ethyl 3-(hydroxymethyl)azetidine-1,3-dicarboxylate (452 mg, 1.74 mmol) and $Et_3N$ (0.34 mL, 2.44 mmol) in dry $CH_2Cl_2$ (12 mL) at 0° C. under $N_2$. The mixture was warmed to rt while stirring for 4 h. The reaction mixture was poured into 2M $K_2CO_3$ (50 mL) and extracted with $CH_2Cl_2$ (3×35 mL). The extracts were dried over $Na_2SO_4$, filtered, and concentrated in vacuo to give the crude product which was carried on as-is.

Step 5: 1-(tert-butyl) 3-ethyl 3-(aminomethyl)azetidine-1,3-dicarboxylate

A mixture of 1-(tert-butyl) 3-ethyl 3-(((methylsulfonyl)oxy)methyl)azetidine-1,3-dicarboxylate (604 mg, 1.743 mmol) and $NaN_3$ (351 mg, 5.40 mmol) in dry DMF (10 mL) was stirred at 50° C. under $N_2$ for 24 h. It was cooled, diluted with $Et_2O$ (100 mL), washed with sat. aq.

$NaHCO_3$ (75 mL) and brine (2×75 mL), dried over $Na_2SO_4$, filtered, and concentrated to dryness to afford the title compound.

Step 6: 1-(tert-butyl) 3-ethyl 3-(aminomethyl)azetidine-1,3-dicarboxylate

A mixture of 1-(tert-butyl) 3-ethyl 3-(azidomethyl)azetidine-1,3-dicarboxylate (453 mg, 1.593 mmol) and 10% Pd (52 mg) in EtOH (20 mL) was stirred under an atmosphere of $H_2$ for 20 h. It was filtered through a pad of Celite®, rinsed with MeOH, and the filtrate was concentrated to dryness to afford the title compound.

Step 7: 1-(tert-butyl) 3-ethyl 3-((((benzyloxy)carbonyl)amino)methyl)azetidine-1,3-dicarboxylate A mixture of 1-(tert-butyl) 3-ethyl 3-(aminomethyl)azetidine-1,3-dicarboxylate (414 mg, 1.593 mmol) and benzyl chloroformate (0.45 mL, 3.15 mmol) in dioxane (16 mL) and sat. aq. $NaHCO_3$(16 mL) was stirred at rt under $N_2$ for 4 days. It was diluted with EtOAc (75 mL), washed with sat. aq. $NaHCO_3$(2×50 mL) and brine (50 mL), dried over $Na_2SO_4$, filtered, and concentrated in vacuo. The residue was purified by flash chromatography (Hexanes/EtOAc) to afford the title compound. $^1H$ NMR (500 MHz, $CDCl_3$) δ 7.28-7.44 (m, 5H), 5.15-5.26 (m, 1H), 5.11 (br.s., 2H), 4.22 (q, 2H), 4.12 (d, 2H), 3.79 (m, 2H), 3.65-3.75 (m, 2H), 1.44 (s, 9H), 1.29 (t, 3H).

Step 8: ethyl 3-((((benzyloxy)carbonyl)amino)methyl)azetidine-3-carboxylate trifluoroacetate salt A mixture of 1-(tert-butyl) 3-ethyl 3-((((benzyloxy)carbonyl)amino)methyl)azetidine-1,3-dicarboxylate (101.5 mg, 0.259 mmol) and TFA (1.0 mL) in dry $CH_2Cl_2$ (3 mL) was stirred at rt for 1.5 h and concentrated to dryness to afford the title compound.

Intermediate 6

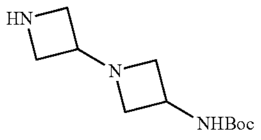 [SMILES: CC(C)(C)OC(=O)NC1CN(C2CNC2)C1]

tert-Butyl [1,3'-biazetidin]-3-ylcarbamate

Scheme I-6

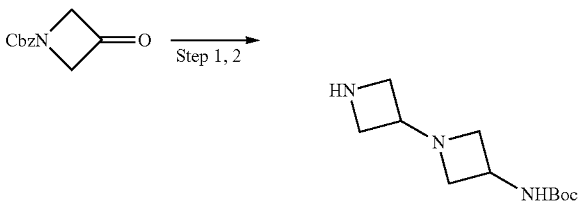

Reagents: 1) tert-butyl azetidin-3-ylcarbamate, $NaBH(OAc)_3$, AcOH, DCE, rt, 20 h 2) $H_2$, Pd/C, EtOH, rt, 2 h.

Step 1: benzyl 3-((tert-butoxycarbonyl)amino)-[1,3'-biazetidine]-1'-carboxylate $NaBH(OAc)_3$ (1.67 g, 7.86 mmol) was added to a mixture of benzyl 3-oxoazetidine-1-carboxylate (522 mg, 2.54 mmol), tert-butyl azetidin-3-ylcarbamate (433 mg, 2.52 mmol), and acetic acid (0.10 mL) in dry DCE (25 mL). The mixture was stirred at rt under $N_2$ for 20 h. It was quenched with sat. aq. $NaHCO_3$(100 mL) and extracted with $CH_2Cl_2$ (2×100 mL). The extracts were dried over $Na_2SO_4$, filtered, and concentrated in vacuo. The residue was purified by flash chromatography (Hexanes/EtOAc/MeOH) to afford the title compound.

Step 2: tert-butyl [1,3'-biazetidin]-3-ylcarbamate

A mixture of benzyl 3-((tert-butoxycarbonyl)amino)-[1,3'-biazetidine]-1'-carboxylate (521 mg, 1.44 mmol) and 10% Pd (61 mg) in EtOH (20 mL) was stirred under an atmosphere of $H_2$ for 2 h. The reaction mixture was filtered through a pad of Celite®, rinsed with MeOH, and the filtrate was concentrated to dryness to afford the title compound.

Intermediate 7

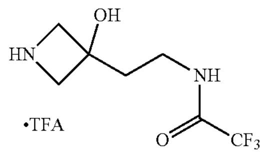 [SMILES: O=C(NCCC1(O)CNC1)C(F)(F)F]

2,2,2-Trifluoro-N-(2-(3-hydroxyazetidin-3-yl)ethyl)acetamide trifluoroacetate salt Scheme I-7

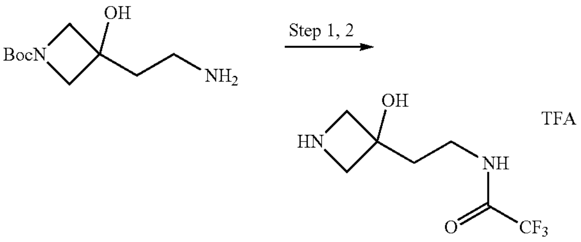

Reagents: 1) Trifluoroacetic anhydride, $Et_3N$, $CH_2Cl_2$, rt, 6 h 2) TFA, $CH_2Cl_2$, rt, 1.5 h.

Step 1: tert-butyl 3-(2-(2,2,2-trifluoroacetamido)ethyl)-3-(2,2,2-trifluoroacetoxy)azetidine-1-carboxylate Trifluoroacetic anhydride (0.16 mL, 1.15 mL) was added dropwise to a solution of tert-butyl 3-(2-aminoethyl)-3-hydroxyazetidine-1-carboxylate (116 mg, 0.54 mmol) and $Et_3N$ (0.22 mL, 1.58 mmol) in dry $CH_2Cl_2$ (5 mL), and the mixture was stirred at rt under $N_2$ for 6 h. The mixture was poured into sat. aq. $NaHCO_3$ (50 mL) and extracted with $CH_2Cl_2$ (2×25 mL). The extracts were dried over $Na_2SO_4$, filtered and concentrated in vacuum. The residue was purified by flash chromatography (Hexanes/EtOAc) to afford the title compound.

Step 2: 2,2,2-trifluoro-N-(2-(3-hydroxyazetidin-3-yl)ethyl)acetamide

A mixture of tert-butyl 3-(2-(2,2,2-trifluoroacetamido)ethyl)-3-(2,2,2-trifluoroacetoxy)azetidine-1-carboxylate (81.1 mg, 0.199 mmol) and TFA (0.5 mL) in dry $CH_2Cl_2$ (2.0 mL) was stirred at rt for 1.5 h and concentrated to dryness to afford the title compound.

Intermediate 8

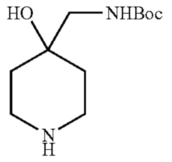 [SMILES: CC(C)(C)OC(=O)NCC1(O)CCNCC1]

tert-Butyl ((4-hydroxypiperidin-4-yl)methyl)carbamate

Scheme I-8

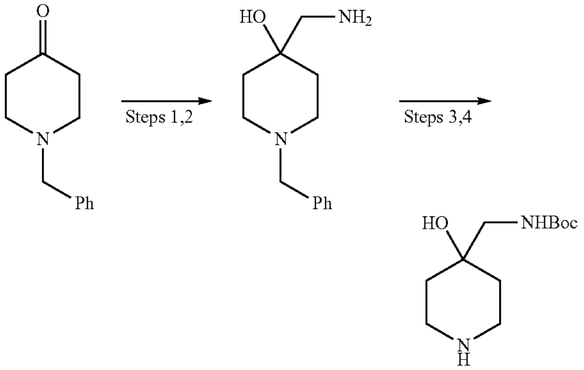

Reagants: 1) NaH, $Me_3SOI$, DMSO 2) $NH_4OH$, MeOH 3) $Boc_2O$, DCM 4) $HCO_2NH_4$, Pd/C, MeOH.

Step 1: 6-benzyl-1-oxa-6-azaspiro[2.5]octane

NaH (60% oil dispersion, 121 mg, 3.16 mmol) was added to a solution of trimethylsulfoxonium iodide (640 mg, 2.91 mmol) in DMSO (2.5 mL) at 0° C. The mixture was warmed to 10° C., stirred for 10 min. and warmed to rt. After 1 h, a solution of N-benzylpiperidone (500 mg, 2.64 mmol) in DMSO (1.5 mL) was added via syringe. The mixture was stirred at rt for 1.5 h, diluted with $Et_2O$ and quenched with sat. aq $NH_4Cl$ solution. The layers were separated and the organic portion was dried over $Na_2SO_4$ and concentrated under reduced pressure to afford the crude epoxide (590 mg). LCMS [M+H] 204.2.

Step 2: 4-(aminomethyl)-1-benzylpiperidin-4-ol

An aqueous ammonia solution (28%, 7 mL) was added to a solution of 6-benzyl-1-oxa-6-azaspiro[2.5]octane (590 mg) in MeOH (3.5 mL) at 0° C. The mixture was warmed to rt and stirred for 16 h. Volatiles were removed under reduced pressure. The residue was dissolved in DCM and the organic portion was washed with 1M aq. NaOH solution. The aqueous portion was extracted with DCM. The combined organic portions were dried and concentrated under reduced pressure to afford (497 mg) the crude aminol. $^1H$ NMR (400 MHz, $CDCl_3$) δ 7.38-7.23 (m, 5H), 3.55 (s, 2H), 2.74-2.58 (m, 4H), 2.48-2.30 (m, 2H), 1.64-1.50 (m, 4H).

Step 3: tert-butyl ((1-benzyl-4-hydroxypiperidin-4-yl)methyl)carbamate

Di-tert-butyl dicarbonate (226 mg, 1.04 mmol) was added to a solution of 4-(aminomethyl)-1-benzylpiperidin-4-ol (230 mg) in DCM (3 mL) and the reaction was stirred at rt for 1 h.

Volatiles were removed under reduced pressure. The crude product was purified by column chromatography (DCM/MeOH) to afford (235 mg) the title compound. $^1H$ NMR (400 MHz, $CDCl_3$) δ 7.38-7.23 (m, 5H), 3.55 (s, 2H), 3.22-3.10 (m, 2H), 2.70-2.56 (m, 2H), 2.49-2.33 (m, 2H), 1.74-1.54 (m, 4H), 1.46 (s, 9H). LCMS [M+H] 321.4.

Step 4: tert-butyl ((4-hydroxypiperidin-4-yl)methyl)carbamate

Ammonium formate (276 mg, 4.78 mmol) and Pd/C (10% wt, 24 mg) were added to a solution of tert-butyl N-[(1-benzyl-4-hydroxypiperidin-4-yl)methyl]carbamate (235 mg, 0.73 mmol) in MeOH (4 mL) and the resulting mixture was refluxed for 1.5 h. Additional Pd/C was added and stirring at reflux was prolonged for 1 h. The cooled mixture was filtered through a pad of Celite® and the solution was concentrated under reduced pressure to afford the crude amine (163 mg), which was directly progressed to the next step. LCMS [M+H] 231.4.

Intermediate 9 cis-Benzyl N-[3-methoxypiperidin-4-yl]carbamate (racemate)

Scheme I-9

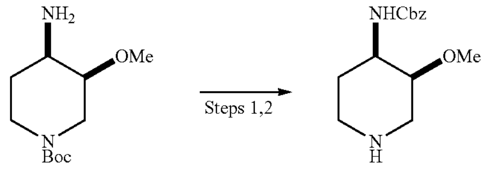

Reagents: 1) Benzyl chloroformate, DIPEA, DCM 2) 3M HCl in MeOH, MeOH.

Step 1: tert-butyl (cis)-4-(((benzyloxy)carbonyl)amino)-3-methoxypiperidine-1-carboxylate Benzyl chloroformate (36 μL, 0.26 mmol) and DIPEA (76 μL, 0.43 mmol) were added to a solution of cis-4-(2-aminopropan-2-yl)-1-boc-piperidine (50 mg, 0.217 mmol) in DCM (4 mL) at 0° C. The reaction was warmed to rt and stirred for 2 h. Benzyl chloroformate (36 μL, 0.26 mmol) and DIPEA (76 μL, 0.434 mmol) were added. The mixture was stirred for 1 h, diluted with DCM and washed with sat. aq. $NaHCO_3$ solution and water. The organic portion was dried over $Na_2SO_4$, filtered and concentrated under reduced pressure. The crude product was purified by column chromatography (cyclohexane-EtOAc, 100:0 to 80:20) to afford the title compound (54 mg, 68%) as a colorless oil. $^1H$ NMR (400 MHz, $CDCl_3$) δ 7.42-7.30 (m, 5H), 5.38-5.20 (m, 1H), 5.12 (s, 2H), 4.55-4.26 (m, 1H), 4.23-3.90 (m, 1H), 3.82-3.58 (m, 1H), 3.44-3.25 (m, 4H), 2.95-2.62 (m, 2H), 1.82-1.59 (m, 2H), 1.48 (s, 9H). LCMS [M+Na] 387.5.

Step 2: benzyl (( )-3-methoxypiperidin-4-yl)carbamate

A 3M solution of HCl in MeOH (246 μL, 0.740 mmol) was added to a solution of cis-tert-butyl 4-(2-{[(benzyloxy)carbonyl]amino} propan-2-yl)piperidine-1-carboxylate (54 mg, 0.148 mmol) in MeOH (3 mL). After 16 h, volatiles were removed under reduced pressure to afford (40 mg) the title compound. LCMS [M+H] 265.3.

Intermediate 10

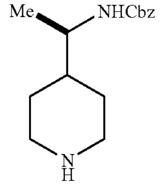 [SMILES: C[C@@H](NC(=O)OCc1ccccc1)C1CCNCC1]

Benzyl N-[(1R)-1-(piperidin-4-yl)ethyl]carbamate

Scheme I-10

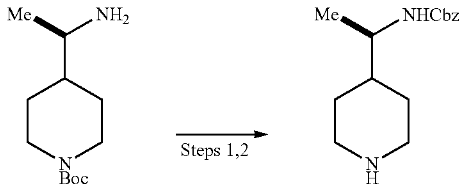

Reagents: 1) Benzyl chloroformate, $K_2CO_3$, THF 2) TFA, DCM.

Step 1: tert-butyl (R)-4-(1-(((benzyloxy)carbonyl)amino)ethyl)piperidine-1-carboxylate Benzyl chloroformate (0.74 mL, 5.26 mmol) was added dropwise to a mixture of tert-butyl 4-[(1R)-1-aminoethyl]piperidine-1-carboxylate (1.0 g, 4.38 mmol) and $K_2CO_3$ (1.21 g, 8.76 mmol) in THF (20 mL). The mixture was stirred at rt for 16 h. Further benzyl chloroformate (0.5 mL) was added. After 5 h, the reaction was diluted with water and extracted with EtOAc. The organic portion was concentrated under reduced pressure to afford (2.30 g) the title compound. LCMS [M+H] 363.4.

Step 2: benzyl (R)-(1-(piperidin-4-yl)ethyl)carbamate

TFA (3 mL) was added to a solution of tert-butyl 4-[(1R)-1-{[(benzyloxy)carbonyl]amino}ethyl]piperidine-1-carboxylate (1 g, crude) in DCM (12 mL). The reaction was stirred at rt for 2 h. Volatiles were removed under reduced pressure and the crude residue was purified by column chromatography (MeOH, 1M $NH_3$ solution in MeOH) to afford (610 mg) the title compound. $^1$H NMR (400 MHz, DMSO) δ 7.41-7.27 (m, 4H), 7.12-7.05 (m, 1H), 5.00-4.97 (m, 2H), 4.17-3.99 (m, 1H), 3.43-3.23 (m, 1H), 2.91 (br.d, 2H), 2.43-2.27 (m, 2H), 1.62-1.46 (m, 2H), 1.39-1.23 (m, 1H), 1.07-0.92 (m, 5H). LCMS [M+H] 263.3.

Intermediate 11

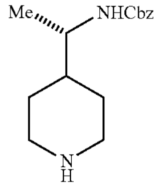 [SMILES: C[C@H](NC(=O)OCc1ccccc1)C1CCNCC1]

Benzyl N-[(1S)-1-(piperidin-4-yl)ethyl]carbamate

Prepared in a similar fashion as Scheme I-10 from tert-butyl 4-[(1S)-1-aminoethyl]piperidine-1-carboxylate. $^1$H NMR (400 MHz, DMSO) δ 7.41-7.27 (m, 4H), 7.14-7.04 (m, 1H), 5.00 (s, 2H), 3.43-3.23 (m, 1H), 2.98-2.85 (m, 2H), 2.44-2.28 (m, 2H), 1.62-1.46 (m, 2H), 1.39-1.23 (m, 1H), 1.07-0.92 (m, 5H).

Intermediate 12

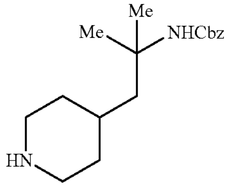 [SMILES: CC(C)(CC1CCNCC1)NC(=O)OCc1ccccc1]

Benzyl N-[2-methyl-1-(piperidin-4-yl)propan-2-yl]carbamate

Scheme I-11

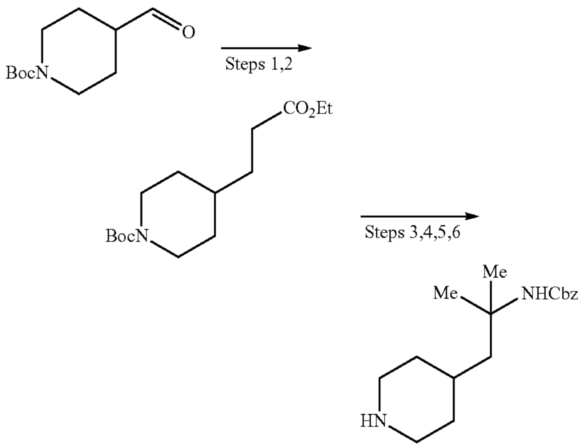

Reagents: 1) Triethyl phophonoacetate, NaH, THF 2) $H_2$, Pd/C, EtOH 3) LDA, MeI, THF; LDA, MeI, THF 4) NaOH, EtOH-$H_2O$ 5) DPPA, TEA, DCE, BnOH 6) TFA, DCM Step 1: tert-butyl (E)-4-(3-ethoxy-3-oxoprop-1-en-1-yl)piperidine-1-carboxylate NaH (60% oil dispersion, 1.09 g, 28.5 mmol) was suspended in THF (20 mL) at 0° C. A solution of triethyl phosphonoacetate (5.6 mL, 28.5 mmol) in THF (10 mL) was added dropwise over 15 min. The reaction was warmed to rt, stirred for 30 min and cooled to 0° C. A solution of 1-Boc-piperidine-4-carboxaldehyde (5.00 g, 23.5 mmol) in THF (10 mL) was added dropwise over 15 min. The reaction was warmed to rt, stirred for 16 h, cooled to 0° C. and water added. The organic solvent was evaporated and the aqueous portion was extracted three times with EtOAc. The combined organic portions were dried over $Na_2SO_4$, filtered, and concentrated under reduced pressure to afford (6.79 g) the crude title compound. LCMS [M+H] 284.4.

Step 2: tert-butyl 4-(3-ethoxy-3-oxopropyl)piperidine-1-carboxylate

A mixture of tert-butyl 4-[3-ethoxy-3-oxoprop-1-en-1-yl]piperidine-1-carboxylate (6.79 g) and Pd/C (10% wt, 180 mg) in EtOH (60 mL) was stirred under $H_2$ atmosphere for 16 h. Further Pd/C (10% wt, 150 mg) was added and stirring under $H_2$ atmosphere was prolonged for 16 h. The reaction was filtered through a pad of Celite®. The solvent was removed under reduced pressure to afford the crude title compound (6.64 g). LCMS [M+H] 286.4.

Step 3: tert-butyl 4-(3-ethoxy-2-methyl-3-oxopropyl)piperidine-1-carboxylate

BuLi (1.6M solution in hexanes, (20 mL, 32 mmol) was added dropwise to a solution of diisopropylamine (4.48 mL, 15 mmol) in THF (40 mL) at −60° C. The mixture was warmed to −20° C. and stirred for 30 min., cooled to −60° C. and a solution of tert-butyl 4-(3-ethoxy-3-oxopropyl)piperidine-1-carboxylate (6.64 g) in THF (10 mL) was added dropwise. The mixture was stirred at −60° C. for 1 h. A solution of MeI (6.7 mL, 108 mmol) in THF (10 mL) was added dropwise. The reaction was warmed to rt, stirred for 16 h, and quenched with sat. aq. $NH_4Cl$ solution. The aqueous portion was extracted three times with EtOAc. The combined organic portions were dried over $Na_2SO_4$, filtered, and concentrated under reduced pressure. The crude product was purified by column chromatography (cyclohexane-EtOAc) to afford (5.53 g, 85%) the title compound. LCMS [M+H] 300.4.

Step 4: tert-butyl 4-(3-ethoxy-2,2-dimethyl-3-oxopropyl)piperidine-1-carboxylate BuLi (1.6M solution in hexanes, 17.3 mL, 27.8 mmol) was added dropwise to a solution of diisopropylamine (3.9 mL, 27.8 mmol) in THF (40 mL) at −60° C. The mixture was warmed to −20° C. and stirred for 30 min. The reaction mixture was cooled to −60° C., and a solution of tert-butyl 4-(3-ethoxy-2-methyl-3-oxopropyl)piperidine-1-carboxylate (5.53 g, 18.5 mmol) in THF (10 mL) was added dropwise. The mixture was stirred at −60° C. for 1 h. A solution of MeI (5.76 mL, 92.5 mmol) in THF (10 mL) was added dropwise. The reaction was allowed to reach rt, stirred for 16 h, and quenched with sat. aq. $NH_4Cl$ solution. The aqueous portion was extracted three times with EtOAc. The combined organic portions were dried over $Na_2SO_4$, filtered, and concentrated under reduced pressure. The crude product was purified by column chromatography (cyclohexane-EtOAc, 100:0 to 70:30) to afford the title compound (4.76 g, 82%). $^1H$ NMR (400 MHz, $CDCl_3$) δ 4.13 (q, 2H), 4.08-3.94 (m, 2H), 2.76-2.59 (m, 2H), 1.62-1.41 (m, 14H), 1.27 (t, 3H), 1.20 (s, 6H), 1.18-1.05 (m, 2H). LCMS [M+H] 314.4.

Step 5: 3-(1-(tert-butoxycarbonyl)piperidin-4-yl)-2,2-dimethylpropanoic acid

NaOH (2.0 g, 50 mmol) was added to a solution of tert-butyl 4-(3-ethoxy-2,2-dimethyl-3-oxopropyl)piperidine-1-carboxylate (4.76 g, 15.2 mmol) in 5:1 EtOH—$H_2O$ (24 mL). The reaction was refluxed for 16 h. The organic solvent was removed under reduced pressure. The aqueous portion was washed twice with $Et_2O$, acidified with 3M HCl and extracted with EtOAc (3×). The combined organic portions were dried over $Na_2SO_4$, filtered, and concentrated under reduced pressure to afford the title compound (2.72 g) as a pale yellow solid. $^1H$ NMR (400 MHz, $CDCl_3$) δ 4.04 (br s, 2H), 2.70 (t, 2H), 1.69-1.50 (m, 5H), 1.47 (s, 9H), 1.30-1.09 (m, 8H). LCMS [M+H] 286.4.

Step 6: benzyl (2-methyl-1-(piperidin-4-yl)propan-2-yl)carbamate $Et_3N$ (1.23 mL, 9.26 mmol) and DPPA (1.10 mL, 5.09 mmol) were sequentially added to a solution of 3-{1-[(tert-butoxy)carbonyl]piperidin-4-yl}-2,2-dimethylpropanoic acid (1.32 g, 4.63 mmol) in DCE (20 mL). The reaction was stirred at 80° C. for 3 h. DPPA (0.50 mL, 2.31 mmol) was added and the reaction mixture heated for 2 h. Benzyl alcohol (0.93 mL, 9.26 mmol) was added and mixture was stirred at 80° C. for 1 h. Benzyl alcohol (3.2 mL, 31 mmol) was added and the solution was stirred at 80° C. for 16 h. Sat. aq. $NaHCO_3$ solution was added and extracted with DCM (3×). The combined organic portions were dried over $Na_2SO_4$, filtered, and concentrated under reduced pressure. The crude product was purified by column chromatography (cyclohexane-EtOAc, 100:0 to 80:20) to afford a mixture of the title compound and benzyl alcohol (~30% wt, 3.1 g), which was progressed to the next step without any further purification. TFA (5 mL) was added to a solution of this mixture in DCM (15 mL) and the resulting solution was stirred at rt for 4 h. Volatiles were removed under reduced pressure. The crude product was purified by column chromatography (MeOH, 1M $NH_3$ in MeOH) to afford the title compound (490 mg, 36% over two steps) as a colorless oil. $^1H$ NMR (400 MHz, $CDCl_3$) δ 7.42-7.30 (m, 5H), 5.18-4.94 (m, 2H), 4.65 (br. s., 1H), 3.09-2.96 (m, 2H), 2.60 (td, 2H), 1.73-1.58 (m, 4H), 1.57-1.41 (m, 1H), 1.38-1.14 (m, 8H). LCMS [M+H] 291.3.

Intermediate 13

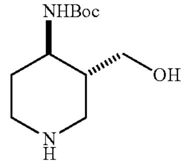 [SMILES: CC(C)(C)OC(=O)N[C@@H]1CCNC[C@H]1CO]

trans-tert-Butyl N-[3-(hydroxymethyl)piperidin-4-yl]carbamate (racemate)

Scheme I-12

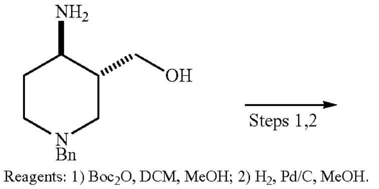

Step 1: tert-butyl ((trans)-1-benzyl-3-(hydroxymethyl)piperidin-4-yl)carbamate

Di-tert-butyl dicarbonate (198 mg, 0.91 mmol) was added to a solution of trans-[4-amino-1-benzylpiperidin-3-yl] methanol (200 mg, 0.91 mmol) in a 3:1 MeOH-DCM solution (10 mL). The reaction was stirred at rt for 16 h and concentrated under reduced pressure. The crude product was purified by column chromatography (DCM-MeOH) to afford the title compound (59 mg, 20%). $^1$H NMR (400 MHz, $CDCl_3$) δ 7.38-7.22 (m, 5H), 4.52 (d, 1H), 3.79-3.62 (m, 2H), 3.59 (d, 1H), 3.52-3.43 (m, 2H), 3.01 (dd, 1H), 2.90 (d, 1H), 2.01 (td, 1H), 1.91-1.71 (m, 2H), 1.68-1.56 (m, 1H), 1.45 (s, 9H), 1.23-1.09 (m, 1H). LCMS [M+H] 321.4.

Step 2: tert-butyl ((trans)-3-(hydroxymethyl)piperidin-4-yl)carbamate

Pd/C (10% wt, 5 mg) was added to a solution of trans-tert-butyl N-[1-benzyl-3-(hydroxymethyl)piperidin-4-yl] carbamate (59 mg, 0.18 mmol) in EtOH (20 mL). The reaction was stirred under $H_2$ atmosphere for 16 h and filtered through Celite®. Volatiles were removed under reduced pressure to afford the title compound (34.5 mg, 83%), which was directly progressed to the next step. LCMS [M+H] 231.3.

Intermediate 14

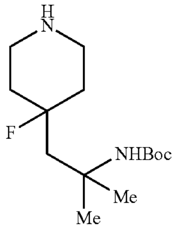

tert-butyl (1-(4-fluoropiperidin-4-yl)-2-methylpropan-2-yl)carbamate

Scheme I-13

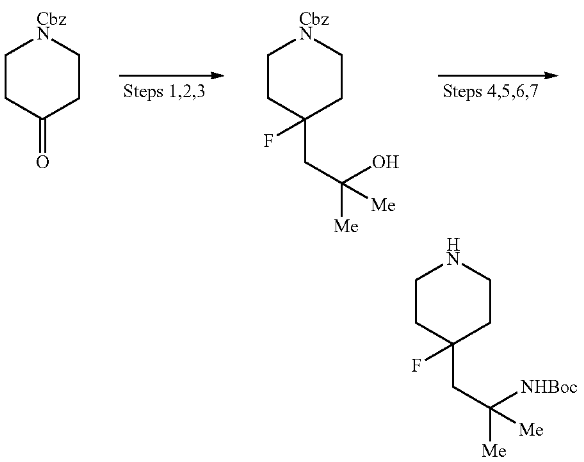

Reagents: 1) LDA, EtOAc, THF; 2) DAST, DCM; 3) MeMgBr, THF; 4) AcOH, $H_2SO_4$, chloroacetonitrile; 5) AcOH, thiourea, EtOH; 6) $Boc_2O$, DCM; 7) $H_2$, Pd/C, MeOH.

Step 1: benzyl 4-(2-ethoxy-2-oxoethyl)-4-hydroxypiperidine-1-carboxylate

Lithium diisopropylamide (1.8M in THF, 7 mL) was added to a solution of EtOAc (1.12 g, 12.7 mmol) in THF (20 mL) at −78° C. After 30 min. a solution of benzyl 4-oxopiperidine-1-carboxylate (2.0 g, 8.5 mmol) in THF (15 mL) was added. The mixture was warmed to −40° C. and stirred for 5 h. The reaction was quenched with sat. aq. $NH_4Cl$ solution (10 mL) and extracted twice with EtOAc. The combined organic portions were dried over $Na_2SO_4$ and concentrated under reduced pressure. The crude product was purified by column chromatography (cyclohexane-EtOAc, 100:0 to 40:60) to afford the title compound (1.3 g, 47%). LCMS [M+H] 322.1.

Step 2: benzyl 4-(2-ethoxy-2-oxoethyl)-4-fluoropiperidine-1-carboxylate

DAST (602 mg, 3.74 mmol) was added to a solution of benzyl 4-(2-ethoxy-2-oxoethyl)-4-hydroxypiperidine-1-carboxylate (600 mg, 1.87 mmol) in DCM (20 mL). The reaction was stirred at rt for 16 h and concentrated under reduced pressure. The crude product was purified by column chromatography (cyclohexane-EtOAc) to afford the title compound (305 mg, 50%). LCMS [M+H] 324.1.

Step 3: benzyl 4-fluoro-4-(2-hydroxy-2-methylpropyl)piperidine-1-carboxylate

Methyl magnesium bromide (3M in $Et_2O$, 0.78 mL) was added dropwise to a solution of benzyl 4-(2-ethoxy-2-oxoethyl)-4-fluoropiperidine-1-carboxylate (305 mg, 0.94 mmol) in THF (10 mL) at 0° C. The reaction was stirred at 0° C. for 1 h, warmed to 20° C. and stirred for 1 h and quenched with sat. aq. $NH_4Cl$ solution. The aqueous portion was extracted twice with DCM. The combined organic portions were concentrated under reduced pressure to afford the title compound (260 mg).

Step 4: benzyl 4-(2-(2-chloroacetamido)-2-methylpropyl)-4-fluoropiperidine-1-carboxylate AcOH (161 mg, 2.7 mmol) and $H_2SO_4$ (172 mg, 3.4 mmol) were added dropwise to a solution of benzyl 4-fluoro-4-(2-hydroxy-2-methylpropyl)piperidine-1-carboxylate (260 mg) in chloroacetonitrile (4 mL) at 0° C. The reaction was stirred at rt for 24 h. An aqueous solution of $Na_2CO_3$ (10%, 10 mL) and THF (15 mL) were added and the mixture was stirred at rt for 20 min. Benzyl chloroformate (1 mL) was added and the mixture was stirred for 2 h. The aqueous portion was extracted with DCM. The organic portion was concentrated under reduced pressure and purified by column chromatography (cyclohexane-EtOAc) to afford the title compound (125 mg). LCMS [M+H] 385.1.

Step 5: benzyl 4-(2-amino-2-methylpropyl)-4-fluoropiperidine-1-carboxylate

ACOH (500 μL) and thiourea (50 mg, 0.65 mmol) were sequentially added to a solution of benzyl 4-[2-(2-chloroacetamido)-2-methylpropyl]-4-fluoropiperidine-1-carboxylate (125 mg, 0.324 mmol) in EtOH (5 mL). The reaction was heated to 80° C. and stirred for 6 h. An aqueous solution of $NaHCO_3$(5%, 10 mL) was added and the mixture was extracted with DCM. The organic portion was concentrated under reduced pressure to afford the title compound (78 mg, 78%). LCMS [M+H] 309.1.

Step 6: benzyl 4-(2-((tert-butoxycarbonyl)amino)-2-methylpropyl)-4-fluoropiperidine-1-carboxylate Di-tert-butyl dicarbonate (110 mg, 0.50 mmol) was added to a solution of benzyl 4-(2-amino-2-methylpropyl)-4-fluoropiperidine-1-carboxylate (78 mg, 0.253 mmol) in DCM (5 mL). The reaction was stirred at rt for 16 h and quenched with sat. aq. $NH_4Cl$ solution. After 1 h, the aqueous phase was extracted with DCM. The organic portion was concentrated under reduced pressure to afford the crude title compound (99 mg). $^1H$ NMR (400 MHz, $CDCl_3$) δ 7.42-7.30 (m, 5H), 5.15 (s, 2H), 4.66-4.53 (m, 1H), 4.08-3.86 (m, 2H), 3.24-3.02 (m, 2H), 2.25-1.91 (m, 4H), 1.77-1.54 (m, 2H), 1.44 (s, 9H), 1.37 (s, 6H).

Step 7: tert-butyl (1-(4-fluoropiperidin-4-yl)-2-methylpropan-2-yl)carbamate

Pd/C (10% wt, 5 mg) was added to a solution of benzyl 4-(2-{[(tert-butoxy)carbonyl]amino}-2-methylpropyl)-4-fluoropiperidine-1-carboxylate (99 mg) in MeOH (2 mL). The reaction was stirred under $H_2$ atmosphere for 5 h, filtered and concentrated under reduced pressure to afford the crude title compound (65 mg). LCMS [M+H] 275.3.

Intermediate 15

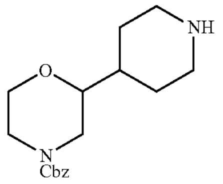 [SMILES: O=C(OCc1ccccc1)N1CCOC(C2CCNCC2)C1]

Benzyl 2-(piperidin-4-yl)morpholine-4-carboxylate

Scheme I-14

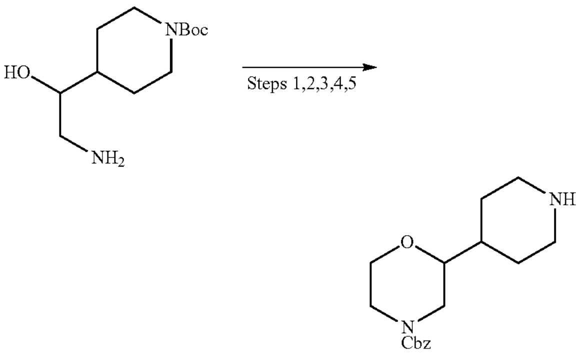

Reagants: 1) 2-Bromoacetyl chloride, DIPEA, DCM; 2) KOtBu, dioxane; 3) $BH_3SMe_2$, THF; 4) benzyl chloroformate, TEA, DCM; 5) TFA, DCM.

Step 1: tert-butyl 4-(2-(2-bromoacetamido)-1-hydroxyethyl)piperidine-1-carboxylate 2-Bromoacetyl chloride (401 mg, 2.55 mmol) was added to a solution of tert-butyl 4-(2-amino-1-hydroxyethyl)piperidine-1-carboxylate (566 mg, 2.32 mmol) and DIPEA (1.6 mL, 9.28 mmol) in DCM (15 mL) at 0° C. The reaction was stirred for 8 h. The mixture was diluted with DCM and washed with 5% aq. citric acid solution. The organic portion was concentrated under reduced pressure to afford the crude title compound (744 mg). LCMS [M+H] 321.1.

Step 2: tert-butyl 4-(5-oxomorpholin-2-yl)piperidine-1-carboxylate

Potassium tert-butoxide (1.04 g, 9.28 mmol) was added to a solution of tert-butyl 4-(2-(2-bromoacetamido)-1-hydroxyethyl)piperidine-1-carboxylate (744 mg) in dioxane (15 mL) and the resulting mixture was stirred at 50° C. for 1 h. Water (20 mL) and sat. aq. $NH_4Cl$ (15 mL) were added and the solution was extracted twice with DCM. The combined organic portions were concentrated under reduced pressure. The crude product was purified by column chromatography (EtOAc-MeOH, 100:0 to 75:25) to afford the title compound (230 mg, 35% over two steps). LCMS [M+H] 285.1.

Step 3: tert-butyl 4-(morpholin-2-yl)piperidine-1-carboxylate

Borane dimethyl sulfide complex (2M in $Et_2O$, 0.425 mL) was added to a solution of tert-butyl 4-(5-oxomorpholin-2-yl)piperidine-1-carboxylate (230 mg, 0.81 mmol) in THF (10 mL) at 0° C. The reaction was warmed to rt and stirred for 1 h. The reaction was cooled to 0° C. and borane dimethyl sulfide complex (2M in $Et_2O$, 0.425 mL) was added. The mixture was warmed to rt and stirred for 2 h. Water (30 mL) was added and the aqueous portion was extracted with DCM. The organic portion was concentrated under reduced pressure to afford the crude title compound (95 mg), which was directly progressed to the next step. LCMS [M+H] 271.1.

Step 4: benzyl 2-(1-(tert-butoxycarbonyl)piperidin-4-yl)morpholine-4-carboxylate Benzyl chloroformate (0.055 mL, 0.39 mmol) was added to a solution of tert-butyl 4-(morpholin-2-yl)piperidine-1-carboxylate (95 mg) and TEA (0.058 mL, 0.42 mmol) in DCM (2 mL) at 0° C. The reaction was warmed to rt and stirred for 2 h. The mixture was diluted with DCM and washed with 5% aq. citric acid. The organic portion was concentrated under reduced pressure. The crude product was purified by column chromatography (cyclohexane-EtOAc) to afford the title compound (117 mg, 36% over two steps). LCMS [M+H] 405.2.

Step 5: benzyl 2-(piperidin-4-yl)morpholine-4-carboxylate

TFA (0.5 mL) was added to a solution of benzyl 2-{1-[(tert-butoxy)carbonyl]piperidin-4-yl}morpholine-4-carboxylate (117 mg, 0.290 mmol) in DCM (0.5 mL). The reaction was stirred at rt for h and concentrated under reduced pressure. The crude solid was washed with 1:1 $Et_2O$-EtOAc solution to afford the title compound as its trifluoroacetate salt (108 mg). LCMS [M+H] 305.1.

Intermediate 16

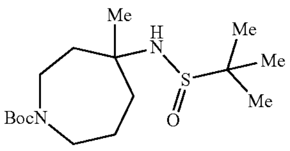 [SMILES: CC1(NS(=O)C(C)(C)C)CCCN(C(=O)OC(C)(C)C)CC1]

2-Methyl-N-(4-methylazepan-4-yl)propane-2-sulfinamide

Scheme I-15

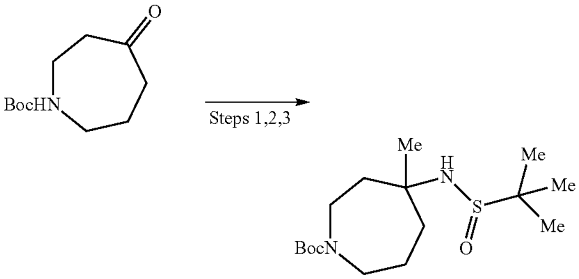

Reagants: 1) 2-methyl-2-propanesulfinamide, $Ti(OEt)_4$, THF, 70° C.; 2) MeLi, $AlMe_3$, THF, -78° C. to rt; 3) TFA, DCM.

Step 1: tert-butyl (Z)-4-((tert-butylsulfinyl)imino) azepane-1-carboxylate

2-Methyl-2-propanesulfinamide (125 mg, 1.03 mmol) and $Ti(OEt)_4$ (428 mg, 1.87 mmol) were added to a solution of tert-butyl 4-oxoazepane-1-carboxylate (400 mg, 1.87 mmol) in THF (4 mL) and the mixture was stirred at 70° C. in a sealed vial for 18 h. The mixture was diluted with DCM. The organic portion was washed with water and filtered from the solid. Volatiles were removed under reduced pressure and the crude product was purified by column chromatography (cyclohexane-EtOAc, 100:0 to 40:60) to afford the title compound (425 mg, 72%) as a yellow oil. $^1H$ NMR (400 MHz, $CDCl_3$) δ 3.88-2.58 (m, 8H), 1.95-1.72 (m, 2H), 1.47 (s, 9H), 1.26 (s, 9H). LCMS [M+H] 317.3.

Step 2: tert-butyl 4-((tert-butylsulfinyl)amino)-4-methylazepane-1-carboxylate

Trimethylaluminum (690 μL, 1.39 mmol) was added to a solution of tert-butyl 4-[(2-methylpropane-2-sulfinyl)imino] azepane-1-carboxylate (200 mg, 0.632 mmol) in toluene (5 mL) at −78° C. After 20 min. methyllithium (1.6M in $Et_2O$, 1.7 mL) was added. The reaction was warmed to rt and stirred for 16 h. The reaction mixture was cooled to −15° C. and methyllithium (1.4 mL, 2.21 mmol) was added. The mixture was warmed to 0° C. and stirred for further 16 h. Water was added. The aqueous portion was extracted twice with EtOAc. The combined organic portions were dried $Na_2SO_4$, filtered, and concentrated under reduced pressure. The crude product was purified by column chromatography (cyclohexane-EtOAc) to afford the title compound (12.0 mg, 6%) as a pale yellow wax. LCMS [M+H] 333.4.

Step 3: 2-methyl-N-(4-methylazepan-4-yl)propane-2-sulfinamide

TFA (400 μL) was added to a solution of tert-butyl 4-methyl-4-[(2-methylpropane-2-sulfinyl)amino]azepane-1-carboxylate (12.0 mg, 0.036 mmol) in DCM (1.6 mL) and the resulting solution was stirred at rt for 1.5 h. Volatiles were removed under reduced pressure to afford the crude 2-methyl-N-(4-methylazepan-4-yl)propane-2-sulfinamide as the trifluoroacetate salt. LCMS [M+H] 233.3.

Intermediate 17

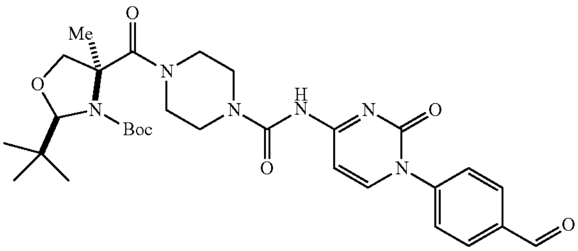

tert-Butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate Scheme I-16

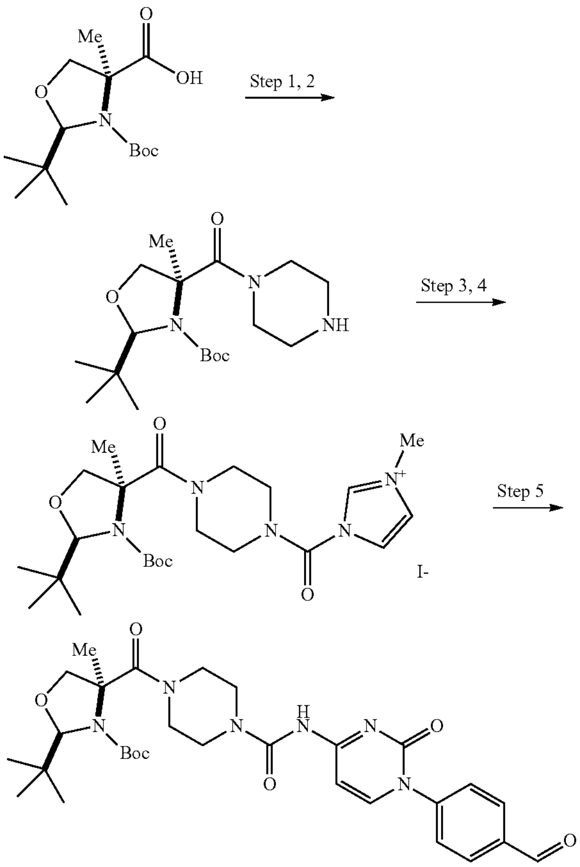

Reagents: 1) benzyl 1-piperzinecarboxylate, HATU, DIPEA, DMF, rt, 16 h 2) 10% Pd/C, MeOH, $H_2$, rt, 16 h 3) CDI, DCM, rt, 16 h 4) MeI, $CH_3CN$, rt, 16 h 5) 4-(4-amino-2-oxopyrimidin-1(2H)-yl)benzaldehyde, $CH_3CN$, reflux, 16 h.

Step 1: tert-butyl (2R,4S)-4-(4-((benzyloxy)carbonyl)piperazine-1-carbonyl)-2-(tert-butyl)-4-methyloxazolidine-3-carboxylate To a stirred solution of (2R,4S)-3-(tert-butoxycarbonyl)-2-(tert-butyl)-4-methyloxazolidine-4-carboxylic acid (0.60 g, 2.11 mmol, Prepared in a similar fashion as Org. Lett. 2011, 13, 5000) in DMF (10 mL) was added DIPEA (0.68 g, 5.28 mmol) and HATU (0.97 g, 2.53 mmol). After 15 min. benzyl 1-piperazinecarboxylate (0.463 g, 2.11 mmol) was added, and the mixture was stirred at rt for 16 h. The reaction mixture was poured into sat. aq. LiCl (30 mL) and stirred for 20 min. The precipitate was filtered and purified by flash chromatography (EtOAc:Hex) to afford the title compound (0.85 g, 82%) as an off-white solid. $^1$H NMR (400 MHz, $CDCl_3$) δ 7.35 (m, 5H), 5.22 (s, 1H), 5.17 (s, 2H), 4.95 (d, 1H), 3.83 (br s, 2H), 3.53 (br s, 3H) 3.31 (d, 1H), 1.61 (s, 3H), 1.51 (s, 9H), 0.89 (s, 12H).

Step 2: tert-Butyl (2R,4S)-2-(tert-butyl)-4-methyl-4-(piperazine-1-carbonyl)oxazolidine-3-carboxylate To a stirred solution of tert-butyl (2R,4S)-4-(4-((benzyloxy)carbonyl)piperazine-1-carbonyl)-2-(tert-butyl)-4-methyloxazolidine-3-carboxylate (0.85 g, 1.73 mmol) in MeOH (20 mL) was added Pd/C 10% wt (0.1 g). The reaction mixture was stirred under hydrogen atmosphere at rt for 16 h, filtered through Celite® and washed with MeOH (50 mL). The filtrate was concentrated under reduced pressure and dried to afford the title compound (0.58 g, 95%) as a viscous oil.

Step 3: tert-butyl (2R,4S)-4-(4-(1H-imidazole-1-carbonyl)piperazine-1-carbonyl)-2-(tert-butyl)-4-methyloxazolidine-3-carboxylate To a stirred solution of tert-butyl (2R,4S)-2-(tert-butyl)-4-methyl-4-(piperazine-1-carbonyl)oxazolidine-3-carboxylate (0.58 g, 1.64 mmol) in $CH_2Cl_2$ (20 mL) was added CDI (0.53 g, 3.27 mmol). The reaction mixture was stirred at rt for 16 h then concentrated under reduced pressure. The residue was purified by column chromatography to afford the title compound (0.66 g, 90%) as an off-white solid.

Step 4: 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide To a stirred solution of tert-butyl (2R,4S)-4-(4-(1H-imidazole-1-carbonyl)piperazine-1-carbonyl)-2-(tert-butyl)-4-methyloxazolidine-3-carboxylate (0.66 g, 1.47 mmol) in $CH_3CN$ (15 mL) was added MeI (20.8 ml, 14.7 mmol). The reaction mixture was stirred at rt for 16 h concentrated under reduced pressure to afford the title compound (0.88 g, quant.) as a pale yellow solid.

Step 5: tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate A mixture of 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide (0.88 g, 1.50 mmol) and 4-(4-amino-2-oxopyrimidin-1(2H)-yl)benzaldehyde in $CH_3CN$ was stirred at reflux for 16 h. The solvent was evaporated and the residue was purified by flash chromatography to afford the title compound (0.54 g, 60%) as a pale yellow solid. LCMS [M+H] 597.2.

Intermediate 18

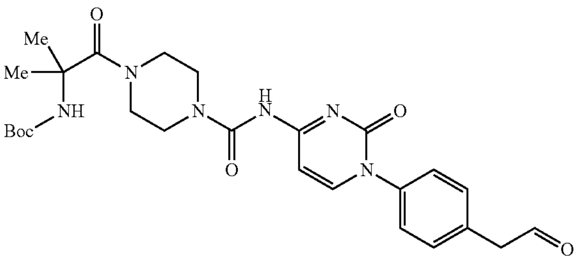 [SMILES: CC(C)(C)OC(=O)NC(C)(C)C(=O)N1CCN(C(=O)Nc2ccn(-c3ccc(CC=O)cc3)c(=O)n2)CC1]

tert-Butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate Scheme I-17

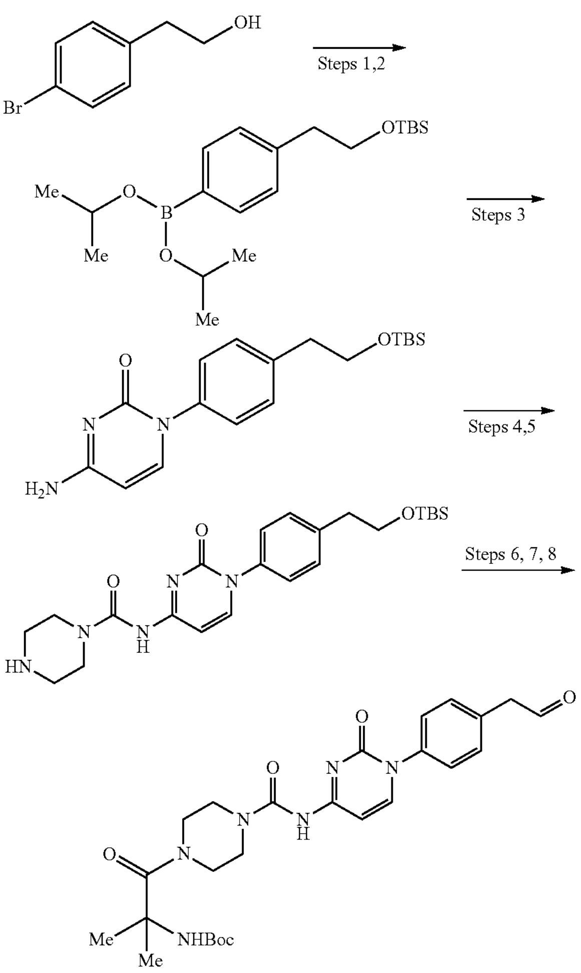

Reagents: 1) TBSCl, imidazole, DMF, rt, 16 h 2) BuLi, THF, -78° C., $(iPro)_3B$, 2NHCl 3) cytosine, TMEDA, $Cu(OAc)_2$•$H_2O$, 4:1 MeOH:$H_2O$, rt, 48 h 4) 3-methyl-1-(4-(2,2,2-trifluoroacetyl)piperazine-1-carbonyl)-1H-imidazol-3-ium iodide, $CH_3CN$, 85° C., 16 h 5) $K_2CO_3$, MeOH, rt, 3 h 6) Boc-AIB-OH,HATU, DIPEA, DMF, rt, 8 h 7) TBAF, THF, 0° C. to rt, 16 h 8) DMP, 1% $CH_2Cl_2$:$H_2O$, rt, 1 h.

Step 1: (4-bromophenethoxy)(tert-butyl)dimethylsilane

To a stirring solution of 2-(4-bromophenyl)ethan-1-ol (7.0 mL, 49.7 mmol) in DMF (50 mL) was added imidazole (5.1 g, 74.6 mmol) and tert-butyldimethylsilyl chloride (9.0 g, 60.0 mmol). The solution was stirred 16 h. The reaction mixture was diluted with EtOAc (100 mL) and extracted with aqueous LiCl (3×50 mL). The organic layer was dried over $Na_2SO_4$ and concentrated under reduced pressure to give an oily residue, which was purified by flash chromatography (Hex:EtOAc) to afford the title compound.

Step 2: bisisopropyl (4-(2-((tert-butyldimethylsilyl)oxy)ethyl)phenyl)boronate

A stirred solution of (4-bromophenethoxy)(tert-butyl)dimethylsilane (9.0 g, 28.0 mmol) in THF (100 mL) was cooled to −78° C. 2.5 M BuLi in Hexanes (28.0 mL, 71.4 mmol) was added dropwise over 30 min. and the temperature maintained below −60° C. After 25 min., triisopropyl borate (10.0 mL, 42.0 mmol) was added dropwise over 30 min. The reaction mixture was warmed to rt and stirred for 15 min. 2NHCl (50 mL) was added and the reaction was stirred for 30 min. The biphasic mixture was separated and the aq. layer extracted with $CH_2Cl_2$ (2×50 mL). The combined organics were dried over $Na_2SO_4$ and concentrated under reduced pressure afford the title compound.

Step 3: 4-amino-1-(4-(2-((tert-butyldimethylsilyl)oxy)ethyl)phenyl)pyrimidin-2(1H)-one A suspension of cytosine (10.5 g, 95.0 mmol) and diisopropyl (4-(2-((tert-butyldimethylsilyl)oxy)ethyl)phenyl)boronate (26.6 g, 95.0 mmol), in MeOH:$H_2O$ (4:1, 600 ml) was stirred at rt in open air for 30 min. TMEDA (17.0 ml, 114.0 mmol) and $Cu(OAc)_2 \cdot H_2O$ (19.0 g, 95.0 mmol) were added and the reaction was stirred in open air for 48 h at rt. The reaction mixture was concentrated under reduced pressure, and cold $H_2O$ (100 mL) was added. The solid was filtered and washed with $H_2O$ (5×50 mL), $Et_2O$ (3×30 mL), and $H_2O$ (2×30 mL) to afford the title compound. LCMS [M+H] 346.2.

Step 4: N-(1-(4-(2-((tert-butyldimethylsilyl)oxy)ethyl)phenyl)-2-oxo-1,2-dihydropyrimidin-4-yl)-4-(2,2,2-trifluoroacetyl)piperazine-1-carboxamide To a stirred solution of 4-amino-1-(4-(2-((tert-butyldimethylsilyl)oxy)ethyl)phenyl)pyrimidin-2(1H)-one (2.41 g, 7.0 mmol) in $CH_3CN$ (50 mL) was added 3-methyl-1-(4-(2,2,2-trifluoroacetyl)piperazine-1-carbonyl)-1H-imidazol-3-ium iodide (3.79 g, 8.4 mmol). The vessel was flushed with nitrogen and heated to 85° C. and refluxed for 16 h. The reaction mixture was concentrated under reduced pressure, which was purified by column chromatography ($CH_2Cl_2$:MeOH:$NH_4OH$) to afford the title compound. LCMS [M+H] 554.3.

Step 5: N-(1-(4-(2-((tert-butyldimethylsilyl)oxy)ethyl)phenyl)-2-oxo-1,2-dihydropyrimidin-4-yl)piperazine-1-carboxamide N-(1-(4-(2-((tert-Butyldimethylsilyl)oxy)ethyl)phenyl)-2-oxo-1,2-dihydropyrimidin-4-yl)-4-(2,2,2-trifluoroacetyl)piperazine-1-carboxamide (4.50 g, 8.1 mmol) and $K_2CO_3$ (3.36 g, 24.3 mmol) were dissolved in MeOH (200 mL), and stirred at rt for 3 h. The reaction mixture was concentrated under reduced pressure to give a solid residue and purified by column chromatography ($CH_2Cl_2$:MeOH:$NH_4OH$) to afford the title compound.

Step 6: tert-butyl (1-(4-((1-(4-(2-((tert-butyldimethylsilyl)oxy)ethyl)phenyl)-2-oxo-1,2-dihydropyrimidin-4-yl)carbamoyl)piperazin-1-yl)-2-methyl-1-oxopropan-2-yl)carbamate To a solution of N-(1-(4-(2-((tert-butyldimethylsilyl)oxy)ethyl)phenyl)-2-oxo-1,2-dihydropyrimidin-4-yl)piperazine-1-carboxamide (3.66 g, 8.1 mmol) in DMF (30 mL) was added 2-((tert-butoxycarbonyl)amino)-2-methylpropanoic acid (1.63 g, 8.1 mmol) followed by DIPEA (3.36 mL, 24.2 mmol). The solution stirred for 5 min, and HATU (5.51 g, 14.5 mmol) was then added and the solution was stirred at rt for an additional 8 h. The crude reaction mixture was dissolved in EtOAc (50 mL) and washed with aqueous LiCl (3×30 mL). The organic layer was dried over $Na_2SO_4$, concentrated under reduced pressure and purified by flash chromatography ($CH_2Cl_2$:MeOH:$NH_4OH$) to afford the desired compound. LCMS [M+H] 643.4.

Step 7: tert-butyl (1-(4-((1-(4-(2-hydroxyethyl)phenyl)-2-oxo-1,2-dihydropyrimidin-4-yl)carbamoyl)piperazin-1-yl)-2-methyl-1-oxopropan-2-yl)carbamate To a solution of tert-butyl (1-(4-((1-(4-(2-((tert-butyldimethylsilyl)oxy)ethyl)phenyl)-2-oxo-1,2-dihydropyrimidin-4-yl)carbamoyl)piperazin-1-yl)-2-methyl-1-oxopropan-2-yl)carbamate (1.0 g, 1.63 mmol) in THF (30 mL) at 0° C. was added TBAF in THF (2M, 3.27 mL) over 20 min. The solution was warmed to rt and stirred for 16 h. The crude reaction mixture was concentrated under reduced pressure to give an oily residue, which was purified by column chromatography ($CH_2Cl_2$:MeOH) to afford the desired compound. LCMS [M+H] 529.4.

Step 8: tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate To a stirred solution of tert-butyl (1-(4-((1-(4-(2-hydroxyethyl)phenyl)-2-oxo-1,2-dihydropyrimidin-4-yl)carbamoyl)piperazin-1-yl)-2-methyl-1-oxopropan-2-yl)carbamate (150.0 mg, 0.28 mmol) in $CH_2Cl_2$:$H_2O$ (100:1, 10 mL) was added Dess-Martin periodinane (361.0 mg, 0.85 mmol). The solution was stirred for 1 h. The crude reaction mixture was dissolved in additional $CH_2Cl_2$ (50 mL) and washed with aq. $NaHCO_3$/$Na_2S_2O_3$ (1×50 mL). The aq. layer was extracted with $CH_2Cl_2$ (1×10 mL). The combined organic layers were dried over $Na_2SO_4$ and concentrated under reduced pressure to afford the title compound which was used immediately.

Intermediate 19

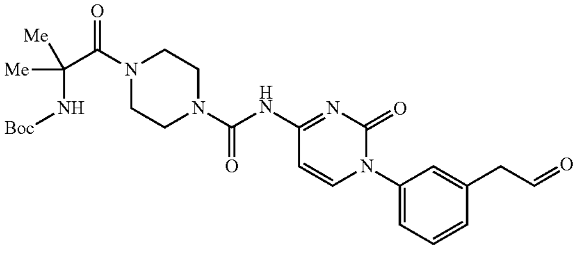 [SMILES: CC(C)(C)OC(=O)NC(C)(C)C(=O)N1CCN(C(=O)Nc2ccn(-c3cccc(CC=O)c3)c(=O)n2)CC1]

tert-Butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate Prepared in a similar fashion to Scheme I-17 from 2-(3-bromophenyl)ethan-1-ol.

Intermediate 20

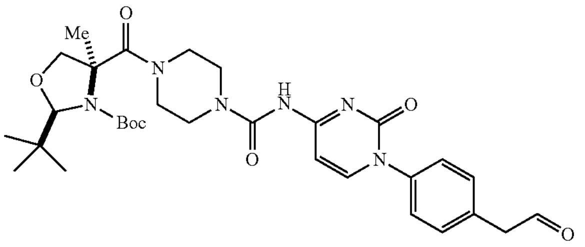

tert-Butyl (2R,4S)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate Prepared in a similar fashion to Scheme I-17 using 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide.

Intermediate 21

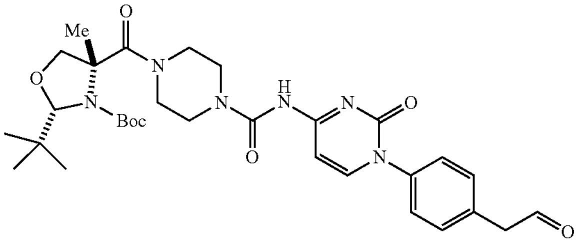

tert-butyl (2S,4R)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate Prepared in a similar fashion to Scheme I-17 using 1-(4-((2S,4R)-3-(tert-butoxycarbonyl)-2-(tert-butyl)-4-methyloxazolidine-4-carbonyl)piperazine-1-carbonyl)-3-methyl-1H-imidazol-3-ium iodide.

Intermediate 22

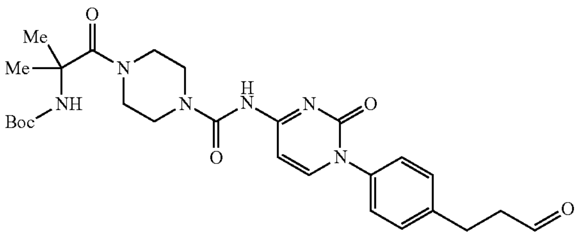 [SMILES: CC(C)(C)OC(=O)NC(C)(C)C(=O)N1CCN(C(=O)Nc2ccn(-c3ccc(CCC=O)cc3)c(=O)n2)CC1]

tert-Butyl (2-methyl-1-oxo-1-(4-((2-oxo-1-(4-(3-oxopropyl)phenyl)-1,2-dihydropyrimidin-4-yl)carbamoyl)piperazin-1-yl)propan-2-yl)carbamate Prepared in a similar fashion to Scheme I-17 from 3-(4-bromophenyl)propan-1-ol.

Intermediate 23

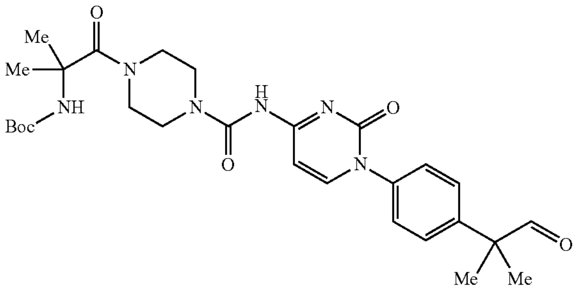 [SMILES: CC(C)(C)OC(=O)NC(C)(C)C(=O)N1CCN(C(=O)Nc2ccn(-c3ccc(C(C)(C)C=O)cc3)c(=O)n2)CC1]

tert-Butyl (2-methyl-1-(4-((1-(4-(2-methyl-1-oxopropan-2-yl)phenyl)-2-oxo-1,2-dihydropyrimidin-4-yl)carbamoyl)piperazin-1-yl)-1-oxopropan-2-yl) carbamate Prepared in a similar fashion to Scheme I-17 from 2-(4-bromophenyl)-2-methylpropan-1-ol.

Intermediate 24

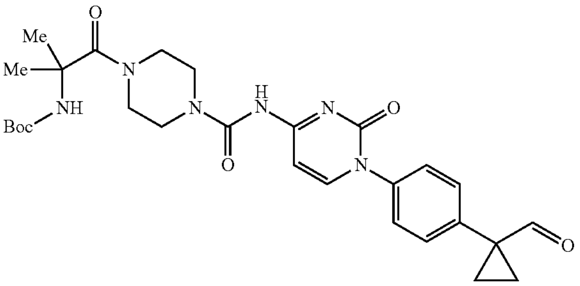 [SMILES: CC(C)(C)OC(=O)NC(C)(C)C(=O)N1CCN(C(=O)Nc2ccn(-c3ccc(C4(C=O)CC4)cc3)c(=O)n2)CC1]

tert-Butyl (1-(4-((1-(4-(1-formylcyclopropyl)phenyl)-2-oxo-1,2-dihydropyrimidin-4-yl)carbamoyl) piperazin-1-yl)-2-methyl-1-oxopropan-2-yl)carbamate Prepared in a similar fashion to Scheme I-17 from (1-(4-bromophenyl)cyclopropyl)methanol.

Intermediate 25

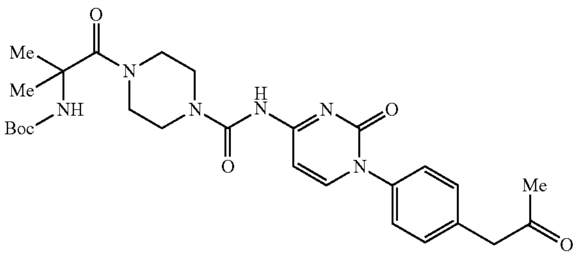 [SMILES: CC(=O)Cc1ccc(-n2ccc(NC(=O)N3CCN(C(=O)C(C)(C)NC(=O)OC(C)(C)C)CC3)nc2=O)cc1]

tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate Scheme I-18

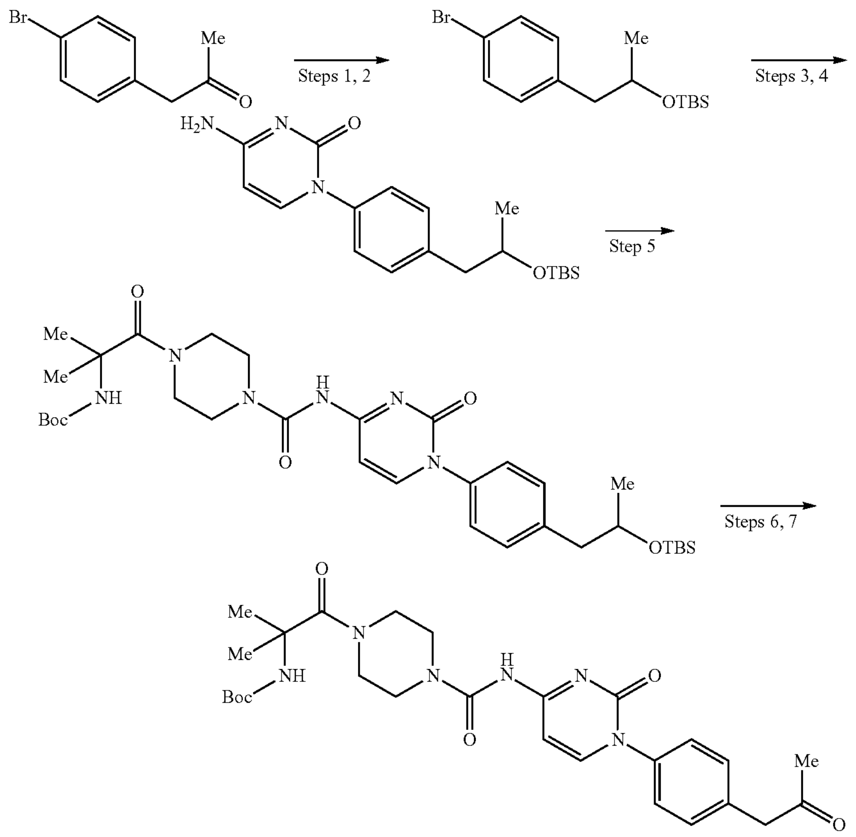

Reagants: 1) $NaBH_4$, MeOH, rt, 3 h 2) TBDMSCl, Imidazole, $CH_2Cl_2$, rt, 16 h 3) n-BuLi, B $(OiPr)_3$, THF, -78° C.-rt, 3 h 4) Cytosine, TMEDA, $Cu(OAc)_2H_2O$, MeOH:$H_2O$ (4:1), $O_2$, rt 16 h 5) 1-(4-(2-((t-iodide, MeCN, 90° C., 16 h 6) TBAF, THF, rt, 16 h 7) DMP, $CH_2Cl_2$, rt, 3 h.

Step 1: 1-(4-bromophenyl) propan-2-ol

To a stirred solution of 1-(4-bromophenyl) propan-2-one (30.0 g, 141 mmol) in MeOH (150 mL) was added $NaBH_4$ (13.3 g, 352 mmol) at 0° C. The reaction mixture was stirred at rt for 3 h. The reaction mixture was poured into $H_2O$ (500 mL) and extracted with EtOAc (3×200 mL). The combined organics were dried over $Na_2SO_4$, filtered and concentrated under reduced pressure to afford the title compound (29.0 g, 95%) as a colorless oil. $^1H$ NMR (DMSO-$d_6$, 400 MHz) δ 7.43 (d, 2H), 7.15 (d, 2H), 4.58 (d, 1H), 3.82-3.73 (m, 1H), 2.64-2.48 (m, 2H), 1.01 (d, 3H).

Step 2: ((1-(4-bromophenyl) propan-2-yl)oxy)(tert-butyl)dimethylsilane

To a stirred solution of 1-(4-bromophenyl) propan-2-ol (29.0 g, 134.9 mmol) in $CH_2Cl_2$ (300 mL) were added imidazole (13.8 g, 202 mmol) and t-butyldimethylsilyl chloride (24.4 g, 161.8 mmol) at 0° C. The reaction mixture was stirred at rt for 16 h. The reaction mixture was poured into $H_2O$ (500 mL) and extracted with $CH_2Cl_2$ (3×700 mL). The combined organics were dried over $Na_2SO_4$, filtered and concentrated under reduced pressure to afford the title compound (40.0 g, 90%) as a yellow oil. $^1H$ NMR (DMSO-$d_6$, 400 MHz) δ 7.43 (d, 2H), 7.13 (d, 2H), 3.98-3.90 (m, 1H), 2.68-2.64 (m, 1H), 2.56-2.48 (m, 1H), 1.09 (d, 3H), 0.76 (s, 9H), 0.10 (s, 3H), −0.27 (s, 3H).

Step 3: diisopropyl (4-(2-((tert-butyldimethylsilyl)oxy)propyl)phenyl)boronate

To a stirred solution of ((1-(4bromophenyl) propan-2-yl)oxy)(t-butyl) dimethylsilane (20.0 g, 60.8 mmol) in THF (300 mL) at −78° C., was added n-BuLi in THF (1.6M, 94 mL). The reaction mixture was stirred −78° C. for 30 min. Triisopropyl borate (21.2 mL, 91.2 mmol) was added at −78° C. The reaction mixture was warmed to rt and stirred for 3 h. The reaction mixture was poured into $NH_4Cl$ solution (100 mL) and extracted with EtOAc (3×300 ml). The combined organics were dried over $Na_2SO_4$, filtered, and concentrated under reduced pressure to afford the title compound (20 g, 86%).

Step 4: 4-amino-1-(4-(2-((tert-butyldimethylsilyl)oxy)propyl)phenyl)pyrimidin-2(1H)-one To a solution of diisopropyl (3-(2-((isopropyldimethylsilyl)oxy)ethyl)phenyl) boronate (20.0 g, 52.9 mmol) and cytosine (5.87 g, 52.9 mmol) in MeOH:$H_2O$ (300 mL, 4:1) was stirred at rt in open air for 30 min. TMEDA (9.58 mL, 63.5 mmol) and $Cu(OAc)_2·H_2O$ (9.6 g, 52.9 mmol) were added and the reaction mixture stirred in open air at rt for 48 h. The reaction mixture was concentrated under reduced pressure and cold $H_2O$ (100 mL) was added into the mixture. The solid was filtered off and washed with $H_2O$ (5×100 mL) and $Et_2O$ (2×60 mL) under reduced pressure. The resulting solid was dried to afford the title compound (9.2 g, 48%) as a white solid. $^1H$ NMR (DMSO-$d_6$, 400 MHz) δ 7.52 (d, 1H), 7.25-7.22 (m, 6H), 5.80 (bs, 1H), 4.00-3.99 (m, 1H), 2.70-2.65 (m, 2H), 1.10 (d, 3H), 0.79 (s, 9H), −0.55 (s, 3H), −0.178 (s, 3H). LCMS [M+H] 360.3.

Step 5: tert-butyl (1-(4-((1-(4(2-hydroxypropyl) phenyl)-2-oxo-1,2-dihydropyrimidine-4-yl)carbamoyl)piperazin-1-yl)-2-methyl-1-oxopropan-2-yl)carbamate To a stirred solution of 4-amino-1-(4-(2-((t-butyldimethylsilyl)oxy)propyl)phenyl) pyrimidin-2(1H)-one (3.0 g, 8.3 mmol) and 1-(4-(2-((t-butoxycarbonyl)amino)-2-methylpropanoyl)piperazine-1-carbonyl)-3-methyl-1H-imidazol-3-ium iodide (6.35 g, 12.5 mmol) in $CH_3CN$ (45 mL) was heated at 90° C. for 16 h. The reaction mixture was concentrated under reduced pressure and the crude material was purified by column chromatography ($CH_3OH/CH_2Cl_2$) to afford the title compound. LCMS [M+H] 357.2.

Step 6: tert-butyl (1-(4-((1-(4-(2-hydroxypropyl) phenyl)-2-oxo-1,2-dihydropyrimidin-4-yl)carbamoyl)piperazin-1-yl)-2-methyl-1-oxopropan-2-yl)carbamate To a stirred solution of t-butyl(1-4-(-2-((t-butyldimethylsilyl)oxy)propyl)phenyl)-2-oxo-1,2-dihydropyrimidin-4-yl) piperazin-1-yl)-2-methyl-1-oxopropan-2-yl)carbamate (3.1 g, 4.72 mmol) in THF (40 mL) was added TBAF (1.0 M in THF, 18.9 mL) at 0° C. The reaction mixture was stirred at rt for 16 h. The reaction mixture was poured in to sat. aq. $NaHCO_3$ (25 mL) and extracted with 9:1 $CH_2Cl_2$:MeOH (3×100 mL). The combined organics were dried over $Na_2SO_4$, filtered and concentrated under reduced pressure. The crude material was purified by column chromatography (5% MeOH in $CH_2Cl_2$) to afford the title compound as an off-white solid (2.4 g, 93%). LCMS [M+H] 543.2.

Step 7: tert-butyl (2-methyl-1-oxo-1-(4-((2-oxo-1-(4-(2-oxopropyl)phenyl)-1,2-dihydropyrimidin-4-yl) carbamoyl)piperazin-1-yl)propan-2-yl)carbamate To a stirred solution of t-butyl (1-(4-((1-(4(2-hydroxypropyl)phenyl)-2-oxo-1,2-dihydropyrimidine-4-yl)carbamoyl) piperazin-1-yl)-2-methyl-1-oxopropan-2-yl)carbamate (0.5 g, 0.92 mmol) in $CH_2Cl_2$ (5 mL) was added DMP (0.78 g, 1.84 mmol) at 0° C. The reaction mixture was stirred at rt for 3 h, poured in to $NaHCO_3$ solution (20 mL) and extracted with $CH_2Cl_2$ (3×50 mL). The combined organics were dried over $Na_2SO_4$, filtered and concentrated under reduced pressure at low temperature (30-35° C.) to afford the title compound (0.7 g, quant.) as an off-white solid. LCMS [M+H] 541.0.

Intermediate 26

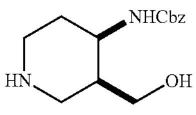 [SMILES: O=C(N[C@@H]1CCNC[C@@H]1CO)OCc1ccccc1]

cis-Benzyl (3-(hydroxymethyl)piperidin-4-yl)carbamate

Scheme I-19

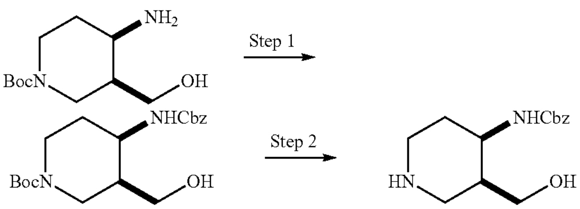

Reagents: Step 1) Cbz—Cl, $NaHCO_3$, dioxane:water, rt, 4 h
2) 4MHCl in dioxane, rt, 4 h.

Step 1: cis-tert-butyl 4-(((benzyloxy)carbonyl) amino)-3-(hydroxymethyl)piperidine-1-carboxylate To a stirred solution of cis-tert-butyl-4-amino-3-(hydroxymethyl)piperidine-1-carboxylate (0.2 g, 0.86 mmol) in 1:1 dioxane: water (4 mL) were added $NaHCO_3$ (0.59 g, 7 mmol) and CBZ-Cl (0.25 mL, 1.73 mmol) at 0° C. The reaction mixture was stirred at rt for 4 h. The reaction mixture was poured into water (20 mL) and extracted with EtOAc (3×10 mL). The combined organic phase was dried over $Na_2SO_4$, filtered and concentrated purified by column chromatography (EtOAc/Hexane) to afford the title compound (0.3 g, 80%) as off white solid. LCMS [M-Boc+H] 265.0.

Step 2: cis-benzyl (3-(hydroxymethyl)piperidin-4-yl)carbamate

To a stirred a solution of cis-tert-butyl 4-(((benzyloxy) carbonyl)amino)-3-(hydroxymethyl)piperidine-1-carboxylate (0.3 g, 0.8 mmol) in dioxane (6 mL) were added 4M HCl in dioxane (3 mL) at 0° C. The reaction mixture was stirred at rt for 4 h. The reaction mixture was concentrated under reduced pressure to afford the title compound (0.2 g, quant.) as yellow oil. LCMS [M+H] 265.6.

Intermediate 27

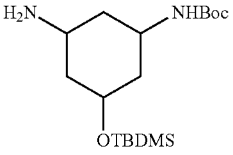

tert-Butyl (3-amino-5-((tert-butyldimethylsilyl)oxy) cyclohexyl)carbamate

Scheme I-20

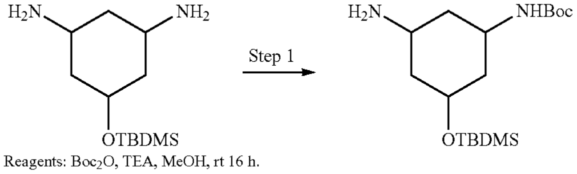

Reagents: $Boc_2O$, TEA, MeOH, rt 16 h.

tert-butyl (3-amino-5-((tert-butyldimethylsilyl)oxy)cyclohexyl)carbamate. To a stirred solution of 5-((tert-butyldimethylsilyl)oxy)cyclohexane-1,3-diamine (0.5 g, 2.1 mmol), prepared according to New J. Chem., 2005, 29, 1152, was added TEA (0.6 ml, 4.1 mmol) and $Boc_2O$ (0.9 g, 4.1 mmol) at rt. The reaction mixture was stirred at rt for 16 h. The reaction mixture was poured into water (50 mL) and extracted with DCM (3×50 mL). The combined organic phase was dried over $Na_2SO_4$, filtered and concentrated under reduced pressure to afford the title compound (0.7 g, quantitative) as brown colored oil. LCMS [M+H] 345.4.

Intermediate 28

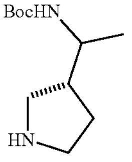

tert-Butyl (1-(R-pyrrolidin-3-yl)ethyl)carbamate

Scheme I-21

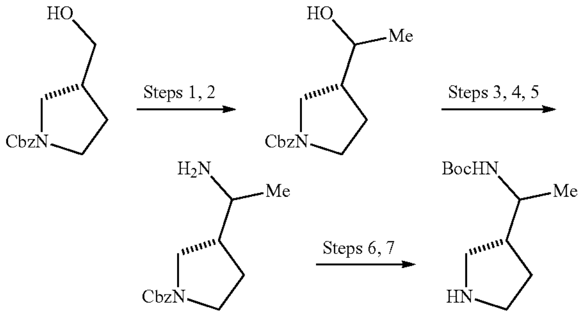

Reagents: 1) PCC, Celite®, $CH_2Cl_2$ 2) MeMgCl, THF, -78° C. 3) MsCl, $NEt_3$, $CH_2Cl_2$, 0° C. 4) $NaN_3$, DMF, 80° C. 5) $PPh_3$, THF, $H_2O$, 45° C. 6) $Boc_2O$, $NEt_3$, THF 7) $H_2$ $Pd(OH)_2/C$, MeOH.

Step 1: benzyl (R)-3-formylpyrrolidine-1-carboxylate

To a solution of benzyl (R)-3-(hydroxymethyl)pyrrolidine-1-carboxylate (1.4 g, 6.0 mmol), in $CH_2Cl_2$ (50 mL) was added PCC (1.95 g, 9.0 mmol) in Celite® (500 mg). The reaction was stirred for 16 h. The solvent was removed and the crude solution was purified by column chromatography (Hex:EtOAc) to afford the title compound.

Step 2: benzyl (3R)-3-(1-hydroxyethyl)pyrrolidine-1-carboxylate

A solution of (R)-3-formylpyrrolidine-1-carboxylate (590 mg, 2.5 mmol) in THF (15 mL) was cooled to −78° C. To the mixture was added 3M MeMgCl (1.69 mL, 5.08 mmol) over 30 min. The solution was warmed to rt and stirred for 16 h. The organic layer was washed with aq. citric acid (1×15 mL) and the organic layer was dried over $Na_2SO_4$, concentrated under reduced pressure to afford the title compound.

Step 3: benzyl (3R)-3-(1-((methylsulfonyl)oxy)ethyl)pyrrolidine-1-carboxylate A solution of benzyl (3R)-3-(1-hydroxyethyl)pyrrolidine-1-carboxylate (330 mg, 1.3 mmol) in $NEt_3$ (0.6 mL, 4.2 mmol) and $CH_2Cl_2$ (10 mL) was cooled to 0° C. and MsCl (0.18 mL, 2.4 mmol) was added dropwise over 5 min. The solution was stirred for 4 h and washed with $NaHCO_3$ (1×20 mL). The aqueous layer was extracted with $CH_2Cl_2$ (1×20 mL). The combined organics were dried over $Na_2SO_4$ and concentrated under reduced pressure to afford the title compound.

Step 4: benzyl (3R)-3-(1-azidoethyl)pyrrolidine-1-carboxylate

To a solution of benzyl (3R)-3-(1-((methylsulfonyl)oxy)ethyl)pyrrolidine-1-carboxylate (1.3 mmol) in DMF (12 mL) was added $NaN_3$ (430 mg, 6.6 mmol). The solution was warmed to 80° C. and stirred for 16 h. The solution was dissolved in EtOAc (50 mL) and washed with sat. LiCl (4×20 mL). The organic layer was dried over $Na_2SO_4$ and concentrated under reduced pressure and purified by column chromatography (Hex:EtOAc) to afford the title compound.

Step 5: benzyl (3R)-3-(1-aminoethyl)pyrrolidine-1-carboxylate

To a solution of benzyl (3R)-3-(1-azidoethyl)pyrrolidine-1-carboxylate (235 mg, 0.85 mmol) in 12:1 THF:$H_2O$ (8 mL) was added $PPh_3$ (448 mg, 1.70 mmol). The solution was warmed to 45° C. and stirred for 16 h. The solution was concentrated under reduced pressure and purified by column chromatography (Hex:EtOAc EtOAc:MeOH:$NH_4OH$) to afford the title compound.

Step 6: benzyl (3R)-3-(1-((tert-butoxycarbonyl)amino)ethyl)pyrrolidine-1-carboxylate To a solution of benzyl (3R)-3-(1-aminoethyl)pyrrolidine-1-carboxylate (200 mg, 0.80 mmol) in THF (20 mL) was added $Boc_2O$ (349 mg, 1.60 mmol) and $NEt_3$ (0.33 mL, 2.4 mmol). The solution was stirred for 16 h. The solution was concentrated under reduced pressure and purified by column chromatography (Hex:EtOAc) to afford the title compound.

Step 7: tert-butyl (1-((R)-pyrrolidin-3-yl)ethyl)carbamate

To a $N_2$ sparged solution of benzyl (3R)-3-(1-((tert-butoxycarbonyl)amino)ethyl)pyrrolidine-1-carboxylate (140 mg, 0.40 mmol) in MeOH (10 mL) was added $Pd(OH)_2$ 10% wt (14 mg). The reaction was stirred for 16 h under $H_2$ atmosphere. The reaction mixture was filtered through a pad of Celite® and washed with MeOH (5×20 mL). The combined organics were concentrated under reduced pressure to afford the title compound.

Intermediate 29

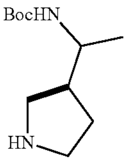

tert-Butyl (1-((S)-pyrrolidin-3-yl)ethyl)carbamate

Prepared in a similar fashion as Scheme I-21 from benzyl (S)-3-(hydroxymethyl)pyrrolidine-1-carboxylate.

Intermediate 30

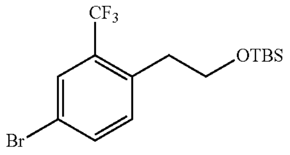 [SMILES: CC(C)(C)[Si](C)(C)OCCc1ccc(Br)cc1C(F)(F)F]

(4-Bromo-2-(trifluoromethyl)phenethoxy)(tert-butyl)dimethylsilane

Scheme I-22

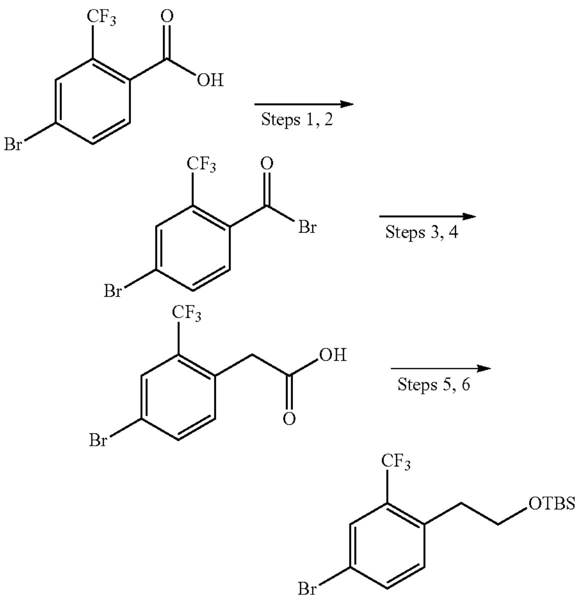

Reagents: 1) $BH_3THF$, THF 0° C. to rt 4 h 2) $CBr_4$, $PPh_3$ DMF, 0° C. to rt 4 h 3) KCN, $EtOH:H_2O$, 70° C. 3 h. 4) LiOH, $H_2O$, 100° C., 16 h. 5) $BH_3THF$, THF 0° C. to rt 4 h 5) TBSCl, $NEt_3$, $CH_2Cl_2$, rt, 16 h.

Step 1: (4-bromo-2-(trifluoromethyl)phenyl)methanol

To a solution of 4-bromo-2-(trifluoromethyl)benzoic acid (2.65 g, 10.0 mmol) in THF (50 mL) stirred at 0° C. was added 1M $BH_3$·THF in THF (20.0 mL) dropwise over 15 min The solution was warmed to rt for 4 h. The reaction mixture was quenched with the addition of 2N HCl, and the biphasic mixture was separated. The aqueous layer was and extracted with EtOAc (2×50 mL), and the combined organics were dried over $Na_2SO_4$. The reaction mixture was purified by flash chromatography (Hexanes:EtOAc) to afford the desired compound.

Step 2: 4-bromo-1-(bromomethyl)-2-(trifluoromethyl)benzene

To a stirred solution of (4-bromo-2-(trifluoromethyl)phenyl)methanol (1.35 g, 5.12 mmol) in DMF (20 mL) at 0° C. was added triphenylphosphine (2.02 g, 7.70 mmol) and carbon tetrabromide (2.54 g, 7.70 mmol). The solution was warmed to rt and stirred for 3 h. The reaction mixture was diluted with EtOAc (100 mL) and washed with sat. LiCl solution (3×100 mL). The crude reaction mixture was purified by flash chromatography (Hexanes:EtOAc) to afford the desired compound.

Step 3: 2-(4-bromo-2-(trifluoromethyl)phenyl)acetonitrile

To a solution of 4-bromo-1-(bromomethyl)-2-(trifluoromethyl)benzene (1.84 g, 5.14 mmol) in $EtOH:H_2O$ 3:1 was added KCN (366 mg, 5.61 mmol). The reaction was heated to 70° C. for 3 h. The reaction mixture was cooled and diluted with EtOAc (100 mL) and $H_2O$ (50 mL). The biphasic mixture was separated and the aqueous layer was and extracted with EtOAc (2×50 mL). The combined organics were dried over $Na_2SO_4$ and concentrated under reduced pressure. The reaction mixture was purified by flash chromatography (Hexanes:EtOAc) to afford the desired compound, Step 4: 2-(4-bromo-2-(trifluoromethyl)phenyl)acetic acid To a suspension of 2-(4-bromo-2-(trifluoromethyl)phenyl)acetonitrile (423 mg, 1.62 mmol) in $H_2O$ (30 mL), was added LiOH (386 mg, 16.2 mmol). The reaction was heated to 100° C. and stirred for 16 h. The reaction mixture was diluted with $H_2O$ (50 mL) and washed with $Et_2O$ (1×50 mL) and the organic layer was discarded. The aqueous layer was acidified with 2N HCl and was extracted with EtOAc, (3×50 mL). The combined organics were dried over $Na_2SO_4$ and concentrated under reduced pressure to afford the desired compound.

Step 5: 2-(4-bromo-2-(trifluoromethyl)phenyl)ethan-1-ol

To a solution of 2-(4-bromo-2-(trifluoromethyl)phenyl) acetic acid (333 mg, 1.18 mmol) in THF (25 mL) stirred at 0° C. was added 1M $BH_3$·THF (2.36 mL) dropwise over 10 min. The solution was warmed and allowed to stir at rt for 4 h. The reaction mixture was quenched with the addition of 2NHCl, and the biphasic mixture was separated. The aqueous layer was and extracted with EtOAc (2×50 mL), and the combined organics were dried over $Na_2SO_4$. The reaction mixture was purified by flash chromatography (Hexanes: EtOAc) to afford the desired compound.

Step 6: (4-bromo-2-(trifluoromethyl)phenethoxy)(tert-butyl)dimethylsilane the desired compound To a solution of 2-(4-bromo-2-(trifluoromethyl)phenyl) ethan-1-ol (317 g, 46.5 mmol) in $CH_2Cl_2$ (150 mL) was added imidazole (4.79 g, 70.5 mmol) and tert-butyldimethylsilyl chloride (10.6 g, 70.5 mmol). The solution was stirred for 16 h at rt. The reaction mixture concentrated under reduced pressure and the solid was dissolved in EtOAc (250 mL) and washed with $H_2O$ (250 mL). The organic layer was dried over $Na_2SO_4$ and concentrated under reduced pressure and purified by flash chromatography (Hexanes:EtOAc) to afford the title compound.

Compound Synthesis

Compound 117

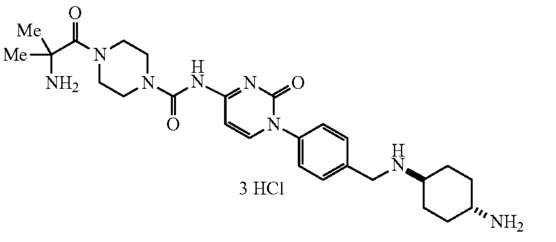

3 HCl 4-(2-Amino-2-methylpropanoyl)-N-(1-(4-(((trans-4-aminocyclohexyl)amino)methyl)phenyl)-2-oxo-1,2-dihydropyrimidin-4-yl)piperazine-1-carboxamide hydrochloride salt Scheme C-1

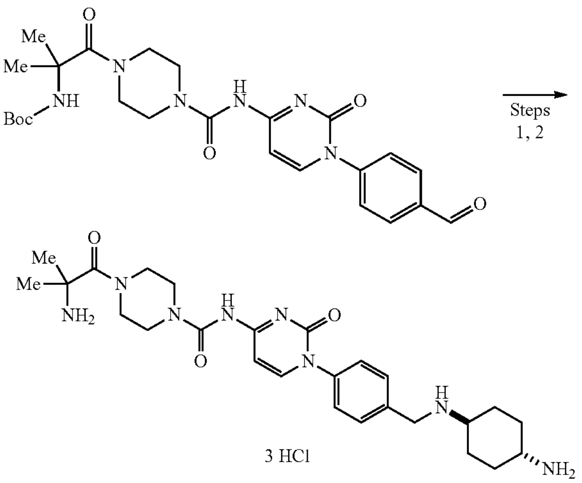

3 HCl

Reagents: 1) N-Boc-trans-1,4-cyclohexanediamine, $NaBH_3CN$, MeOH, rt, 3 d
2) 2MHCl in MeOH, rt, 17 h.

Step 1: tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)carbamate $NaBH_3CN$ (379 mg, 6.03 mmol) was added to a mixture of tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate (1.03 g, 2.01 mmol) and N-boc-trans-1,4-cyclohexanediamine (527 mg, 2.46 mmol) in dry MeOH (20 mL), and the mixture was stirred at rt for 3 days. It was directly dry-loaded onto silica and Celite®, and the residue was purified by flash chromatography (MeOH/EtOAc) to afford the title compound (804 mg, 1.13 mmol) as a white solid.

Step 2: 4-(2-amino-2-methylpropanoyl)-N-(1-(4-(((trans-4-aminocyclohexyl)amino)methyl)phenyl)-2-oxo-1,2-dihydropyrimidin-4-yl)piperazine-1-carboxamide hydrochloride salt A mixture of tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)carbamate (369 mg, 0.519 mmol) and 2M HCl in MeOH (12 mL, 24 mmol) was stirred at rt for 17 h. The precipitate was collected by vacuum filtration to afford the title compound (270 mg, 0.435 mmol) as a white solid. $^1H$ NMR (500 MHz, $D_2O$) δ 7.82 (d, 1H), 7.51 (d, 2H), 7.39 (d, 2H), 6.70 (d, 1H), 4.22 (s, 2H), 3.51-3.76 (m, 8H), 3.06-3.21 (m, 2H), 2.15-2.24 (m, 2H), 2.02-2.10 (m, 2H), 1.58 (s, 6H), 1.33-1.52 (m, 4H). LCMS [M+H] 511.4.

Compound 112

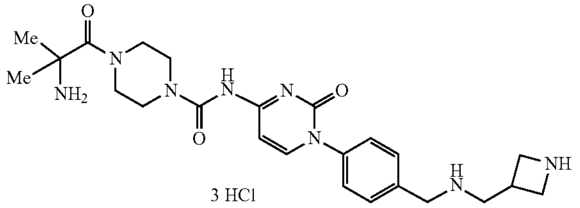

3 HCl 4-(2-Amino-2-methylpropanoyl)-N-(1-(4-(((azetidin-3-ylmethyl)amino)methyl)phenyl)-2-oxo-1,2-dihydropyrimidin-4-yl)piperazine-1-carboxamide hydrochloride salt Prepared in a similar fashion to Scheme C-1 using tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 3-(aminomethyl)azetidine-1-carboxylate. $^1H$ NMR (400 MHz, $D_2O$) δ 7.78 (d, 1H), 7.49 (d, 2H), 7.38 (d, 2H), 6.69 (d, 1H), 4.18 (s, 2H), 4.09 (t, 2H), 3.90 (t, 2H), 3.72-3.55 (m, 8H), 3.35-3.31 (m, 2H), 3.30-3.18 (m, 1H), 1.56 (s, 6H). LCMS [M+H] 483.

Compound 114

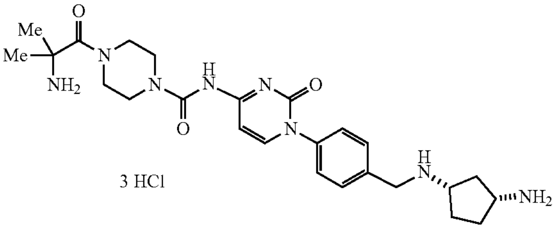

3 HCl 4-(2-Amino-2-methylpropanoyl)-N-(1-(4-((((1S,3R)-3-aminocyclopentyl)amino)methyl)phenyl)-2-oxo-1,2-dihydropyrimidin-4-yl)piperazine-1-carboxamide hydrochloride salt Prepared in a similar fashion to Scheme C-1 using tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((1R,3S)-3-aminocyclopentyl) carbamate. $^1H$ NMR (400 MHz, $D_2O$) δ 7.81 (d, 1H), 7.50 (d, 2H), 7.38 (d, 2H), 6.69 (d, 1H), 4.20 (s, 2H), 3.68-3.57

(m, 9H), 2.63-2.55 (m, 1H), 2.17-2.04 (m, 2H), 1.85-1.63 (m, 4H), 1.59 (s, 6H). LCMS [M+H] 497.3.

Compound 44

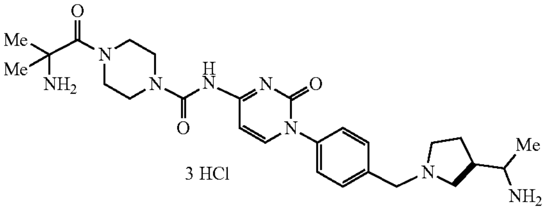

4-(2-Amino-2-methylpropanoyl)-N-(1-(4-(((3R)-3-(1-aminoethyl)pyrrolidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (1-((R)-pyrrolidin-3-yl)ethyl) carbamate. $^1$H NMR (500 MHz, $D_2O$) δ 8.07 (d, 1H), 7.70 (d, 2H), 7.58 (d, 2H), 6.82 (d, 1H), 4.52 (s, 2H), 3.85-3.64 (m, 8H), 3.64-3.35 (m, 3H), 3.24-3.03 (m, 1H), 2.99-2.70 (m, 1H), 2.67-2.51 (m, 1H), 2.48-2.21 (m, 1H), 2.18-2.01 (m, 1H), 1.72 (s, 6H), 1.35-1.28 (m, 3H) LCMS [M+H] 511.2.

Compound 45

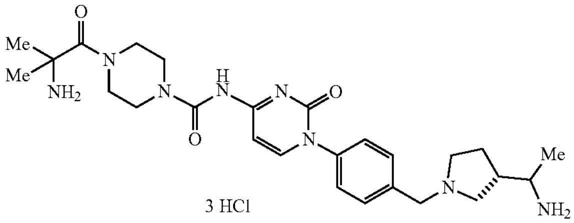

4-(2-Amino-2-methylpropanoyl)-N-(1-(4-(((3S)-3-(1-aminoethyl)pyrrolidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (1-((S)-pyrrolidin-3-yl)ethyl) carbamate. $^1$H NMR (500 MHz, $D_2O$) δ 8.01 (d, 1H), 7.69 (d, 2H), 7.57 (d, 2H), 6.84 (d, 1H), 4.52 (s, 2H), 3.83-3.63 (m, 8H), 3.60 (t, 1H), 3.53-3.36 (m, 2H), 3.22-3.10 (m, 1H), 2.91-2.79 (m, 1H), 2.68-2.52 (m, 1H), 2.48-2.19 (m, 1H), 2.15-2.02 (m, 1H), 1.73 (s, 6H), 1.38-1.28 (m, 3H). LCMS [M+H] 511.2.

Compound 107

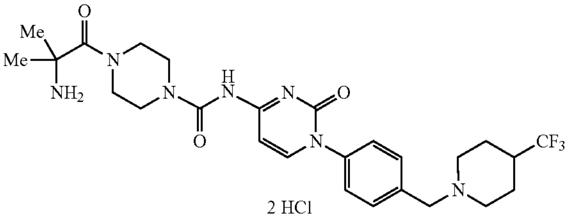

4-(2-Amino-2-methylpropanoyl)-N-(2-oxo-1-(4-((4-(trifluoromethyl)piperidin-1-yl)methyl)phenyl)-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and 4-(trifluoromethyl)piperidine. $^1$H NMR (500 MHz, $D_2O$) δ 7.99 (d, 1H), 7.69 (d, 2H), 7.58 (d, 2H), 6.85 (d, 1H), 4.44 (s, 2H), 3.83-3.75 (m, 4H), 3.74-3.70 (m, 4H), 3.68 (d, 2H), 3.13 (t, 2H), 2.66-2.60 (m, 1H), 2.22 (d, 2H), 1.88-1.78 (m, 2H), 1.74 (s, 6H). LCMS [M+H] 550.3.

Compound 383

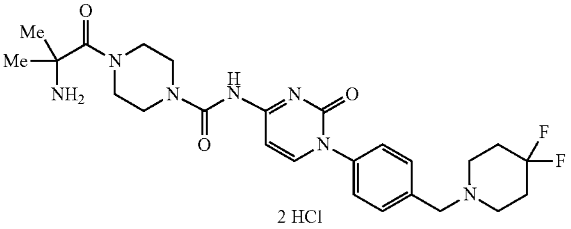

4-(2-Amino-2-methylpropanoyl)-N-(1-(4-((4,4-difluoropiperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and 4,4-difluoropiperidine. $^1$H NMR (500 MHz, $D_2O$) δ 8.09 (d, 1H), 7.82 (d, 2H), 7.70 (d, 2H), 6.96 (d, 1H), 4.61 (s, 2H), 3.94-3.86 (m, 4H), 3.85-3.83 (m, 4H), 3.82-3.79 (m, 2H), 3.54-3.50 (m, 2H), 2.64-2.50 (m, 2H), 2.49-2.32 (m, 2H), 1.86 (s, 6H). LCMS [M+H] 417.3.

Compound 109

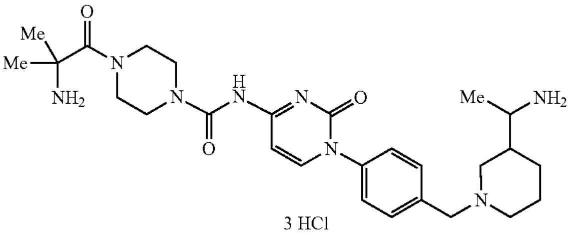

4-(2-Amino-2-methylpropanoyl)-N-(1-(4-((3-(1-aminoethyl)piperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (1-(piperidin-3-yl)ethyl) carbamate. $^{1}$H NMR (400 MHz, $D_2O$) δ 7.98 (d, 1H), 7.71 (d, 2H), 7.59 (d, 2H), 6.87 (d, 1H), 4.48 (s, 2H), 3.79 (br. s, 2H), 3.74 (s, 6H), 3.60 (t, 2H), 3.35 (t, 1H), 3.11-2.86 (m, 2H), 2.24-2.03 (m, 2H), 1.98 (t, 1H), 1.75 (s, 6H), 1.49-1.12 (m, 4H). LCMS [M+H] 525.3.

Compound 110

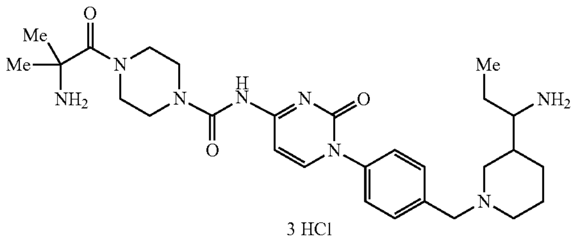

4-(2-Amino-2-methylpropanoyl)-N-(1-(4-((3-(1-aminopropyl)piperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (1-(piperidin-3-yl)propyl) carbamate. $^{1}$H NMR (400 MHz, $D_2O$) δ 8.09 (d, 1H), 7.72 (d, 2H), 7.61 (d, 2H), 6.85 (d, 1H), 4.47 (s, 2H), 3.81 (br. s, 2H), 3.69 (br.s, 6H), 3.59 (d, 2H), 3.29-3.13 (m, 1H), 3.00 (t, 2H), 2.22 (t, 1H), 2.11 (d, 1H), 1.98 (d, 1H), 1.83-1.56 (m, 8H), 1.50-1.23 (m, 2H), 1.09-0.90 (m, 3H). LCMS [M+H] 539.2.

Compound 342

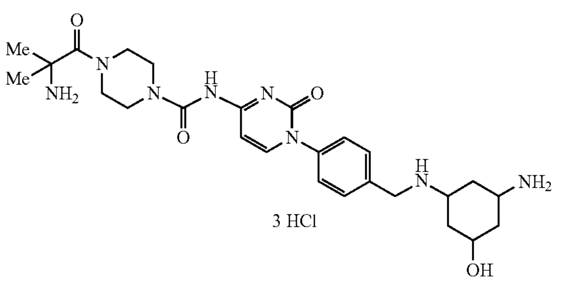

4-(2-amino-2-methylpropanoyl)-N-(1-(4-(((3-amino-5-hydroxycyclohexyl)amino)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3-amino-5-((tert-butyldimethylsilyl)oxy)cyclohexyl)carbamate. $^{1}$H NMR (400 MHz, $D_2O$) δ 7.89 (d, 1H), 7.55 (d, 2H), 7.41 (d, 2H), 6.70 (d, 1H), 4.27 (m, 3H), 3.79-3.76 (m, 2H), 3.63-3.50 (m, 8H), 2.34-2.23 (m, 2H), 2.00-1.72 (m, 4H), 1.58 (s, 6H). LCMS [M+H] 527.3.

Compound 120

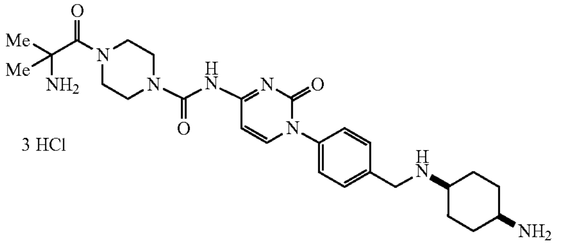

cis-4-(2-Amino-2-methylpropanoyl)-N-(1-(4-(((4-aminocyclohexyl)amino)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and 1-N-Boc-cis-1,4-cyclohexyldiamine. $^{1}$H NMR (400 MHz, $D_2O$) δ 7.77 (d, 1H), 7.53 (d, 2H), 7.39 (d, 2H), 6.72 (d, 1H), 4.25 (s, 2H), 3.68-6.55 (m, 8H), 3.47-3.40 (m, 1H), 3.34-3.28 (m, 1H), 1.99-1.92 (m, 2H), 1.85-1.65 (m, 6H), 1.58 (s, 6H). LCMS [(M+2H)/2] 256.2.

Compound 123

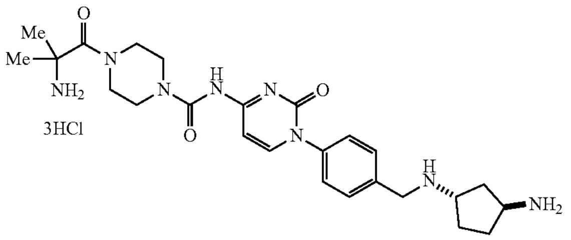

4-(2-Amino-2-methylpropanoyl)-N-(1-(4-((((1S,3S)-3-aminocyclopentyl)amino)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((1S,3S)-3-aminocyclopentyl) carbamate. $^{1}$H NMR (400 MHz, $D_2O$) δ 7.79 (d, 1H), 7.52 (d, 2H), 7.40 (d, 2H), 6.73 (d, 1H), 4.22 (s, 2H), 3.82-3.73 (m, 2H), 3.68-3.55 (m, 8H), 2.32-2.15 (m, 4H), 1.78-1.60 (m, 2H), 1.57 (s, 6H). LCMS [(M+2H/2] 249.0.

Compound 126

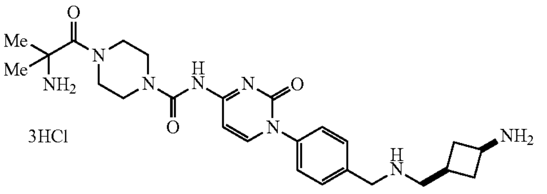

4-(2-Amino-2-methylpropanoyl)-N-(1-(4-((((cis-3-aminocyclobutyl)methyl)amino)methyl)phenyl)-2-oxo-1,2-dihydropyrimidin-4-yl)piperazine 1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (cis-3-(aminomethyl) cyclobutyl)carbamate. $^1$H NMR (400 MHz, $D_2O$) δ 7.81 (d, 1H), 7.49 (d, 2H), 7.38 (d, 2H), 6.70 (d, 1H), 4.15 (s, 2H), 3.68-3.57 (m, 8H), 3.10-3.05 (m, 2H), 2.49-2.35 (m, 4H), 1.88-1.79 (m, 2H), 1.57 (s, 6H). LCMS [(M+2H)/2] 249.1.

Compound 100

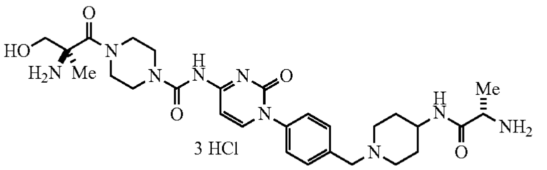

4-((S)-2-Amino-3-hydroxy-2-methylpropanoyl)-N-(1-(4-((4-((S)-2-aminopropanamido)piperidin-1-yl) methyl)phenyl)-2-oxo-1,2-dihydropyrimidin-4-yl) piperazine-1-carboxamide hydrochloride salt Prepared in a similar fashion to Scheme C-1 from tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate and tert-butyl (S)-(1-oxo-1-(piperidin-4-ylamino)propan-2-yl)carbamate. $^1$H NMR (400 MHz, $D_2O$) δ 8.01 (d, 1H), 7.72 (d, 2H), 7.60 (d, 2H), 6.87 (d, 1H), 4.47 (d, 2H), 4.19 (d, 1H), 4.09-3.98 (m, 1H), 3.93 (d, 1H), 3.87-3.70 (m, 8H), 3.65 (d, 2H), 3.22 (t, 2H), 2.23 (d, 2H), 1.85-1.74 (m, 1H), 1.71 (s, 3H), 1.54 (d, 3H), 1.12 (d, 2H). LCMS [M+H] 584.4.

Compound 102

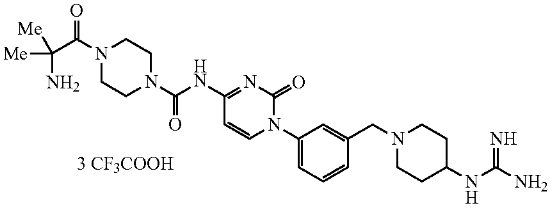

4-(2-Amino-2-methylpropanoyl)-N-(1-(3-((4-guanidinopiperidin-1-yl)methyl)phenyl)-2-oxo-1,2-dihydropyrimidin-4-yl)piperazine-1-carboxamide trifluoroacetate salt Prepared in a similar fashion as Scheme C-1 from tert-butyl (1-(4-((1-(3-formylphenyl)-2-oxo-1,2-dihydropyrimidin-4-yl)carbamoyl)piperazin-1-yl)-2-methyl-1-oxopropan-2-yl)carbamate and 1,2-bis(tert-butoxycarbonyl)-3-(piperidin-4-yl)guanidine. LCMS [M+H] 539.4.

Compound 105

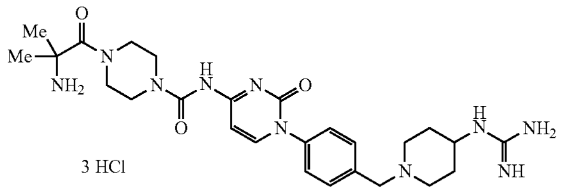

4-(2-Amino-2-methylpropanoyl)-N-(1-(4-((4-guanidinopiperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and 1,2-bis(tert-butoxycarbonyl)-3-(piperidin-4-yl)guanidine. $^1$H NMR (500 MHz, $CD_3OD$) δ 7.75 (d, 1H), 7.71 (d, 2H), 7.57 (d, 2H), 6.65 (s, 1H), 4.43 (s, 2H), 3.76-3.65 (m, 9H), 3.60 (d, 2H), 3.16 (dd, 2H), 2.21 (d, 2H), 1.93-1.81 (m, 2H), 1.70 (s, 6H). LCMS [M+H] 539.4.

Compound 362

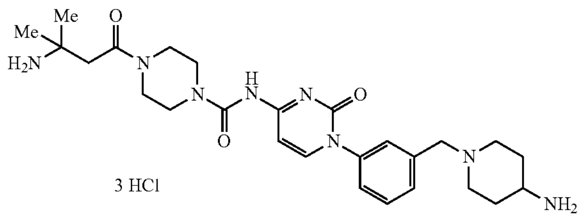

4-(3-Amino-3-methylbutanoyl)-N-(1-(3-((4-aminopiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (4-(4-((1-(3-formylphenyl)-2-oxo-1,2-dihydropyrimidin-4-yl)carbamoyl)piperazin-1-yl)-2-methyl-4-oxobutan-2-yl)carbamate and tert-butyl piperidin-4-ylcarbamate. $^1$H NMR (400 MHz, $CD_3OD$) δ 8.47 (d, 1H), 7.88 (s, 1H), 7.79 (t, 1H), 7.71 (d, 2H), 6.86 (d, 1H), 4.48 (s, 2H), 3.86-3.69 (m, 8H), 3.64 (d, 2H), 3.53 (t, 1H), 3.26 (t, 2H), 2.84 (s, 2H), 2.29 (d, 2H), 2.11 (q, 2H), 1.45 (s, 6H). LCMS [M+H] 511.3.

Compound 363

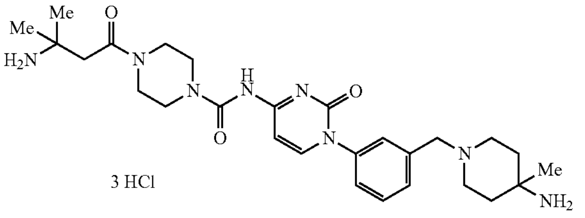

4-(3-Amino-3-methylbutanoyl)-N-(1-(3-((4-amino-4-methylpiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (4-(4-((1-(3-formylphenyl)-2-oxo-1,2-dihydropyrimidin-4-yl)carbamoyl)piperazin-1-yl)-2-methyl-4-oxobutan-2-yl)carbamate and tert-butyl (4-methylpiperidin-4-yl) carbamate. $^1$H NMR (400 MHz, $CD_3OD$) δ 8.53 (d, 1H), 7.91 (s, 1H), 7.82 (s, 1H), 7.71 (d, 2H), 6.89 (s, 1H), 4.55 (s, 2H), 3.89-3.63 (m, 8H), 3.54 (s, 2H), 3.47-3.33 (m, 2H), 2.86 (d, 2H), 2.28 (d, 2H), 2.18-2.00 (m, 2H), 1.59 (s, 3H), 1.46 (s, 6H). LCMS [M+H] 525.3.

Compound 350

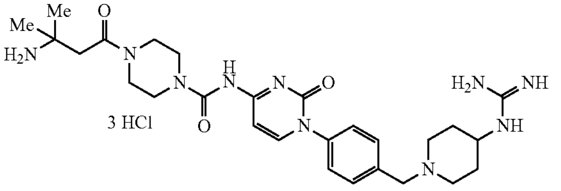

4-(3-Amino-3-methylbutanoyl)-N-(1-(4-((4-guanidinopiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (4-(4-((1-(4-formylphenyl)-2-oxo-1,2-dihydropyrimidin-4-yl)carbamoyl)piperazin-1-yl)-2-methyl-4-oxobutan-2-yl)carbamate and 1,2-bis(tert-butoxycarbonyl)-3-(piperidin-4-yl)guanidine. $^1$H NMR (400 MHz, $CD_3OD$) δ 8.42 (d, 1H), 7.86 (d, 2H), 7.68 (d, 2H), 6.89 (d, 1H), 3.96 (s, 2H), 3.90-3.64 (m, 9H), 3.58 (d, 2H), 3.25 (d, 2H), 2.84 (s, 2H), 2.28-2.16 (m, 2H), 1.95 (d, 2H), 1.48-1.38 (m, 6H). LCMS [M+H] 553.3.

Compound 351

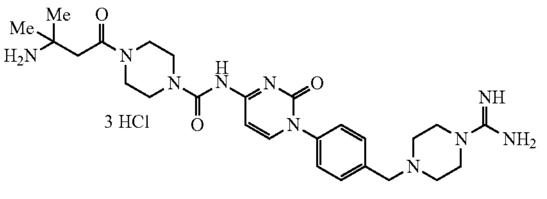

4-(3-Amino-3-methylbutanoyl)-N-(1-(4-((4-carbamimidoylpiperazin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (4-(4-((1-(4-formylphenyl)-2-oxo-1,2-dihydropyrimidin-4-yl)carbamoyl)piperazin-1-yl)-2-methyl-4-oxobutan-2-yl)carbamate and 1-[N,N'-bis(tert-butoxycarbonyl) amidino]piperazine. $^1$H NMR (400 MHz, $CD_3OD$) δ 8.37 (d, 1H), 7.89 (d, 2H), 7.69 (d, 2H), 6.87 (d, 1H), 3.97 (s, 2H), 3.91-3.52 (m, 16H), 2.84 (s, 2H), 1.52-1.41 (m, 6H). LCMS [M+H] 539.3.

Compound 133

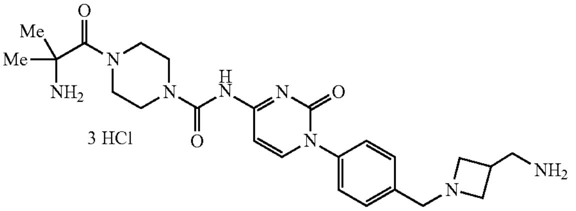

4-(2-Amino-2-methylpropanoyl)-N-(1-(4-((3-(aminomethyl)azetidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (azetidin-3-ylmethyl) carbamate. $^1$H NMR (500 MHz, $CD_3OD$) δ 8.35 (d, 1H), 7.77 (m, 2H), 7.60-7.68 (m, 2H), 6.82 (d, 1H), 4.56 (m, 2H), 4.34-4.42 (m, 1H), 4.16-4.29 (m, 2H), 4.06-4.14 (m, 1H), 3.78 (m, 8H), 3.38-3.43 (m, 1H), 3.32-3.36 (m, 1H), 3.18-3.28 (m, 1H), 1.71 (s, 6H). LCMS [M+H] 483.3.

Compound 134

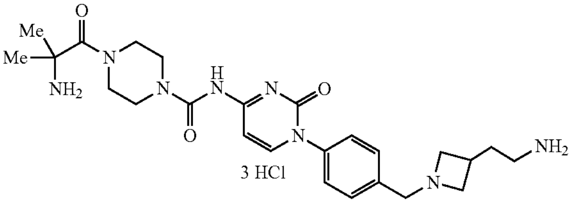

4-(2-Amino-2-methylpropanoyl)-N-(1-(4-((3-(2-aminoethyl)azetidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan- 2-yl)carbamate and tert-butyl (2-(azetidin-3-yl)ethyl)carbamate hydrochloride. $^1$H NMR (500 MHz, $CD_3OD$) δ 8.33-8.44 (m, 1H), 7.77 (m, 2H), 7.59-7.70 (m, 2H), 6.80-6.90 (m, 1H), 4.52 (m, 2H), 4.28-4.36 (m, 1H), 4.18-4.27 (m, 1H), 4.05-4.15 (m, 1H), 3.93-4.02 (m, 1H), 3.78 (m, 8H), 2.95-3.08 (m, 1H), 2.84-2.95 (m, 2H), 2.10-2.18 (m, 1H), 2.03-2.10 (m, 1H), 1.71 (s, 6H). LCMS [M+H] 497.3.

Compound 374

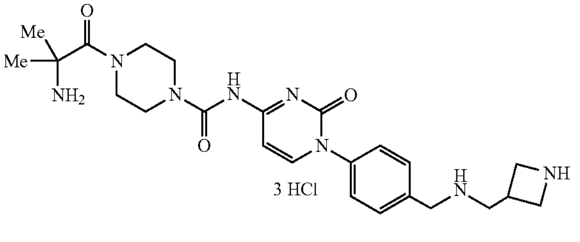

4-(2-Amino-2-methylpropanoyl)-N-(1-(4-(((azetidin-3-ylmethyl)amino)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 3-(aminomethyl)azetidine-1-carboxylate. $^1$H NMR (500 MHz, $D_2O$) δ 7.79 (d, 1H), 7.51 (d, 2H), 7.40 (d, 2H), 6.71 (d, 1H), 4.20 (s, 2H), 4.07-4.16 (m, 2H), 3.87-3.96 (m, 2H), 3.50-3.72 (m, 8H), 3.34 (d, 2H), 3.22-3.31 (m, 1H), 1.58 (s, 6H). LCMS [M+H] 483.4.

Compound 376

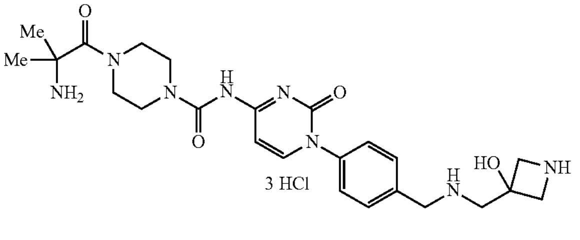

4-(2-Amino-2-methylpropanoyl)-N-(1-(4-((((3-hydroxyazetidin-3-yl)methyl)amino)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 3-(aminomethyl)-3-hydroxyazetidine-1-carboxylate. $^1$H NMR (500 MHz, $D_2O$) δ 7.80 (d, 1H), 7.55 (d, 2H), 7.42 (d, 2H), 6.73 (d, 1H), 4.28 (s, 2H), 4.13 (d, 2H), 4.04 (d, 2H), 3.51-3.72 (m, 8H), 3.42 (s, 2H), 1.59 (s, 6H). LCMS [M+H] 499.4.

Compound 375

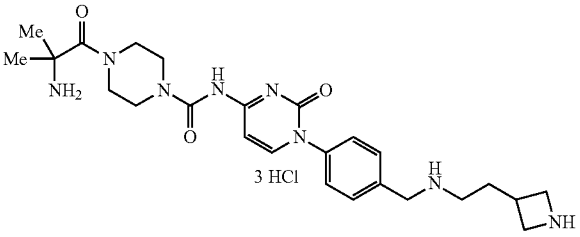

4-(2-Amino-2-methylpropanoyl)-N-(1-(4-(((2-(azetidin-3-yl)ethyl)amino)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 3-(2-aminoethyl)azetidine-1-carboxylate. $^1$H NMR (500 MHz, $D_2O$) δ 7.78 (d, 1H), 7.50 (d, 2H), 7.39 (d, 2H), 6.71 (d, 1H), 4.18 (s, 2H), 4.00-4.09 (m, 2H), 3.70-3.79 (m, 2H), 3.50-3.70 (m, 8H), 2.83-2.96 (m, 3H), 1.91-2.00 (m, 2H), 1.58 (s, 6H). LCMS [M+H] 497.3.

Compound 135

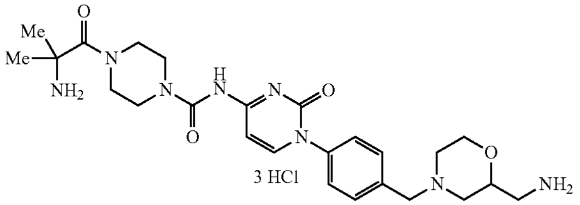

4-(2-Amino-2-methylpropanoyl)-N-(1-(4-((2-(aminomethyl)morpholino)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (morpholin-2-ylmethyl) carbamate. $^1$H NMR (500 MHz, $CD_3OD$) δ 8.32-8.41 (m, 1H), 7.87 (d, 2H), 7.68 (d, 2H), 6.82-6.89 (m, 1H), 4.46-4.59 (m, 2H), 4.15-4.26 (m, 2H), 3.97-4.07 (m, 1H), 3.69-3.86 (m, 8H), 3.44-3.58 (m, 2H), 3.26-3.36 (m, 1H), 3.16-3.25 (m, 1H), 3.05-3.15 (m, 1H), 2.95-3.04 (m, 1H), 1.71 (s, 6H). LCMS [M+H] 513.3.

Compound 136

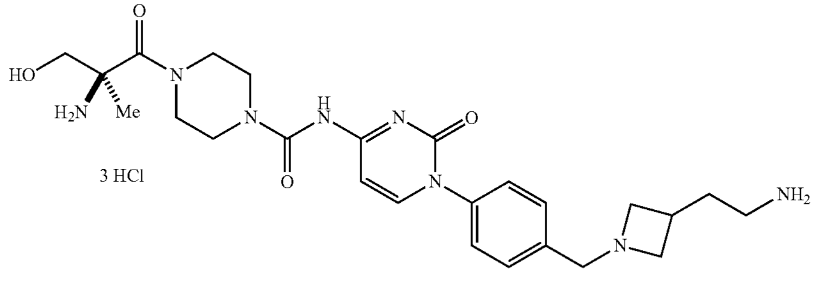

(S)-4-(2-Amino-3-hydroxy-2-methylpropanoyl)-N-(1-(4-((3-(2-aminoethyl)azetidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate and tert-butyl (2-(azetidin-3-yl)ethyl)carbamate hydrochloride. $^{1}H$ NMR (500 MHz, $D_2O$) δ 7.44 (d, 1H), 7.33 (d, 2H), 7.22 (d, 2H), 6.28 (d, 1H), 3.45-3.76 (m, 11H), 3.41 (d, 1H), 3.28 (dd, 1H), 3.14-3.24 (m, 2H), 3.02-3.11 (m, 1H), 2.70 (dd, 1H), 2.48-2.54 (m, 1H), 2.29-2.40 (m, 1H), 1.98-2.08 (m, 1H), 1.43-1.54 (m, 1H), 1.22 (s, 3H). LCMS [M+H] 513.3.

Compound 377

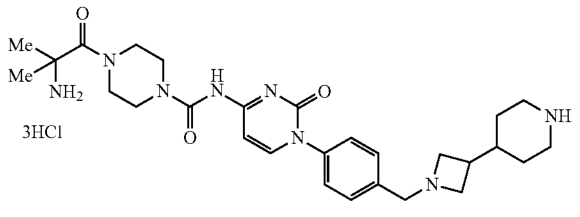

4-(2-Amino-2-methylpropanoyl)-N-(2-oxo-1-(4-((3-(piperidin-4-yl)azetidin-1-yl)methyl)phenyl)-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 4-(azetidin-3-yl)piperidine-1-carboxylate. $^{1}H$ NMR (400 MHz, $D_2O$) δ 8.23 (d, 1H), 7.67 (d, 2H), 7.60 (d, 2H), 6.82 (d, 1H), 4.46 (s, 2H), 4.29-4.43 (m, 2H), 4.42-4.04 (m, 2H), 3.83-3.76 (m, 8H), 3.45 (d, 2H), 3.01 (t, 2H), 2.83-2.75 (m, 1H), 2.04-1.84 (m, 3H), 1.74 (s, 6H), 1.39-1.28 (m, 2H). LC-MS [M+H] 537.3.

Compound 288

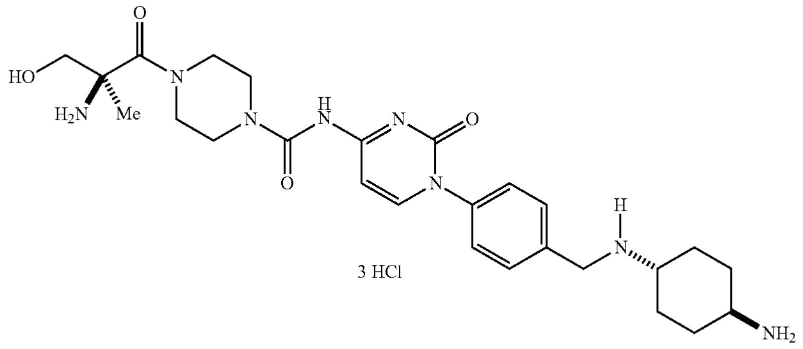

4-((S)-2-Amino-3-hydroxy-2-methylpropanoyl)-N-(1-(4-(((trans-4-aminocyclohexyl)amino)methyl)phenyl)-2-oxo-1,2-dihydropyrimidin-4-yl)piperazine-1-carboxamide hydrochloride salt Prepared in a similar fashion as Scheme C-1 using tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate and tert-butyl (trans-4-aminocyclohexyl)carbamate. $^{1}H$ NMR (500 MHz, $D_2O$) δ 7.94 (d, 1H), 7.63 (d, 2H), 7.51 (d, 2H), 6.83 (d, 1H), 4.34 (s, 2H), 4.14 (d, 1H), 3.87 (d, 1H), 3.76-3.69 (m, 8H), 3.32-3.21 (m, 2H), 2.32 (d, 2H), 2.19 (d, 2H), 1.66 (s, 3H), 1.62-1.48 (m, 4H). LCMS [M+H] 527.3.

Compound 201

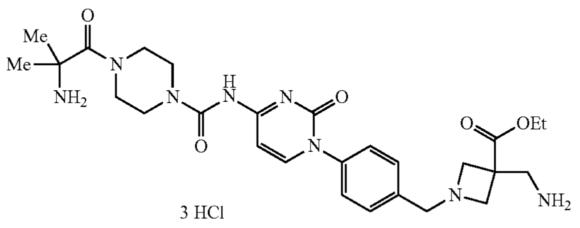

Ethyl 1-(4-(4-(4-(2-amino-2-methylpropanoyl)piperazine-1-carboxamido)-2-oxopyrimidin-1(2H)-yl) benzyl)-3-(aminomethyl)azetidine-3-carboxylate hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and ethyl 3-((((benzyloxy)carbonyl)amino) methyl)azetidine-3-carboxylate trifluoroacetate salt. $^{1}H$ NMR (500 MHz, $CD_3OD$) δ 7.69 (d, 1H), 7.45 (d, 2H), 7.38 (d, 2H), 6.52-6.72 (m, 1H), 4.21 (q, 2H), 3.61-3.88 (m, 12H), 3.50 (d, 2H), 3.11 (s, 2H), 1.42 (s, 6H), 1.29 (t, 3H). LCMS [M+H] 555.3.

Compound 137

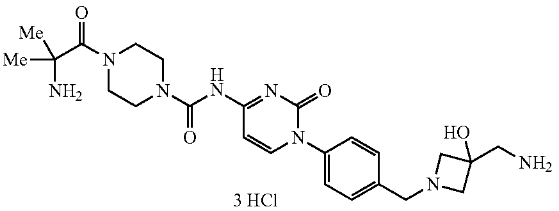

Compound 380

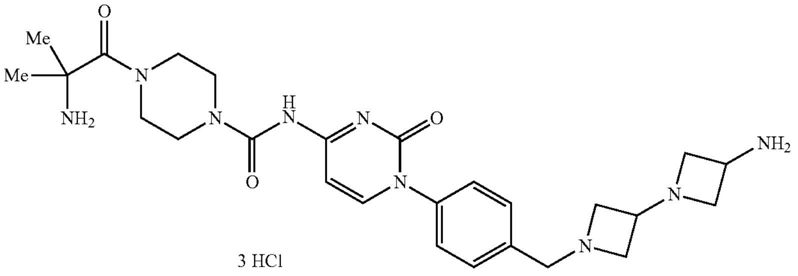

4-(2-Amino-2-methylpropanoyl)-N-(1-(4-((3-(aminomethyl)-3-hydroxyazetidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((3-hydroxyazetidin-3-yl) methyl)carbamate. $^{1}H$ NMR (500 MHz, $D_2O$) δ 7.78 (d, 1H), 7.47-7.56 (m, 2H), 7.42 (d, 2H), 6.71 (d, 1H), 4.36-4.51 (m, 2H), 4.24-4.33 (m, 2H), 4.01-4.20 (m, 2H), 3.51-3.72 (m, 8H), 3.29 (s, 2H), 1.59 (s, 6H). LCMS [M+H] 499.3.

4-(2-Amino-2-methylpropanoyl)-N-(1-(4-((3-amino-[1,3'-biazetidin]-1'-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl [1,3'-biazetidin]-3-ylcarbamate. $^{1}H$ NMR (500 MHz, $D_2O$) δ 7.60 (d, 1H), 7.29 (d, 2H), 7.24 (d, 2H), 6.54 (d, 1H), 3.46-3.73 (m, 10H), 3.34-3.44 (m, 3H), 3.21-3.33 (m, 3H), 2.93 (t, 2H), 2.69-2.80 (m, 2H), 1.32 (s, 6H). LCMS [M+H] 524.2.

Compound 205

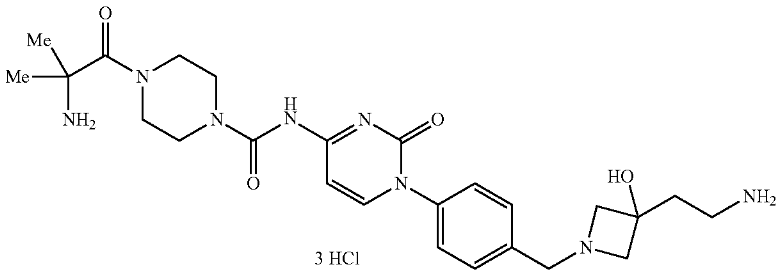

4-(2-Amino-2-methylpropanoyl)-N-(1-(4-((3-(2-aminoethyl)-3-hydroxyazetidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and 2,2,2-trifluoro-N-(2-(3-hydroxyazetidin-3-yl)ethyl)acetamide trifluoroacetate salt. $^{1}$H NMR (500 MHz, $D_2O$) δ 7.81 (d, 1H), 7.46-7.54 (m, 2H), 7.41 (d, 2H), 6.70 (d, 1H), 4.33-4.46 (m, 2H), 4.13-4.21 (m, 2H), 3.95-4.10 (m, 2H), 3.48-3.74 (m, 8H), 2.90-3.03 (m, 2H), 2.04-2.14 (m, 2H), 1.58 (s, 6H). LCMS [M+H] 513.3.

Compound 132

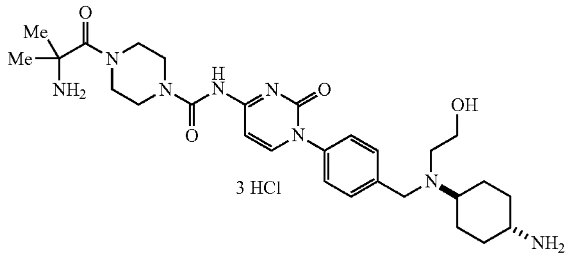

Compound 369

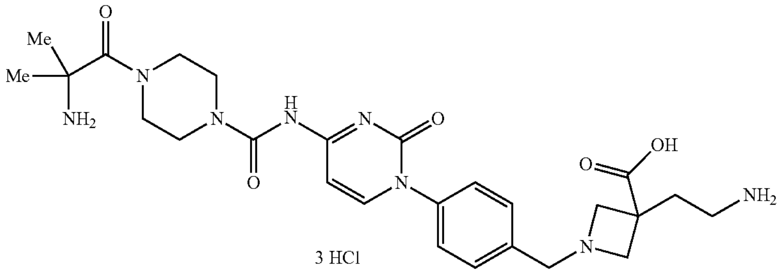

1-(4-(4-(4-(2-Amino-2-methylpropanoyl)piperazine-1-carboxamido)-2-oxopyrimidin-1(2H)-yl)benzyl)-3-(2-aminoethyl)azetidine-3-carboxylic acid hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 3-(2-((tert-butoxycarbonyl)amino)ethyl)azetidine-3-carboxylate. $^{1}$H NMR (500 MHz, $CD_3OD$) δ 7.71-7.86 (m, 1H), 7.61-7.70 (m, 2H), 7.48-7.59 (m, 2H), 5.78-5.84 (m, 1H), 4.38-4.59 (m, 4H), 4.17-4.34 (m, 2H), 3.58-3.86 (m, 7H), 3.41-3.51 (m, 1H), 2.88-3.02 (m, 2H), 2.32-2.48 (m, 2H), 1.69 (s, 6H). LCMS [M+H] 541.4.

4-(2-Amino-2-methylpropanoyl)-N-(1-(4-(((trans-4-aminocyclohexyl)(2-hydroxyethyl)amino)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (trans-4-((2-((tert-butyldimethylsilyl)oxy)ethyl)amino)cyclohexyl)carbamate. $^{1}$H NMR (500 MHz, $D_2O$) δ 7.85 (d, 1H), 7.60 (d, 2H), 7.45 (d, 2H), 6.73 (d, 1H), 4.36-4.48 (m, 2H), 3.54-3.81 (m, 10H), 3.32-3.44 (m, 2H), 3.06-3.20 (m, 2H), 2.02-2.28 (m, 4H), 1.67-1.82 (m, 2H), 1.60 (s, 6H), 1.35-1.51 (m, 2H). LCMS [M+H] 555.3.

Compound 138

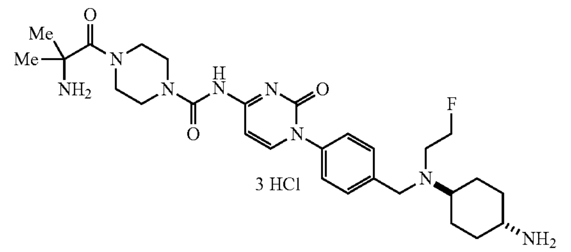

4-(2-Amino-2-methylpropanoyl)-N-(1-(4-(((trans-4-aminocyclohexyl)(2-fluoroethyl)amino)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (trans-4-((2-fluoroethyl)amino)cyclohexyl)carbamate. $^{1}$H NMR (500 MHz, $D_2O$) δ 7.83-7.92 (m, 1H), 7.55-7.66 (m, 2H), 7.41-7.53 (m, 2H), 6.69-6.77 (m, 1H), 4.35-4.54 (m, 2H), 3.49-3.80 (m, 10H), 3.36-3.48 (m, 2H), 3.09-3.28 (m, 2H), 2.05-2.28 (m, 4H), 1.68-1.85 (m, 2H), 1.61 (s, 6H), 1.36-1.52 (m, 2H). LCMS [M+H] 557.2.

Compound 319

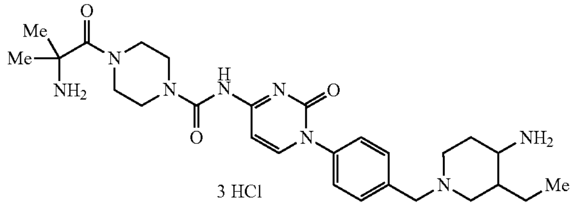

4-(2-Amino-2-methylpropanoyl)-N-(1-(4-((4-amino-3-ethylpiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3-ethylpiperidin-4-yl) carbamate. $^{1}$H NMR (400 MHz, $D_2O$) δ 7.78 (d, 1H), 7.56 (d, 2H), 7.43 (d, 2H), 6.73 (d, 1H), 4.36-4.28 (m, 2H), 3.61-3.58 (m, 6H), 3.08-3.04 (m, 2H), 2.92-2.86 (m, 1H), 2.20-2.04 (m, 3H), 1.59 (s, 6H), 1.39 (m, 1H) 1.28 (s, 2H), 0.84-0.72 (m, 4H). LCMS [M+H] 525.4.

Compound 297

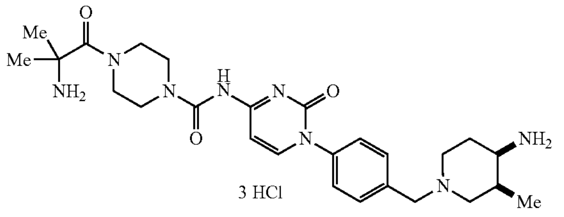

cis-4-(2-Amino-2-methylpropanoyl)-N-(1-(4-((4-amino-3-methylpiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and cis-tert-butyl (3-methylpiperidin-4-yl) carbamate. $^{1}$H NMR (400 MHz, $D_2O$) δ 7.78 (d, 1H), 7.52 (s, 2H), 7.41 (d, 2H), 6.69 (d, 1H), 4.33-4.22 (m, 2H), 3.61-3.48 (m, 11H), 3.31 (t, 2H), 3.20 (d, 1H), 3.02 (d, 1H), 2.85 (t, 1H), 2.44 (bs, 1H) 2.11 (s, 1H), 1.99 (s, 1H), 1.56 (s, 6H), 2.85 (t, 1H), 0.98 (d, 2H) 0.90 (d, 2H). LCMS [M+H] 511.3.

Compound 296

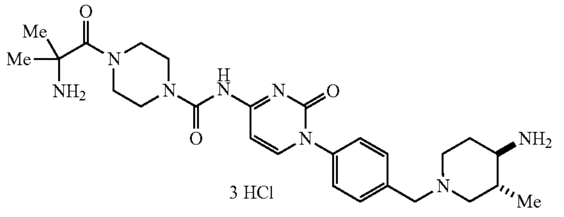

trans-4-(2-Amino-2-methylpropanoyl)-N-(1-(4-((4-amino-3-methylpiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and trans-tert-butyl (3-methylpiperidin-4-yl) carbamate. $^{1}$H NMR (400 MHz, $D_2O$) δ 7.8 (d, 1H), 7.55 (d, 2H), 7.44 (d, 2H), 6.73 (d, 1H), 4.35-4.26 (m, 2H), 3.64-3.59 (m, 8H), 3.5 (d, 1H), 3.40 (d, 1H), 3.24-2.98 (m, 3H), 2.81 (t, 1H), 2.22 (d, 1H) 2.04-1.98 (m, 2H), 1.86-1.65 (m, 2H) 1.55 (s, 6H), 0.96-0.88 (m, 3H). LCMS [M+H] 511.3.

Compound 300

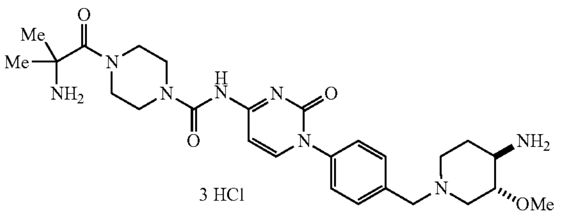

trans-4-(2-Amino-2-methylpropanoyl)-N-(1-(4-((4-amino-3-methoxypiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and trans-4-(Boc-amino)-3-methoxypiperidine. $^1H$ NMR (400 MHz, $D_2O$) δ 7.76 (d, 1H), 7.55 (d, 2H), 7.42 (d, 2H), 6.72 (d, 1H), 4.35-4.26 (m, 2H), 3.85-3.70 (m, 1H), 3.65-3.49 (m, 10H), 3.42-3.29 (m, 4H), 3.07 (t, 1H), 2.88-2.81 (m, 1H), 2.25 (d, 1H) 1.91-1.75 (m, 1H), 1.57 (s, 6H). LCMS [M+H] 527.8.

Compound 336

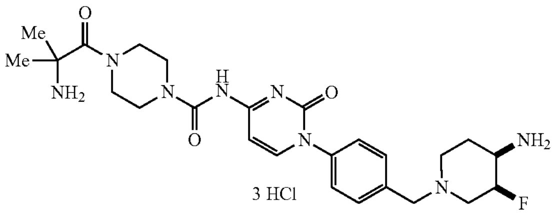

cis-4-(2-Amino-2-methylpropanoyl)-N-(1-(4-((4-amino-3-fluoropiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and cis-4-(Boc-amino)-3-fluoropiperidine. $^1H$ NMR (400 MHz, $D_2O$) δ 7.78 (d, 1H), 7.54 (d, 2H), 7.42 (d, 2H), 6.71 (d, 1H), 5.22 (s, 1H), 5.11 (m, 1H), 4.36 (s, 2H), 3.84 (t, 1H), 3.71-3.56 (m, 8H), 3.49-3.30 (m, 2H), 3.18-3.12 (m, 1H) 2.14-2.05 (m, 2H), 1.57 (s, 6H). LCMS [M+H] 515.3.

Compound 344

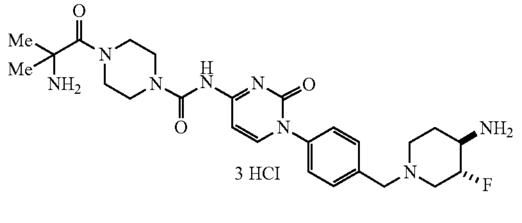

trans-4-(2-Amino-2-methylpropanoyl)-N-(1-(4-((4-amino-3-fluoropiperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and trans-4-(Boc-amino)-3-fluoropiperidine. $^1H$ NMR (400 MHz, $D_2O$) δ 7.86 (d, 1H), 7.59 (d, 2H), 7.47 (d, 2H), 6.73 (d, 1H), 4.82-4.81 (m, 1H), 4.49-4.38 (m, 2H), 3.82-3.79 (m, 1H), 3.65-3.53 (m, 10H), 3.24-3.15 (m, 2H), 2.39-3.35 (m, 1H), 1.96-1.86 (m, 1H) 1.60 (s 6H). LCMS [(M+2H)/2] 258.3.

Compound 320

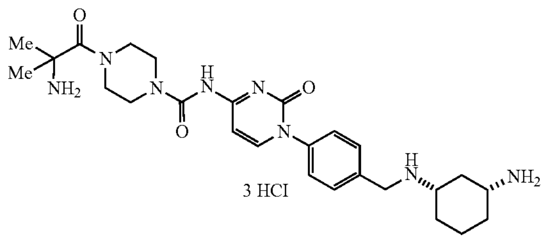

cis-4-(2-Amino-2-methylpropanoyl)-N-(1-(4-(((3-aminocyclohexyl)amino)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and cis-tert-butyl (3-aminocyclohexyl) carbamate. $^1H$ NMR (400 MHz, $D_2O$) δ 7.83 (d, 1H), 7.52 (d, 2H), 7.40 (d, 2H), 6.72 (d, 1H), 5.75-5.55 (m, 1H), 4.25 (s, 2H), 3.75-3.59 (m, 8H), 3.33-3.19 (m, 2H), 2.51-2.40 (m, 1H), 2.13 (bs, 1H), 2.05-1.89 (m, 3H) 1.59 (s, 6H), 1.52-1.43 (m, 2H), 1.30-1.19 (m, 4H). LCMS [M+H] 511.3.

Compounds 298 and 299

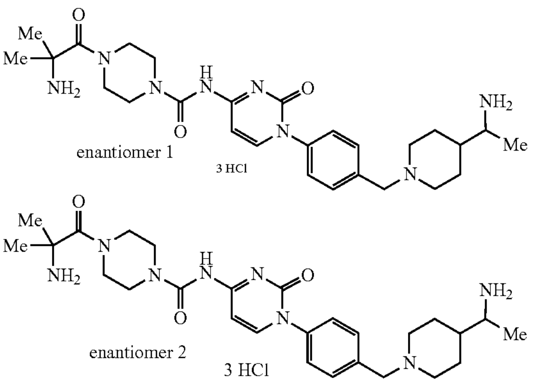

4-(2-Amino-2-methylpropanoyl)-N-(1-(4-((4-(1-aminoethyl)piperidin-1-yl)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (1-(piperidin-4-yl)ethyl) carbamate. Prior to Boc-deprotection the two enantiomers were separated by Chiral Prep-HPLC and used separately in the final step.

Isomer 1: $^1H$ NMR (400 MHz, $D_2O$) δ 7.76 (t, 1H), 7.52 (t, 2H), 7.42 (t, 2H), 6.71 (t, 1H), 4.25 (d, 2H), 3.61-3.56 (m, 9H), 3.5 (d, 4H), 3.16-3.14 (m, 1H), 2.91 (bs, 2H), 1.89 (bs, 2H), 1.81 (s, 1H) 1.28 (s, 2H), 1.55 (d, 5H) 1.43 (s, 2H), 1.15-1.08 (m, 4H). LCMS [M+H] 525.3.

Isomer 2: $^1$H NMR (400 MHz, $D_2O$) δ 7.80 (d, 1H), 7.52 (s, 2H), 7.40 (d, 2H), 6.69 (d, 1H), 4.24 (s, 3H), 4.12-4.06 (m, 2H), 3.58-3.48 (m, 5H), 3.13 (bs, 2H), 2.92 (bs, 3H), 1.79-1.87 (m, 4H), 1.56 (s, 6H) 1.12 (s, 8H), 0.71 (s, 3H). LCMS [M+H] 525.5.

Compound 335

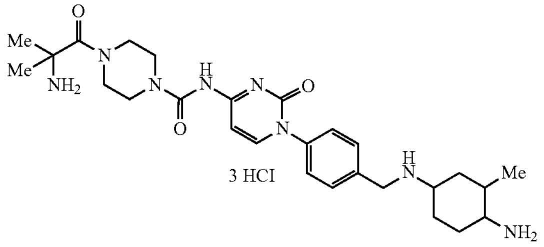

4-(2-Amino-2-methylpropanoyl)-N-(1-(4-(((4-amino-3-methylcyclohexyl)amino)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (4-amino-2-methylcyclohexyl)carbamate (prepared according to WO2012101062A1). $^1$H NMR (400 MHz, $D_2O$) Mixture of diastereomers δ 7.83 (d, 1H), 7.55 (d, 2H), 7.44 (d, 2H), 6.76 (d, 1H), 4.29 (s, 2H), 3.67-3.56 (m, 8H), 3.28 (bs, 1H), 2.87 (bs, 1H), 2.26-2.14 (m, 2H), 2.12-2.10 (m, 2H), 1.70-1.76 (bs, 1H), 1.63 (s, 6H), 1.53-1.47 (m, 2H), 1.33 (d, 1H), 1.19 (d, 1H), 1.10 (d, 3H). LCMS [M+H] 525.3.

Compound 339

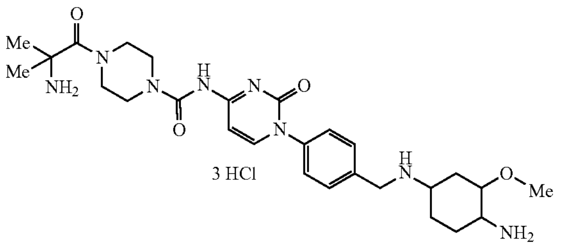

4-(2-Amino-2-methylpropanoyl)-N-(1-(4-(((4-amino-3-methoxycyclohexyl)amino)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (4-amino-2-methoxycyclohexyl)carbamate (prepared according to WO2012101062A1). $^1$H NMR (400 MHz, $D_2O$) Mixture of diastereomers δ 7.84 (d, 1H), 7.54 (d, 2H), 7.41 (d, 2H), 6.71 (d, 1H), 4.26 (s, 2H), 3.63-3.50 (m, 8H), 3.34 (br s, 2H), 3.29 (s, 3H), 2.27 (d, 1H), 2.10-1.95 (m, 3H), 1.79-1.76 (m, 1H), 1.58 (s, 6H), 1.51-1.46 (m, 2H). LCMS [M+H] 541.5.

Compound 321

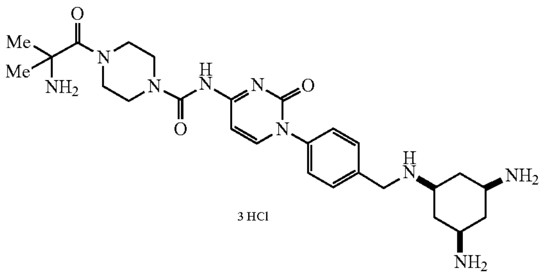

cis-4-(2-Amino-2-methylpropanoyl)-N-(1-(4-(((3,5-diaminocyclohexyl)amino)methyl)phenyl)-2-oxo-1,2-dihydropyrimidin-4-yl)piperazine-1-carboxamide hydrochloride salt Prepared in a similar fashion to Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and cis-di-tert-butyl (5-aminocyclohexane-1,3-diyl)dicarbamate (prepared according to J. Am. Chem. Soc. 2004, 126, 4543). $^1$H NMR (400 MHz, $D_2O$) Mixture of rotamers δ 7.83 (d, 1H), 7.55 (d, 2H), 7.42 (d, 2H), 6.73 (d, 1H), 4.31 (s, 2H), 3.64-3.51 (m, 8H), 3.49-3.46 (m, 1H), 3.42-3.33 (m, 2H), 3.27 (m, 1H), 2.51 (d, 2H), 2.38 (d, 1H), 1.65-1.52 (m, 9H). LCMS [M+H] 526.6.

Compound 208

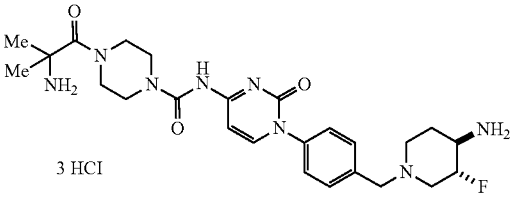

trans-4-(2-Amino-2-methylpropanoyl)-N-[1-(4-{[4-amino-3-fluoropiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((trans)-3-fluoropiperidin-4-yl)carbamate to give the title compound as the hydrochloride salt (8.8 mg, 56%). $^1$H NMR (400 MHz, $D_2O$) δ 7.86 (d, 1H), 7.66 (d, 2H), 7.53 (d, 2H), 6.82 (d, 1H), 5.06-4.82 (m, 1H), 4.53 (d, 1H), 4.47 (d, 1H), 3.94-3.82 (m, 1H), 3.81-3.57 (m, 10H), 3.39-3.16 (m, 2H), 2.55-2.33 (m, 1H), 2.06-1.89 (m, 1H), 1.68 (s, 6H). LCMS [M+H] 515.5.

Compound 212

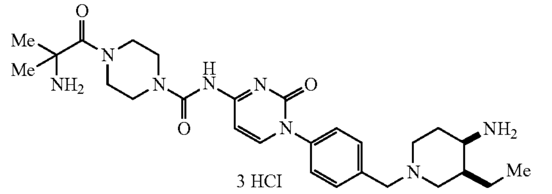

4-(2-Amino-2-methylpropanoyl)-N-(1-(4-(((cis)-4-amino-3-ethylpiperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3-ethylpiperidin-4-yl) carbamate. The two isomers were separated by semi-preparative HPLC on a Gemini 5 μm C18 110A AXIA (100x30 mm) column using a mobile phase of A: 10 mM ammonium bicarbonate aq. solution adjusted to pH 10 with ammonia/B: $CH_3CN$, flow rate: 40 mL/min, runtime=15.0 min., gradient: t=0 min. 10% B, t=10 min. 60% B, t=10.5 min. 100% B, t=14.5 min. 100% B, t=15 min. 10% B. Structural assignments were performed on free bases. $^1$H NMR ($D_2O$, 400 MHz) δ 7.90 (d, 1H), 7.66 (d, 2H), 7.53 (d, 2H), 6.81 (d, 1H), 4.51-4.30 (m, 2H), 3.81-3.43 (m, 11H), 3.26-2.90 (m, 2H), 2.38-2.00 (m, 3H), 1.68 (s, 6H), 1.54-1.30 (m, 2H), 1.00-0.72 (m, 3H). LCMS [M+H] 525.6.

Compound 213

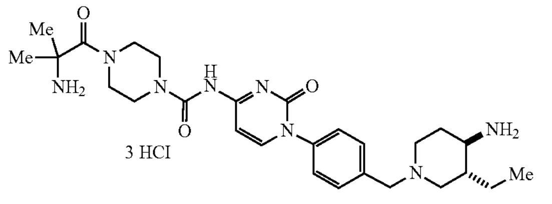

4-(2-Amino-2-methylpropanoyl)-N-(1-(4-(((trans)-4-amino-3-ethylpiperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3-ethylpiperidin-4-yl) carbamate. The two isomers were separated by semi-preparative HPLC on a Gemini 5 μm C18 110A AXIA (100x30 mm) column using a mobile phase of A: 10 mM ammonium bicarbonate aq. solution adjusted to pH 10 with ammonia B: $CH_3CN$, flow rate: 40 mL/min, runtime=15.0 min., gradient: t=0 min. 10% B, t=10 min. 60% B, t=10.5 min 100% B, t=14.5 min 100% B, t=15 min 10% B. Structural assignments were performed on free bases. $^1$H NMR ($D_2O$, 400 MHz) δ 7.84 (d, 1H), 7.64 (d, 2H), 7.52 (d, 2H), 6.84-6.78 (m, 1H), 4.41 (d, 1H), 4.38 (d, 1H), 3.80-3.54 (m, 10H), 3.38-3.26 (m, 1H), 3.20-3.07 (m, 1H), 2.96 (t, 1H), 2.38-2.25 (m, 1H), 2.10-1.81 (m, 2H), 1.68 (s, 7H), 1.43-1.29 (m, 1H), 0.86 (t, 3H). LCMS [M+H] 525.6.

Compound 365

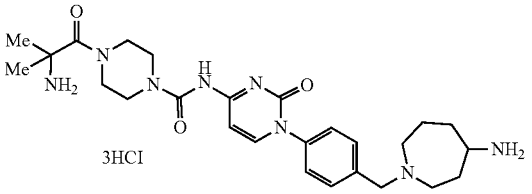

4-(2-Amino-2-methylpropanoyl)-N-(1-(4-((4-aminoazepan-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl azepan-4-ylcarbamate. LCMS [M+H] 511.3.

Compound 370

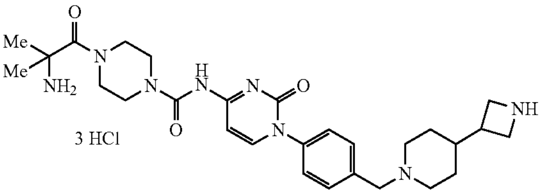

4-(2-Amino-2-methylpropanoyl)-N-(1-(4-((4-(azetidin-3-yl)piperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 3-(piperidin-4-yl)azetidine-1-carboxylate. LCMS [M+H] 537.4.

Compound 292

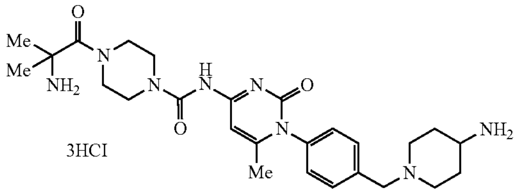

4-(2-Amino-2-methylpropanoyl)-N-(1-(4-((4-aminopiperidin-1-yl)methyl)phenyl)-6-methyl-2-oxo-1,2-dihydropyrimidin-4-yl)piperazine-1-carboxamide hydrochloride salt Prepared in a similar fashion as Scheme C-1. LCMS [M+H] 511.3.

Compound 209

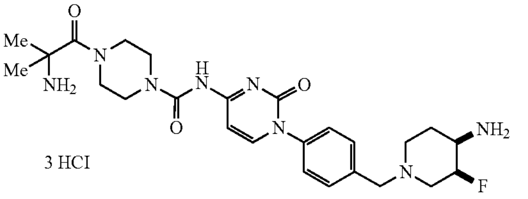

cis-4-(2-Amino-2-methylpropanoyl)-N-[1-(4-{[4-amino-3-fluoropiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((cis)-3-fluoropiperidin-4-yl) carbamate. $^1$H NMR (400 MHz, $D_2O$) δ 7.83 (d, 1H), 7.64 (d, 2H), 7.53 (d, 2H), 6.82 (d, 1H), 5.27 (d, 1H), 4.53-4.38 (m, 2H), 4.02-3.88 (m, 1H), 3.85-3.57 (m, 10H), 3.55-3.18 (m, 2H), 2.32-2.16 (m, 2H), 1.68 (s, 6H). LCMS [M+H] 515.5.

Compound 210

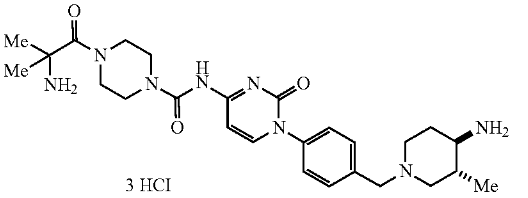

trans-4-(2-Amino-2-methylpropanoyl)-N-[1-(4-{[4-amino-3-methylpiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((trans)-3-methylpiperidin-4-yl)carbamate. $^1$H NMR (400 MHz, $D_2O$) δ 7.88 (d, 1H), 7.64 (d, 2H), 7.52 (d, 2H), 6.81 (d, 1H), 4.42 (d, 1H), 4.37 (d, 1H), 3.81-3.58 (m, 9H), 3.57-3.44 (m, 1H), 3.27-3.07 (m, 2H), 2.90 (t, 1H), 2.36-2.25 (m, 1H), 2.14-2.01 (m, 1H), 1.98-1.82 (m, 1H), 1.68 (s, 6H), 1.04 (d, 3H). LCMS [M+H] 511.5.

Compound 211

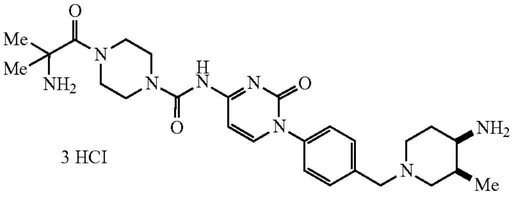

cis-4-(2-Amino-2-methylpropanoyl)-N-[1-(4-{[4-amino-3-methylpiperidin-1-yl]methyl}phenyl)-2-oxo-1,2-dihydropyrimidin-4-yl]piperazine-1-carboxamide (racemate) hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((cis)-3-methylpiperidin-4-yl) carbamate. $^1$H NMR (400 MHz, $D_2O$) δ 7.85 (d, 1H), 7.64 (d, 2H), 7.52 (d, 2H), 6.82 (d, 1H), 4.49-4.30 (m, 2H), 3.81-3.54 (m, 10H), 3.48-3.37 (m, 1H), 3.35-2.90 (m, 2H), 2.63-2.32 (m, 1H), 2.29-2.05 (m, 2H), 1.68 (s, 6H), 1.13-0.98 (m, 3H). LCMS [M+H] 511.5.

Compound 214

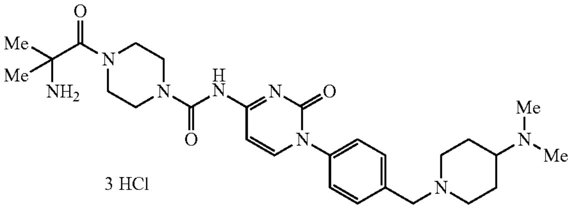

4-(2-Amino-2-methylpropanoyl)-N-[1-(4-{[4-(dimethylamino)piperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and N,N-dimethylpiperidin-4-amine. $^1$H NMR (400 MHz, $D_2O$) δ 7.89 (d, 1H), 7.65 (d, 2H), 7.53 (d, 2H), 6.81 (d, 1H), 4.41 (s, 2H), 3.81-3.50 (m, 11H), 3.17 (br. s., 2H), 2.86 (s, 6H), 2.36 (br s, 2H), 2.05-1.86 (m, 2H), 1.69 (s, 6H). LCMS [M+H] 525.3.

Compound 215

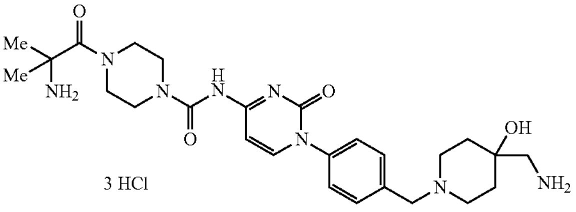

4-(2-Amino-2-methylpropanoyl)-N-[1-(4-{[4-(aminomethyl)-4-hydroxypiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((4-hydroxypiperidin-4-yl)methyl)carbamate. $^1$H NMR (400 MHz, $D_2O$) δ 7.86 (d, 1H), 7.64 (d, 2H), 7.52 (d, 2H), 6.81 (d, 1H), 4.40 (s, 2H), 3.80-3.61 (m, 8H), 3.51-3.41 (m, 2H), 3.37-3.23 (m, 2H), 3.05 (s, 2H), 2.00-1.78 (m, 4H), 1.68 (s, 6H). LCMS [M+H] 527.4.

Compound 218

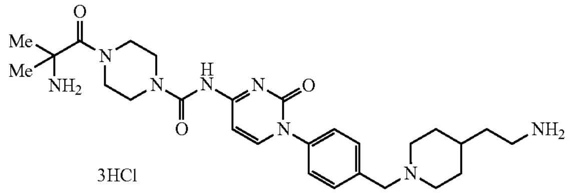

4-(2-Amino-2-methylpropanoyl)-N-[1-(4-{[4-(2-aminoethyl)piperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (2-(piperidin-4-yl)ethyl) carbamate. $^1$H NMR (400 MHz, $D_2O$) δ 7.84 (d, 1H), 7.65-7.58 (m, 2H), 7.53-7.47 (m, 2H), 6.82 (d, 1H), 4.33 (s, 2H), 3.81-3.60 (m, 8H), 3.56-3.48 (m, 2H), 3.08-2.93 (m, 4H), 2.01-1.91 (m, 2H), 1.90-1.54 (m, 9H), 1.49-1.32 (m, 2H). LCMS [M+H] 525.4.

Compound 223

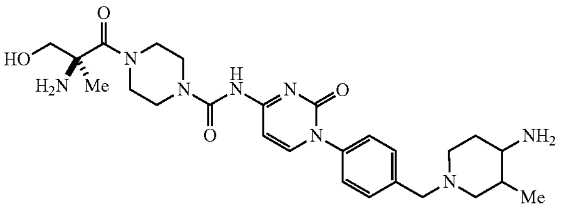

4-[(2S)-2-Amino-3-hydroxy-2-methylpropanoyl]-N-(1-{4-[(4-amino-3-methylpiperidin-1-yl)methyl]phenyl}-2-oxo-1,2-dihydropyrimidin-4-yl)piperazine-1-carboxamide hydrochloride salt Prepared in a similar fashion as Scheme C-1 from tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate and tert-butyl (3-methylpiperidin-4-yl)carbamate. $^1$H NMR (400 MHz, $D_2O$) δ 7.80 (d, 1H), 7.56 (d, 2H), 7.44 (d, 2H), 6.73 (d, 1H), 4.39-4.21 (m, 2H), 4.02 (d, 1H), 3.77 (d, 1H), 3.73-2.81 (m, 13H), 2.56-2.24 (m, 1H), 2.22-1.92 (m, 2H), 1.55 (s, 3H), 1.09-0.87 (m, 3H). LCMS [M+H] 527.5.

Compound 224

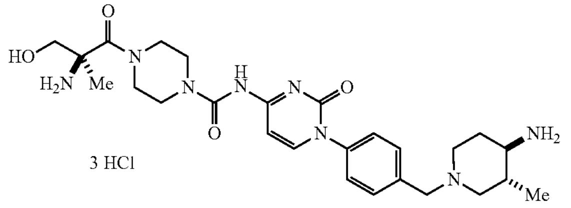

trans-4-[(2S)-2-Amino-3-hydroxy-2-methylpropanoyl]-N-(1-{4-[(4-amino-3-methylpiperidin-1-yl)methyl]phenyl}-2-oxo-1,2-dihydropyrimidin-4-yl)piperazine-1-carboxamide hydrochloride salt Prepared in a similar fashion as Scheme C-1 from tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate and tert-butyl ((trans)-3-methylpiperidin-4-yl)carbamate. $^1$H NMR (400 MHz, $D_2O$) δ 7.86 (d, 1H), 7.63 (d, 2H), 7.51 (d, 2H), 6.81 (d, 1H), 4.46-4.30 (m, 2H), 4.18-3.81 (m, 2H), 3.80-3.58 (m, 8H), 3.69-3.57 (m, 1H), 3.57-3.38 (m, 1H), 3.24-3.03 (m, 2H), 2.89 (t, 1H), 2.30 (d, 1H), 2.09 (br. s., 1H), 1.90 (q, 1H), 1.63 (s, 3H), 1.16-0.83 (m, 3H). LCMS [M+H] 527.5.

Compound 225

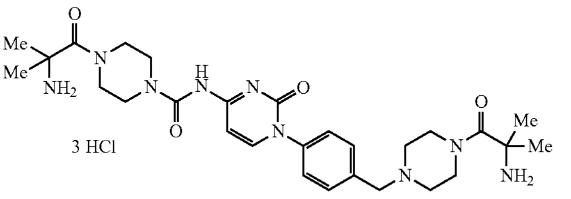

4-(2-Amino-2-methylpropanoyl)-N-[1-(4-{[4-(2-amino-2-methylpropanoyl)piperazin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (2-methyl-1-oxo-1-(piperazin-1-yl)propan-2-yl)carbamate. $^1$H NMR (400 MHz, $D_2O$) δ 7.84 (d, 1H), 7.64 (d, 2H), 7.53 (d, 2H), 6.82 (d, 1H), 4.43 (s, 2H), 3.85-3.26 (m, 16H), 1.68 (s, 6H), 1.66 (s, 6H). LCMS [M+H] 568.5.

Compound 227

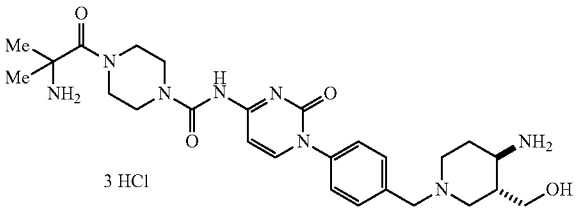

trans-4-(2-Amino-2-methylpropanoyl)-N-[1-(4-{[4-amino-3-(hydroxymethyl)piperidin-1-yl] methyl}phenyl)-2-oxo-1,2-dihydropyrimidin-4-yl] piperazine-1-carboxamide (racemate) hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((trans)-3-(hydroxymethyl) piperidin-4-yl)carbamate. $^1$H NMR (400 MHz, $D_2O$) δ 7.97 (d, 1H), 7.71 (d, 2H), 7.59 (d, 2H), 6.85 (d, 1H), 4.53 (s, 2H), 3.90-3.58 (m, 13H), 3.29-3.08 (m, 2H), 2.09 (d, 2H), 1.80-1.53 (m, 7H). LCMS [M+H] 527.6.

Compound 237

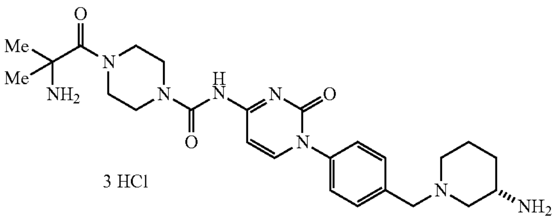

3 HCl 4-(2-Amino-2-methylpropanoyl)-N-[1-(4-{[(3S)-3-aminopiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (S)-piperidin-3-ylcarbamate. $^1$H NMR (400 MHz, $D_2O$) δ 7.84 (d, 1H), 7.64 (d, 2H), 7.53 (d, 2H), 6.82 (d, 1H), 4.47 (s, 2H), 3.77-3.62 (m, 9H), 3.62-3.49 (m, 2H), 3.20-2.92 (m, 2H), 2.25-2.15 (m, 1H), 2.13-2.04 (m, 1H), 1.87-1.72 (m, 1H), 1.71-1.56 (m, 7H). LCMS [M+H] 497.4.

Compound 238

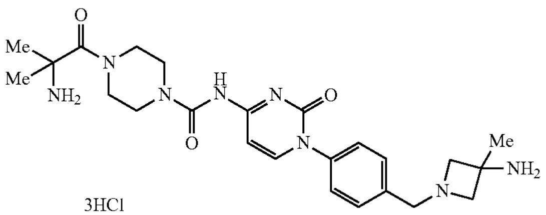

3HCl 4-(2-Amino-2-methylpropanoyl)-N-(1-(4-((3-amino-3-methylazetidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3-methylazetidin-3-yl) carbamate. $^1$H NMR (400 MHz, $D_2O$) δ 7.83 (d, 1H), 7.62-7.57 (m, 2H), 7.54-7.48 (m, 2H), 6.81 (d, 1H), 4.57-4.50 (m, 4H), 4.32-4.25 (m, 2H), 3.76-3.62 (m, 8H), 1.71 (s, 3H), 1.68 (s, 6H). LCMS [M+H] 483.4.

Compound 239

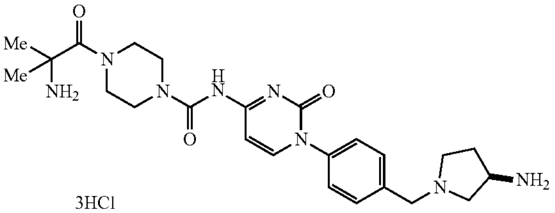

3HCl 4-(2-Amino-2-methylpropanoyl)-N-[1-(4-{[(3R)-3-aminopyrrolidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (R)-pyrrolidin-3-ylcarbamate. $^1$H NMR (400 MHz, $D_2O$) δ 7.85 (d, 1H), 7.65 (d, 2H), 7.52 (d, 2H), 6.81 (d, 1H), 4.53 (s, 2H), 4.27-4.12 (m, 1H), 4.00-3.40 (m, 12H), 2.69-2.52 (m, 1H), 2.30-2.12 (m, 1H), 1.67 (s, 6H). LCMS [M+H] 483.4.

Compound 240

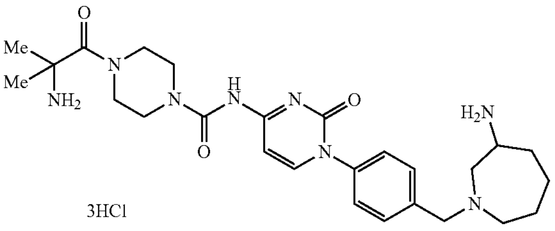

3HCl 4-(2-Amino-2-methylpropanoyl)-N-(1-{4-[(3-amino-azepan-1-yl)methyl]phenyl}-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl azepan-3-ylcarbamate. $^1$H NMR (400 MHz, $D_2O$) δ 7.83 (d, 1H), 7.65 (d, 2H), 7.51 (d, 2H), 6.80 (d, 1H), 4.50 (d, 2H), 4.43 (d, 2H), 3.85-3.25 (m, 11H), 2.26-2.08 (m, 1H), 1.96-1.60 (m, 11H). LCMS [M+H] 511.4.

Compound 241

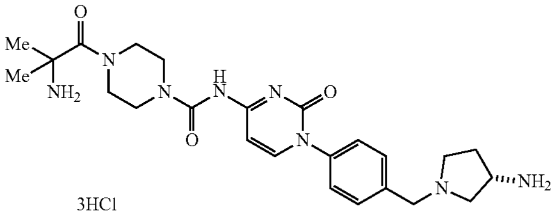

4-(2-Amino-2-methylpropanoyl)-N-[1-(4-{[(3S)-3-aminopyrrolidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (S)-pyrrolidin-3-ylcarbamate. $^1$H NMR ($D_2O$, 400 MHz) δ 7.85 (d, 1H), 7.65 (d, 2H), 7.53 (d, 2H), 6.82 (d, 1H), 4.53 (s, 2H), 4.29-4.13 (m, 1H), 3.99-3.82 (m, 1H), 3.44-3.82 (m, 11H), 2.71-2.51 (m, 1H), 2.30-2.10 (m, 1H), 1.68 (s, 6H). LCMS [M+H] 483.3.

Compound 242

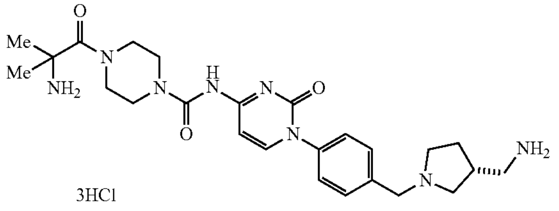

4-(2-Amino-2-methylpropanoyl)-N-[1-(4-{[(3R)-3-(aminomethyl)pyrrolidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (S)-(pyrrolidin-3-ylmethyl) carbamate. $^1$H NMR (400 MHz, $D_2O$) δ 7.85 (d, 1H), 7.64 (d, 2H), 7.51 (d, 2H), 6.86-6.79 (m, 1H), 4.51-4.43 (m, 2H), 3.84-2.21 (m, 14H), 2.05-1.63 (m, 9H). LCMS [M+H] 497.5.

Compound 243

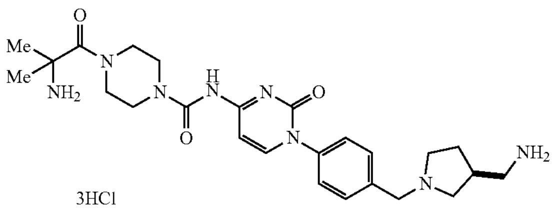

4-(2-Amino-2-methylpropanoyl)-N-[1-(4-{[(3S)-3-(aminomethyl)pyrrolidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (R)-(pyrrolidin-3-ylmethyl) carbamate. $^1$H NMR (400 MHz, $D_2O$) δ 7.88 (d, 1H), 7.66 (d, 2H), 7.53 (d, 2H), 6.83 (d, 1H), 4.56-4.42 (m, 2H), 3.92-1.64 (m, 23H). LCMS [M+H] 497.4.

Compound 244

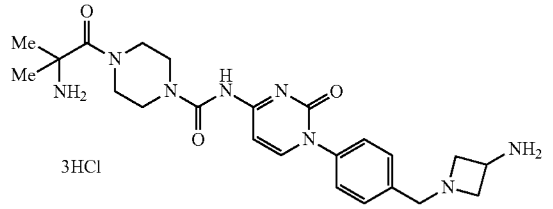

4-(2-Amino-2-methylpropanoyl)-N-(1-{4-[(3-aminoazetidin-1-yl)methyl]phenyl}-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl azetidin-3-ylcarbamate. $^1$H NMR (400 MHz, $D_2O$) δ 7.90 (d, 1H), 7.61 (d, 2H), 7.52 (d, 2H), 6.79 (d, 1H), 4.59-4.40 (m, 7H), 3.79-3.61 (m, 8H), 1.67 (s, 6H). LCMS [M+H] 469.3.

Compound 245

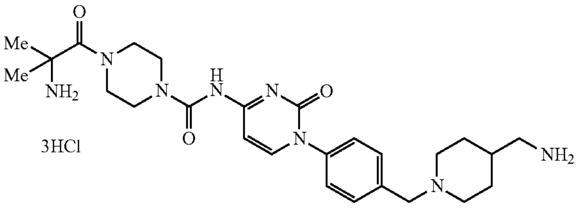

4-(2-Amino-2-methylpropanoyl)-N-[1-(4-{[4-(aminomethyl)piperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (piperidin-4-ylmethyl) carbamate. $^1$H NMR (400 MHz, $D_2O$) δ 7.86 (d, 1H), 7.63 (d, 2H), 7.51 (d, 2H), 6.81 (d, 1H), 4.36 (s, 2H), 3.81-3.63 (m, 8H), 3.62-3.51 (m, 2H), 3.13-2.99 (m, 2H), 2.92 (d, 2H), 2.09-1.93 (m, 3H), 1.69 (s, 6H), 1.58-1.40 (m, 2H). LCMS [M+H] 511.3.

Compound 246

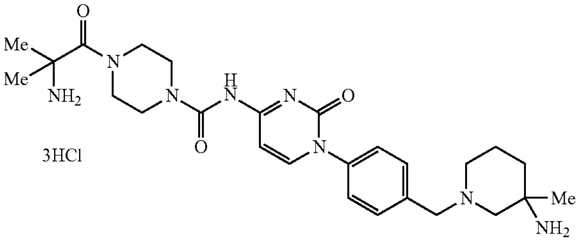

4-(2-Amino-2-methylpropanoyl)-N-(1-{4-[(3-amino-3-methylpiperidin-1-yl)methyl]phenyl}-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3-methylpiperidin-3-yl) carbamate. $^{1}$H NMR (400 MHz, $D_2O$) δ 7.88 (d, 1H), 7.66 (d, 2H), 7.54 (d, 2H), 6.82 (d, 1H), 4.50 (d, 1H), 4.44 (d, 1H), 3.95-2.91 (m, 12H), 2.24-1.61 (m, 10H), 1.47 (br s, 3H). LCMS [M+H] 511.5.

Compound 247

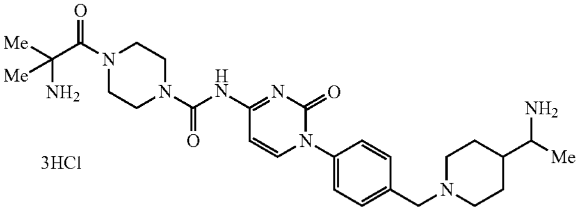

4-(2-Amino-2-methylpropanoyl)-N-[1-(4-{[4-(1-aminoethyl)piperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (1-(piperidin-4-yl)ethyl) carbamate. LCMS [M+H] 525.4.

Compound 248

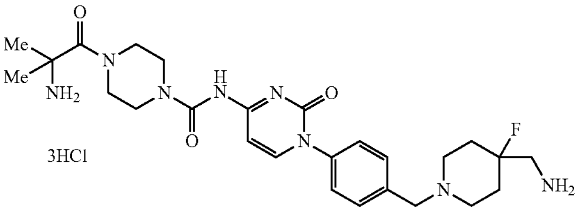

4-(2-Amino-2-methylpropanoyl)-N-[1-(4-{[4-(aminomethyl)-4-fluoropiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((4-fluoropiperidin-4-yl) methyl)carbamate. $^{1}$H NMR (400 MHz, $D_2O$) δ 7.86 (d, 1H), 7.65 (d, 2H), 7.53 (d, 2H), 6.82 (d, 1H), 4.43 (s, 2H), 3.82-3.62 (m, 8H), 3.61-3.50 (m, 2H), 3.42-3.24 (m, 4H), 2.35-2.17 (m, 2H), 2.13-1.86 (m, 2H), 1.69 (s, 6H). LCMS [M+H] 529.5.

Compound 249

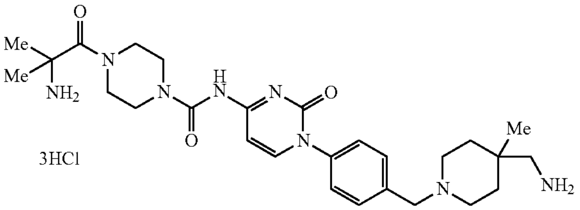

4-(2-Amino-2-methylpropanoyl)-N-[1-(4-{[4-(aminomethyl)-4-methylpiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((4-methylpiperidin-4-yl) methyl)carbamate. $^{1}$H NMR (400 MHz, $D_2O$) δ 7.84 (d, 1H), 7.63 (d, 2H), 7.51 (d, 2H), 6.82 (d, 1H), 4.39 (s, 2H), 3.84-3.57 (m, 8H), 3.52-3.37 (m, 2H), 3.27-2.86 (m, 4H), 1.99-1.55 (m, 10H), 1.21-1.04 (m, 3H). LCMS [M+H] 525.4.

Compound 250

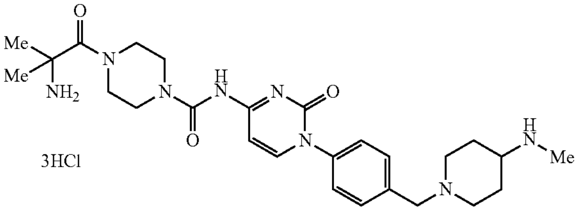

4-(2-amino-2-methylpropanoyl)-N-(1-(4-((4-(methylamino)piperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl methyl(piperidin-4-yl) carbamate. $^{1}$H NMR (400 MHz, $D_2O$) δ 7.85 (d, 1H), 7.63 (d, 2H), 7.52 (d, 2H), 6.81 (d, 1H), 4.39 (s, 2H), 3.78-3.57

(m, 10H), 3.49-3.34 (m, 1H), 3.21-3.05 (m, 2H), 2.70 (s, 3H), 2.44-2.29 (m, 2H), 1.94-1.76 (m, 2H), 1.68 (s, 6H). LCMS [M+H] 511.7.

Compound 251

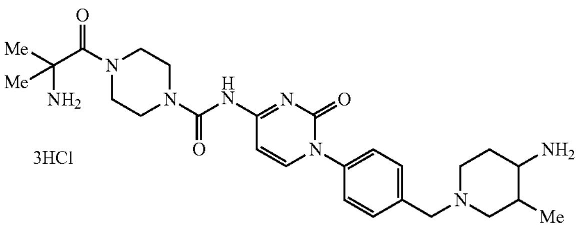

4-(2-amino-2-methylpropanoyl)-N-(1-(4-((4-amino-3-methylpiperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3-methylpiperidin-4-yl) carbamate. $^1$H NMR (400 MHz, $D_2O$) δ 7.86 (d, 1H), 7.64 (d, 2H), 7.52 (d, 2H), 6.81 (d, 1H), 4.50-4.29 (m, 2H), 3.87-2.82 (m, 13H), 2.66-1.81 (m, 3H), 1.68 (m, 6H), 1.22-0.94 (m, 3H). LCMS [M+H] 511.5.

Compound 252

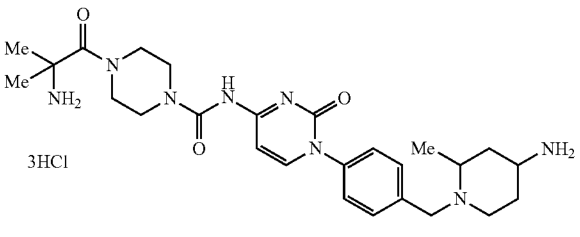

N-(1-(4-((4-amino-2-methylpiperidin-1-yl)methyl)phenyl)-2-oxo-1,2-dihydropyrimidin-4-yl)-4-(2-amino-2-methylpropanoyl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (2-methylpiperidin-4-yl) carbamate. $^1$H NMR (400 MHz, $D_2O$) δ 7.85 (d, 1H), 7.59-7.70 (m, 2H), 7.52 (d, 2H), 6.82 (d, 1H), 4.91-4.07 (m, 2H), 4.02-2.95 (m, 12H), 2.44-1.66 (m, 10H), 1.63-1.45 (m, 3H). LCMS [M+H] 511.5.

Compound 267

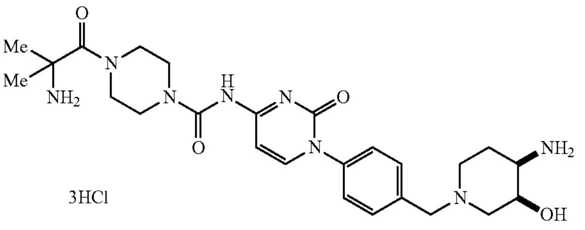

4-(2-amino-2-methylpropanoyl)-N-(1-(4-((cis-4-amino-3-hydroxypiperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl ((cis)-3-hydroxypiperidin-4-yl)carbamate. $^1$H NMR (400 MHz, $D_2O$) δ 7.83 (d, 1H), 7.63 (d, 2H), 7.52 (d, 2H), 6.82 (d, 1H), 4.45 (d, 1H), 4.37 (d, 1H), 4.29 (br. s., 1H), 3.83-3.44 (m, 11H), 3.34-3.07 (m, 2H), 2.32-2.16 (m, 1H), 2.15-2.06 (m, 1H), 1.68 (s, 6H). LCMS [M+H] 513.4.

Compound 268

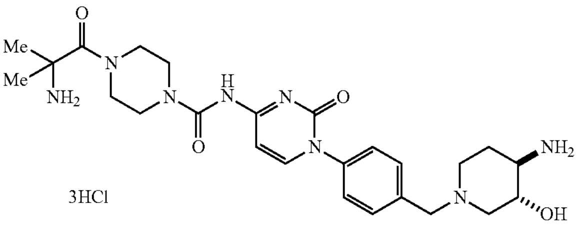

4-(2-amino-2-methylpropanoyl)-N-(1-(4-((trans-4-amino-3-hydroxypiperidin-1-yl)methyl)phenyl)-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (trans-3-hydroxypiperidin-4-yl)carbamate. $^1$H NMR (400 MHz, $D_2O$) δ 7.85 (d, 1H), 7.65 (d, 2H), 7.53 (d, 2H), 6.82 (d, 1H), 4.45 (s, 2H), 4.01-3.89 (m, 1H), 3.82-3.56 (m, 10H), 3.41-3.28 (m, 1H), 3.25-3.13 (m, 1H), 3.01 (t, 1H), 2.43-2.30 (m, 1H), 2.00-1.83 (m, 1H), 1.69 (s, 6H). LCMS [M+H] 513.5.

Compound 254

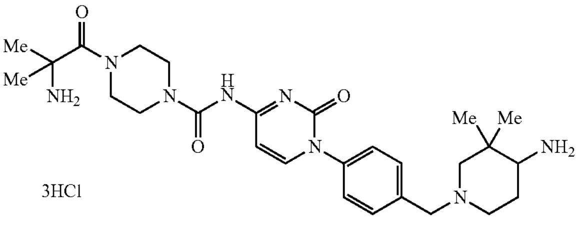

4-(2-Amino-2-methylpropanoyl)-N-(1-{4-[(4-amino-3,3-dimethylpiperidin-1-yl)methyl]phenyl}-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (3,3-dimethylpiperidin-4-yl) carbamate. $^1$H NMR (400 MHz, $D_2O$) δ 7.85 (d, 1H), 7.64 (d, 2H), 7.52 (d, 2H), 6.82 (d, 1H), 4.45 (d, 1H), 4.34 (d, 1H), 383-3.57 (m, 9H), 3.35 (dd, 1H), 3.30-3.22 (m, 1H), 3.20-3.09 (m, 1H), 2.98 (d, 1H), 2.23-2.00 (m, 2H), 1.68 (s, 6H), 1.09 (s, 6H). LCMS [M+H] 525.5.

Compound 255

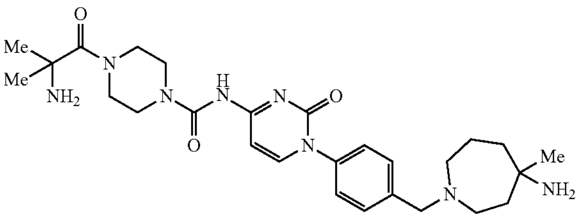

4-(2-Amino-2-methylpropanoyl)-N-(1-{4-[(4-amino-4-methylazepan-1-yl)methyl]phenyl}-2-oxo-1,2-dihydropyrimidin-4-yl)piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and 2-methyl-N-(4-methylazepan-4-yl) propane-2-sulfinamide. $^1$H NMR (400 MHz, $D_2O$) δ 7.83 (d, 1H), 7.63 (d, 2H), 7.51 (d, 2H), 6.81 (d, 1H), 4.42 (s, 2H), 3.89-3.00 (m, 12H), 2.30-1.75 (m, 6H), 1.68 (s, 6H), 1.38 (br. s., 3H). LCMS [M+H] 525.5.

Compound 236

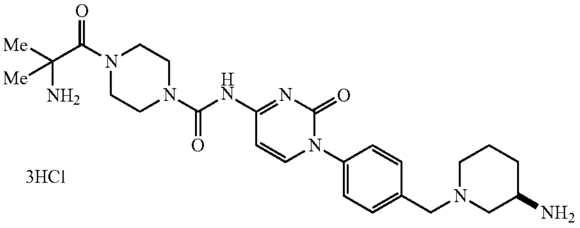

4-(2-Amino-2-methylpropanoyl)-N-[1-(4-{[(3R)-3-aminopiperidin-1-yl]methyl}phenyl)-2-oxo-1,2-dihydropyrimidin-4-yl]piperazine-1-carboxamide hydrochloride salt Prepared in a similar fashion as Scheme C-1 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (R)-piperidin-3-ylcarbamate. $^1$H NMR (400 MHz, $D_2O$) δ 7.84 (d, 1H), 7.68-7.60 (m, 2H), 7.57-7.47 (m, 2H), 6.82 (d, 1H), 4.47 (s, 2H), 3.81-3.47 (m, 11H), 3.19-2.93 (m, 2H), 2.25-2.04 (m, 2H), 1.91-1.54 (m, 8H). LCMS [M+H] 497.4.

Compound 253

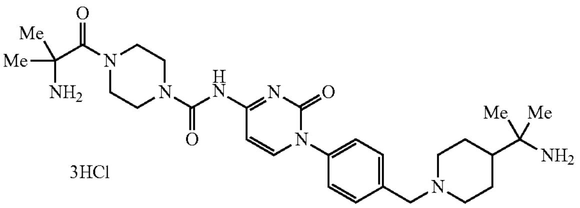

4-(2-Amino-2-methylpropanoyl)-N-(1-(4-((4-(2-aminopropan-2-yl)piperidin-1-yl)methyl)phenyl)-2-oxo-1,2-dihydropyrimidin-4-yl)piperazine-1-carboxamide hydrochloride salt Scheme C-2

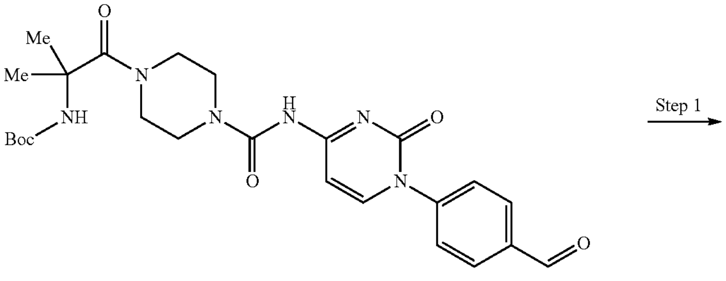

-continued

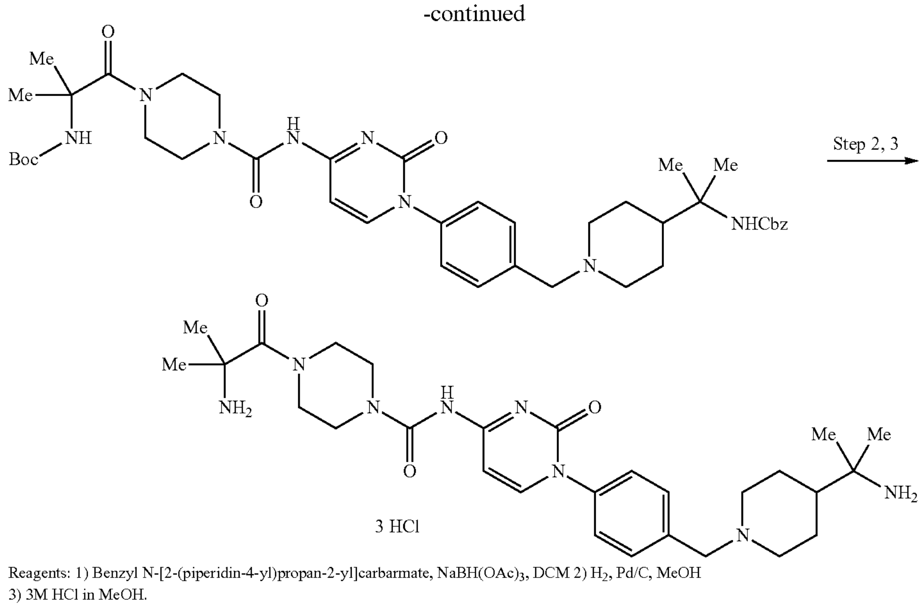

Step 1: Benzyl (2-(1-(4-(4-(4-(2-((tert-butoxycarbonyl)amino)-2-methylpropanoyl)piperazine-1-carboxamido)-2-oxopyrimidin-1(2H)-yl)benzyl)piperidin-4-yl)propan-2-yl)carbamate Benzyl (2-(piperidin-4-yl)propan-2-yl)carbamate (11.5 mg, 0.054 mmol) was added to a suspension of tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate (40 mg, 0.078 mmol) in DCM (3 mL). The reaction mixture was stirred at rt for 15 min and NaBH$(OAc)_3$ (195 mg, 0.090 mmol) was added. The reaction was stirred at rt for 7 h. Additional $NaBH(OAc)_3$ (20 mg) was added and the reaction was stirred overnight. The reaction was diluted with DCM and washed with sat. aq. $NaHCO_3$. The organic layer was dried over $Na_2SO_4$, filtered, and concentrated under reduced pressure. The crude product was purified by reverse phase chromatography ($H_2O$: 0.1% aq. $NH_4OH$ in $CH_3CN$, 20:80) and the recovered fractions purified by reverse phase chromatography ($H_2O$:$CH_3CN$, 20:80) to afford the title compound (12.0 mg, 33%). $^1H$ NMR (400 MHz, $CDCl_3$) δ 12.94 (br s, 1H), 7.44 (d, 2H), 7.40-7.22 (m, 8H), 5.84 (d, 1H), 5.06 (s, 2H), 4.94-4.80 (m, 1H), 4.66 (s, 1H), 3.97-3.57 (m, 8H), 3.52 (s, 2H), 3.01-2.90 (m, 2H), 2.02-1.82 (m, 3H), 1.70-1.59 (m, 2H), 1.54 (s, 6H), 1.46 (s, 9H), 1.43-1.25 (m, 8H). LCMS [M+H] 773.7.

Step 2: tert-Butyl (1-(4-((1-(4-((4-(2-aminopropan-2-yl)piperidin-1-yl)methyl)phenyl)-2-oxo-1,2-dihydropyrimidin-4-yl)carbamoyl)piperazin-1-yl)-2-methyl-1-oxopropan-2-yl)carbamate Pd/C Degussa type (10% wt, 3.0 mg) was added to a solution of benzyl (2-(1-(4-(4-(4-(2-((tert-butoxycarbonyl)amino)-2-methylpropanoyl)piperazine-1-carboxamido)-2-oxopyrimidin-1(2H)-yl)benzyl)piperidin-4-yl)propan-2-yl)carbamate (12.0 mg, 0.015 mmol) in EtOAc (4 mL). The mixture was stirred under $H_2$ atmosphere for 24 h. The reaction was filtered and concentrated under reduced pressure. The crude product was purified (EtOAc-MeOH, 90:10) to afford the title compound (4.5 mg, 47%). $^1H$ NMR (400 MHz, $CDCl_3$) δ 7.45 (d, 2H), 7.33-7.24 (m, 3H), 5.84 (d, 1H), 4.86 (br. s., 1H), 3.98-3.58 (m, 8H), 3.54 (br.s., 2H), 3.03-2.94 (m, 2H), 2.04-1.90 (m, 2H), 1.79-1.13 (m, 20H), 1.08 (s, 6H). LCMS [M+H] 639.7.

Step 3: 4-(2-Amino-2-methylpropanoyl)-N-(1-(4-((4-(2-aminopropan-2-yl)piperidin-1-yl)methyl)phenyl)-2-oxo-1,2-dihydropyrimidin-4-yl)piperazine-1-carboxamide hydrochloride salt A solution of tert-butyl (1-(4-((1-(4-((4-(2-aminopropan-2-yl)piperidin-1-yl)methyl)phenyl)-2-oxo-1,2-dihydropyrimidin-4-yl)carbamoyl)piperazin-1-yl)-2-methyl-1-oxopropan-2-yl)carbamate (4.5 mg, 0.007 mmol) in 3M HCl in MeOH (1.5 mL) was stirred at rt for 16 h. The reaction mixture was concentrated under reduced pressure, dissolved in MeOH and precipitated with EtOAc. The solid was filtered washed with $Et_2O$ and dried to afford the title compound (3.9 mg, 86%) as a colorless wax. $^1H$ NMR (400 MHz, $D_2O$) δ 7.83 (d, 1H), 7.62 (d, 2H), 7.50 (d, 2H), 6.81 (d, 1H), 4.35 (s, 2H), 3.84-3.53 (m, 10H), 3.11-2.97 (m, 2H), 2.04-1.94 (m, 2H), 1.93-1.82 (m, 1H), 1.72-1.50 (m, 8H), 1.27 (s, 6H). LCMS [M+H] 539.5.

Compound 217

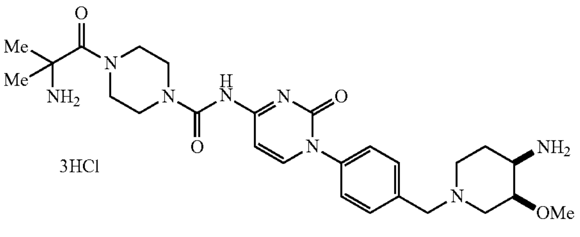

cis-4-(2-Amino-2-methylpropanoyl)-N-[1-(4-{[4-amino-3-methoxypiperidin-1-yl]methyl}phenyl)-2-oxo-1,2-dihydropyrimidin-4-yl]piperazine-1-carboxamide (racemate) hydrochloride salt Prepared in a similar fashion as Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and benzyl ((cis)-3-methoxypiperidin-4-yl) carbamate. $^1$H NMR (400 MHz, $D_2O$) δ 7.62 (d, 2H), 7.56-7.48 (m, 3H), 7.46-7.41 (m, 1H), 4.42-4.22 (m, 2H), 3.99-2.80 (m, 17H), 2.21-2.03 (m, 2H), 1.68 (s, 3H), 1.66 (s, 3H). LCMS [M+H] 527.6.

Compound 216

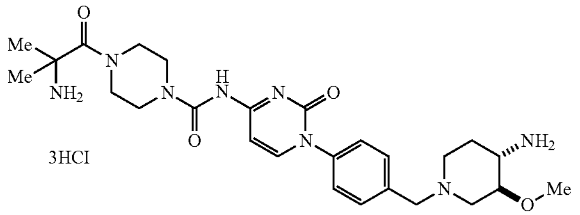

trans-4-(2-Amino-2-methylpropanoyl)-N-[1-(4-{[4-amino-3-methoxypiperidin-1-yl]methyl}phenyl)-2-oxo-1,2-dihydropyrimidin-4-yl]piperazine-1-carboxamide (racemate) hydrochloride salt Prepared in a similar fashion as Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and benzyl ((trans)-3-methoxypiperidin-4-yl)carbamate. $^1$H NMR (400 MHz, $D_2O$) δ 7.86 (d, 1H), 7.65 (d, 2H), 7.53 (d, 2H), 6.81 (d, 1H), 4.46 (s, 2H), 3.94-3.82 (m, 1H), 3.80-3.55 (m, 10H), 3.48-3.32 (m, 4H), 3.11-3.25 (m, 1H), 3.07-2.91 (m, 1H), 2.44-2.28 (m, 1H), 2.02-1.85 (m, 1H), 1.67 (s, 6H). LCMS [M+H] 527.6.

Compound 219

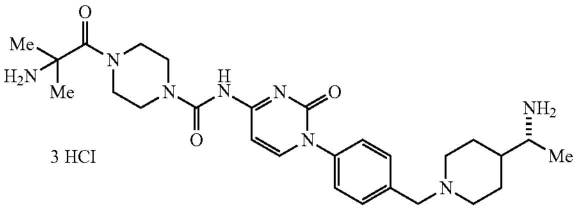

4-(2-Amino-2-methylpropanoyl)-N-{1-[4-({4-[(1R)-1-aminoethyl]piperidin-1-yl}methyl)phenyl]-2-oxo-1,2-dihydropyrimidin-4-yl}piperazine-1-carboxamide hydrochloride salt Prepared in a similar fashion as Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and benzyl (R)-(1-(piperidin-4-yl)ethyl) carbamate. $^1$H NMR (600 MHz, $D_2O$) δ 8.06-8.02 (m, 1H), 7.73-7.67 (m, 2H), 7.61-7.56 (m, 2H), 6.84 (d, 1H), 4.42 (s, 2H), 3.88-3.68 (m, 8H), 3.65 (d, 2H), 3.35-3.28 (m, 1H), 3.14-3.06 (m, 2H), 2.10-1.91 (m, 3H), 1.74 (s, 6H), 1.66-1.55 (m, 2H), 1.40-1.28 (m, 3H). LCMS [M+H] 525.4.

Compound 220

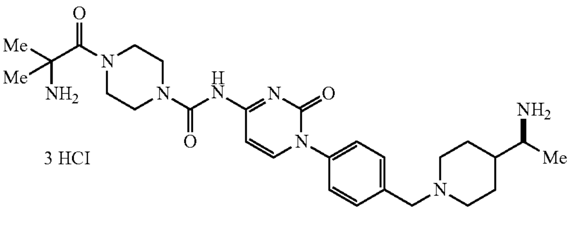

4-(2-Amino-2-methylpropanoyl)-N-{1-[4-({4-[(1S)-1-aminoethyl]piperidin-1-yl}methyl)phenyl]-2-oxo-1,2-dihydropyrimidin-4-yl}piperazine-1-carboxamide hydrochloride salt Prepared in a similar fashion as Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and benzyl (S)-(1-(piperidin-4-yl)ethyl) carbamate. $^1$H NMR (600 MHz, $D_2O$) δ 7.91 (d, 1H), 7.68 (d, 2H), 7.56 (d, 2H), 6.86 (d, 1H), 4.55-4.38 (m, 2H), 3.85-3.68 (m, 8H), 3.65 (d, 2H), 3.31 (quin, 1H), 3.09 (t, 2H), 2.05 (t, 2H), 2.00-1.89 (m, 1H), 1.75-1.71 (m, 6H), 1.65-1.54 (m, 2H), 1.39-1.26 (m, 3H). LCMS [M+H] 525.4.

Compound 221

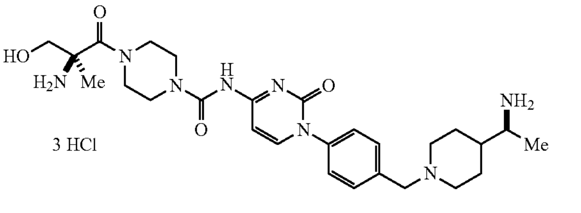

4-[(2S)-2-Amino-3-hydroxy-2-methylpropanoyl]-N-{1-[4-({4-[(1S)-1-aminoethyl]piperidin-1-yl}methyl)phenyl]-2-oxo-1,2-dihydropyrimidin-4-yl}piperazine-1-carboxamide hydrochloride salt Prepared in a similar fashion as Scheme C-2 from tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate and benzyl (S)-(1-(piperidin-4-yl)ethyl)carbamate. $^1$H NMR (400 MHz, $D_2O$) δ 7.84 (d, 1H), 7.62 (d, 2H), 7.51 (d, 2H), 6.81 (d, 1H), 4.36 (s, 2H), 4.11 (d, 1H), 3.85 (d, 1H), 3.79-3.54 (m, 10H), 3.31-3.20 (m, 1H), 3.04 (t, 2H), 2.07-1.95 (m, 2H), 1.95-1.83 (m, 1H), 1.63 (s, 3H), 1.61-1.47 (m, 2H), 1.24 (d, 3H). LCMS [M+H] 541.3.

Compound 222

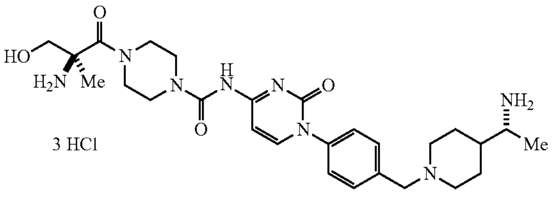

4-[(2S)-2-Amino-3-hydroxy-2-methylpropanoyl]-N-{1-[4-({4-[(1R)-1-aminoethyl]piperidin-1-yl}methyl)phenyl]-2-oxo-1,2-dihydropyrimidin-4-yl}piperazine-1-carboxamide hydrochloride salt Prepared in a similar fashion as Scheme C-2 tert-butyl (2R,4S)-2-(tert-butyl)-4-(4-((1-(4-formylphenyl)-2-oxo-1,2-dihydropyrimidin-4-yl)carbamoyl)piperazine-1-carbonyl)-4-methyloxazolidine-3-carboxylate and benzyl (R)-(1-(piperidin-4-yl)ethyl)carbamate. $^1$H NMR (400 MHz, $D_2O$) δ 7.85 (d, 1H), 7.62 (d, 2H), 7.51 (d, 2H), 6.81 (d, 1H), 4.35 (s, 2H), 4.10 (d, 1H), 3.85 (d, 1H), 3.79-3.53 (m, 10H), 3.30-3.22 (m, 1H), 3.04 (t, 2H), 2.06-1.82 (m, 3H), 1.63 (s, 3H), 1.61-1.45 (m, 2H), 1.24 (d, 3H). LCMS [M+H] 541.3.

Compound 226

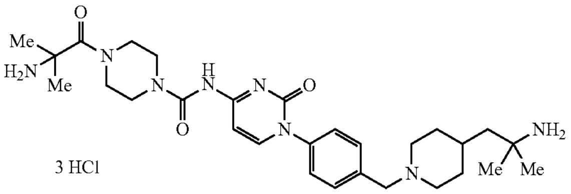

4-(2-Amino-2-methylpropanoyl)-N-[1-(4-{[4-(2-amino-2-methylpropyl)piperidin-1-yl]methyl}phenyl)-2-oxo-1,2-dihydropyrimidin-4-yl]piperazine-1-carboxamide hydrochloride salt Prepared in a similar fashion as Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and benzyl (2-methyl-1-(piperidin-4-yl)propan-2-yl)carbamate. $^1$H NMR (400 MHz, $D_2O$) δ 7.83 (d, 1H), 7.61 (d, 2H), 7.50 (d, 2H), 6.88-6.75 (m, 1H), 4.32 (s, 2H), 3.81-3.61 (m, 8H), 3.52-3.41 (m, 2H), 3.09-2.94 (m, 2H), 2.04-1.93 (m, 2H), 1.84-1.40 (m, 11H), 1.32 (s, 6H). LCMS [M+H] 553.6.

Compound 322

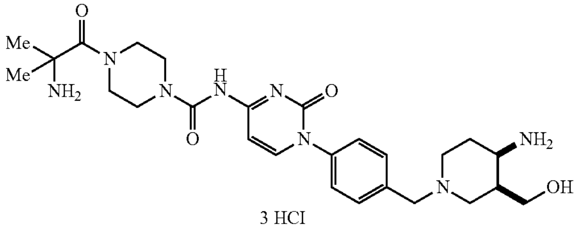

cis-4-(2-Amino-2-methylpropanoyl)-N-(1-(4-((4-amino-3-(hydroxymethyl)piperidin-1-yl)methyl)phenyl)-2-oxo-1,2-dihydropyrimidin-4-yl)piperazine-1-carboxamide hydrochloride salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and benzyl (cis-3-(hydroxymethyl)piperidin-4-yl)carbamate. $^1$H NMR (400 MHz, $D_2O$) δ 7.88 (d, 1H), 7.62-7.59 (m, 2H), 7.48 (d, 2H), 6.75 (d, 1H), 4.41-4.39 (m, 2H), 4.27 (d, 1H), 3.84-3.81 (m, 2H), 3.78-3.74 (m, 4H), 3.67-3.55 (m, 6H), 3.44 (m, 1H), 1.59 (s, 6H), 3.24-3.17 (m, 2H), 2.17 (s, 2H), 1.63 (s, 6H). LCMS [M+H] 527.6.

Compound 293

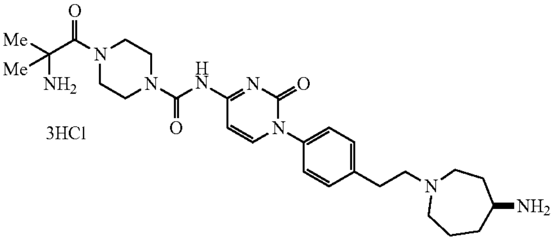

(S)-4-(2-Amino-2-methylpropanoyl)-N-(1-(4-(2-(4-aminoazepan-1-yl)ethyl)phenyl)-2-oxo-1,2-dihydropyrimidin-4-yl)piperazine-1-carboxamide hydrochloride salt Prepared in a similar fashion as Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and benzyl (S)-azepan-4-ylcarbamate. $^1$H NMR (400 MHz, $D_2O$) δ 7.88 (d, 1H), 7.51-7.45 (m, 2H), 7.45-7.39 (m, 2H), 6.83 (d, 1H), 3.83-3.66 (m, 9H), 3.64-3.46 (m, 5H), 3.45-3.13 (m, 4H), 2.44-2.21 (m, 2H), 2.18-1.97 (m, 2H), 1.90-1.76 (m, 1H), 1.72 (s, 6H). LCMS [M+H] 525.4. e.e.>99% as determined on a Chiralpak AD-H (25x0.46 cm, 5 μm); mobile phase: n-hexane/EtOH:MeOH, 1:1+0.1% isopropylamine, 10/90% v/v; flow rate:1 mL/min; retention time: 27.1 min.

Compound 294

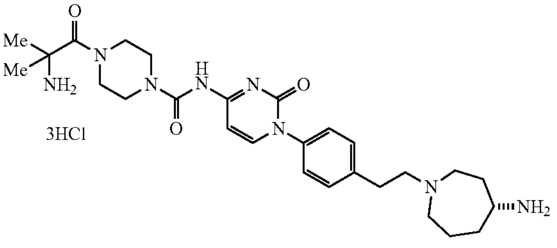

(R)-4-(2-Amino-2-methylpropanoyl)-N-(1-(4-(2-(4-aminoazepan-1-yl)ethyl)phenyl)-2-oxo-1,2-dihydropyrimidin-4-yl)piperazine-1-carboxamide hydrochloride salt Prepared in a similar fashion as Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl) propan-2-yl)carbamate and benzyl (R)-azepan-4-ylcarbamate. $^1H$ NMR (400 MHz, $D_2O$) δ 7.88 (d, 1H), 7.51-7.45 (m, 2H), 7.45-7.39 (m, 2H), 6.83 (d, 1H), 3.83-3.66 (m, 9H), 3.64-3.46 (m, 5H), 3.45-3.13 (m, 4H), 2.44-2.21 (m, 2H), 2.18-1.97 (m, 2H), 1.90-1.76 (m, 1H), 1.72 (s, 6H). LCMS [M+H] 525.4. e.e.=100% as determined on a Chiralpak AD-H (25x0.46 cm, 5 μm); mobile phase: n-hexane/EtOH:MeOH, 1:1+0.1% isopropylamine, 10/90% v/v; flow rate:1 mL/min; retention time: 30.3 min.

Compound 119

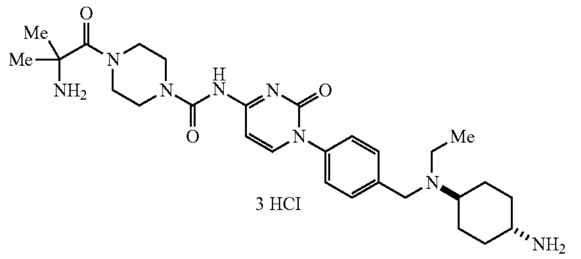

4-(2-Amino-2-methylpropanoyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt Step 1: tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)(ethyl)amino)cyclohexyl)carbamate $NaBH_3CN$ (96 mg, 1.53 mmol) was added to a mixture of tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)carbamate (488 mg, 0.69 mmol) and acetaldehyde (0.5 mL) in dry MeOH (8 mL), and the mixture was stirred at rt for 18 h. The mixture was concentrated to about 2 mL, added to 2 M aq. $K_2CO_3$ (50 mL), and extracted with DCM (3x50 mL). The extracts were dried over $Na_2SO_4$, decanted, concentrated, and the residue was purified by flash chromatography (MeOH/EtOAc/Hexanes) to afford the title compound as a white solid (365 mg, 0.494 mmol).

Step 2: 4-(2-amino-2-methylpropanoyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt A mixture of tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)(ethyl)amino)cyclohexyl)carbamate (365 mg, 0.49 mmol) and 2 MHCl in MeOH (20 mL, 40 mmol) was stirred at rt for 18 h and concentrated. The residue was purified by flash chromatography (DCM/MeOH/$NH_4OH$). Product fractions were concentrated to dryness, converted to the HCl salt with 2 M HCl in MeOH, and concentrated to dryness to afford the title compound (264 mg, 0.407 mmol) as a white solid. $^1H$ NMR (500 MHz, $D_2O$) δ 7.97 (d, 1H), 7.63 (d, 2H), 7.52 (d, 2H), 6.78 (d, 1H), 4.50 (d, 1H), 4.32 (d, 1H), 3.59-3.82 (m, 8H), 3.35-3.45 (m, 1H), 3.14-3.33 (m, 3H), 2.11-2.27 (m, 4H), 1.71-1.89 (m, 2H), 1.67 (s, 6H), 1.43-1.57 (m, 2H), 1.25 (t, 3H). LCMS [M+H] 539.4.

Scheme C-3

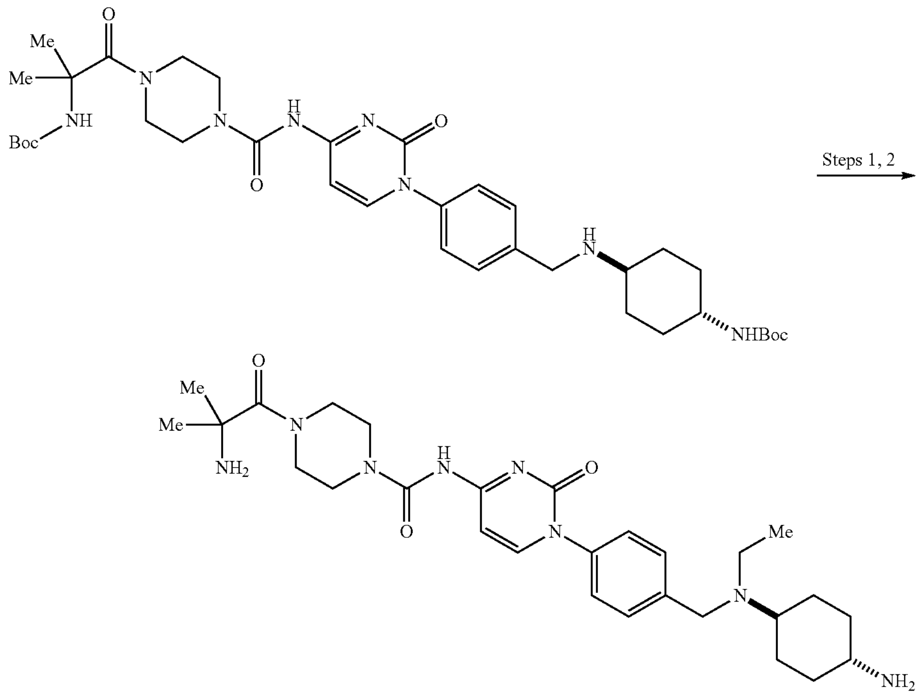

Reagents: 1) $CH_3CHO$, $NaBH_3CN$, MeOH, rt, 18 h 2) 2M HCl in MeOH, rt, 18 h.

Alternatively, 4-(2-Amino-2-methylpropanoyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt may be prepared according to Scheme C-4.

Scheme C-4

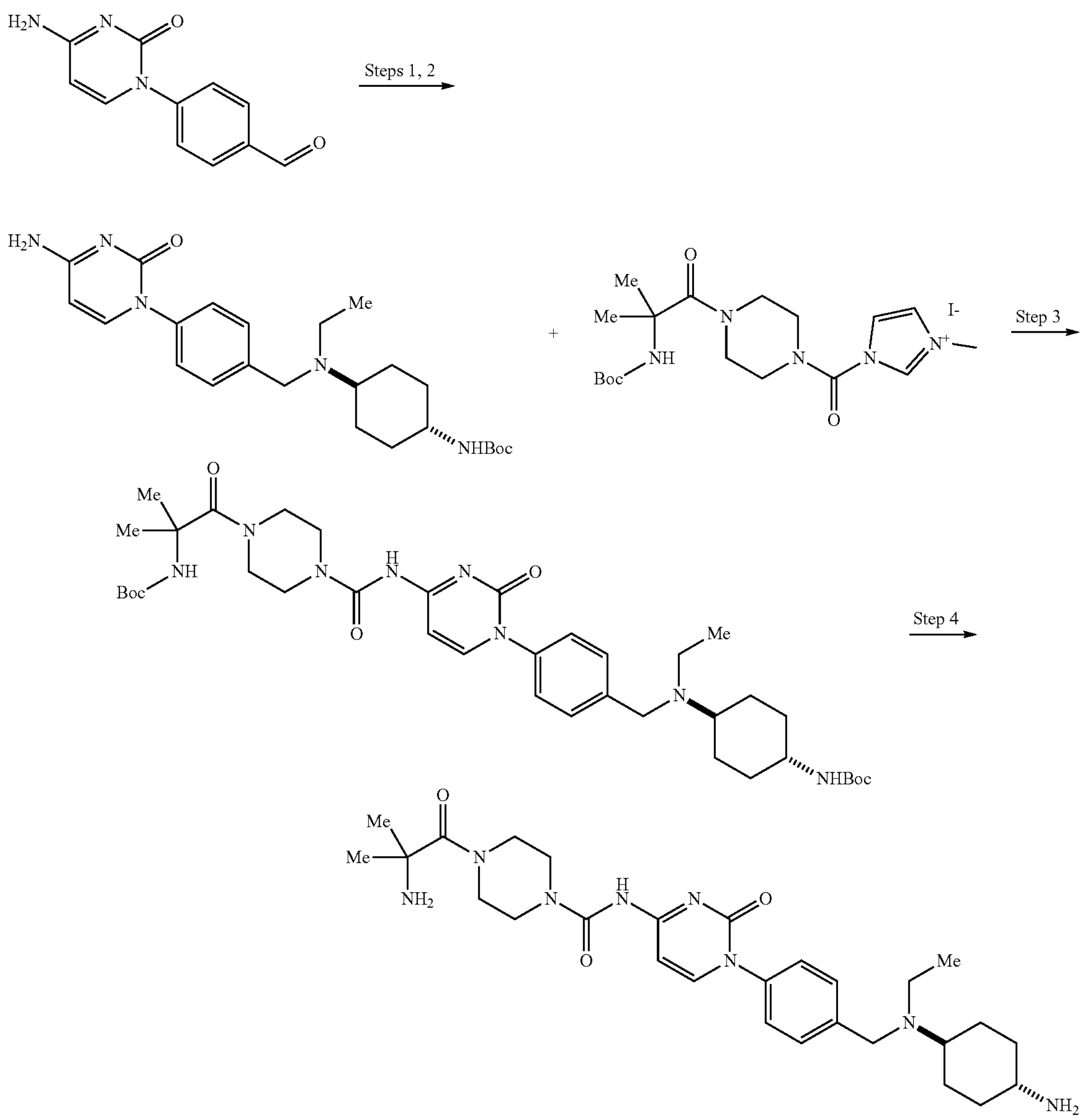

Reagents: Step 1) N-Boc-trans-1,4-cyclohexanediamine, $NaBH_4$, MeOH, rt, 22 h 2) $CH_3CHO$, $NaBH_3CN$, MeOH, rt, 44 h 3) $CH_3CN$, reflux, 18 h 4) 2M HCl in MeOH, rt, 18 h.

Step 1: tert-butyl (trans-4-((4-(4-amino-2-oxopyrimidin-1(2H)-yl)benzyl)amino)cyclohexyl)carbamate A mixture of 4-(4-amino-2-oxopyrimidin-1(2H)-yl)benzaldehyde (1.38 g, 6.38 mmol) and N-Boc-trans-1,4-cyclohexanediamine (1.51 g, 7.04 mmol) in dry MeOH (75 mL) was stirred at rt for 30 min. The mixture was concentrated to dryness and resuspended in dry MeOH (75 mL). $NaBH_4$ (750 mg, 19.8 mmol) was added portionwise, and the mixture was stirred at rt for 22 hours. It was concentrated to about 10 mL total volume and $H_2O$ (100 mL) was added. The precipitate was collected by vacuum filtration to provide the title compound (1.21 g, 2.92 mmol) as a white solid.

Step 2: tert-butyl (trans-4-((4-(4-amino-2-oxopyrimidin-1(2H)-yl)benzyl)(ethyl)amino)cyclohexyl) carbamate $NaBH_3CN$ (1.03 g, 16.4 mmol) was added to a mixture of tert-butyl (trans-4-((4-(4-amino-2-oxopyrimidin-1(2H)-yl) benzyl)amino)cyclohexyl)carbamate (3.23 g, 7.81 mmol) and acetaldehyde (1 mL) in dry MeOH (100 mL), and the mixture was stirred at rt for 44 h. It was concentrated to 25 mL total volume, and 1 M NaOH (150 mL) was added. The precipitate was collected by vacuum filtration to afford the title compound (3.55 g) as a white solid.

Step 3: tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)(ethyl)amino)cyclohexyl)carbamate A mixture of tert-butyl (trans-4-((4-(4-amino-2-oxopyrimidin-1(2H)-yl)benzyl)(ethyl)amino)cyclohexyl)carbamate (674 mg, 1.53 mmol) and 1-(4-(2-((tert-butoxycarbonyl)amino)-2-methylpropanoyl)piperazine-1-carbonyl)-3-methyl-1H-imidazol-3-ium iodide (1.01 g, 1.99 mmol) in dry $CH_3CN$ (20 mL) was stirred at reflux for 18 h. The reaction mixture was cooled and concentrated in vacuo, EtOAc (75 mL) added and the organic layer washed with sat. aq. $NaHCO_3$ (2×50 mL), brine (50 mL), dried over $Na_2SO_4$, decanted and concentrated. The residue was purified by flash chromatography (MeOH/EtOAc/Hexanes) to afford the title compound (726 mg) as a white solid.

Step 4: 4-(2-amino-2-methylpropanoyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt A mixture of tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)(ethyl)amino)cyclohexyl)carbamate (726 mg, 0.98 mmol) and 2 M HCl in MeOH (25 mL, 50 mmol) was stirred at rt for 18 h. The reaction mixture was concentrated and purified by flash chromatography ($DCM/MeOH/NH_4OH$) followed by reverse-phase HPLC ($CH_3CN/H_2O/TFA$). Product fractions were concentrated to dryness, converted to the HCl salt with 2M HCl in MeOH, and again concentrated to dryness to afford the title compound (437 mg) as a white solid. $^1H$ NMR (500 MHz, $D_2O$) δ 7.89 (d, 1H), 7.54 (d, 2H), 7.43 (d, 2H), 6.69 (d, 1H), 4.41 (d, 1H), 4.23 (d, 1H), 3.48-3.76 (m, 8H), 3.26-3.37 (m, 1H), 3.16-3.24 (m, 1H), 3.06-3.16 (m, 2H), 2.02-2.19 (m, 4H), 1.61-1.81 (m, 2H), 1.58 (s, 6H), 1.34-1.48 (m, 2H), 1.16 (t, 3H). LCMS [M+H] 539.4.

Compound 118

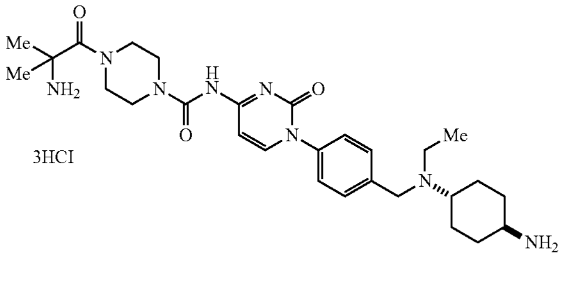

trans-4-(2-Amino-2-methylpropanoyl)-N-(1-(4-(((4-aminocyclohexyl)(methyl)amino)methyl)phenyl)-2-oxo-1,2-dihydropyrimidin-4-yl)piperazine-1-carboxamide hydrochloride salt Prepared in a similar fashion as Scheme C-3 using tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)carbamate and formaldehyde. $^1H$ NMR (400 MHz, $D_2O$) mixture of rotamers, δ 7.80 (d, 1H), 7.53 (d, 2H), 7.42 (d, 2H), 6.71 (d, 1H), 4.45 (d, 1H), 4.16 (d, 1H), 3.57-3.70 (m, 8H), 3.33-3.27 (m, 1H), 3.15-3.09 (m, 1H), 2.63 (s, 3H), 2.18-2.07 (m, 4H), 1.74-1.69, (m, 2H), 1.58 (s, 6H), 1.46-1.37 (m, 2H). LCMS [M+H] 525.2.

Compound 279

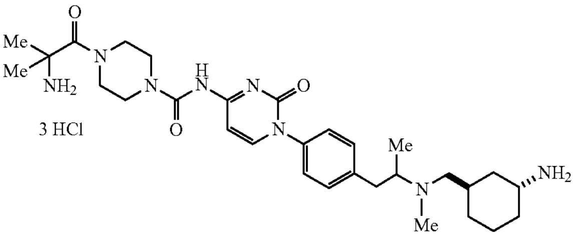

trans-4-(2-Amino-2-methylpropanoyl)-N-(1-(4-(2-(((3-aminocyclohexyl)methyl)(methyl)amino)propyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(2-((((trans)-3-((tert-butoxycarbonyl)amino)cyclohexyl)methyl)amino)propyl)phenyl)-2-oxo-1,2-dihydropyrimidin-4-yl)carbamoyl)piperazin-1-yl)-2-methyl-1-oxopropan-2-yl)carbamate and formaldehyde. $^1H$ NMR (400 MHz, $D_2O$) mixture of rotamers, δ 7.78 (d, 1H), 7.36-7.29 (m, 4H), 6.70 (d, 1H), 3.63-3.58 (m, 8H), 3.45-3.38 (m, 1H), 3.20-3.10 (m, 3H), 3.00-2.97 (m, 3H), 2.89-2.75 (m, 3H), 2.22-2.15 (m, 1H), 1.90-1.40 (m, 12H), 1.31-1.25 (m, 1H), 1.15 (t, 3H). LCMS [M+H] 567.3.

Compound 280

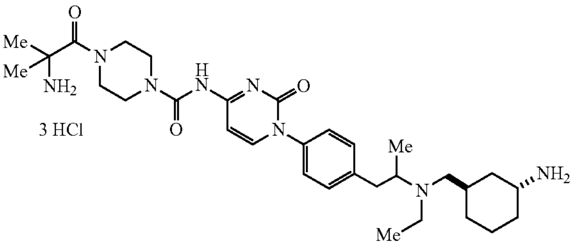

trans-4-(2-Amino-2-methylpropanoyl)-N-(1-(4-(2-(((3-aminocyclohexyl)methyl)(ethyl)amino)propyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(2-((((trans)-3-((tert-butoxycarbonyl)amino)cyclohexyl)methyl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. $^1H$ NMR (400 MHz, $D_2O$) mixture of rotamers, δ 7.85 (d, 1H), 7.37-7.10 (m, 4H), 6.70 (d, 1H), 3.75-3.60 (m, 8H), 3.49-3.36 (m, 1H), 3.36-3.11 (m, 4H), 3.09-2.76 (m, 3H), 2.31-2.11 (m, 1H), 1.76-1.66 (m, 4H), 1.60 (s, 6H), 1.55-1.50 (m, 3H), 1.32-1.23 (m, 3H), 1.50 (t, 3H). LCMS [M+H] 581.3.

Compound 281

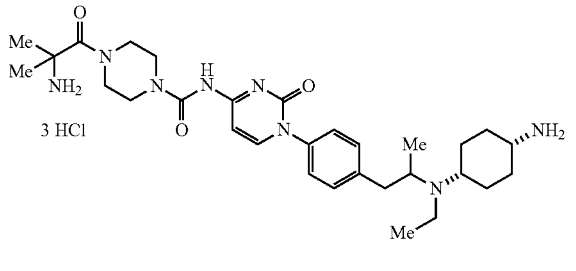

4-(2-Amino-2-methylpropanoyl)-N-(1-(4-(2-(((cis)-4-aminocyclohexyl)(ethyl)amino)propyl)phenyl)-2-oxo-1,2-dihydropyrimidin-4-yl)piperazine-1-carboxamide hydrochloride salt Prepared in a similar fashion as Scheme C-3 from tert-butyl (cis-4-((1-(4-(4-(4-(2-((tert-butoxycarbonyl)amino)-2-methylpropanoyl)piperazine-1-carboxamido)-2-oxopyrimidin-1(2H)-yl)phenyl)propan-2-yl)amino)cyclohexyl) carbamate and acetaldehyde. $^1$H NMR (400 MHz, $D_2O$) Mixture of rotamers, δ 8.43 (d, 1H), 8.08-8.02 (m, 4H), 7.34 (d, 1H), 4.54 (m, 2H), 4.33-4.29 (m, 8H), 4.20-3.79 (m, 4H), 3.63-3.57 (m, 1H), 2.70-2.67 (m, 4H), 2.56-2.46 (m, 4H), 2.32 (s, 6H), 2.15-1.85 (m, 6H). LCMS [M+H] 567.3.

Compound 281

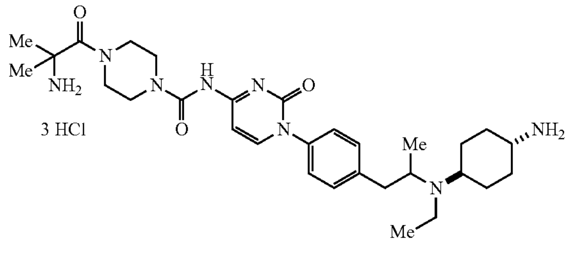

4-(2-Amino-2-methylpropanoyl)-N-(1-(4-(2-(((trans)-4-aminocyclohexyl)(ethyl)amino)propyl)phenyl)-2-oxo-1,2-dihydropyrimidin-4-yl)piperazine-1-carboxamide hydrochloride salt Prepared in a similar fashion as Scheme C-3 from tert-butyl (trans-4-((1-(4-(4-(4-(2-((tert-butoxycarbonyl)amino)-2-methylpropanoyl)piperazine-1-carboxamido)-2-oxopyrimidin-1(2H)-yl)phenyl)propan-2-yl)amino)cyclohexyl) carbamate and acetaldehyde. LCMS [M+H] 567.4.

Compound 111

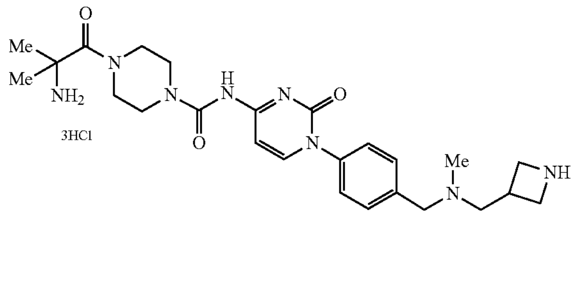

4-(2-Amino-2-methylpropanoyl)-N-(1-(4-(((azetidin-3-ylmethyl)(methyl)amino)methyl)phenyl)-2-oxo-1,2-dihydropyrimidin-4-yl)piperazine-1-carboxamide hydrochloride salt Prepared in a similar fashion to Scheme C-3 from tert-butyl 3-(((4-(4-(4-(2-((tert-butoxycarbonyl)amino)-2-methylpropanoyl)piperazine-1-carboxamido)-2-oxopyrimidin-1(2H)-yl)benzyl)amino)methyl)azetidine-1-carboxylate and formaldehyde. $^1$H NMR (400 MHz, $D_2O$) mixture of rotamers, δ 7.80 (d, 1H), 7.53 (d, 2H), 7.43 (d, 2H), 6.71 (d, 1H), 4.39-4.22 (m, 2H), 4.20-4.00 (m, 2H), 3.95-3.85 (m, 2H), 3.70-3.50 (m, 9H), 3.42-3.41 (m, 2H), 2.66 (s, 3H), 1.57 (s, 6H). LCMS [M+H] 497.1.

Compound 301

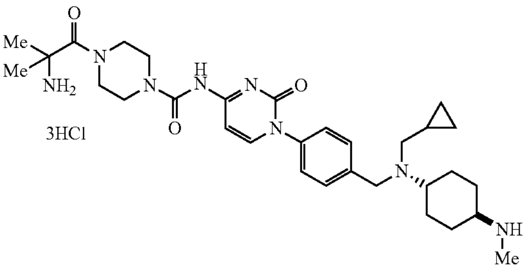

4-(2-Amino-2-methylpropanoyl)-N-(1-(4-(((cyclopropylmethyl)(trans-4-(methylamino)cyclohexyl)amino)methyl)phenyl)-2-oxo-1,2-dihydropyrimidin-4-yl)piperazine-1-carboxamide hydrochloride salt Prepared in a similar fashion as a similar fashion to Scheme C-3 from tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)(methyl)carbamate and cyclopropanecarbaldehyde. $^1$H NMR (500 MHz, $D_2O$) δ 7.98 (d, 1H), 7.73-7.67 (m, 2H), 7.57 (d, 2H), 6.85 (d, 1H), 4.53 (q, 2H), 3.87-3.63 (m, 8H), 3.58 (t, 1H), 3.31-3.02 (m, 3H), 2.75-2.71 (m, 3H), 2.37-1.76 (m, 6H), 1.72 (s, 6H), 1.61-1.48 (m, 2H), 0.72 (d, 1H), 0.36-0.22 (m, 4H).

Compound 305

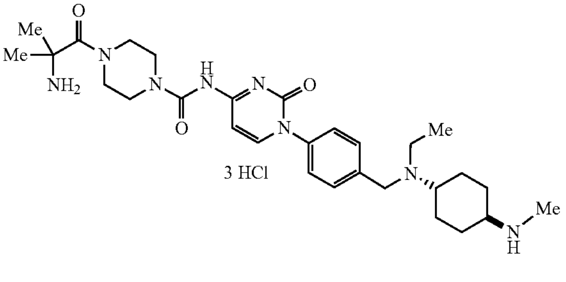

4-(2-Amino-2-methylpropanoyl)-N-(1-(4-((ethyl(trans-4-(methylamino)cyclohexyl)amino)methyl)phenyl)-2-oxo-1,2-dihydropyrimidin-4-yl)piperazine-1-carboxamide hydrochloride salt Prepared in a similar fashion as a similar fashion to Scheme C-3 from tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)(methyl)carbamate and acetaldehyde. $^1$H NMR (500 MHz, $D_2O$) δ 8.14 (d, 1H), 7.78-7.72 (m, 2H), 7.65 (d, 2H), 6.89 (d, 1H), 4.79 (m under $D_2O$, 2H) 3.89-3.77 (m, 8H), 3.60-3.16 (m, 4H), 2.83-2.75 (m, 3H), 2.41-1.80 (m, 6H), 1.78 (s, 6H), 1.69-1.47 (m, 2H), 1.37 (t, 3H). LCMS [M+H] 553.4.

Compound 113

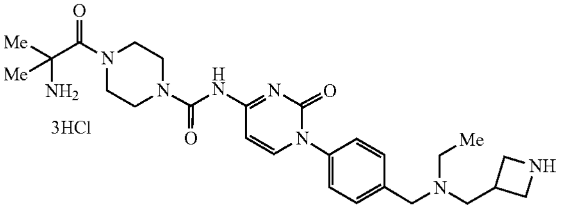

4-(2-Amino-2-methylpropanoyl)-N-(1-(4-(((azetidin-3-ylmethyl)(ethyl)amino)methyl)phenyl)-2-oxo-1,2-dihydropyrimidin-4-yl)piperazine-1-carboxamide hydrochloride salt Prepared in a similar fashion as Scheme C-3 from tert-butyl 3-(((4-(4-(4-(2-((tert-butoxycarbonyl)amino)-2-methylpropanoyl)piperazine-1-carboxamido)-2-oxopyrimidin-1(2H)-yl)benzyl)amino)methyl)azetidine-1-carboxylate and acetaldehyde. $^1$H NMR (400 MHz, $D_2O$) Mixture of rotamers, δ 7.74 (d, 1H), 7.52 (d, 2H), 7.42 (d, 2H), 6.72 (d, 1H), 4.35-4.20 (m, 2H), 4.19-4.08 (m, 2H), 3.91-3.81 (m, 2H), 3.65-3.55 (m, 8H), 3.45-3.35 (m, 3H), 3.11-3.05 (m, 2H), 1.57 (s, 6H), 1.21 (t, 3H). LCMS [M+H] 511.1.

Compound 115

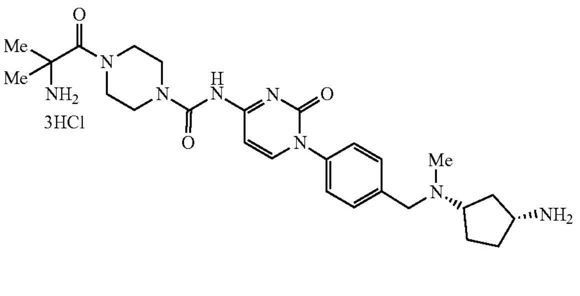

4-(2-Amino-2-methylpropanoyl)-N-(1-(4-((((1S,3R)-3-aminocyclopentyl)(methyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-((((1S,3R)-3-((tert-butoxycarbonyl)amino)cyclopentyl)amino)methyl)phenyl)-2-oxo-1,2-dihydropyrimidin-4-yl)carbamoyl)piperazin-1-yl)-2-methyl-1-oxopropan-2-yl)carbamate and formalin. $^1$H NMR (400 Mz, $D_2O$) Mixture of rotamers, δ 7.90 (d, 1H), 7.58 (d, 2H), 7.47 (d, 2H), 6.72 (d, 1H), 4.55 (d, 1H), 4.16 (d, 1H), 3.80-3.78 (m, 1H), 3.76-3.51 (m, 8H), 2.68 (s, 3H), 2.62-2.59 (m, 1H), 2.29-2.27 (m, 1H), 2.16-2.11 (m, 1H), 2.10-2.01 (m, 4H), 1.61 (s, 6H). LCMS [M+H] 511.0.

Compound 16

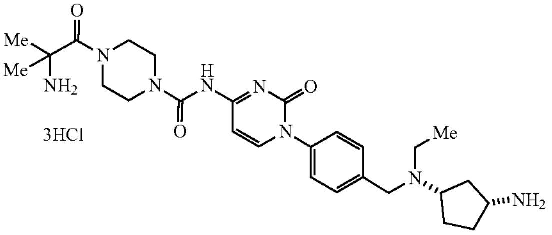

4-(2-Amino-2-methylpropanoyl)-N-(1-(4-((((1S,3R)-3-aminocyclopentyl)(ethyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-((((1S,3R)-3-((tert-butoxycarbonyl)amino)cyclopentyl)amino)methyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$) Mixture of rotamers, δ 7.74 (d, 1H), 7.54 (d, 2H), 7.42 (d, 2H), 6.73 (d, 1H), 4.45-4.2 (m, 2H), 3.92-3.81 (m, 1H), 3.68-3.52 (m, 8H), 3.19-3.06 (m, 3H), 2.60-2.57 (m, 1H), 2.25-1.7 (m, 5H), 1.58 (s, 6H), 1.31-1.18 (m, 3H). LCMS [M+H] 525.2.

Compound 121

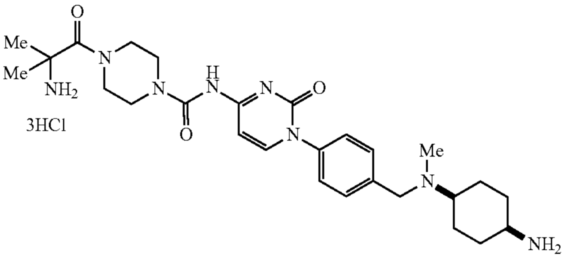

cis-4-(2-Amino-2-methylpropanoyl)-N-(1-(4-(((4-aminocyclohexyl)(methyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((cis-4-((tert-butoxycarbonyl)amino)cyclohexyl)amino)methyl)phenyl)-2-oxo-1,2-dihydropyrimidin-4-yl)carbamoyl)piperazin-1-yl)-2-methyl-1-oxopropan-2-yl)carbamate and formalin. $^1$H NMR (400 MHz, $D_2O$) Mixture of rotamers, δ 7.76 (d, 1H), 7.53 (d, 2H), 7.41 (d, 2H), 6.71 (d, 1H), 4.44 (d, 1H), 4.21 (d, 1H), 3.68-3.515 (m, 8H), 3.51-3.49 (m, 1H), 3.41-3.32 (m, 1H), 2.65 (s, 3H), 2.15-1.93 (m, 4H), 1.82-1.72 (m, 4H), 1.57 (s, 6H). LCMS [(M+2H)/2] 263.3.

Compound 122

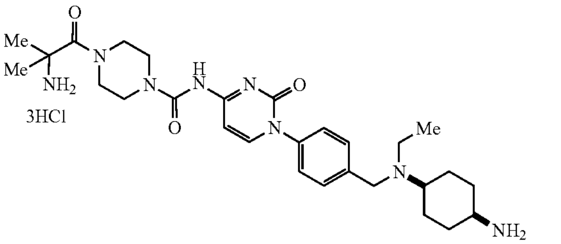

cis-4-(2-Amino-2-methylpropanoyl)-N-(1-(4-(((4-aminocyclohexyl)(ethyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((cis-4-((tert-butoxycarbonyl)amino)cyclohexyl)amino)methyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$) Mixture of rotamers, δ 7.78 (d, 1H), 7.53 (d, 2H), 7.41 (d, 2H), 6.70 (d, 1H), 4.42 (d, 1H), 3.68-3.45 (m, 10H), 3.49-3.41 (m, 1H), 3.39-3.30 (m, 1H), 3.28-3.05 (m, 1H), 2.10-1.90 (m, 4H), 1.88-1.72 (m, 4H), 1.57 (s, 6H), 1.16 (t, 3H). LCMS [(M+2H)/2]270.3

Compound 124

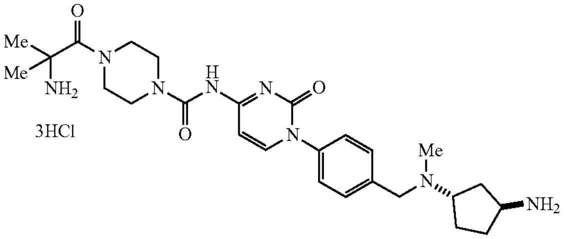

4-(2-Amino-2-methylpropanoyl)-N-(1-(4-((((1S,3S)-3-aminocyclopentyl)(methyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-((((1S,3S)-3-((tert-butoxycarbonyl)amino)cyclopentyl)amino)methyl)phenyl)-2-oxo-1,2-dihydropyrimidin-4-yl)carbamoyl)piperazin-1-yl)-2-methyl-1-oxopropan-2-yl)carbamate and formalin. $^1$H NMR (400 MHz, $D_2O$) mixture of rotamers, δ 7.84 (d, 1H), 7.59 (d, 2H), 7.48 (d, 2H), 6.76 (d, 1H), 4.55-4.50 (m, 1H), 4.22-4.15 (m, 1H), 3.95-3.80 (m, 2H), 3.65-3.55 (m, 8H), 2.69 (s, 3H), 2.45-2.20 (m, 4H), 1.95-1.64 (m, 2H), 1.63 (s, 6H). LCMS [M+H] 511.

Compound 125

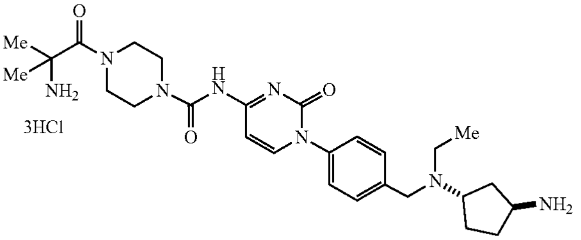

4-(2-Amino-2-methylpropanoyl)-N-(1-(4-((((1S,3S)-3-aminocyclopentyl)(ethyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-((((1S,3S)-3-((tert-butoxycarbonyl)amino)cyclopentyl)amino)methyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$) mixture of rotamers, δ 7.80 (d, 1H), 7.56 (d, 2H), 7.44 (d, 2H), 6.72 (d, 1H), 4.45-4.38 (m, 1H), 4.35-4.25 (m, 1H), 4.00-3.94 (m, 1H), 3.85-3.75 (m, 1H), 3.70-3.55 (m, 8H), 3.13-3.05 (m, 2H), 2.38-2.15 (m, 4H), 1.90-1.70 (m, 1H), 1.68-1.58 (m, 1H), 1.59 (s, 6H), 1.23-1.17 (m, 3H). LCMS [(M+2H)/2] 263.2.

Compound 127

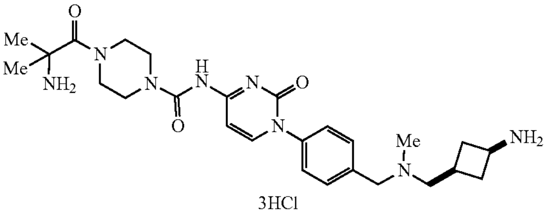

4-(2-Amino-2-methylpropanoyl)-N-(1-(4-(((((cis)-3-aminocyclobutyl)methyl)(methyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((((cis)-3-((tert-butoxycarbonyl)amino)cyclobutyl)methyl)amino)methyl)phenyl)-2-oxo-1,2-dihydropyrimidin-4-yl)carbamoyl)piperazin-1-yl)-2-methyl-1-oxopropan-2-yl)carbamate and formalin. $^1$H NMR (400 MHz, $D_2O$) mixture of rotamers, δ 7.84 (d, 1H), 7.52 (d, 2H), 7.42 (d, 2H), 6.69 (d, 1H), 4.32 (d, 1H), 4.19 (d, 1H), 3.68-3.55 (m, 8H), 3.30-3.21 (m, 2H), 2.66 (s, 3H), 2.60-2.2.40 (m, 4H), 1.92-1.75 (m, 2H), 1.79 (s, 6H). LCMS [(M+2H)/2] 256.1.

Compound 128

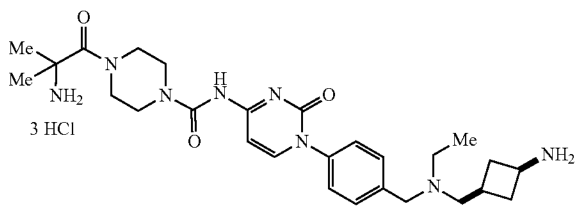

4-(2-Amino-2-methylpropanoyl)-N-(1-(4-(((((cis)-3-aminocyclobutyl)methyl)(ethyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((((cis)-3-((tert-butoxycarbonyl)amino)cyclobutyl)methyl)amino)methyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$) mixture of rotamers, δ 7.81 (d, 1H), 7.52 (d, 2H), 7.42 (d, 2H), 6.70 (d, 1H), 4.32-4.22 (m, 2H), 3.76-3.55 (m, 8H), 3.17 (t, 2H), 3.08 (q, 2H) 2.52-2.43 (m, 4H), 1.86-1.75 (m, 2H), 1.56 (s, 6H)), 1.27 (t, 3H). LCMS [(M+2H)/2] 263.2.

Compound 129

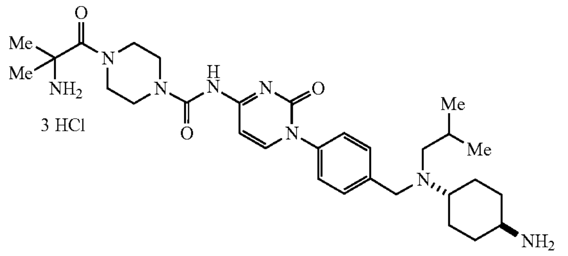

4-(2-Amino-2-methylpropanoyl)-N-(1-(4-(((trans-4-aminocyclohexyl)(isobutyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((trans-4-((tert-butoxycarbonyl)amino)cyclohexyl)amino)methyl)phenyl)-2-oxo-1,2-dihydropyrimidin-4-yl)carbamoyl)piperazin-1-yl)-2-methyl-1-oxopropan-2-yl)carbamate and isobutyraldehyde. $^1$H NMR (500 MHz, $D_2O$) δ 7.95 (d, 1H), 7.74 (d, 2H), 7.59 (d, 2H), 6.87 (d, 1H), 4.57 (d, 1H), 4.45 (d, 1H), 3.86-3.71 (m, 8H), 3.46 (t, 1H), 3.29 (t, 1H), 3.22-3.15 (m, 1H), 3.05-2.99 (m, 1H), 2.41-2.16 (m, 4H), 1.94-1.83 (m, 3H), 1.75 (s, 6H), 1.65-1.49 (m, 2H), 0.98 (d, 3H), 0.86 (d, 3H). LCMS [M+H] 567.2.

Compound 130

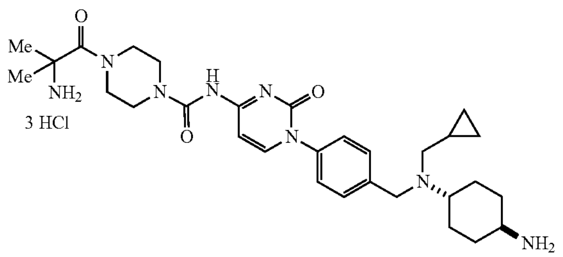

4-(2-Amino-2-methylpropanoyl)-N-(1-(4-(((trans-4-aminocyclohexyl)(cyclopropylmethyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((trans-4-((tert-butoxycarbonyl)amino)cyclohexyl)amino)methyl)phenyl)-2-oxo-1,2-dihydropyrimidin-4-yl)carbamoyl)piperazin-1-yl)-2-methyl-1-oxopropan-2-yl)carbamate and cyclopropanecarbaldehyde. $^1$H NMR (500 MHz, $D_2O$) δ 8.01 (d, 1H), 7.72 (d, 2H), 7.59 (d, 2H), 6.87 (d, 1H), 4.54 (q, 2H), 3.85-3.70 (m, 8H), 3.60 (t, 1H), 3.32-3.22 (m, 2H), 3.11-3.04 (m, 1H), 2.36-2.17 (m, 4H), 1.96-1.79 (m, 2H), 1.74 (s, 6H), 1.64-1.50 (m, 2H), 1.08-1.02 (m, 1H), 0.74 (d, 2H), 0.39-0.26 (m, 2H). LCMS [M+H] 565.3.

Compound 131

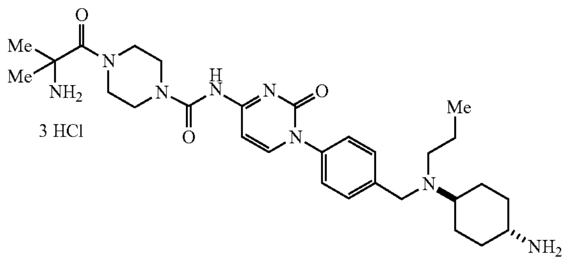

4-(2-Amino-2-methylpropanoyl)-N-(1-(4-(((trans-4-aminocyclohexyl)(propyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((trans-4-((tert-butoxycarbonyl)amino)cyclohexyl)amino)methyl)phenyl)-2-oxo-1,2-dihydropyrimidin-4-yl)carbamoyl)piperazin-1-yl)-2-methyl-1-oxopropan-2-yl)carbamate and propionaldehyde. $^1$H NMR (500 MHz, $D_2O$) δ 8.00 (d, 1H), 7.71 (d, 2H), 7.60 (d, 2H), 6.87 (d, 1H), 4.58 (d, 1H), 4.40 (d, 1H), 3.85-3.69 (m, 8H), 3.47 (t, 1H), 3.33-3.19 (m, 2H), 3.18-3.07 (m, 1H), 2.37-2.21 (m, 4H), 1.97-1.81 (m, 2H), 1.75 (s, 6H), 1.71-1.50 (m, 4H), 0.92 (t, 3H). LCMS [M+H] 553.3.

Compound 348

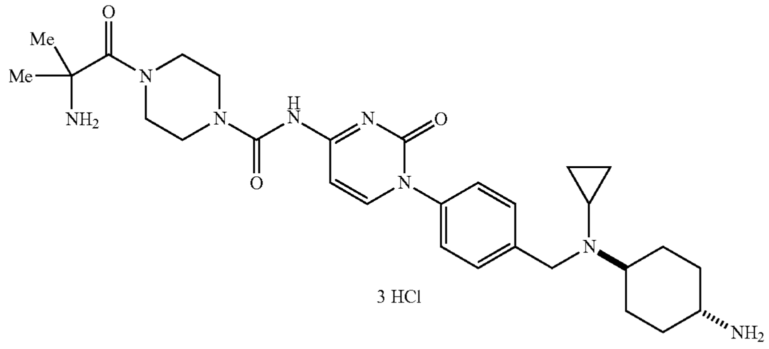

4-(2-Amino-2-methylpropanoyl)-N-(1-(4-(((trans-4-aminocyclohexyl)(cyclopropyl)amino)methyl)phenyl)-2-oxo-1,2-dihydropyrimidin-4-yl)piperazine-1-carboxamide hydrochloride salt Prepared in a similar fashion as Scheme C-3 from tert-butyl (1-(4-((1-(4-(((trans-4-((tert-butoxycarbonyl)amino) cyclohexyl)amino)methyl)phenyl)-2-oxo-1,2-dihydropyrimidin-4-yl)carbamoyl)piperazin-1-yl)-2-methyl-1-oxopropan-2-yl)carbamate and (1-ethoxycyclopropoxy) trimethylsilane. 1H NMR (500 MHz, D2O) δ 7.99 (d, 1H), 7.72 (d, 2H), 7.56 (d, 2H), 6.86 (d, 1H), 4.63-4.46 (m, 2H), 3.89-3.60 (m, 8H), 3.56-3.41 (m, 1H), 3.38-3.22 (m, 1H), 3.01-2.86 (m, 1H), 2.46-2.32 (m, 2H), 2.31-2.19 (m, 2H), 2.00-1.89 (m, 2H), 1.74 (s, 6H), 1.63-1.47 (m, 2H), 1.09-0.80 (m, 4H). LCMS [M+H] 551.5.

Compound 337

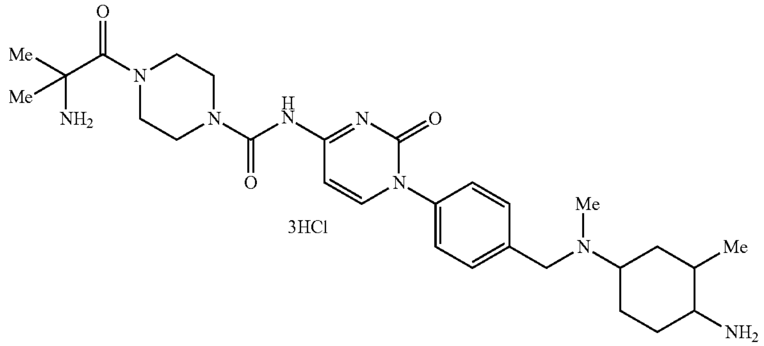

4-(2-Amino-2-methylpropanoyl)-N-(1-(4-(((4-amino-3-methylcyclohexyl)(methyl)amino)methyl) phenyl)-2-oxo-1,2-dihydropyrimidin-4-yl)piperazine-1-carboxamide hydrochloride salt Prepared in a similar fashion to Scheme C-3 from tert-butyl (4-((4-(4-(4-(2-((tert-butoxycarbonyl)amino)-2-methylpropanoyl)piperazine-1-carboxamido)-2-oxopyrimidin-1 (2H)-yl)benzyl)amino)-2-methylcyclohexyl)carbamate and formaldehyde. $^1$H NMR (400 MHz, $D_2O$) Mixture of diastereomers δ 7.82 (d, 1H), 7.55 (d, 2H), 7.44 (d, 2H), 6.73 (d, 1H), 4.63 (d, 1H), 4.49-4.46 (m, 2H), 4.20-4.08 (m, 3H), 3.94 (d, 1H), 3.65-3.59 (m, 8H), 3.42-3.36 (m, 3H), 2.86-2.81 (m, 1H), 2.67-2.58 (m, 4H), 2.12-1.93 (m, 4H), 1.60 (s, 6H), 1.46 (m, 1H), 1.22-1.14 (m, 1H), 1.03-0.99 (m, 3H). LCMS [(M+2H)/2] 270.3.

Compound 323

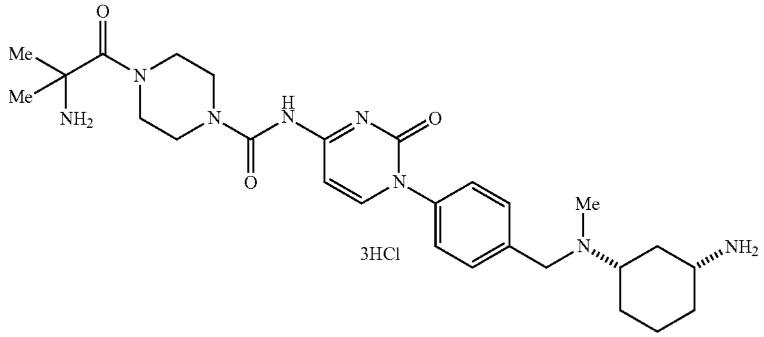

cis-4-(2-Amino-2-methylpropanoyl)-N-(1-(4-(((3-aminocyclohexyl)(methyl)amino)methyl)phenyl)-2-oxo-1,2-dihydropyrimidin-4-yl)piperazine-1-carboxamide hydrochloride salt Prepared in a similar fashion to Scheme C-3 from cis-tert-butyl (3-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)carbamate and formaldehyde. $^1$H NMR (400 MHz, $D_2O$) δ 7.89 (d, 1H), 7.58 (d, 2H), 7.47 (d, 2H), 4.51 (d, 2H), 4.31-4.23 (m, 1H), 3.75-3.61 (m, 7H), 3.42-3.39 (m, 1H), 3.41-3.22 (m, 1H), 2.69 (s, 3H), 2.42-2.32 (m, 1H), 2.15-2.09 (m, 1H) 2.05-1.97 (m, 3H), 1.61 (s, 1H) 1.60-1.59 (m, 2H), 1.33-1.21 (m, 2H). LCMS [M+H] 525.5.

Compound 340

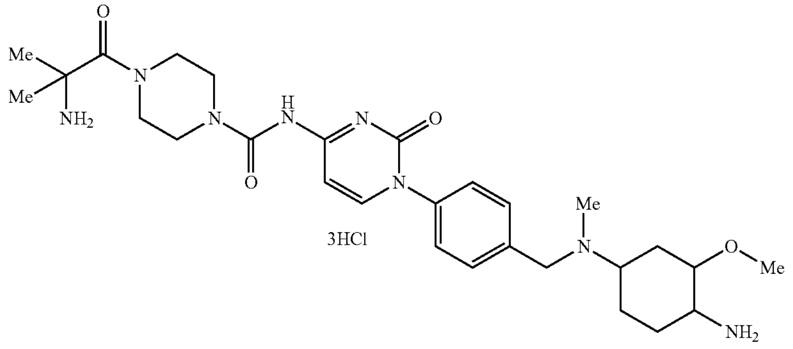

4-(2-Amino-2-methylpropanoyl)-N-(1-(4-(((4-amino-3-methoxycyclohexyl)(methyl)amino)methyl) phenyl)-2-oxo-1,2-dihydropyrimidin-4-yl)piperazine-1-carboxamide hydrochloride salt Prepared in a similar fashion to Scheme C-3 from tert-butyl (4-((4-(4-(4-(2-((tert-butoxycarbonyl)amino)-2-methylpropanoyl)piperazine-1-carboxamido)-2-oxopyrimidin-1(2H)-yl)benzyl)amino)-2-methoxycyclohexyl)carbamate and formaldehyde. $^1$H NMR (400 MHz, $D_2O$) mixture of diastereomers, δ 7.82 (d, 1H), 7.55 (d, 2H), 7.44 (d, 2H), 6.73 (d, 1H), 4.63 (d, 1H), 4.49-4.46 (m, 2H), 4.20-4.08 (m, 3H), 3.94 (d, 1H), 3.65-3.59 (m, 8H), 3.42-3.36 (m, 3H), 2.86-2.81 (m, 1H), 2.67-2.58 (m, 4H), 2.12-1.93 (m, 4H), 1.60 (s, 6H), 1.46 (m, 1H), 1.22-1.14 (m, 1H), 1.03-0.99 (m, 3H). LCMS [(M+2H)/2] 278.3.

Compound 325

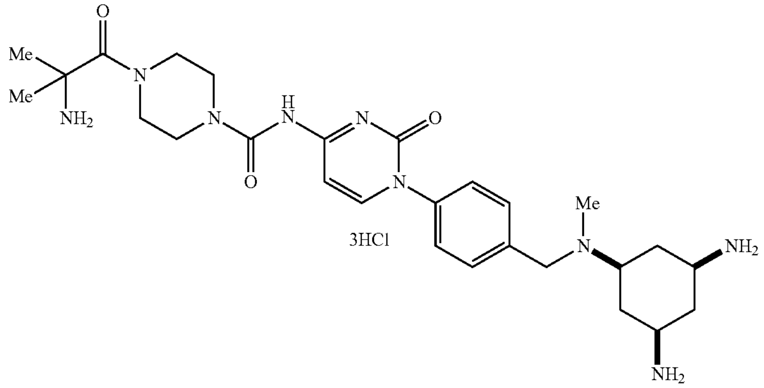

cis-4-(2-Amino-2-methylpropanoyl)-N-(1-(4-(((3,5-diaminocyclohexyl)(methyl)amino)methyl)phenyl)-2-oxo-1,2-dihydropyrimidin-4-yl)piperazine-1-carboxamide hydrochloride salt Prepared in a similar fashion to Scheme C-3 from cis-tert-butyl (2-hydroxypropan-2-yl) (5-((4-(4-(4-(2-((tert-butoxycarbonyl)amino)-2-methylpropanoyl)piperazine-1-carboxamido)-2-oxopyrimidin-1(2H)-yl)benzyl)amino) cyclohexane-1,3-diyl)dicarbamate and formaldehyde. $^1$H NMR (400 MHz, $D_2O$) Mixture of rotamers, δ 7.86 (d, 1H), 7.56 (d, 2H), 7.44 (d, 2H), 6.70 (d, 1H), 4.41 (bs, 2H), 3.57-3.62 (m, 10H), 3.38 (t, 3H), 3.24 (s, 1H), 2.70 (s, 3H), 2.44 (s, 2H), 2.35 (d, 1H), 1.82-1.73 (m, 2H) 1.62-1.52 (m, 6H). LCMS [M+H] 540.4.

Compound 338

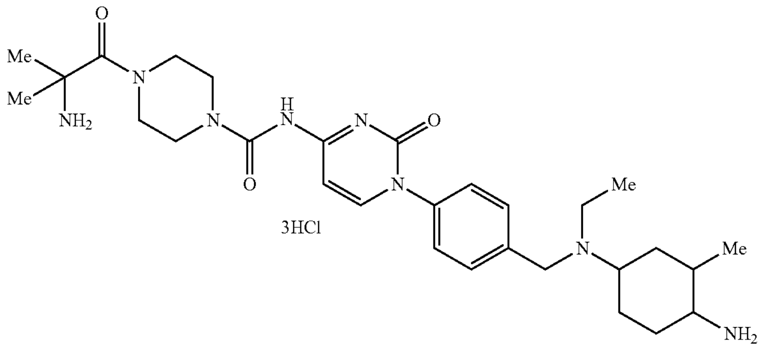

4-(2-Amino-2-methylpropanoyl)-N-(1-(4-(((4-amino-3-methylcyclohexyl)(ethyl)amino)methyl) phenyl)-2-oxo-1,2-dihydropyrimidin-4-yl)piperazine-1-carboxamide hydrochloride salt Prepared in a similar fashion to Scheme C-3 from tert-butyl (4-((4-(4-(4-(2-((tert-butoxycarbonyl)amino)-2-methylpropanoyl)piperazine-1-carboxamido)-2-oxopyrimidin-1(2H)-yl)benzyl)amino)-2-methylcyclohexyl)carbamate and acetaldehyde. $^1$H NMR (400 MHz, $D_2O$) Mixture of diastereomers, δ 7.82 (d, 1H), 7.53 (d, 2H), 7.42 (d, 2H), 6.70 (d, 1H) 4.41 (d, 2H), 4.29 (d, 2H), 3.62-3.58 (m, 8H), 3.50 (s, 2H), 3.40-3.37 (m, 2H), 3.20-3.12 (m, 3H), 2.81 (t, 1H), 2.10-2.00 (m, 3H), 1.58 (s, 6H), 1.48-1.41 (m, 1H), 1.22-1.11 (m, 3H), 0.92-0.87 (m, 3H). LCMS [(M+2H)/2] 277.3.

Compound 324

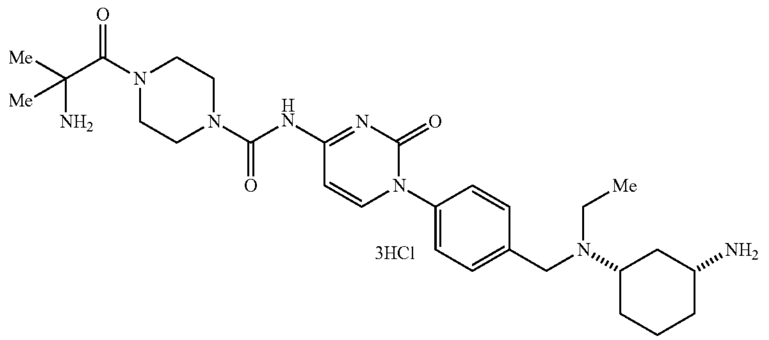

cis-4-(2-Amino-2-methylpropanoyl)-N-(1-(4-(((3-aminocyclohexyl)(ethyl)amino)methyl)phenyl)-2-oxo-1,2-dihydropyrimidin-4-yl)piperazine-1-carboxamide hydrochloride salt Prepared in a similar fashion to Scheme C-3 from cis-tert-butyl (3-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)carbamate and acetaldehyde. $^{1}$H NMR (400 MHz, $D_2O$) δ 7.88-7.46 (d, 1H), 7.58 (d, 2H), 7.47 (d, 2H), 6.75 (d, 1H), 4.47 (d, 1H), 4.29 (d, 1H), 3.64 (d, 1H), 3.40 (d, 8H), 3.42-3.40 (m, 2H), 3.25-3.17 (m, 3H), 2.40-2.30 (m, 1H) 2.10-1.96 (m, 3H), 1.81-1.65 (m, 1H) 1.62 (s, 6H), 1.40-1.25 (m, 2H), 1.21 (t, 3H). LCMS [M+H] 539.5.

Compound 341

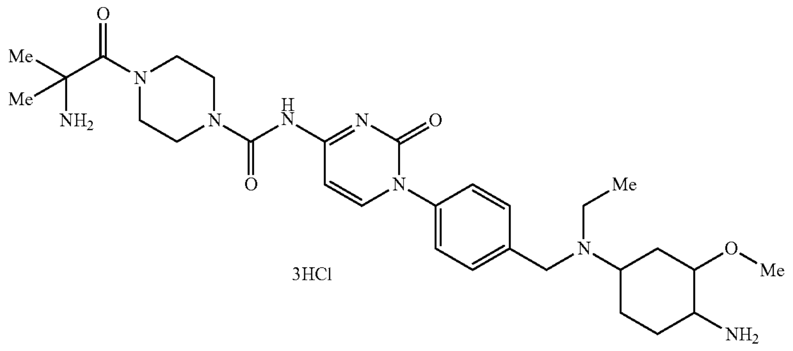

4-(2-Amino-2-methylpropanoyl)-N-(1-(4-(((4-amino-3-methoxycyclohexyl)(ethyl)amino)methyl)phenyl)-2-oxo-1,2-dihydropyrimidin-4-yl)piperazine-1-carboxamide hydrochloride salt Prepared in a similar fashion to Scheme C-3 from tert-butyl (4-((4-(4-(4-(2-((tert-butoxycarbonyl)amino)-2-methylpropanoyl)piperazine-1-carboxamido)-2-oxopyrimidin-1(2H)-yl)benzyl)amino)-2-methoxycyclohexyl)carbamate and acetaldehyde. $^{1}$H NMR (400 MHz, $D_2O$) Mixture of diastereomers, δ 8.01 (d, 1H), 7.60 (d, 2H), 7.48 (d, 2H), 6.71 (d, 1H), 4.53-4.48 (m, 1H), 4.31-4.26 (m, 1H), 3.66-3.61 (m, 4H), 3.51-3.49 (m, 8H), 3.30 (s, 3H), 3.17 (bs, 2H), 2.31-2.28 (m, 1H), 2.09 (d, 1H) 1.94-1.89 (m, 3H), 1.76 (bs, 1H), 1.60 (s, 6H), 1.21 (m, 3H). LCMS [M+H] 569.6.

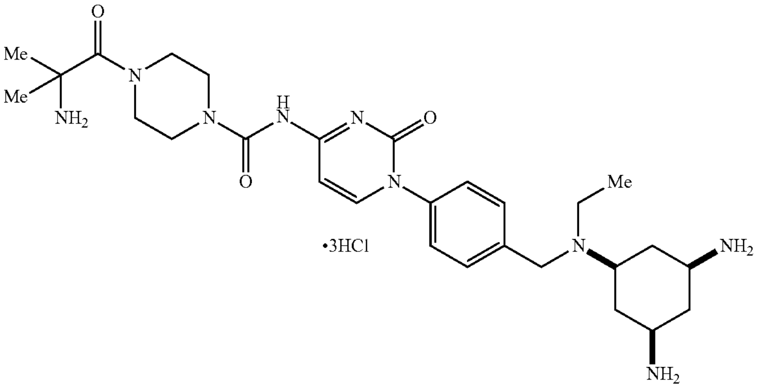

cis-4-(2-Amino-2-methylpropanoyl)-N-(1-(4-(((3,5-diaminocyclohexyl)(ethyl)amino)methyl)phenyl)-2-oxo-1,2-dihydropyrimidin-4-yl)piperazine-1-carboxamide hydrochloride salt Prepared in a similar fashion to Scheme C-3 from cis-tert-butyl (2-hydroxypropan-2-yl) (5-((4-(4-(4-(2-((tert-butoxycarbonyl)amino)-2-methylpropanoyl)piperazine-1-carboxamido)-2-oxopyrimidin-1(2H)-yl)benzyl)amino) cyclohexane-1,3-diyl)dicarbamate and acetaldehyde. $^1$H NMR (400 MHz, $D_2O$) Mixture of rotamers, δ 7.91 (d, 1H), 7.55 (d, 2H), 7.45 (d, 2H), 6.70 (d, 1H), 4.42 (bs, 2H), 3.62-3.46 (m, 9H), 3.38-3.35 (m, 2H), 3.24 (bs, 2H), 2.42-2.33 (m, 4H), 1.82 (d, 2H), 1.57 (s, 6H), 1.19 (t, 3H). LCMS [M+H] 554.4.

Compound 333

4-(2-Amino-2-methylpropanoyl)-N-(1-(4-(((3-amino-5-hydroxycyclohexyl)(methyl)amino)methyl) phenyl)-2-oxo-1,2-dihydropyrimidin-4-yl)piperazine-1-carboxamide hydrochloride salt Prepared in a similar fashion to Scheme C-3 from tert-butyl (1-(4-((1-(4-(((3-((tert-butoxycarbonyl)amino)-5-((tert-butyldimethylsilyl)oxy)cyclohexyl)(methyl)amino) methyl)phenyl)-2-oxo-1,2-dihydropyrimidin-4-yl)carbamoyl)piperazin-1-yl)-2-methyl-1-oxopropan-2-yl)carbamate and formaldehyde. $^1$H NMR (400 MHz, $D_2O$) δ 7.77 (d, 1H), 7.58 (d, 2H), 7.44 (d, 1H), 7.30 (d, 1H), 6.73 (d, 1H), 4.33 (m, 3H), 4.25-4.23 (m, 2H), 3.98-3.96 (m, 3H), 3.86-3.59 (m, 7H), 3.52-3.36 (m, 3H), 3.27 (m, 2H), 2.71-2.64 (m, 4H), 2.61-2.58 (m, 2H), 2.02-1.90 (m, 3H), 1.78 (m, 3H), 1.59 (s, 6H), 1.29-1.25 (d, 6H), 1.21-1.19 (m, 1H). LCMS [(M+2H)/2] 271.2.

Compound 343

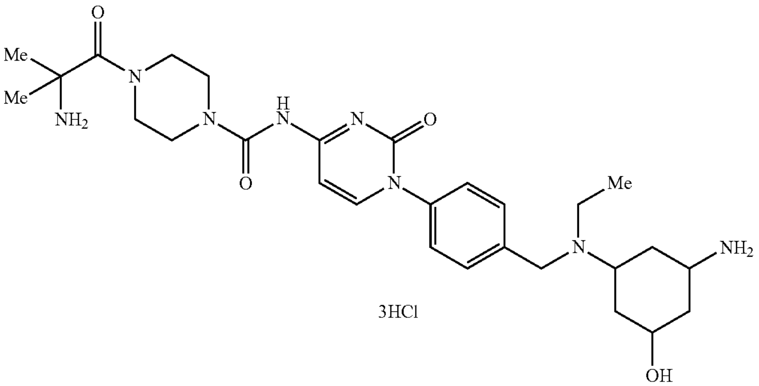

Compound 286

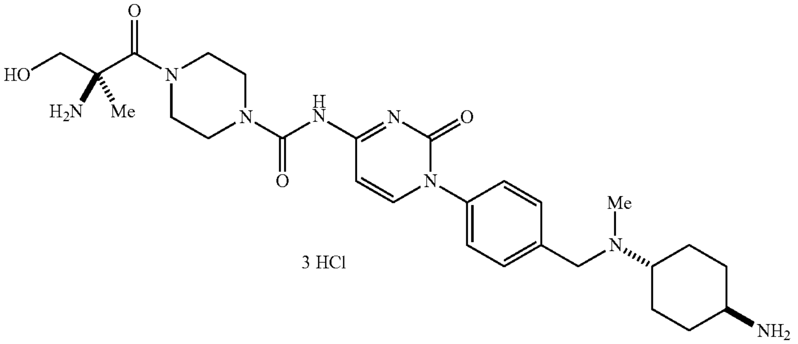

4-((S)-2-Amino-3-hydroxy-2-methylpropanoyl)-N-(1-(4-(((trans-4-aminocyclohexyl)(methyl)amino)methyl)phenyl)-2-oxo-1,2-dihydropyrimidin-4-yl)piperazine-1-carboxamide hydrochloride salt Prepared in a similar fashion as Scheme C-3 from tert-butyl (2R,4S)-4-(4-((1-(4-(((trans-4-((tert-butoxycarbonyl)amino)cyclohexyl)amino)methyl)phenyl)-2-oxo-1,2-dihydropyrimidin-4-yl)carbamoyl)piperazine-1-carbonyl)-2-(tert-butyl)-4-methyloxazolidine-3-carboxylate and formalin. $^1$H NMR (500 MHz, $D_2O$) δ 7.97 (d, 1H), 7.65 (d, 2H), 7.54 (d, 2H), 6.81 (d, 1H), 4.56 (d, 1H), 4.28 (d, 1H), 4.12 (d, 1H), 3.86 (d, 1H), 3.76-3.68 (m, 8H), 3.41 (t, 1H), 3.23 (t, 1H), 2.74 (s, 3H), 2.29-2.18 (m, 4H), 1.83-1.76 (m, 2H), 1.64 (s, 3H), 1.53 (q, 2H). LCMS [M+H] 541.3.

Compound 287

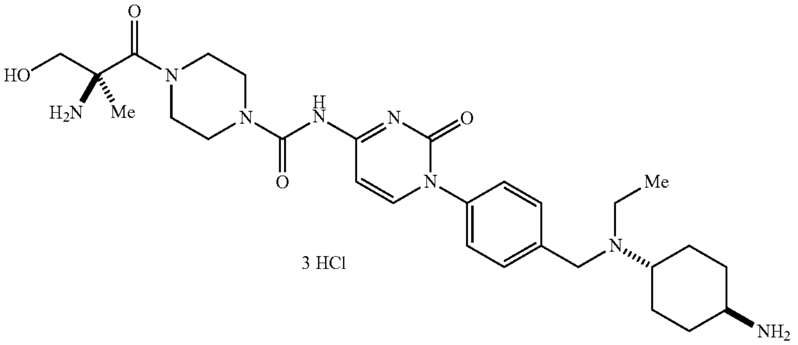

4-((S)-2-Amino-3-hydroxy-2-methylpropanoyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt Prepared in a similar fashion as scheme C-3 from tert-butyl (2R,4S)-4-(4-((1-(4-(((trans-4-((tert-butoxycarbonyl)amino)cyclohexyl)amino)methyl)phenyl)-2-oxo-1,2-dihydropyrimidin-4-yl)carbamoyl)piperazine-1-carbonyl)-2-(tert-butyl)-4-methyloxazolidine-3-carboxylate and acetaldehyde. $^1$H NMR (500 MHz, $D_2O$) δ 8.00 (d, 1H), 7.65 (d, 2H), 7.54 (d, 2H), 6.81 (d, 1H), 4.52 (d, 1H), 4.33 (d, 1H), 4.11 (d, 1H), 3.86 (d, 1H), 3.76-3.68 (m, 8H), 3.41 (t, 1H), 3.31-3.20 (m, 3H), 2.24-2.18 (m, 4H), 1.86-1.76 (m, 2H), 1.64 (s, 3H), 1.51 (q, 2H), 1.27 (t, 3H). LCMS [M+H] 555.4.

Compound 277

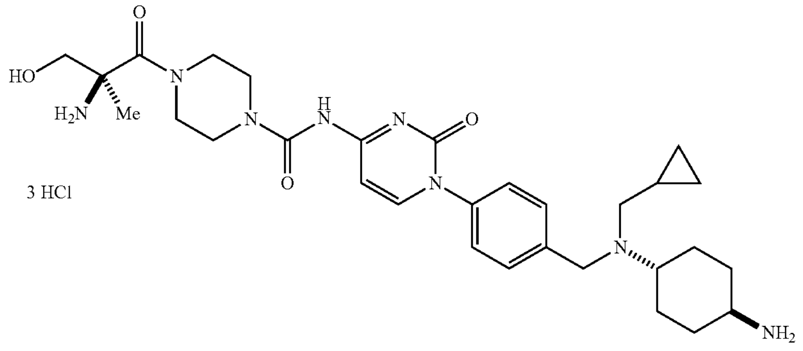

4-((S)-2-Amino-3-hydroxy-2-methylpropanoyl)-N-(1-(4-(((trans-4-aminocyclohexyl)(cyclopropylmethyl)amino)methyl)phenyl)-2-oxo-1,2-dihydropyrimidin-4-yl)piperazine-1-carboxamide hydrochloride salt Prepared in a similar fashion as Scheme C-3 from tert-butyl (2R,4S)-4-(4-((1-(4-(((trans-4-((tert-butoxycarbonyl)amino)cyclohexyl)amino)methyl)phenyl)-2-oxo-1,2-dihydropyrimidin-4-yl)carbamoyl)piperazine-1-carbonyl)-2-(tert-butyl)-4-methyloxazolidine-3-carboxylate and cyclopropane carboxaldehyde. $^1$H NMR (500 MHz, $D_2O$) δ 7.95 (d, 1H), 7.69 (d, 2H), 7.56 (d, 2H), 6.85 (d, 1H), 4.55 (d, 1H), 4.50 (d, 1H), 4.15 (d, 1H), 3.90 (d, 1H), 3.79-3.68 (m, 8H), 3.60-3.54 (m, 1H), 3.28-3.23 (m, 2H), 3.08-3.03 (m, 1H), 2.33-2.16 (m, 4H), 1.90-1.79 (m, 2H), 1.68 (s, 3H), 1.61-1.49 (m, 2H), 1.08-0.99 (m, 1H), 0.74-0.67 (m, 2H), 0.36-0.25 (m, 2H). LCMS [M+H] 581.4.

Compound 356

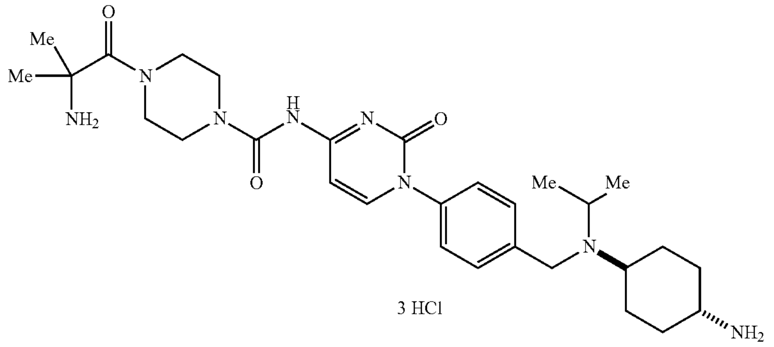

4-(2-Amino-2-methylpropanoyl)-N-(1-(4-(((trans-4-aminocyclohexyl)(isopropyl)amino)methyl)phenyl)-2-oxo-1,2-dihydropyrimidin-4-yl)piperazine-1-carboxamide hydrochloride salt Scheme C-5

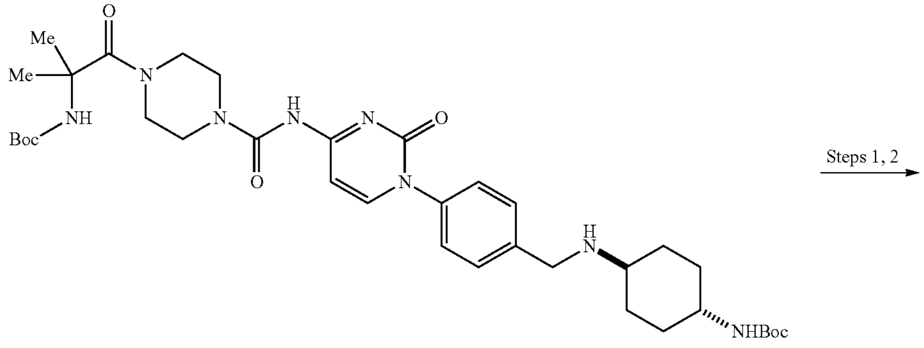

-continued

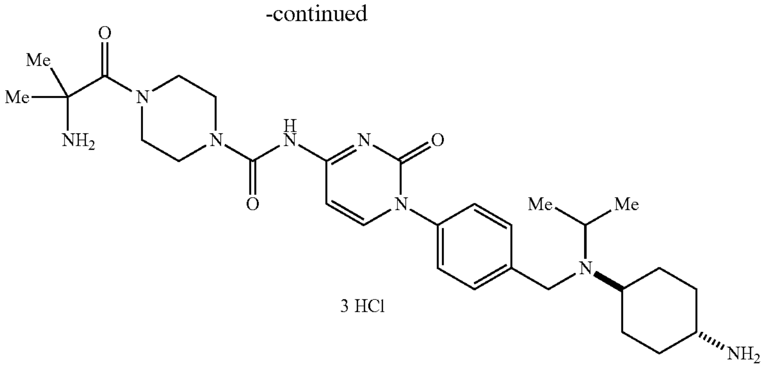

3 HCl

Reagents: 1) i-PrBr, $K_2CO_3$, DMF, 55° C., 40 h 2) HCl in MeOH, rt, 22 h.

Step 1. tert-butyl (trans-4-((4-(4-(4-(2-((tert-butoxycarbonyl)amino)-2-methylpropanoyl) piperazine-1-carboxamido)-2-oxopyrimidin-1(2H)yl)benzyl)(isopropyl)amino)cyclohexyl) carbamate A mixture of tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)amino)cyclohexyl)carbamate (71.1 mg, 0.10 mmol), $K_2CO_3$ (44.1 mg, 0.32 mmol), and 2-bromopropane (30 μL, 0.32 mmol) in DMF (0.5 mL) was stirred at 55° C. for 18 h. Another portion of 2-bromopropane (30 μL, 0.32 mmol) was added and stirring continued at 55° C. for 22 h. The mixture was cooled, diluted with EtOAc (10 mL), washed with sat. aq. $NaHCO_3$(2×10 mL) and brine (2×10 mL), dried over $Na_2SO_4$, decanted, and concentrated. The residue was purified by flash chromatography (Hexanes/EtOAc/MeOH) to provide the title compound (44.5 mg, 59%) as a white solid. LCMS [M+H] 753.9.

Step 2. 4-(2-amino-2-methylpropanoyl)-N-(1-(4-(((trans-4-aminocyclohexyl)(isopropyl)amino) methyl)phenyl)-2-oxo-1,2-dihydropyrimidin-4-yl) piperazine-1-carboxamide hydrochloride salt A mixture of tert-butyl (trans-4-((4-(4-(4-(2-((tert-butoxycarbonyl)amino)-2-methylpropanoyl)piperazine-1-carboxamido)-2-oxopyrimidin-1(2H)-yl)benzyl)(isopropyl) amino)cyclohexyl)carbamate (44.5 mg, 0.059 mmol) and 2M HCl in MeOH (3 mL) was stirred at rt for 22 h and concentrated. The residue was purified by reverse phase HPLC ($CH_3CN/H_2O$/TFA), and the product fractions were converted to the HCl salt with 2M HCl in MeOH to afford the title compound (22.3 mg, 57.0%) as a white solid. $^1H$ NMR (500 MHz, $D_2O$) δ 7.67 (d, 2H), 7.53 (d, 2H), 7.40 (d, 1H), 6.07 (d, 1H), 5.39-5.26 (m, 1H), 4.40 (s, 2H), 3.91-3.59 (m, 8H), 3.43-3.23 (m, 2H), 2.47-2.33 (m, 2H), 2.32-2.19 (m, 2H), 1.77 (s, 6H), 1.71-1.55 (m, 4H), 1.52 (d, 6H). LCMS [(M+2H)/2] 277.3.

Compound 367

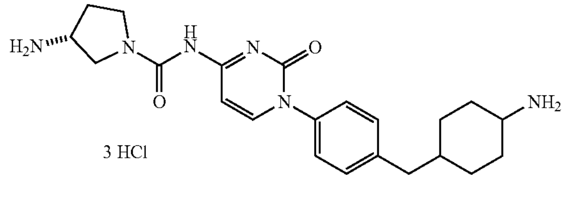

3 HCl (R)-3-Amino-N-(1-(4-((4-aminopiperidin-1-yl) methyl)phenyl)-2-oxo-1,2-dihydropyrimidin-4-yl) pyrrolidine-1-carboxamide hydrochloride salt Scheme C-6

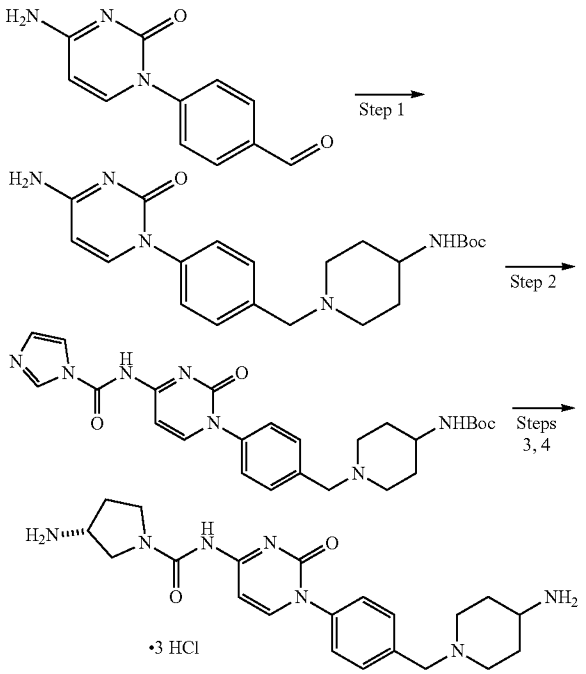

Reagents: 1) tert-butyl piperidin-4-ylcarbamate, DIPEA, $NaBH(OAc)_3$, DCE, $CH_3CN$, rt, 16 h 2) CDI, $CH_2Cl_2$, rt, 16 h 3) tert-butyl (R)-pyrrolidin-3-ylcarbamate, $CH_3CN$, rt, 20 h 4) HCl, MeOH, rt, 4 h.

Step 1: tert-butyl (1-(4-(4-amino-2-oxopyrimidin-1 (2H)-yl)benzyl)piperidin-4-yl)carbamate To a suspension of 4-(4-amino-2-oxopyrimidin-1(2H)-yl) benzaldehyde (1.00 g 4.6 mmol) and tert-butyl piperidin-4-ylcarbamate (1.39 g, 7.0 mmol) in 1:1 DCE:MeCN (25 mL) was added DIPEA (1.61 mL, 9.2 mmol) and $NaBH(OAc)_3$ (1.97 g, 9.3 mmol). The reaction was stirred at rt for 16 h. The reaction mixture was concentrated under reduced pressure, the residue was dissolved in $CHCl_3$ and washed with 10% NaOH. Purification by column chromatography (MeOH:$CHCl_3$) afforded the title compound.

Step 2: tert-butyl (1-(4-(4-(1H-imidazole-1-carboxamido)-2-oxopyrimidin-1(2H)-yl)benzyl)piperidin-4-yl)carbamate A suspension of tert-butyl (1-(4-(4-amino-2-oxopyrimidin-1(2H)-yl)benzyl)piperidin-4-yl)carbamate (350 mg, 0.82 mmol) and CDI (195 mg, 0.84 mmol) in $CH_2Cl_2$ was stirred at rt for 16 h. The solvent was removed under reduced pressure, and the residue was triturated with EtOAc. The solid was collected by filtration to give the title compound.

Step 3: tert-butyl (R)-(1-(4-(4-(3-((tert-butoxycarbonyl)amino)pyrrolidine-1-carboxamido)-2-oxopyrimidin-1(2H)-yl)benzyl)piperidin-4-yl)carbamate A mixture of tert-butyl (1-(4-(4-(1H-imidazole-1-carboxamido)-2-oxopyrimidin-1(2H)-yl)benzyl)piperidin-4-yl) carbamate (60 mg, 0.12 mmol) and tert-butyl (R)-pyrrolidin-3-ylcarbamate (22.6 mg, 0.12 mmol) in MeCN (2 mL) was stirred at rt for 20 h. The reaction mixture was concentrated under reduced pressure and purified by column chromatography (Hexanes:EtOAc:MeOH) to afford the title compound.

Step 4. (R)-3-amino-N-(1-(4-((4-aminopiperidin-1-yl)methyl)phenyl)-2-oxo-1,2-dihydropyrimidin-4-yl) pyrrolidine-1-carboxamide hydrochloride salt A mixture of tert-utyl (R)-(1-(4-(4-(3-((tert-butoxycarbonyl)amino)pyrrolidine-1-carboxamido)-2-oxopyrimidin-1 (2H)-yl)benzyl)piperidin-4-yl)carbamate (63.1 mg, 0.10 mmol) and 2M HCl in MeOH (4.0 mL) was stirred at rt for 4 h. The mixture was concentrated to dryness and dry MeOH added and removed under reduced pressure to give the title compound. $^1H$ NMR (500 MHz, $D_2O$) δ 7.87 (d, 1H), 7.56 (d, 2H), 7.45 (d, 2H), 7.00 (d, 1H), 4.32 (s, 2H), 3.92-4.03 (m, 1H), 3.72-3.88 (m, 1H), 3.50-3.70 (m, 5H), 3.37-3.49 (m, 1H), 3.02-3.14 (m, 2H), 2.29-2.44 (m, 1H), 2.17-2.26 (m, 2H), 2.03-2.16 (m, 1H), 1.73-1.87 (m, 2H). LCMS [M+H] 412.3.

Compound 366

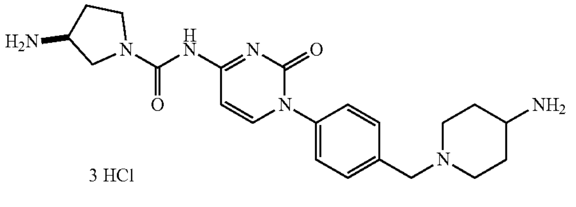

3 HCl (S)-3-Amino-N-(1-(4-((4-aminopiperidin-1-yl)methyl)phenyl)-2-oxo-1,2-dihydropyrimidin-4-yl) pyrrolidine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (S)-pyrrolidin-3-ylcarbamate. LCMS [M+H] 412.3.

Compound 46

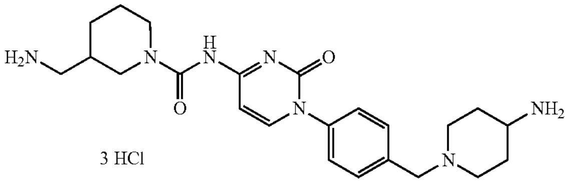

3 HCl 3-(Aminomethyl)-N-(1-(4-((4-aminopiperidin-1-yl) methyl)phenyl)-2-oxo-1,2-dihydropyrimidin-4-yl) piperidine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (piperidin-3-ylmethyl)carbamate. $^1H$ NMR (500 MHz, $D_2O$) δ 7.81 (d, 1H), 7.56 (d, 2H), 7.44 (d, 2H), 6.71 (d, 1H), 4.31 (s, 2H), 3.93-4.01 (m, 1H), 3.78-3.89 (m, 1H), 3.52-3.61 (m, 2H), 3.39-3.49 (m, 1H), 3.07 (m, 3H), 2.88-2.95 (m, 1H), 2.79-2.87 (m, 2H), 2.16-2.27 (m, 2H), 1.67-1.94 (m, 5H), 1.40-1.53 (m, 1H), 1.21-1.33 (m, 1H). LCMS [M+H] 440.3.

Compound 47

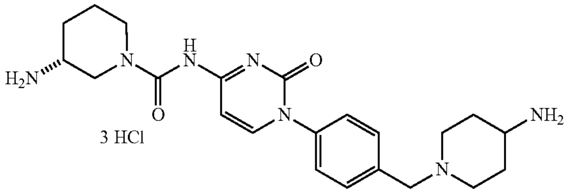

3 HCl (R)-3-Amino-N-(1-(4-((4-aminopiperidin-1-yl) methyl)phenyl)-2-oxo-1,2-dihydropyrimidin-4-yl) piperidine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (R)-piperidin-3-ylcarbamate. $^1H$ NMR (500 MHz, $D_2O$) δ 7.81 (d, 1H), 7.56 (d, 2H), 7.44 (d, 2H), 6.70 (d, 1H), 4.31 (s, 2H), 3.91-3.98 (m, 1H), 3.62-3.70 (m, 1H), 3.52-3.61 (m, 2H), 3.25-3.48 (m, 4H), 3.03-3.13 (m, 2H), 2.16-2.26 (m, 2H), 1.98-2.07 (m, 1H), 1.70-1.86 (m, 3H), 1.51-1.69 (m, 2H). LCMS [M+H] 426.2.

Compound 48

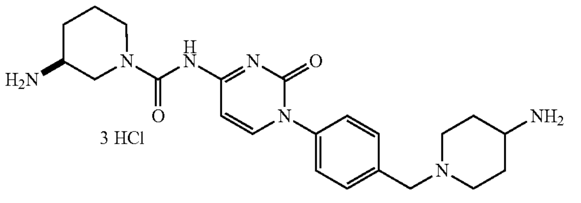

3 HCl (S)-3-Amino-N-(1-(4-((4-aminopiperidin-1-yl)methyl)phenyl)-2-oxo-1,2-dihydropyrimidin-4-yl)piperidine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (S)-piperidin-3-ylcarbamate. $^1$H NMR (500 MHz, $D_2O$) δ 7.81 (d, 1H), 7.56 (d, 2H), 7.44 (d, 2H), 6.70 (d, 1H), 4.31 (br. s., 1H), 3.90-3.99 (m, 1H), 3.62-3.72 (m, 1H), 3.52-3.61 (m, 2H), 3.23-3.49 (m, 4H), 3.01-3.14 (m, 2H), 2.16-2.28 (m, 2H), 1.97-2.08 (m, 1H), 1.70-1.87 (m, 3H), 1.51-1.70 (m, 2H). LCMS [M+H] 426.1.

Compound 49

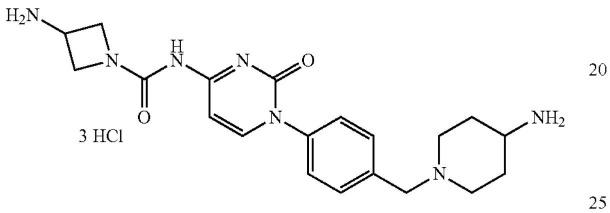

3 HCl

3-Amino-N-(1-(4-((4-aminopiperidin-1-yl)methyl)phenyl)-2-oxo-1,2-dihydropyrimidin-4-yl)azetidine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl azetidin-3-ylcarbamate. $^1$H NMR (500 MHz, $D_2O$) δ 7.89 (d, 1H), 7.56 (d, 2H), 7.44 (d, 2H), 7.02 (d, 1H), 4.41-4.48 (m, 2H), 4.31 (s, 2H), 4.07-4.20 (m, 3H), 3.51-3.61 (m, 2H), 3.38-3.49 (m, 1H), 3.02-3.13 (m, 2H), 2.17-2.26 (m, 2H), 1.74-1.87 (m, 2H). LCMS [M+H] 398.2.

Compound 50

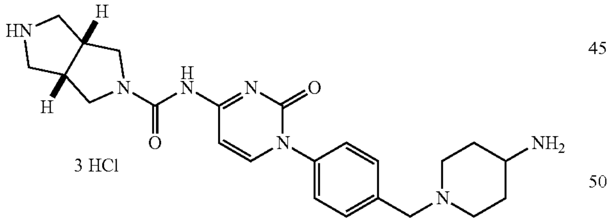

3 HCl cis-N-(1-(4-((4-Aminopiperidin-1-yl)methyl)phenyl)-2-oxo-1,2-dihydropyrimidin-4-yl)hexahydropyrrolo[3,4-c]pyrrole-2(1H)-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (cis)-hexahydropyrrolo[3,4-c]pyrrole-2(1H)-carboxylate. $^1$H NMR (500 MHz, $D_2O$) δ 7.91 (d, 1H), 7.57 (d, 2H), 7.45 (d, 2H), 6.94 (d, 1H), 4.32 (s, 2H), 3.67-3.79 (m, 2H), 3.39-3.62 (m, 7H), 3.13-3.21 (m, 4H), 3.03-3.12 (m, 2H), 2.17-2.27 (m, 2H), 1.73-1.88 (m, 2H). LCMS [M+H] 438.1.

Compound 51

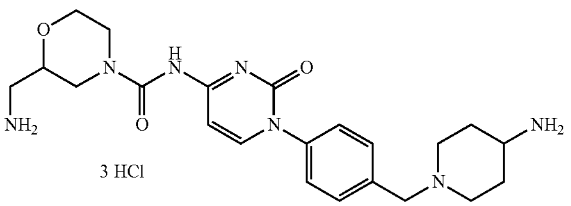

3 HCl 2-(Aminomethyl)-N-(1-(4-((4-aminopiperidin-1-yl)methyl)phenyl)-2-oxo-1,2-dihydropyrimidin-4-yl)morpholine-4-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (morpholin-2-ylmethyl)carbamate. $^1$H NMR (500 MHz, $D_2O$) δ 7.72 (d, 1H), 7.50 (d, 2H), 7.38 (d, 2H), 6.66 (d, 1H), 4.25 (s, 2H), 3.95 (d, 1H), 3.79-3.91 (m, 2H), 3.62-3.72 (m, 1H), 3.44-3.58 (m, 3H), 3.31-3.43 (m, 1H), 2.97-3.13 (m, 4H), 2.88-2.96 (m, 1H), 2.74-2.86 (m, 1H), 2.09-2.21 (m, 2H), 1.67-1.82 (m, 2H). LCMS [M+H] 442.2.

Compound 52

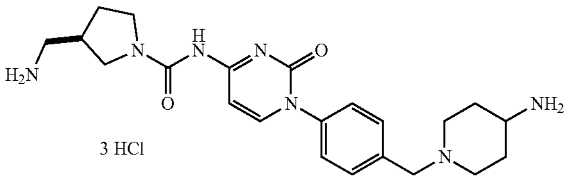

3 HCl (R)-3-(Aminomethyl)-N-(1-(4-((4-aminopiperidin-1-yl)methyl)phenyl)-2-oxo-1,2-dihydropyrimidin-4-yl)pyrrolidine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (S)-(pyrrolidin-3-ylmethyl)carbamate. $^1$H NMR (500 MHz, $D_2O$) δ 7.94 (d, 1H), 7.59 (d, 2H), 7.47 (d, 2H), 6.98 (d, 1H), 4.34 (s, 2H), 3.34-3.83 (m, 7H), 2.95-3.21 (m, 4H), 2.47-2.68 (m, 1H), 2.05-2.31 (m, 3H), 1.62-1.91 (m, 3H). LCMS [M+H] 426.3.

Compound 53

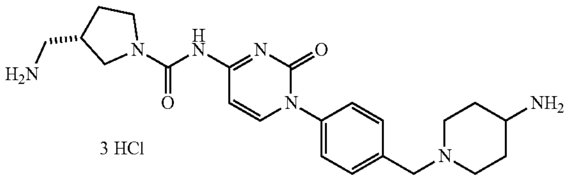

3 HCl (S)-3-(Aminomethyl)-N-(1-(4-((4-aminopiperidin-1-yl)methyl)phenyl)-2-oxo-1,2-dihydropyrimidin-4-yl)pyrrolidine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (R)-(pyrrolidin-3-ylmethyl)carbamate. $^{1}$H NMR (500 MHz, $D_2O$) δ 7.92 (d, 1H), 7.59 (d, 2H), 7.47 (d, 2H), 7.00 (d, 1H), 4.33 (s, 2H), 3.36-3.83 (m, 7H), 2.96-3.21 (m, 4H), 2.47-2.68 (m, 1H), 2.06-2.30 (m, 3H), 1.62-1.90 (m, 3H). LCMS [M+H] 426.4.

Compound 54

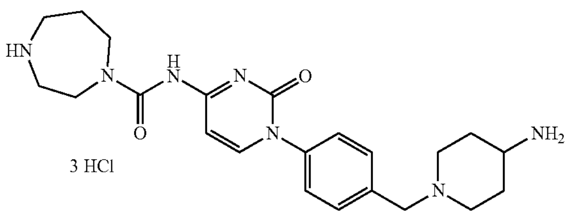

N-(1-(4-((4-Aminopiperidin-1-yl)methyl)phenyl)-2-oxo-1,2-dihydropyrimidin-4-yl)-1,4-diazepane-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl 1,4-diazepane-1-carboxylate. $^{1}$H NMR (500 MHz, $D_2O$) δ 7.86 (d, 1H), 7.59 (d, 2H), 7.47 (d, 2H), 6.72-6.85 (m, 1H), 4.33 (s, 2H), 3.74-3.88 (m, 2H), 3.65 (t, 2H), 3.58 (d, 2H), 3.41-3.51 (m, 1H), 3.32-3.39 (m, 2H), 3.26-3.32 (m, 2H), 3.04-3.15 (m, 2H), 2.19-2.29 (m, 2H), 2.03-2.14 (m, 2H), 1.75-1.89 (m, 2H). LCMS [M+H] 426.4.

Compound 55

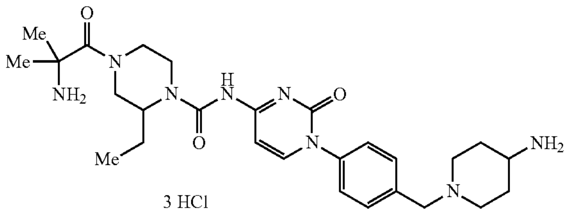

4-(2-Amino-2-methylpropanoyl)-N-(1-(4-((4-aminopiperidin-1-yl)methyl)phenyl)-2-oxo-1,2-dihydropyrimidin-4-yl)-2-ethylpiperazine-1-carboxamide hydrochloride salt Prepared in a similar fashion to Scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-(3-ethylpiperazin-1-yl)-2-methyl-1-oxopropan-2-yl)carbamate. $^{1}$H NMR (500 MHz, $D_2O$) δ 7.82 (d, 1H), 7.59 (d, 2H), 7.47 (d, 2H), 6.70 (d, 1H), 4.34 (s, 2H), 4.22-4.31 (m, 1H), 4.06-4.18 (m, 1H), 3.95-4.05 (m, 1H), 3.55-3.64 (m, 2H), 3.41-3.51 (m, 1H), 3.16-3.41 (m, 3H), 2.92-3.16 (m, 3H), 2.19-2.29 (m, 2H), 1.76-1.90 (m, 2H), 1.57-1.70 (m, 7H), 1.45-1.56 (m, 1H), 0.78 (t, 3H). LCMS [M+H] 525.3.

Compound 56

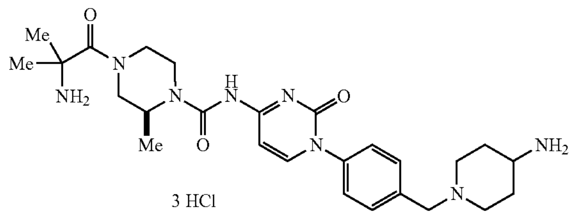

(S)-4-(2-Amino-2-methylpropanoyl)-N-(1-(4-((4-aminopiperidin-1-yl)methyl)phenyl)-2-oxo-1,2-dihydropyrimidin-4-yl)-2-methylpiperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (S)-(2-methyl-1-(3-methylpiperazin-1-yl)-1-oxopropan-2-yl)carbamate. $^{1}$H NMR (400 MHz, Methanol-$d_4$) δ 8.26 (s, 1H), 7.84 (d, 2H), 7.67 (d, 2H), 6.82 (s, 1H), 4.66 (s, 1H), 4.47 (s, 2H), 4.29 (d, 3H), 3.64 (d, 2H), 3.57-3.18 (m, 4H), 2.29 (d, 2H), 2.09 (t, 2H), 1.75 (s, 3H), 1.72 (s, 3H), 1.30 (s, 3H). LCMS [M+H] 511.3.

Compound 57

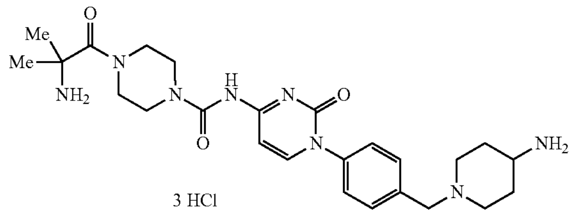

4-(2-Amino-2-methylpropanoyl)-N-(1-(4-((4-aminopiperidin-1-yl)methyl)phenyl)-2-oxo-1,2-dihydropyrimidin-4-yl)piperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (2-methyl-1-oxo-1-(piperazin-1-yl)propan-2-yl)carbamate. LCMS [M+H] 497.3.

Compound 96

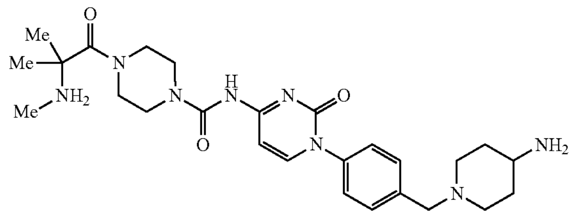

N-(1-(4-((4-Aminopiperidin-1-yl)methyl)phenyl)-2-oxo-1,2-dihydropyrimidin-4-yl)-4-(2-methyl-2-(methylamino)propanoyl)piperazine-1-carboxamide Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and benzyl methyl(2-methyl-1-oxo-1-(piperazin-1-yl)propan-2-yl)carbamate. $^1$H NMR (500 MHz, $CD_3OD$) δ 7.71 (d, 1H), 7.52 (d, 2H), 7.41 (d, 2H), 6.37-6.76 (m, 1H), 3.64-3.78 (m, 10H), 3.10-3.20 (m, 1H), 2.99-3.09 (m, 2H), 2.67 (s, 3H), 2.22-2.32 (m, 2H), 1.98-2.05 (m, 2H), 1.65-1.76 (m, 8H). LCMS [M+H] 511.3.

Compound 58

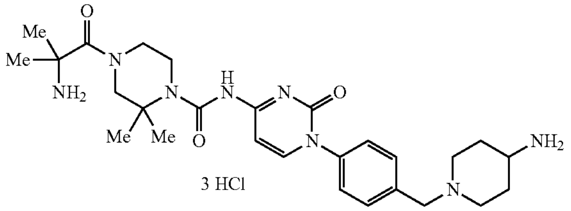

4-(2-Amino-2-methylpropanoyl)-N-(1-(4-((4-aminopiperidin-1-yl)methyl)phenyl)-2-oxo-1,2-dihydropyrimidin-4-yl)-2,2-dimethylpiperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-(3,3-dimethylpiperazin-1-yl)-2-methyl-1-oxopropan-2-yl)carbamate. $^1$H NMR (400 MHz, $D_2O$) δ 8.06 (d, 1H), 7.72 (d, 2H), 7.60 (d, 2H), 6.76 (d, 1H), 4.46 (s, 2H), 4.05-3.63 (m, 8H), 3.63-3.50 (m, 1H), 3.22 (t, 2H), 2.35 (d, 2H), 2.03-1.88 (m, 2H), 1.75 (s, 6H), 1.56 (s, 6H). LCMS [M+H] 525.3.

Compound 59

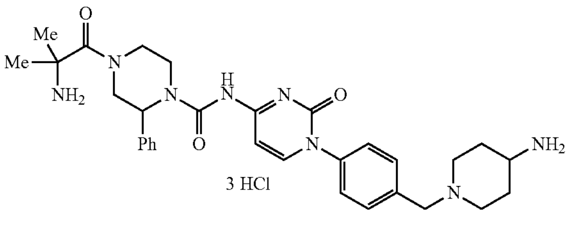

4-(2-Amino-2-methylpropanoyl)-N-(1-(4-((4-aminopiperidin-1-yl)methyl)phenyl)-2-oxo-1,2-dihydropyrimidin-4-yl)-2-phenylpiperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (2-methyl-1-oxo-1-(3-phenylpiperazin-1-yl)propan-2-yl) carbamate. $^1$H NMR (400 MHz, Methanol-$d_4$) δ 8.39 (d, 1H), 7.84 (d, 2H), 7.65 (d, 2H), 7.38 (d, 4H), 7.34-7.24 (m, 1H), 6.92 (d, 1H), 5.71 (s, 1H), 4.45 (s, 2H), 4.31 (d, 1H), 4.06 (d, 1H), 3.70-3.44 (m, 6H), 3.32 (s, 1H), 3.24 (d, 2H), 2.26 (d, 2H), 2.08 (d, 2H), 1.53 (d, 6H). LCMS [M+H] 573.2.

Compound 60

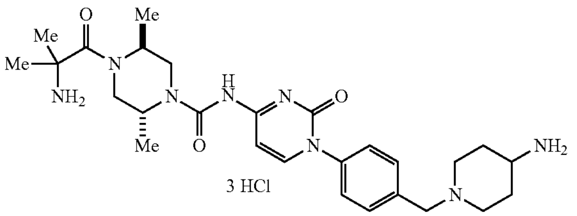

(2R,5S)-4-(2-Amino-2-methylpropanoyl)-N-(1-(4-((4-aminopiperidin-1-yl)methyl)phenyl)-2-oxo-1,2-dihydropyrimidin-4-yl)-2,5-dimethylpiperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-((2S,5R)-2,5-dimethylpiperazin-1-yl)-2-methyl-1-oxopropan-2-yl)carbamate. $^1$H NMR (400 MHz, $D_2O$) δ 8.12 (d, 1H), 7.73 (d, 2H), 7.62 (d, 2H), 6.86 (d, 1H), 4.57 (s, 2H), 4.47 (s, 2H), 4.04 (d, 2H), 3.72 (d, 2H), 3.67-3.53 (m, 1H), 3.53-3.32 (m, 2H), 3.30-3.16 (m, 2H), 2.37 (d, 2H), 2.05-1.88 (m, 2H), 1.78 (s, 6H), 1.32 (d, 6H). LCMS [M+H] 525.3.

Compound 61

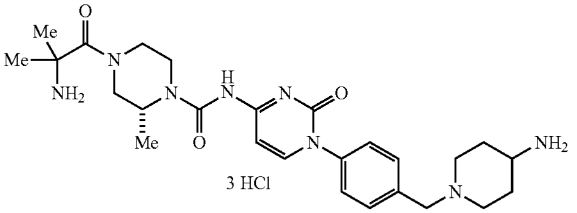

(R)-4-(2-Amino-2-methylpropanoyl)-N-(1-(4-((4-aminopiperidin-1-yl)methyl)phenyl)-2-oxo-1,2-dihydropyrimidin-4-yl)-2-methylpiperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (R)-(2-methyl-1-(3-methylpiperazin-1-yl)-1-oxopropan-2-yl)carbamate. LCMS [M+H] 511.3.

Compound 62

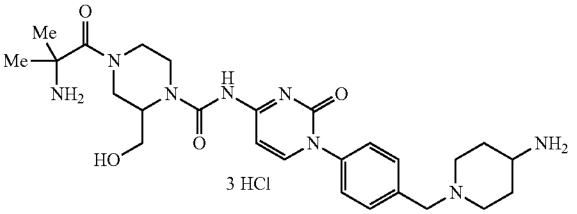

4-(2-Amino-2-methylpropanoyl)-N-(1-(4-((4-aminopiperidin-1-yl)methyl)phenyl)-2-oxo-1,2-dihydropyrimidin-4-yl)-2-(hydroxymethyl)piperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-(3-(((tert-butyldimethylsilyl)oxy)methyl)piperazin-1-yl)-2-methyl-1-oxopropan-2-yl)carbamate. LCMS [M+H] 527.2.

Compound 63

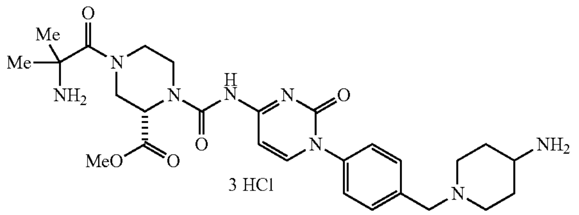

Methyl (S)-4-(2-amino-2-methylpropanoyl)-1-((1-(4-((4-aminopiperidin-1-yl)methyl)phenyl)-2-oxo-1,2-dihydropyrimidin-4-yl)carbamoyl)piperazine-2-carboxylate hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and methyl (S)-4-(2-((tert-butoxycarbonyl)amino)-2-methylpropanoyl)piperazine-2-carboxylate. LCMS [M+H] 555.4.

Compound 64

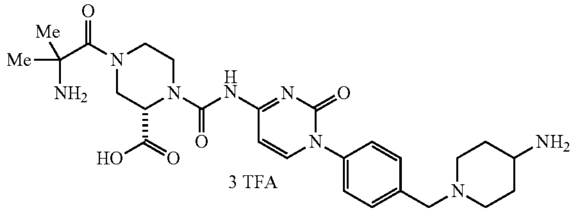

(S)-4-(2-Amino-2-methylpropanoyl)-1-((1-(4-((4-aminopiperidin-1-yl)methyl)phenyl)-2-oxo-1,2-dihydropyrimidin-4-yl)carbamoyl)piperazine-2-carboxylic acid trifluroacetetate salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and methyl (S)-4-(2-((tert-butoxycarbonyl)amino)-2-methylpropanoyl)piperazine-2-carboxylate. $^1$H NMR (400 MHz, $CD_3OD$) δ 7.73-7.56 (m, 3H), 7.59-7.31 (m, 2H), 6.47 (s, 1H) 4.37 (s, 2H), 4.21 (d, 1H), 3.58 (d, 2H), 3.50-3.20 (m, 7H), 3.14 (t, 2H), 2.24 (d, 2H), 1.96 (d, H), 1.68 (s, 3H), 1.65 (s, 3H). LCMS [M+H] 541.2.

Compound 82

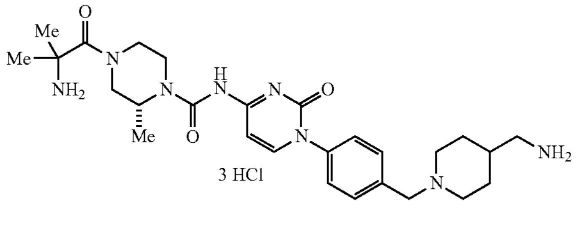

(R)-4-(2-Amino-2-methylpropanoyl)-N-(1-(4-((4-(aminomethyl)piperidin-1-yl)methyl)phenyl)-2-oxo-1,2-dihydropyrimidin-4-yl)-2-methylpiperazine-1-carboxamide hydrochloride salt Prepared as is scheme C-6 from tert-butyl ((1-(4-(4-(1H-imidazole-1-carboxamido)-2-oxopyrimidin-1(2H)-yl)benzyl)piperidin-4-yl)methyl)carbamate and (R)-tert-butyl (2-methyl-1-(3-methylpiperazin-1-yl)-1-oxopropan-2-yl) carbamate. $^1$H NMR (400 MHz, $D_2O$) δ 8.01 (d, 1H), 7.71 (d, 2H), 7.59 (d, 2H), 6.85 (d, 1H), 4.55 (d, 1H), 4.43 (s, 2H), 4.23 (d, 1H), 4.10 (d, 1H), 3.64 (d, 2H), 3.56-3.25 (d, 2H), 3.12 (t, 2H), 2.99 (d, 2H), 2.10 (d, 3H), 1.77 (d, 6H), 1.62-1.45 (m, 2H), 1.29 (s, 5H). LCMS [M+H] 525.3.

Compound 83

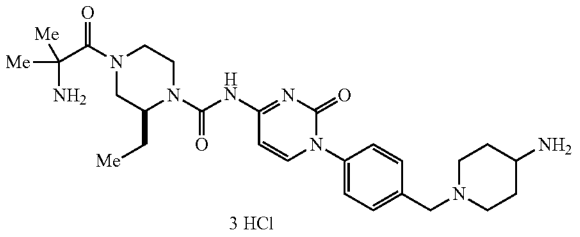

(S)-4-(2-Amino-2-methylpropanoyl)-N-(1-(4-((4-aminopiperidin-1-yl)methyl)phenyl)-2-oxo-1,2-dihydropyrimidin-4-yl)-2-ethylpiperazine-1-carboxamide hydrochloride salt Prepared as is scheme C-6 from tert-butyl (1-(4-(4-(1H-imidazole-1-carboxamido)-2-oxopyrimidin-1(2H)-yl)benzyl)piperidin-4-yl)carbamate and (S)-tert-butyl (1-(3-ethylpiperazin-1-yl)-2-methyl-1-oxopropan-2-yl)carbamate. $^1$H NMR (400 MHz, $D_2O$) δ 8.15 (d, 1H), 7.73 (d, 2H), 7.62 (d, 2H), 6.81 (d, 1H), 4.46 (s, 2H), 4.43-4.35 (m, 2H), 4.23 (s, 1H), 4.12 (d, 1H), 3.75-3.66 (m, 2H), 3.65-3.51 (m, 2H), 3.46-3.32 (m, 2H), 3.23 (t, 2H), 2.35 (d, 2H), 2.04-1.89 (m, 2H), 1.75 (d, 6H), 1.70-1.55 (d, 2H), 0.90 (t, 3H). LCMS [M+H] 525.3.

Compound 84

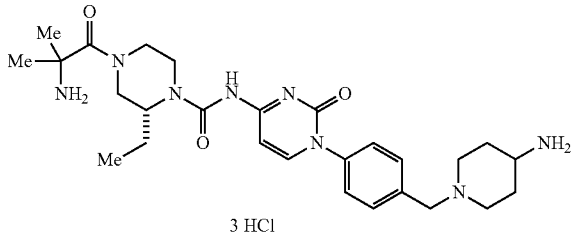

(R)-4-(2-Amino-2-methylpropanoyl)-N-(1-(4-((4-aminopiperidin-1-yl)methyl)phenyl)-2-oxo-1,2-dihydropyrimidin-4-yl)-2-ethylpiperazine-1-carboxamide hydrochloride salt Prepared as is scheme C-6 from tert-butyl (1-(4-(4-(1H-imidazole-1-carboxamido)-2-oxopyrimidin-1(2H)-yl)benzyl)piperidin-4-yl)carbamate and (R)-tert-butyl (1-(3-ethylpiperazin-1-yl)-2-methyl-1-oxopropan-2-yl)carbamate. $^1$H NMR (400 MHz, $D_2O$) δ 8.00 (d, 1H), 7.71 (d, 2H), 7.60 (d, 2H), 6.82 (d, 1H), 4.44 (d, 2H), 4.43-4.33 (m, 2H), 4.23 (s, 1H), 4.12 (d, 1H), 3.79-3.65 (m, 3H), 3.65-3.53 (m, 1H), 3.36 (s, 2H), 3.22 (t, 2H), 2.36 (d, 2H), 2.03-1.87 (m, 2H), 1.76 (d, 6H), 1.70-1.56 (m, 2H), 0.90 (t, 3H). LCMS [M+H] 525.3.

Compound 85

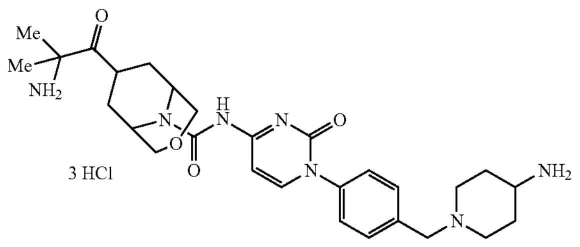

7-(2-Amino-2-methylpropanoyl)-N-(1-(4-((4-aminopiperidin-1-yl)methyl)phenyl)-2-oxo-1,2-dihydropyrimidin-4-yl)-3-oxa-7,9-diazabicyclo[3.3.1]nonane-9-carboxamide hydrochloride salt Prepared as is scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-(3-oxa-7,9-diazabicyclo[3.3.1]nonan-7-yl)-2-methyl-1-oxopropan-2-yl)carbamate. LCMS [M+H] 539.2.

Compound 86

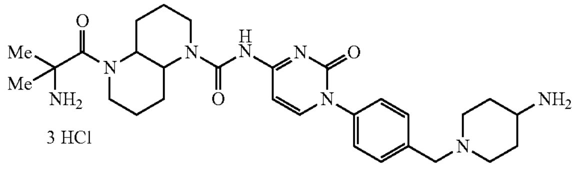

5-(2-Amino-2-methylpropanoyl)-N-(1-(4-((4-aminopiperidin-1-yl)methyl)phenyl)-2-oxo-1,2-dihydropyrimidin-4-yl)octahydro-1,5-naphthyridine-1(2H)-carboxamide hydrochloride salt Prepared as is scheme C-6 from tert-butyl (1-(4-(4-(1H-imidazole-1-carboxamido)-2-oxopyrimidin-1(2H)-yl)benzyl)piperidin-4-yl)carbamate and tert-butyl (2-methyl-1-(octahydro-1,5-naphthyridin-1(2H)-yl)-1-oxopropan-2-yl) carbamate. $^1$H NMR (400 MHz, $D_2O$) δ 8.02 (d, 1H), 7.70 (d, 2H), 7.59 (d, 2H), 6.81 (d, 1H), 4.62 (s, 2H), 4.46 (s, 2H), 3.92 (s, 2H), 3.71 (d, 2H), 3.58 (t, 2H), 3.38-3.15 (m, 3H), 2.36 (d, 2H), 2.16 (br. s, 2H), 2.03-1.86 (m, 4H), 1.82-1.56 (m, 10H). LCMS [M+H] 551.2.

Compound 87

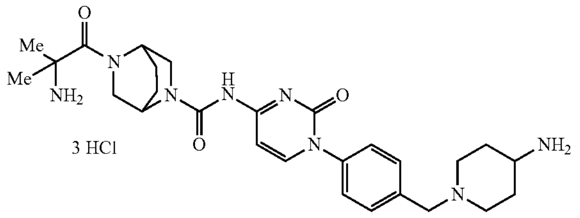

5-(2-Amino-2-methylpropanoyl)-N-(1-(4-((4-aminopiperidin-1-yl)methyl)phenyl)-2-oxo-1,2-dihydropyrimidin-4-yl)-2,5-diazabicyclo[2.2.2]octane-2-carboxamide hydrochloride salt Prepared as is scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-(2,5-diazabicyclo[2.2.2]octan-2-yl)-2-methyl-1-oxopropan-2-yl) carbamate. $^1$H NMR (400 MHz, $D_2O$) δ 8.13 (d, 1H), 7.72 (d, 2H), 7.61 (d, 2H), 7.07 (d, 1H), 4.61 (d, 2H), 4.47 (s, 2H), 4.18-3.76 (m, 2H), 3.71 (d, 2H), 3.67-3.43 (m, 3H), 3.23 (t, 2H), 2.36 (d, 2H), 2.15 (s, 2H), 2.06-1.84 (m, 4H), 1.74 (s, 6H). LCMS [M+H] 523.3.

Compound 88

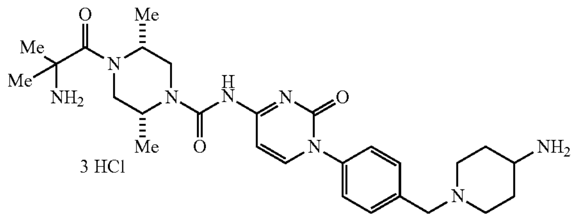

(2R,5R)-4-(2-Amino-2-methylpropanoyl)-N-(1-(4-((4-aminopiperidin-1-yl)methyl)phenyl)-2-oxo-1,2-dihydropyrimidin-4-yl)-2,5-dimethylpiperazine-1-carboxamide hydrochloride salt Prepared as is scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-((2R,5R)-2,5-dimethylpiperazin-1-yl)-2-methyl-1-oxopropan-2-yl) carbamate. $^1$H NMR (400 MHz, $D_2O$) δ 7.97 (d, 1H), 7.71 (d, 2H), 7.60 (d, 2H), 6.88 (d, 1H), 4.46 (s, 2H), 4.43-4.28

(m, 2H), 4.22 (d, 1H), 4.10 (d, 1H), 3.71 (d, 2H), 3.59 (s, 1H), 3.51-3.39 (m, 1H), 3.23 (t, 3H), 2.36 (d, 2H), 2.02-1.88 (m, 2H), 1.74 (d, 6H), 1.28 (d, 3H), 1.18 (d, 3H). LCMS [M+H] 525.3.

Compound 89

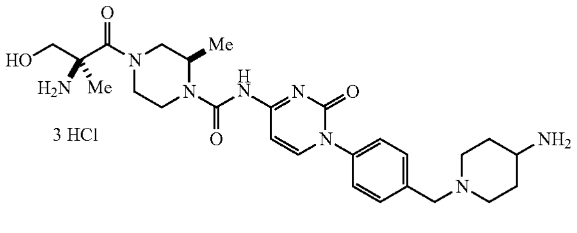

(R)-4-((S)-2-Amino-3-hydroxy-2-methylpropanoyl)-N-(1-(4-((4-aminopiperidin-1-yl)methyl)phenyl)-2-oxo-1,2-dihydropyrimidin-4-yl)-2-methylpiperazine-1-carboxamide hydrochloride salt Prepared as is scheme C-6 from tert-butyl (1-(4-(4-(1H-imidazole-1-carboxamido)-2-oxopyrimidin-1(2H)-yl)benzyl)piperidin-4-yl)carbamate and (2R,4S)-tert-butyl 2-(tert-butyl)-4-methyl-4-((R)-3-methylpiperazine-1-carbonyl)oxazolidine-3-carboxylate. $^1$H NMR (400 MHz, $D_2O$) δ 7.98 (d, 1H), 7.71 (d, 2H), 7.60 (d, 2H), 6.85 (d, 1H), 4.57 (s, 1H), 4.46 (s, 2H), 4.23 (d, 1H), 4.18 (d, 1H), 4.10 (d, 1H), 3.93 (d, 1H), 3.71 (d, 3H), 3.63-3.53 (m, 1H), 3.53-3.33 (m, 3H), 3.22 (t, 2H), 2.36 (d, 2H), 1.99-1.87 (m, 2H), 1.73 (s, 3H), 1.29 (d, 3H). LCMS [M+H] 527.3.

Compound 274

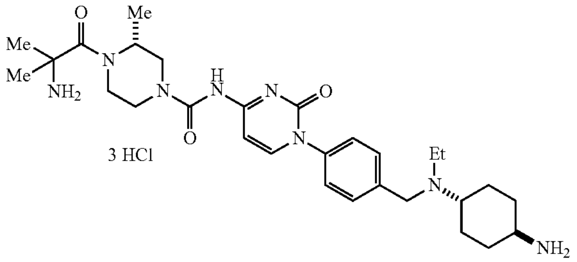

(R)-4-(2-Amino-2-methylpropanoyl)-N-(1-(4-((((trans)-4-aminocyclohexyl) (ethyl)amino)methyl)phenyl)-2-oxo-1,2-dihydropyrimidin-4-yl)-3-methylpiperazine-1-carboxamide hydrochloride salt Prepared in a similar fashion as Scheme C-6 from tert-butyl ((trans)-4-((4-(4-(1H-imidazole-1-carboxamido)-2-oxopyrimidin-1(2H)-yl)benzyl)(ethyl)amino)cyclohexyl) carbamate and tert-butyl (R)-(2-methyl-1-(2-methylpiperazin-1-yl)-1-oxopropan-2-yl)carbamate. $^1$H NMR (400 MHz, D2O) δ 8.00 (d, 1H), 7.71 (d, 2H), 7.60 (d, 2H), 6.87 (d, 1H), 4.69 (s, 1H), 4.58 (d, 1H), 4.39 (d, 1H), 4.19 (s, 1H), 4.00 (s, 2H), 3.69 (s, 1H), 3.53-3.41 (m, 1H), 3.40-3.18 (m, 5H), 2.41-2.19 (m, 4H), 1.99-1.80 (m, 2H), 1.74 (s, 6H), 1.58 (t, 2H), 1.33 (t, 3H), 1.26 (s, 3H). LCMS [M+H] 553.4.

Compound 275

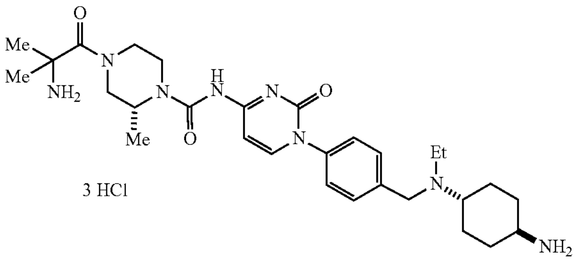

(R)-4-(2-Amino-2-methylpropanoyl)-N-(1-(4-((((trans)-4-aminocyclohexyl)(ethyl)amino)methyl)phenyl)-2-oxo-1,2-dihydropyrimidin-4-yl)-2-methylpiperazine-1-carboxamide hydrochloride salt Prepared in a similar fashion as Scheme C-6 from tert-butyl ((trans)-4-((4-(4-(1H-imidazole-1-carboxamido)-2-oxopyrimidin-1(2H)-yl)benzyl)(ethyl)amino)cyclohexyl) carbamate and tert-butyl (R)-(2-methyl-1-(3-methylpiperazin-1-yl)-1-oxopropan-2-yl)carbamate. $^1$H NMR (400 MHz, $D_2O$) δ 7.94 (d, 1H), 7.70 (d, 2H), 7.59 (d, 2H), 6.85 (d, 1H), 4.57 (d, 2H), 4.39 (d, 1H), 4.23 (d, 1H), 4.09 (d, 1H), 3.48 (s, 3H), 3.41-3.21 (m, 5H), 2.37-2.15 (m, 4H), 1.98-1.81 (m, 2H), 1.77 (s, 6H), 1.70-1.50 (m, 2H), 1.33 (t, 3H), 1.28 (s, 3H). LCMS [M+H] 553.4.

Compound 233

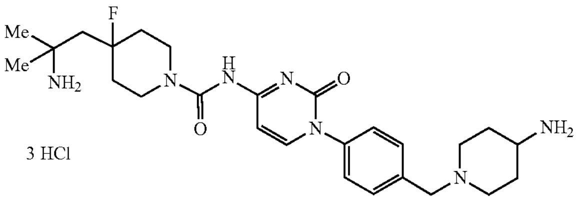

4-(2-Amino-2-methylpropyl)-N-(1-{4-[(4-aminopiperidin-1-yl)methyl]phenyl}-2-oxo-1,2-dihydropyrimidin-4-yl)-4-fluoropiperidine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (1-(4-fluoropiperidin-4-yl)-2-methylpropan-2-yl)carbamate. $^1$H NMR (400 MHz, $D_2O$) δ 7.92-7.83 (m, 1H), 7.64 (d, 2H), 7.52 (d, 2H), 6.89-6.77 (m, 1H), 4.39 (s, 2H), 4.11-3.93 (m, 2H), 3.70-3.62 (m, 2H), 3.57-3.46 (m, 1H), 3.37-3.23 (m, 2H), 3.22-3.08 (m, 2H), 2.34-2.24 (m, 2H), 2.18-2.04 (m, 4H), 1.96-1.69 (m, 4H), 1.45 (s, 6H). LCMS [M+H] 500.4.

Compound 384

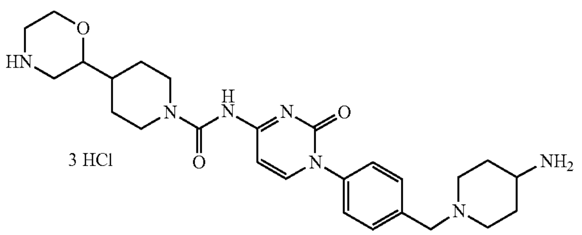

N-(1-{4-[(4-Aminopiperidin-1-yl)methyl]phenyl}-2-oxo-1,2-dihydropyrimidin-4-yl)-4-(morpholin-2-yl)piperidine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl 2-(piperidin-4-yl)morpholine-4-carboxylate. $^1$H NMR (400 MHz, $D_2O$) δ 7.86 (d, 1H), 7.63 (d, 2H), 7.51 (d, 2H), 6.80 (d, 1H), 4.38 (s, 2H), 4.21-4.02 (m, 3H), 3.84-3.79 (m, 1H), 3.71-3.58 (m, 3H), 3.57-3.45 (m, 1H), 3.38 (d, 1H), 3.28 (d, 1H), 3.20-3.07 (m, 3H), 3.06-2.84 (m, 3H), 2.35-2.18 (m, 2H), 1.98-1.75 (m, 4H), 1.74-1.63 (m, 1H), 1.44-1.24 (m, 2H). LCMS [M+H] 496.4.

Compound 230

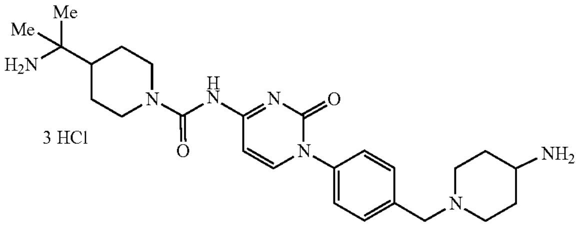

N-(1-{4-[(4-Aminopiperidin-1-yl)methyl]phenyl}-2-oxo-1,2-dihydropyrimidin-4-yl)-4-(2-aminopropan-2-yl)piperidine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (2-(piperidin-4-yl)propan-2-yl)carbamate. $^1$H NMR (400 MHz, $D_2O$) δ 7.87 (d, 1H), 7.63 (d, 2H), 7.51 (d, 2H), 6.80 (d, 1H), 4.38 (s, 2H), 4.30-4.15 (m, 2H), 3.72-3.58 (m, 2H), 3.57-3.44 (m, 1H), 3.21-3.09 (m, 2H), 3.03-2.88 (m, 2H), 2.33-2.22 (m, 2H), 1.96-1.73 (m, 5H), 1.45-1.21 (m, 8H). LCMS [M+H] 468.5.

Compound 231

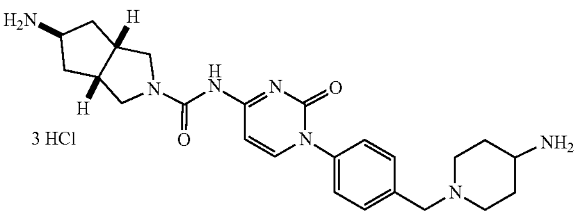

(3aR,5S,6aS)-5-Amino-N-(1-{4-[(4-aminopiperidin-1-yl)methyl]phenyl}-2-oxo-1,2-dihydropyrimidin-4-yl)-octahydrocyclopenta[c]pyrrole-2-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl ((3aR,5s,6aS)-octahydrocyclopenta[c]pyrrol-5-yl)carbamate. $^1$H NMR (400 MHz, $D_2O$) δ 7.99 (d, 1H), 7.69 (d, 2H), 7.57 (d, 2H), 7.12 (d, 1H), 4.51-4.33 (m, 2H), 4.01-3.86 (m, 1H), 3.83-3.64 (m, 4H), 3.63-3.33 (m, 3H), 3.20 (t, 2H), 3.04 (br. s., 2H), 2.34 (d, 2H), 2.18-1.84 (m, 6H). LCMS [M+H] 452.4.

Compound 295

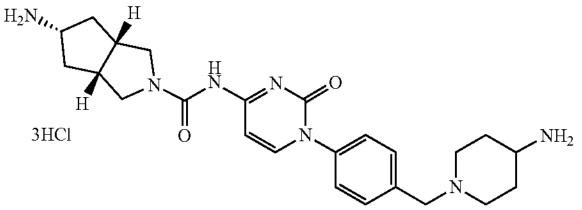

(3aR,5R,6aS)-5-Amino-N-(1-{4-[(4-aminopiperidin-1-yl)methyl]phenyl}-2-oxo-1,2-dihydropyrimidin-4-yl)-octahydrocyclopenta[c]pyrrole-2-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl ((3aR,5r,6aS)-octahydrocyclopenta[c]pyrrol-5-yl)carbamate. $^1$H NMR (400 MHz, $D_2O$) δ 7.92 (d, 1H), 7.64 (d, 2H), 7.52 (d, 2H), 7.09 (d, 1H), 4.39 (s, 2H), 3.81-3.41 (m, 8H), 3.23-3.09 (m, 2H), 2.91-2.75 (m, 2H), 2.50-2.36 (m, 2H), 2.34-2.24 (m, 2H), 1.94-1.78 (m, 2H), 1.57-1.44 (m, 2H). LCMS [M+H] 452.4.

Compound 234

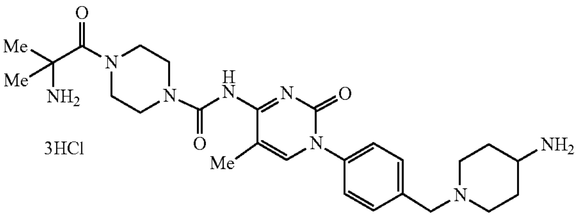

4-(2-Amino-2-methylpropanoyl)-N-(1-(4-((4-aminopiperidin-1-yl)methyl)phenyl)-5-methyl-2-oxo-1,2-dihydropyrimidin-4-yl)piperazine-1-carboxamide hydrochloride salt Prepared in a similar fashion as Scheme C-6 from tert-butyl (1-(4-(4-(1H-imidazole-1-carboxamido)-5-methyl-2-oxopyrimidin-1(2H)-yl)benzyl)piperidin-4-yl)carbamate and tert-butyl (2-methyl-1-oxo-1-(piperazin-1-yl)propan-2-yl)carbamate. $^1$H NMR (400 MHz, $D_2O$) δ 7.62 (d, 2H), 7.53-7.45 (m, 3H), 4.38 (br.s., 2H), 3.86-3.40 (m, 11H), 3.14 (br. t., 2H), 2.34-2.22 (m, 2H), 2.01-1.78 (m, 5H), 1.68 (s, 6H). LCMS [M+H] 511.5.

Compound 289

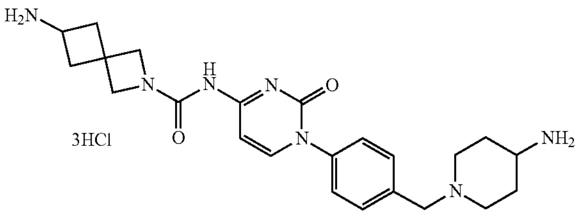

6-Amino-N-(1-(4-((4-aminopiperidin-1-yl)methyl)phenyl)-2-oxo-1,2-dihydropyrimidin-4-yl)-2-azaspiro[3.3]heptane-2-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (2-azaspiro[3.3]heptan-6-yl)carbamate. LCMS [M+H] 438.3.

Compound 291

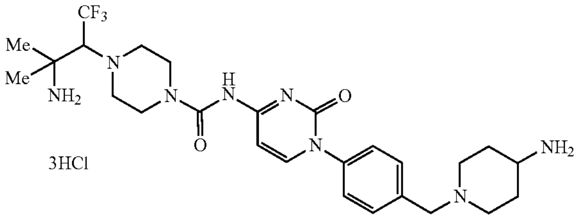

4-(3-Amino-1,1,1-trifluoro-3-methylbutan-2-yl)-N-(1-(4-((4-aminopiperidin-1-yl)methyl)phenyl)-2-oxo-1,2-dihydropyrimidin-4-yl)piperazine-1-carboxamide hydrochloride salt Prepared in a similar fashion as Scheme C-6 from tert-butyl (1-(4-(4-(1H-imidazole-1-carboxamido)-2-oxopyrimidin-1(2H)-yl)benzyl)piperidin-4-yl)carbamate and tert-butyl (4,4,4-trifluoro-2-methyl-3-(piperazin-1-yl)butan-2-yl)carbamate. LCMS [M+H] 551.4.

Compound 78

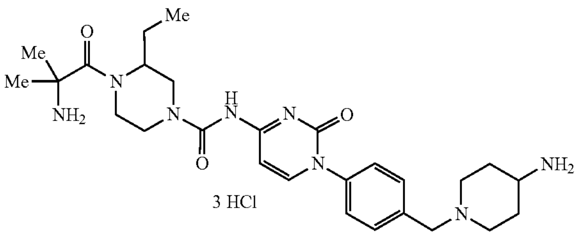

4-(2-Amino-2-methylpropanoyl)-N-(1-(4-((4-aminopiperidin-1-yl)methyl)phenyl)-2-oxo-1,2-dihydropyrimidin-4-yl)-3-ethylpiperazine-1-carboxamide hydrochloride salt Scheme C-7

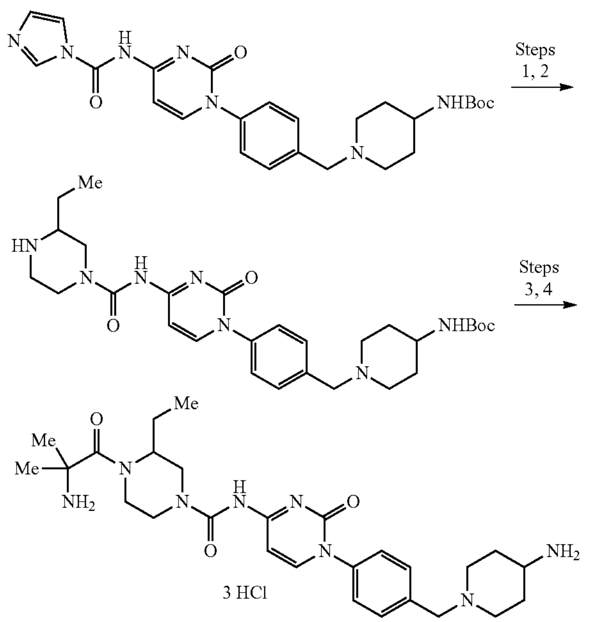

Reagents: 1) 1-(2-ethylpiperazin-1-yl)-2,2,3-trifluoroethan-1-one trifluoroacetate, $CH_3CN$, 85° C., 2 h 2) LiOH•$H_2O$, THF:$H_2O$, rt, 2 h 3) 2-((tert-butoxycarbonyl)amino)-2-methylpropanoic acid, HATU, DIPEA, DMF, 50° C., 16 h 4) HCl, MeOH, rt, 4 h.

Step 1: tert-butyl (1-(4-(4-(3-ethyl-4-(2,2,2-trifluoroacetyl)piperazine-1-carboxamido)-2-oxopyrimidin-1(2H)-yl)benzyl)piperidin-4-yl)carbamate tert-Butyl (1-(4-(4-(1H-imidazole-1-carboxamido)-2-oxopyrimidin-1(2H)-yl)benzyl)piperidin-4-yl)carbamate (135 mg, 0.26 mmol) and 1-(2-ethylpiperazin-1-yl)-2,2,2-trifluoroethan-1-one triflouroacetate (91 mg, 0.26 mmol) were dissolved in $CH_3CN$ and heated to reflux for 2 h.

The solvent was removed under reduced pressure. The crude reaction mixture was dissolved in EtOAc (25 mL) and washed with water (3×25 mL). Purification by column chromatography ($CHCl_3$:MeOH) afforded the title compound.

Step 2: tert-butyl (1-(4-(4-(3-ethylpiperazine-1-carboxamido)-2-oxopyrimidin-1(2H)-yl)benzyl)piperidin-4-yl)carbamate tert-Butyl (1-(4-(4-(3-ethyl-4-(2,2,2-trifluoroacetyl)piperazine-1-carboxamido)-2-oxopyrimidin-1(2H)-yl)benzyl)piperidin-4-yl)carbamate (138 mg, 0.21 mmol.) and LiOH·$H_2O$ (97 mg, 2.1 mmol) were suspended in THF:$H_2O$ (1:1) and stirred at rt for 2 h. The reaction mixture was concentrated under reduced pressure, and the residue was diluted with $H_2O$ (50 mL) and the extracted with $CHCl_3$ (3×50 mL). The organic layers were dried over $Na_2SO_4$, filtered and concentrated under reduced pressure to yield the title compound.

Step 3: tert-butyl (1-(4-(4-(4-(2-((tert-butoxycarbonyl)amino)-2-methylpropanoyl)-3-ethylpiperazine-1-carboxamido)-2-oxopyrimidin-1(2H)-yl)benzyl)piperidin-4-yl)carbamate To a suspension of 2-((tert-butoxycarbonyl)amino)-2-methylpropanoic acid (28 mg, 0.14 mmol) and HATU (52 mg, 0.14 mmol) in DMF, was added DIPEA (0.03 mL, 0.17 mmol). The suspension was stirred for 10 min, a solution of tert-butyl (1-(4-(4-(3-ethylpiperazine-1-carboxamido)-2-oxopyrimidin-1(2H)-yl)benzyl)piperidin-4-yl)carbamate (75 mg, 0.14 mmol) in DMF was added dropwise. The mixture was stirred at 50° C. for 16 h. Sat. aq. LiCl (10 mL) was added and the mixture was extracted with EtOAc (1×15 mL). The organic layer was concentrated under reduced pressure and purified by column chromatography ($CHCl_3$: MeOH) to afford the title compound.

Step 4: 4-(2-amino-2-methylpropanoyl)-N-(1-(4-((4-aminopiperidin-1-yl)methyl)phenyl)-2-oxo-1,2-dihydropyrimidin-4-yl)-3-ethylpiperazine-1-carboxamide hydrochloride salt tert-Butyl (1-(4-(4-(4-(2-((tert-butoxycarbonyl)amino)-2-methylpropanoyl)-3-ethylpiperazine-1-carboxamido)-2-oxopyrimidin-1(2H)-yl)benzyl)piperidin-4-yl)carbamate (80 mg, 0.11 mmol) in HCl in MeOH (2N, 10 mL) was stirred at rt for 4 h, concentrated under reduced pressure to afford the title compound as a white solid. $^1$H NMR (400 MHz, $CD_3OD$) δ 8.35 (s, 1H), 7.85 (d, 2H), 7.67 (d, 2H), 6.90 (s, 1H), 4.47 (s, 2H), 4.35 (s, 2H), 3.63 (d, 2H), 3.52 (t, 2H), 3.28-3.11 (s, 5H), 2.29 (d, 3H), 2.11 (t, 2H), 1.74 (s, 3H), 1.58 (s, 3H), 1.29 (s, 2H), 0.95 (t, 3H). LCMS [M+H] 525.2.

Compound 72

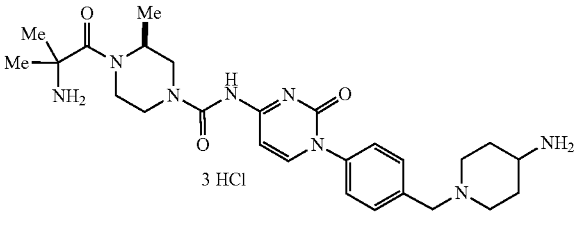

(S)-4-(2-Amino-2-methylpropanoyl)-N-(1-(4-((4-aminopiperidin-1-yl)methyl)phenyl)-2-oxo-1,2-dihydropyrimidin-4-yl)-3-methylpiperazine-1-carboxamide hydrochloride salt Prepared in a similar fashion as scheme C-7 from tert-butyl (1-(4-(4-(1H-imidazole-1-carboxamido)-2-oxopyrimidin-1(2H)-yl)benzyl)piperidin-4-yl)carbamate and 2-((tert-butoxycarbonyl)amino)-2-methylpropanoic acid. $^1$H NMR (400 MHz, Methanol-$d_4$) δ 8.34 (s, 1H), 7.86 (d, 2H), 7.68 (d, 2H), 6.91 (s, 1H), 4.48 (s, 2H), 4.27 (d, 2H), 3.73-3.16 (m, 10H), 2.29 (d, 2H), 2.11 (t, 2H), 1.73 (s, 3H), 1.71 (s, 3H), 1.31 (d, 3H). LCMS [M+H] 511.3.

Compound 65

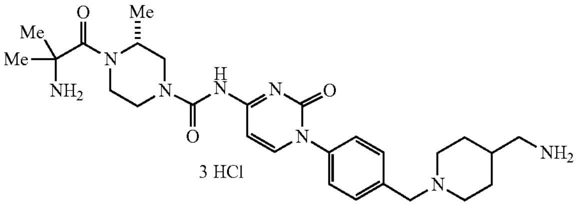

(R)-4-(2-Amino-2-methylpropanoyl)-N-(1-(4-((4-(aminomethyl)piperidin-1-yl)methyl)phenyl)-2-oxo-1,2-dihydropyrimidin-4-yl)-3-methylpiperazine-1-carboxamide hydrochloride salt Prepared in a similar fashion as Scheme C-7 from (R)-tert-butyl ((1-(4-(4-(3-methylpiperazine-1-carboxamido)-2-oxopyrimidin-1(2H)-yl)benzyl)piperidin-4-yl)methyl)carbamate and 2-((tert-butoxycarbonyl)amino)-2-methylpropanoic acid. $^1$H NMR (400 MHz, $D_2O$) δ 7.95 (d, 1H), 7.73 (d, 2H), 7.62 (d, 2H), 6.93 (d, 1H), 4.53 (s, 2H), 4.24 (s, 1H), 4.14-3.97 (m, 2H), 3.87-3.64 (m, 3H), 3.41 (s, 2H), 3.27 (d, 2H), 2.97 (s, 1H) 2.50 (s, 2H), 1.93-1.72 (m, 6H), 1.68 (s, 3H), 1.55 (s, 2H), 1.34 (d, 3H).

Compound 73

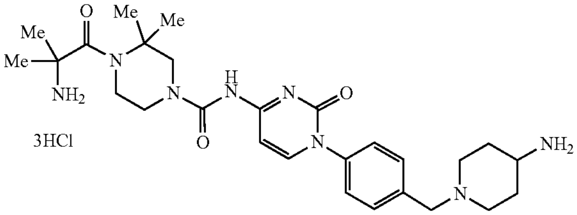

4-(2-Amino-2-methylpropanoyl)-N-(1-(4-((4-aminopiperidin-1-yl)methyl)phenyl)-2-oxo-1,2-dihydropyrimidin-4-yl)-3,3-dimethylpiperazine-1-carboxamide hydrochloride salt Prepared in a similar fashion as scheme C-7 from tert-butyl (1-(4-(4-(3,3-dimethylpiperazine-1-carboxamido)-2-oxopyrimidin-1(2H)-yl)benzyl)piperidin-4-yl)carbamate and 2-((tert-butoxycarbonyl)amino)-2-methylpropanoic acid. $^1$H NMR (400 MHz, Methanol-$d_4$) δ 7.94 (d, 1H), 7.81 (d, 2H), 7.63 (d, 2H), 6.64 (s, 1H), 4.47 (s, 2H), 3.97 (s, 2H), 3.77 (d, 2H), 3.66 (d, 2H), 3.52 (s, 2H), 3.25 (s, 2H), 2.30 (d, 2H), 2.11 (t, 2H), 1.71 (s, 2H), 1.49 (d, 6H), 1.31 (s, 6H). LCMS [M+H] 525.3.

Compound 66

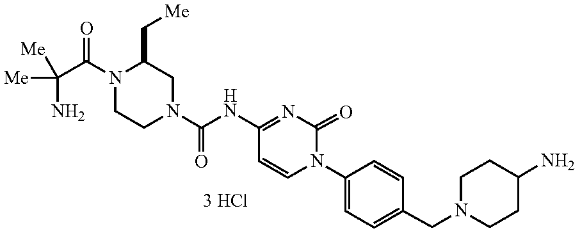

(S)-4-(2-Amino-2-methylpropanoyl)-N-(1-(4-((4-aminopiperidin-1-yl)methyl)phenyl)-2-oxo-1,2-dihydropyrimidin-4-yl)-3-ethylpiperazine-1-carboxamide hydrochloride salt Prepared in a similar fashion as Scheme C-7 from (S)-tert-butyl (1-(4-(4-(3-ethylpiperazine-1-carboxamido)-2-oxopyrimidin-1(2H)-yl)benzyl)piperidin-4-yl)carbamate and 2-((tert-butoxycarbonyl)amino)-2-methylpropanoic acid. $^1$H NMR (400 MHz, $D_2O$) δ 7.93 (d, 1H), 7.71 (d, 2H), 7.59 (d, 2H), 6.84 (d, 1H), 4.46 (s, 2H), 4.19 (d, 2H), 4.00 (d, 1H), 3.77-3.63 (m, 2H), 3.58 (s, 2H), 3.35-3.30 (m, 1H) 3.30-3.15 (m, 4H), 2.36 (d, 2H), 2.02-1.85 (m, 2H),), 1.60 (d, 6H), 1.37-1.23 (m, 2H) 0.86 (s, 3H). LCMS [M+H] 525.3.

Compound 67

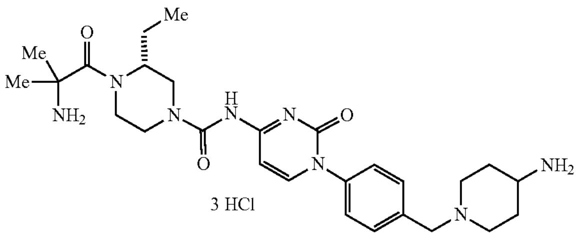

(R)-4-(2-Amino-2-methylpropanoyl)-N-(1-(4-((4-aminopiperidin-1-yl)methyl)phenyl)-2-oxo-1,2-dihydropyrimidin-4-yl)-3-ethylpiperazine-1-carboxamide hydrochloride salt Prepared in a similar fashion as Scheme C-7 from (R)-tert-butyl (1-(4-(4-(3-ethylpiperazine-1-carboxamido)-2-oxopyrimidin-1(2H)-yl)benzyl)piperidin-4-yl)carbamate and 2-((tert-butoxycarbonyl)amino)-2-methylpropanoic acid. $^1$H NMR (400 MHz, $D_2O$) δ 7.98 (d, 1H), 7.71 (d, 2H), 7.60 (d, 2H), 6.84 (d, 1H), 4.58 (s, 1H), 4.46 (s, 2H), 4.22 (d, 2H), 4.02 (d, 1H), 3.71 (d, 2H), 3.62-3.55 (m, 2H), 3.22 (t, 4H), 2.36 (d, 2H), 1.00-1.90 (m, 2H), 1.76 (d, 6H), 1.73-1.63 (m, 2H), 0.86 (s, 3H). LCMS [M+H] 525.2.

Compound 68

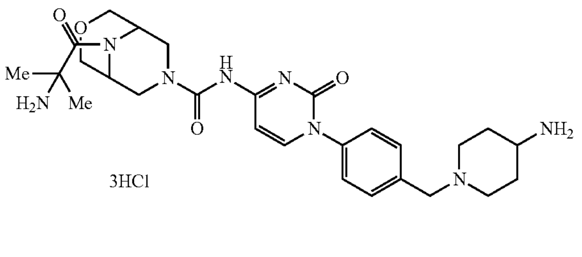

9-(2-Amino-2-methylpropanoyl)-N-(1-(4-((4-aminopiperidin-1-yl)methyl)phenyl)-2-oxo-1,2-dihydropyrimidin-4-yl)-3-oxa-7,9-diazabicyclo[3.3.1] nonane-7-carboxamide hydrochloride salt Prepared in a similar fashion as Scheme C-7 from tert-butyl (1-(4-(4-(3-oxa-8,10-diazabicyclo[4.3.1]decane-8-carboxamido)-2-oxopyrimidin-1(2H)-yl)benzyl)piperidin-4-yl) carbamate and 2-((tert-butoxycarbonyl)amino)-2-methylpropanoic acid. $^1$H NMR (400 MHz, $D_2O$) δ 8.05 (d, 1H), 7.72 (d, 2H), 7.61 (d, 2H), 6.79 (d, 1H), 4.64-4.37 (m, 6H), 4.17 (d, 2H), 3.94 (s, 2H), 3.71 (d, 2H), 3.59 (t, 2H), 3.21 (t, 2H), 2.36 (d, 2H), 2.07-1.88 (m, 2H), 1.75 (s, 6H), 1.59 (d, 1H). LCMS [M+H] 539.2.

Compound 69

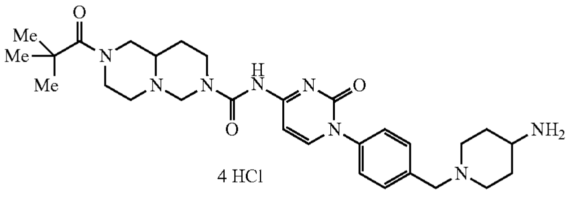

8-(2-Amino-2-methylpropanoyl)-N-(1-(4-((4-aminopiperidin-1-yl)methyl)phenyl)-2-oxo-1,2-dihydropyrimidin-4-yl)hexahydro-1H-pyrazino[1,2-a]pyrazine-2(6H)-carboxamide hydrochloride salt Prepared in a similar fashion as Scheme C-7 from tert-butyl (1-(4-(4-(octahydro-1H-pyrazino[1,2-a]pyrazine-2-carboxamido)-2-oxopyrimidin-1(2H)-yl)benzyl)piperidin-4-yl)carbamate and 2-((tert-butoxycarbonyl)amino)-2-methylpropanoic acid. $^1$H NMR (400 MHz, $D_2O$) δ 7.90 (d, 1H), 7.71 (d, 2H), 7.59 (d, 2H), 6.76 (d, 1H), 4.56 (s, 2H), 4.46 (s, 2H), 3.76-3.66 (m, 4H), 3.66-3.45 (m, 2H), 3.22 (d, 4H), 2.36 (d, 2H), 2.02-1.86 (m, 2H), 1.75 (s, 6H), 1.35 (d, 4H), 1.29 (t, 2H). LCMS [M+H] 552.2.

Compound 70

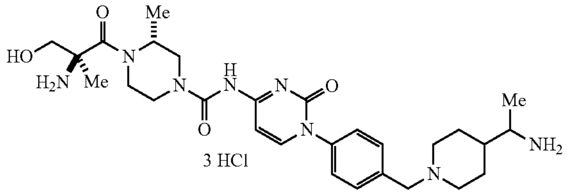

(3R)-4-((S)-2-Amino-3-hydroxy-2-methylpropanoyl)-N-(1-(4-((4-(1-aminoethyl)piperidin-1-yl)methyl)phenyl)-2-oxo-1,2-dihydropyrimidin-4-yl)-3-methylpiperazine-1-carboxamide hydrochloride salt Prepared in a similar fashion as Scheme C-7 from tert-butyl (1-(1-(4-(4-((R)-3-methylpiperazine-1-carboxamido)-2-oxopyrimidin-1(2H)-yl)benzyl)piperidin-4-yl)ethyl)carbamate and (2R,4S)-2-(tert-butyl)-4-methyloxazolidine-4-carboxylic acid. LCMS [M+H] 555.4.

Compound 71

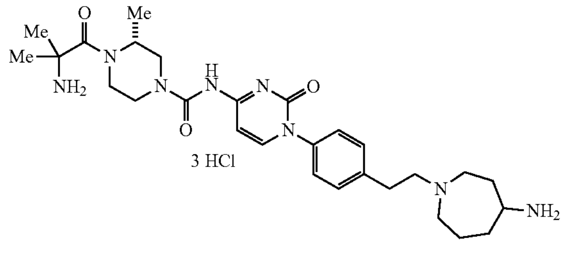

(3R)-4-(2-Amino-2-methylpropanoyl)-N-(1-(4-(2-(4-aminoazepan-1-yl)ethyl)phenyl)-2-oxo-1,2-dihydropyrimidin-4-yl)-3-methylpiperazine-1-carboxamide hydrochloride salt Prepared in a similar fashion as Scheme C-7 from tert-butyl (1-(4-(4-((R)-3-methylpiperazine-1-carboxamido)-2-oxopyrimidin-1(2H)-yl)phenethyl)azepan-4-yl)carbamate and 2-((tert-butoxycarbonyl)amino)-2-methylpropanoic acid. $^1H$ NMR (400 MHz, $D_2O$) δ 7.78 (d, 1H), 7.36 (d, 2H), 7.29 (d, 2H), 6.70 (d, 1H), 4.01 (s, 1H), 3.87 (s, 1H), 3.58 (s, 2H), 3.49-3.32 (m, 5H), 3.33-2.95 (m, 7H), 2.18 (s, 2H), 2.04-1.79 (m, 2H), 1.59 (d, 7H), 1.41-0.95 (m, 4H). LCMS [M+H] 539.3.

Compound 74

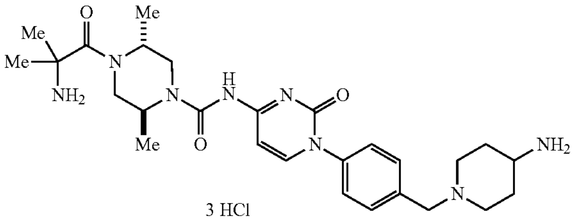

(2S,5R)-4-(2-Amino-2-methylpropanoyl)-N-(1-(4-((4-aminopiperidin-1-yl)methyl)phenyl)-2-oxo-1,2-dihydropyrimidin-4-yl)-2,5-dimethylpiperazine-1-carboxamide hydrochloride salt Prepared in a similar fashion as scheme C-7 from tert-butyl (1-(4-(4-((2S,5R)-2,5-dimethylpiperazine-1-carboxamido)-2-oxopyrimidin-1(2H)-yl)benzyl)piperidin-4-yl) carbamate and 2-((tert-butoxycarbonyl)amino)-2-methylpropanoic acid. $^1H$ NMR (400 MHz, $D_2O$) δ 7.89 (d, 1H), 7.71 (d, 2H), 7.60 (d, 2H), 6.85 (d, 1H), 4.61 (s, 2H), 4.47 (s, 2H), 4.03 (d, 2H), 3.72 (d, 2H), 3.59 (t, 1H), 3.37 (s, 2H), 3.23 (s, 2H), 2.37 (d, 2H), 1.96 (d, 2H), 1.78 (s, 6H), 1.47-1.15 (m, 6H). LCMS [M+H] 525.3.

Compound 75

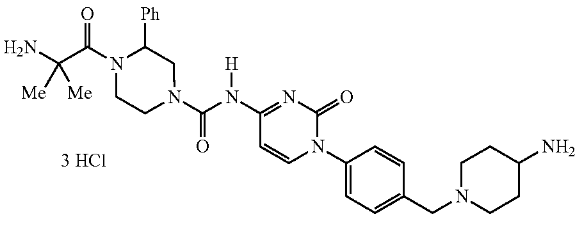

4-(2-Amino-2-methylpropanoyl)-N-(1-(4-((4-aminopiperidin-1-yl)methyl)phenyl)-2-oxo-1,2-dihydropyrimidin-4-yl)-3-phenylpiperazine-1-carboxamide hydrochloride salt Prepared in a similar fashion as scheme C-7 from tert-butyl (1-(4-(2-oxo-4-(3-phenylpiperazine-1-carboxamido) pyrimidin-1(2H)-yl)benzyl)piperidin-4-yl)carbamate and 2-((tert-butoxycarbonyl)amino)-2-methylpropanoic acid. LCMS [M+H] 573.2.

Compound 76

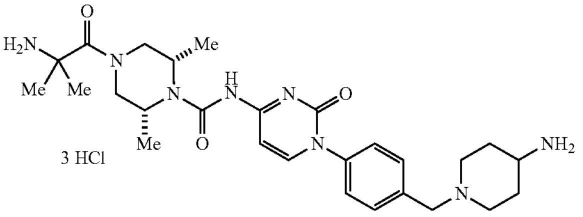

cis-4-(2-Amino-2-methylpropanoyl)-N-(1-(4-((4-aminopiperidin-1-yl)methyl)phenyl)-2-oxo-1,2-dihydropyrimidin-4-yl)-2,6-dimethylpiperazine-1-carboxamide hydrochloride salt Prepared in a similar fashion as scheme C-7 from tert-butyl (1-(4-(4-(cis-2,6-dimethylpiperazine-1-carboxamido)-2-oxopyrimidin-1(2H)-yl)benzyl)piperidin-4-yl)carbamate and 2-((tert-butoxycarbonyl)amino)-2-methylpropanoic acid. $^1H$ NMR (500 MHz, $CD_3OD$) δ 8.27-8.40 (m, 1H), 7.85 (d, 2H), 7.66 (d, 2H), 6.89-7.01 (m, 1H), 4.55-4.69 (m, 2H), 4.46 (s, 2H), 4.23-4.39 (m, 2H), 3.58-3.68 (m, 2H), 3.45-3.57 (m, 1H), 3.19-3.40 (m, 4H), 2.22-2.35 (m, 2H), 2.03-2.17 (m, 2H), 1.74 (s, 6H), 1.34-1.45 (m, 6H). LCMS [M+H] 525.3.

Compound 77

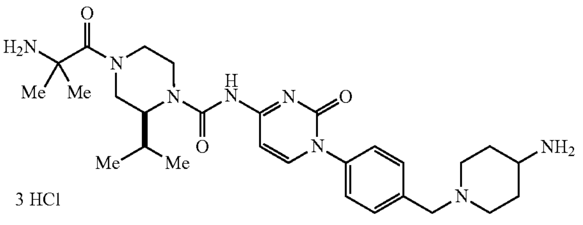

(S)-4-(2-Amino-2-methylpropanoyl)-N-(1-(4-((4-aminopiperidin-1-yl)methyl)phenyl)-2-oxo-1,2-dihydropyrimidin-4-yl)-2-isopropylpiperazine-1-carboxamide hydrochloride salt Prepared in a similar fashion as scheme C-7 from tert-butyl (S)-(1-(4-(4-(2-isopropylpiperazine-1-carboxamido)-2-oxopyrimidin-1(2H)-yl)benzyl)piperidin-4-yl)carbamate and 2-((tert-butoxycarbonyl)amino)-2-methylpropanoic acid. $^1H$ NMR (500 MHz, $CD_3OD$) δ 8.39 (d, 1H), 7.85 (d, 2H), 7.67 (d, 2H), 6.85-7.08 (m, 1H), 4.47 (s, 2H), 4.25-4.37 (m, 1H), 4.14-4.24 (m, 2H), 3.58-3.68 (m, 2H), 3.37-3.57 (m, 3H), 3.19-3.28 (m, 2H), 2.94-3.17 (m, 2H), 2.28 (d, 2H), 2.04-2.17 (m, 2H), 1.90-2.04 (m, 1H), 1.75 (s, 3H), 1.69 (s, 3H), 1.05-1.17 (m, 3H), 0.92 (d, 3H). LCMS [M+H] 539.3.

Compound 79

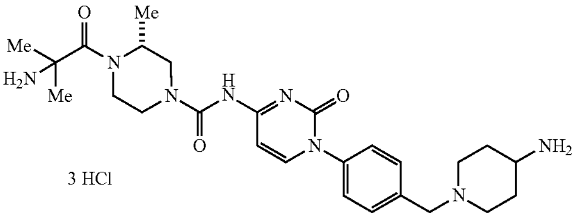

3 HCl (R)-4-(2-Amino-2-methylpropanoyl)-N-(1-(4-((4-aminopiperidin-1-yl)methyl)phenyl)-2-oxo-1,2-dihydropyrimidin-4-yl)-3-methylpiperazine-1-carboxamide hydrochloride salt Prepared in a similar fashion as scheme C-7 from tert-butyl (R)-(1-(4-(4-(3-methylpiperazine-1-carboxamido)-2-oxopyrimidin-1(2H)-yl)benzyl)piperidin-4-yl)carbamate and 2-((tert-butoxycarbonyl)amino)-2-methylpropanoic acid. LCMS [M+H] 511.3.

Compound 80

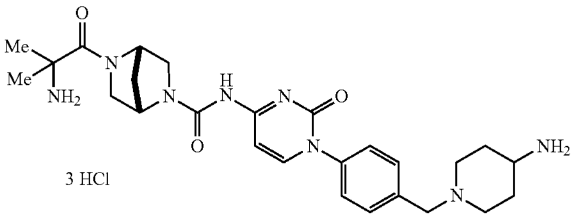

3 HCl cis-5-(2-Amino-2-methylpropanoyl)-N-(1-(4-((4-aminopiperidin-1-yl)methyl)phenyl)-2-oxo-1,2-dihydropyrimidin-4-yl)-2,5-diazabicyclo[2.2.1]heptane-2-carboxamide hydrochloride salt Prepared in a similar fashion as scheme C-7 from tert-butyl (1-(4-(4-(cis-2,5-diazabicyclo[2.2.1]heptane-2-carboxamido)-2-oxopyrimidin-1(2H)-yl)benzyl)piperidin-4-yl) carbamate and 2-((tert-butoxycarbonyl)amino)-2-methylpropanoic acid. LCMS [M+H] 509.3.

Compound 81

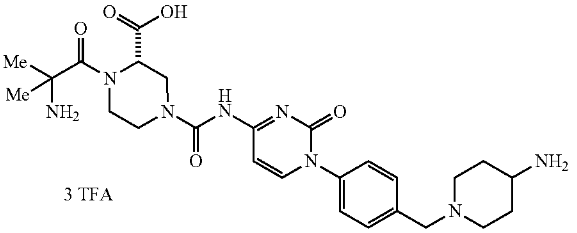

3 TFA (S)-1-(2-Amino-2-methylpropanoyl)-4-((1-(4-((4-aminopiperidin-1-yl)methyl)phenyl)-2-oxo-1,2-dihydropyrimidin-4-yl)carbamoyl)piperazine-2-carboxylic acid trifluoroacetate salt Prepared in a similar fashion as scheme C-7 from methyl (S)-4-((1-(4-((4-((tert-butoxycarbonyl)amino)piperidin-1-yl)methyl)phenyl)-2-oxo-1,2-dihydropyrimidin-4-yl)carbamoyl)piperazine-2-carboxylate and 2-((tert-butoxycarbonyl)amino)-2-methylpropanoic acid. LCMS [M+H] 456.3.

Compound 206

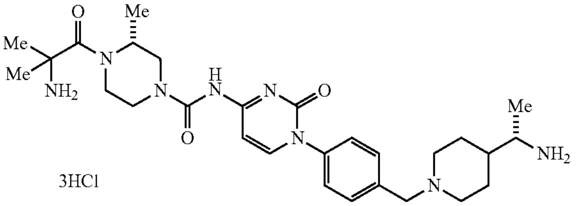

3HCl (R)-4-(2-Amino-2-methylpropanoyl)-N-(1-(4-((4-((S)-1-aminoethyl)piperidin-1-yl)methyl)phenyl)-2-oxo-1,2-dihydropyrimidin-4-yl)-3-methylpiperazine-1-carboxamide hydrochloride salt Scheme C-8

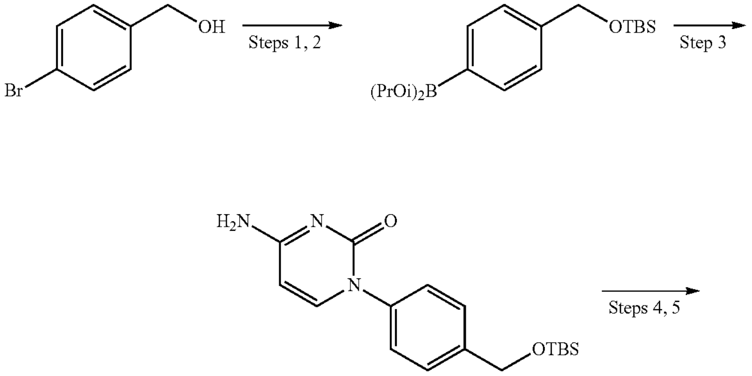

-continued

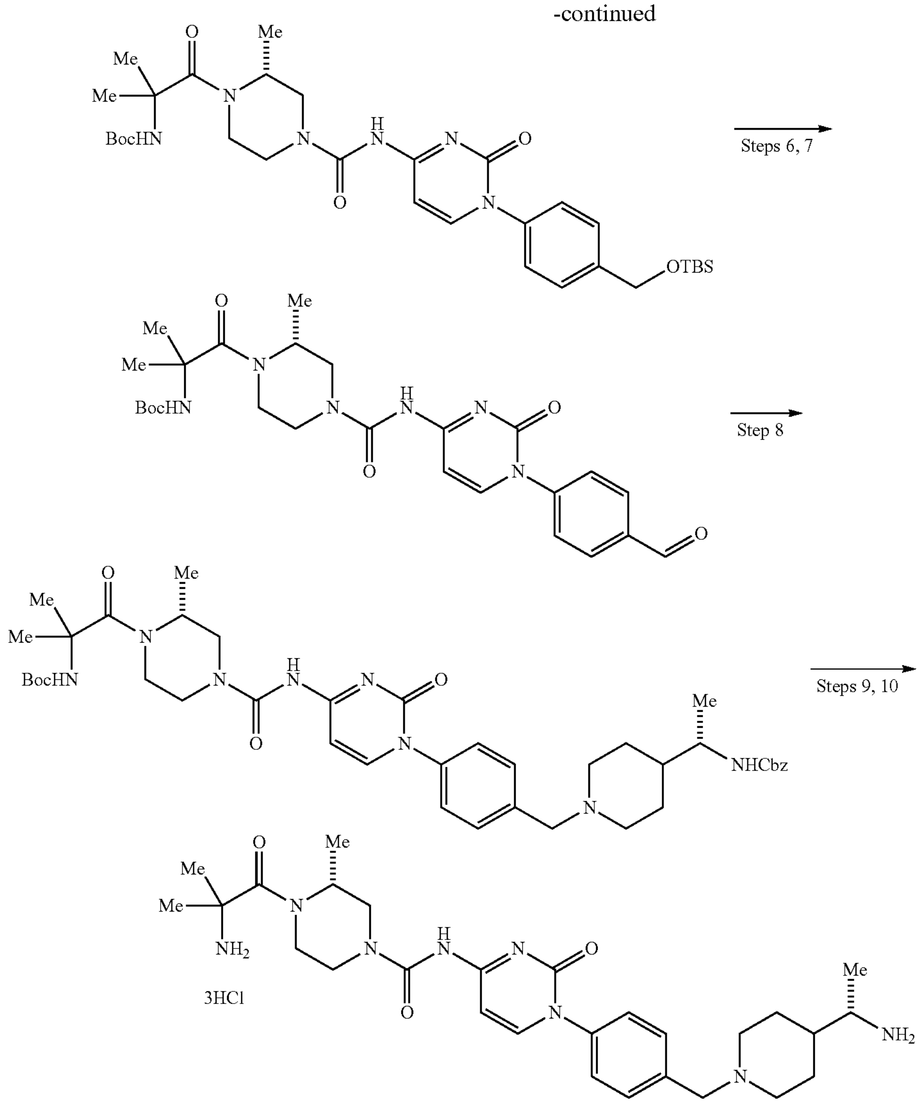

Reagents: 1) TBSCl, imidazole, $CH_2Cl_2$, rt, 16 h 2) BuLi, THF, -78° C. $(iPrO)_3B$ 3) cytosine, TMEDA, $Cu(OAc)_2{\cdot}H_2O$, 4:1 MeOH:$H_2O$ rt, 48 h 4) CDI, $CH_2Cl_2$, rt, 4 h 5) tert-butyl (R)-(2-methyl-1-(2-methylpiperazin-1-yl)-1-oxopropan-2-yl)carbamate, $CH_3CN$, 85° C., 16 h 6) TBAF, THF 0° C. to rt, 16 h 7) Dess-Martin periodinane, 0.1% $H_2O$:$CH_2Cl_2$ 8) benzyl (S)-(1 (piperidin-4-yl)ethyl)carbamate, $Na(OAc)_3BH$, DIPEA, DCE, rt, 16 h 9) Degussa type Pd/C, $H_2$, MeOH, rt 16 h 10) HCl in MeOH, rt, 8 h.

Step 1: ((4-bromobenzyl)oxy)(tert-butyl)dimethylsilane

To a solution of (4-bromophenyl)methanol (2.0 g, 10.6 mmol) in $CH_2Cl_2$ (50 mL) was added imidazole (1.4 g, 21.2 mmol) and tert-butyldimethylsilyl chloride (1.9 g, 12.6 mmol). The solution was stirred for 16 h. The reaction mixture was concentrated under reduced pressure and the solid dissolved in EtOAc (100 mL) and washed with $H_2O$ (100 mL). The organic layer was dried over $Na_2SO_4$ and concentrated under reduced pressure and purified by flash chromatography (Hexanes:EtOAc) to afford the title compound.

Step 2: diisopropyl (4-(((tert-butyldimethylsilyl)oxy)methyl)phenyl)boronate A solution of ((4-bromobenzyl)oxy)(tert-butyl)dimethylsilane (2.0 g, 6.67 mmol) in THF (50 mL) was cooled to −78° C. 2.5M BuLi in Hexanes (8.0 mL) was added dropwise over 30 min. and the temperature maintained below −60° C. The reaction was stirred for 25 min. Triisopropyl borate (2.3 mL, 10.0 mmol) was added dropwise over 30 min. The reaction mixture was warmed to rt and stirred for 15 min. 2N HCl (50 mL) was added and the reaction was stirred for 30 min. The biphasic mixture was separated and the aq. layer extracted with $CH_2Cl_2$ (2×50 mL). The combined organics were dried over $Na_2SO_4$ and concentrated under reduced pressure to afford the title compound.

Step 3: 4-amino-1-(4-(((tert-butyldimethylsilyl)oxy)methyl)phenyl)pyrimidin-2(1H)-one A suspension of cytosine (0.74 g, 6.67 mmol) and diisopropyl (4-(((tert-butyldimethylsilyl)oxy)methyl)phenyl)boronate (2.3 g, 6.67 mmol), in MeOH:$H_2O$ (4:1, 60 ml) was stirred at rt in open air for 30 min. TMEDA (1.2 ml, 8.0 mmol) and $Cu(OAc)_2H_2O$ (1.33 g, 6.67 mmol) were added and the reaction was stirred in open air for 48 h at rt. The reaction mixture was concentrated under reduced pressure, and cold $H_2O$ (100 mL) was added. The solid was filtered and washed with $H_2O$ (2×15 mL) and $Et_2O$ (3×10 mL) to afford the title compound.

Step 4: N-(1-(4-(((tert-butyldimethylsilyl)oxy)methyl)phenyl)-2-oxo-1,2-dihydropyrimidin-4-yl)-1H-imidazole-1-carboxamide A suspension of 4-amino-1-(4-(((tert-butyldimethylsilyl)oxy)methyl)phenyl)pyrimidin-2(1H)-one (500 mg, 1.5 mmol) and 1,1'-carbonyldiimidazole (365 mg, 2.25 mmol) in dry $CH_2Cl_2$ was stirred for 16 h at rt. The solvent was removed under reduced pressure, and the solid was triturated with EtOAc to give the title compound which was used in the next step without further purification.

Step 5: (R)-tert-butyl (1-(4-((1-(4-(((tert-butyldimethylsilyl)oxy)methyl)phenyl)-2-oxo-1,2-dihydropyrimidin-4-yl)carbamoyl)-2-methylpiperazin-1-yl)-2-methyl-1-oxopropan-2-yl)carbamate N-(1-(4-(((tert-butyldimethylsilyl)oxy)methyl)phenyl)-2-oxo-1,2-dihydropyrimidin-4-yl)-1H-imidazole-1-carboxamide (141 mg, 0.33 mmol) and (R)-tert-butyl (2-methyl-1-(2-methylpiperazin-1-yl)-1-oxopropan-2-yl)carbamate as prepared in Scheme 1 step 2, (95 mg, 0.33 mmol) were dissolved in $CH_3CN$ and heated to reflux for 2 h. The reaction mixture was concentrated under reduced pressure and the crude reaction mixture was dissolved in EtOAc (25 mL) and washed with water (3×25 mL). Purification by flash chromatography ($MeOH/CHCl_3$) yielded the title compound.

Step 6: (R)-tert-butyl (1-(4-((1-(4-(hydroxymethyl)phenyl)-2-oxo-1,2-dihydropyrimidin-4-yl)carbamoyl)-3-methylpiperazin-1-yl)-2-methyl-1-oxopropan-2-yl)carbamate To a solution of (R)-tert-butyl (1-(4-((1-(4-(((tert-butyldimethylsilyl)oxy)methyl)phenyl)-2-oxo-1,2-dihydropyrimidin-4-yl)carbamoyl)-2-methylpiperazin-1-yl)-2-methyl-1-oxopropan-2-yl)carbamate (90 mg, 0.14 mmol) in THF (10 mL) at 0° C. was added 2M TBAF in THF (0.28 mL) over 5 min. The solution was stirred for 16 h. The crude reaction mixture was concentrated under reduced pressure to give an oily residue, which was purified by flash chromatography to afford the title compound.

Step 7: (R)-tert-butyl (1-(4-((1-(4-formylphenyl)-2-oxo-1,2-dihydropyrimidin-4-yl)carbamoyl)-2-methylpiperazin-1-yl)-2-methyl-1-oxopropan-2-yl)carbamate To a stirred solution of (R)-tert-butyl (1-(4-((1-(4-(hydroxymethyl)phenyl)-2-oxo-1,2-dihydropyrimidin-4-yl)carbamoyl)-3-methylpiperazin-1-yl)-2-methyl-1-oxopropan-2-yl)carbamate (150.0 mg, 0.24 mmol) in 0.1% $H_2O:CH_2Cl_2$ (10 mL) was added Dess-Martin periodinane (100 mg, 0.25 mmol). The solution was stirred for 1 h. The crude reaction mixture was dissolved in additional $CH_2Cl_2$(20 mL) and washed with aq. $NaHCO_3/Na_2SO_2O_3$ (1×20 mL). The aq. layer was extracted with $CH_2Cl_2$(1×10 mL). The combined organic layers were dried over $Na_2SO_4$ and concentrated under reduced pressure to give the title compound.

Step 8: tert-butyl (1-((R)-4-((1-(4-((4-((S)-1-(((benzyloxy)carbonyl)amino)ethyl)piperidin-1-yl)methyl)phenyl)-2-oxo-1,2-dihydropyrimidin-4-yl)carbamoyl)-2-methylpiperazin-1-yl)-2-methyl-1-oxopropan-2-yl)carbamate To a stirred solution (R)-tert-butyl (1-(4-((1-(4-formylphenyl)-2-oxo-1,2-dihydropyrimidin-4-yl)carbamoyl)-2-methylpiperazin-1-yl)-2-methyl-1-oxopropan-2-yl)carbamate (15 mg, 0.03 mmol) in DCE (10 mL) was added (S)-benzyl (1-(piperidin-4-yl)ethyl)carbamate (7.8 mg, 0.035 mmol) followed by $Na(OAc)_3BH$ (13 mg, 0.06 mmol) and DIPEA (0.01 mL, 0.06 mmol). The reaction was stirred for 16 h. The reaction mixture was treated with 1 N NaOH (10 mL) and extracted with $CH_2Cl_2$ (2×20 mL). The combined organics were dried over $Na_2SO_4$ and concentrated under reduced pressure to afford the title compound, which was used in the next reaction without further purification Step 9: tert-butyl (1-((R)-4-((1-(4-((4-((S)-1-aminoethyl)piperidin-1-yl)methyl)phenyl)-2-oxo-1,2-dihydropyrimidin-4-yl)carbamoyl)-2-methylpiperazin-1-yl)-2-methyl-1-oxopropan-2-yl)carbamate To a mixture of tert-butyl (1-((R)-4-((1-(4-((4-((S)-1-(((benzyloxy)carbonyl)amino)ethyl)piperidin-1-yl)methyl)phenyl)-2-oxo-1,2-dihydropyrimidin-4-yl)carbamoyl)-2-methylpiperazin-1-yl)-2-methyl-1-oxopropan-2-yl)carbamate (12 mg, 0.03 mmol) and Degussa type Pd/C (10% wt, 2.4 mg) at rt was added MeOH under $N_2$. The reaction mixture was flushed with $H_2$ and stirred for 16 h under $H_2$ atmosphere. The reaction mixture was filtered through Celite®. The organic layer was concentrated under reduced pressure to afford the title compound.

Step 10: (R)-4-(2-amino-2-methylpropanoyl)-N-(1-(4-((4-((S)-1-aminoethyl)piperidin-1-yl)methyl)phenyl)-2-oxo-1,2-dihydropyrimidin-4-yl)-3-methylpiperazine-1-carboxamide hydrochloride salt tert-Butyl tert-butyl (1-((R)-4-((1-(4-((4-((S)-1-aminoethyl)piperidin-1-yl)methyl)phenyl)-2-oxo-1,2-dihydropyrimidin-4-yl)carbamoyl)-2-methylpiperazin-1-yl)-2-methyl-1-oxopropan-2-yl)carbamate was dissolved in a solution of HCl/MeOH (5 mL) and stirred for 8 h. The solvent was evaporated and the crude solid was purified by RPHPLC ($H_2O:CH_3CN:TFA$) and concentrated under reduced pressure. Addition of HCl/MeOH (3×15 mL) and evaporation under reduced pressure afforded the title compound. $^1H$ NMR (400 MHz, $D_2O$) δ 7.84 (d, 1H), 7.63 (d, 2H), 7.51 (d, 2H), 7.39 (d, 1H), 4.36 (s, 2H), 4.09 (d, 1H), 3.93 (t, 2H), 3.64-3.55 (m, 4H), 3.26 (s, 2H), 3.05 (t, 2H), 2.57 (s, 1H), 2.03 (d, 4H), 1.90 (s, 1H), 1.67 (d, 6H), 1.56 (s, 2H), 1.23 (d, 4H). LCMS [M+H] 539.4.

Compound 207

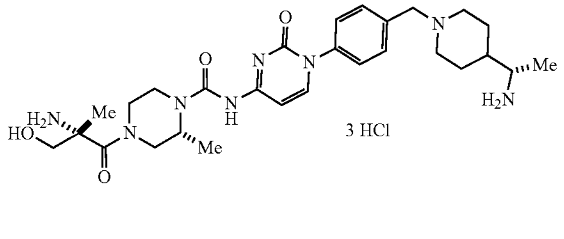
3 HCl (R)-4-((S)-2-Amino-3-hydroxy-2-methylpropanoyl)-N-(1-(4-((4-((S)-1-aminoethyl)piperidin-1-yl)methyl)phenyl)-2-oxo-1,2-dihydropyrimidin-4-yl)-2-methylpiperazine-1-carboxamide hydrochloride salt Prepared as is scheme C-8 from tert-butyl (2R,4S)-2-(tert-butyl)-4-((R)-4-((1-(4-formylphenyl)-2-oxo-1,2-dihydropyrimidin-4-yl)carbamoyl)-3-methylpiperazine-1-carbonyl)-4-methyloxazolidine-3-carboxylate and (S)-benzyl (1-(piperidin-4-yl)ethyl)carbamate. $^1$H NMR (400 MHz, $D_2O$) δ 7.83 (d, 1H), 7.63 (d, 2H), 7.51 (d, 2H), 6.80 (d, 1H), 4.50 (s, 2H), 4.36 (s, 2H), 4.18 (s, 1H), 4.13 (d, 1H), 4.02 (s, 1H), 3.86 (d, 1H), 3.60 (d, 2H), 3.40 (s, 2H), 3.29-3.21 (m, 1H), 3.05 (t, 2H), 2.03 (d, 2H), 2.01-1.96 (m, 1H), 1.89 (s, 1H), 1.67 (s, 3H), 1.55 (s, 2H), 1.26-1.17 (m, 6H). LCMS [M+H] 555.3.

Compound 91

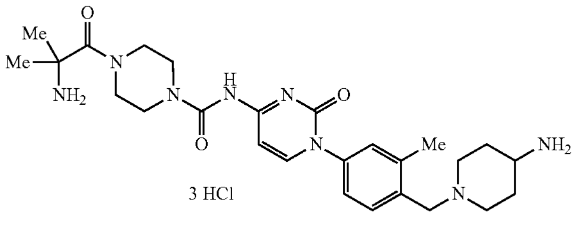

3 HCl 4-(2-Amino-2-methylpropanoyl)-N-(1-(4-((4-aminopiperidin-1-yl)methyl)-3-methylphenyl)-2-oxo-1,2-dihydropyrimidin-4-yl)piperazine-1-carboxamide hydrochloride salt Scheme C-9

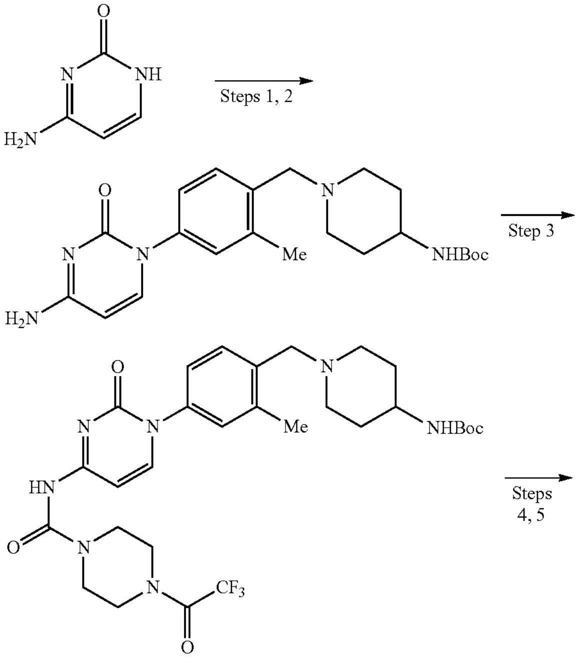

-continued

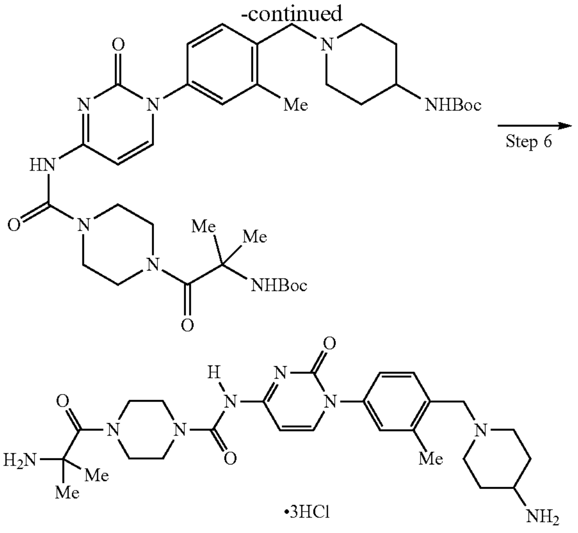

Reagents: 1) (4-formyl-3-methylphenyl)boronic acid, TMEDA, $Cu(OAc)_2$•$H_2O$, MeOH:$H_2O$, rt, 16 h 2) DIPEA, $Na(OAc)_3BH$, DCE:$CH_3CN$, rt, 16 h 3) $CH_3CN$, 85° C., 16 h 4) $K_2CO_3$, MeOH, rt, 2 h 5) 2-((tert-butoxycarbonyl)amino)-2-methylpropanoic acid, HATU, DIPEA, $CH_2Cl_2$, rt, 16 h 6) HCl, MeOH, rt, 4 h.

Step 1: 4-(4-amino-2-oxopyrimidin-1(2H)-yl)-2-methylbenzaldehyde

A suspension of cytosine (2.60 g, 24 mmol) and (4-formyl-3-methylphenyl)boronic acid (3.53 g 24 mmol), in a mixture of solvents MeOH:$H_2O$ (4:1, 25 ml) was stirred at rt in open air. After 30 min., TMEDA (6.70 ml, 28 mmol) and $Cu(OAc)_2 \cdot H_2O$ (4.70 g, 24 mmol) were added. The reaction was stirred at rt in open air for 16 h. The MeOH was evaporated reduced pressure, and the remaining mixture was diluted with $H_2O$ and stirred for 15 min at 0° C., allowing a solid to precipitate. The solid was filtered and washed with $H_2O$ (lx 25 mL) and $Et_2O$ (1×25 mL) to yield the title compound.

Step 2: tert-butyl (1-(4-(4-amino-2-oxopyrimidin-1(2H)-yl)-2-methylbenzyl)piperidin-4-yl)carbamate To stirring suspension of 4-(4-amino-2-oxopyrimidin-1(2H)-yl)-3-methylbenzaldehyde (1.00 g 4.6 mmol) and tert-butyl piperidin-4-ylcarbamate (1.39 g, 7.0 mmol) in DCE: $CH_3CN$ (1:1, 25 mL), were added N,N-diisopropylethylamine (1.61 mL, 9.2 mmol) and $Na(OAc)_3BH$ (1.97 g, 9.3 mmol). The reaction was stirred for 16 h at rt and the solvent was evaporated reduced pressure. The solid was dissolved in $CHCl_3$ and washed with 10% NaOH. Purification via flash chromatography (MeOH/$CHCl_3$) yielded the title compound.

Step 3: tert-butyl (1-(2-methyl-4-(2-oxo-4-(4-(2,2,2-trifluoroacetyl)piperazine-1-carboxamido)pyrimidin-1(2H)-yl)benzyl)piperidin-4-yl)carbamate A solution of 3-methyl-1-(4-(2,2,2-trifluoroacetyl)piperazine-1-carbonyl)-1H-imidazol-3-ium iodide (211 mg, 0.72 mmol) and tert-butyl (1-(4-(4-amino-2-oxopyrimidin-1(2H)-yl)-3-methylbenzyl)piperidin-4-yl)carbamate (300 mg, 0.72 mmol), in dry $CH_3CN$ (12 mL) was heated to 85° C. and refluxed for 8 h. The solvent was removed under reduced pressure and the crude reaction mixture was partitioned between $CHCl_3$ (125 mL) and $H_2O$ (125 mL). The organic layer was concentrated under reduced pressure and purified by flash chromatography ($MeOH/CHCl_3$) to afford the title compound.

Step 4: tert-butyl (1-(3-methyl-4-(2-oxo-4-(piperazine-1-carboxamido)pyrimidin-1(2H)-yl)benzyl)piperidin-4-yl)carbamate tert-Butyl (1-(2-methyl-4-(2-oxo-4-(4-(2,2,2-trifluoroacetyl)piperazine-1-carboxamido)pyrimidin-1(2H)-yl)benzyl)piperidin-4-yl)carbamate (125 mg, 0.2 mmol) and $K_2CO_3$ (83 mg, 0.6 mmol) were dissolved in MeOH, and stirred at rt for 2 h and the solvent was removed under reduced pressure. The crude solid was dissolved in $H_2O$ (25 mL) and the aqueous layer was extracted with $CHCl_3$ (3×25 mL). The organic layers were dried over $Na_2SO_4$ and concentrated under reduced pressure to yield title compound.

Step 5: tert-butyl (1-(4-(4-(4-(2-((tert-butoxycarbonyl)amino)-3-methylpropanoyl)piperazine-1-carboxamido)-2-oxopyrimidin-1(2H)-yl)-2-methylbenzyl)piperidin-4-yl)carbamate To a suspension of 2-((tert-butoxycarbonyl)amino)-2-methylpropanoic acid (37 mg, 0.18 mmol) and HATU (68.4 mg, 0.18 mmol) in $CH_2Cl_2$ (10 mL), was added N,N-diisopropylethylamine (0.03 mL, 0.22 mmol). The suspension was stirred for 15 min. Solid tert-butyl (1-(3-methyl-4-(2-oxo-4-(piperazine-1-carboxamido)pyrimidin-1(2H)-yl)benzyl)piperidin-4-yl)carbamate was added and the solution and was stirred at rt for 16 h. The solution was diluted with $CH_2Cl_2$ (10 mL) and washed with $H_2O$ (1×25 mL). The combined organics were concentrated and purified by flash chromatography ($MeOH/CHCl_3$) to yield the title compound.

Step 6: 4-(2-amino-2-methylpropanoyl)-N-(1-(4-((4-aminopiperidin-1-yl)methyl)-3-methylphenyl)-2-oxo-1,2-dihydropyrimidin-4-yl)piperazine-1-carboxamide hydrochloride salt The tert-butyl (1-(4-(4-(4-(2-((tert-butoxycarbonyl)amino)-2-methylpropanoyl)piperazine-1-carboxamido)-2-oxopyrimidin-1(2H)-yl)-2-methylbenzyl)piperidin-4-yl)carbamate (95 mg, 0.14 mmol), was dissolved in 2M HCl/MeOH (10 mL) at rt for 4 h. The reaction mixture was concentrated under reduced pressure, and the solid was triturated with diethyl ether to afford the title compound. $^1H$ NMR (500 MHz, $CD_3OD$): δ 8.37 (s, 1H), 7.89 (d, 1H), 7.55 (s, 1H), 7.54 (d, 1H), 6.89 (s, 1H), 4.52 (s, 2H), 3.86-3.76 (m, 8H), 3.69 (d, 2H), 3.61-3.51 (m, 1H), 3.44-3.34 (m, 1H), 3.37 (s, 1H), 2.60 (s, 3H), 2.31 (d, 2H), 2.22-2.12 (m, 2H), 1.74 (s, 6H). LCMS [M+H] 511.3.

Compound 92

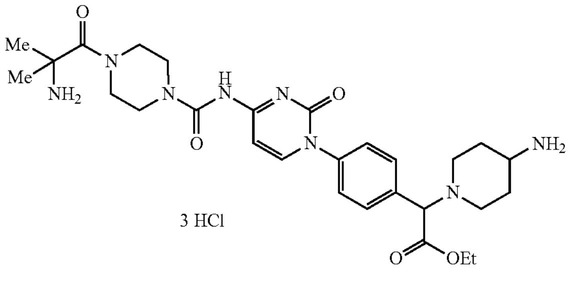

3 HCl

Ethyl 2-(4-(4-(4-(2-amino-2-methylpropanoyl)piperazine-1-carboxamido)-2-oxopyrimidin-1(2H)-yl)phenyl)-2-(4-aminopiperidin-1-yl)acetate hydrochloride salt Prepared in a similar fashion as scheme C-9 from ethyl 2-(4-((tert-butoxycarbonyl)amino)piperidin-1-yl)-2-(4-(2-oxo-4-(piperazine-1-carboxamido)pyrimidin-1(2H)-yl)phenyl)acetate and 2-((tert-butoxycarbonyl)amino)-2-methylpropanoic acid. LCMS [M+H] 569.4.

Compound 93

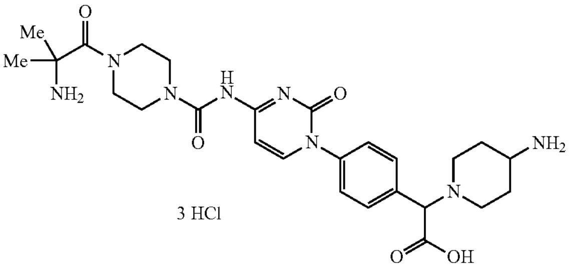

3 HCl 2-(4-(4-(4-(2-Amino-2-methylpropanoyl)piperazine-1-carboxamido)-2-oxopyrimidin-1(2H)-yl)phenyl)-2-(4-aminopiperidin-1-yl)acetic acid hydrochloride salt Prepared in a similar fashion as scheme C-9 from ethyl 2-(4-((tert-butoxycarbonyl)amino)piperidin-1-yl)-2-(4-(2-oxo-4-(piperazine-1-carboxamido)pyrimidin-1(2H)-yl)phenyl)acetate and 2-((tert-butoxycarbonyl)amino)-2-methylpropanoic acid. $^1H$ NMR (500 MHz, $CD_3OD$): δ 8.24 (s, 1H), 7.81 (d, 2H), 7.72 (d, 2H), 6.81 (s, 1H), 5.38 (s, 1H), 3.82-3.72 (m, 8H), 3.35 (s, 5H), 2.38-2.03 (m, 4H), 1.71 (s, 3H), 1.19 (s, 3H). LCMS [M+H] 541.3.

Compound 95

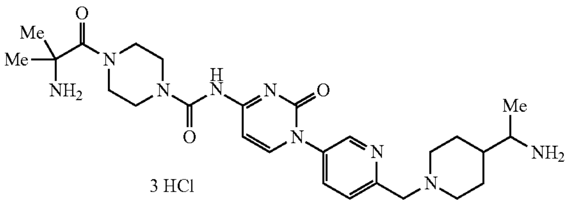

3 HCl 4-(2-Amino-2-methylpropanoyl)-N-(1-(6-((4-(1-aminoethyl)piperidin-1-yl)methyl)pyridin-3-yl)-2-oxo-1,2-dihydropyrimidin-4-yl)piperazine-1-carboxamide hydrochloride salt Prepared in a similar fashion as scheme C-9 from tert-butyl (1-(4-((1-(6-formylpyridin-3-yl)-2-oxo-1,2-dihydropyrimidin-4-yl)carbamoyl)piperazin-1-yl)-2-methyl-1-oxopropan-2-yl)carbamate and tert-butyl (1-(piperidin-4-yl)ethyl)carbamate. $^1H$ NMR (400 MHz, $D_2O$) δ 8.73 (d, 1H), 8.07-8.01 (m, 1H), 7.98 (d, 1H), 7.72 (d, 1H), 6.84 (d, 1H), 4.53 (s, 2H), 3.83-3.61 (m, 10H), 3.47 (s, 1H), 3.30 (d, 2H), 3.25-3.10 (m, 2H), 2.02 (s, 2H), 1.95 (s, 1H), 1.70 (s, 6H), 1.32-1.28 (m, 3H). LCMS [M+H] 526.4.

Compound 97

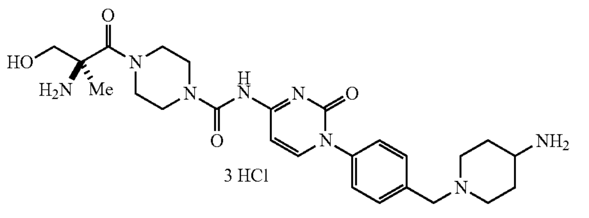

3 HCl (S)-4-(2-Amino-3-hydroxy-2-methylpropanoyl)-N-(1-(4-((4-aminopiperidin-1-yl)methyl)phenyl)-2-oxo-1,2-dihydropyrimidin-4-yl)piperazine-1-carboxamide hydrochloride salt Scheme C-10

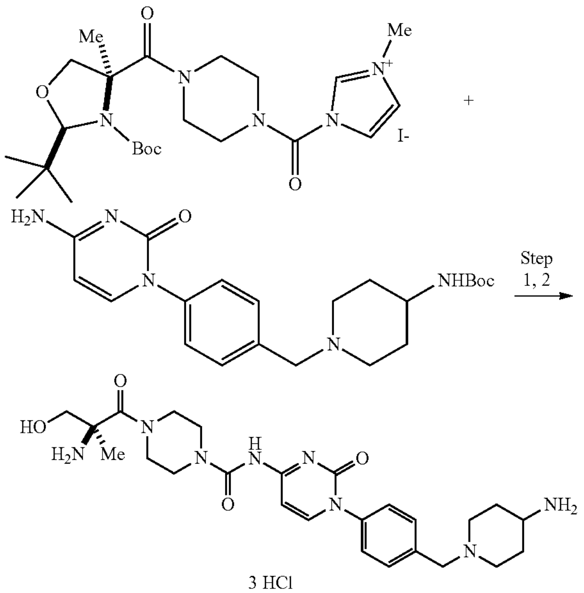

3 HCl

Reagents: 1) $CH_3CN$, 85° C., 8 h 2) HCl, MeOH, rt, 4 h.

Step 1: tert-butyl (2R,4S)-4-(4-((1-(4-((4-((tert-butoxycarbonyl)amino)piperidin-1-yl)methyl)phenyl)-2-oxo-1,2-dihydropyrimidin-4-yl)carbamoyl)piperazine-1-carbonyl)-2-(tert-butyl)-4-methyloxazolidine-3-carboxylate A mixture of 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide (48 mg, 0.08 mmol) and tert-butyl (1-(4-(4-amino-2-oxopyrimidin-1(2H)-yl)benzyl)piperidin-4-yl)carbamate (34 mg, 0.08 mmol) in $CH_3CN$ (12 mL) was stirred at reflux for 8 h. The solvent was removed under reduced pressure and the residue was partitioned between $CHCl_3$ (50 mL) and $H_2O$ (50 mL). The organic layer was concentrated under reduced pressure and purified by flash chromatography (MeOH/$CHCl_3$) to afford the title compound.

Step 2: (S)-4-(2-amino-3-hydroxy-2-methylpropanoyl)-N-(1-(4-((4-aminopiperidin-1-yl)methyl)phenyl)-2-oxo-1,2-dihydropyrimidin-4-yl)piperazine-1-carboxamide hydrochloride salt A mixture of tert-butyl (2R,4S)-4-(4-((1-(4-((4-((tert-butoxycarbonyl)amino)piperidin-1-yl)methyl)phenyl)-2-oxo-1,2-dihydropyrimidin-4-yl)carbamoyl)piperazine-1-carbonyl)-2-(tert-butyl)-4-methyloxazolidine-3-carboxylate (28 mg, 0.04 mmol) and HCl in MeOH (1.5 M, 10 mL) was stirred at rt for 4 h. The solvent was removed under reduced pressure, and the solid was triturated with diethyl ether to yield the title compound. $^1H$ NMR (400 MHz, $CD_3OD$) δ 8.38 (s, 1H), 7.85 (d, 2H), 7.68 (d, 2H), 6.87 (s, 1H), 4.47 (s, 2H), 4.11 (d, 1H), 3.94-3.69 (m, 9H), 3.63 (d, 2H), 3.52 (s, 1H), 3.28 (d, 2H), 2.29 (d, 2H), 2.17-2.03 (m, 2H), 2.17 (s, 3H). LCMS [M+H] 513.3.

Compound 98

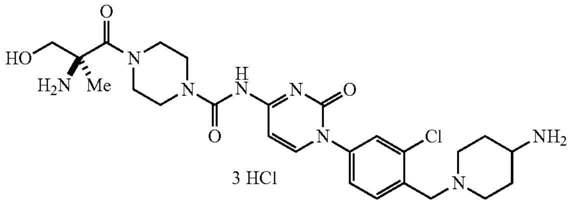

3 HCl (S)-4-(2-Amino-3-hydroxy-2-methylpropanoyl)-N-(1-(4-((4-aminopiperidin-1-yl)methyl)-3-chlorophenyl)-2-oxo-1,2-dihydropyrimidin-4-yl)piperazine-1-carboxamide hydrochloride salt Prepared in a similar fashion as scheme C-10 from 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide and tert-butyl (1-(4-(4-amino-2-oxopyrimidin-1(2H)-yl)-2-chlorobenzyl)piperidin-4-yl)carbamate. $^1H$ NMR (500 MHz, $D_2O$) δ 7.67-7.83 (m, 1H), 7.50-7.58 (m, 2H), 7.28-7.37 (m, 1H), 6.62-6.87 (m, 1H), 4.04 (d, 1H), 3.83-3.97 (m, 2H), 3.78 (d, 1H), 3.67 (br. s., 4H), 3.61 (br. s., 4H), 3.20-3.30 (m, 1H), 3.07-3.20 (m, 2H), 2.39-2.63 (m, 2H), 1.94-2.06 (m, 2H), 1.59-1.72 (m, 2H), 1.57 (s, 3H). LCMS [M+H] 547.3.

Compound 99

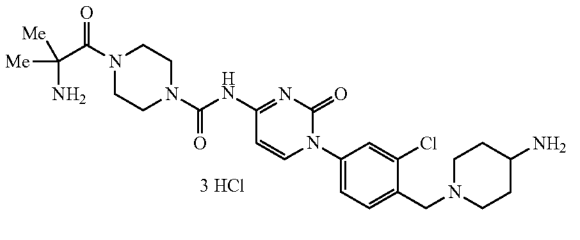

3 HCl 4-(2-Amino-2-methylpropanoyl)-N-(1-(4-((4-aminopiperidin-1-yl)methyl)-3-chlorophenyl)-2-oxo-1,2-dihydropyrimidin-4-yl)piperazine-1-carboxamide hydrochloride salt Scheme C-11

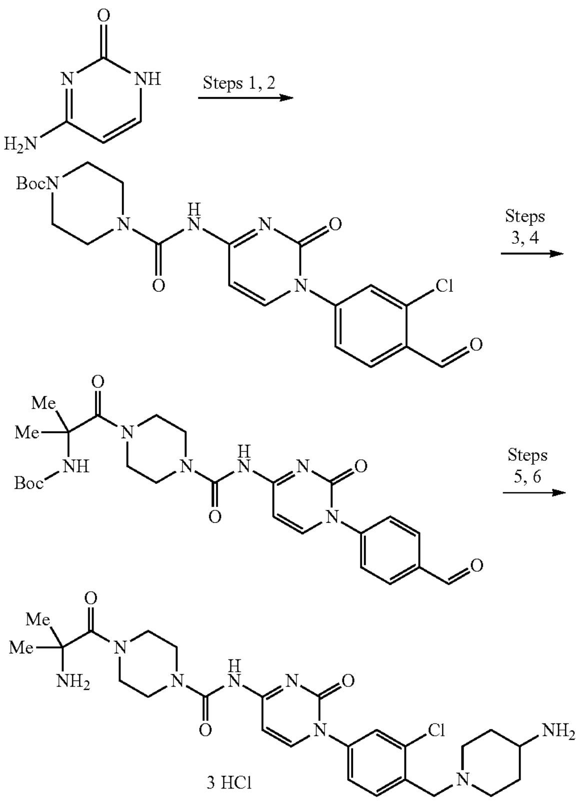

Reagents: 1) (3-chloro-4-formylphenyl)boronic acid, TMEDA, $Cu(OAc)_2$•$H_2O$, MeOH:$H_2O$, 16 h, rt, 2) 1-(4-(tert-butoxycarbonyl)piperazine-1-carbonyl)-3-methyl-1H-imidazol-3-ium iodide, $CH_3CN$, 16 h, rt 3) TFA, $CH_2Cl_2$, 1.5 h 4) 2-((tert-butoxycarbonyl)amino)-2-methylpropanoic acid, HATU, DIPEA, $CH_2Cl_2$, rt, 16 h 5) tert-butyl piperidin-4-ylcarbamate, DIPEA, $Na(OAc)_3BH$, DCE:$CH_3CN$, rt, 16 h 6) HCl, MeOH, rt, 4 h.

Step 1: 4-(4-amino-2-oxopyrimidin-1(2H)-yl)-2-chlorobenzaldehyde

A suspension of cytosine and (3-chloro-4-formylphenyl) boronic acid, in a mixture of MeOH:$H_2O$ (4:1, 25 ml) was stirred at rt in an open atmosphere. After 30 min., TMEDA and $Cu(OAc)_2 \cdot H_2O$ were added. The reaction was stirred in an open atmosphere for 16 h at rt. The MeOH was evaporated reduced pressure, and the remaining mixture was diluted with $H_2O$ (25 ml) and left to stir at 0° C. for 15 minutes. The mixture was filtered and the title compound was collected as a white solid.

Step 2: tert-butyl 4-((1-(3-chloro-4-formylphenyl)-2-oxo-1,2-dihydropyrimidin-4-yl)carbamoyl)piperazine-1-carboxylate 1-(4-(tert-butoxycarbonyl)piperazine-1-carbonyl)-3-methyl-1H-imidazol-3-ium iodide and 4-(4-amino-2-oxopyrimidin-1(2H)-yl)-2-chlorobenzaldehyde dissolved in dry $CH_3CN$ (12 mL). The solution was heated to reflux for 16 h under an atmosphere of nitrogen. After, the solvent was removed under reduced pressure and the crude reaction mixture was partitioned between $CHCl_3$ (50 mL) and water (50 mL). The organic layer was concentrated and purified via flash chromatography to afford the title compound (85%) as a white solid.

Step 3: N-(1-(3-chloro-4-formylphenyl)-2-oxo-1,2-dihydropyrimidin-4-yl)piperazine-1-carboxamide trifluoroacetate salt tert-Butyl 4-((1-(3-chloro-4-formylphenyl)-2-oxo-1,2-dihydropyrimidin-4-yl)carbamoyl)piperazine-1-carboxylate was dissolved in a solution of 1:1 trifluoroacetic acid: $CH_2Cl_2$ (10 mL). The reaction was stirred for 1.5 h at rt. The solvent and trifluoroacetic acid were removed reduced pressure. The crude reaction mixture was triturated with diethyl ether to yield a solid precipitate. The precipitate was filtered and washed with diethyl ether to yield the title compound as a white solid.

Step 4: tert-butyl (1-(4-((1-(3-chloro-4-formylphenyl)-2-oxo-1,2-dihydropyrimidin-4-yl)carbamoyl)piperazin-1-yl)-2-methyl-1-oxopropan-2-yl)carbamate To a suspension of 2-((tert-butoxycarbonyl)amino)-24-methylpropanoic acid and HATU in dry $CH_2Cl_2$ was added DIPEA. The suspension was stirred for 10 min. Solid N-(1-(3-chloro-4-formylphenyl)-2-oxo-1,2-dihydropyrimidin-4-yl)piperazine-1-carboxamide trifluoroacetate salt was added and the solution was stirred at rt for 16 h. The solution was diluted with $CH_2Cl_2$ (25 mL) and washed with water. The organic layers were concentrated and purification via flash chromatography yielded the title compound as a white solid.

Step 5: tert-butyl (1-(4-((1-(4-((4-((tert-butoxycarbonyl)amino)piperidin-1-yl)methyl)-3-chlorophenyl)-2-oxo-1,2-dihydropyrimidin-4-yl)carbamoyl)piperazin-1-yl)-2-methyl-1-oxopropan-2-yl)carbamate To suspension of tert-butyl (1-(4-((1-(3-chloro-4-formylphenyl)-2-oxo-1,2-dihydropyrimidin-4-yl)carbamoyl)piperazin-1-yl)-2-methyl-1-oxopropan-2-yl)carbamate and tert-butyl piperidin-4-ylcarbamate in 1:1 DCE:MeCN (25 mL), DIPEA and $Na(OAc)_3BH$ were added. The reaction was left to stir for 16 h at rt, after which the solvent was removed reduced pressure. The solid was dissolved in $CHCl_3$ and washed with 10% NaOH. Purification via flash chromatography yielded the title compound as a white solid.

Step 6: 4-(2-amino-2-methylpropanoyl)-N-(1-(4-((4-aminopiperidin-1-yl)methyl)-3-chlorophenyl)-2-oxo-1,2-dihydropyrimidin-4-yl)piperazine-1-carboxamide hydrochloride The tert-butyl (1-(4-((1-(4-((4-((tert-butoxycarbonyl)amino)piperidin-1-yl)methyl)-3-chlorophenyl)-2-oxo-1,2-dihydropyrimidin-4-yl)carbamoyl)piperazin-1-yl)-2-methyl-1-oxopropan-2-yl)carbamate was treated with 2M HCl in MeOH (10 mL) and stirred at rt for 4 h. The solvent and excess HCl were removed under reduced pressure and the solid was triturated with diethyl ether and dried under high vacuum to yield the title compound. $^1H$ NMR (400 MHz, $CD_3OD$) δ 8.29 (d, 1H), 8.06 (d, 1H), 7.86 (s, 1H), 7.65 (d, 1H), 6.85 (d, 1H), 4.64 (s, 2H), 3.79 (br. s, 9H), 3.72 (d, 2H), 3.41 (t, 2H), 2.30 (d, 2H), 2.13 (q, 2H), 1.72 (d 6H). LCMS [M+H] 531.3.

Compound 101

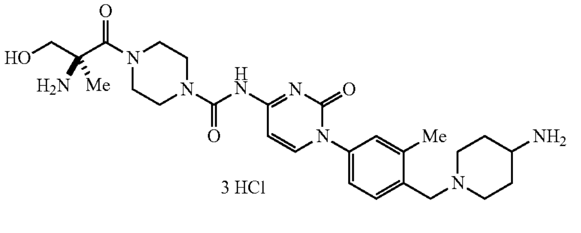

(S)-4-(2-Amino-3-hydroxy-2-methylpropanoyl)-N-(1-(4-((4-aminopiperidin-1-yl)methyl)-3-methylphenyl)-2-oxo-1,2-dihydropyrimidin-4-yl)piperazine-1-carboxamide hydrochloride salt Prepared in a similar fashion as scheme C-11 from tert-butyl (2R,4S)-2-(tert-butyl)-4-(4-((1-(4-formyl-3-methylphenyl)-2-oxo-1,2-dihydropyrimidin-4-yl)carbamoyl)piperazine-1-carbonyl)-4-methyloxazolidine-3-carboxylate and tert-butyl piperidin-4-ylcarbamate. $^1$H NMR (500 MHz, $CD_3OD$): δ 7.79 (d, 1H), 7.81-7.74 (m, 1H), 7.42-7.34 (m, 3H), 4.23 (s, 2H), 4.10 (d, 1H), 3.84 (d, 1H), 3.78-3.67 (m, 8H), 3.65-3.28 (m, 1H), 2.54 (s, 3H), 2.28 (d, 2H), 2.19-2.06 (m, 2H). LCMS [M+H] 527.4.

Compound 94

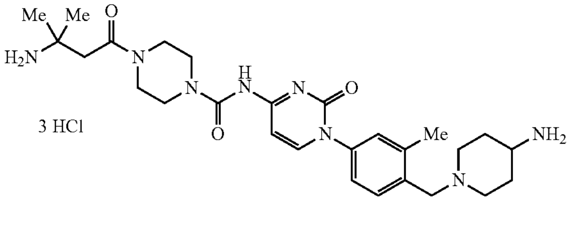

4-(3-Amino-3-methylbutanoyl)-N-(1-(4-((4-aminopiperidin-1-yl)methyl)-3-methylphenyl)-2-oxo-1,2-dihydropyrimidin-4-yl)piperazine-1-carboxamide hydrochloride salt Prepared in a similar fashion to Scheme C-11 from tert-butyl (4-(4-((1-(4-formyl-3-methylphenyl)-2-oxo-1,2-dihydropyrimidin-4-yl)carbamoyl)piperazin-1-yl)-2-methyl-4-oxobutan-2-yl)carbamate and tert-butyl piperidin-4-ylcarbamate. $^1$H NMR (500 MHz, $D_2O$) δ 8.00 (d, 1H), 7.66 (d, 1H), 7.47 (s, 1H), 7.42 (d 1H), 6.87 (d, 1H), 4.50 (s, 2H), 3.76 (br s. 2H), 3.74 (br s, 8H), 3.65-3.56 (m, 1H), 3.32 (t, 2H), 2.88 (s, 2H), 2.51 (s, 3H), 2.36 (d, 2H), 2.03-1.94 (m, 2H), 1.46 (s, 6H). LCMS [M+H] 525.3.

Compound 103

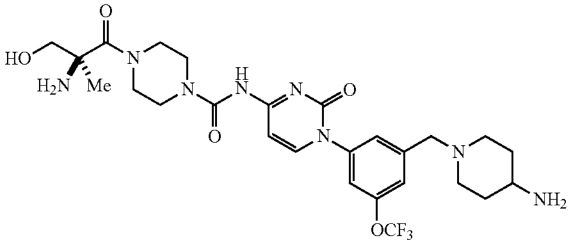

(S)-4-(2-Amino-3-hydroxy-2-methylpropanoyl)-N-(1-(3-((4-aminopiperidin-1-yl)methyl)-5-(trifluoromethoxy)phenyl)-2-oxo-1,2-dihydropyrimidin-4-yl)piperazine-1-carboxamide Prepared in a similar fashion as scheme C-11 from tert-butyl (2R,4S)-2-(tert-butyl)-4-(4-((1-(3-formyl-5-(trifluoromethoxy)phenyl)-2-oxo-1,2-dihydropyrimidin-4-yl)carbamoyl)piperazine-1-carbonyl)-4-methyloxazolidine-3-carboxylate and tert-butyl piperidin-4-ylcarbamate. LCMS [M+H] 597.3.

Compound 104

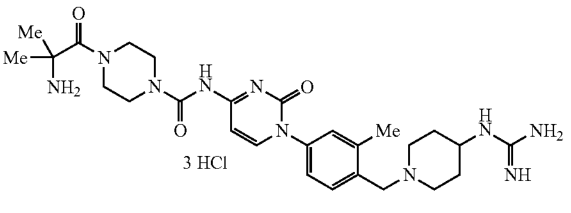

4-(2-Amino-2-methylpropanoyl)-N-(1-(4-((4-guanidinopiperidin-1-yl)methyl)-3-methylphenyl)-2-oxo-1,2-dihydropyrimidin-4-yl)piperazine-1-carboxamide hydrochloride salt Prepared in a similar fashion as scheme C-11 from tert-butyl (1-(4-((1-(4-formyl-3-methylphenyl)-2-oxo-1,2-dihydropyrimidin-4-yl)carbamoyl)piperazin-1-yl)-2-methyl-1-oxopropan-2-yl)carbamate and 1,2-bis(tert-butoxycarbonyl)-3-(piperidin-4-yl)guanidine. $^1$H NMR (500 MHz, $CD_3OD$) δ 8.40 (s, 1H), 7.83 (s, 1H), 7.71 (s, 1H), 7.50 (d, 2H), 6.87 (s, 1H), 4.49 (s, 1H), 3.83-3.71 (m, 10H), 3.64-3.55 (m, 3H), 3.3 (s, 8H), 2.56 (s, 3H), 2.56 (s, 3H), 2.26-2.13 (m, 3H), 2.03-1.91 (m, 3H), 1.69 (s, 6H), 1.55 (s, 6H), 1.26 (s, 2H). LCMS [M+H] 553.3.

Compound 106

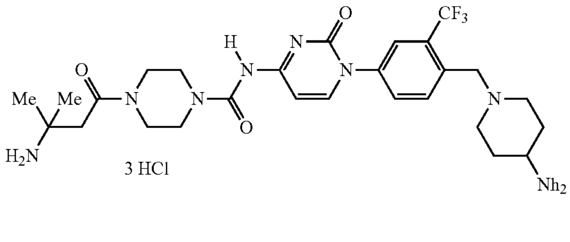

4-(3-Amino-3-methylbutanoyl)-N-(1-(4-((4-aminopiperidin-1-yl)methyl)-3-(trifluoromethyl)phenyl)-2-oxo-1,2-dihydropyrimidin-4-yl)piperazine-1-carboxamide hydrochloride salt Prepared in a similar fashion as scheme C-11 from tert-butyl (4-(4-((1-(4-formyl-3-(trifluoromethyl)phenyl)-2-oxo-1,2-dihydropyrimidin-4-yl)carbamoyl)piperazin-1-yl)-2-methyl-4-oxobutan-2-yl)carbamate and tert-butyl piperidin-4-ylcarbamate. LCMS [M+H] 579.3.

Compound 357

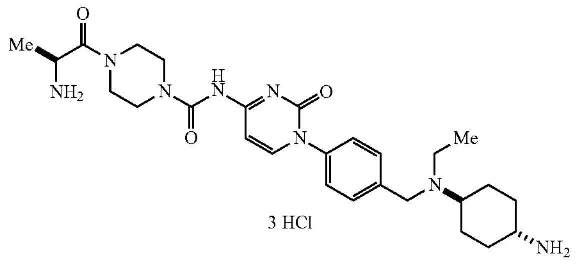

4-(L-Alanyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt Scheme C-12

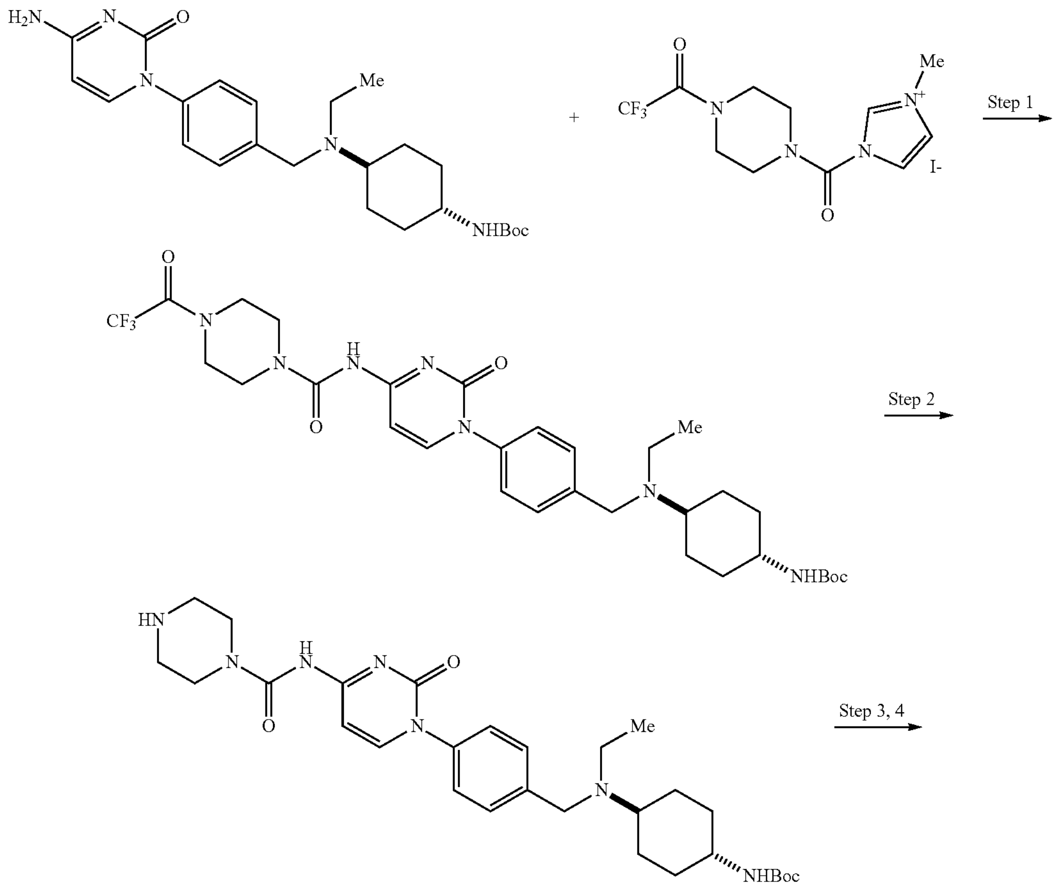

-continued

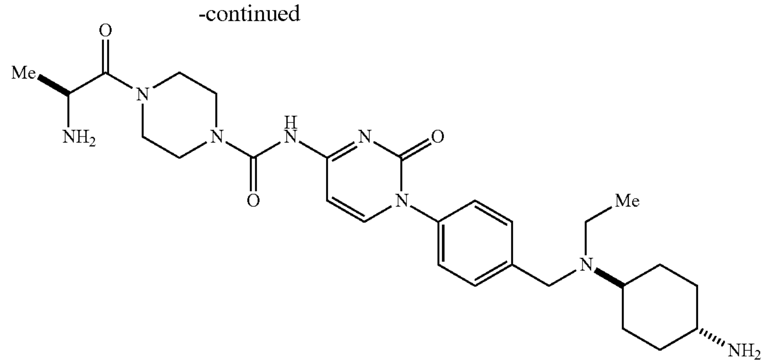

Reagents: 1) $CH_3CN$, reflux, 20 h 2) $K_2CO_3$, MeOH, rt 2 d 3) Boc-L-Ala, HATU, DIPEA, DMF, rt, 17 h 4) 2.0M HCl in MeOH, rt, 18 h.

Step 1. tert-butyl (trans-4-(ethyl(4-(2-oxo-4-(4-(2,2,2-trifluoroacetyl)piperazine-1-carboxamido)pyrimidin-1(2H)-yl)benzyl)amino)cyclohexyl)carbamate A mixture of tert-butyl (trans-4-((4-(4-amino-2-oxopyrimidin-1(2H)-yl)benzyl)(ethyl)amino)cyclohexyl) carbamate (605 mg, 1.37 mmol) and 3-methyl-1-(4-(2,2,2-trifluoroacetyl)piperazine-1-carbonyl)-1H-imidazol-3-ium iodide (687 mg, 1.64 mmol) in $CH_3CN$ (20 mL) was stirred at reflux for 20 h. The reaction mixture was concentrated and EtOAc (75 mL) added, washed with sat. aq. $NaHCO_3$ (3×50 mL) and brine (1×50 mL), dried over $Na_2SO_4$, decanted and concentrated. The residue was purified by flash chromatography (Hexanes/EtOAc/MeOH) to afford the title compound (515 mg, 58%) as a white solid. $^1$H NMR (500 MHz, $CDCl_3$) δ 12.87 (br s, 1H), 7.46 (d, 2H), 7.34-7.18 (m, 3H), 5.88-5.75 (m, 1H), 4.35-4.31 (m, 1H), 4.02-3.88 (m, 2H), 3.77-3.66 (m, 4H), 3.65-3.56 (m, 4H), 3.44-3.24 (m, 1H), 2.59-2.44 (m, 3H), 2.10-1.98 (m, 2H), 1.83 (d, 2H), 1.50-1.32 (m, 11H), 1.14-1.02 (m, 2H), 0.98 (t, 3H).

Step 2. tert-butyl (trans-4-(ethyl(4-(2-oxo-4-(piperazine-1-carboxamido)pyrimidin-1(2H)-yl)benzyl)amino)cyclohexyl)carbamate A mixture of tert-butyl (trans-4-(ethyl(4-(2-oxo-4-(4-(2,2,2-trifluoroacetyl)piperazine-1-carboxamido)pyrimidin-1(2H)-yl)benzyl)amino)cyclohexyl)carbamate (515 mg, 0.79 mmol) and $K_2CO_3$ (349 mg, 2.53 mmol) in MeOH (10 mL) was stirred at rt for 2 d. The solvent was removed, sat. aq. $NaHCO_3$(50 mL) was added and the aqueous layer was extracted with DCM (3×75 mL). The extracts were concentrated to dryness to give the title compound (456 mg, 93%) as a white solid.

Step 3. tert-butyl (trans-4-((4-(4-(4-((tert-butoxycarbonyl)-L-alanyl)piperazine-1-carboxamido)-2-oxopyrimidin-1(2H)-yl)benzyl)(ethyl)amino)cyclohexyl)carbamate A mixture of tert-butyl (trans-4-(ethyl(4-(2-oxo-4-(piperazine-1-carboxamido)pyrimidin-1(2H)-yl)benzyl)amino) cyclohexyl)carbamate (75 mg, 0.13 mmol), (tert-butoxycarbonyl)-L-alanine (33 mg, 0.17 mmol), HATU (64.9 mg, 0.17 mmol), and DIPEA (0.07 mL, 0.4 mmol) in DMF (0.5 mL) was stirred at rt for 17 h. The mixture was diluted with EtOAc (10 mL), washed with sat. aq. $NaHCO_3$(2×8 mL) and brine (2×8 mL). The organic layer along with the remaining emulsion was concentrated, water (5 mL) was added, and the solid was collected by vacuum filtration to give the title compound (68.8 mg, 70.5%) as a white solid.

Step 4. 4-(L-Alanyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt A mixture of tert-butyl (trans-4-((4-(4-(4-((tert-butoxycarbonyl)-L-alanyl)piperazine-1-carboxamido)-2-oxopyrimidin-1(2H)-yl)benzyl)(ethyl)amino)cyclohexyl)carbamate (69 mg, 0.10 mmol) and 2M HCl in MeOH (2 mL, 4 mmol) was stirred at rt for 18 h, concentrated. The residue was purified by HPLC ($CH_3CN/H_2O$/TFA) and by flash chromatography (DCM/MeOH/$NH_4OH$). The product fractions were converted to the HCl salt with 2M HCl in MeOH to afford the title compound (21.9 mg, 36.4%) as a white solid. $^1$H NMR (500 MHz, $D_2O$) δ 8.10-7.95 (m, 1H), 7.81-7.68 (m, 2H), 7.68-7.55 (m, 2H), 6.97-6.81 (m, 1H), 4.64-4.54 (m, 1H), 4.42 (d, 1H), 3.89-3.64 (m, 8H), 3.63-3.55 (m, 1H), 3.55-3.45 (m, 1H), 3.45-3.23 (m, 3H), 2.43-2.19 (m, 4H), 2.03-1.79 (m, 2H), 1.71-1.49 (m, 5H), 1.44-1.29 (m, 3H). LCMS [M+H] 525.4.

Compound 358

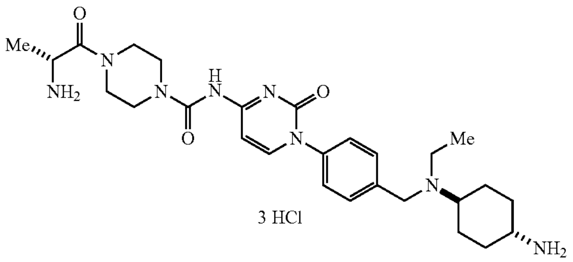

3 HCl

4-(D-Alanyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and (tert-butoxycarbonyl)-L-alanine. $^1$H NMR (500 MHz, $D_2O$) δ 8.07 (d, 1H), 7.74 (d, 2H), 7.63 (d, 2H), 6.89

(d, 1H), 4.65-4.55 (m, 2H), 4.42 (d, 1H), 3.86-3.69 (m, 8H), 3.56-3.46 (m, 1H), 3.44-3.25 (m, 3H), 2.39-2.22 (m, 4H), 2.00-1.81 (m, 2H), 1.69-1.51 (m, 5H), 1.36 (t, 3H). LCMS [M+H] 525.3.

Compound 359

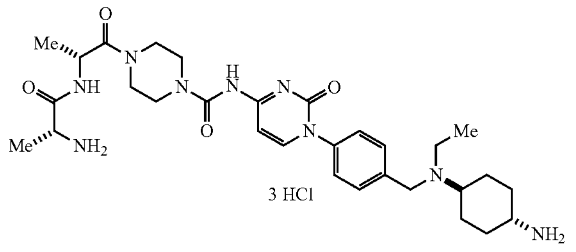

4-(D-Alanyl-D-alanyl)-N-(1-(4-(((trans-4-aminocyclohexyl)(ethyl)amino)methyl)phenyl)-2-oxo-1,2-dihydropyrimidin-4-yl)piperazine-1-carboxamidehydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and (tert-butoxycarbonyl)-D-alanyl-D-alanine. $^1$H NMR (500 MHz, $D_2O$) δ 8.06 (d, 1H), 7.74 (d, 2H), 7.63 (d, 2H), 6.90 (d, 1H), 4.95-4.87 (m, 1H), 4.61 (d, 1H), 4.43 (d, 1H), 4.16 (q, 1H), 3.92-3.66 (m, 8H), 3.56-3.45 (m, 1H), 3.44-3.25 (m, 3H), 2.40-2.21 (m, 4H), 2.01-1.81 (m, 2H), 1.69-1.53 (m, 5H), 1.43 (d, 3H), 1.36 (t, 3H). LCMS [M+H] 596.4.

Compound 311

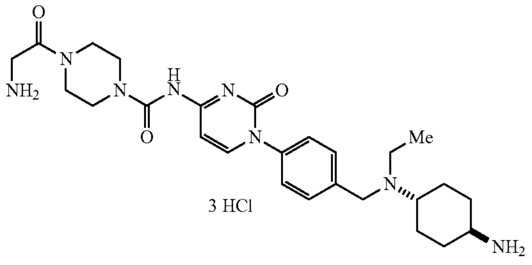

N-(1-(4-(((trans-4-Aminocyclohexyl)(ethyl)amino)methyl)phenyl)-2-oxo-1,2-dihydropyrimidin-4-yl)-4-glycylpiperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and (tert-butoxycarbonyl)glycine. $^1$H NMR (500 MHz, $CD_3OD$) δ 7.84 (d, 1H), 7.71 (d, 2H), 7.59 (d, 2H), 6.66 (d, 1H), 4.58 (s, 1H), 4.38 (s, 1H), 4.00 (s, 2H), 3.74-3.68 (m, 6H), 3.51 (t, 2H), 3.46-3.41 (m, 1H), 3.28-3.17 (m, 3H), 2.31-2.21 (m, 4H), 1.92-1.82 (m, 2H), 1.60-1.52 (m, 2H), 1.32 (t, 3H). LCMS [M+H] 511.3.

Compound 312

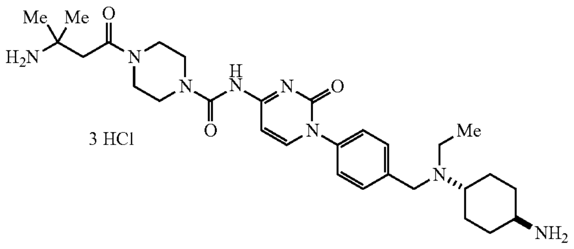

4-(3-Amino-3-methylbutanoyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and 3-((tert-butoxycarbonyl)amino)-3-methylbutanoic acid. $^1$H NMR (500 MHz, $CD_3OD$) δ 7.83 (d, 1H), 7.71 (d, 2H), 7.59 (d, 2H), 6.67 (d, 1H), 4.56 (s, 1H), 4.37 (s, 1H), 3.76-3.68 (m, 8H), 3.43 (t, 1H), 3.28-3.17 (m, 3H), 3.03 (s, 2H), 2.31-2.21 (m, 4H), 1.92-1.82 (m, 2H), 1.60-1.52 (m, 2H), 1.44 (s, 6H), 1.33 (t, 3H). LCMS [M+H] 553.4.

Compound 313

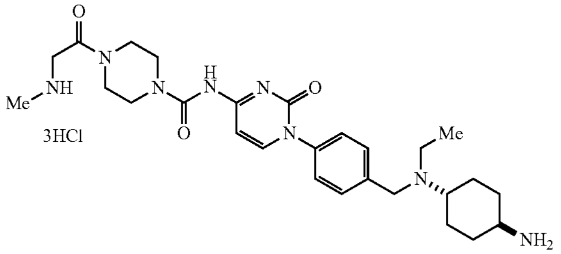

N-(1-(4-(((trans-4-Aminocyclohexyl)(ethyl)amino)methyl)phenyl)-2-oxo-1,2-dihydropyrimidin-4-yl)-4-(methylglycyl)piperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and N-(tert-butoxycarbonyl)-N-methylglycine. $^1$H NMR (500 MHz, $CD_3OD$) δ 7.83 (d, 1H), 7.71 (d, 2H), 7.59 (d, 2H), 6.66 (d, 1H), 4.56 (s, 1H), 4.37 (s, 1H), 4.13 (s, 2H), 3.74-3.68 (m, 6H), 3.50 (t, 2H), 3.46-3.41 (m, 1H), 3.28-3.17 (m, 3H), 2.76 (s, 3H), 2.31-2.21 (m, 4H), 1.92-1.82 (m, 2H), 1.61-1.52 (m, 2H), 1.33 (t, 3H). LCMS [M+H] 525.3.

Compound 314

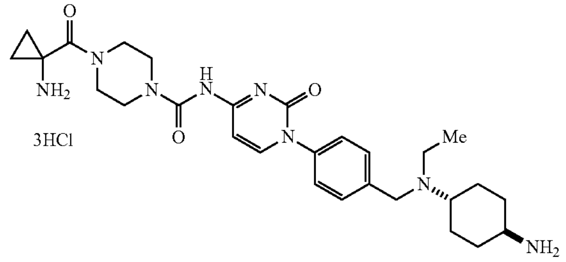

N-(1-(4-(((trans-4-Aminocyclohexyl)(ethyl)amino)methyl)phenyl)-2-oxo-1,2-dihydropyrimidin-4-yl)-4-(1-aminocyclopropane-1-carbonyl)piperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and 1-((tert-butoxycarbonyl)amino)cyclopropane-1-carboxylic acid. $^1$H NMR (500 MHz, $CD_3OD$) δ 7.74 (d, 1H), 7.70 (d, 2H), 7.59 (d, 2H), 6.54 (d, 1H), 4.56 (s, 1H), 4.37 (s, 1H), 3.92 (t, 4H), 3.43 (t, 1H), 3.40 (t, 8H), 3.28-3.17 (m, 3H), 2.31-2.21 (m, 4H), 1.92-1.82 (m, 2H), 1.60-1.52 (m, 2H), 1.34 (t, 3H).

Compound 315

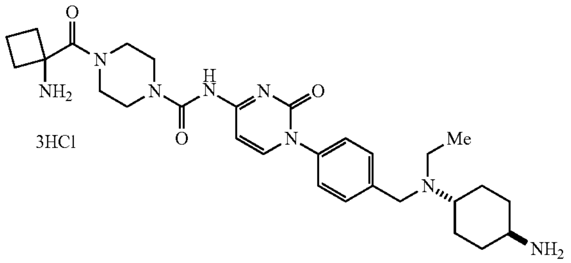

4-(1-Aminocyclobutane-1-carbonyl)-N-(1-(4-(((trans-4-aminocyclohexyl)(ethyl)amino)methyl)phenyl)-2-oxo-1,2-dihydropyrimidin-4-yl)piperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and 1-((tert-butoxycarbonyl)amino)cyclobutane-1-carboxylic acid. $^1$H NMR (500 MHz, $CD_3OD$) δ 7.84 (d, 1H), 7.71 (d, 2H), 7.59 (d, 2H), 6.66 (d, 1H), 4.56 (s, 1H), 4.37 (s, 1H), 3.75-3.61 (m, 8H), 3.44 (t, 1H), 3.28-3.17 (m, 3H), 2.92-2.85 (m, 2H), 2.45-2.37 (m, 2H), 2.36-2.32 (m, 1H), 2.31-2.21 (m, 4H), 2.12-2.05 (m, 1H), 1.92-1.82 (m, 2H), 1.60-1.52 (m, 2H), 1.34 (t, 3H). LCMS [M+H] 551.4.

Compound 316

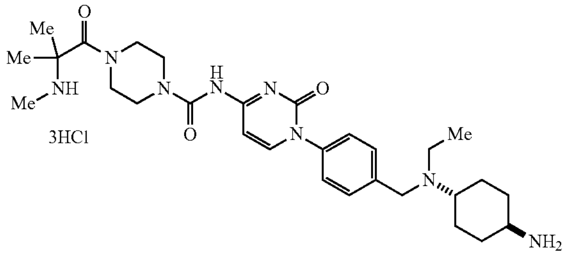

N-(1-(4-(((trans-4-Aminocyclohexyl)(ethyl)amino)methyl)phenyl)-2-oxo-1,2-dihydropyrimidin-4-yl)-4-(2-methyl-2-(methylamino)propanoyl)piperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate and 2-((tert-butoxycarbonyl)(methyl)amino)-2-methylpropanoic acid. $^1$H NMR (500 MHz, $CD_3OD$) δ 7.77 (d, 1H), 7.70 (d, 2H), 7.59 (d, 2H), 6.65 (d, 1H), 4.56 (s, 1H), 4.37 (s, 1H), 3.71 (s, 8H), 3.43 (t, 1H), 3.35 (s, 3H), 3.28-3.17 (m, 3H), 2.31-2.21 (m, 4H), 1.92-1.82 (m, 2H), 1.70 (s, 6H), 1.61-1.52 (m, 2H), 1.33 (t, 3H).

Compound 326

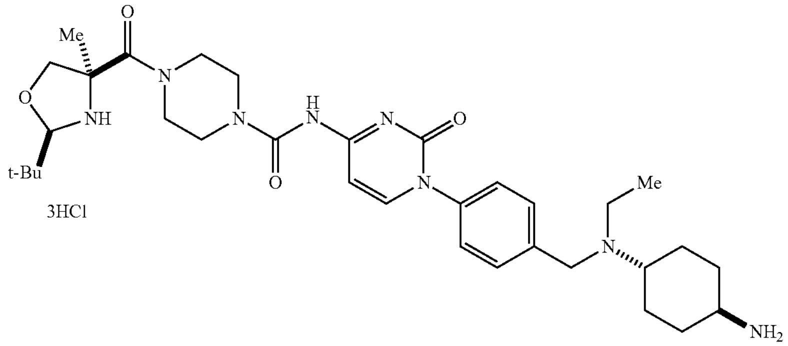

N-(1-(4-(((trans-4-Aminocyclohexyl)(ethyl)amino)methyl)phenyl)-2-oxo-1,2-dihydropyrimidin-4-yl)-4-((2R,4S)-2-(tert-butyl)-4-methyloxazolidine-4-carbonyl)piperazine-1-carboxamide hydrochloride salt Prepared in a similar fashion to Scheme C-12 from tert-butyl (trans-4-(ethyl(4-(2-oxo-4-(piperazine-1-carboxamido)pyrimidin-1(2H)-yl)benzyl)amino)cyclohexyl)carbamate, and (2R,4S)-3-(tert-butoxycarbonyl)-2-(tert-butyl)-4-methyloxazolidine-4-carboxylic acid. $^{1}$H NMR (500 MHz, $CD_3OD$) δ 7.71 (d, 1H), 7.50 (d, 2H), 7.35 (d, 2H), 6.62 (d, 1H), 4.50 (s, 1H), 4.23 (s, 1H), 4.05 (s, 1H), 3.89-3.63 (m, 8H), 3.56 (d, 1H), 3.52-3.38 (m, 1H), 3.27 (d, 1H), 2.70 (t, 1H), 2.62-2.54 (m, 3H), 1.99-1.84 (m, 4H), 1.49 (s, 3H), 1.48-1.38 (m, 2H), 1.24-1.15 (m, 2H), 1.02 (t, 3H), 0.95 (d, 9H). LCMS [M+H] 623.4.

Compound 364

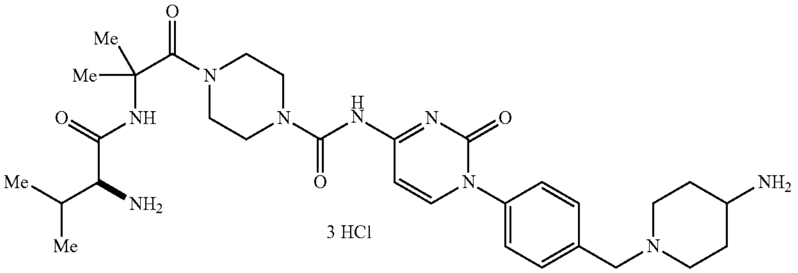

(S)-4-(2-(2-Amino-3-methylbutanamido)-2-methylpropanoyl)-N-(1-(4-((4-aminopiperidin-1-yl)methyl)phenyl)-2-oxo-1,2-dihydropyrimidin-4-yl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)benzyl)piperidin-4-yl)carbamate and (S)-2-(2-((tert-butoxycarbonyl)amino)-3-methylbutanamido)-2-methylpropanoic acid. LCMS [M+H] 569.4.

Compound 385

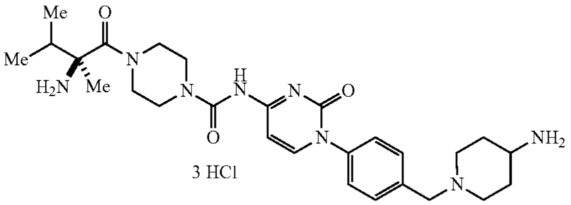

(S)-4-(2-Amino-2,3-dimethylbutanoyl)-N-(1-(4-((4-aminopiperidin-1-yl)methyl)phenyl)-2-oxo-1,2-dihydropyrimidin-4-yl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)benzyl)piperidin-4-yl)carbamate and (S)-2-((tert-butoxycarbonyl)amino)-2,3-dimethylbutanoic acid.

Compound 303

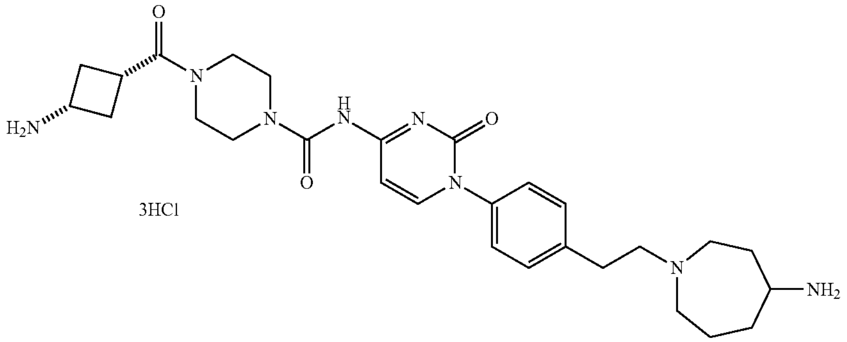

N-(1-(4-(2-(4-Aminoazepan-1-yl)ethyl)phenyl)-2-oxo-1,2-dihydropyrimidin-4-yl)-4-(cis-3-aminocyclobutane-1-carbonyl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)phenethyl)azepan-4-yl)carbamate and 1-(tert-butoxycarbonyl)azetidine-3-carboxylic acid. $^1$H NMR (500 MHz, $D_2O$) δ 8.12 (d, 1H), 7.57 (d, 2H), 7.51 (d, 2H), 6.87 (d, 1H), 3.82-3.45 (m, 17H), 3.25 (t, 2H), 2.76-2.66 (m, 4H), 2.48-1.75 (m, 6H). LCMS [M+H] 537.4.

Compound 304

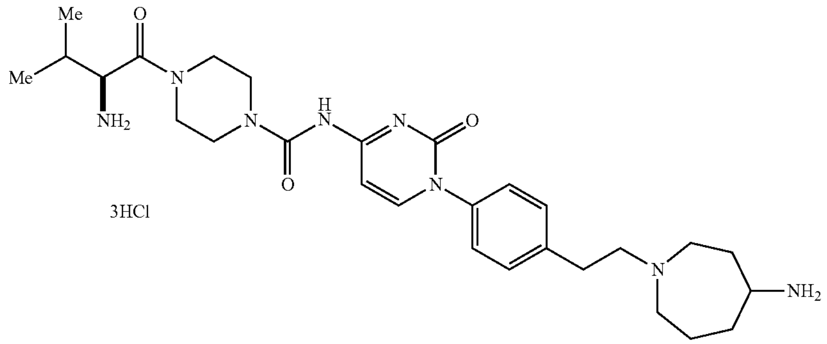

4-(L-Valyl)-N-(1-(4-(2-(4-minoazepan-1-yl)ethyl)phenyl)-2-oxo-1,2-dihydropyrimidin-4-yl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)phenethyl)azepan-4-yl)carbamate and (tert-butoxycarbonyl)-L-valine. $^1$H NMR (500 MHz, $D_2O$) δ 8.10 (d, 1H), 7.56 (d, 2H), 7.51 (d, 2H), 6.86 (d, 1H), 3.86-3.51 (m, 16H), 3.25 (t, 2H), 2.48-2.24 (m, 3H), 2.23-2.00 (m, 2H), 1.98-1.73 (m, 2H), 1.15 (d, 3H), 1.06 (d, 3H). LCMS [M+H] 539.4.

Compound 306

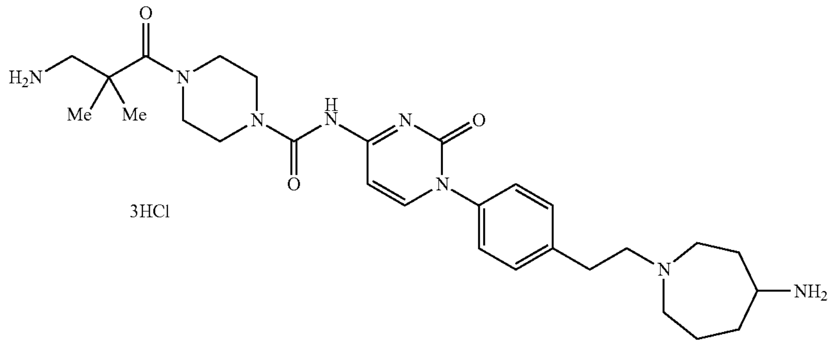

4-(3-Amino-2,2-dimethylpropanoyl)-N-(1-(4-(2-(4-aminoazepan-1-yl)ethyl)phenyl)-2-oxo-1,2-dihydropyrimidin-4-yl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)phenethyl)azepan-4-yl)carbamate and 3-((tert-butoxycarbonyl)amino)-2,2-dimethylpropanoic acid. $^1$H NMR (500 MHz, $D_2O$) δ 8.04 (d, 1H), 7.50 (d, 2H), 7.44 (d, 2H), 6.81 (d, 1H), 3.88-3.62 (m, 8H), 3.64-3.34 (m, 6H), 3.27-3.16 (m, 3H), 3.10 (s, 2H), 2.42-1.97 (m, 4H), 1.90-1.60 (m, 2H), 1.43 (s, 6H). LCMS [M+H] 539.4.

Compound 307

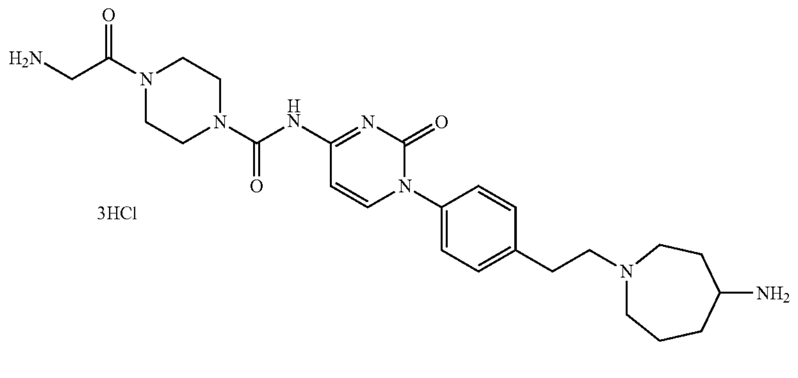

N-(1-(4-(2-(4-Aminoazepan-1-yl)ethyl)phenyl)-2-oxo-1,2-dihydropyrimidin-4-yl)-4-glycylpiperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)phenethyl)azepan-4-yl)carbamate and (tert-butoxycarbonyl)glycine. $^1$H NMR (500 MHz, $D_2O$) δ 8.15 (d, 1H), 7.53 (d, 2H), 7.47 (d, 2H), 6.80 (d, 1H), 4.10 (s, 2H), 3.78-3.49 (m, 15H), 3.20 (t, 2H), 2.43-1.61 (m, 6H). LCMS [M+H] 497.3.

Compound 308

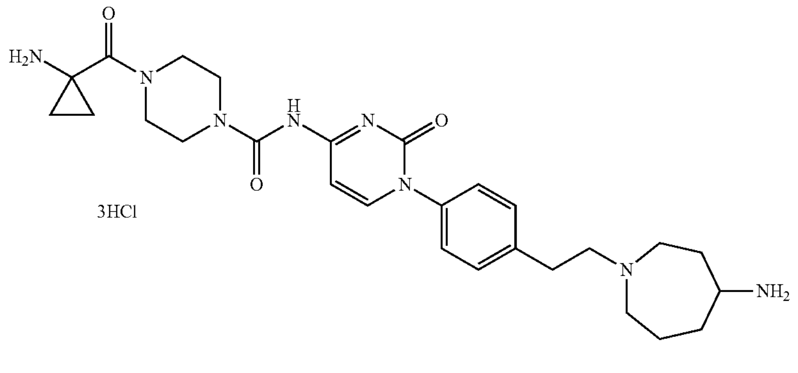

N-(1-(4-(2-(4-Aminoazepan-1-yl)ethyl)phenyl)-2-oxo-1,2-dihydropyrimidin-4-yl)-4-(1-aminocyclopropane-1-carbonyl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)phenethyl)azepan-4-yl)carbamate and 1-((tert-butoxycarbonyl)amino)cyclopropane-1-carboxylic acid. $^1$H NMR (500 MHz, $D_2O$) δ 8.08 (d, 1H), 7.50 (d, 2H), 7.45 (d, 2H), 6.80 (d, 1H), 3.84-3.67 (m, 8H), 3.63-3.47 (m, 5H), 3.43-3.27 (m, 2H), 3.18 (t, 2H), 2.40-1.63 (m, 6H), 1.47-1.14 (m, 4H). LCMS [M+H] 523.4.

Compound 309

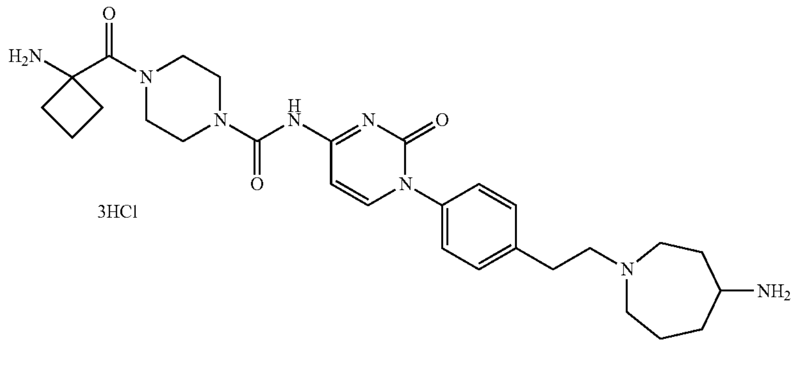

N-(1-(4-(2-(4-Aminoazepan-1-yl)ethyl)phenyl)-2-oxo-1,2-dihydropyrimidin-4-yl)-4-(1-aminocyclobutane-1-carbonyl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)phenethyl)azepan-4-yl)carbamate and 1-((tert-butoxycarbonyl)amino)cyclobutane-1-carboxylic acid. $^1$H NMR (500 MHz, $D_2O$) δ 8.05 (d, 1H), 7.54 (d, 2H), 7.48 (d, 2H), 6.86 (d, 1H), 3.83-3.74 (m, 8H), 3.67-3.53 (m, 5H), 3.23 (t, 2H), 2.97-2.88 m, 2H), 2.55-1.66 (m, 12H) LCMS [M+H] 537.4.

Compound 310

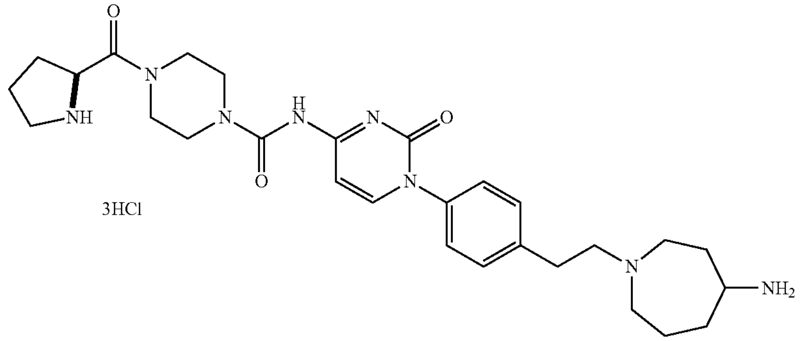

4-(L-Prolyl)-N-(1-(4-(2-(4-aminoazepan-1-yl)ethyl)phenyl)-2-oxo-1,2-dihydropyrimidin-4-yl)piperazine-1-carboxamide hydrochloride salt Prepared in a similar fashion to Scheme C-12 from tert-butyl (1-(4-(2-oxo-4-(piperazine-1-carboxamido)pyrimidin-1(2H)-yl)phenethyl)azepan-4-yl)carbamate and (tert-butoxycarbonyl)-L-proline. LCMS [M+H] 537.3.

Compound 352

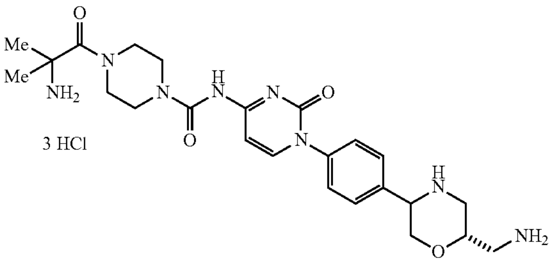

4-(2-Amino-2-methylpropanoyl)-N-(1-(4-((6S)-6-(aminomethyl)morpholin-3-yl)phenyl)-2-oxo-1,2-dihydropyrimidin-4-yl)piperazine-1-carboxamide hydrochloride salt Scheme C-13

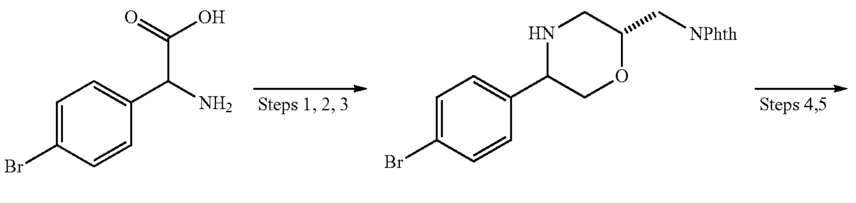

-continued

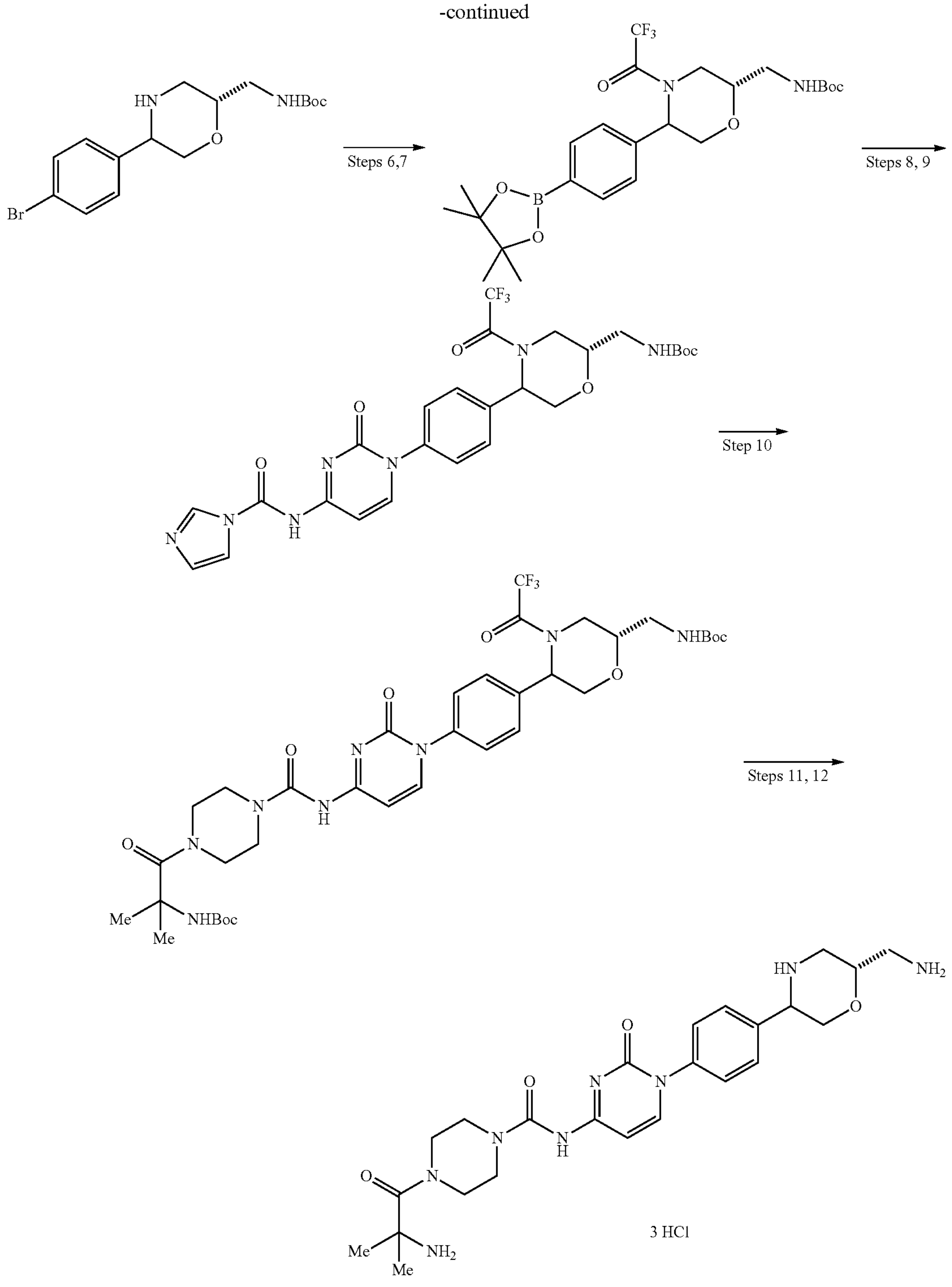

Reagents: 1) $NaBH_4$, $I_2$, THF, 65° C., 16 h 2) (S)-glycidyl phthalimide, EtOH, 65° C., 24 h 3) DIAD, $PPh_3$ 0° C. to rt, 4 h 4) hydrazine monohydrate, EtOH, 70° C., 4 h 5) $Boc_2O$, $Et_3N$, $CH_2Cl_2$, rt, 16 h 6) TFAA, $Et_3N$, $CH_2Cl_2$, 0° C. to rt, 16 h 7) $(B(pin))_2$, $Pd(dppf)Cl_2$•$CH_2Cl_2$, KOAc, dioxane, 100° C., 16 h 8) cytosine, TMEDA, $Cu(OAc)_2$•$H_2O$, 4:1 MeOH:$H_2O$ rt. 48 h 9) 1,1'-carbonyldiimidazole, $CH_2Cl_2$, rt. 4 h 10) tert-butyl (2-methyl-1-oxo-1-(piperazine-1-yl)propan-2-yl)carbamate $CH_3CN$, 85° C., 3 h 11) LiOH, 1:1 THF:$H_2O$ rt, 16 h 12) HCl in MeOH, rt, 4 h.

Step 1: 2-amino-2-(4-bromophenyl)ethan-1-ol

To a suspension of 2-amino-2-(4-bromophenyl)acetic acid in THF (2.0 g, 8.6 mmol) at 0° C., was added $NaBH_4$ (826 mg, 21.7 mmol). A solution of $I_2$ (2.2 g, 8 mmol) in THF was added dropwise over 10 min. and the reaction was heated to 65° C. for 16 h. The reaction was cooled to rt and quenched with the addition of MeOH (5 mL). The reaction mixture was concentrated under reduced pressure and diluted with 10% NaOH (100 mL) and stirred for 2 h. The aqueous phase was extracted with $CHCl_3$ (3×150 mL), and the combined organics were concentrated under reduced pressure. The crude reaction mixture was purified by column chromatography ($NH_4OH$:MeOH:$CHCl_3$) to afford the title compound.

Step 2: 2-((2R)-3-((1-(4-bromophenyl)-2-hydroxy-ethyl)amino)-2-hydroxypropyl)isoindoline-1,3-dione A solution of 2-amino-2-(4-bromophenyl)ethan-1-ol (214 mg, 1.0 mmol) and (S)-glycidyl phthalimide (203 mg, 1.0 mmol) in EtOH (20 mL) was heated to 80° C. for 24 h. The reaction mixture was concentrated under reduced pressure and the crude solid was purified by column chromatography (Hexanes:EtOAc) to afford the title compound.

Step 3: 2-(((2R)-5-(4-bromophenyl)morpholin-2-yl) methyl)isoindoline-1,3-dione

To a stirred solution of 2-((2R)-3-((1-(4-bromophenyl)-2-hydroxyethyl)amino)-2-hydroxypropyl)isoindoline-1,3-dione (100 mg, 0.23 mmol) and triphenylphosphine (60 mg, 0.23 mmol) in THF (10 mL) at 0° C., was added DIAD (0.048 mL, 0.23 mmol) dropwise over 5 min. The reaction mixture was warmed to rt and stirred for 4 h. The reaction was concentrated under reduced pressure and purified by column chromatography (Hexanes:EtOAc) to afford the title compound.

Step 4: ((2S)-5-(4-bromophenyl)morpholin-2-yl) methanamine

To a solution of 2-(((2R)-5-(4-bromophenyl)morpholin-2-yl)methyl)isoindoline-1,3-dione (100 mg, 0.25 mmol) in EtOH (5 mL) was added hydrazine monohydrate (0.025 mL, 0.50 mmol). The reaction mixture was heated to 70° C. for 4 h, concentrated and diluted with $CHCl_3$ (5 mL). The solid filtered and the filtrate concentrated under reduced pressure. The crude residue was dissolved in $CHCl_3$ (25 mL) and washed with $H_2O$ (10 mL) and sat. aq. NaCl (15 mL). The organic layer was dried over $Na_2SO_4$ and concentrated under reduced pressure to afford the title compound.

Step 5: tert-butyl (((2R)-5-(4-bromophenyl)morpholin-2-yl)methyl)carbamate

To a suspension of ((2S)-5-(4-bromophenyl)morpholin-2-yl)methanamine (312 mg, 1.16 mmol) in $CH_2Cl_2$ (10 mL) was added $Et_3N$ (0.65 mL, 4.6 mmol) and di-tert-butyl-dicarbonate (503 mg, 2.30 mmol) and was stirred at rt for 16 h. The reaction mixture was diluted with $CH_2Cl_2$ (50 mL), washed with $H_2O$ (50 mL) and concentrated under reduced pressure. The crude reaction mixture was purified by column chromatography (Hexanes:EtOAc) to afford the title compound.

Step 6: tert-butyl (((2S)-5-(4-bromophenyl)-4-(2,2,2-trifluoroacetyl)morpholin-2-yl)methyl)carbamate To a solution of tert-butyl (((2R)-5-(4-bromophenyl)morpholin-2-yl)methyl)carbamate (180 mg, 0.49 mmol) in $CH_2Cl_2$ (10 mL) at 0° C., was added $Et_3N$ (0.10 mL, 0.73 mmol) and TFAA (0.082 mL, 0.085 mmol). The reaction was warmed to rt and stirred for 16 h. The reaction mixture was diluted with $CH_2Cl_2$ (50 mL) and washed with $H_2O$ (1×50 mL). The organic layer was dried over $Na_2SO_4$ and concentrated under reduced pressure to afford the title compound.

Step 7: tert-butyl (((2S)-5-(4-(4,4,5,5-tetramethyl-1,3,2-dioxaborolan-2-yl)phenyl)-4-(2,2,2-trifluoroacetyl)morpholin-2-yl)methyl)carbamate A suspension of tert-butyl (((2S)-5-(4-bromophenyl)-4-(2,2,2-trifluoroacetyl)morpholin-2-yl)methyl)carbamate (210 mg, 0.49 mmol), bis-pinacolato diboron (150 mg, 0.58 mmol), $Pd(dppf)Cl_2 \cdot CH_2Cl_2$ (10 mg, 0.014 mmol), and KOAc (143 mg, 1.46 mmol) in dioxane was degassed and heated to 100° C. for 16 h. The crude reaction mixture was filtered through Celite® and the filtrate was concentrated under reduced pressure. Purification by column chromatography (Hexanes:EtOAc) afforded the title compound.

Step 8: tert-butyl (((2S)-5-(4-(4-amino-2-oxopyrimidin-1(2H)-yl)phenyl)-4-(2,2,2-trifluoroacetyl)morpholin-2-yl)methyl)carbamate A suspension of cytosine (37 mg, 0.33 mmol) and tert-butyl (((2S)-5-(4-(4,4,5,5-tetramethyl-1,3,2-dioxaborolan-2-yl)phenyl)-4-(2,2,2-trifluoroacetyl)morpholin-2-yl) methyl)carbamate (110 mg, 0.33 mmol), in MeOH:$H_2O$ (4:1, 100 mL) was stirred at rt in open air for 30 min. TMEDA (0.090 mL, 0.40 mmol) and $Cu(OAc)_2 \cdot H_2O$ (66 mg, 0.33 mmol) were added and the reaction was stirred in open air for 48 h at rt. The reaction mixture was concentrated under reduced pressure and $H_2O$ (10 mL) was added. The aqueous phase was extracted with $CHCl_3$ (3×15 mL), and the combined organics were concentrated under reduced pressure. The crude reaction mixture was purified by column chromatography ($CHCl_3$:MeOH) to afford the title compound.

Step 9: tert-butyl (((2S)-5-(4-(4-(1H-imidazole-1-carboxamido)-2-oxopyrimidin-1(2H)-yl)phenyl)-4-(2,2,2-trifluoroacetyl)morpholin-2-yl)methyl)carbamate A suspension of tert-butyl (((2S)-5-(4-(4-amino-2-oxopyrimidin-1(2H)-yl)phenyl)-4-(2,2,2-trifluoroacetyl)morpholin-2-yl)methyl)carbamate (45 mg, 0.09 mmol) and 1,1'-carbonyldiimidazole (24 mg, 0.14 mmol) in $CH_2Cl_2$ (12 mL) was stirred for 16 h at rt. The reaction mixture was concentrated under reduced pressure, and the residue was triturated with EtOAc. The solid was collected to afford the title compound.

Step 10: tert-butyl (1-(4-((1-(4-((6S)-6-(((tert-butoxycarbonyl)amino)methyl)-4-(2,2,2-trifluoroacetyl)morpholin-3-yl)phenyl)-2-oxo-1,2-dihydropyrimidin-4-yl)carbamoyl)piperazin-1-yl)-2-methyl-1-oxopropan-2-yl)carbamate tert-butyl (((2S)-5-(4-(4-(1H-imidazole-1-carboxamido)-2-oxopyrimidin-1(2H)-yl)phenyl)-4-(2,2,2-trifluoroacetyl) morpholin-2-yl)methyl)carbamate (53 mg, 0.09 mmol) and tert-butyl (2-methyl-1-oxo-1-(piperazin-1-yl)propan-2-yl) carbamate (24 mg, 0.09 mmol) were dissolved in MeCN (5 mL) and heated to reflux for 2 h. The reaction mixture was concentrated under reduced pressure and the crude reaction mixture was dissolved in EtOAc (25 mL) and washed with $H_2O$ (3×20 mL). The reaction mixture was purified by column chromatography (Hexanes:EtOAc) to afford the title compound.

Step 11: tert-butyl (1-(4-((1-(4-((6R)-6-(((tert-butoxycarbonyl)amino)methyl)morpholin-3-yl)phenyl)-2-oxo-1,2-dihydropyrimidin-4-yl)carbamoyl)piperazin-1-yl)-2-methyl-1-oxopropan-2-yl)carbamate To a solution of tert-butyl (1-(4-((1-(4-((6S)-6-(((tert-butoxycarbonyl)amino)methyl)-4-(2,2,2-trifluoroacetyl)morpholin-3-yl)phenyl)-2-oxo-1,2-dihydropyrimidin-4-yl)carbamoyl)piperazin-1-yl)-2-methyl-1-oxopropan-2-yl)carbamate (75 mg, 0.09 mmol) in 1:1 THF:$H_2O$ (2 mL) was added LiOH (10 mg, 0.45 mmol). The reaction was stirred at rt for 16 h, diluted with $H_2O$ (5 mL) and acidified by the addition of 2N HCl. The organic layer was separated and the aqueous layer was extracted with $CHCl_3$ (3×10 mL). The combined organics were dried over $Na_2SO_4$ and concentrated under reduced pressure to give the title compound.

Step 12: 4-(2-amino-2-methylpropanoyl)-N-(1-(4-((6S)-6-(aminomethyl)morpholin-3-yl)phenyl)-2-oxo-1,2-dihydropyrimidin-4-yl)piperazine-1-carboxamide tert-Butyl (1-(4-((1-(4-((6R)-6-(((tert-butoxycarbonyl)amino)methyl)morpholin-3-yl)phenyl)-2-oxo-1,2-dihydropyrimidin-4-yl)carbamoyl)piperazin-1-yl)-2-methyl-1-oxopropan-2-yl)carbamate was dissolved in a solution of HCl/MeOH (5 mL) and stirred for 4 h. The reaction mixture was concentrated under reduced pressure and the crude solid was purified by RPHPLC ($H_2O$:$CH_3CN$:TFA). Addition of 2N HCl in MeOH (5 mL) and evaporation under reduced pressure afforded the title compound. $^1H$ NMR (400 MHz, $D_2O$) δ 8.14 (d, 1H), 7.64 (d, 2H), 7.53 (d, 2H), 6.81 (d, 1H), 5.21 (d, 1H), 4.32 (s, 1H), 3.79 (s, 3H), 3.75 (s, 5H), 3.48 (s, 1H), 3.45-3.33 (m, 2H), 3.25 (d, 2H), 3.10-2.99 (m, 1H), 1.73 (s, 6H).

Compound 330

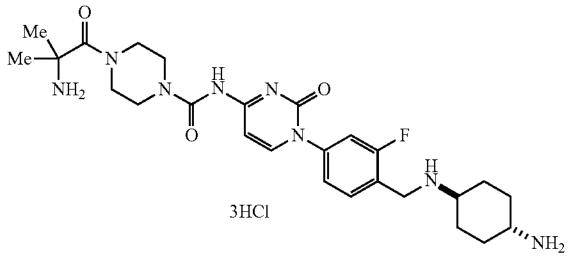

3HCl 4-(2-Amino-2-methylpropanoyl)-N-(1-(4-(((trans-4-aminocyclohexyl)amino)methyl)-3-fluorophenyl)-2-oxo-1,2-dihydropyrimidin-4-yl)piperazine-1-carboxamide hydrochloride salt Scheme C-14

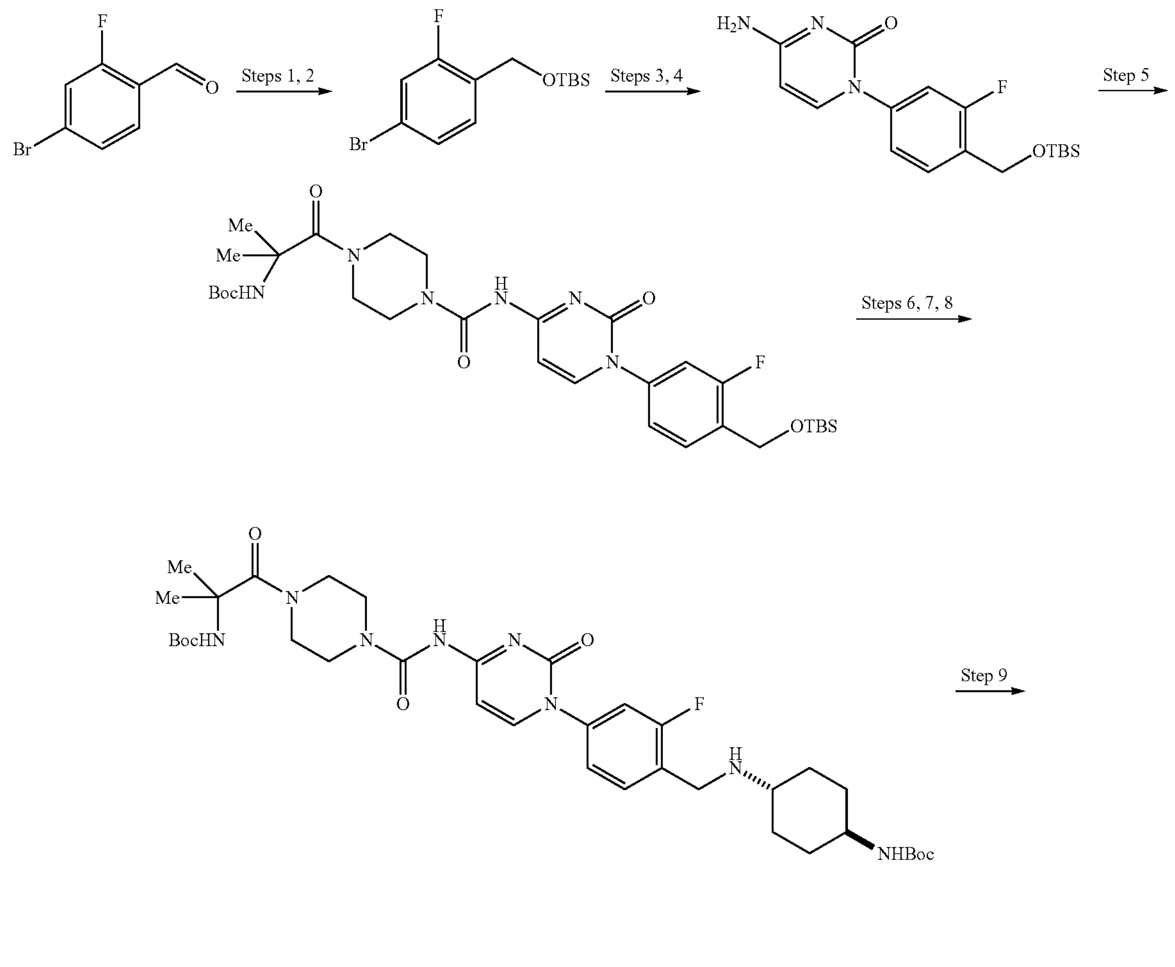

-continued

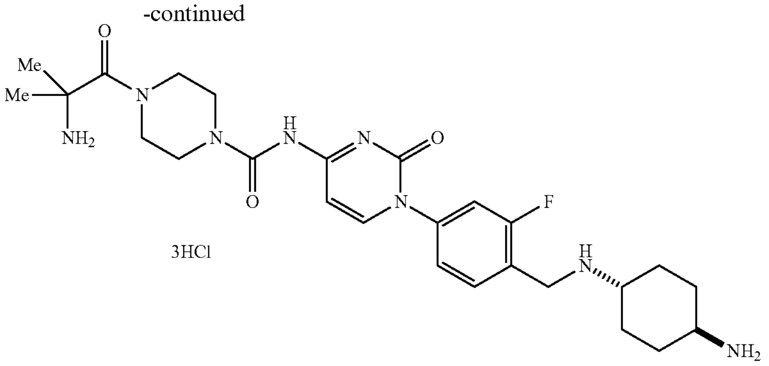

3HCl

Reagents: 1) $NaBH_4$, MeOH, 2 h 2) TBSCl, imidazole, DMF, 16 h 3) BuLi, THF, -78° C. $(iPrO)_3B$, NaHCO3, 3 h 4) cytosine, TMEDA, $Cu(OAc)_2$•$H_2O$, 4:1 MeOH:$H_2O$, 16-48 h 5) 1-(4-(2-((tert-butoxycarbonyl)amino)-2-methylpropanoyl)piperazine-1-carbonyl)-3-methyl-1H-imidazol-3-ium iodide, $CH_3CN$, 80° C., 16 h 6) TsOH, MeOH, 45 min 7) Dess-Martin periodinane, $CH_2Cl_2$, 1 h 8) tert-butyl (trans-4-aminocyclohexyl)carbamate, $NaBH_4$, MeOH, 16 h 9) HCl, MeOH, rt, 4 h.

Step 1: (4-bromo-2-fluorophenyl)methanol

A solution of 4-bromo-2-fluorobenzaldehyde (10.2 g, 50 mmol) in MeOH (500 mL) was cooled to 0° C. and $NaBH_4$ (5.70 g, 151 mmol) added over 10 min. The solution was stirred for 16 h. The excess MeOH was removed and the crude mixture was partitioned between EtOAc (500 mL) and 1N NaOH (500 mL). The 1N NaOH was washed with an additional portion of EtOAc (300 mL). The combined organics were dried over $Na_2SO_4$ and concentrated to afford the title compound as a viscous oil to white solid which was in the next step without further purification.

Step 2: ((4-bromo-2-fluorobenzyl)oxy)(tert-butyl) dimethylsilane

To a crude solution of 4-bromo-2-fluorophenyl)methanol (10.1 g, 49.3 mmol) in DMF (250 mL) was added TBSCl (11.1 g, 73.9 mmol) followed by Imidizole (6.71 g, 98.5 mmol). The solution was stirred for 16 h. The crude solution was partitioned between EtOAc (500 mL) and LiCl (500 mL). The LiCl was discarded and the organic layer was washed with additional LiCl (2×250 mL). The combined organics were dried over $Na_2SO_4$ and concentrated to afford a crude oil which was purified via column chromatography (Hexanes:EtOAc) to afford the title compound as a clear oil.

Step 3: tert-butyl((2-fluoro-4-(4,4,5,5-tetramethyl-1,3,2-dioxaborolan-2-yl)benzyl)oxy)dimethylsilane A stirred solution of ((4-bromo-2-fluorobenzyl)oxy)(tert-butyl)dimethylsilane (15.0 g, 47.0 mmol) in THF (350 mL) was cooled to −78° C. 1 M BuLi in Hexanes (47.0 mL, 117 mmol) was added dropwise over 30 min. and the temperature maintained below −60° C. After 25 min triisopropyl borate (16.0 mL, 70.5 mmol) was added dropwise over 30 min. The reaction mixture was warmed to rt and stirred for 15 min. 150 mL of $NaHCO_3$ aq. (freshly made) was added and the reaction was stirred for 30 min. The biphasic mixture was separated and the aq. layer washed with $CH_2Cl_2$(2×250 mL). The combined organics were dried over $Na_2SO_4$ and concentrated under reduced pressure to afford the title compound.

Step 4: 4-amino-1-(4-(((tert-butyldimethylsilyl)oxy) methyl)-3-fluorophenyl)pyrimidin-2(1H)-one A suspension of cytosine (17.25 g, 47.0 mmol) and tert-butyl((2-fluoro-4-(4,4,5,5-tetramethyl-1,3,2-dioxaborolan-2-yl)benzyl)oxy)dimethylsilane (17.3 g, 47.1 mmol), in MeOH:$H_2O$ (4:1, 500 ml) was stirred at rt in open air for 30 min. TMEDA (6.0 g, 51.8 mmol) and $Cu(OAc)_2H_2O$ (9.4 g, 47.1 mmol) were added and the reaction was stirred in open air for 48 h at rt. The reaction mixture was concentrated under reduced pressure, and cold $H_2O$ (100 mL) was added. The solid was filtered and washed with $H_2O$ (5×50 mL), $Et_2O$ (3×30 mL), and $H_2O$ (2×30 mL) to afford the title compound.

Step 5: tert-butyl (1-(4-((1-(4-(((tert-butyldimethylsilyl)oxy)methyl)-3-fluorophenyl)-2-oxo-1,2-dihydropyrimidin-4-yl)carbamoyl)piperazin-1-yl)-2-methyl-1-oxopropan-2-yl)carbamate To a stirred solution 4-amino-1-(4-(((tert-butyldimethylsilyl)oxy)methyl)-3-fluorophenyl)pyrimidin-2(1H)-one (1.93 g, 5.5 mmol) and 1-(4-(2-((tert-butoxycarbonyl)amino)-2-methylpropanoyl)piperazine-1-carbonyl)-3-methyl-1H-imidazol-3-ium iodide (3.92 g, 7.7 mmol) in $CH_3CN$ (75 mL) was heated at 80° C. for 16 h. The reaction mixture was concentrated under reduced pressure and the crude material was purified by column chromatography (EtOAc:MeOH) to afford the title compound. LCMS [M+H] 647.4.

Step 6: tert-butyl (1-(4-((1-(3-fluoro-4-formylphenyl)-2-oxo-1,2-dihydropyrimidin-4-yl)carbamoyl) piperazin-1-yl)-2-methyl-1-oxopropan-2-yl)carbamate A solution of tert-butyl (1-(4-((1-(4-(((tert-butyldimethylsilyl)oxy)methyl)-3-fluorophenyl)-2-oxo-1,2-dihydropyrimidin-4-yl)carbamoyl)piperazin-1-yl)-2-methyl-1-oxopropan-2-yl)carbamate (550 mg, 0.85 mmol) and TsOH (323 mg, 1.70 mmol) in MeOH (20 mL) were stirred for 1 h. The excess MeOH was removed in vacuo. The crude mixture was partitioned between $CH_2Cl_2$ (75 mL) and $NaHCO_3$(150 mL). The $CH_2Cl_2$(75 mL) solution was taken and to this was added DMP (652 mg, 1.54 mmol) and stirred for 1 h. The solution was partitioned between $CH_2Cl_2$ and $NaHCO_3$ and $Na_2SO_2O_3$ (100 mL). The organic layer was dried over $Na_2SO_4$ and concentrated under reduced pressure to afford the title compound. LCMS [M+H] 531.2.

Step 7: tert-butyl (1-(4-((1-(4-(((trans-4-((tert-butoxycarbonyl)amino)cyclohexyl)amino)methyl)-3-fluorophenyl)-2-oxo-1,2,5,6-tetrahydropyrimidin-4-yl)carbamoyl)piperazin-1-yl)-2-methyl-1-oxopropan-2-yl)carbamate To a solution of tert-butyl (1-(4-((1-(3-fluoro-4-formylphenyl)-2-oxo-1,2-dihydropyrimidin-4-yl)carbamoyl)piperazin-1-yl)-2-methyl-1-oxopropan-2-yl)carbamate (80 mg, 0.15 mmol) in MeOH (15 mL) was added tert-butyl (trans-4-aminocyclohexyl)carbamate (32 mg, 0.15 mmol). The solution was stirred for 16 h and to this was added $NaBH_4$ (17 mg, 0.45 mmol) and the solution was stirred an additional 1 h. The excess MeOH was removed and the crude mixture was partitioned between EtOAc (100 mL) and 1 N NaOH (100 mL) and the aqueous layer washed with additional EtOAc (2×100 mL). The combined organics were dried over $Na_2SO_4$ and concentrated under reduced pressure. The crude material was purified via column chromatography (EtOAc:MeOH) to afford the title compound. LCMS [M+H] 729.8

Step 8: 4-(2-amino-2-methylpropanoyl)-N-(1-(4-(((trans-4-aminocyclohexyl)amino)methyl)-3-fluorophenyl)-2-oxo-1,2,5,6-tetrahydropyrimidin-4-yl)piperazine-1-carboxamide hydrochloride salt To solid tert-butyl (1-(4-((1-(4-(((trans-4-((tert-butoxycarbonyl)amino)cyclohexyl)amino)methyl)-3-fluorophenyl)-2-oxo-1,2,5,6-tetrahydropyrimidin-4-yl)carbamoyl)piperazin-1-yl)-2-methyl-1-oxopropan-2-yl)carbamate (0.15 mmol) was added HCl in MeOH (50 mL). The solution was stirred for 4 h and the excess MeOH was removed in vacuo. The crude solid was purified by recrystallization from water and isopropanol by dissolution into water, heating to 80° C. with stirring and adding antisolvent until cloudy and allowing to cool to rt or via RPHPLC and conversion to the hydrochloride salt with the addition of 2N HCl in MeOH (5 mL) and evaporation under reduced pressure. $^1H$ NMR (500 MHz, $D_2O$) δ 8.04 (d, 1H), 7.69 (t, 1H), 7.46-7.37 (m, 2H), 6.83 (d, 1H), 4.42 (s, 2H), 3.85-3.67 (m, 8H), 3.38-3.22 (m, 2H), 2.39-2.19 (m, 4H), 1.72 (s, 6H), 1.68-1.49 (m, 4H). LCMS [M+H] 529.3.

Alternatively, compound 330 may be prepared according to Scheme C-14a.

Scheme C-14a

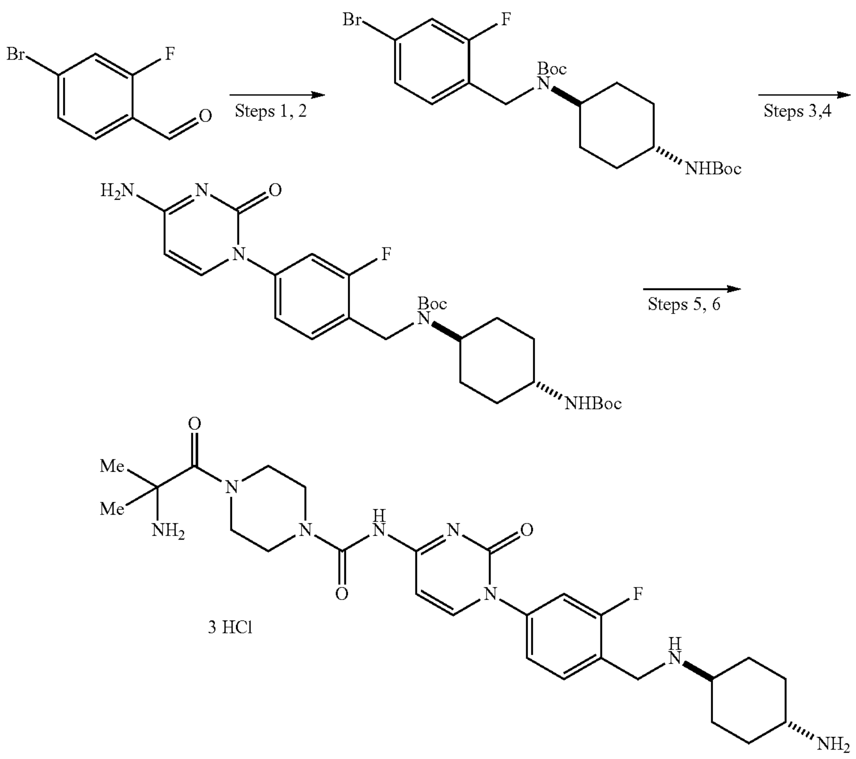

Reagents: 1) tert-butyl (trans-4-aminocyclohexyl)carbamate, $NaBH_4$, MeOH, 0° C. to rt, 16 h 2) $Boc_2O$, $K_2CO_3$, THF:$H_2O$, rt, 16 h 3) Pd(dppf)$Cl_2$•$CH_2Cl_2$, $B_2pin_2$, KOAc, dioxane, reflux, 16 h 4) cytosine, $Cu(OAc)_2$•$H_2O$, TMEDA, MeOH:$H_2O$, rt, 4 d 5) 1-(4-(2-((tert-butoxycarbonyl)amino)-2-methylpropanoyl)piperazine-1-carbonyl)-3-methyl-1H-imidazol-3-ium iodide, $CH_3CN$, reflux,2 d 6) 2M HCl/MeOH, rt, 18 h.

Step 1: tert-butyl (trans-4-((4-bromo-2-fluorobenzyl)amino)cyclohexyl)carbamate

To a solution of 4-bromo-2-fluorobenzaldehyde (5.0 g, 25 mmol) in MeOH (30 mL) at 0° C., was added tert-butyl (trans-4-aminocyclohexyl)carbamate (7.9 g, 37 mmol) followed by $NaBH_4$ (0.47 g, 12 mmol). The reaction was warmed to rt and stirred for 16 h. The reaction mixture was concentrated under reduced pressure, diluted with $CH_2Cl_2$ (500 mL), and washed with 10% NaOH (1×500 mL) which was back extracted with $CH_2Cl_2$ (500 mL). The combined organics were dried over $Na_2SO_4$ and concentrated under reduced pressure to afford the crude title compound. LCMS [M+H] 401.2.

Step 2: tert-butyl (4-bromo-2-fluorobenzyl)(trans-4-((tert-butoxycarbonyl)amino)cyclohexyl)carbamate To a solution of tert-butyl (trans-4-((4-bromo-2-fluorobenzyl)amino)cyclohexyl)carbamate (9.0 g, 22 mmol) in THF:$H_2O$ (1:1, 30 mL) was added $Boc_2O$ (7.3 g, 34 mmol) and $K_2CO_3$ (15 g, 110 mmol). The reaction was stirred at rt for 16 h. The organic layer was separated, and the aqueous layer was extracted with EtOAc (2×50 mL). The combined organics were washed with sat. aq. NaCl (1×100 mL) and dried over $Na_2SO_4$. The crude was purified by flash chromatography (Hex:EtOAc) to afford the title compound (9.8 g, 20 mmol). $^1H$ NMR (500 MHz, $CDCl_3$) δ 7.25-7.16 (m, 2H), 7.11 (br s, 1H), 4.32 (s, 3H), 4.06 (br. s, 1H), 3.31 (br. s, 1H), 2.00 (d, 2H), 1.70 (br. s, 2H), 1.42 (s, 9H), 1.36 (br. s, 11H), 1.19 (s, 2H).

Step 3: tert-butyl (trans-4-((tert-butoxycarbonyl)amino)cyclohexyl)(2-fluoro-4-(4,4,5,5-tetramethyl-1,3,2-dioxaborolan-2-yl)benzyl)carbamate A flask containing tert-butyl (4-bromo-2-fluorobenzyl)(trans-4-((tert-butoxycarbonyl)amino)cyclohexyl)carbamate (9.8 g, 20 mmol), $Pd(dppf)Cl_2 \cdot CH_2Cl_2$ (0.48 g, 0.59 mmol), potassium acetate (5.8 g, 59 mmol), and $B_2pin_2$ (5.5 g, 21 mmol) was evacuated and back-filled with $N_2$. Dioxane (6 mL) was added, the mixture was de-gassed with $N_2$, then heated to 105° C. for 16 h. The reaction mixture was diluted with EtOAc (30 mL) and filtered through a pad of Celite®. The filtrate was concentrated in vacuo and purified by flash chromatography (Hex:EtOAc) to afford the title compound (9.9 g 18 mmol), which was immediately carried-on to the next step. $^1H$ NMR (500 MHz, $CDCl_3$) δ 7.50 (d, 1H), 7.41 (d, 1H), 7.22 (br. s, 1H), 4.35 (br s, 2H), 4.07 (br. s, 1H), 3.29 (br. s, 1H), 1.98 (d, 2H), 1.73 (br. s, 2H), 1.55-1.02 (m, 34H).

Step 4: tert-butyl (4-(4-amino-2-oxopyrimidin-1(2H)-yl)-2-fluorobenzyl)(trans-4-((tert-butoxycarbonyl)amino)cyclohexyl)carbamate A mixture of tert-butyl (trans-4-((tert-butoxycarbonyl)amino)cyclohexyl)(2-fluoro-4-(4,4,5,5-tetramethyl-1,3,2-dioxaborolan-2-yl)benzyl)carbamate (9.9 g 18 mmol) and cytosine (2.0 g, 18 mmol) in MeOH (450 mL) and $H_2O$ (150 mL) was stirred at rt for 30 min. $Cu(OAc)_2 \cdot H_2O$ (3.6 g, 18 mmol) and TMEDA (3.3 mL, 22 mmol) were added to the reaction and it was stirred open to the air at rt for 4 days. The reaction mixture was concentrated under reduced pressure to remove the MeOH, $H_2O$ was added (ca. 650 mL), and the suspension was stirred vigorously for several hours and scraped with a spatula until the gummy residue had turned into a solid. The precipitate was collected by vacuum filtration to give the title compound in about 60% purity (6.56 g, 69%) as an off-white solid. LCMS [M+H] 532.3.

Step 5: tert-butyl (4-(4-(4-(2-((tert-butoxycarbonyl)amino)-2-methylpropanoyl)piperazine-1-carboxamido)-2-oxopyrimidin-1(2H)-yl)-2-fluorobenzyl)((trans)-4-((tert-butoxycarbonyl)amino)cyclohexyl)carbamate A mixture of tert-butyl (4-(4-amino-2-oxopyrimidin-1(2H)-yl)-2-fluorobenzyl)((trans)-4-((tert-butoxycarbonyl)amino)cyclohexyl)carbamate (6.56 g, 12.3 mmol) and 1-(4-(2-((tert-butoxycarbonyl)amino)-2-methylpropanoyl)piperazine-1-carbonyl)-3-methyl-1H-imidazol-3-ium iodide (8.20 g, 16.2 mmol) in $CH_3CN$ (125 mL) was stirred at reflux for 2 days. The mixture was cooled, diluted with EtOAc (500 mL), washed with sat. aq. $NaHCO_3$(2×350 mL) and brine (350 mL), dried ($Na_2SO_4$), filtered, and concentrated. The residue was purified by flash chromatography (MeOH/EtOAc/Hexanes) to give the title compound (4.38 g, 42.8%) as a light yellow solid. $^1H$ NMR (500 MHz, $CDCl_3$) δ 12.94 (s, 1H), 7.41-7.29 (m, 1H), 7.28-7.21 (m, 1H), 7.13-7.05 (m, 2H), 5.87-5.79 (m, 1H), 4.91-4.82 (m, 1H), 4.50-4.28 (m, 3H), 4.15-3.98 (m, 1H), 3.92-3.55 (m, 8H), 3.38-3.24 (m, 1H), 2.05-1.95 (m, 2H), 1.77-1.67 (m, 2H), 1.58-1.28 (m, 33H), 1.26-1.11 (m, 4H). LCMS [M+H] 829.6.

Step 6: 4-(2-amino-2-methylpropanoyl)-N-(1-(4-((((trans)-4-aminocyclohexyl)amino)methyl)-3-fluorophenyl)-2-oxo-1,2-dihydropyrimidin-4-yl)piperazine-1-carboxamide hydrochloride salt A mixture of tert-butyl (4-(4-(4-(2-((tert-butoxycarbonyl)amino)-2-methylpropanoyl)piperazine-1-carboxamido)-2-oxopyrimidin-1(2H)-yl)-2-fluorobenzyl)((trans)-4-((tert-butoxycarbonyl)amino)cyclohexyl)carbamate (3.88 g, 4.68 mmol) and 2 M HCl in MeOH (100 mL, 200 mmol) was stirred at rt for 18 h. The precipitate was collected by vacuum filtration, and the solid was washed with isopropanol then $Et_2O$. The solid was recrystallized from $H_2O$/isopropanol to give the title compound as a white solid. Analytical data was consistent with previous data.

Compound 332

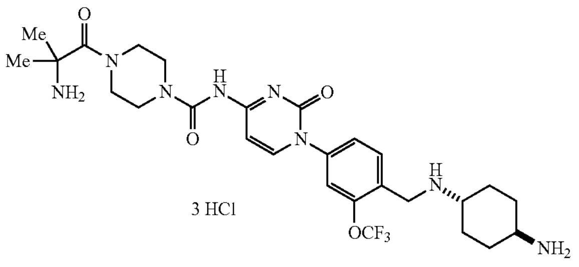

4-(2-Amino-2-methylpropanoyl)-N-(1-(4-(((trans-4-aminocyclohexyl)amino)methyl)-3-(trifluoromethoxy)phenyl)-2-oxo-1,2-dihydropyrimidin-4-yl)piperazine-1-carboxamide hydrochloride salt Prepared in a similar fashion to Scheme C-14 from tert-butyl (1-(4-((1-(4-formyl-3-(trifluoromethoxy)phenyl)-2-oxo-1,2-dihydropyrimidin-4-yl)carbamoyl)piperazin-1-yl)-2-methyl-1-oxopropan-2-yl)carbamate and N-boc-trans-1,4-cyclohexanediamine. $^1H$ NMR (500 MHz, $D_2O$) δ 7.90 (d, 1H), 7.75 (d, 1H), 7.64 (s, 1H), 7.50 (d, 1H), 6.84 (d, 1H), 4.44 (s, 2H), 3.79-3.65 (m, 8H), 3.36-3.21 (m, 2H), 2.39-2.18 (m, 4H), 1.71 (s, 6H), 1.67-1.48 (m, 4H). LCMS [M+H] 595.2.

Compound 334

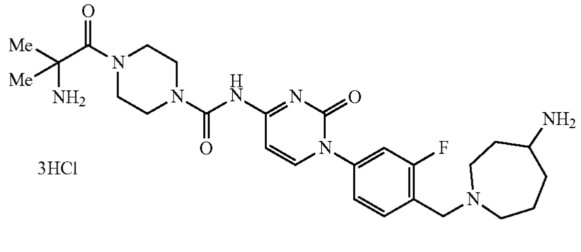

4-(2-Amino-2-methylpropanoyl)-N-(1-(4-((4-amino-azepan-1-yl)methyl)-3-fluorophenyl)-2-oxo-1,2-dihydropyrimidin-4-yl)piperazine-1-carboxamide hydrochloride salt Prepared in a similar fashion to Scheme C-14 from tert-butyl (1-(4-((1-(3-fluoro-4-formylphenyl)-2-oxo-1,2-dihydropyrimidin-4-yl)carbamoyl)piperazin-1-yl)-2-methyl-1-oxopropan-2-yl)carbamate and tert-butyl azepan-4-ylcarbamate. $^{1}H$ NMR (500 MHz, $D_2O$) δ 8.18 (d, 1H), 7.76 (t, 1H), 7.49 (d, 1H), 7.44 (d, 1H), 6.80 (d, 1H), 4.54 (s, 2H), 3.82-3.69 (m, 8H), 3.64-3.44 (m, 4H), 3.41-3.19 (m, 1H), 2.42-1.96 (m, 5H), 1.84 (m, 1H), 1.71 (s, 6H). LCMS [M+H] 529.3.

Compound 360

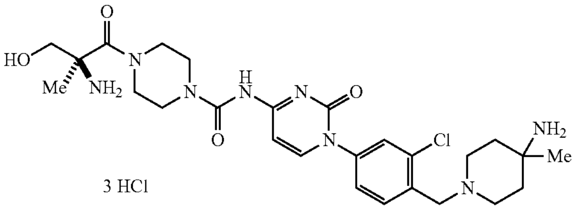

(S)-4-(2-Amino-3-hydroxy-2-methylpropanoyl)-N-(1-(4-((4-amino-4-methylpiperidin-1-yl)methyl)-3-chlorophenyl)-2-oxo-1,2-dihydropyrimidin-4-yl)piperazine-1-carboxamide hydrochloride salt Prepared in a similar fashion to Scheme C-14 from tert-butyl (2R,4S)-2-(tert-butyl)-4-(4-((1-(3-chloro-4-formylphenyl)-2-oxo-1,2-dihydropyrimidin-4-yl)carbamoyl)piperazine-1-carbonyl)-4-methyloxazolidine-3-carboxylate and tert-butyl (4-methylpiperidin-4-yl)carbamate. LCMS [M+H] 561.2.

Compound 353

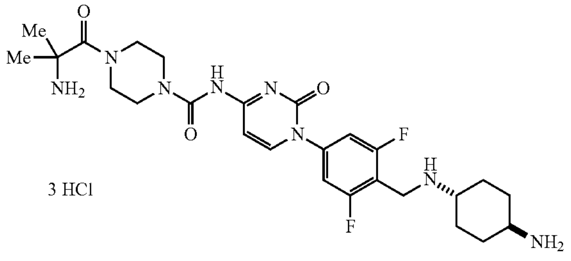

4-(2-Amino-2-methylpropanoyl)-N-(1-(4-(((trans-4-aminocyclohexyl)amino)methyl)-3,5-difluorophenyl)-2-oxo-1,2-dihydropyrimidin-4-yl)piperazine-1-carboxamide hydrochloride salt Prepared in a similar fashion to Scheme C-14 from tert-butyl (1-(4-((1-(3,5-difluoro-4-formylphenyl)-2-oxo-1,2-dihydropyrimidin-4-yl)carbamoyl)piperazin-1-yl)-2-methyl-1-oxopropan-2-yl)carbamate and N-boc-trans-1,4-cyclohexanediamine. 1H NMR 7.86 (d, 1H), 7.31 (d, 2H), 6.85 (d, 1H), 4.46 (s, 2H), 3.86-3.66 (m, 8H), 3.41-3.23 (m, 2H), 2.41-2.20 (m, 4H), 1.72 (s, 6H), 1.68-1.49 (m, 4H). LCMS [M+H] 547.4.

Compound 283

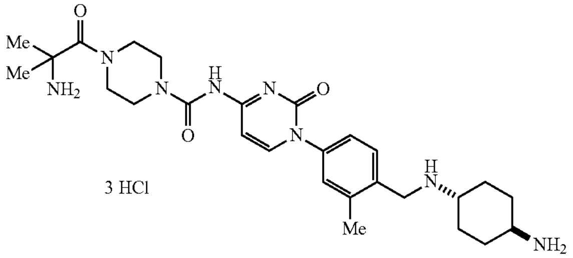

4-(2-Amino-2-methylpropanoyl)-N-(1-(4-((((trans)-4-aminocyclohexyl)amino)methyl)-3-methylphenyl)-2-oxo-1,2-dihydropyrimidin-4-yl)piperazine-1-carboxamide hydrochloride salt Prepared in a similar fashion as scheme C-14 from tert-butyl (1-(4-((1-(4-formyl-3-methylphenyl)-2-oxo-1,2-dihydropyrimidin-4-yl)carbamoyl)piperazin-1-yl)-2-methyl-1-oxopropan-2-yl)carbamate and tert-butyl ((trans)-4-aminocyclohexyl)carbamate. LCMS [M+H] 525.36.

Compound 271

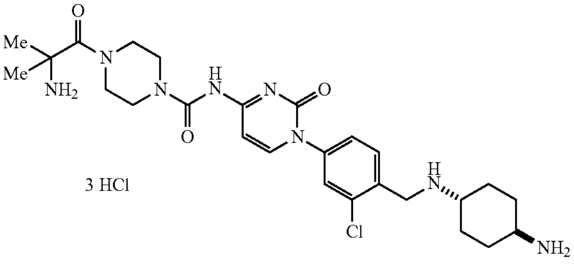

4-(2-Amino-2-methylpropanoyl)-N-(1-(4-((((trans)-4-aminocyclohexyl)amino)methyl)-3-chlorophenyl)-2-oxo-1,2-dihydropyrimidin-4-yl)piperazine-1-carboxamide hydrochloride salt Prepared in a similar fashion as scheme C-14 from tert-butyl (1-(4-((1-(3-chloro-4-formylphenyl)-2-oxo-1,2-dihydropyrimidin-4-yl)carbamoyl)piperazin-1-yl)-2-methyl-1-oxopropan-2-yl)carbamate and tert-butyl ((trans)-4-aminocyclohexyl)carbamate. $^{1}H$ NMR (400 MHz, D2O) δ 8.00 (d, 1H), 7.75 (t, 2H), 7.57-7.52 (m, 1H), 6.86 (d, 1H), 4.53 (s, 2H), 3.79 (s, 3H), 3.74 (s, 5H), 3.48-3.38 (m, 1H), 3.36-3.24 (m, 1H), 2.41 (d, 2H), 2.25 (d, 2H), 1.74 (d, 6H), 1.71-1.52 (m, 4H). LCMS [M+H] 545.3.

Compound 272

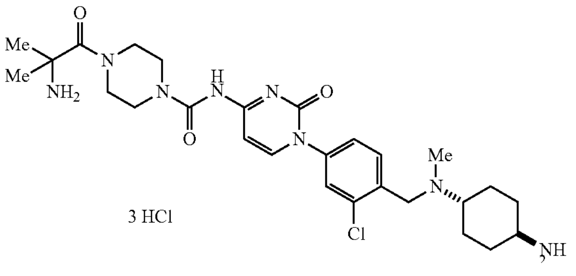

4-(2-Amino-2-methylpropanoyl)-N-(1-(4-((((trans)-4-aminocyclohexyl)(methyl)amino)methyl)-3-chlorophenyl)-2-oxo-1,2-dihydropyrimidin-4-yl)piperazine-1-carboxamide Prepared in a similar fashion as in Scheme C-14 from tert-butyl (1-(4-((1-(3-chloro-4-formylphenyl)-2-oxo-1,2-dihydropyrimidin-4-yl)carbamoyl)piperazin-1-yl)-2-methyl-1-oxopropan-2-yl)carbamate. $^1$H NMR (400 MHz, D2O) δ 8.06 (d, 1H), 7.82-7.77 (m, 2H), 7.61-7.55 (m, 1H), 6.85 (d, 1H), 4.83 (d, 1H), 4.37 (d, 1H), 3.78 (s, 3H), 3.75 (s, 5H), 3.63-3.48 (m, 2H), 3.34-3.26 (m, 1H), 2.85 (s, 3H), 2.42-2.23 (m, 4H), 2.03-1.78 (m, 2H), 1.74 (s, 6H), 1.70-1.55 (in, 2H). LCMS [M+H] 559.3.

Compound 278

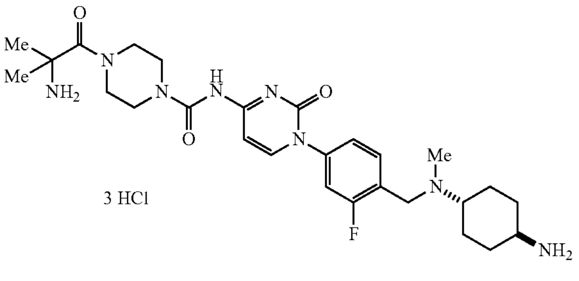

4-(2-Amino-2-methylpropanoyl)-N-(1-(4-(((trans-4-aminocyclohexyl)(methyl)amino)methyl)-3-fluorophenyl)-2-oxo-1,2-dihydropyrimidin-4-yl)piperazine-1-carboxamide hydrochloride salt Prepared in a similar fashion as in Scheme C-14 from tert-butyl (1-(4-((1-(3-fluoro-4-formylphenyl)-2-oxo-1,2-dihydropyrimidin-4-yl)carbamoyl)piperazin-1-yl)-2-methyl-1-oxopropan-2-yl)carbamate. $^1$H NMR (500 MHz, $D_2O$) δ 7.88 (d, 1H), 7.71 (t, 1H), 7.50-7.33 (m, 2H), 6.86 (d, 1H), 4.69 (d, 1H), 4.32 (d, 1H), 3.92-3.59 (m, 8H), 3.49 (t, 1H), 3.28 (t, 1H), 2.83 (s, 3H), 2.36-2.22 (m, 2H), 1.92-1.76 (m, 2H), 1.73 (s, 6H), 1.64-1.53 (m, 4H). LCMS [M+H] 543.3.

Compound 355

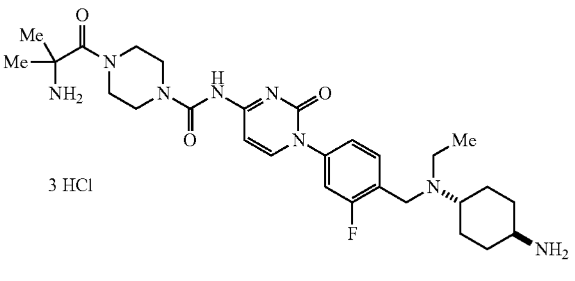

4-(2-Amino-2-methylpropanoyl)-N-(1-(4-(((trans-4-aminocyclohexyl)(ethyl)amino)methyl)-3-fluorophenyl)-2-oxo-1,2-dihydropyrimidin-4-yl)piperazine-1-carboxamide hydrochloride salt Prepared in a similar fashion as in Scheme C-14 from tert-butyl (1-(4-((1-(3-fluoro-4-formylphenyl)-2-oxo-1,2-dihydropyrimidin-4-yl)carbamoyl)piperazin-1-yl)-2-methyl-1-oxopropan-2-yl)carbamate. $^1$H NMR (400 MHz, $D_2O$) δ 7.74 (d, 1H), 7.56 (dd, 1H), 7.30 (dd, 1H), 7.25 (dd, 1H), 6.70 (d, 1H), 4.49 (d, 1H), 4.21 (d, 1H), 3.61 (br s, 3H), 3.58-3.50 (m, 5H), 3.39-3.29 (m, 1H), 3.25-3.07 (m, 3H), 2.17-2.03 (m, 4H), 1.85-1.59 (m, 2H), 1.57 (s, 6H), 1.49-1.35 (m, 2H), 1.17 (t, 3H). LCMS [M+H] 557.3.

Compound 302

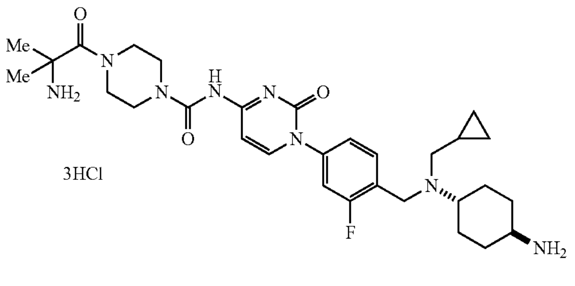

4-(2-Amino-2-methylpropanoyl)-N-(1-(4-(((trans-4-aminocyclohexyl)(cyclopropylmethyl)amino)methyl)-3-fluorophenyl)-2-oxo-1,2-dihydropyrimidin-4-yl)piperazine-1-carboxamide hydrochloride salt Prepared in a similar fashion as in Scheme C-14 from tert-butyl (1-(4-((1-(3-fluoro-4-formylphenyl)-2-oxo-1,2-dihydropyrimidin-4-yl)carbamoyl)piperazin-1-yl)-2-methyl- 1-oxopropan-2-yl)carbamate and cyclopropanecarbaldehyde. LCMS [M+H] 583.3.

Compound 317

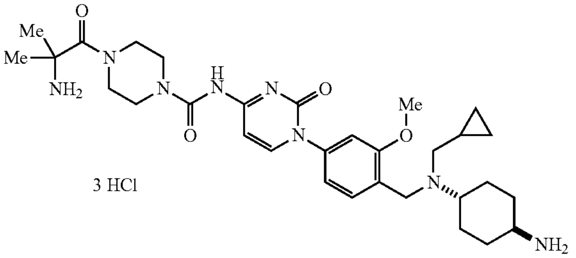

3 HCl 4-(2-Amino-2-methylpropanoyl)-N-(1-(4-(((trans-4-aminocyclohexyl)(cyclopropylmethyl)amino)methyl)-3-methoxyphenyl)-2-oxo-1,2-dihydropyrimidin-4-yl)piperazine-1-carboxamide hydrochloride salt Prepared in a similar fashion as in Scheme C-14 from tert-butyl (1-(4-((1-(4-formyl-3-methoxyphenyl)-2-oxo-1,2-dihydropyrimidin-4-yl)carbamoyl)piperazin-1-yl)-2-methyl-1-oxopropan-2-yl)carbamate and cyclopropanecarbaldehyde. $^1$H NMR (500 MHz, $D_2O$) δ 8.01 (d, 1H), 7.57 (d, 1H), 7.23 (s, 1H), 7.12 (d, 1H), 6.83 (d, 1H), 4.61-4.39 (m, 2H), 3.93 (s, 3H), 3.84-3.65 (m, 8H), 3.57 (t, 2H), 3.29-3.04 (m, 3H), 2.32-2.16 (m, 4H), 1.98-1.78 (m, 2H), 1.72 (s, 6H), 1.62-1.48 (m, 1H), 1.11-1.02 (m, 1H), 0.75-0.69 (m, 2H), 0.40-0.27 (m, 2H). LCMS [M+H] 595.4

Compound 318

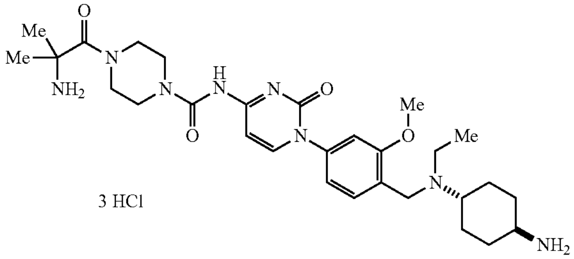

3 HCl 4-(2-Amino-2-methylpropanoyl)-N-(1-(4-(((trans-4-aminocyclohexyl)(ethyl)amino)methyl)-3-methoxyphenyl)-2-oxo-1,2-dihydropyrimidin-4-yl)piperazine-1-carboxamide hydrochloride salt Prepared in a similar fashion as in Scheme C-14 from tert-butyl (1-(4-((1-(4-formyl-3-methoxyphenyl)-2-oxo-1,2-dihydropyrimidin-4-yl)carbamoyl)piperazin-1-yl)-2-methyl-1-oxopropan-2-yl)carbamate. $^1$H NMR (500 MHz, $D_2O$) δ 7.95 (d, 1H), 7.56 (d, 1H), 7.21 (s, 1H), 7.10 (d, 1H), 6.83 (d, 1H), 4.61-4.22 (m, 2H), 3.92 (s, 3H), 3.83-3.66 (m, 8H), 3.50-3.23 (m, 4H), 2.28-2.18 (m, 4H), 1.97-1.75 (m, 2H), 1.72 (s, 6H), 1.66-1.49 (m, 2H), 1.30 (t, 3H). LCMS [M+H] 569.4.

Compound 327

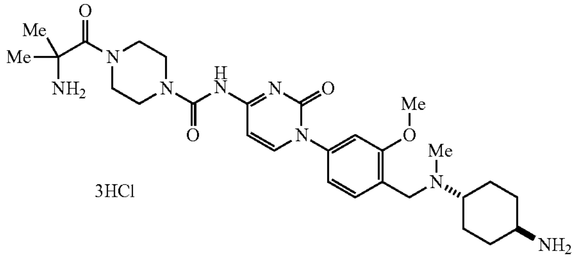

3HCl 4-(2-Amino-2-methylpropanoyl)-N-(1-(4-(((trans-4-aminocyclohexyl)(methyl)amino)methyl)-3-methoxyphenyl)-2-oxo-1,2-dihydropyrimidin-4-yl)piperazine-1-carboxamide hydrochloride salt Prepared in a similar fashion as Scheme C-14 from tert-butyl (1-(4-((1-(4-formyl-3-methoxyphenyl)-2-oxo-1,2-dihydropyrimidin-4-yl)carbamoyl)piperazin-1-yl)-2-methyl-1-oxopropan-2-yl)carbamate. $^1$H NMR (500 MHz, $D_2O$) δ 8.02 (d, 1H), 7.58 (d, 1H), 7.23 (s, 1H), 7.13 (d, 1H), 6.83 (d, 1H), 4.66 (d, 1H), 4.12 (d, 1H), 3.92 (s, 3H), 3.87-3.69 (m, 8H), 3.42 (t, 1H), 3.26 (t, 1H), 2.79 (s, 3H), 2.33-2.23 (m, 4H), 1.99-1.75 (m, 2H), 1.73 (s, 6H), 1.65-1.51 (m, 2H). LCMS [M+H] 555.4.

Compound 328

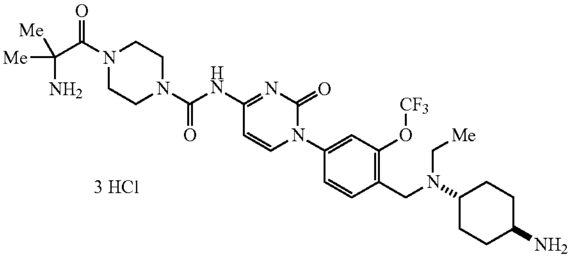

3 HCl 4-(2-Amino-2-methylpropanoyl)-N-(1-(4-(((trans-4-aminocyclohexyl)(ethyl)amino)methyl)-3-(trifluoromethoxy)phenyl)-2-oxo-1,2-dihydropyrimidin-4-yl)piperazine-1-carboxamide hydrochloride salt Prepared in a similar fashion as in Scheme C-14 from tert-butyl (1-(4-((1-(4-formyl-3-(trifluoromethoxy)phenyl)-2-oxo-1,2-dihydropyrimidin-4-yl)carbamoyl)piperazin-1-yl)-2-methyl-1-oxopropan-2-yl)carbamate. $^1$H NMR (500 MHz, $D_2O$) δ 8.00 (d, 1H), 7.81 (d, 1H), 7.69 (s, 1H), 7.55 (d, 1H), 6.83 (d, 1H), 4.69 (d, 1H), 4.34 (d, 1H), 3.80-3.65 (m, 8H), 3.49 (t, 1H), 3.38-3.23 (m, 3H), 2.32-2.17 (m, 4H), 2.01-1.78 (m, 2H), 1.72 (s, 6H), 1.64-1.54 (m, 2H), 1.32 (t, 3H). LCMS [M+H] 623.4.

Compound 329

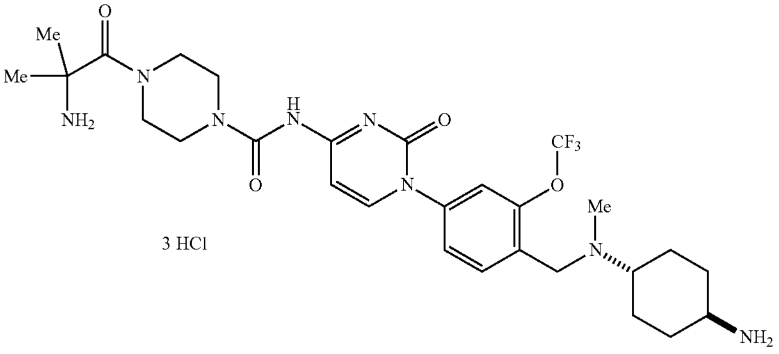

3 HCl 4-(2-Amino-2-methylpropanoyl)-N-(1-(4-(((trans-4-aminocyclohexyl)(methyl)amino)methyl)-3-(trifluoromethoxy)phenyl)-2-oxo-1,2-dihydropyrimidin-4-yl)piperazine-1-carboxamide hydrochloride salt Prepared in a similar fashion as in Scheme C-14 from tert-butyl (1-(4-((1-(4-formyl-3-(trifluoromethoxy)phenyl)-2-oxo-1,2-dihydropyrimidin-4-yl)carbamoyl)piperazin-1-yl)-2-methyl-1-oxopropan-2-yl)carbamate. $^1H$ NMR (500 MHz, $D_2O$) δ 8.05 (d, 1H), 7.82 (d, 1H), 7.69 (s, 1H), 7.56 (d, 1H), 6.83 (d, 1H), 4.78-4.71 (m, 1H), 4.27 (d, 1H), 3.82-3.68 (m, 8H), 3.48 (t, 1H), 3.28 (t, 1H), 2.82 (s, 3H), 2.36-2.20 (m, 4H), 1.97-1.76 (m, 2H), 1.72 (s, 6H), 1.64-1.51 (m, 2H). LCMS [M+H] 609.4.

Compound 331

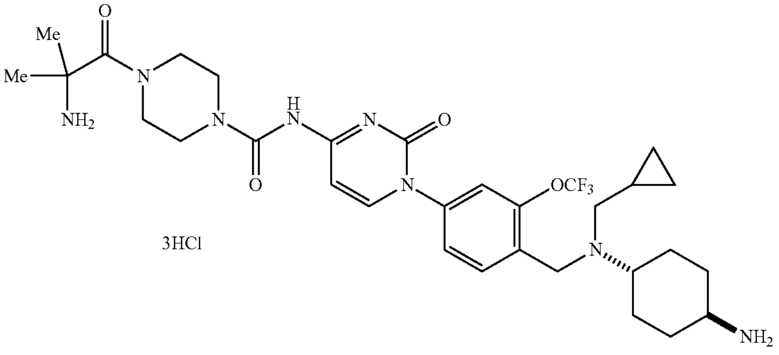

3HCl 4-(2-Amino-2-methylpropanoyl)-N-(1-(4-(((trans-4-aminocyclohexyl)(cyclopropylmethyl)amino)methyl)-3-(trifluoromethoxy)phenyl)-2-oxo-1,2-dihydropyrimidin-4-yl)piperazine-1-carboxamide hydrochloride salt Prepared in a similar fashion as in Scheme C-14 from tert-butyl (1-(4-((1-(4-formyl-3-(trifluoromethoxy)phenyl)-2-oxo-1,2-dihydropyrimidin-4-yl)carbamoyl)piperazin-1-yl)-2-methyl-1-oxopropan-2-yl)carbamate and cyclopropanecarbaldehyde. $^1H$ NMR (500 MHz, $D_2O$) δ 7.96 (d, 1H), 7.81 (d, 1H), 7.69 (s, 1H), 7.55 (d, 1H), 6.85 (d, 1H), 4.68 (d, 2H), 4.52 (d, 2H), 3.87-3.67 (m, 8H), 3.64 (t, 1H), 3.29-3.10 (m, 1H), 2.36-2.17 (m, 4H), 2.01-1.78 (m, 2H), 1.72 (s, 6H), 1.67-1.50 (m, 2H), 1.11-1.04 (m, 1H), 0.74 (d, 2H), 0.36 (d, 2H). LCMS [M+H] 649.4.

Compound 354

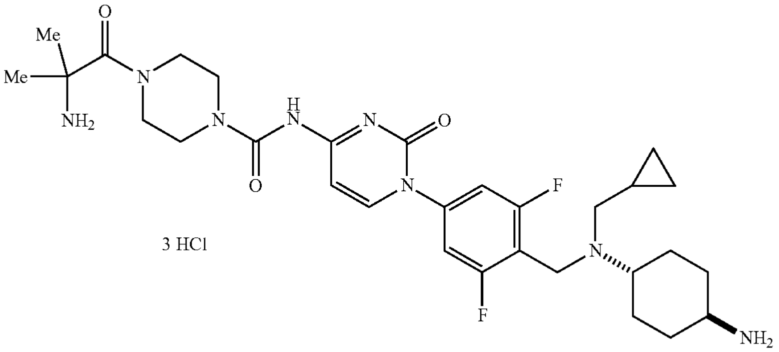

3 HCl 4-(2-Amino-2-methylpropanoyl)-N-(1-(4-(((trans-4-aminocyclohexyl)(cyclopropylmethyl)amino)methyl)-3,5-difluorophenyl)-2-oxo-1,2-dihydropyrimidin-4-yl)piperazine-1-carboxamide hydrochloride salt Prepared in a similar fashion as in Scheme C-14 from tert-butyl (1-(4-((1-(3,5-difluoro-4-formylphenyl)-2-oxo-1,2-dihydropyrimidin-4-yl)carbamoyl)piperazin-1-yl)-2-methyl-1-oxopropan-2-yl)carbamate and cyclopropanecarbaldehyde. $^1$H (400 MHz, $D_2O$) NMR δ 7.86 (d, 1H), 7.34 (d, 2H), 6.85 (d, 1H), 4.65-4.50 (m, 2H), 3.83-3.61 (m, 8H), 3.32-3.13 (m, 4H), 3.39-1.77 (m, 5H), 1.71 (s, 6H), 1.64-0.95 (m, 4) 0.80-0.35 (m, 4H). LCMS [M+H] 601.5.

Compound 284

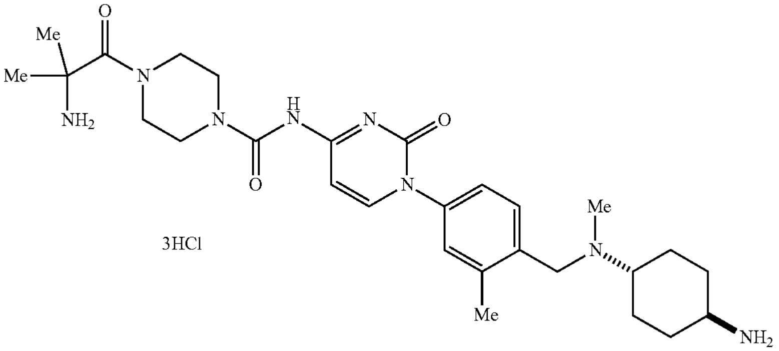

3HCl 4-(2-Amino-2-methylpropanoyl)-N-(1-(4-((((trans)-4-aminocyclohexyl)(methyl)amino)methyl)-3-methylphenyl)-2-oxo-1,2-dihydropyrimidin-4-yl)piperazine-1-carboxamide hydrochloride salt Prepared in a similar fashion as Scheme C-14 from tert-butyl (1-(4-((1-(4-formyl-3-methylphenyl)-2-oxo-1,2-dihydropyrimidin-4-yl)carbamoyl)piperazin-1-yl)-2-methyl-1-oxopropan-2-yl)carbamate and formalin. $^1$H NMR (400 MHz, $D_2O$) δ 8.08 (d, 1H), 7.63 (d, 1H), 7.47 (s, 1H), 7.45-7.40 (m, 1H), 6.84 (d, 1H), 4.68 (d, 1H), 4.28 (d, 1H), 3.79 (s, 3H), 3.76 (s, 5H), 3.59-3.50 (m, 1H), 3.35-3.26 (m, 1H), 2.81 (s, 3H), 2.49 (s, 3H), 2.39-2.24 (m, 4H), 2.02-1.79 (m, 2H), 1.74 (s, 6H), 1.70-1.56 (m, 2H). LCMS [M+H] 539.3.

Compound 285

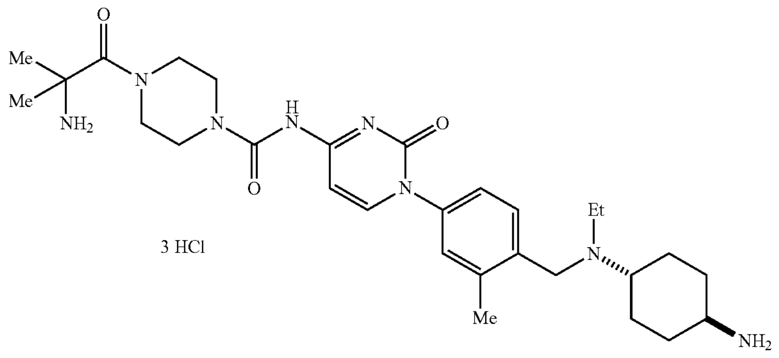

4-(2-Amino-2-methylpropanoyl)-N-(1-(4-((((trans)-4-aminocyclohexyl)(ethyl)amino)methyl)-3-methylphenyl)-2-oxo-1,2-dihydropyrimidin-4-yl)piperazine-1-carboxamide hydrochloride salt Prepared in a similar fashion as in Scheme C-14 from tert-butyl (1-(4-((1-(4-formyl-3-methylphenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$) δ 8.01 (d, 1H), 7.62 (d, 1H), 7.46 (s, 1H), 7.44-7.39 (m, 1H), 6.85 (d, 1H), 4.62 (d, 1H), 4.33 (d, 1H), 3.79 (s, 3H), 3.75 (s, 5H), 3.60-3.50 (m, 1H), 3.43-3.26 (m, 3H), 2.48 (s, 3H), 2.36-2.23 (m, 4H), 2.12-1.96 (m, 1H), 1.96-1.80 (m, 1H), 1.75 (s, 6H), 1.71-1.56 (m, 2H), 1.33 (t, 3H). LCMS [M+H] 553.4.

Compound 270

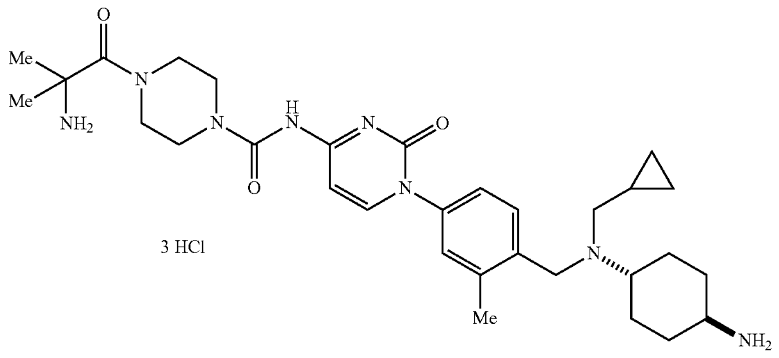

4-(2-Amino-2-methylpropanoyl)-N-(1-(4-((((trans)-4-aminocyclohexyl)(cyclopropylmethyl)amino)methyl)-3-methylphenyl)-2-oxo-1,2-dihydropyrimidin-4-yl)piperazine-1-carboxamide hydrochloride salt Prepared in a similar fashion as in Scheme C-14 from tert-butyl (1-(4-((1-(4-formyl-3-methylphenyl)-2-oxo-1,2-dihydropyrimidin-4-yl)carbamoyl)piperazin-1-yl)-2-methyl-1-oxopropan-2-yl)carbamate and cyclopropanecarbaldehyde. $^1$H NMR (400 MHz, $D_2O$) δ 8.01 (d, 1H), 7.63 (d, 1H), 7.46 (s, 1H), 7.42 (d, 1H), 6.85 (d, 1H), 4.60 (d, 1H), 4.46 (d, 1H), 3.79 (s, 3H), 3.74 (d, 6H), 3.34-3.22 (m, 2H), 3.18-3.05 (m, 1H), 2.50 (s, 3H), 2.41-2.20 (m, 4H), 2.10-1.94 (m, 1H), 1.94-1.81 (m, 1H), 1.74 (d, 6H), 1.72-1.51 (m, 2H), 1.17-1.02 (m, 1H), 0.82-0.70 (m, 2H), 0.42-0.27 (m, 2H). LCMS [M+H] 579.6.

Compound 273

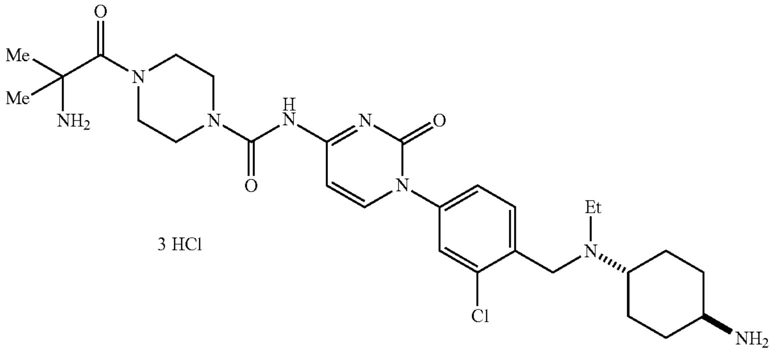

4-(2-Amino-2-methylpropanoyl)-N-(1-(4-((((trans)-4-aminocyclohexyl)(ethyl)amino)methyl)-3-chlorophenyl)-2-oxo-1,2-dihydropyrimidin-4-yl)piperazine-1-carboxamide hydrochloride salt Prepared in a similar fashion as in Scheme C-14 from tert-butyl (1-(4-((1-(3-chloro-4-formylphenyl)-2-oxo-1,2-dihydropyrimidin-4-yl)carbamoyl)piperazin-1-yl)-2-methyl-1-oxopropan-2-yl)carbamate and acetaldehyde. $^{1}H$ NMR (400 MHz, $D_2O$) δ 8.02 (d, 1H), 7.83-7.77 (m, 2H), 7.57 (dd, 1H), 6.86 (d, 1H), 4.76 (d, 1H), 4.46 (d, 1H), 3.79 (br. s, 3H), 3.74 (br. s, 5H), 3.62-3.50 (m, 1H), 3.43-3.25 (m, 3H), 2.39-2.25 (m, 4H), 2.10-1.95 (m, 1H), 1.95-1.81 (m, 1H), 1.75 (s, 6H), 1.69-1.56 (m, 2H), 1.35 (t, 3H). LCMS [M+H] 573.6.

Compound 276

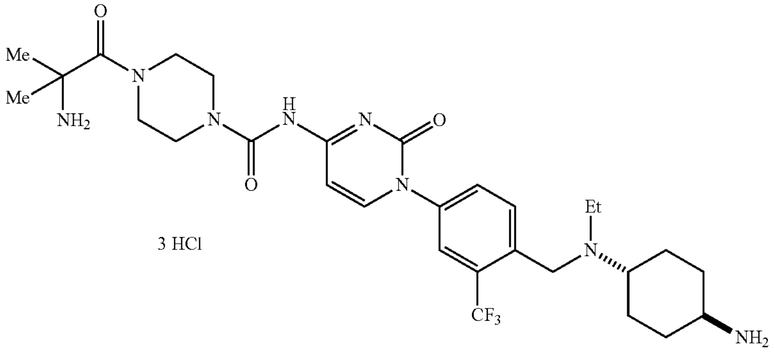

4-(2-Amino-2-methylpropanoyl)-N-(1-(4-((((trans)-4-aminocyclohexyl)(ethyl)amino)methyl)-3-(trifluoromethyl)phenyl)-2-oxo-1,2-dihydropyrimidin-4-yl) piperazine-1-carboxamide hydrochloride salt Prepared in a similar fashion as in Scheme C-14 from tert-butyl (1-(4-((1-(4-formyl-3-(trifluoromethyl)phenyl)-2-oxo-1,2-dihydropyrimidin-4-yl)carbamoyl)piperazin-1-yl)-2-methyl-1-oxopropan-2-yl)carbamate and acetaldehyde. $^{1}H$ NMR (400 MHz, $D_2O$) δ 8.05 (s, 1H), 7.96 (d, 1H), 7.94-7.82 (m, 2H), 6.89 (d, 1H), 4.83 (d, 1H), 4.51 (d, 1H), 3.79 (s, 3H), 3.74 (s, 5H), 3.64-3.55 (m, 1H), 3.44-3.22 (m, 3H), 2.30 (d, 4H), 2.05-1.82 (m, 2H), 1.75 (s, 6H), 1.72-1.54 (m, 2H), 1.33 (t, 3H). LCMS [M+H] 607.4.

Compound 21

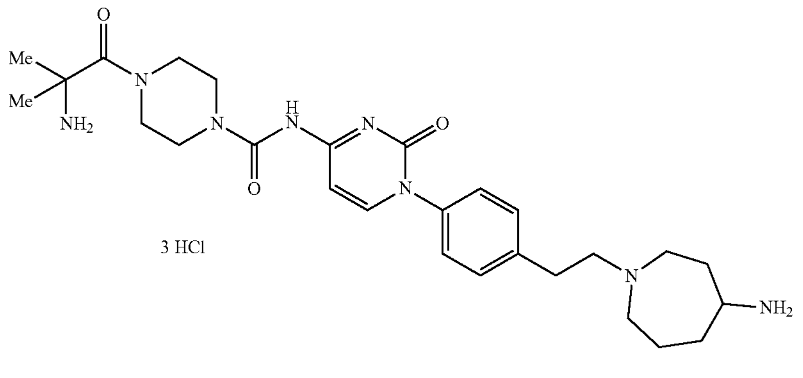

4-(2-Amino-2-methylpropanoyl)-N-(1-(4-(2-(4-aminoazepan-1-yl)ethyl)phenyl)-2-oxo-1,2-dihydropyrimidin-4-yl)piperazine-1-carboxamide hydrochloride salt Scheme C-15

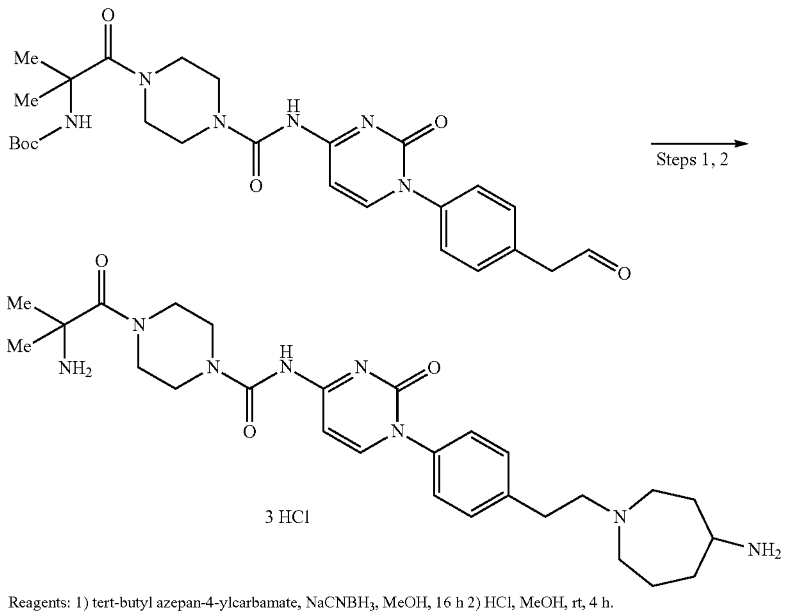

Step 1: tert-butyl (1-(4-((1-(4-(2-(4-((tert-butoxycarbonyl)amino)azepan-1-yl)ethyl)phenyl)-2-oxo-1,2-dihydropyrimidin-4-yl)carbamoyl)piperazin-1-yl)-2-methyl-1-oxopropan-2-yl)carbamate To a solution of tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate (50.0 mg, 0.10 mmol) in MeOH (10 mL) was added tert-butyl azepan-4-ylcarbamate (30.0 mg, 0.14 mmol) followed by $NaCNBH_3$ (25.0 mg, 0.4 mmol). The reaction was stirred at rt for 16 h. The excess MeOH was removed and the crude solution was partitioned between EtOAc (50 mL) and 1N NaOH (50 mL). The organic layer was dried over $Na_2SO_4$ and concentrated under reduced pressure to afford the title compound.

Step 2: 4-(2-amino-2-methylpropanoyl)-N-(1-(4-(2-(4-aminoazepan-1-yl)ethyl)phenyl)-2-oxo-1,2-dihydropyrimidin-4-yl)piperazine-1-carboxamide hydrochloride salt Tert-butyl (1-(4-((1-(4-(2-(4-((tert-butoxycarbonyl)amino)azepan-1-yl)ethyl)phenyl)-2-oxo-1,2-dihydropyrimidin-4-yl)carbamoyl)piperazin-1-yl)-2-methyl-1-oxopropan-2-yl)carbamate was dissolved in a solution of HCl/MeOH (50 mL) and stirred for 4 h. The solvent was evaporated and the crude solid was purified by RPHPLC ($H_2O$:$CH_3CN$:TFA) and concentrated under reduced pressure. Product fractions were converted to the HCl salt with the addition of HCl in MeOH and removal under reduced pressure to afford the title compound. $^1H$ NMR (500 MHz, $D_2O$) δ 8.05 (d, 1H), 7.55 (d, 2H), 7.49 (d, 2H), 6.86 (d, 1H), 3.85-3.74 (m, 8H), 3.65-3.54 (m, 5H), 3.23 (t, 2H), 3.03-3.00 (m, 1H), 2.44-2.31 (m, 2H), 2.19-2.02 (m, 3H), 1.77 (s, 6H), 1.37 (t, 2H). LCMS [M+H] 525.3.

Compound 1

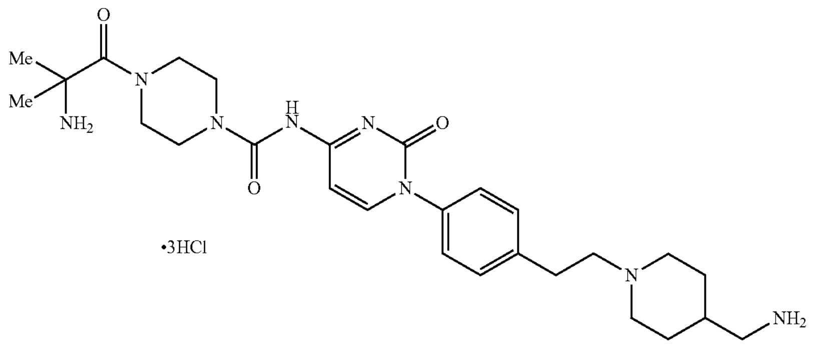

4-(2-Amino-2-methylpropanoyl)-N-(1-(4-(2-(4-(aminomethyl)piperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and tert-butyl (piperidin-4-ylmethyl)carbamate. LCMS [M+H] 525.3.

Compound 2

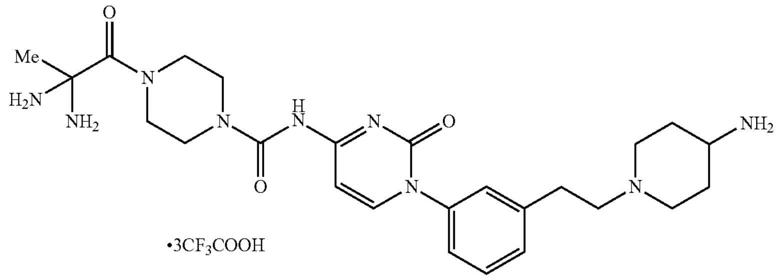

4-(2-Amino-2-methylpropanoyl)-N-(1-(3-(2-(4-aminopiperidin-1-yl)ethyl)phenyl)-2-oxo-1,2-dihydropyrimidin-4-yl)piperazine-1-carboxamide tri-trifluroacetetate Prepared in a similar fashion as Scheme C-15 from tert-butyl (2-methyl-1-oxo-1-(4-((2-oxo-1-(3-(2-oxoethyl) phenyl)-1,2-dihydropyrimidin-4-yl)carbamoyl)piperazin-1-yl)propan-2-yl)carbamate and tert-butyl piperidin-4-ylcarbamate. $^1H$ NMR (500 MHz, $D_2O$) δ 7.89 (d, 1H), 7.59 (t, 1H), 7.51-7.48 (m, 1H), 7.42 (s, 1H), 7.39 (d, 1H), 6.89 (d, 1H), 3.84-3.70 (m, 8H), 3.52-3.47 (m, 2H), 3.23-3.16 (m, 3H), 2.41-2.34 (m, 4H), 2.01-1.91 (m, 4H), 1.75 (s, 6H) LCMS [M+H] 511.3.

Compound 3

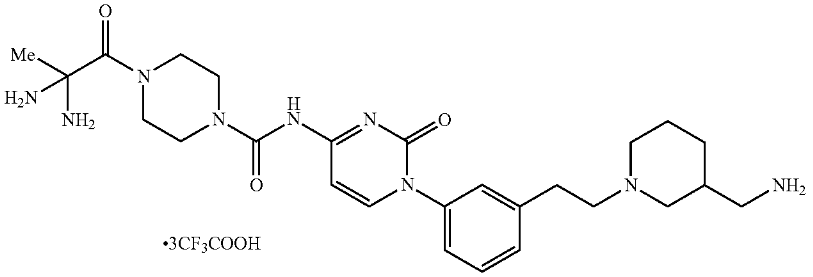

4-(2-Amino-2-methylpropanoyl)-N-(1-(3-(2-(3-(aminomethyl)piperidin-1-yl)ethyl)phenyl)-2-oxo-1,2-dihydropyrimidin-4-yl)piperazine-1-carboxamide triflouroacetate salt Prepared in a similar fashion as Scheme C-15 from tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and tert-butyl (piperidin-3-ylmethyl)carbamate. $^1$H NMR (500 MHz, $D_2O$) δ 8.02 (d, 1H), 7.59 (t, 1H), 7.50 (d, 1H), 7.43 (s, 1H), 7.39 (d, 1H), 6.84 (d, 1H), 3.85-3.67 (m, 8H), 3.48 (t, 2H), 3.21 (t, 2H), 3.09-2.95 (m, 3H), 2.86 (t, 2H), 2.32-2.22. (m, 1H), 2.13-2.02 (m, 2H), 1.75 (s, 6H), 1.43-1.33 (m, 3H). LCMS [M+H] 525.4.

Compound 4

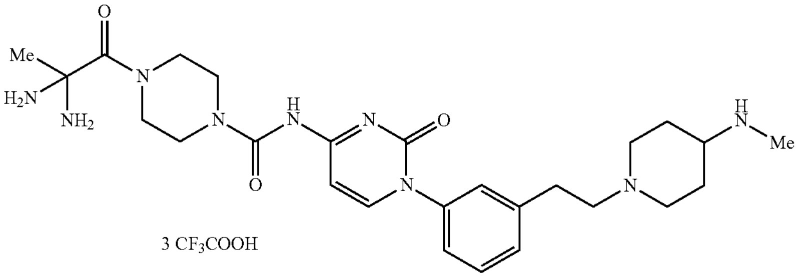

4-(2-Amino-2-methylpropanoyl)-N-(1-(3-(2-(4-(methylamino)piperidin-1-yl)ethyl)phenyl)-2-oxo-1,2-dihydropyrimidin-4-yl)piperazine-1-carboxamide triflouroacetate salt Prepared in a similar fashion as Scheme C-15 from tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and tert-butyl methyl(piperidin-4-yl)carbamate. $^1$H NMR (500 MHz, $D_2O$) δ 8.05 (d, 1H), 7.60 (t, 1H), 7.51 (d, 1H), 7.43 (s, 1H), 7.40 (d, 1H), 6.84 (d, 1H), 3.88-3.71 (m, 10H), 3.52-3.47 (m, 2H), 3.23-3.16 (m, 4H), 2.77 (s, 3H), 2.46 (d, 2H), 2.00-1.91 (m, 2H), 1.75 (s, 6H). LCMS [M+H] 525.4.

Compound 5

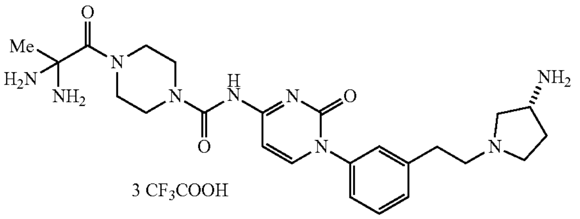

(R)-4-(2-Amino-2-methylpropanoyl)-N-(1-(3-(2-(3-aminopyrrolidin-1-yl)ethyl)phenyl)-2-oxo-1,2-dihydropyrimidin-4-yl)piperazine-1-carboxamide triflouroacetate salt Prepared in a similar fashion as Scheme C-15 from tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and tert-butyl (R)-pyrrolidin-3-ylcarbamate. LCMS [M+H] 497.4.

Compound 6

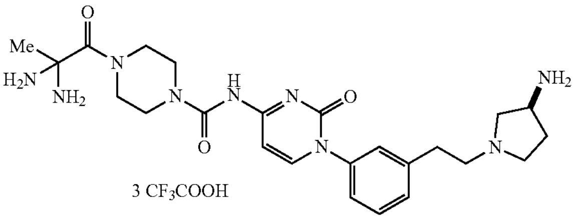

(S)-4-(2-Amino-2-methylpropanoyl)-N-(1-(3-(2-(3-aminopyrrolidin-1-yl)ethyl)phenyl)-2-oxo-1,2-dihydropyrimidin-4-yl)piperazine-1-carboxamide triflouroacetate salt Prepared in a similar fashion as Scheme C-15 from tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and tert-butyl (S)-pyrrolidin-3-ylcarbamate. LCMS [M+H] 497.3.

Compound 7

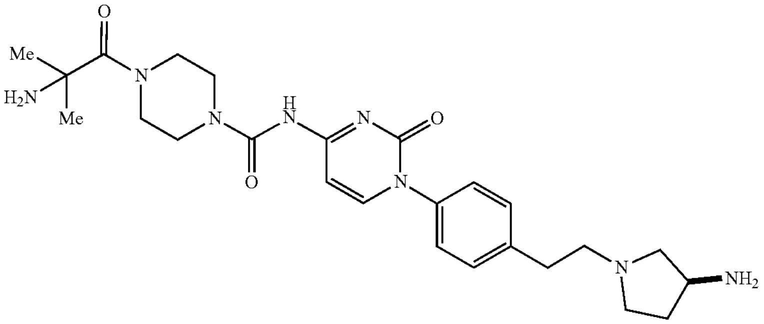

3 $CF_3COOH$ (S)-4-(2-Amino-2-methylpropanoyl)-N-(1-(4-(2-(3-aminopyrrolidin-1-yl)ethyl)phenyl)-2-oxo-1,2-dihydropyrimidin-4-yl)piperazine-1-carboxamide triflouroacetate salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (S)-pyrrolidin-3-ylcarbamate $^1H$ NMR (500 MHz, $D_2O$) δ 8.09 (d, 1H), 7.54 (d, 2H), 7.48 (d, 2H), 6.82 (d, 1H), 4.38-4.10 (m, 2H), 3.83-3.64 (m, 11H), 3.59-3.31 (m, 2H), 3.22 (t, 2H), 2.83-2.08 (m, 2H), 1.75 (s, 6H). LCMS [M+H] 497.3.

Compound 8

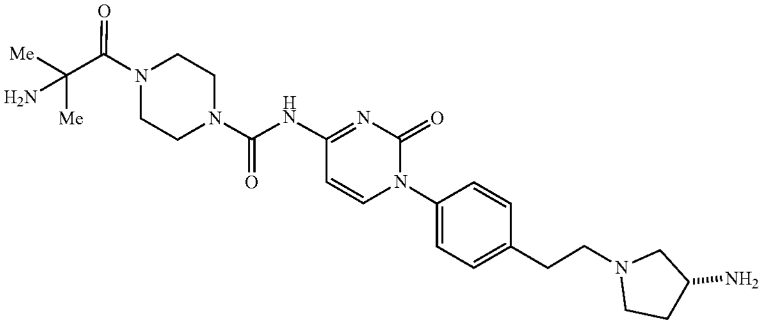

3 $CF_3COOH$ (R)-4-(2-Amino-2-methylpropanoyl)-N-(1-(4-(2-(3-aminopyrrolidin-1-yl)ethyl)phenyl)-2-oxo-1,2-dihydropyrimidin-4-yl)piperazine-1-carboxamide triflouroacetate salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (R)-pyrrolidin-3-ylcarbamate $^1H$ NMR (500 MHz, $D_2O$) δ 8.09 (d, 1H), 7.54 (d, 2H), 7.48 (d, 2H), 6.82 (d, 1H), 4.38-4.10 (m, 2H), 3.83-3.64 (m, 11H), 3.59-3.31 (m, 2H), 3.22 (t, 2H), 2.83-2.08 (m, 2H), 1.75 (s, 6H). LCMS [M+H] 497.3.

Compound 9

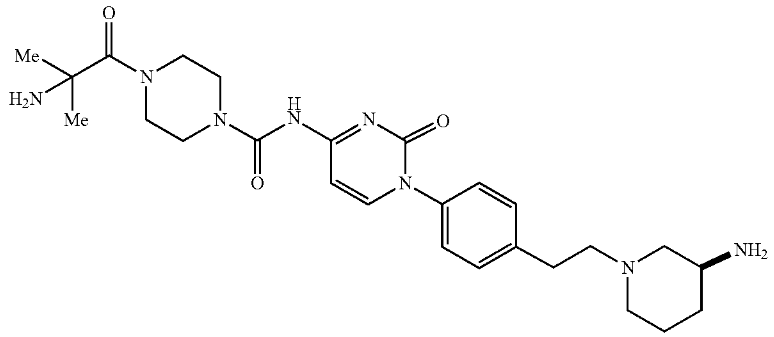

3 $CF_3COOH$ (S)-4-(2-Amino-2-methylpropanoyl)-N-(1-(4-(2-(3-aminopiperidin-1-yl)ethyl)phenyl)-2-oxo-1,2-dihydropyrimidin-4-yl)piperazine-1-carboxamide triflouroacetate salt Prepared in a similar fashion as Scheme C-15 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and tert-butyl (S)-piperidin-3-yl-carbamate. $^1$H NMR (500 MHz, $D_2O$) δ 8.19 (d, 1H), 7.52 (d, 2H), 7.46 (d, 2H), 6.78 (d, 1H), 3.91-3.61 (m, 12H), 3.55 (t, 2H), 3.22 (t, 2H), 3.17-3.00 (m, 2H), 2.29-2.13 (m, 2H), 1.95-1.78 (m, 1H), 1.72 (s, 6H). LCMS [M+H] 511.4.

Compound 10

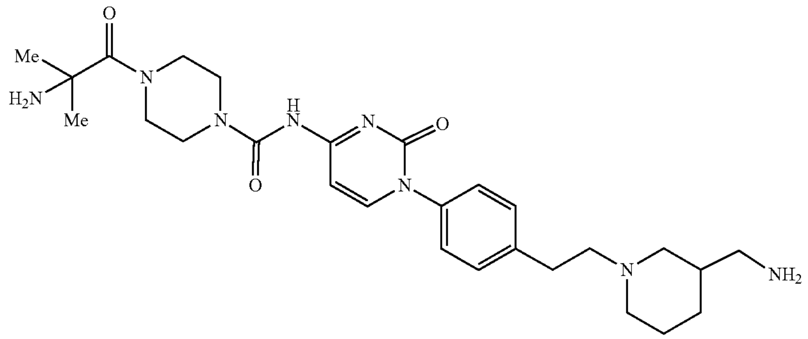

3 HCl 4-(2-Amino-2-methylpropanoyl)-N-(1-(4-(2-(3-(aminomethyl)piperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and tert-butyl (piperidin-3-ylmethyl)carbamate. $^1$H NMR (500 MHz, $D_2O$) δ 8.13 (d, 1H), 7.52 (d, 2H), 7.47 (d, 2H), 6.81 (d, 1H), 3.84-3.69 (m, 10H), 3.48 (t, 2H), 3.21 (t, 2H), 3.11-3.05 (m, 1H), 3.03-2.95 (m, 2H), 2.88 (t, 1H), 2.27 (bs, 1H), 2.14-2.02 (m, 2H), 1.88-1.78 (m, 1H), 1.74 (s, 6H), 1.39-1.29 (m, 1H).

Compound 372

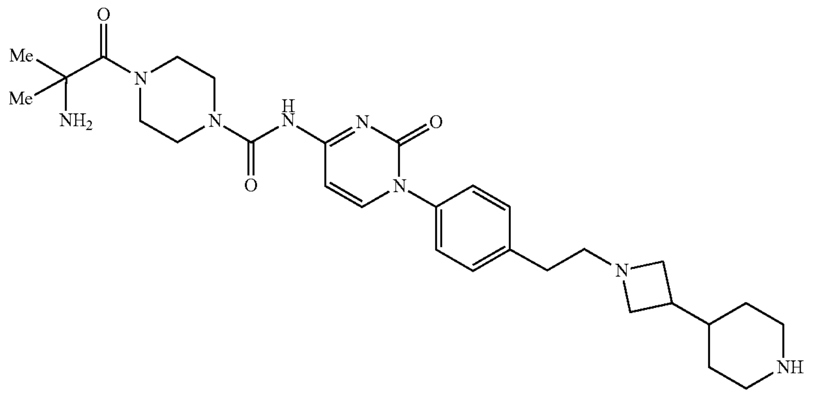

3 HCl 4-(2-Amino-2-methylpropanoyl)-N-(2-oxo-1-(4-(2-(3-(piperidin-4-yl)azetidin-1-yl)ethyl)phenyl)-1,2-dihydropyrimidin-4-yl)piperazine-1-carboxamide hydrochloride salt Prepared in a similar fashion to Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl 4-(azetidin-3-yl)piperidine-1-carboxylate. $^1$H NMR (400 MHz, $D_2O$) δ 8.13 (d, 1H), 7.54-7.44 (m, 4H), 6.80 (d, 1H), 4.29 (t, 1H), 4.13 (d, 1H), 3.91 (t, 1H), 3.79 (s, 3H), 3.75 (s, 5H), 3.62 (t, 1H), 3.55 (t, 2H), 3.43 (d, 2H), 3.09-2.93 (m, 4H), 2.82-2.69 (m, 1H), 2.01-1.80 (m, 3H), 1.74 (s, 6H), 1.41-1.24 (m, 2H). LCMS [M+H] 551.3.

Compound 177

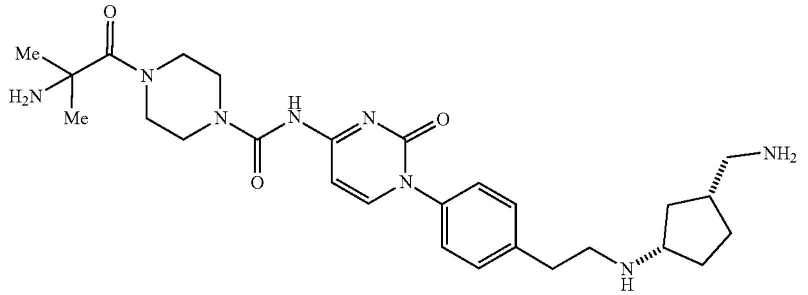

3 HCl 4-(2-Amino-2-methylpropanoyl)-N-(1-(4-(2-(((1S,3R)-3-(aminomethyl)cyclopentyl)amino) ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate. $^1$H NMR (500 MHz, $D_2O$) δ 8.00 (d, 1H), 7.57 (d, 2H), 7.51 (d, 2H), 6.91 (d, 1H), 3.88-3.75 (m, 8H), 3.46 (t, 2H), 3.22-3.08 (m, 5H), 2.55-2.45 (m, 1H), 2.40-2.32 (m, 1H), 2.30-2.22 (m, 1H), 2.11-2.01 (m, 1H), 1.92-1.85 (m, 1H), 1.81 (s, 6H), 1.66-1.52 (m, 1H), 1.49-1.37 (m, 1H). LCMS [M+H] 525.1.

Compound 179

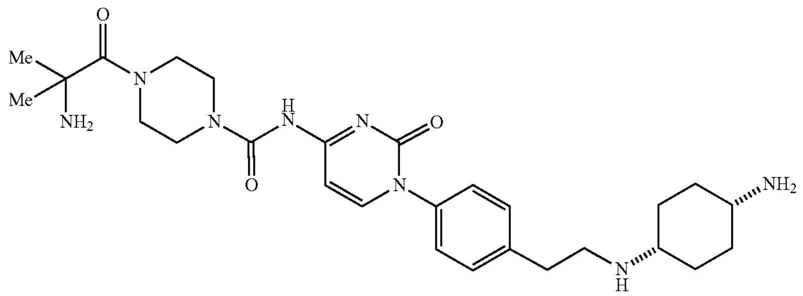

3 HCl 4-(2-Amino-2-methylpropanoyl)-N-(1-(4-(2-((cis-4-aminocyclohexyl)amino)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and boc-cis-1,4-cyclohexanediamine. $^1H$ NMR (500 MHz, $D_2O$) δ 8.08 (d, 1H), 7.50 (d, 2H), 7.44 (d, 2H), 6.80 (d, 1H), 3.86-3.67 (m, 8H), 3.55-3.49 (m, 1H), 3.43-3.35 (m, 3H), 3.12 (t, 2H), 2.07-1.98 (m, 2H), 1.98-1.85 (m, 4H), 1.84-1.74 (m, 2H), 1.72 (s, 6H). LCMS [M+H] 525.3.

Compound 180

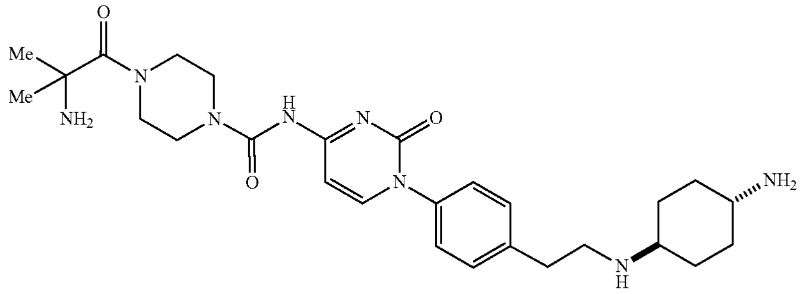

3 HCl 4-(2-Amino-2-methylpropanoyl)-N-(1-(4-(2-((trans-4-aminocyclohexyl)amino)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and boc-trans-1,4-cyclohexanediamine. $^1H$ NMR (500 MHz, $D_2O$) δ 7.98 (d, 1H), 7.49 (d, 2H), 7.43 (d, 2H), 6.82 (d, 1H), 3.81-3.68 (m, 8H), 3.39 (t, 2H), 3.27-3.18 (m, 2H), 3.10 (t, 2H), 2.21 (d, 4H), 1.72 (s, 6H), 1.59-1.47 (m, 4H). [M+H] 525.3.

Compound 181

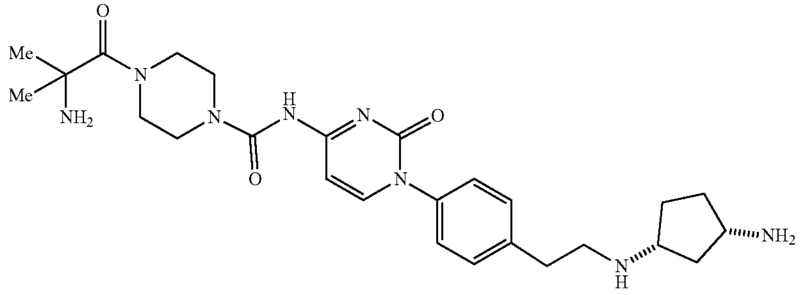

3 HCl 4-(2-Amino-2-methylpropanoyl)-N-(1-(4-(2-(((1R,3S)-3-aminocyclopentyl)amino)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl ((1R,3S)-3-aminocyclopentyl)carbamate. $^{1}H$ NMR (500 MHz, $D_2O$) δ 7.98 (d, 1H), 7.50 (d, 2H), 7.44 (d, 2H), 6.82 (d, 1H), 3.84-3.65 (m, 10H), 3.40 (t, 2H), 3.13 (t, 2H), 2.69 (p, 1H), 2.22 (sept, 2H), 1.95-1.83 (m, 2H), 1.79-1.70 (m, 7H). [M+H] 511.4.

Compound 11

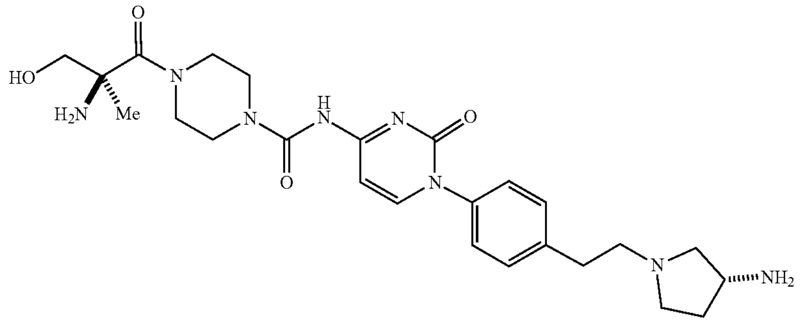

3 HCl 4-((S)-2-Amino-3-hydroxy-2-methylpropanoyl)-N-(1-(4-(2-((R)-3-aminopyrrolidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2R,4S)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate and tert-butyl (R)-pyrrolidin-3-ylcarbamate. $^{1}H$ NMR (500 MHz, $D_2O$) δ 8.10 (d, 1H), 7.55 (d, 2H), 7.48 (d, 2H), 6.83 (d, 1H), 4.33-4.13 (m, 3H), 4.04-3.63 (m, 12H), 3.55.3.37 (m, 2H), 3.22 (t, 2H), 2.86-2.10 (m, 2H), 1.70 (s, 3H). LCMS [M+H] 513.4.

Compound 12

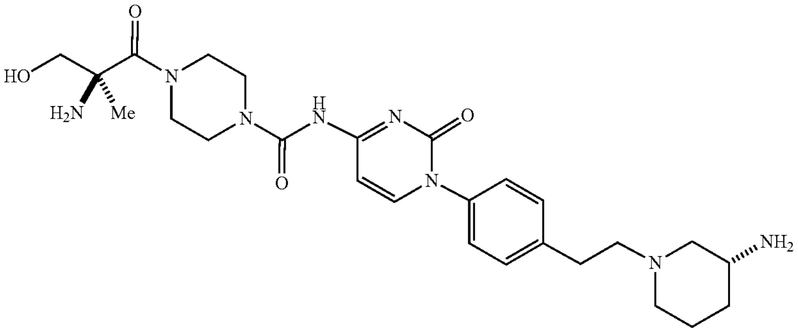

3 HCl 4-((S)-2-Amino-3-hydroxy-2-methylpropanoyl)-N-(1-(4-(2-((R)-3-aminopiperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2R,4S)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate and tert-butyl (R)-piperidin-3-ylcarbamate. $^1$H NMR (500 MHz, $D_2O$) δ 8.11 (d, 1H), 7.53 (d, 2H), 7.48 (d, 2H), 6.82 (d, 1H), 4.17 (d, 1H), 3.91 (d, 2H), 3.85-3.64 (m, 10H), 3.58 (t, 2H), 3.24 (t, 2H), 3.19-3.04 (m, 2H), 2.31-2.16 (m, 2H), 1.96-1.82 (m, 1H), 1.77-1.67 (m, 4H). LCMS [M+H] 527.3.

Compound 13

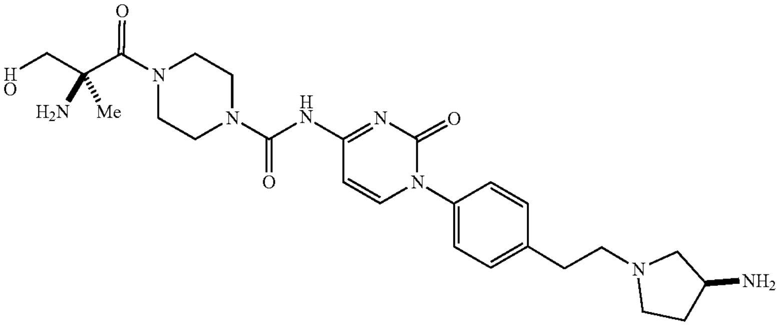

3 HCl 4-((S)-2-Amino-3-hydroxy-2-methylpropanoyl)-N-(1-(4-(2-((S)-3-aminopyrrolidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2R,4S)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate and tert-butyl (S)-pyrrolidin-3-ylcarbamate. $^1$H NMR (500 MHz, $D_2O$) δ 8.10 (d, 1H), 7.55 (d, 2H), 7.48 (d, 2H), 6.83 (d, 1H), 4.33-4.13 (m, 3H), 4.04-3.63 (m, 12H), 3.55.3.37 (m, 2H), 3.22 (t, 2H), 2.86-2.10 (m, 2H), 1.70 (s, 3H). LCMS [M+H] 513.4.

Compound 381

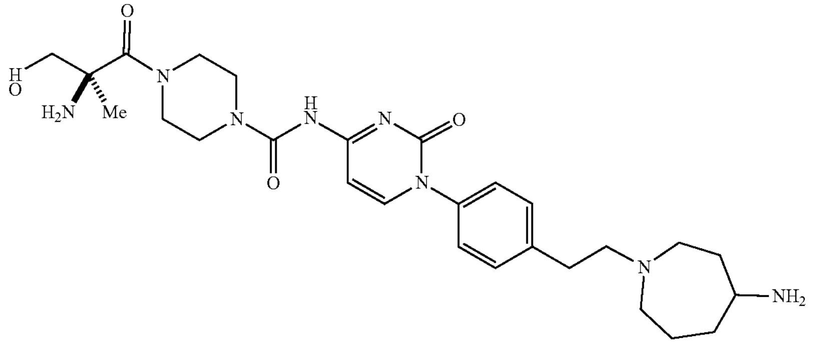

3 HCl 4-((S)-2-Amino-3-hydroxy-2-methylpropanoyl)-N-(1-(4-(2-(4-aminoazepan-1-yl)ethyl) phenyl)-2-oxo-1,2-dihydropyrimidin-4-yl)piperazine-1-carboxamide hydrochloride salt Prepared in a similar fashion as Scheme C-15 from tert-butyl (2R,4S)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate and tert-butyl azepan-4-ylcarbamate. LCMS [M+H] 541.4.

Compound 361

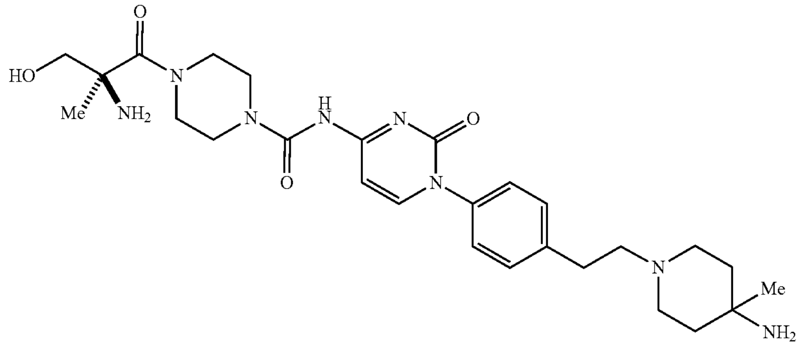

3 HCl (S)-4-(2-Amino-3-hydroxy-2-methylpropanoyl)-N-(1-(4-(2-(4-amino-4-methylpiperidin-1-yl)ethyl)phenyl)-2-oxo-1,2-dihydropyrimidin-4-yl)piperazine-1-carboxamide hydrochloride salt Prepared in a similar fashion to Scheme SC-15 from tert-butyl (1-(4-(4-amino-2-oxopyrimidin-1(2H)-yl)phenethyl)-4-methylpiperidin-4-yl)carbamate and 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide. LCMS [M+H] 541.3.

Compound 14

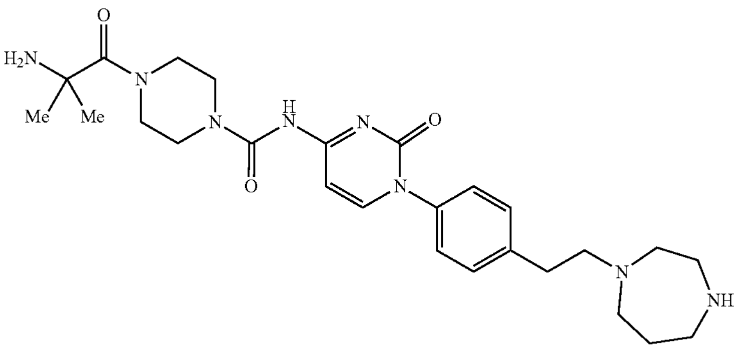

3 HCl

N-(1-(4-(2-(1,4-Diazepan-1-yl)ethyl)phenyl)-2-oxo-1,2-dihydropyrimidin-4-yl)-4-(2-amino-2-methyl-propanoyl)piperazine-1-carboxamide hydrochloride salt Prepared in a similar fashion as Scheme C-15 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and tert-butyl 1,4-diazepane-1-carboxylate. $^{1}H$ NMR (500 MHz, $D_2O$) δ 8.21 (d, 1H), 7.53 (d, 2H), 7.48 (d, 2H), 6.79 (d, 1H), 3.87-3.67 (m, 14H), 3.61 (t, 2H), 3.51 (t, 2H), 3.23 t, 2H), 2.33 (s, 2H), 1.73 (s, 6 h). LCMS [M+H] 511.3.

Compound 15

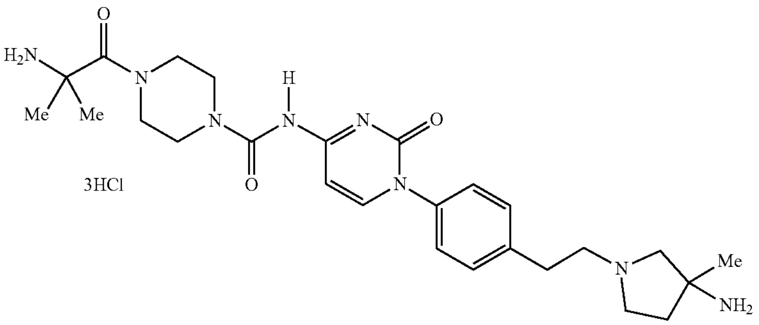

3HCl 4-(2-Amino-2-methylpropanoyl)-N-(1-(4-(2-(3-amino-3-methylpyrrolidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and tert-butyl (3-methylpyrrolidin-3-yl)carbamate. $^{1}H$ NMR (500 MHz, $D_2O$) δ 8.09 (d, 1H), 7.54 (d, 2H), 7.48 (d, 2H), 6.82 (d, 1H), 3.80-3.72 (m, 10H), 3.68 (t, 2H), 3.63-3.42 (m, 2H), 3.21 (t, 2H), 2.44 (bs, 2H), 1.74 (s, 6H), 1.65 (s, 3H). LCMS [M+H] 511.4.

Compound 16

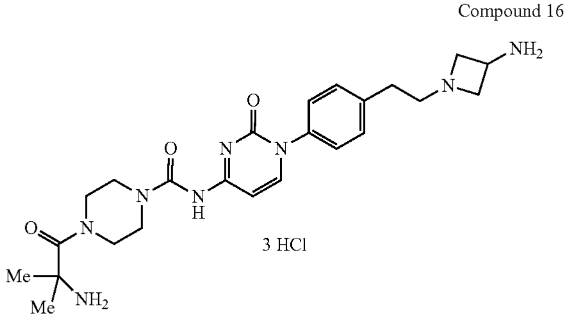 [SMILES: CC(C)(N)C(=O)N1CCN(C(=O)Nc2ccn(-c3ccc(CCN4CC(N)C4)cc3)c(=O)n2)CC1]

3 HCl 4-(2-Amino-2-methylpropanoyl)-N-(1-(4-(2-(3-aminoazetidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl azetidin-3-ylcarbamate. $^1$H NMR (500 MHz, $D_2O$) δ 8.14 (d, 1H), 7.53 (d, 2H), 7.48 (d, 2H), 6.81 (d, 1H), 4.65-4.34 (m, 5H), 3.84-3.70 (m, 10H), 3.10 (t, 2H), 1.74 (s, 6H). LCMS [M+H] 483.4.

Compound 17

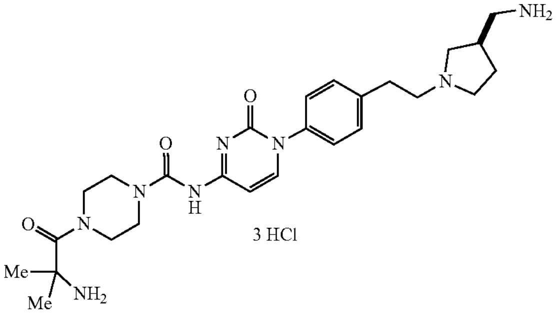

(R)-4-(2-Amino-2-methylpropanoyl)-N-(1-(4-(2-(3-(aminomethyl)pyrrolidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (S)-(pyrrolidin-3-ylmethyl)carbamate. $^1$H NMR (500 MHz, $D_2O$) δ 8.23 (d, 1H), 7.54 (d, 2H), 7.48 (d, 2H), 6.79 (d, 1H), 3.97-3.93 (m, 1H), 3.84-3.73 (m, 8H) 3.63-3.57 (m, 2H), 3.55-3.51 (m, 1H), 3.18 (t, 2 h), 3.12-3.07 (m, 1H), 3.02-2.90 (m, 1H), 2.77-2.69 (m, 1H), 2.51-2.45 (m, 1H), 2.37-2.29 (m, 1H), 2.04-1.96 (m, 1H), 1.84-1.77 (m, 1H), 1.73 (s, 6H). LCMS [M+H] 511.5.

Compound 18

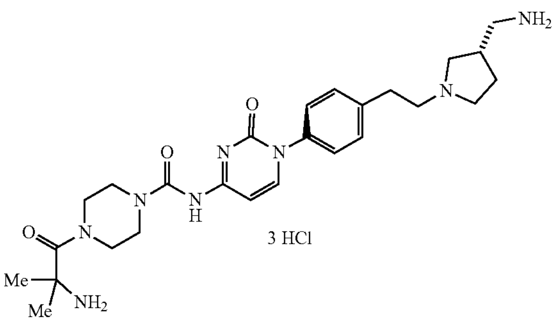

(S)-4-(2-Amino-2-methylpropanoyl)-N-(1-(4-(2-(3-(aminomethyl)pyrrolidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (R)-(pyrrolidin-3-ylmethyl)carbamate. $^1$H NMR (500 MHz, $D_2O$) δ 8.23 (d, 1H), 7.54 (d, 2H), 7.48 (d, 2H), 6.79 (d, 1H), 3.97-3.93 (m, 1H), 3.84-3.73 (m, 8H) 3.63-3.57 (m, 2H), 3.55-3.51 (m, 1H), 3.18 (t, 2 h), 3.12-3.07 (m, 1H), 3.02-2.90 (m, 1H), 2.77-2.69 (m, 1H), 2.51-2.45 (m, 1H), 2.37-2.29 (m, 1H), 2.04-1.96 (m, 1H), 1.84-1.77 (m, 1H), 1.73 (s, 6H). LCMS [M+H] 511.4.

Compound 22

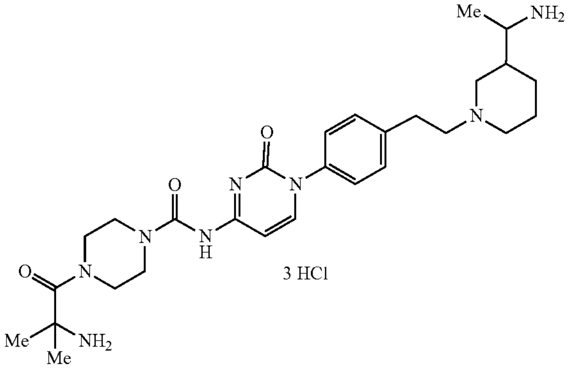

4-(2-Amino-2-methylpropanoyl)-N-(1-(4-(2-(3-(1-aminoethyl)piperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (1-(piperidin-3-yl)ethyl)carbamate. $^1$H NMR (500 MHz, $D_2O$) δ 8.02 (d, 1H), 7.55 (d, 2H), 7.49 (d, 2H), 6.87 (d, 1H), 3.82-3.71 (m, 10H), 3.55-3.52 (m, 2H), 3.45-3.41 (m, 2H), 3.25 (t, 2H), 2.17 (d, 2H), 2.11-1.95 (m, 2H), 1.96-1.88 (m, 1H), 1.77 (s, 6H), 1.52-1.41 (m, 1H), 1.38 (d, 3H). LCMS [M+H] 539.4.

Compound 23

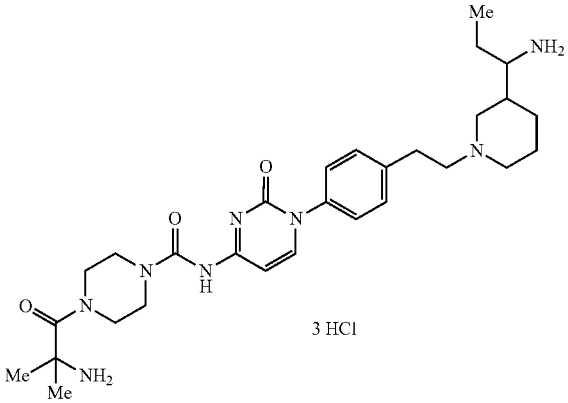

4-(2-Amino-2-methylpropanoyl)-N-(1-(4-(2-(3-(1-aminopropyl)piperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (1-(piperidin-3-yl)propyl)carbamate. $^1H$ NMR (500 MHz, $D_2O$) δ 8.06 (d, 1H), 7.55 (d, 2H), 7.49 (d, 2H), 6.86 (d, 1H), 3.82-3.66 (m, 10H), 3.55-3.52 (m, 2H), 3.27-3.25 (m, 3H), 3.06-2.98 (q, 2H), 2.38-2.22 (m, 1H), 2.19-2.12 (m, 1H), 2.06-1.99 (m, 1H), 1.90-1.81 (m, 2H), 1.77 (s, 6H), 1.74-1.67 (m, 1H), 1.56-1.37 (m, 1H), 1.04 (t, 3H). LCMS [M+H] 553.4.

Compound 24

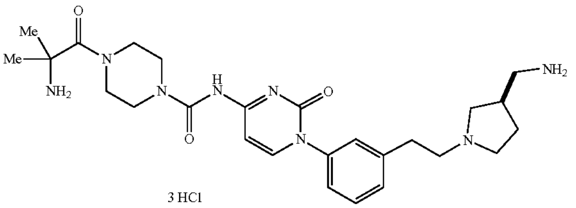

3 HCl (R)-4-(2-Amino-2-methylpropanoyl)-N-(1-(3-(2-(3-(aminomethyl)pyrrolidin-1-yl)ethyl)phenyl)-2-oxo-1,2-dihydropyrimidin-4-yl)piperazine-1-carboxamide hydrochloride Prepared in a similar fashion as scheme C-15 from tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and tert-butyl (S)-(pyrrolidin-3-ylmethyl)carbamate. $^1H$ NMR (400 MHz, $D_2O$) mixture of rotamers δ 7.86 (d, 1H), 7.43 (t, 1H), 7.36 (d, 1H), 7.31-7.21 (m, 2H), 6.71 (d, 1H), 3.81-3.77 (m, 1H), 3.64-3.59 (m, 8H), 3.51-3.45 (m, 4H), 3.25-2.92 (m, 6H), 2.89-2.75 (m, 1H), 2.62-2.53 (m, 1H), 2.34-2.30 (m, 1H), 2.20-2.15 (m, 1H), 1.90-1.81 (m, 1H), 1.59 (s, 6H). LCMS [(M+2H)/2] 256.1.

Compound 25

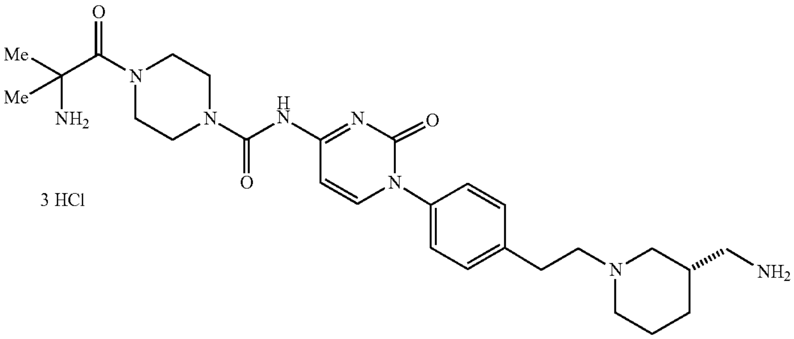

3 HCl (S)-4-(2-Amino-2-methylpropanoyl)-N-(1-(4-(2-(3-(aminomethyl)piperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (R)-(piperidin-3-ylmethyl)carbamate. $^1H$ NMR (500 MHz, $D_2O$) δ 7.97 (d, 1H), 7.51 (d, 2H), 7.45 (d, 2H), 6.84 (d, 1H), 3.86-3.67 (m, 10H), 3.48 (t, 2H), 3.21 (t, 2H), 3.11-2.95 (m, 3H), 2.87 (t, 1H), 2.34-2.20 (m, 1H), 2.15-2.01 (m, 2H), 1.89-1.77 (m, 1H), 1.74 (s, 6H), 1.41-1.30 (m, 1H). LCMS [M+H] 525.3.

Compound 168

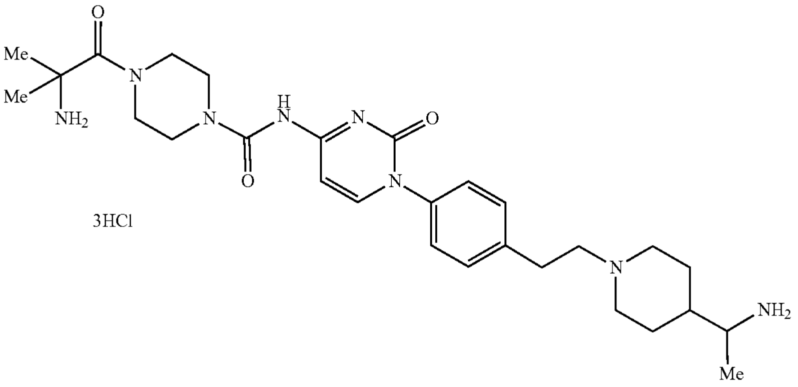

3HCl 4-(2-Amino-2-methylpropanoyl)-N-(1-(4-(2-(4-(1-aminoethyl)piperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and tert-butyl (1-(piperidin-4-yl) ethyl)carbamate. LCMS [M+H] 539.2.

Compound 26

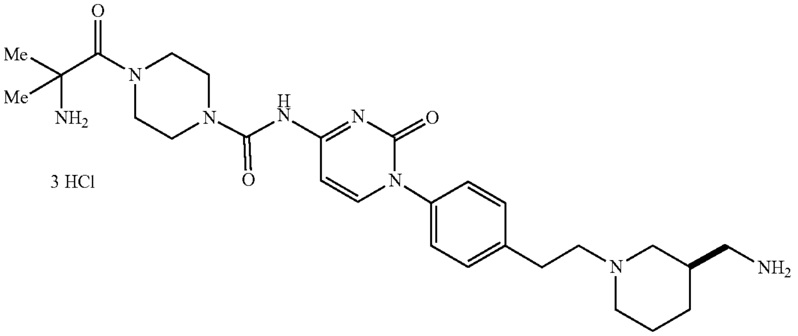

3 HCl (R)-4-(2-Amino-2-methylpropanoyl)-N-(1-(4-(2-(3-(aminomethyl)piperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and tert-butyl (S)-(piperidin-3-yl-methyl)carbamate. $^1$H NMR (500 MHz, $D_2O$) δ 7.97 (d, 1H), 7.51 (d, 2H), 7.45 (d, 2H), 6.84 (d, 1H), 3.86-3.67 (m, 10H), 3.48 (t, 2H), 3.21 (t, 2H), 3.11-2.95 (m, 3H), 2.87 (t, 1H), 2.34-2.20 (m, 1H), 2.15-2.01 (m, 2H), 1.89-1.77 (m, 1H), 1.74 (s, 6H), 1.41-1.30 (m, 1H). LCMS [M+H] 525.3.

Compound 349

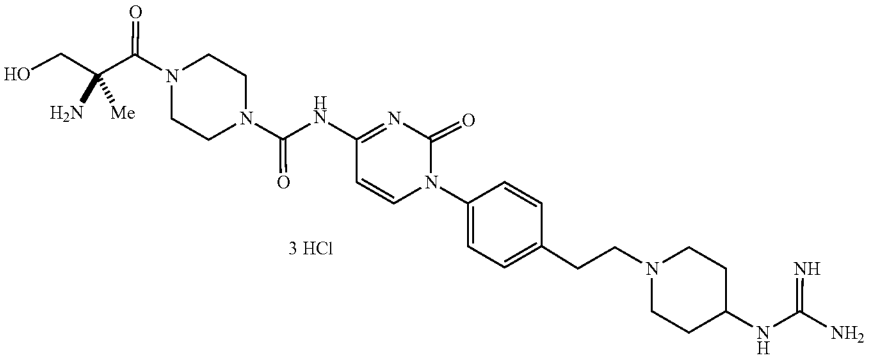

3 HCl (S)-4-(2-Amino-3-hydroxy-2-methylpropanoyl)-N-(1-(4-(2-(4-guanidinopiperidin-1-yl)ethyl)phenyl)-2-oxo-1,2-dihydropyrimidin-4-yl)piperazine-1-carboxamide hydrochloride salt Prepared in a similar fashion as Scheme C-15 from 4-((2S,4S)-2-(tert-butyl)-4-methyloxazolidine-4-carbonyl)-N-(2-oxo-1-(4-(2-oxoethyl)phenyl)-1,2-dihydropyrimidin-4-yl)piperazine-1-carboxamide and 1,2-bis(tert-butoxycarbonyl)-3-(piperidin-4-yl)guanidine. LCMS [M+H] 553.4.

Compound 27

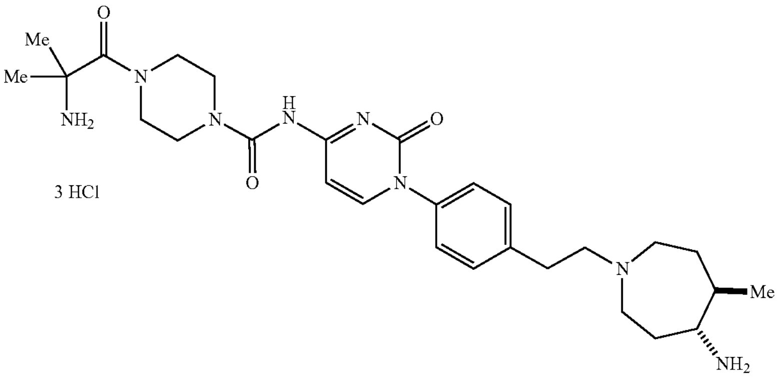

3 HCl 4-(2-Amino-2-methylpropanoyl)-N-(1-(4-(2-(trans-4-amino-5-methylazepan-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and trans-tert-butyl (5-methylazepan-4-yl)carbamate. $^1$H NMR (500 MHz, $D_2O$) δ 7.86 (d, 1H), 7.46 (d, 2H), 7.40 (d, 2H), 6.81 (d, 1H), 3.80-3.65 (m, 8H), 3.58-3.43 (m, 5H), 3.26-3.11 (m, 4H), 2.30-2.21 (m, 2H), 2.08-1.85 (m, 3H), 1.70 (s, 6H), 1.15-1.09 (m, 3H). LCMS [M+H] 539.2.

Compound 28

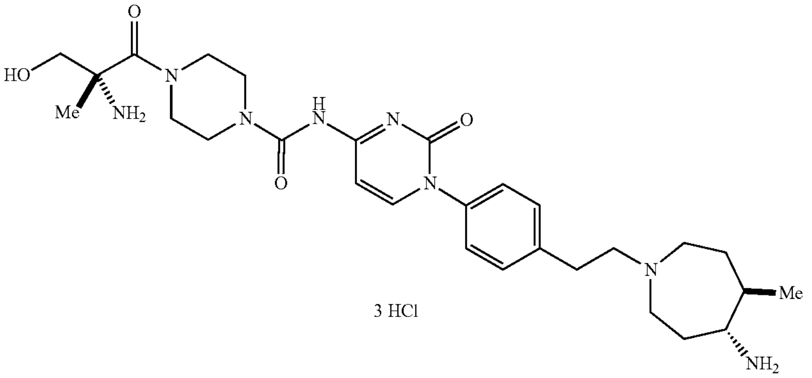

3 HCl 4-((R)-2-Amino-3-hydroxy-2-methylpropanoyl)-N-(1-(4-(2-(trans-4-amino-5-methylazepan-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2S,4R)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate and trans-tert-butyl (5-methylazepan-4-yl)carbamate. $^1$H NMR (500 MHz, $D_2O$) δ 8.01 (d, 1H), 7.50 (d, 2H), 7.44 (d, 2H), 6.82 (d, 1H), 4.15 (d, 1H), 3.89 (d, 1H), 3.81-3.69 (m, 9H), 3.60-3.47 (m, 4H), 3.30-3.13 (m, 4H), 2.33-2.11 (m, 2H), 2.09-1.88 (m, 3H), 1.68 (s, 3H), 1.15 (t, 3H). LCMS [M+H] 555.4.

Compound 35

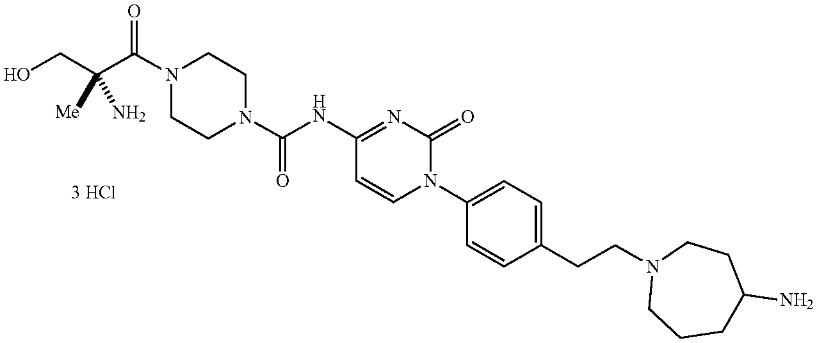

3 HCl 4-((R)-2-Amino-3-hydroxy-2-methylpropanoyl)-N-(1-(4-(2-(4-aminoazepan-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2S,4R)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate and tert-butyl azepan-4-ylcarbamate. $^1$H NMR (500 MHz, $D_2O$) δ 8.18 (d, 1H), 7.56 (d, 2H), 7.51 (d, 2H), 6.84 (d, 1H), 4.20 (d, 1H), 3.94 (d, 1H), 3.87-3.72 (m, 8H), 3.65-3.48 (m, 3H), 3.28-3.21 (m, 2H), 2.44-1.98 (m, 8H), 1.72 (s, 3H), 1.41-1.24 (m, 2H).

Compound 29

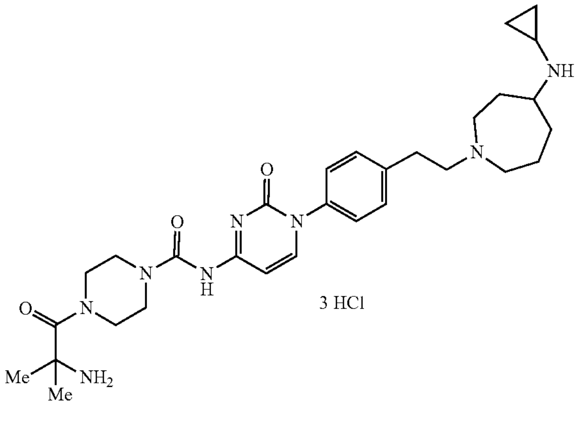

4-(2-Amino-2-methylpropanoyl)-N-(1-(4-(2-(4-(cyclopropylamino)azepan-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl azepan-4-yl(cyclopropyl)carbamate. $^1$H NMR (500 MHz, $D_2O$) δ 8.05 (d, 1H), 7.51 (d, 2H), 7.46 (d, 2H), 6.82 (d, 1H), 3.84-3.68 (m, 10H), 3.68-3.37 (m, 6H), 3.20 (t, 2H), 2.80-2.72 (m, 1H), 2.62-2.38 (m, 2H), 2.34-1.98 (m, 2H), 1.91-1.77 (m, 1H), 1.73 (s, 6H), 1.00-0.84 (m, 4H). LCMS [M+H] 565.4.

Compound 30

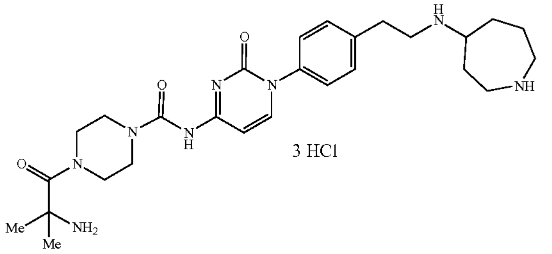

4-(2-Amino-2-methylpropanoyl)-N-(1-(4-(2-(azepan-4-ylamino)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl) carbamate and tert-butyl 4-aminoazepane-1-carboxylate. $^1$H NMR (500 MHz, $D_2O$) δ 7.94 (d, 1H), 7.51 (d, 2H), 7.44 (d, 2H), 6.85 (d, 1H), 3.85-3.69 (m, 8H), 3.58-3.48 (m, 2H), 3.47-3.38 (m, 2H), 3.30-3.18 (m, 2H), 3.14 (t, 2H), 2.49-2.32 (m, 2H), 2.16-2.00 (m, 2H), 1.93-1.75 (m, 2H), 1.74 (s, 6H). MS [M+H] 525.4.

Compound 368

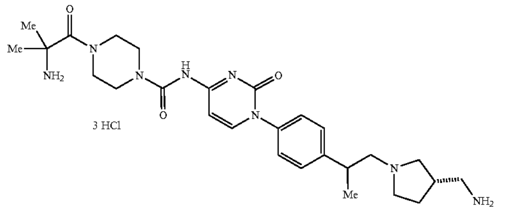

4-(2-Amino-2-methylpropanoyl)-N-(1-(4-(1-((S)-3-(aminomethyl)pyrrolidin-1-yl)propan-2-yl)phenyl)-2-oxo-1,2-dihydropyrimidin-4-yl)piperazine-1-carboxamide Prepared in a similar fashion as in Scheme C-15 from 2-(4-bromophenyl)propan-1-ol and tert-butyl (R)-(pyrrolidin-3-ylmethyl)carbamate in Scheme 5. $^1$H NMR (500 MHz, $D_2O$) δ 7.96 (d, 1H), 7.57 (d, 2H), 7.48 (d, 2H), 6.84 (d, 1H), 3.82-3.69 (m, 8H), 3.68-3.58 (m, 2H), 3.56-3.34 (m, 2H), 3.22-3.06 (m, 2H), 3.05-2.96 (m, 1H), 2.94-2.82 (m, 1H), 2.71-2.59 (m, 1H), 2.46-2.34 (m, 1H), 2.30-2.20 (m, 1H), 2.01-1.88 (m, 1H), 1.73 (s, 6H), 1.36 (d, 3H) LCMS [M+H] 525.3.

Compound 290

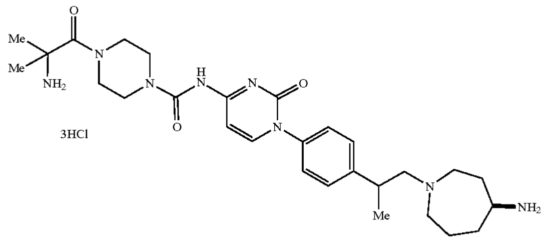

4-(2-Amino-2-methylpropanoyl)-N-(1-(4-(1-((S)-4-aminoazepan-1-yl)propan-2-yl)phenyl)-2-oxo-1,2-dihydropyrimidin-4-yl)piperazine-1-carboxamide hydrochloride salt Prepared in a similar fashion as in Scheme C-15 from tert-butyl (2-methyl-1-oxo-1-(4-((2-oxo-1-(4-(1-oxopropan-2-yl)phenyl)-1,2-dihydropyrimidin-4-yl)carbamoyl)piperazin-1-yl)propan-2-yl)carbamate and tert-butyl (S)-azepan-4-ylcarbamate. LCMS [M+H] 539.4.

Compound 31

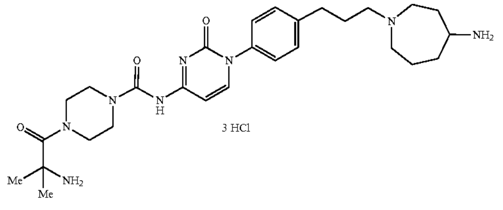

4-(2-Amino-2-methylpropanoyl)-N-(1-(4-(3-(4-aminoazepan-1-yl)propyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(3-oxopropyl)phenyl)-1,2-dihydropyrimidin-4-yl)carbamoyl)piperazin-1-yl)propan-2-yl)carbamate and tert-butyl azepan-4-ylcarbamate. $^{1}H$ NMR (500 MHz, $D_2O$) δ 8.18 (d, 1H), 7.45 (d, 2H), 7.41 (d, 2H), 6.76 (d, 1H), 3.82-3.69 (m, 8H), 3.64-3.57 (m, 1H), 3.57-3.41 (m, 2H), 3.29-3.06 (m, 4H), 2.79 (t, 2H), 2.35-1.90 (m, 7H), 1.81-1.61 (m, 7H). LCMS [M+H] 539.4.

Compound 32

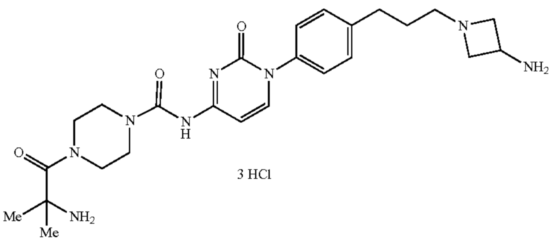

4-(2-Amino-2-methylpropanoyl)-N-(1-(4-(3-(3-aminoazetidin-1-yl)propyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(3-oxopropyl)phenyl)-1,2-dihydropyrimidin-4-yl)carbamoyl)piperazin-1-yl)propan-2-yl)carbamate and tert-butyl azetidin-3-ylcarbamate. $^{1}H$ NMR (500 MHz, $D_2O$) δ 8.02 (d, 1H), 7.43 (d, 2H), 7.38 (d, 2H), 6.79 (d, 1H), 4.70-4.56 (m, 2H), 4.56-4.36 (m, 2H), 4.32-4.22 (m, 1H), 3.85-3.68 (m, 8H), 3.36 (t, 2H), 2.80 (t, 2H), 2.01-1.92 (m, 2H), 1.73 (s, 6H). LCMS [M+H] 497.4.

Compound 33

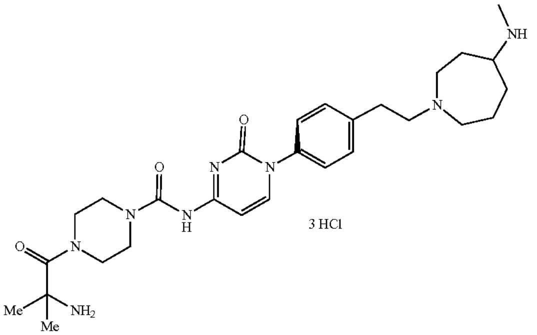

4-(2-Amino-2-methylpropanoyl)-N-(1-(4-(2-(4-(methylamino)azepan-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl) carbamate and tert-butyl azepan-4-yl(methyl)carbamate. $^{1}H$ NMR (500 MHz, $D_2O$) δ 7.92 (d, 1H), 7.50 (d, 2H), 7.44 (d, 2H), 6.84 (d, 1H), 3.85-3.67 (m, 8H), 3.63-3.39 (m, 6H), 3.28-3.17 (m, 3H), 2.74 (s, 3H), 2.56-2.30 (m, 2H), 2.29-1.96 (m, 3H), 1.88-1.75 (m, 1H), 1.73 (s, 6H). LCMS [M+H] 539.3.

Compound 34

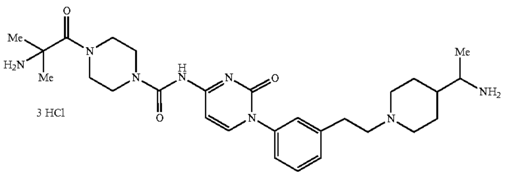

4-(2-Amino-2-methylpropanoyl)-N-(1-(3-(2-(4-(1-aminoethyl)piperidin-1-yl)ethyl)phenyl)-2-oxo-1,2-dihydropyrimidin-4-yl)piperazine-1-carboxamide hydrochloride Prepared in a similar fashion as Scheme C-15 from tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and tert-butyl (1-(piperidin-4-yl)ethyl)carbamate. $^{1}H$ NMR (400 MHz, $D_2O$) δ 7.85 (d, 1H), 7.46 (t, 1H), 7.39-7.24 (m, 3H), 6.71 (d, 1H), 3.63-3.60 (m, 8H), 3.32 (t, 2H), 3.25-3.15 (m, 1H), 3.05 (t, 2H), 2.95 (t, 2H), 1.97-1.93 (m, 2H), 1.88-1.82 (m, 1H), 1.60 (s, 6H), 1.51-1.48 (m, 4H), 1.17 (d, 3H). LCMS [M+H] 539.2.

Compound 36

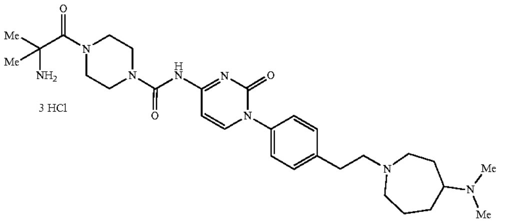

4-(2-Amino-2-methylpropanoyl)-N-(1-(4-(2-(4-(dimethylamino)azepan-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and N,N-dimethylazepan-4-amine. $^{1}H$ NMR (500 MHz, $D_2O$) δ 7.87 (d, 1H), 7.50 (d, 2H), 7.44 (d, 2H), 6.86 (d, 1H), 3.82-3.69 (m, 8H), 3.68-3.51 (m, 4H), 3.24-3.18 (m, 2H), 2.86 (d, 1H), 2.44-2.29 (m, 4H), 2.09-1.84 (m, 4H), 1.74 (s, 6H), 1.35 (d, 6H) LCMS [M+H] 553.3.

Compound 37

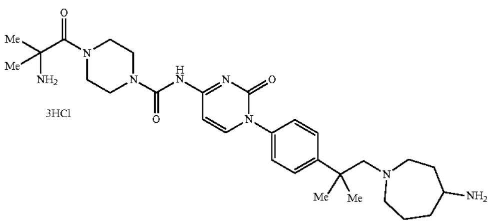

4-(2-Amino-2-methylpropanoyl)-N-(1-(4-(1-(4-aminoazepan-1-yl)-2-methylpropan-2-yl)phenyl)-2-oxo-1,2-dihydropyrimidin-4-yl)piperazine-1-carboxamide hydrochloride salt Prepared in a similar fashion as Scheme C-15 from tert-butyl (2-methyl-1-(4-((1-(4-(2-methyl-1-oxopropan-2-yl)phenyl)-2-oxo-1,2-dihydropyrimidin-4-yl)carbamoyl)piperazin-1-yl)-1-oxopropan-2-yl)carbamate and tert-butyl azepan-4-ylcarbamate. $^1$H NMR (500 MHz, $D_2O$) δ 7.91 (d, 1H), 7.69 (d, 2H), 7.48 (d, 2H), 6.83 (d, 1H), 3.79-3.67 (m, 8H), 3.65-3.37 (m, 4H), 3.29-2.97 (m, 5H), 2.26-2.10 (m, 2H), 2.01-1.78 (m, 2H), 1.71 (s, 6H), 1.50 (d, 6H). LCMS [M+H] 553.2.

Compound 38

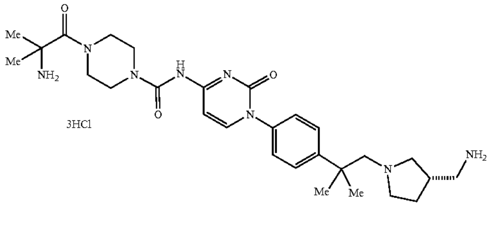

(S)-4-(2-Amino-2-methylpropanoyl)-N-(1-(4-(1-(3-(aminomethyl)pyrrolidin-1-yl)-2-methylpropan-2-yl)phenyl)-2-oxo-1,2-dihydropyrimidin-4-yl)piperazine-1-carboxamide hydrochloride salt Prepared in a similar fashion as Scheme C-15 from tert-butyl (2-methyl-1-(4-((1-(4-(2-methyl-1-oxopropan-2-yl)phenyl)-2-oxo-1,2-dihydropyrimidin-4-yl)carbamoyl)piperazin-1-yl)-1-oxopropan-2-yl)carbamate and tert-butyl (R)-(pyrrolidin-3-ylmethyl)carbamate. $^1$H NMR (500 MHz, $D_2O$) δ 7.89 (d, 1H), 7.71 (d, 2H), 7.51 (d, 2H), 6.88 (d, 1H), 3.84-3.69 (m, 8H), 3.61-3.42 (m, 2H), 3.34-3.16 (m, 2H), 3.14-3.00 (m, 1H), 2.85-2.54 (m, 2H), 2.40-2.02 (m, 1H), 1.94-1.80 (m, 1H), 1.75 (s, 6H), 1.54 (s, 6H), 1.35 (d, 2H). LCMS [M+H] 539.2.

Compound 39

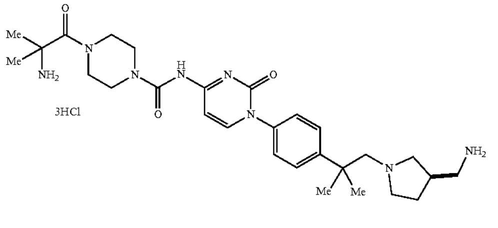

(R)-4-(2-Amino-2-methylpropanoyl)-N-(1-(4-(1-(3-(aminomethyl)pyrrolidin-1-yl)-2-methylpropan-2-yl)phenyl)-2-oxo-1,2-dihydropyrimidin-4-yl)piperazine-1-carboxamide hydrochloride salt Prepared in a similar fashion as Scheme C-15 from tert-butyl (2-methyl-1-(4-((1-(4-(2-methyl-1-oxopropan-2-yl)phenyl)-2-oxo-1,2-dihydropyrimidin-4-yl)carbamoyl)piperazin-1-yl)-1-oxopropan-2-yl)carbamate and tert-butyl (S)-(pyrrolidin-3-ylmethyl)carbamate. $^1$H NMR (500 MHz, $D_2O$) δ 7.89 (d, 1H), 7.71 (d, 2H), 7.51 (d, 2H), 6.88 (d, 1H), 3.84-3.69 (m, 8H), 3.61-3.42 (m, 2H), 3.34-3.16 (m, 2H), 3.14-3.00 (m, 1H), 2.85-2.54 (m, 2H), 2.40-2.02 (m, 1H), 1.94-1.80 (m, 1H), 1.75 (s, 6H), 1.54 (s, 6H), 1.35 (d, 2H). LCMS [M+H] 539.2.

Compound 40

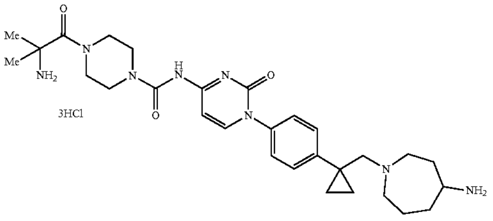

4 4-(2-Amino-2-methylpropanoyl)-N-(1-(4-(1-((4-aminoazepan-1-yl)methyl)cyclopropyl)phenyl)-2-oxo-1,2-dihydropyrimidin-4-yl)piperazine-1-carboxamide hydrochloride salt Prepared in a similar fashion as Scheme C-15 from tert-butyl (1-(4-((1-(4-(1-formylcyclopropyl)phenyl)-2-oxo-1,2-dihydropyrimidin-4-yl)carbamoyl)piperazin-1-yl)-2-methyl-1-oxopropan-2-yl)carbamate and tert-butyl azepan-4-ylcarbamate. $^1$H NMR (500 MHz, $D_2O$) δ 7.99 (d, 1H), 7.69 (d, 2H), 7.46 (d, 2H), 6.81 (d, 1H), 3.82-3.67 (m, 8H), 3.67-3.54 (m, 3H), 3.50-3.33 (m, 3H), 3.19-3.01 (m, 1H), 2.29-2.18 (m, 2H), 2.03-1.85 (m, 2H), 1.72 (s, 6H), 1.69-1.54 (m, 2H), 1.25-1.06 (m, 4H). LCMS [M+H] 551.2.

Compound 41

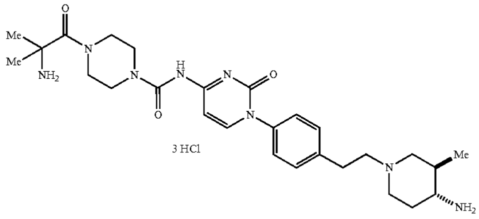

4-(2-Amino-2-methylpropanoyl)-N-(1-(4-(2-(trans-4-amino-3-methylpiperidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl ((trans)-3-methylpiperidin-4-yl)carbamate. $^1$H NMR (500 MHz, $D_2O$) δ 7.90 (d, 1H), 7.50 (d, 2H), 7.44 (d, 2H), 6.85 (d, 1H), 3.85-3.68 (m, 8H), 3.49 (t, 2H), 3.31-3.26 (m, 1H), 3.20 (t, 1H), 2.97 (t, 1H), 2.42-2.36 (m, 1H), 2.22-2.14 (m, 2H), 2.08 (s, 3H), 2.04-1.98 (m, 1H), 1.74 (s, 6H), 1.35 (d, 1H), 1.25 (t, 1H), 1.14 (d, 1H). LCMS [M+H] 525.4.

Compound 42

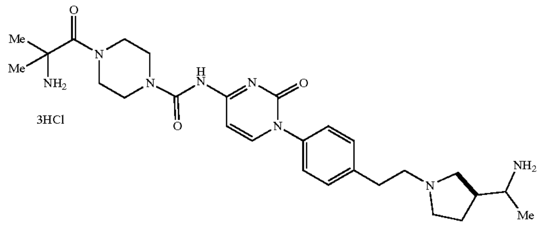

4-(2-Amino-2-methylpropanoyl)-N-(1-(4-(2-((3S)-3-(1-aminoethyl)pyrrolidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (1-((S)-pyrrolidin-3-yl)ethyl)carbamate. $^{1}H$ NMR (500 MHz, $D_2O$) δ 7.93 (d, 1H), 7.50 (d, 2H), 7.43 (d, 2H), 6.83 (d, 1H), 3.82-3.68 (m, 8H), 3.63-3.56 (m, 2H), 3.54-3.42 (m, 1H), 3.17 (t, 2H), 3.10-3.00 (m, 2H), 2.87-2.78 (m, 1H), 2.66-2.54 (m, 1H), 2.42-2.22 (m, 1H), 2.09-2.01 (m, 1H), 1.86-1.79 (m, 1H), 1.72 (s, 6H), 1.38-1.31 (m, 3H) LCMS [M+H] 525.3.

Compound 43

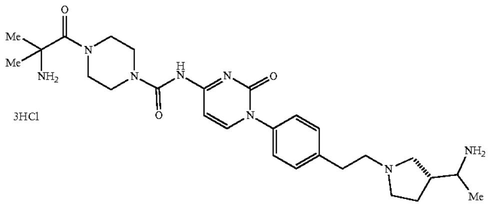

4-(2-Amino-2-methylpropanoyl)-N-(1-(4-(2-((3R)-3-(1-aminoethyl)pyrrolidin-1-yl)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (1-((R)-pyrrolidin-3-yl)ethyl)carbamate. $^{1}H$ NMR (500 MHz, $D_2O$) δ 7.93 (d, 1H), 7.50 (d, 2H), 7.43 (d, 2H), 6.83 (d, 1H), 3.82-3.68 (m, 8H), 3.63-3.56 (m, 2H), 3.54-3.42 (m, 1H), 3.17 (t, 2H), 3.10-3.00 (m, 2H), 2.87-2.78 (m, 1H), 2.66-2.54 (m, 1H), 2.42-2.22 (m, 1H), 2.09-2.01 (m, 1H), 1.86-1.79 (m, 1H), 1.72 (s, 6H), 1.38-1.31 (m, 3H) LCMS [M+H] 525.3.

Compound 345

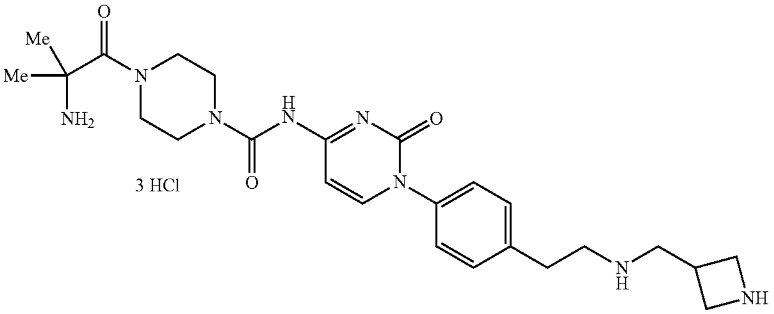

4-(2-Amino-2-methylpropanoyl)-N-(1-(4-(2-((azetidin-3-ylmethyl)amino)ethyl)phenyl)-2-oxo-1,2-dihydropyrimidin-4-yl)piperazine-1-carboxamide hydrochloride salt Prepared in a similar fashion as Scheme C-15 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl 3-(aminomethyl)azetidine-1-carboxylate. $^{1}H$ NMR (500 MHz, $D_2O$) δ 8.04 (d, 1H), 7.52 (d, 2H), 7.47 (d, 2H), 6.85 (d, 1H), 4.28 (t, 2H), 4.09 (t, 2H), 3.88-3.72 (m, 8H), 3.49-3.38 (m, 5H), 3.15 (t, 2H), 1.76 (s, 6H). LCMS [M+H] 497.27

Compound 90

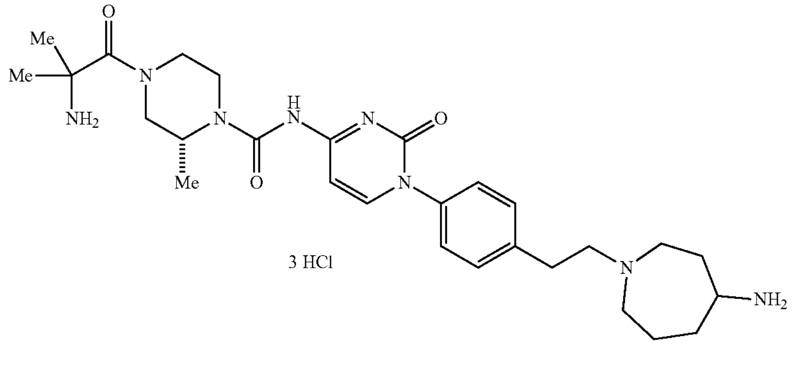

3 HCl (2R)-4-(2-Amino-2-methylpropanoyl)-N-(1-(4-(2-(4-aminoazepan-1-yl)ethyl)phenyl)-2-oxo-1,2-dihydropyrimidin-4-yl)-2-methylpiperazine-1-carboxamide hydrochloride salt Prepared in a similar fashion as scheme C-15 from (R)-tert-butyl (2-methyl-1-(3-methyl-4-((2-oxo-1-(4-(2-oxoethyl)phenyl)-1,2-dihydropyrimidin-4-yl)carbamoyl)piperazin-1-yl)-1-oxopropan-2-yl)carbamate and tert-butyl azepan-4-ylcarbamate. $^{1}H$ NMR (400 MHz, $D_2O$) δ 7.98 (d, 1H), 7.52 (d, 2H), 7.46 (d, 2H), 6.83 (d, 1H), 4.57 (s, 1H), 4.22 (d, 1H), 4.09 (d, 1H), 3.72 (s, 1H), 3.65-3.11 (m, 13H), 2.34 (s, 2H), 2.08 (d, 2H), 1.76 (d, 7H), 1.31 (d, 3H) LCMS [M+H] 539.3.

Compound 204

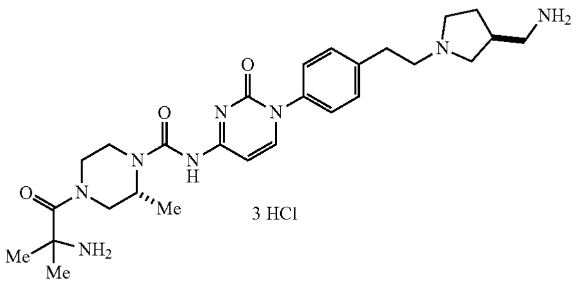

3 HCl (R)-4-(2-Amino-2-methylpropanoyl)-N-(1-(4-(2-((S)-3-(aminomethyl)pyrrolidin-1-yl)ethyl)phenyl)-2-oxo-1,2-dihydropyrimidin-4-yl)-2-methylpiperazine-1-carboxamide hydrochloride salt Scheme C-16

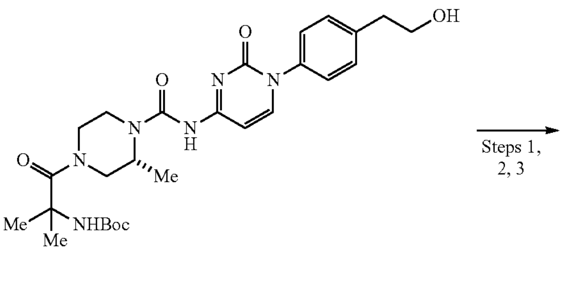

-continued

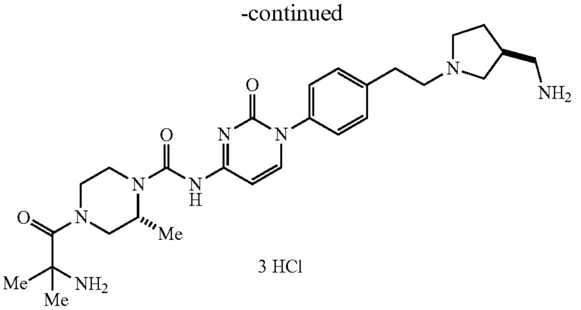

3 HCl

Reagents: 1) TsCl, $Et_3N$, DMAP $CH_2Cl_2$, rt. 16 h 2) $K_2CO_3$, (S)-tert-butyl (pyrrolidin-3-ylmethyl)carbamate, $CH_3CN$, 70° C., 16 h 3) HCl, $CH_3OH$, rt. 4 h.

Step 1: (R)-4-(4-(4-(2-((tert-butoxycarbonyl)amino)-2-methylpropanoyl)-2-methylpiperazine-1-carboxamido)-2-oxopyrimidin-1(2H)-yl)phenethyl 4-methylbenzenesulfonate To a solution of (R)-tert-butyl (1-(4-((1-(4-(2-hydroxyethyl)phenyl)-2-oxo-1,2-dihydropyrimidin-4-yl)carbamoyl)-3-methylpiperazin-1-yl)-2-methyl-1-oxopropan-2-yl)carbamate (52 mg, 0.10 mmol) and $Et_3N$ (0.04 mL, 0.28 mmol) in $CH_2Cl_2$ at rt were added tosyl chloride (28.5 mg, 0.15 mmol) and DMAP (0.2 mg, 0.002 mmol). The reaction was stirred for 16 h and concentrated under reduced pressure. The crude solid was dissolved in EtOAc (15 mL) and washed with saturated $NaHCO_3$ (1×15 mL) and $H_2O$ (15 mL). The organic layer was dried with $Na_2SO_4$ and concentrated under reduced pressure to afford the title compound.

Step 2: tert-butyl (((R)-1-(4-(4-((R)-4-(2-amino-2-methylpropanoyl)-2-methylpiperazine-1-carboxamido)-2-oxopyrimidin-1(2H)-yl)phenethyl)pyrrolidin-3-yl)methyl)carbamate To a solution of (R)-4-(4-(4-(2-((tert-butoxycarbonyl)amino)-2-methylpropanoyl)-2-methylpiperazine-1-carboxamido)-2-oxopyrimidin-1(2H)-yl)phenethyl 4-methylbenzenesulfonate (54 mg, 0.08 mmol) in MeCN, was added (S)-tert-butyl (pyrrolidin-3-ylmethyl)carbamate (19 mg, 0.10 mmol) and $K_2CO_3$ (21 mg, 0.16 mmol). The reaction was heated to 70° C. for 16 h, and the solvent was removed under reduced pressure. The crude solid was dissolved in $CHCl_3$, filtered and the filtrate was purified via flash chromatography ($CHCl_3$/MeOH) to afford the title compound.

Step 3: (R)-4-(2-amino-2-methylpropanoyl)-N-(1-(4-(2-((R)-3-(aminomethyl)pyrrolidin-1-yl)ethyl)phenyl)-2-oxo-1,2-dihydropyrimidin-4-yl)-2-methylpiperazine-1-carboxamide hydrochloride salt tert-Butyl (((R)-1-(4-(4-((R)-4-(2-amino-2-methylpropanoyl)-2-methylpiperazine-1-carboxamido)-2-oxopyrimidin-1(2H)-yl)phenethyl)pyrrolidin-3-yl)methyl)carbamate was treated with a solution of HCl/MeOH (10 mL) and stirred at rt for 4 h. The reaction mixture was concentrated under reduced pressure and the solid was triturated with $Et_2O$ to afford the title compound. $^1H$ NMR (400 MHz, $D_2O$) δ 7.87 (d, 1H), 7.38 (d, 2H), 7.31 (d, 2H), 6.67 (d, 1H), 4.41 (s, 1H), 4.07 (d, 1H), 3.94 (d, 1H), 3.85-3.73 (m, 1H), 3.73-3.55 (m, 1H), 3.46 (d, 2H), 3.41-2.91 (m, 9H), 2.78 (m, 2H), 2.39-2.11 (m, 1H), 1.91-1.62 (m, 1H), 1.60 (s, 6H), 1.12 (s, 3H). LCMS [M+H] 525.3.

Compound 196

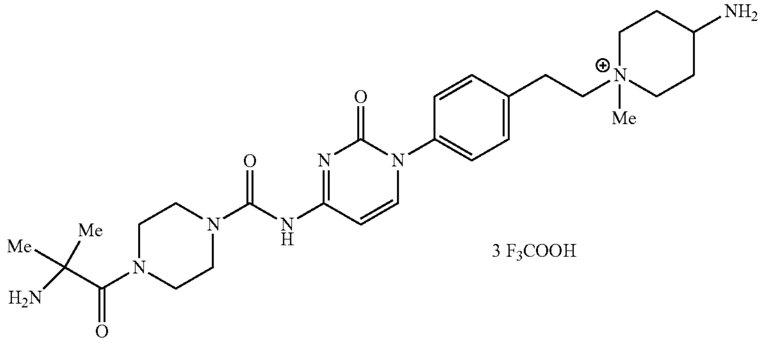

4-Amino-1-(4-(4-(4-(2-amino-2-methylpropanoyl)piperazine-1-carboxamido)-2-oxopyrimidin-1(2H)-yl)phenethyl)-1-methylpiperidin-1-ium trifluoroacetate salt Scheme C-17

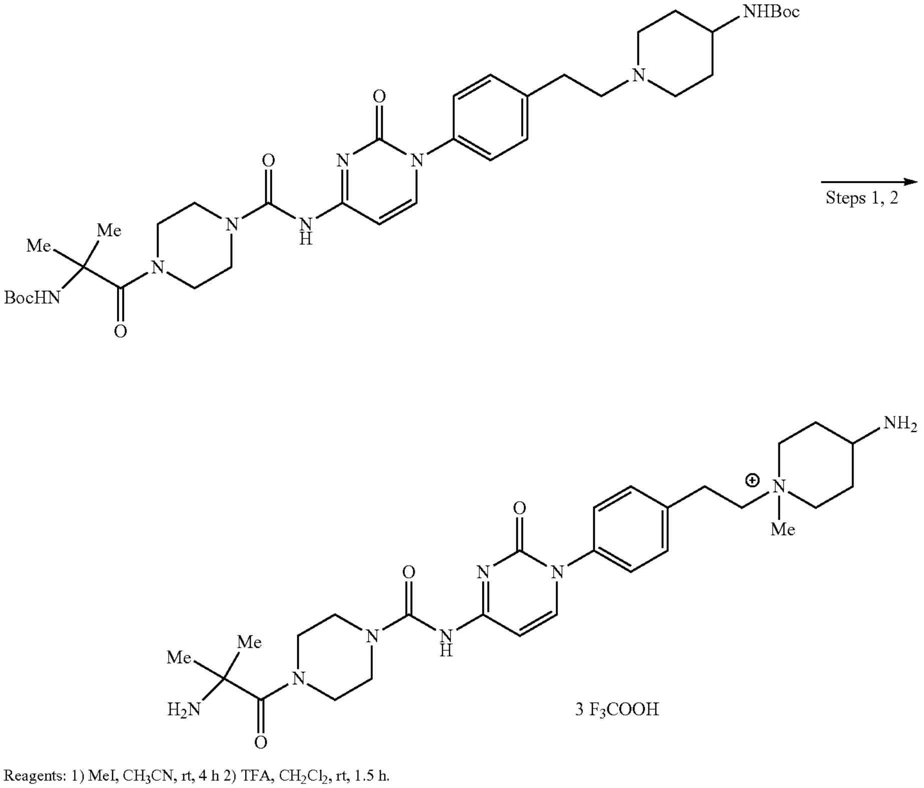

Step 1: 4-((tert-butoxycarbonyl)amino)-1-(4-(4-(4-(2-((tert-butoxycarbonyl)amino)-2-methylpropanoyl)piperazine-1-carboxamido)-2-oxopyrimidin-1(2H)-yl)phenethyl)-1-methylpiperidin-1-ium iodide To a solution of tert-butyl (1-(4-((1-(4-(2-(4-((tert-butoxycarbonyl)amino)piperidin-1-yl)ethyl)phenyl)-2-oxo-1,2-dihydropyrimidin-4-yl)carbamoyl)piperazin-1-yl)-2-methyl-1-oxopropan-2-yl)carbamate (10 mg, 0.014 mmol) in $CH_3CN$ (1 mL), was added MeI (4.4 μL, 0.070 mmol). The solution was stirred for 4 h at rt, forming a white precipitate. The solid was collected and triturated with EtOAc, to afford the title compound.

Step 2: 4-amino-1-(4-(4-(4-(2-amino-2-methylpropanoyl)piperazine-1-carboxamido)-2-oxopyrimidin-1(2H)-yl)phenethyl)-1-methylpiperidin-1-ium trifluoroacetate salt To a suspension of 4-((tert-butoxycarbonyl)amino)-1-(4-(4-(4-(2-((tert-butoxycarbonyl)amino)-2-methylpropanoyl)piperazine-1-carboxamido)-2-oxopyrimidin-1(2H)-yl)phenethyl)-1-methylpiperidin-1-ium iodide (8 mg, 0.011 mmol) in DCM (0.5 mL) was added triflouroacetic acid (0.5 mL). The solution was stirred for 1.5 h at rt, after which the reaction mixture was concentrated under reduced pressure. Purification with HPLC. $^1$H NMR (400 MHz, $D_2O$) δ 8.10 (d, 1H), 7.49 (d, 2H), 7.44 (s, 2H), 6.77 (d, 1H), 3.88-3.64 (m, 10H), 3.63-3.42 (m, 3H), 3.32-3.12 (m, 5H), 2.38-2.08 (m, 4H), 2.06-1.88 (m, 2H), 1.70 (s, 6H). LCMS [M+H] 526.2.

Compound 197

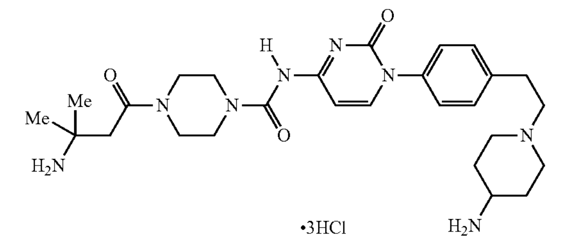

4-(3-Amino-3-methylbutanoyl)-N-(1-(4-(2-(4-aminopiperidin-1-yl)ethyl)phenyl)-2-oxo-1,2-dihydropyrimidin-4-yl)piperazine-1-carboxamide hydrochloride salt Scheme C-18

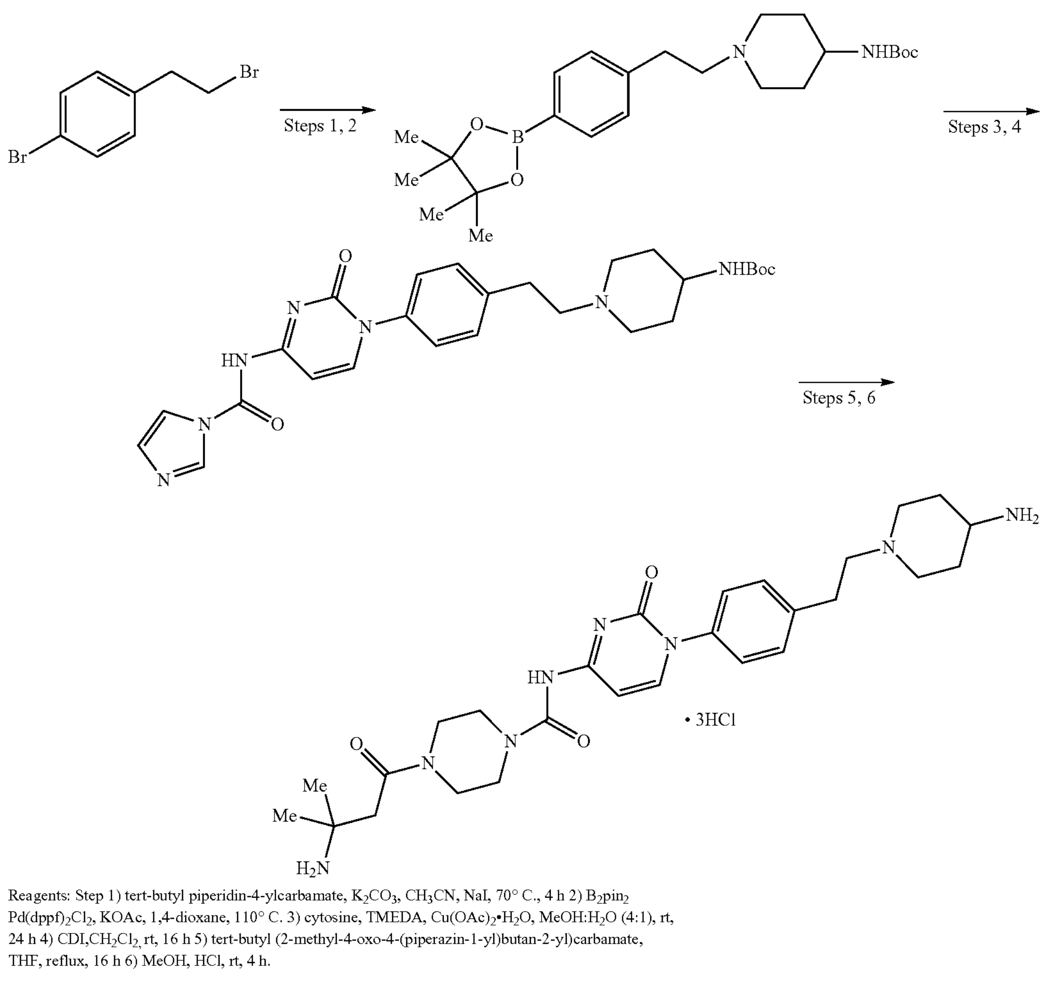

Step 1: tert-butyl (1-(4-bromophenethyl)piperidin-4-yl)carbamate

To a suspension of potassium carbonate (2.10 g, 15.2 mmol), sodium iodide (0.57 g, 3.8 mmol) and 4-(N-Boc-amino)piperidine (0.76 mg, 3.8 mmol) in dry $CH_3CN$ (22 mL) at 70° C. under $N_2$ was added 1-bromo-4-(2-bromo-ethyl)benzene (1.0 g, 3.8 mmol) dropwise over 3 min. The reaction was stirred for 16 h at 70° C., cooled and the solid was filtered. The filtrate was concentrated and purified by flash chromatography to afford the title compound.

Step 2: tert-butyl (1-(4-(4,4,5,5-tetramethyl-1,3,2-dioxaborolan-2-yl)phenethyl)piperidin-4-yl)carbamate An oven dried pressure flask was charged with tert-butyl (1-(4-bromophenethyl)piperidin-4-yl)carbamate (0.30 mg, 0.78 mmol), bis(pinacolato)diboron (0.24 g, 0.94 mmol), KOAc (0.22 g, 2.19 mmol), $Pd(dppf)_2Cl_2$ (0.13 mg, 0.02 mmol), and dry dioxane (10 mL). The reaction mixture was degassed and flushed with nitrogen (3×). The reaction was placed in a preheated oil bath at 110° C. and stirred for 16 h. The mixture was cooled, concentrated under reduced pressure and $CHCl_3$ (10 mL) was added. The solution was washed with sat. aq. $NaHCO_3$(30 mL) and the aqueous layer was extracted (2×10 mL chloroform). The organic layers were combined, dried over sodium sulfate and concentrated under reduced pressure. The residue was purified by flash chromatography to afford the title compound.

Step 3: tert-butyl (1-(4-(4-amino-2-oxopyrimidin-1(2H)-yl)phenethyl)piperidin-4-yl)carbamate A mixture of cytosine (52.0 mg, 0.47 mmol) and tert-butyl (1-(4-(4,4,5,5-tetramethyl-1,3,2-dioxaborolan-2-yl)phenethyl)piperidin-4-yl)carbamate (0.20 g, 0.47 mmol) were dissolved in a stirring solution of 4:1 MeOH:water (15 mL) open to air. After 30 minutes $Cu(OAc)_2 \cdot H_2O$ (93.0 mg, 0.47 mmol) and N,N,N',N'-tetramethylethylenediamine (64.0 mg, 0.55 mmol) were added and the solution was stirred for 12 h. The methanol was evaporated under reduced pressure. Ice (20 g) was added and the mixture stirred for 30 min. The precipitate was collected by vacuum filtration to afford the title compound.

Step 4: tert-butyl (1-(4-(4-(1H-imidazole-1-carboxamido)-2-oxopyrimidin-1(2H)-yl)phenethyl)piperidin-4-yl)carbamate An oven dried round bottom flask equipped with a stir bar, was charged with tert-butyl (1-(4-(4-amino-2-oxopyrimidin-1(2H)-yl)phenethyl)piperidin-4-yl)carbamate (50 mg, 0.21 mmol) and CDI (33 mg, 0.21 mmol), and dry $CH_2Cl_2$ (10 mL) was added under nitrogen atmosphere. The reaction mixture was stirred for 16 h at rt under $N_2$. The mixture was concentrated under reduced pressure to afford the title compound.

Step 5: tert-butyl (4-(4-((1-(4-(2-(4-((tert-butoxycarbonyl)amino)piperidin-1-yl)ethyl)phenyl)-2-oxo-1,2-dihydropyrimidin-4-yl)carbamoyl)piperazin-1-yl)-2-methyl-4-oxobutan-2-yl)carbamate To a stirring solution of tert-butyl (1-(4-(4-(1H-imidazole-1-carboxamido)-2-oxopyrimidin-1(2H)-yl)phenethyl)piperidin-4-yl)carbamate (0.21 mmol) in dry THF (6 mL), tert-butyl (2-methyl-4-oxo-4-(piperazin-1-yl)butan-2-yl)carbamate (51 mg, 0.18 mmol) dissolved in dry THF (2 mL) was added dropwise. The reaction mixture was stirred at reflux for 16 h, after which the solvent was evaporated reduced pressure. The residue was dissolved in EtOAc and partitioned between EtOAc and water. The organic layer was washed with water (3×50 mL) and brine (15 mL), dried over $Na_2SO_4$, filtered and concentrated reduced pressure. Purification via flash chromatography afforded the title compound.

Step 6: 4-(3-amino-3-methylbutanoyl)-N-(1-(4-(2-(4-aminopiperidin-1-yl)ethyl)phenyl)-2-oxo-1,2-dihydropyrimidin-4-yl)piperazine-1-carboxamide hydrochloride salt tert-Butyl (4-(4-((1-(4-(2-(4-((tert-butoxycarbonyl)amino)piperidin-1-yl)ethyl)phenyl)-2-oxo-1,2-dihydropyrimidin-4-yl)carbamoyl)piperazin-1-yl)-2-methyl-4-oxobutan-2-yl)carbamate (90 mg, 0.13 mmol) was dissolved in a solution of 2M methanolic HCl (10 mL). The reaction mixture was stirred for 4 h and concentrated reduced pressure. The solid was triturated with diethyl ether and dried to afford the title compound. LCMS [M+H] 525.4.

Compound 198

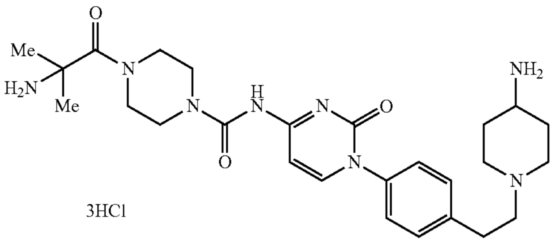

4-(2-Amino-2-methylpropanoyl)-N-(1-(4-(2-(4-aminopiperidin-1-yl)ethyl)phenyl)-2-oxo-1,2-dihydropyrimidin-4-yl)piperazine-1-carboxamide hydrochloride salt Prepared in a similar fashion as Scheme C-18 from tert-butyl (1-(4-(4-(1H-imidazole-1-carboxamido)-2-oxopyrimidin-1(2H)-yl)phenethyl)piperidin-4-yl)carbamate and tert-butyl (2-methyl-1-oxo-1-(piperazin-1-yl)propan-2-yl)carbamate. $^1H$ NMR (400 MHz, $D_2O$) δ 8.06-7.94 (m, 1H), 7.53 (d, 2H), 7.50-7.40 (m, 2H), 6.85 (d, 1H), 3.79 (d, 10H), 3.67-3.57 (m, 1H), 3.56-3.46 (m, 2H), 3.24 (d, 4H), 2.40 (d, 2H), 2.07-1.91 (m, 2H), 1.76 (d, 6H). LCMS [M+H] 511.5.

Compound 199

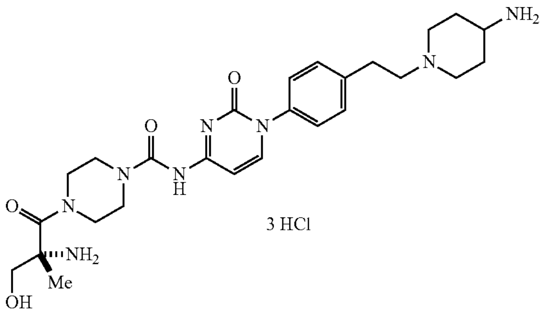

(R)-4-(2-Amino-3-hydroxy-2-methylpropanoyl)-N-(1-(4-(2-(4-aminopiperidin-1-yl)ethyl)phenyl)-2-oxo-1,2-dihydropyrimidin-4-yl)piperazine-1-carboxamide hydrochloride salt Prepared in a similar fashion as Scheme C-18 from tert-butyl (1-(4-(4-(1H-imidazole-1-carboxamido)-2-oxopyrimidin-1(2H)-yl)phenethyl)piperidin-4-yl)carbamate and (2S,4R)-tert-butyl 2-(tert-butyl)-4-methyl-4-(piperazine-1-carbonyl)oxazolidine-3-carboxylate. $^1$H NMR (400 MHz, $D_2O$) δ 8.12 (d, 1H), 7.53 (d, 2H), 7.47 (d, 2H), 6.82 (d, 1H), 4.17 (d, 1H), 3.92 (d, 1H), 3.85-3.70 (m, 10H) 3.66-3.54 (m, 1H), 3.54-3.46 (m, 2H), 3.26-3.15 (m, 4H), 2.39 (d, 2H), 2.06-1.91 (m, 2H), 1.70 (s, 3H). LCMS [M+H] 527.4.

Compound 192

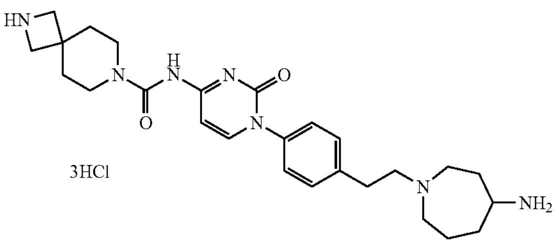

N-(1-(4-(2-(4-Aminoazepan-1-yl)ethyl)phenyl)-2-oxo-1,2-dihydropyrimidin-4-yl)-2,7-diazaspiro[3.5]nonane-7-carboxamide hydrochloride salt Scheme C-19

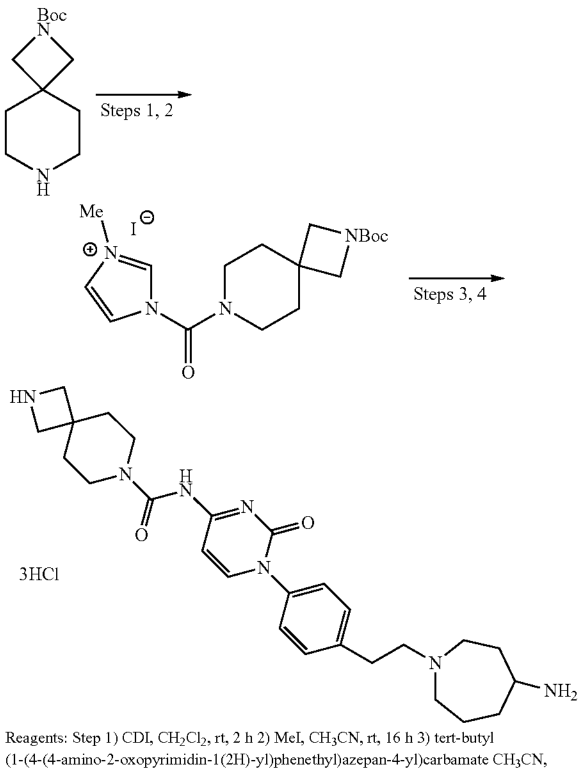

Reagents: Step 1) CDI, $CH_2Cl_2$, rt, 2 h 2) MeI, $CH_3CN$, rt, 16 h 3) tert-butyl (1-(4-(4-amino-2-oxopyrimidin-1(2H)-yl)phenethyl)azepan-4-yl)carbamate $CH_3CN$, 90° C., 16 h 4) 4M HCl in dioxane, rt, 4 h.

Step 1: tert-butyl 7-(1H-imidazole-1-carbonyl)-2,7-diazaspiro[3.5]nonane-2-carboxylate To a stirred solution of tert-butyl 2,7-diazaspiro[3.5]nonane-2-carboxylate (0.2 g, 0.88 mmol) in $CH_2Cl_2$ (5 mL) was added CDI (0.172 g, 1.06 mmol), and the mixture was stirred at rt for 2 h. It was poured into $H_2O$ (50 mL) and extracted with $CH_2Cl_2$ (3×20 mL). The extracts were dried over $Na_2SO_4$, filtered and concentrated in vacuo to afford the title compound. $^1$H NMR (DMSO-$d_6$, 400 MHz) δ 7.98 (d, 1H), 7.42 (t, 1H), 7.02 (t, 1H), 3.65-3.55 (m, 4H), 3.45-3.35 (m, 4H), 1.75 (t, 4H), 1.37 (s, 9H). LCMS [M+H] 321.1.

Step 2: 1-(2-(tert-butoxycarbonyl)-2,7-diazaspiro[3.5]nonane-7-carbonyl)-3-methyl-1H-imidazol-3-ium iodide To a stirred solution of tert-butyl 7-(1H-imidazole-1-carbonyl)-2,7-diazaspiro[3.5]nonane-2-carboxylate (0.28 g, 0.87 mmol) in $CH_3CN$ (3 mL) was added MeI (0.74 g, 0.34 mL, 5.25 mmol). The mixture was stirred at rt for 16 h concentrated in vacuo to afford the title compound. LCMS [M+H] 335.1.

Step 3: tert-butyl 7-((1-(4-(2-(4-((tert-butoxycarbonyl)amino)azepan-1-yl)ethyl)phenyl)-2-oxo-1,2-dihydropyrimidin-4-yl)carbamoyl)-2,7-diazaspiro[3.5]nonane-2-carboxylate A mixture of tert-butyl (1-(4-(4-amino-2-oxopyrimidin-1(2H)-yl)phenethyl)azepan-4-yl)carbamate (0.2 g, 0.46 mmol) and 1-(2-(tert-butoxycarbonyl)-2,7-diazaspiro[3.5]nonane-7-carbonyl)-3-methyl-1H-imidazol-3-ium iodide (0.26 g, 0.56 mmol) in $CH_3CN$ (3 mL) was stirred at 90° C. for 16 h. The mixture was concentrated in vacuo and the residue was purified by flash chromatography ($CH_3OH$/$CH_2Cl_2$) to afford the title compound. LCMS [M+H] 680.2.

Step 4: N-(1-(4-(2-(4-aminoazepan-1-yl)ethyl)phenyl)-2-oxo-1,2-dihydropyrimidin-4-yl)-2,7-diazaspiro[3.5]nonane-7-carboxamide hydrochloride salt A mixture of tert-butyl 7-((1-(4-(2-(4-((tert-butoxycarbonyl)amino)azepan-1-yl)ethyl)phenyl)-2-oxo-1,2-dihydropyrimidin-4-yl)carbamoyl)-2,7-diazaspiro[3.5]nonane-2-carboxylate (0.09 g, 0.13 mmol) and 4 M HCl in dioxane (5 mL, 20 mmol) in 1,4-dioxane (3 mL) was stirred at rt for 4 h. It was concentrated in vacuo, triturated with diethyl ether (10 mL), and the residue was purified by prepHPLC to afford the title compound. $^1$H NMR (400 MHz, $D_2O$) δ 7.74 (d, 1H), 7.34 (d, 2H), 7.27 (d, 2H), 6.67 (d, 1H), 3.83 (s, 4H), 3.59-3.55 (m, 1H), 3.43-3.37 (m, 7H), 3.05-3.07 (m, 2H), 2.18-2.07 (m, 2H), 1.97-1.87 (m, 3H), 1.98-1.89 (m, 2H), 1.82-1.79 (m, 4H), 1.70-1.55 (m, 2H). LCMS [M+H] 480.2.

Compound 193

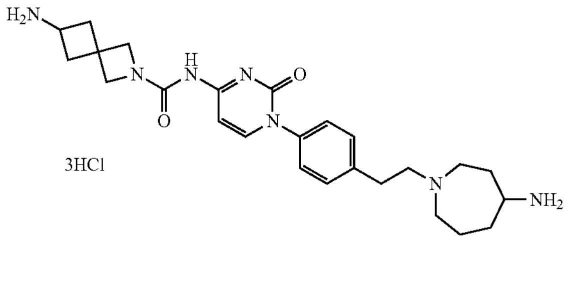

6-Amino-N-(1-(4-(2-(4-aminoazepan-1-yl)ethyl) phenyl)-2-oxo-1,2-dihydropyrimidin-4-yl)-2-azaspiro[3.3]heptane-2-carboxamide hydrochloride salt Prepared in a similar fashion as Scheme C-19 from tert-butyl (1-(4-(4-amino-2-oxopyrimidin-1(2H)-yl)phenethyl)azepan-4-yl)carbamate and tert-butyl (2-azaspiro[3.3] heptan-6-yl)carbamate hydrochloride. LCMS [M+H] 466.2.

5-Amino-N-(1-(4-(2-(4-aminoazepan-1-yl)ethyl) phenyl)-2-oxo-1,2-dihydropyrimidin-4-yl)-2-azaspiro[3.3]heptane-2-carboxamide hydrochloride salt Prepared in a similar fashion as Scheme C-19 from tert-butyl (1-(4-(4-amino-2-oxopyrimidin-1(2H)-yl)phenethyl)azepan-4-yl)carbamate and tert-butyl azepan-4-ylcarbamate and tert-butyl (2-azaspiro[3.3]heptan-5-yl)carbamate. $^1$H NMR (400 MHz, $D_2O$) δ 7.84 (d, 1H), 7.34 (d, 2H), 7.27 (d, 2H), 6.99 (d, 1H), 4.05-3.96 (m, 4H), 3.79 (t, 1H), 3.58-3.55 (m, 2H), 3.41-3.37 (m, 4H), 3.28-3.11 (m, 2H), 3.05-3.01 (m, 2H), 2.18-2.04 (m, 4H), 1.95-1.83 (m, 3H), 1.70-1.55 (m, 2H). LCMS [M+H] 466.2.

Compound 371

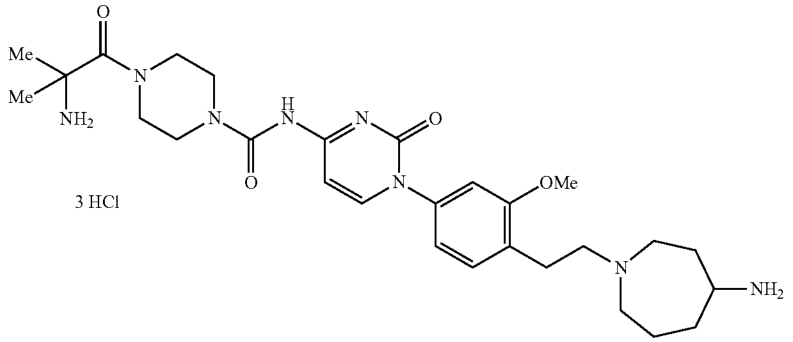

4-(2-Amino-2-methylpropanoyl)-N-(1-(4-(2-(4-aminoazepan-1-yl)ethyl)-3-methoxyphenyl)-2-oxo-1,2-dihydropyrimidin-4-yl)piperazine-1-carboxamide hydrochloride salt Compound 194

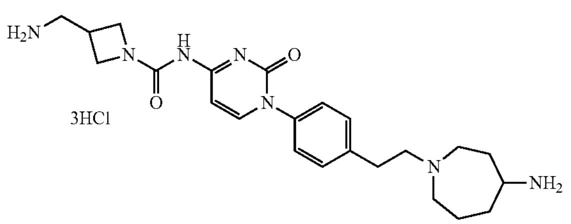

N-(1-(4-(2-(4-Aminoazepan-1-yl)ethyl)phenyl)-2-oxo-1,2-dihydropyrimidin-4-yl)-3-(aminomethyl) azetidine-1-carboxamide hydrochloride salt Prepared in a similar fashion as Scheme C-19 from tert-butyl (1-(4-(4-amino-2-oxopyrimidin-1(2H)-yl)phenethyl)azepan-4-yl)carbamate and tert-butyl (azetidin-3-ylmethyl)carbamate. LCMS [M+H] 440.4.

Compound 195

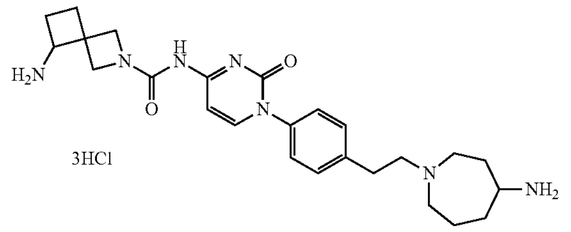

Scheme C-20

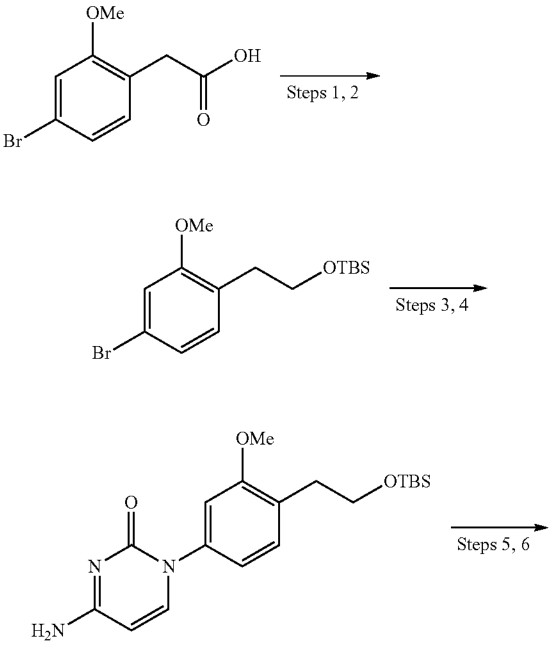

-continued

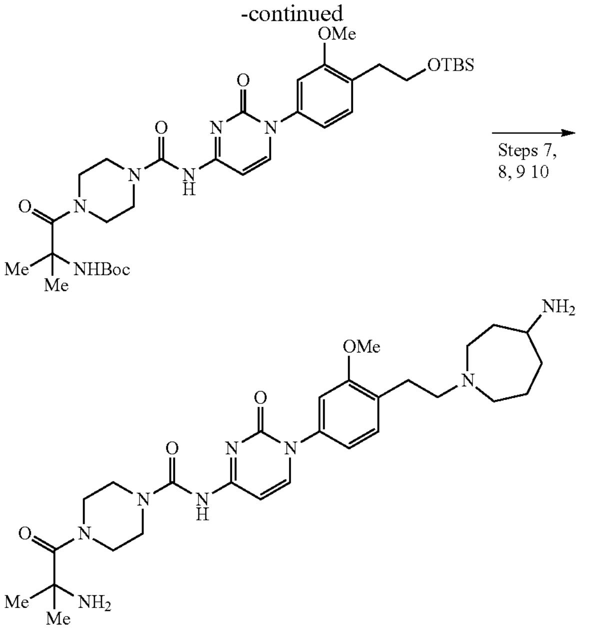

Reagents 1) $BH_3THF$, THF 0° C. 2) TBSCl, $NEt_3$, DMF 3) BuLi, THF, -78° C. $(iPrO)_3B$, 2N HCl 4) cystosine, TMEDA, $Cu(OAc)_2$•H2O, 4:1 MeOH:$H_2O$ 5) CDI, $CH_2Cl_2$ 6) tert-butyl (2-methyl-1-oxo-1-(piperazin-1-yl)propan-2-yl)carbamate, $CH_3CN$, 80° C. 7) TBAF, THF 0° C. to rt 8) DMP, 0.1% $H_2O$:$CH_2Cl_2$, 15 min 9) tert-butyl azepan-4-ylcarbamate, $NaH(OAc)_3$, DIPEA, DCE, 16 h 10) HCl in MeOH, 4-8 h.

Step 1: 2-(4-bromo-2-methoxyphenyl)ethan-1-ol

A solution of 2-(4-bromo-2-methoxyphenyl)acetic acid (2.00 g, 8.23 mmol) in THF (100 mL) was cooled to 0° C. to this was added $BH_3THF$ (16.46 ml, 16.46 mmol) drop wise over 30 min. The solution was stirred for 16 h. The excess $BH_3THF$ was quenched with MeOH (100 mL) and the solvent evaporated to afford the title compound.

Step 2: (4-bromo-2-methoxyphenethoxy)(tert-butyl)dimethylsilane

To a solution of 2-(4-bromo-2-methoxyphenyl)ethan-1-ol (8.23 mmol) in DMF (25 mL) was added $NEt_3$ (2.2 ml, 16.5 mmol) and TBSCl (1.48 g, 9.9 mmol). The reaction was stirred for 16 h. The reaction mixture was partitioned between EtOAc (50 mL) and LiCl (50 mL). The organic layer was washed with LiCl (2×50 mL). The organic layer was dried over $Na_2SO_4$ and concentrated under reduced pressure to give an oily residue, which was purified by column chromatography (Hexanes:EtOAc) to afford the title compound.

Step 3: diisopropyl (4-(2-((tert-butyldimethylsilyl)oxy)ethyl)-3-methoxyphenyl)boronate A stirred solution of (4-bromo-2-methoxyphenethoxy)(tert-butyl)dimethylsilane (1.2 g, 3.5 mmol) in THF (30 mL) was cooled to −78° C. 1M BuLi in Hexanes (3.5 mL, 8.8 mmol) was added dropwise over 30 min. and the temperature maintained below −60° C. After 25 min triisopropyl borate (1.2 mL, 5.3 mmol) was added dropwise over 30 min. The reaction mixture was warmed to rt and stirred for 15 min. 2N HCl (20 mL) was added and the reaction was stirred for 30 min. The biphasic mixture was separated and the aq. layer washed with $CH_2Cl_2$ (2×50 mL). The combined organics were dried over $Na_2SO_4$ and concentrated under reduced pressure to afford the title compound.

Step 4: 4-amino-1-(4-(2-((tert-butyldimethylsilyl)oxy)ethyl)-3-methoxyphenyl)pyrimidin-2(1H)-one A suspension of cytosine (0.39 g, 3.5 mmol) and diisopropyl (4-(2-((tert-butyldimethylsilyl)oxy)ethyl)-3-methoxyphenyl)boronate (3.5 mmol), in MeOH:$H_2O$ (4:1, 40 ml) was stirred at rt in open air for 30 min. TMEDA (0.67 ml, 3.7 mmol) and $Cu(OAc)_2 \cdot H_2O$ (0.69 g, 3.5 mmol) were added and the reaction was stirred in open air for 48 h at rt. The reaction mixture was concentrated under reduced pressure, and cold $H_2O$ (50 mL) was added. The solid was filtered and washed with $H_2O$ (5×50 mL), $Et_2O$ (3×30 mL) and $H_2O$ (2×30 mL) to afford the title compound.

Step 5: N-(1-(4-(2-((tert-butyldimethylsilyl)oxy)ethyl)-3-methoxyphenyl)-2-oxo-1,2-dihydropyrimidin-4-yl)-1H-imidazole-1-carboxamide A suspension of 4-amino-1-(4-(2-((tert-butyldimethylsilyl)oxy)ethyl)-3-methoxyphenyl)pyrimidin-2(1H)-one (200 mg, 0.53 mmol) and 1,1'-carbonyldiimidazole (146 mg, 0.90 mmol) in $CH_2Cl_2$ (12 mL) was stirred at rt for 16 h. The solvent was removed under reduced pressure to afford the title compound.

Step 6: tert-butyl (1-(4-((1-(4-(2-((tert-butyldimethylsilyl)oxy)ethyl)-3-methoxyphenyl)-2-oxo-1,2-dihydropyrimidin-4-yl)carbamoyl)piperazin-1-yl)-2-methyl-1-oxopropan-2-yl)carbamate N-(1-(4-(2-((tert-Butyldimethylsilyl)oxy)ethyl)-3-methoxyphenyl)-2-oxo-1,2-dihydropyrimidin-4-yl)-1H-imidazole-1-carboxamide (0.81 mmol) and tert-butyl (2-methyl-1-oxo-1-(piperazin-1-yl)propan-2-yl)carbamate as prepared in scheme 1 (329 mg, 1.2 mmol) were dissolved in $CH_3CN$ (30 mL) and heated to reflux for 2 h. The reaction mixture was concentrated under reduced pressure and the solid was dissolved in EtOAc (25 mL) and washed with water (3×20 mL). The reaction mixture was purified by flash chromatography (Hexanes:EtOAc) to afford the title compound.

Step 7: tert-butyl (1-(4-((1-(4-(2-hydroxyethyl)-3-methoxyphenyl)-2-oxo-1,2-dihydropyrimidin-4-yl)carbamoyl)piperazin-1-yl)-2-methyl-1-oxopropan-2-yl)carbamate To a stirred solution of tert-butyl (1-(4-((1-(4-(2-((tert-butyldimethylsilyl)oxy)ethyl)-3-methoxyphenyl)-2-oxo-1,2-dihydropyrimidin-4-yl)carbamoyl)piperazin-1-yl)-2-methyl-1-oxopropan-2-yl)carbamate (300 mg, 0.45 mmol) in THF (30 mL) at 0° C. was added 2M TBAF in THF (1.0 mL) over of 20 min. The solution was stirred for 16 h. The crude reaction mixture was concentrated under reduced pressure to give an oily residue, which was purified by column chromatography ($CH_2Cl_2$:MeOH) to afford the title compound.

Step 8: tert-butyl (1-(4-((1-(3-methoxy-4-(2-oxoethyl)phenyl)-2-oxo-1,2-dihydropyrimidin-4-yl)carbamoyl)piperazin-1-yl)-2-methyl-1-oxopropan-2-yl)carbamate To a stirred solution of tert-butyl (1-(4-((1-(4-(2-hydroxyethyl)-3-methoxyphenyl)-2-oxo-1,2-dihydropyrimidin-4-yl)carbamoyl)piperazin-1-yl)-2-methyl-1-oxopropan-2-yl)carbamate (45 mg, 0.08 mmol) in 0.1% $H_2O$:$CH_2Cl_2$ (20 mL) was added Dess-Martin periodinane (55 mg, 0.13 mmol). The solution was stirred for 15 min. The crude reaction mixture was dissolved in additional $CH_2Cl_2$ (50 mL) and washed with aq. $NaHCO_3/Na_2SO_2O_3$ (1×50 mL). The aq. layer was extracted with $CH_2Cl_2$ (1×10 mL). The combined organic layers were dried over $Na_2SO_4$ and concentrated under reduced pressure to afford the title compound.

Step 9: tert-butyl (1-(4-((1-(4-(2-(4-((tert-butoxycarbonyl)amino)azepan-1-yl)ethyl)-3-methoxyphenyl)-2-oxo-1,2-dihydropyrimidin-4-yl)carbamoyl)piperazin-1-yl)-2-methyl-1-oxopropan-2-yl)carbamate To a stirred solution tert-butyl (1-(4-((1-(3-methoxy-4-(2-oxoethyl)phenyl)-2-oxo-1,2-dihydropyrimidin-4-yl)carbamoyl)piperazin-1-yl)-2-methyl-1-oxopropan-2-yl)carbamate (22 mg, 0.04 mmol) was added tert-butyl azepan-4-ylcarbamate (13 mg, 0.06 mmol) followed by $NaH(OAc)_3$ (17 mg, 0.08 mmol) and DIPEA (1 drop). The reaction was stirred for 16 h. The reaction mixture was treated with 1N NaOH (10 mL) and extracted with $CH_2Cl_2$ (2×20 mL). The combined organics were dried over $Na_2SO_4$ and concentrated under reduced pressure to afford the title compound.

Step 10: 4-(2-amino-2-methylpropanoyl)-N-(1-(4-(2-(4-aminoazepan-1-yl)ethyl)-3-methoxyphenyl)-2-oxo-1,2-dihydropyrimidin-4-yl)piperazine-1-carboxamide hydrochloride salt tert-Butyl (1-(4-((1-(4-(2-(4-((tert-butoxycarbonyl)amino)azepan-1-yl)ethyl)-3-methoxyphenyl)-2-oxo-1,2-dihydropyrimidin-4-yl)carbamoyl)piperazin-1-yl)-2-methyl-1-oxopropan-2-yl)carbamate was dissolved in a solution of HCl/MeOH (50 mL) and stirred for 4 h. The HCl/MeOH was evaporated and the crude solid was purified by RPHPLC ($H_2O$:$CH_3CN$:TFA) and concentrated under reduced pressure. Addition of HCl/MeOH (3×15 mL) and evaporation under reduced pressure afforded the title compound. $^1H$ NMR (500 MHz, $D_2O$) δ 8.01 (d, 1H), 7.41 (d, 1H), 7.12 (s, 1H), 7.03 (d, 1H), 6.82 (d, 1H), 3.88 (s, 3H), 3.84-3.70 (m, 8H), 3.62-3.53 (m, 3H), 3.48-3.38 (m, 3H), 3.32-3.20 (m, 1H), 3.14 (t, 2H), 2.41-2.20 (m, 3H), 2.22-1.98 (m, 2H), 1.89-1.75 (m, 1H), 1.73 (s, 6H). LCMS [M+H] 555.2.

Compound 139

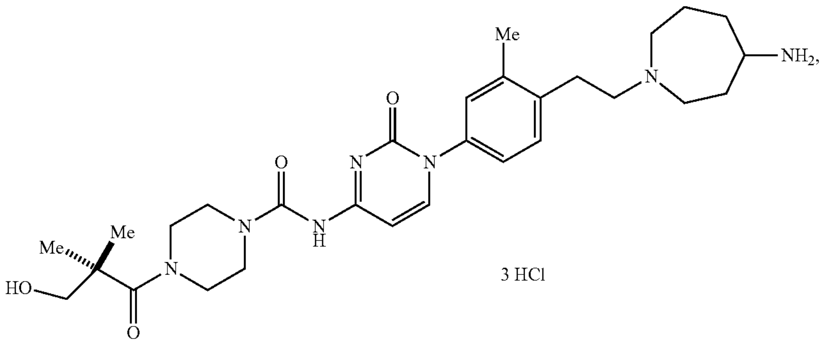

3 HCl 4-((S)-2-Amino-3-hydroxy-2-methylpropanoyl)-N-(1-(4-(2-(4-aminoazepan-1-yl)ethyl)-3-methylphenyl)-2-oxo-1,2-dihydropyrimidin-4-yl)piperazine-1-carboxamide hydrochloride salt Prepared in a similar fashion as Scheme C-20 from 2-(4-bromo-2-methylphenyl)ethan-1-ol, 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide, and tert-butyl azepan-4-ylcarbamate. $^1H$ NMR (400 MHz, $D_2O$) δ 8.00 (d, 1H), 7.38 (d, 1H), 7.30 (s, 1H), 7.25 (d, 1H), 6.78 (d, 1H), 4.13 (d, 1H), 3.87 (d, 1H), 3.76 (s, 2H), 3.71 (s, 7H), 3.58 (s, 2H), 3.39 (t, 3H), 3.32 (s, 2H), 3.19-3.11 (m, 2H), 2.37 (s, 3H), 2.34-2.20 (m, 2H), 2.19-1.96 (m, 2H), 1.91-1.68 (m, 1H), 1.65 (s, 3H). LCMS [M+H] 555.3.

Compound 140

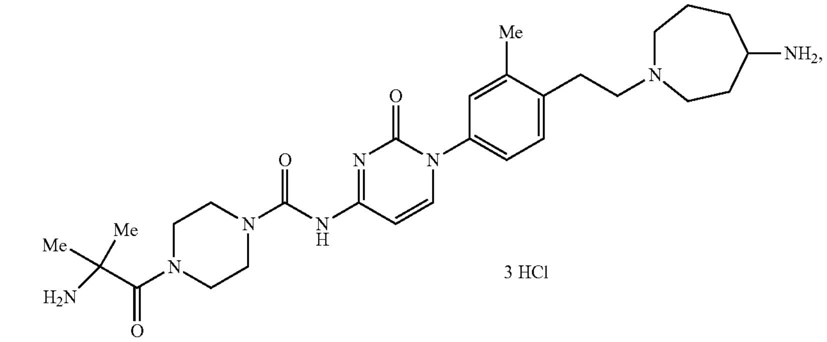

3 HCl 4-(2-Amino-2-methylpropanoyl)-N-(1-(4-(2-(4-aminoazepan-1-yl)ethyl)-3-methylphenyl)-2-oxo-1,2-dihydropyrimidin-4-yl)piperazine-1-carboxamide hydrochloride salt Prepared in a similar fashion as Scheme C-20 from tert-butyl (2-methyl-1-(4-((1-(3-methyl-4-(2-oxoethyl)phenyl)-2-oxo-1,2-dihydropyrimidin-4-yl)carbamoyl)piperazin-1-yl)-1-oxopropan-2-yl)carbamate and tert-butyl azepan-4-ylcarbamate. $^1$H NMR (400 MHz, $D_2O$) δ 7.98 (d, 1H), 7.38 (d, 1H), 7.30 (s, 1H), 7.25 (d, 1H), 6.78 (d, 1H), 3.75, (s, 2H), 3.71 (s, 8H), 3.58 (s, 2H), 3.41 (t, 2H), 3.31 (s, 2H), 3.15 (t, 2H), 2.37 (s, 3H), 2.36-2.19, (m, 2H), 2.18-1.98 (m, 2H), 1.90-1.73 (m, 1H), 1.70 (s, 6H). LCMS [M+H] 539.4.

Compound 141

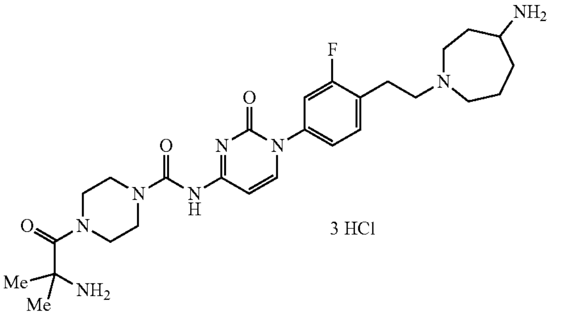

4-(2-Amino-2-methylpropanoyl)-N-(1-(4-(2-(4-aminoazepan-1-yl)ethyl)-3-fluorophenyl)-2-oxo-1,2-dihydropyrimidin-4-yl)piperazine-1-carboxamide hydrochloride salt Prepared in a similar fashion as Scheme C-20 from tert-butyl (1-(4-((1-(3-fluoro-4-(2-oxoethyl)phenyl)-2-oxo-1,2-dihydropyrimidin-4-yl)carbamoyl)piperazin-1-yl)-2-methyl-1-oxopropan-2-yl)carbamate and tert-butyl azepan-4-ylcarbamate. $^1$H NMR (500 MHz, $D_2O$) δ 8.26-8.22 (m, 1H), 7.51 (t, 1H), 7.35-7.24 (m, 2H), 6.73 (d, 1H), 3.79-3.66 (m, 8H), 3.59-3.39 (m, 5H), 3.39-3.33 (m, 1H), 3.22-3.12 (m, 3H), 2.38-1.70 (m, 6H), 1.67 (s, 6H). LCMS [M+H] 543.3.

Compound 142

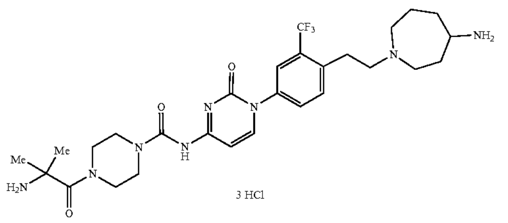

4-(2-Amino-2-methylpropanoyl)-N-(1-(4-(2-(4-aminoazepan-1-yl)ethyl)-3-(trifluoromethyl)phenyl)-2-oxo-1,2-dihydropyrimidin-4-yl)piperazine-1-carboxamide hydrochloride salt Prepared in a similar fashion as Scheme C-20 from tert-butyl (2-methyl-1-oxo-1-(4-((2-oxo-1-(4-(2-oxoethyl)-3-(trifluoromethyl)phenyl)-1,2-dihydropyrimidin-4-yl)carbamoyl)piperazin-1-yl)propan-2-yl)carbamate and tert-butyl azepan-4-ylcarbamate. $^1$H NMR (400 MHz, $D_2O$) δ 7.90 (d, 1H), 7.85 (d, 1H), 7.72-7.60 (m, 2H), 6.82 (d, 1H), 3.74 (s, 4H), 3.69 (s, 6H), 3.63-3.52 (m, 4H), 3.51-3.41 (m, 2H), 3.36-3.26 (m, 2H), 2.41-2.20 (m, 2H), 2.18-1.92 (m, 2H) 1.91-1.72 (m, 1H), 1.70 (s, 6H). LCMS [M+H] 593.2.

Compound 150

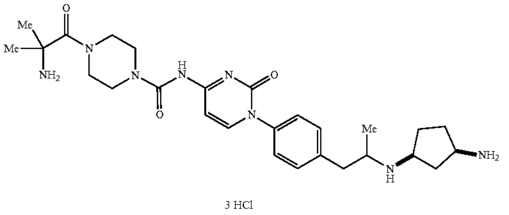

4-(2-Amino-2-methylpropanoyl)-N-(1-(4-(2-(((1S,3R)-3-aminocyclopentyl)amino)propyl)phenyl)-2-oxo-1,2-dihydropyrimidin-4-yl)piperazine-1-carboxamide hydrochloride salt Scheme C-21

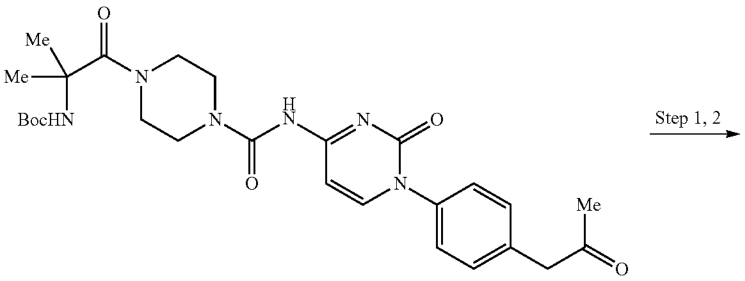

-continued

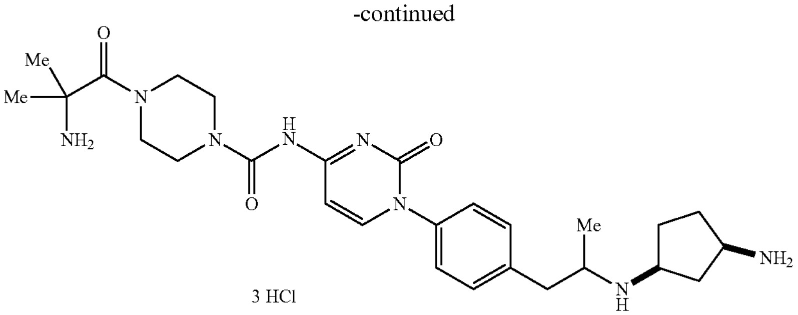

3 HCl

Reagents: 1) tert-butyl ((1R,3S)-3-aminocyclopentyl)carbamate, $NaBH_3CN$, 4Å ms, MeOH, rt, 16 h
2) HCl in dioxane, dioxane, rt, 4 h.

Step 1: tert-butyl (1-(4-((1-(4-(2-(((1S,3R)-3-((tert-butoxycarbonyl)amino)cyclopentyl)amino)propyl)phenyl)-2-oxo-1,2-dihydropyrimidin-4-yl)carbamoyl)piperazin-1-yl)-2-methyl-1-oxopropan-2-yl)carbamate To a stirred solution of tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate (0.45 g, 0.74 mmol) and tert-butyl ((1R,3S)-3-aminocyclopentyl)carbamate (177 mg, 0.88 mmol) in methanol (10 mL) were added activated 4 Å ms (3.0 g) and $NaBH_3CN$ (0.105 g, 1.66 mmol) at 0° C. under $N_2$ atmosphere. The reaction mixture was stirred at rt for 24 h. The resulting reaction mixture was concentrated under reduced pressure and purified by flash chromatography ($MeOH/CH_2Cl_2$) to afford the title compound (0.36 g, 60%) as a pale yellow solid. LCMS [M+H] 725.2.

Step 10: 4-(2-amino-2-methylpropanoyl)-N-(1-(4-(2-(((1S,3R)-3-aminocyclopentyl)amino)propyl)phenyl)-2-oxo-1,2-dihydropyrimidin-4-yl)piperazine-1-carboxamide hydrochloride salt To a stirred solution of tert-butyl (1-(4-((1-(4-(2-(((1S,3R)-3-((tert-butoxycarbonyl)amino)cyclopentyl)amino)propyl)phenyl)-2-oxo-1,2-dihydropyrimidin-4-yl)carbamoyl)piperazin-1-yl)-2-methyl-1-oxopropan-2-yl)carbamate (0.09 g, 0.12 mmol) in 1,4-dioxane (3 mL) was added 4 M HCl in dioxane (5 ml). The mixture was stirred at rt for 4 h concentrated under reduced pressure and triturated with diethyl ether (10 mL). The resulting crude material was purified by semi-preparative HPLC to afford the title compound. $^1H$ NMR (400 MHz, $D_2O$) δ 7.89 (d, 1H), 7.31-7.25 (m, 4H), 6.62 (d, 1H), 3.76-3.72 (m, 1H), 3.58-3.49 (m, 10H), 3.12-3.07 (m, 1H), 2.75-2.70 (m, 1H), 2.53-2.50 (m, 1H), 2.09-2.01 (m, 2H), 1.76-1.72 (m, 2H), 1.64-1.58 (m, 1H), 1.53 (s, 6H), 1.09 (d, 3H). LCMS [M+H] 525.2.

Compound 152

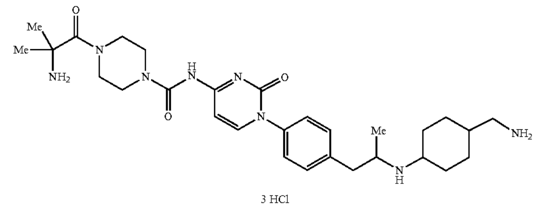

3 HCl

4-(2-Amino-2-methylpropanoyl)-N-(1-(4-(2-((4-(aminomethyl)cyclohexyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and tert-butyl ((4-aminocyclohexyl)methyl)carbamate. $^1H$ NMR (400 MHz, $D_2O$) δ 7.72 (d, 1H), 7.34-7.27 (m, 4H), 6.71 (d, 1H), 3.62-3.51 (m, 8H), 3.38-3.34 (m, 1H), 3.22-3.10 (m, 2H), 3.95-2.85 (m, 2H), 2.76-2.22 (m, 2H), 2.10-2.00 (m, 1H), 1.95-1.75 (m, 3H), 1.59 (s, 6H), 1.55-1.45 (m, 1H), 1.35-1.25 (m, 1H), 1.22 (t, 3H), 1.05-0.90 (in, 2H). LCMS [M+H] 553.3.

Compound 155

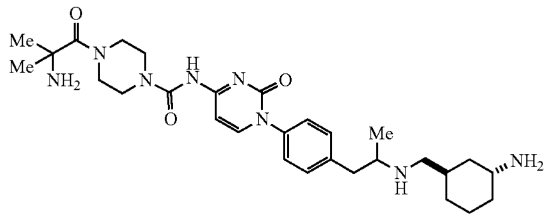

3 HCl trans-4-(2-Amino-2-methylpropanoyl)-N-(1-(4-(2-(((3-aminocyclohexyl)methyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate. $^1H$ NMR (400 MHz, $D_2O$) δ 7.77 (d, 1H), 7.33-7.27 (m, 4H), 6.68 (d, 1H), 3.70-3.40 (m, 8H), 3.40-3.30 (m, 2H), 31.7-3.10 (m, 1H), 2.80-2.65 (m, 2H), 2.10-2.01 (m, 1H), 1.75-1.41 (m, 13H), 1.26-1.19 (m, 2H), 1.12 (d, 3H). LCMS [M+H] 553.3.

Compound 156

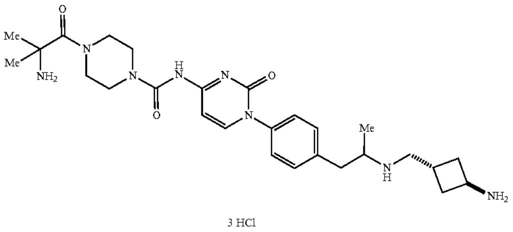

trans-4-(2-Amino-2-methylpropanoyl)-N-(1-(4-(2-(((3-aminocyclobutyl)methyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate. $^1$H NMR ($D_2O$, 400 MHz) δ 7.83 (d, 1H), 7.83-7.29 (m, 4H), 6.75-6.70 (br s, 1H), 3.82-3.79 (m, 1H), 3.63-3.48 (m, 8H), 3.24-3.10 (m, 3H), 2.79-2.55 (m, 3H), 2.25-2.33 (m, 2H), 2.22-2.17 (m, 2H), 1.58 (s, 6H), 1.13 (d, 3H). LCMS[(M+2H)/2] 263.1.

Compound 159

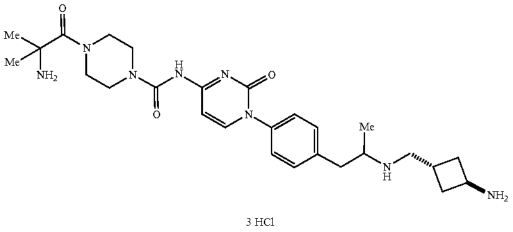

cis-4-(2-Amino-2-methylpropanoyl)-N-(1-(4-(2-(((3-aminocyclobutyl)methyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate. $^1$H NMR (400 MHz, $D_2O$) δ 7.80 (d, 1H), 7.36-7.30 (m, 4H), 6.72 (d, 1H), 3.68-3.48 (m, 10H), 3.15-3.11 (m, 3H), 2.89-2.72 (m, 1H), 2.50-2.39 (m, 3H), 1.87-1.84 (m, 2H), 1.59 (s, 6H), 1.14 (d, 3H). LCMS [(M+2H)/2] 263.1.

Compound 162

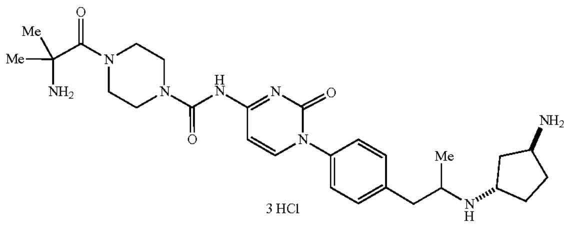

4-(2-Amino-2-methylpropanoyl)-N-(1-(4-(2-(((1S,3S)-3-aminocyclopentyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and tert-butyl ((1S,3S)-3-aminocyclopentyl)carbamate. $^1$H NMR ($D_2O$, 400 MHz) δ 7.76 (d, 1H), 7.34-7.27 (m, 4H), 6.79 (d, 1H), 3.93-3.88 (m, 1H), 3.79-3.71 (m, 2H), 3.68-3.51 (m, 8H), 3.16-3.10 (in, 1H), 2.80-2.71 (m, 1H), 2.25-2.23 (m, 2H), 2.11 (t, 2H), 1.67-1.52 (m, 8H), 1.14-1.12 (m, 3H). LCMS [M+H] 525.4

Compound 165

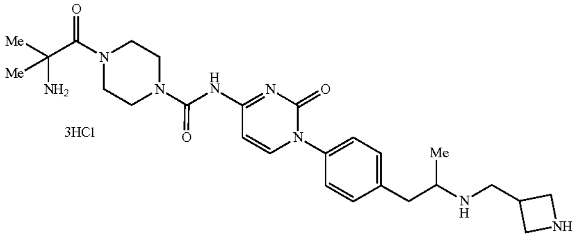

4-(2-Amino-2-methylpropanoyl)-N-(1-(4-(2-((azetidin-3-ylmethyl)amino)propyl)phenyl)-2-oxo-1,2-dihydropyrimidin-4-yl)piperazine-1-carboxamide hydrochloride Prepared in a similar fashion as Scheme C-21 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and tert-butyl 3-(aminomethyl)azetidine-1-carboxylate. $^1$H NMR (400 MHz, $D_2O$): δ 7.86 (d, 1H), 7.35-7.29 (m, 4H), 6.68 (d, 1H), 4.15-4.11 (m, 2H), 3.95-3.89 (m, 2H), 3.69-3.48 (m, 9H), 3.41-3.21 (m, 4H), 2.79-2.73 (m, 1H), 1.58 (s, 6H), 1.13 (d, 3H). LCMS [M+2H]/2 256.1.

Compound 169

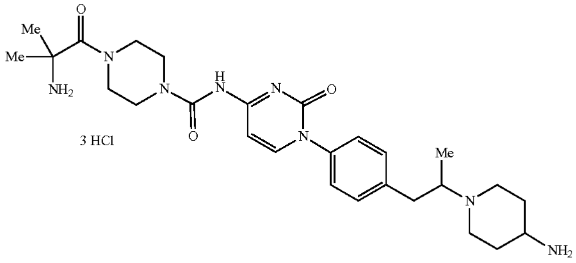

4-(2-Amino-2-methylpropanoyl)-N-(1-(4-(2-(4-aminopiperidin-1-yl)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and 4-Boc amino piperidine. $^1$H NMR (400 MHz, $D_2O$) δ 7.96 (d, 1H), 7.50 (d, 2H), 7.46 (d, 2H), 6.85 (d, 1H), 3.84-3.67 (m, 11H), 3.67-3.55 (m, 1H), 3.44-3.31 (m, 3H), 3.04-2.91 (m, 1H), 2.44 (d, 2H), 2.15-1.97 (m, 2H), 1.75 (s, 6H), 1.39-1.15 (m, 3H). LCMS [M+H] 525.3.

Compound 170

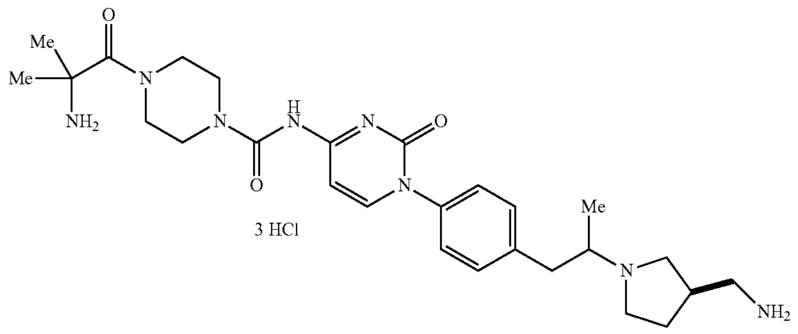

4-(2-Amino-2-methylpropanoyl)-N-(1-(4-(2-((R)-3-(aminomethyl)pyrrolidin-1-yl)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl (S)-(pyrrolidin-3-ylmethyl)carbamate. $^1$H NMR (400 MHz, $D_2O$) δ 7.95 (d, 1H), 7.44 (d, 2H), 7.40 (d, 2H), 6.78 (d, 1H), 3.97-3.55 (m, 9H), 3.51-3.39 (m, 1H), 3.38-3.25 (m, 2H), 3.27-2.96 (m, 3H), 2.93-2.64 (m, 3H), 2.49-2.26 (m, 1H), 1.99-1.71 (m, 1H), 1.68 (d, 6H), 1.24 (d, 3H). LCMS [M+H] 525.3.

Compound 200

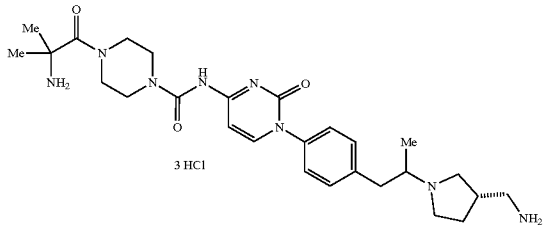

4-(2-Amino-2-methylpropanoyl)-N-(1-(4-(2-((S)-3-(aminomethyl)pyrrolidin-1-yl)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl (R)-(pyrrolidin-3-ylmethyl)carbamate. $^1$H NMR (500 MHz, $D_2O$) δ 7.96 (d, 1H), 7.57 (d, 2H), 7.48 (d, 2H), 6.84 (d, 1H), 3.82-3.69 (m, 9H), 3.58-3.43 (m, 1H), 3.43-3.30 (m, 2H), 3.30-3.00 (m, 3H), 2.99-2.68 (m, 3H), 2.71-2.59 (m, 1H), 2.50-2.29 (m, 1H), 2.05-1.76 (m, 1H), 1.73 (s, 6H), 1.30 (d, 3H). LCMS [M+H] 525.3.

Compound 171

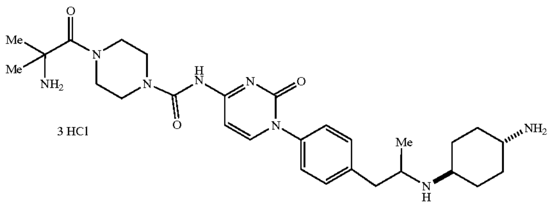

4-(2-Amino-2-methylpropanoyl)-N-(1-(4-(2-((trans-4-aminocyclohexyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and N-Boc-trans-1,4-cyclohexanediaminet. $^1$H NMR (400 MHz, $D_2O$) δ 7.89 (d, 1H), 7.48 (s, 2H), 7.45 (d, 2H), 6.86 (d, 1H), 3.78 (s, 4H), 3.74 (s, 5H), 3.39 (s, 1H), 3.26 (s, 2H), 2.91 (s, 1H), 2.31-2.16 (m, 4H), 1.75 (s, 6H), 1.65-1.50 (m, 4H), 1.29 (d, 3H). LCMS [M+H] 539.3.

Compound 172

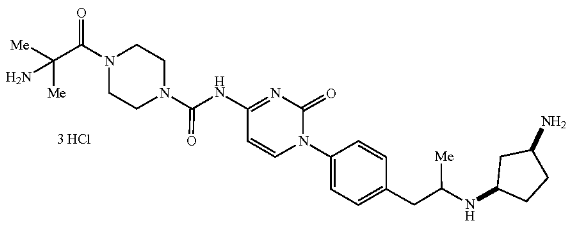

4-(2-Amino-2-methylpropanoyl)-N-(1-(4-(2-(((1R,3S)-3-aminocyclopentyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl ((1R,3S)-3-aminocyclopentyl)carbamate. $^{1}$H NMR (400 MHz, $D_2O$) δ 7.95 (d, 1H), 7.49 (s, 2H), 7.46 (d, 2H), 6.85 (d, 1H), 3.94 (s, 1H), 3.79 (s, 4H), 3.74 (s, 6H), 3.34-3.23 (m, 1H), 3.04-2.88 (m, 1H), 2.80-2.66 (m, 1H), 2.34-2.17 (m, 2H), 1.99-1.76 (m, 3H), 1.75 (s, 6H), 1.30 (d, 3H). LCMS [M+H] 525.4.

Compound 173

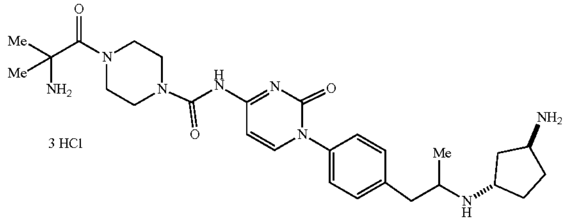

4-(2-Amino-2-methylpropanoyl)-N-(1-(4-(2-(((1S,3S)-3-aminocyclopentyl)amino)propyl)phenyl)-2-oxo-1,2-dihydropyrimidin-4-yl)piperazine-1-carboxamidehydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl ((1R,3S)-3-aminocyclopentyl)carbamate. $^{1}$H NMR (400 MHz, $D_2O$) δ 7.92 (d, 1H), 7.53-7.43 (m, 4H), 6.86 (d, 1H), 4.13-3.99 (m, 1H), 3.95-3.88 (m, 1H), 3.78 (s, 3H), 3.73 (s, 6H), 3.35-3.23 (m, 1H), 2.97-2.87 (m, 1H), 2.40 (s, 2H), 2.28 (t, 2H), 1.79 (s, 2H), 1.75 (s, 6H), 1.29 (d, 3H). LCMS [M+H] 525.3.

Compound 174

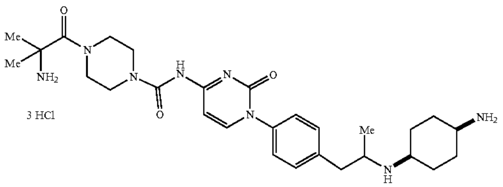

4-(2-Amino-2-methylpropanoyl)-N-(1-(4-(2-((cis-4-aminocyclohexyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and N-Boc-cis-1,4-cyclohexanediamine. $^{1}$H NMR (400 MHz, $D_2O$) δ 7.98 (d 1H), 7.51 (d, 2H), 7.46 (d, 2H), 6.85 (d, 1H), 3.80 (s, 4H), 3.75 (s, 5H), 3.63-3.50 (m, 2H), 3.35-3.29 (m, 1H), 2.91 (t, 1H), 2.08 (s, 2H), 1.97 (s, 4H), 1.86-1.75 (m, 2H), 1.75 (s, 6H), 1.29 (d, 3H). LCMS [M+H] 539.3.

Compound 346

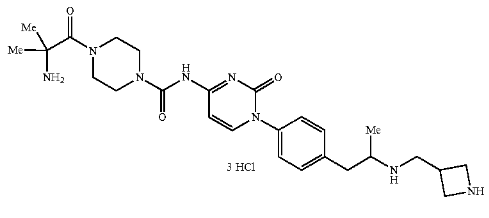

4-(2-Amino-2-methylpropanoyl)-N-(1-(4-(2-((azetidin-3-ylmethyl)amino)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl 3-(aminomethyl) azetidine-1-carboxylate. $^{1}$H NMR (400 MHz, $D_2O$) δ 8.11 (d, 1H), 7.48 (s, 4H), 6.81 (d, 1H), 4.28 (s, 2H), 4.07 (s, 2H), 3.79 (s, 3H), 3.75 (s, 5H), 3.66 (s, 1H), 3.58-3.43 (m, 2H), 3.43-3.33 (m, 1H), 3.28 (d, 1H), 2.91 (t, 1H), 1.74 (d, 6H), 1.28 (d, 3H). LCMS [M+H] 511.2.

Compound 347

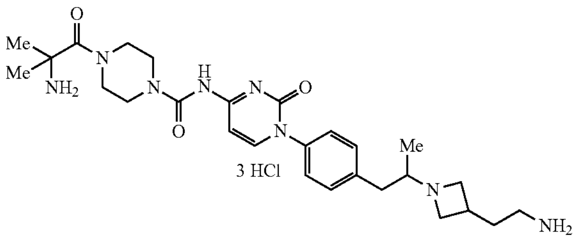

4-(2-Amino-2-methylpropanoyl)-N-(1-(4-(2-(3-(2-aminoethyl)azetidin-1-yl)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl (2-(azetidin-3-yl) ethyl)carbamate. $^{1}$H NMR (400 MHz, D2O) δ 7.96 (d, 1H), 7.53-7.39 (m, 4H), 6.85 (d, 1H), 4.36-4.18 (m, 2H), 4.07-3.84 (m, 2H), 3.79 (br. s, 3H), 3.73 (br. s, 5H), 3.05-2.89 (m, 2H), 2.84 (s, 2H), 2.16-1.93 (m, 2H), 1.74 (d, 6H), 1.28 (t 2H) 1.21 (d, 3H). LCMS [M+H] 525.3.

Compound 378

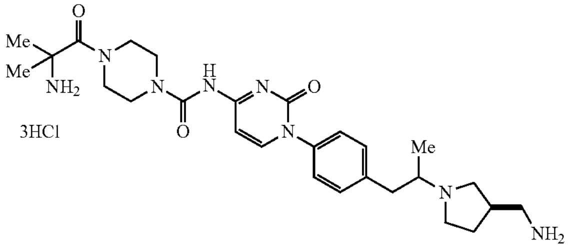

4-(2-Amino-2-methylpropanoyl)-N-(1-(4-(2-((R)-3-(aminomethyl)pyrrolidin-1-yl)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl (S)-(pyrrolidin-3-ylmethyl)carbamate. LCMS [M+H] 525.4.

Compound 382

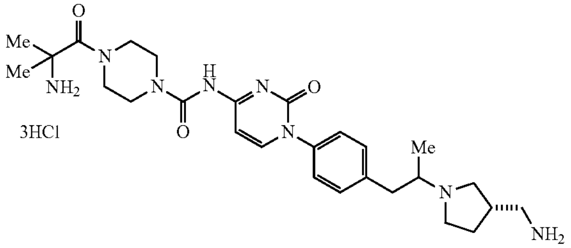

4-(2-Amino-2-methylpropanoyl)-N-(1-(4-(2-((R)-3-(aminomethyl)pyrrolidin-1-yl)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl (R)-(pyrrolidin-3-ylmethyl)carbamate. LCMS [M+H] 525.3.

Compound 379

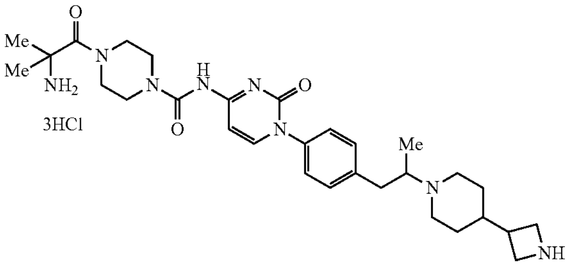

4-(2-Amino-2-methylpropanoyl)-N-(1-(4-(2-(4-(azetidin-3-yl)piperidin-1-yl)propyl)phenyl)-2-oxo-1,2-dihydropyrimidin-4-yl)piperazine-1-carboxamide hydrochloride salt Prepared in a similar fashion as Scheme C-21 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl 3-(piperidin-4-yl) azetidine-1-carboxylate. LCMS [M+H] 565.4.

Compound 149

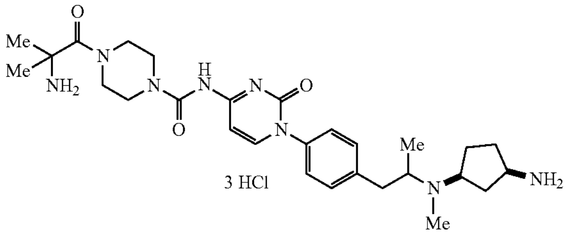

4-(2-Amino-2-methylpropanoyl)-N-(1-(4-(2-(((1S,3R)-3-aminocyclopentyl)(methyl)amino)propyl) phenyl)-2-oxo-1,2-dihydropyrimidin-4-yl)piperazine-1-carboxamide hydrochloride salt Scheme C-22

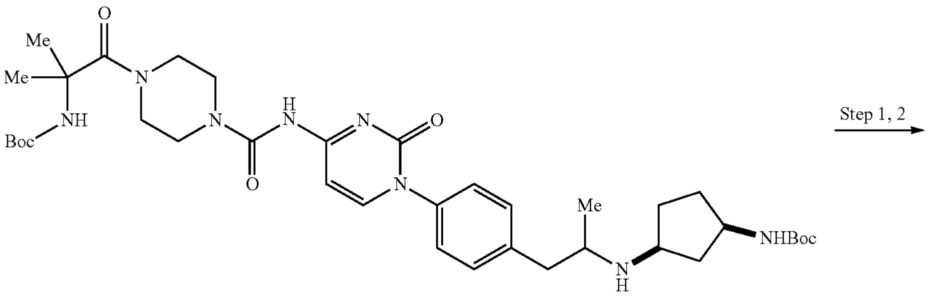

-continued

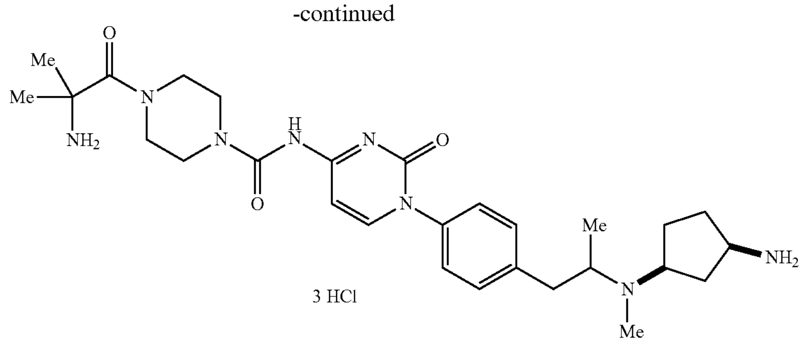

Reagents: 1) formaldehyde (37%), $NaCNBH_3$, 4Å ms, MeOH, rt, 16 h 2) HCl in dioxane, dioxane, rt, 3 h.

Step 1: tert-butyl (1-(4-((1-(4-(2-(((1S,3R)-3-((tert-butoxycarbonyl)amino)cyclopentyl)(methyl)amino)propyl)phenyl)-2-oxo-1,2-dihydropyrimidin-4-yl)carbamoyl)piperazin-1-yl)-2-methyl-1-oxopropan-2-yl)carbamate To a stirred solution of tert-butyl (1-(4-((1-(4-(2-(((1S,3R)-3-((tert-butoxycarbonyl)amino)cyclopentyl)amino)propyl)phenyl)-2-oxo-1,2-dihydropyrimidin-4-yl)carbamoyl)piperazin-1-yl)-2-methyl-1-oxopropan-2-yl)carbamate (0.110 g, 0.15 mmol) and formaldehyde (37% in water, 0.12 ml, 1.51 mmol) in MeOH (3.0 ml) at 0° C. were added activated 4 Å molecular sieves (0.80 g) and $NaCNBH_3$ (0.019 g, 0.30 mmol), and the mixture was stirred at rt for 16 h. The resulting reaction mixture was concentrated under reduced pressure and the residue was purified by flash chromatography ($MeOH:CH_2Cl_2$) to afford the title compound. LCMS [(M+2H-Boc)/2] 320.0.

Step 2: 4-(2-amino-2-methylpropanoyl)-N-(1-(4-(2-(((1S,3R)-3-aminocyclopentyl)(methyl)amino)propyl)phenyl)-2-oxo-1,2-dihydropyrimidin-4-yl)piperazine-1-carboxamide hydrochloride salt To a stirred solution of tert-butyl (1-(4-((1-(4-(2-(((1S,3R)-3-((tert-butoxycarbonyl)amino)cyclopentyl)(methyl)amino)propyl)phenyl)-2-oxo-1,2-dihydropyrimidin-4-yl)carbamoyl)piperazin-1-yl)-2-methyl-1-oxopropan-2-yl)carbamate (0.09 g, 0.12 mmol) in 1,4-dioxane (3 mL) was added 4 MHCl in dioxane (5 mL). The mixture was stirred at rt for 3 h, concentrated under reduced pressure and triturated by diethyl ether (10 mL). The resulting crude material was purified by PrepHPLC to afford the title compound. $^1H$ NMR (400 MHz, $D_2O$, 80° C.) mixture of rotamers, δ 7.40-8.39 (m, 1H), 8.05-8.01 (m, 4H), 7.33-7.30 (m, 1H), 4.50-4.27 (m, 12H), 4.05-4.01 (m, 1H), 3.83-3.81 (m, 1H), 3.53-3.46 (m, 4H), 3.30-3.23 (m, 2H), 2.87-2.79 (m, 3H), 2.61-2.49 (m, 4H), 2.31-2.29 (m, 6H), 1.87-1.84 (m, 3H). LCMS [M+H] 539.4.

Compound 151

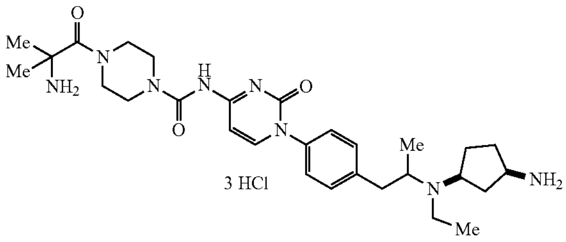

4-(2-Amino-2-methylpropanoyl)-N-(1-(4-(2-(((1S,3R)-3-aminocyclopentyl)(ethyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((1S,3R)-3-((tert-butoxycarbonyl)amino)cyclopentyl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. $^1H$ NMR (400 MHz, $D_2O$) mixture of rotamers, δ 7.77 (d, 1H), 7.33-7.27 (m, 4H), 6.69 (d, 1H), 3.97-3.50 (m, 12H), 3.46-3.39 (m, 2H), 3.22-3.11 (m, 3H), 2.95-2.75 (m, 2H), 2.68-2.50 (m, 2H), 2.20-1.70 (m, 6H), 1.57 (s, 6H), 1.31-1.26 (m, 3H), 1.17-1.11 (m, 3H). LCMS [M+H] 553.1.

Compound 153

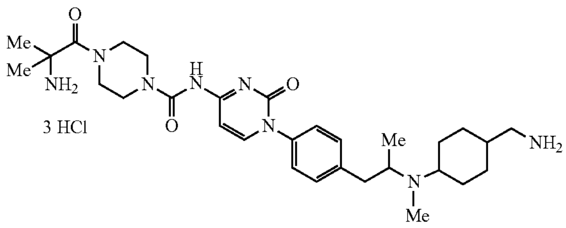

4-(2-Amino-2-methylpropanoyl)-N-(1-(4-(2-((4-(aminomethyl)cyclohexyl)(methyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-((4-(((tert-butoxycarbonyl)amino)methyl)cyclohexyl)amino)propyl)phenyl)-2-oxo-1,2-dihydropyrimidin-4-yl)carbamoyl)piperazin-1-yl)-2-methyl-1-oxopropan-2-yl)carbamate and formalin. $^1H$ NMR (400 MHz, $D_2O$+1 drop TFA) mixture of rotamers, δ 8.03 (d, 1H), 7.40-7.30 (m, 3H), 7.08-7.23 (m, 1H), 6.64 (d, 1H), 3.81-3.50 (m, 9H), 3.34-3.08 (m, 3H), 2.92-2.56 (m, 6H), 2.20-1.81 (m, 5H), 1.58-1.41 (m, 9H) 1.26-1.00 (m, 5H). LCMS [M+H] 567.3.

Compound 154

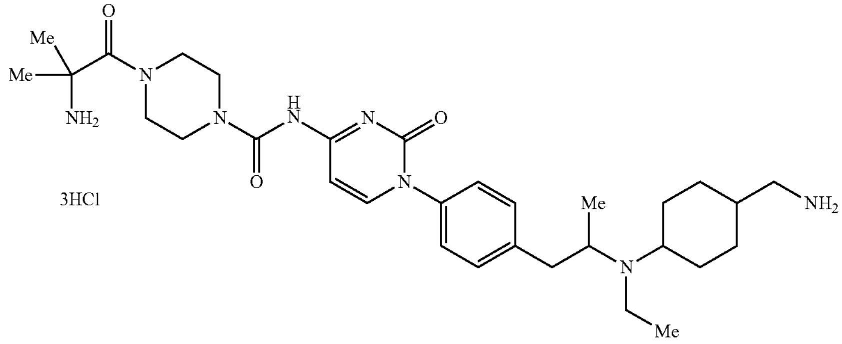

4-(2-Amino-2-methylpropanoyl)-N-(1-(4-(2-((4-(aminomethyl)cyclohexyl)(ethyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-((4-(((tert-butoxycarbonyl)amino)methyl)cyclohexyl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$) mixture of rotamers, δ 7.74 (d, 1H), 7.34-7.27 (m, 4H), 6.70 (d, 2H), 3.85-3.75 (m, 2H), 3.65-3.51 (m, 7H), 3.40-3.10 (m, 5H), 2.95-2.72 (m, 4H), 2.15-1.61 (m, 6H), 1.60-1.41 (m, 8H), 1.27-1.24 (m, 3H), 1.18-1.04 (m, 5H). LCMS [M+H] 581.2.

Compound 157

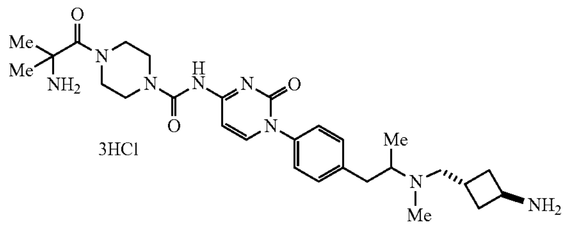

4-(2-Amino-2-methylpropanoyl)-N-(1-(4-(2-(((trans-3-aminocyclobutyl)methyl)(methyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((trans-3-((tert-butoxycarbonyl)amino)cyclobutyl)methyl)amino)propyl)phenyl)-2-oxo-1,2-dihydropyrimidin-4-yl)carbamoyl)piperazin-1-yl)-2-methyl-1-oxopropan-2-yl)carbamate and formalin. $^1$H NMR ($D_2O$, 400 MHz) mixture of rotamers, δ 7.77 (d, 1H), 7.35-7.28 (m, 4H), 6.70 (d, 1H), 3.85-3.75 (m, 1H), 3.65-3.55 (m, 8H), 3.45-3.34 (m, 2H), 3.23-3.10 (m, 2H), 2.84 (t, 2H), 2.71 (d, 3H), 2.32-2.20 (m, 4H), 1.58 (s, 6H), 1.12 (t, 3H). LCMS [(M+2H)/2]270.2.

Compound 158

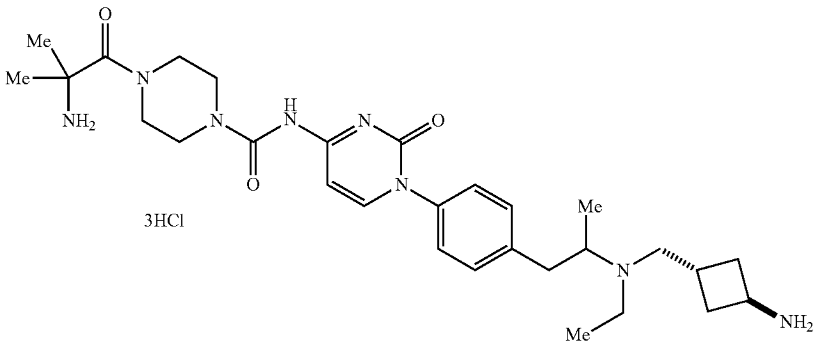

4-(2-Amino-2-methylpropanoyl)-N-(1-(4-(2-(((trans-3-aminocyclobutyl)methyl)(ethyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((trans-3-((tert-butoxycarbonyl)amino)cyclobutyl)methyl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR ($D_2O$, 400 MHz) mixture of rotamers, δ 7.82 (d, 1H), 7.35-7.28 (m, 4H), 6.72 (br s, 1H), 3.78-87 (m, 1H), 3.76-3.52 (m, 9H), 3.48-3.10 (m, 7H), 2.88-2.79 (m, 2H), 2.32-2.20 (m, 4H), 1.55 (s, 6H), 1.25-1.17 (m, 3H), 1.14-1.09 (m, 3H). LCMS [(M+2H)/2] 277.2.

Compound 160

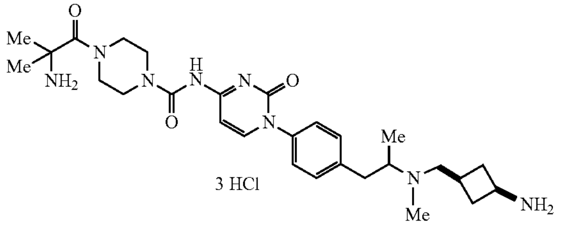

4-(2-Amino-2-methylpropanoyl)-N-(1-(4-(2-(((cis-3-aminocyclobutyl)methyl)(methyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((cis-3-((tert-butoxycarbonyl)amino)cyclobutyl)methyl)amino)propyl)phenyl)-2-oxo-1,2-dihydropyrimidin-4-yl)carbamoyl)piperazin-1-yl)-2-methyl-1-oxopropan-2-yl)carbamate and formalin. $^1$H NMR (400 MHz, $D_2O$, 80° C.) mixture of rotamers, δ 8.42 (d, 1H), 8.07-8.02 (m, 4H), 7.34 (d, 1H), 4.66-4.28 (m, 12H), 3.85-3.95 (m, 3H), 3.57-3.51 (m, 1H), 3.44 (s, 3H), 3.28-3.14 (m, 3H), 2.63-2.61 (m, 2H), 2.32 (s, 6H) 1.87 (d, 3H). LCMS [M+H] 539.2.

4-(2-Amino-2-methylpropanoyl)-N-(1-(4-(2-(((cis-3-aminocyclobutyl)methyl)(ethyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((cis-3-((tert-butoxycarbonyl)amino)cyclobutyl)methyl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$, 80° C.) mixture of rotamers, δ 8.38 (d, 1H), 8.12-7.95 (m, 4H), 7.31 (d, 1H), 4.40-4.27 (m, 11H), 3.95-3.75 (m, 4H), 3.58-3.48 (m, 1H), 3.23-3.16 (m, 3H), 2.65-2.55 (m, 2H), 2.30 (s, 6H), 1.92-1.99 (m, 3H), 1.84 (d, 3H). LCMS [M+H] 553.3.

Compound 163

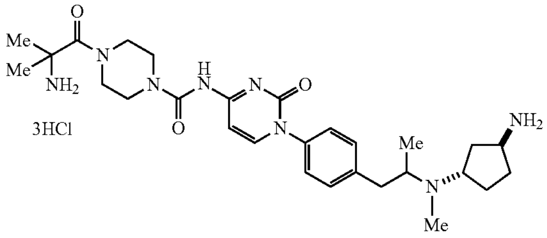

4-(2-Amino-2-methylpropanoyl)-N-(1-(4-(2-(((1S,3S)-3-aminocyclopentyl)(methyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((1S,3S)-3-((tert-butoxycarbonyl)amino)cyclopentyl)amino)propyl)phenyl)-2-oxo-1,2-dihy Compound 161

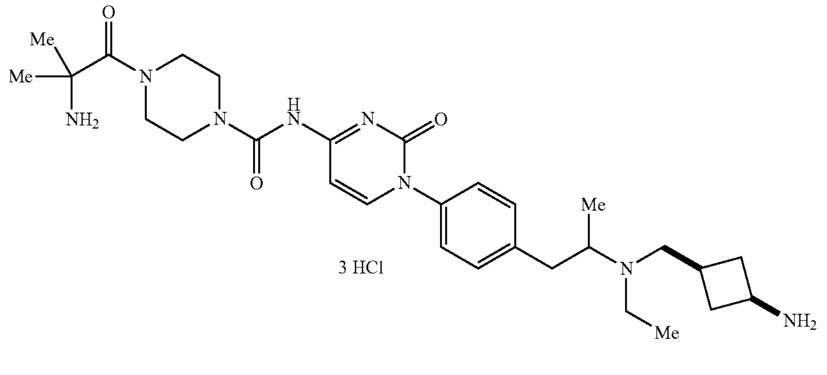

dropyrimidin-4-yl)carbamoyl)piperazin-1-yl)-2-methyl-1-oxopropan-2-yl)carbamate and formalin. LCMS [M+H] 539.6.

Compound 164

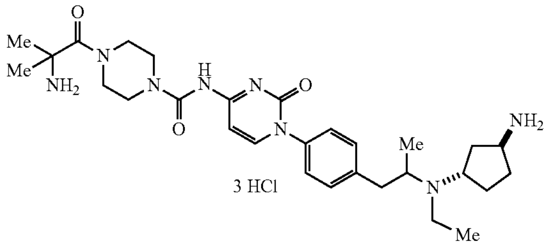

4-(2-Amino-2-methylpropanoyl)-N-(1-(4-(2-(((1S,3S)-3-aminocyclopentyl)(ethyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((1S,3S)-3-((tert-butoxycarbonyl)amino)cyclopentyl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. LCMS [(M+2H)/2] 277.2.

Compound 166

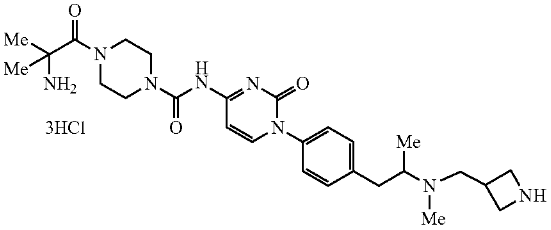

4-(2-Amino-2-methylpropanoyl)-N-(1-(4-(2-((azetidin-3-ylmethyl)(methyl)amino)propyl)phenyl)-2-oxo-1,2-dihydropyrimidin-4-yl)piperazine-1-carboxamide hydrochloride salt Prepared in a similar fashion as Scheme C-22 from tert-butyl 3-(((1-(4-(4-(4-(2-((tert-butoxycarbonyl)amino)-2-methylpropanoyl)piperazine-1-carboxamido)-2-oxopyrimidin-1(2H)-yl)phenyl)propan-2-yl)amino)methyl)azetidine-1-carboxylate and formalin. $^1$H NMR (400 MHz, $D_2O$) mixture of rotamers, δ 7.75 (d, 1H), 7.36-7.29 (m, 4H), 6.71 (d, 1H), 4.21-4.10 (m, 2H), 4.13-3.96 (m, 2H), 3.90-3.53 (m, 8H), 3.41-3.39 (m, 3H), 3.15-3.11 (m, 2H), 2.87-2.81 (m, 1H), 2.72 (s, 3H), 1.59 (s, 6H), 1.14 (d, 3H). LCMS [(M+2H)/2] 263.1.

Compound 167

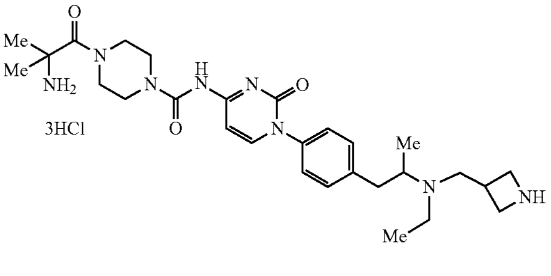

4-(2-Amino-2-methylpropanoyl)-N-(1-(4-(2-((azetidin-3-ylmethyl)(ethyl)amino)propyl)phenyl)-2-oxo-1,2-dihydropyrimidin-4-yl)piperazine-1-carboxamide hydrochloride salt Prepared in a similar fashion as Scheme C-22 from tert-butyl 3-(((1-(4-(4-(4-(2-((tert-butoxycarbonyl)amino)-2-methylpropanoyl)piperazine-1-carboxamido)-2-oxopyrimidin-1(2H)-yl)phenyl)propan-2-yl)amino)methyl)azetidine-1-carboxylate and acetaldehyde. $^1$H NMR (400 MHz, $D_2O$) mixture of rotamers, δ 7.75 (d, 1H), 7.36-7.29 (m, 4H), 6.71 (d, 1H), 4.17 (t, 2H), 3.40-3.90 (m, 2H), 3.80-3.55 (m, 9H), 3.49-3.33 (m, 4H), 3.20-3.11 (m, 4H), 2.95-2.70 (m, 2H), 1.59 (s, 6H), 1.30-1.18 (m, 3H), 1.15-1.11 (m, 3H). LCMS [(M+2H)/2] 269.9.

Compound 175

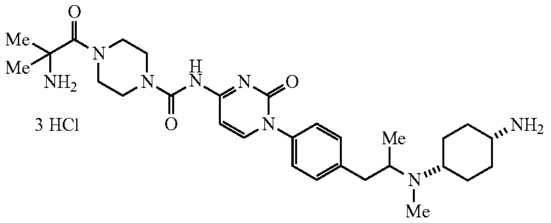

4-(2-Amino-2-methylpropanoyl)-N-(1-(4-(2-((cis-4-aminocyclohexyl)(methyl)amino)propyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-((cis-4-((tert-butoxycarbonyl)amino)cyclohexyl)amino)propyl)phenyl)-2-oxo-1,2-dihydropyrimidin-4-yl)carbamoyl)piperazin-1-yl)-2-methyl-1-oxopropan-2-yl)carbamate and formalin. $^1$H NMR (400 MHz, $D_2O$) δ 7.97 (d, 1H), 7.55-7.42 (m, 4H), 6.84 (d, 1H), 4.05-3.95 (m, 1H), 3.78 (s, 3H), 3.74 (s, 5H), 3.65 (s, 2H), 3.54 (s, 1H), 3.41-3.26 (m, 1H), 3.11-3.02 (m, 1H), 2.92 (d, 3H), 2.23-1.78 (m, 7H), 1.74 (s, 6H), 1.37-1.24 (m, 3H). LCMS [M+H] 553.2.

Compound 176

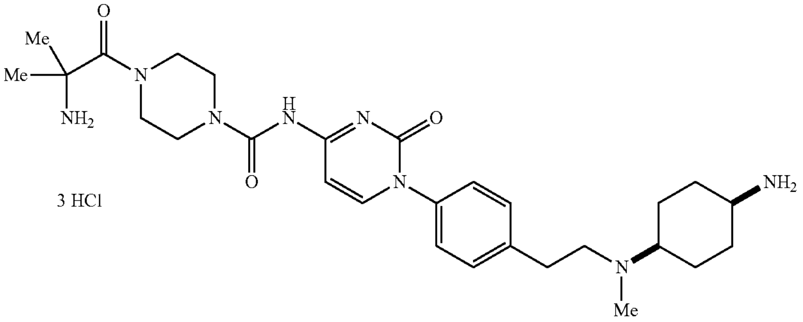

4-(2-Amino-2-methylpropanoyl)-N-(1-(4-(2-((cis-4-aminocyclohexyl) (methyl)amino)ethyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-((cis-4-((tert-butoxycarbonyl)amino)cyclohexyl)amino)ethyl)phenyl)-2-oxo-1,2-dihydropyrimidin-4-yl)carbamoyl)piperazin-1-yl)-2-methyl-1-oxopropan-2-yl)carbamate and formalin. $^1$H NMR (500 MHz, $D_2O$) δ 7.94 (d, 1H), 7.52 (d, 2H), 7.45 (d, 2H), 6.85 (d, 1H), 3.83-3.70 (m, 8H), 3.68-3.57 (m, 2H), 3.55-3.42 (m, 2H), 3.30-3.21 (m, 1H), 3.20-3.12 (m, 1H), 2.94 (s, 3H), 2.12-1.80 (m, 8H), 1.74 (s, 6H). LCMS [M+H] 539.4.

Compound 178

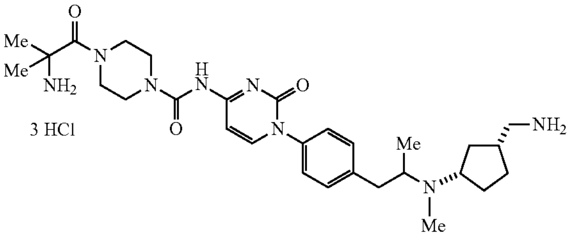

4-(2-Amino-2-methylpropanoyl)-N-(1-(4-(2-(((1S,3R)-3-(aminomethyl)cyclopentyl) (methyl)amino)ethyl)phenyl)-2-oxo-1,2-dihydropyrimidin-4-yl)piperazine-1-carboxamide hydrochloride salt Prepared in a similar fashion as Scheme C-22 from tert-butyl (1-(4-((1-(4-(2-(((1S,3R)-3-(((tert-butoxycarbonyl)amino)methyl)cyclopentyl)amino)ethyl)phenyl)-2-oxo-1,2-dihydropyrimidin-4-yl)carbamoyl)piperazin-1-yl)-2-methyl-1-oxopropan-2-yl)carbamate and formalin. $^1$H NMR (500 MHz, $D_2O$) δ 8.13 (d, 1H), 7.52 (d, 2H), 7.45 (d, 2H), 6.79 (d, 1H), 3.87-3.68 (m, 8H), 3.61-3.50 (m, 1H), 3.42-3.35 (m, 1H), 3.32 (s, 3H), 3.30-3.21 (m, 1H), 3.15-2.99 (m, 2H), 2.94 (d, 2H), 2.45-2.15 (m, 3H), 2.03-1.82 (m, 2H), 1.72 (s, 6H), 1.56-1.44 (m, 1H), 0.91 (t, 1H). LCMS [M+H] 539.7.

Compound 182

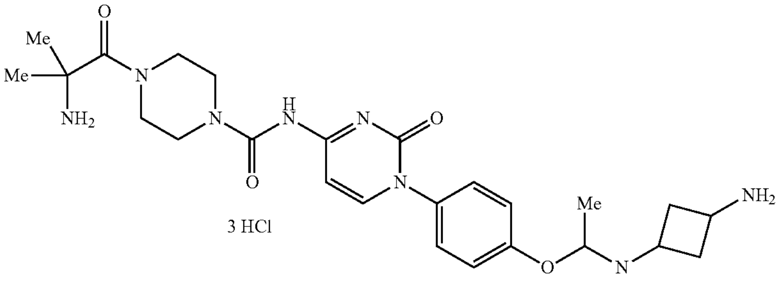

4-(2-Amino-2-methylpropanoyl)-N-(1-(4-((1-(3-aminoazetidin-1-yl)propan-2-yl)oxy)phenyl)-2-oxo-1,2-dihydropyrimidin-4-yl)piperazine-1-carboxamide hydrochloride salt Scheme C-23

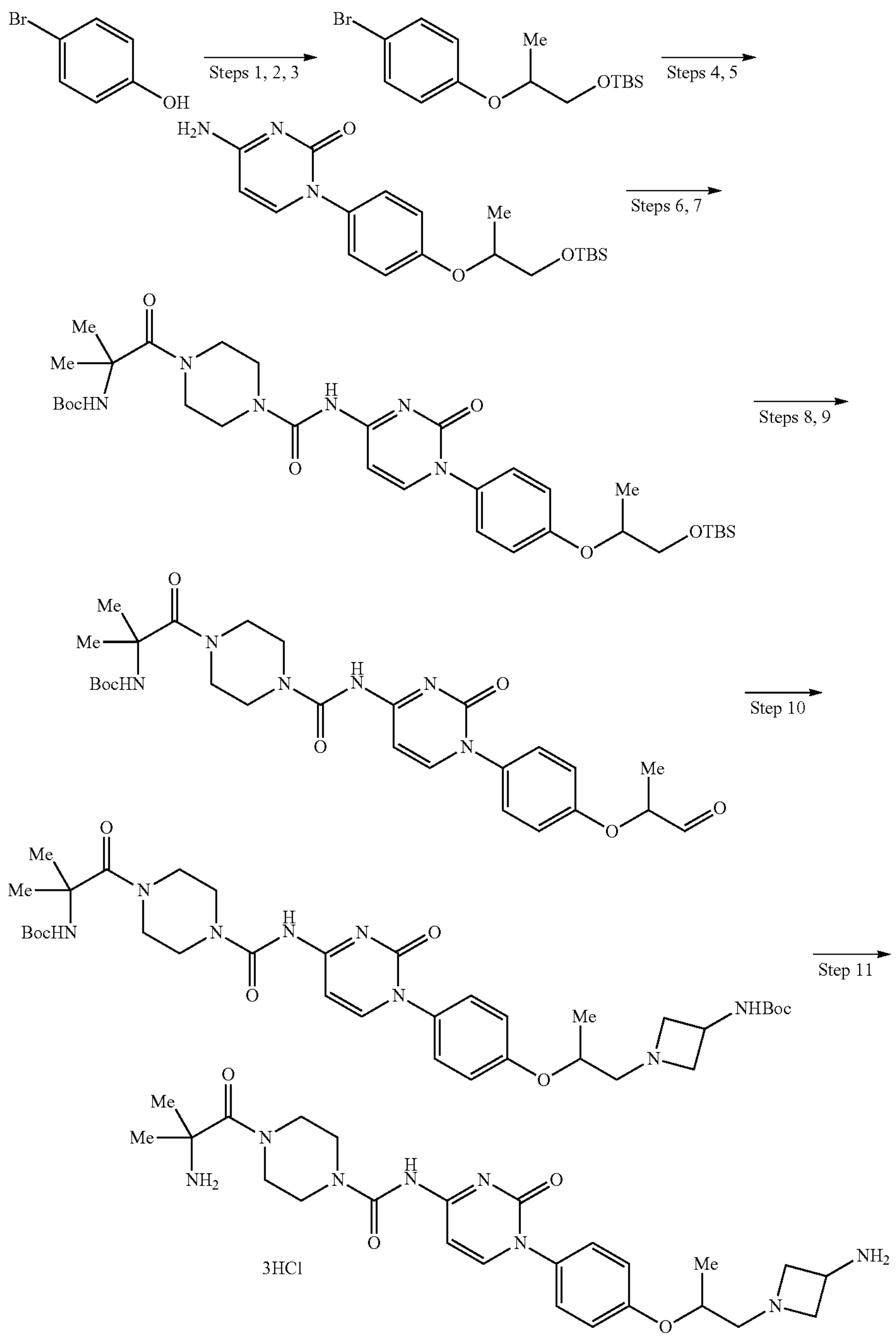

Reagents: 1) methyl 2-hydroxypropanoate, DIAD, $PPh_3$, 0° C. to rt, 16 h 2) $NaBH_4$, EtOH, 0° C. to rt, 16 h 3) TBSCl, imidazole, $CH_2Cl_2$, rt, 16 h 4) BuLi, THF, -78° C., $(iPrO)_3B$ 5) cytosine, TMEDA, $Cu(OAc)_2$•$H_2O$, 4:1 MeOH:$H_2O$, rt, 48 h 6) CDI, $CH_2Cl_2$, rt, 4 h 7) tert-butyl (2-methyl-1-oxo-1-(piperazin-1-yl)propan-2-yl)carbamate, $CH_3CN$, 85° C., 3 h 8) TBAF, THF, 0° C. to rt, 16 h 9) DMP, 0.1% $CH_2Cl_2$:$H_2O$, rt, 15 min. 10) tert-butyl azetidin-3-ylcarbamate, $NaBH_3CN$, MeOH, rt, 16 h 11) HCl in MeOH, rt, 4 h.

Step 1: methyl 2-(4-bromophenoxy)propanoate

To a stirred solution of 4-bromophenol (2.50 g, 14.4 mmol), methyl 2-hydroxypropanoate (1.50 g, 14.4 mmol), and triphenylphosphine (3.77 g 14.4 mmol) at 0° C. was added DIAD (2.9 mL, 1.4 mmol) dropwise over 15 min. The reaction was stirred at rt for 16 h. The volatiles were removed under reduced pressure and the reaction mixture was purified by flash chromatography to afford the title compound.

Step 2: 2-(4-bromophenoxy)propan-1-ol

To a stirred solution of methyl 2-(4-bromophenoxy)propanoate (1.2 g, 4.6 mmol) in EtOH (40 mL) at 0° C. was added $NaBH_4$ (521 mg, 13.8 mmol). The solution was warmed to rt and stirred for 36 h. The reaction mixture was concentrated under reduced pressure, dissolved in $CHCl_3$ (100 mL) and washed with 10% NaOH solution (100 mL). The organic layer was dried over $Na_2SO_4$, filtered, and concentrated under reduced pressure to afford the title compound.

Step 3: (2-(4-bromophenoxy)propoxy)(tert-butyl) dimethylsilane

To a solution of 2-(4-bromophenoxy)propan-1-ol (1.07 g, 4.6 mmol) in $CH_2Cl_2$(50 mL) was added imidazole (468 mg, 6.9 mmol) and t-butyldimethylsilyl chloride (1.03 g, 6.9 mmol). The solution was stirred at rt for 16 h. The reaction mixture was concentrated under reduced pressure, EtOAc (100 mL) was added and washed with $H_2O$ (100 mL). The organic layer was dried over $Na_2SO_4$, concentrated under reduced pressure, and purified by flash chromatography (Hexanes:EtOAc) to afford the title compound.

Step 4: tert-butyldimethyl(2-(4-(4,4,5,5-tetramethyl-1,3,2-dioxaborolan-2-yl)phenoxy)propoxy)silane A solution of (2-(4-bromophenoxy)propoxy)(tert-butyl) dimethylsilane (350 mg, 3.21 mmol) in THF (50 mL) was cooled to −78° C. and 2.5M BuLi in hexanes (3.80 mL) was added dropwise over 30 min. The temperature was maintained below −60° C. The reaction was stirred for 25 min. and triisopropyl borate (1.12 mL, 4.82 mmol) was added dropwise over 30 min. The reaction mixture was warmed to rt and stirred for 15 min. 2N HCl (50 mL) was added and the reaction was stirred for 30 min. The biphasic mixture was separated and the aq. layer extracted with $CH_2Cl_2$(2×50 mL). The combined organics were dried over $Na_2SO_4$ and concentrated under reduced pressure to afford the title compound.

Step 5: 4-amino-1-(4-((1-((t-butyldimethylsilyl)oxy) propan-2-yl)oxy)phenyl)pyrimidin-2(1H)-one A suspension of cytosine (355 mg, 3.2 mmol) and tert-butyldimethyl(2-(4-(4,4,5,5-tetramethyl-1,3,2-dioxaborolan-2-yl)phenoxy)propoxy)silane (992 mg, 3.2 mmol), in 4:1, MeOH:$H_2O$ (100 mL) was stirred at rt in open air for 30 min. TMEDA (0.87 mL, 3.8 mmol) and $Cu(OAc)_2 \cdot H_2O$ (640 mg, 3.2 mmol) were added and the reaction was stirred in open air at rt for 48 h. The reaction mixture was concentrated under reduced pressure and cold $H_2O$ (100 mL) was added. The solid was filtered and washed with $H_2O$ (2×20 mL) and $Et_2O$ (3×20 mL) to afford the title compound.

Step 6: N-(1-(4-((1-((t-butyldimethylsilyl)oxy)propan-2-yl)oxy)phenyl)-2-oxo-1,2-dihydropyrimidin-4-yl)-1H-imidazole-1-carboxamide A suspension of 4-amino-1-(4-((1-((t-butyldimethylsilyl) oxy)propan-2-yl)oxy)phenyl)pyrimidin-2(1H)-one (100 mg, 0.27 mmol) and 1,1'-carbonyldiimidazole (68 mg, 0.37 mmol) in $CH_2Cl_2$ (12 mL) was stirred at rt for 16 h. The solvent was removed under reduced pressure, and the solid was triturated with EtOAc. The solid was collected to afford the title compound.

Step 7: t-butyl (1-(4-((1-(4-((1-((t-butyldimethylsilyl)oxy)propan-2-yl)oxy)phenyl)-2-oxo-1,2-dihydropyrimidin-4-yl)carbamoyl)piperazin-1-yl)-2-methyl-1-oxopropan-2-yl)carbamate N-(1-(4-((1-((t-butyldimethylsilyl)oxy)propan-2-yl)oxy) phenyl)-2-oxo-1,2-dihydropyrimidin-4-yl)-1H-imidazole-1-carboxamide (122 mg, 0.260 mmol) and t-butyl (2-methyl-1-oxo-1-(piperazin-1-yl)propan-2-yl)carbamate (72 mg, 0.26 mmol) were dissolved in $CH_3CN$ (10 mL) and heated to reflux for 2 h. The reaction mixture was concentrated under reduced pressure and the residue was dissolved in EtOAc (25 mL) and washed with water (3×20 mL). The reaction mixture was purified by flash chromatography (Hexanes:EtOAc) to afford the title compound.

Step 8: t-butyl (1-(4-((1-(4-((1-hydroxypropan-2-yl) oxy)phenyl)-2-oxo-1,2-dihydropyrimidin-4-yl)carbamoyl)piperazin-1-yl)-2-methyl-1-oxopropan-2-yl) carbamate To a solution of t-butyl (1-(4-((1-(4-((1-((t-butyldimethylsilyl)oxy)propan-2-yl)oxy)phenyl)-2-oxo-1,2-dihydropyrimidin-4-yl)carbamoyl)piperazin-1-yl)-2-methyl-1-oxopropan-2-yl)carbamate (150 mg, 0.22 mmol) in THF (50 mL) at 0° C. was added 1M TBAF in THF (0.45 mL) dropwise over 5 min. The solution was warmed to rt and stirred for 16 h. The crude reaction mixture was concentrated under reduced pressure to give an oily residue, which was purified by flash chromatography to afford the title compound.

Step 9: t-butyl (2-methyl-1-oxo-1-(4-((2-oxo-1-(4-((1-oxopropan-2-yl)oxy)phenyl)-1,2-dihydropyrimidin-4-yl)carbamoyl)piperazin-1-yl)propan-2-yl)carbamate To a stirred solution of t-butyl (1-(4-((1-(4-((1-hydroxypropan-2-yl)oxy)phenyl)-2-oxo-1,2-dihydropyrimidin-4-yl) carbamoyl)piperazin-1-yl)-2-methyl-1-oxopropan-2-yl)carbamate (40 mg, 0.07 mmol) in 0.1% $H_2O$:$CH_2Cl_2$ (10 mL) was added Dess-Martin periodinane (44 mg, 0.01 mmol). The solution was stirred for 1 h. $CH_2Cl_2$ (15 mL) was added the reaction mixture washed with aq. $NaHCO_3$/$Na_2S_2O_3$ (15 mL). The aq. layer was extracted with $CH_2Cl_2$ (15 mL). The combined organic layers were dried over $Na_2SO_4$ and concentrated under reduced pressure to the title compound.

Step 10: tert-butyl (1-(4-((1-(4-((1-(3-((tert-butoxycarbonyl)amino)azetidin-1-yl)propan-2-yl)oxy)phenyl)-2-oxo-1,2-dihydropyrimidin-4-yl)carbamoyl) piperazin-1-yl)-2-methyl-1-oxopropan-2-yl) carbamate To a stirred solution of tert-butyl (2-methyl-1-oxo-1-(4-((2-oxo-1-(4-((1-oxopropan-2-yl)oxy)phenyl)-1,2-dihydropyrimidin-4-yl)carbamoyl)piperazin-1-yl)propan-2-yl)carbamate (28 mg, 0.05 mmol) in MeOH, was added tert-butyl azetidin-3-ylcarbamate (13 mg, 0.075 mmol) and $NaBH_3CN$ (5.0 mg, 0.08 mmol). The reaction mixture was stirred for 16 h at rt. The reaction mixture was concentrated under reduced pressure, $CHCl_3$ (15 mL) added and washed with 10%

NaOH solution (15 mL). The organic layer was dried over $Na_2SO_4$ and concentrated under reduced pressure to afford the title compound.

Step 11: 4-(2-amino-2-methylpropanoyl)-N-(1-(4-((1-(3-aminoazetidin-1-yl)propan-2-yl)oxy)phenyl)-2-oxo-1,2-dihydropyrimidin-4-yl)piperazine-1-carboxamide hydrochloride salt A mixture of tert-butyl (1-(4-((1-(4-((1-(3-((tert-butoxycarbonyl)amino)azetidin-1-yl)propan-2-yl)oxy)phenyl)-2-oxo-1,2-dihydropyrimidin-4-yl)carbamoyl)piperazin-1-yl)-2-methyl-1-oxopropan-2-yl)carbamate (0.05 mmol) and a solution of HCl/MeOH (5 mL) was stirred at rt for 4 h. The solvent was evaporated and the crude solid was purified by RPHPLC ($H_2O$:$CH_3CN$:TFA) and concentrated under reduced pressure. Addition of HCl/MeOH and evaporation under reduced pressure afforded the title compound. $^1$H NMR (400 MHz, $D_2O$) δ 8.06 (d, 1H), 7.44 (d, 2H), 7.18 (d, 2H), 6.81 (d, 1H), 4.94-4.85 (m, 2H), 4.70 (s, 2H), 4.65-4.47 (m, 2H), 3.79 (s, 4H), 3.74 (s, 6H), 1.74 (s, 6H), 1.38 (d, 3H). LCMS [M+H] 513.3.

Compound 183

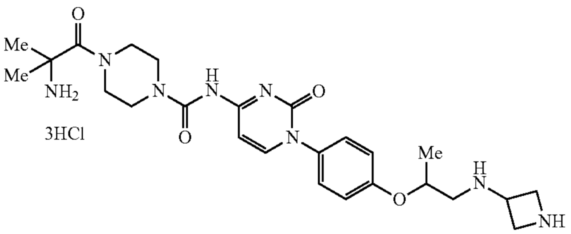

4-(2-Amino-2-methylpropanoyl)-N-(1-(4-((1-(azetidin-3-ylamino)propan-2-yl)oxy)phenyl)-2-oxo-1,2-dihydropyrimidin-4-yl)piperazine-1-carboxamide hydrochloride salt Prepared in a similar fashion as Scheme C-23 from tert-butyl (2-methyl-1-oxo-1-(4-((2-oxo-1-(4-((1-oxopropan-2-yl)oxy)phenyl)-1,2-dihydropyrimidin-4-yl)carbamoyl)piperazin-1-yl)propan-2-yl)carbamate and tert-butyl-3-amino-azetidine-1-carboxylate. $^1$H NMR (400 MHz, $D_2O$) δ 8.12 (d, 1H), 7.46 (d, 2H), 7.22 (d, 2H), 6.80 (d, 1H), 4.92 (s, 1H), 4.62-4.42 (m, 5H), 3.80 (br. s, 4H), 3.76 (br. s, 4H), 3.47-3.37 (m, 2H), 1.74 (s, 6H), 1.40 (d, 3H). LCMS [M+H] 513.3.

Compound 184

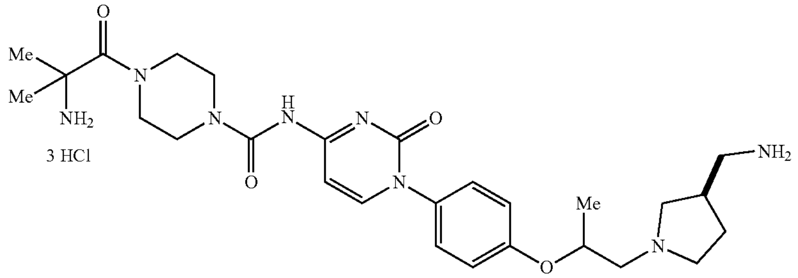

4-(2-Amino-2-methylpropanoyl)-N-(1-(4-((1-((R)-3-(aminomethyl)pyrrolidin-1-yl)propan-2-yl)oxy)phenyl)-2-oxo-1,2-dihydropyrimidin-4-yl)piperazine-1-carboxamide hydrochloride salt Prepared in a similar fashion as Scheme C-23 from tert-butyl (2-methyl-1-oxo-1-(4-((2-oxo-1-(4-((1-oxopropan-2-yl)oxy)phenyl)-1,2-dihydropyrimidin-4-yl)carbamoyl)piperazin-1-yl)propan-2-yl)carbamate and tert-butyl (S)-(pyrrolidin-3-ylmethyl)carbamate. $^1$H NMR (400 MHz, $D_2O$) δ 8.11 (d, 1H), 7.46 (d, 2H), 7.22 (d, 2H), 6.81 (d, 1H), 4.97 (s, 1H), 3.96-3.53 (m, 12H), 3.52-3.29 (m, 1H), 3.26-3.02 (m, 3H), 3.01-2.66 (m, 1H), 2.53-2.29 (m, 1H), 2.09-1.76 (m, 1H), 1.74 (s, 6H), 1.39 (d, 3H). LCMS [M+H] 541.2.

Compound 185

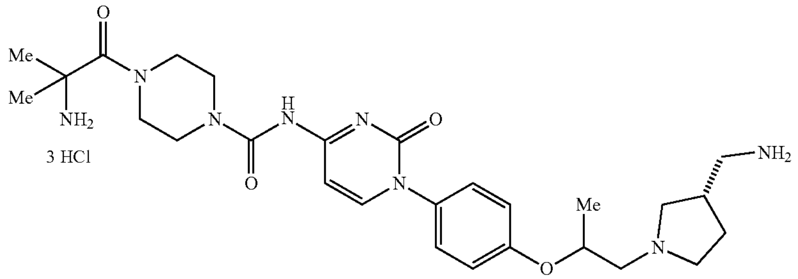

4-(2-Amino-2-methylpropanoyl)-N-(1-(4-((1-((S)-3-(aminomethyl)pyrrolidin-1-yl)propan-2-yl)oxy)phenyl)-2-oxo-1,2-dihydropyrimidin-4-yl)piperazine-1-carboxamide hydrochloride salt Prepared in a similar fashion as Scheme C-23 from tert-butyl (2-methyl-1-oxo-1-(4-((2-oxo-1-(4-((1-oxopropan-2-yl)oxy)phenyl)-1,2-dihydropyrimidin-4-yl)carbamoyl)piperazin-1-yl)propan-2-yl)carbamate and tert-butyl (R)-(pyrrolidin-3-ylmethyl)carbamate. $^1$H NMR (400 MHz, $D_2O$) δ 8.11 (d, 1H), 7.46 (d, 2H), 7.22 (d, 2H), 6.81 (d1H), 4.98 (s, 1H), 4.05-3.50 (m, 12H), 3.50-3.33 (m, 1H), 3.26-3.03 (m, 3H), 3.02-2.71 (m, 1H), 2.55-2.26 (m, 1H), 2.10-1.78 (m, 1H), 1.74 (s, 6H), 1.39 (d, 3H). LCMS [M+H] 541.3.

Compound 186

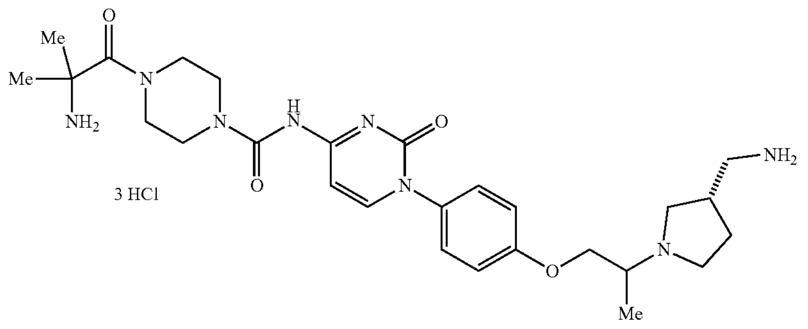

4-(2-Amino-2-methylpropanoyl)-N-(1-(4-(2-((S)-3-(aminomethyl)pyrrolidin-1-yl)propoxy)phenyl)-2-oxo-1,2-dihydropyrimidin-4-yl)piperazine-1-carboxamide hydrochloride salt Scheme C-24

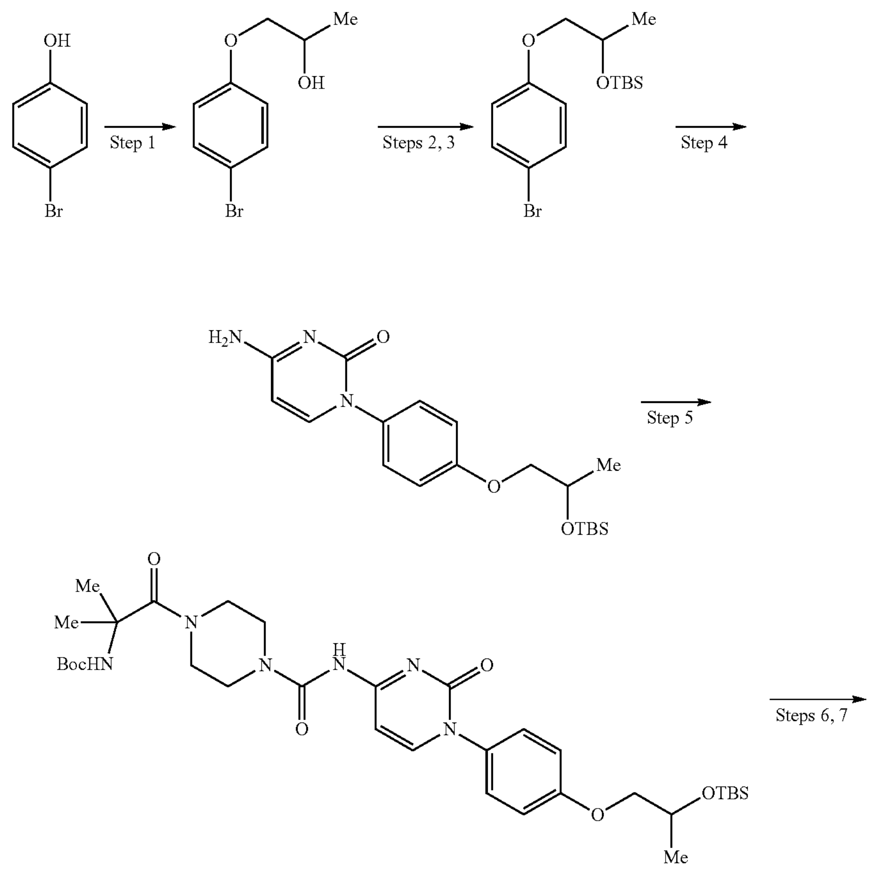

-continued

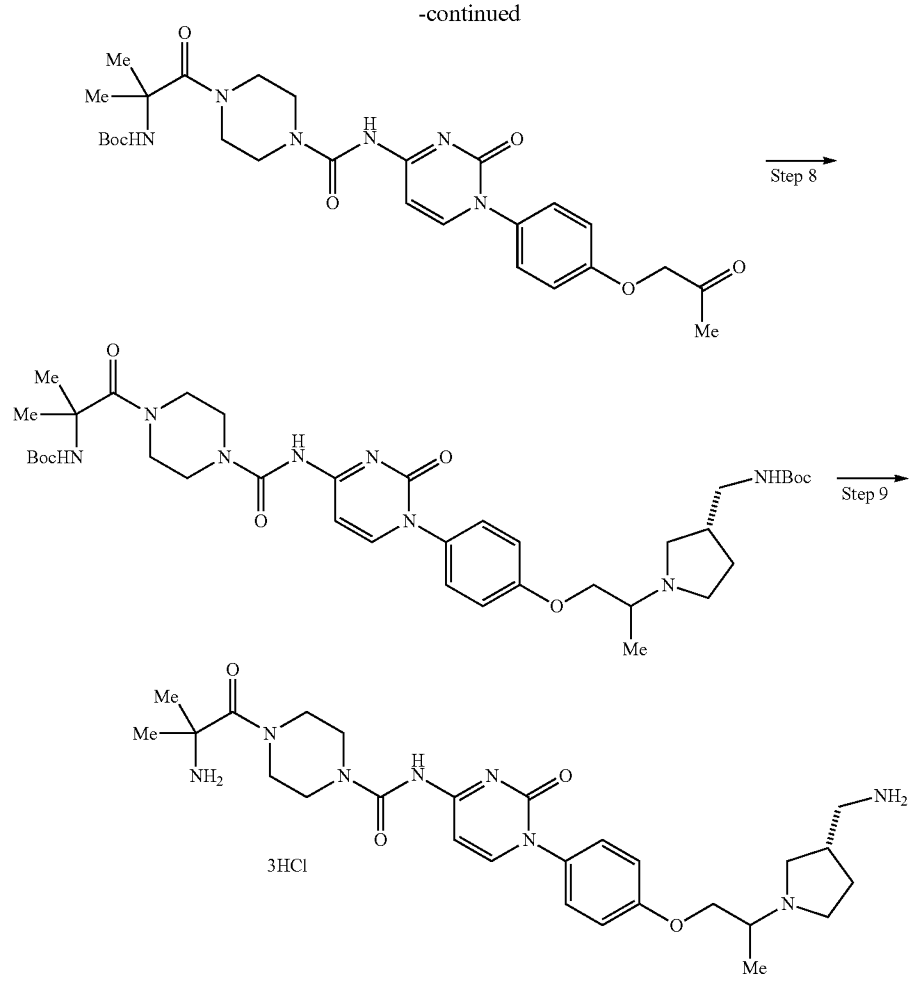

Reagents: Step 1) Propylene glycol, $K_2CO_3$, diethyl carbonate, 110° C., 8 days 2) TBSCl, imidazole, $CH_2Cl_2$, rt, 16 h 3) nBuLi, $B(OiPr)_3$, THF, -78° C. to rt, 3 h 4) Cytosine, TMEDA, $Cu(OAc)_2 \cdot H_2O$, $CH_3OH$:$H_2O$ (4:1), rt, 16 h 5) 1-(4-(2-((tert-butoxycarbonyl)amino)-2-methylpropanoyl)piperazine-1-carbonyl)-3-methyl-1H-imidazol-3-ium iodide, $CH_3CN$, 90° C., 16 h 6) TBAF, THF, rt, 16 h 7) Dess-Martin periodinane, $CH_2Cl_2$, rt, 3 h 8) tert-butyl (R)-(pyrrolidin-3-ylmethyl)carbamate, $NaBH_3CN$, 4Å MS, $CH_3OH$, rt, 16 h 9) 4.0 MHCl in dioxane, dioxane, rt, 3 h.

Step 1: 1-(4-bromophenoxy)propan-2-ol

A mixture of 4-bromophenol (25 g, 145 mmol), propane-1,2-diol (32.9 g, 434 mmol), and $K_2CO_3$ (2.0 g, 14.5 mmol) in diethyl carbonate (25 mL, 202 mmol) was stirred at 110° C. for 8 days. The resulting reaction mixture was poured into 1N NaOH (200 mL) and extracted with EtOAc (3×200 mL). The extracts were dried over $Na_2SO_4$, filtered, and concentrated in vacuo to afford the title compound. $^1H$ NMR (400 MHz, DMSO-$d_6$) δ 7.44-7.39 (m, 2H), 6.91-6.87 (m, 2H), 4.89 (d, 1H), 3.95-3.90 (m, 1H), 3.81-3.73 (m, 2H), 1.14 (d, 3H).

Step 2: ((1-(4-bromophenoxy)propan-2-yl)oxy)(t-butyl)dimethylsilane

To a stirred solution of 1-(4-bromophenoxy)propan-2-ol (18 g, 78 mmol) in $CH_2Cl_2$ (200 mL) at 0° C. was added imidazole (7.94 g, 117 mmol) and t-butyldimethylsilyl chloride (14.1 g, 93 mmol). The reaction mixture was stirred at rt for 16 h, poured into $H_2O$ (200 mL) and extracted with $CH_2Cl_2$ (3×200 mL). The extracts were dried over $Na_2SO_4$, filtered, and concentrated in vacuo to afford the title compound. $^1H$ NMR (400 MHz, DMSO-$d_6$) δ 7.44-7.40 (m, 2H), 6.89-6.86 (m, 2H), 4.13-4.08 (m, 1H), 3.86-3.66 (m, 2H), 1.14 (d, 3H), 0.84 (s, 9H), 0.06 (s, 3H), 0.02 (s, 3H).

Step 3: diisopropyl (4-(2-((t-butyldimethylsilyl) oxy) propoxy) phenyl) boronate To a stirred solution of ((1-(4-bromophenoxy)propan-2-yl)oxy)(t-butyl)dimethylsilane (5.0 g, 14.5 mmol) in THF (300 mL) at −78° C. under $N_2$ was added n-BuLi (1.6M in THF, 22.64 mL) dropwise. The reaction mixture was stirred for 30 min. Triisopropyl borate (5.04 mL, 21.7 mmol) was added dropwise. The reaction mixture was warmed to rt and stirred for 3 h. The reaction mixture was poured into sat. aq. $NH_4Cl$ (400 mL) and extracted with EtOAc (3×1000 mL). The combined organic phases were dried over $Na_2SO_4$, filtered, and concentrated in vacuo to afford the title compound.

Step 4: 4-amino-1-(4-(2-((t-butyldimethylsilyl)oxy)propoxy)phenyl)pyrimidin-2(1H)-one A mixture of diisopropyl (4-(2-((t-butyldimethylsilyl)oxy)propoxy) phenyl)boronate (6.5 g, 16.5 mmol) and cytosine (1.8 g, 16.5 mmol) in 4:1 $CH_3OH$:$H_2O$ (50 mL) was stirred at rt open to air for 30 min. TMEDA (2.3 mL, 19.8 mmol) and $Cu(OAc)_2 \cdot H_2O$ (2.3 g, 16.5 mmol) were added and the mixture was stirred at rt open to air for 48 h. It was concentrated in vacuo to remove the $CH_3OH$, and cold $H_2O$ (100 mL) was added.

The precipitate was collected by vacuum filtration, washed with $H_2O$ (5×50 mL) and $Et_2O$ (2×20 mL) and dried to yield the title compound. $^1H$ NMR (400 MHz, DMSO-$d_6$) δ 7.57 (d, 1H), 7.21 (d, 2H), 6.94 (d, 2H), 5.73 (d, 1H), 4.13-4.08 (m, 1H), 3.87-3.86 (m, 1H), 3.81-3.80 (m, 1H), 1.17 (d, 3H), 0.86 (s, 9H), 0.09 (s, 3H), 0.05 (s, 3H). LCMS [M+H] 376.1.

Step 5: t-butyl (1-(4-((1-(4-(2-((t-butyldimethylsilyl)oxy)propoxy)phenyl)-2-oxo-1,2-dihydropyrimidin-4-yl)carbamoyl)piperazin-1-yl)-2-methyl-1-oxopropan-2-yl)carbamate A mixture of 4-amino-1-(4-(2-((t-butyldimethylsilyl)oxy)propoxy)phenyl) pyrimidin-2(1H)-one (0.5 g, 1.33 mmol) and 1-(4-(2-((tert-butoxycarbonyl)amino)-2-methylpropanoyl)piperazine-1-carbonyl)-3-methyl-1H-imidazol-3-ium iodide (1.01 g, 2.0 mmol) in $CH_3CN$ (15 mL) was stirred at 90° C. for 16 h. The reaction mixture was concentrated in vacuo and the residue was purified by flash chromatography ($CH_3OH$:$CH_2Cl_2$) to afford the title compound. LCMS [M+H] 673.1.

Step 6: t-butyl (1-(4-((1-(4-(2-hydroxypropoxy)phenyl)-2-oxo-1,2-dihydropyrimidin-4-yl)carbamoyl)piperazin-1-yl)-2-methyl-1-oxopropan-2-yl)carbamate To a stirred solution of t-butyl (1-(4-((1-(4-(2-((t-butyldimethylsilyl)oxy) propoxy)phenyl)-2-oxo-1,2-dihydropyrimidin-4-yl)carbamoyl)piperazin-1-yl)-2-methyl-1-oxopropan-2-yl)carbamate (0.4 g, 0.59 mmol) in THF (10 mL) at 0° C. was added 1M TBAF in THF (2.4 mL). The reaction mixture was warmed to rt and stirred for 16 h. The reaction mixture was poured into sat. aq. $NaHCO_3$ (10 mL) and extracted with 9:1 $CH_2Cl_2$:$CH_3OH$ (3×50 mL). The extracts were dried over $Na_2SO_4$, filtered, and concentrated in vacuo, and the residue purified by flash chromatography ($CH_3OH$:$CH_2Cl_2$) to afford the title compound. LCMS [M+H] 559.1.

Step 7: tert-butyl (2-methyl-1-oxo-1-(4-((2-oxo-1-(4-(2-oxopropoxy)phenyl)-1,2-dihydropyrimidin-4-yl)carbamoyl)piperazin-1-yl)propan-2-yl)carbamate To a stirred solution of t-butyl (1-(4-((1-(4-(2-hydroxypropoxy)phenyl)-2-oxo-1,2-dihydropyrimidin-4-yl)carbamoyl)piperazin-1-yl)-2-methyl-1-oxopropan-2-yl)carbamate (0.3 g, 0.53 mmol) in $CH_2Cl_2$(5.0 mL) at 0° C. under $N_2$ was added Dess-Martin periodinane (1.36 g, 3.22 mmol). The reaction mixture was stirred at rt for 3 h, poured into sat. aq. $NaHCO_3$ (20 mL) and extracted with $CH_2Cl_2$(3×50 mL). The extracts were dried over $Na_2SO_4$, filtered and concentrated in vacuo at <35° C. to afford the title compound. LCMS [M+H] 557.1.

Step 8: tert-butyl (1-(4-((1-(4-(2-((S)-3-(((tert-butoxycarbonyl)amino)methyl)pyrrolidin-1-yl)propoxy)phenyl)-2-oxo-1,2-dihydropyrimidin-4-yl)carbamoyl)piperazin-1-yl)-2-methyl-1-oxopropan-2-yl)carbamate To a stirred solution of tert-butyl (2-methyl-1-oxo-1-(4-((2-oxo-1-(4-(2-oxopropoxy)phenyl)-1,2-dihydropyrimidin-4-yl)carbamoyl)piperazin-1-yl)propan-2-yl)carbamate (0.28 g, 0.50 mmol) and tert-butyl (R)-(pyrrolidin-3-ylmethyl)carbamate (0.12 g, 0.60 mmol) in $CH_3OH$ (10 mL) at 0° C. under $N_2$ was added activated 4 Å molecular sieves followed by $NaBH_3CN$ (0.67 g, 1.07 mmol). The mixture was stirred at rt for 16 h concentrated in vacuo. The residue was purified by flash chromatography ($CH_3OH$:$CH_2Cl_2$) to afford the title compound.

Step 9: 44-(2-amino-2-methylpropanoyl)-N-(1-(4-(2-((S)-3-(aminomethyl)pyrrolidin-1-yl)propoxy)phenyl)-2-oxo-1,2-dihydropyrimidin-4-yl)piperazine-1-carboxamide hydrochloride salt To a stirred solution of tert-butyl (1-(4-((1-(4-(2-((S)-3-(((tert-butoxycarbonyl)amino)methyl)pyrrolidine-1-yl)propoxy)phenyl)-2-oxo-1,2-dihydropyrimidin-4-yl)carbamoyl)piperazin-1-yl)-2-methyl-1-oxopropan-2-yl)carbamate (0.2 g, 0.26 mmol) in dioxane (3 mL) was added 4M HCl in dioxane (5 mL). The mixture was stirred at rt for 3 h, concentrated in vacuo, and triturated with $Et_2O$ (10 mL). The residue was purified by HPLC ($CH_3CN/H_2O$/TFA). Addition of HCl/MeOH (3×15 mL) and evaporation under reduced pressure afforded the title compound. $^1H$ NMR (400 MHz, $D_2O$) mixture of rotamers, mixture of diastereomers, δ 7.86 (d, 1H), 7.28 (d, 2H), 7.03 (d, 2H), 6.67 (d, 1H), 4.33-4.30 (m, 1H), 4.15-4.10 (m, 1H), 3.80-3.50 (m, 11H), 3.45-3.20 (m, 2H), 3.12-2.93 (m, 3H), 2.83-2.55 (m, 2H), 2.40-2.15 (m, 2H), 1.91-1.60 (m, 2H), 1.59 (s, 6H), 1.40 (d, 3H). LCMS[(M+2H)/2] 271.1.

Compound 187

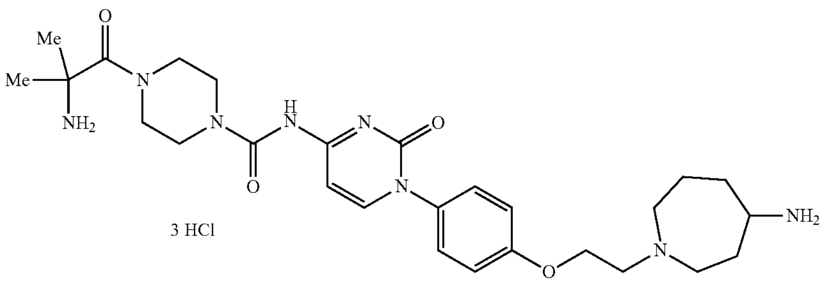

3 HCl 4-(2-Amino-2-methylpropanoyl)-N-(1-(4-(2-(4-aminoazepan-1-yl)ethoxy)phenyl)-2-oxo-1,2-dihydropyrimidin-4-yl)piperazine-1-carboxamide hydrochloride salt Prepared in a similar fashion as Scheme C-24 from tert-butyl (2-methyl-1-oxo-1-(4-((2-oxo-1-(4-(2-oxoethoxy)phenyl)-1,2-dihydropyrimidin-4-yl)carbamoyl)piperazin-1-yl)propan-2-yl)carbamate and tert-butyl azepan-4-ylcarbamate. $^1$H NMR (400 MHz, $D_2O$) δ 7.95 (d, 1H), 7.43 (d, 2H), 7.18 (d, 2H), 6.84 (d, 1H), 4.47 (s, 2H), 3.79 (s, 4H), 3.73 (s, 6H), 3.68-3.55 (m, 3H), 3.55-3.42 (m, 1H), 3.42-3.25 (m, 2H), 2.43-2.27 (m, 2H), 2.25-2.09 (m, 2H), 2.09-1.85 (m, 1H, 1.75 (s, 6H). LCMS [M+H] 541.4.

Compound 188

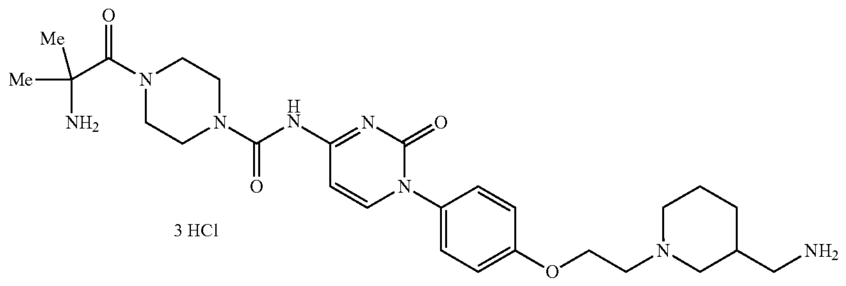

4-(2-Amino-2-methylpropanoyl)-N-(1-(4-(2-(3-(aminomethyl)piperidin-1-yl)ethoxy)phenyl)-2-oxo-1,2-dihydropyrimidin-4-yl)piperazine-1-carboxamide hydrochloride salt Prepared in a similar fashion as Scheme C-24 from tert-butyl (2-methyl-1-oxo-1-(4-((2-oxo-1-(4-(2-oxoethoxy)phenyl)-1,2-dihydropyrimidin-4-yl)carbamoyl)piperazin-1-yl)propan-2-yl)carbamate and tert-butyl (piperidin-3-ylmethyl)carbamate. $^1$H NMR (400 MHz, $D_2O$) δ 7.96 (d, 1H), 7.43 (d, 2H), 7.18 (d, 2H), 6.84 (d, 1H), 4.51-4.46 (m, 2H), 3.78 (s, 4H), 3.74 (s, 6H), 3.71-3.65 (m, 2H), 3.12-3.02 (m, 2H), 3.02-2.89 (m, 2H), 2.33 (s, 1H), 2.18-2.01 (m, 2H), 1.96-1.83 (m, 1H), 1.75 (s, 6H), 1.43-1.30 (m, 1H). LCMS [M+H] 541.3.

Compound 190

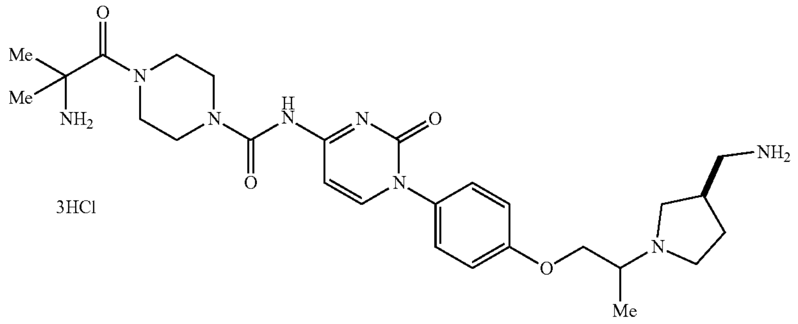

4-(2-Amino-2-methylpropanoyl)-N-(1-(4-(2-((R)-3-(aminomethyl)pyrrolidin-1-yl)propoxy)phenyl)-2-oxo-1,2-dihydropyrimidin-4-yl)piperazine-1-carboxamide hydrochloride salt Prepared in a similar fashion as Scheme C-24 from tert-butyl (2-methyl-1-oxo-1-(4-((2-oxo-1-(4-(2-oxopropoxy)phenyl)-1,2-dihydropyrimidin-4-yl)carbamoyl)piperazin-1-yl)propan-2-yl)carbamate and tert-butyl (S)-(pyrrolidin-3-ylmethyl)carbamate. $^1$H NMR (400 MHz, $D_2O$) mixture of rotamers, mixture of diastereomers, δ 7.82 (d, 1H), 7.27 (d, 2H), 7.02 (d, 2H), 6.67 (d, 1H), 4.31-4.29 (m, 1H), 4.14-4.12 (m, 1H), 3.80-3.51 (m, 10H), 3.38-3.31 (m, 1H), 3.25-3.21 (m, 2H), 3.08-2.92 (m, 3H), 2.79-2.74 (m, 1H), 2.64-2.62 (m, 1H), 2.36-2.33 (m, 1H), 2.23-2.21 (m, 1H), 1.87-1.85 (m, 1H), 1.70-1.59 (m, 1H), 1.58 (s, 6H), 1.39 (d, 3H). LCMS [(M+2H)/2] 271.2.

Compound 191

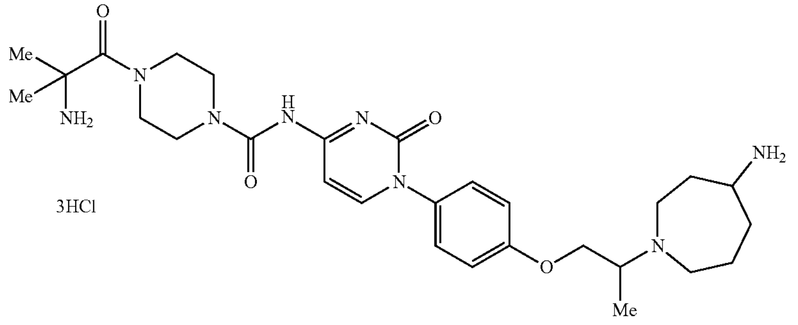

4-(2-Amino-2-methylpropanoyl)-N-(1-(4-(2-(4-aminoazepan-1-yl)propoxy)phenyl)-2-oxo-1,2-dihydropyrimidin-4-yl)piperazine-1-carboxamide hydrochloride salt Prepared in a similar fashion as Scheme C-24 from tert-butyl (2-methyl-1-oxo-1-(4-((2-oxo-1-(4-(2-oxopropoxy)phenyl)-1,2-dihydropyrimidin-4-yl)carbamoyl)piperazin-1-yl)propan-2-yl)carbamate and tert-butyl azepan-4-ylcarbamate. $^1H$ NMR (400 MHz, $D_2O$) mixture of rotamers, mixture of diastereomers, δ 7.77 (d, 1H), 7.31 (d, 2H), 7.06 (d, 2H), 6.74 (d, 1H), 4.76-4.70 (m, 3H), 4.30-4.20 (m, 2H), 3.98-3.90 (m, 1H), 3.67-3.61 (m, 8H), 3.51-3.45 (m, 3H), 2.40-2.10 (m, 3H), 1.63 (s, 6H), 1.45-1.35 (m, 3H). LCMS [M+H] 555.3.

Compound 269

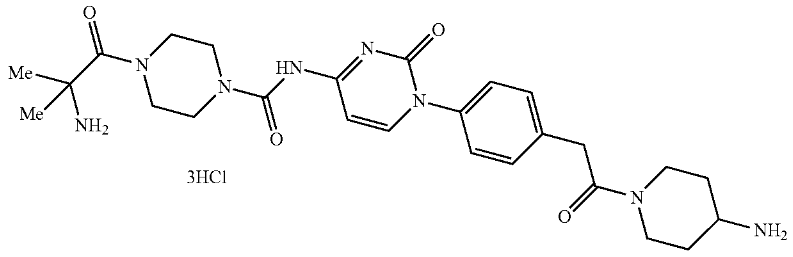

4-(2-Amino-2-methylpropanoyl)-N-(1-(4-(2-(4-aminopiperidin-1-yl)-2-oxoethyl) phenyl)-2-oxo-1,2-dihydropyrimidin-4-yl)piperazine-1-carboxamide hydrochloride salt Scheme C-25

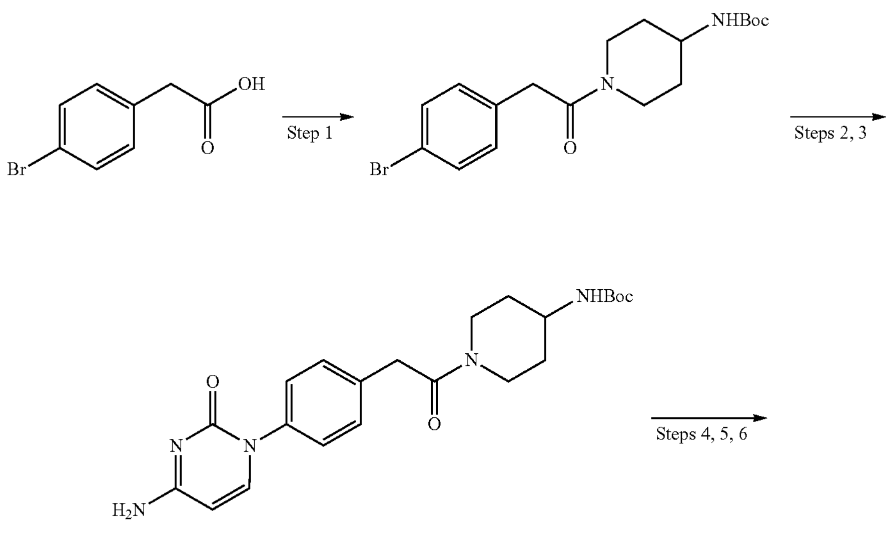

-continued

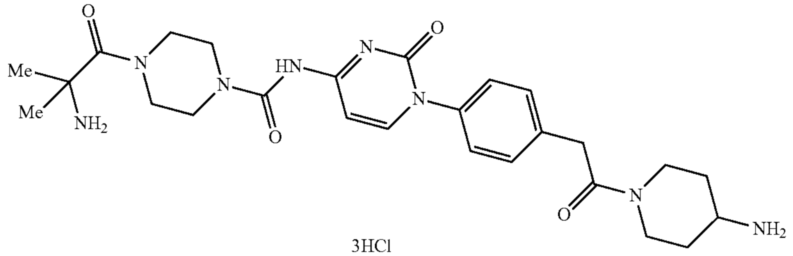

Step 1: tert-butyl (1-(2-(4-bromophenyl)acetyl)piperidin-4-yl)carbamate

To a stirred solution of 4-bromo phenylacetic acid (2.15 g, 10 mmol), 4-Boc amino piperidine (2.0 g, 10 mmol) and HATU (4.5 g, 12 mmol) in DMF was added DIPEA (2.61 mL, 15 mmol) and the reaction mixture stirred for 6 h at rt. Saturated LiCl solution was added and the solid was filtered and vacuum dried to afford the title compound (3.5 g, 90%) as gray solid.

Step 2: tert-butyl (1-(2-(4-(4,4,5,5-tetramethyl-1,3,2-dioxaborolan-2-yl)phenyl)acetyl)piperidin-4-yl) carbamate To a stirred suspension of tert-butyl (1-(2-(4-bromophenyl)acetyl)piperidin-4-yl)carbamate (0.39 g, 1 mmol) in a flame dried pressure flask was added bis(pinacolato) diboron (0.31 g, 1.2 mmol), KOAc (0.30 g, 3 mmol) and Pd(dppf)$Cl_2$ (25 mg, 0.03 mmol). The reaction mixture was degassed and purged with $N_2$ (g) (3×). The pressure flask was sealed and stirred at 110° C. for 16 h. The mixture was diluted with EtOAc and filtered through Celite®. The filtrate was concentrated and purified using flash column chromatography to afford the title compound ad a brown colored sticky solid.

Step 3: tert-butyl (1-(2-(4-(4-amino-2-oxopyrimidin-1(2H)-yl)phenyl)acetyl)piperidin-4-yl)carbamate A suspension of cytosine (0.093 g, 0.84 mmol) and tert-butyl (1-(2-(4-(4,4,5,5-tetramethyl-1,3,2-dioxaborolan-2-yl)phenyl)acetyl)piperidin-4-yl)carbamate (0.38 g, 0.84 mmol), in a mixture of solvents 4:1 MeOH:$H_2O$ (12 ml) was stirred at rt in open air. After 30 min. TMEDA (0.15 ml, 1.10 mmol) and Cu(OAc)$_2$H$_2$O (0.17 g, 0.84 mmol) were added. The reaction was stirred in open air for 48 h at rt. The solvent was evaporated reduced pressure, and the residue was crystallized with EtOH to afford the title compound.

Step 4: tert-butyl (1-(2-(4-(4-(1H-imidazole-1-carboxamido)-2-oxopyrimidin-1(2H)-yl)phenyl)acetyl) piperidin-4-yl)carbamate To a suspension of tert-butyl (1-(2-(4-(4-amino-2-oxopyrimidin-1(2H)-yl)phenyl)acetyl)piperidin-4-yl)carbamate (0.21 g, 0.5 mmol) in dichloromethane (12 mL) was added CDI (98 mg, 0.6 mmol) and the reaction mixture stirred for 16 h at rt. The solvent was evaporated under reduced pressure and the solid was used in the next step without further purification.

Step 5: tert-butyl (1-(2-(4-(4-(4-(2-((tert-butoxycarbonyl)amino)-2-methylpropanoyl)piperazine-1-carboxamido)-2-oxopyrimidin-1(2H)-yl)phenyl)acetyl) piperidin-4-yl)carbamate tert-Butyl (1-(2-(4-(4-(1H-imidazole-1-carboxamido)-2-oxopyrimidin-1(2H)-yl)phenyl)acetyl)piperidin-4-yl)carbamate (90 mg, 0.17 mmol) and tert-butyl (2-methyl-1-oxo-1-(piperazin-1-yl)propan-2-yl)carbamate (56 mg, 0.172 mmol) were suspended in acetonitrile and refluxed for 16 h. The solvent was evaporated and the residue was diluted with EtOAc (15 mL) and the excess imidazole was removed by water wash (3×10 mL). The organic layer was dried over $Na_2SO_4$, filtered and concentrated under reduced pressure to afford the title compound.

Step 6: 4-(2-amino-2-methylpropanoyl)-N-(1-(4-(2-(4-aminopiperidin-1-yl)-2-oxoethyl)phenyl)-2-oxo-1,2-dihydropyrimidin-4-yl)piperazine-1-carboxamide hydrochloride salt tert-Butyl (1-(2-(4-(4-(4-(2-((tert-butoxycarbonyl) amino)-2-methylpropanoyl)piperazine-1-carboxamido)-2-oxopyrimidin-1(2H)-yl)phenyl)acetyl)piperidin-4-yl)carbamate (56 mg, 0.08 mmol) was dissolved in methanolic HCl and stirred for 4 h. The solvent was evaporated and the residue was purified by RPHPLC and converted to the hydrochloride salt with the addition of 2N HCl in MeOH (5 mL) and evaporation under reduced pressure. $^1$H NMR (500 MHz, $D_2O$) δ 8.11 (d, 1H), 7.41 (br s, 4H), 6.77 (d, 1H), 4.50 (d, 1H), 4.11 (d, 1H), 3.93 (s, 2H), 3.83-3.73 (m, 8H), 3.45 (t, 1H), 3.21 (t, 1H), 2.80 (t, 1H), 2.12-1.98 (m, 2H), 1.73 (s, 6H), 1.57-1.49 (m, 2H). LCMS [M+H] 525.43

Compound 143

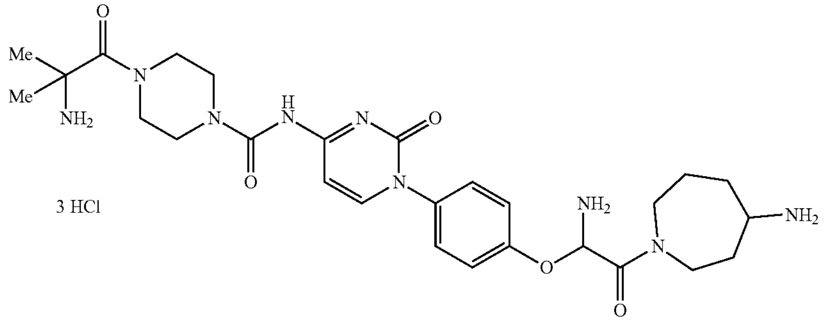

4-(2-Amino-2-methylpropanoyl)-N-(1-(4-((2R)-2-amino-3-(4-aminoazepan-1-yl)-3-oxopropyl)phenyl)-2-oxo-1,2-dihydropyrimidin-4-yl)piperazine-1-carboxamide hydrochloride salt Scheme C-26

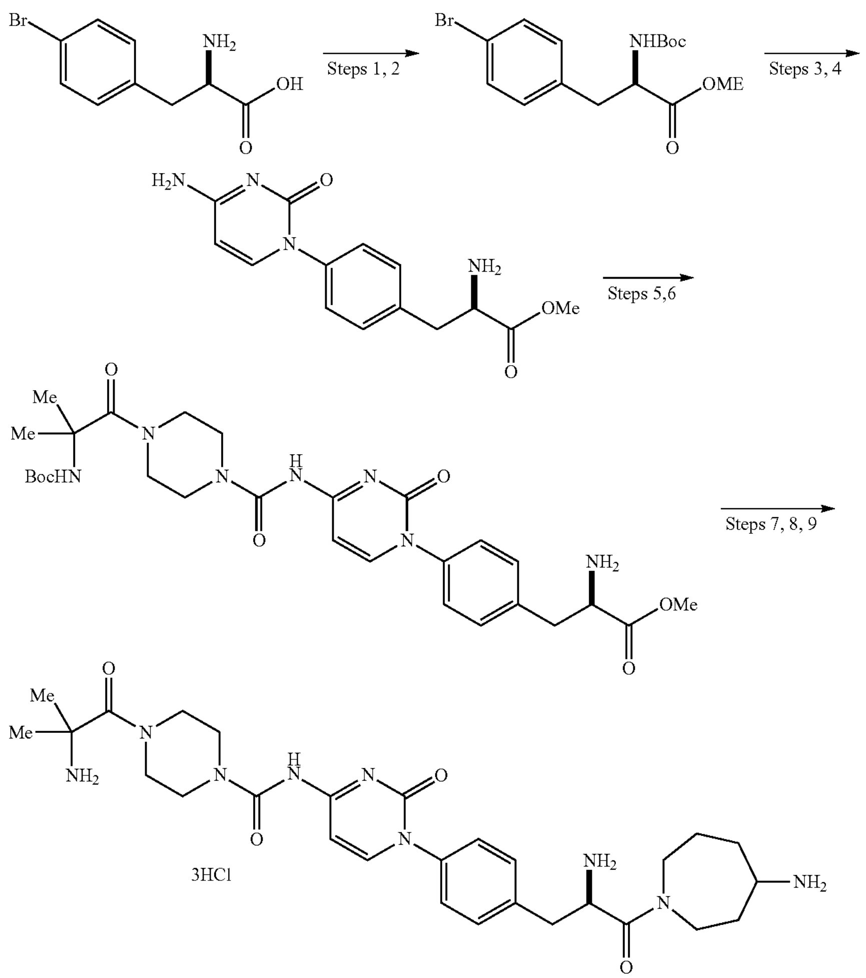

Reagents: 1) HCl, MeOH, rt, 16 h 2) $Boc_2O$, $Et_3N$, $CH_2Cl_2$, rt, 16 h 3) $Pd(dppf)_2$, KOAc, $B_2Pin_2$, dioxane, 100° C., 16 h 4) cytosine, $Cu(OAc)_2$, TMEDA, MeOH, $H_2O$ rt, 48 h 5) CDI, $CH_2Cl_2$, rt, 16 h 6) tert-butyl (2-methyl-1-oxo-1-(piperazin-1-yl)propan-2-yl)carbamate, $CH_3CN$, 80° C., 2 h 7) LiOH, THF, $H_2O$, 2 h 8) tert-butyl azepan-4-ylcarbamate, HATU, DIPEA, DMF, rt, 3 h 9) HCl, MeOH, rt, 4 h.

Step 1: methyl (R)-2-amino-3-(4-bromophenyl)propanoate (R)-2-Amino-3-(4-bromophenyl)propanoic acid (2.5 g, 10.2 mmol) was added to a solution of HCl in MeOH (100 mL) and the reaction was stirred for 16 h. The reaction mixture was concentrated under reduced pressure to afford the title compound.

Step 2: methyl (R)-3-(4-bromophenyl)-2-((tert-butoxycarbonyl)amino)propanoate

To a solution of methyl (R)-2-amino-3-(4-bromophenyl) propanoate (1.10 g, 3.74 mmol) in $CH_2Cl_2$ (100 mL) was added $NEt_3$ (2.0 mL, 14.96 mmol) followed by $Boc_2O$ (1.05 g, 4.86 mmol). The reaction mixture was stirred for 16 h and concentrated under reduced pressure and purified via column chromatography (hexanes:EtOAc) to afford the title compound.

Step 3: methyl (R)-2-((tert-butoxycarbonyl)amino)-3-(4-(4,4,5,5-tetramethyl-1,3,2-dioxaborolan-2-yl) phenyl)propanoate A mixture of (R)-3-(4-bromophenyl)-2-((tert-butoxycarbonyl)amino)propanoate (0.68 g, 1.9 mmol), bis(pinacolato) diboron (0.96 g, 3.8 mmol), $Pd(dppf)_2$ (0.07 g, 5 mol %), and KOAc (0.46 g, 4.76 mmol) was evacuated and flushed with $N_2$ (3×). Dioxane (30 mL) was added and the mixture was subjected to 3 freeze pump thaw cycles. The mixture was placed under $N_2$ and heated to 100° C. for 16 h, concentrated under reduced pressure and purified via column chromatography (hexanes:EtOAc) to afford the title compound.

Step 4: methyl (R)-3-(4-(4-amino-2-oxopyrimidin-1(2H)-yl)phenyl)-2-((tert-butoxycarbonyl)amino)propanoate A suspension of cytosine (0.14 g, 1.3 mmol) and methyl (R)-2-((tert-butoxycarbonyl)amino)-3-(4-(4,4,5,5-tetramethyl-1,3,2-dioxaborolan-2-yl)phenyl)propanoate (0.50 g, 1.3 mmol), in 4:1 MeOH:$H_2O$ (60 ml) was stirred at rt in open air for 30 min. TMEDA (0.2 ml, 1.6 mmol) and $Cu(OAc)_2 \cdot H_2O$ (0.3 g, 1.3 mmol) were added and the reaction was stirred in open air for 48 h at rt. The reaction mixture was concentrated under reduced pressure, and cold $H_2O$ (50 mL) was added. The solid was filtered and washed with $H_2O$ (5×50 mL), $Et_2O$ (3×30 mL), and $H_2O$ (2×30 mL) to afford the title compound.

Step 5: methyl (R)-3-(4-(4-(1H-imidazole-1-carboxamido)-2-oxopyrimidin-1(2H)-yl)phenyl)-2-((tert-butoxycarbonyl)amino)propanoate A suspension of methyl (R)-3-(4-(4-amino-2-oxopyrimidin-1(2H)-yl)phenyl)-2-((tert-butoxycarbonyl)amino)propanoate (100 mg, 0.25 mmol) and 1,1'-carbonyldiimidazole (70 mg, 0.42 mmol) in $CH_2Cl_2$ (20 mL) was stirred at rt for 16 h. The solvent was removed under reduced pressure to afford the title compound.

Step 6: methyl (R)-2-((tert-butoxycarbonyl)amino)-3-(4-(4-(4-(2-((tert-butoxycarbonyl)amino)-2-methylpropanoyl)piperazine-1-carboxamido)-2-oxopyrimidin-1(2H)-yl)phenyl)propanoate Methyl (R)-3-(4-(4-(1H-imidazole-1-carboxamido)-2-oxopyrimidin-1(2H)-yl)phenyl)-2-((tert-butoxycarbonyl) amino)propanoate (0.25 mmol) and tert-butyl (2-methyl-1-oxo-1-(piperazin-1-yl)propan-2-yl)carbamate (115 mg, 0.42 mmol) were dissolved in $CH_3CN$ (20 mL) and heated to reflux for 2 h. The reaction mixture was concentrated under reduced pressure and the solid was dissolved in EtOAc (25 mL) and washed with water (3×20 mL). The reaction mixture was purified by flash chromatography (Hexanes: EtOAc) to afford the title compound.

Step 7: (R)-2-((tert-butoxycarbonyl)amino)-3-(4-(4-(4-(2-((tert-butoxycarbonyl)amino)-2-methylpropanoyl)piperazine-1-carboxamido)-2-oxopyrimidin-1(2H)-yl)phenyl)propanoic acid To a solution of methyl (R)-2-((tert-butoxycarbonyl) amino)-3-(4-(4-(4-(2-((tert-butoxycarbonyl)amino)-2-methylpropanoyl)piperazine-1-carboxamido)-2-oxopyrimidin-1 (2H)-yl)phenyl)propanoate (50 mg, 0.07 mmol) in 1:1 THF: $H_2O$ (10 ml) was added LiOH (10 mg, 0.44 mmol) and the reaction was stirred for 2 h. The reaction mixture was acidified to pH 4 and extracted with EtOAc (3×20 mL) to afford the title compound.

Step 8: tert-butyl ((2R)-3-(4-(4-(4-(2-((tert-butoxycarbonyl)amino)-2-methylpropanoyl)piperazine-1-carboxamido)-2-oxopyrimidin-1(2H)-yl)phenyl)-1-(4-((tert-butoxycarbonyl)amino)azepan-1-yl)-1-oxopropan-2-yl)carbamate To a solution of (R)-2-((tert-butoxycarbonyl)amino)-3-(4-(4-(4-(2-((tert-butoxycarbonyl)amino)-2-methylpropanoyl) piperazine-1-carboxamido)-2-oxopyrimidin-1(2H)-yl)phenyl)propanoic acid (22 mg, 0.03 mmol) in DMF (5 mL) was added tert-butyl azepan-4-ylcarbamate (8 mg, 0.04 mmol), DIPEA (1 drop), and HATU (18 mg, 0.05 mmol). The reaction mixture was stirred for 3 h and partitioned between EtOAc (50 mL) and LiCl (50 mL). The organic layer was washed with LiCl (2×50 mL), dried over $Na_2SO_4$ and concentrated under reduced pressure. The residue was purified by column chromatography ($CH_2Cl_2$:MeOH) to afford the title compound.

Step 9: 4-(2-amino-2-methylpropanoyl)-N-(1-(4-((2R)-2-amino-3-(4-aminoazepan-1-yl)-3-oxopropyl) phenyl)-2-oxo-1,2-dihydropyrimidin-4-yl)piperazine-1-carboxamide hydrochloride salt A mixture of HCl in MeOH (100 ml) was added to tert-butyl ((2R)-3-(4-(4-(4-(2-((tert-butoxycarbonyl) amino)-2-methylpropanoyl)piperazine-1-carboxamido)-2-oxopyrimidin-1(2H)-yl)phenyl)-1-(4-((tert-butoxycarbonyl) amino)azepan-1-yl)-1-oxopropan-2-yl)carbamate (8 mg, 0.01 mmol) and the reaction was stirred for 4 h. The reaction mixture was concentrated under reduced pressure to afford the title compound. $^1H$ NMR (500 MHz, $D_2O$): δ 8.01 (d, 1H), 7.50-7.45 (m, 4H), 6.81 (d, 1H), 3.85-3.66 (m, 8H), 3.65-3.38 (m, 3H), 3.34-3.02 (m, 5H), 2.27-1.83 (m, 6H), 1.72 (s, 6H). LCMS [M+H] 568.3.

Compound 144

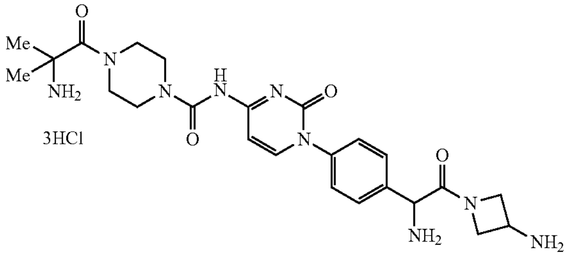

N-(1-(4-(1-Amino-2-(3-aminoazetidin-1-yl)-2-oxoethyl)phenyl)-2-oxo-1,2-dihydropyrimidin-4-yl)-4-(2-amino-2-methylpropanoyl)piperazine-1-carboxamide hydrochloride salt Prepared in a similar fashion as Scheme C-26 from 2-amino-2-(4-bromophenyl)acetic acid. $^1$H NMR (400 MHz, $D_2O$) δ 7.92 (d, 1H), 7.69 (d, 2H), 7.65 (d, 2H), 6.89 (d, 1H), 5.34 (d, 1H), 4.56-4.36 (m, 1H), 4.33-4.20 (m, 2H), 4.15-4.01 (m, 2H), 3.79 (s, 2H), 3.74 (s, 6H), 1.75 (s, 6H). LCMS [M+H] 512.2.

Compound 145

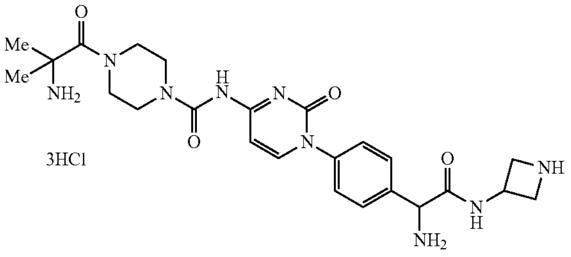

N-(1-(4-(1-Amino-2-(azetidin-3-ylamino)-2-oxoethyl)phenyl)-2-oxo-1,2-dihydropyrimidin-4-yl)-4-(2-amino-2-methylpropanoyl)piperazine-1-carboxamide hydrochloride salt Prepared in a similar fashion as Scheme C-26 from 2-amino-2-(4-bromophenyl)acetic acid. $^1$H NMR (400 MHz, $D_2O$) δ 7.95 (d, 1H), 7.70 (d, 2H), 7.61 (d, 2H), 6.88 (d, 1H), 5.28 (s, 1H), 4.43-4.30 (m, 3H), 4.17 (d, 2H), 3.79 (s, 4H), 3.73 (s, 4H), 1.75 (s, 6H). LCMS [M+H] 512.2.

Compound 146

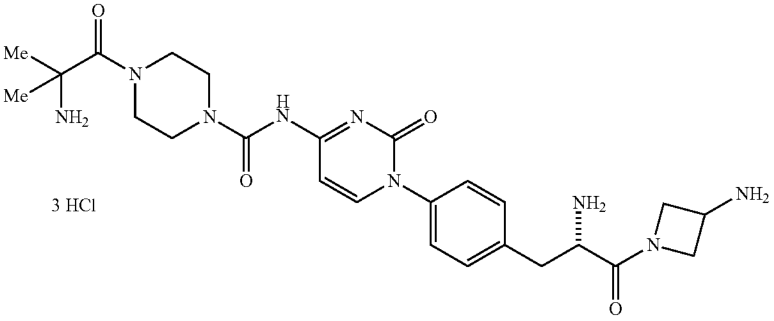

(S)-4-(2-Amino-2-methylpropanoyl)-N-(1-(4-(2-amino-3-(3-aminoazetidin-1-yl)-3-oxopropyl)phenyl)-2-oxo-1,2-dihydropyrimidin-4-yl)piperazine-1-carboxamide hydrochloride salt Prepared in a similar fashion as Scheme C-26 from (S)-2-amino-3-(4-bromophenyl)propanoic acid. $^1$H NMR (400 MHz, $D_2O$) δ 8.16 (d, 1H), 7.58-7.49 (m, 4H), 6.86-6.80 (m, 1H), 4.66 (t, 1H), 4.51-4.24 (m, 2H), 4.17-4.00 (m, 2H), 3.88-3.66 (m, 9H), 3.32-3.18 (m, 2H), 1.75 (s, 6H). LCMS [M+H] 526.4.

Compound 147

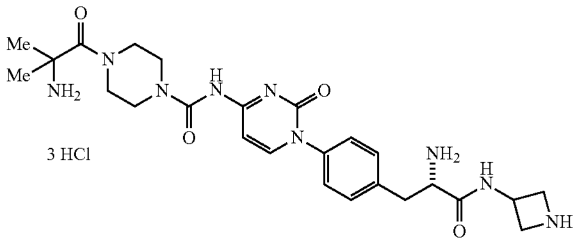

(S)-4-(2-Amino-2-methylpropanoyl)-N-(1-(4-(2-amino-3-(azetidin-3-ylamino)-3-oxopropyl)phenyl)-2-oxo-1,2-dihydropyrimidin-4-yl)piperazine-1-carboxamide hydrochloride salt Prepared in a similar fashion as Scheme C-26 from (S)-2-amino-3-(4-bromophenyl)propanoic acid. $^1H$ NMR (400 MHz, $D_2O$) δ 8.08 (d, 1H), 7.50 (s, 4H), 6.83 (d, 1H), 4.74 (d, 1H), 4.38-4.24 (m, 3H), 4.17-4.09 (m, 1H), 3.98-3.90 (m, 1H), 3.80 (s, 3H), 3.75 (s, 5H), 3.38-3.24 (m, 2H), 1.75 (s, 6H). LCMS [M+H] 526.3.

Compound 148

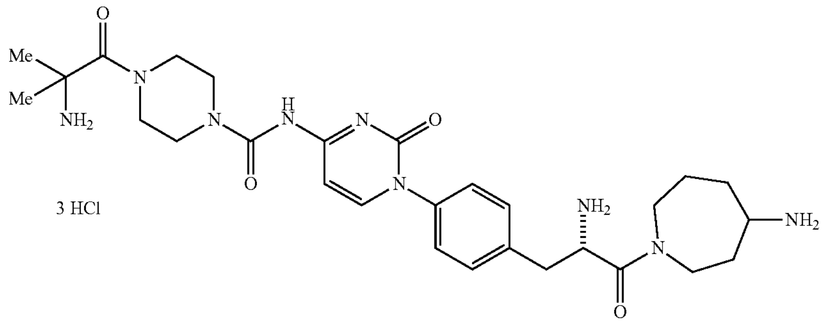

4-(2-Amino-2-methylpropanoyl)-N-(1-(4-((2S)-2-amino-3-(4-aminoazepan-1-yl)-3-oxopropyl)phenyl)-2-oxo-1,2-dihydropyrimidin-4-yl)piperazine-1-carboxamide hydrochloride salt Prepared in a similar fashion as Scheme C-26 from (S)-2-amino-3-(4-bromophenyl)propanoic acid. $^1H$ NMR (400 MHz, $D_2O$) δ 8.02 (d, 1H), 7.49 (d, 4H), 6.83 (d, 1H), 3.93-3.41 (m, 12H), 3.39-3.05 (m, 4H), 2.30-2.11 (m, 1H), 2.11-1.87 (m, 2H), 1.75 (s, 6H), 1.70-1.22 (m, 3H. LCMS [M+H] 568.4.

Compound 373

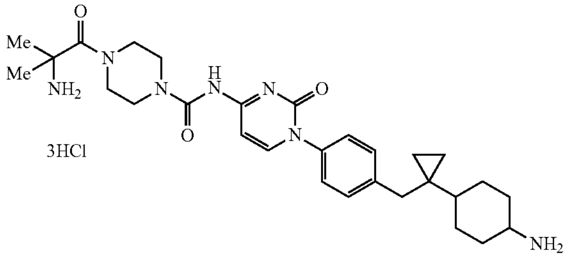

4-(2-Amino-2-methylpropanoyl)-N-(1-(4-((1-(4-aminopiperidin-1-yl)cyclopropyl)methyl)phenyl)-2-oxo-1,2-dihydropyrimidin-4-yl)piperazine-1-carboxamide hydrochloride salt Scheme C-27

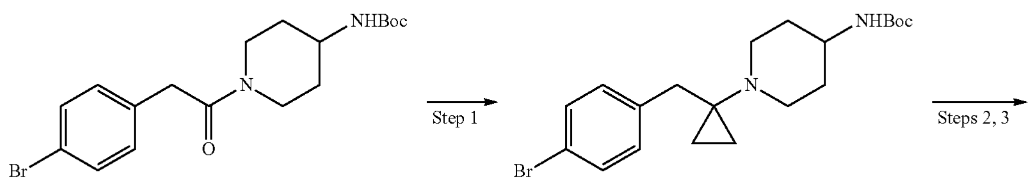

-continued

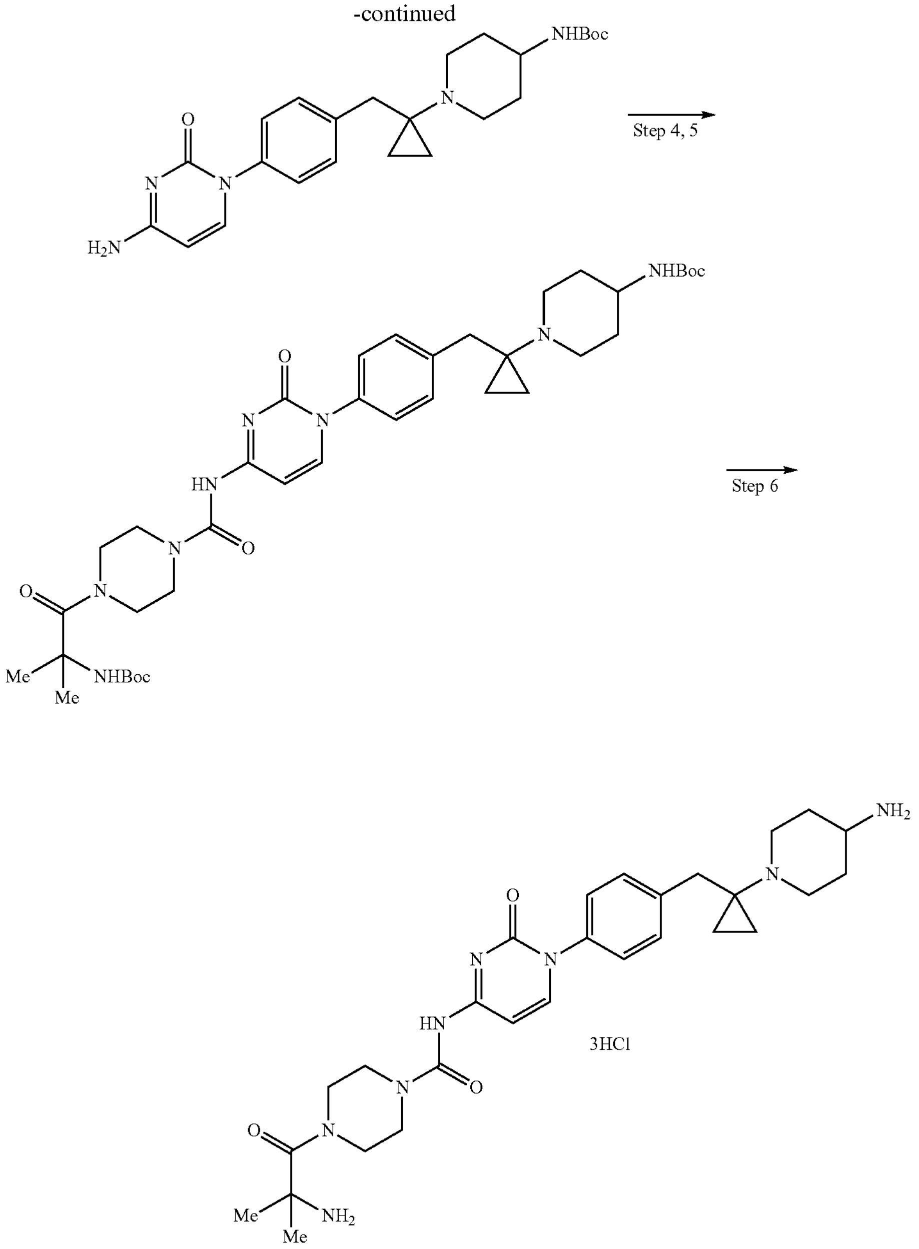

Reagents: 1) Ti($^i$OPr)$_4$, EtMgBr, THF, rt, 16 h 2) B(Pin)$_2$, KOAc, Pd(dppf)$Cl_2$, Dioxane, 110° C., 16 h 3) Cu(OAc)$_2$•$H_2O$, TMEDA, MeOH:$H_2O$ (4:1), rt, 48 h 4) CDI, $CH_2Cl_2$, 16 h 5) $CH_3CN$, reflux, 16 h 6) HCl MeOH, rt, 4 h.

Step 1

To a stirred solution of tert-butyl (1-(2-(4-bromophenyl) acetyl)piperidin-4-yl)carbamate (0.5 g, 1.26 mmol) and Ti(iOPr)$_4$ (0.76 mL, 2.52 mmol) was added ethyl magnesium bromide solution (3M in $Et_2O$, 2.1 mL, 6.30 mmol). The reaction mixture was stirred for 16 h at rt followed by the addition of a solution of Rochelle salt and dilution with ethyl acetate. The mixture was stirred for 96 h. The organic layer was separated, dried over $Na_2SO_4$, filtered and evaporated under reduced pressure to yield tert-butyl (1-(1-(4-bromobenzyl)cyclopropyl)piperidin-4-yl)carbamate as a yellow colored sticky solid which was used in next step without further purification.

Step 2: tert-butyl (1-(1-(4-(4,4,5,5-tetramethyl-1,3,2-dioxaborolan-2-yl)benzyl)cyclopropyl)piperidin-4-yl)carbamate To a stirred suspension of tert-butyl (1-(1-(4-bromobenzyl)cyclopropyl)piperidin-4-yl)carbamate (0.21 g, 0.5 mmol), bis (pinacolato) diboron (0.15 g, 0.6 mmol), and KOAc (0.15 g, 1.5 mmol) in a flame dried pressure flask was added Pd(dppf)$Cl_2$ (13 mg, 0.02 mmol) and the reaction mixture was purged with nitrogen. The pressure flask was sealed and stirred at 110° C. for 16 h. The mixture was diluted with ethyl acetate and filtered through celite. The filtrate was concentrated to give the title compound as a brown colored sticky solid.

Step 3. tert-butyl (1-(1-(4-(4-amino-2-oxopyrimidin-1(2H)-yl)benzyl)cyclopropyl)piperidin-4-yl) carbamate A suspension of cytosine (0.06 g, 0.5 mmol) and tert-butyl (1-(1-(4-(4,4,5,5-tetramethyl-1,3,2-dioxaborolan-2-yl)benzyl)cyclopropyl)piperidin-4-yl)carbamate (0.23 g, 0.5 mmol), in a mixture of 4:1 MeOH:$H_2O$ (10 ml) was stirred at rt in open air. After 30 min. TMEDA (0.09 ml, 0.6 mmol) and $Cu(OAc)_2 \cdot H_2O$ (0.10 g, 0.5 mmol) were added. The reaction was stirred in open air for 48 h at rt. The MeOH was evaporated reduced pressure, and the residue was crystallized with EtOH to yield the title compound.

Step 4. tert-butyl (1-(1-(4-(4-(1H-imidazole-1-carboxamido)-2-oxopyrimidin-1(2H)-yl)benzyl)cyclopropyl)piperidin-4-yl)carbamate To a stirred suspension of tert-butyl (1-(1-(4-(4-amino-2-oxopyrimidin-1(2H)-yl)benzyl)cyclopropyl)piperidin-4-yl) carbamate (0.05 g, 0.11 mmol) in dichloromethane (12 mL) was added CDI (24 mg, 0.14 mmol) and the mixture stirred for 16 h at rt. The solvent was evaporated under reduced pressure and the resultant solid was used in the next step without further purification.

Step 5. tert-butyl (1-(1-(4-(4-(4-(2-((tert-butoxycarbonyl)amino)-2-methylpropanoyl)piperazine-1-carboxamido)-2-oxopyrimidin-1(2H)-yl)benzyl)cyclopropyl) piperidin-4-yl)carbamate tert-Butyl (1-(1-(4-(4-(1H-imidazole-1-carboxamido)-2-oxopyrimidin-1(2H)-yl)benzyl)cyclopropyl)piperidin-4-yl) carbamate (60 mg, 0.11 mmol) and tert-butyl (2-methyl-1-oxo-1-(piperazin-1-yl)propan-2-yl)carbamate (37 mg, 0.14 mmol) were suspended in acetonitrile and refluxed for 16 h. The solvent was evaporated and the residue was diluted with ethyl acetate (12 mL) and extracted (3×8 mL). The organic layer was dried over $Na_2SO_4$, filtered and concentrated under reduced pressure to afford the title compound.

Step 6. 4-(2-amino-2-methylpropanoyl)-N-(1-(4-((1-(4-aminopiperidin-1-yl)cyclopropyl)methyl)phenyl)-2-oxo-1,2-dihydropyrimidin-4-yl)piperazine-1-carboxamide hydrochloride salt tert-Butyl (1-(1-(4-(4-(4-(2-((tert-butoxycarbonyl) amino)-2-methylpropanoyl)piperazine-1-carboxamido)-2-oxopyrimidin-1(2H)-yl)benzyl)cyclopropyl) piperidin-4-yl) carbamate (60 mg, 0.08 mmol) was dissolved in methanolic HCl and stirred for 4 h. The solvent was evaporated and the residue was purified using HPLC. Collection and evaporation of the desired fraction, addition and removal of methanolic HCl yielded the title compound as a brown solid. $^1H$ NMR (500 MHz, $D_2O$) δ 7.95 (d, 1H), 7.44 (br s, 2H), 7.41 (br s, 2H), 6.78 (d, 1H), 3.80-3.63 (m, 9H), 3.68-3.43 (m, 4H), 3.32 (s, 2H), 2.32 (d, 2H), 1.99-1.84 (m, 2H), 1.69 (s, 6H), 1.13 (br s, 2H), 0.86 (br s, 2H). LCMS [M+H] 537.36.

Biological Examples

Standard Microbiological Activity:

A certified BSL-2 laboratory was used for testing. Compounds were evaluated using the broth microdilution minimum inhibitory concentration (MIC) and minimum bactericidal concentration (MBC) assays defined by Clinical and Laboratory Standards Institute (CLSI) in the M26-A guideline against *S. aureus* (Sa), *E. coli* (Ec), *K. pneumoniae* (Kp), *A. baumannii* (Ab), *E. faecalis* (Ef) and *P. aeruginosa* (Pa).

*E. coli* S30 extract: Inhibition of bacterial protein synthesis was determined using the *E. coli* S30 Extract System for Circular DNA (Promega catalog #L-2010) and Luciferase Assay Reagent (Promega catalog #E1500) with slight modifications to a published protocol. Fyfe, C., Sutcliffe, J. A. and Grossman, T. H. (2012) "Development and characterization of a *Pseudomonas aeruginosa* in vitro coupled transcription-translation assay system for evaluation of translation inhibitors" J. Microbiol. Methods 90(3), 256-261.

Compounds were serial diluted in 0.5 mL microcentrifuge tubes by mixing and transferring 50 μL from the highest concentration to 50 μL of water, mixing and transferring 50 μL of this 2-fold dilution to 50 μL of water. This mixing and transferring was repeated so that there are a total of 8 tubes with serial dilutions of compound at 10× the desired screening concentration that are ultimately diluted to 1× by the addition of S30 luciferase synthesis mixture. Serial dilutions of compounds were added (2 μL) to wells in a black round bottom 96-well plate. Water (2 μL) was used as a "no inhibitor" control in 4 wells/plate. No DNA control reaction mixture (20 μL; see below) was used as a control in 4 wells/plate for background luminescence. S30 luciferase synthesis mixture (18 μL; see below) was added to wells with compounds or water mixture and incubated at 37° C. for 1 hour. Reactions were stopped by transferring to 4° C. refrigerator for 5 minutes then 25 μL of luciferase activity mix was added. Luminescence was measured using a BioTek Synergy HTX plate reader. % Inhibition was determined relative to no inhibitor controls.

S30 luciferase synthesis mixture:
- 445 μL S30 extract, circular
- 712 μL S30 Premix without amino acids
- 4.45 μL pBESTluc™ DNA (1 μg/μL)
- 78 μL complete amino acid mixture
- 267 μL water No DNA control:
- 20 μL S30 extract, circular
- 32 μL S30 Premix without amino acids
- 7 μL complete amino acid mixture
- 21 μL water Rabbit Reticulocyte lysate Inhibition of eukaryotic protein synthesis was determined using the Rabbit Reticulocyte Lysate System, Nuclease-Treated from Promega (catalog #L-4960) with slight modifications to the manufacturer's protocol. Compounds were serial diluted in 0.5 mL microcentrifuge tubes by mixing and transferring 50 μL from the highest concentration to 50 μL of water, mixing and transferring 50 μL of this 2-fold dilution to 50 μL of water. This mixing and transferring was repeated so that there are a total of 8 tubes with serial dilutions of compound at 10× the desired screening concentration that are ultimately diluted to 1× by the addition of rabbit reticulocyte luciferase synthesis mixture. Serial dilutions of compounds were added (2.5 L) to wells in a black round bottom 96-well plate. Water (2.5 μL) was used as a "no inhibitor" control in 4 wells/plate. No RNA control reaction mixture (2 μL; see below) was used as a control in 4 wells/plate for background luminescence. Rabbit reticulocyte luciferase synthesis mixture (22.5 μL; see below) was added to wells with compounds or water mixture and incubated at 30° C. for 90 minutes. Luciferase assay reagent (25 μL) was added with luminescence measured using a BioTek Synergy HTX plate reader. % Inhibition was determined relative to no inhibitor controls.

Rabbit reticulocyte luciferase synthesis mixture:
- 1,000 μL rabbit reticulocyte lysate
- 5.7 μL Luciferase Control RNA (1 μg/μL)
- 26 μL complete amino acid mixture
- 395 μL water No RNA Control
- 70 μL rabbit reticulocyte lysate
- 2 μL complete amino acid mixture
- 28 μL water Minimum Inhibitory Concentration (MIC)

MICs were determined using the Clinical Laboratory and Standards Institute (CLSI) Broth Microdilution Method with slight modification. Clinical and Laboratory Standards Institute (2012). "Methods for dilution antimicrobial susceptibility tests for bacteria that grow aerobically; approved standard, 9th ed. M07-A9. Clinical and Laboratory Standards Institute, Wayne, PA" Serial two-fold dilutions of compounds are prepared in sterile clear round-bottom 96-well plates.

To prepare microdilution trays, two-fold dilutions of antimicrobial agent are prepared in growth medium: Cation-Adjusted Mueller-Hinton Broth (CAMHB), or CAMHB supplemented with sodium bicarbonate (6.25 or 25 mM final concentration prepared from a 1.0M stock solution) or CAMHB supplemented with heat inactivated human serum (Fisher Cat. #BP2657100) 0-50% by adding 200 μL of the highest concentration to be tested (64 μg/mL, for example) in row A, mixing and transferring 100 μL from row A to 100 μL growth medium in row B, then repeating the mixing and transferring through row H of the 96-well plate, discarding the excess 100 μL remaining. This slight modification to the CLSI protocol enables evaluation of MICs for 3 compounds per plate in triplicate, albeit with only 8 compound dilutions (CLSI protocol enables 2 compounds in triplicate with 10 dilutions). Bacterial suspensions are added to a final concentration of $5\times10^4$ CFU/well by adding 5 μL of a 1:10 dilution of a 0.5 McFarland suspension ($1\times10^8$ CFU/mL) for each bacterium evaluated. Bacterial suspensions were prepared using the growth method described by CLSI. Well-isolated colonies (3-5 from an agar plate) were selected using a sterile loop and used to inoculate a tube containing 4 mL of CAMHB. The cultures are incubated at 35±2° C. until it achieves or exceeds the turbidity of the 0.5 McFarland standard, determined by measuring $A_{600nm}$ (usually two to six hours). When growth exceeds a 0.5 McFarland standard, the turbidity is adjusted with broth to be equivalent to a 0.5 McFarland standard.

Data for compounds is provided in Table 16. An $IC_{50}$ value (μM) that is 1 μM or greater (% inhibition is <50% @ 1 μM) is designated by a "+". An $IC_{50}$ value that is 0.5 μM or greater and less than 1 μM (% inhibition is >50% and <90% @ 1 μM) is designated by a "++". An $IC_{50}$ value that is less than 0.5 μM (% inhibition is >90% @ 1 μM) is designated by "+++". An MIC value (μg/mL) that is 32 μg/mL or greater is designated by a "+". An MIC value (μg/mL) that is 8 μg/mL or greater and less than 32 μg/mL is designated by a "++". An MIC value (μg/mL) that is less than 8 μg/mL is designated by "+++". "NA" means not available.

TABLE 16

Biological Activity of Compounds of Formula I or a pharmaceutically acceptable salt thereof

| No. | Sa + bicarb MIC | *E. coli* + bicarb MIC | Kp (1705) + bicarb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 1 | NA | NA | NA | NA | NA | NA | NA | ++ | + |
| 2 | NA | ++ | NA | + | + | NA | NA | +++ | + |
| 3 | NA | NA | NA | NA | NA | NA | NA | + | NA |
| 4 | NA | NA | NA | NA | NA | NA | NA | + | NA |
| 5 | NA | NA | NA | NA | NA | NA | NA | + | + |
| 6 | NA | NA | NA | NA | NA | NA | NA | + | + |
| 7 | NA | NA | NA | NA | NA | NA | NA | + | NA |
| 8 | NA | NA | NA | NA | NA | NA | NA | NA | NA |
| 9 | NA | NA | NA | NA | NA | NA | NA | + | NA |
| 10 | NA | NA | NA | NA | NA | NA | NA | +++ | + |
| 11 | NA | NA | NA | NA | NA | NA | NA | ++ | + |
| 12 | NA | + | + | NA | + | + | NA | ++ | + |
| 13 | NA | NA | NA | NA | NA | NA | NA | + | + |
| 14 | NA | NA | NA | NA | NA | NA | NA | NA | NA |
| 15 | NA | NA | NA | NA | NA | NA | NA | NA | NA |
| 16 | NA | NA | NA | NA | NA | NA | NA | + | + |
| 17 | NA | NA | NA | NA | NA | NA | NA | +++ | + |
| 18 | NA | NA | NA | NA | NA | NA | NA | +++ | + |
| 21 | +++ | +++ | +++ | +++ | ++ | + | +++ | +++ | + |
| 22 | +++ | +++ | ++ | NA | + | NA | NA | +++ | + |
| 23 | ++ | +++ | ++ | +++ | + | + | + | + | + |
| 24 | ++ | ++ | + | + | + | + | + | +++ | + |
| 25 | +++ | +++ | ++ | ++ | + | + | + | ++ | + |
| 26 | +++ | +++ | ++ | +++ | + | + | ++ | +++ | + |
| 27 | +++ | +++ | +++ | +++ | ++ | + | +++ | +++ | + |
| 28 | +++ | +++ | +++ | +++ | + | + | +++ | +++ | + |
| 29 | ++ | +++ | + | ++ | + | + | + | + | + |
| 30 | +++ | +++ | ++ | ++ | + | + | + | +++ | + |
| 31 | +++ | +++ | ++ | +++ | + | + | ++ | +++ | + |
| 32 | ++ | ++ | + | ++ | + | + | + | + | + |
| 33 | ++ | +++ | + | + | + | + | + | ++ | + |
| 34 | +++ | +++ | ++ | ++ | + | + | +++ | +++ | + |
| 35 | +++ | +++ | ++ | ++ | ++ | + | +++ | + | + |
| 36 | NA | NA | NA | NA | NA | NA | NA | + | + |
| 37 | NA | NA | NA | NA | NA | NA | NA | + | + |

TABLE 16-continued

Biological Activity of Compounds of Formula I or a pharmaceutically acceptable salt thereof

| No. | Sa + bicarb MIC | *E. coli* + bicarb MIC | Kp (1705) + bicarb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 38 | NA | NA | NA | NA | NA | NA | NA | + | + |
| 39 | NA | NA | NA | NA | NA | NA | NA | + | + |
| 40 | NA | NA | NA | NA | NA | NA | NA | + | + |
| 41 | NA | NA | NA | ++ | NA | + | ++ | +++ | + |
| 42 | NA | +++ | ++ | ++ | ++ | + | ++ | +++ | + |
| 43 | NA | +++ | +++ | ++ | ++ | + | ++ | +++ | + |
| 44 | NA | NA | NA | ++ | NA | + | +++ | +++ | + |
| 45 | NA | NA | NA | +++ | NA | + | +++ | +++ | + |
| 46 | NA | NA | NA | NA | NA | NA | NA | + | + |
| 47 | NA | NA | NA | NA | NA | NA | NA | + | + |
| 48 | NA | NA | NA | NA | NA | NA | NA | + | + |
| 49 | NA | + | + | NA | + | + | NA | + | + |
| 50 | NA | NA | NA | NA | NA | NA | NA | + | + |
| 51 | NA | NA | NA | NA | NA | NA | NA | + | + |
| 52 | NA | NA | NA | NA | NA | NA | NA | + | + |
| 53 | NA | NA | NA | NA | NA | NA | NA | + | + |
| 54 | NA | NA | NA | NA | NA | NA | NA | + | + |
| 55 | NA | NA | NA | NA | NA | NA | NA | ++ | + |
| 56 | NA | +++ | NA | + | + | NA | NA | +++ | + |
| 57 | +++ | +++ | ++ | +++ | + | + | ++ | +++ | + |
| 58 | NA | ++ | + | NA | + | + | NA | +++ | + |
| 59 | NA | + | + | NA | + | + | NA | + | + |
| 60 | NA | NA | NA | NA | NA | NA | NA | NA | + |
| 61 | +++ | +++ | + | ++ | + | + | ++ | +++ | + |
| 62 | + | +++ | + | + | + | + | + | +++ | + |
| 63 | NA | NA | NA | NA | NA | NA | NA | ++ | + |
| 64 | NA | + | NA | + | + | NA | NA | +++ | + |
| 65 | NA | +++ | NA | + | + | NA | NA | +++ | + |
| 66 | NA | NA | NA | NA | NA | NA | NA | + | + |
| 67 | NA | NA | NA | NA | NA | NA | NA | + | + |
| 68 | + | +++ | + | NA | + | NA | NA | ++ | + |
| 69 | NA | NA | NA | NA | NA | NA | NA | + | + |
| 70 | +++ | +++ | +++ | ++ | + | + | +++ | +++ | + |
| 71 | +++ | +++ | +++ | +++ | ++ | +++ | +++ | +++ | + |
| 72 | NA | NA | NA | NA | NA | NA | NA | ++ | + |
| 73 | NA | NA | NA | NA | NA | NA | NA | NA | + |
| 74 | NA | + | + | NA | + | + | NA | NA | + |
| 75 | NA | NA | NA | NA | NA | NA | NA | NA | + |
| 76 | NA | NA | NA | NA | NA | NA | NA | NA | + |
| 77 | NA | NA | NA | NA | NA | NA | NA | + | + |
| 78 | NA | NA | NA | NA | NA | NA | NA | + | + |
| 79 | +++ | +++ | ++ | ++ | + | + | ++ | +++ | + |
| 80 | NA | NA | NA | NA | NA | NA | NA | ++ | + |
| 81 | NA | NA | NA | NA | NA | NA | NA | + | + |
| 82 | +++ | +++ | ++ | ++ | + | ++ | +++ | +++ | + |
| 83 | NA | NA | NA | NA | NA | NA | NA | + | + |
| 84 | NA | NA | NA | NA | NA | NA | NA | + | + |
| 85 | + | +++ | + | NA | + | NA | NA | + | + |
| 86 | NA | NA | NA | NA | NA | NA | NA | + | + |
| 87 | NA | NA | NA | NA | NA | NA | NA | + | + |
| 88 | NA | NA | NA | NA | NA | NA | NA | + | + |
| 89 | NA | NA | NA | + | NA | + | + | +++ | + |
| 90 | +++ | +++ | +++ | +++ | + | +++ | +++ | +++ | + |
| 91 | NA | +++ | +++ | ++ | + | + | +++ | +++ | + |
| 92 | NA | + | NA | NA | NA | NA | NA | + | NA |
| 93 | NA | + | NA | NA | NA | NA | NA | + | NA |
| 94 | NA | NA | NA | NA | NA | NA | NA | + | + |
| 95 | ++ | +++ | ++ | ++ | + | + | + | +++ | + |
| 96 | +++ | +++ | + | NA | + | NA | NA | + | + |
| 97 | NA | ++ | NA | NA | NA | NA | NA | +++ | + |
| 98 | +++ | +++ | + | NA | + | NA | NA | +++ | + |
| 99 | NA | +++ | ++ | ++ | + | NA | NA | +++ | + |
| 100 | NA | NA | NA | NA | NA | NA | NA | ++ | + |
| 101 | NA | NA | NA | NA | NA | NA | NA | ++ | + |
| 102 | NA | NA | NA | NA | NA | NA | NA | + | + |
| 103 | NA | + | NA | NA | NA | + | NA | + | + |
| 104 | NA | NA | + | NA | NA | NA | NA | +++ | + |
| 105 | NA | NA | NA | NA | NA | NA | NA | +++ | +++ |
| 106 | NA | NA | NA | NA | NA | NA | NA | + | + |
| 107 | NA | NA | NA | NA | NA | NA | NA | + | + |
| 108 | NA | + | + | NA | NA | NA | NA | ++ | + |
| 109 | +++ | +++ | +++ | NA | + | NA | NA | +++ | + |
| 110 | +++ | +++ | ++ | +++ | + | + | ++ | +++ | + |

TABLE 16-continued

Biological Activity of Compounds of Formula I or a pharmaceutically acceptable salt thereof

| No. | Sa + bicarb MIC | *E. coli* + bicarb MIC | Kp (1705) + bicarb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 111 | ++ | ++ | + | + | + | + | + | ++ | + |
| 112 | ++ | ++ | + | + | + | + | + | +++ | + |
| 113 | ++ | ++ | + | + | + | + | + | +++ | + |
| 114 | + | +++ | ++ | ++ | + | + | + | +++ | + |
| 115 | +++ | +++ | + | + | + | + | ++ | +++ | + |
| 116 | ++ | +++ | ++ | ++ | + | + | ++ | +++ | + |
| 117 | +++ | +++ | +++ | +++ | + | + | +++ | +++ | + |
| 118 | +++ | +++ | +++ | +++ | ++ | ++ | +++ | +++ | + |
| 119 | +++ | +++ | +++ | +++ | +++ | +++ | +++ | +++ | + |
| 120 | +++ | +++ | ++ | ++ | + | + | ++ | +++ | + |
| 121 | +++ | +++ | +++ | +++ | + | + | +++ | +++ | + |
| 122 | +++ | +++ | +++ | +++ | + | + | +++ | +++ | + |
| 123 | +++ | +++ | ++ | +++ | + | + | + | +++ | + |
| 124 | +++ | +++ | +++ | +++ | + | + | +++ | +++ | + |
| 125 | +++ | +++ | +++ | +++ | + | + | +++ | +++ | + |
| 126 | ++ | +++ | ++ | ++ | + | + | + | +++ | + |
| 127 | +++ | +++ | +++ | +++ | + | + | +++ | +++ | + |
| 128 | +++ | +++ | ++ | +++ | ++ | + | +++ | +++ | + |
| 129 | +++ | +++ | +++ | +++ | ++ | +++ | +++ | +++ | + |
| 130 | +++ | +++ | +++ | +++ | ++ | ++ | +++ | +++ | + |
| 131 | +++ | +++ | +++ | +++ | ++ | +++ | +++ | +++ | + |
| 132 | +++ | +++ | + | + | + | + | + | +++ | + |
| 133 | NA | NA | NA | + | NA | + | + | +++ | + |
| 134 | NA | +++ | NA | ++ | + | + | ++ | +++ | + |
| 135 | NA | NA | NA | NA | NA | NA | NA | + | + |
| 136 | ++ | ++ | ++ | + | + | + | ++ | +++ | + |
| 137 | ++ | +++ | ++ | + | + | + | + | +++ | + |
| 138 | +++ | +++ | + | + | + | + | + | ++ | + |
| 139 | +++ | +++ | ++ | ++ | ++ | + | +++ | +++ | + |
| 140 | +++ | +++ | +++ | +++ | ++ | ++ | +++ | +++ | + |
| 141 | +++ | +++ | +++ | ++ | ++ | + | +++ | +++ | + |
| 142 | +++ | +++ | ++ | + | ++ | ++ | +++ | +++ | + |
| 143 | + | + | + | + | + | + | + | + | + |
| 144 | + | + | + | + | + | + | + | + | + |
| 145 | + | + | + | + | + | + | + | ++ | + |
| 146 | + | + | + | + | + | + | + | + | + |
| 147 | + | + | + | + | + | + | + | + | + |
| 148 | + | + | + | + | + | + | + | +++ | + |
| 149 | +++ | +++ | ++ | ++ | + | + | ++ | +++ | + |
| 150 | +++ | +++ | + | + | + | + | + | ++ | + |
| 151 | +++ | +++ | ++ | +++ | ++ | + | +++ | +++ | + |
| 152 | +++ | +++ | ++ | +++ | + | + | + | + | + |
| 153 | +++ | +++ | ++ | ++ | + | + | + | + | + |
| 154 | +++ | +++ | +++ | +++ | + | + | +++ | +++ | + |
| 155 | ++ | +++ | + | ++ | + | + | + | + | + |
| 156 | +++ | +++ | ++ | +++ | + | + | ++ | +++ | + |
| 157 | +++ | +++ | ++ | +++ | + | + | +++ | +++ | + |
| 158 | +++ | +++ | +++ | +++ | ++ | + | +++ | +++ | + |
| 159 | +++ | +++ | ++ | +++ | + | + | ++ | +++ | + |
| 160 | +++ | +++ | +++ | +++ | + | + | +++ | +++ | + |
| 161 | +++ | +++ | +++ | +++ | + | ++ | +++ | +++ | + |
| 162 | +++ | +++ | ++ | ++ | + | + | ++ | +++ | + |
| 163 | ++ | ++ | + | + | + | + | + | + | + |
| 164 | +++ | +++ | +++ | +++ | + | ++ | +++ | +++ | + |
| 165 | + | ++ | + | ++ | + | + | + | + | + |
| 166 | ++ | ++ | + | + | + | + | + | + | + |
| 167 | ++ | +++ | + | + | + | + | ++ | + | + |
| 168 | NA | NA | NA | ++ | NA | + | ++ | +++ | + |
| 169 | +++ | +++ | +++ | +++ | ++ | ++ | +++ | +++ | + |
| 170 | ++ | +++ | +++ | ++ | ++ | + | + | +++ | + |
| 171 | ++ | +++ | + | + | + | + | + | + | + |
| 172 | +++ | +++ | + | ++ | + | + | +++ | +++ | + |
| 173 | +++ | +++ | + | ++ | + | + | ++ | +++ | + |
| 174 | +++ | +++ | ++ | ++ | + | ++ | +++ | +++ | + |
| 175 | +++ | +++ | +++ | +++ | ++ | + | +++ | +++ | + |
| 176 | +++ | +++ | ++ | ++ | + | + | +++ | +++ | + |
| 177 | +++ | +++ | ++ | ++ | + | + | + | + | + |
| 178 | ++ | +++ | + | ++ | + | + | + | + | + |
| 179 | +++ | +++ | ++ | ++ | + | + | ++ | +++ | + |
| 180 | ++ | +++ | + | ++ | + | + | + | ++ | + |
| 181 | +++ | +++ | ++ | ++ | + | + | ++ | +++ | + |
| 182 | + | ++ | + | + | + | + | + | + | + |
| 183 | + | + | + | + | + | + | + | + | + |

TABLE 16-continued

Biological Activity of Compounds of Formula I or a pharmaceutically acceptable salt thereof

| No. | Sa + bicarb MIC | *E. coli* + bicarb MIC | Kp (1705) + bicarb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 184 | +++ | +++ | + | ++ | + | + | ++ | +++ | + |
| 185 | +++ | +++ | + | ++ | + | + | ++ | +++ | + |
| 186 | +++ | +++ | ++ | ++ | + | + | ++ | +++ | + |
| 187 | +++ | +++ | +++ | +++ | + | ++ | +++ | +++ | + |
| 188 | +++ | +++ | ++ | ++ | + | + | +++ | +++ | + |
| 190 | +++ | +++ | ++ | ++ | + | + | +++ | +++ | + |
| 191 | +++ | +++ | + | ++ | + | + | ++ | ++ | + |
| 192 | +++ | +++ | ++ | ++ | + | + | ++ | + | + |
| 193 | +++ | +++ | ++ | ++ | + | + | ++ | +++ | + |
| 194 | + | +++ | + | + | + | + | + | ++ | + |
| 195 | ++ | + | + | + | + | + | + | ++ | + |
| 196 | NA | NA | NA | NA | NA | NA | NA | +++ | + |
| 197 | NA | NA | NA | NA | NA | NA | NA | + | NA |
| 198 | ++ | +++ | ++ | +++ | + | + | ++ | +++ | + |
| 199 | ++ | +++ | + | ++ | + | + | + | +++ | + |
| 200 | ++ | ++ | ++ | ++ | ++ | + | ++ | +++ | + |
| 201 | + | + | + | + | + | + | + | + | + |
| 204 | NA | NA | NA | NA | NA | NA | NA | ++ | + |
| 205 | ++ | +++ | ++ | + | + | + | + | +++ | + |
| 206 | NA | NA | NA | NA | NA | NA | NA | + | + |
| 207 | NA | NA | NA | NA | NA | NA | NA | + | + |
| 208 | NA | ++ | + | NA | NA | NA | NA | + | NA |
| 209 | + | +++ | + | + | + | + | + | + | + |
| 210 | +++ | +++ | ++ | ++ | + | + | +++ | +++ | + |
| 211 | +++ | +++ | + | ++ | + | + | ++ | ++ | + |
| 212 | +++ | +++ | + | + | + | + | +++ | ++ | + |
| 213 | +++ | +++ | ++ | ++ | + | + | +++ | +++ | + |
| 214 | NA | +++ | + | NA | NA | NA | NA | +++ | NA |
| 215 | NA | +++ | + | NA | NA | NA | NA | +++ | NA |
| 216 | NA | ++ | + | NA | NA | NA | NA | + | NA |
| 217 | NA | NA | NA | NA | NA | NA | NA | NA | NA |
| 218 | NA | +++ | +++ | NA | NA | NA | NA | +++ | + |
| 219 | +++ | +++ | ++ | ++ | + | + | ++ | ++ | + |
| 220 | +++ | +++ | ++ | +++ | + | ++ | ++ | +++ | + |
| 221 | NA | +++ | +++ | NA | NA | NA | NA | +++ | + |
| 222 | NA | +++ | +++ | NA | NA | NA | NA | +++ | + |
| 223 | NA | +++ | ++ | ++ | + | + | +++ | ++ | + |
| 224 | NA | +++ | + | NA | NA | NA | NA | +++ | + |
| 225 | NA | NA | NA | NA | NA | NA | NA | + | + |
| 226 | NA | +++ | +++ | NA | NA | NA | NA | +++ | + |
| 227 | + | ++ | + | + | + | + | + | + | + |
| 230 | NA | ++ | + | NA | NA | NA | NA | + | + |
| 231 | NA | NA | NA | NA | NA | NA | NA | + | + |
| 233 | +++ | +++ | + | + | + | + | + | + | + |
| 234 | NA | + | + | NA | NA | NA | NA | + | + |
| 235 | NA | + | + | NA | NA | NA | NA | + | + |
| 236 | NA | +++ | + | NA | NA | NA | NA | + | + |
| 237 | NA | +++ | + | NA | NA | NA | NA | ++ | + |
| 238 | NA | +++ | ++ | NA | NA | NA | NA | + | + |
| 239 | NA | +++ | ++ | NA | NA | NA | NA | +++ | + |
| 240 | NA | + | + | NA | NA | NA | NA | ++ | + |
| 241 | NA | ++ | + | NA | NA | NA | NA | +++ | + |
| 242 | +++ | +++ | + | + | + | + | ++ | +++ | + |
| 243 | +++ | +++ | ++ | ++ | + | + | ++ | +++ | + |
| 244 | NA | +++ | + | NA | NA | NA | NA | + | + |
| 245 | +++ | +++ | +++ | +++ | + | + | +++ | +++ | + |
| 246 | NA | +++ | + | NA | NA | NA | NA | + | + |
| 247 | +++ | +++ | +++ | +++ | + | + | +++ | +++ | + |
| 248 | NA | +++ | + | NA | NA | NA | NA | +++ | + |
| 249 | +++ | +++ | ++ | +++ | + | + | ++ | +++ | + |
| 250 | NA | +++ | + | NA | NA | NA | NA | +++ | + |
| 251 | +++ | +++ | ++ | ++ | + | + | +++ | +++ | + |
| 252 | NA | +++ | ++ | NA | NA | NA | NA | +++ | + |
| 253 | NA | +++ | + | NA | NA | NA | NA | +++ | + |
| 254 | +++ | +++ | ++ | ++ | + | +++ | +++ | ++ | + |
| 255 | NA | +++ | ++ | NA | NA | NA | NA | +++ | + |
| 267 | NA | +++ | + | NA | NA | NA | NA | +++ | + |
| 268 | ++ | ++ | + | + | + | + | + | + | + |
| 269 | + | ++ | + | ++ | + | + | + | + | + |
| 270 | +++ | +++ | +++ | +++ | ++ | +++ | +++ | +++ | + |
| 271 | +++ | +++ | +++ | +++ | + | + | +++ | +++ | + |
| 272 | +++ | +++ | +++ | +++ | ++ | +++ | +++ | +++ | + |
| 273 | +++ | +++ | +++ | +++ | ++ | +++ | +++ | +++ | + |

TABLE 16-continued

Biological Activity of Compounds of Formula I or a pharmaceutically acceptable salt thereof

| No. | Sa + bicarb MIC | *E. coli* + bicarb MIC | Kp (1705) + bicarb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 274 | +++ | +++ | +++ | +++ | ++ | +++ | +++ | +++ | + |
| 275 | +++ | +++ | +++ | +++ | ++ | +++ | +++ | +++ | + |
| 276 | +++ | +++ | + | + | + | + | +++ | ++ | + |
| 277 | +++ | +++ | +++ | +++ | + | + | +++ | +++ | + |
| 278 | +++ | +++ | +++ | +++ | ++ | ++ | +++ | +++ | + |
| 279 | +++ | +++ | ++ | ++ | + | + | ++ | + | + |
| 280 | +++ | +++ | ++ | +++ | + | + | +++ | ++ | + |
| 281 | +++ | +++ | ++ | +++ | ++ | + | +++ | +++ | + |
| 282 | +++ | +++ | + | ++ | + | + | + | + | + |
| 283 | +++ | +++ | ++ | +++ | + | + | +++ | +++ | + |
| 284 | +++ | +++ | +++ | +++ | ++ | +++ | +++ | +++ | + |
| 285 | +++ | +++ | +++ | +++ | ++ | +++ | +++ | +++ | + |
| 286 | +++ | +++ | +++ | +++ | + | + | +++ | +++ | + |
| 287 | +++ | +++ | +++ | +++ | ++ | + | +++ | +++ | + |
| 288 | +++ | +++ | +++ | +++ | + | + | +++ | +++ | + |
| 289 | +++ | +++ | + | ++ | + | + | + | ++ | + |
| 290 | +++ | +++ | ++ | +++ | + | +++ | +++ | ++ | + |
| 291 | +++ | ++ | + | + | + | ++ | ++ | + | + |
| 292 | + | + | + | + | + | + | + | + | + |
| 293 | +++ | +++ | +++ | +++ | + | ++ | +++ | +++ | + |
| 294 | +++ | +++ | +++ | +++ | + | + | ++ | +++ | + |
| 295 | + | + | + | + | + | + | + | + | + |
| 296 | +++ | +++ | ++ | ++ | + | + | +++ | +++ | + |
| 297 | +++ | +++ | + | + | + | + | ++ | ++ | + |
| 298 | +++ | +++ | + | ++ | + | + | ++ | +++ | + |
| 299 | +++ | +++ | + | ++ | + | + | ++ | ++ | + |
| 300 | ++ | + | + | + | + | + | + | + | + |
| 301 | +++ | +++ | +++ | +++ | + | ++ | +++ | ++ | + |
| 302 | +++ | +++ | +++ | +++ | + | +++ | +++ | +++ | + |
| 303 | +++ | +++ | + | + | + | + | + | + | + |
| 304 | +++ | +++ | ++ | ++ | + | + | +++ | +++ | + |
| 305 | +++ | +++ | +++ | +++ | + | + | +++ | +++ | + |
| 306 | +++ | +++ | + | + | + | + | + | + | + |
| 307 | +++ | +++ | ++ | +++ | ++ | + | + | +++ | + |
| 308 | + | + | + | + | + | + | + | + | + |
| 309 | + | + | + | + | + | + | + | ++ | + |
| 310 | ++ | +++ | + | + | + | + | + | ++ | + |
| 311 | +++ | +++ | + | ++ | + | + | ++ | +++ | + |
| 312 | +++ | +++ | + | + | + | + | + | + | + |
| 313 | +++ | +++ | + | + | + | + | + | ++ | + |
| 314 | + | +++ | + | + | + | + | + | + | + |
| 315 | ++ | ++ | + | + | + | + | + | + | + |
| 316 | +++ | +++ | + | ++ | + | + | ++ | +++ | + |
| 317 | +++ | +++ | + | + | + | + | ++ | +++ | + |
| 318 | +++ | +++ | + | + | + | + | + | +++ | + |
| 319 | ++ | ++ | + | + | + | + | + | ++ | + |
| 320 | ++ | +++ | + | + | + | + | + | +++ | + |
| 321 | + | ++ | ++ | ++ | + | + | + | +++ | + |
| 322 | + | ++ | + | + | + | + | + | ++ | + |
| 323 | ++ | +++ | + | + | + | + | + | +++ | + |
| 324 | ++ | +++ | + | + | + | + | + | +++ | + |
| 325 | + | ++ | + | + | + | + | + | +++ | + |
| 326 | ++ | +++ | + | + | + | + | + | +++ | + |
| 327 | ++ | +++ | + | ++ | + | + | + | +++ | + |
| 328 | +++ | +++ | + | + | + | + | +++ | +++ | + |
| 329 | +++ | +++ | + | + | + | + | +++ | +++ | + |
| 330 | ++ | +++ | + | ++ | + | + | + | +++ | + |
| 331 | ++ | +++ | + | + | + | + | ++ | +++ | + |
| 332 | ++ | +++ | + | + | + | + | ++ | +++ | + |
| 333 | ++ | ++ | + | + | + | + | + | +++ | + |
| 334 | ++ | +++ | + | + | + | + | + | +++ | + |
| 335 | +++ | +++ | ++ | ++ | + | + | + | +++ | + |
| 336 | + | ++ | + | + | + | + | + | + | + |
| 337 | +++ | +++ | + | + | + | + | ++ | +++ | + |
| 338 | +++ | +++ | + | ++ | + | + | ++ | +++ | + |
| 339 | ++ | +++ | + | + | + | + | + | +++ | + |
| 340 | ++ | +++ | + | + | + | + | + | ++ | + |
| 341 | ++ | ++ | + | + | + | + | + | ++ | + |
| 342 | + | ++ | + | + | + | + | + | +++ | + |
| 343 | + | ++ | + | + | + | + | + | ++ | + |
| 344 | + | + | + | + | + | + | + | + | + |
| 345 | + | + | + | + | + | + | + | ++ | + |
| 346 | + | + | + | + | + | + | + | ++ | + |

TABLE 16-continued

Biological Activity of Compounds of Formula I or a pharmaceutically acceptable salt thereof

| No. | Sa + bicarb MIC | *E. coli* + bicarb MIC | Kp (1705) + bicarb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 347 | ++ | +++ | + | + | + | + | + | ++ | + |
| 348 | ++ | +++ | + | + | + | + | + | +++ | + |
| 349 | ++ | +++ | + | NA | NA | NA | NA | +++ | ++ |
| 350 | NA | NA | NA | NA | NA | NA | NA | + | + |
| 351 | NA | NA | NA | NA | NA | NA | NA | + | + |
| 352 | + | ++ | + | + | + | + | + | +++ | + |
| 353 | ++ | +++ | + | + | + | + | + | +++ | + |
| 354 | +++ | +++ | + | + | + | + | ++ | +++ | + |
| 355 | +++ | +++ | + | + | + | + | +++ | +++ | + |
| 356 | + | + | + | + | + | + | + | + | + |
| 357 | +++ | +++ | + | + | + | + | ++ | +++ | + |
| 358 | +++ | +++ | + | + | + | + | ++ | ++ | + |
| 359 | ++ | + | + | + | + | + | + | + | + |
| 360 | NA | NA | NA | NA | NA | NA | NA | +++ | + |
| 361 | NA | NA | NA | NA | NA | NA | NA | + | + |
| 362 | NA | NA | NA | NA | NA | NA | NA | + | + |
| 363 | NA | NA | NA | NA | NA | NA | NA | + | + |
| 364 | NA | NA | NA | NA | NA | NA | NA | +++ | + |
| 365 | +++ | +++ | ++ | +++ | + | + | +++ | +++ | + |
| 366 | NA | NA | NA | NA | NA | NA | NA | + | NA |
| 367 | NA | NA | NA | NA | NA | NA | NA | + | + |
| 368 | NA | NA | NA | NA | NA | NA | NA | + | + |
| 369 | NA | NA | NA | NA | NA | NA | NA | + | + |
| 370 | +++ | +++ | ++ | ++ | + | + | +++ | +++ | + |
| 371 | ++ | +++ | ++ | ++ | + | + | ++ | +++ | + |
| 372 | +++ | +++ | ++ | +++ | + | + | + | + | + |
| 373 | +++ | +++ | + | ++ | + | + | ++ | + | + |
| 374 | ++ | +++ | + | ++ | + | + | ++ | +++ | + |
| 376 | +++ | +++ | ++ | +++ | + | + | +++ | +++ | + |
| 376 | + | ++ | + | + | + | + | + | +++ | + |
| 377 | +++ | +++ | ++ | ++ | + | + | + | +++ | + |
| 378 | +++ | +++ | ++ | ++ | + | + | ++ | +++ | + |
| 379 | +++ | +++ | + | + | + | + | + | + | + |
| 380 | +++ | +++ | ++ | ++ | + | + | ++ | +++ | + |
| 381 | NA | +++ | NA | NA | NA | NA | NA | +++ | + |
| 382 | +++ | +++ | +++ | +++ | ++ | + | +++ | +++ | + |
| 383 | NA | NA | NA | NA | NA | NA | NA | + | + |

The invention claimed is:

1. A compound of formula I:

I

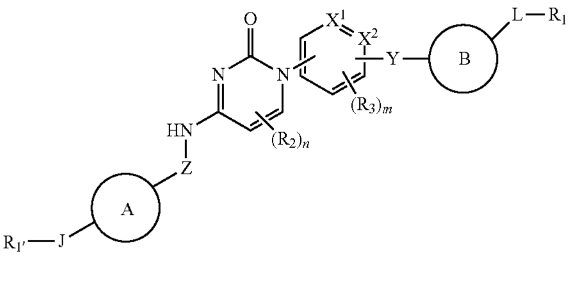

or a pharmaceutically acceptable salt thereof, wherein:

Z is (C═O), (C═S), (C═$NR_z$), (S═O), or $SO_2$; wherein $R_z$ is H, $C_1$-$C_6$ alkyl, or CN;

ring A is a monocyclic heterocycloalkylene or bicyclic heterocycloalkylene, wherein the monocyclic heterocycloalkylene or bicyclic heterocycloalkylene are optionally substituted with up to three substituents independently selected from the group consisting of $C_1$-$C_6$ alkyl, $C_1$-$C_6$ alkoxy, $C_1$-$C_6$ hydroxyalkyl, halo, CN, $C_1$-$C_6$ haloalkyl, phenyl, OH, $NH_2$, NH($C_1$-$C_6$ alkyl), N($C_1$-$C_6$ alkyl)$_2$, COOH, COO($C_1$-$C_6$ alkyl), $CONH_2$, and oxo;

J is absent or is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to three substituents independently selected from the group consisting of halo, $C_1$-$C_6$ alkyl, $C_1$-$C_6$ alkoxy, $C_1$-$C_6$ haloalkyl, $NH_2$, CN, and OH; wherein at each occurrence of $C_1$-$C_6$ alkylene, up to two methylene units of the $C_1$-$C_6$ alkylene may independently and optionally be replaced with O, S, $SO_2$, C═O, or

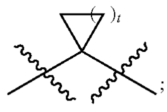

;

wherein t is 1, 2, 3, or 4;

$X^1$ and $X^2$ are each independently C—H or N;

Y is a linear $C_1$-$C_8$ alkylene, $C_2$-$C_8$ alkenylene, or $C_2$-$C_8$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), N—($C_{3-8}$ cycloalkyl), NH(C═O), N—($C_{1-6}$ alkyl) (C═O), (C═O), or

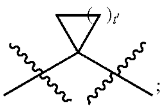;

wherein t' is 1, 2, 3, or 4;

ring B is a monocyclic cycloalkylene or monocyclic heterocycloalkylene, either of which is optionally substituted with up to three substituents independently selected from the group consisting of $C_1$-$C_6$ alkyl, $C_1$-$C_6$ alkoxy, halo, CN, $NH_2$, $C_1$-$C_6$ haloalkyl, OH, COOH, COO($C_1$-$C_6$ alkyl), $CONH_2$, and $C_1$-$C_6$ hydroxyalkyl;

L is absent, or is a $C_1$-$C_6$ alkylene, wherein up to two methylene units of the $C_1$-$C_6$ alkylene may independently be replaced with O, NH, (C═O), NH(C═O), N—($C_{1-6}$ alkyl)(C═O), (C═NH), NH(C═N), or N—($C_{1-6}$ alkyl);

$R_1$ is H, halo, $C_1$-$C_6$ haloalkyl, $NR_{x'}R_{y'}$, or monocyclic heterocycloalkyl optionally substituted with $NH_2$, NH($C_1$-$C_6$ alkyl), N($C_1$-$C_6$ alkyl)$_2$, wherein $R_{x'}$ and $R_{y'}$ are each independently H, $C_1$-$C_6$ alkyl, $C_3$-$C_8$ cycloalkyl, or an amino protecting group, wherein the $C_1$-$C_6$ alkyl and $C_3$-$C_8$ cycloalkyl are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$CONH_2$, and oxo; or $R_1$ is NH(C═O)-($C_1$-$C_6$) alkyl, or NH—(C═NH)—$NH_2$, either of which may be optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, COO($C_1$-$C_6$ alkyl), $CONH_2$, and oxo;

$R_{1'}$ is H or $NR_xR_y$, wherein $R_x$ and $R_y$ are each independently H, $C_1$-$C_6$ alkyl, $C_1$-$C_6$ alkyl-$SO_3$, CO($C_1$-$C_6$ alkyl), CO—($C_1$-$C_6$ alkylene)-$NH_2$, or an amino protecting group;

$R_2$ and $R_3$ are each independently selected from the group consisting of $C_1$-$C_6$ alkyl, halo, CN, OH, $NH_2$, O($C_1$-$C_6$ haloalkyl), NH($C_1$-$C_6$ alkyl), N($C_1$-$C_6$ alkyl)$_2$, —COO($C_1$-$C_6$ alkyl), —$CONH_2$, $C_1$-$C_6$ haloalkyl, $C_1$-$C_6$ alkoxy, and $C_1$-$C_6$ haloalkoxy; and m and n are each independently 0, 1, 2, or 3.

2. The compound of claim 1 or a pharmaceutically acceptable salt thereof, wherein Z is —(C═O)—;

ring A is a 4 to 8 membered monocyclic heterocycloalkylene or 6 to 12 membered bicyclic heterocycloalkylene, wherein the monocyclic heterocycloalkylene and bicyclic heterocycloalkylene are optionally substituted with up to three substituents independently selected from the group consisting of $C_1$-$C_6$ alkyl, $C_1$-$C_6$ alkoxy, $C_1$-$C_6$ hydroxyalkyl, halo, $C_1$-$C_6$ haloalkyl, phenyl, OH, $NH_2$, COOH, COO($C_1$-$C_6$ alkyl), and —$CONH_2$; and wherein J is absent or J is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to two substituents independently selected from the group consisting of halo, $C_1$-$C_6$ alkyl, $C_1$-$C_6$ alkoxy, $C_1$-$C_6$ haloalkyl, $NH_2$, CN, and OH; wherein at each occurrence of $C_1$-$C_6$ alkylene, one or two methylene units of the $C_1$-$C_6$ alkylene may independently and optionally be replaced with C═O or

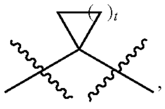, wherein t is 1, 2, or 3; and $R_{1'}$ is H, $NH_2$, NH($C_1$-$C_6$ alkyl), or NH($C_1$-$C_6$ alkyl)$_2$.

3. The compound of claim 2 or a pharmaceutically acceptable salt thereof, wherein:

ring A is selected from the group consisting of

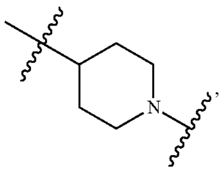, 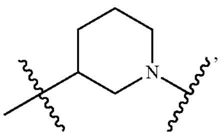,

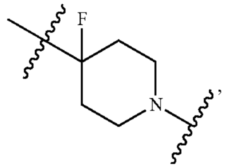, 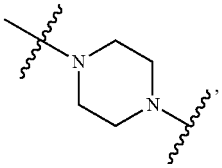,

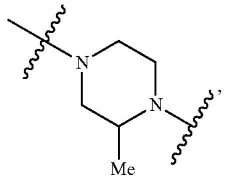, 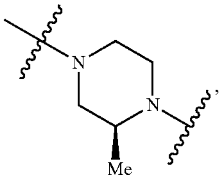,

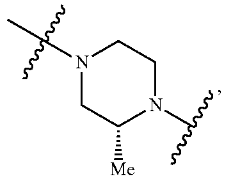, 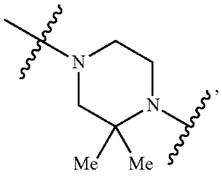,

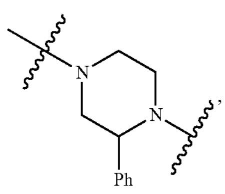, 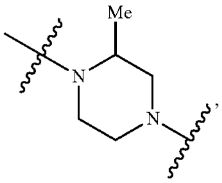,

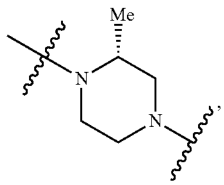, 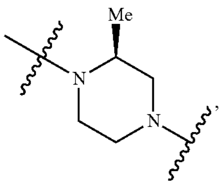,

-continued
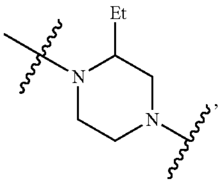
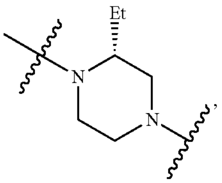
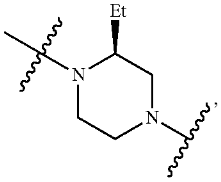
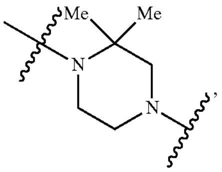
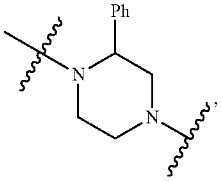
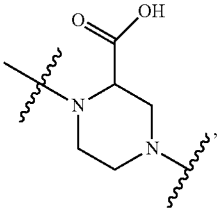
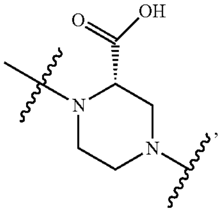
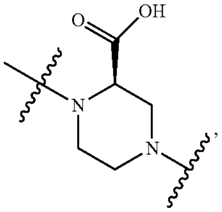
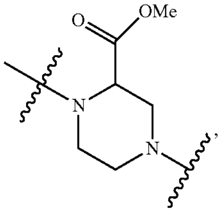
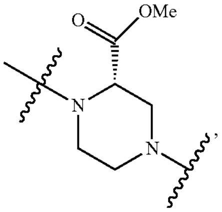
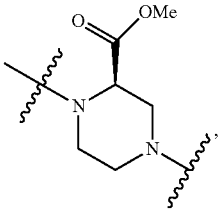
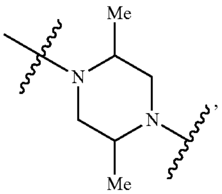
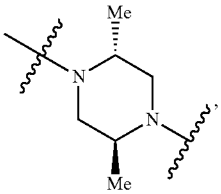
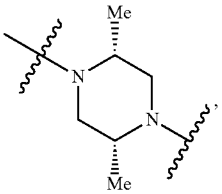
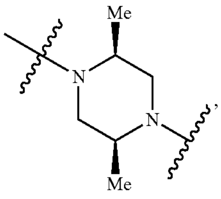
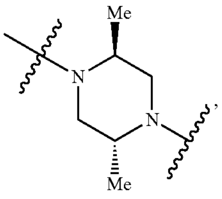
-continued
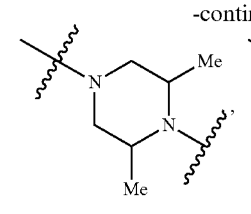
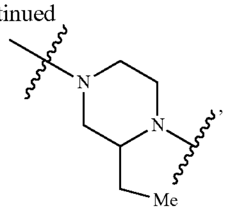
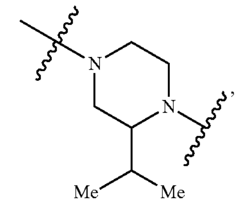
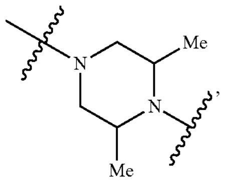
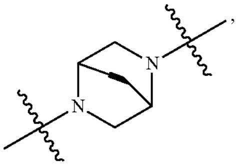
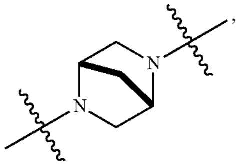
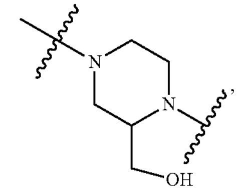
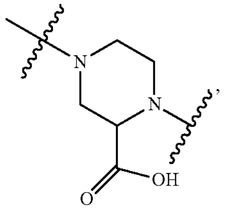
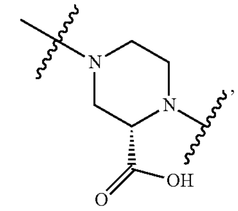
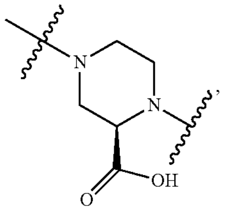
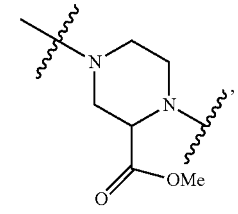
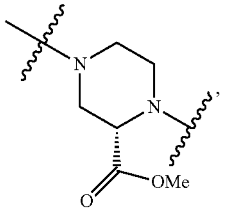
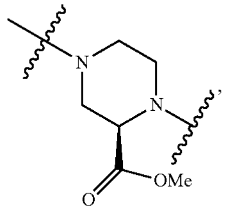
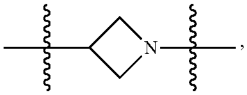
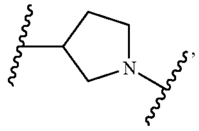
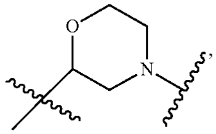

-continued
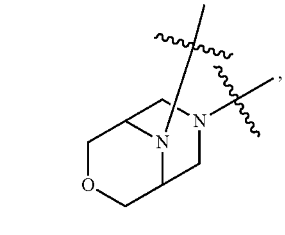,
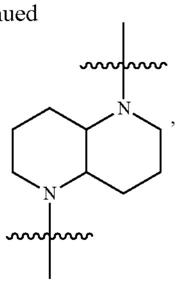,
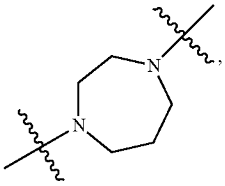,
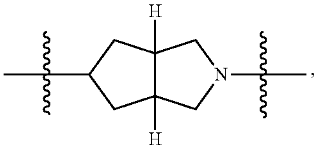,
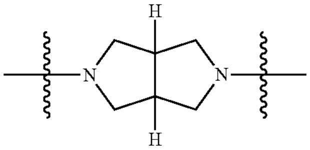,
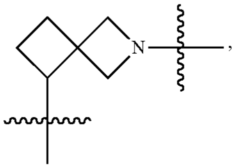,
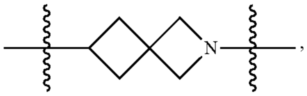,
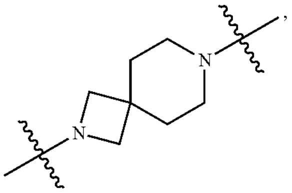, and
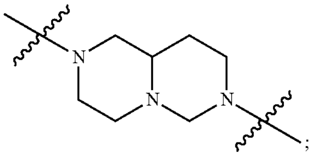;
and
J is selected from the group consisting of —$CH_2$—,
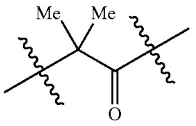,
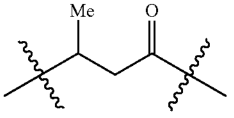,
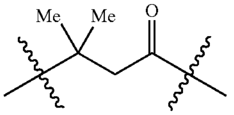,
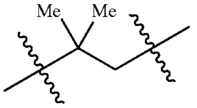,
-continued
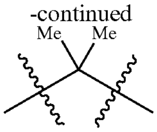
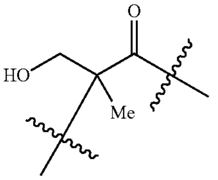,
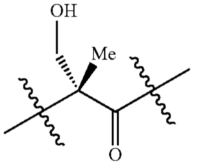,
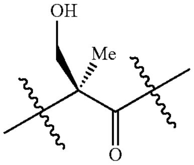,
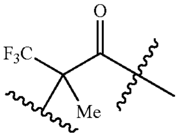,
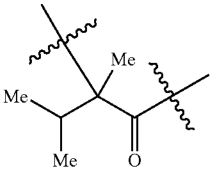,
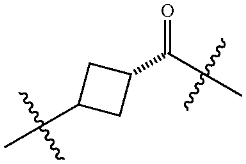,
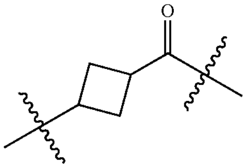,
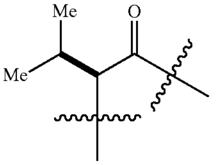,
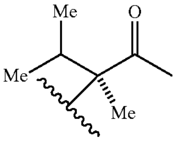,
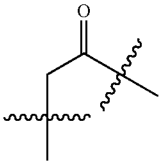,
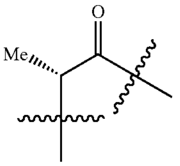,
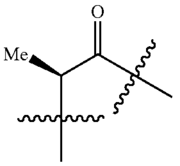, -continued
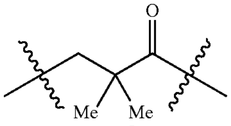
,
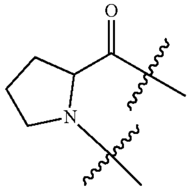
,
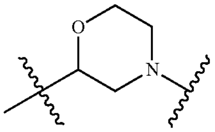
,
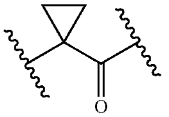
,
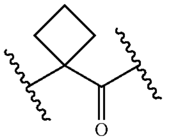
,
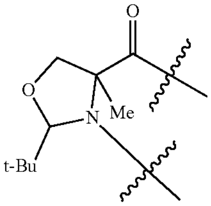
,
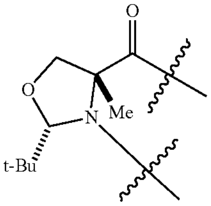
, and
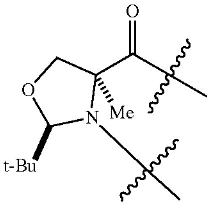
.
4. The compound of claim 3 or a pharmaceutically acceptable salt thereof, wherein
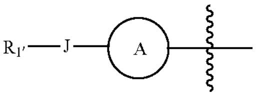
is selected from the group consisting of
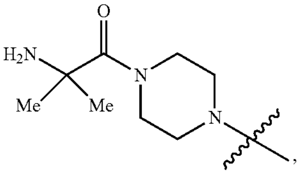
,
-continued
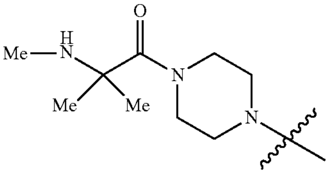
,
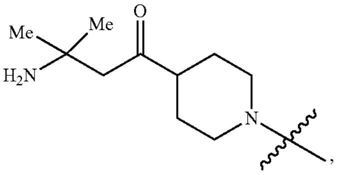
,
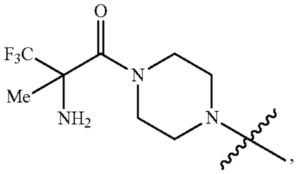
,
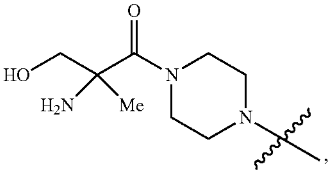
,
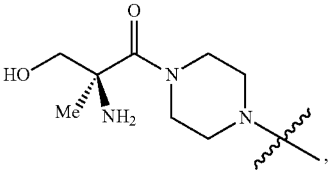
,
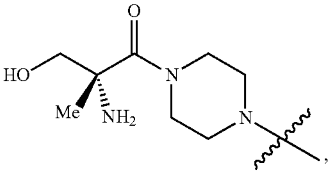
,
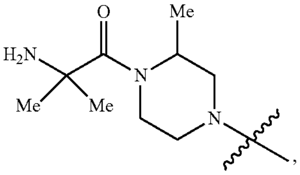
,
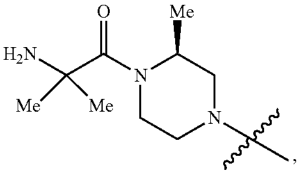
,
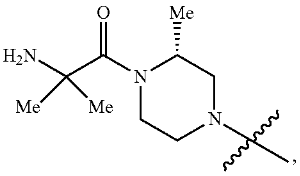
, -continued
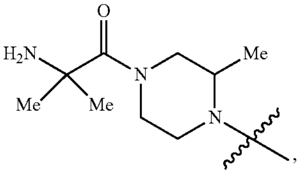,
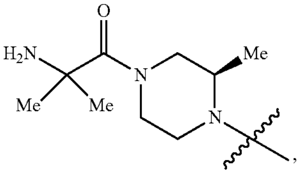,
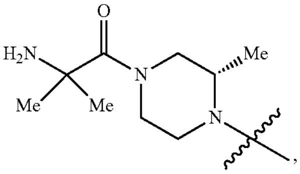, 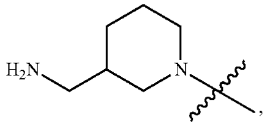,
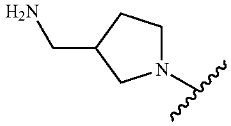, 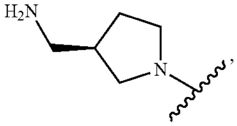,
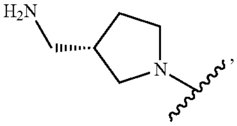, 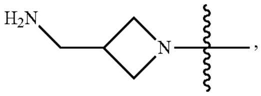,
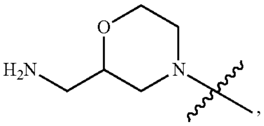, 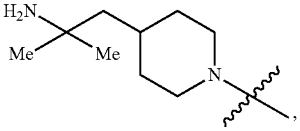,
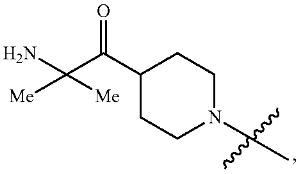,
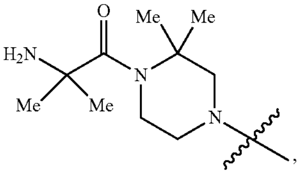,
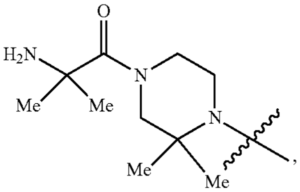,
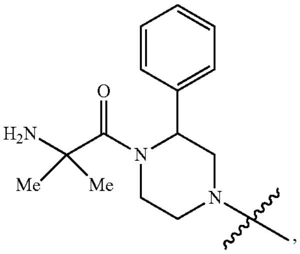,
-continued
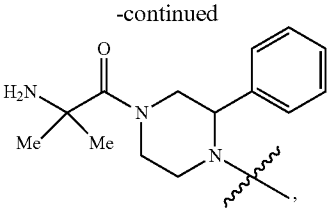,
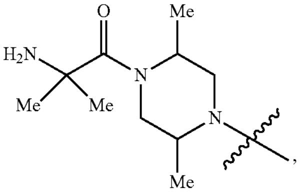,
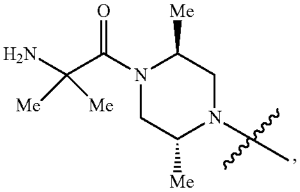,
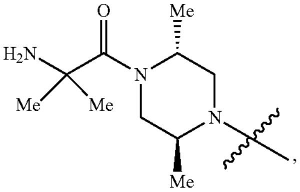,
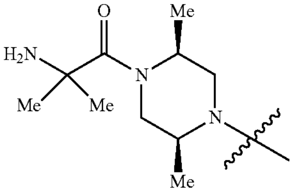
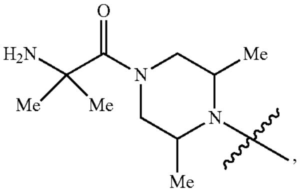,
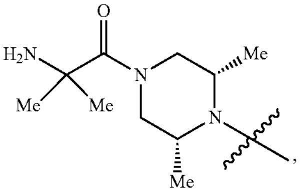,
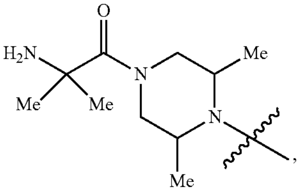,
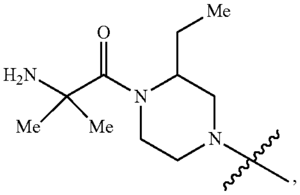, -continued
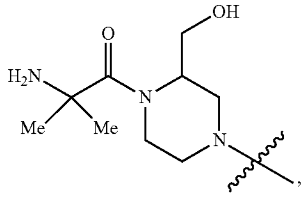
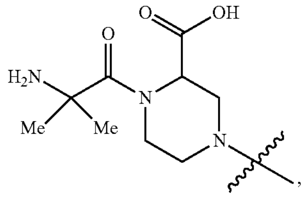
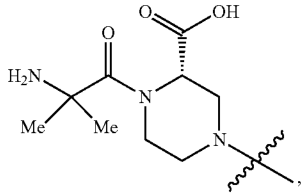
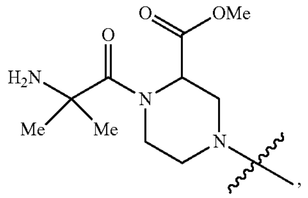
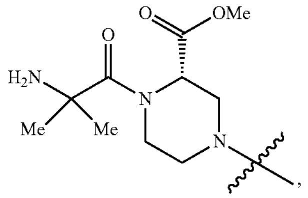
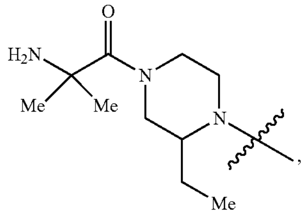
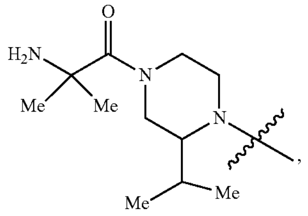
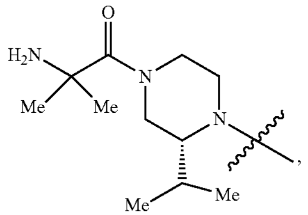
-continued
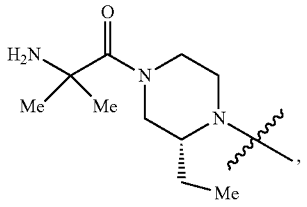
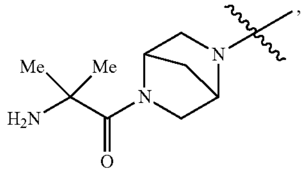
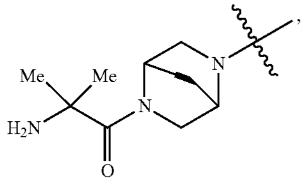
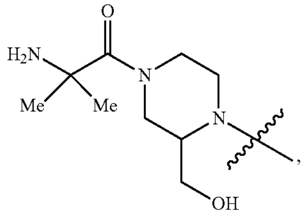
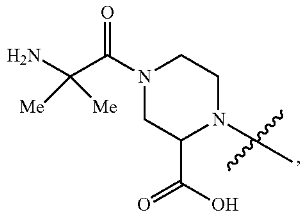
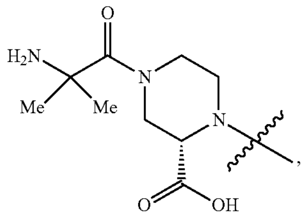
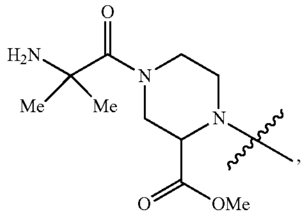
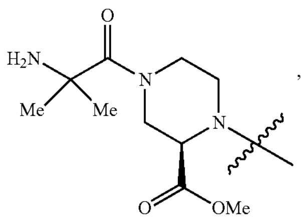
,
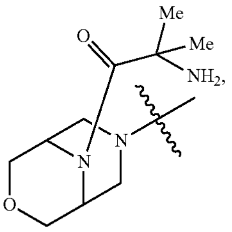

-continued
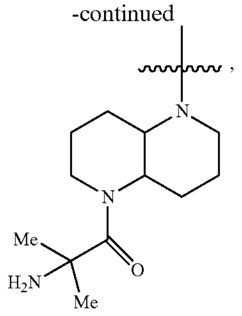
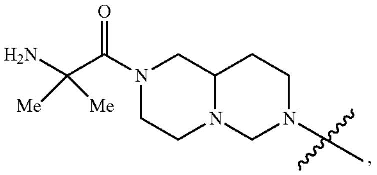
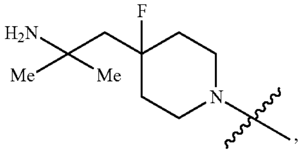 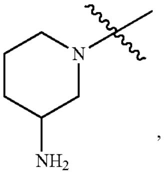 ,
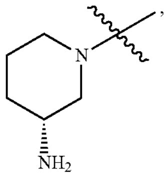 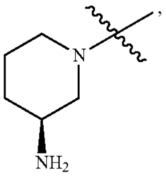 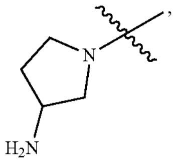
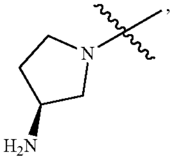 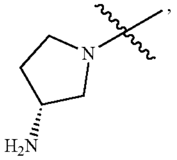
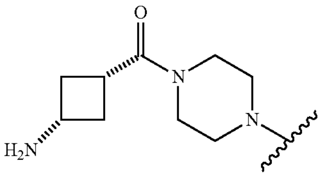 , 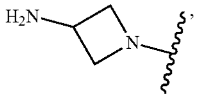
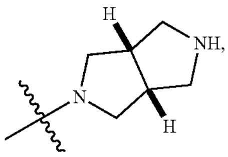 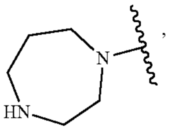
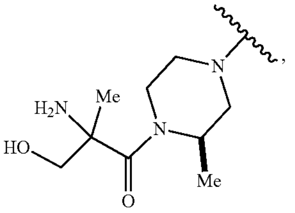
-continued
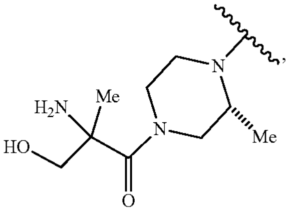
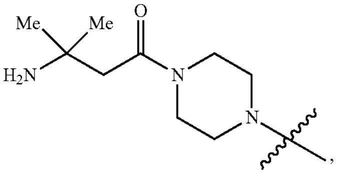
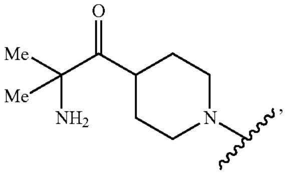 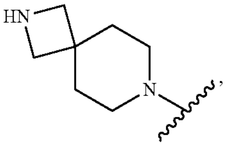
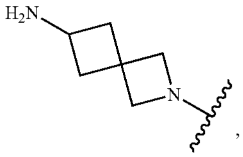 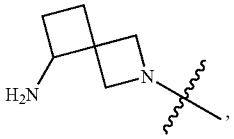
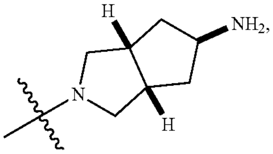 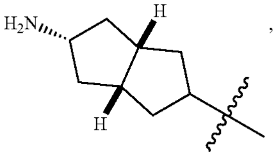 ,
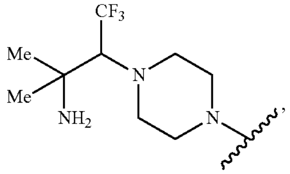
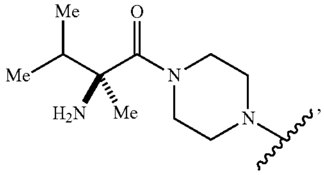
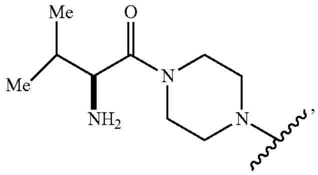
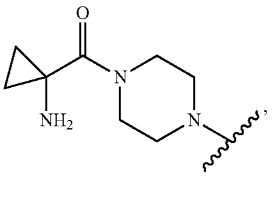 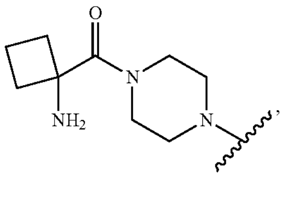

-continued

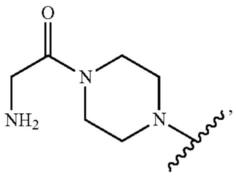, 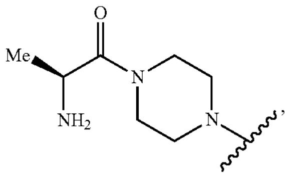,

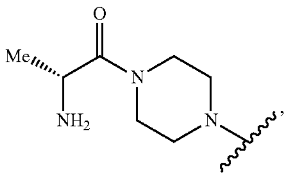,

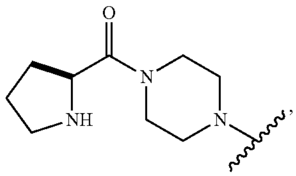,

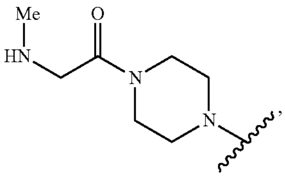, 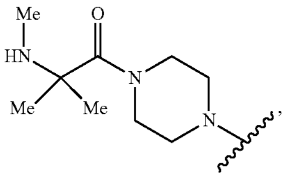,

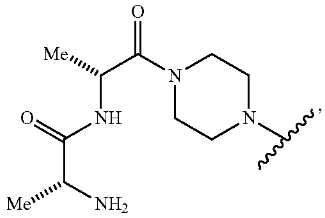,

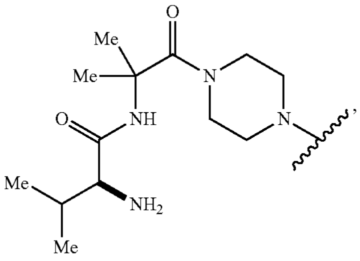,

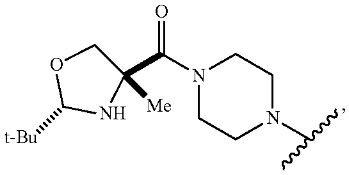,

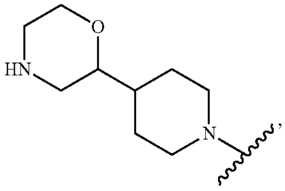, and

-continued

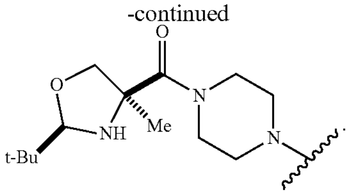.

5. The compound of claim 4 or a pharmaceutically acceptable salt thereof, wherein

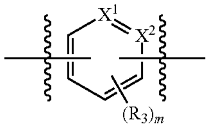 is 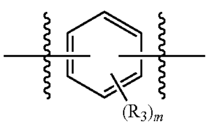 or

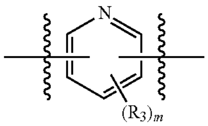, wherein each $R_3$ is independently selected from the group consisting of $C_1$-$C_6$ alkyl, $C_1$-$C_6$ alkoxy, halo, O($C_1$-$C_6$ haloalkyl), and $C_1$-$C_6$ haloalkyl, wherein m is 0, 1 or 2; and Y is a linear $C_1$-$C_8$ alkylene optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two methylene units of the $C_1$-$C_8$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-$C_{3-8}$ cycloalkyl), N—($C_{3-8}$ cycloalkyl), NH(C═O), N—($C_{1-6}$ alkyl) (C═O), (C═O), or

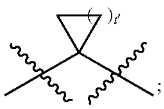;

wherein t' is 1 or 2.

6. The compound of claim 5 or a pharmaceutically acceptable salt thereof, wherein:

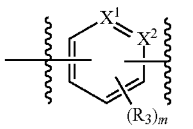

is selected from the group consisting of

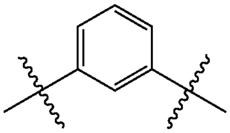, 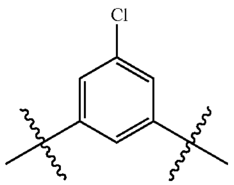,

-continued
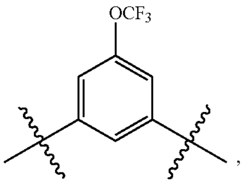
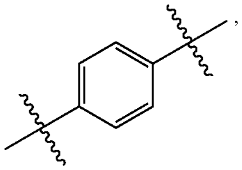
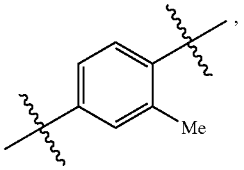
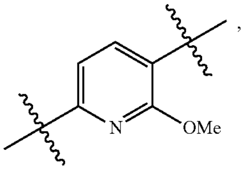
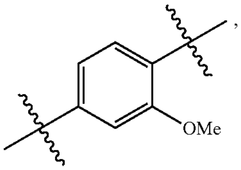
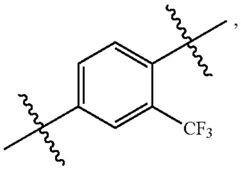
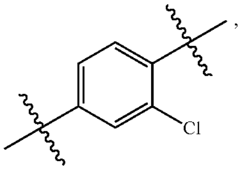
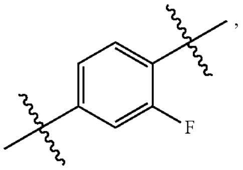
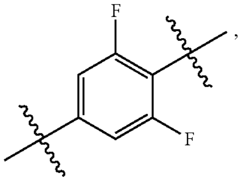
and
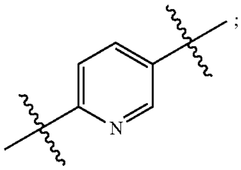
and
Y is selected from the group consisting of $CH_2$, $CH(CH_3)$, CH(COOEt), CH(COOH),
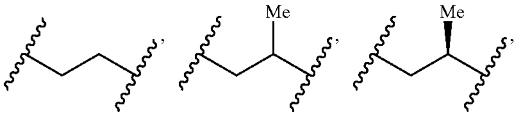
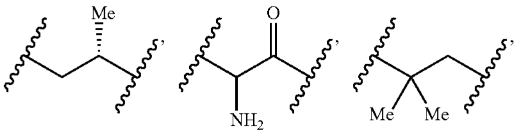
-continued
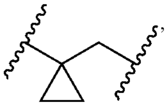
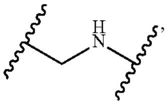
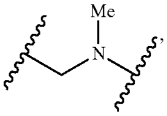
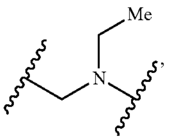
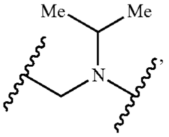
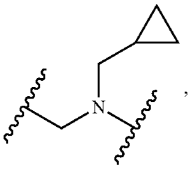
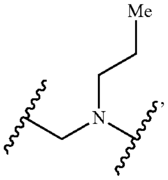
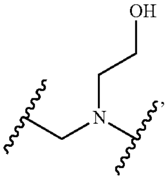
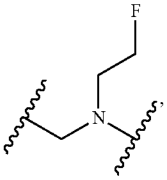
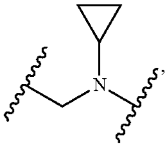
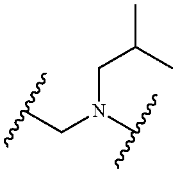
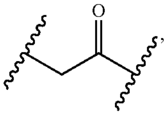
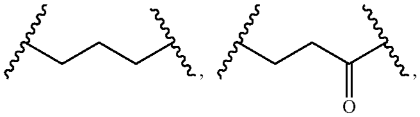
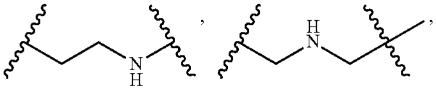
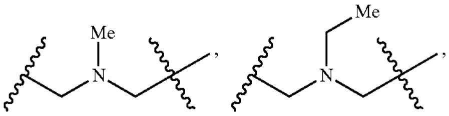
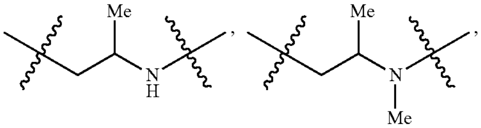
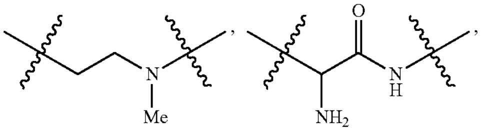
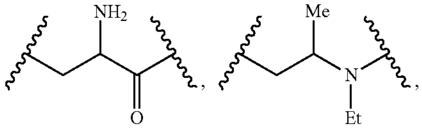
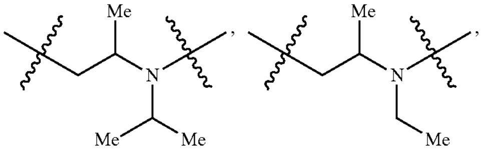
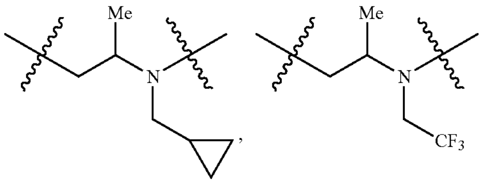

-continued
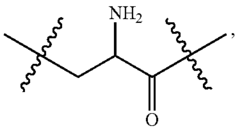, 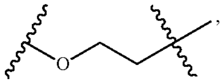,
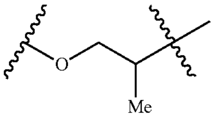, 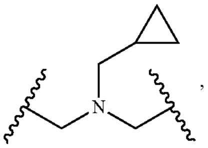,
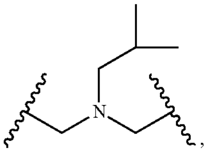, 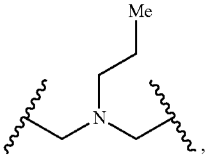,
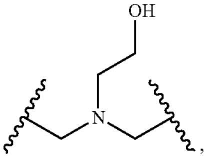, 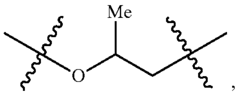,
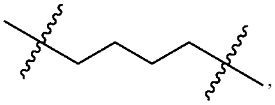, 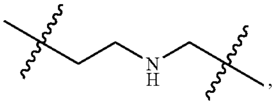,
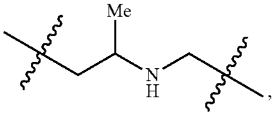, 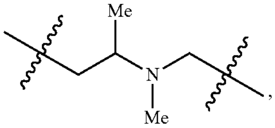,
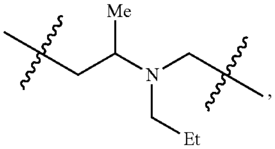, 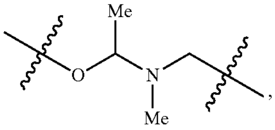,
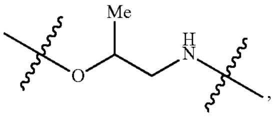, 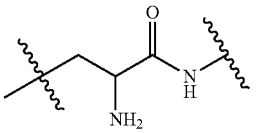 and
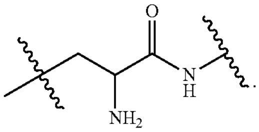.
7. The compound of claim 6 wherein
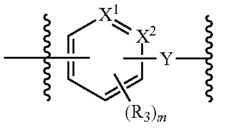
is selected from the group consisting of
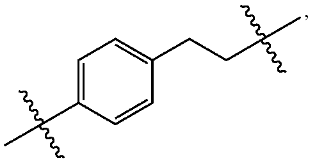,
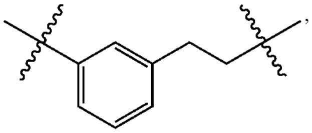,
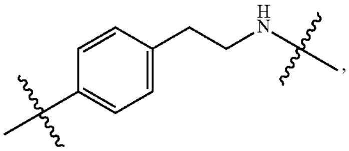,
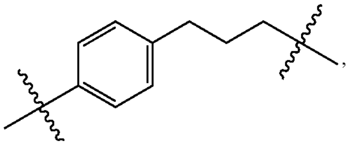,
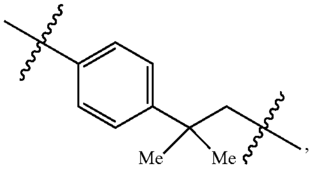,
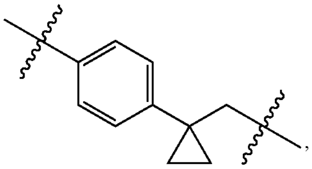,
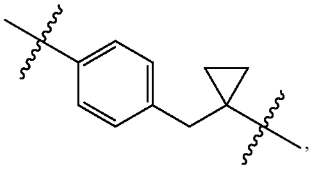,
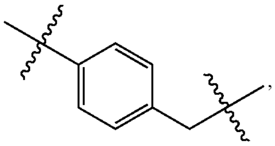, 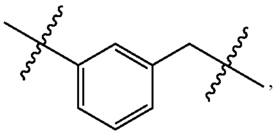,
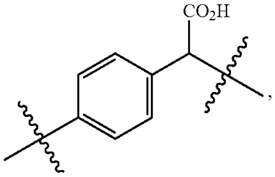,
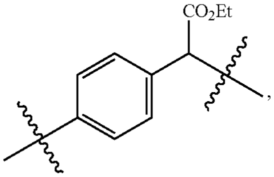, 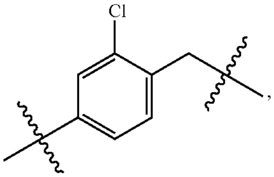, -continued
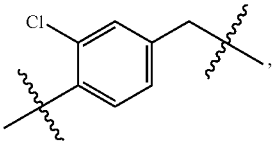,
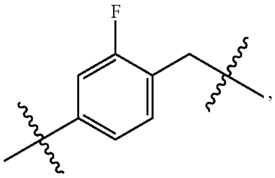,
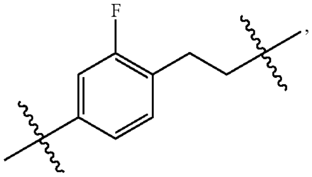,
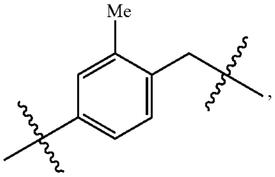,
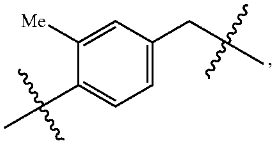,
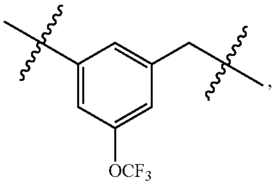,
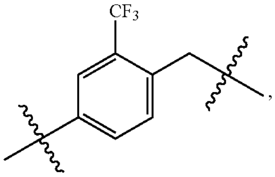,
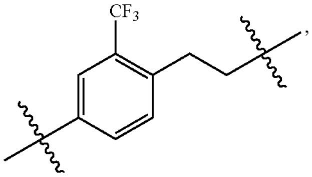,
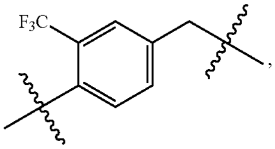,
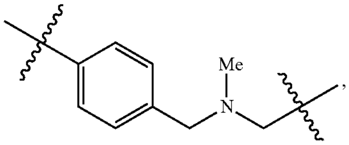,
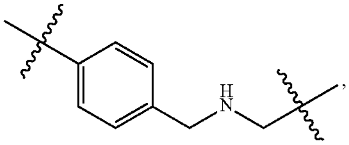,
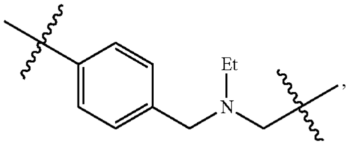,
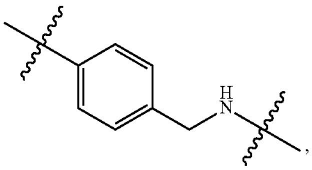,
-continued
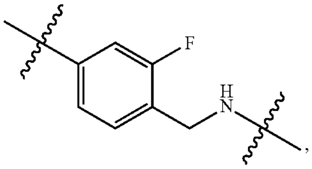,
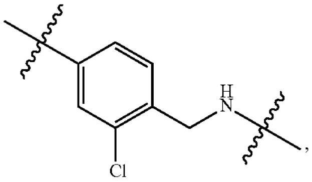,
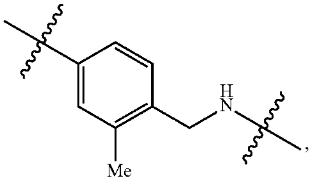,
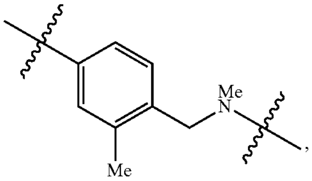,
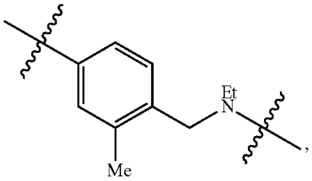,
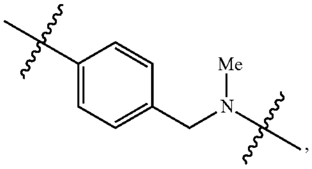,
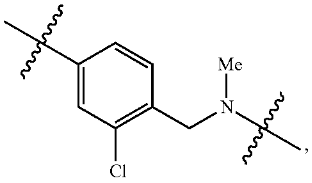,
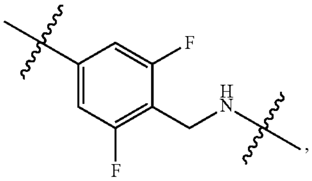,
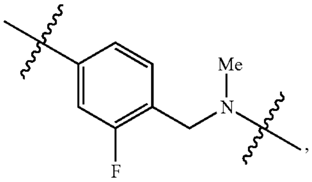, -continued
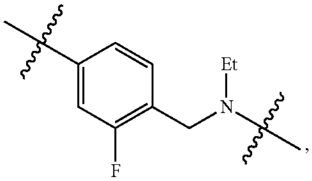
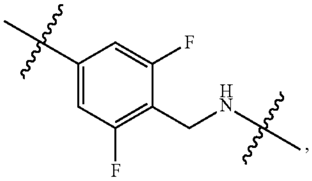
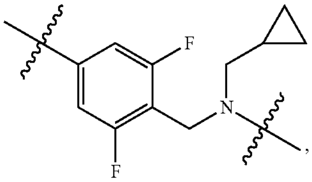
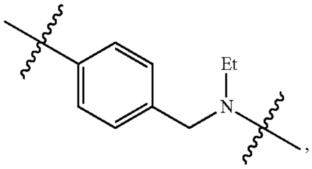
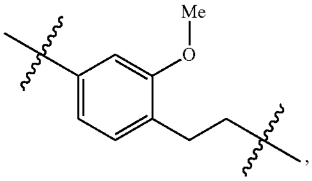
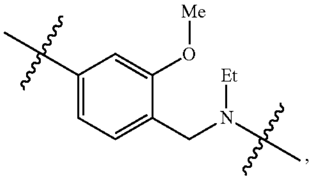
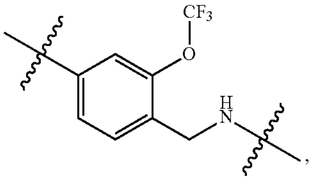
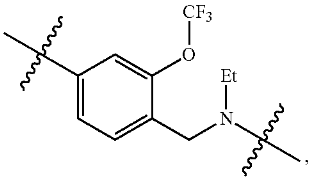
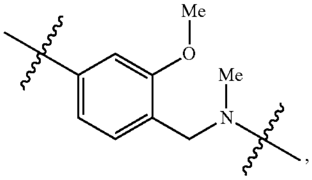
-continued
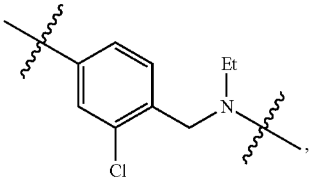
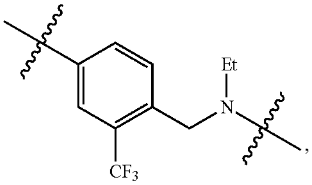
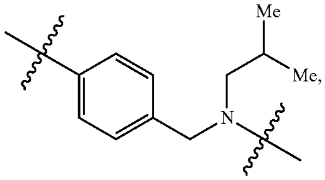
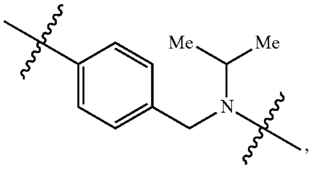
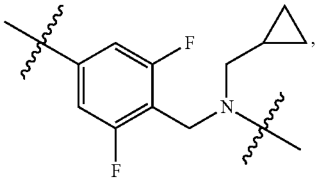
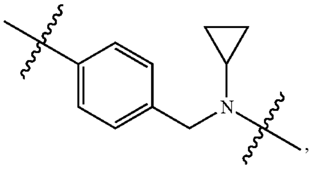
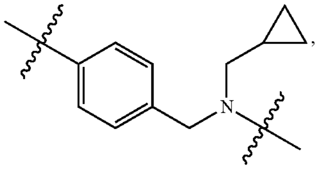
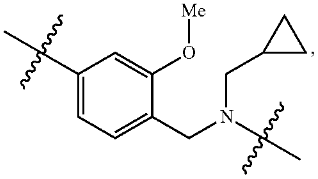
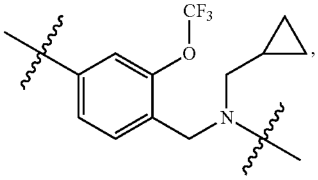

-continued
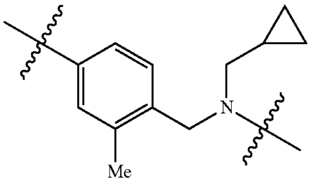,
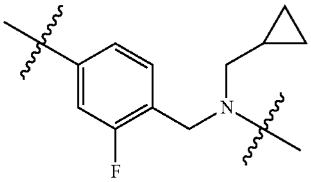,
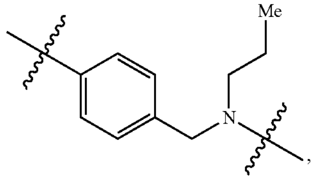,
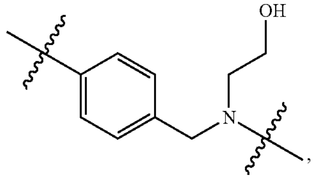,
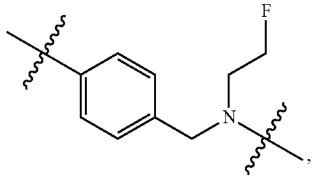,
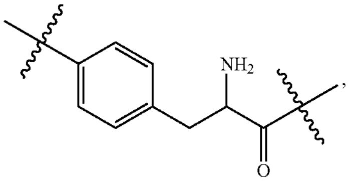,
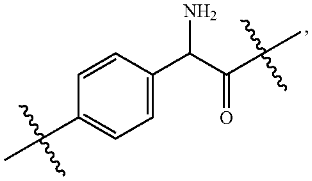,
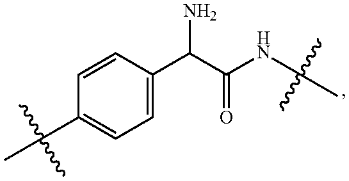,
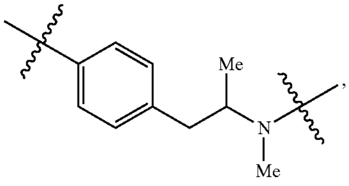,
-continued
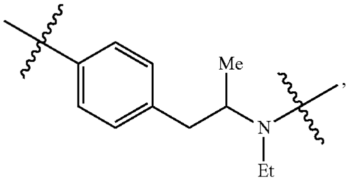,
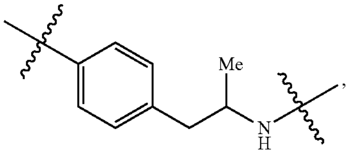,
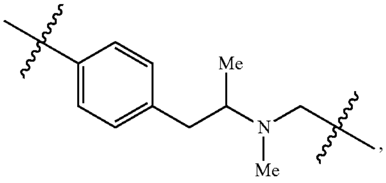,
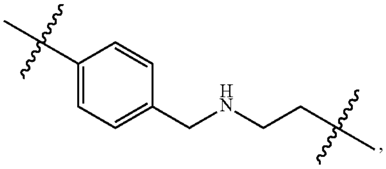,
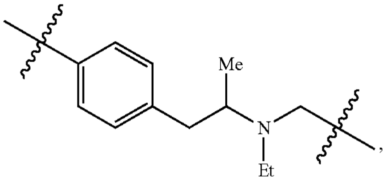,
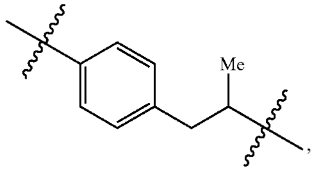,
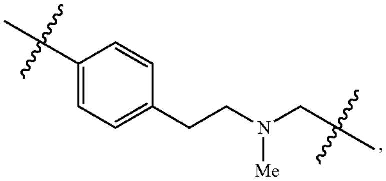,
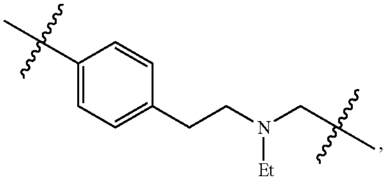,
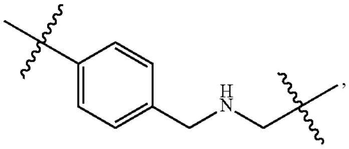,
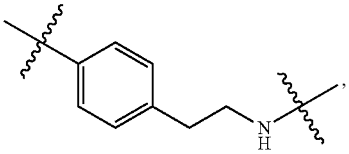, -continued

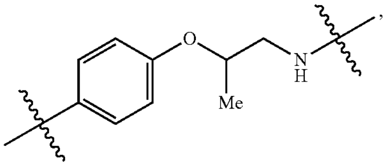

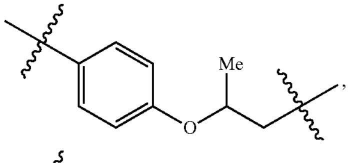

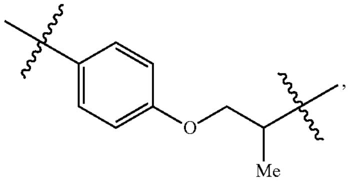

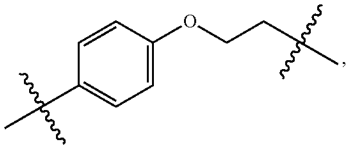

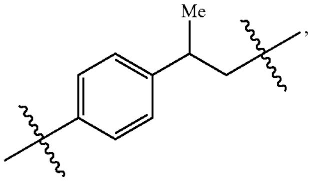

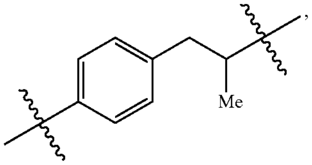

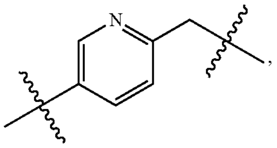

and

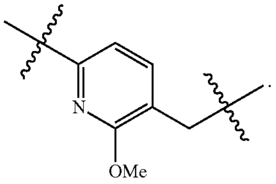

8. The compound of claim 7 or a pharmaceutically acceptable salt thereof, wherein:

ring B is a 4-7 membered monocyclic cycloalkylene or 4-7 membered monocyclic heterocycloalkylene, either of which is optionally substituted with up to three substituents independently selected from the group consisting of $C_1$-$C_6$ alkyl, $C_1$-$C_6$ alkoxy, halo, $NH_2$, $C_1$-$C_6$ haloalkyl, OH, COO($C_1$-$C_6$ alkyl), COOH, and $C_1$-$C_6$ hydroxyalkyl;

L is absent or L is a linear or branched $C_1$-$C_6$ alkylene, wherein up to two methylene units of the $C_1$-$C_6$ alkylene are optionally and independently replaced with O, NH, (C═O), NH(C═O), N—($C_{1-6}$ alkyl)(C═O), (C═NH), NH(C═N), or N—($C_{1-6}$ alkyl); and $R_1$ is selected from the group consisting of H, $NH_2$, NH($C_1$-$C_6$ alkyl), NH($C_1$-$C_6$ alkyl)$_2$, NH($C_3$-$C_6$ cycloalkyl), $CF_3$, and a 4 to 6 membered monocyclic heterocycloalkyl optionally substituted with $NH_2$.

9. The compound of claim 8 or a pharmaceutically acceptable salt thereof, wherein ring B is selected from the group consisting of,

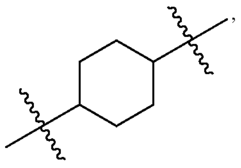
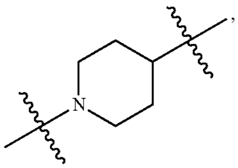

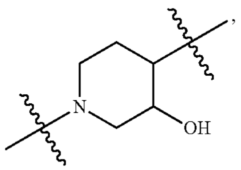
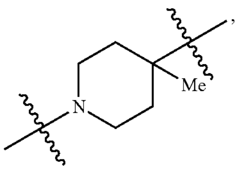

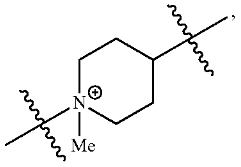
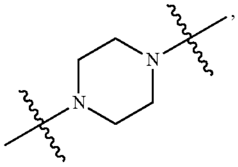

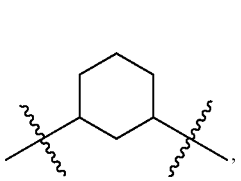
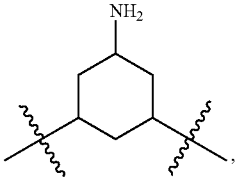

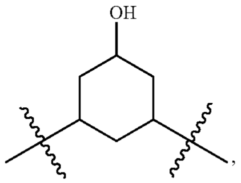
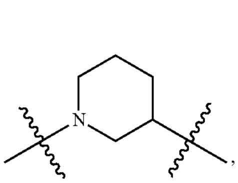

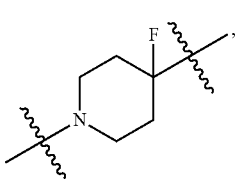
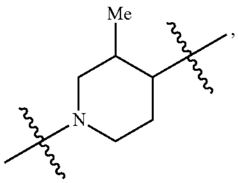

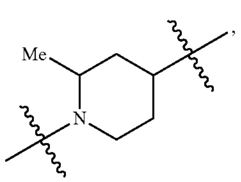
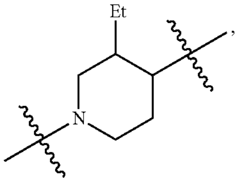

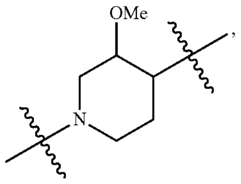
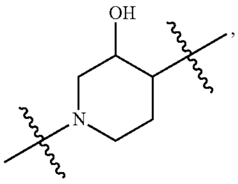

-continued

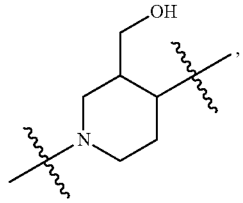,
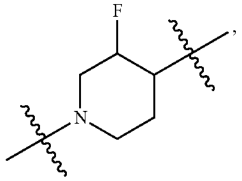,
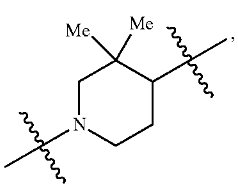,
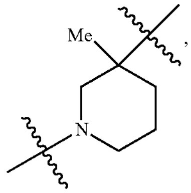,
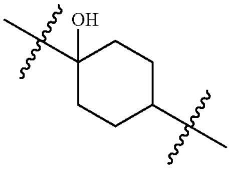,
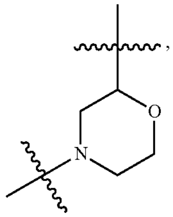,
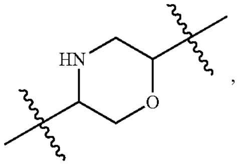,
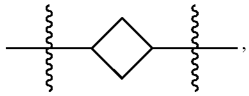,
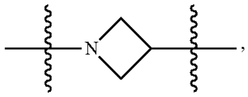,
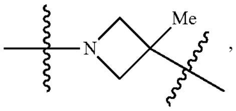,
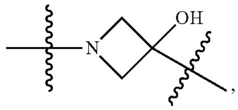,
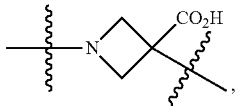,
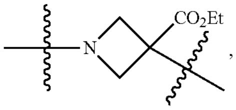,
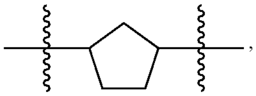,
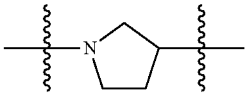,
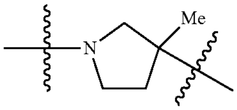,
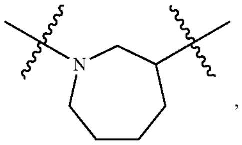,
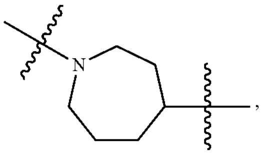,
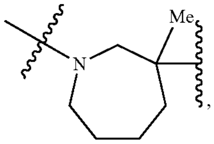,
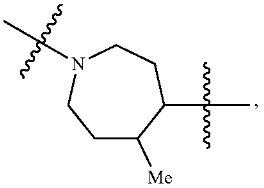, -continued

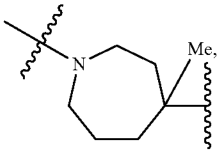 and 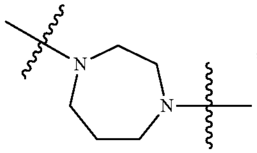;

and

L is absent or is selected from the group consisting of $CH_2$, $CH_2CH_2$, $C(Me)_2$, CH(Me), CH(Et), (C=NH),

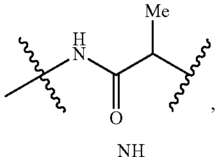,
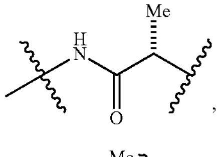,
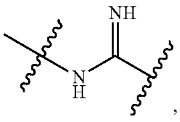, and
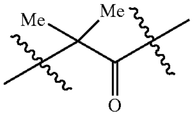;

and $R_2$ and $R_3$ are each independently selected from the group consisting of $C_1$-$C_6$ alkyl, halo, $C_1$-$C_6$ haloalkyl, O($C_1$-$C_6$ haloalkyl), and $C_1$-$C_6$ alkoxy, and m and n are each independently 0, 1, or 2.

10. The compound of claim 9 or a pharmaceutically acceptable salt thereof, wherein

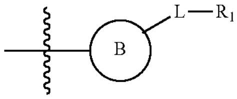

is selected from the group consisting of

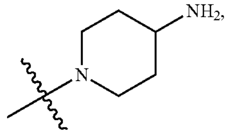
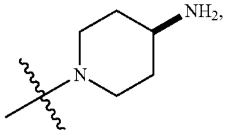
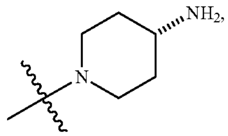
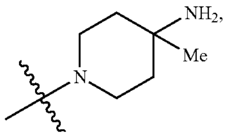
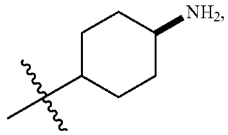
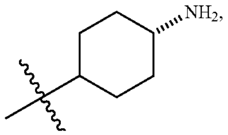
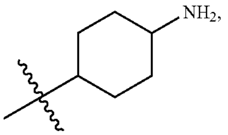
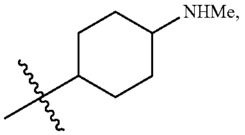

-continued
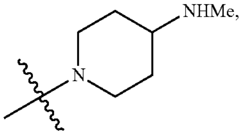
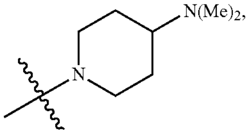
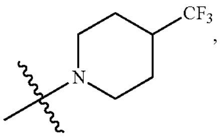
,
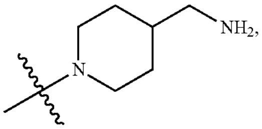
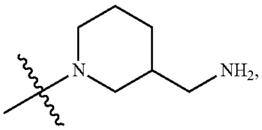
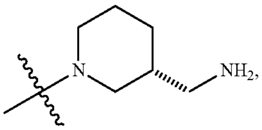
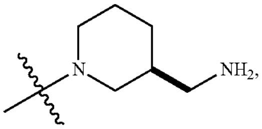
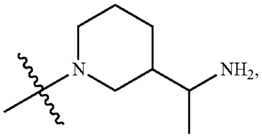
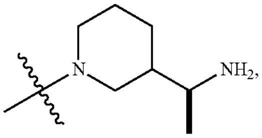
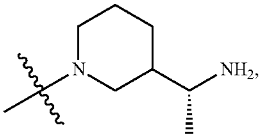
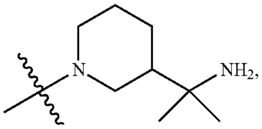
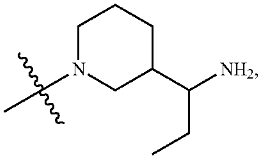
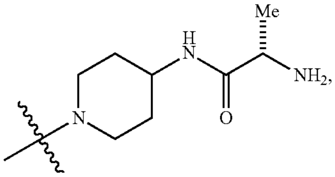
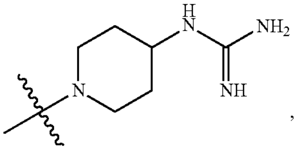
,
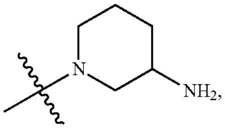
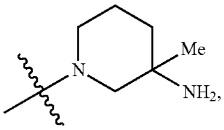
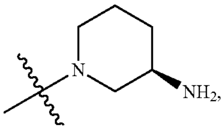
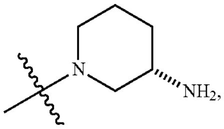
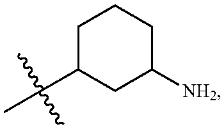
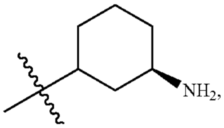
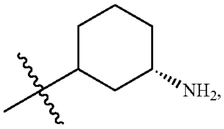
-continued
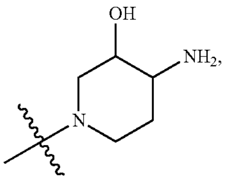
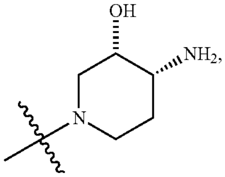
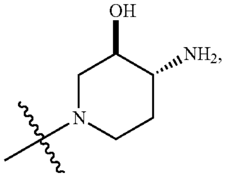
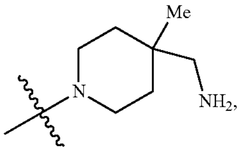
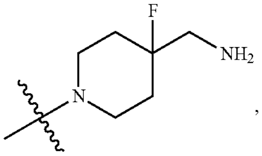
,
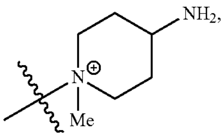
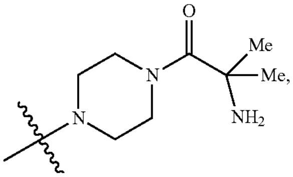
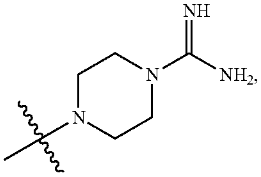
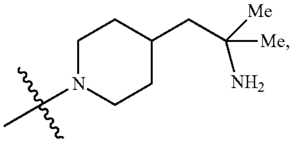
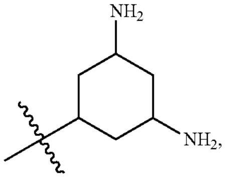
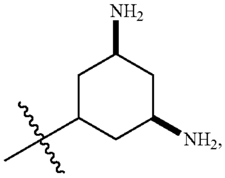
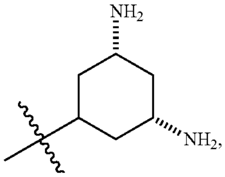
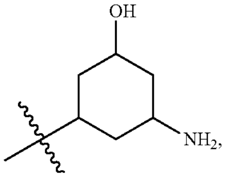
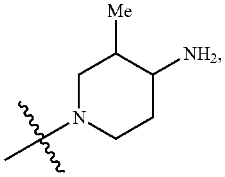
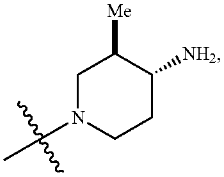
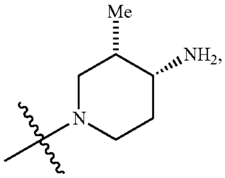
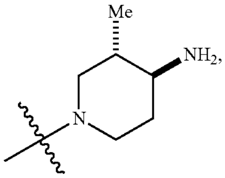

-continued
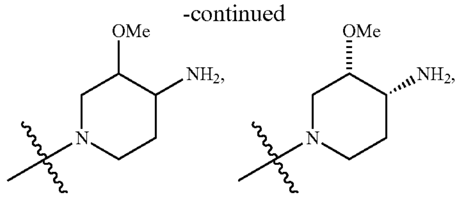
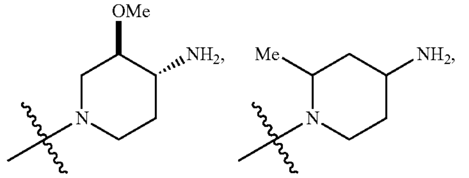
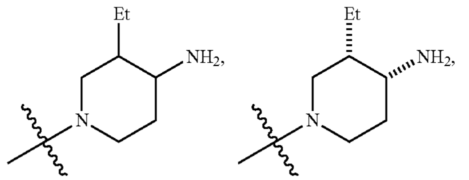
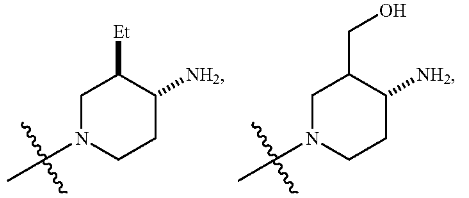
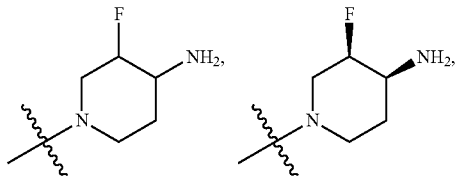
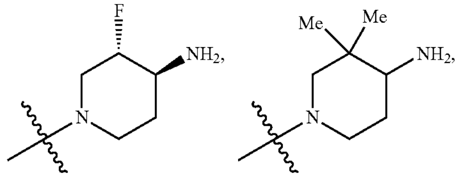
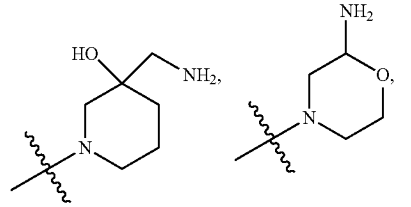
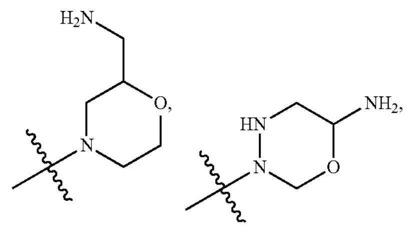
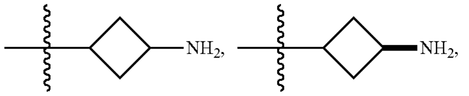
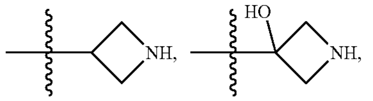
-continued
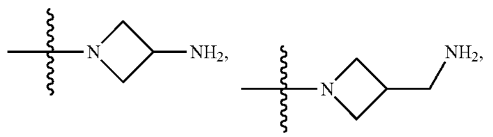
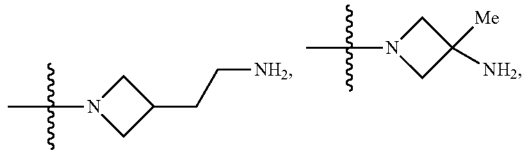
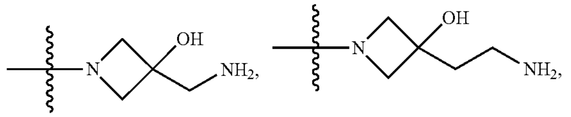
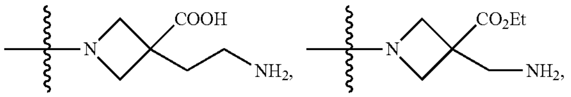
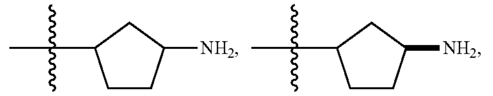
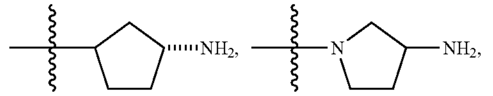
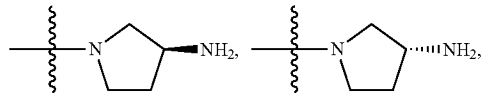
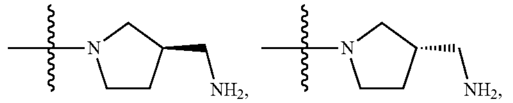
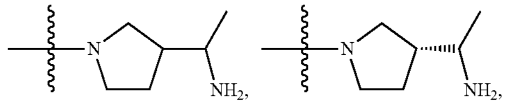
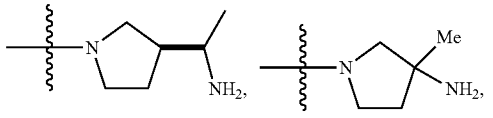
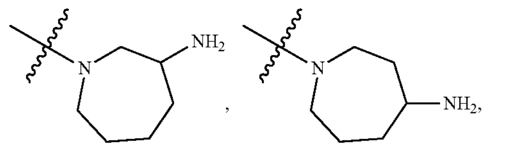
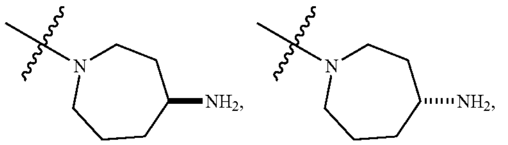
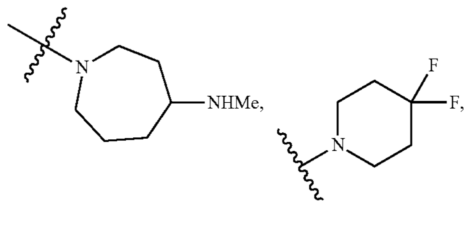

-continued

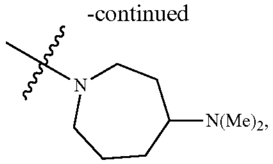

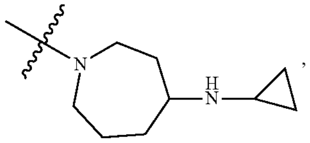

,

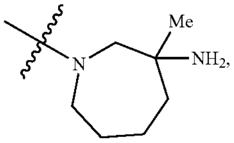

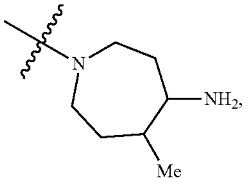

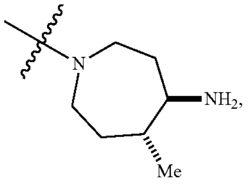

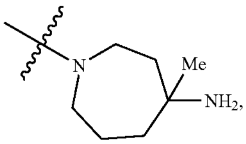

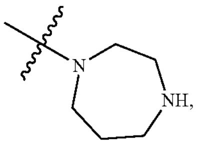

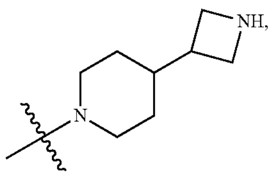

and

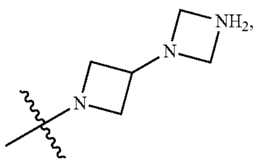

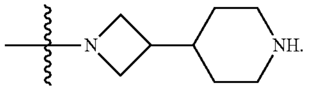

11. The compound of claim 1 or a pharmaceutically acceptable salt thereof which is:

a compound of formula I-1:

I-1

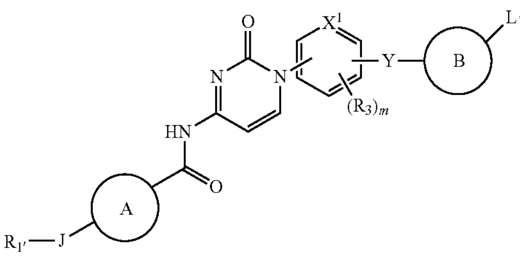

wherein $X^1$ is CH or N.

12. The compound of claim 1 or a pharmaceutically acceptable salt thereof which is a compound of formula II:

II

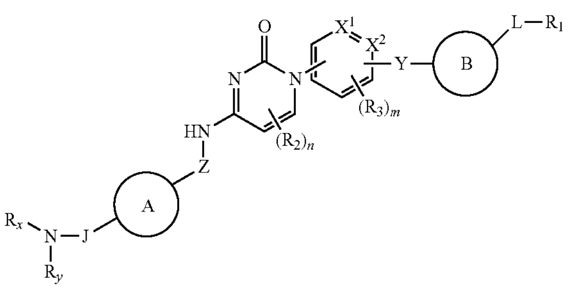

wherein:

Z is (C═O);

ring A is a monocyclic heterocycloalkylene or bicyclic heterocycloalkylene, wherein the monocyclic heterocycloalkylene or bicyclic heterocycloalkylene are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, COO($C_1$-$C_6$ alkyl), —$CONH_2$, and oxo;

J is $C_1$-$C_6$ alkylene optionally substituted with halo, hydroxy, or alkoxy, wherein one or two methylene units of the $C_1$-$C_6$ alkylene may optionally be replaced with O, S, $SO_2$, or C═O;

$R_x$ and $R_y$ are each independently H, $C_1$-$C_6$ alkyl, or an amino protecting group;

Y is a linear $C_1$-$C_8$ alkylene, $C_2$-$C_8$ alkenylene, or $C_2$-$C_8$ alkynylene, any of which are optionally substituted with OH, $NH_2$, halo, $C_1$-$C_6$ alkyl, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O);

ring B is a monocyclic cycloalkylene or monocyclic heterocycloalkylene which is optionally substituted with up to three substituents selected from the group consisting of $C_1$-$C_6$ alkyl, $C_1$-$C_6$ alkoxy, halo, CN, $C_1$-$C_6$ haloalkyl, OH, —COO($C_1$-$C_6$ alkyl), —$CONH_2$, and $C_1$-$C_6$ hydroxyalkyl;

L is absent or L is a linear or branched $C_1$-$C_6$ alkylene, wherein up to two carbon atoms of the $C_1$-$C_6$ alkylene may be replaced with O, NH, (C═O), NH(C═O), N—($C_{1-6}$ alkyl)(C═O), (C═NH), NH(C═N), or N—($C_{1-6}$ alkyl);

$R_1$ is H, halo, $C_1$-$C_6$ haloalkyl, or $NR_{x'}R_{y'}$, wherein $R_{x'}$ and $R_{y'}$ are each independently H, $C_1$-$C_6$ alkyl which may be optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$COONH_2$, and oxo, or a or a protecting group; or $R_1$ is NH(C═O)-($C_1$-$C_6$) alkyl, or NH—(C═NH)—$NH_2$, either of which may be optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$CONH_2$, and oxo; and $R_2$ and $R_3$ are each independently selected from the group consisting of $C_1$-$C_6$ alkyl, halo, CN, OH, $NH_2$, NH($C_1$-

$C_6$ alkyl), $N(C_1$-$C_6$ alkyl$)_2$, —COO($C_1$-$C_6$ alkyl), —$CONH_2$, $C_1$-$C_6$ haloalkyl, $C_1$-$C_6$ alkoxy, and $C_1$-$C_6$ haloalkoxy.
13. The compound of claim 12 or a pharmaceutically acceptable salt thereof, wherein ring A is selected from the group consisting of
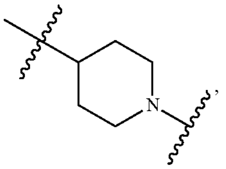
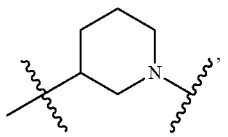
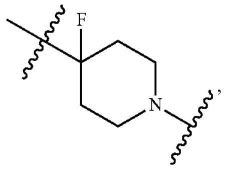
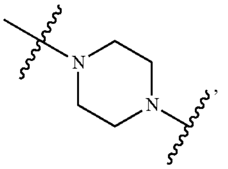
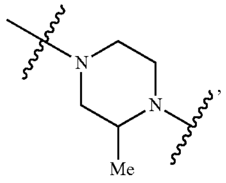
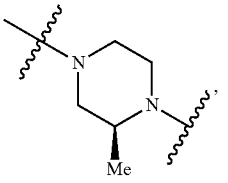
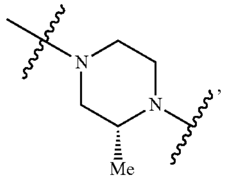
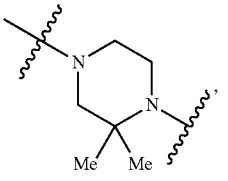
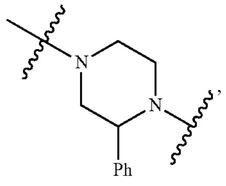
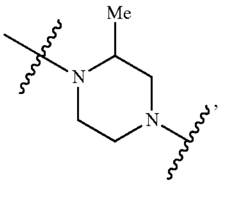
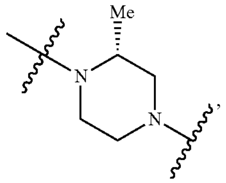
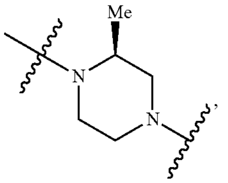
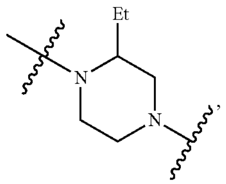
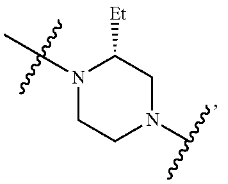
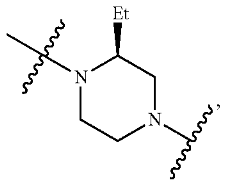
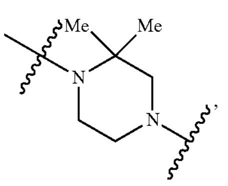
-continued
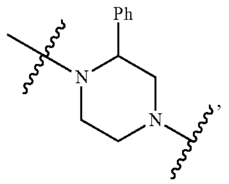
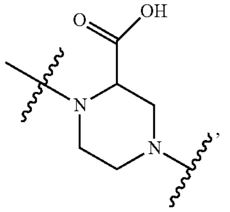
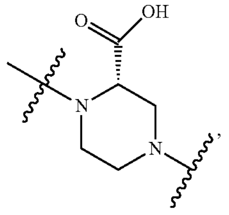
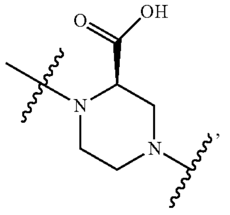
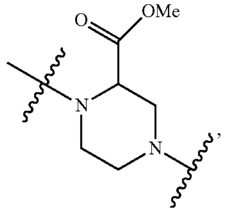
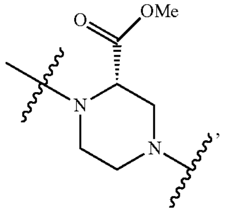
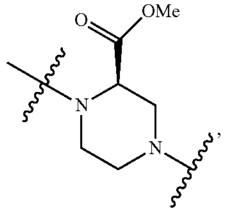
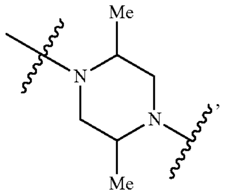
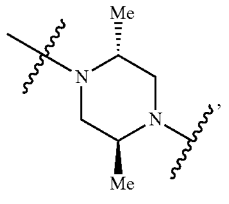
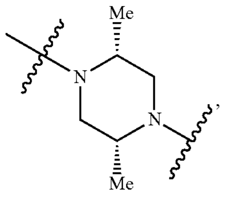
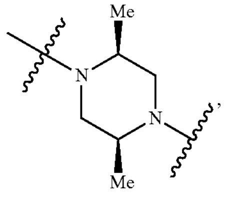
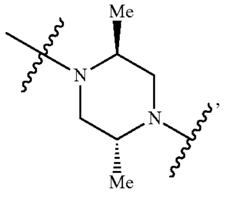
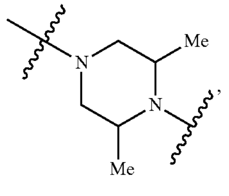
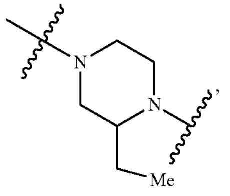
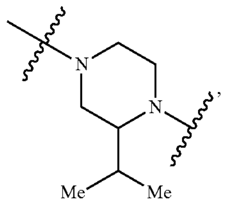
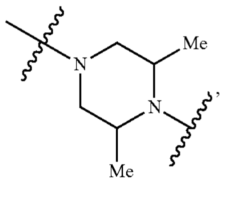

-continued
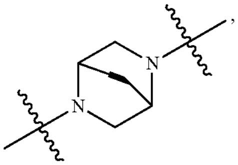,
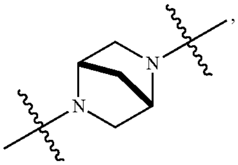,
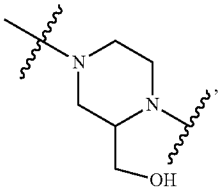,
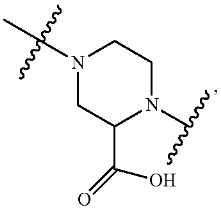,
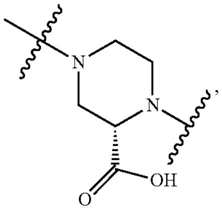,
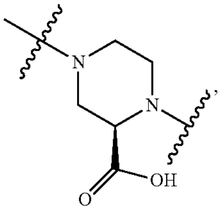,
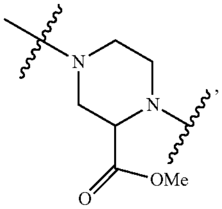,
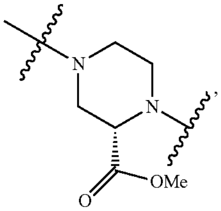,
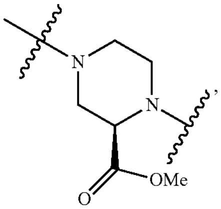,
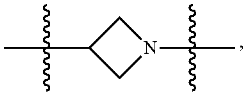,
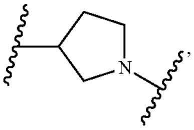,
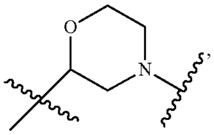,
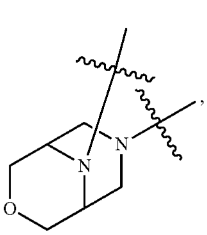,
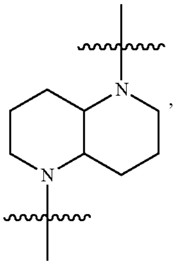,
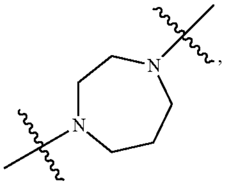,
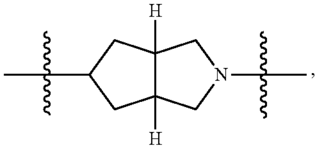,
-continued
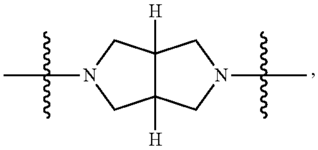,
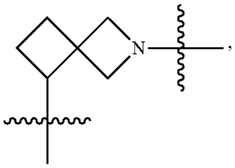,
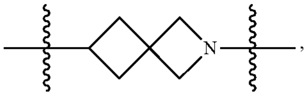,
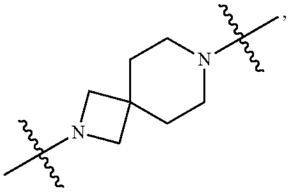, and
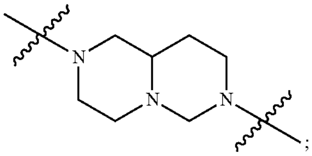;
J is selected from the group consisting of $-CH_2-$,
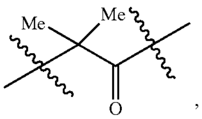,
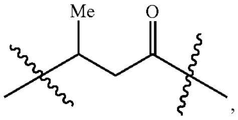,
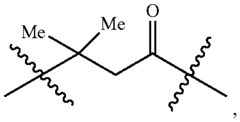,
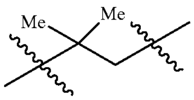,
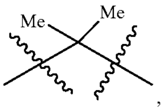,
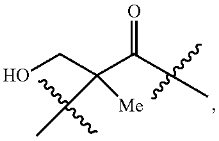, and
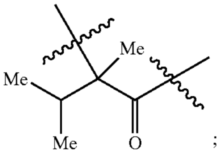;
$NR_xR_y$ is $NH_2$, NHMe, NHEt, NHPG, $N(Me)_2$, or $N(Et)_2$, wherein PG is the amino protecting group;
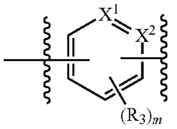

is selected from the group consisting of
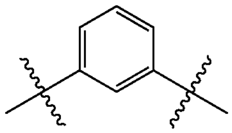,
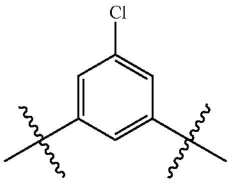,
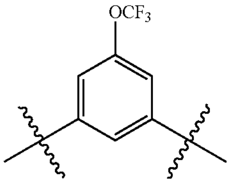,
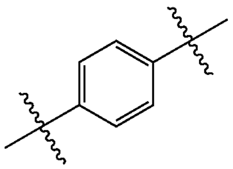,
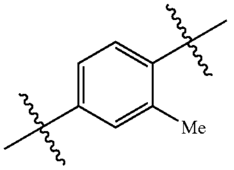,
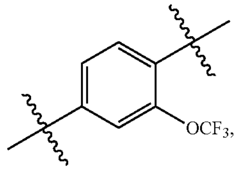,
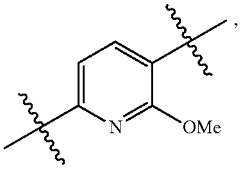,
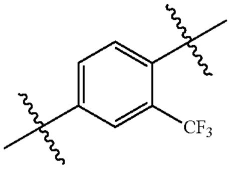,
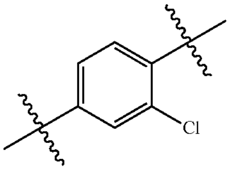,
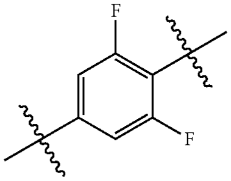, and
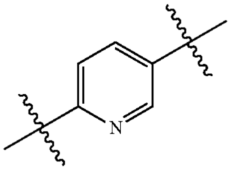;
ring B is selected from the group consisting of
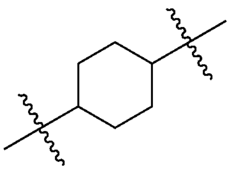,
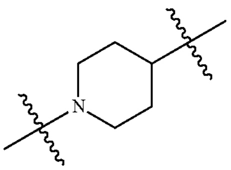,
-continued
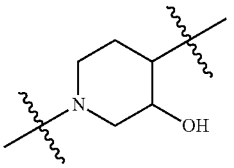,
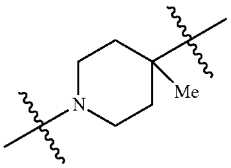,
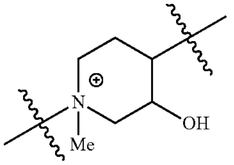,
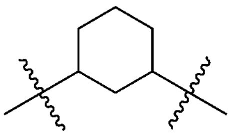,
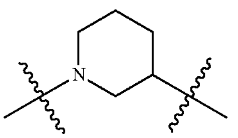,
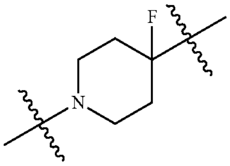,
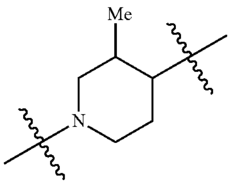,
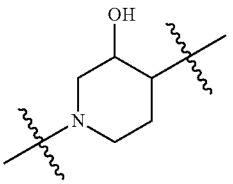,
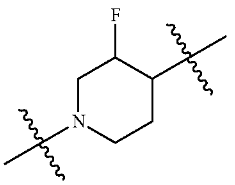,
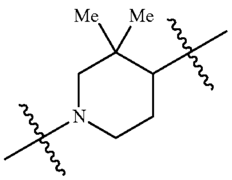,
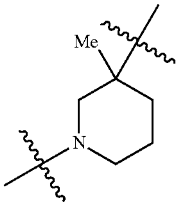
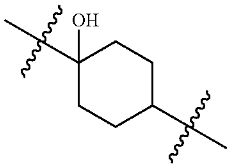
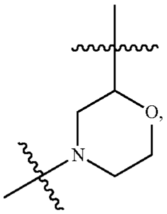,
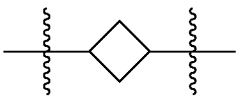,
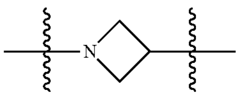,
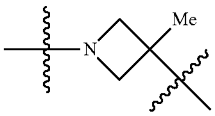,
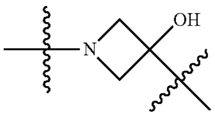, -continued

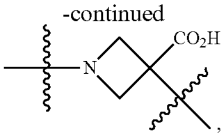
,

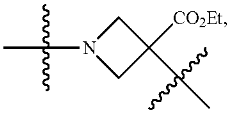

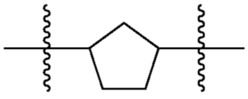
,

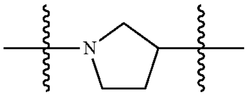
,
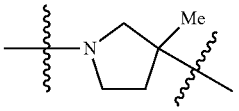
,

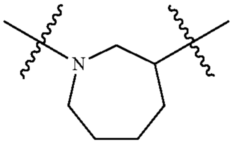
,

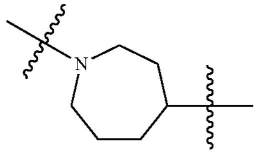
,
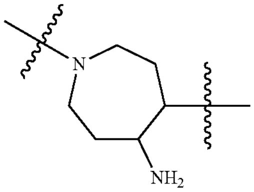
,

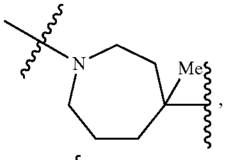
, and

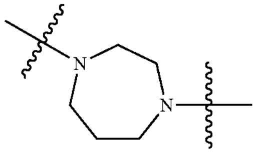
.

14. The compound of claim 13 or a pharmaceutically acceptable salt thereof, wherein:

$R_1$ is H, fluoro, $NH_2$, NH($C_1$-$C_6$ alkyl), or NH($C_3$-$C_6$ cycloalkyl); and $R_2$ and $R_3$ are each independently selected from the group consisting of $C_1$-$C_6$ alkyl, halo, $C_1$-$C_6$ haloalkyl, and $C_1$-$C_6$ alkoxy and m and n are each independently 0, 1, or 2.

15. The compound of claim 14 or a pharmaceutically acceptable salt thereof which is a compound of formula IIA-9:

IIA-9

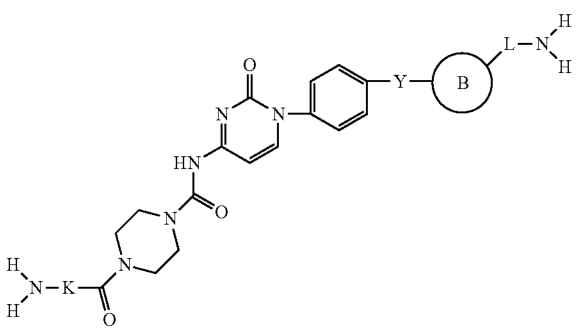

wherein K is $C_1$-$C_4$ alkylene optionally substituted with hydroxy or alkoxy.

16. The compound of claim 1, or a pharmaceutically acceptable salt thereof, which is a compound of formula III:

III

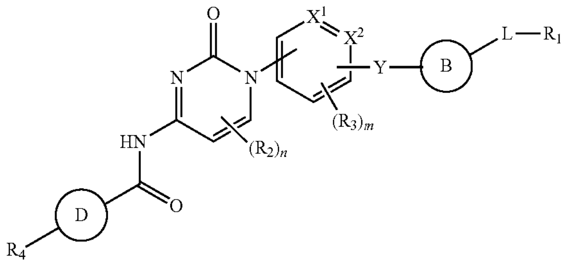

wherein:

Y is a linear $C_1$-$C_8$ alkylene, $C_2$-$C_8$ alkenylene, or $C_2$-$C_8$ alkynylene, any of which are optionally substituted with OH, $NH_2$, halo, $C_1$-$C_6$ alkyl, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O);

$R_1$ is H, halo, $C_1$-$C_6$ haloalkyl, or $NR_{x'}R_{y'}$, wherein $R_{x'}$ and $R_{y'}$ are each independently H, $C_1$-$C_6$ alkyl which may be optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$CONH_2$, and oxo, or a or a protecting group; or $R_1$ is NH(C═O)-($C_1$-$C_6$) alkyl, or NH—(C═NH)—$NH_2$, either of which may be optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, —COO($C_1$-$C_6$ alkyl), —$CONH_2$, and oxo;

ring D is a monocyclic heterocycloalkylene or bicyclic heterocycloalkylene, wherein the bicyclic heterocycloalkylene, and bicyclic heterocycloalkylene are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, NH($C_1$-$C_6$ alkyl), N($C_1$-$C_6$ alkyl)$_2$, COO($C_1$-$C_6$ alkyl), $CONH_2$, and oxo; and $R_2$ and $R_3$ are each independently selected from the group consisting of $C_1$-$C_6$ alkyl, halo, CN, OH, $NH_2$, NH($C_1$-$C_6$ alkyl), N($C_1$-$C_6$ alkyl)$_2$, COO($C_1$-$C_6$ alkyl), $CONH_2$, $C_1$-$C_6$ haloalkyl, $C_1$-$C_6$ alkoxy, and $C_1$-$C_6$ haloalkoxy;

$R_4$ is H or $NR_{x''}R_{y''}$, wherein $R_{x''}$ and $R_{y''}$ are each independently H or $C_1$-$C_6$ alkyl.

17. The compound of claim 16 or a pharmaceutically acceptable salt thereof wherein ring D is selected from the group consisting of

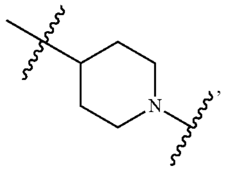
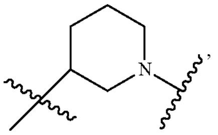
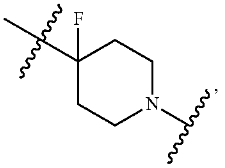
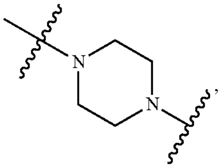
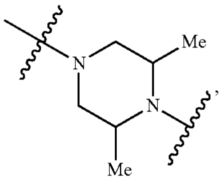
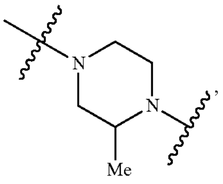
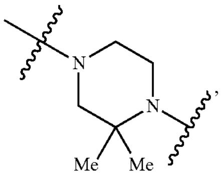
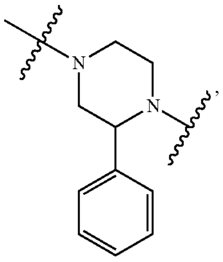
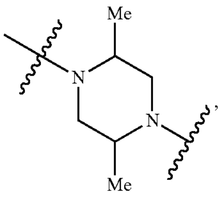
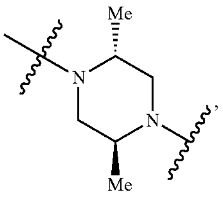
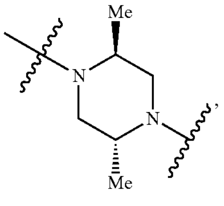
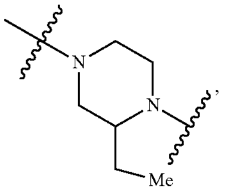

-continued

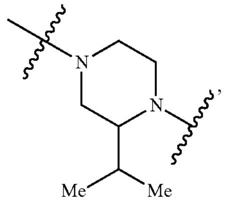
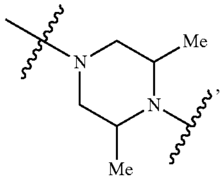
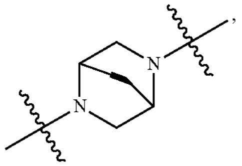
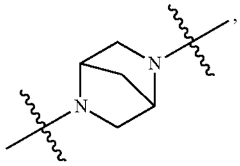
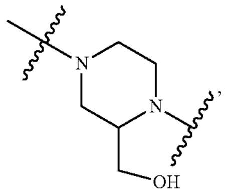
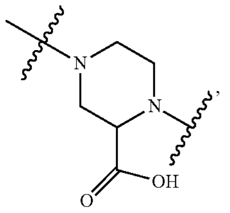
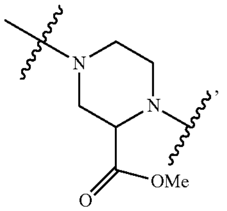
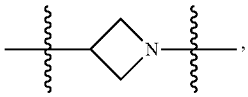
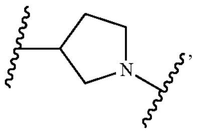
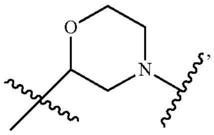
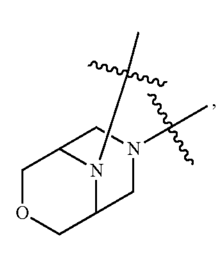
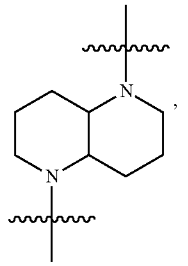
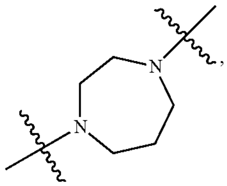
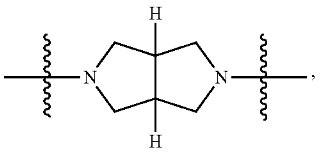
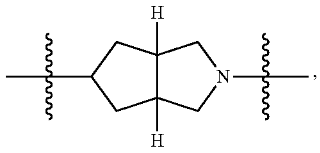
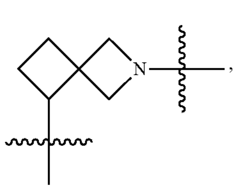
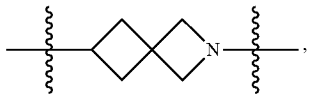

-continued
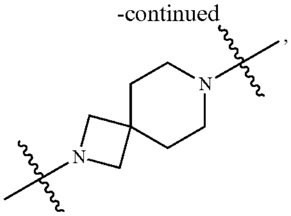
, and
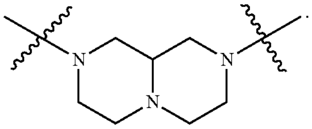
.
18. A compound or a pharmaceutically acceptable salt thereof, wherein the compound is selected from the compounds listed in Table 10 and Table 11:

TABLE 10
| Compounds of Formula I | | |
|---|---|---|
| No. | Salt Structure | Free Base Structure |
| 1 | 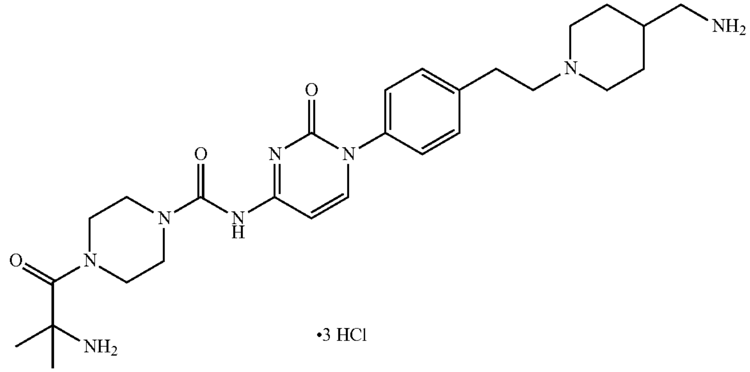 [SMILES: CC(C)(N)C(=O)N1CCN(C(=O)Nc2ccn(-c3ccc(CCN4CCC(CN)CC4)cc3)c(=O)n2)CC1] •3 HCl | 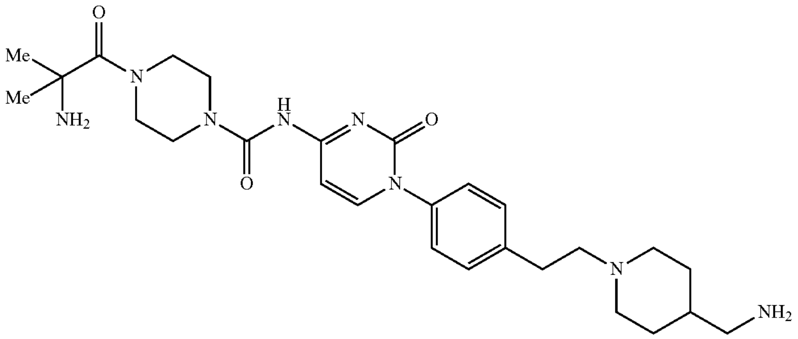 [SMILES: CC(C)(N)C(=O)N1CCN(C(=O)Nc2ccn(-c3ccc(CCN4CCC(CN)CC4)cc3)c(=O)n2)CC1] |
| 2 | 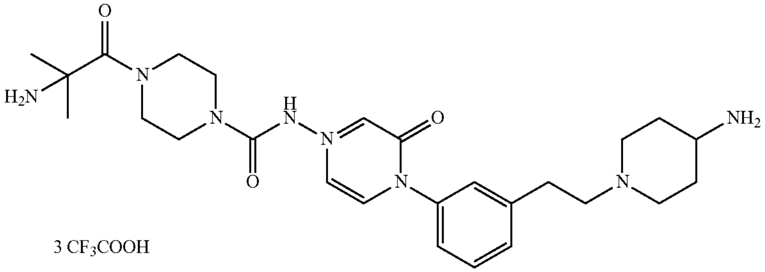 3 $CF_3COOH$ | 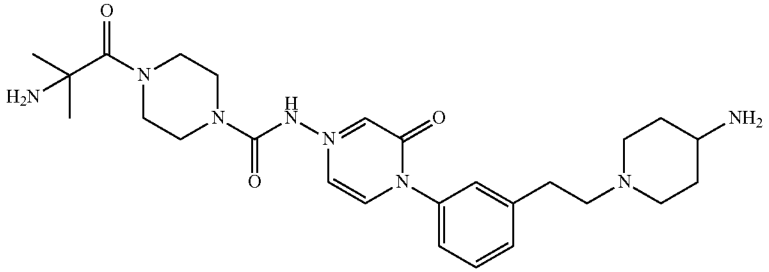 |
| 3 | 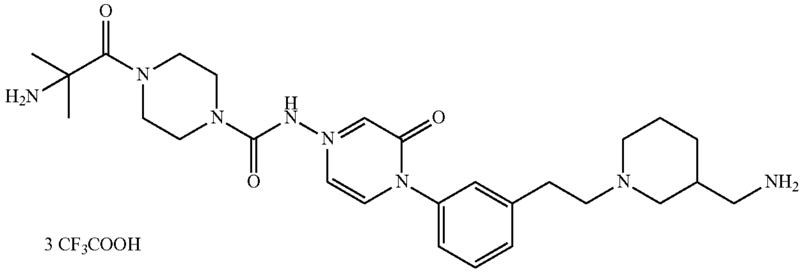 3 $CF_3COOH$ | 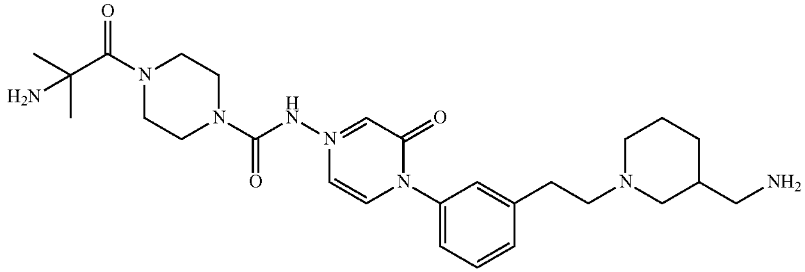 |

TABLE 10-continued
| Compounds of Formula I | | |
|---|---|---|
| No. | Salt Structure | Free Base Structure |
| 4 | 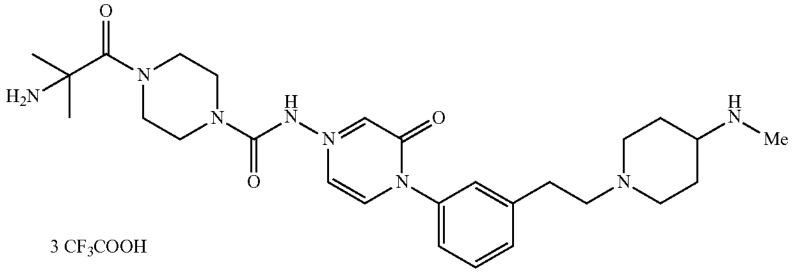 3 $CF_3COOH$ | 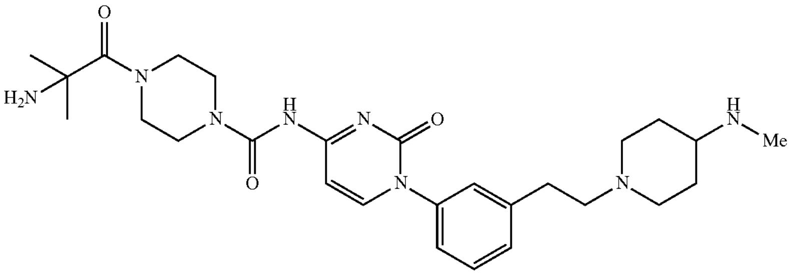 [SMILES: CNC1CCN(CCc2cccc(-n3ccc(NC(=O)N4CCN(C(=O)C(C)(C)N)CC4)nc3=O)c2)CC1] |
| 5 | 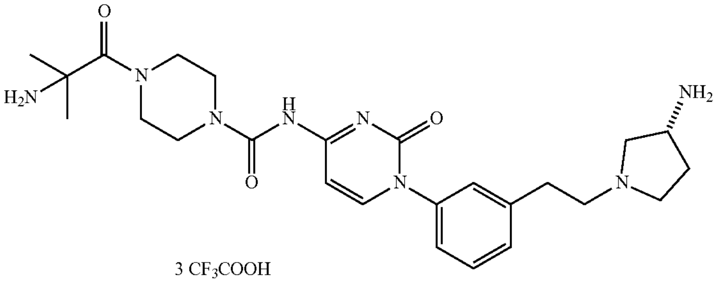 [SMILES: CC(C)(N)C(=O)N1CCN(C(=O)Nc2ccn(-c3cccc(CCN4CC[C@@H](N)C4)c3)c(=O)n2)CC1] 3 $CF_3COOH$ | 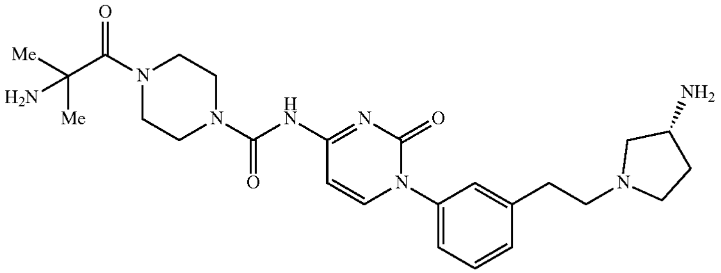 [SMILES: CC(C)(N)C(=O)N1CCN(C(=O)Nc2ccn(-c3cccc(CCN4CC[C@@H](N)C4)c3)c(=O)n2)CC1] |
| 6 | 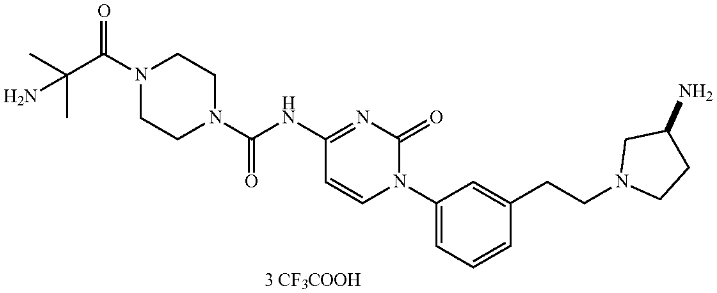 [SMILES: CC(C)(N)C(=O)N1CCN(C(=O)Nc2ccn(-c3cccc(CCN4CC[C@H](N)C4)c3)c(=O)n2)CC1] 3 $CF_3COOH$ | 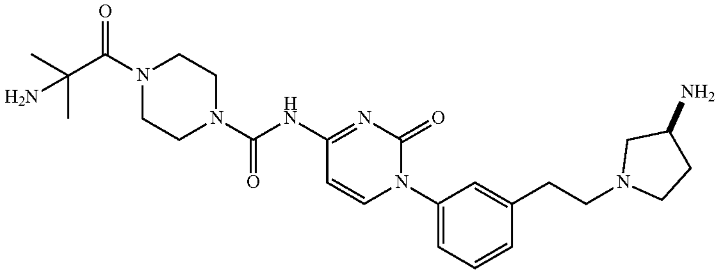 [SMILES: CC(C)(N)C(=O)N1CCN(C(=O)Nc2ccn(-c3cccc(CCN4CC[C@H](N)C4)c3)c(=O)n2)CC1] |

TABLE 10-continued
Compounds of Formula I
| No. | Salt Structure | Free Base Structure |
|---|---|---|
| 7 | 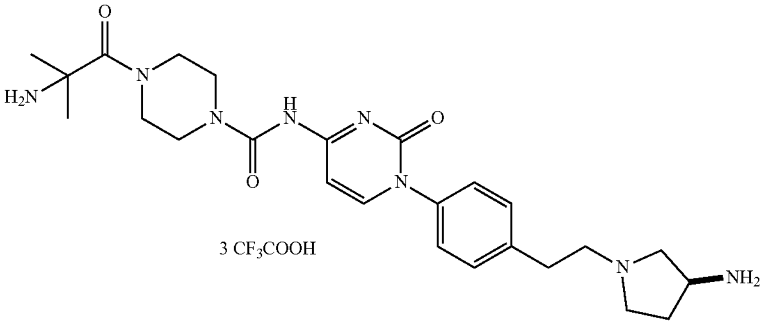 [SMILES: CC(C)(N)C(=O)N1CCN(C(=O)Nc2ccn(-c3ccc(CCN4CC[C@H](N)C4)cc3)c(=O)n2)CC1] 3 $CF_3COOH$ | 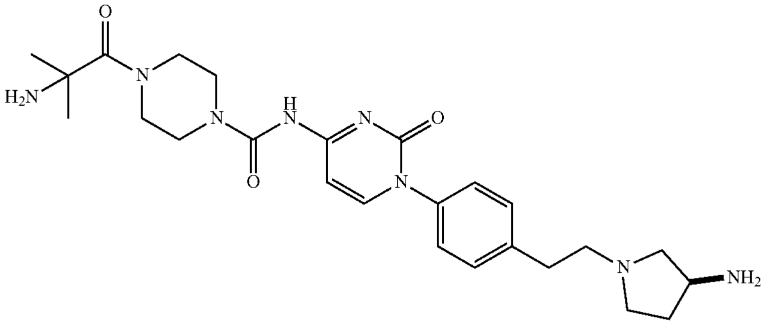 [SMILES: CC(C)(N)C(=O)N1CCN(C(=O)Nc2ccn(-c3ccc(CCN4CC[C@H](N)C4)cc3)c(=O)n2)CC1] |
| 8 | 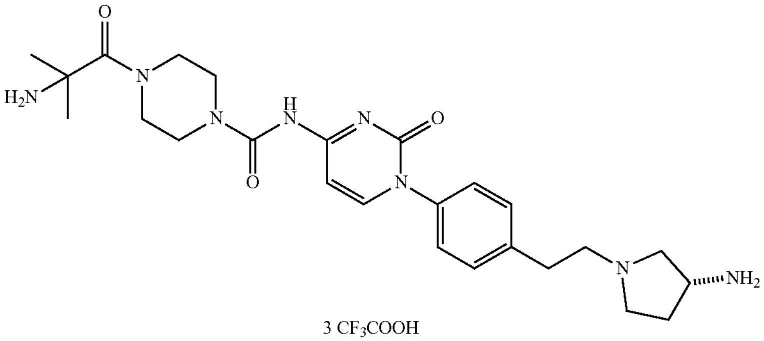 [SMILES: CC(C)(N)C(=O)N1CCN(C(=O)Nc2ccn(-c3ccc(CCN4CC[C@@H](N)C4)cc3)c(=O)n2)CC1] 3 $CF_3COOH$ | 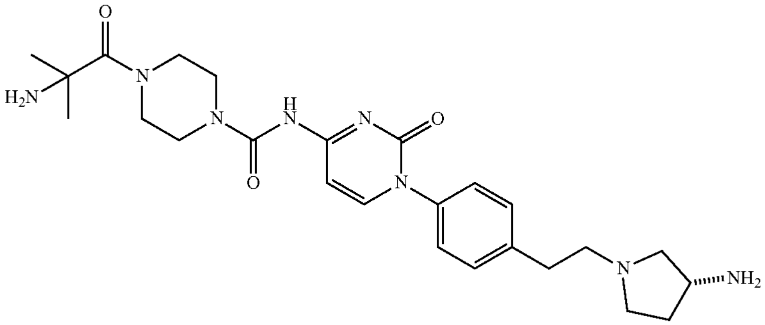 [SMILES: CC(C)(N)C(=O)N1CCN(C(=O)Nc2ccn(-c3ccc(CCN4CC[C@@H](N)C4)cc3)c(=O)n2)CC1] |

TABLE 10-continued
| Compounds of Formula I | | |
|---|---|---|
| No. | Salt Structure | Free Base Structure |
| 9 | 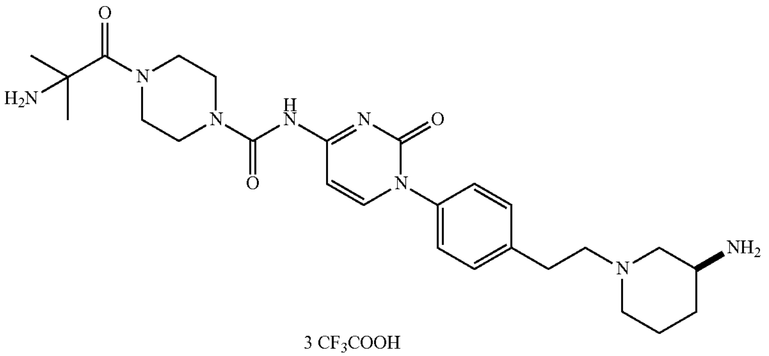 [SMILES: CC(C)(N)C(=O)N1CCN(C(=O)Nc2ccn(-c3ccc(CCN4CCC[C@H](N)C4)cc3)c(=O)n2)CC1] 3 $CF_3COOH$ | 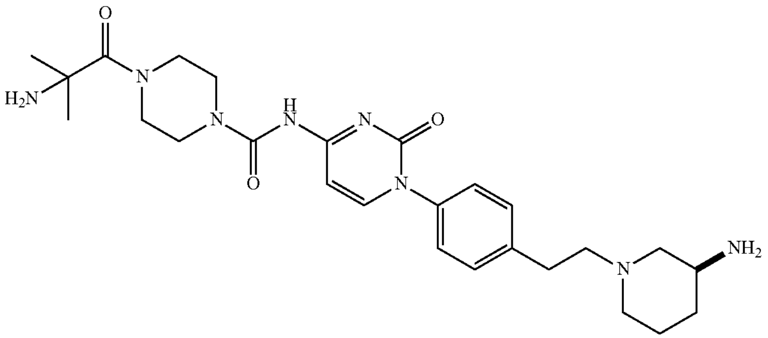 [SMILES: CC(C)(N)C(=O)N1CCN(C(=O)Nc2ccn(-c3ccc(CCN4CCC[C@H](N)C4)cc3)c(=O)n2)CC1] |
| 10 | 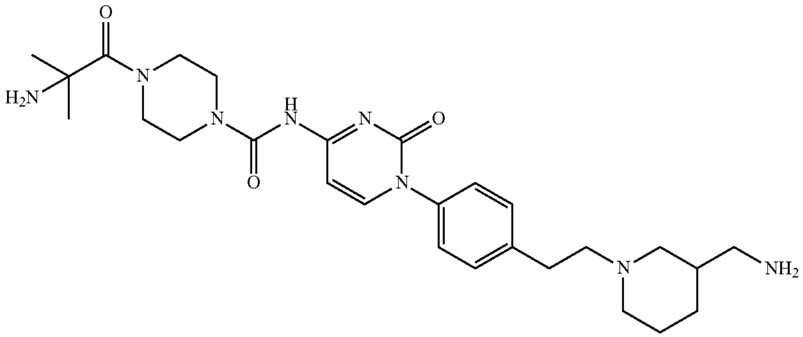 [SMILES: CC(C)(N)C(=O)N1CCN(C(=O)Nc2ccn(-c3ccc(CCN4CCCC(CN)C4)cc3)c(=O)n2)CC1] 3 HCl | 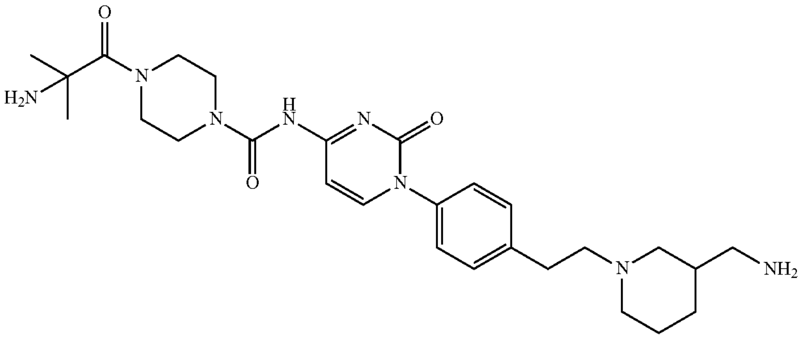 |

TABLE 10-continued
| Compounds of Formula I | | |
|---|---|---|
| No. | Salt Structure | Free Base Structure |
| 11 | 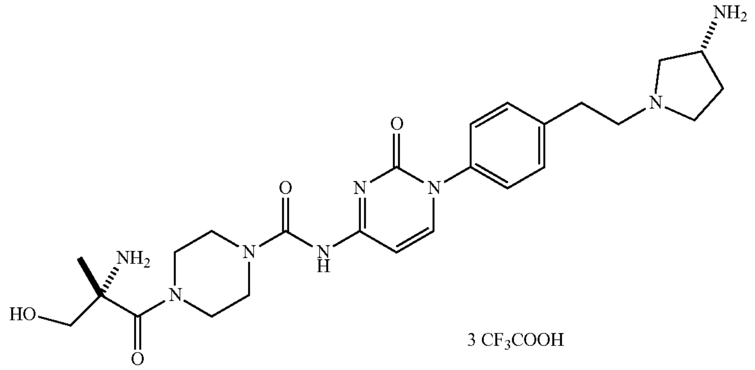 [SMILES: C[C@](N)(CO)C(=O)N1CCN(C(=O)Nc2ccn(-c3ccc(CCN4CC[C@@H](N)C4)cc3)c(=O)n2)CC1] 3 $CF_3COOH$ | 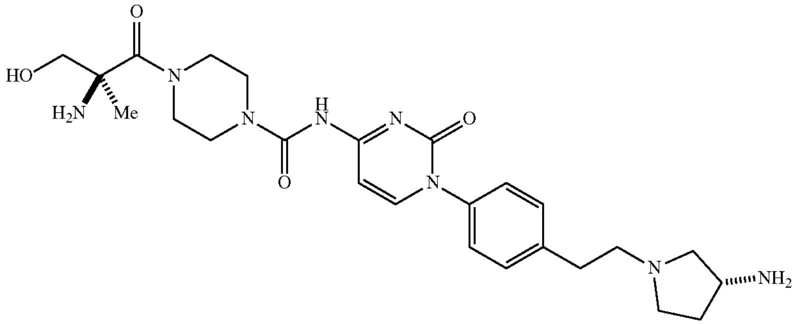 [SMILES: C[C@](N)(CO)C(=O)N1CCN(C(=O)Nc2ccn(-c3ccc(CCN4CC[C@@H](N)C4)cc3)c(=O)n2)CC1] |
| 12 | 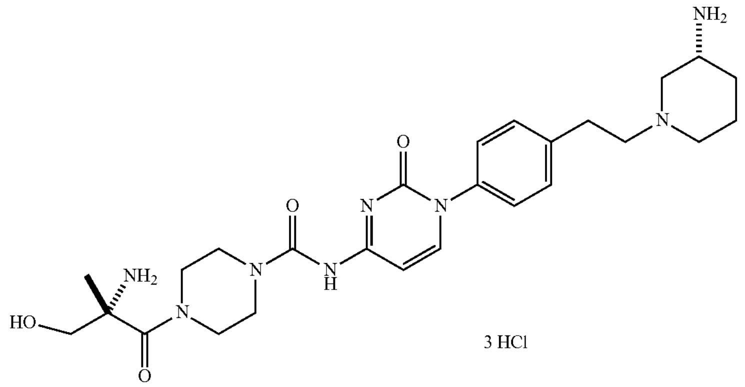 [SMILES: C[C@](N)(CO)C(=O)N1CCN(C(=O)Nc2ccn(-c3ccc(CCN4CCC[C@@H](N)C4)cc3)c(=O)n2)CC1] 3 HCl | 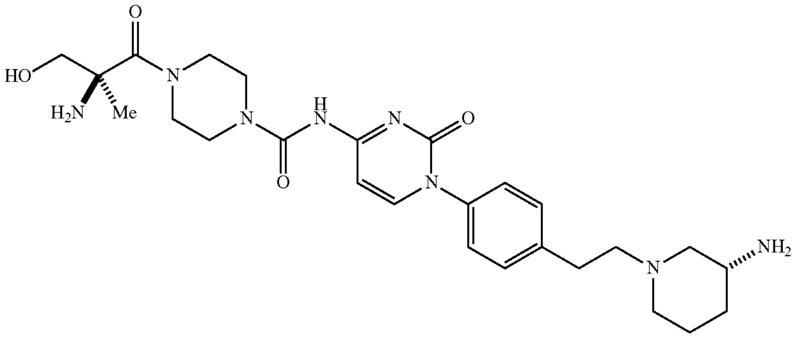 [SMILES: C[C@](N)(CO)C(=O)N1CCN(C(=O)Nc2ccn(-c3ccc(CCN4CCC[C@@H](N)C4)cc3)c(=O)n2)CC1] |

TABLE 10-continued
| Compounds of Formula I | | |
|---|---|---|
| No. | Salt Structure | Free Base Structure |
| 13 | 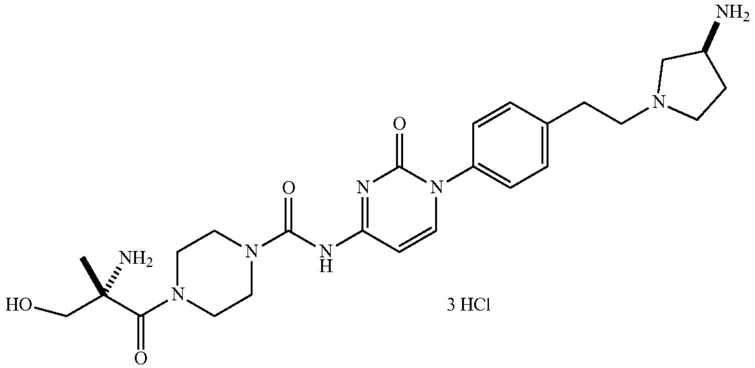 [SMILES: C[C@](N)(CO)C(=O)N1CCN(C(=O)Nc2ccn(-c3ccc(CCN4CC[C@H](N)C4)cc3)c(=O)n2)CC1] 3 HCl | 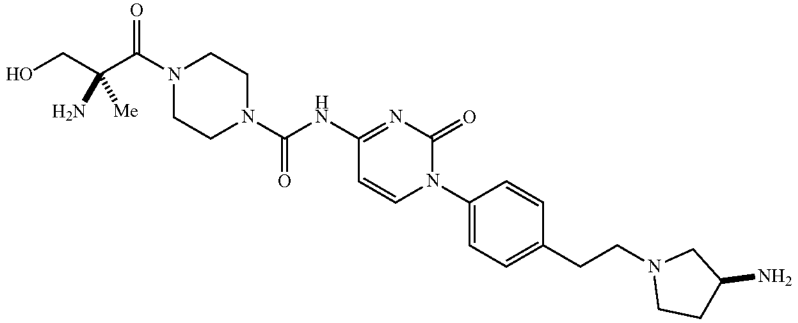 [SMILES: C[C@](N)(CO)C(=O)N1CCN(C(=O)Nc2ccn(-c3ccc(CCN4CC[C@H](N)C4)cc3)c(=O)n2)CC1] |
| 14 | 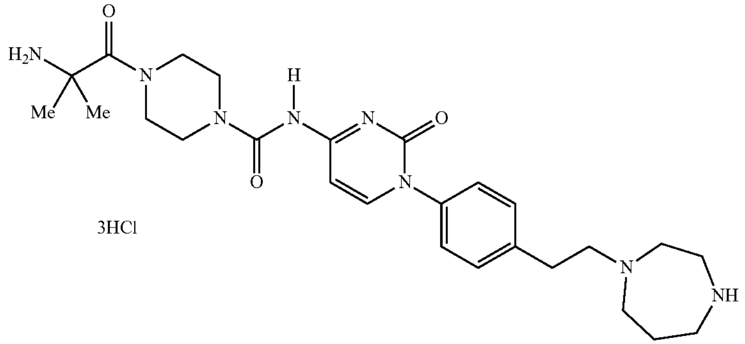 [SMILES: CC(C)(N)C(=O)N1CCN(C(=O)Nc2ccn(-c3ccc(CCN4CCCNCC4)cc3)c(=O)n2)CC1] 3HCl | 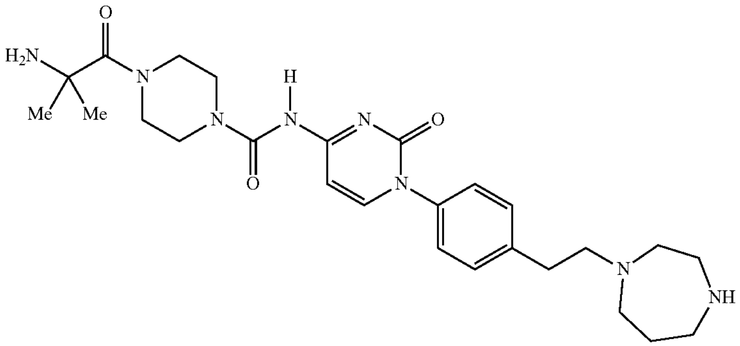 [SMILES: CC(C)(N)C(=O)N1CCN(C(=O)Nc2ccn(-c3ccc(CCN4CCCNCC4)cc3)c(=O)n2)CC1] |

TABLE 10-continued
| Compounds of Formula I | | |
|---|---|---|
| No. | Salt Structure | Free Base Structure |
| 15 | 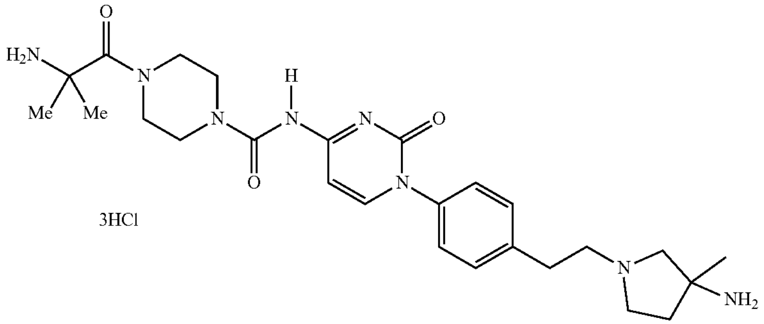 [SMILES: CC1(N)CCN(CCc2ccc(-n3ccc(NC(=O)N4CCN(C(=O)C(C)(C)N)CC4)nc3=O)cc2)C1] 3HCl | 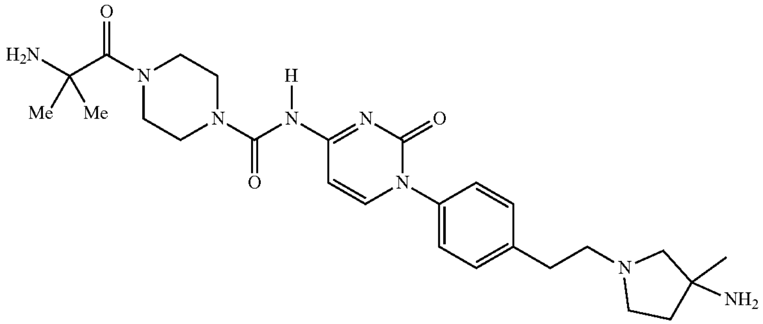 [SMILES: CC1(N)CCN(CCc2ccc(-n3ccc(NC(=O)N4CCN(C(=O)C(C)(C)N)CC4)nc3=O)cc2)C1] |
| 16 | 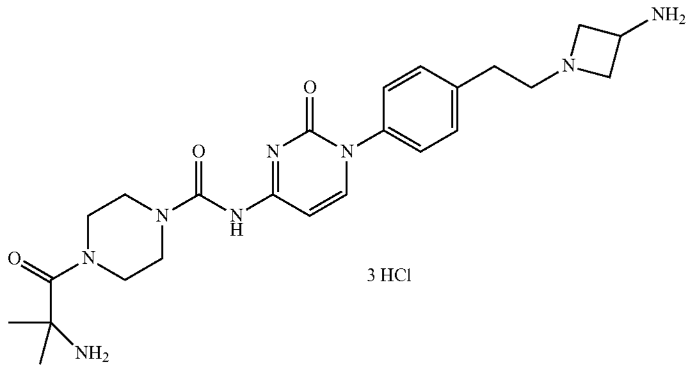 [SMILES: CC(C)(N)C(=O)N1CCN(C(=O)Nc2ccn(-c3ccc(CCN4CC(N)C4)cc3)c(=O)n2)CC1] 3 HCl | 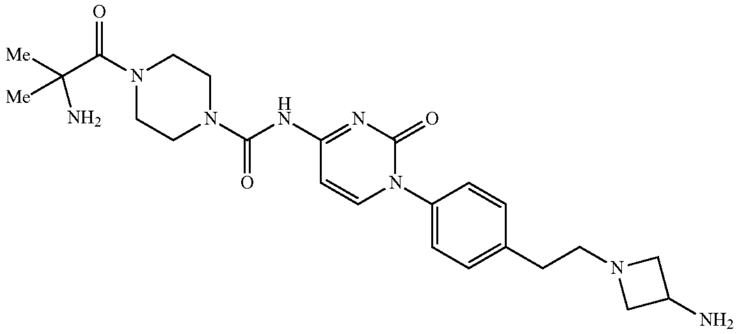 [SMILES: CC(C)(N)C(=O)N1CCN(C(=O)Nc2ccn(-c3ccc(CCN4CC(N)C4)cc3)c(=O)n2)CC1] |

TABLE 10-continued
| Compounds of Formula I | | |
|---|---|---|
| No. | Salt Structure | Free Base Structure |
| 17 | 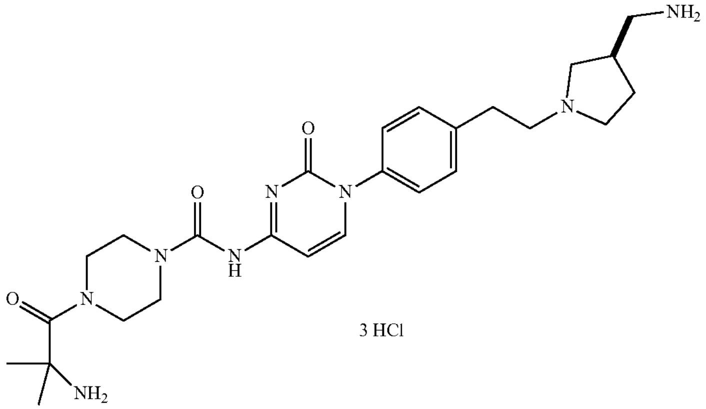 [SMILES: CC(C)(N)C(=O)N1CCN(C(=O)Nc2ccn(-c3ccc(CCN4CC[C@H](CN)C4)cc3)c(=O)n2)CC1] 3 HCl | 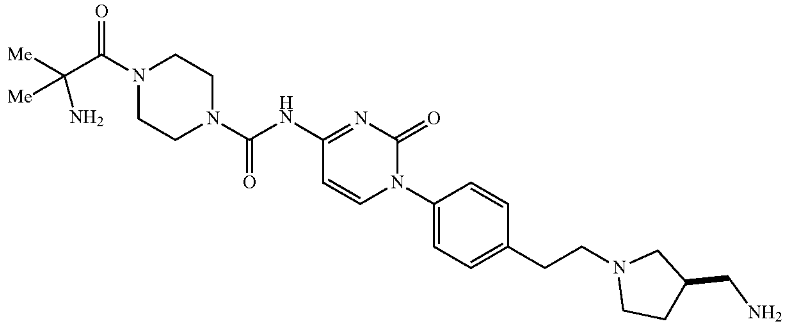 [SMILES: CC(C)(N)C(=O)N1CCN(C(=O)Nc2ccn(-c3ccc(CCN4CC[C@H](CN)C4)cc3)c(=O)n2)CC1] |
| 18 | 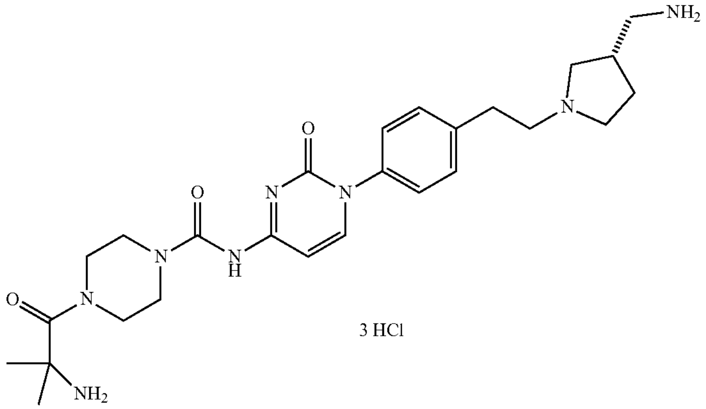 [SMILES: CC(C)(N)C(=O)N1CCN(C(=O)Nc2ccn(-c3ccc(CCN4CC[C@@H](CN)C4)cc3)c(=O)n2)CC1] 3 HCl | 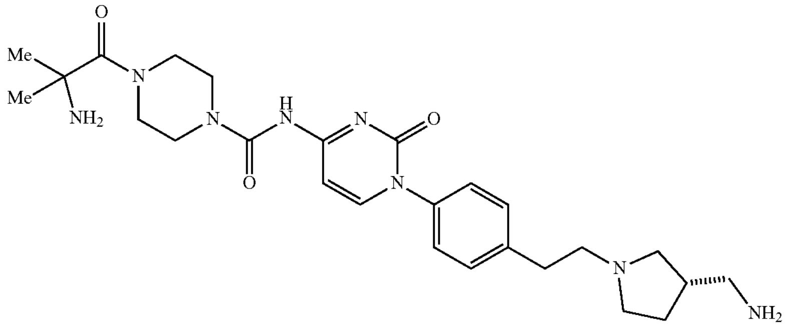 [SMILES: CC(C)(N)C(=O)N1CCN(C(=O)Nc2ccn(-c3ccc(CCN4CC[C@@H](CN)C4)cc3)c(=O)n2)CC1] |

TABLE 10-continued
| Compounds of Formula I | | |
|---|---|---|
| No. | Salt Structure | Free Base Structure |
| 21 | 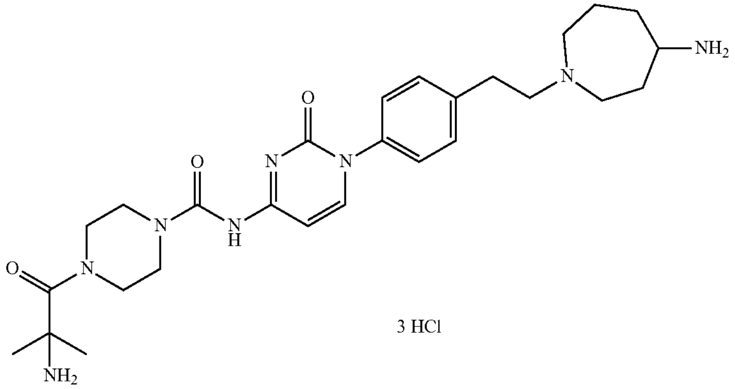 [SMILES: CC(C)(N)C(=O)N1CCN(C(=O)Nc2ccn(-c3ccc(CCN4CCCC(N)CC4)cc3)c(=O)n2)CC1] 3 HCl | 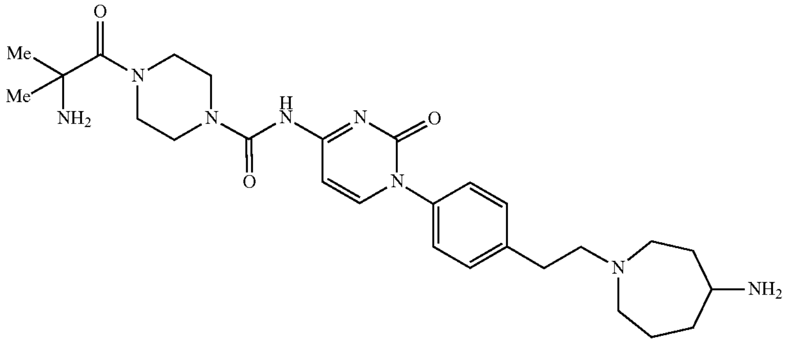 [SMILES: CC(C)(N)C(=O)N1CCN(C(=O)Nc2ccn(-c3ccc(CCN4CCCC(N)CC4)cc3)c(=O)n2)CC1] |
| 22 | 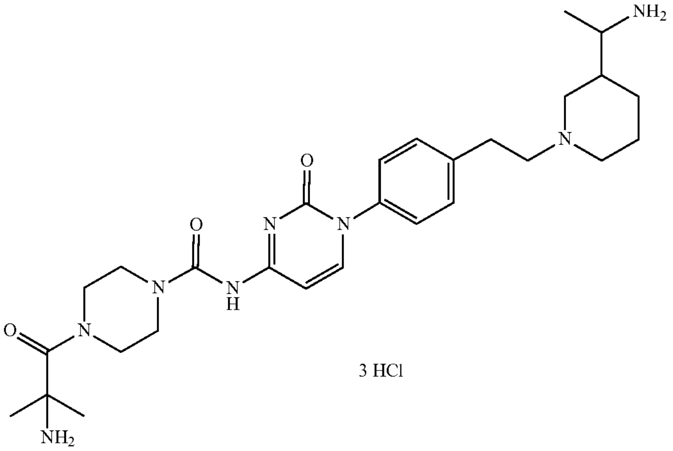 [SMILES: CC(N)C1CCCN(CCc2ccc(-n3ccc(NC(=O)N4CCN(C(=O)C(C)(C)N)CC4)nc3=O)cc2)C1] 3 HCl | 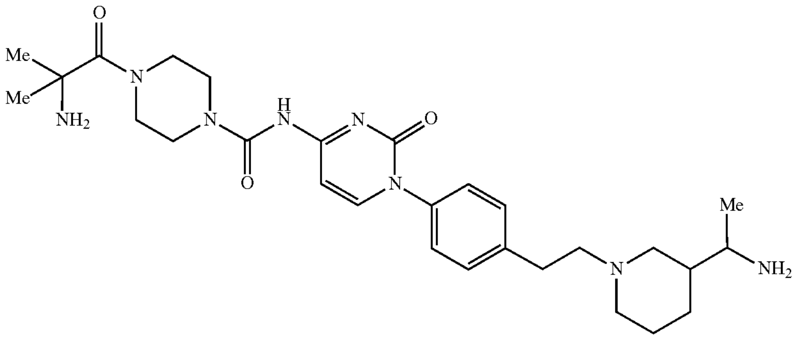 [SMILES: CC(N)C1CCCN(CCc2ccc(-n3ccc(NC(=O)N4CCN(C(=O)C(C)(C)N)CC4)nc3=O)cc2)C1] |

TABLE 10-continued
Compounds of Formula I
| No. | Salt Structure | Free Base Structure |
| --- | --- | --- |
| 23 | 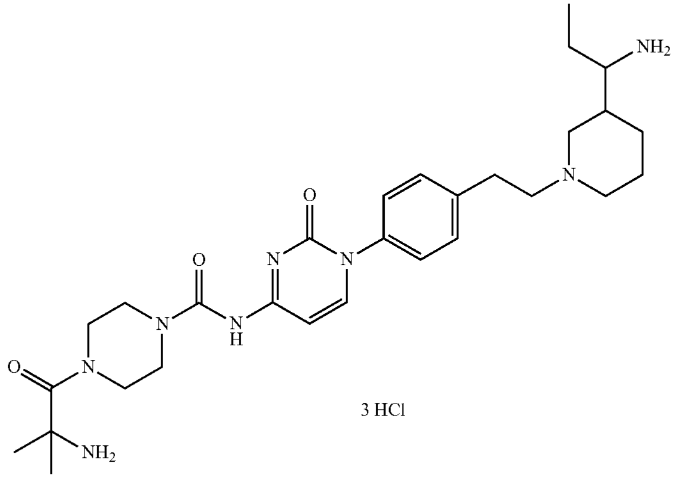 [SMILES: CCC(N)C1CCCN(CCc2ccc(-n3ccc(NC(=O)N4CCN(C(=O)C(C)(C)N)CC4)nc3=O)cc2)C1] 3 HCl | 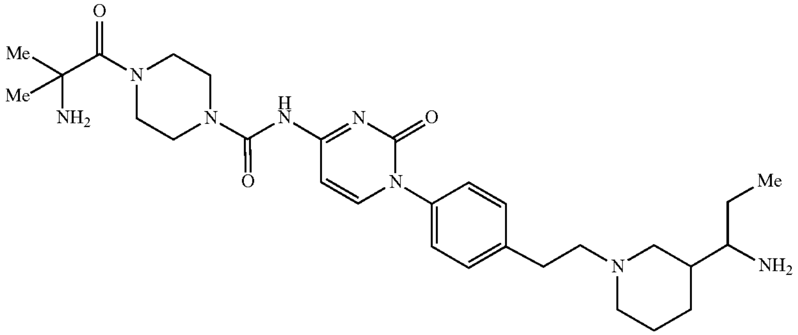 [SMILES: CCC(N)C1CCCN(CCc2ccc(-n3ccc(NC(=O)N4CCN(C(=O)C(C)(C)N)CC4)nc3=O)cc2)C1] |
| 24 | 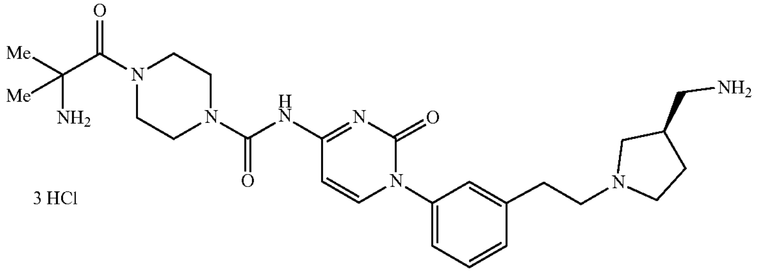 [SMILES: CC(C)(N)C(=O)N1CCN(C(=O)Nc2ccn(-c3cccc(CCN4CC[C@H](CN)C4)c3)c(=O)n2)CC1] 3 HCl | 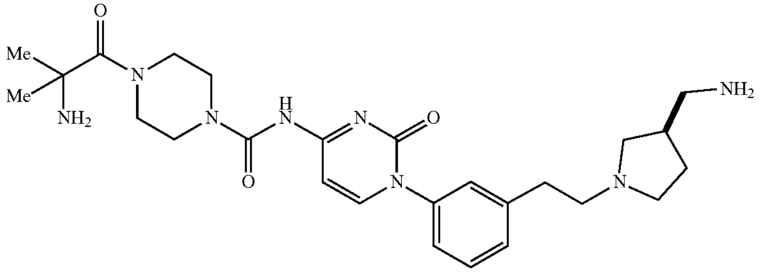 [SMILES: CC(C)(N)C(=O)N1CCN(C(=O)Nc2ccn(-c3cccc(CCN4CC[C@H](CN)C4)c3)c(=O)n2)CC1] |

TABLE 10-continued
| Compounds of Formula I | | |
|---|---|---|
| No. | Salt Structure | Free Base Structure |
| 25 | 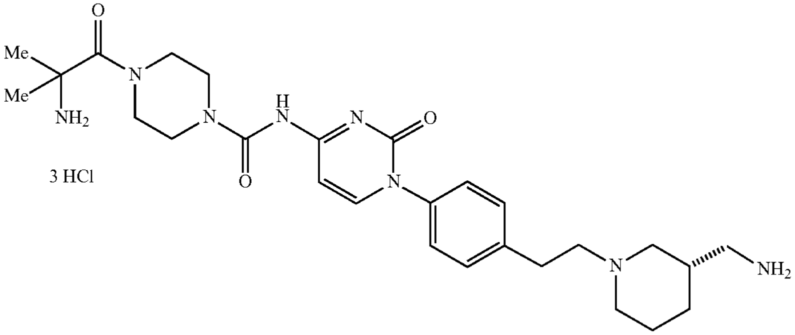 [SMILES: CC(C)(N)C(=O)N1CCN(C(=O)Nc2ccn(-c3ccc(CCN4CCC[C@@H](CN)C4)cc3)c(=O)n2)CC1] 3 HCl | 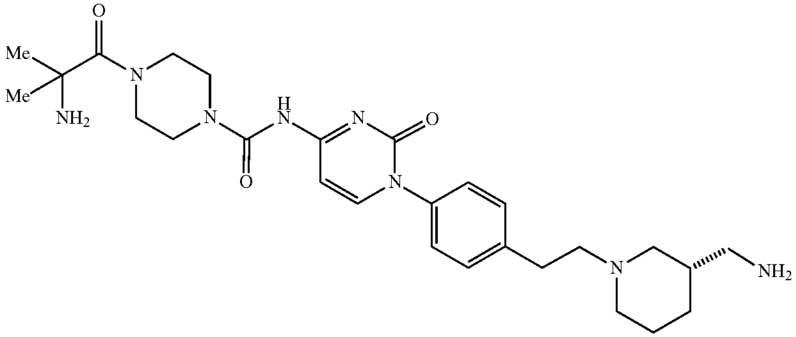 [SMILES: CC(C)(N)C(=O)N1CCN(C(=O)Nc2ccn(-c3ccc(CCN4CCC[C@@H](CN)C4)cc3)c(=O)n2)CC1] |
| 26 | 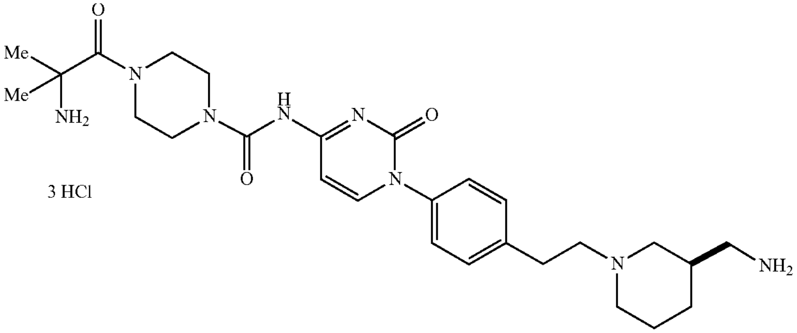 [SMILES: CC(C)(N)C(=O)N1CCN(C(=O)Nc2ccn(-c3ccc(CCN4CCC[C@H](CN)C4)cc3)c(=O)n2)CC1] 3 HCl | 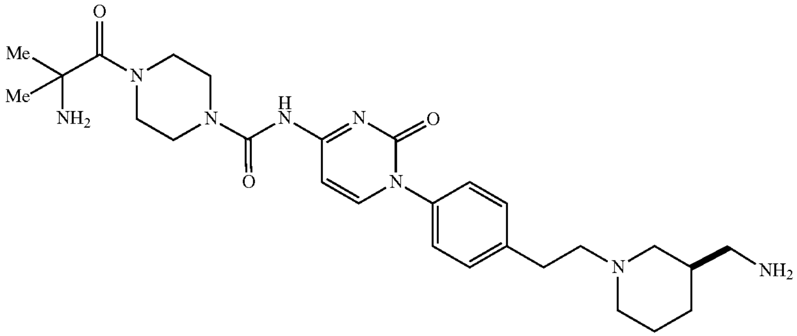 [SMILES: CC(C)(N)C(=O)N1CCN(C(=O)Nc2ccn(-c3ccc(CCN4CCC[C@H](CN)C4)cc3)c(=O)n2)CC1] |

TABLE 10-continued
| Compounds of Formula I | | |
|---|---|---|
| No. | Salt Structure | Free Base Structure |
| 27 | 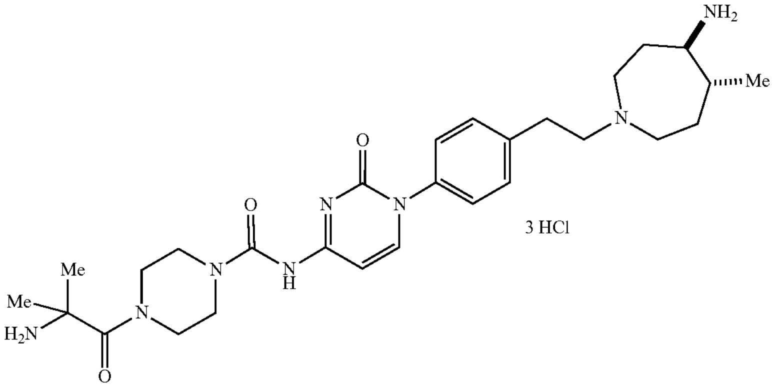 [SMILES: C[C@@H]1CCN(CCc2ccc(-n3ccc(NC(=O)N4CCN(C(=O)C(C)(C)N)CC4)nc3=O)cc2)CC[C@H]1N] 3 HCl | 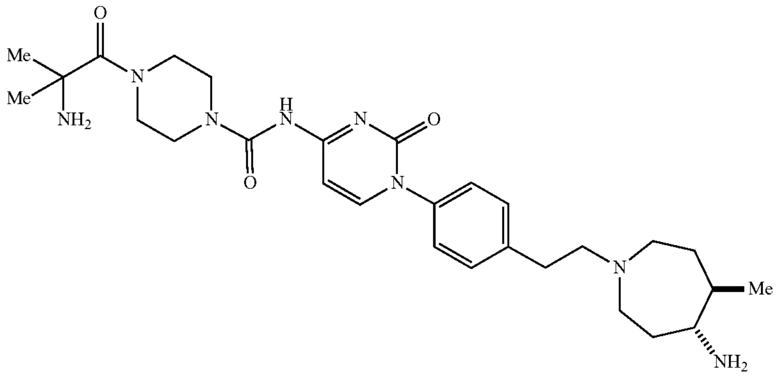 [SMILES: C[C@@H]1CCN(CCc2ccc(-n3ccc(NC(=O)N4CCN(C(=O)C(C)(C)N)CC4)nc3=O)cc2)CC[C@H]1N] |
| 28 | 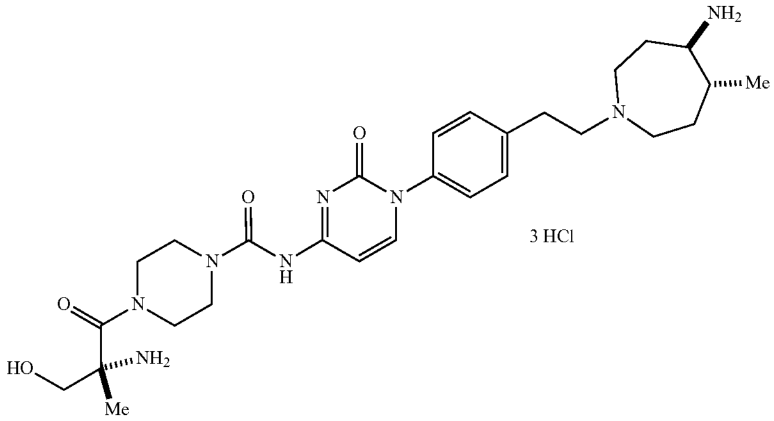 [SMILES: C[C@@H]1CCN(CCc2ccc(-n3ccc(NC(=O)N4CCN(C(=O)[C@](C)(N)CO)CC4)nc3=O)cc2)CC[C@H]1N] 3 HCl | 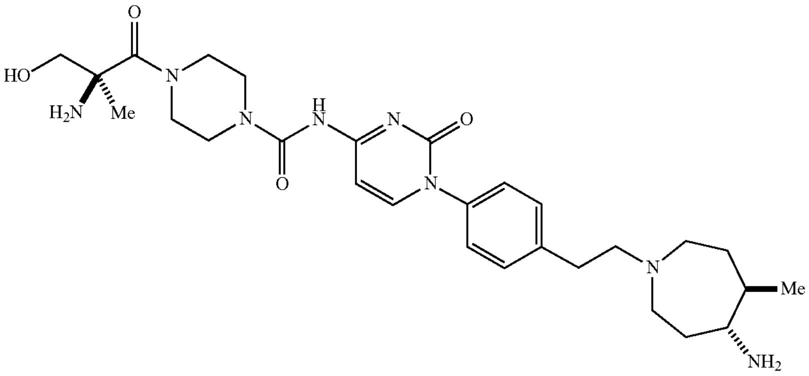 [SMILES: C[C@@H]1CCN(CCc2ccc(-n3ccc(NC(=O)N4CCN(C(=O)[C@@](C)(N)CO)CC4)nc3=O)cc2)CC[C@H]1N] |

TABLE 10-continued
| Compounds of Formula I | | |
|---|---|---|
| No. | Salt Structure | Free Base Structure |
| 29 | 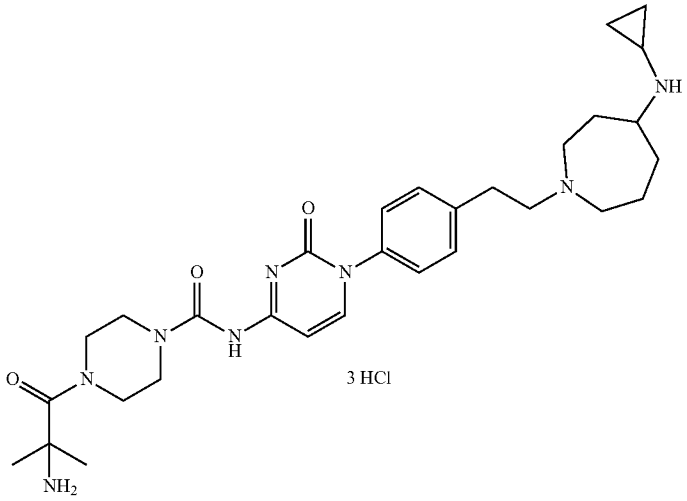 [SMILES: CC(C)(N)C(=O)N1CCN(C(=O)Nc2ccn(-c3ccc(CCN4CCCC(NC5CC5)CC4)cc3)c(=O)n2)CC1] 3 HCl | 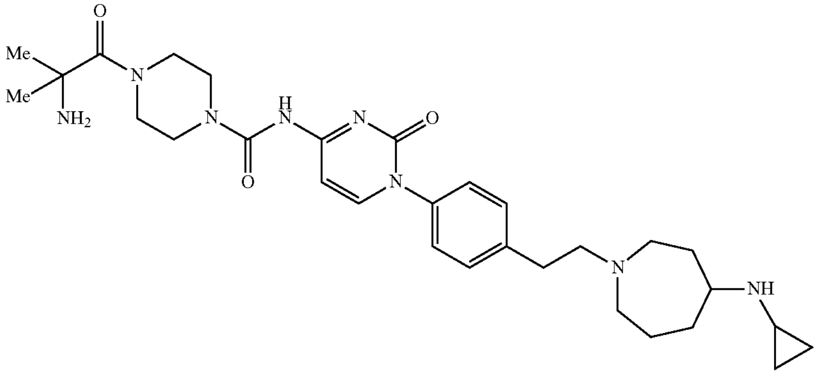 [SMILES: CC(C)(N)C(=O)N1CCN(C(=O)Nc2ccn(-c3ccc(CCN4CCCC(NC5CC5)CC4)cc3)c(=O)n2)CC1] |
| 30 | 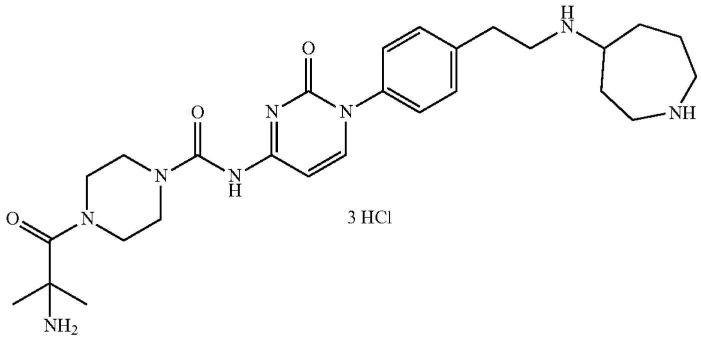 [SMILES: CC(C)(N)C(=O)N1CCN(C(=O)Nc2ccn(-c3ccc(CCNC4CCCNCC4)cc3)c(=O)n2)CC1] 3 HCl | 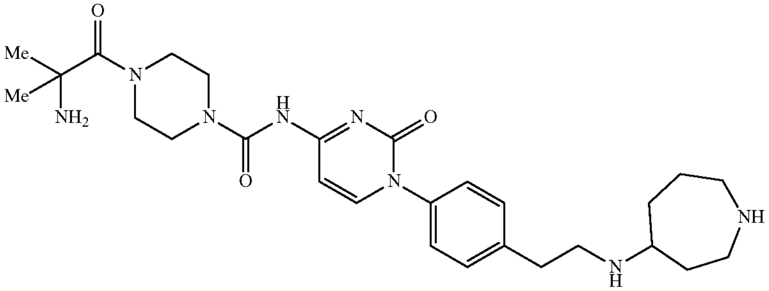 [SMILES: CC(C)(N)C(=O)N1CCN(C(=O)Nc2ccn(-c3ccc(CCNC4CCCNCC4)cc3)c(=O)n2)CC1] |

TABLE 10-continued
| Compounds of Formula I | | |
|---|---|---|
| No. | Salt Structure | Free Base Structure |
| 31 | 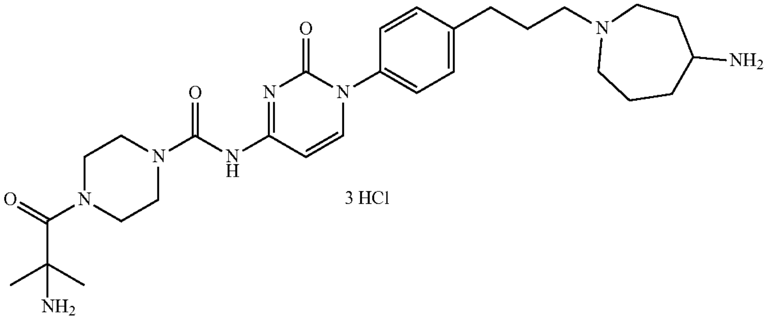 [SMILES: CC(C)(N)C(=O)N1CCN(C(=O)Nc2ccn(-c3ccc(CCCN4CCCC(N)CC4)cc3)c(=O)n2)CC1] 3 HCl | 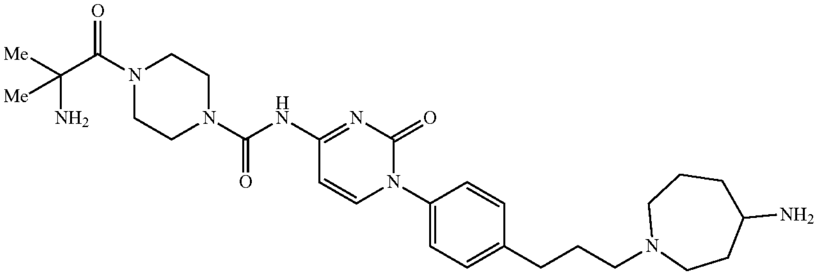 [SMILES: CC(C)(N)C(=O)N1CCN(C(=O)Nc2ccn(-c3ccc(CCCN4CCCC(N)CC4)cc3)c(=O)n2)CC1] |
| 32 | 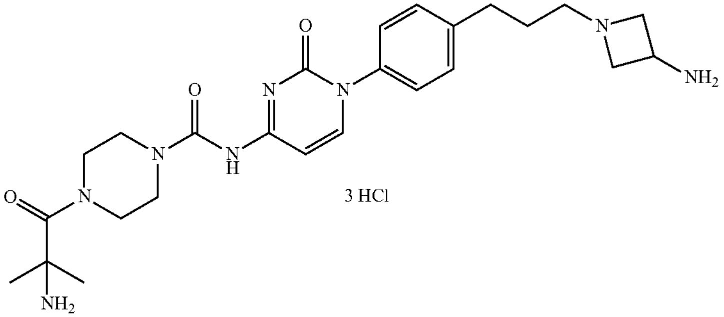 [SMILES: CC(C)(N)C(=O)N1CCN(C(=O)Nc2ccn(-c3ccc(CCCN4CC(N)C4)cc3)c(=O)n2)CC1] 3 HCl | 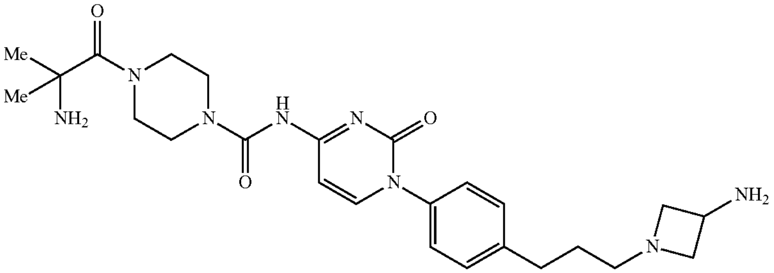 [SMILES: CC(C)(N)C(=O)N1CCN(C(=O)Nc2ccn(-c3ccc(CCCN4CC(N)C4)cc3)c(=O)n2)CC1] |

TABLE 10-continued
| Compounds of Formula I | | |
|---|---|---|
| No. | Salt Structure | Free Base Structure |
| 33 | 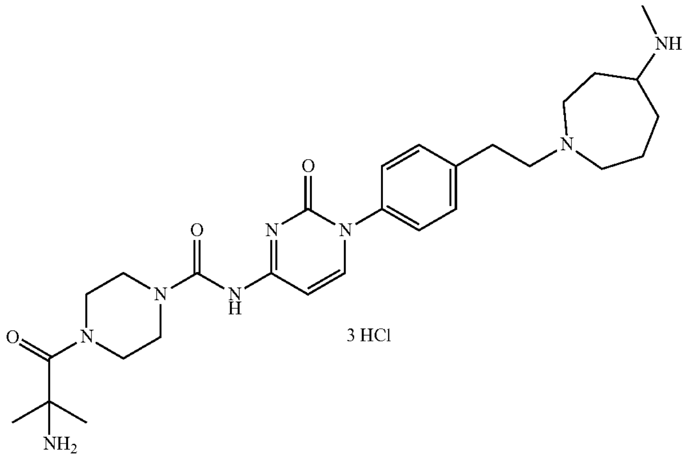 [SMILES: CNC1CCCN(CCc2ccc(-n3ccc(NC(=O)N4CCN(C(=O)C(C)(C)N)CC4)nc3=O)cc2)CC1] 3 HCl | 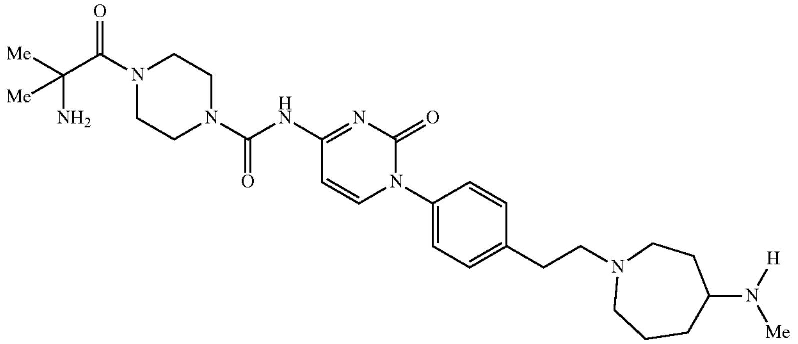 [SMILES: CNC1CCCN(CCc2ccc(-n3ccc(NC(=O)N4CCN(C(=O)C(C)(C)N)CC4)nc3=O)cc2)CC1] |
| 34 | 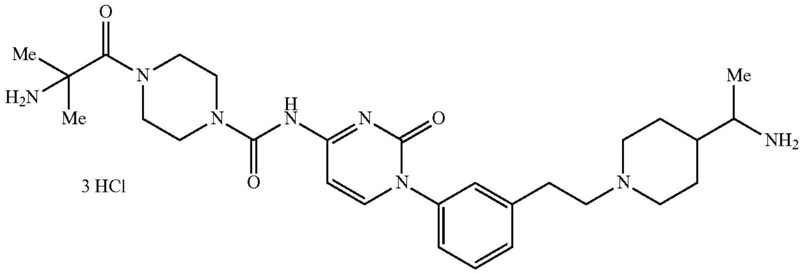 [SMILES: CC(N)C1CCN(CCc2cccc(-n3ccc(NC(=O)N4CCN(C(=O)C(C)(C)N)CC4)nc3=O)c2)CC1] 3 HCl | 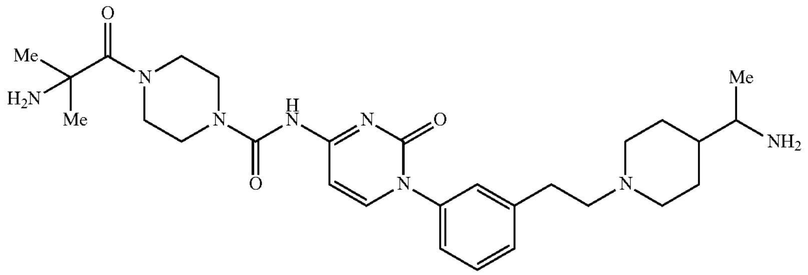 [SMILES: CC(N)C1CCN(CCc2cccc(-n3ccc(NC(=O)N4CCN(C(=O)C(C)(C)N)CC4)nc3=O)c2)CC1] |

TABLE 10-continued
| Compounds of Formula I | | |
|---|---|---|
| No. | Salt Structure | Free Base Structure |
| 35 | 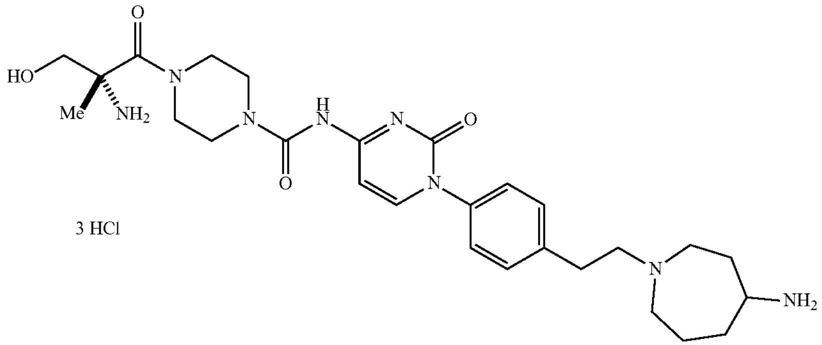 3 HCl | 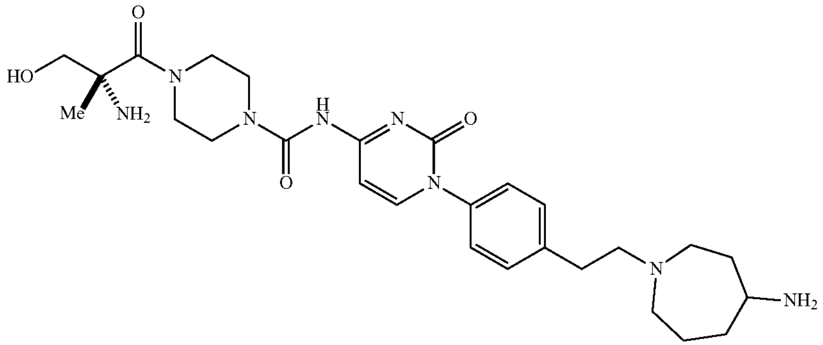 |
| 36 | 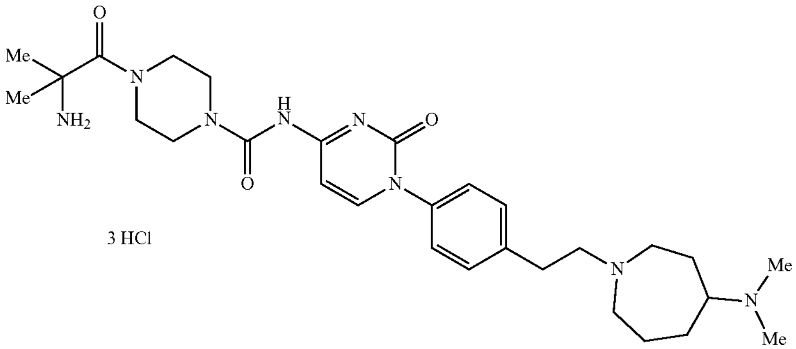 [SMILES: CN(C)C1CCCN(CCc2ccc(-n3ccc(NC(=O)N4CCN(C(=O)C(C)(C)N)CC4)nc3=O)cc2)CC1] 3 HCl | 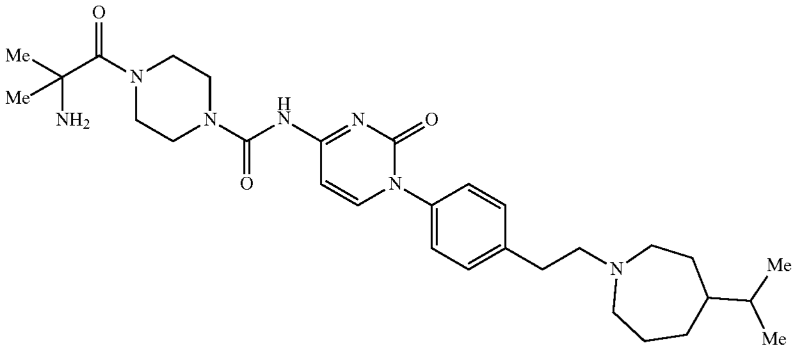 [SMILES: CC(C)C1CCCN(CCc2ccc(-n3ccc(NC(=O)N4CCN(C(=O)C(C)(C)N)CC4)nc3=O)cc2)CC1] |

TABLE 10-continued
| Compounds of Formula I | | |
|---|---|---|
| No. | Salt Structure | Free Base Structure |
| 37 | 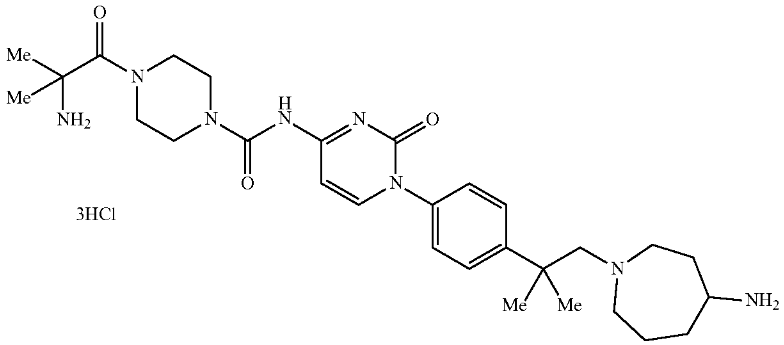 [SMILES: CC(C)(N)C(=O)N1CCN(C(=O)Nc2ccn(-c3ccc(C(C)(C)CN4CCCC(N)CC4)cc3)c(=O)n2)CC1] 3HCl | 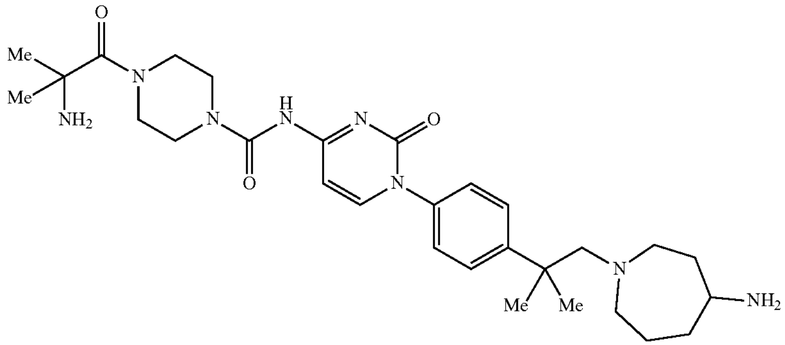 [SMILES: CC(C)(N)C(=O)N1CCN(C(=O)Nc2ccn(-c3ccc(C(C)(C)CN4CCCC(N)CC4)cc3)c(=O)n2)CC1] |
| 38 | 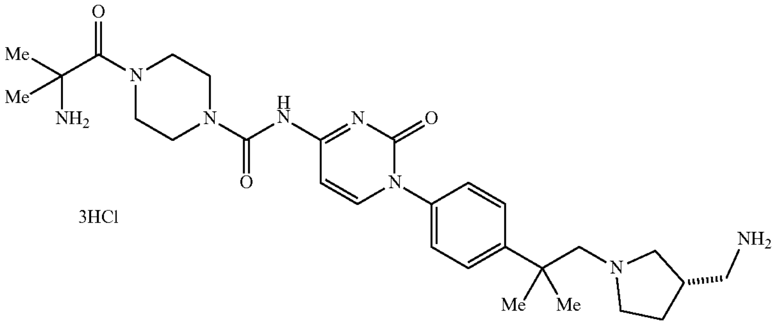 [SMILES: CC(C)(N)C(=O)N1CCN(C(=O)Nc2ccn(-c3ccc(C(C)(C)CN4CC[C@@H](CN)C4)cc3)c(=O)n2)CC1] 3HCl | 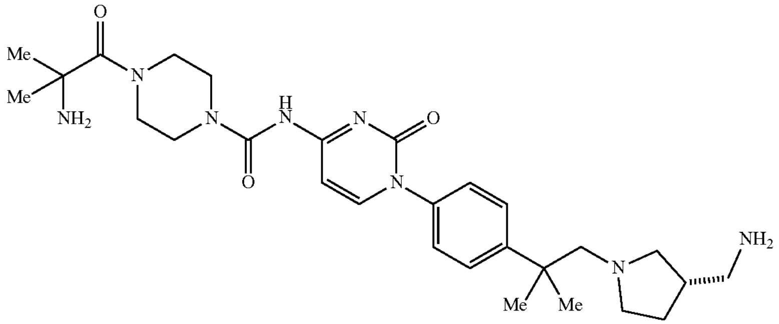 [SMILES: CC(C)(N)C(=O)N1CCN(C(=O)Nc2ccn(-c3ccc(C(C)(C)CN4CC[C@@H](CN)C4)cc3)c(=O)n2)CC1] |
| 39 | 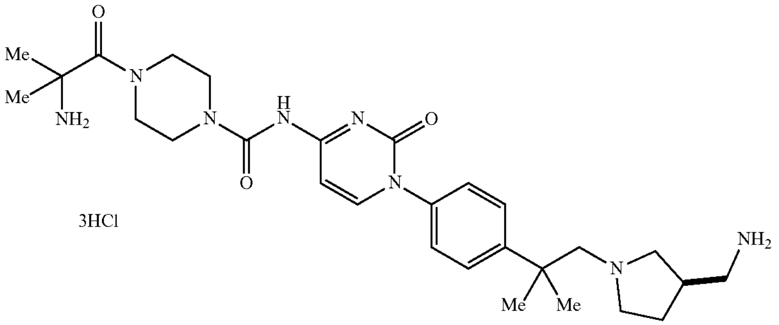 [SMILES: CC(C)(N)C(=O)N1CCN(C(=O)Nc2ccn(-c3ccc(C(C)(C)CN4CC[C@H](CN)C4)cc3)c(=O)n2)CC1] 3HCl | 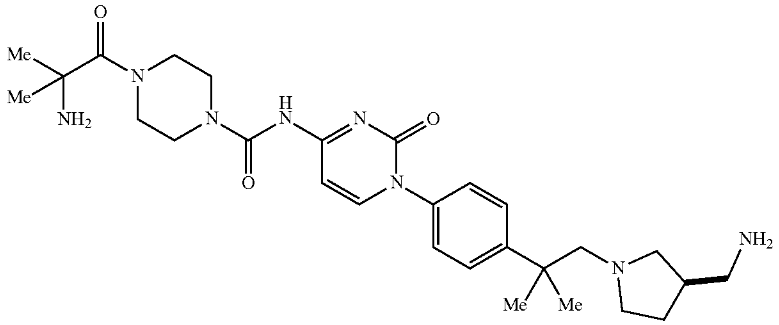 [SMILES: CC(C)(N)C(=O)N1CCN(C(=O)Nc2ccn(-c3ccc(C(C)(C)CN4CC[C@H](CN)C4)cc3)c(=O)n2)CC1] |

TABLE 10-continued
| Compounds of Formula I | | |
|---|---|---|
| No. | Salt Structure | Free Base Structure |
| 40 | 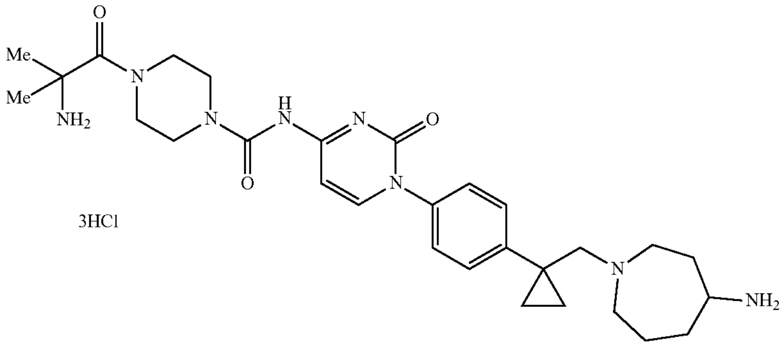 [SMILES: CC(C)(N)C(=O)N1CCN(C(=O)Nc2ccn(-c3ccc(C4(CN5CCCC(N)CC5)CC4)cc3)c(=O)n2)CC1] 3HCl | 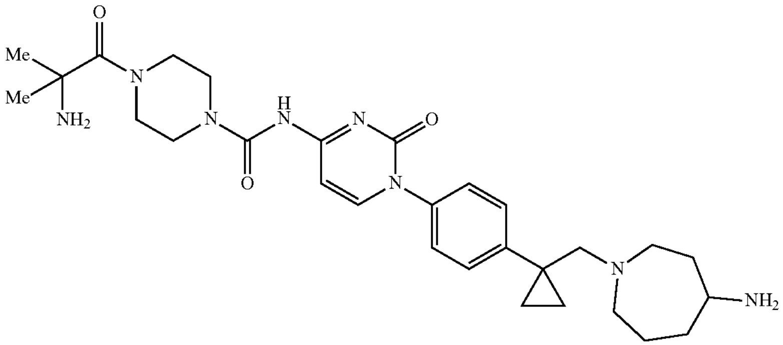 [SMILES: CC(C)(N)C(=O)N1CCN(C(=O)Nc2ccn(-c3ccc(C4(CN5CCCC(N)CC5)CC4)cc3)c(=O)n2)CC1] |
| 41 | 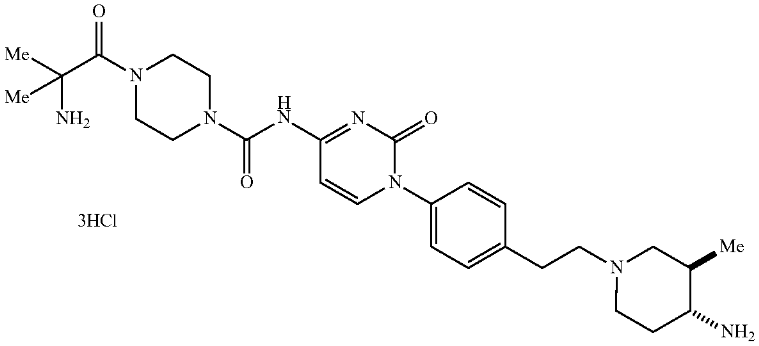 [SMILES: C[C@@H]1CN(CCc2ccc(-n3ccc(NC(=O)N4CCN(C(=O)C(C)(C)N)CC4)nc3=O)cc2)CC[C@H]1N] 3HCl | 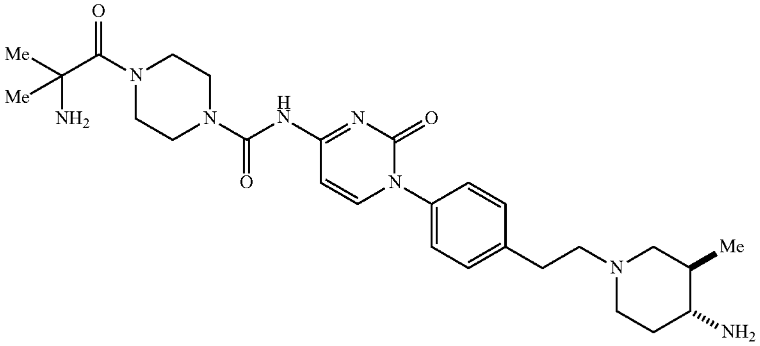 |
| 42 | 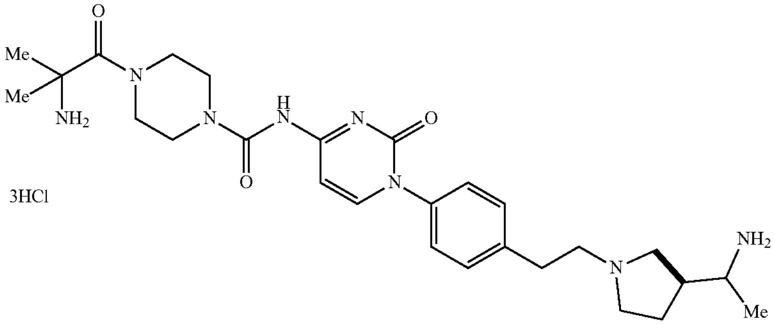 [SMILES: CC(N)[C@H]1CCN(CCc2ccc(-n3ccc(NC(=O)N4CCN(C(=O)C(C)(C)N)CC4)nc3=O)cc2)C1] 3HCl | 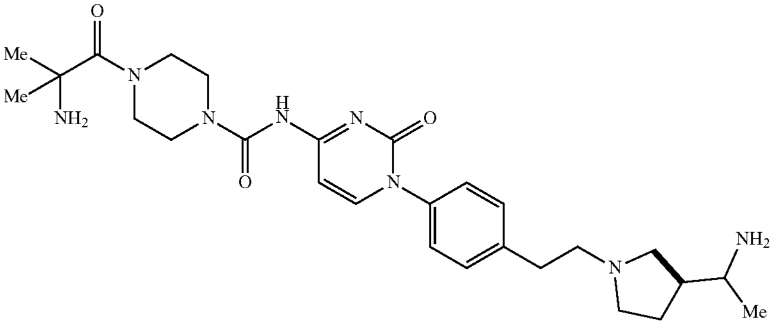 [SMILES: CC(N)[C@H]1CCN(CCc2ccc(-n3ccc(NC(=O)N4CCN(C(=O)C(C)(C)N)CC4)nc3=O)cc2)C1] |

TABLE 10-continued
| Compounds of Formula I | | |
|---|---|---|
| No. | Salt Structure | Free Base Structure |
| 43 | 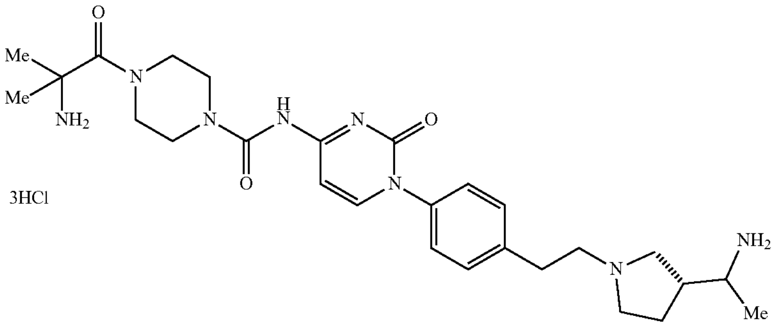 [SMILES: CC(N)[C@@H]1CCN(CCc2ccc(-n3ccc(NC(=O)N4CCN(C(=O)C(C)(C)N)CC4)nc3=O)cc2)C1] 3HCl | 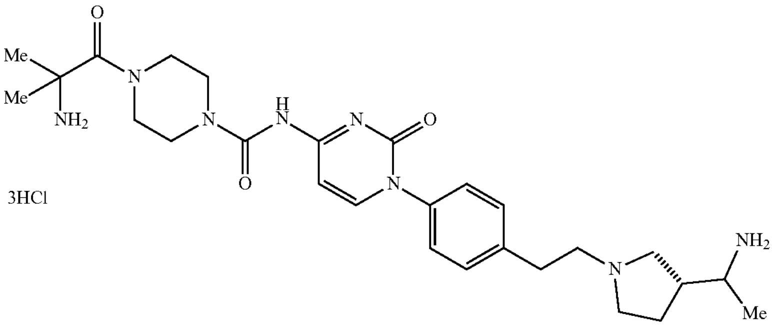 [SMILES: CC(N)[C@@H]1CCN(CCc2ccc(-n3ccc(NC(=O)N4CCN(C(=O)C(C)(C)N)CC4)nc3=O)cc2)C1] |
| 44 | 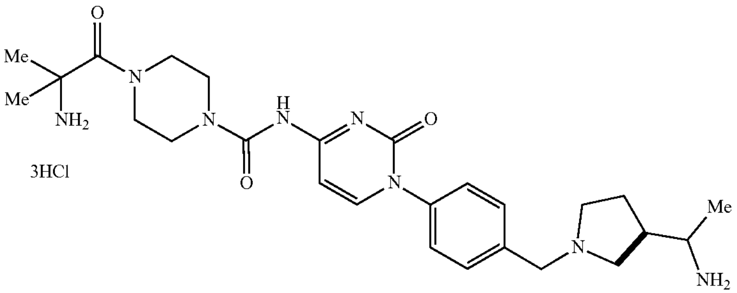 [SMILES: CC(N)[C@@H]1CCN(Cc2ccc(-n3ccc(NC(=O)N4CCN(C(=O)C(C)(C)N)CC4)nc3=O)cc2)C1] 3HCl | 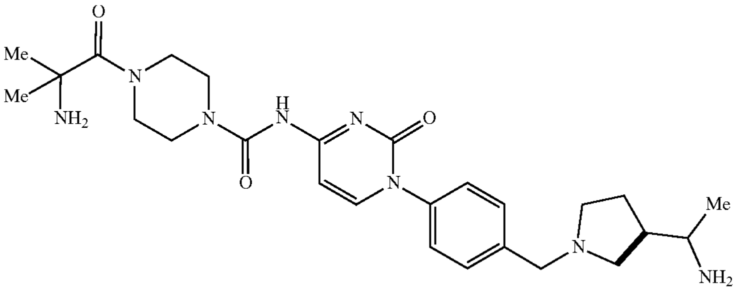 |
| 45 | 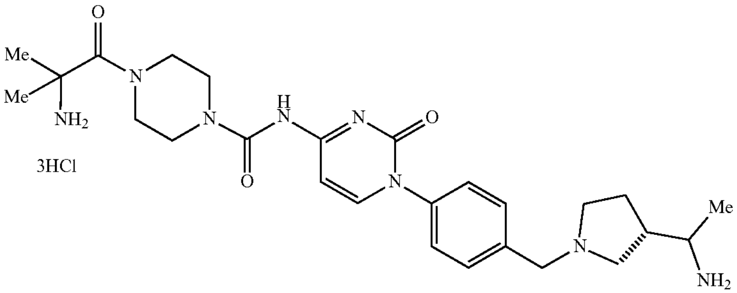 [SMILES: CC(N)[C@H]1CCN(Cc2ccc(-n3ccc(NC(=O)N4CCN(C(=O)C(C)(C)N)CC4)nc3=O)cc2)C1] 3HCl | 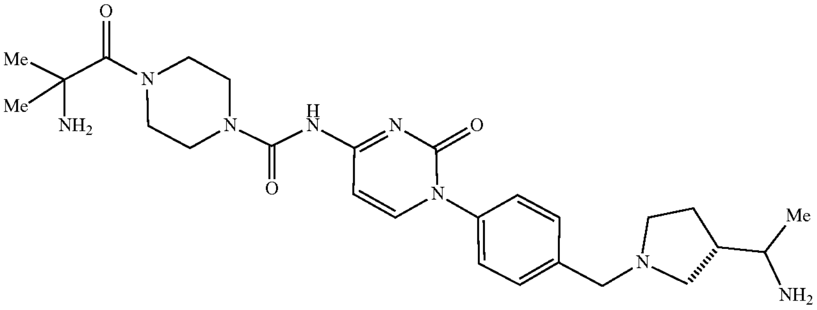 [SMILES: CC(N)[C@H]1CCN(Cc2ccc(-n3ccc(NC(=O)N4CCN(C(=O)C(C)(C)N)CC4)nc3=O)cc2)C1] |

TABLE 10-continued
Compounds of Formula I
| No. | Salt Structure | Free Base Structure |
| --- | --- | --- |
| 46 | 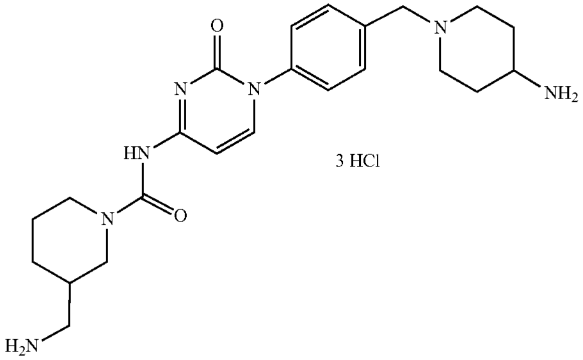 [SMILES: NCC1CCCN(C(=O)Nc2ccn(-c3ccc(CN4CCC(N)CC4)cc3)c(=O)n2)C1] 3 HCl | 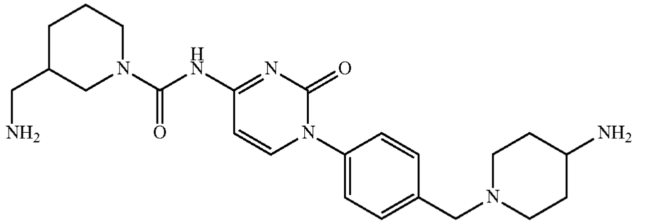 [SMILES: NCC1CCCN(C(=O)Nc2ccn(-c3ccc(CN4CCC(N)CC4)cc3)c(=O)n2)C1] |
| 47 | 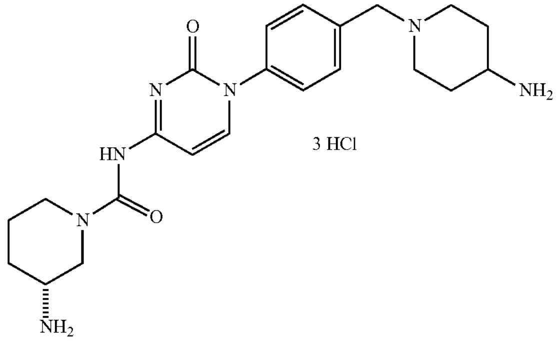 [SMILES: NC1CCN(Cc2ccc(-n3ccc(NC(=O)N4CCC[C@@H](N)C4)nc3=O)cc2)CC1] 3 HCl | 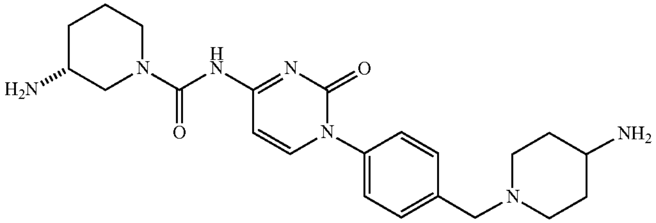 [SMILES: NC1CCN(Cc2ccc(-n3ccc(NC(=O)N4CCC[C@@H](N)C4)nc3=O)cc2)CC1] |

TABLE 10-continued
| Compounds of Formula I | | |
| --- | --- | --- |
| No. | Salt Structure | Free Base Structure |
| 48 | 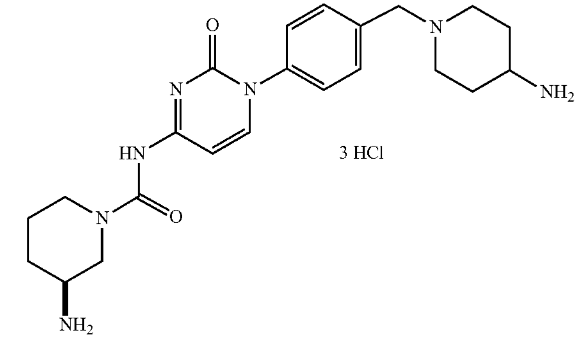 [SMILES: NC1CCN(Cc2ccc(-n3ccc(NC(=O)N4CCC[C@H](N)C4)nc3=O)cc2)CC1] 3 HCl | 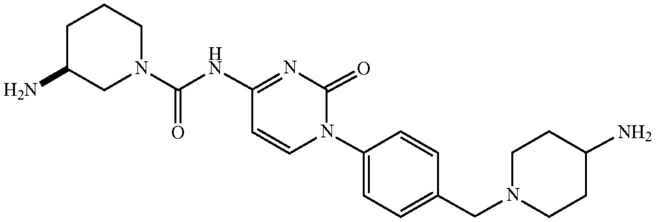 [SMILES: NC1CCN(Cc2ccc(-n3ccc(NC(=O)N4CCC[C@H](N)C4)nc3=O)cc2)CC1] |
| 49 | 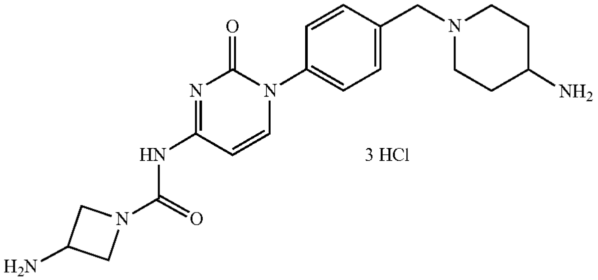 [SMILES: NC1CCN(Cc2ccc(-n3ccc(NC(=O)N4CC(N)C4)nc3=O)cc2)CC1] 3 HCl | 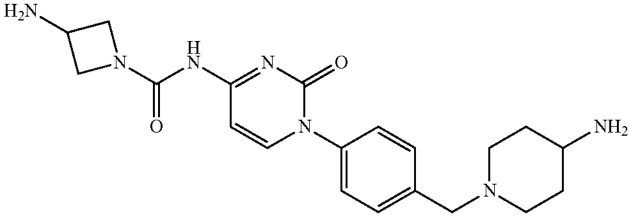 [SMILES: NC1CCN(Cc2ccc(-n3ccc(NC(=O)N4CC(N)C4)nc3=O)cc2)CC1] |
| 50 | 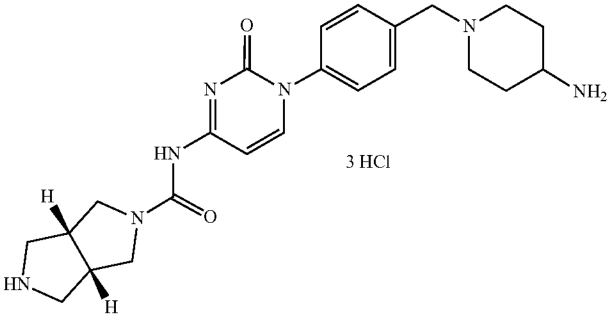 [SMILES: NC1CCN(Cc2ccc(-n3ccc(NC(=O)N4C[C@H]5CNC[C@H]5C4)nc3=O)cc2)CC1] 3 HCl | 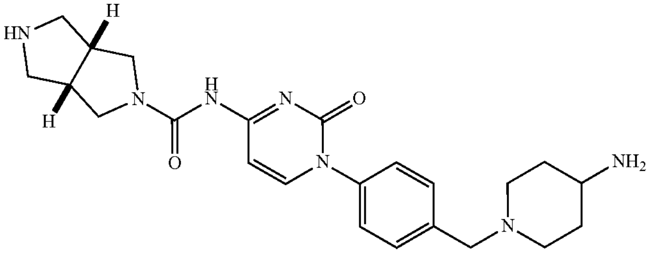 [SMILES: NC1CCN(Cc2ccc(-n3ccc(NC(=O)N4C[C@H]5CNC[C@H]5C4)nc3=O)cc2)CC1] |

TABLE 10-continued
| Compounds of Formula I | | |
|---|---|---|
| No. | Salt Structure | Free Base Structure |
| 51 | 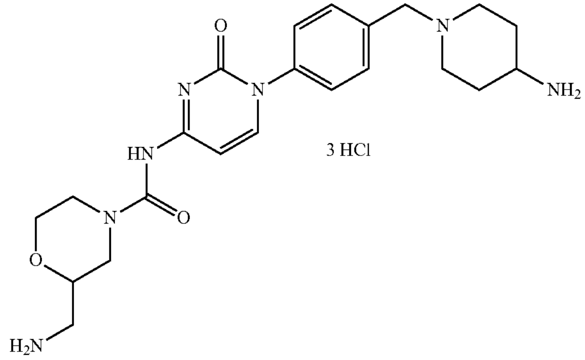 [SMILES: NCC1CN(C(=O)Nc2ccn(-c3ccc(CN4CCC(N)CC4)cc3)c(=O)n2)CCO1] 3 HCl | 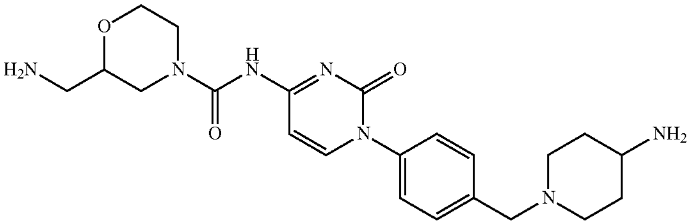 [SMILES: NCC1CN(C(=O)Nc2ccn(-c3ccc(CN4CCC(N)CC4)cc3)c(=O)n2)CCO1] |
| 52 | 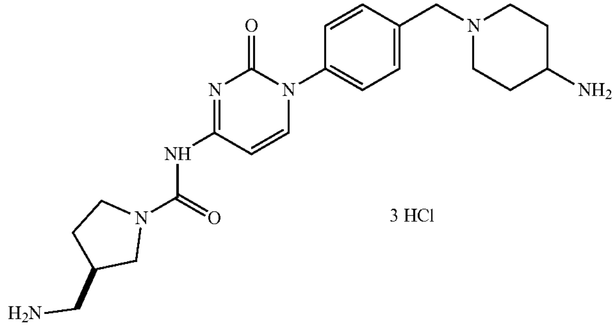 [SMILES: NC[C@H]1CCN(C(=O)Nc2ccn(-c3ccc(CN4CCC(N)CC4)cc3)c(=O)n2)C1] 3 HCl | 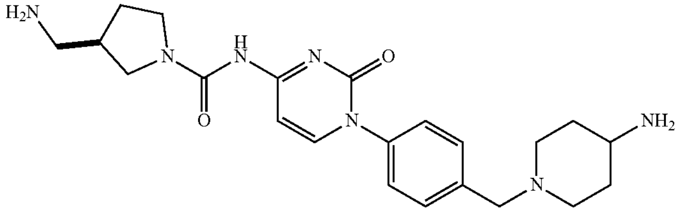 [SMILES: NC[C@H]1CCN(C(=O)Nc2ccn(-c3ccc(CN4CCC(N)CC4)cc3)c(=O)n2)C1] |
| 53 | 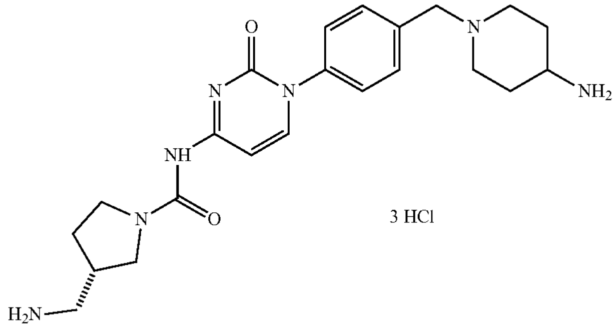 [SMILES: NC[C@@H]1CCN(C(=O)Nc2ccn(-c3ccc(CN4CCC(N)CC4)cc3)c(=O)n2)C1] 3 HCl | 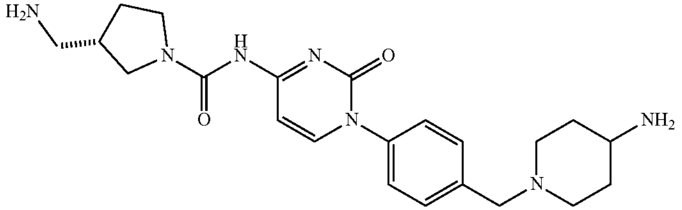 [SMILES: NC[C@@H]1CCN(C(=O)Nc2ccn(-c3ccc(CN4CCC(N)CC4)cc3)c(=O)n2)C1] |

TABLE 10-continued
Compounds of Formula I
| No. | Salt Structure | Free Base Structure |
|---|---|---|
| 54 | 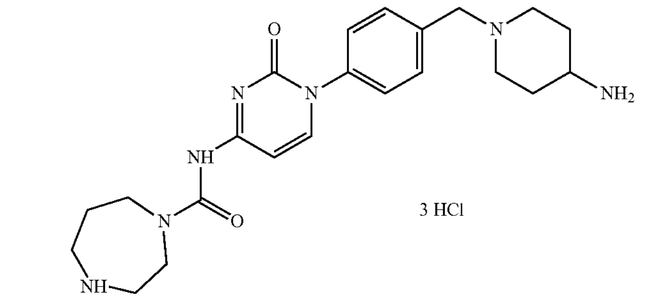 [SMILES: NC1CCN(Cc2ccc(-n3ccc(NC(=O)N4CCCNCC4)nc3=O)cc2)CC1] 3 HCl | 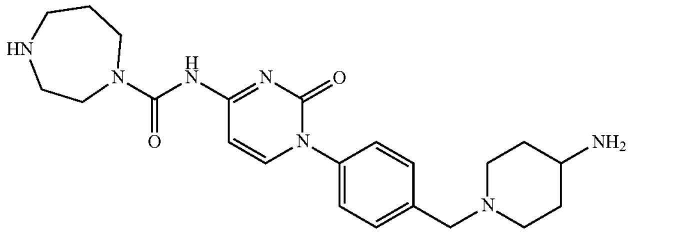 [SMILES: NC1CCN(Cc2ccc(-n3ccc(NC(=O)N4CCCNCC4)nc3=O)cc2)CC1] |
| 55 | 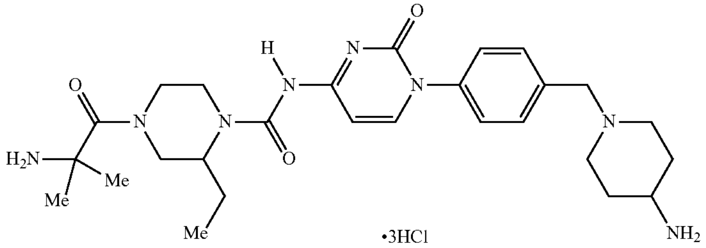 [SMILES: CCC1CN(C(=O)C(C)(C)N)CCN1C(=O)Nc1ccn(-c2ccc(CN3CCC(N)CC3)cc2)c(=O)n1] •3HCl | 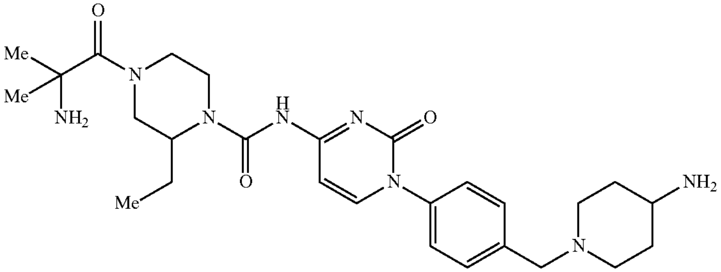 [SMILES: CCC1CN(C(=O)C(C)(C)N)CCN1C(=O)Nc1ccn(-c2ccc(CN3CCC(N)CC3)cc2)c(=O)n1] |
| 56 | 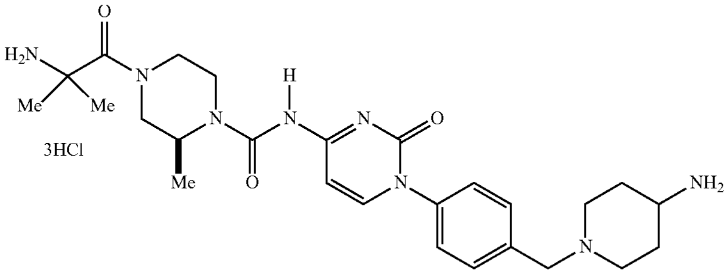 [SMILES: C[C@H]1CN(C(=O)C(C)(C)N)CCN1C(=O)Nc1ccn(-c2ccc(CN3CCC(N)CC3)cc2)c(=O)n1] 3HCl | 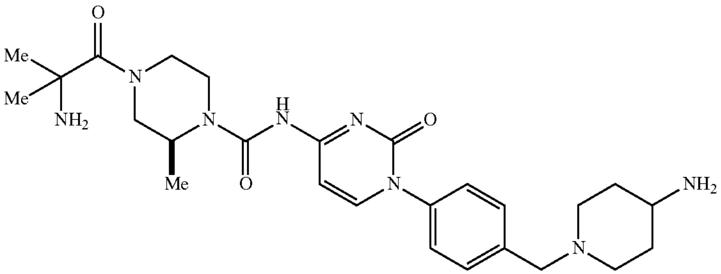 [SMILES: C[C@H]1CN(C(=O)C(C)(C)N)CCN1C(=O)Nc1ccn(-c2ccc(CN3CCC(N)CC3)cc2)c(=O)n1] |

TABLE 10-continued
| Compounds of Formula I | | |
|---|---|---|
| No. | Salt Structure | Free Base Structure |
| 57 | 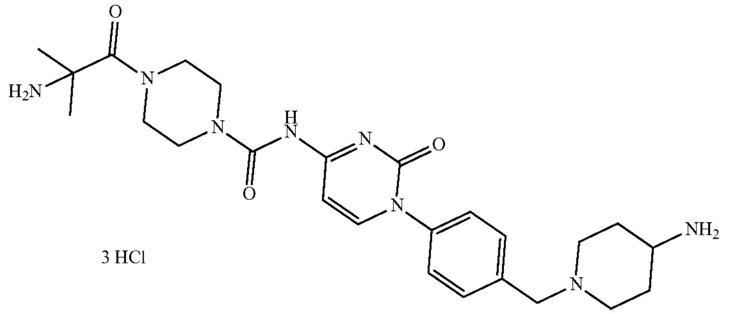 [SMILES: CC(C)(N)C(=O)N1CCN(C(=O)Nc2ccn(-c3ccc(CN4CCC(N)CC4)cc3)c(=O)n2)CC1] 3 HCl | 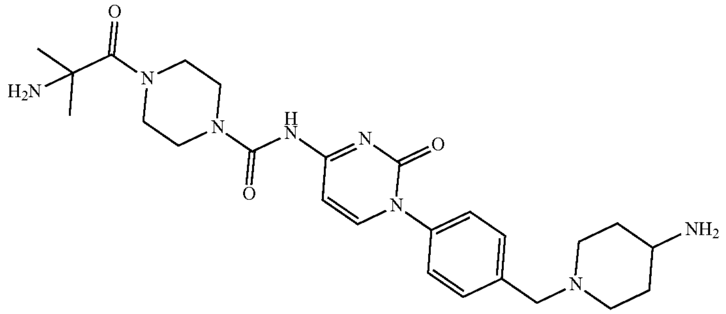 [SMILES: CC(C)(N)C(=O)N1CCN(C(=O)Nc2ccn(-c3ccc(CN4CCC(N)CC4)cc3)c(=O)n2)CC1] |
| 58 | 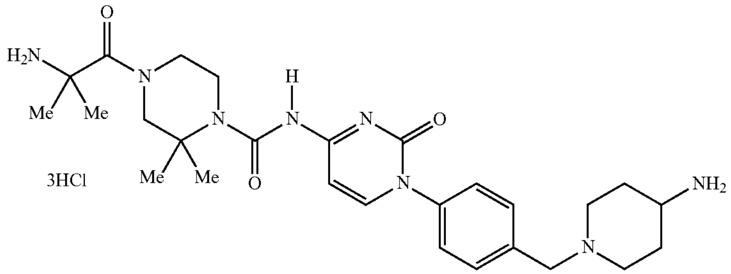 [SMILES: CC(C)(N)C(=O)N1CCN(C(=O)Nc2ccn(-c3ccc(CN4CCC(N)CC4)cc3)c(=O)n2)C(C)(C)C1] 3HCl | 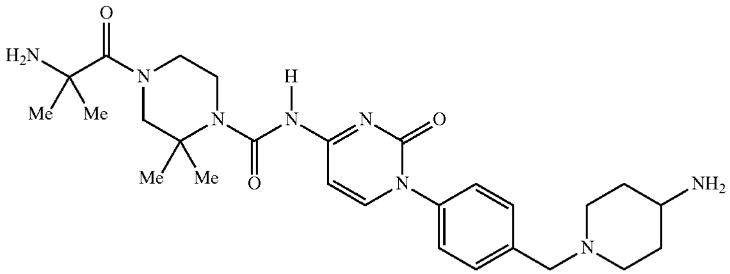 [SMILES: CC(C)(N)C(=O)N1CCN(C(=O)Nc2ccn(-c3ccc(CN4CCC(N)CC4)cc3)c(=O)n2)C(C)(C)C1] |
| 59 | 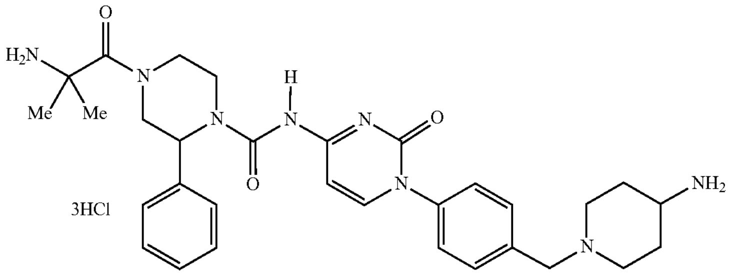 [SMILES: CC(C)(N)C(=O)N1CCN(C(=O)Nc2ccn(-c3ccc(CN4CCC(N)CC4)cc3)c(=O)n2)C(c2ccccc2)C1] 3HCl | 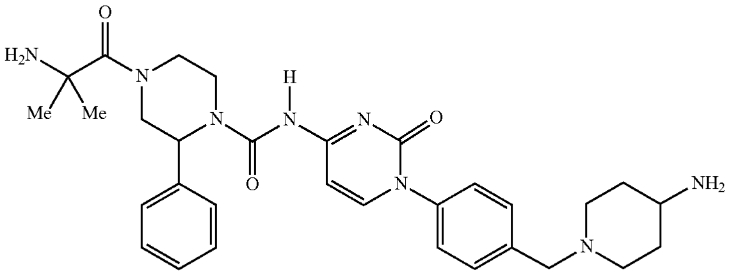 [SMILES: CC(C)(N)C(=O)N1CCN(C(=O)Nc2ccn(-c3ccc(CN4CCC(N)CC4)cc3)c(=O)n2)C(c2ccccc2)C1] |

TABLE 10-continued
| Compounds of Formula I | | |
|---|---|---|
| No. | Salt Structure | Free Base Structure |
| 60 | 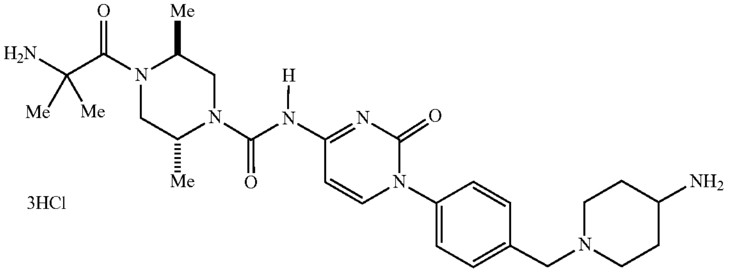 [SMILES: C[C@@H]1CN(C(=O)C(C)(C)N)[C@@H](C)CN1C(=O)Nc1ccn(-c2ccc(CN3CCC(N)CC3)cc2)c(=O)n1] 3HCl | 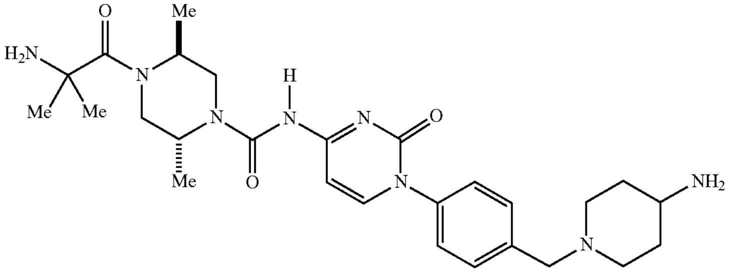 [SMILES: C[C@@H]1CN(C(=O)C(C)(C)N)[C@@H](C)CN1C(=O)Nc1ccn(-c2ccc(CN3CCC(N)CC3)cc2)c(=O)n1] |
| 61 | 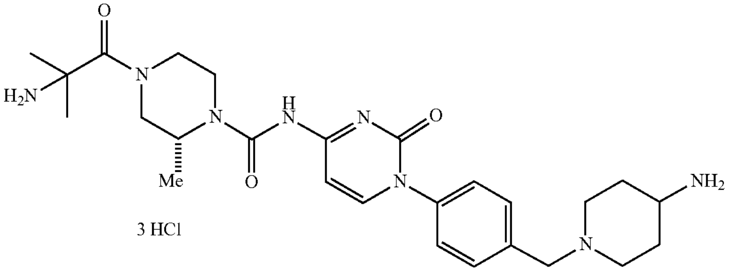 [SMILES: C[C@@H]1CN(C(=O)C(C)(C)N)CCN1C(=O)Nc1ccn(-c2ccc(CN3CCC(N)CC3)cc2)c(=O)n1] 3 HCl | 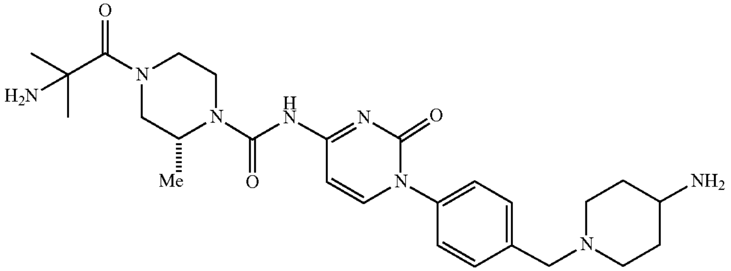 [SMILES: C[C@@H]1CN(C(=O)C(C)(C)N)CCN1C(=O)Nc1ccn(-c2ccc(CN3CCC(N)CC3)cc2)c(=O)n1] |
| 62 | 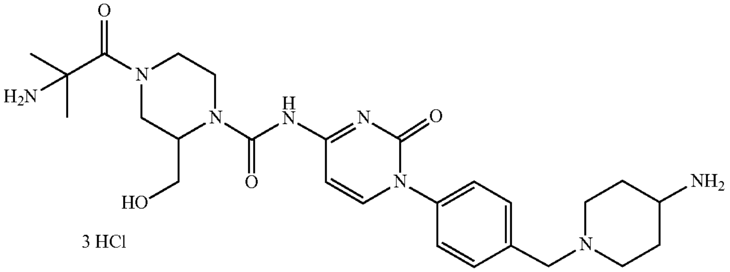 [SMILES: CC(C)(N)C(=O)N1CCN(C(=O)Nc2ccn(-c3ccc(CN4CCC(N)CC4)cc3)c(=O)n2)C(CO)C1] 3 HCl | 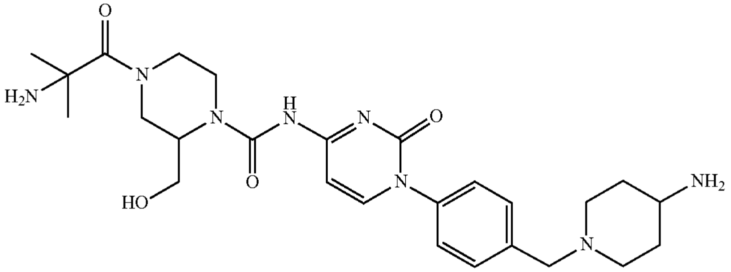 [SMILES: CC(C)(N)C(=O)N1CCN(C(=O)Nc2ccn(-c3ccc(CN4CCC(N)CC4)cc3)c(=O)n2)C(CO)C1] |

TABLE 10-continued
Compounds of Formula I
| No. | Salt Structure | Free Base Structure |
|---|---|---|
| 63 | 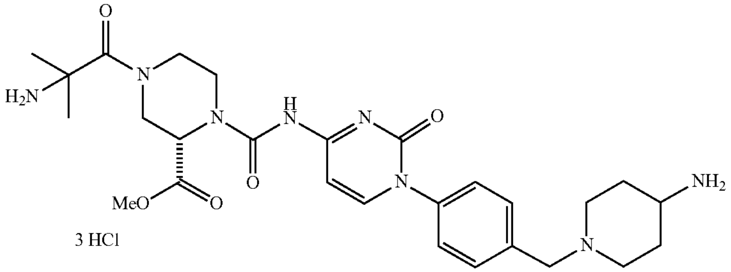 [SMILES: COC(=O)[C@@H]1CN(C(=O)C(C)(C)N)CCN1C(=O)Nc1ccn(-c2ccc(CN3CCC(N)CC3)cc2)c(=O)n1] 3 HCl | 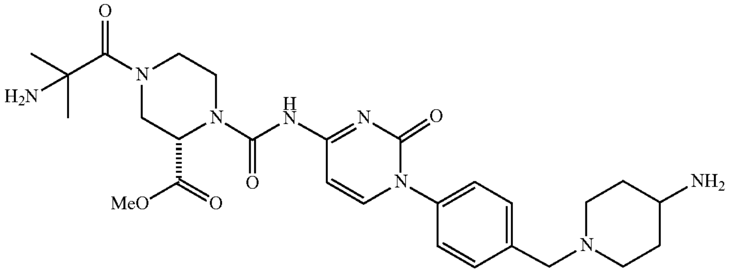 [SMILES: COC(=O)[C@@H]1CN(C(=O)C(C)(C)N)CCN1C(=O)Nc1ccn(-c2ccc(CN3CCC(N)CC3)cc2)c(=O)n1] |
| 64 | 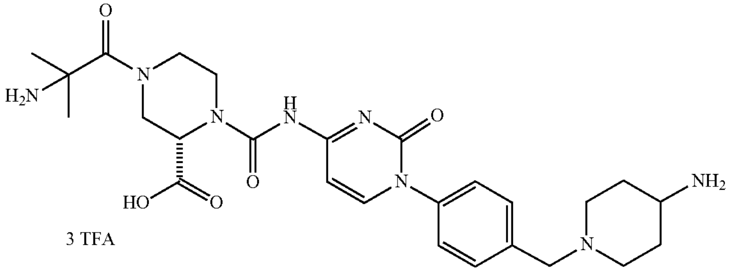 [SMILES: CC(C)(N)C(=O)N1CCN(C(=O)Nc2ccn(-c3ccc(CN4CCC(N)CC4)cc3)c(=O)n2)[C@H](C(=O)O)C1] 3 TFA | 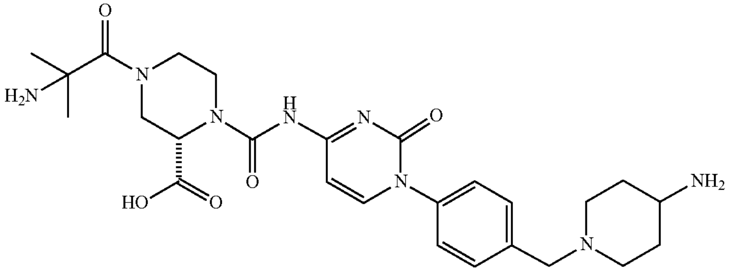 [SMILES: CC(C)(N)C(=O)N1CCN(C(=O)Nc2ccn(-c3ccc(CN4CCC(N)CC4)cc3)c(=O)n2)[C@H](C(=O)O)C1] |
| 65 | 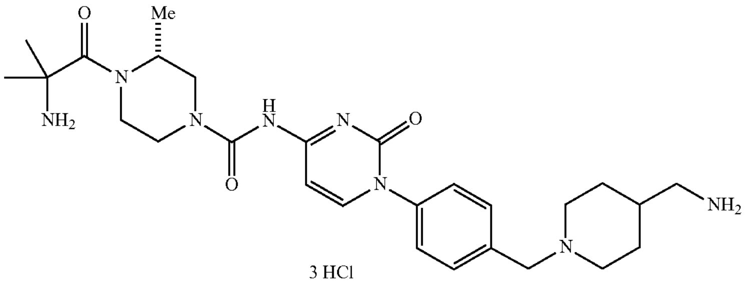 [SMILES: C[C@@H]1CN(C(=O)Nc2ccn(-c3ccc(CN4CCC(CN)CC4)cc3)c(=O)n2)CCN1C(=O)C(C)(C)N] 3 HCl | 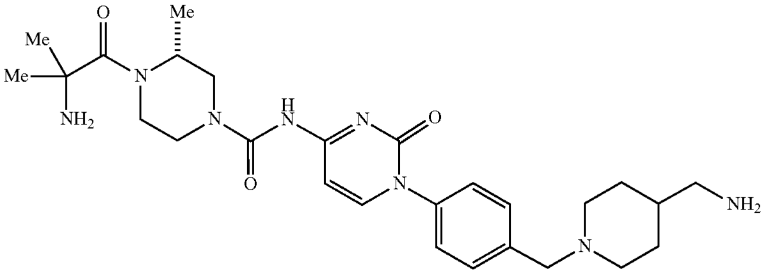 [SMILES: C[C@@H]1CN(C(=O)Nc2ccn(-c3ccc(CN4CCC(CN)CC4)cc3)c(=O)n2)CCN1C(=O)C(C)(C)N] |

TABLE 10-continued
| Compounds of Formula I | | |
|---|---|---|
| No. | Salt Structure | Free Base Structure |
| 66 | 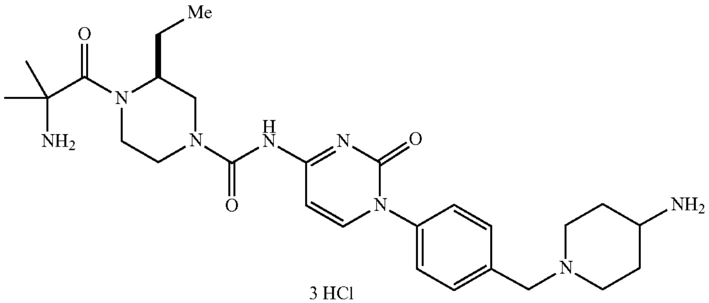 [SMILES: CC[C@H]1CN(C(=O)Nc2ccn(-c3ccc(CN4CCC(N)CC4)cc3)c(=O)n2)CCN1C(=O)C(C)(C)N] 3 HCl | 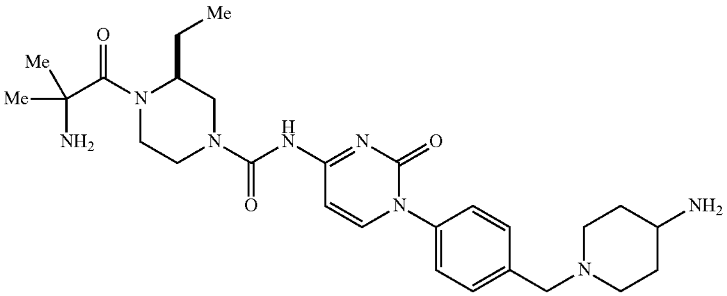 |
| 67 | 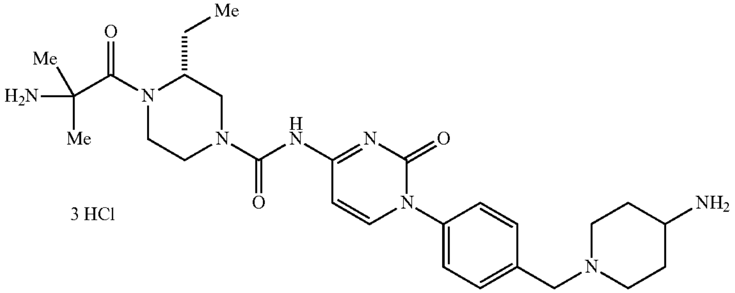 [SMILES: CC[C@@H]1CN(C(=O)Nc2ccn(-c3ccc(CN4CCC(N)CC4)cc3)c(=O)n2)CCN1C(=O)C(C)(C)N] 3 HCl | 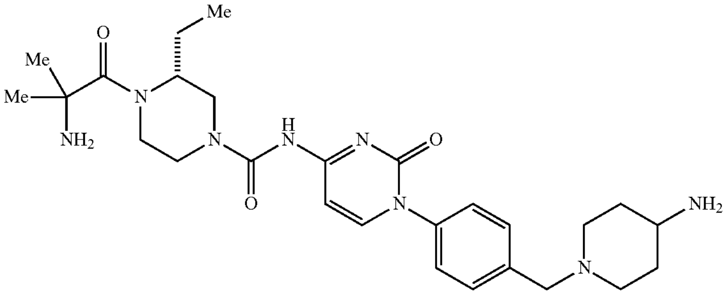 |
| 68 | 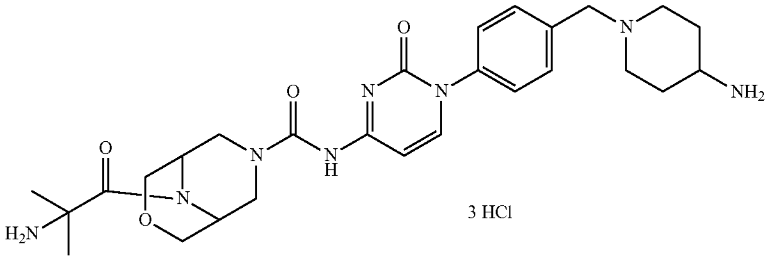 [SMILES: CC(C)(N)C(=O)N1C2COCC1CN(C(=O)Nc1ccn(-c3ccc(CN4CCC(N)CC4)cc3)c(=O)n1)C2] 3 HCl | 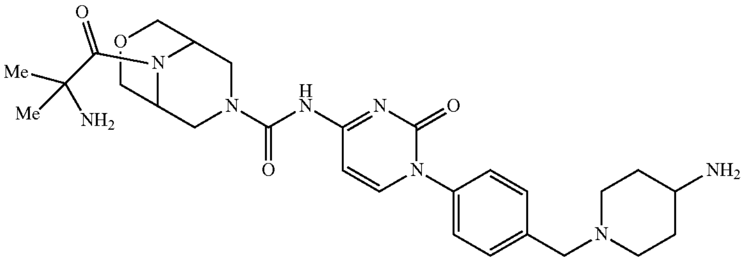 [SMILES: CC(C)(N)C(=O)N1C2COCC1CN(C(=O)Nc1ccn(-c3ccc(CN4CCC(N)CC4)cc3)c(=O)n1)C2] |

TABLE 10-continued
| Compounds of Formula I | | |
|---|---|---|
| No. | Salt Structure | Free Base Structure |
| 69 | 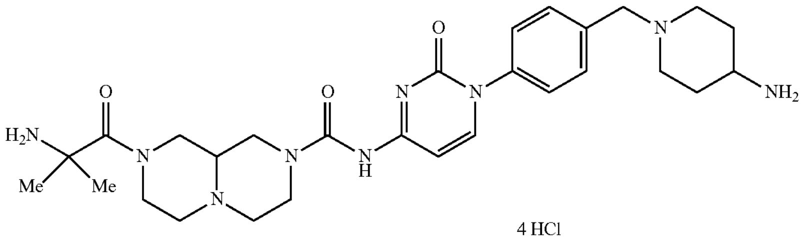 [SMILES: CC(C)(N)C(=O)N1CCN2CCN(C(=O)Nc3ccn(-c4ccc(CN5CCC(N)CC5)cc4)c(=O)n3)CC2C1] 4 HCl | 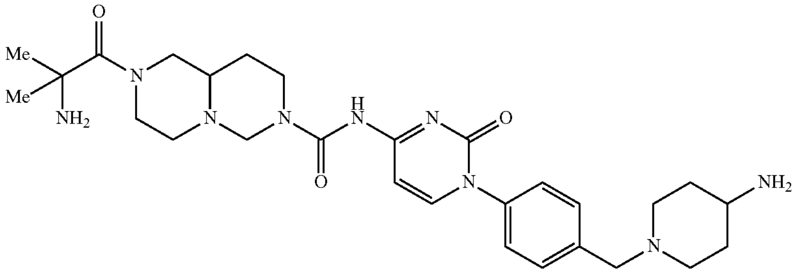 [SMILES: CC(C)(N)C(=O)N1CCN2CN(C(=O)Nc3ccn(-c4ccc(CN5CCC(N)CC5)cc4)c(=O)n3)CCC2C1] |
| 70 | 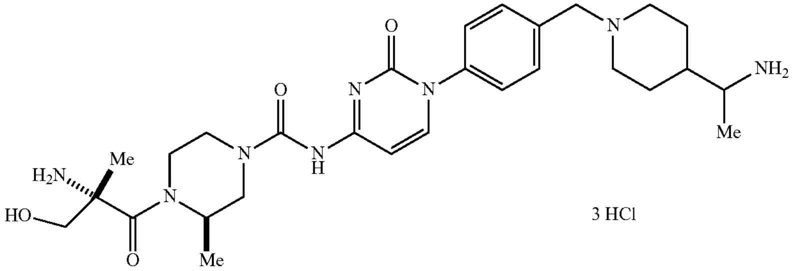 [SMILES: CC(N)C1CCN(Cc2ccc(-n3ccc(NC(=O)N4CCN(C(=O)[C@@](C)(N)CO)[C@H](C)C4)nc3=O)cc2)CC1] 3 HCl | 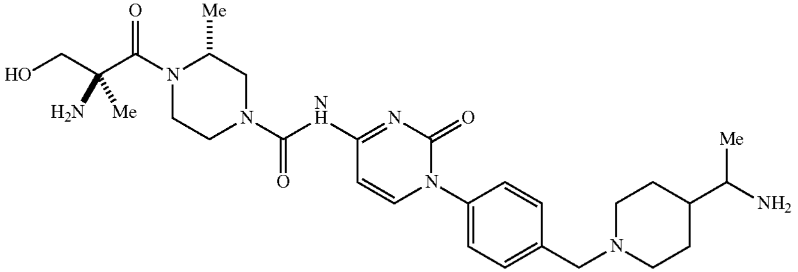 [SMILES: CC(N)C1CCN(Cc2ccc(-n3ccc(NC(=O)N4CCN(C(=O)[C@@](C)(N)CO)[C@H](C)C4)nc3=O)cc2)CC1] |
| 71 | 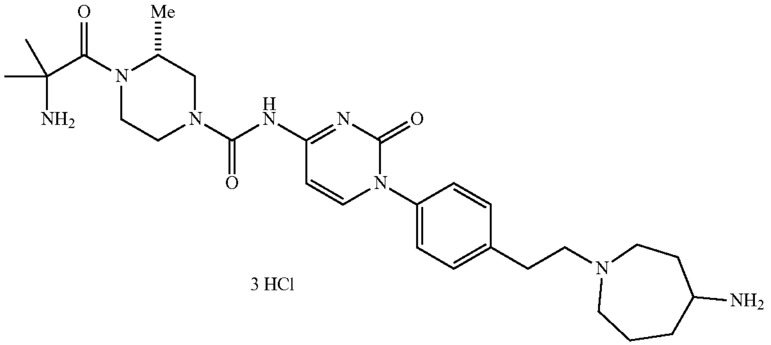 [SMILES: C[C@@H]1CN(C(=O)Nc2ccn(-c3ccc(CCN4CCCC(N)CC4)cc3)c(=O)n2)CCN1C(=O)C(C)(C)N] 3 HCl | 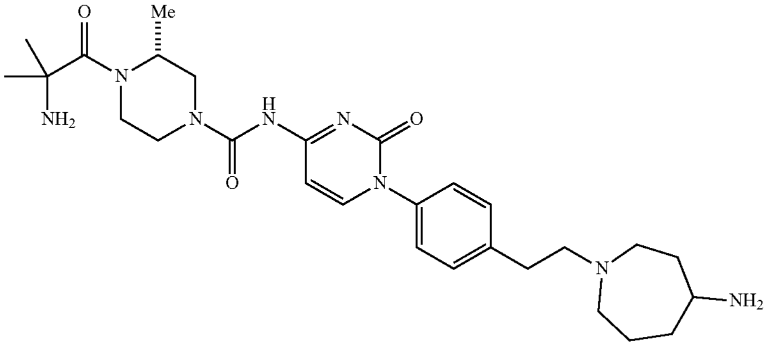 [SMILES: C[C@@H]1CN(C(=O)Nc2ccn(-c3ccc(CCN4CCCC(N)CC4)cc3)c(=O)n2)CCN1C(=O)C(C)(C)N] |

TABLE 10-continued
| Compounds of Formula I | | |
|---|---|---|
| No. | Salt Structure | Free Base Structure |
| 72 | 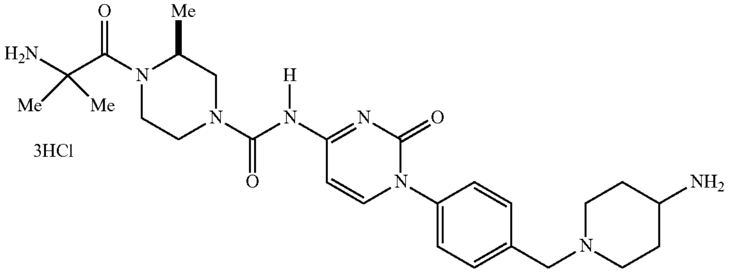 [SMILES: C[C@H]1CN(C(=O)Nc2ccn(-c3ccc(CN4CCC(N)CC4)cc3)c(=O)n2)CCN1C(=O)C(C)(C)N] 3HCl | 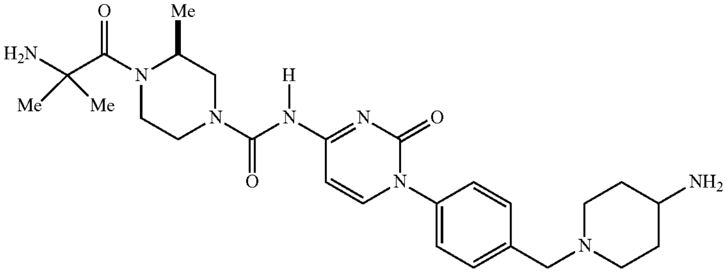 [SMILES: C[C@H]1CN(C(=O)Nc2ccn(-c3ccc(CN4CCC(N)CC4)cc3)c(=O)n2)CCN1C(=O)C(C)(C)N] |
| 73 | 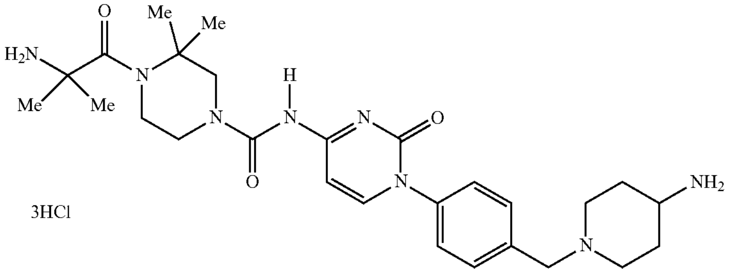 [SMILES: CC(C)(N)C(=O)N1CCN(C(=O)Nc2ccn(-c3ccc(CN4CCC(N)CC4)cc3)c(=O)n2)CC1(C)C] 3HCl | 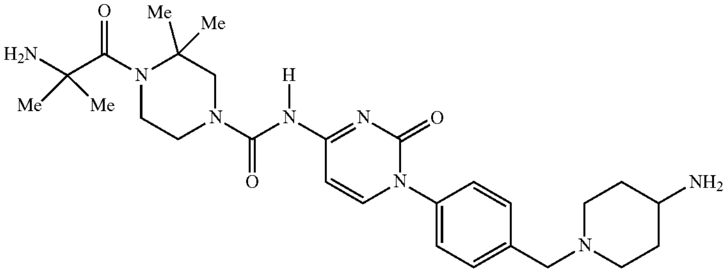 [SMILES: CC(C)(N)C(=O)N1CCN(C(=O)Nc2ccn(-c3ccc(CN4CCC(N)CC4)cc3)c(=O)n2)CC1(C)C] |
| 74 | 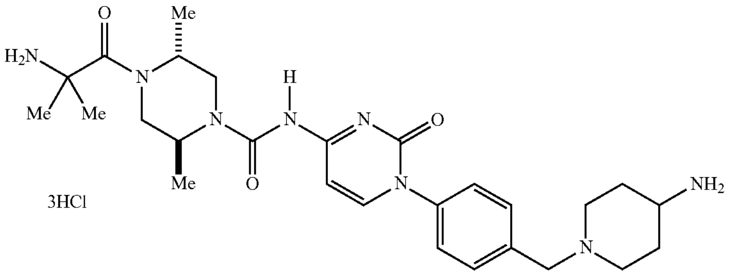 [SMILES: C[C@@H]1CN(C(=O)Nc2ccn(-c3ccc(CN4CCC(N)CC4)cc3)c(=O)n2)[C@@H](C)CN1C(=O)C(C)(C)N] 3HCl | 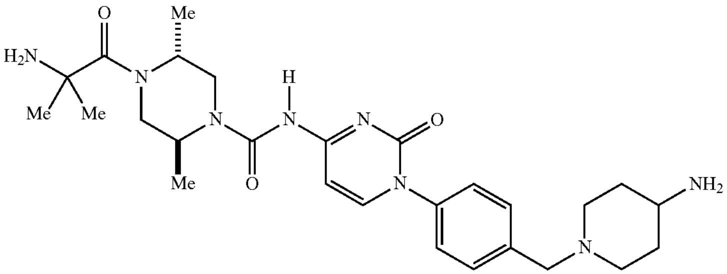 [SMILES: C[C@@H]1CN(C(=O)Nc2ccn(-c3ccc(CN4CCC(N)CC4)cc3)c(=O)n2)[C@@H](C)CN1C(=O)C(C)(C)N] |

TABLE 10-continued
| Compounds of Formula I | | |
|---|---|---|
| No. | Salt Structure | Free Base Structure |
| 75 | 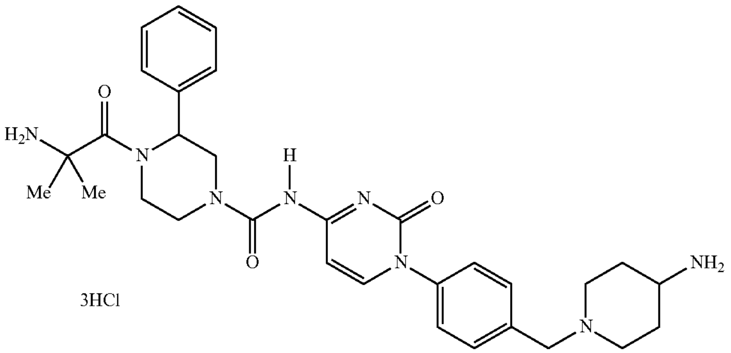 [SMILES: CC(C)(N)C(=O)N1CCN(C(=O)Nc2ccn(-c3ccc(CN4CCC(N)CC4)cc3)c(=O)n2)CC1c1ccccc1] 3HCl | 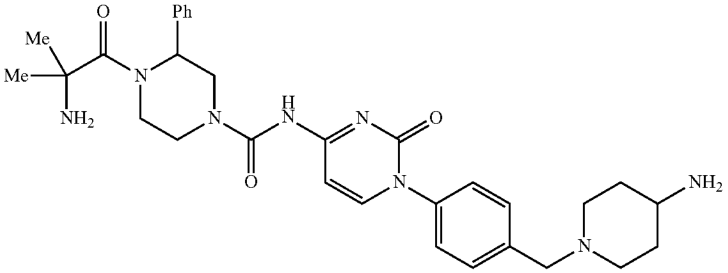 [SMILES: CC(C)(N)C(=O)N1CCN(C(=O)Nc2ccn(-c3ccc(CN4CCC(N)CC4)cc3)c(=O)n2)CC1c1ccccc1] |
| 76 | 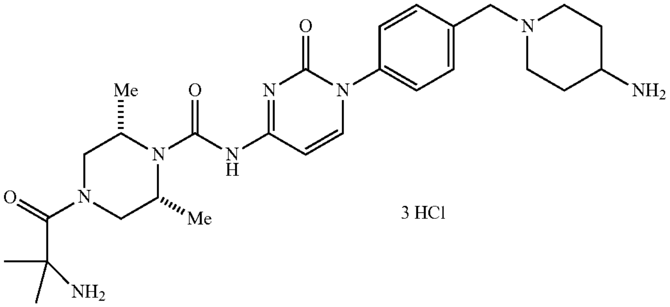 [SMILES: C[C@@H]1CN(C(=O)C(C)(C)N)C[C@H](C)N1C(=O)Nc1ccn(-c2ccc(CN3CCC(N)CC3)cc2)c(=O)n1] 3 HCl | 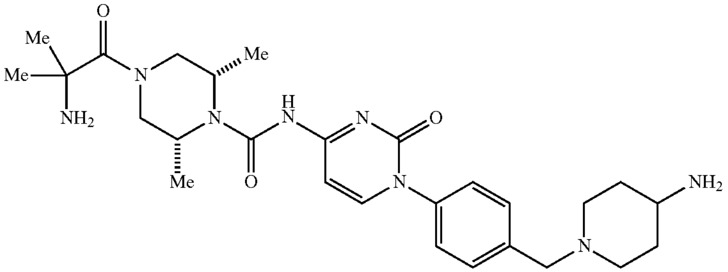 [SMILES: C[C@@H]1CN(C(=O)C(C)(C)N)C[C@H](C)N1C(=O)Nc1ccn(-c2ccc(CN3CCC(N)CC3)cc2)c(=O)n1] |
| 77 | 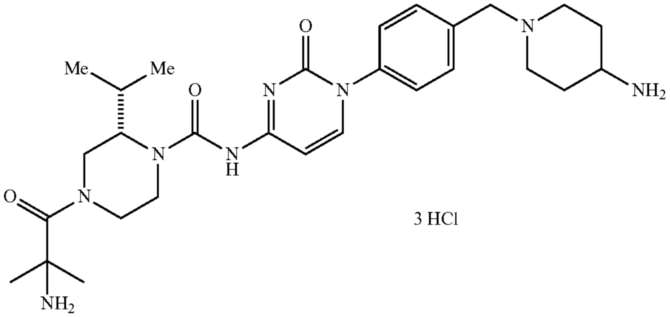 [SMILES: CC(C)[C@H]1CN(C(=O)C(C)(C)N)CCN1C(=O)Nc1ccn(-c2ccc(CN3CCC(N)CC3)cc2)c(=O)n1] 3 HCl | 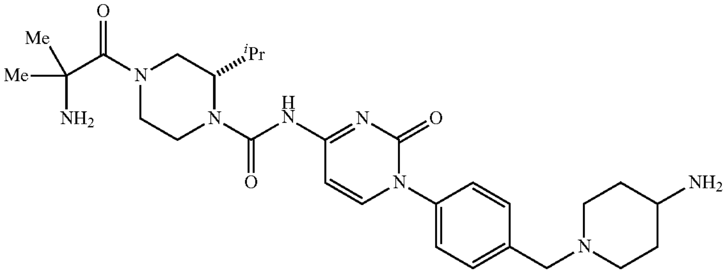 [SMILES: CC(C)[C@H]1CN(C(=O)C(C)(C)N)CCN1C(=O)Nc1ccn(-c2ccc(CN3CCC(N)CC3)cc2)c(=O)n1] |

TABLE 10-continued
| Compounds of Formula I | | |
|---|---|---|
| No. | Salt Structure | Free Base Structure |
| 78 | 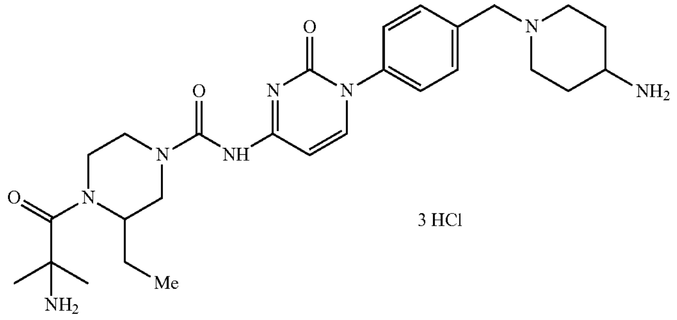 [SMILES: CCC1CN(C(=O)Nc2ccn(-c3ccc(CN4CCC(N)CC4)cc3)c(=O)n2)CCN1C(=O)C(C)(C)N] 3 HCl | 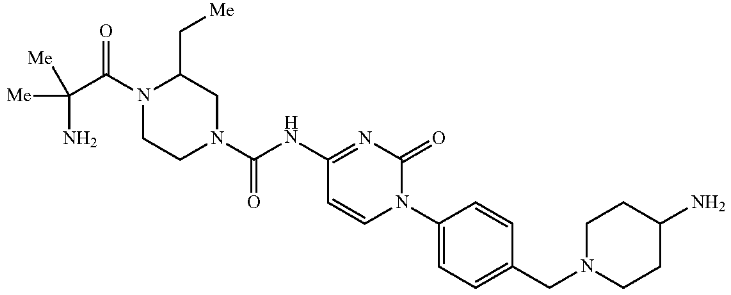 [SMILES: CCC1CN(C(=O)Nc2ccn(-c3ccc(CN4CCC(N)CC4)cc3)c(=O)n2)CCN1C(=O)C(C)(C)N] |
| 79 | 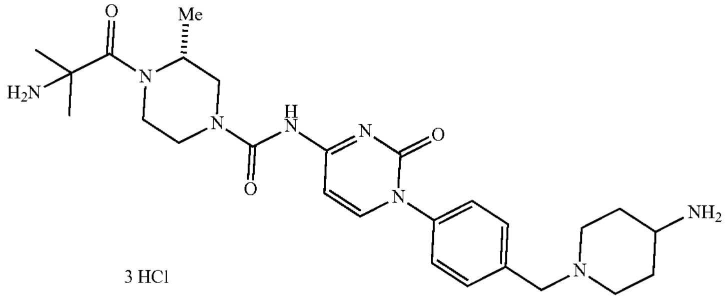 [SMILES: C[C@@H]1CN(C(=O)Nc2ccn(-c3ccc(CN4CCC(N)CC4)cc3)c(=O)n2)CCN1C(=O)C(C)(C)N] 3 HCl | 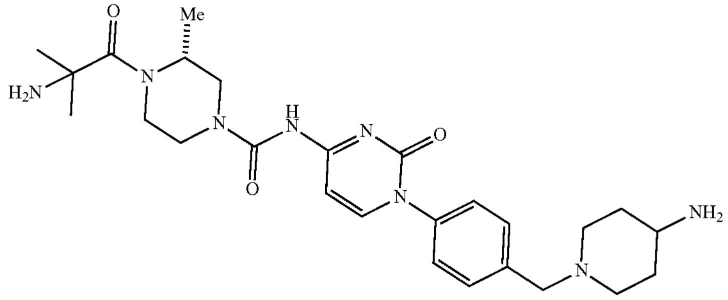 [SMILES: C[C@@H]1CN(C(=O)Nc2ccn(-c3ccc(CN4CCC(N)CC4)cc3)c(=O)n2)CCN1C(=O)C(C)(C)N] |
| 80 | 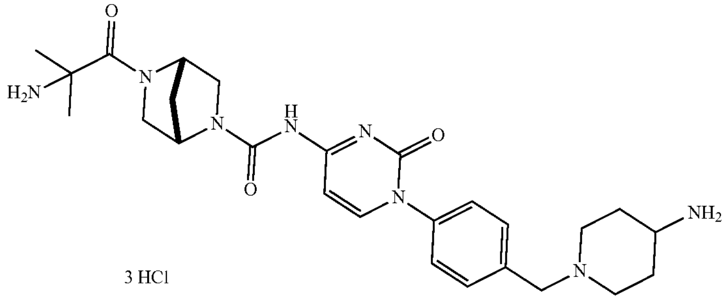 3 HCl | 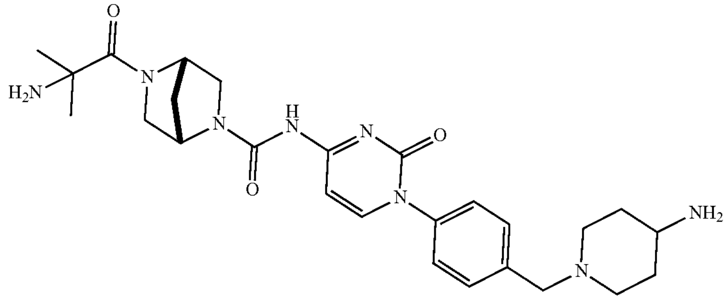 |

TABLE 10-continued
| Compounds of Formula I | | |
|---|---|---|
| No. | Salt Structure | Free Base Structure |
| 81 | 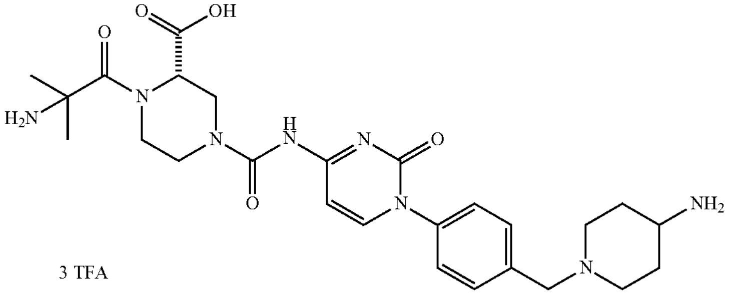 [SMILES: CC(C)(N)C(=O)N1CCN(C(=O)Nc2ccn(-c3ccc(CN4CCC(N)CC4)cc3)c(=O)n2)C[C@H]1C(=O)O] 3 TFA | 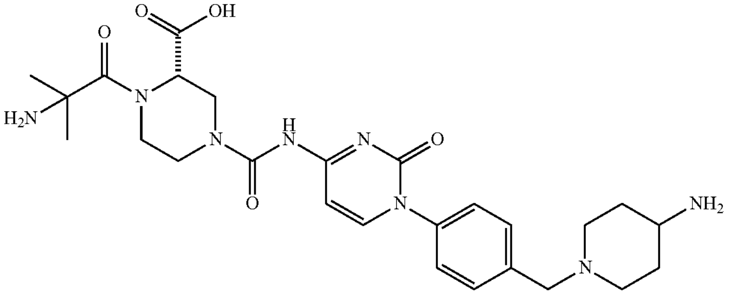 [SMILES: CC(C)(N)C(=O)N1CCN(C(=O)Nc2ccn(-c3ccc(CN4CCC(N)CC4)cc3)c(=O)n2)C[C@H]1C(=O)O] |
| 82 | 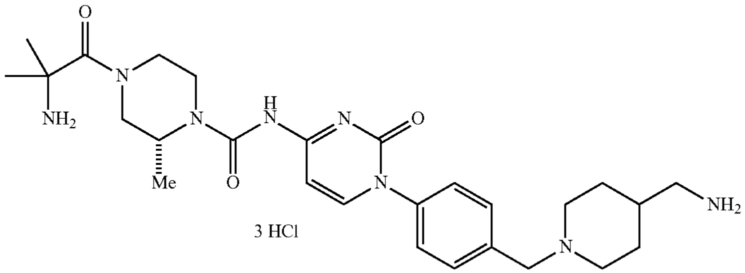 [SMILES: C[C@@H]1CN(C(=O)C(C)(C)N)CCN1C(=O)Nc1ccn(-c2ccc(CN3CCC(CN)CC3)cc2)c(=O)n1] 3 HCl | 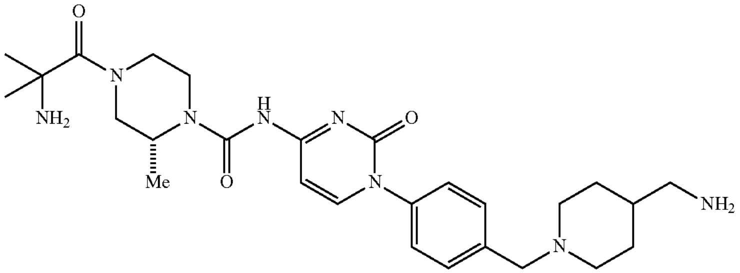 [SMILES: C[C@@H]1CN(C(=O)C(C)(C)N)CCN1C(=O)Nc1ccn(-c2ccc(CN3CCC(CN)CC3)cc2)c(=O)n1] |
| 83 | 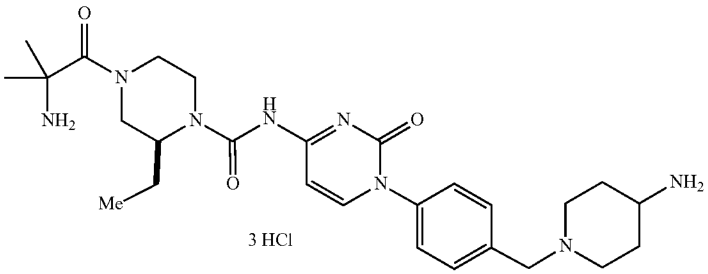 [SMILES: CC[C@H]1CN(C(=O)C(C)(C)N)CCN1C(=O)Nc1ccn(-c2ccc(CN3CCC(N)CC3)cc2)c(=O)n1] 3 HCl | 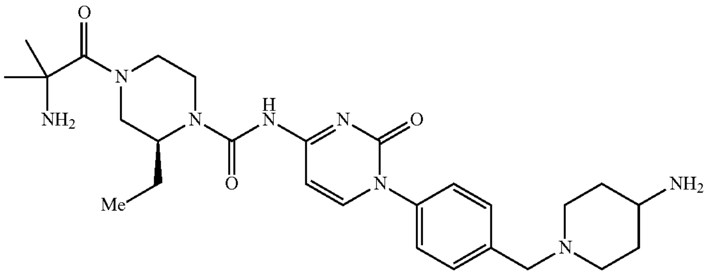 [SMILES: CC[C@H]1CN(C(=O)C(C)(C)N)CCN1C(=O)Nc1ccn(-c2ccc(CN3CCC(N)CC3)cc2)c(=O)n1] |

TABLE 10-continued
| Compounds of Formula I | | |
|---|---|---|
| No. | Salt Structure | Free Base Structure |
| 84 | 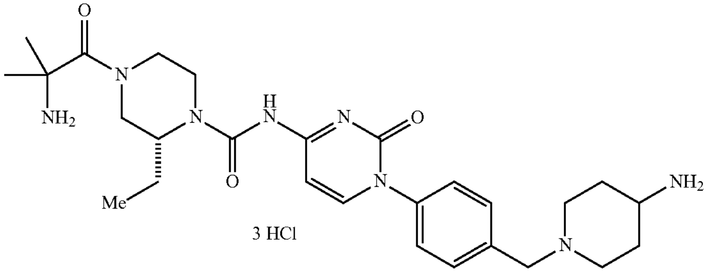 [SMILES: CC[C@@H]1CN(C(=O)C(C)(C)N)CCN1C(=O)Nc1ccn(-c2ccc(CN3CCC(N)CC3)cc2)c(=O)n1] 3 HCl | 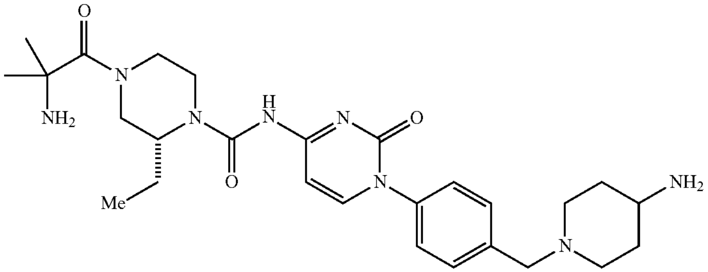 [SMILES: CC[C@@H]1CN(C(=O)C(C)(C)N)CCN1C(=O)Nc1ccn(-c2ccc(CN3CCC(N)CC3)cc2)c(=O)n1] |
| 85 | 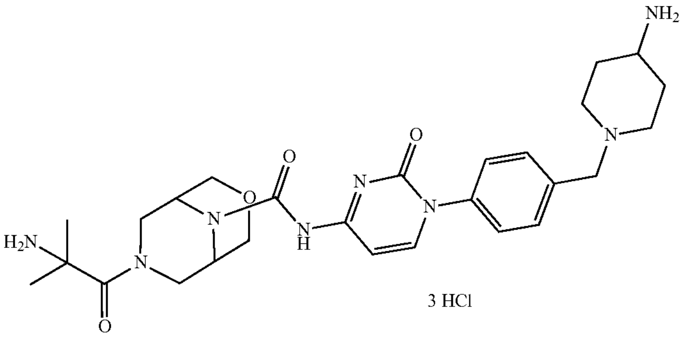 [SMILES: CC(C)(N)C(=O)N1CC2COCC(C1)N2C(=O)Nc1ccn(-c2ccc(CN3CCC(N)CC3)cc2)c(=O)n1] 3 HCl | 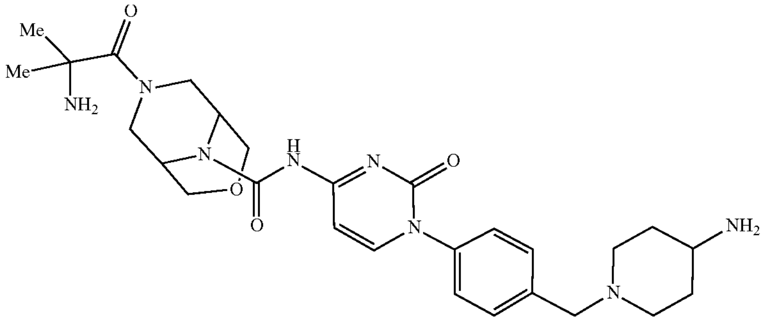 [SMILES: CC(C)(N)C(=O)N1CC2COCC(C1)N2C(=O)Nc1ccn(-c2ccc(CN3CCC(N)CC3)cc2)c(=O)n1] |
| 86 | 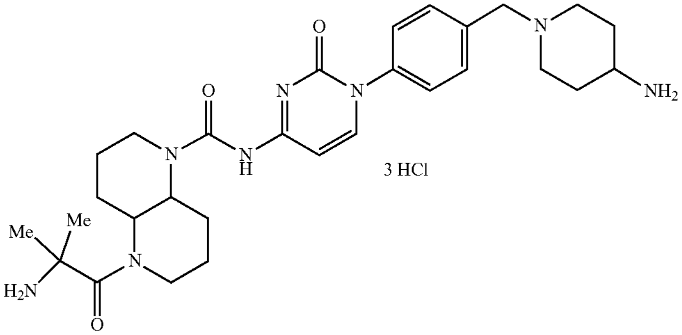 [SMILES: CC(C)(N)C(=O)N1CCCC2C1CCCN2C(=O)Nc1ccn(-c2ccc(CN3CCC(N)CC3)cc2)c(=O)n1] 3 HCl | 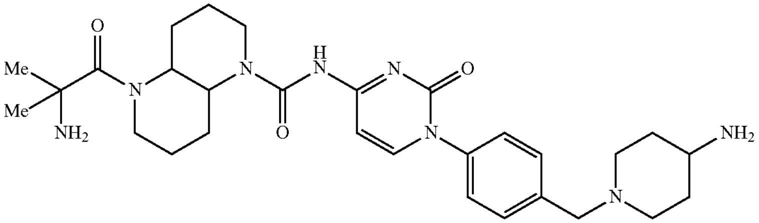 [SMILES: CC(C)(N)C(=O)N1CCCC2C1CCCN2C(=O)Nc1ccn(-c2ccc(CN3CCC(N)CC3)cc2)c(=O)n1] |

TABLE 10-continued
| Compounds of Formula I | | |
|---|---|---|
| No. | Salt Structure | Free Base Structure |
| 87 | 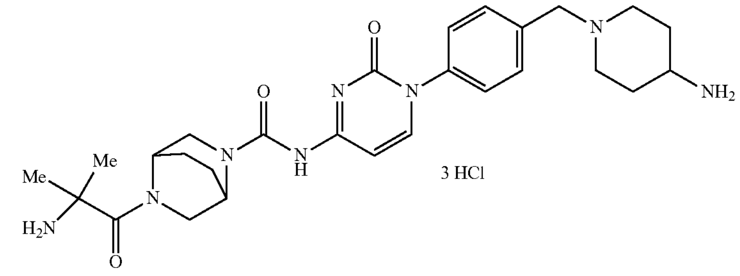 [SMILES: CC(C)(N)C(=O)N1CC2CCC1CN2C(=O)Nc1ccn(-c2ccc(CN3CCC(N)CC3)cc2)c(=O)n1] 3 HCl | 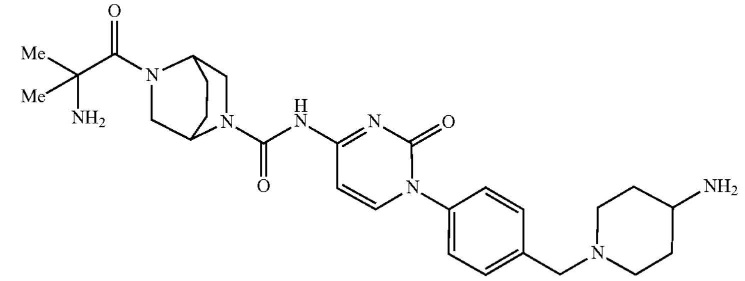 [SMILES: CC(C)(N)C(=O)N1CC2CCC1CN2C(=O)Nc1ccn(-c2ccc(CN3CCC(N)CC3)cc2)c(=O)n1] |
| 88 | 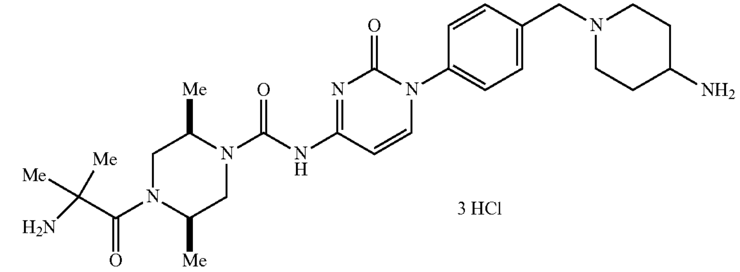 [SMILES: C[C@@H]1CN(C(=O)C(C)(C)N)[C@H](C)CN1C(=O)Nc1ccn(-c2ccc(CN3CCC(N)CC3)cc2)c(=O)n1] 3 HCl | 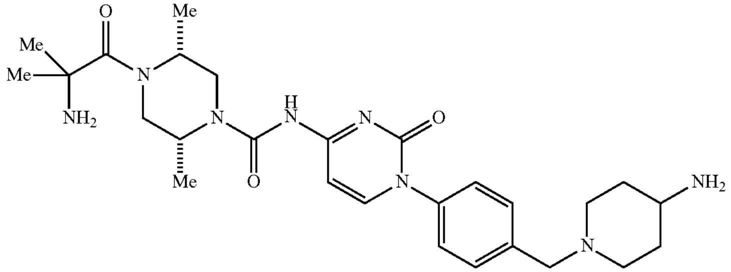 [SMILES: C[C@@H]1CN(C(=O)C(C)(C)N)[C@H](C)CN1C(=O)Nc1ccn(-c2ccc(CN3CCC(N)CC3)cc2)c(=O)n1] |
| 89 | 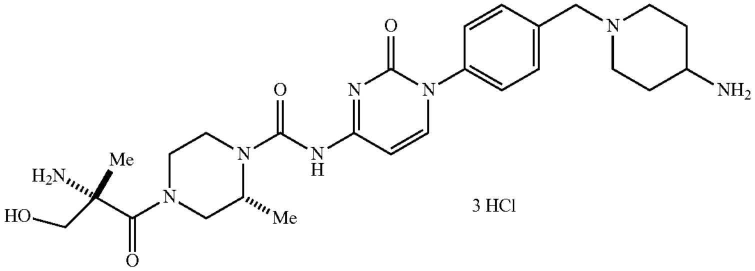 [SMILES: C[C@@H]1CN(C(=O)[C@@](C)(N)CO)CCN1C(=O)Nc1ccn(-c2ccc(CN3CCC(N)CC3)cc2)c(=O)n1] 3 HCl | 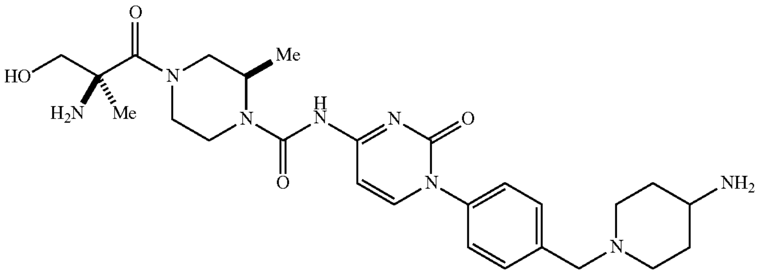 [SMILES: C[C@@H]1CN(C(=O)[C@@](C)(N)CO)CCN1C(=O)Nc1ccn(-c2ccc(CN3CCC(N)CC3)cc2)c(=O)n1] |

TABLE 10-continued
| Compounds of Formula I | | |
|---|---|---|
| No. | Salt Structure | Free Base Structure |
| 90 | 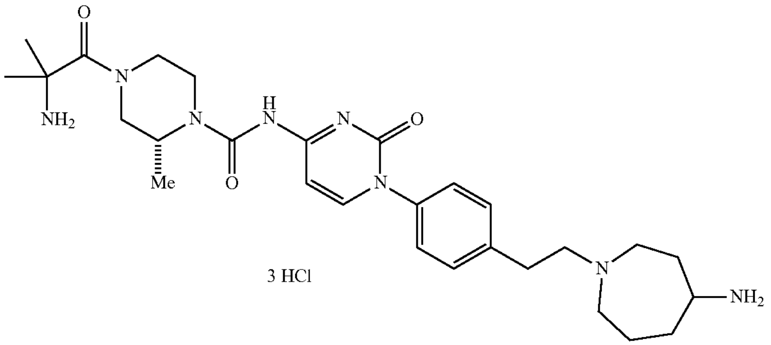 [SMILES: C[C@@H]1CN(C(=O)C(C)(C)N)CCN1C(=O)Nc1ccn(-c2ccc(CCN3CCCC(N)CC3)cc2)c(=O)n1] 3 HCl | 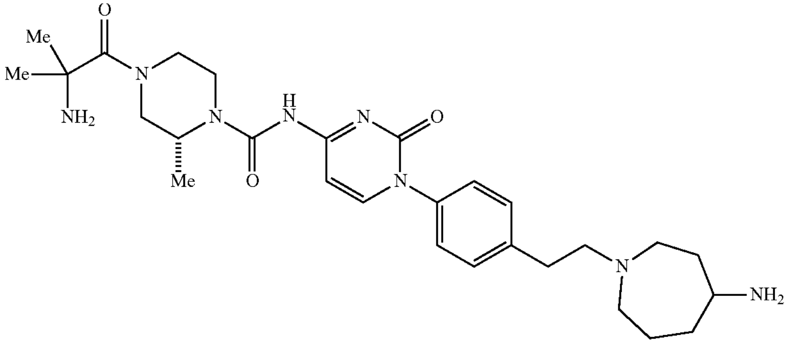 [SMILES: C[C@@H]1CN(C(=O)C(C)(C)N)CCN1C(=O)Nc1ccn(-c2ccc(CCN3CCCC(N)CC3)cc2)c(=O)n1] |
| 91 | 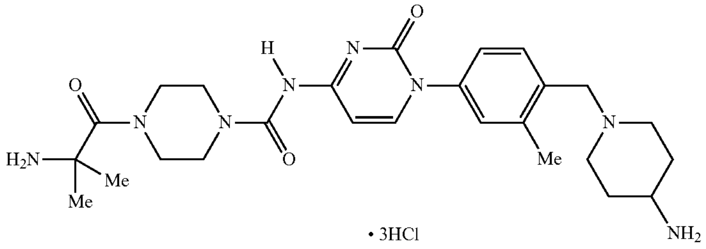 [SMILES: Cc1cc(-n2ccc(NC(=O)N3CCN(C(=O)C(C)(C)N)CC3)nc2=O)ccc1CN1CCC(N)CC1] • 3HCl | 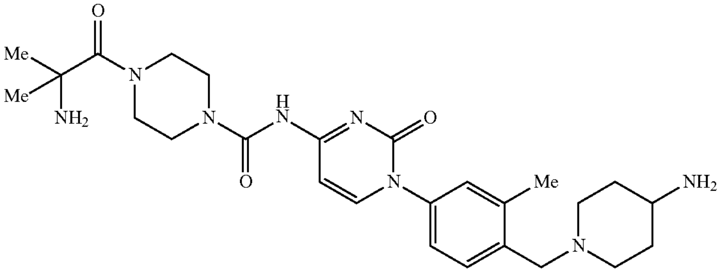 [SMILES: Cc1cc(-n2ccc(NC(=O)N3CCN(C(=O)C(C)(C)N)CC3)nc2=O)ccc1CN1CCC(N)CC1] |
| 92 | 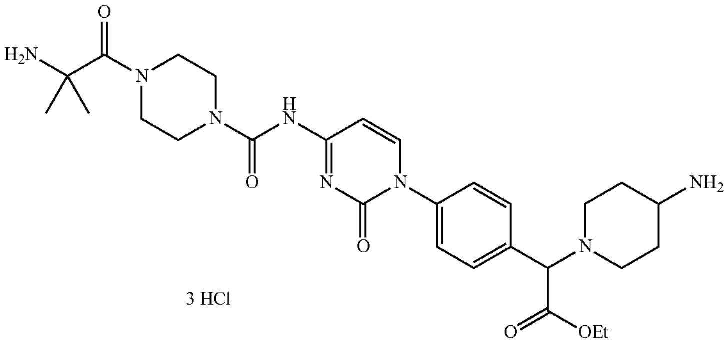 [SMILES: CCOC(=O)C(c1ccc(-n2ccc(NC(=O)N3CCN(C(=O)C(C)(C)N)CC3)nc2=O)cc1)N1CCC(N)CC1] 3 HCl | 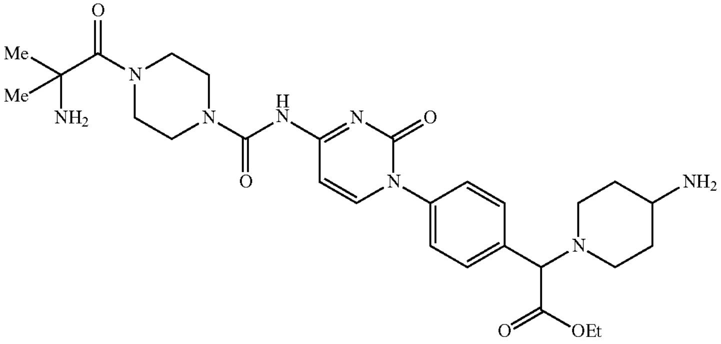 |

TABLE 10-continued
| Compounds of Formula I | | |
|---|---|---|
| No. | Salt Structure | Free Base Structure |
| 93 | 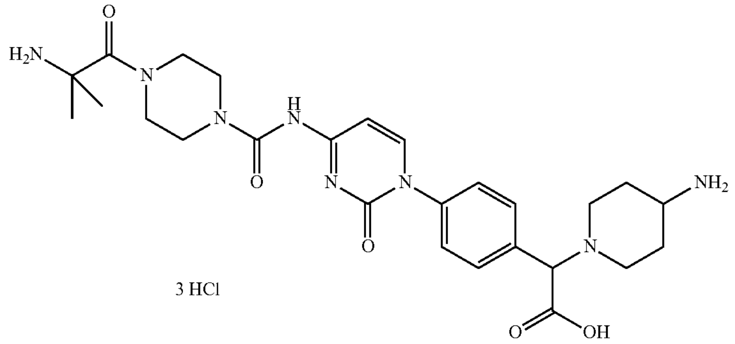 [SMILES: CC(C)(N)C(=O)N1CCN(C(=O)Nc2ccn(-c3ccc(C(C(=O)O)N4CCC(N)CC4)cc3)c(=O)n2)CC1] 3 HCl | 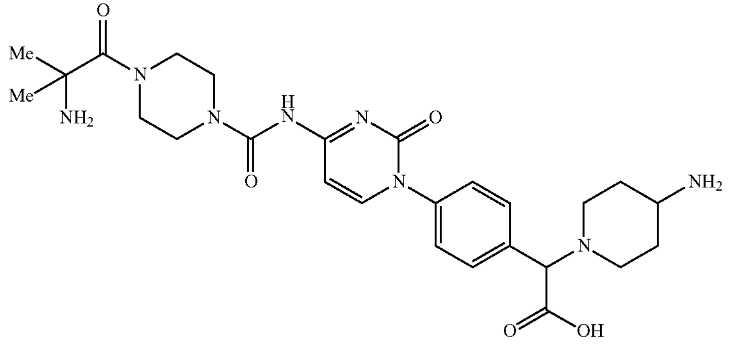 [SMILES: CC(C)(N)C(=O)N1CCN(C(=O)Nc2ccn(-c3ccc(C(C(=O)O)N4CCC(N)CC4)cc3)c(=O)n2)CC1] |
| 94 | 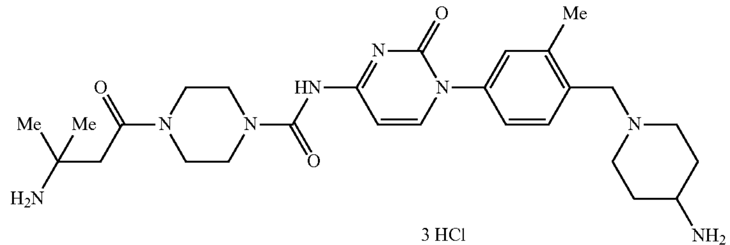 3 HCl | 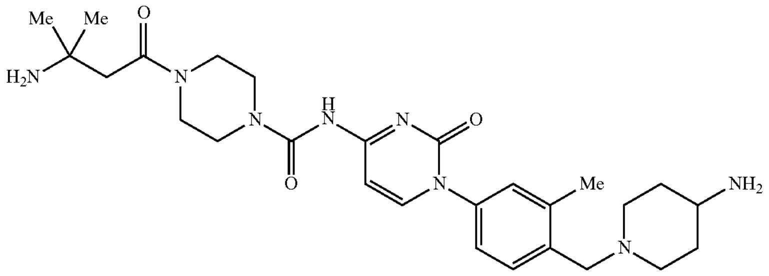 [SMILES: Cc1cc(-n2ccc(NC(=O)N3CCN(C(=O)CC(C)(C)N)CC3)nc2=O)ccc1CN1CCC(N)CC1] |
| 95 | 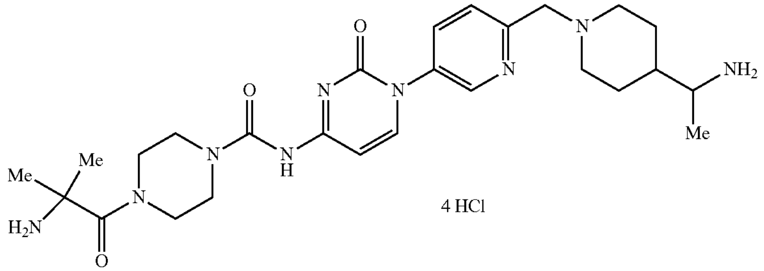 [SMILES: CC(N)C1CCN(Cc2ccc(-n3ccc(NC(=O)N4CCN(C(=O)C(C)(C)N)CC4)nc3=O)cn2)CC1] 4 HCl | 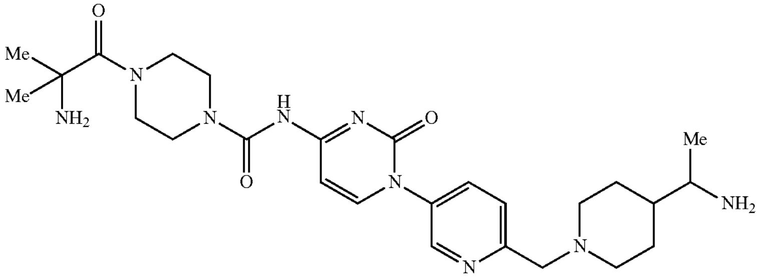 [SMILES: CC(N)C1CCN(Cc2ccc(-n3ccc(NC(=O)N4CCN(C(=O)C(C)(C)N)CC4)nc3=O)cn2)CC1] |

TABLE 10-continued
| Compounds of Formula I | | |
|---|---|---|
| No. | Salt Structure | Free Base Structure |
| 96 | 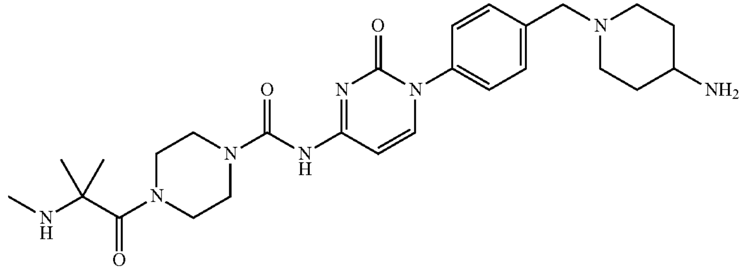 [SMILES: CNC(C)(C)C(=O)N1CCN(C(=O)Nc2ccn(-c3ccc(CN4CCC(N)CC4)cc3)c(=O)n2)CC1] | 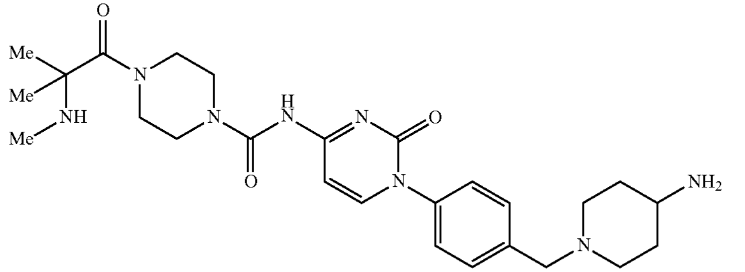 [SMILES: CNC(C)(C)C(=O)N1CCN(C(=O)Nc2ccn(-c3ccc(CN4CCC(N)CC4)cc3)c(=O)n2)CC1] |
| 97 | 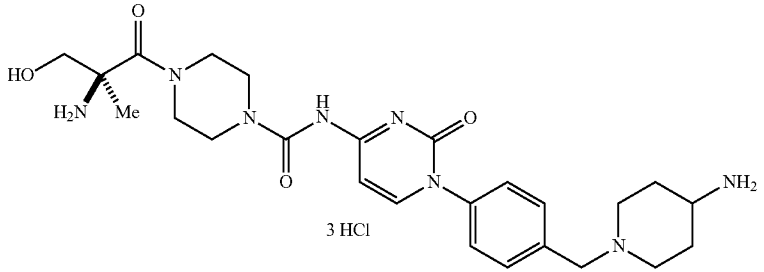 [SMILES: C[C@](N)(CO)C(=O)N1CCN(C(=O)Nc2ccn(-c3ccc(CN4CCC(N)CC4)cc3)c(=O)n2)CC1] 3 HCl | 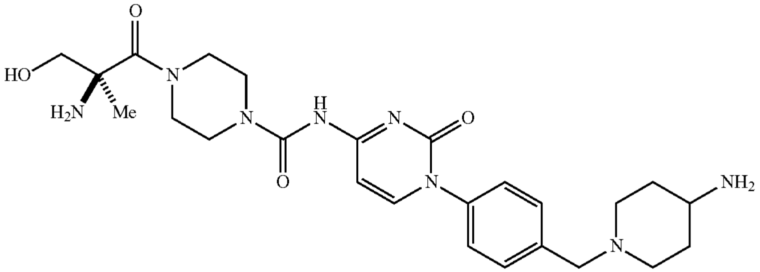 [SMILES: C[C@](N)(CO)C(=O)N1CCN(C(=O)Nc2ccn(-c3ccc(CN4CCC(N)CC4)cc3)c(=O)n2)CC1] |
| 98 | 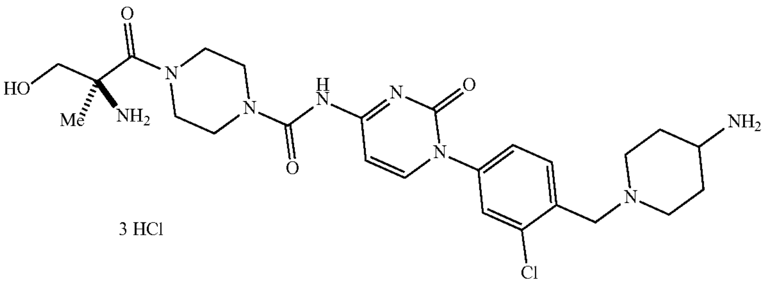 3 HCl | 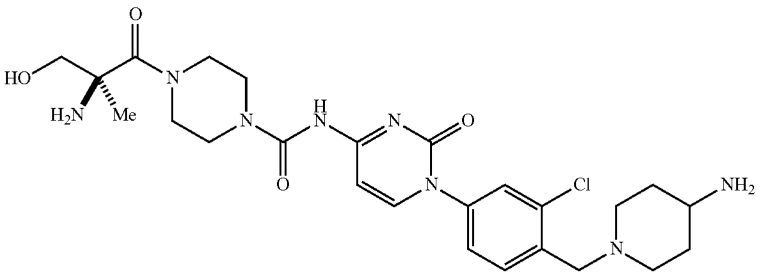 [SMILES: C[C@](N)(CO)C(=O)N1CCN(C(=O)Nc2ccn(-c3ccc(CN4CCC(N)CC4)c(Cl)c3)c(=O)n2)CC1] |

TABLE 10-continued
| Compounds of Formula I | | |
|---|---|---|
| No. | Salt Structure | Free Base Structure |
| 99 | 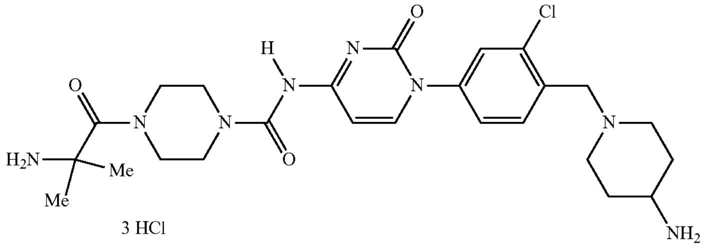 [SMILES: CC(C)(N)C(=O)N1CCN(C(=O)Nc2ccn(-c3ccc(CN4CCC(N)CC4)c(Cl)c3)c(=O)n2)CC1] 3 HCl | 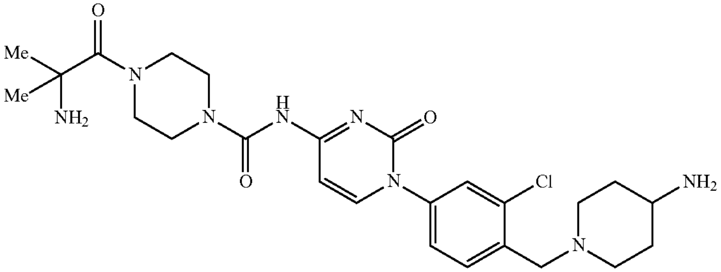 [SMILES: CC(C)(N)C(=O)N1CCN(C(=O)Nc2ccn(-c3ccc(CN4CCC(N)CC4)c(Cl)c3)c(=O)n2)CC1] |
| 100 | 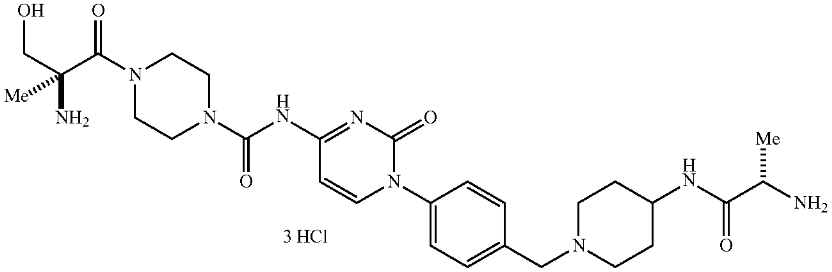 [SMILES: C[C@H](N)C(=O)NC1CCN(Cc2ccc(-n3ccc(NC(=O)N4CCN(C(=O)[C@@](C)(N)CO)CC4)nc3=O)cc2)CC1] 3 HCl | 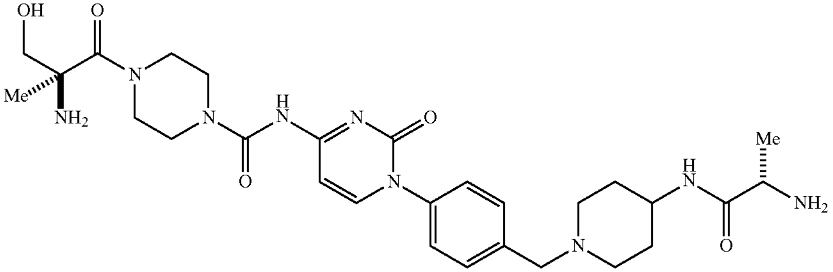 [SMILES: C[C@H](N)C(=O)NC1CCN(Cc2ccc(-n3ccc(NC(=O)N4CCN(C(=O)[C@@](C)(N)CO)CC4)nc3=O)cc2)CC1] |
| 101 | 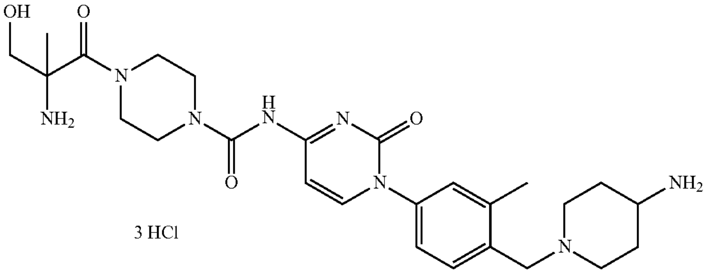 [SMILES: Cc1cc(-n2ccc(NC(=O)N3CCN(C(=O)C(C)(N)CO)CC3)nc2=O)ccc1CN1CCC(N)CC1] 3 HCl | 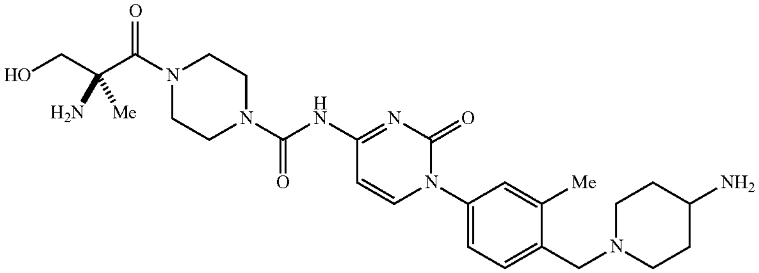 [SMILES: Cc1cc(-n2ccc(NC(=O)N3CCN(C(=O)[C@@](C)(N)CO)CC3)nc2=O)ccc1CN1CCC(N)CC1] |

TABLE 10-continued
| Compounds of Formula I | | |
|---|---|---|
| No. | Salt Structure | Free Base Structure |
| 102 | 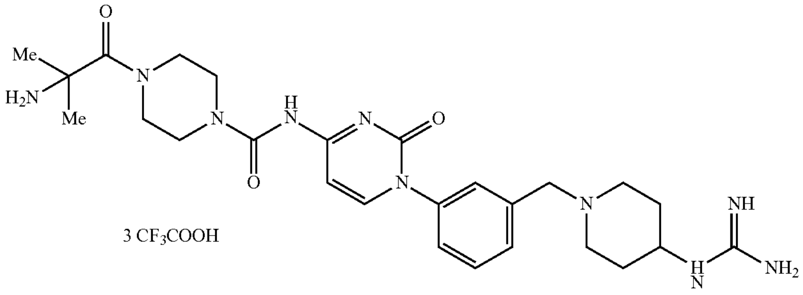 [SMILES: CC(C)(N)C(=O)N1CCN(C(=O)Nc2ccn(-c3cccc(CN4CCC(NC(=N)N)CC4)c3)c(=O)n2)CC1] 3 $CF_3COOH$ | 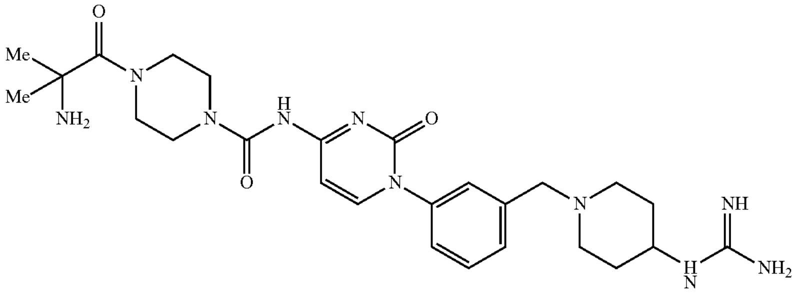 [SMILES: CC(C)(N)C(=O)N1CCN(C(=O)Nc2ccn(-c3cccc(CN4CCC(NC(=N)N)CC4)c3)c(=O)n2)CC1] |
| 103 | 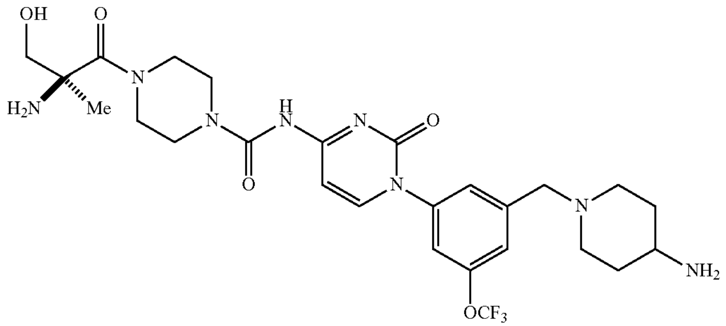 [SMILES: C[C@](N)(CO)C(=O)N1CCN(C(=O)Nc2ccn(-c3cc(CN4CCC(N)CC4)cc(OC(F)(F)F)c3)c(=O)n2)CC1] | 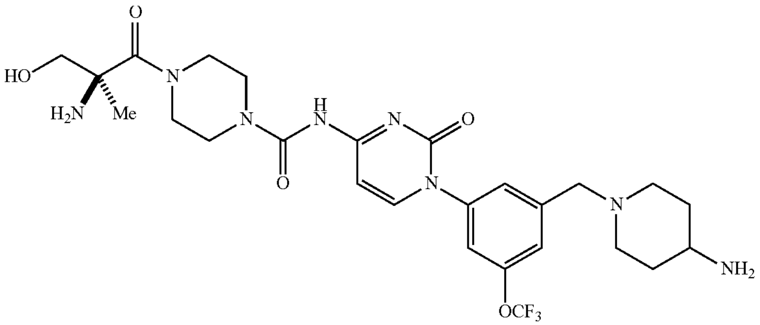 [SMILES: C[C@](N)(CO)C(=O)N1CCN(C(=O)Nc2ccn(-c3cc(CN4CCC(N)CC4)cc(OC(F)(F)F)c3)c(=O)n2)CC1] |
| 104 | 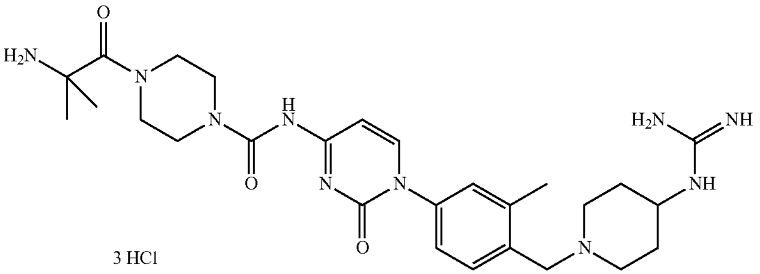 [SMILES: Cc1cc(-n2ccc(NC(=O)N3CCN(C(=O)C(C)(C)N)CC3)nc2=O)ccc1CN1CCC(NC(=N)N)CC1] 3 HCl | 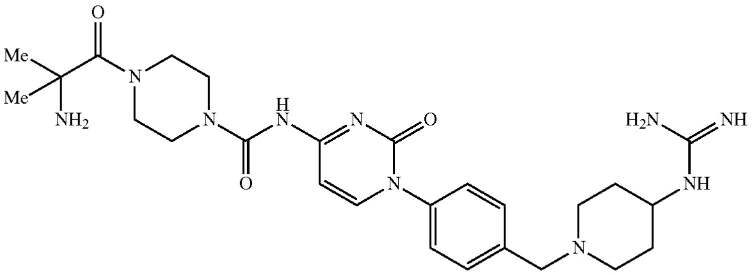 [SMILES: CC(C)(N)C(=O)N1CCN(C(=O)Nc2ccn(-c3ccc(CN4CCC(NC(=N)N)CC4)cc3)c(=O)n2)CC1] |

TABLE 10-continued
| Compounds of Formula I | | |
|---|---|---|
| No. | Salt Structure | Free Base Structure |
| 105 | 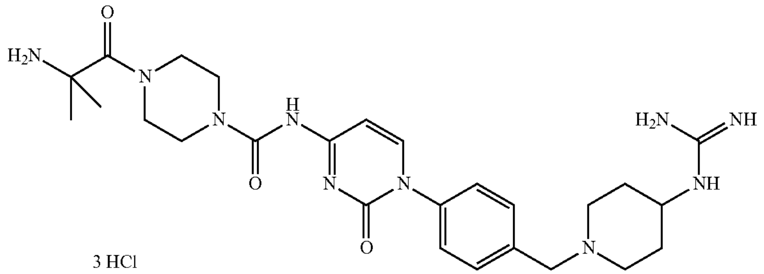 [SMILES: CC(C)(N)C(=O)N1CCN(C(=O)Nc2ccn(-c3ccc(CN4CCC(NC(=N)N)CC4)cc3)c(=O)n2)CC1] 3 HCl | 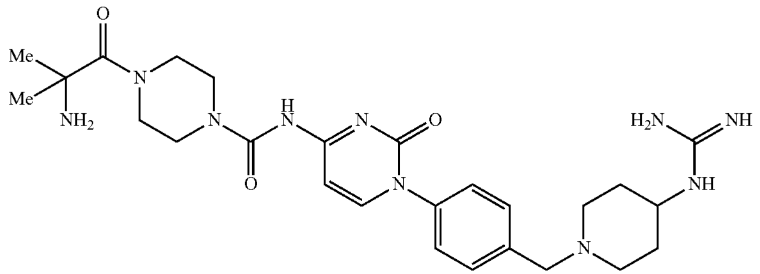 [SMILES: CC(C)(N)C(=O)N1CCN(C(=O)Nc2ccn(-c3ccc(CN4CCC(NC(=N)N)CC4)cc3)c(=O)n2)CC1] |
| 106 | 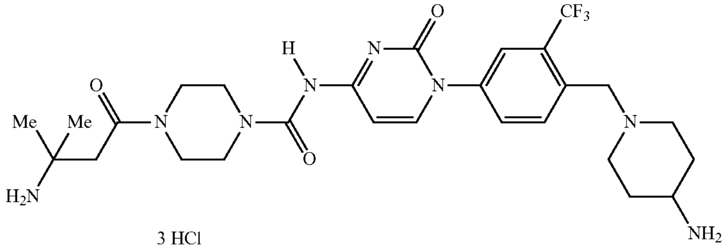 [SMILES: CC(C)(N)CC(=O)N1CCN(C(=O)Nc2ccn(-c3ccc(CN4CCC(N)CC4)c(C(F)(F)F)c3)c(=O)n2)CC1] 3 HCl | 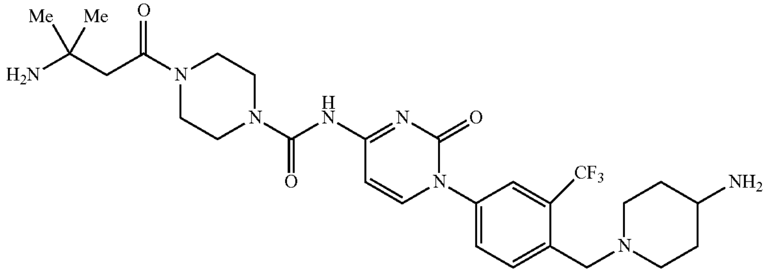 [SMILES: CC(C)(N)CC(=O)N1CCN(C(=O)Nc2ccn(-c3ccc(CN4CCC(N)CC4)c(C(F)(F)F)c3)c(=O)n2)CC1] |
| 107 | 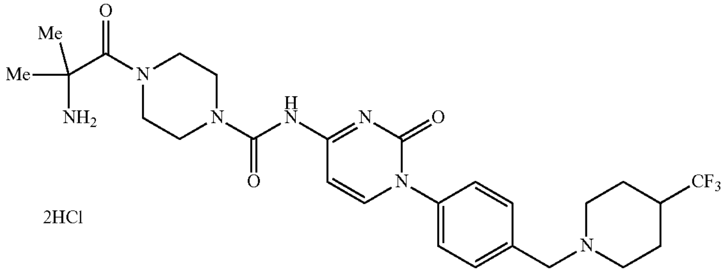 [SMILES: CC(C)(N)C(=O)N1CCN(C(=O)Nc2ccn(-c3ccc(CN4CCC(C(F)(F)F)CC4)cc3)c(=O)n2)CC1] 2HCl | 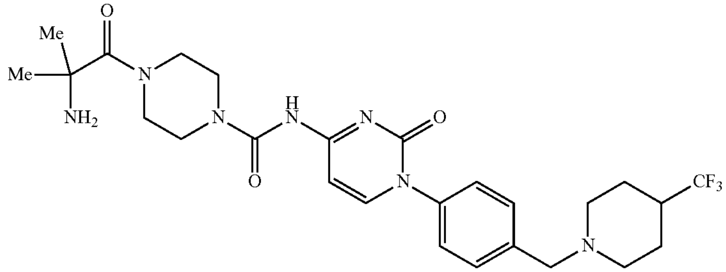 [SMILES: CC(C)(N)C(=O)N1CCN(C(=O)Nc2ccn(-c3ccc(CN4CCC(C(F)(F)F)CC4)cc3)c(=O)n2)CC1] |

TABLE 10-continued
| Compounds of Formula I | | |
|---|---|---|
| No. | Salt Structure | Free Base Structure |
| 108 | 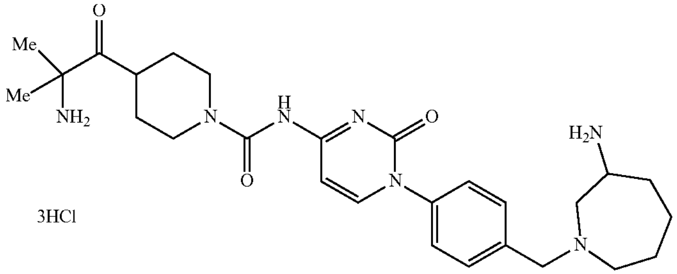 [SMILES: CC(C)(N)C(=O)C1CCN(C(=O)Nc2ccn(-c3ccc(CN4CCCCC(N)C4)cc3)c(=O)n2)CC1] 3HCl | 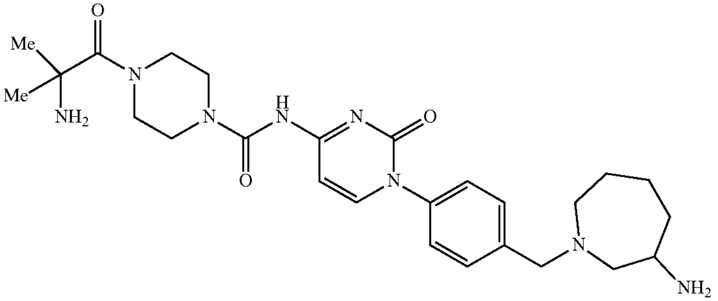 [SMILES: CC(C)(N)C(=O)N1CCN(C(=O)Nc2ccn(-c3ccc(CN4CCCCC(N)C4)cc3)c(=O)n2)CC1] |
| 109 | 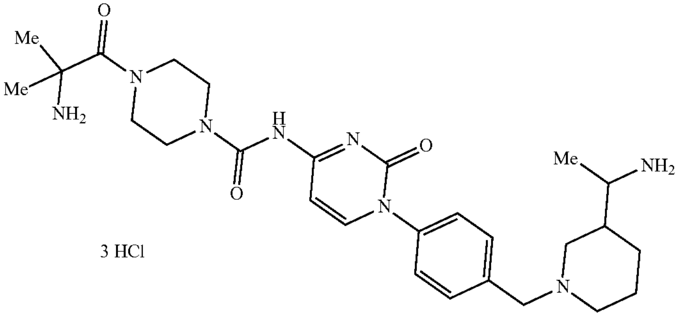 [SMILES: CC(N)C1CCCN(Cc2ccc(-n3ccc(NC(=O)N4CCN(C(=O)C(C)(C)N)CC4)nc3=O)cc2)C1] 3 HCl | 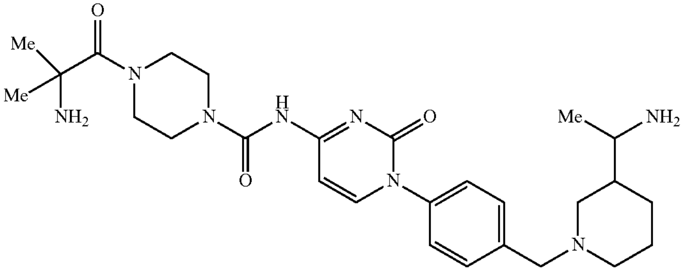 [SMILES: CC(N)C1CCCN(Cc2ccc(-n3ccc(NC(=O)N4CCN(C(=O)C(C)(C)N)CC4)nc3=O)cc2)C1] |
| 110 | 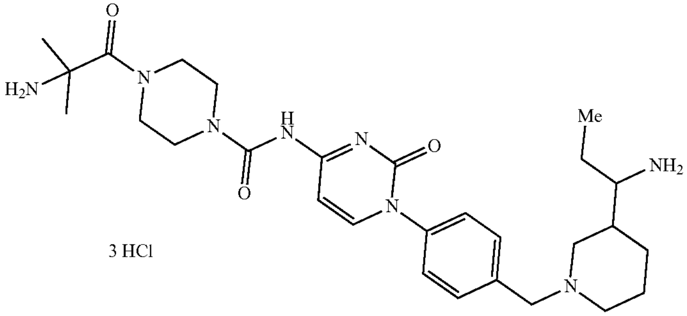 [SMILES: CCC(N)C1CCCN(Cc2ccc(-n3ccc(NC(=O)N4CCN(C(=O)C(C)(C)N)CC4)nc3=O)cc2)C1] 3 HCl | 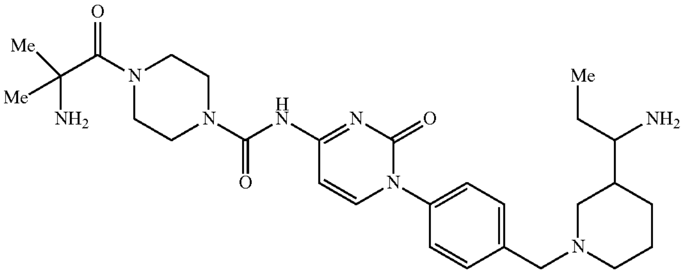 [SMILES: CCC(N)C1CCCN(Cc2ccc(-n3ccc(NC(=O)N4CCN(C(=O)C(C)(C)N)CC4)nc3=O)cc2)C1] |

TABLE 10-continued
| Compounds of Formula I | | |
| --- | --- | --- |
| No. | Salt Structure | Free Base Structure |
| 111 | 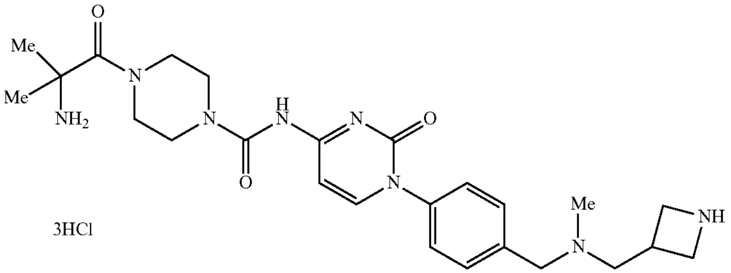 [SMILES: CN(Cc1ccc(-n2ccc(NC(=O)N3CCN(C(=O)C(C)(C)N)CC3)nc2=O)cc1)CC1CNC1] 3HCl | 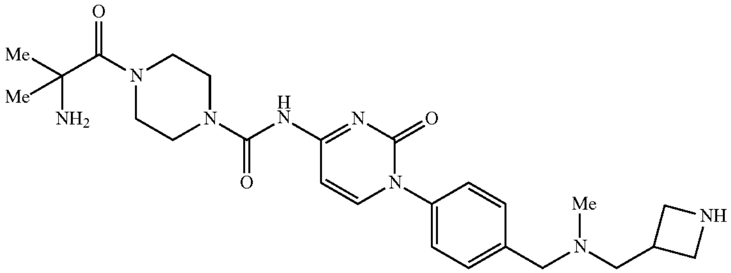 [SMILES: CN(Cc1ccc(-n2ccc(NC(=O)N3CCN(C(=O)C(C)(C)N)CC3)nc2=O)cc1)CC1CNC1] |
| 112 | 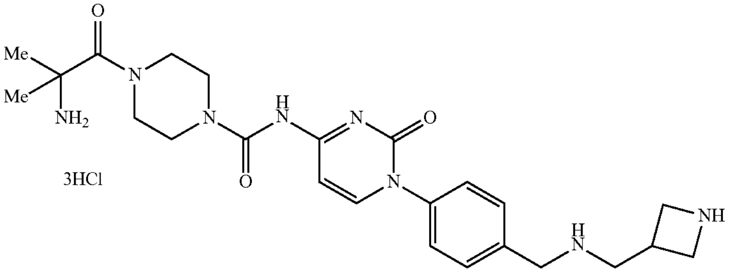 [SMILES: CC(C)(N)C(=O)N1CCN(C(=O)Nc2ccn(-c3ccc(CNCC4CNC4)cc3)c(=O)n2)CC1] 3HCl | 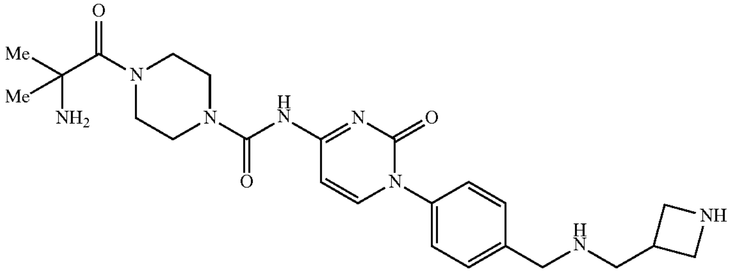 [SMILES: CC(C)(N)C(=O)N1CCN(C(=O)Nc2ccn(-c3ccc(CNCC4CNC4)cc3)c(=O)n2)CC1] |
| 114 | 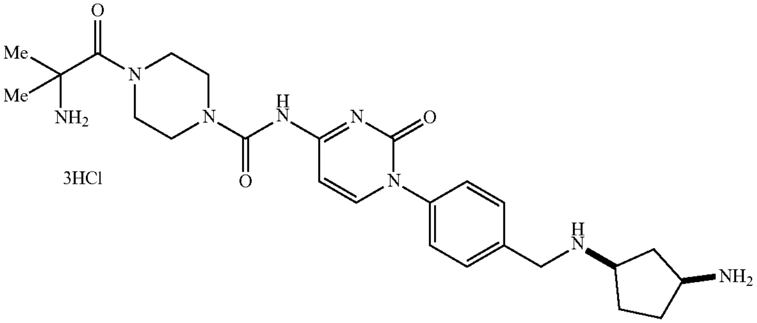 3HCl | 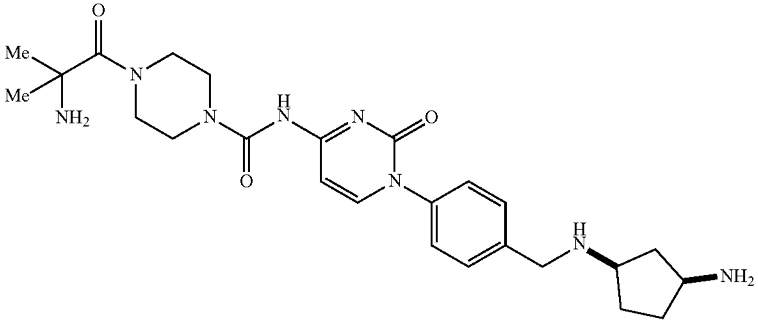 |

TABLE 10-continued
| Compounds of Formula I | | |
|---|---|---|
| No. | Salt Structure | Free Base Structure |
| 115 | 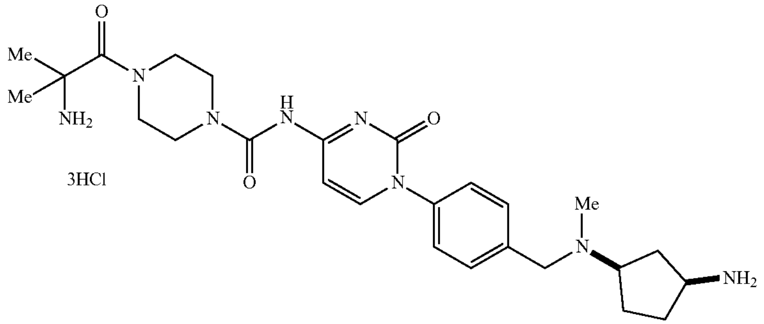 3HCl | 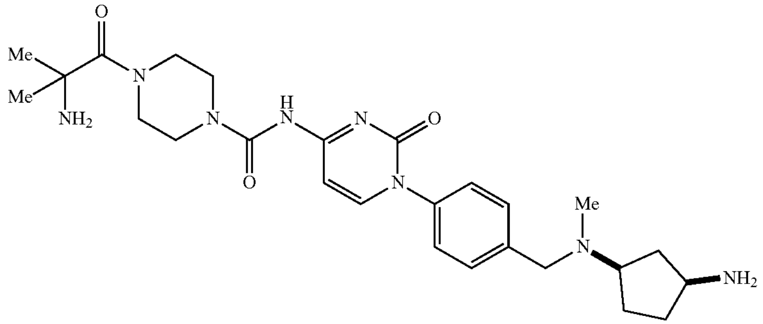 |
| 116 | 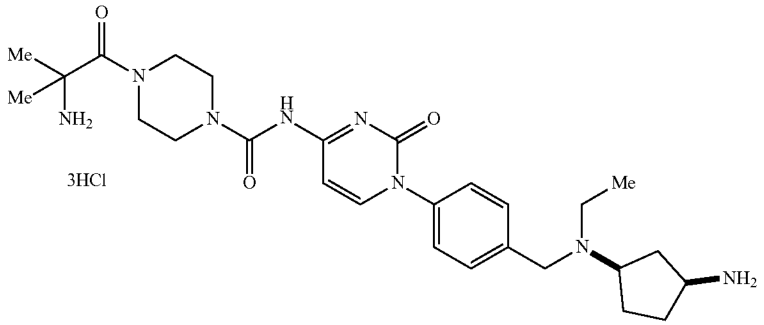 3HCl | 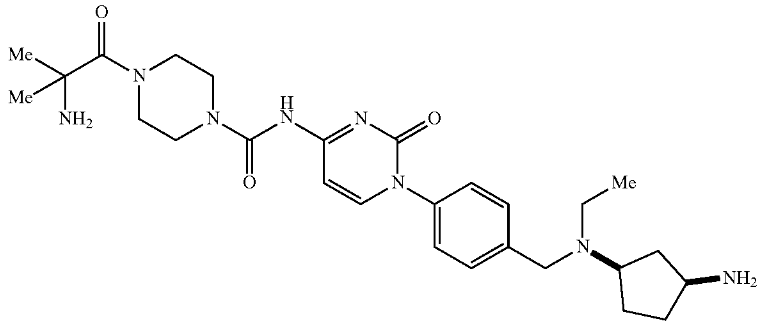 |
| 117 | 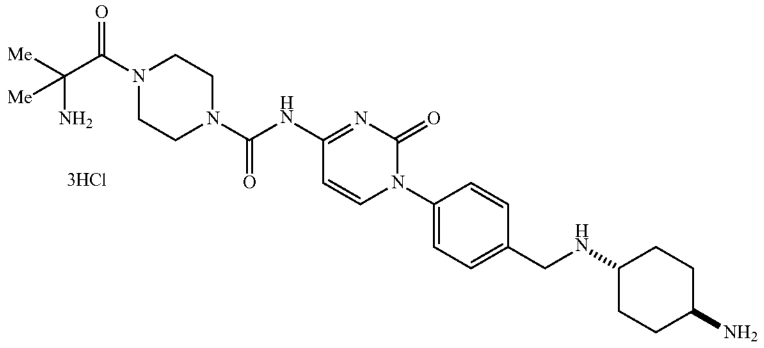 3HCl | 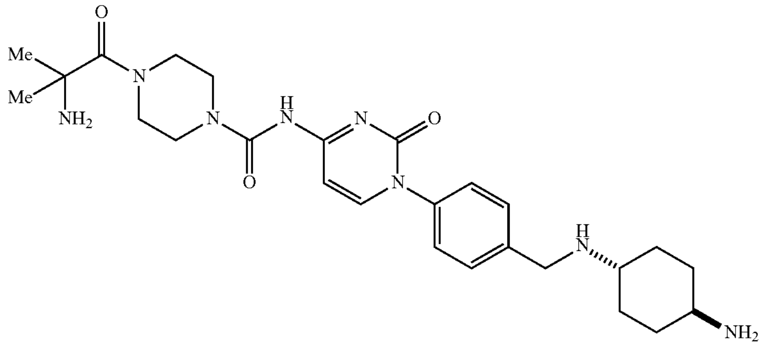 |

TABLE 10-continued
| Compounds of Formula I | | |
|---|---|---|
| No. | Salt Structure | Free Base Structure |
| 118 | 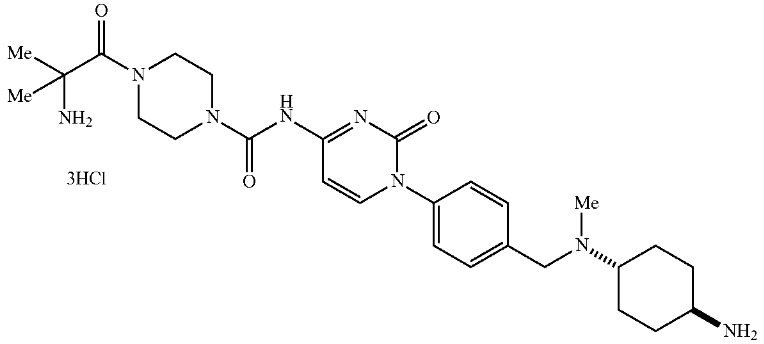 3HCl | 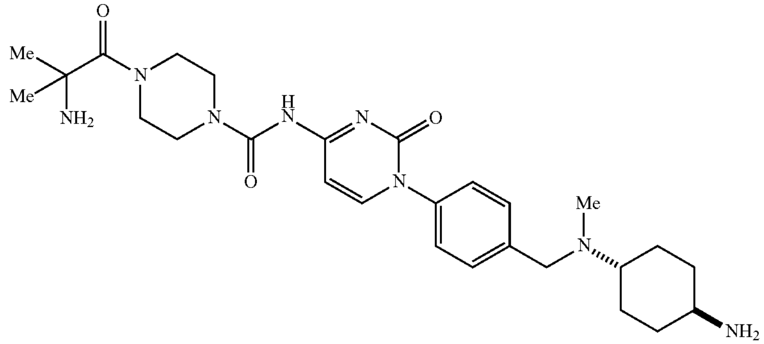 |
| 119 | 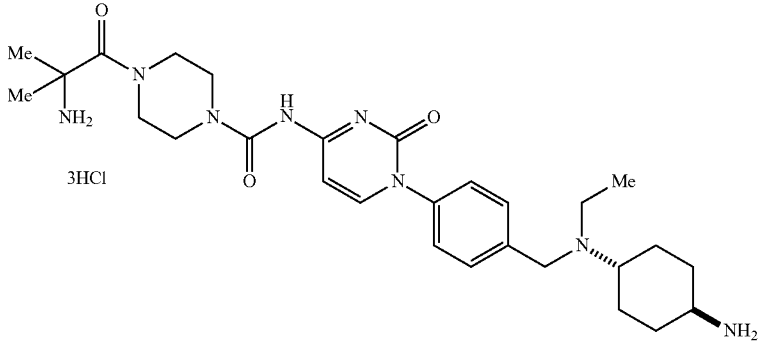 3HCl | 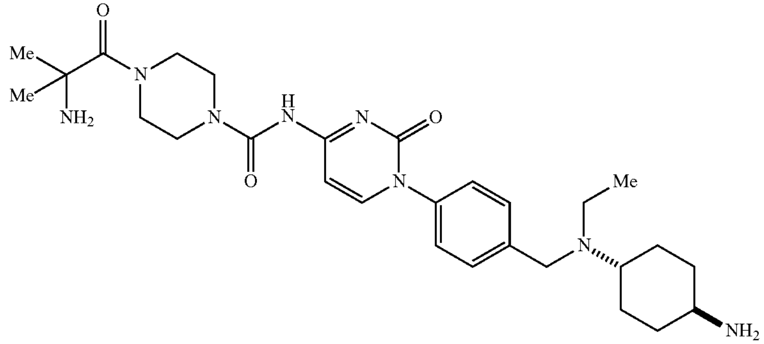 |

TABLE 10-continued
| Compounds of Formula I | | |
|---|---|---|
| No. | Salt Structure | Free Base Structure |
| 120 | 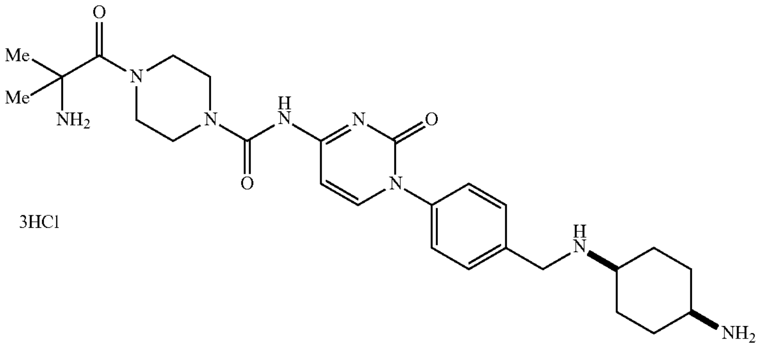 [SMILES: CC(C)(N)C(=O)N1CCN(C(=O)Nc2ccn(-c3ccc(CN[C@H]4CC[C@@H](N)CC4)cc3)c(=O)n2)CC1] 3HCl | 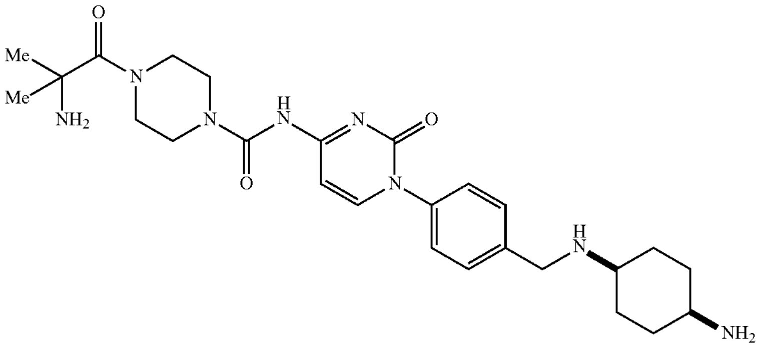 |
| 121 | 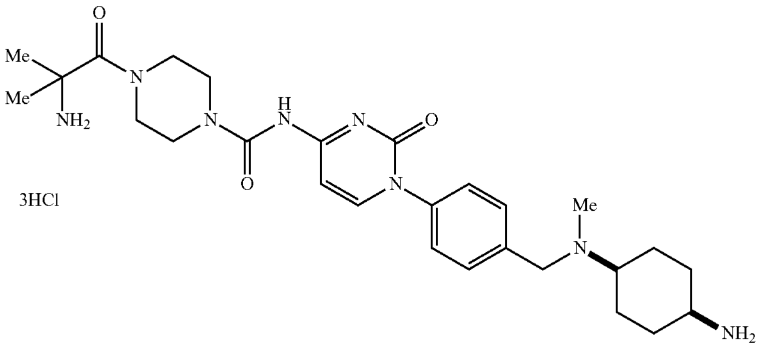 [SMILES: CN(Cc1ccc(-n2ccc(NC(=O)N3CCN(C(=O)C(C)(C)N)CC3)nc2=O)cc1)[C@H]1CC[C@@H](N)CC1] 3HCl | 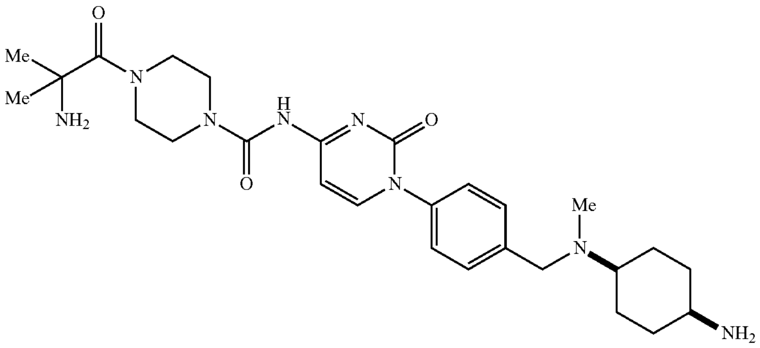 |

TABLE 10-continued
| Compounds of Formula I | | |
|---|---|---|
| No. | Salt Structure | Free Base Structure |
| 122 | 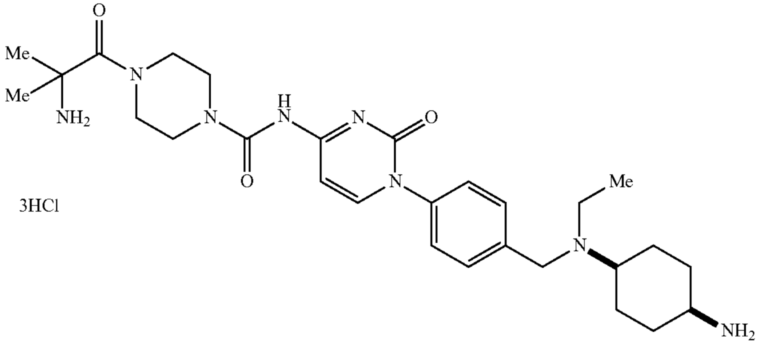 [SMILES: CCN(Cc1ccc(-n2ccc(NC(=O)N3CCN(C(=O)C(C)(C)N)CC3)nc2=O)cc1)[C@H]1CC[C@@H](N)CC1] 3HCl | 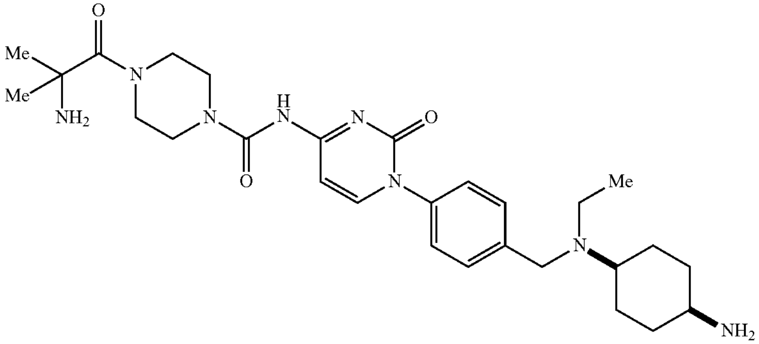 [SMILES: CCN(Cc1ccc(-n2ccc(NC(=O)N3CCN(C(=O)C(C)(C)N)CC3)nc2=O)cc1)[C@H]1CC[C@@H](N)CC1] |
| 123 | 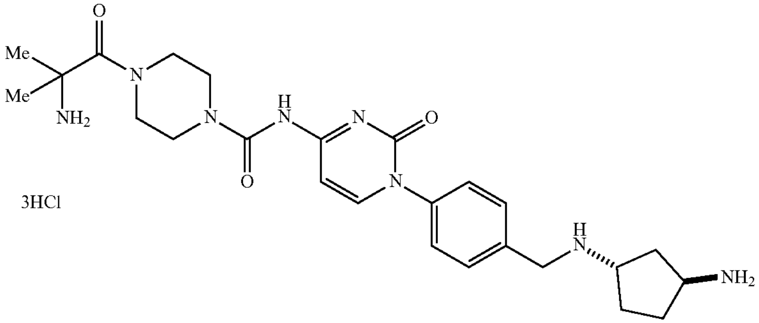 [SMILES: CC(C)(N)C(=O)N1CCN(C(=O)Nc2ccn(-c3ccc(CN[C@H]4CC[C@H](N)C4)cc3)c(=O)n2)CC1] 3HCl | 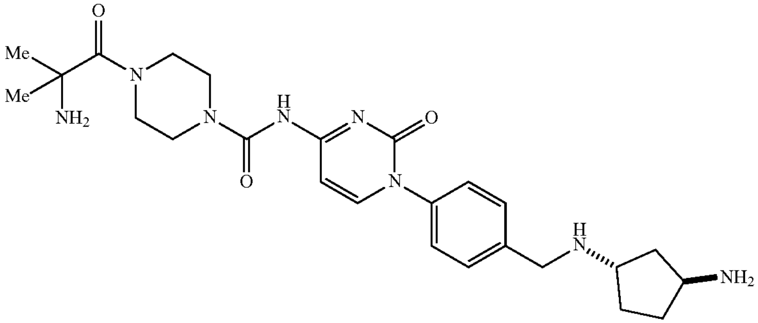 [SMILES: CC(C)(N)C(=O)N1CCN(C(=O)Nc2ccn(-c3ccc(CN[C@H]4CC[C@H](N)C4)cc3)c(=O)n2)CC1] |
| 124 | 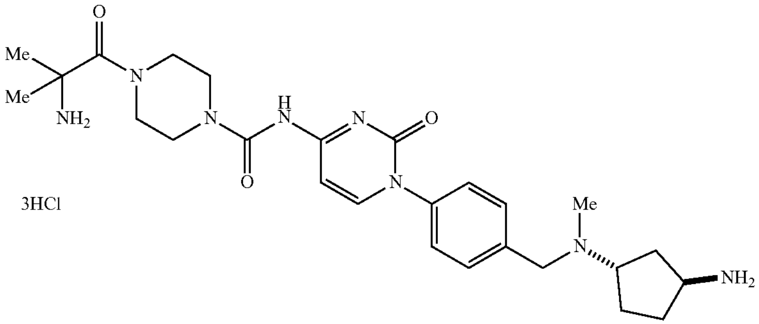 [SMILES: CN(Cc1ccc(-n2ccc(NC(=O)N3CCN(C(=O)C(C)(C)N)CC3)nc2=O)cc1)[C@H]1CC[C@H](N)C1] 3HCl | 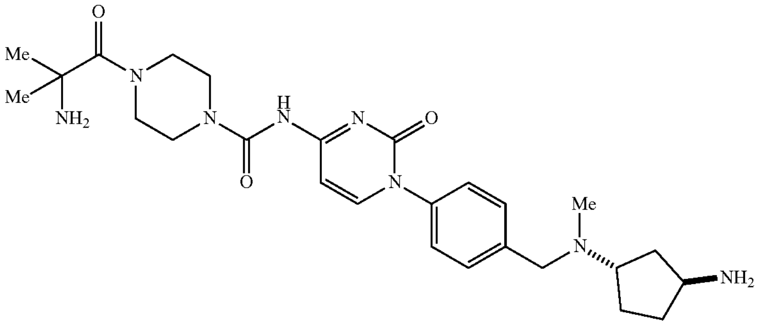 [SMILES: CN(Cc1ccc(-n2ccc(NC(=O)N3CCN(C(=O)C(C)(C)N)CC3)nc2=O)cc1)[C@H]1CC[C@H](N)C1] |

TABLE 10-continued
| Compounds of Formula I | | |
|---|---|---|
| No. | Salt Structure | Free Base Structure |
| 125 | 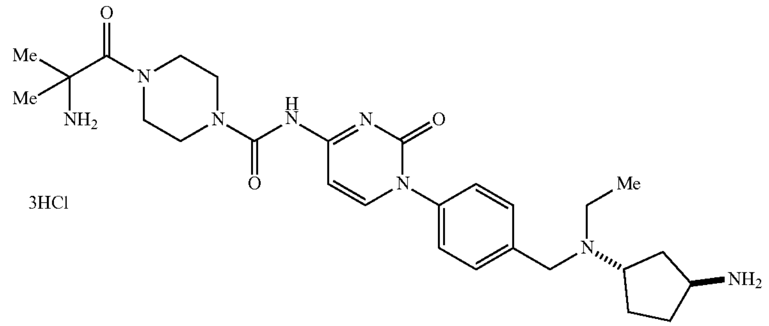 [SMILES: CCN(Cc1ccc(-n2ccc(NC(=O)N3CCN(C(=O)C(C)(C)N)CC3)nc2=O)cc1)[C@H]1CC[C@H](N)C1] 3HCl | 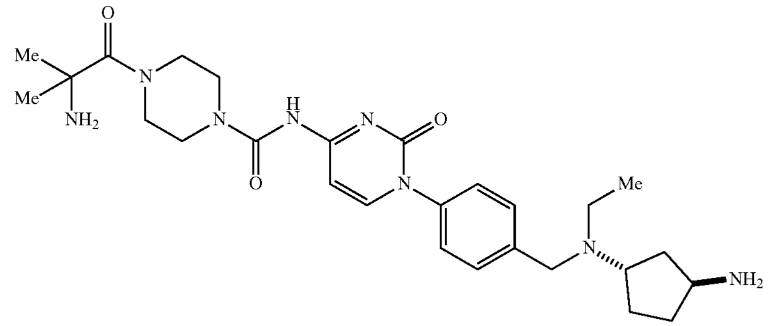 [SMILES: CCN(Cc1ccc(-n2ccc(NC(=O)N3CCN(C(=O)C(C)(C)N)CC3)nc2=O)cc1)[C@H]1CC[C@H](N)C1] |
| 126 | 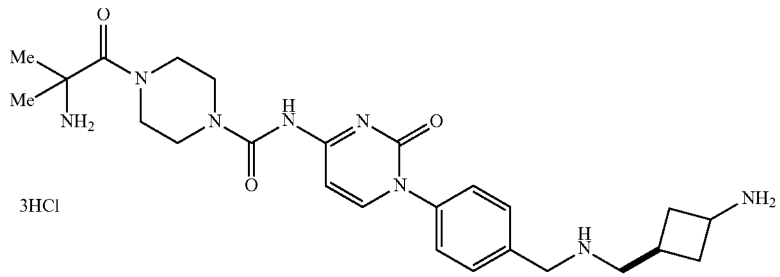 3HCl | 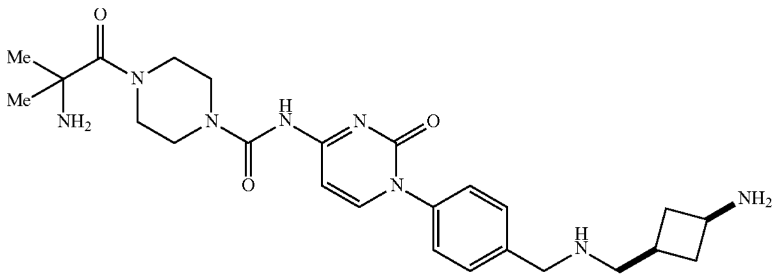 [SMILES: CC(C)(N)C(=O)N1CCN(C(=O)Nc2ccn(-c3ccc(CNC[C@H]4C[C@@H](N)C4)cc3)c(=O)n2)CC1] |
| 127 | 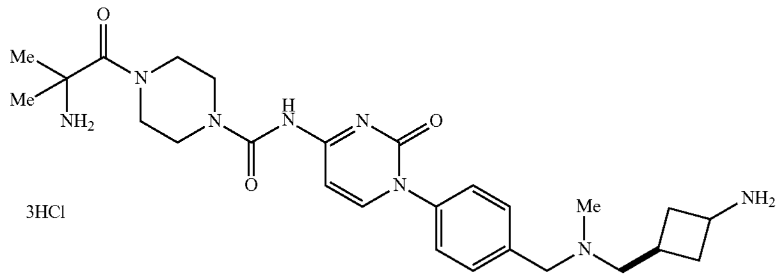 3HCl | 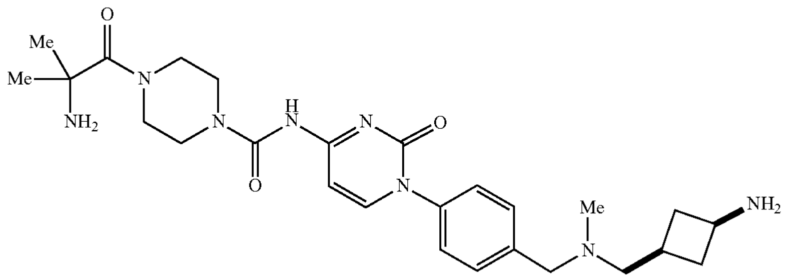 [SMILES: CN(Cc1ccc(-n2ccc(NC(=O)N3CCN(C(=O)C(C)(C)N)CC3)nc2=O)cc1)C[C@H]1C[C@@H](N)C1] |

TABLE 10-continued
| Compounds of Formula I | | |
| --- | --- | --- |
| No. | Salt Structure | Free Base Structure |
| 128 | 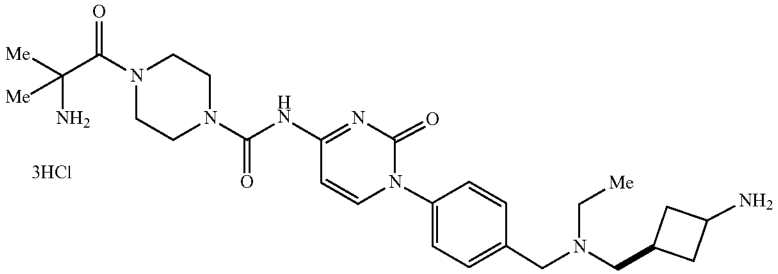 3HCl | 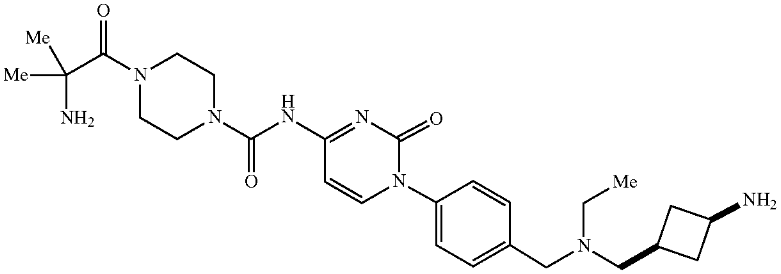 [SMILES: CCN(Cc1ccc(-n2ccc(NC(=O)N3CCN(C(=O)C(C)(C)N)CC3)nc2=O)cc1)C[C@H]1C[C@@H](N)C1] |
| 129 | 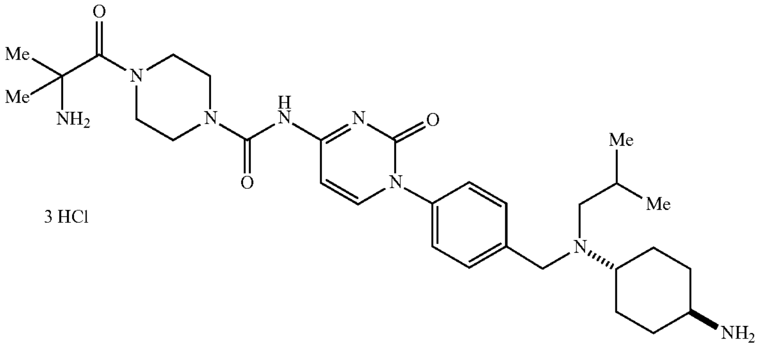 3 HCl | 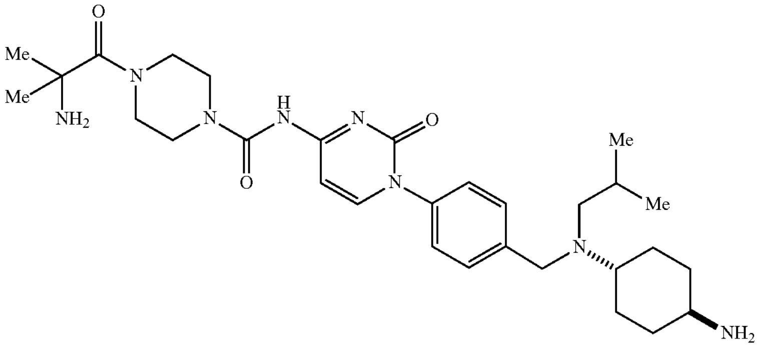 |
| 130 | 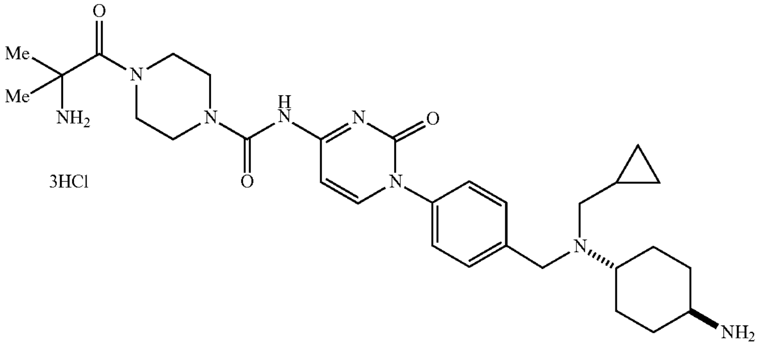 3HCl | 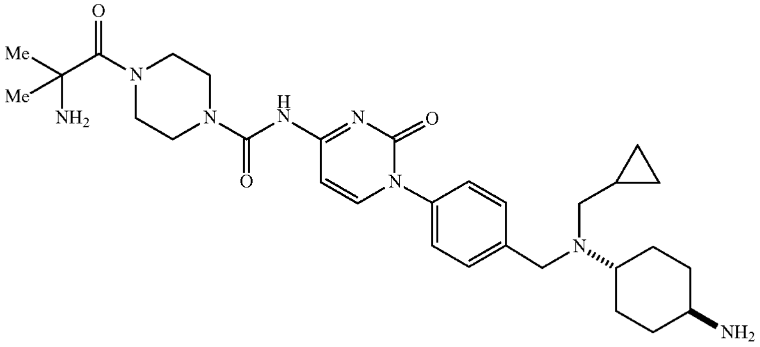 |

TABLE 10-continued
| Compounds of Formula I | | |
|---|---|---|
| No. | Salt Structure | Free Base Structure |
| 131 | 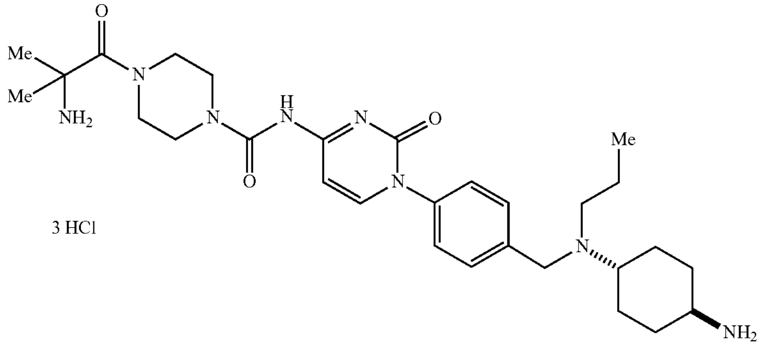 3 HCl | 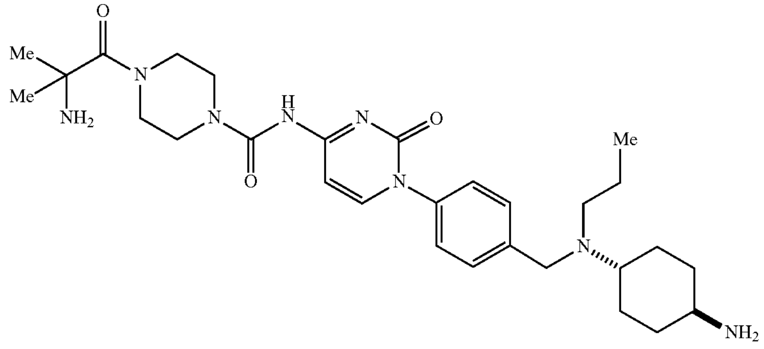 |
| 132 | 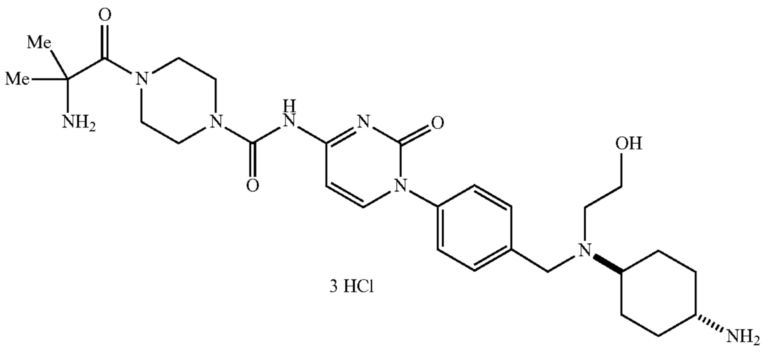 3 HCl | 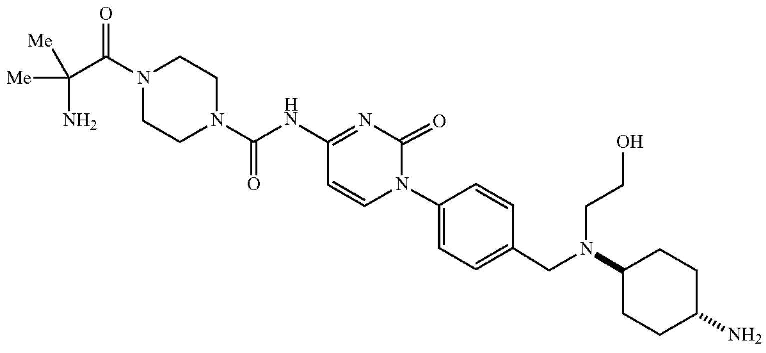 |

TABLE 10-continued
| Compounds of Formula I | | |
|---|---|---|
| No. | Salt Structure | Free Base Structure |
| 133 | 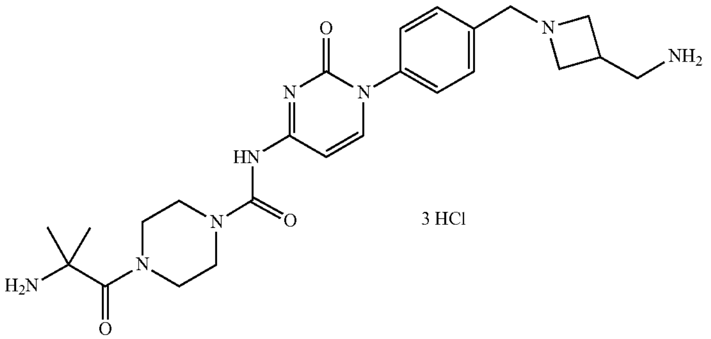 [SMILES: CC(C)(N)C(=O)N1CCN(C(=O)Nc2ccn(-c3ccc(CN4CC(CN)C4)cc3)c(=O)n2)CC1] 3 HCl | 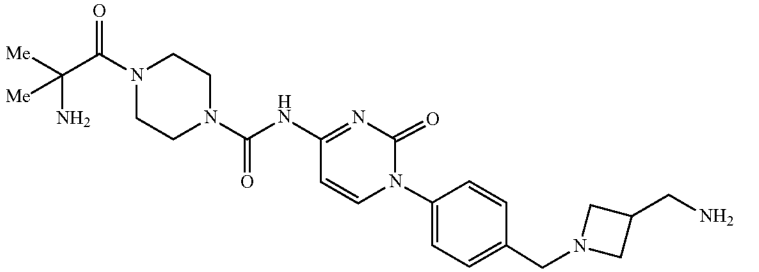 [SMILES: CC(C)(N)C(=O)N1CCN(C(=O)Nc2ccn(-c3ccc(CN4CC(CN)C4)cc3)c(=O)n2)CC1] |
| 134 | 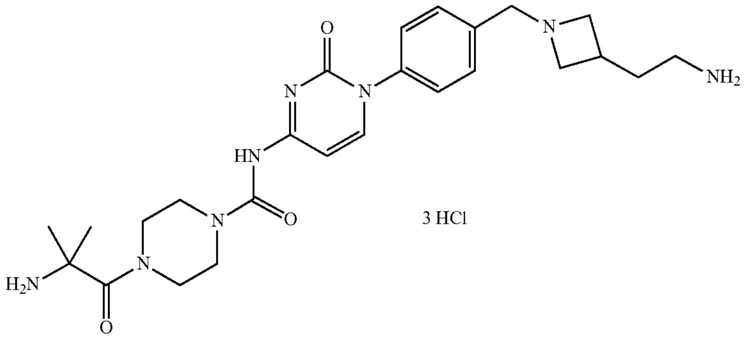 [SMILES: CC(C)(N)C(=O)N1CCN(C(=O)Nc2ccn(-c3ccc(CN4CC(CCN)C4)cc3)c(=O)n2)CC1] 3 HCl | 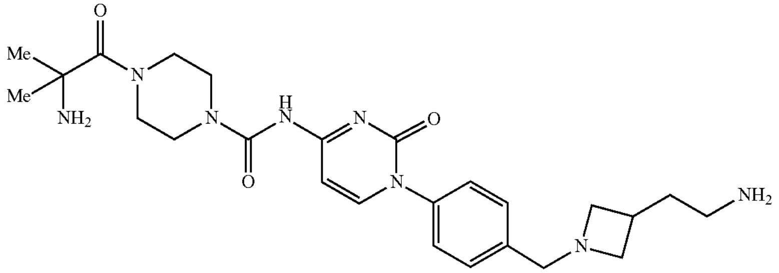 [SMILES: CC(C)(N)C(=O)N1CCN(C(=O)Nc2ccn(-c3ccc(CN4CC(CCN)C4)cc3)c(=O)n2)CC1] |
| 135 | 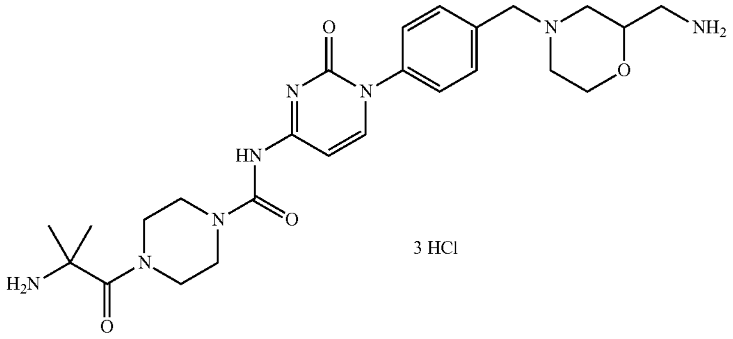 [SMILES: CC(C)(N)C(=O)N1CCN(C(=O)Nc2ccn(-c3ccc(CN4CCOC(CN)C4)cc3)c(=O)n2)CC1] 3 HCl | 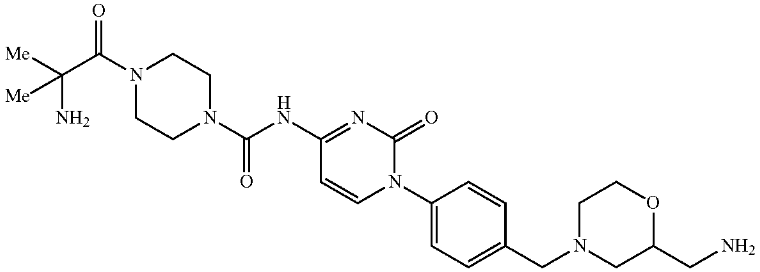 [SMILES: CC(C)(N)C(=O)N1CCN(C(=O)Nc2ccn(-c3ccc(CN4CCOC(CN)C4)cc3)c(=O)n2)CC1] |

TABLE 10-continued
Compounds of Formula I
| No. | Salt Structure | Free Base Structure |
| --- | --- | --- |
| 136 | 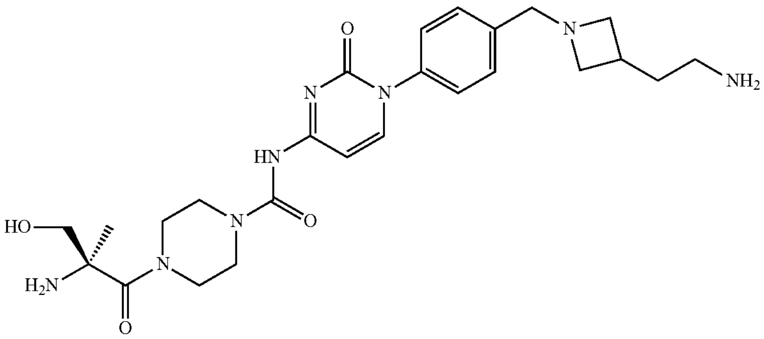 [SMILES: C[C@](N)(CO)C(=O)N1CCN(C(=O)Nc2ccn(-c3ccc(CN4CC(CCN)C4)cc3)c(=O)n2)CC1] | 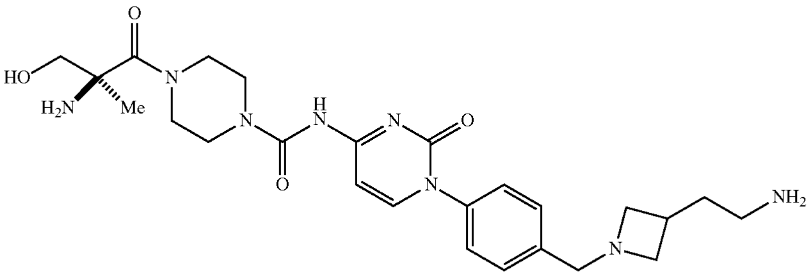 |
| 137 | 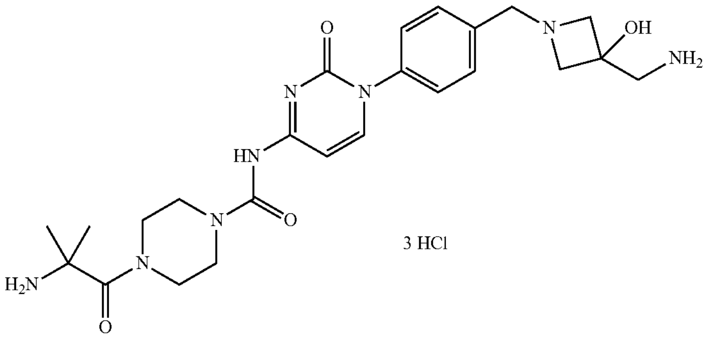 [SMILES: CC(C)(N)C(=O)N1CCN(C(=O)Nc2ccn(-c3ccc(CN4CC(O)(CN)C4)cc3)c(=O)n2)CC1] 3 HCl | 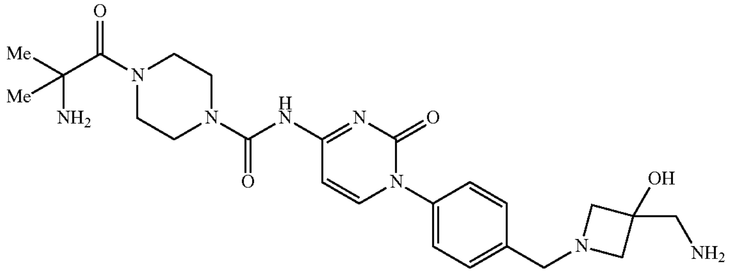 [SMILES: CC(C)(N)C(=O)N1CCN(C(=O)Nc2ccn(-c3ccc(CN4CC(O)(CN)C4)cc3)c(=O)n2)CC1] |

TABLE 10-continued
| Compounds of Formula I | | |
|---|---|---|
| No. | Salt Structure | Free Base Structure |
| 138 | 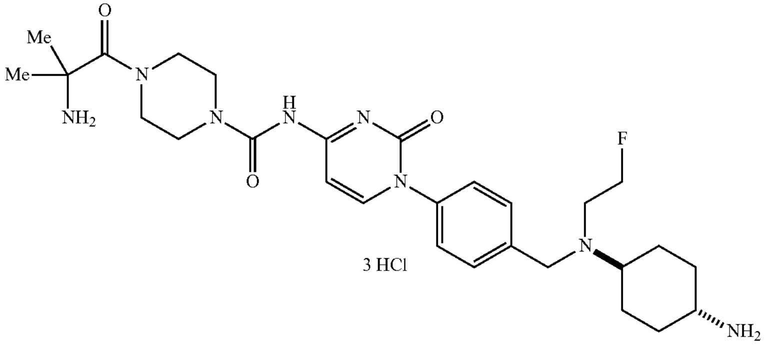 3 HCl | 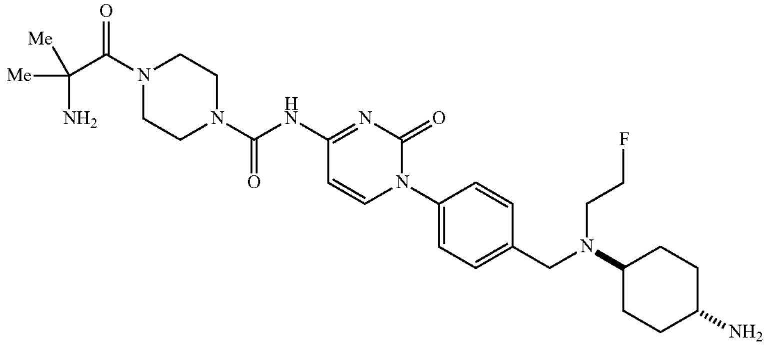 |
| 139 | 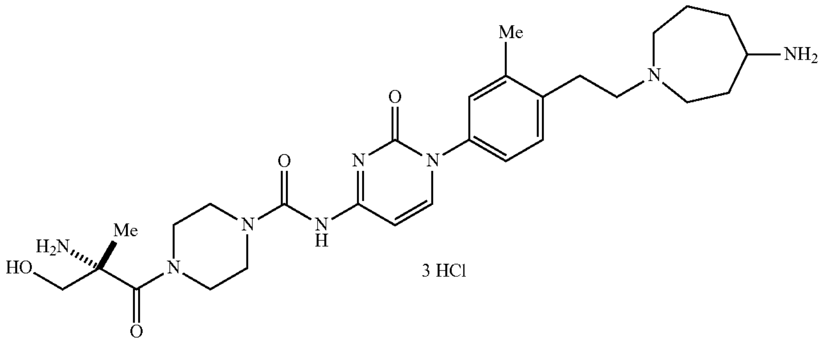 3 HCl | 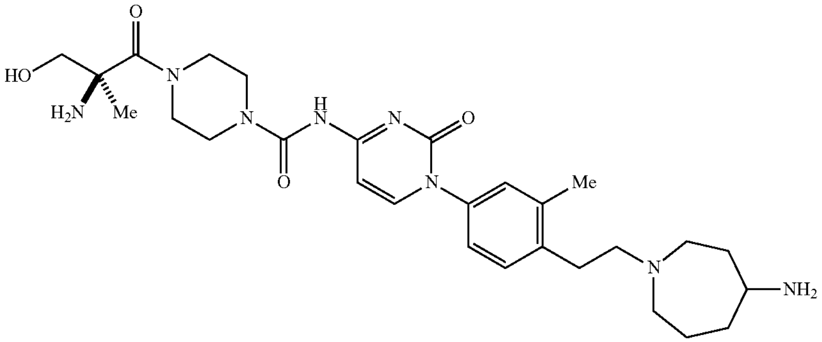 [SMILES: Cc1cc(-n2ccc(NC(=O)N3CCN(C(=O)[C@@](C)(N)CO)CC3)nc2=O)ccc1CCN1CCCC(N)CC1] |

TABLE 10-continued
| Compounds of Formula I | | |
|---|---|---|
| No. | Salt Structure | Free Base Structure |
| 140 | 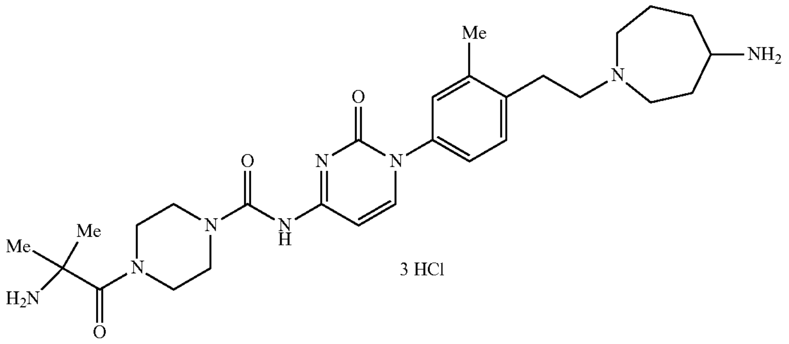 [SMILES: Cc1cc(-n2ccc(NC(=O)N3CCN(C(=O)C(C)(C)N)CC3)nc2=O)ccc1CCN1CCCC(N)CC1] 3 HCl | 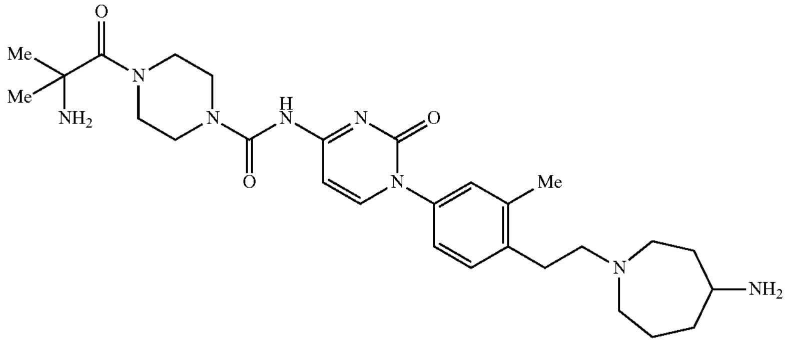 [SMILES: Cc1cc(-n2ccc(NC(=O)N3CCN(C(=O)C(C)(C)N)CC3)nc2=O)ccc1CCN1CCCC(N)CC1] |
| 141 | 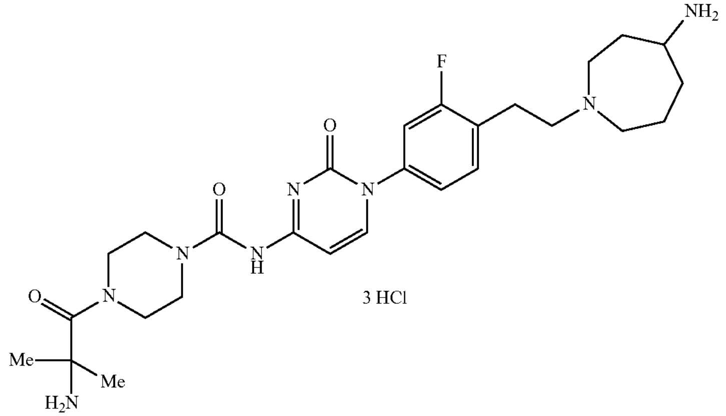 [SMILES: CC(C)(N)C(=O)N1CCN(C(=O)Nc2ccn(-c3ccc(CCN4CCCC(N)CC4)c(F)c3)c(=O)n2)CC1] 3 HCl | 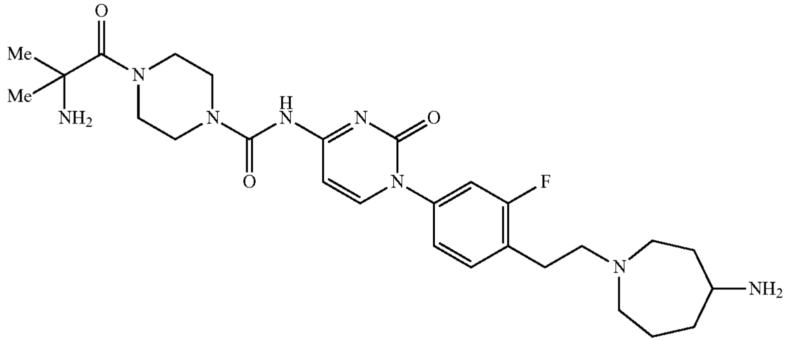 [SMILES: CC(C)(N)C(=O)N1CCN(C(=O)Nc2ccn(-c3ccc(CCN4CCCC(N)CC4)c(F)c3)c(=O)n2)CC1] |

TABLE 10-continued
| Compounds of Formula I | | |
|---|---|---|
| No. | Salt Structure | Free Base Structure |
| 142 | 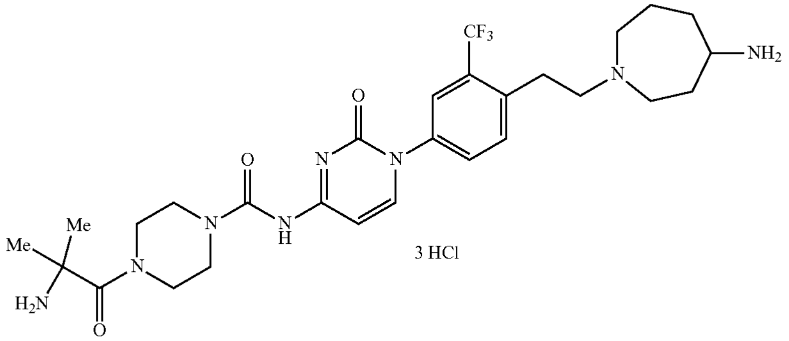 [SMILES: CC(C)(N)C(=O)N1CCN(C(=O)Nc2ccn(-c3ccc(CCN4CCCC(N)CC4)c(C(F)(F)F)c3)c(=O)n2)CC1] 3 HCl | 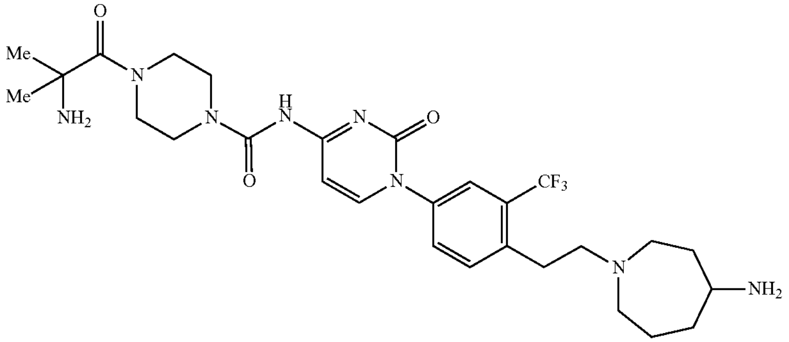 [SMILES: CC(C)(N)C(=O)N1CCN(C(=O)Nc2ccn(-c3ccc(CCN4CCCC(N)CC4)c(C(F)(F)F)c3)c(=O)n2)CC1] |
| 143 | 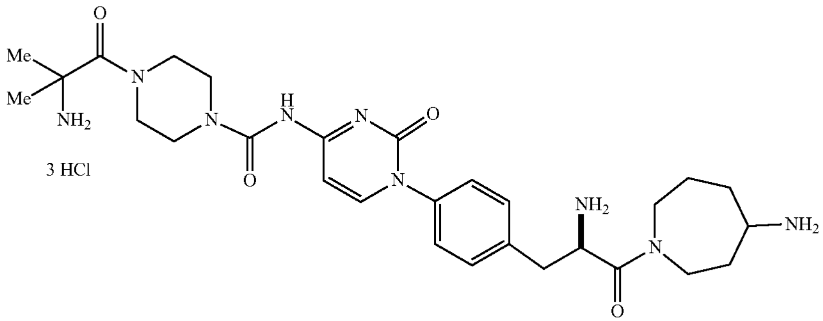 [SMILES: CC(C)(N)C(=O)N1CCN(C(=O)Nc2ccn(-c3ccc(C[C@@H](N)C(=O)N4CCCC(N)CC4)cc3)c(=O)n2)CC1] 3 HCl | 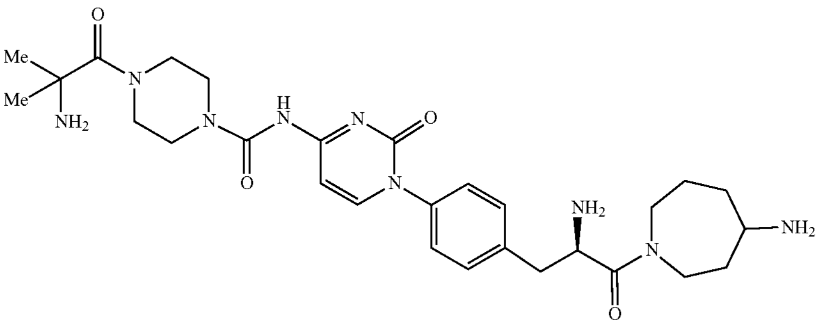 [SMILES: CC(C)(N)C(=O)N1CCN(C(=O)Nc2ccn(-c3ccc(C[C@@H](N)C(=O)N4CCCC(N)CC4)cc3)c(=O)n2)CC1] |
| 144 | 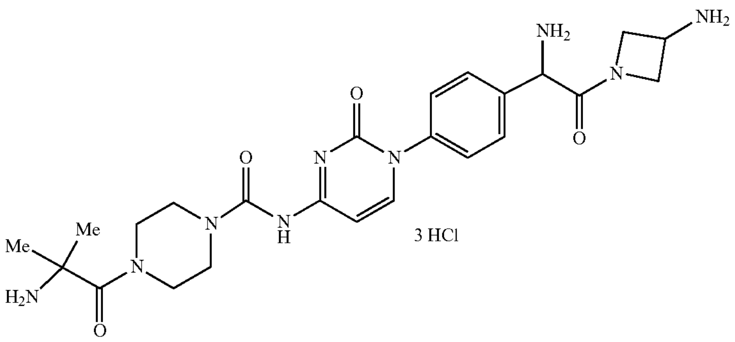 [SMILES: CC(C)(N)C(=O)N1CCN(C(=O)Nc2ccn(-c3ccc(C(N)C(=O)N4CC(N)C4)cc3)c(=O)n2)CC1] 3 HCl | 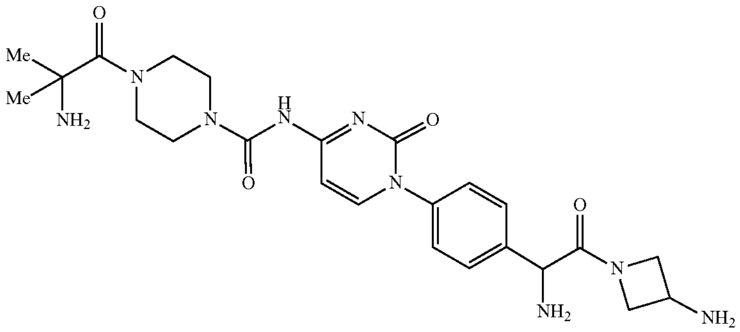 |

TABLE 10-continued
| Compounds of Formula I | | |
|---|---|---|
| No. | Salt Structure | Free Base Structure |
| 145 | 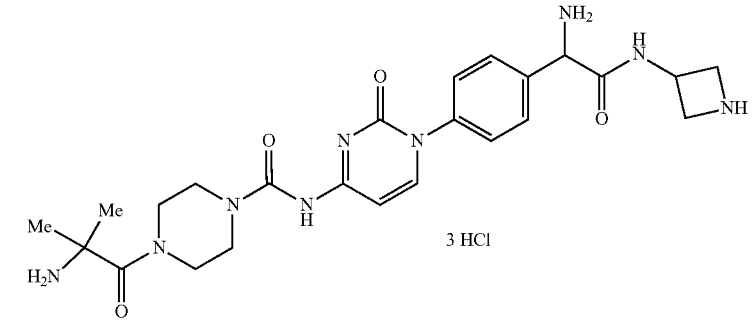 [SMILES: CC(C)(N)C(=O)N1CCN(C(=O)Nc2ccn(-c3ccc(C(N)C(=O)NC4CNC4)cc3)c(=O)n2)CC1] 3 HCl | 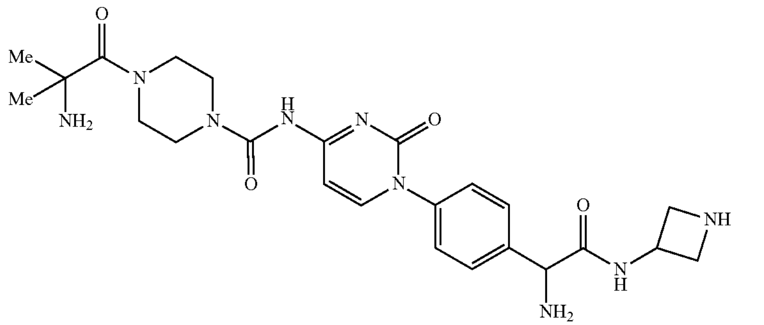 [SMILES: CC(C)(N)C(=O)N1CCN(C(=O)Nc2ccn(-c3ccc(C(N)C(=O)NC4CNC4)cc3)c(=O)n2)CC1] |
| 146 | 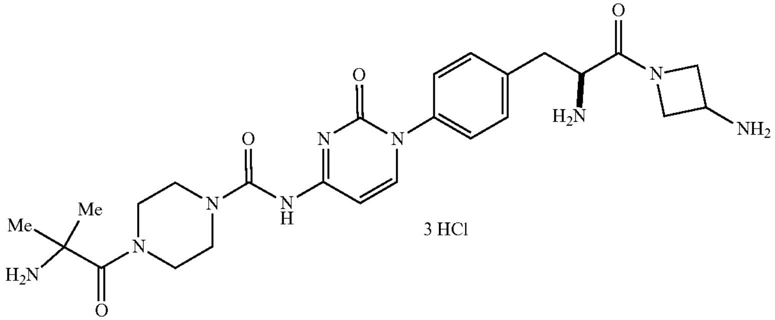 [SMILES: CC(C)(N)C(=O)N1CCN(C(=O)Nc2ccn(-c3ccc(C[C@H](N)C(=O)N4CC(N)C4)cc3)c(=O)n2)CC1] 3 HCl | 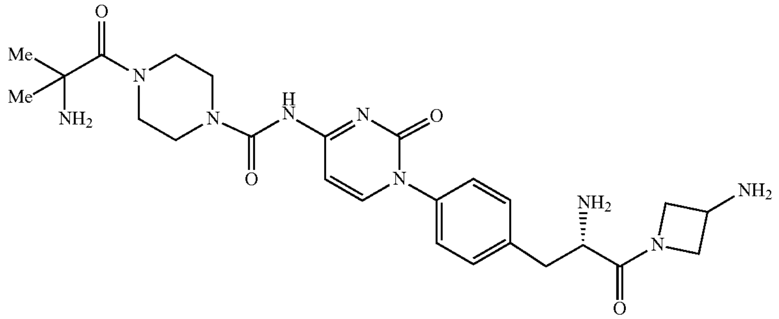 [SMILES: CC(C)(N)C(=O)N1CCN(C(=O)Nc2ccn(-c3ccc(C[C@H](N)C(=O)N4CC(N)C4)cc3)c(=O)n2)CC1] |
| 147 | 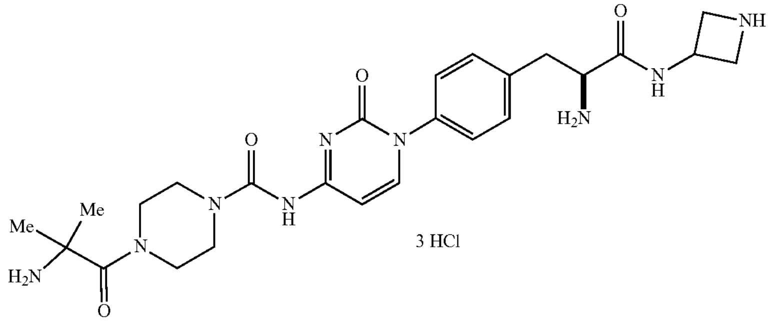 [SMILES: CC(C)(N)C(=O)N1CCN(C(=O)Nc2ccn(-c3ccc(C[C@H](N)C(=O)NC4CNC4)cc3)c(=O)n2)CC1] 3 HCl | 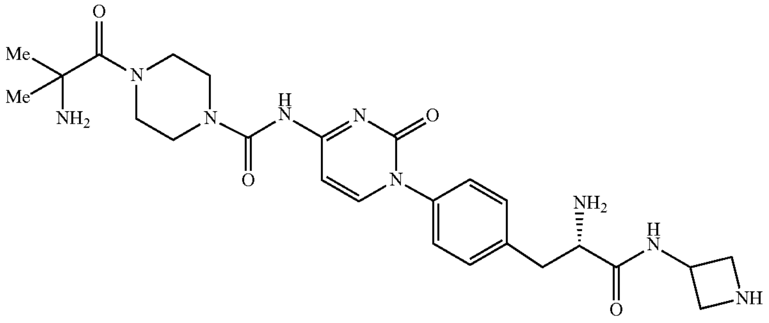 [SMILES: CC(C)(N)C(=O)N1CCN(C(=O)Nc2ccn(-c3ccc(C[C@H](N)C(=O)NC4CNC4)cc3)c(=O)n2)CC1] |

TABLE 10-continued
| Compounds of Formula I | | |
|---|---|---|
| No. | Salt Structure | Free Base Structure |
| 148 | 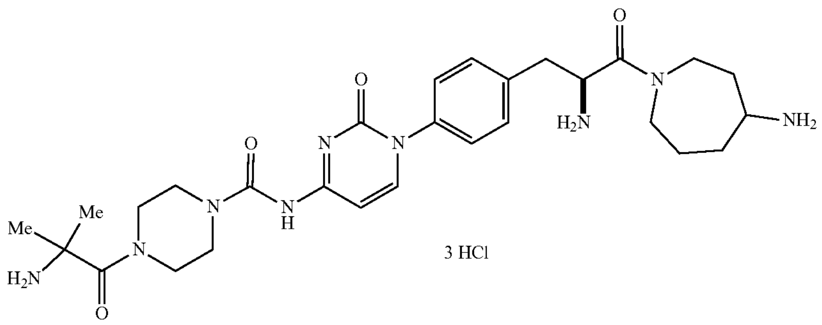 [SMILES: CC(C)(N)C(=O)N1CCN(C(=O)Nc2ccn(-c3ccc(C[C@H](N)C(=O)N4CCCC(N)CC4)cc3)c(=O)n2)CC1] 3 HCl | 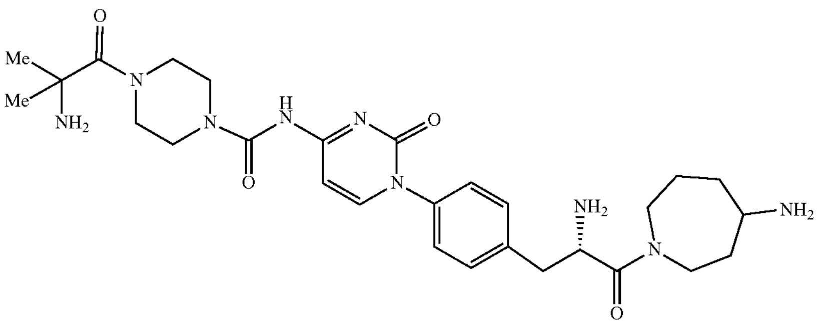 [SMILES: CC(C)(N)C(=O)N1CCN(C(=O)Nc2ccn(-c3ccc(C[C@H](N)C(=O)N4CCCC(N)CC4)cc3)c(=O)n2)CC1] |
| 149 | 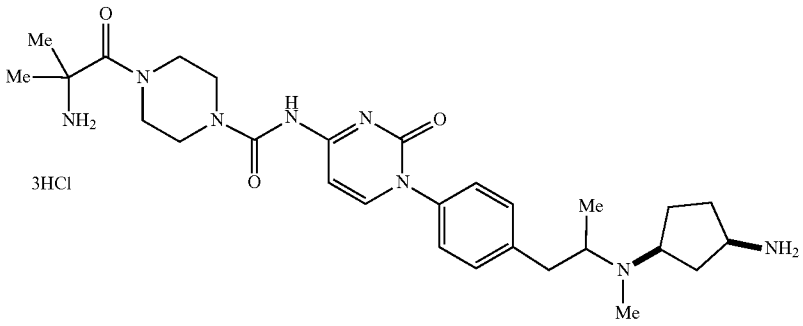 [SMILES: CC(Cc1ccc(-n2ccc(NC(=O)N3CCN(C(=O)C(C)(C)N)CC3)nc2=O)cc1)N(C)[C@H]1CC[C@@H](N)C1] 3HCl | 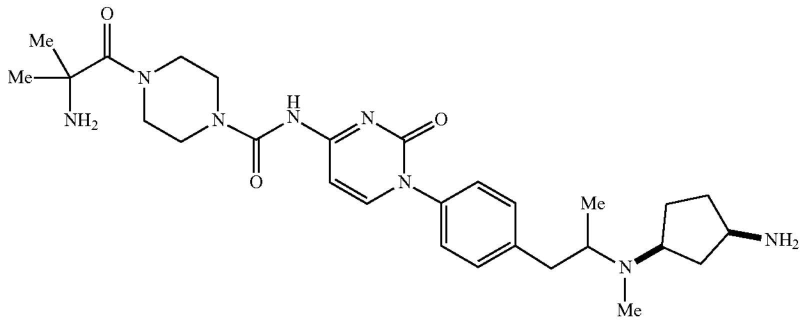 [SMILES: CC(Cc1ccc(-n2ccc(NC(=O)N3CCN(C(=O)C(C)(C)N)CC3)nc2=O)cc1)N(C)[C@H]1CC[C@@H](N)C1] |

TABLE 10-continued
| Compounds of Formula I | | |
|---|---|---|
| No. | Salt Structure | Free Base Structure |
| 150 | 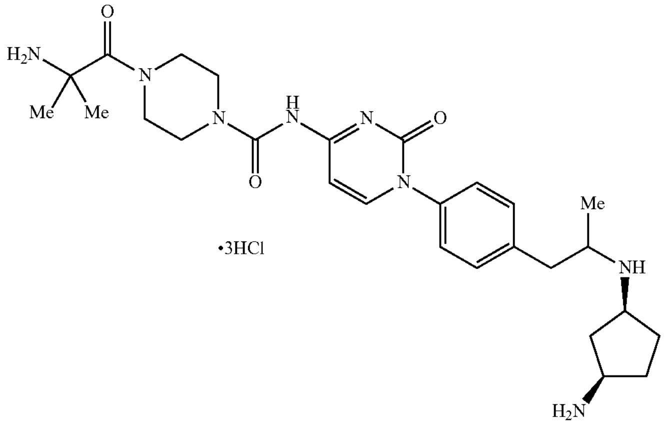 [SMILES: CC(Cc1ccc(-n2ccc(NC(=O)N3CCN(C(=O)C(C)(C)N)CC3)nc2=O)cc1)N[C@H]1CC[C@@H](N)C1] •3HCl | 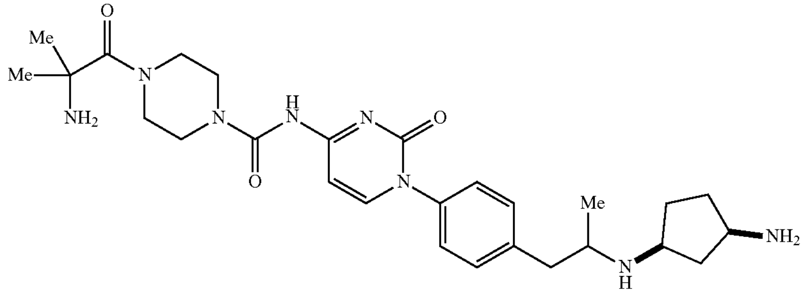 [SMILES: CC(Cc1ccc(-n2ccc(NC(=O)N3CCN(C(=O)C(C)(C)N)CC3)nc2=O)cc1)N[C@H]1CC[C@@H](N)C1] |
| 151 | 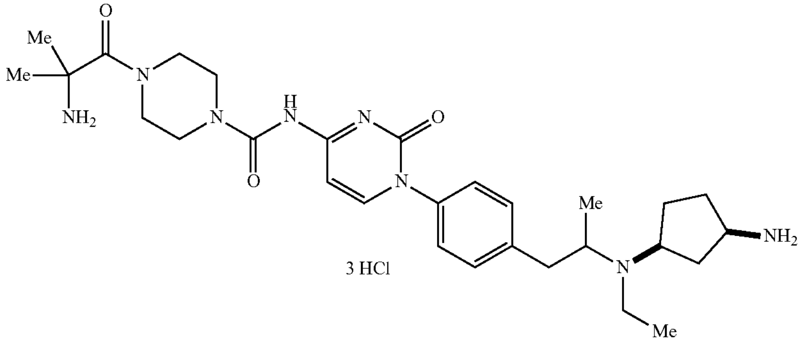 [SMILES: CCN(C(C)Cc1ccc(-n2ccc(NC(=O)N3CCN(C(=O)C(C)(C)N)CC3)nc2=O)cc1)[C@H]1CC[C@@H](N)C1] 3 HCl | 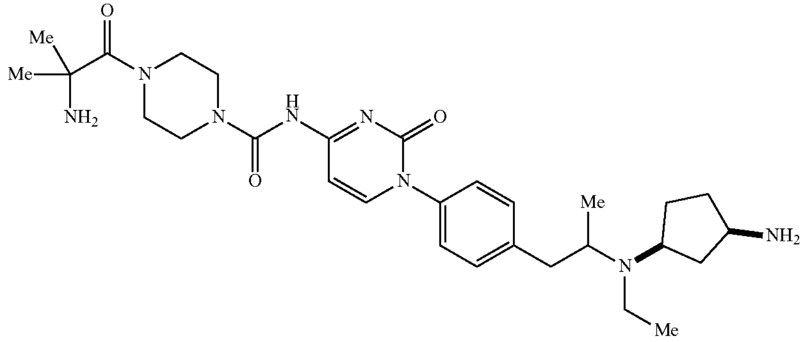 [SMILES: CCN(C(C)Cc1ccc(-n2ccc(NC(=O)N3CCN(C(=O)C(C)(C)N)CC3)nc2=O)cc1)[C@H]1CC[C@@H](N)C1] |

TABLE 10-continued
| Compounds of Formula I | | |
| --- | --- | --- |
| No. | Salt Structure | Free Base Structure |
| 152 | 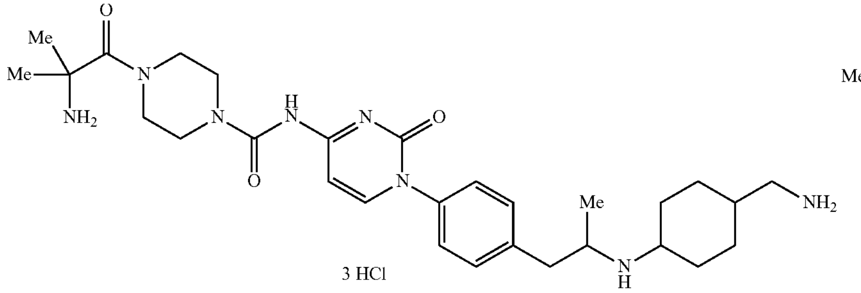 3 HCl | 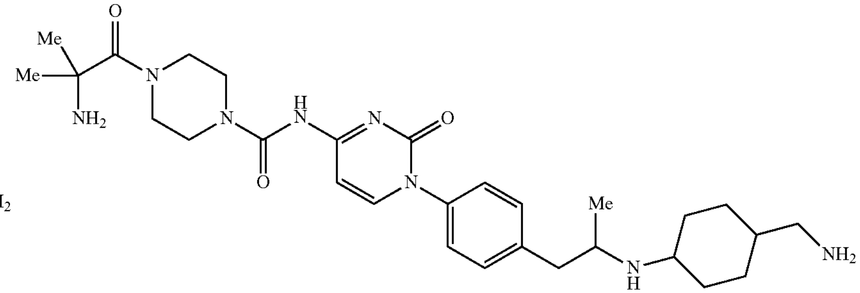 |
| 153 | 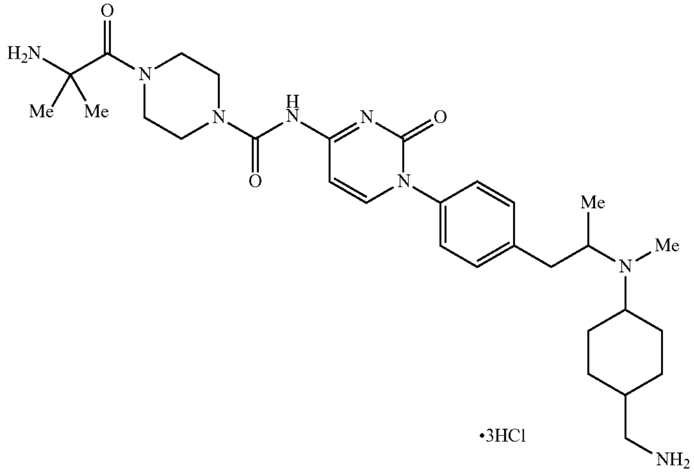 [SMILES: CC(Cc1ccc(-n2ccc(NC(=O)N3CCN(C(=O)C(C)(C)N)CC3)nc2=O)cc1)N(C)C1CCC(CN)CC1] •3HCl | 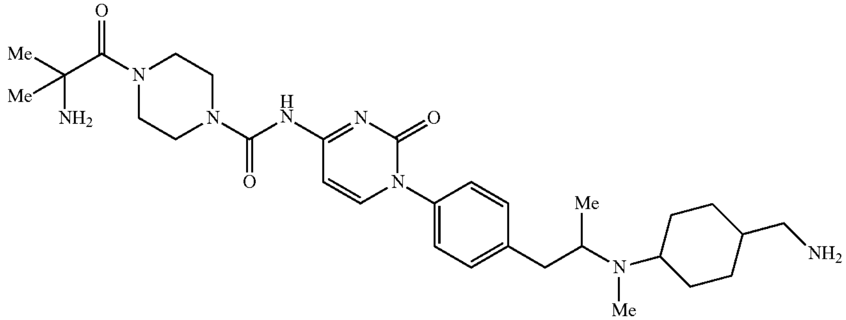 [SMILES: CC(Cc1ccc(-n2ccc(NC(=O)N3CCN(C(=O)C(C)(C)N)CC3)nc2=O)cc1)N(C)C1CCC(CN)CC1] |

TABLE 10-continued
| Compounds of Formula I | | |
|---|---|---|
| No. | Salt Structure | Free Base Structure |
| 154 | 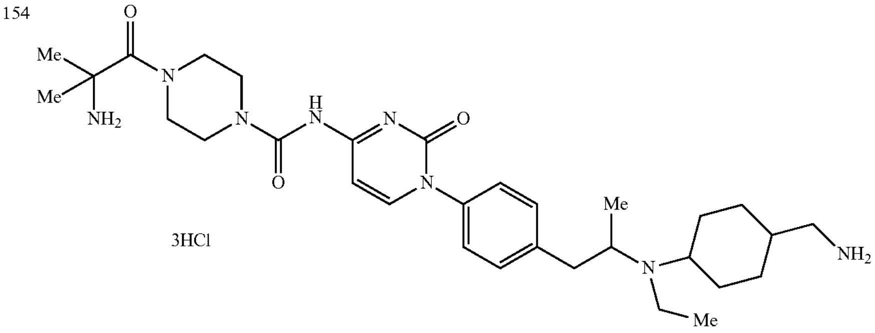 3HCl | 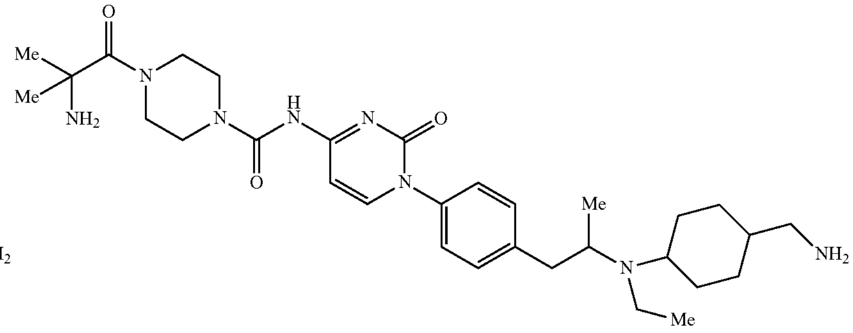 |
| 155 | 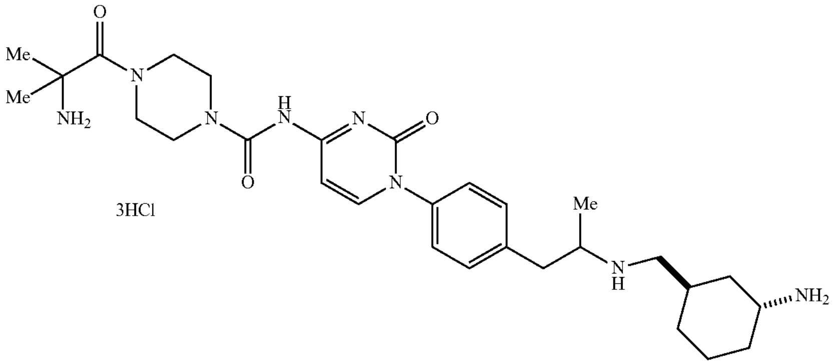 3HCl (trans-racemic) | 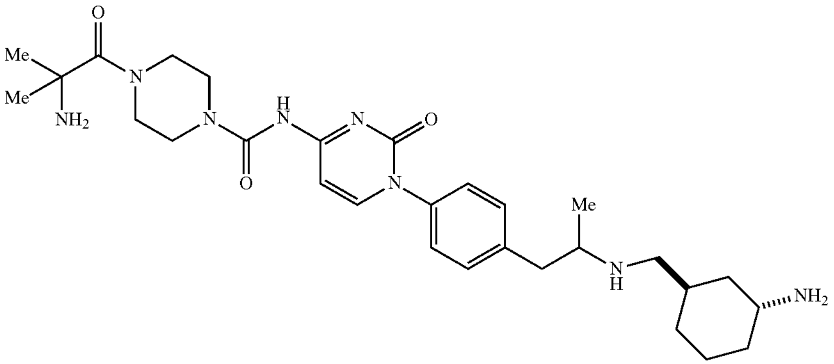 (trans-racemic) |

TABLE 10-continued
| Compounds of Formula I | | |
|---|---|---|
| No. | Salt Structure | Free Base Structure |
| 156 | 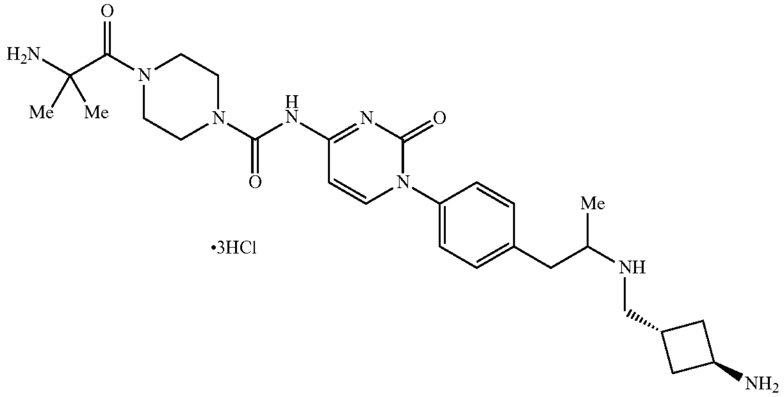 [SMILES: CC(Cc1ccc(-n2ccc(NC(=O)N3CCN(C(=O)C(C)(C)N)CC3)nc2=O)cc1)NC[C@H]1C[C@H](N)C1] •3HCl | 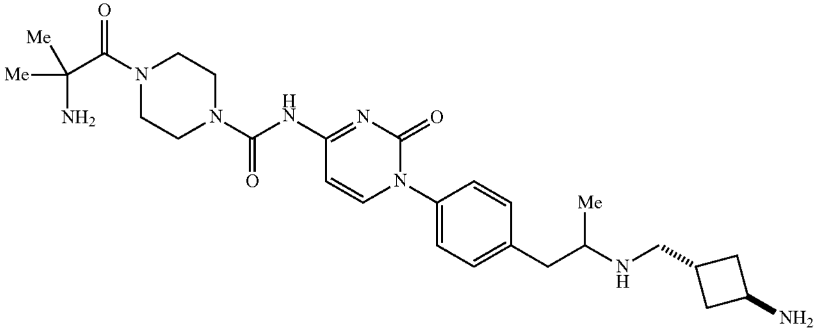 |
| 157 | 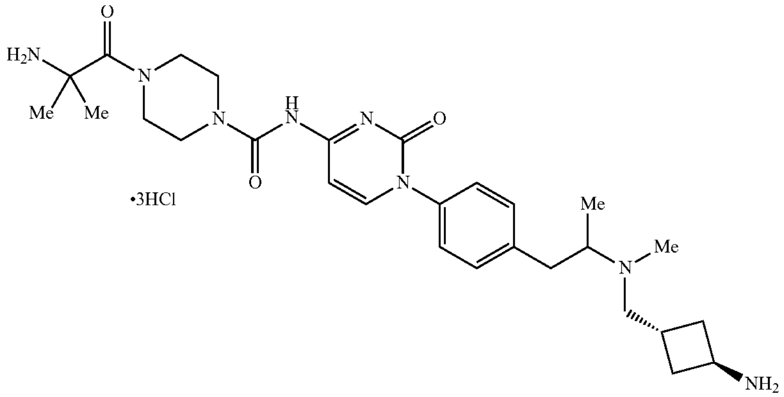 [SMILES: CC(Cc1ccc(-n2ccc(NC(=O)N3CCN(C(=O)C(C)(C)N)CC3)nc2=O)cc1)N(C)C[C@H]1C[C@H](N)C1] •3HCl | 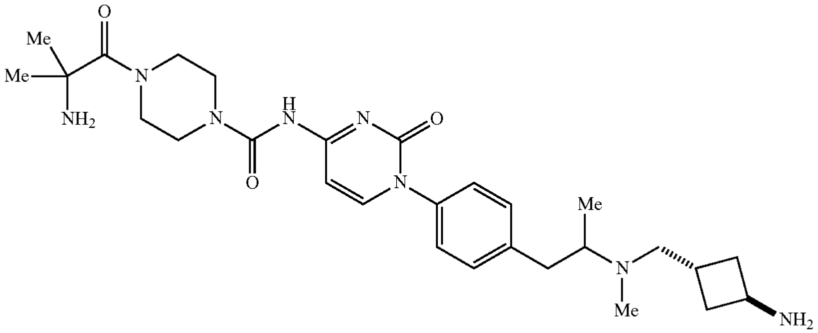 |

TABLE 10-continued
| Compounds of Formula I | | |
|---|---|---|
| No. | Salt Structure | Free Base Structure |
| 158 | 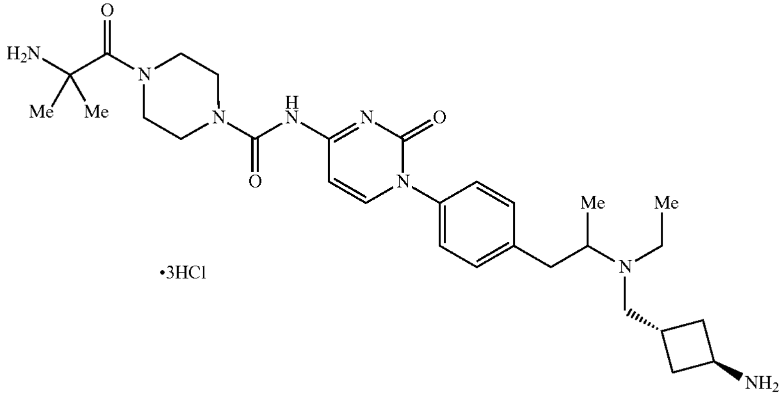 [SMILES: CCN(C[C@H]1C[C@H](N)C1)C(C)Cc1ccc(-n2ccc(NC(=O)N3CCN(C(=O)C(C)(C)N)CC3)nc2=O)cc1] •3HCl | 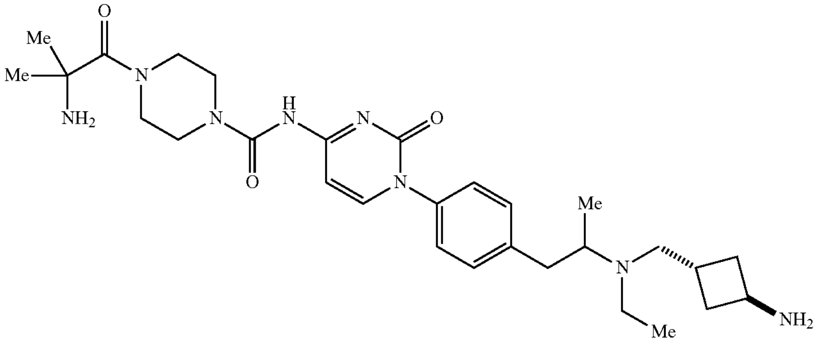 |
| 159 | 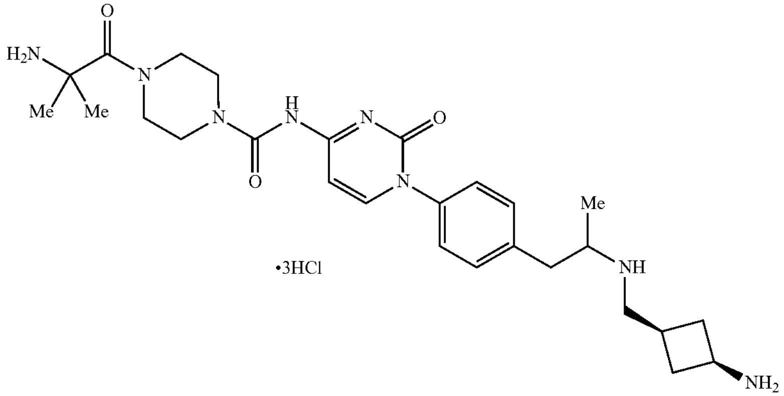 [SMILES: CC(Cc1ccc(-n2ccc(NC(=O)N3CCN(C(=O)C(C)(C)N)CC3)nc2=O)cc1)NC[C@H]1C[C@@H](N)C1] •3HCl | 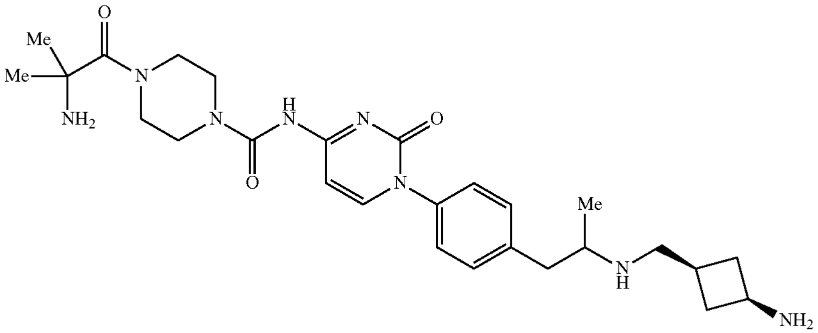 |

TABLE 10-continued
| Compounds of Formula I | | |
|---|---|---|
| No. | Salt Structure | Free Base Structure |
| 160 | 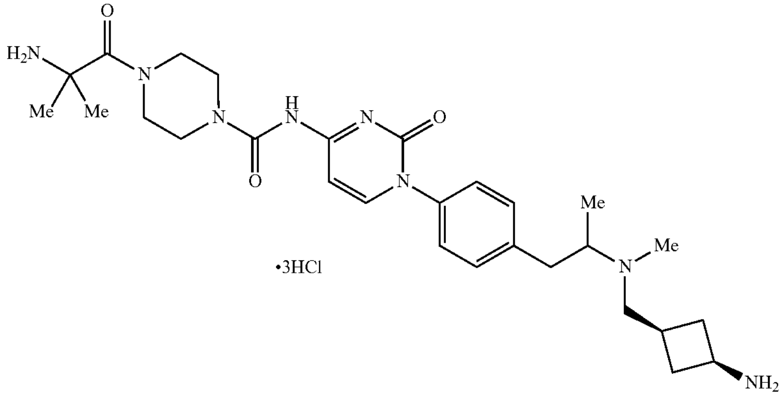 [SMILES: CC(Cc1ccc(-n2ccc(NC(=O)N3CCN(C(=O)C(C)(C)N)CC3)nc2=O)cc1)N(C)C[C@H]1C[C@@H](N)C1] •3HCl | 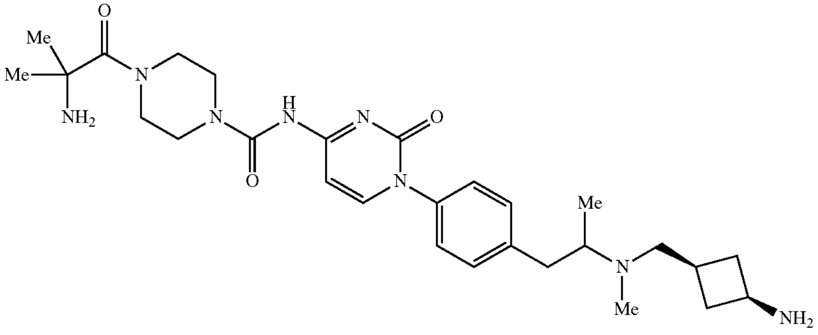 |
| 161 | 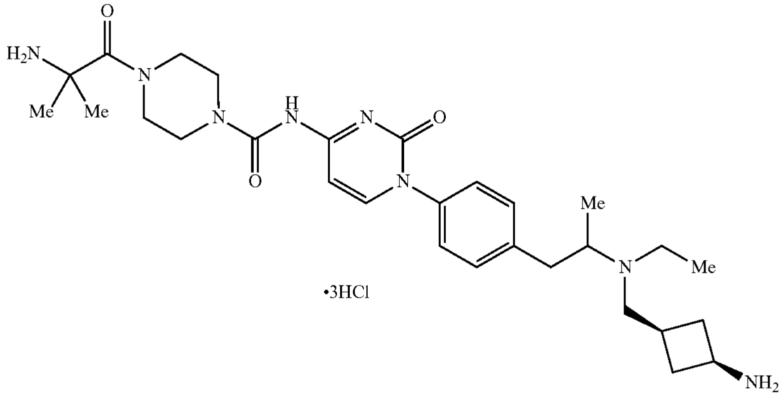 [SMILES: CCN(C[C@H]1C[C@@H](N)C1)C(C)Cc1ccc(-n2ccc(NC(=O)N3CCN(C(=O)C(C)(C)N)CC3)nc2=O)cc1] •3HCl | 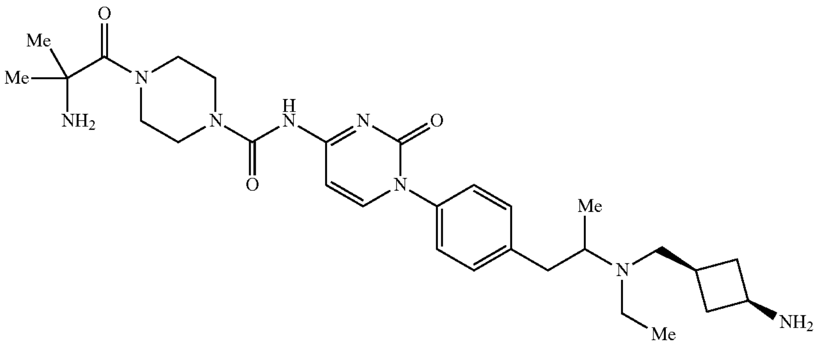 [SMILES: CCN(C[C@H]1C[C@@H](N)C1)C(C)Cc1ccc(-n2ccc(NC(=O)N3CCN(C(=O)C(C)(C)N)CC3)nc2=O)cc1] |

TABLE 10-continued
Compounds of Formula I
| No. | Salt Structure | Free Base Structure |
| --- | --- | --- |
| 162 | 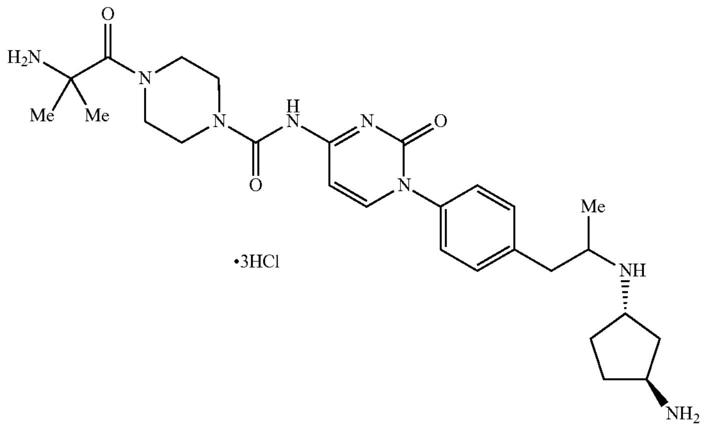 [SMILES: CC(Cc1ccc(-n2ccc(NC(=O)N3CCN(C(=O)C(C)(C)N)CC3)nc2=O)cc1)N[C@H]1CC[C@H](N)C1] •3HCl | 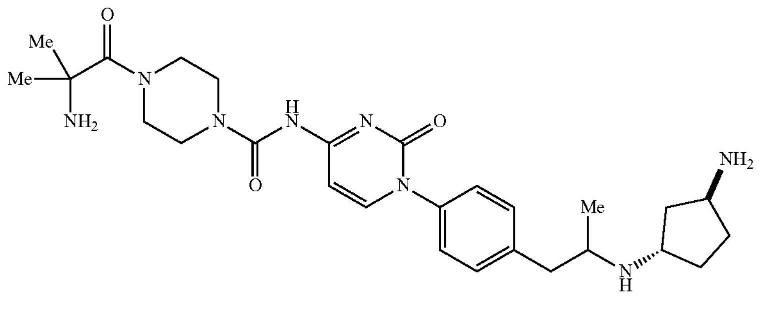 [SMILES: CC(Cc1ccc(-n2ccc(NC(=O)N3CCN(C(=O)C(C)(C)N)CC3)nc2=O)cc1)N[C@H]1CC[C@H](N)C1] |
| 163 | 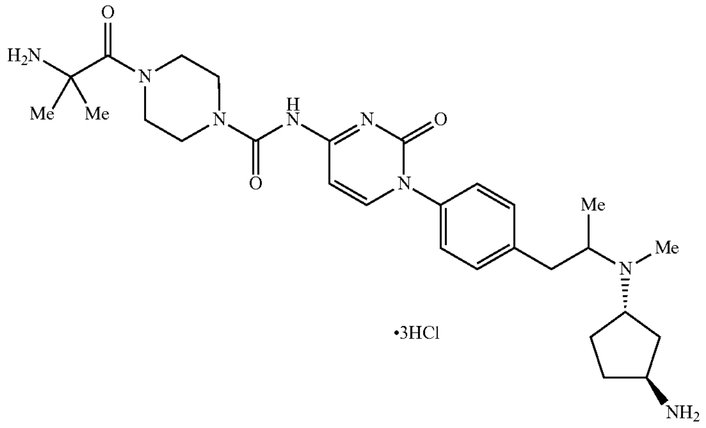 [SMILES: CC(Cc1ccc(-n2ccc(NC(=O)N3CCN(C(=O)C(C)(C)N)CC3)nc2=O)cc1)N(C)[C@H]1CC[C@H](N)C1] •3HCl | 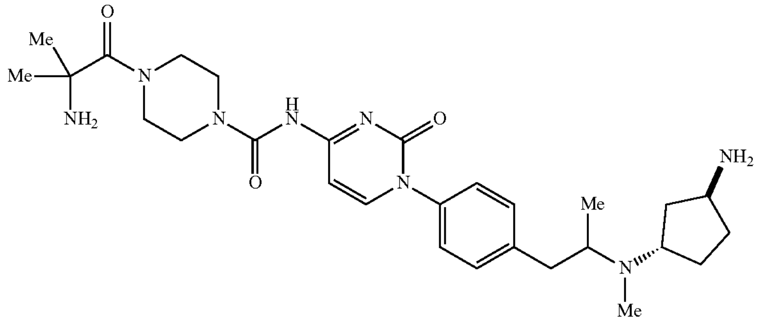 |

TABLE 10-continued
| Compounds of Formula I | | |
|---|---|---|
| No. | Salt Structure | Free Base Structure |
| 164 | 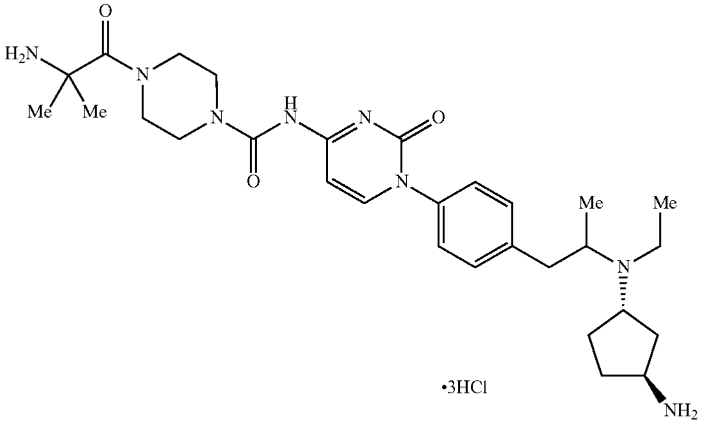 [SMILES: CCN(C(C)Cc1ccc(-n2ccc(NC(=O)N3CCN(C(=O)C(C)(C)N)CC3)nc2=O)cc1)[C@H]1CC[C@H](N)C1] •3HCl | 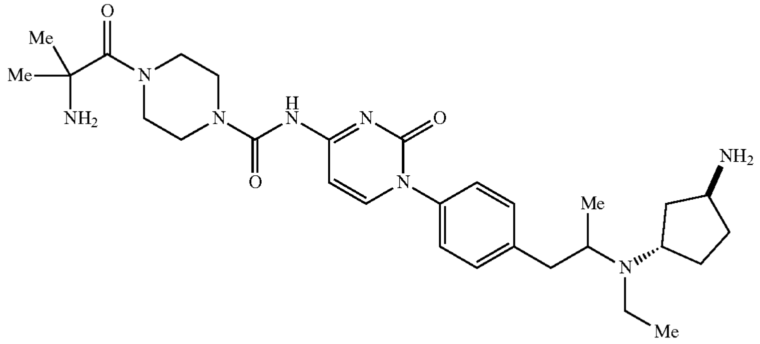 [SMILES: CCN(C(C)Cc1ccc(-n2ccc(NC(=O)N3CCN(C(=O)C(C)(C)N)CC3)nc2=O)cc1)[C@H]1CC[C@H](N)C1] |
| 165 | 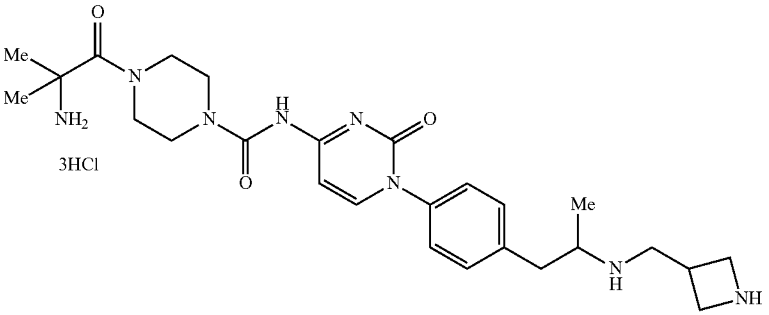 [SMILES: CC(Cc1ccc(-n2ccc(NC(=O)N3CCN(C(=O)C(C)(C)N)CC3)nc2=O)cc1)NCC1CNC1] 3HCl | 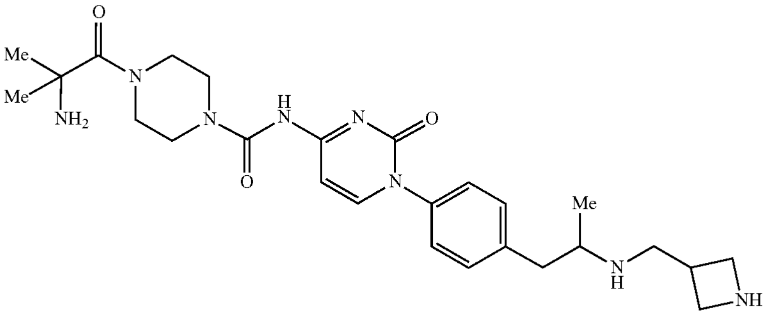 [SMILES: CC(Cc1ccc(-n2ccc(NC(=O)N3CCN(C(=O)C(C)(C)N)CC3)nc2=O)cc1)NCC1CNC1] |

TABLE 10-continued
Compounds of Formula I
| No. | Salt Structure | Free Base Structure |
|---|---|---|
| 166 | 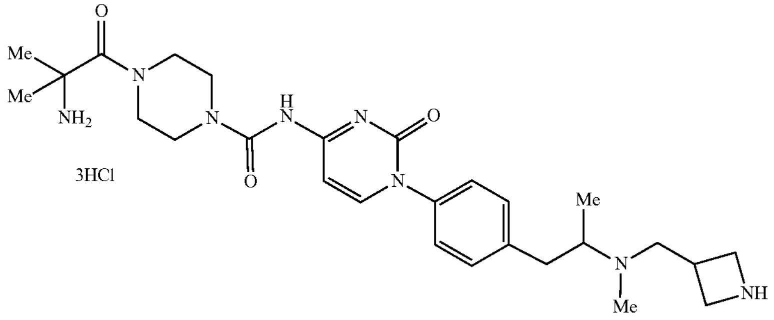 [SMILES: CC(Cc1ccc(-n2ccc(NC(=O)N3CCN(C(=O)C(C)(C)N)CC3)nc2=O)cc1)N(C)CC1CNC1] 3HCl | 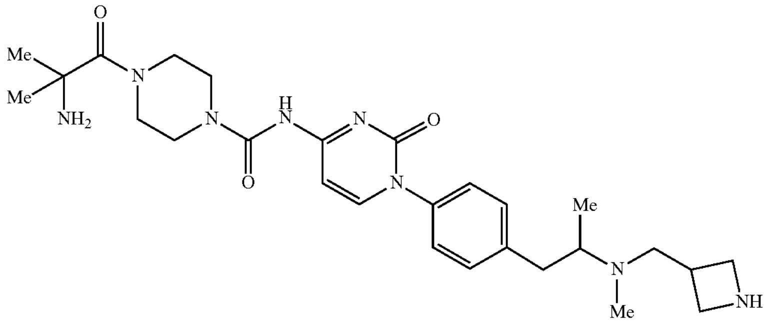 [SMILES: CC(Cc1ccc(-n2ccc(NC(=O)N3CCN(C(=O)C(C)(C)N)CC3)nc2=O)cc1)N(C)CC1CNC1] |
| 167 | 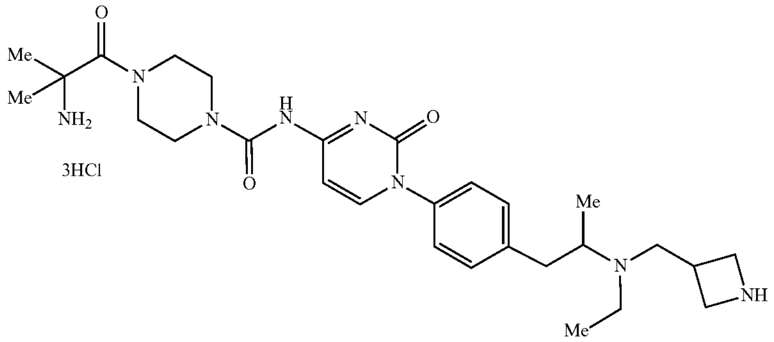 [SMILES: CCN(CC1CNC1)C(C)Cc1ccc(-n2ccc(NC(=O)N3CCN(C(=O)C(C)(C)N)CC3)nc2=O)cc1] 3HCl | 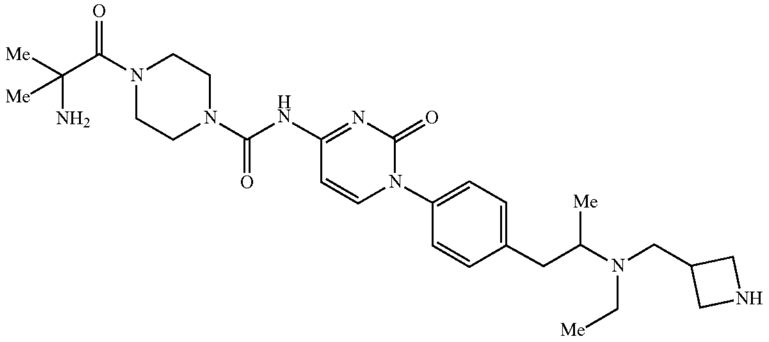 [SMILES: CCN(CC1CNC1)C(C)Cc1ccc(-n2ccc(NC(=O)N3CCN(C(=O)C(C)(C)N)CC3)nc2=O)cc1] |

TABLE 10-continued
Compounds of Formula I
| No. | Salt Structure | Free Base Structure |
|---|---|---|
| 168 | 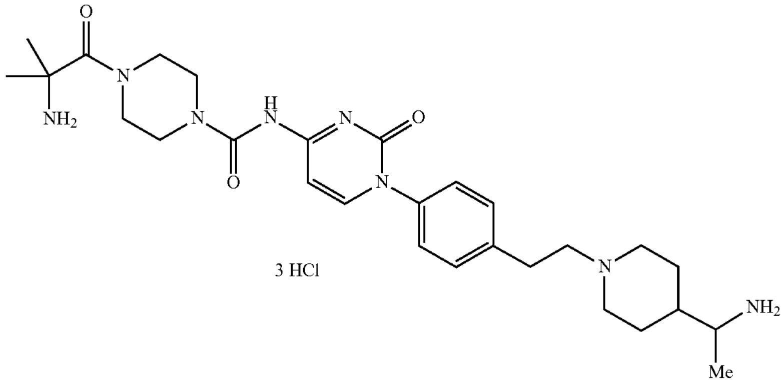 [SMILES: CC(N)C1CCN(CCc2ccc(-n3ccc(NC(=O)N4CCN(C(=O)C(C)(C)N)CC4)nc3=O)cc2)CC1] 3 HCl | 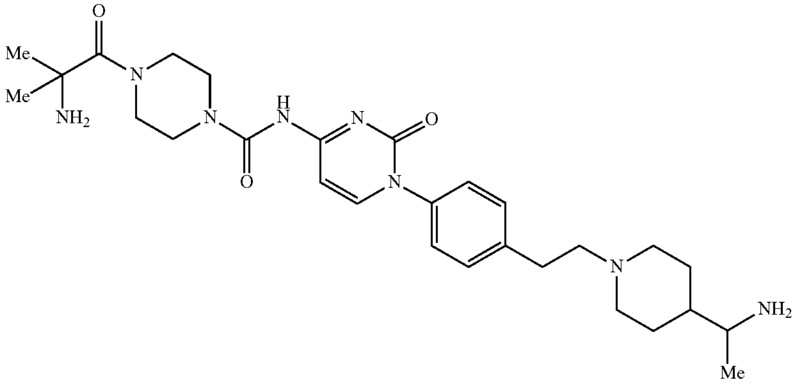 [SMILES: CC(N)C1CCN(CCc2ccc(-n3ccc(NC(=O)N4CCN(C(=O)C(C)(C)N)CC4)nc3=O)cc2)CC1] |
| 169 | 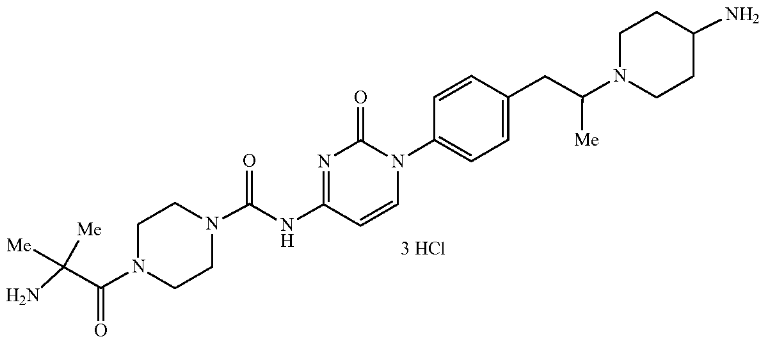 [SMILES: CC(Cc1ccc(-n2ccc(NC(=O)N3CCN(C(=O)C(C)(C)N)CC3)nc2=O)cc1)N1CCC(N)CC1] 3 HCl | 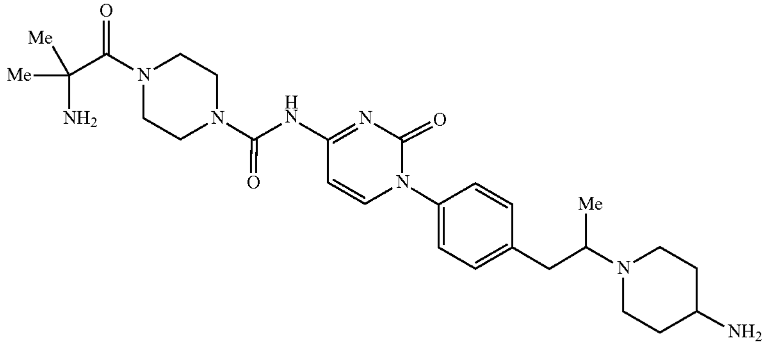 |

TABLE 10-continued
| Compounds of Formula I | | |
|---|---|---|
| No. | Salt Structure | Free Base Structure |
| 170 | 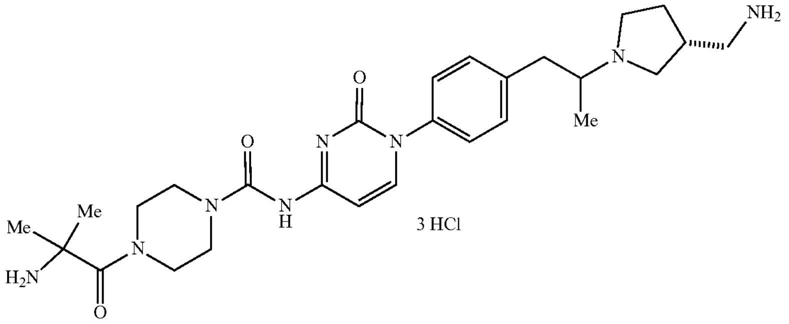 [SMILES: CC(Cc1ccc(-n2ccc(NC(=O)N3CCN(C(=O)C(C)(C)N)CC3)nc2=O)cc1)N1CC[C@H](CN)C1] 3 HCl | 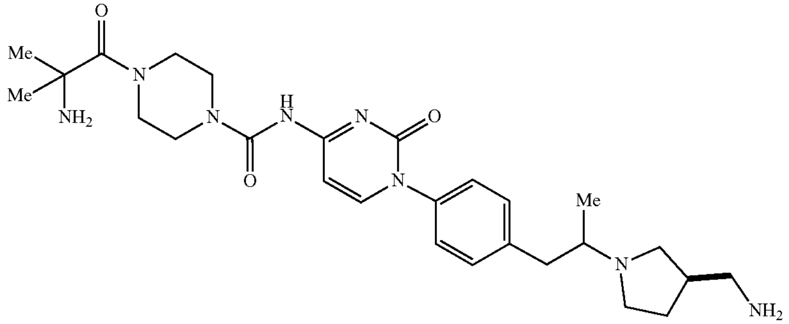 |
| 171 | 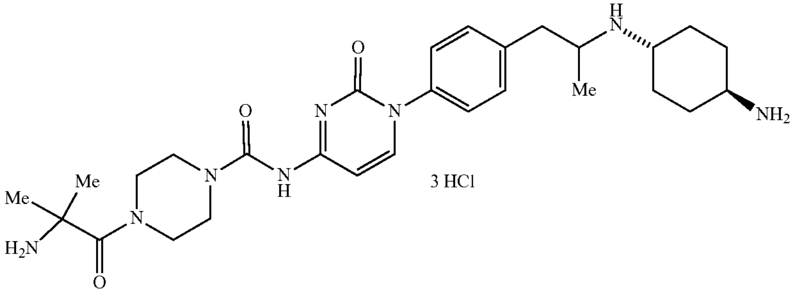 [SMILES: CC(Cc1ccc(-n2ccc(NC(=O)N3CCN(C(=O)C(C)(C)N)CC3)nc2=O)cc1)N[C@H]1CC[C@H](N)CC1] 3 HCl | 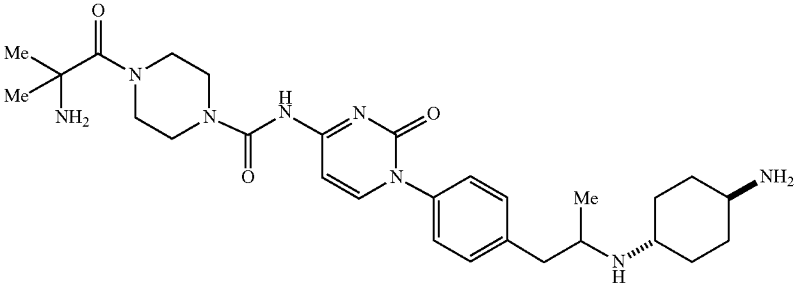 [SMILES: CC(Cc1ccc(-n2ccc(NC(=O)N3CCN(C(=O)C(C)(C)N)CC3)nc2=O)cc1)N[C@H]1CC[C@H](N)CC1] |
| 172 | 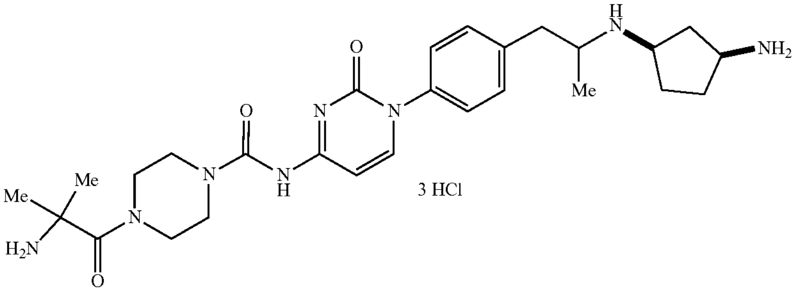 [SMILES: CC(Cc1ccc(-n2ccc(NC(=O)N3CCN(C(=O)C(C)(C)N)CC3)nc2=O)cc1)N[C@@H]1CC[C@H](N)C1] 3 HCl | 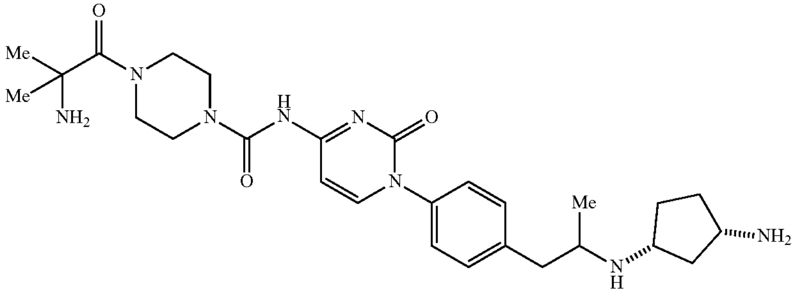 [SMILES: CC(Cc1ccc(-n2ccc(NC(=O)N3CCN(C(=O)C(C)(C)N)CC3)nc2=O)cc1)N[C@@H]1CC[C@H](N)C1] |

TABLE 10-continued
Compounds of Formula I
| No. | Salt Structure | Free Base Structure |
|---|---|---|
| 173 | 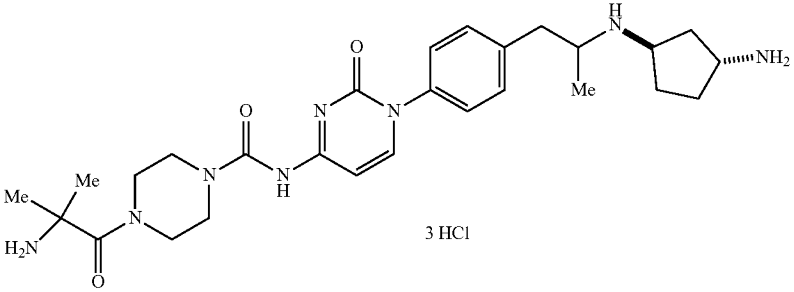 [SMILES: CC(Cc1ccc(-n2ccc(NC(=O)N3CCN(C(=O)C(C)(C)N)CC3)nc2=O)cc1)N[C@@H]1CC[C@@H](N)C1] 3 HCl | 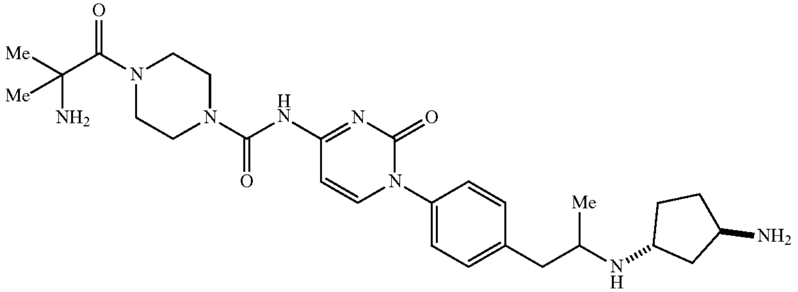 [SMILES: CC(Cc1ccc(-n2ccc(NC(=O)N3CCN(C(=O)C(C)(C)N)CC3)nc2=O)cc1)N[C@@H]1CC[C@@H](N)C1] |
| 174 | 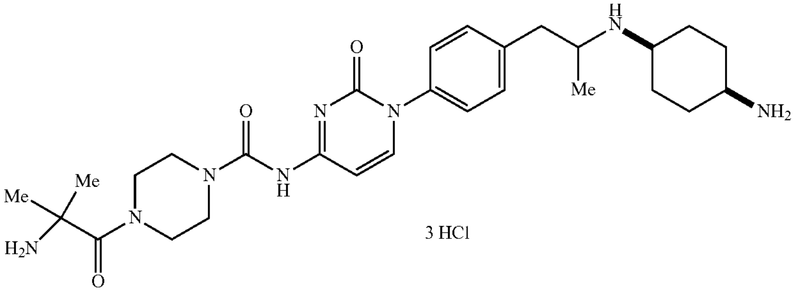 [SMILES: CC(Cc1ccc(-n2ccc(NC(=O)N3CCN(C(=O)C(C)(C)N)CC3)nc2=O)cc1)N[C@H]1CC[C@@H](N)CC1] 3 HCl | 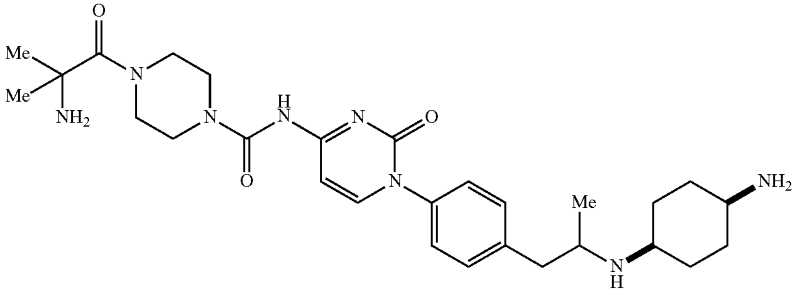 [SMILES: CC(Cc1ccc(-n2ccc(NC(=O)N3CCN(C(=O)C(C)(C)N)CC3)nc2=O)cc1)N[C@H]1CC[C@@H](N)CC1] |
| 175 | 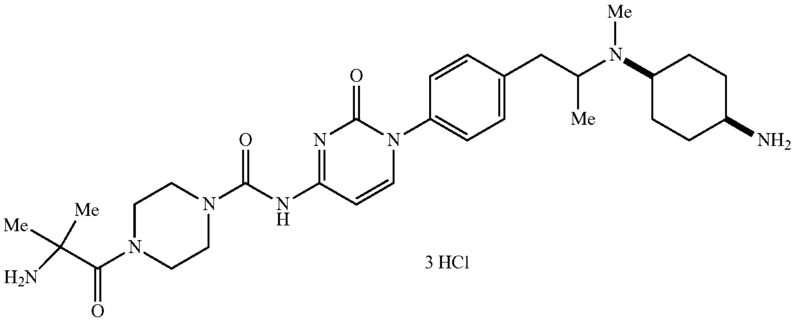 [SMILES: CC(Cc1ccc(-n2ccc(NC(=O)N3CCN(C(=O)C(C)(C)N)CC3)nc2=O)cc1)N(C)[C@H]1CC[C@@H](N)CC1] 3 HCl | 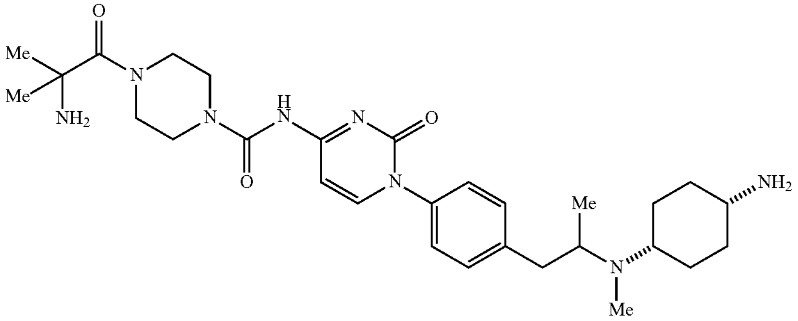 |

TABLE 10-continued
Compounds of Formula I
| No. | Salt Structure | Free Base Structure |
| --- | --- | --- |
| 176 | 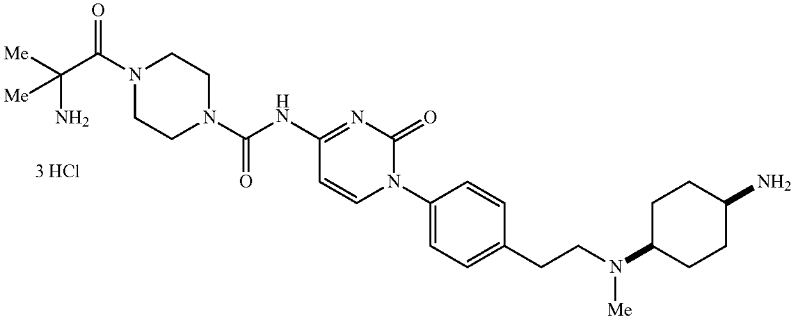 [SMILES: CN(CCc1ccc(-n2ccc(NC(=O)N3CCN(C(=O)C(C)(C)N)CC3)nc2=O)cc1)[C@H]1CC[C@@H](N)CC1] 3 HCl | 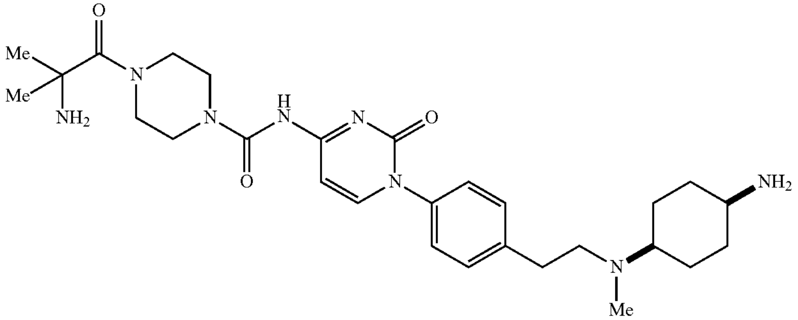 [SMILES: CN(CCc1ccc(-n2ccc(NC(=O)N3CCN(C(=O)C(C)(C)N)CC3)nc2=O)cc1)[C@H]1CC[C@@H](N)CC1] |
| 177 | 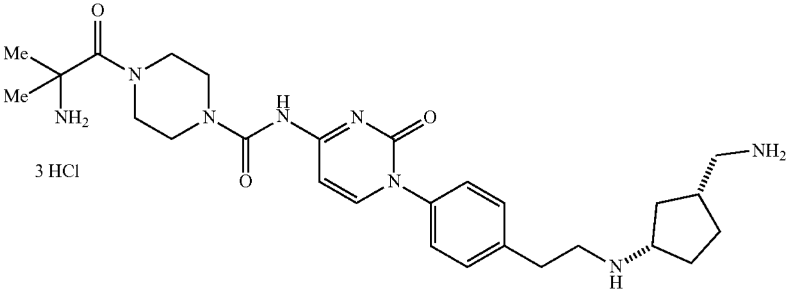 [SMILES: CC(C)(N)C(=O)N1CCN(C(=O)Nc2ccn(-c3ccc(CCN[C@H]4CC[C@@H](CN)C4)cc3)c(=O)n2)CC1] 3 HCl | 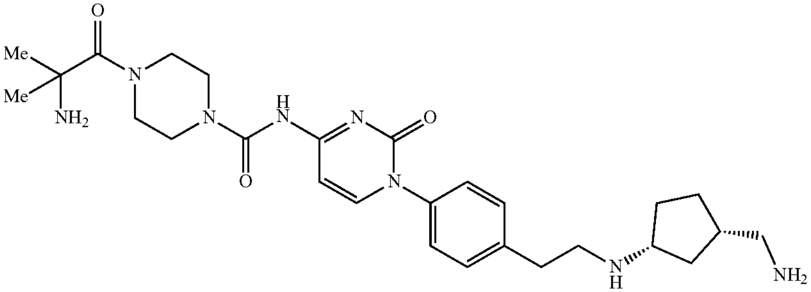 [SMILES: CC(C)(N)C(=O)N1CCN(C(=O)Nc2ccn(-c3ccc(CCN[C@@H]4CC[C@H](CN)C4)cc3)c(=O)n2)CC1] |
| 178 | 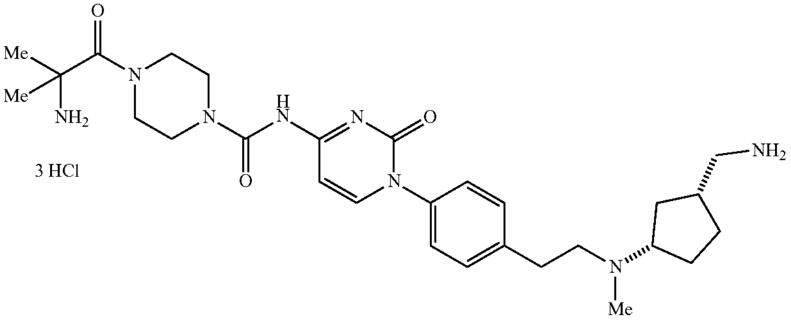 [SMILES: CN(CCc1ccc(-n2ccc(NC(=O)N3CCN(C(=O)C(C)(C)N)CC3)nc2=O)cc1)[C@H]1CC[C@@H](CN)C1] 3 HCl | 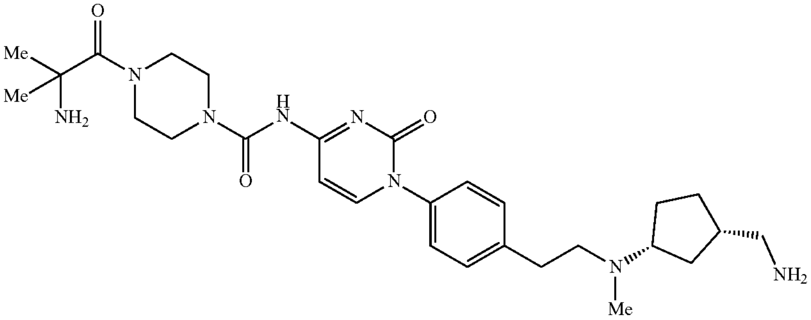 [SMILES: CN(CCc1ccc(-n2ccc(NC(=O)N3CCN(C(=O)C(C)(C)N)CC3)nc2=O)cc1)[C@@H]1CC[C@H](CN)C1] |

TABLE 10-continued
Compounds of Formula I
| No. | Salt Structure | Free Base Structure |
|---|---|---|
| 179 | 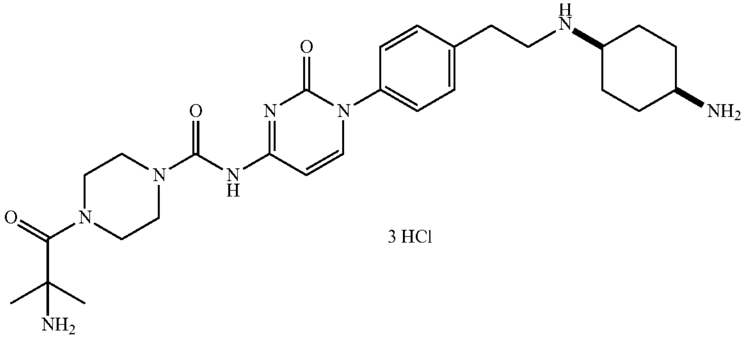 [SMILES: CC(C)(N)C(=O)N1CCN(C(=O)Nc2ccn(-c3ccc(CCN[C@H]4CC[C@@H](N)CC4)cc3)c(=O)n2)CC1] 3 HCl | 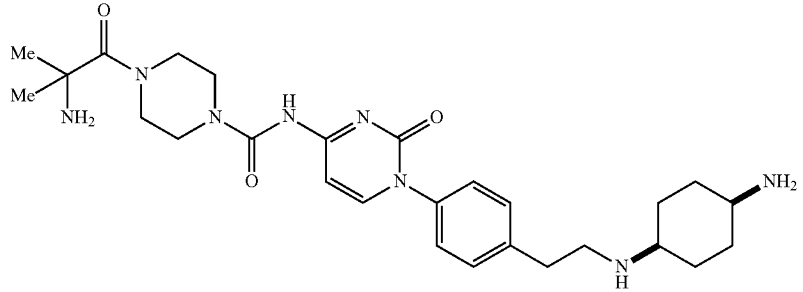 [SMILES: CC(C)(N)C(=O)N1CCN(C(=O)Nc2ccn(-c3ccc(CCN[C@H]4CC[C@@H](N)CC4)cc3)c(=O)n2)CC1] |
| 180 | 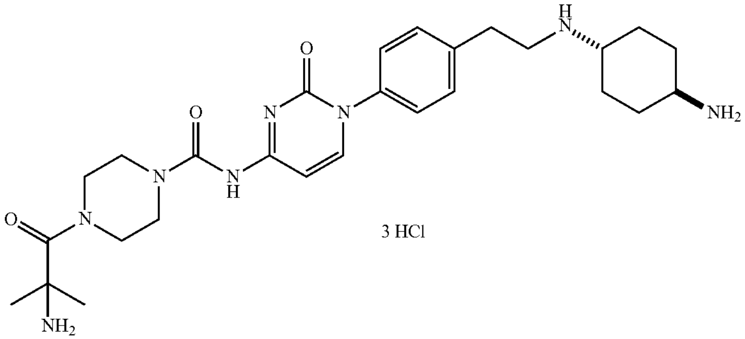 [SMILES: CC(C)(N)C(=O)N1CCN(C(=O)Nc2ccn(-c3ccc(CCN[C@H]4CC[C@H](N)CC4)cc3)c(=O)n2)CC1] 3 HCl | 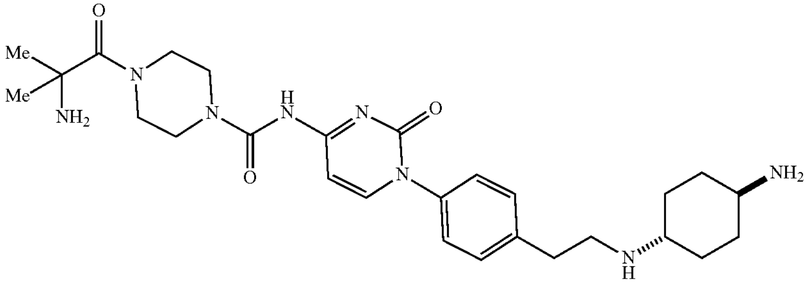 |
| 181 | 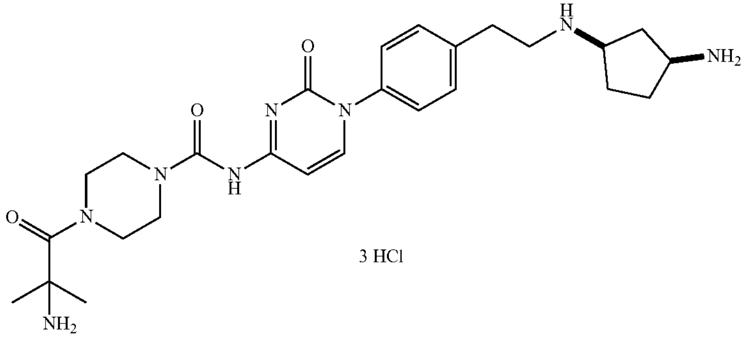 [SMILES: CC(C)(N)C(=O)N1CCN(C(=O)Nc2ccn(-c3ccc(CCN[C@@H]4CC[C@H](N)C4)cc3)c(=O)n2)CC1] 3 HCl | 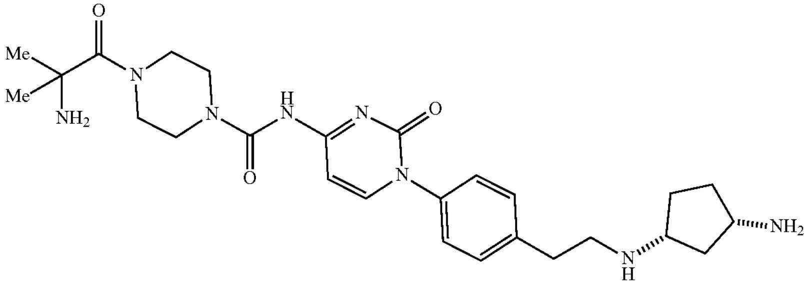 [SMILES: CC(C)(N)C(=O)N1CCN(C(=O)Nc2ccn(-c3ccc(CCN[C@@H]4CC[C@H](N)C4)cc3)c(=O)n2)CC1] |

TABLE 10-continued
| Compounds of Formula I | | |
|---|---|---|
| No. | Salt Structure | Free Base Structure |
| 182 | 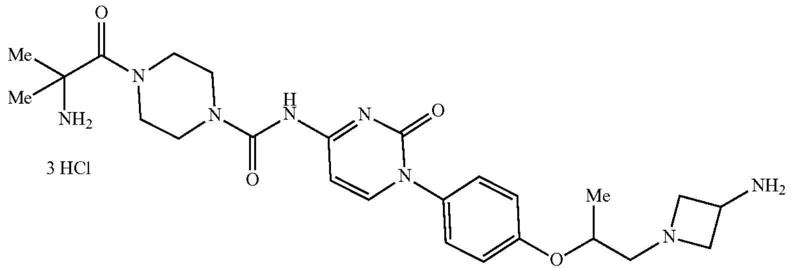 [SMILES: CC(CN1CC(N)C1)Oc1ccc(-n2ccc(NC(=O)N3CCN(C(=O)C(C)(C)N)CC3)nc2=O)cc1] 3 HCl | 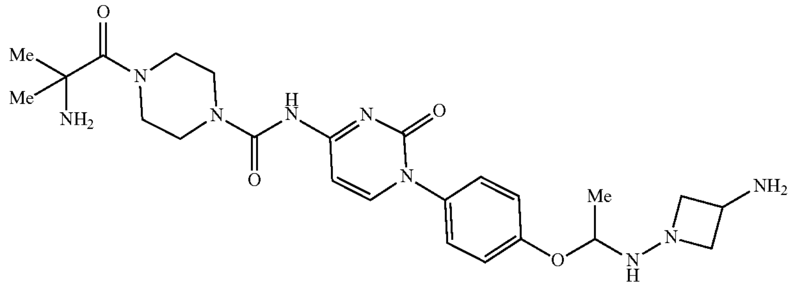 [SMILES: CC(NN1CC(N)C1)Oc1ccc(-n2ccc(NC(=O)N3CCN(C(=O)C(C)(C)N)CC3)nc2=O)cc1] |
| 183 | 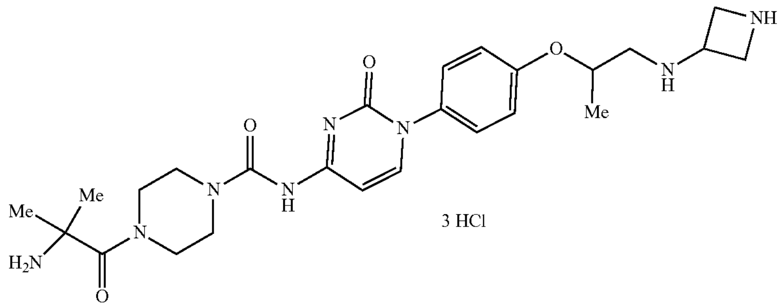 [SMILES: CC(CNC1CNC1)Oc1ccc(-n2ccc(NC(=O)N3CCN(C(=O)C(C)(C)N)CC3)nc2=O)cc1] 3 HCl | 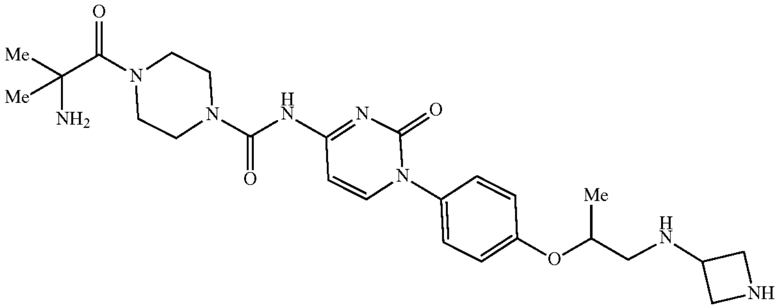 [SMILES: CC(CNC1CNC1)Oc1ccc(-n2ccc(NC(=O)N3CCN(C(=O)C(C)(C)N)CC3)nc2=O)cc1] |
| 184 | 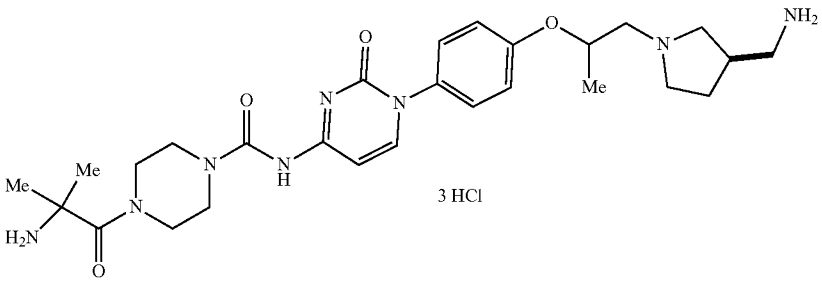 [SMILES: CC(CN1CC[C@H](CN)C1)Oc1ccc(-n2ccc(NC(=O)N3CCN(C(=O)C(C)(C)N)CC3)nc2=O)cc1] 3 HCl | 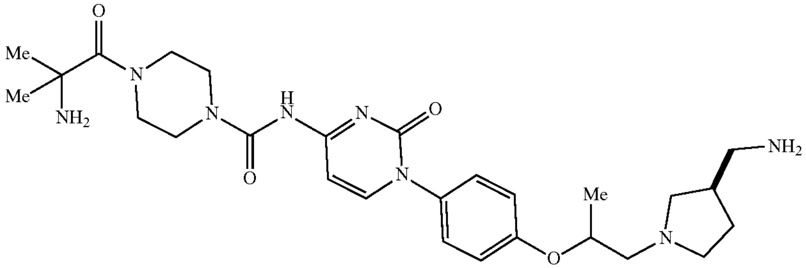 [SMILES: CC(CN1CC[C@H](CN)C1)Oc1ccc(-n2ccc(NC(=O)N3CCN(C(=O)C(C)(C)N)CC3)nc2=O)cc1] |

TABLE 10-continued
| Compounds of Formula I | | |
|---|---|---|
| No. | Salt Structure | Free Base Structure |
| 185 | 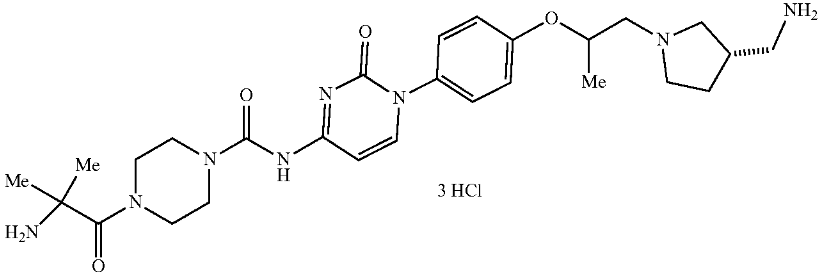 [SMILES: CC(CN1CC[C@@H](CN)C1)Oc1ccc(-n2ccc(NC(=O)N3CCN(C(=O)C(C)(C)N)CC3)nc2=O)cc1] 3 HCl | 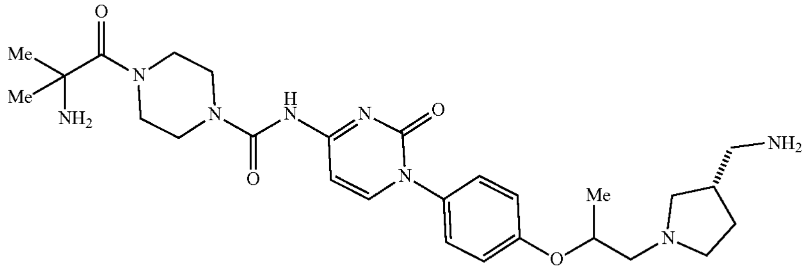 [SMILES: CC(CN1CC[C@@H](CN)C1)Oc1ccc(-n2ccc(NC(=O)N3CCN(C(=O)C(C)(C)N)CC3)nc2=O)cc1] |
| 186 | 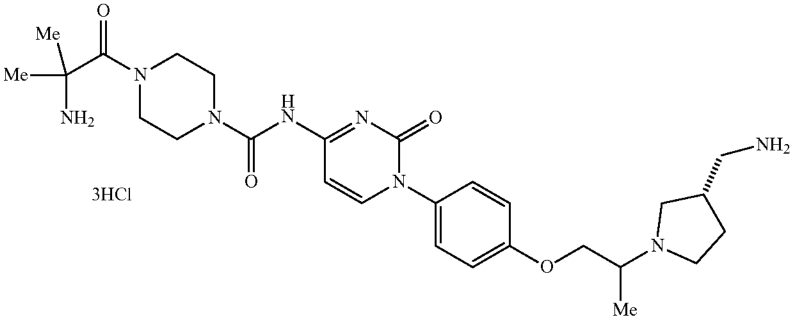 [SMILES: CC(COc1ccc(-n2ccc(NC(=O)N3CCN(C(=O)C(C)(C)N)CC3)nc2=O)cc1)N1CC[C@@H](CN)C1] 3HCl | 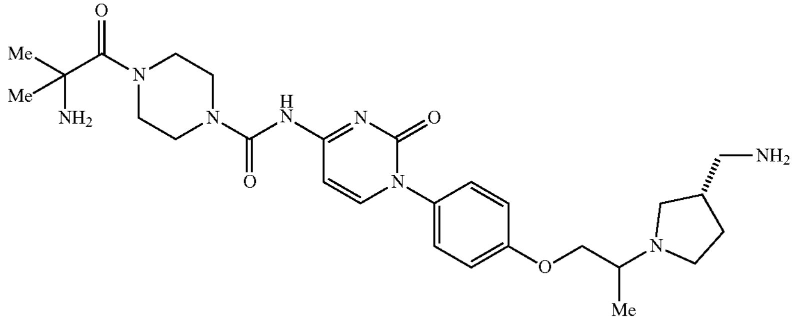 [SMILES: CC(COc1ccc(-n2ccc(NC(=O)N3CCN(C(=O)C(C)(C)N)CC3)nc2=O)cc1)N1CC[C@@H](CN)C1] |
| 187 | 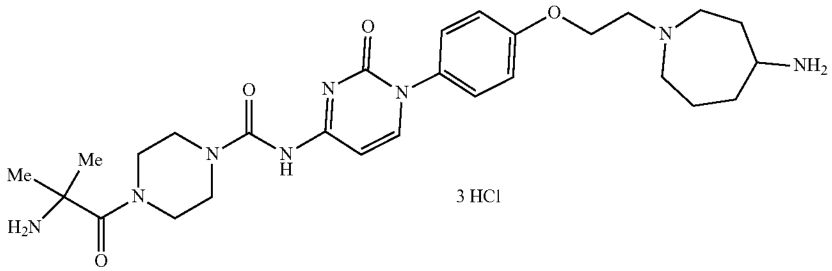 [SMILES: CC(C)(N)C(=O)N1CCN(C(=O)Nc2ccn(-c3ccc(OCCN4CCCC(N)CC4)cc3)c(=O)n2)CC1] 3 HCl | 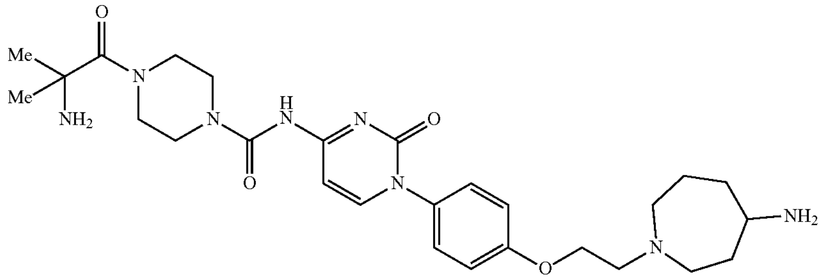 [SMILES: CC(C)(N)C(=O)N1CCN(C(=O)Nc2ccn(-c3ccc(OCCN4CCCC(N)CC4)cc3)c(=O)n2)CC1] |

TABLE 10-continued
| Compounds of Formula I | | |
|---|---|---|
| No. | Salt Structure | Free Base Structure |
| 188 | 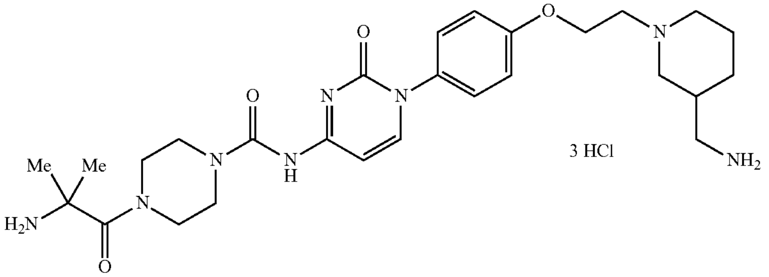 [SMILES: CC(C)(N)C(=O)N1CCN(C(=O)Nc2ccn(-c3ccc(OCCN4CCCC(CN)C4)cc3)c(=O)n2)CC1] 3 HCl | 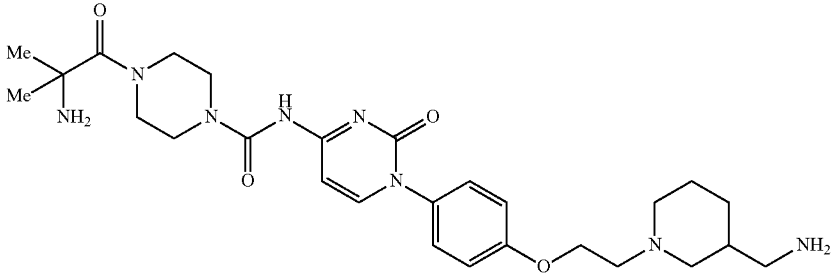 [SMILES: CC(C)(N)C(=O)N1CCN(C(=O)Nc2ccn(-c3ccc(OCCN4CCCC(CN)C4)cc3)c(=O)n2)CC1] |
| 190 | 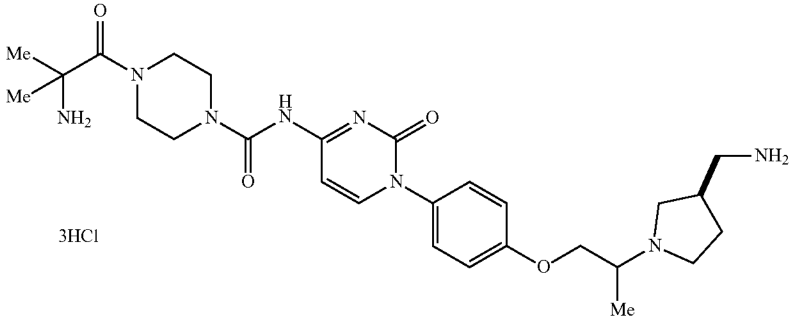 [SMILES: CC(COc1ccc(-n2ccc(NC(=O)N3CCN(C(=O)C(C)(C)N)CC3)nc2=O)cc1)N1CC[C@H](CN)C1] 3HCl | 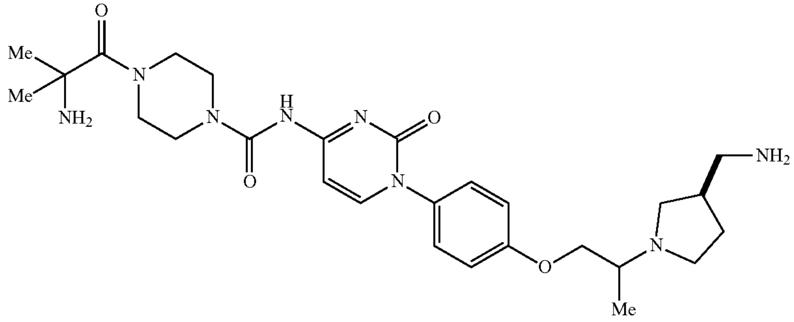 [SMILES: CC(COc1ccc(-n2ccc(NC(=O)N3CCN(C(=O)C(C)(C)N)CC3)nc2=O)cc1)N1CC[C@H](CN)C1] |
| 191 | 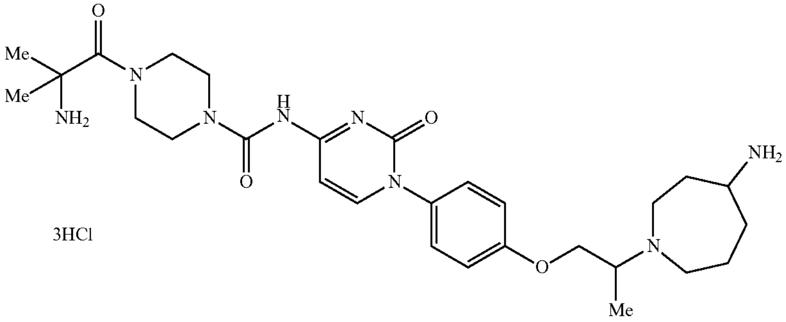 [SMILES: CC(COc1ccc(-n2ccc(NC(=O)N3CCN(C(=O)C(C)(C)N)CC3)nc2=O)cc1)N1CCCC(N)CC1] 3HCl | 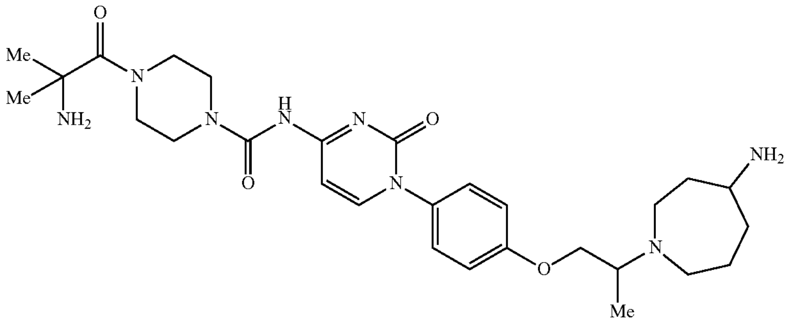 [SMILES: CC(COc1ccc(-n2ccc(NC(=O)N3CCN(C(=O)C(C)(C)N)CC3)nc2=O)cc1)N1CCCC(N)CC1] |

TABLE 10-continued
| Compounds of Formula I | | |
|---|---|---|
| No. | Salt Structure | Free Base Structure |
| 192 | 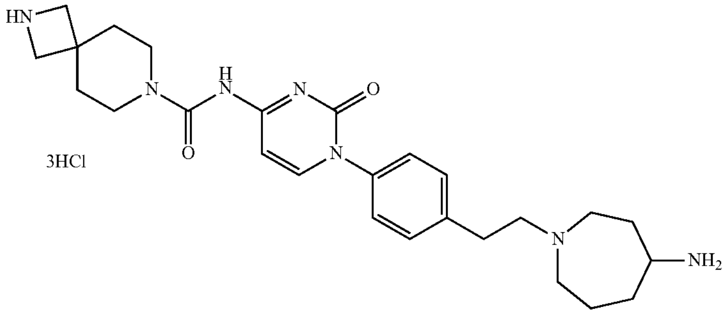 [SMILES: NC1CCCN(CCc2ccc(-n3ccc(NC(=O)N4CCC5(CC4)CNC5)nc3=O)cc2)CC1] 3HCl | 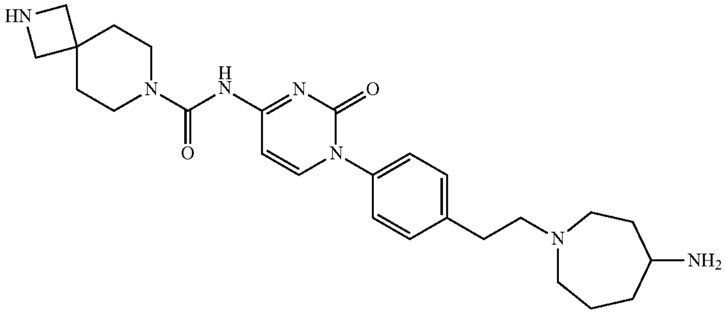 [SMILES: NC1CCCN(CCc2ccc(-n3ccc(NC(=O)N4CCC5(CC4)CNC5)nc3=O)cc2)CC1] |
| 193 | 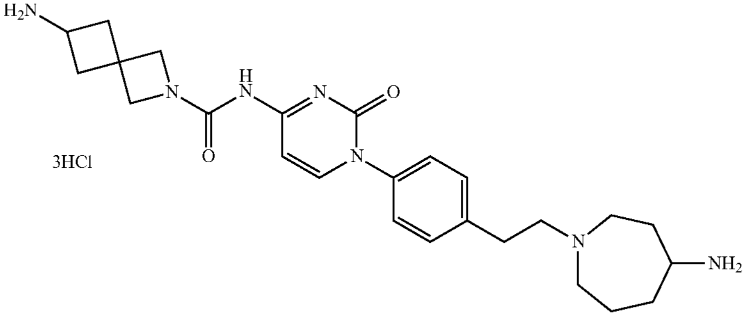 [SMILES: NC1CCCN(CCc2ccc(-n3ccc(NC(=O)N4CC5(CC(N)C5)C4)nc3=O)cc2)CC1] 3HCl | 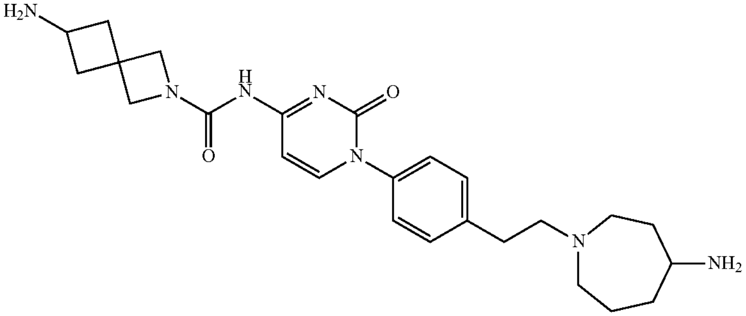 [SMILES: NC1CCCN(CCc2ccc(-n3ccc(NC(=O)N4CC5(CC(N)C5)C4)nc3=O)cc2)CC1] |
| 194 | 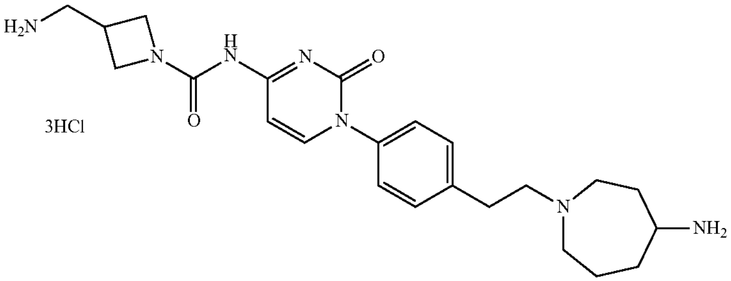 [SMILES: NCC1CN(C(=O)Nc2ccn(-c3ccc(CCN4CCCC(N)CC4)cc3)c(=O)n2)C1] 3HCl | 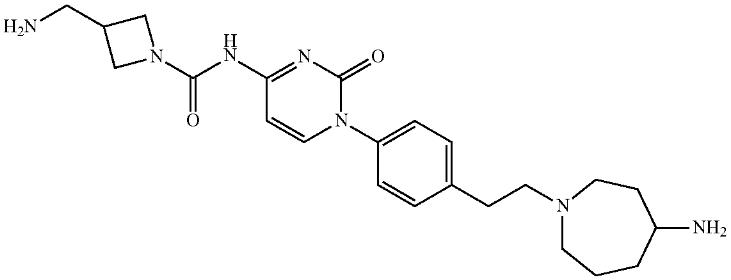 [SMILES: NCC1CN(C(=O)Nc2ccn(-c3ccc(CCN4CCCC(N)CC4)cc3)c(=O)n2)C1] |

TABLE 10-continued
| Compounds of Formula I | | |
|---|---|---|
| No. | Salt Structure | Free Base Structure |
| 195 | 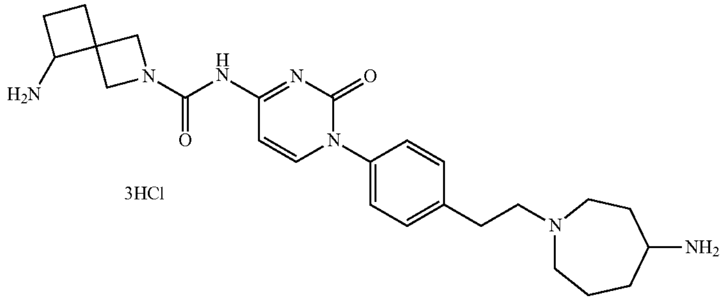 [SMILES: NC1CCCN(CCc2ccc(-n3ccc(NC(=O)N4CC5(CCC5N)C4)nc3=O)cc2)CC1] 3HCl | 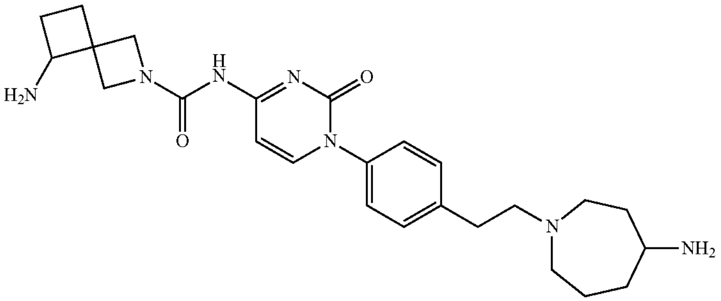 [SMILES: NC1CCCN(CCc2ccc(-n3ccc(NC(=O)N4CC5(CCC5N)C4)nc3=O)cc2)CC1] |
| 196 | 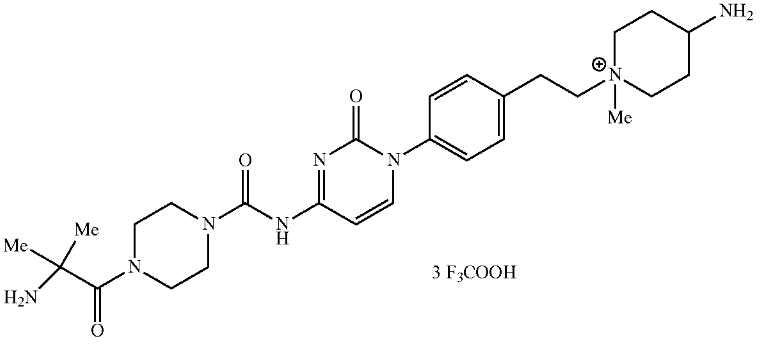 [SMILES: CC(C)(N)C(=O)N1CCN(C(=O)Nc2ccn(-c3ccc(CC[N+]4(C)CCC(N)CC4)cc3)c(=O)n2)CC1] 3 $F_3COOH$ | 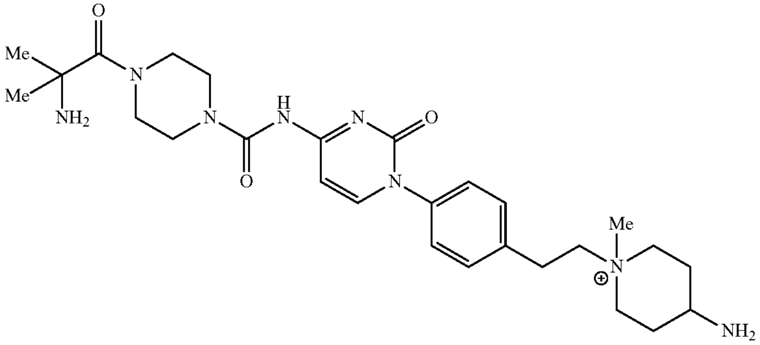 [SMILES: CC(C)(N)C(=O)N1CCN(C(=O)Nc2ccn(-c3ccc(CC[N+]4(C)CCC(N)CC4)cc3)c(=O)n2)CC1] |
| 197 | 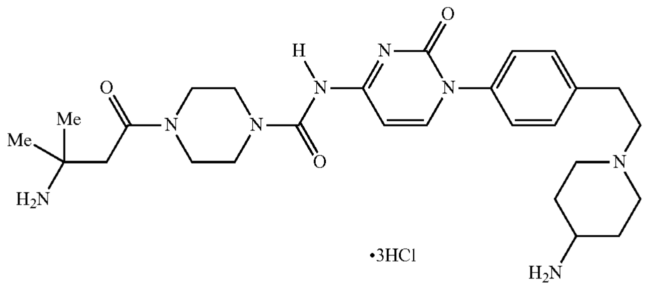 •3HCl | 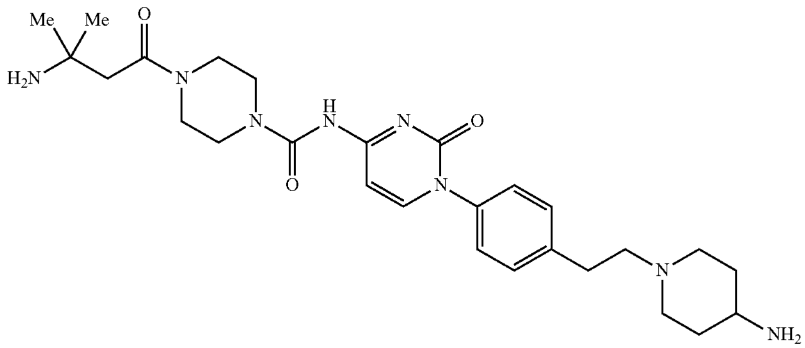 [SMILES: CC(C)(N)CC(=O)N1CCN(C(=O)Nc2ccn(-c3ccc(CCN4CCC(N)CC4)cc3)c(=O)n2)CC1] |

TABLE 10-continued
| Compounds of Formula I | | |
|---|---|---|
| No. | Salt Structure | Free Base Structure |
| 198 | 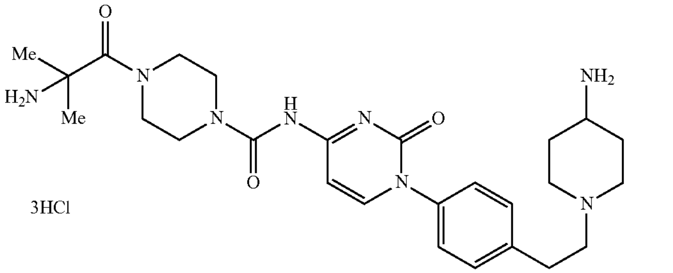 [SMILES: CC(C)(N)C(=O)N1CCN(C(=O)Nc2ccn(-c3ccc(CCN4CCC(N)CC4)cc3)c(=O)n2)CC1] 3HCl | 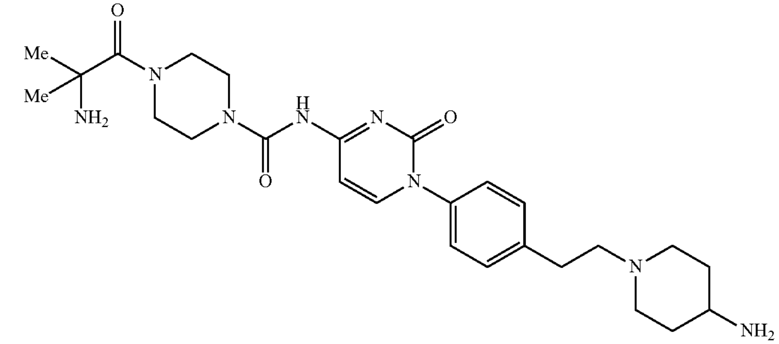 [SMILES: CC(C)(N)C(=O)N1CCN(C(=O)Nc2ccn(-c3ccc(CCN4CCC(N)CC4)cc3)c(=O)n2)CC1] |
| 199 | 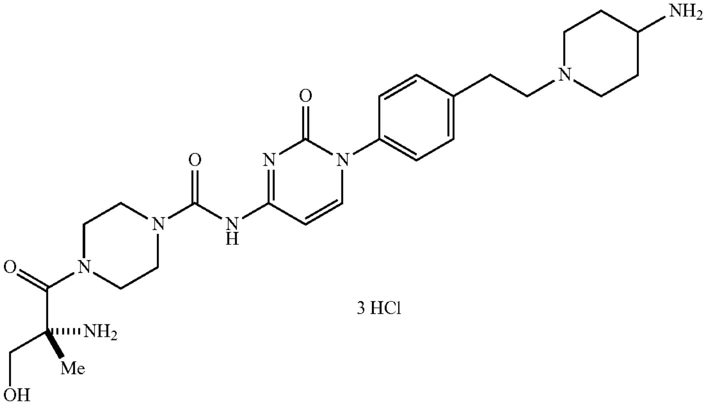 [SMILES: C[C@@](N)(CO)C(=O)N1CCN(C(=O)Nc2ccn(-c3ccc(CCN4CCC(N)CC4)cc3)c(=O)n2)CC1] 3 HCl | 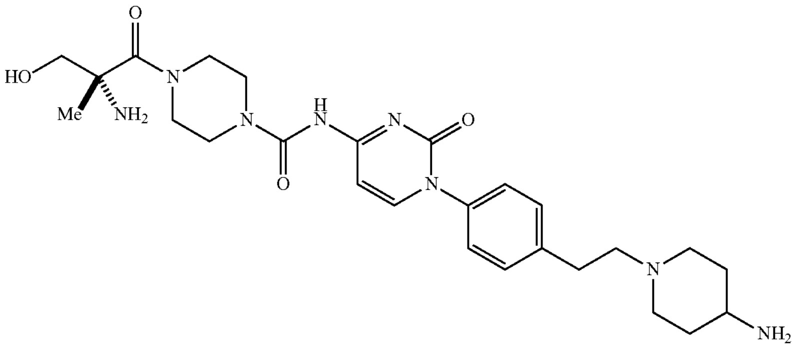 |

TABLE 10-continued
| Compounds of Formula I | | |
|---|---|---|
| No. | Salt Structure | Free Base Structure |
| 200 | 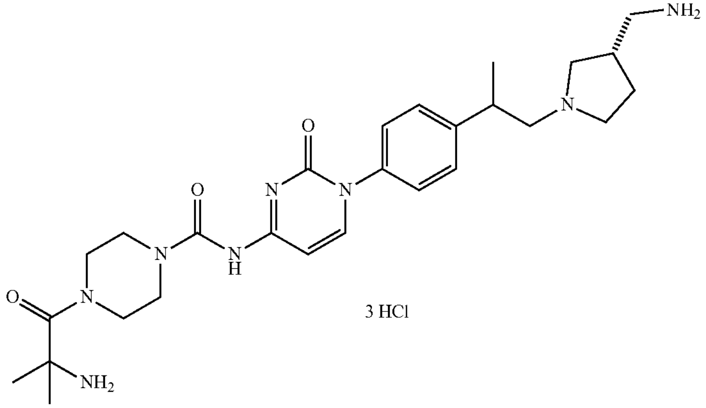 [SMILES: CC(CN1CC[C@@H](CN)C1)c1ccc(-n2ccc(NC(=O)N3CCN(C(=O)C(C)(C)N)CC3)nc2=O)cc1] 3 HCl | 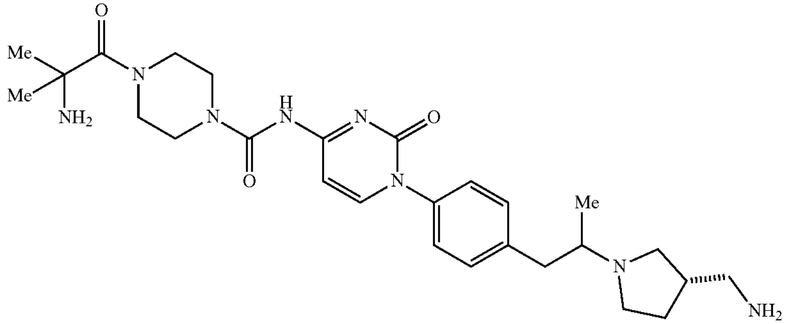 [SMILES: CC(Cc1ccc(-n2ccc(NC(=O)N3CCN(C(=O)C(C)(C)N)CC3)nc2=O)cc1)N1CC[C@@H](CN)C1] |
| 201 | 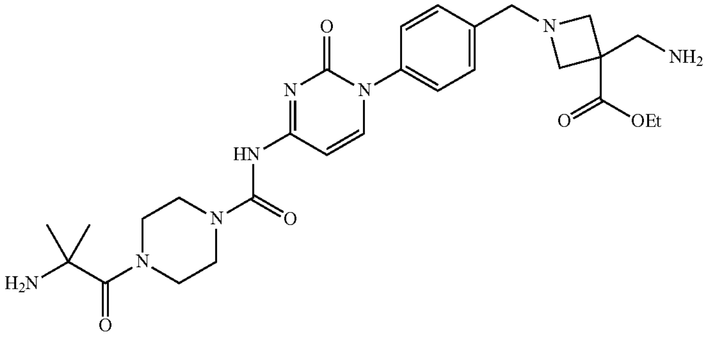 [SMILES: CCOC(=O)C1(CN)CN(Cc2ccc(-n3ccc(NC(=O)N4CCN(C(=O)C(C)(C)N)CC4)nc3=O)cc2)C1] | 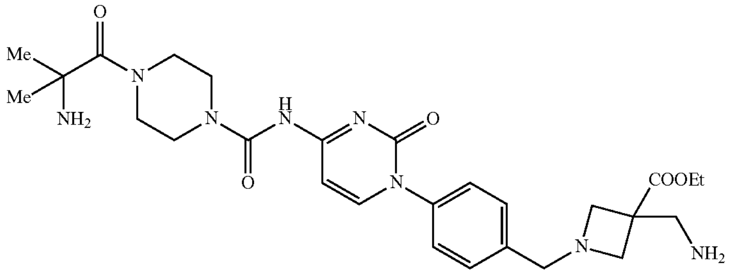 [SMILES: CCOC(=O)C1(CN)CN(Cc2ccc(-n3ccc(NC(=O)N4CCN(C(=O)C(C)(C)N)CC4)nc3=O)cc2)C1] |

TABLE 10-continued
Compounds of Formula I
| No. | Salt Structure | Free Base Structure |
|---|---|---|
| 204 | 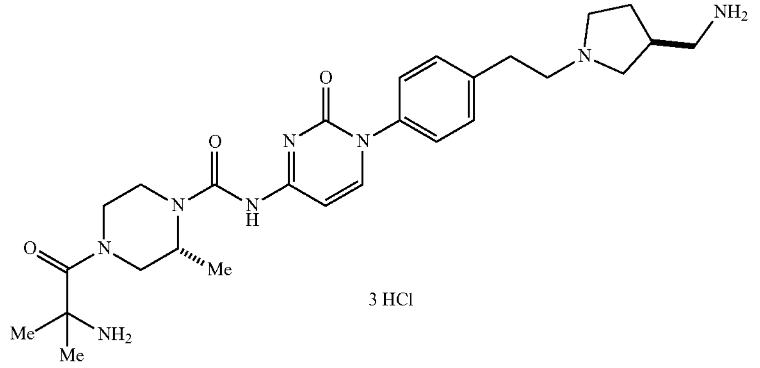 [SMILES: C[C@@H]1CN(C(=O)C(C)(C)N)CCN1C(=O)Nc1ccn(-c2ccc(CCN3CC[C@@H](CN)C3)cc2)c(=O)n1] 3 HCl | 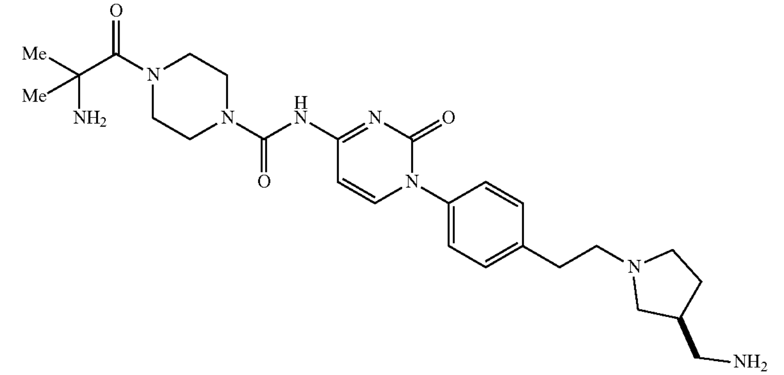 [SMILES: CC(C)(N)C(=O)N1CCN(C(=O)Nc2ccn(-c3ccc(CCN4CC[C@@H](CN)C4)cc3)c(=O)n2)CC1] |
| 205 | 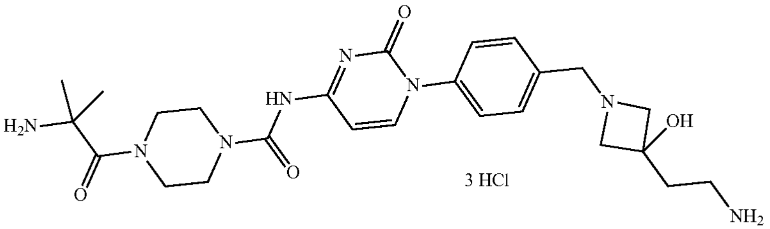 [SMILES: CC(C)(N)C(=O)N1CCN(C(=O)Nc2ccn(-c3ccc(CN4CC(O)(CCN)C4)cc3)c(=O)n2)CC1] 3 HCl | 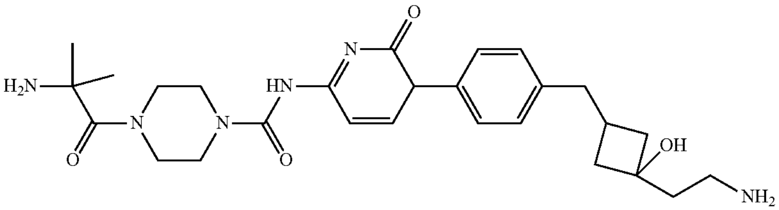 [SMILES: CC(C)(N)C(=O)N1CCN(C(=O)NC2=NC(=O)C(c3ccc(CC4CC(O)(CCN)C4)cc3)C=C2)CC1] |
| 206 | 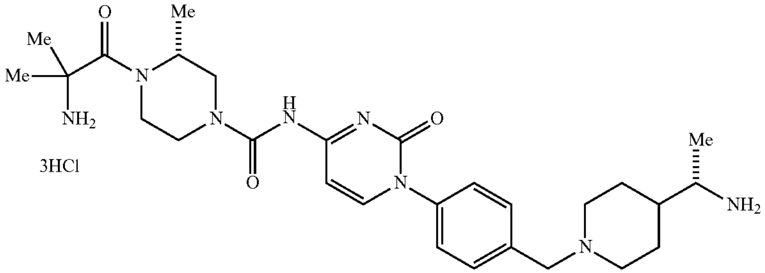 [SMILES: C[C@H](N)C1CCN(Cc2ccc(-n3ccc(NC(=O)N4CCN(C(=O)C(C)(C)N)[C@H](C)C4)nc3=O)cc2)CC1] 3HCl | 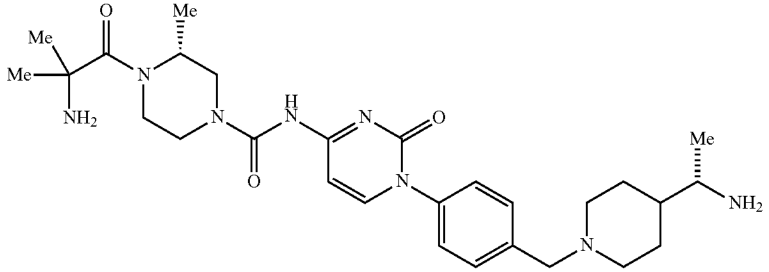 [SMILES: C[C@H](N)C1CCN(Cc2ccc(-n3ccc(NC(=O)N4CCN(C(=O)C(C)(C)N)[C@H](C)C4)nc3=O)cc2)CC1] |

TABLE 10-continued
| Compounds of Formula I | | |
|---|---|---|
| No. | Salt Structure | Free Base Structure |
| 207 | 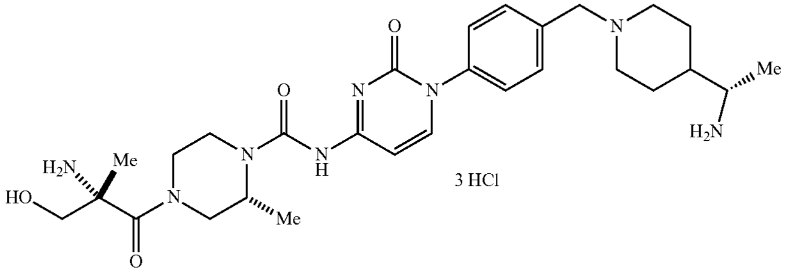 [SMILES: C[C@H](N)C1CCN(Cc2ccc(-n3ccc(NC(=O)N4CCN(C(=O)[C@@](C)(N)CO)C[C@H]4C)nc3=O)cc2)CC1] 3 HCl | 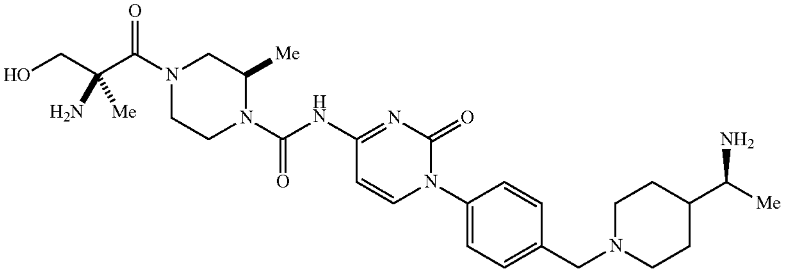 [SMILES: C[C@H](N)C1CCN(Cc2ccc(-n3ccc(NC(=O)N4CCN(C(=O)[C@@](C)(N)CO)C[C@H]4C)nc3=O)cc2)CC1] |
| 208 | 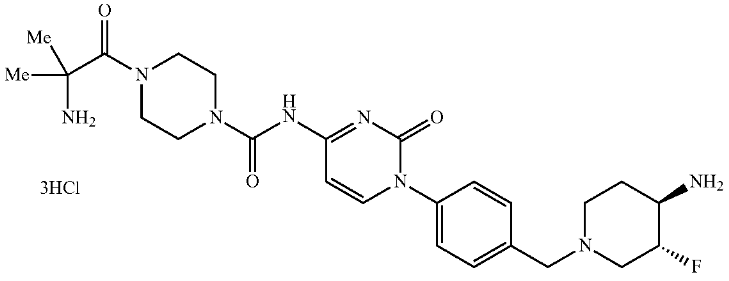 [SMILES: CC(C)(N)C(=O)N1CCN(C(=O)Nc2ccn(-c3ccc(CN4CC[C@@H](N)[C@H](F)C4)cc3)c(=O)n2)CC1] 3HCl | 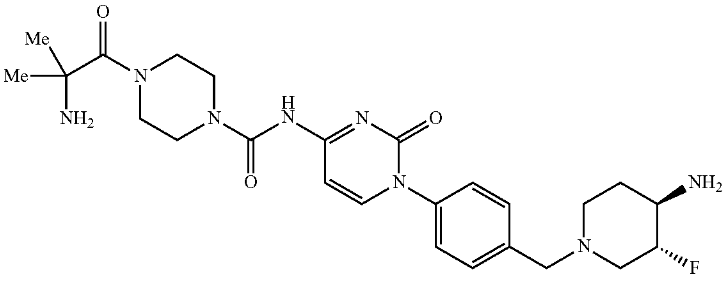 [SMILES: CC(C)(N)C(=O)N1CCN(C(=O)Nc2ccn(-c3ccc(CN4CC[C@@H](N)[C@H](F)C4)cc3)c(=O)n2)CC1] |
| 209 | 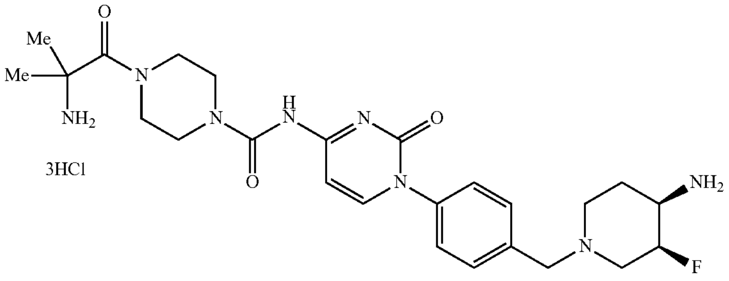 [SMILES: CC(C)(N)C(=O)N1CCN(C(=O)Nc2ccn(-c3ccc(CN4CC[C@@H](N)[C@@H](F)C4)cc3)c(=O)n2)CC1] 3HCl | 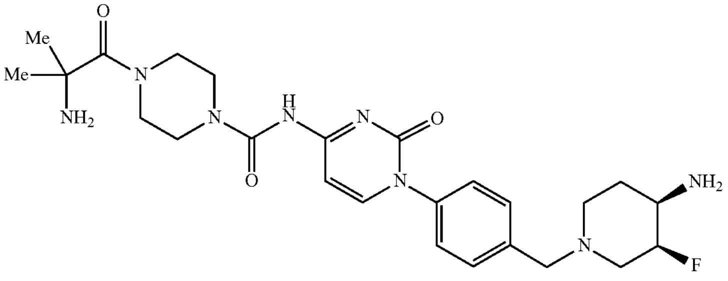 |

TABLE 10-continued
| Compounds of Formula I | | |
|---|---|---|
| No. | Salt Structure | Free Base Structure |
| 210 | 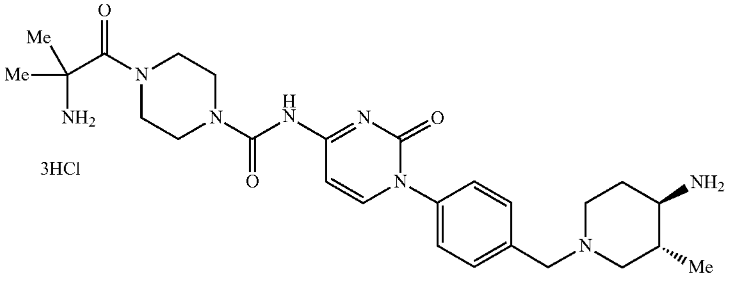 [SMILES: C[C@@H]1CN(Cc2ccc(-n3ccc(NC(=O)N4CCN(C(=O)C(C)(C)N)CC4)nc3=O)cc2)CC[C@H]1N] 3HCl | 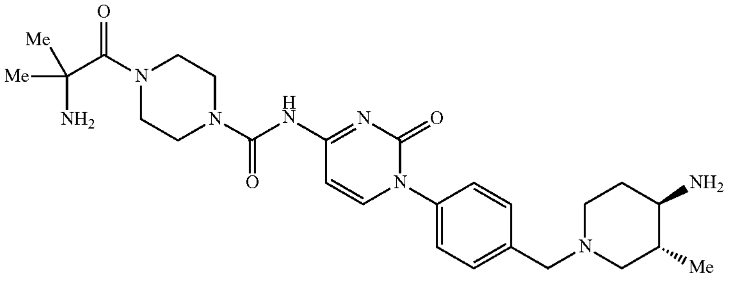 [SMILES: C[C@@H]1CN(Cc2ccc(-n3ccc(NC(=O)N4CCN(C(=O)C(C)(C)N)CC4)nc3=O)cc2)CC[C@H]1N] |
| 211 | 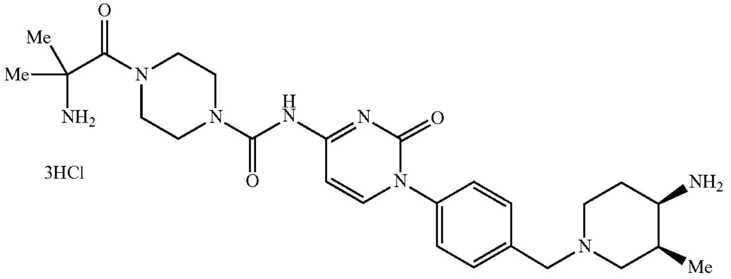 [SMILES: C[C@H]1CN(Cc2ccc(-n3ccc(NC(=O)N4CCN(C(=O)C(C)(C)N)CC4)nc3=O)cc2)CC[C@H]1N] 3HCl | 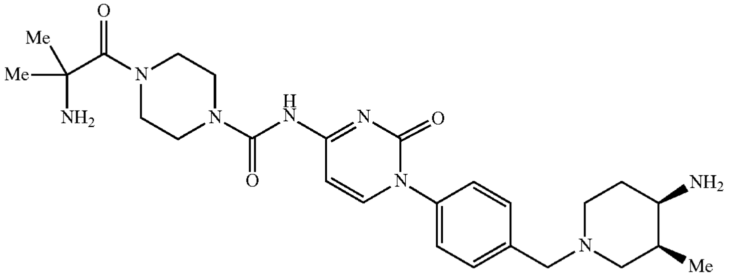 [SMILES: C[C@H]1CN(Cc2ccc(-n3ccc(NC(=O)N4CCN(C(=O)C(C)(C)N)CC4)nc3=O)cc2)CC[C@H]1N] |
| 212 | 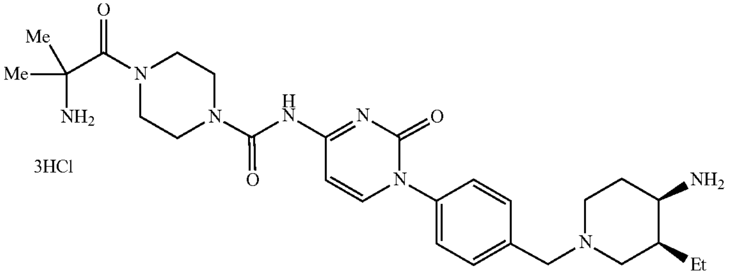 [SMILES: CC[C@H]1CN(Cc2ccc(-n3ccc(NC(=O)N4CCN(C(=O)C(C)(C)N)CC4)nc3=O)cc2)CC[C@H]1N] 3HCl | 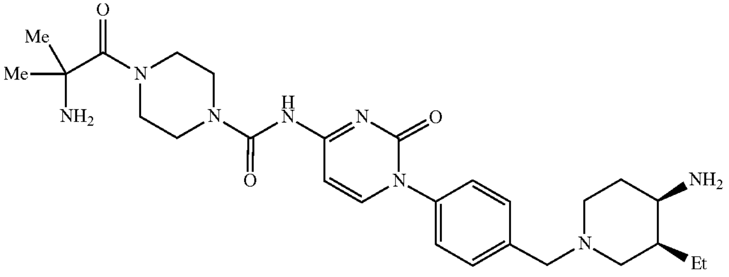 [SMILES: CC[C@H]1CN(Cc2ccc(-n3ccc(NC(=O)N4CCN(C(=O)C(C)(C)N)CC4)nc3=O)cc2)CC[C@H]1N] |

TABLE 10-continued
| Compounds of Formula I | | |
|---|---|---|
| No. | Salt Structure | Free Base Structure |
| 213 | 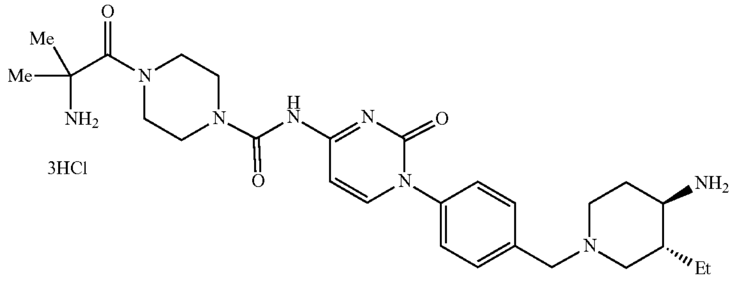 [SMILES: CC[C@@H]1CN(Cc2ccc(-n3ccc(NC(=O)N4CCN(C(=O)C(C)(C)N)CC4)nc3=O)cc2)CC[C@H]1N] 3HCl | 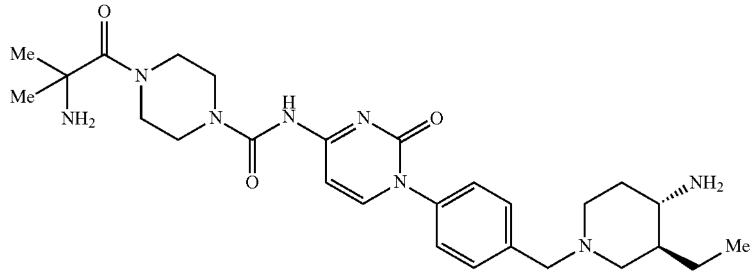 [SMILES: CC[C@H]1CN(Cc2ccc(-n3ccc(NC(=O)N4CCN(C(=O)C(C)(C)N)CC4)nc3=O)cc2)CC[C@@H]1N] |
| 214 | 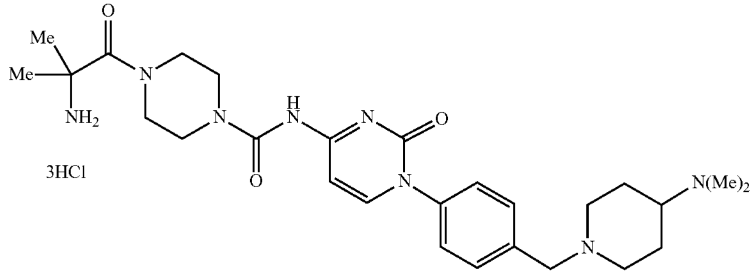 3HCl | 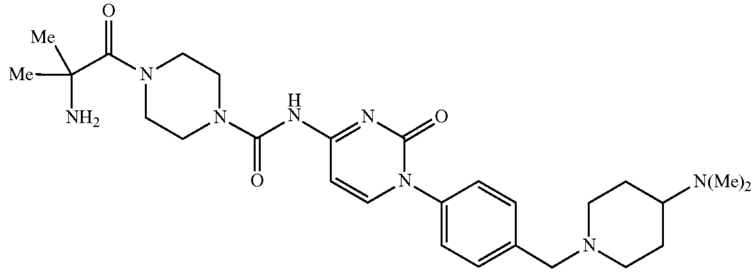 |
| 215 | 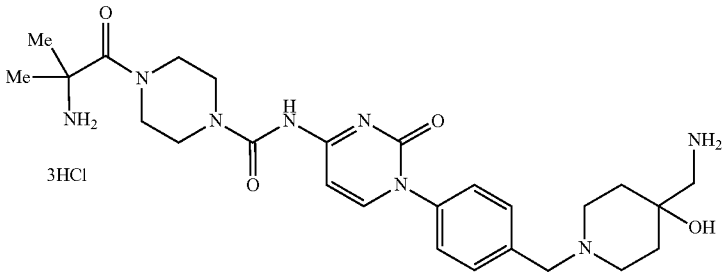 [SMILES: CC(C)(N)C(=O)N1CCN(C(=O)Nc2ccn(-c3ccc(CN4CCC(O)(CN)CC4)cc3)c(=O)n2)CC1] 3HCl | 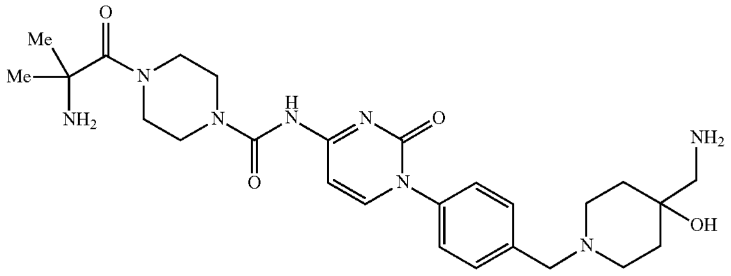 [SMILES: CC(C)(N)C(=O)N1CCN(C(=O)Nc2ccn(-c3ccc(CN4CCC(O)(CN)CC4)cc3)c(=O)n2)CC1] |

TABLE 10-continued
| Compounds of Formula I | | |
|---|---|---|
| No. | Salt Structure | Free Base Structure |
| 216 | 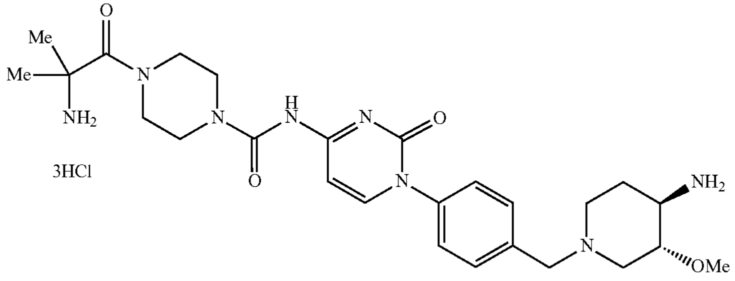 [SMILES: CO[C@@H]1CN(Cc2ccc(-n3ccc(NC(=O)N4CCN(C(=O)C(C)(C)N)CC4)nc3=O)cc2)CC[C@H]1N] 3HCl | 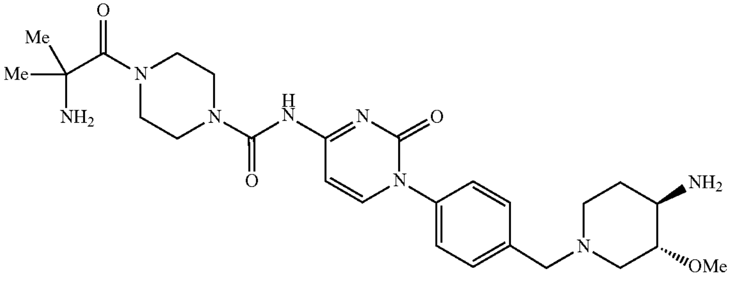 [SMILES: CO[C@@H]1CN(Cc2ccc(-n3ccc(NC(=O)N4CCN(C(=O)C(C)(C)N)CC4)nc3=O)cc2)CC[C@H]1N] |
| 217 | 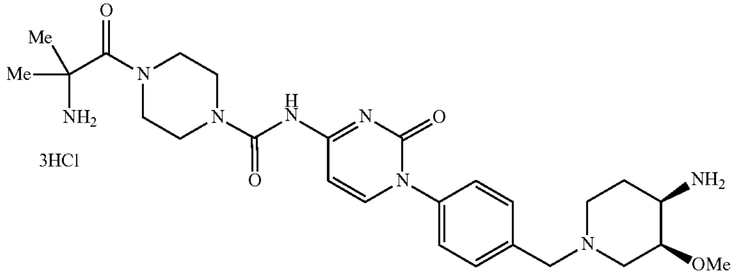 [SMILES: CO[C@H]1CN(Cc2ccc(-n3ccc(NC(=O)N4CCN(C(=O)C(C)(C)N)CC4)nc3=O)cc2)CC[C@H]1N] 3HCl | 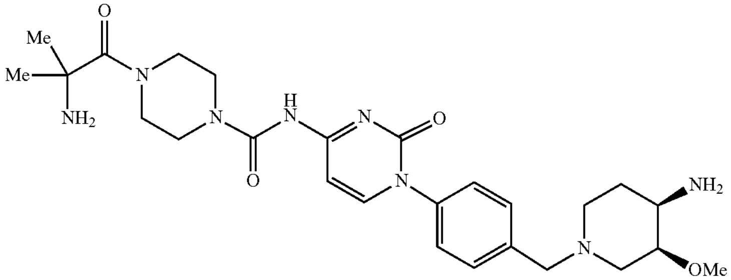 [SMILES: CO[C@H]1CN(Cc2ccc(-n3ccc(NC(=O)N4CCN(C(=O)C(C)(C)N)CC4)nc3=O)cc2)CC[C@H]1N] |
| 218 | 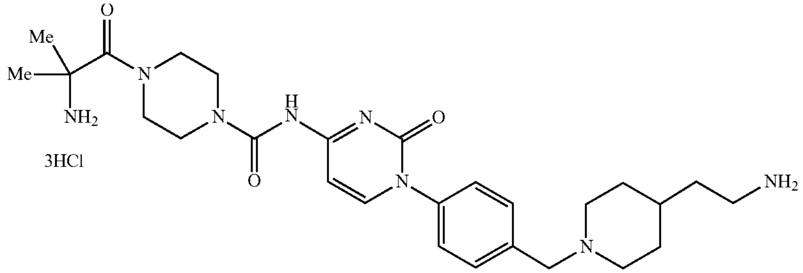 [SMILES: CC(C)(N)C(=O)N1CCN(C(=O)Nc2ccn(-c3ccc(CN4CCC(CCN)CC4)cc3)c(=O)n2)CC1] 3HCl | 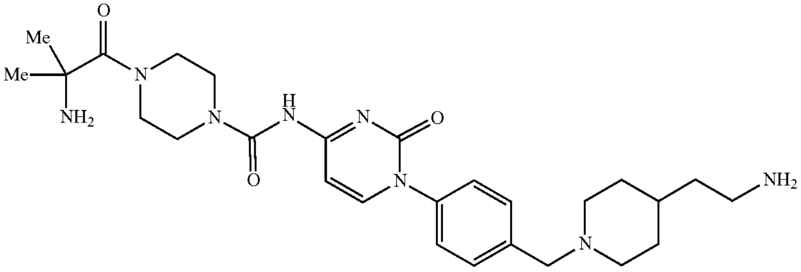 [SMILES: CC(C)(N)C(=O)N1CCN(C(=O)Nc2ccn(-c3ccc(CN4CCC(CCN)CC4)cc3)c(=O)n2)CC1] |

TABLE 10-continued
| Compounds of Formula I | | |
|---|---|---|
| No. | Salt Structure | Free Base Structure |
| 219 | 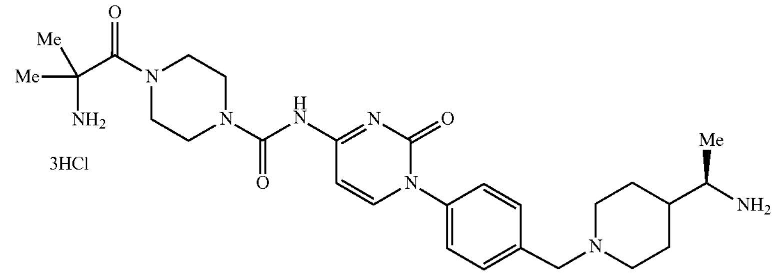 [SMILES: C[C@@H](N)C1CCN(Cc2ccc(-n3ccc(NC(=O)N4CCN(C(=O)C(C)(C)N)CC4)nc3=O)cc2)CC1] 3HCl | 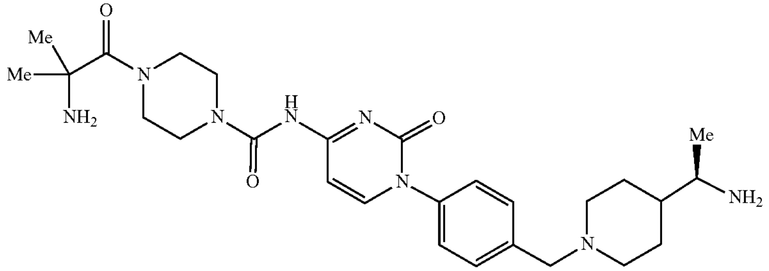 [SMILES: C[C@@H](N)C1CCN(Cc2ccc(-n3ccc(NC(=O)N4CCN(C(=O)C(C)(C)N)CC4)nc3=O)cc2)CC1] |
| 220 | 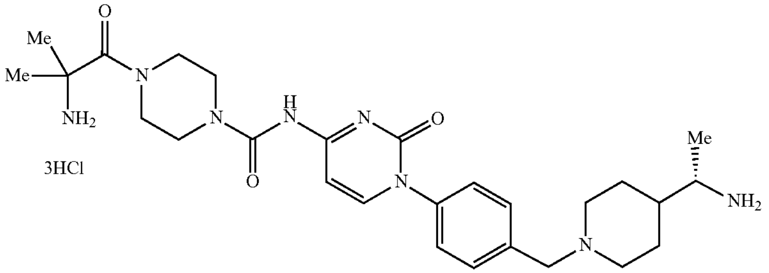 [SMILES: C[C@H](N)C1CCN(Cc2ccc(-n3ccc(NC(=O)N4CCN(C(=O)C(C)(C)N)CC4)nc3=O)cc2)CC1] 3HCl | 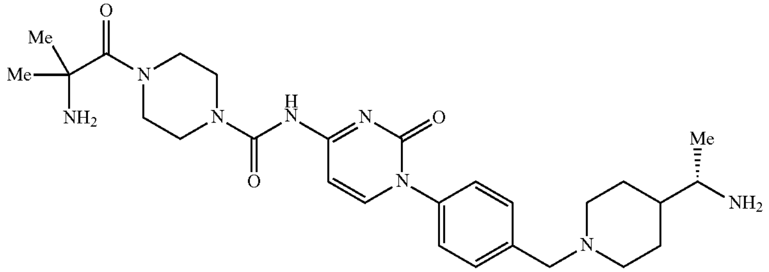 [SMILES: C[C@H](N)C1CCN(Cc2ccc(-n3ccc(NC(=O)N4CCN(C(=O)C(C)(C)N)CC4)nc3=O)cc2)CC1] |
| 221 | 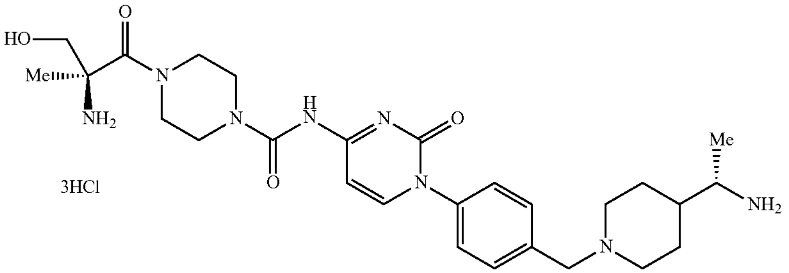 [SMILES: C[C@H](N)C1CCN(Cc2ccc(-n3ccc(NC(=O)N4CCN(C(=O)[C@@](C)(N)CO)CC4)nc3=O)cc2)CC1] 3HCl | 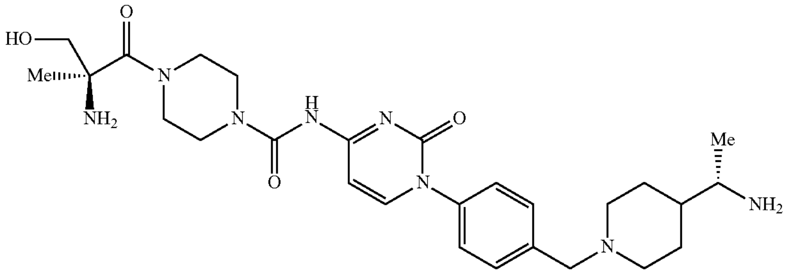 [SMILES: C[C@H](N)C1CCN(Cc2ccc(-n3ccc(NC(=O)N4CCN(C(=O)[C@@](C)(N)CO)CC4)nc3=O)cc2)CC1] |

TABLE 10-continued
| Compounds of Formula I | | |
|---|---|---|
| No. | Salt Structure | Free Base Structure |
| 222 | 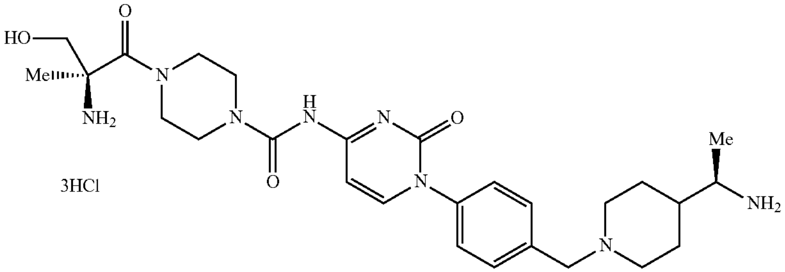 [SMILES: C[C@@H](N)C1CCN(Cc2ccc(-n3ccc(NC(=O)N4CCN(C(=O)[C@@](C)(N)CO)CC4)nc3=O)cc2)CC1] 3HCl | 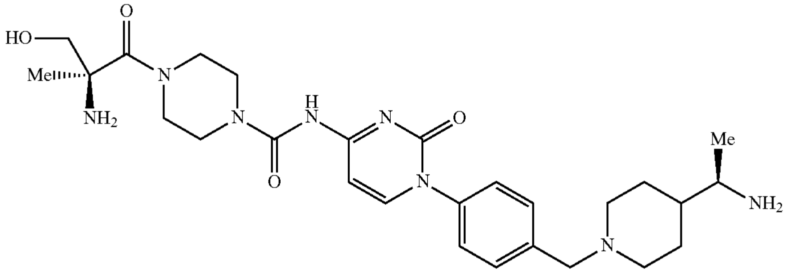 [SMILES: C[C@@H](N)C1CCN(Cc2ccc(-n3ccc(NC(=O)N4CCN(C(=O)[C@@](C)(N)CO)CC4)nc3=O)cc2)CC1] |
| 223 | 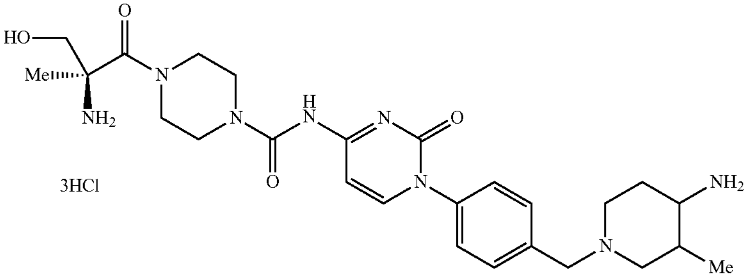 [SMILES: CC1CN(Cc2ccc(-n3ccc(NC(=O)N4CCN(C(=O)[C@@](C)(N)CO)CC4)nc3=O)cc2)CCC1N] 3HCl | 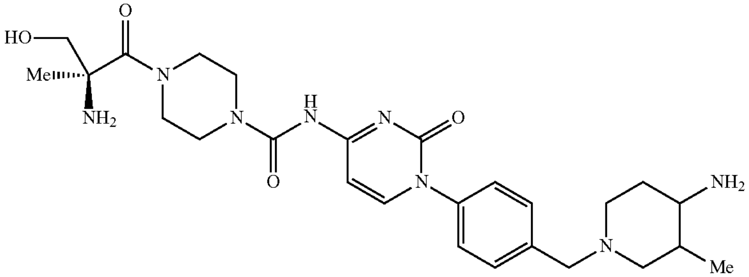 [SMILES: CC1CN(Cc2ccc(-n3ccc(NC(=O)N4CCN(C(=O)[C@@](C)(N)CO)CC4)nc3=O)cc2)CCC1N] |
| 224 | 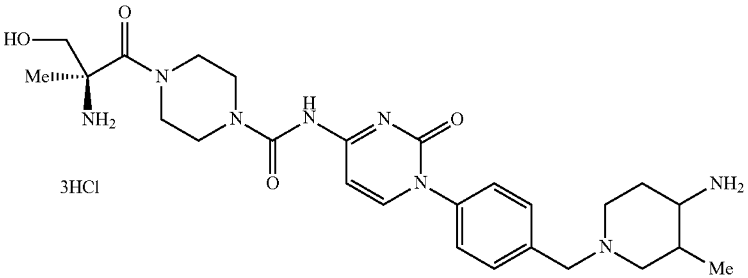 [SMILES: CC1CN(Cc2ccc(-n3ccc(NC(=O)N4CCN(C(=O)[C@@](C)(N)CO)CC4)nc3=O)cc2)CCC1N] 3HCl | 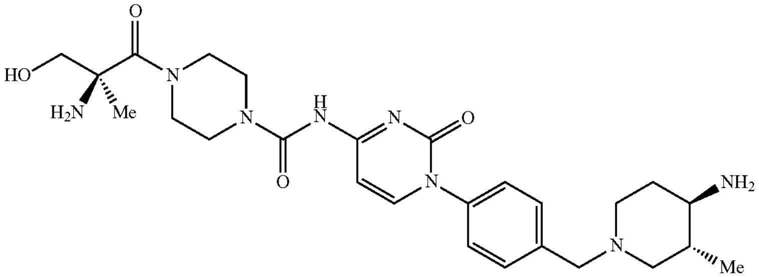 |

TABLE 10-continued
| Compounds of Formula I | | |
|---|---|---|
| No. | Salt Structure | Free Base Structure |
| 225 | 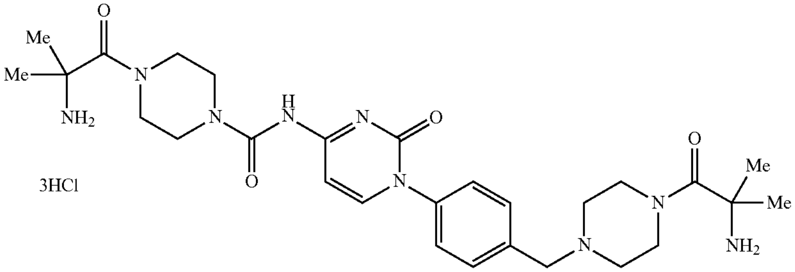 [SMILES: CC(C)(N)C(=O)N1CCN(Cc2ccc(-n3ccc(NC(=O)N4CCN(C(=O)C(C)(C)N)CC4)nc3=O)cc2)CC1] 3HCl | 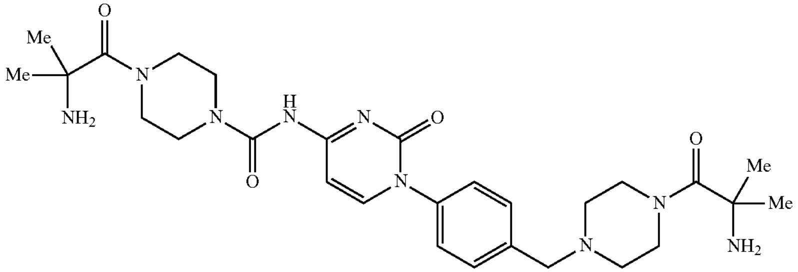 [SMILES: CC(C)(N)C(=O)N1CCN(Cc2ccc(-n3ccc(NC(=O)N4CCN(C(=O)C(C)(C)N)CC4)nc3=O)cc2)CC1] |
| 226 | 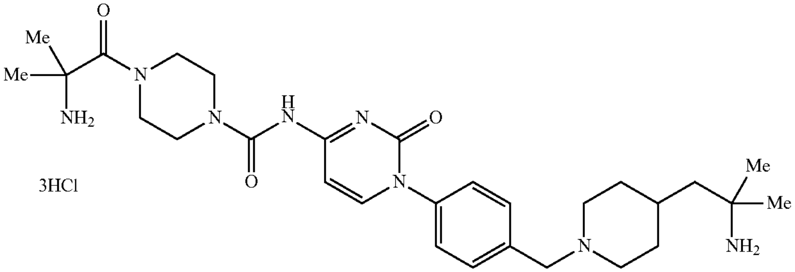 [SMILES: CC(C)(N)CC1CCN(Cc2ccc(-n3ccc(NC(=O)N4CCN(C(=O)C(C)(C)N)CC4)nc3=O)cc2)CC1] 3HCl | 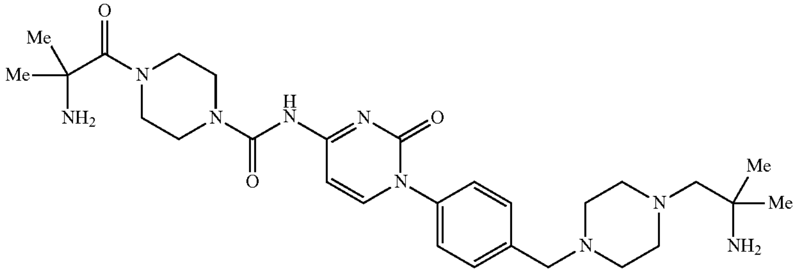 [SMILES: CC(C)(N)CN1CCN(Cc2ccc(-n3ccc(NC(=O)N4CCN(C(=O)C(C)(C)N)CC4)nc3=O)cc2)CC1] |
| 227 | 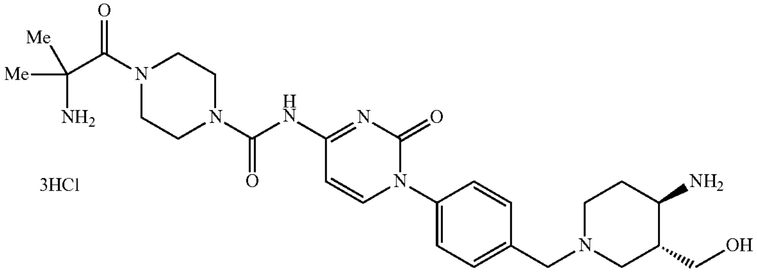 [SMILES: CC(C)(N)C(=O)N1CCN(C(=O)Nc2ccn(-c3ccc(CN4CC[C@@H](N)[C@H](CO)C4)cc3)c(=O)n2)CC1] 3HCl | 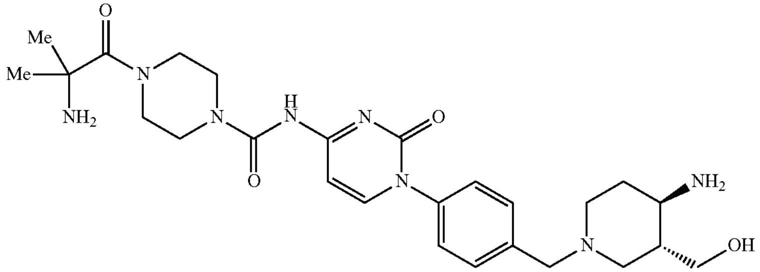 [SMILES: CC(C)(N)C(=O)N1CCN(C(=O)Nc2ccn(-c3ccc(CN4CC[C@@H](N)[C@H](CO)C4)cc3)c(=O)n2)CC1] |

TABLE 10-continued
| Compounds of Formula I | | |
|---|---|---|
| No. | Salt Structure | Free Base Structure |
| 230 | 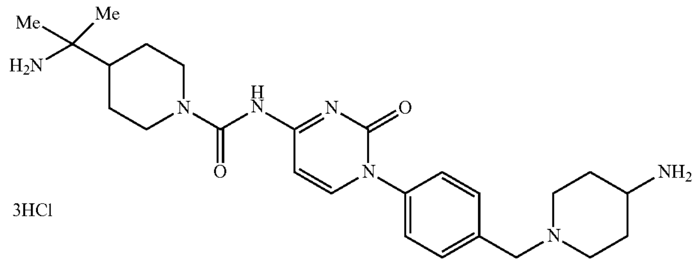 [SMILES: CC(C)(N)C1CCN(C(=O)Nc2ccn(-c3ccc(CN4CCC(N)CC4)cc3)c(=O)n2)CC1] 3HCl | 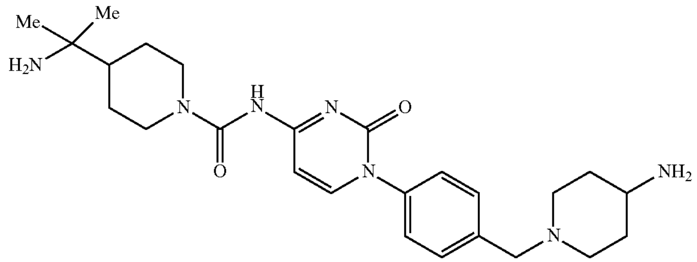 [SMILES: CC(C)(N)C1CCN(C(=O)Nc2ccn(-c3ccc(CN4CCC(N)CC4)cc3)c(=O)n2)CC1] |
| 231 | 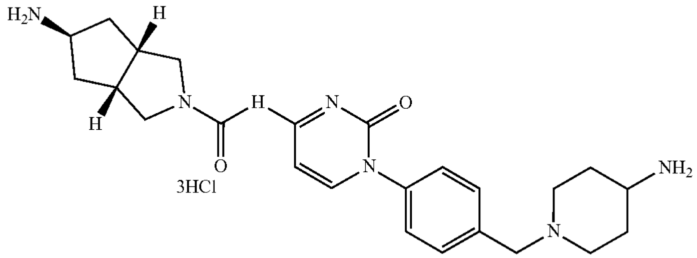 3HCl | 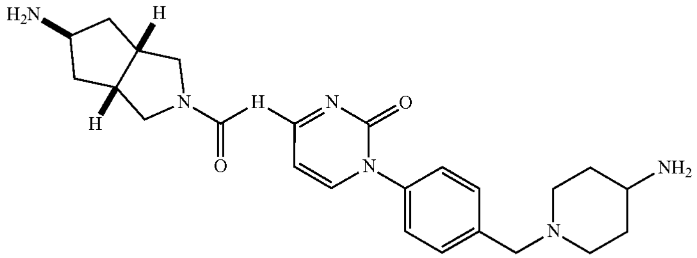 |
| 233 | 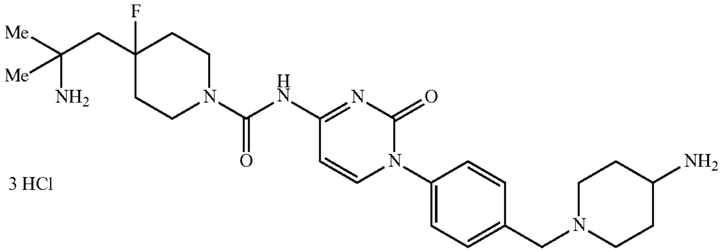 [SMILES: CC(C)(N)CC1(F)CCN(C(=O)Nc2ccn(-c3ccc(CN4CCC(N)CC4)cc3)c(=O)n2)CC1] 3 HCl | 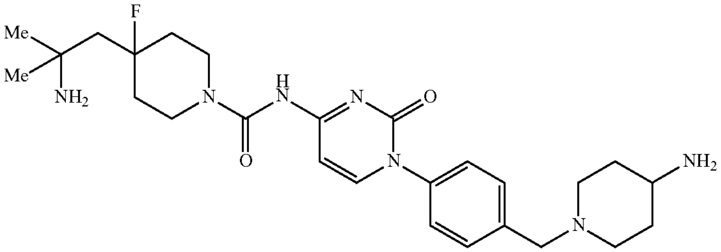 [SMILES: CC(C)(N)CC1(F)CCN(C(=O)Nc2ccn(-c3ccc(CN4CCC(N)CC4)cc3)c(=O)n2)CC1] |

TABLE 10-continued
| Compounds of Formula I | | |
|---|---|---|
| No. | Salt Structure | Free Base Structure |
| 234 | 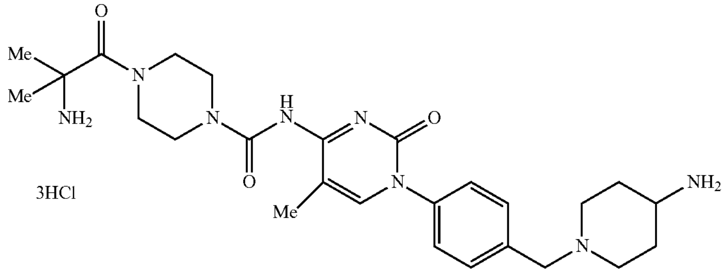 [SMILES: Cc1cn(-c2ccc(CN3CCC(N)CC3)cc2)c(=O)nc1NC(=O)N1CCN(C(=O)C(C)(C)N)CC1] 3HCl | 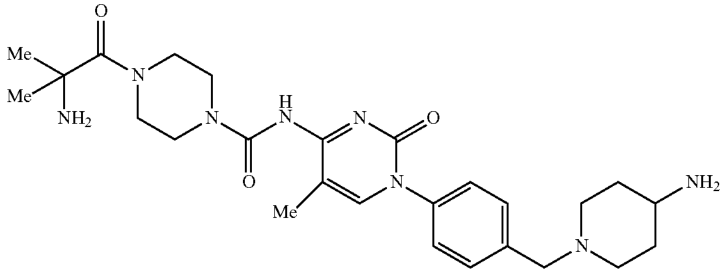 [SMILES: Cc1cn(-c2ccc(CN3CCC(N)CC3)cc2)c(=O)nc1NC(=O)N1CCN(C(=O)C(C)(C)N)CC1] |
| 235 | 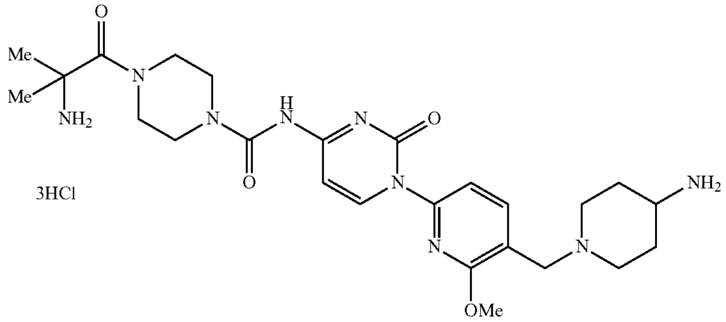 [SMILES: COc1nc(-n2ccc(NC(=O)N3CCN(C(=O)C(C)(C)N)CC3)nc2=O)ccc1CN1CCC(N)CC1] 3HCl | 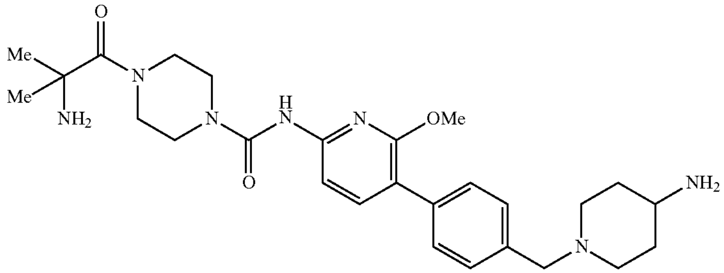 [SMILES: COc1nc(NC(=O)N2CCN(C(=O)C(C)(C)N)CC2)ccc1-c1ccc(CN2CCC(N)CC2)cc1] |
| 236 | 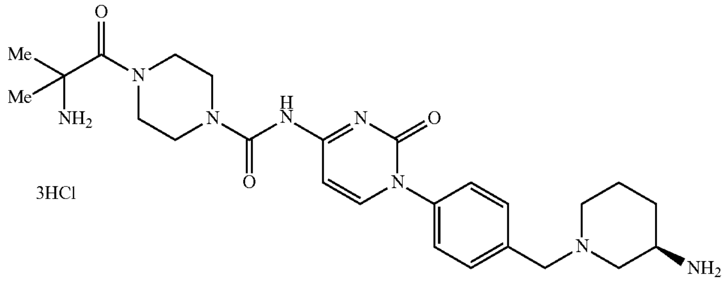 3HCl | 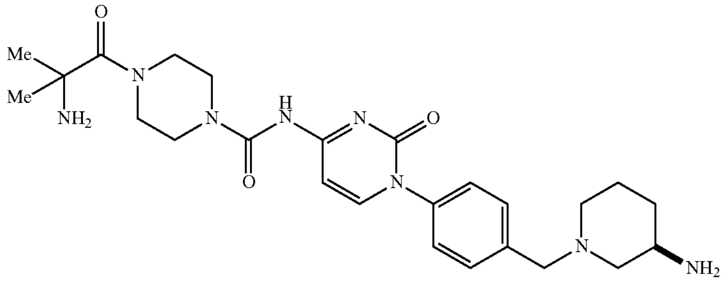 |

TABLE 10-continued
| Compounds of Formula I | | |
| --- | --- | --- |
| No. | Salt Structure | Free Base Structure |
| 237 | 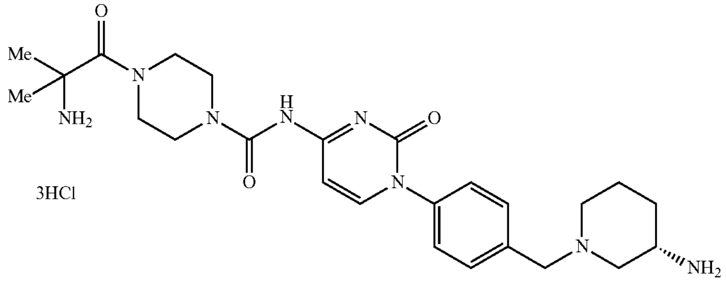 [SMILES: CC(C)(N)C(=O)N1CCN(C(=O)Nc2ccn(-c3ccc(CN4CCC[C@H](N)C4)cc3)c(=O)n2)CC1] 3HCl | 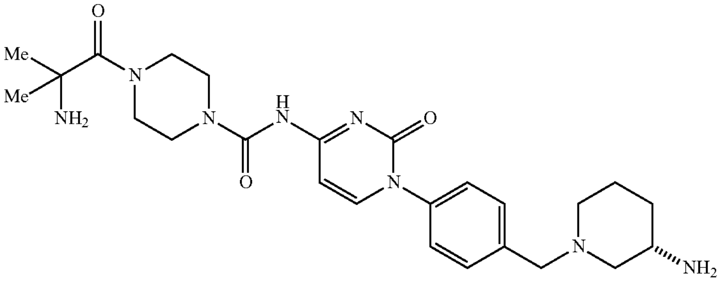 |
| 238 | 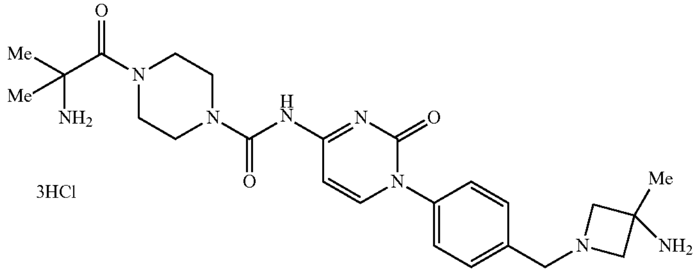 [SMILES: CC1(N)CN(Cc2ccc(-n3ccc(NC(=O)N4CCN(C(=O)C(C)(C)N)CC4)nc3=O)cc2)C1] 3HCl | 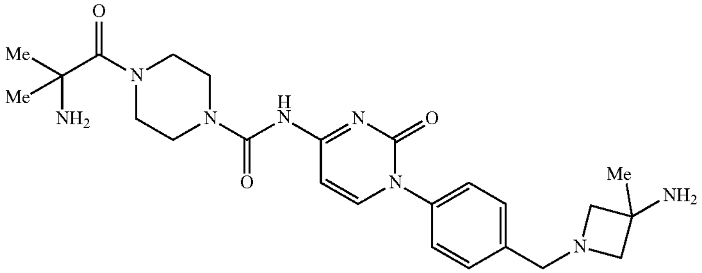 [SMILES: CC1(N)CN(Cc2ccc(-n3ccc(NC(=O)N4CCN(C(=O)C(C)(C)N)CC4)nc3=O)cc2)C1] |
| 239 | 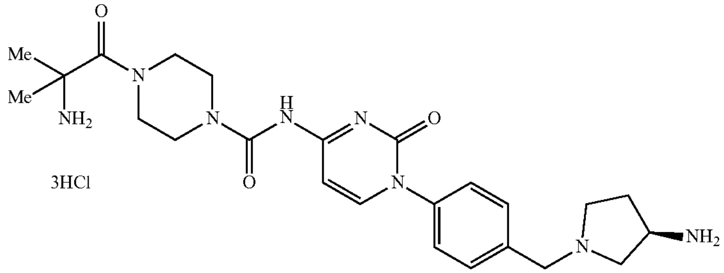 [SMILES: CC(C)(N)C(=O)N1CCN(C(=O)Nc2ccn(-c3ccc(CN4CC[C@@H](N)C4)cc3)c(=O)n2)CC1] 3HCl | 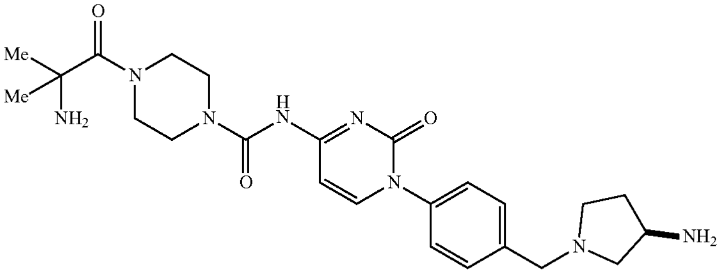 [SMILES: CC(C)(N)C(=O)N1CCN(C(=O)Nc2ccn(-c3ccc(CN4CC[C@@H](N)C4)cc3)c(=O)n2)CC1] |

TABLE 10-continued
| Compounds of Formula I | | |
|---|---|---|
| No. | Salt Structure | Free Base Structure |
| 240 | 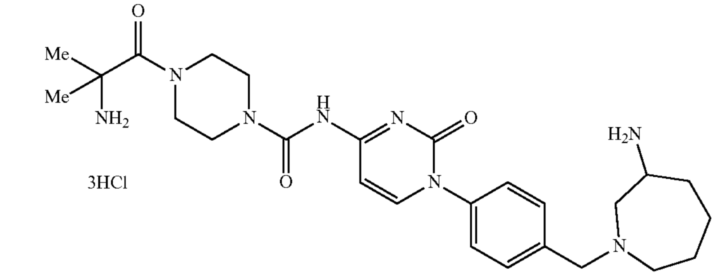 [SMILES: CC(C)(N)C(=O)N1CCN(C(=O)Nc2ccn(-c3ccc(CN4CCCCC(N)C4)cc3)c(=O)n2)CC1] 3HCl | 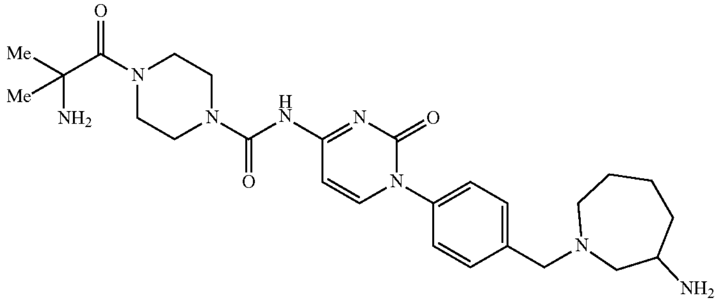 |
| 241 | 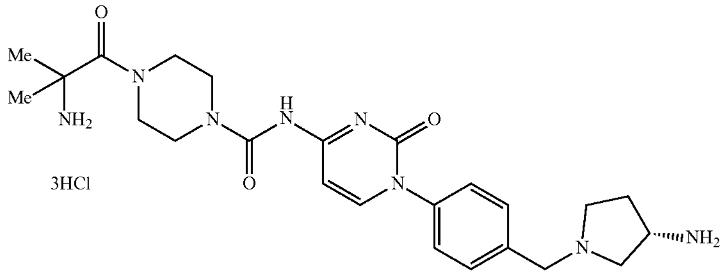 [SMILES: CC(C)(N)C(=O)N1CCN(C(=O)Nc2ccn(-c3ccc(CN4CC[C@H](N)C4)cc3)c(=O)n2)CC1] 3HCl | 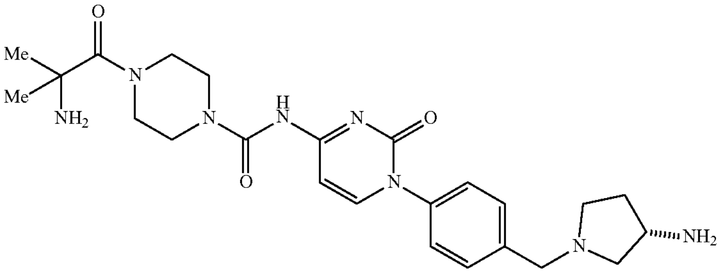 [SMILES: CC(C)(N)C(=O)N1CCN(C(=O)Nc2ccn(-c3ccc(CN4CC[C@H](N)C4)cc3)c(=O)n2)CC1] |
| 242 | 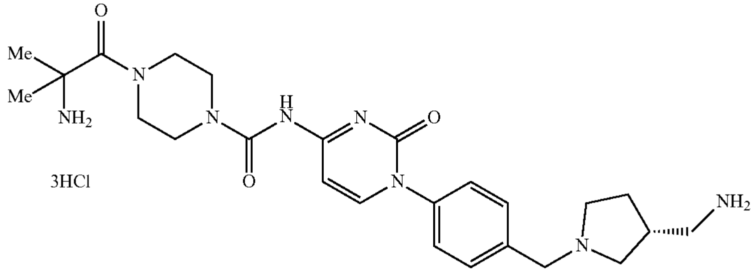 [SMILES: CC(C)(N)C(=O)N1CCN(C(=O)Nc2ccn(-c3ccc(CN4CC[C@H](CN)C4)cc3)c(=O)n2)CC1] 3HCl | 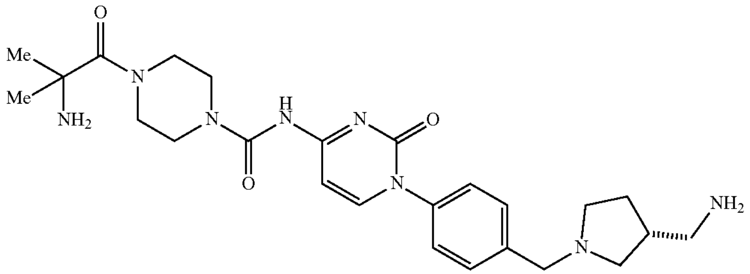 [SMILES: CC(C)(N)C(=O)N1CCN(C(=O)Nc2ccn(-c3ccc(CN4CC[C@H](CN)C4)cc3)c(=O)n2)CC1] |

TABLE 10-continued
| Compounds of Formula I | | |
|---|---|---|
| No. | Salt Structure | Free Base Structure |
| 243 | 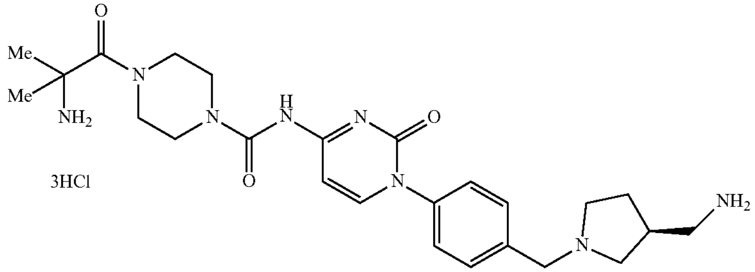 [SMILES: CC(C)(N)C(=O)N1CCN(C(=O)Nc2ccn(-c3ccc(CN4CC[C@@H](CN)C4)cc3)c(=O)n2)CC1] 3HCl | 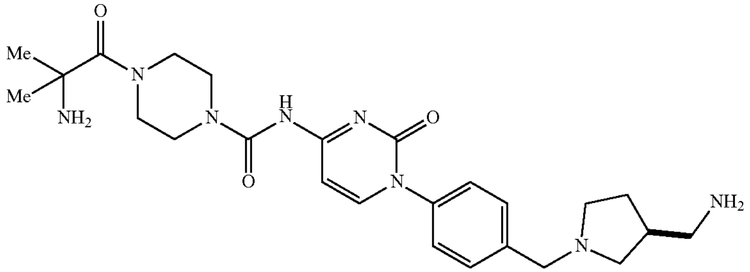 [SMILES: CC(C)(N)C(=O)N1CCN(C(=O)Nc2ccn(-c3ccc(CN4CC[C@@H](CN)C4)cc3)c(=O)n2)CC1] |
| 244 | 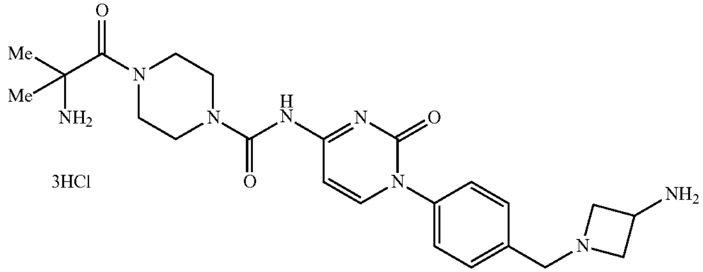 [SMILES: CC(C)(N)C(=O)N1CCN(C(=O)Nc2ccn(-c3ccc(CN4CC(N)C4)cc3)c(=O)n2)CC1] 3HCl | 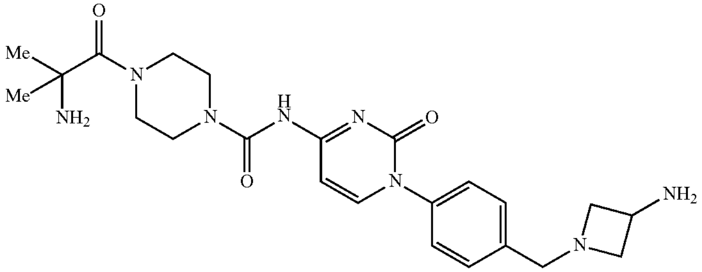 [SMILES: CC(C)(N)C(=O)N1CCN(C(=O)Nc2ccn(-c3ccc(CN4CC(N)C4)cc3)c(=O)n2)CC1] |
| 245 | 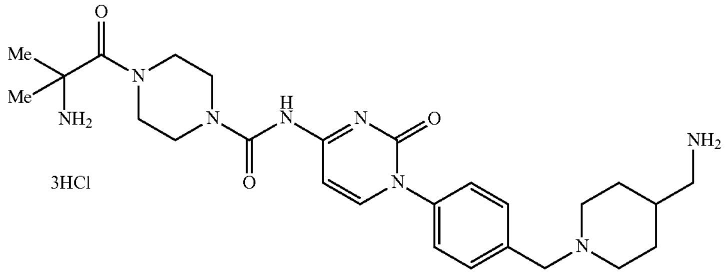 [SMILES: CC(C)(N)C(=O)N1CCN(C(=O)Nc2ccn(-c3ccc(CN4CCC(CN)CC4)cc3)c(=O)n2)CC1] 3HCl | 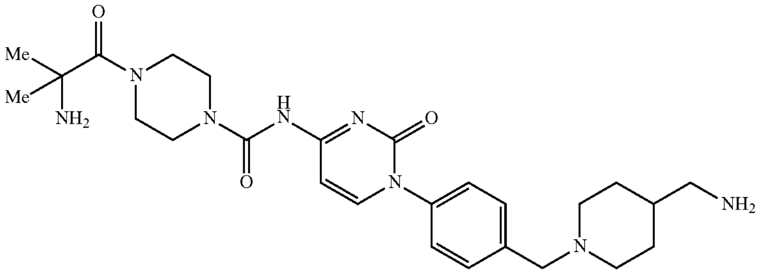 [SMILES: CC(C)(N)C(=O)N1CCN(C(=O)Nc2ccn(-c3ccc(CN4CCC(CN)CC4)cc3)c(=O)n2)CC1] |

TABLE 10-continued
Compounds of Formula I
| No. | Salt Structure | Free Base Structure |
| --- | --- | --- |
| 246 | 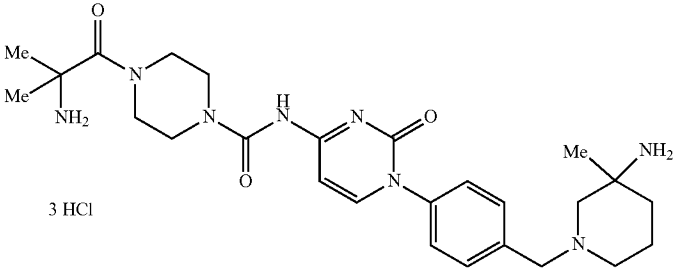 [SMILES: CC1(N)CCCN(Cc2ccc(-n3ccc(NC(=O)N4CCN(C(=O)C(C)(C)N)CC4)nc3=O)cc2)C1] 3 HCl | 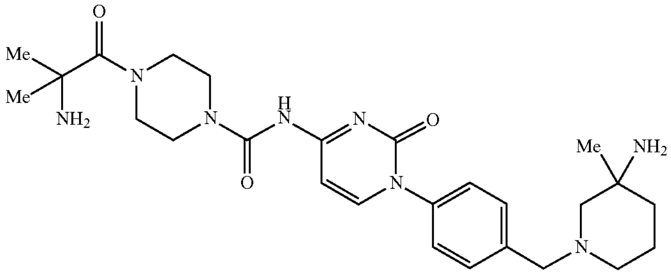 |
| 247 | 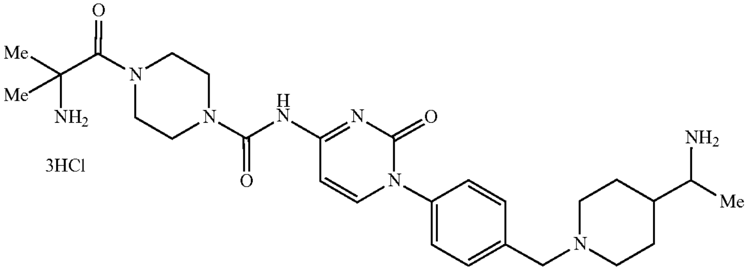 [SMILES: CC(N)C1CCN(Cc2ccc(-n3ccc(NC(=O)N4CCN(C(=O)C(C)(C)N)CC4)nc3=O)cc2)CC1] 3HCl | 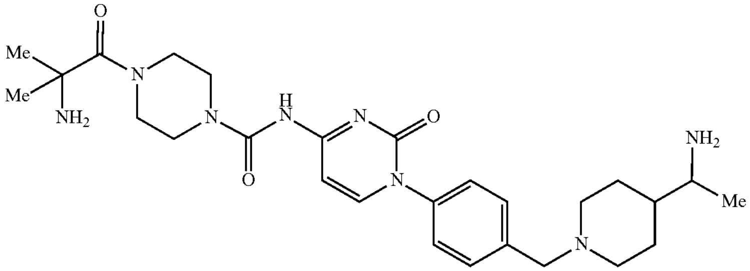 [SMILES: CC(N)C1CCN(Cc2ccc(-n3ccc(NC(=O)N4CCN(C(=O)C(C)(C)N)CC4)nc3=O)cc2)CC1] |
| 248 | 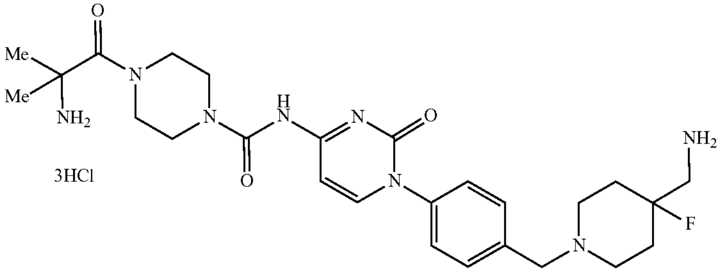 [SMILES: CC(C)(N)C(=O)N1CCN(C(=O)Nc2ccn(-c3ccc(CN4CCC(F)(CN)CC4)cc3)c(=O)n2)CC1] 3HCl | 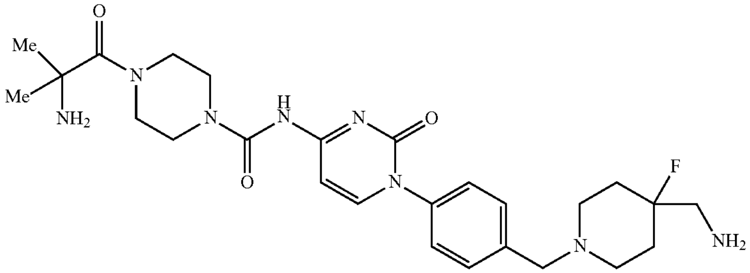 [SMILES: CC(C)(N)C(=O)N1CCN(C(=O)Nc2ccn(-c3ccc(CN4CCC(F)(CN)CC4)cc3)c(=O)n2)CC1] |

TABLE 10-continued
| Compounds of Formula I | | |
|---|---|---|
| No. | Salt Structure | Free Base Structure |
| 249 | 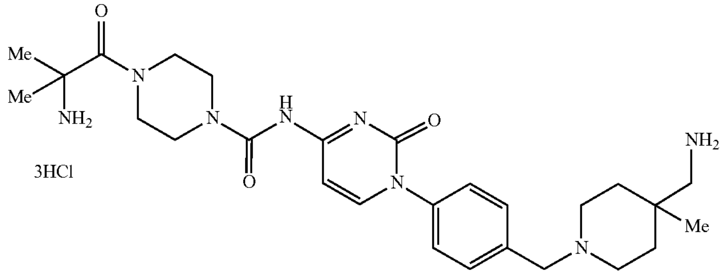 [SMILES: CC1(CN)CCN(Cc2ccc(-n3ccc(NC(=O)N4CCN(C(=O)C(C)(C)N)CC4)nc3=O)cc2)CC1] 3HCl | 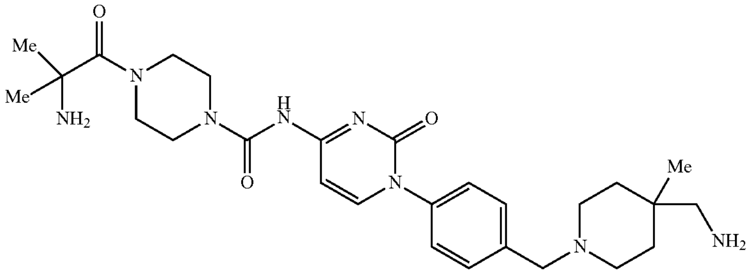 [SMILES: CC1(CN)CCN(Cc2ccc(-n3ccc(NC(=O)N4CCN(C(=O)C(C)(C)N)CC4)nc3=O)cc2)CC1] |
| 250 | 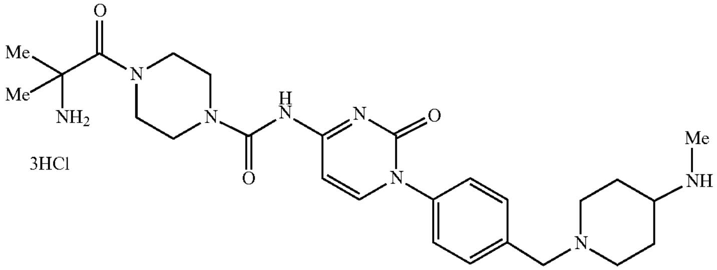 [SMILES: CNC1CCN(Cc2ccc(-n3ccc(NC(=O)N4CCN(C(=O)C(C)(C)N)CC4)nc3=O)cc2)CC1] 3HCl | 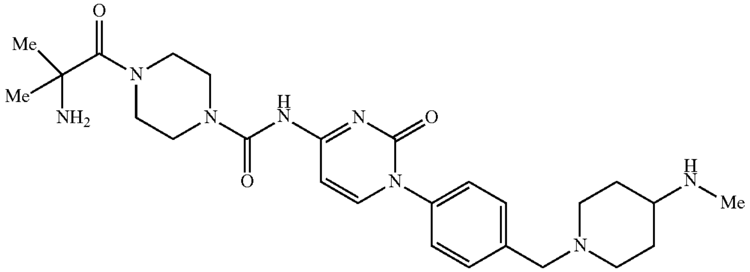 [SMILES: CNC1CCN(Cc2ccc(-n3ccc(NC(=O)N4CCN(C(=O)C(C)(C)N)CC4)nc3=O)cc2)CC1] |
| 251 | 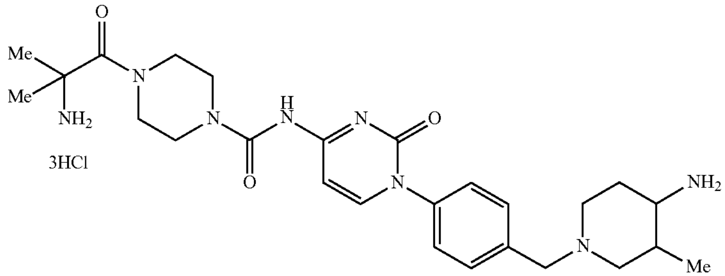 [SMILES: CC1CN(Cc2ccc(-n3ccc(NC(=O)N4CCN(C(=O)C(C)(C)N)CC4)nc3=O)cc2)CCC1N] 3HCl | 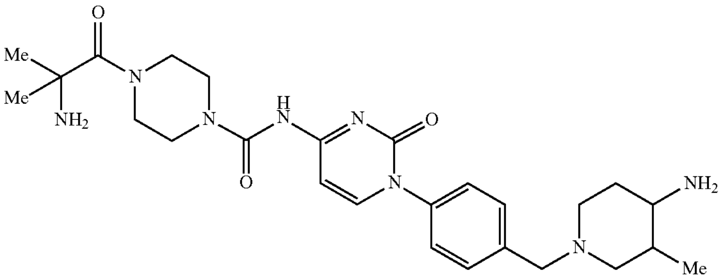 [SMILES: CC1CN(Cc2ccc(-n3ccc(NC(=O)N4CCN(C(=O)C(C)(C)N)CC4)nc3=O)cc2)CCC1N] |

TABLE 10-continued
| Compounds of Formula I | | |
|---|---|---|
| No. | Salt Structure | Free Base Structure |
| 252 | 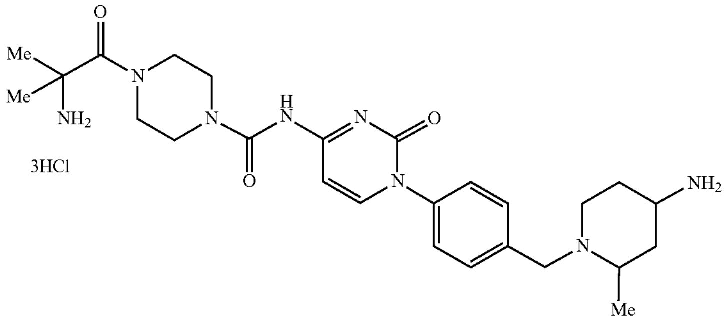 [SMILES: CC1CC(N)CCN1Cc1ccc(-n2ccc(NC(=O)N3CCN(C(=O)C(C)(C)N)CC3)nc2=O)cc1] 3HCl | 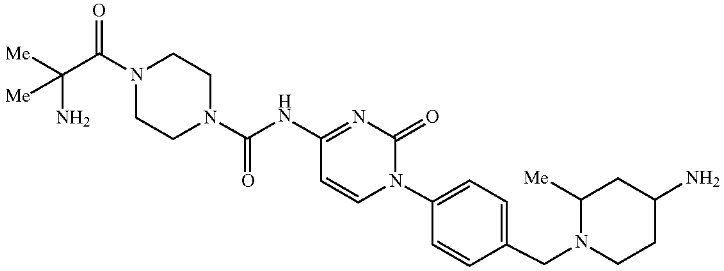 [SMILES: CC1CC(N)CCN1Cc1ccc(-n2ccc(NC(=O)N3CCN(C(=O)C(C)(C)N)CC3)nc2=O)cc1] |
| 253 | 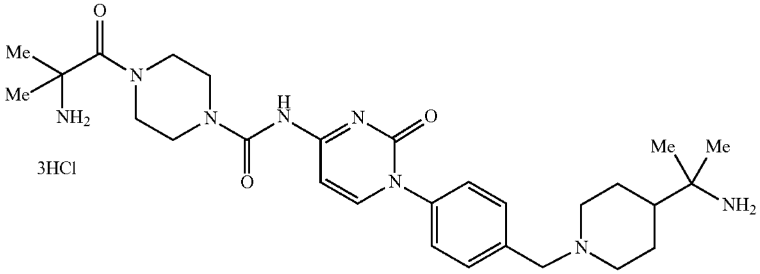 [SMILES: CC(C)(N)C(=O)N1CCN(C(=O)Nc2ccn(-c3ccc(CN4CCC(C(C)(C)N)CC4)cc3)c(=O)n2)CC1] 3HCl | 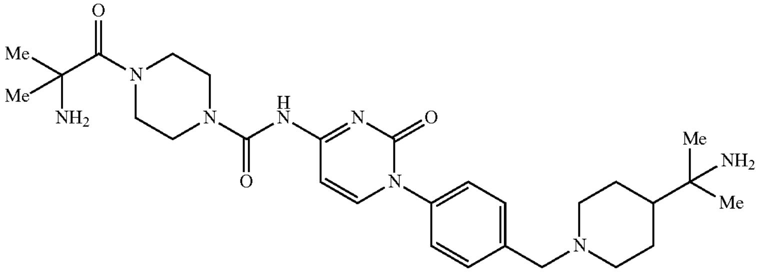 [SMILES: CC(C)(N)C(=O)N1CCN(C(=O)Nc2ccn(-c3ccc(CN4CCC(C(C)(C)N)CC4)cc3)c(=O)n2)CC1] |
| 254 | 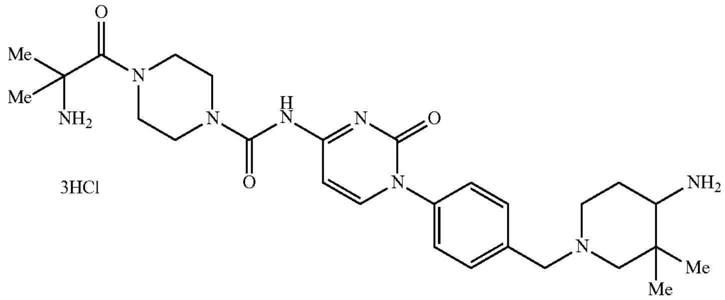 [SMILES: CC(C)(N)C(=O)N1CCN(C(=O)Nc2ccn(-c3ccc(CN4CCC(N)C(C)(C)C4)cc3)c(=O)n2)CC1] 3HCl | 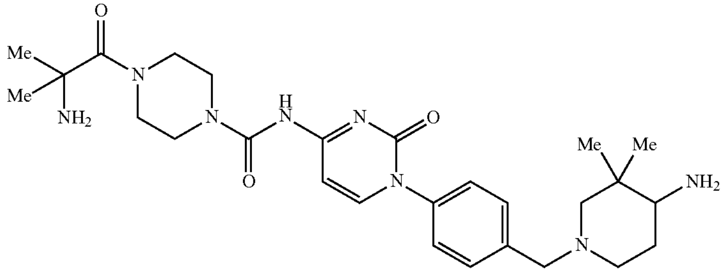 [SMILES: CC(C)(N)C(=O)N1CCN(C(=O)Nc2ccn(-c3ccc(CN4CCC(N)C(C)(C)C4)cc3)c(=O)n2)CC1] |

TABLE 10-continued
| Compounds of Formula I | | |
| --- | --- | --- |
| No. | Salt Structure | Free Base Structure |
| 255 | 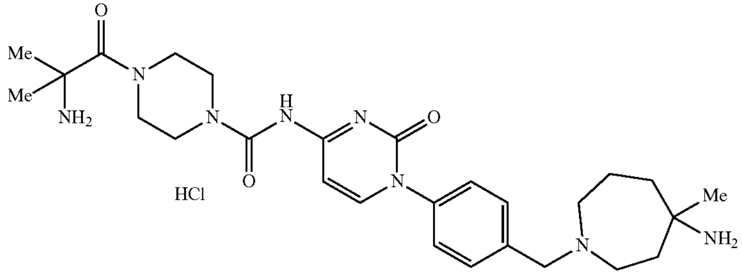 [SMILES: CC1(N)CCCN(Cc2ccc(-n3ccc(NC(=O)N4CCN(C(=O)C(C)(C)N)CC4)nc3=O)cc2)CC1 ; Cl] HCl | 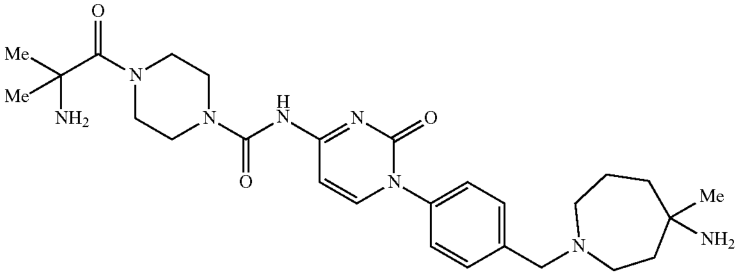 [SMILES: CC1(N)CCCN(Cc2ccc(-n3ccc(NC(=O)N4CCN(C(=O)C(C)(C)N)CC4)nc3=O)cc2)CC1] |
| 265 | 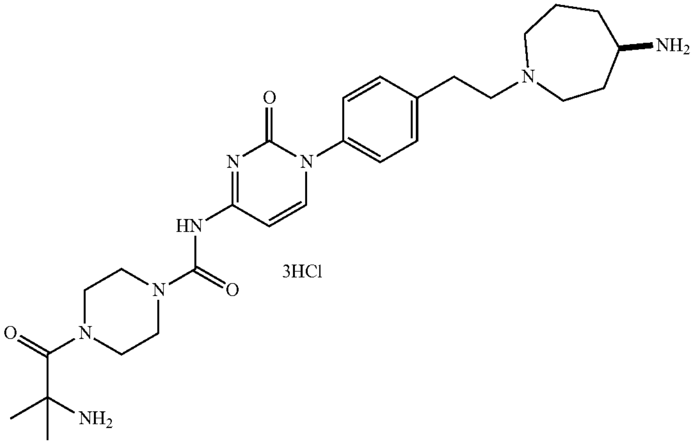 [SMILES: CC(C)(N)C(=O)N1CCN(C(=O)Nc2ccn(-c3ccc(CCN4CCC[C@@H](N)CC4)cc3)c(=O)n2)CC1] 3HCl | 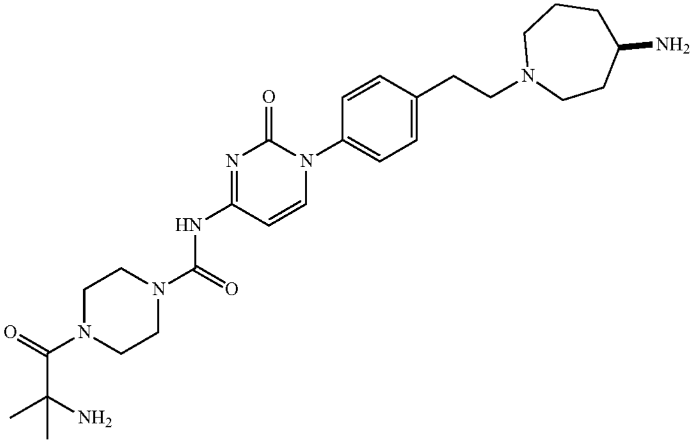 [SMILES: CC(C)(N)C(=O)N1CCN(C(=O)Nc2ccn(-c3ccc(CCN4CCC[C@@H](N)CC4)cc3)c(=O)n2)CC1] |

TABLE 10-continued
| Compounds of Formula I | | |
|---|---|---|
| No. | Salt Structure | Free Base Structure |
| 266 | 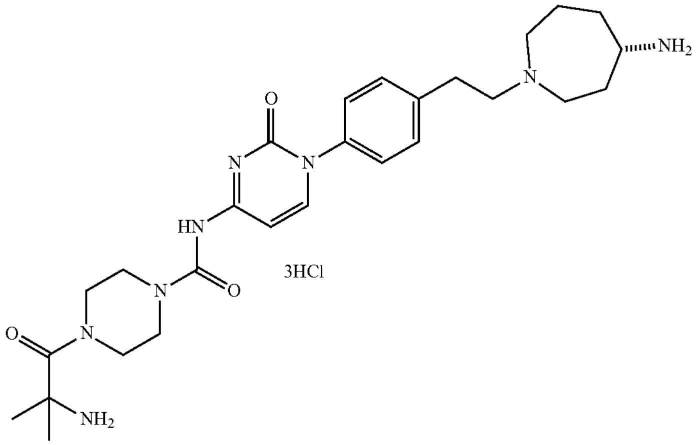 [SMILES: CC(C)(N)C(=O)N1CCN(C(=O)Nc2ccn(-c3ccc(CCN4CCC[C@H](N)CC4)cc3)c(=O)n2)CC1] 3HCl | 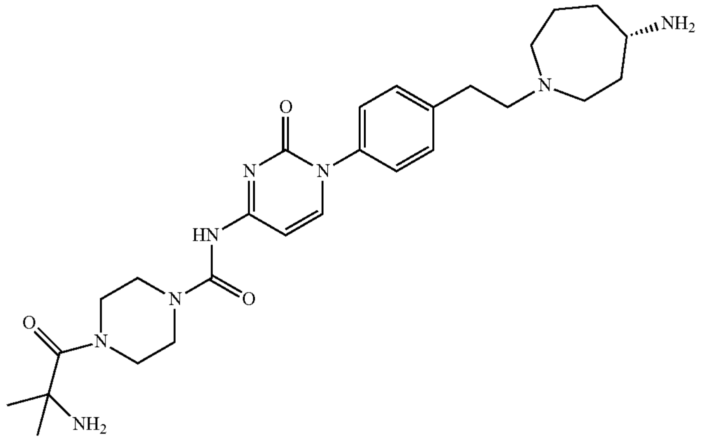 [SMILES: CC(C)(N)C(=O)N1CCN(C(=O)Nc2ccn(-c3ccc(CCN4CCC[C@H](N)CC4)cc3)c(=O)n2)CC1] |
| 267 | 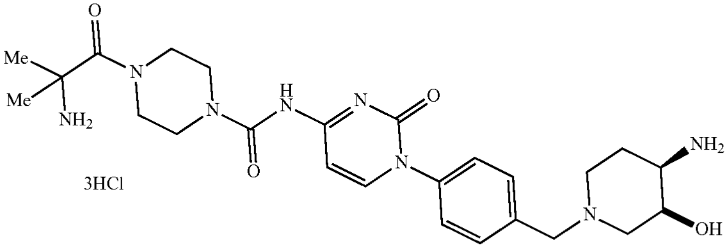 [SMILES: CC(C)(N)C(=O)N1CCN(C(=O)Nc2ccn(-c3ccc(CN4CC[C@@H](N)[C@@H](O)C4)cc3)c(=O)n2)CC1] 3HCl | 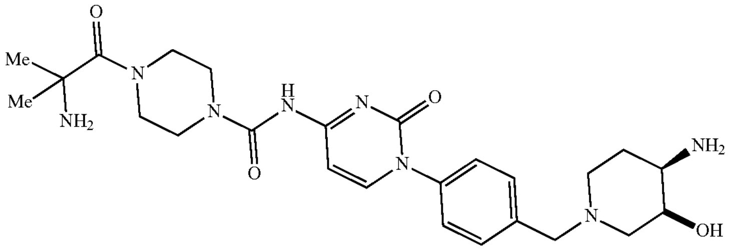 [SMILES: CC(C)(N)C(=O)N1CCN(C(=O)Nc2ccn(-c3ccc(CN4CC[C@@H](N)[C@@H](O)C4)cc3)c(=O)n2)CC1] |
| 268 | 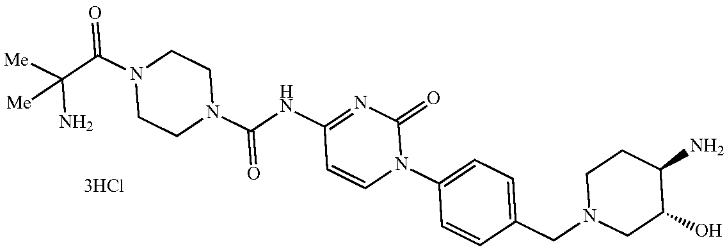 [SMILES: CC(C)(N)C(=O)N1CCN(C(=O)Nc2ccn(-c3ccc(CN4CC[C@@H](N)[C@H](O)C4)cc3)c(=O)n2)CC1] 3HCl | 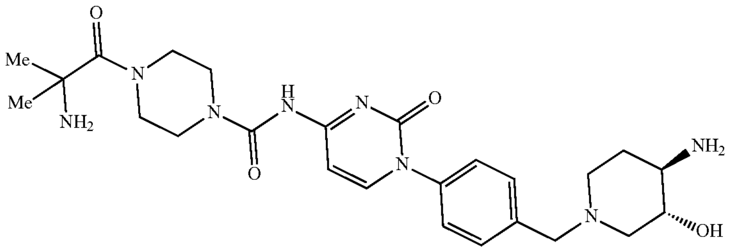 [SMILES: CC(C)(N)C(=O)N1CCN(C(=O)Nc2ccn(-c3ccc(CN4CC[C@@H](N)[C@H](O)C4)cc3)c(=O)n2)CC1] |

TABLE 10-continued
| Compounds of Formula I | | |
|---|---|---|
| No. | Salt Structure | Free Base Structure |
| 269 | 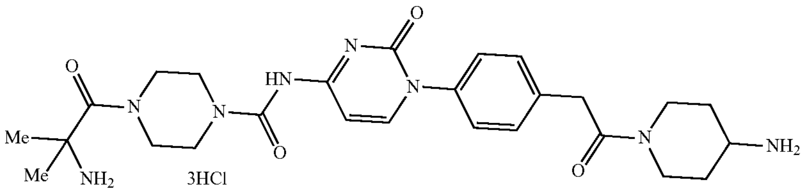 3HCl | 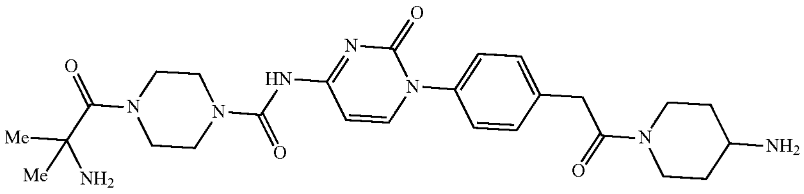 [SMILES: CC(C)(N)C(=O)N1CCN(C(=O)Nc2ccn(-c3ccc(CC(=O)N4CCC(N)CC4)cc3)c(=O)n2)CC1] |

TABLE 11
| Compounds of Formula I Continued | |
|---|---|
| No. Salt Structure | Free Base Structure |
| 270 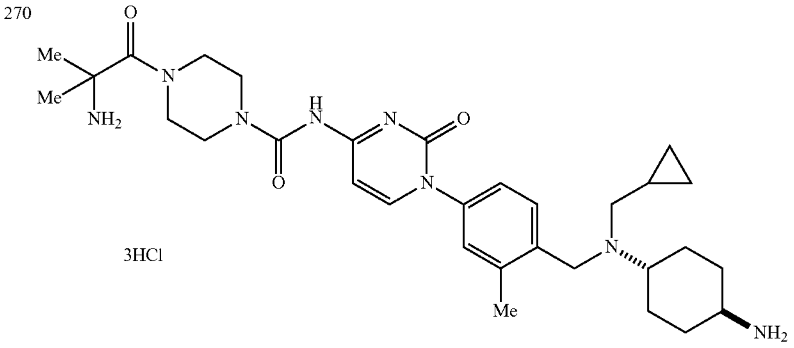 3HCl | 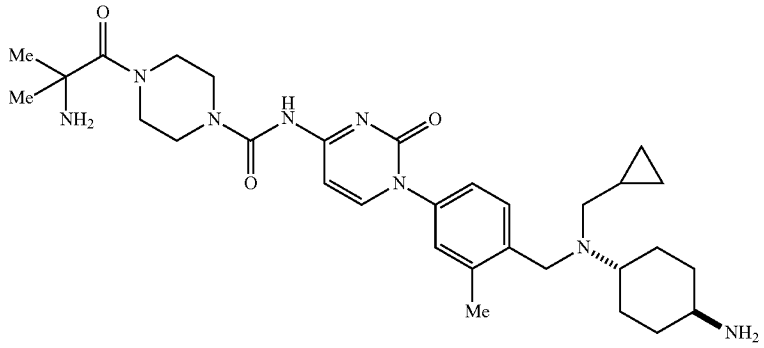 |
| 271 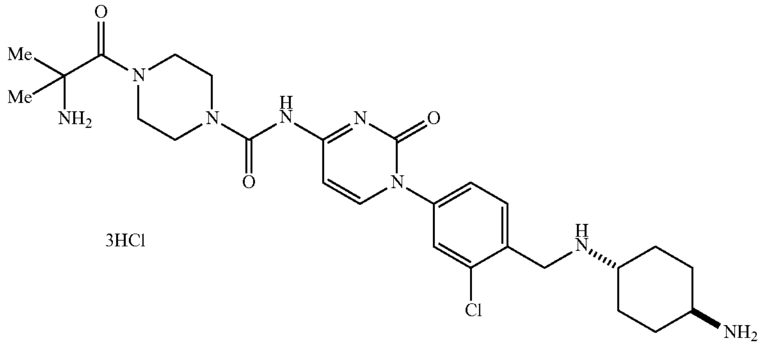 3HCl | 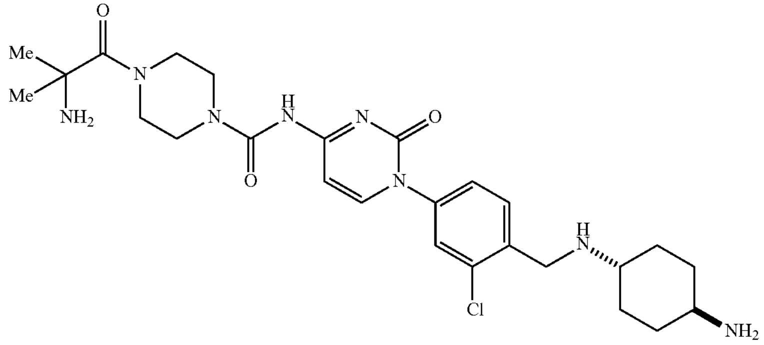 |

TABLE 11-continued
| Compounds of Formula I Continued | | |
|---|---|---|
| No. | Salt Structure | Free Base Structure |
| 272 | 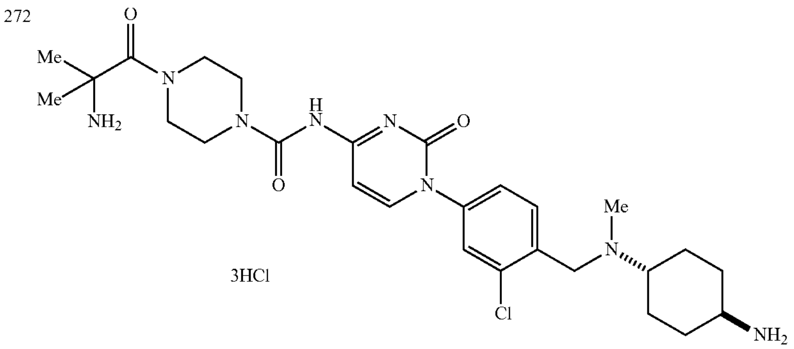 3HCl | 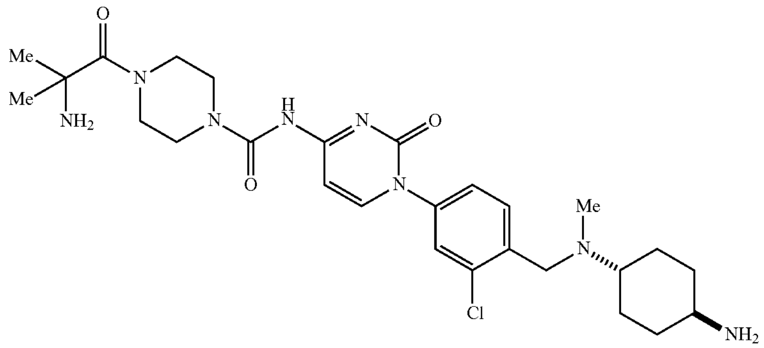 |
| 273 | 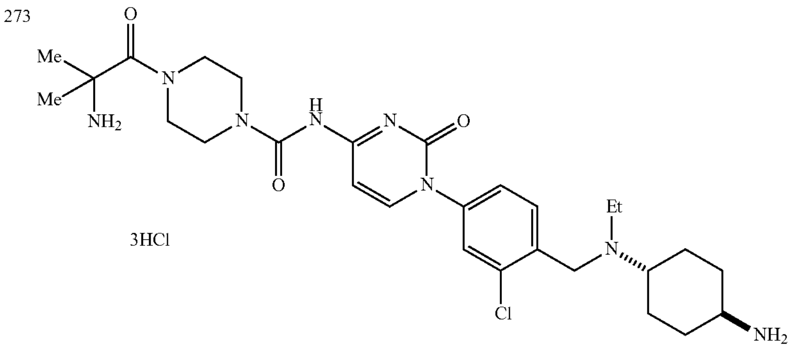 3HCl | 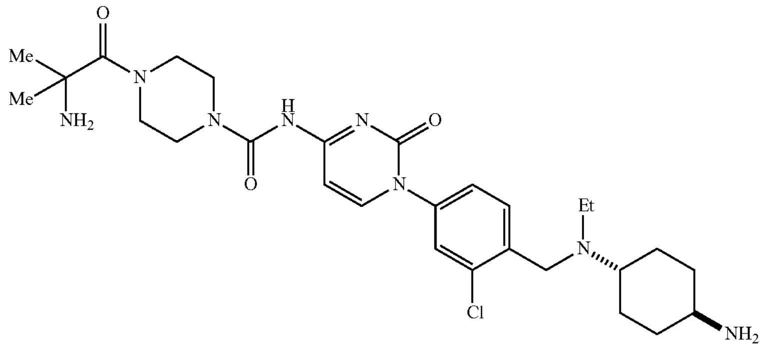 |

TABLE 11-continued
| Compounds of Formula I Continued | | |
|---|---|---|
| No. | Salt Structure | Free Base Structure |
| 274 | 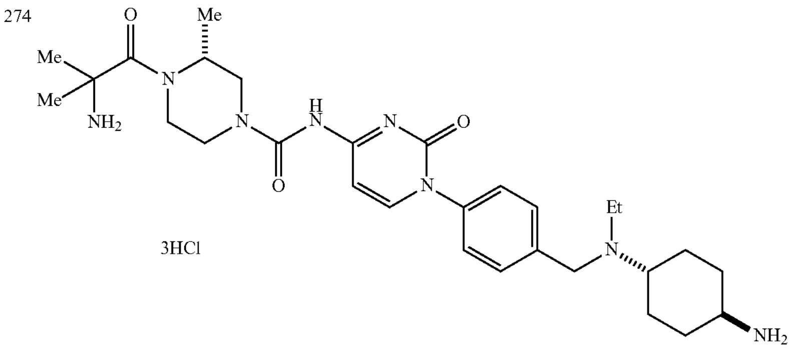 3HCl | 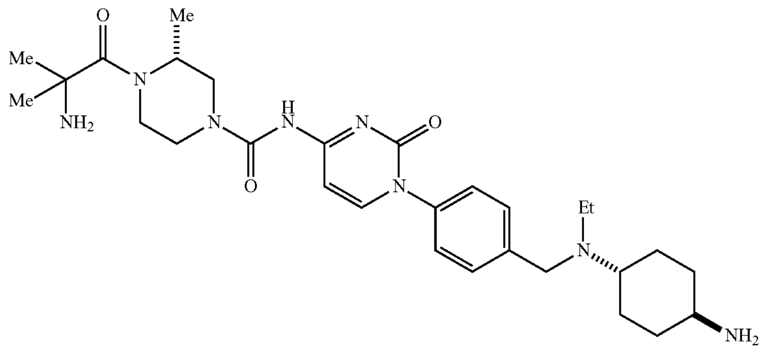 |
| 275 | 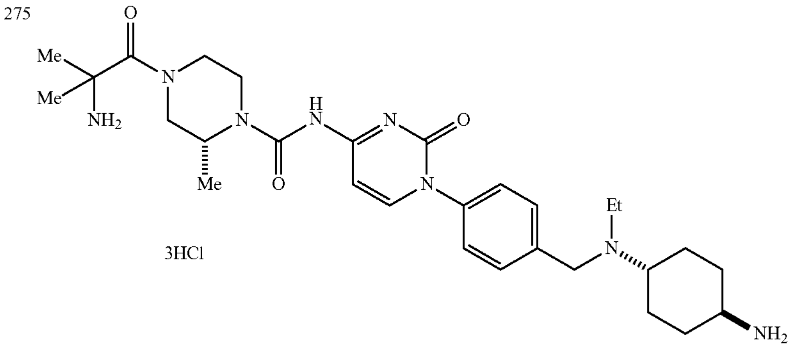 3HCl | 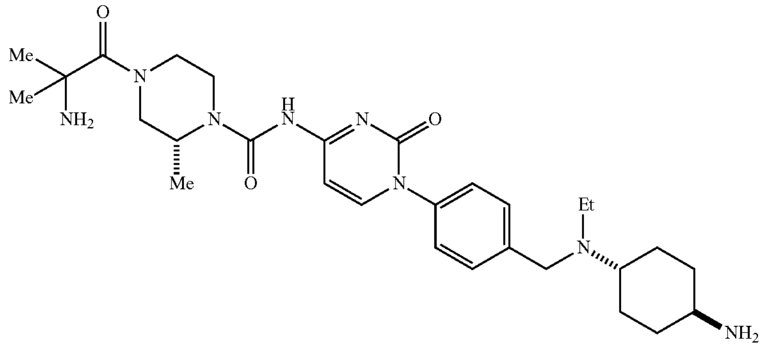 |

TABLE 11-continued
| Compounds of Formula I Continued | | |
|---|---|---|
| No. | Salt Structure | Free Base Structure |
| 276 | 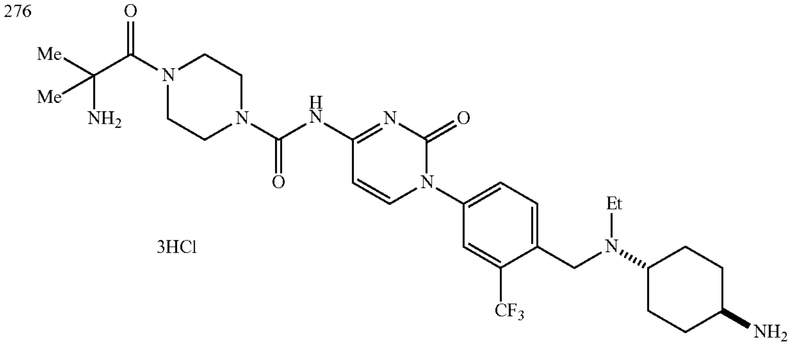 3HCl | 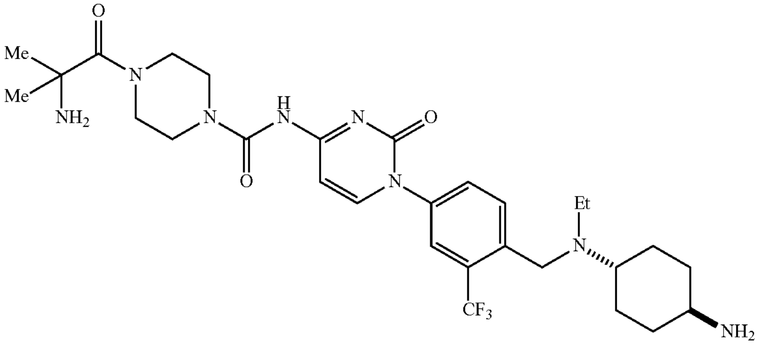 |
| 277 | 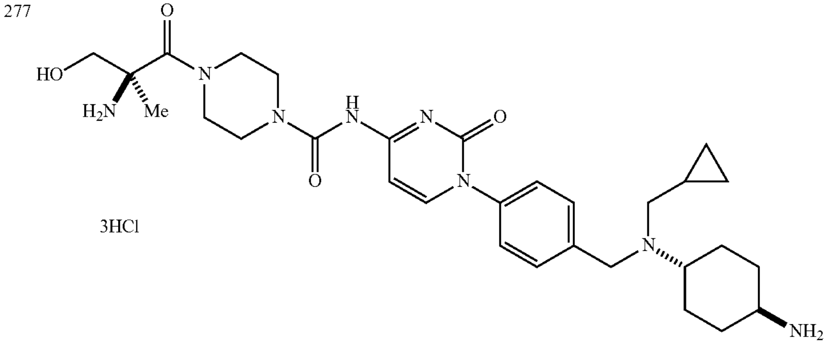 3HCl | 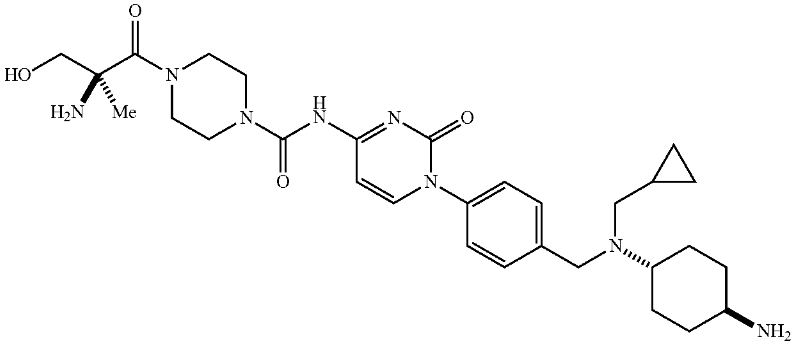 |

TABLE 11-continued
| Compounds of Formula I Continued | | |
|---|---|---|
| No. | Salt Structure | Free Base Structure |
| 278 | 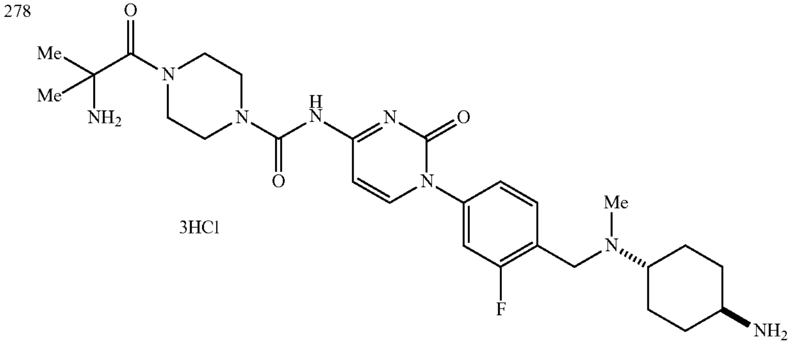 3HCl | 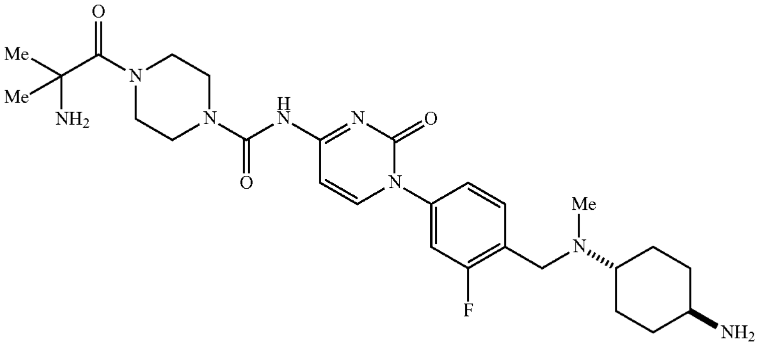 |
| 279 | 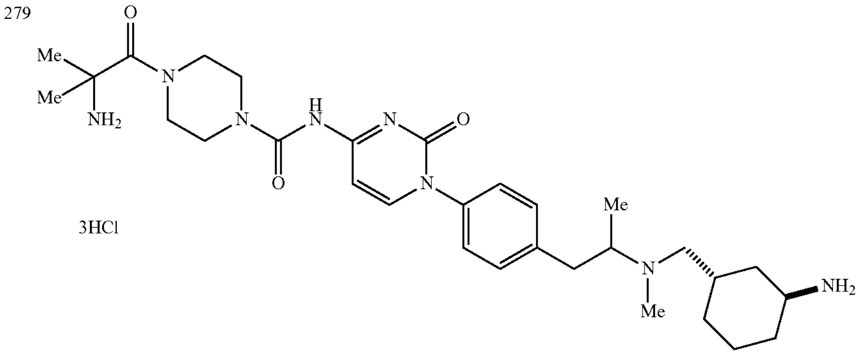 3HCl | 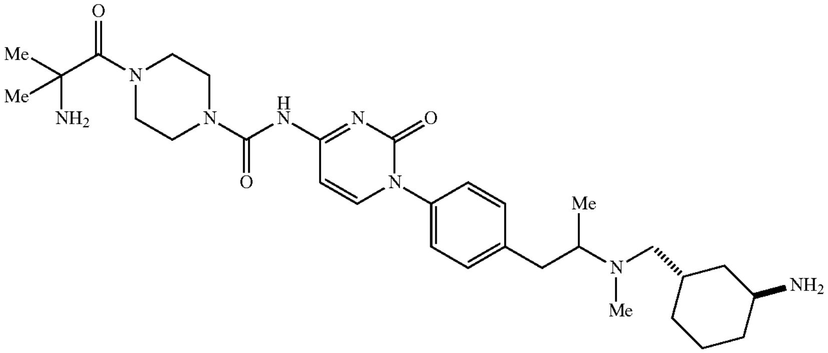 |

TABLE 11-continued
| Compounds of Formula I Continued | |
|---|---|
| No. Salt Structure | Free Base Structure |
| 280 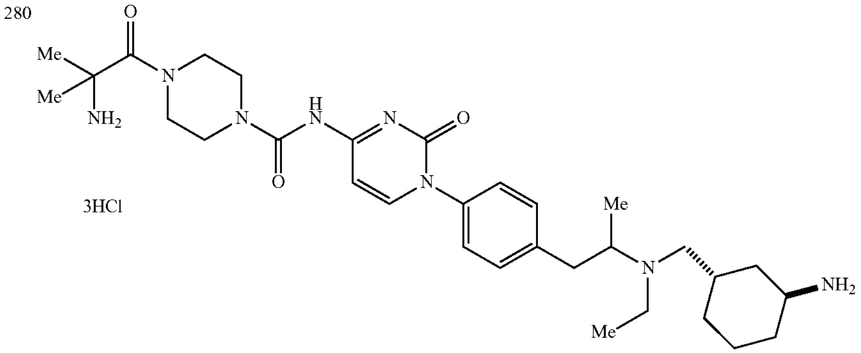 3HCl | 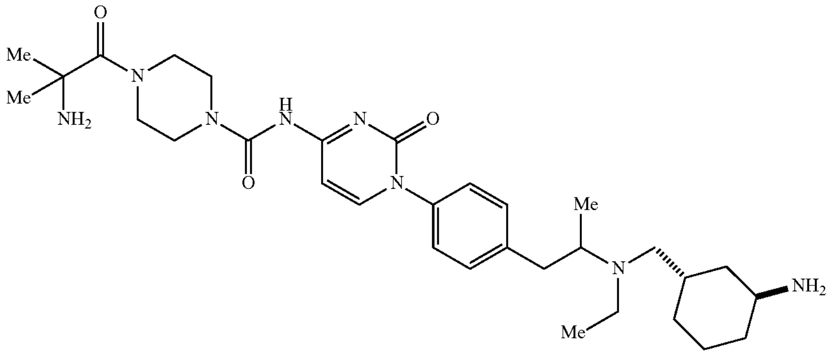 |
| 281 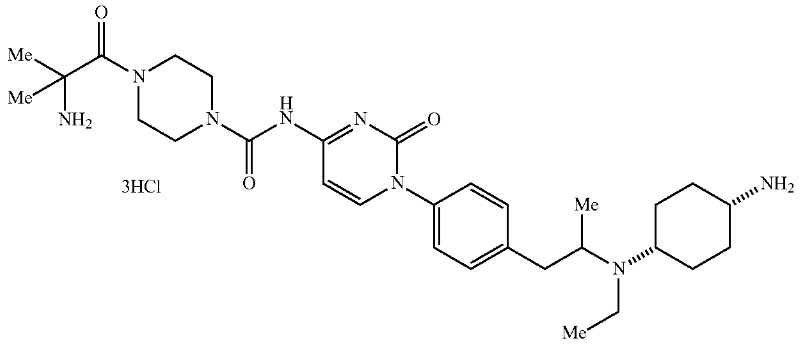 [SMILES: CCN(C(C)Cc1ccc(-n2ccc(NC(=O)N3CCN(C(=O)C(C)(C)N)CC3)nc2=O)cc1)[C@H]1CC[C@@H](N)CC1] 3HCl | 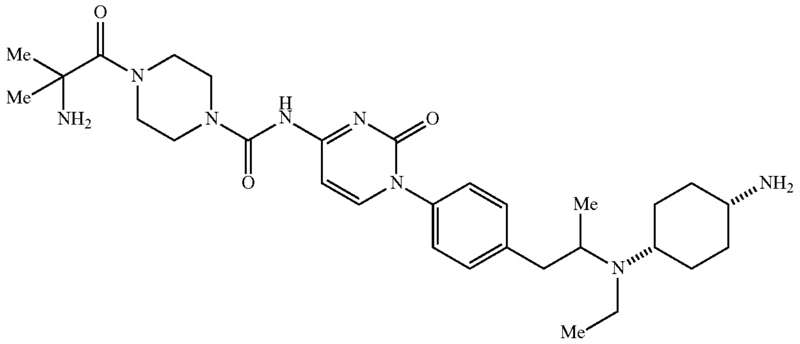 [SMILES: CCN(C(C)Cc1ccc(-n2ccc(NC(=O)N3CCN(C(=O)C(C)(C)N)CC3)nc2=O)cc1)[C@H]1CC[C@@H](N)CC1] |

TABLE 11-continued
| Compounds of Formula I Continued | |
|---|---|
| No. Salt Structure | Free Base Structure |
| 282 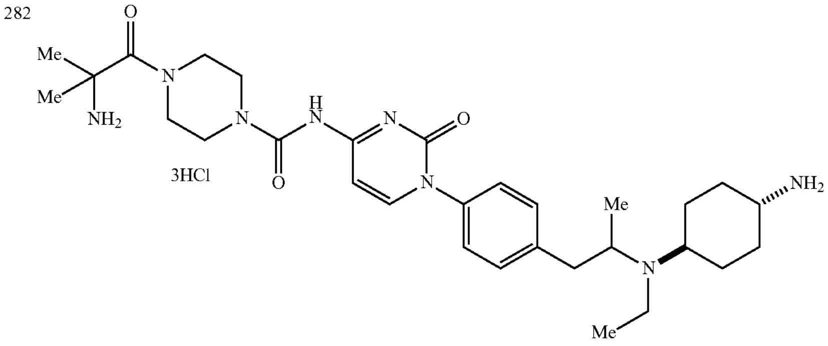 3HCl | 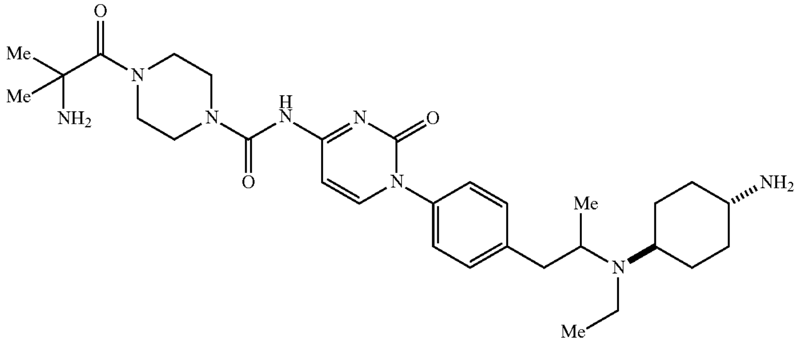 |
| 283 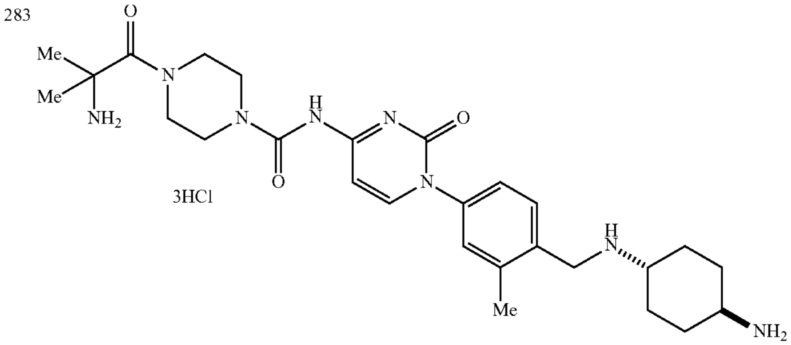 3HCl | 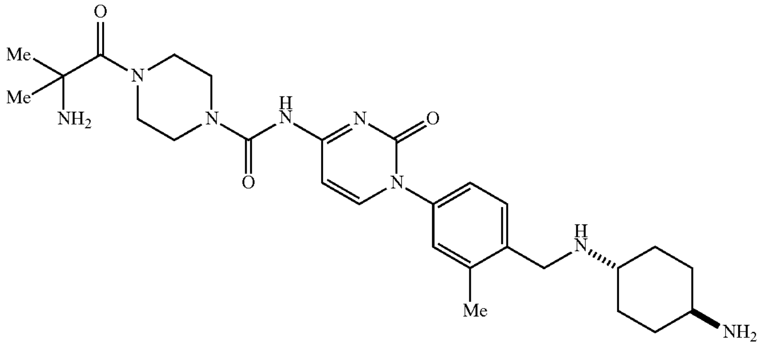 |

TABLE 11-continued
| Compounds of Formula I Continued | | |
|---|---|---|
| No. | Salt Structure | Free Base Structure |
| 284 | 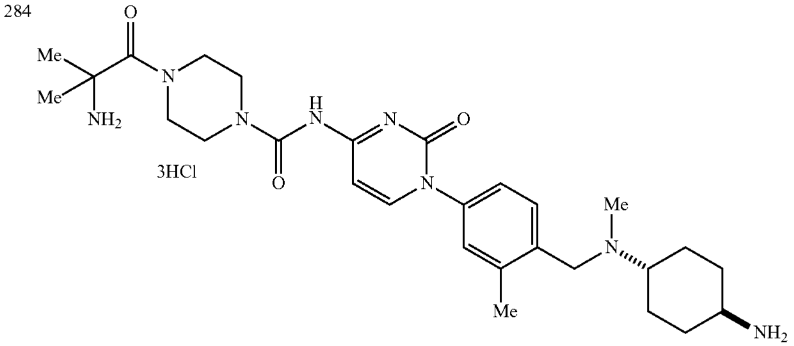 3HCl | 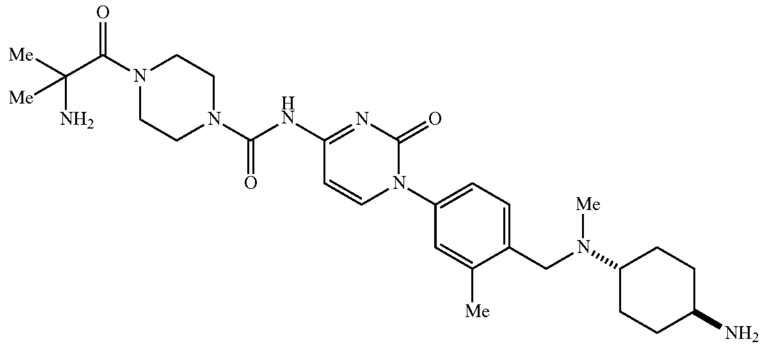 |
| 285 | 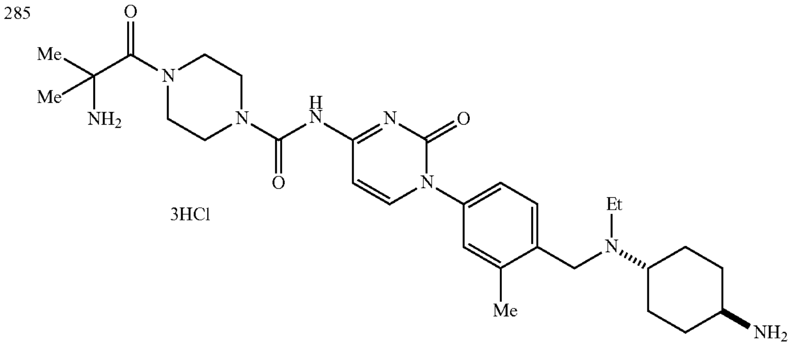 3HCl | 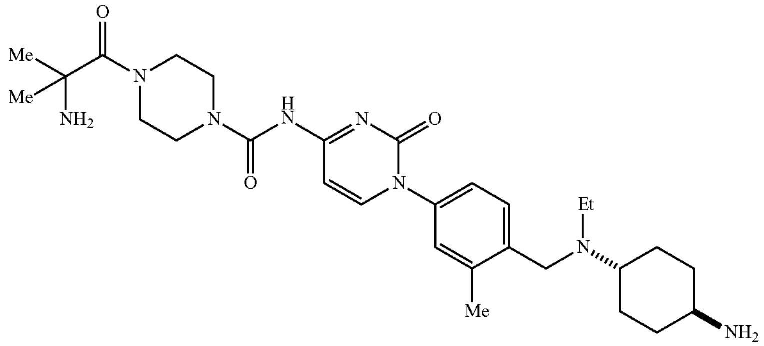 |

TABLE 11-continued
| Compounds of Formula I Continued | |
|---|---|
| No. Salt Structure | Free Base Structure |
| 286 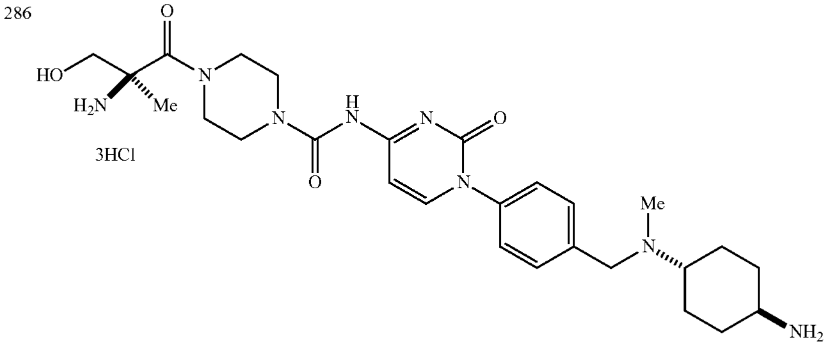 3HCl | 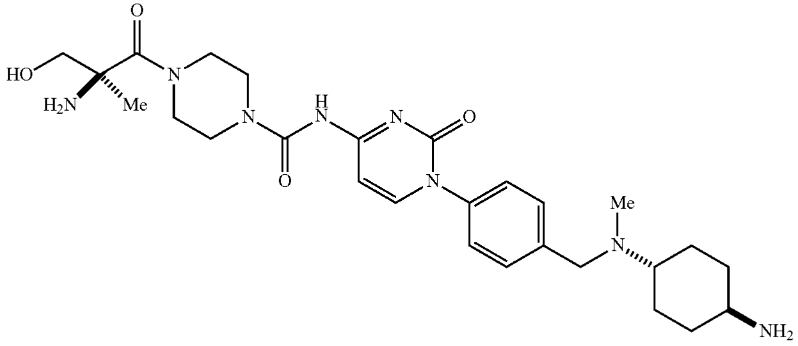 |
| 287 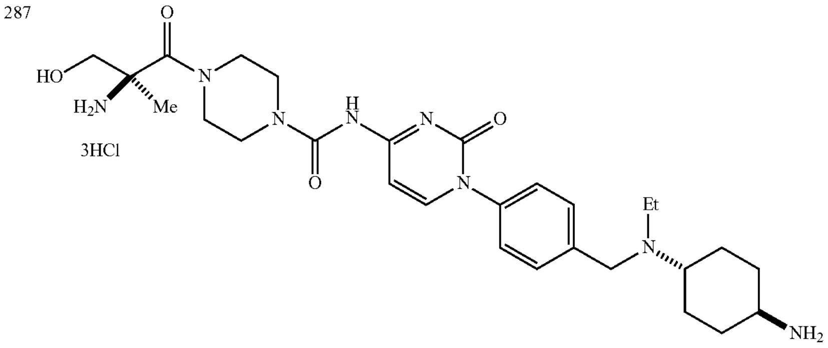 3HCl | 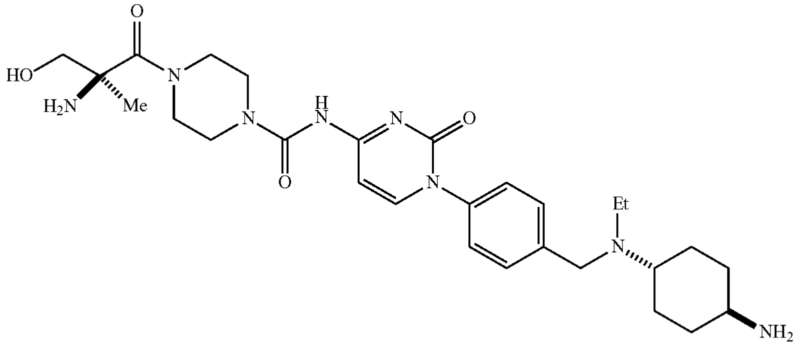 |

TABLE 11-continued
| Compounds of Formula I Continued | |
|---|---|
| No. Salt Structure | Free Base Structure |
| 288 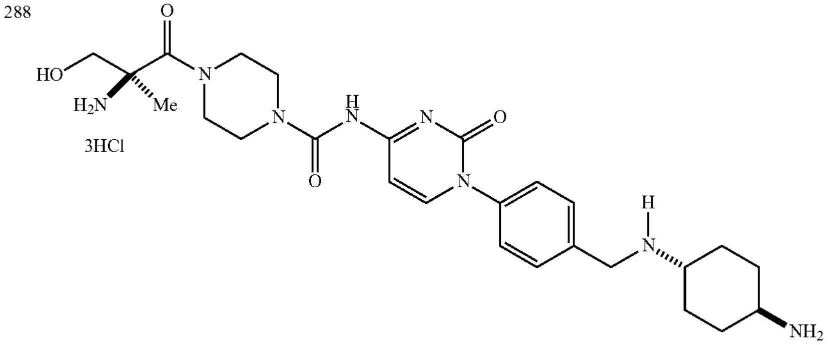 3HCl | 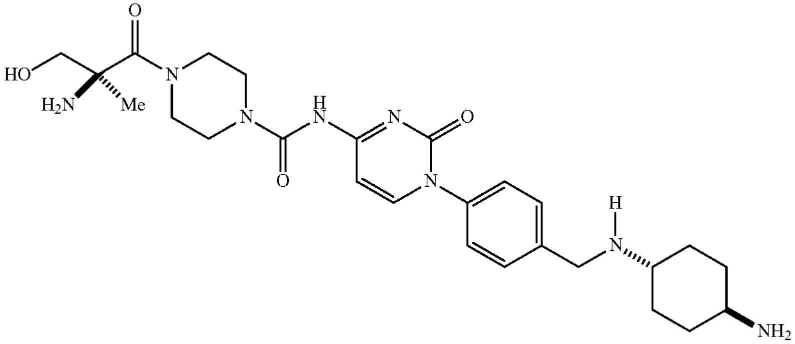 |
| 289 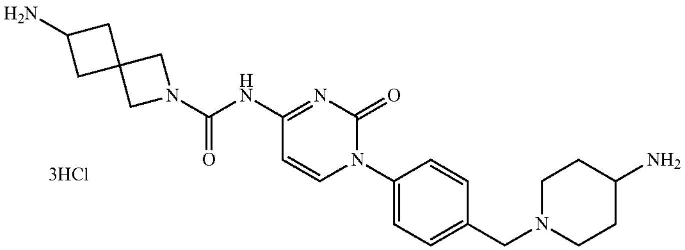 [SMILES: NC1CCN(Cc2ccc(-n3ccc(NC(=O)N4CC5(CC(N)C5)C4)nc3=O)cc2)CC1] 3HCl | 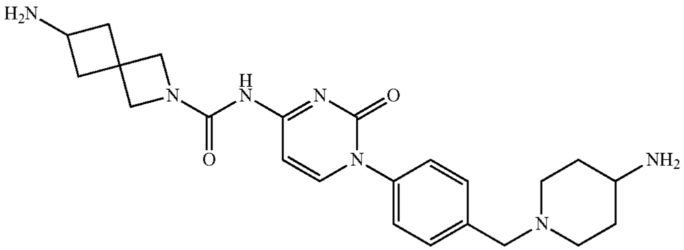 [SMILES: NC1CCN(Cc2ccc(-n3ccc(NC(=O)N4CC5(CC(N)C5)C4)nc3=O)cc2)CC1] |
| 290 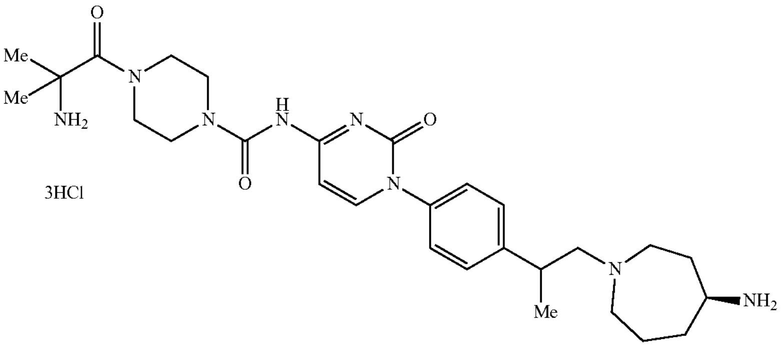 [SMILES: CC(CN1CCC[C@H](N)CC1)c1ccc(-n2ccc(NC(=O)N3CCN(C(=O)C(C)(C)N)CC3)nc2=O)cc1] 3HCl | 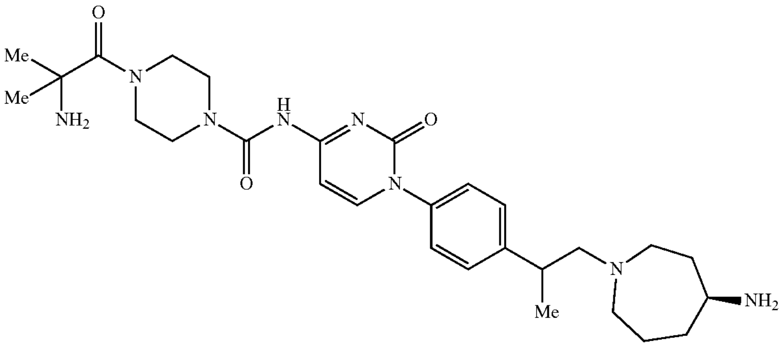 [SMILES: CC(CN1CCC[C@H](N)CC1)c1ccc(-n2ccc(NC(=O)N3CCN(C(=O)C(C)(C)N)CC3)nc2=O)cc1] |

TABLE 11-continued
| Compounds of Formula I Continued | | |
|---|---|---|
| No. | Salt Structure | Free Base Structure |
| 291 | 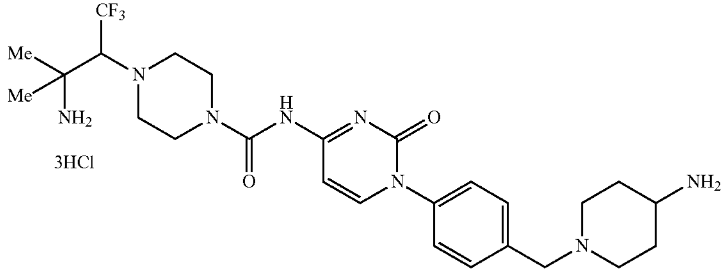 [SMILES: CC(C)(N)C(N1CCN(C(=O)Nc2ccn(-c3ccc(CN4CCC(N)CC4)cc3)c(=O)n2)CC1)C(F)(F)F] 3HCl | 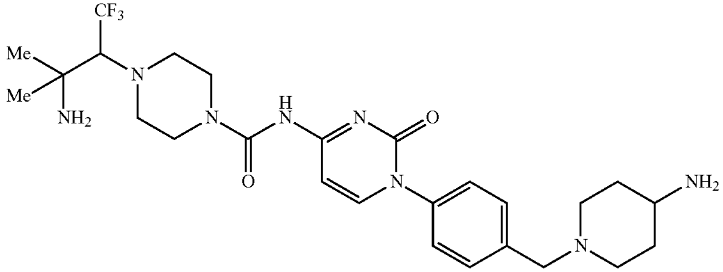 [SMILES: CC(C)(N)C(N1CCN(C(=O)Nc2ccn(-c3ccc(CN4CCC(N)CC4)cc3)c(=O)n2)CC1)C(F)(F)F] |
| 292 | 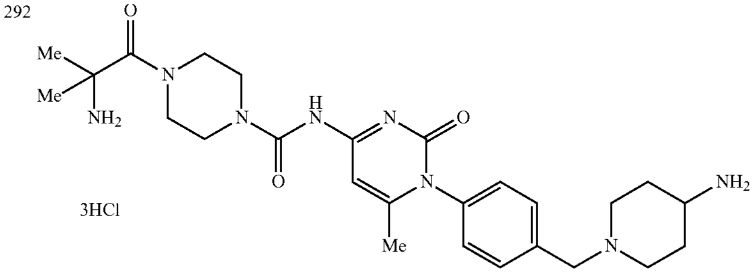 3HCl | 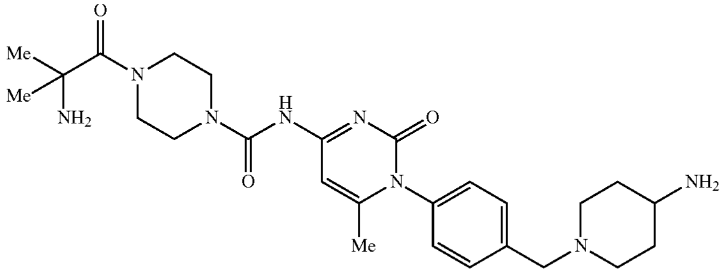 [SMILES: Cc1cc(NC(=O)N2CCN(C(=O)C(C)(C)N)CC2)nc(=O)n1-c1ccc(CN2CCC(N)CC2)cc1] |
| 293 | 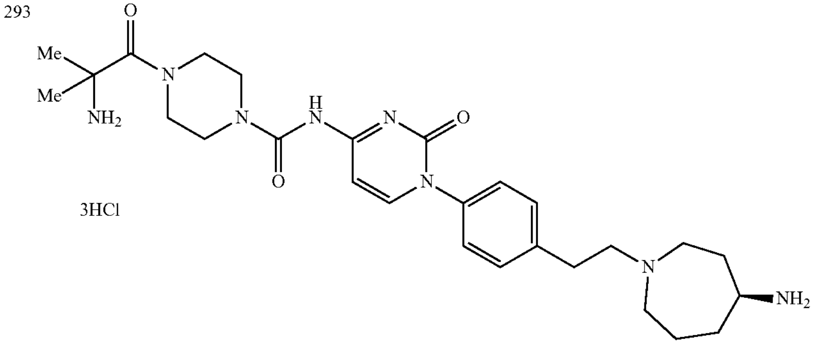 3HCl | 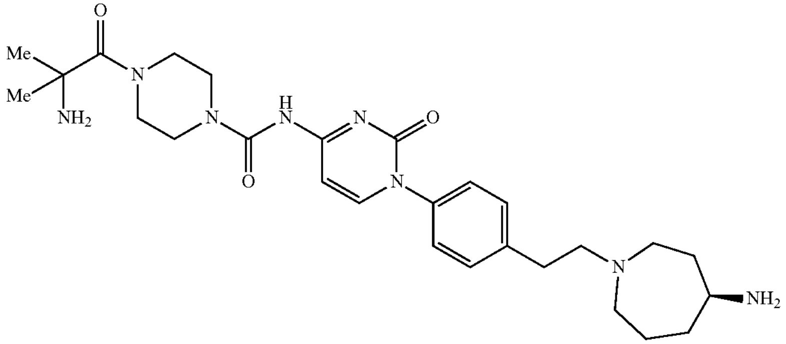 |

TABLE 11-continued
Compounds of Formula I Continued
| No. | Salt Structure | Free Base Structure |
|---|---|---|
| 294 | 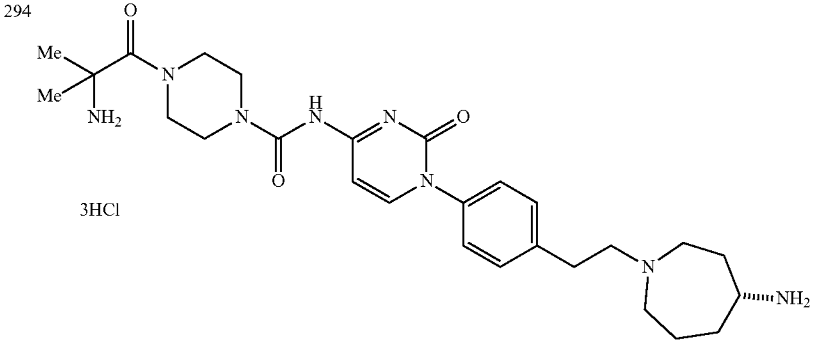 3HCl | 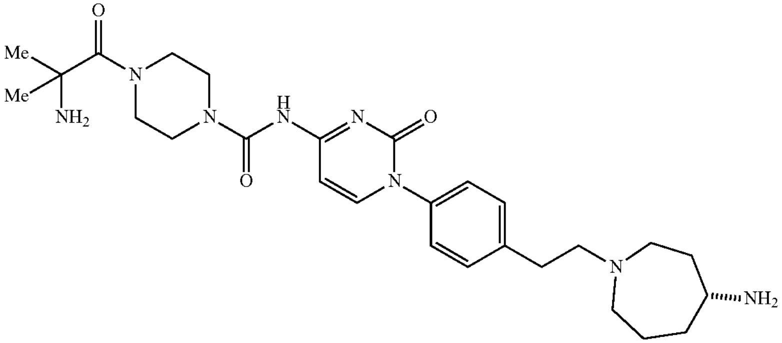 [SMILES: CC(C)(N)C(=O)N1CCN(C(=O)Nc2ccn(-c3ccc(CCN4CCC[C@@H](N)CC4)cc3)c(=O)n2)CC1] |
| 295 | 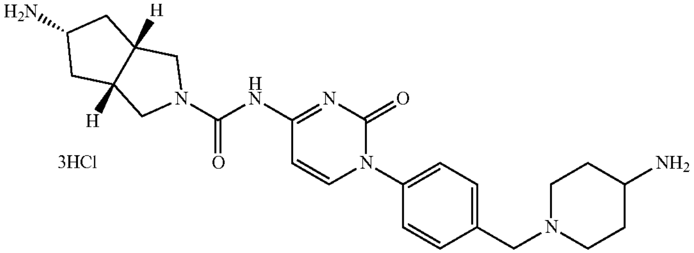 [SMILES: NC1CCN(Cc2ccc(-n3ccc(NC(=O)N4C[C@H]5C[C@@H](N)C[C@H]5C4)nc3=O)cc2)CC1] 3HCl | 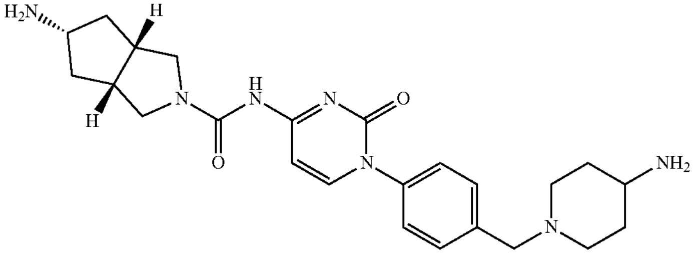 [SMILES: NC1CCN(Cc2ccc(-n3ccc(NC(=O)N4C[C@H]5C[C@@H](N)C[C@H]5C4)nc3=O)cc2)CC1] |
| 296 | 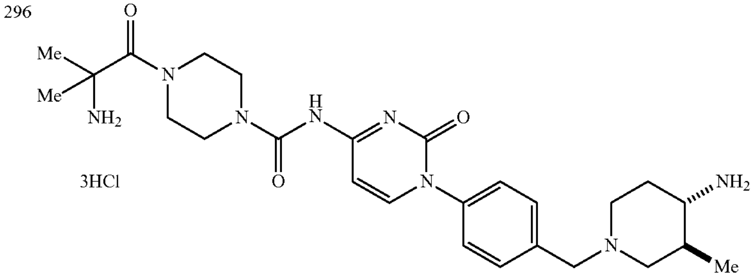 3HCl | 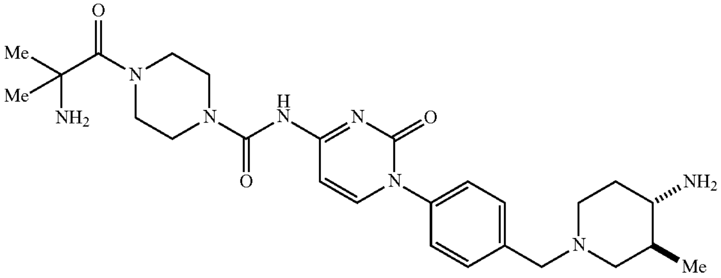 |

TABLE 11-continued
| Compounds of Formula I Continued | | |
|---|---|---|
| No. | Salt Structure | Free Base Structure |
| 297 | 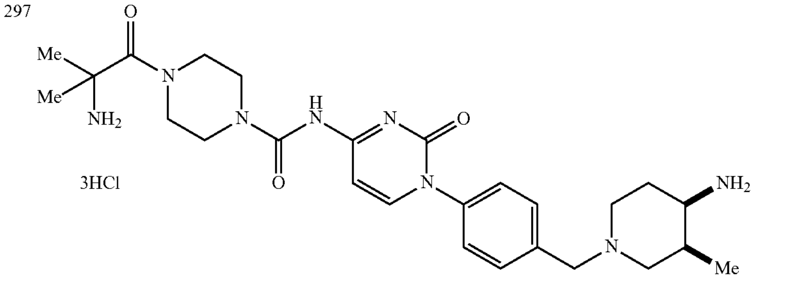 3HCl | 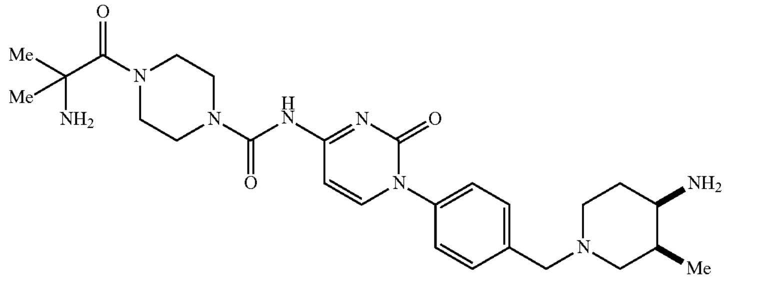 |
| 298 | 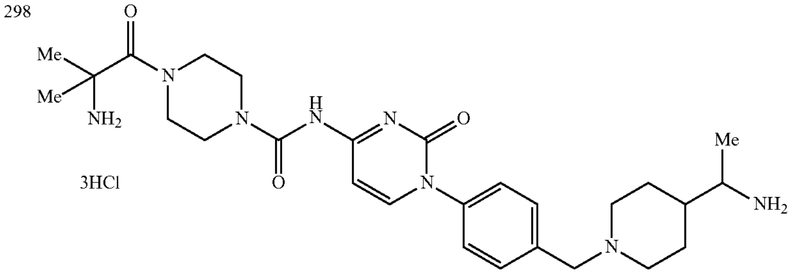 3HCl | 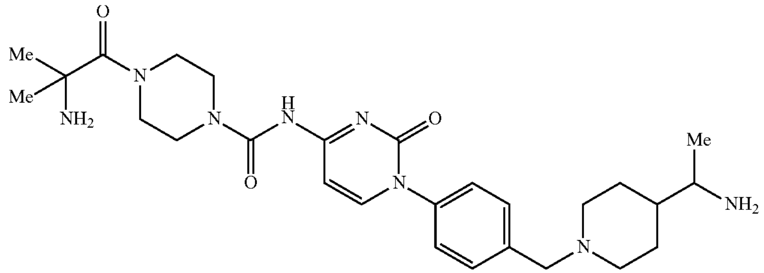 |
| 299 | 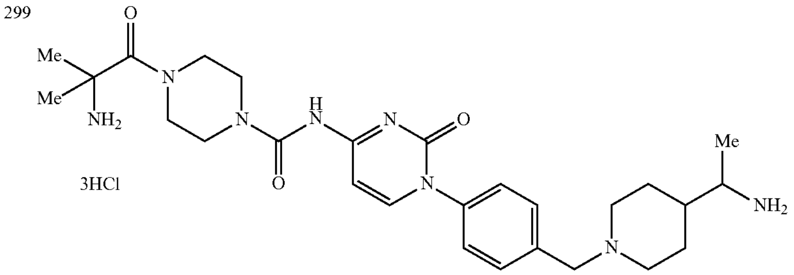 3HCl | 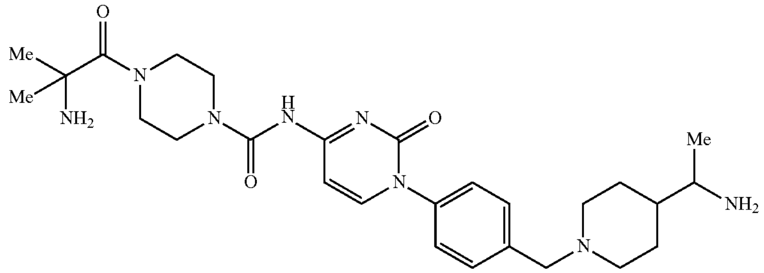 [SMILES: CC(N)C1CCN(Cc2ccc(-n3ccc(NC(=O)N4CCN(C(=O)C(C)(C)N)CC4)nc3=O)cc2)CC1] |

TABLE 11-continued
Compounds of Formula I Continued
| No. | Salt Structure | Free Base Structure |
|---|---|---|
| 300 | 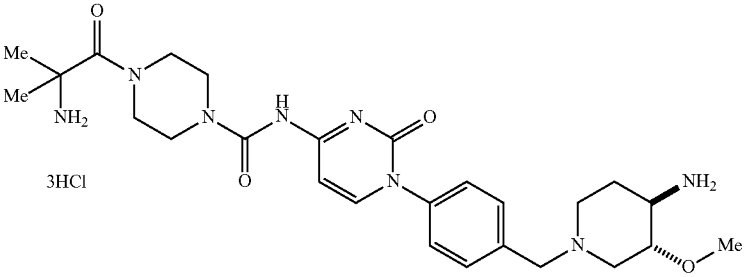 [SMILES: CO[C@@H]1CN(Cc2ccc(-n3ccc(NC(=O)N4CCN(C(=O)C(C)(C)N)CC4)nc3=O)cc2)CC[C@H]1N] 3HCl | 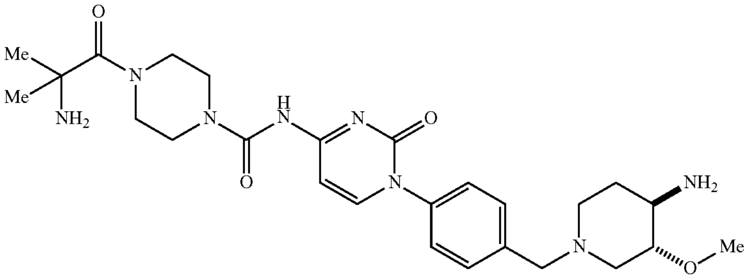 [SMILES: CO[C@@H]1CN(Cc2ccc(-n3ccc(NC(=O)N4CCN(C(=O)C(C)(C)N)CC4)nc3=O)cc2)CC[C@H]1N] |
| 301 | 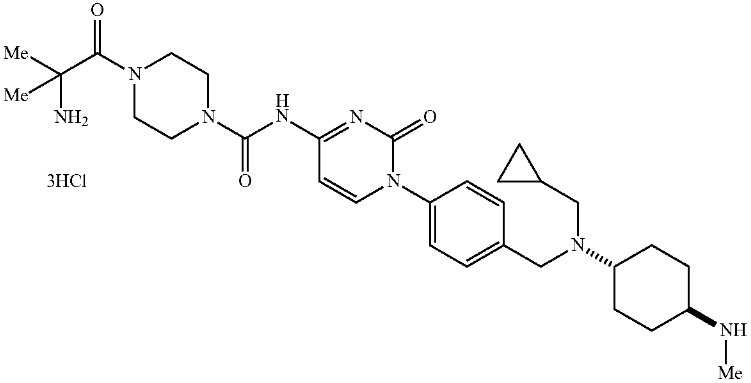 3HCl | 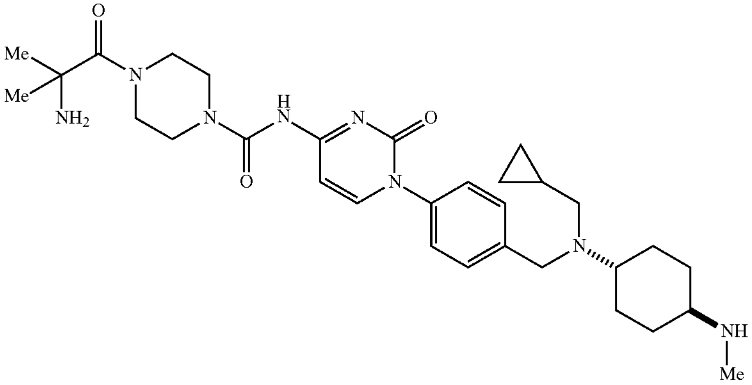 |
| 302 | 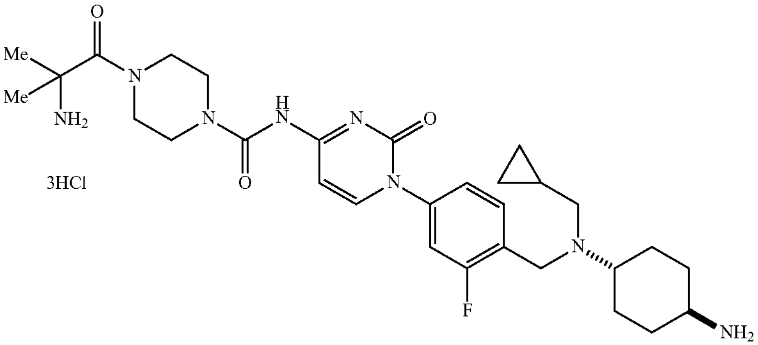 3HCl | 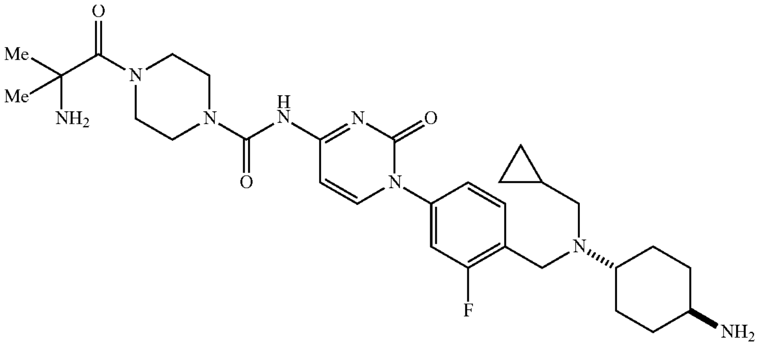 |

TABLE 11-continued
| Compounds of Formula I Continued | | |
|---|---|---|
| No. | Salt Structure | Free Base Structure |
| 303 | 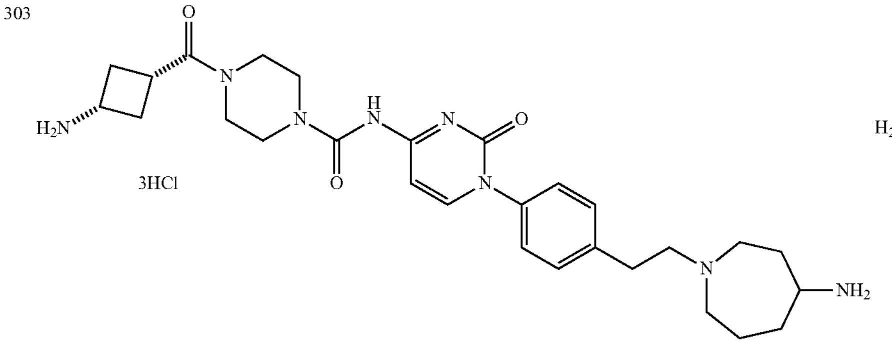 3HCl | 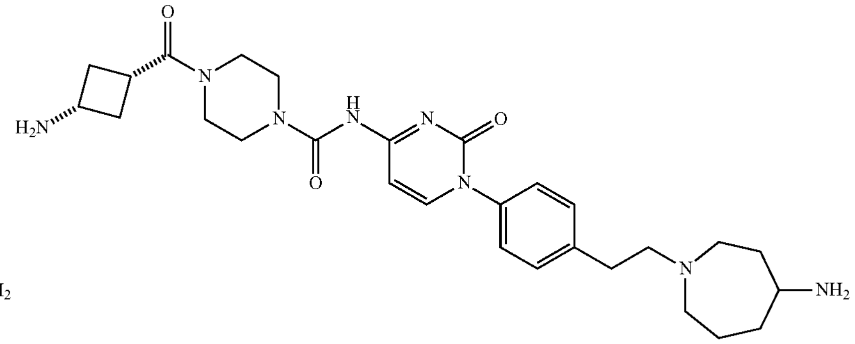 |
| 304 | 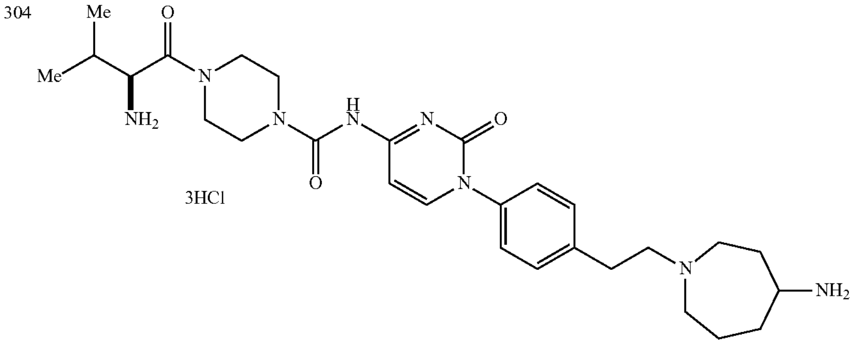 3HCl | 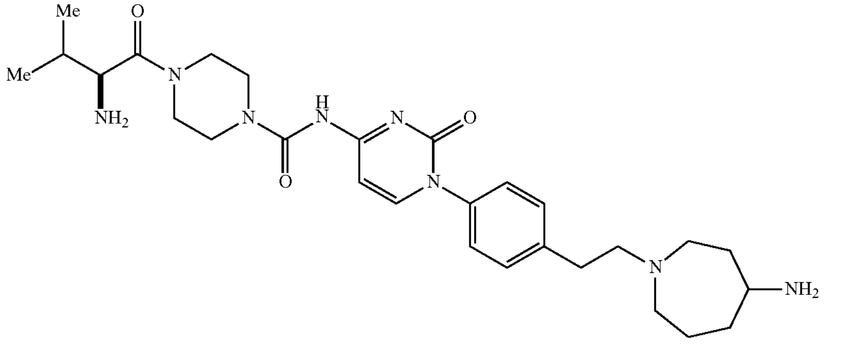 [SMILES: CC(C)[C@H](N)C(=O)N1CCN(C(=O)Nc2ccn(-c3ccc(CCN4CCCC(N)CC4)cc3)c(=O)n2)CC1] |

TABLE 11-continued
| Compounds of Formula I Continued | |
|---|---|
| No. Salt Structure | Free Base Structure |
| 305 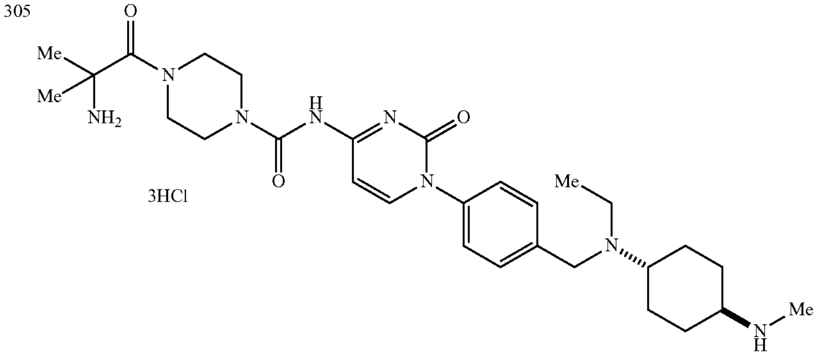 3HCl | 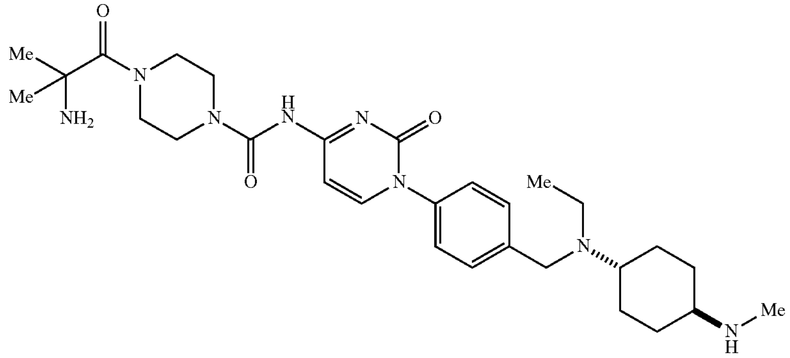 |
| 306 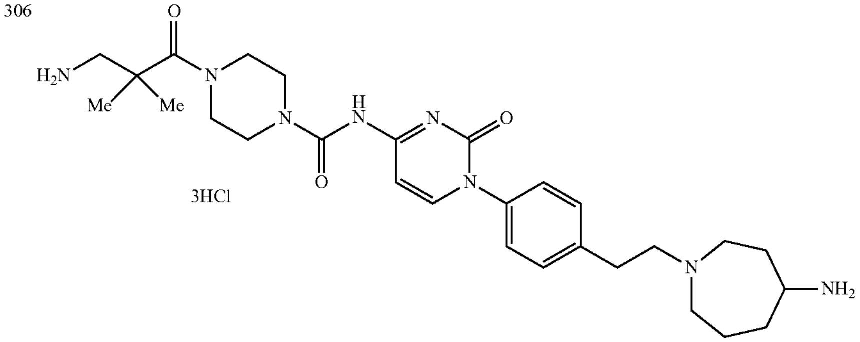 3HCl | 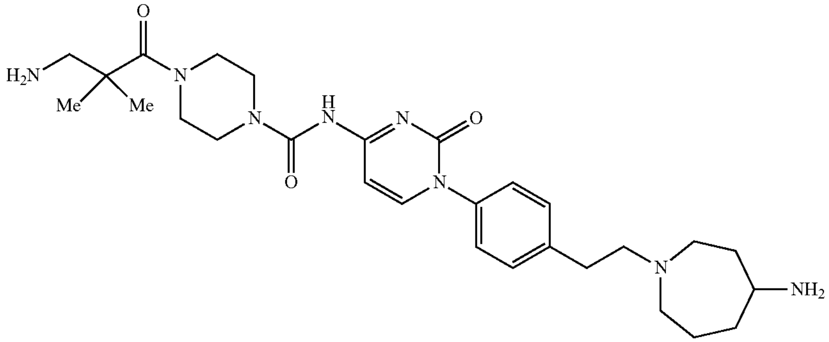 [SMILES: CC(C)(CN)C(=O)N1CCN(C(=O)Nc2ccn(-c3ccc(CCN4CCCC(N)CC4)cc3)c(=O)n2)CC1] |

TABLE 11-continued
| Compounds of Formula I Continued | |
|---|---|
| No. Salt Structure | Free Base Structure |
| 307 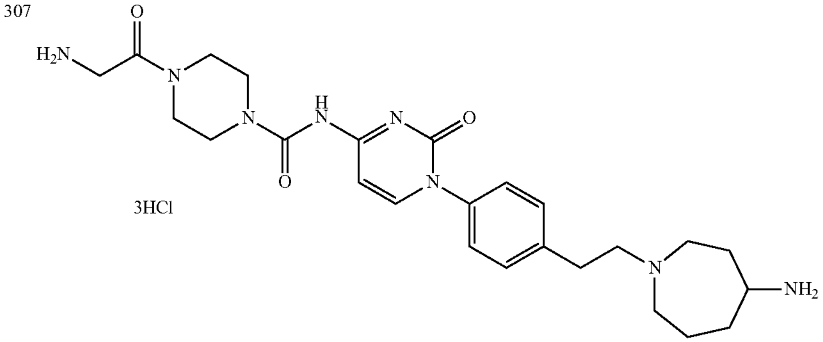 3HCl | 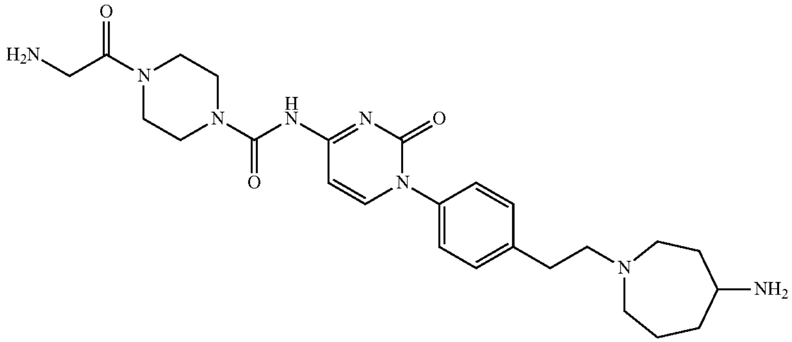 |
| 308 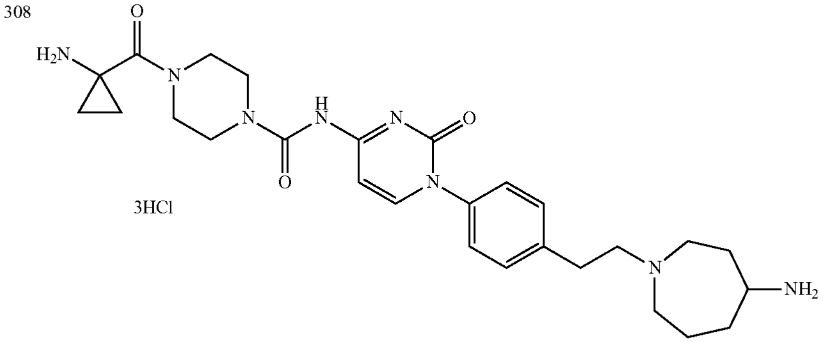 3HCl | 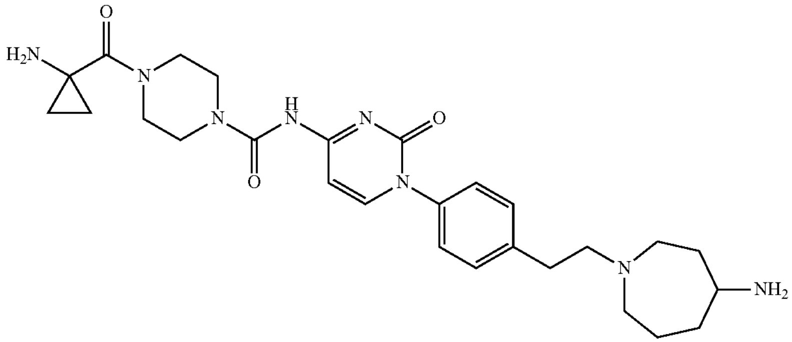 [SMILES: NC1CCCN(CCc2ccc(-n3ccc(NC(=O)N4CCN(C(=O)C5(N)CC5)CC4)nc3=O)cc2)CC1] |

TABLE 11-continued
| Compounds of Formula I Continued | |
|---|---|
| No. Salt Structure | Free Base Structure |
| 309 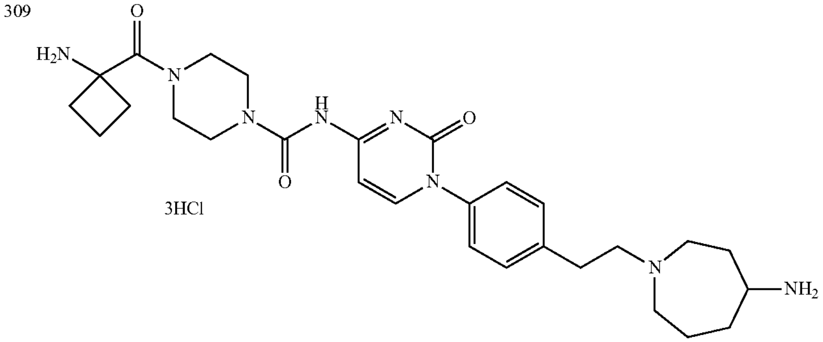 3HCl | 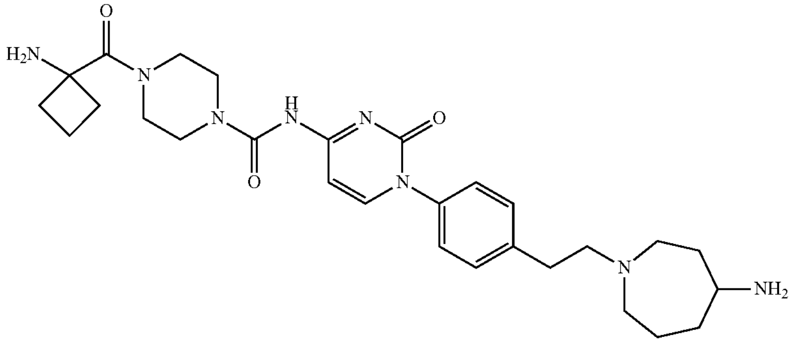 [SMILES: NC1CCCN(CCc2ccc(-n3ccc(NC(=O)N4CCN(C(=O)C5(N)CCC5)CC4)nc3=O)cc2)CC1] |
| 310 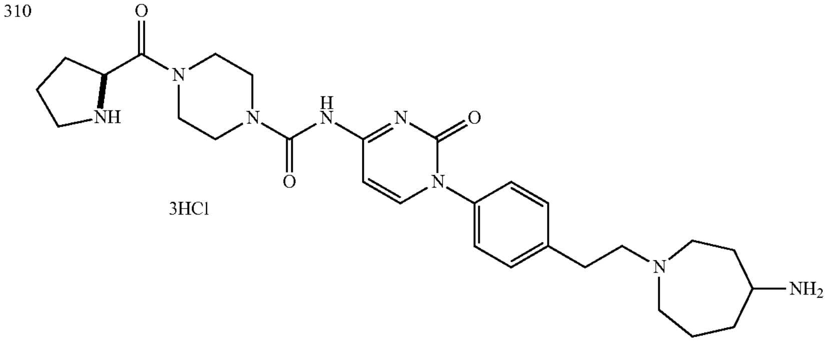 3HCl | 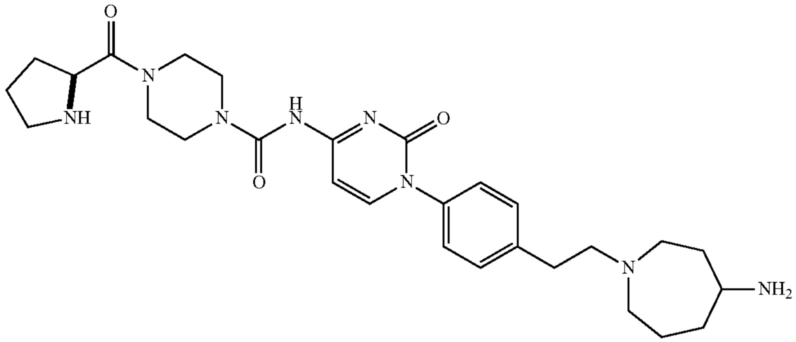 |

TABLE 11-continued
| Compounds of Formula I Continued | | |
| --- | --- | --- |
| No. | Salt Structure | Free Base Structure |
| 311 | 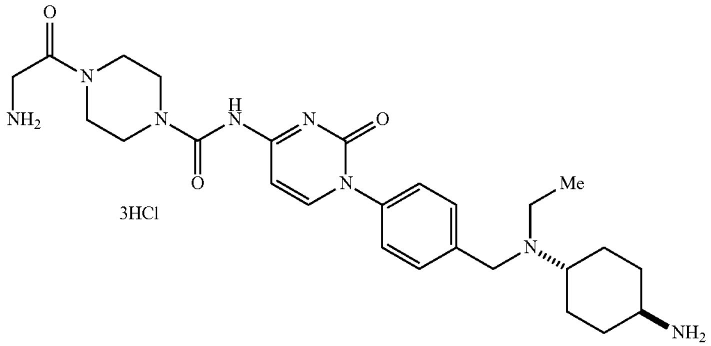 3HCl | 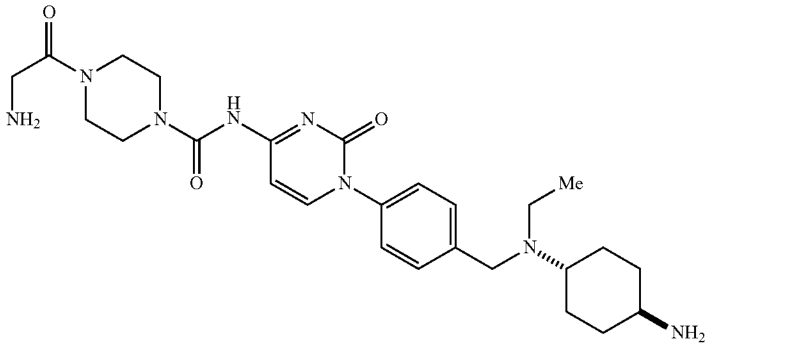 |
| 312 | 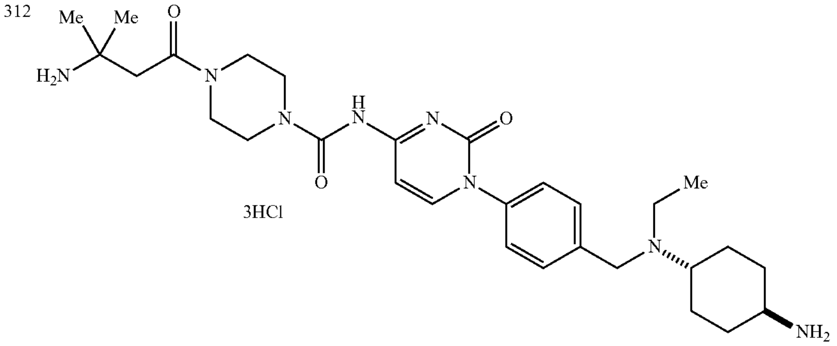 3HCl | 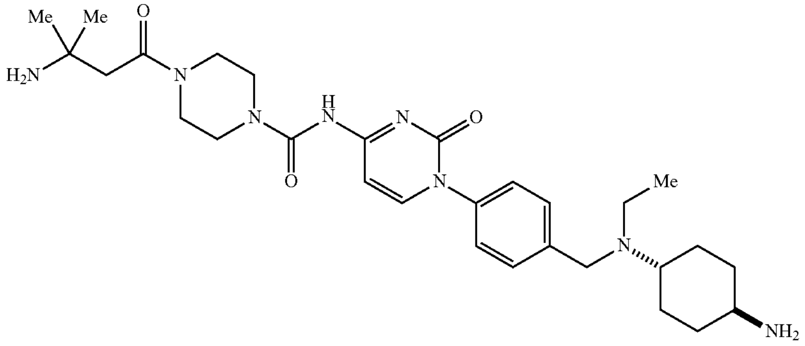 |

TABLE 11-continued
| Compounds of Formula I Continued | | |
|---|---|---|
| No. | Salt Structure | Free Base Structure |
| 313 | 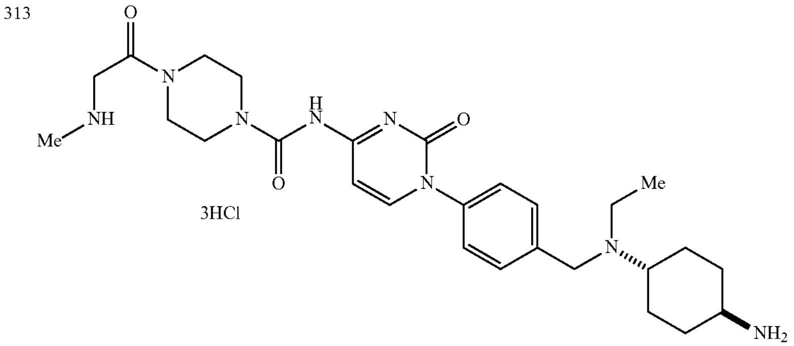 3HCl | 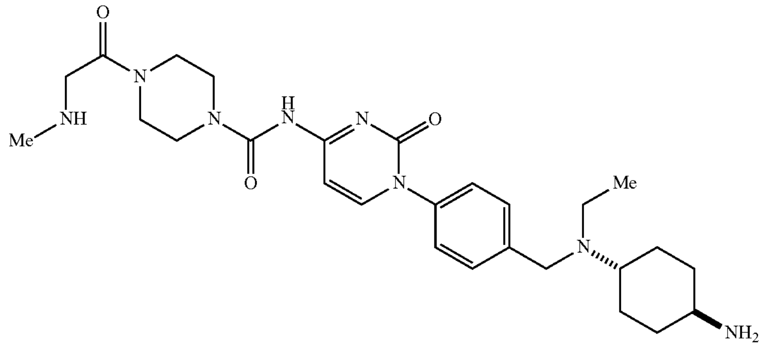 |
| 314 | 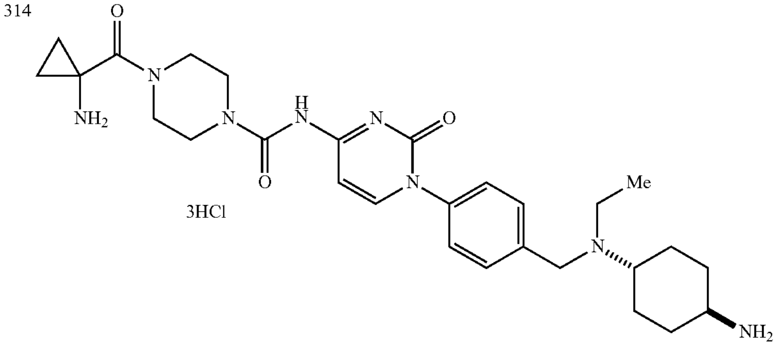 3HCl | 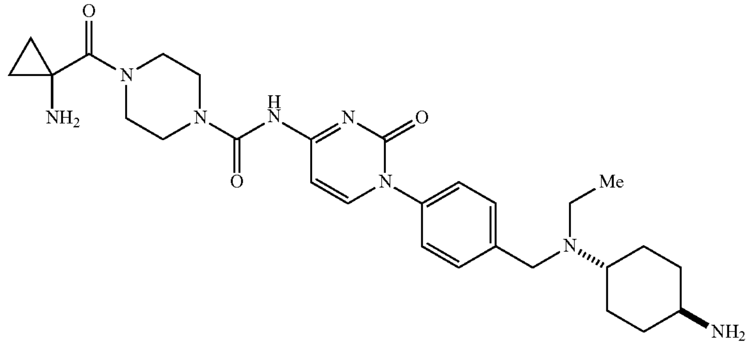 |

TABLE 11-continued
| Compounds of Formula I Continued | | |
|---|---|---|
| No. | Salt Structure | Free Base Structure |
| 315 | 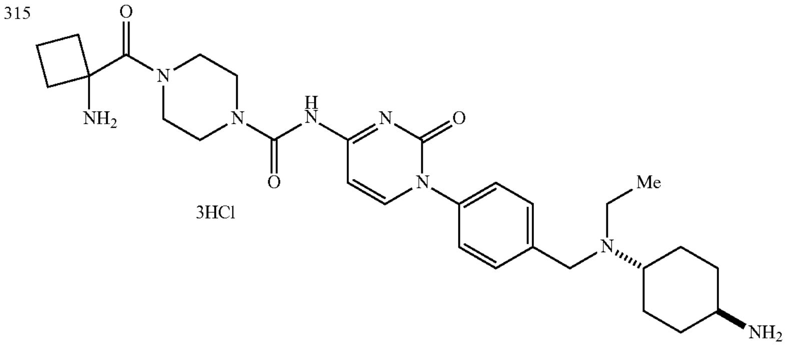 3HCl | 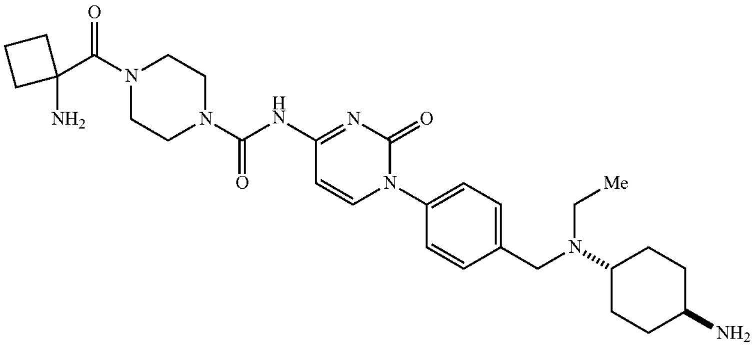 |
| 316 | 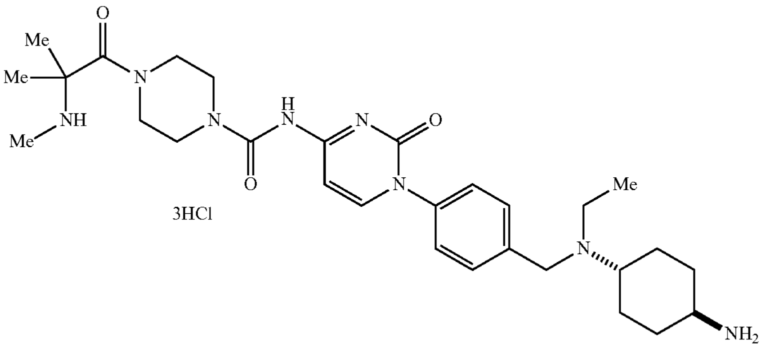 3HCl | 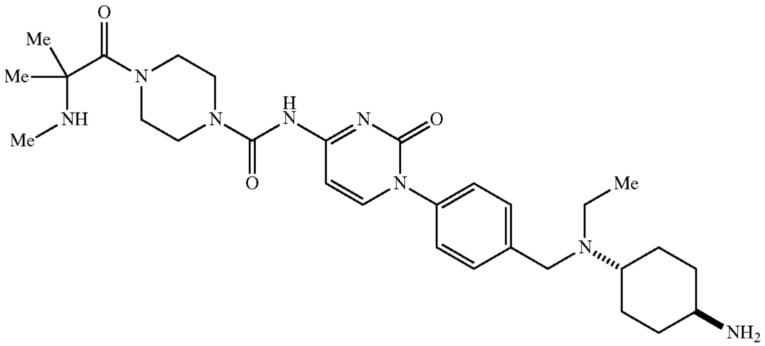 |

TABLE 11-continued
| Compounds of Formula I Continued | |
|---|---|
| No. Salt Structure | Free Base Structure |
| 317 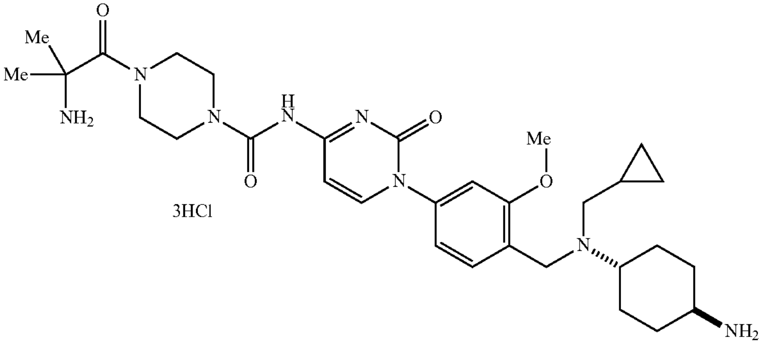 3HCl | 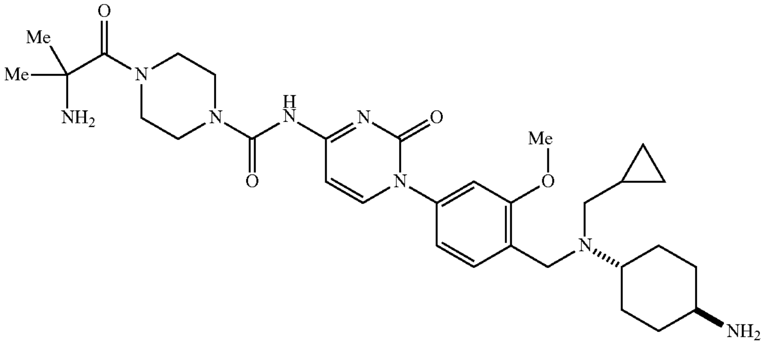 |
| 318 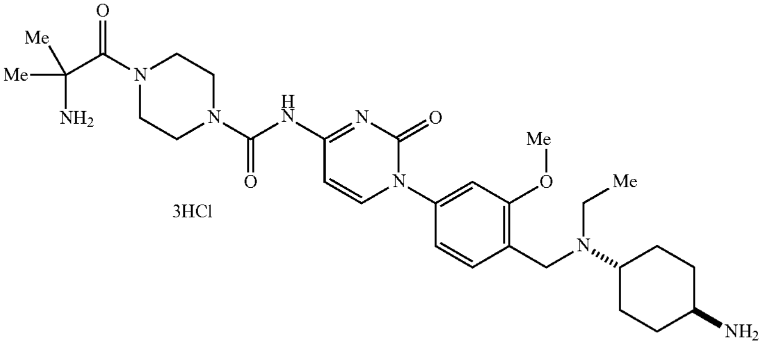 3HCl | 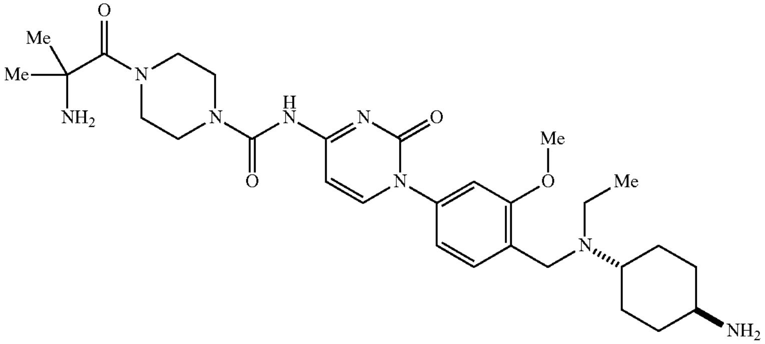 |
| 319 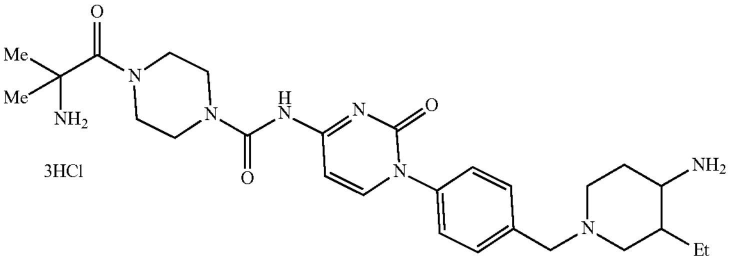 [SMILES: CCC1CN(Cc2ccc(-n3ccc(NC(=O)N4CCN(C(=O)C(C)(C)N)CC4)nc3=O)cc2)CCC1N] 3HCl | 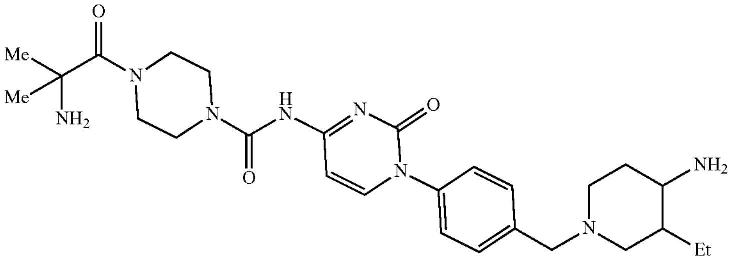 [SMILES: CCC1CN(Cc2ccc(-n3ccc(NC(=O)N4CCN(C(=O)C(C)(C)N)CC4)nc3=O)cc2)CCC1N] |

TABLE 11-continued
| Compounds of Formula I Continued | | | |
|---|---|---|---|
| No. | Salt Structure | | Free Base Structure |
| 320 | 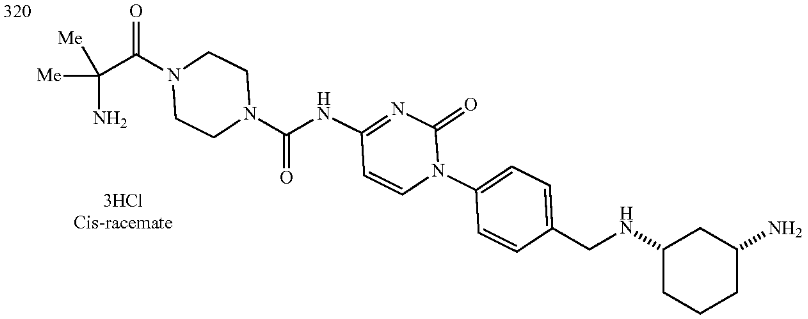 | 3HCl Cis-racemate | 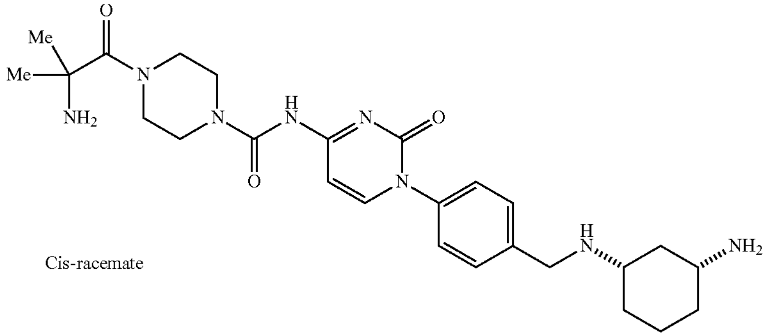 Cis-racemate |
| 321 | 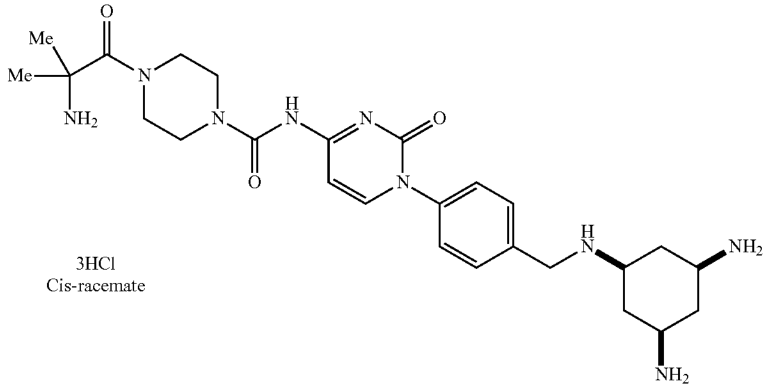 | 3HCl Cis-racemate | 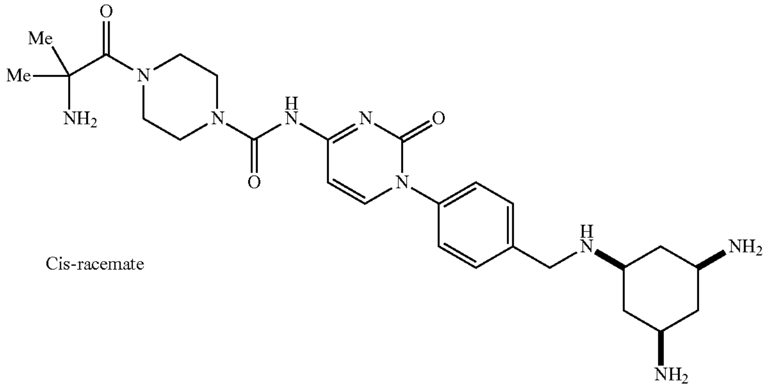 Cis-racemate |
| 322 | 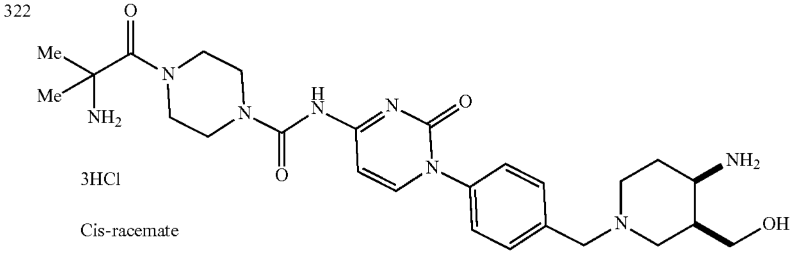 | 3HCl Cis-racemate | 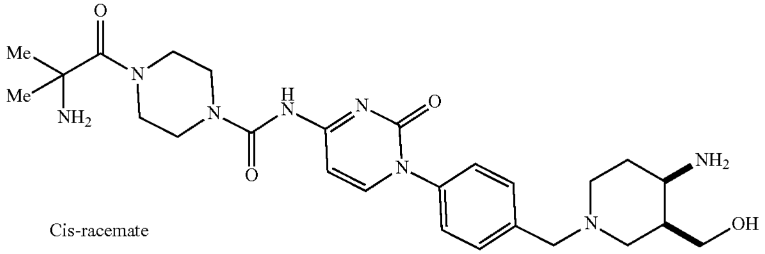 [SMILES: CC(C)(N)C(=O)N1CCN(C(=O)Nc2ccn(-c3ccc(CN4CC[C@@H](N)[C@@H](CO)C4)cc3)c(=O)n2)CC1] Cis-racemate |

TABLE 11-continued
| Compounds of Formula I Continued | |
|---|---|
| No. Salt Structure | Free Base Structure |
| 323 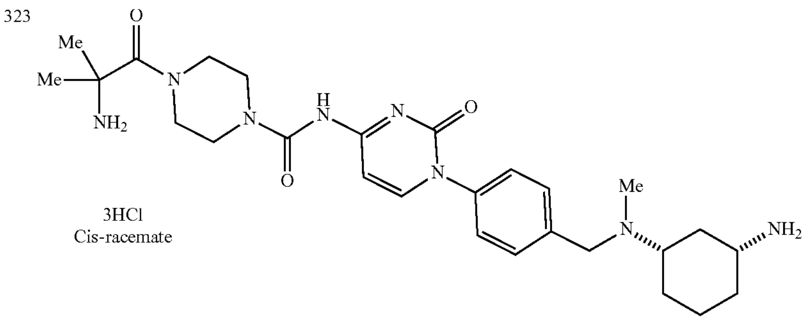 3HCl Cis-racemate | 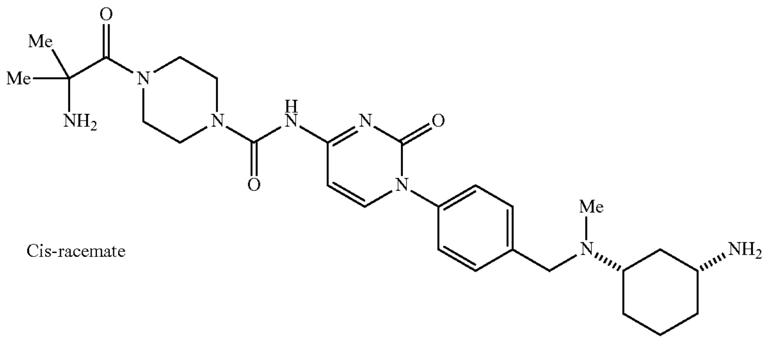 Cis-racemate |
| 324 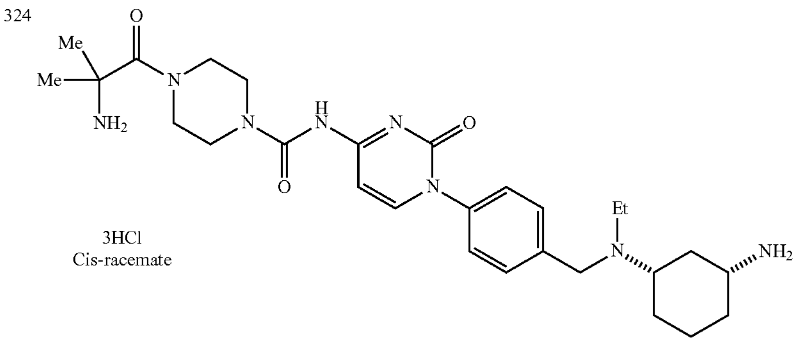 3HCl Cis-racemate | 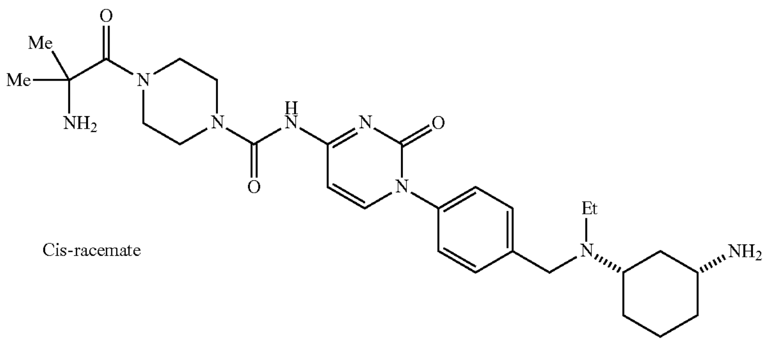 Cis-racemate |

TABLE 11-continued
| Compounds of Formula I Continued | | |
|---|---|---|
| No. | Salt Structure | Free Base Structure |
| 325 | 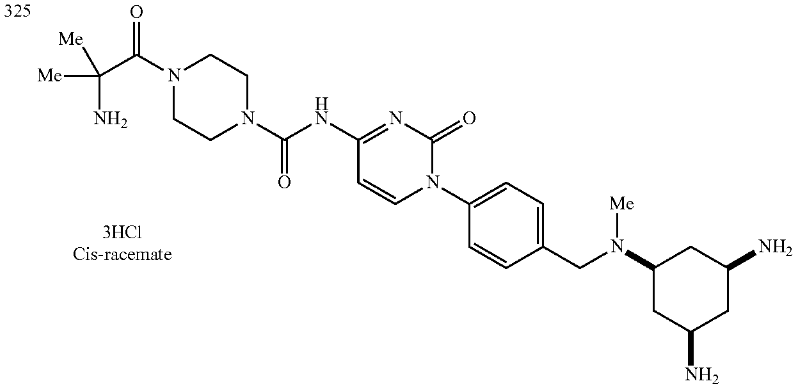 3HCl Cis-racemate | 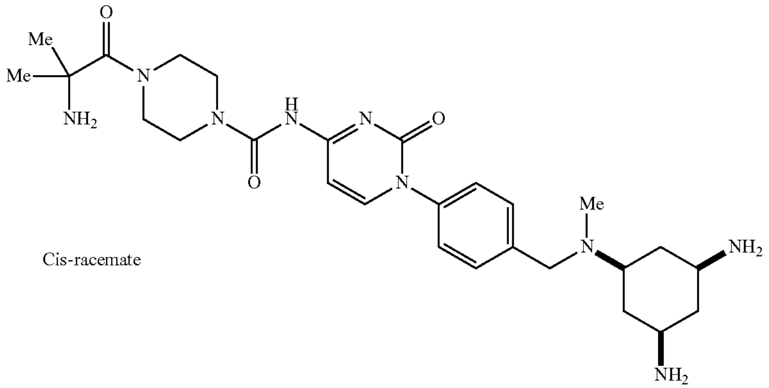 Cis-racemate |
| 326 | 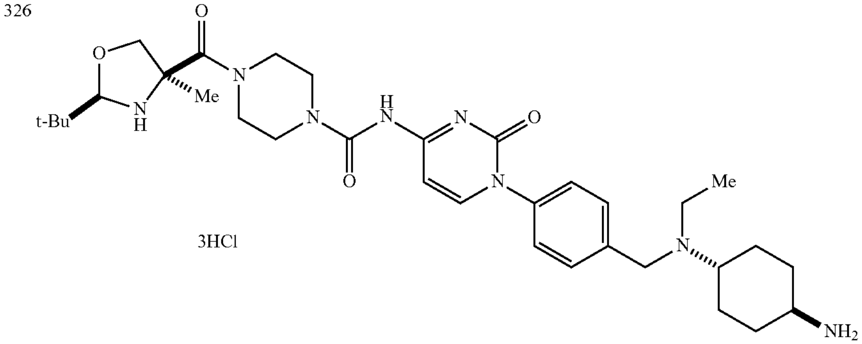 3HCl | 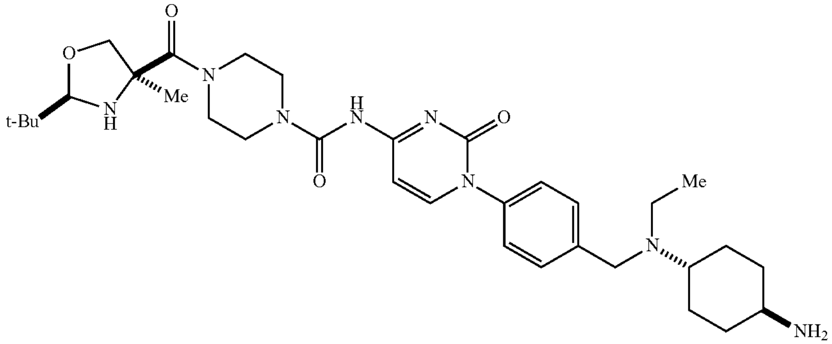 |

TABLE 11-continued
Compounds of Formula I Continued
| No. | Salt Structure | Free Base Structure |
|---|---|---|
| 327 | 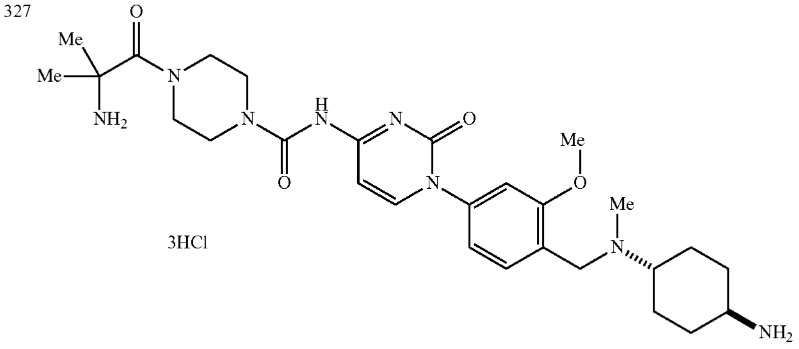 3HCl | 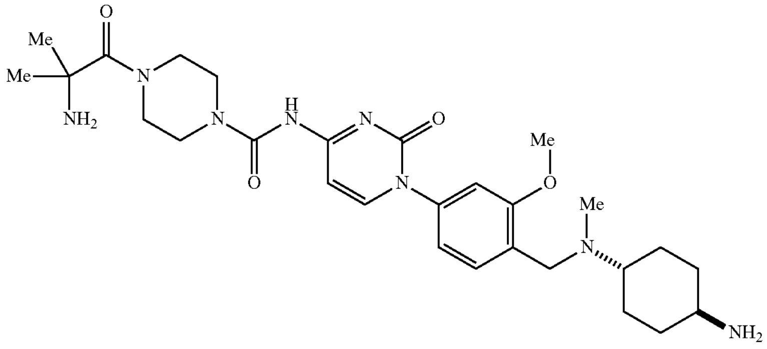 |
| 328 | 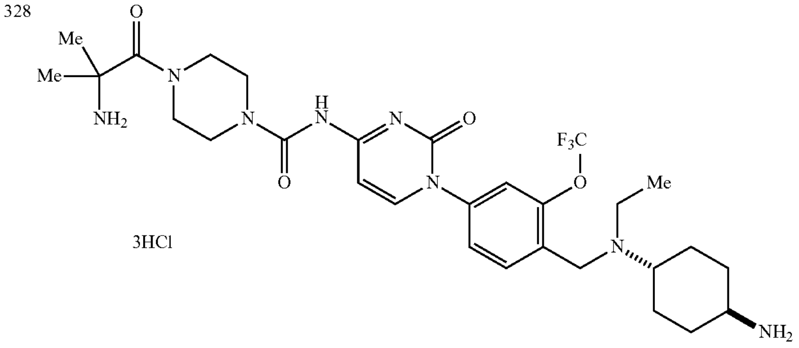 3HCl | 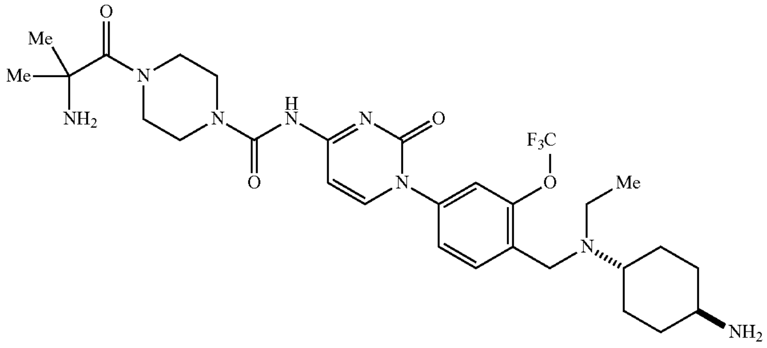 |

TABLE 11-continued
| Compounds of Formula I Continued | |
|---|---|
| No. Salt Structure | Free Base Structure |
| 329 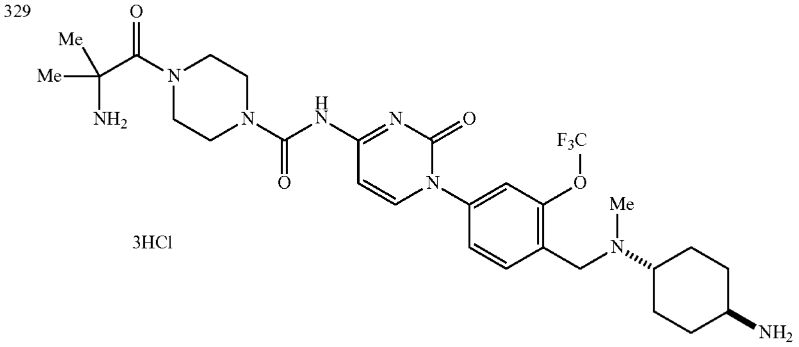 3HCl | 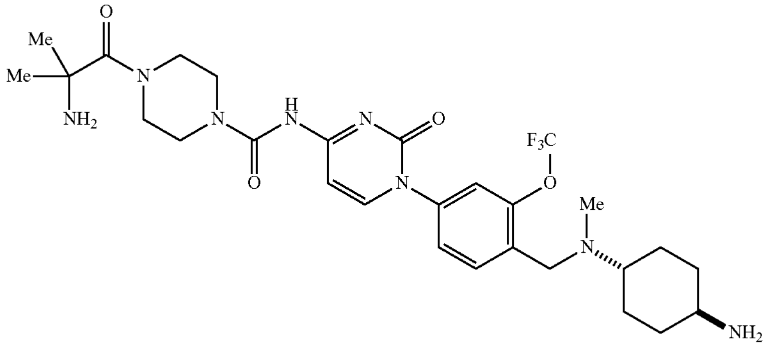 |
| 330 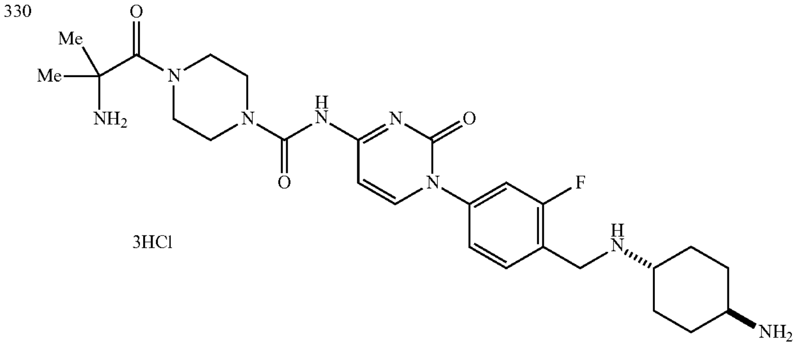 3HCl | 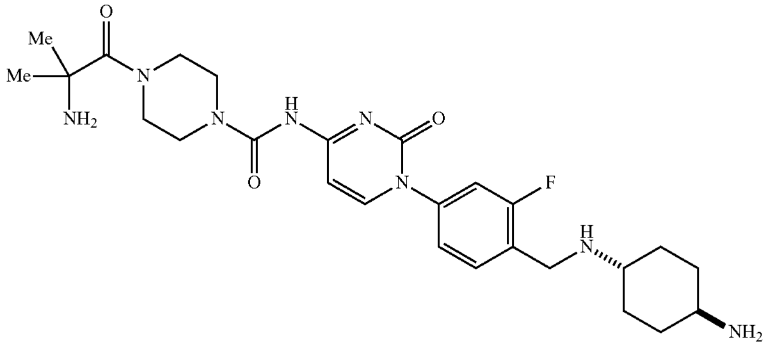 |

TABLE 11-continued
| Compounds of Formula I Continued | | |
|---|---|---|
| No. | Salt Structure | Free Base Structure |
| 331 | 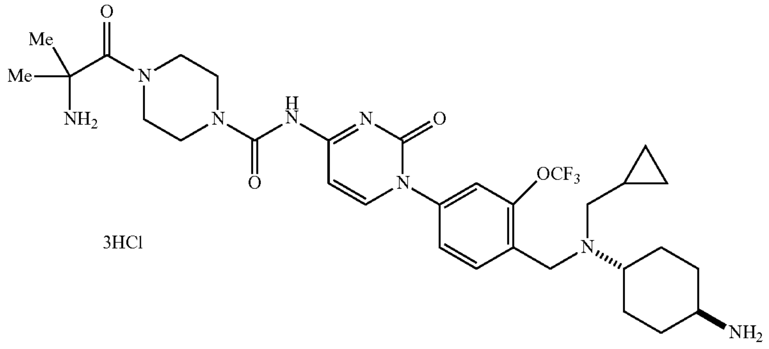 3HCl | 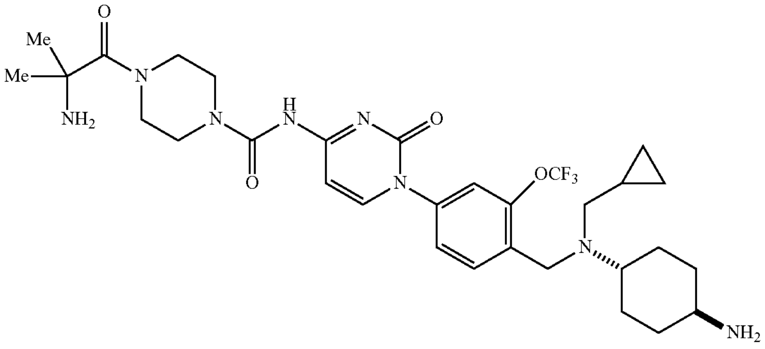 |
| 332 | 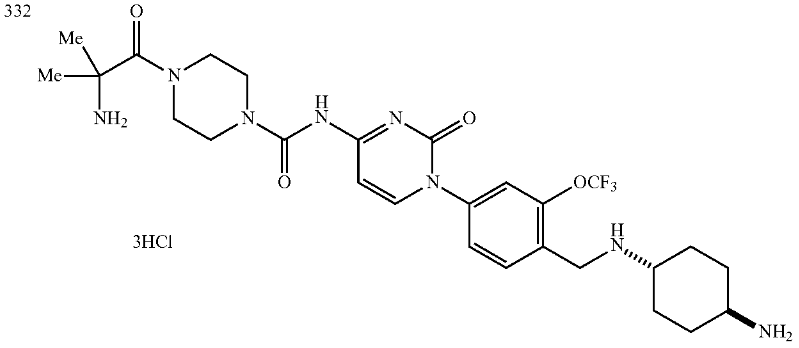 3HCl | 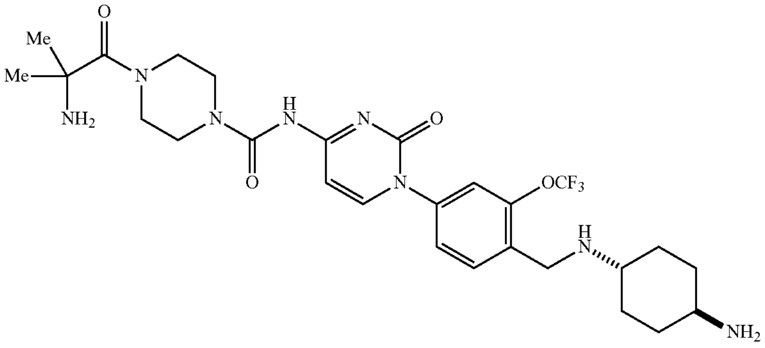 |

TABLE 11-continued
| Compounds of Formula I Continued | |
|---|---|
| No. Salt Structure | Free Base Structure |
| 333 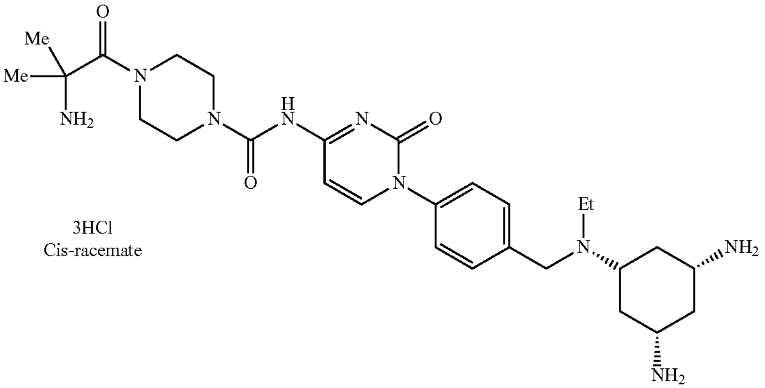 3HCl Cis-racemate | 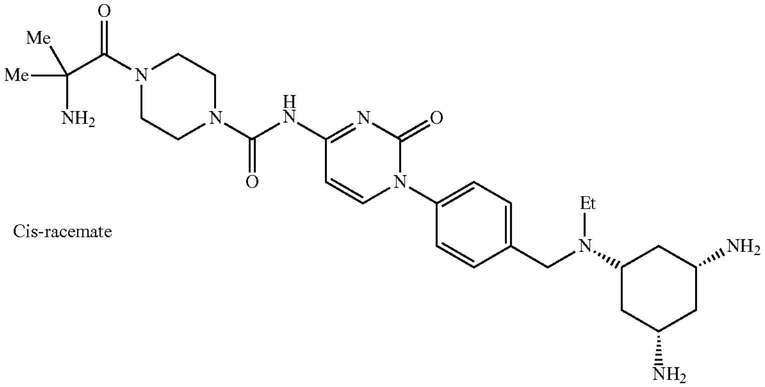 Cis-racemate |
| 334 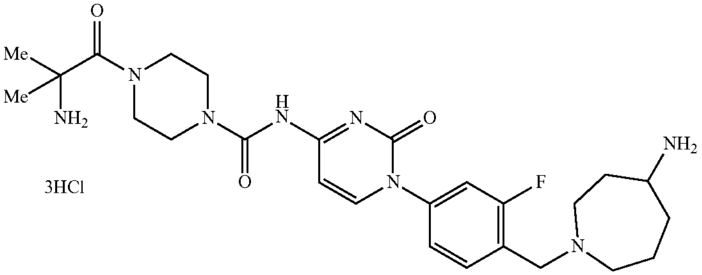 [SMILES: CC(C)(N)C(=O)N1CCN(C(=O)Nc2ccn(-c3ccc(CN4CCCC(N)CC4)c(F)c3)c(=O)n2)CC1] 3HCl | 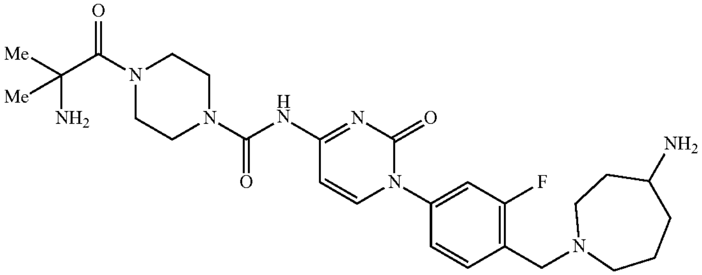 [SMILES: CC(C)(N)C(=O)N1CCN(C(=O)Nc2ccn(-c3ccc(CN4CCCC(N)CC4)c(F)c3)c(=O)n2)CC1] |
| 335 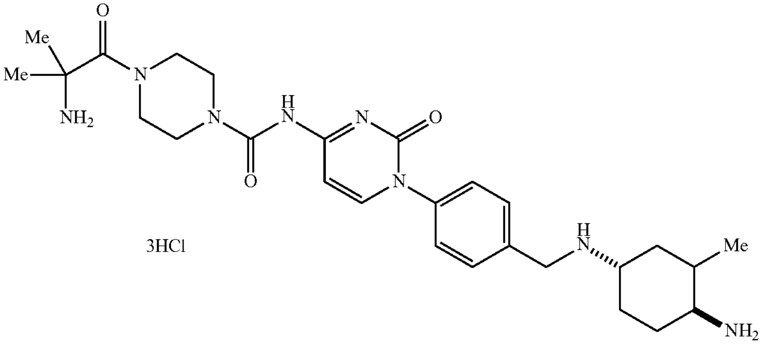 [SMILES: CC1C[C@@H](NCc2ccc(-n3ccc(NC(=O)N4CCN(C(=O)C(C)(C)N)CC4)nc3=O)cc2)CC[C@@H]1N] 3HCl | 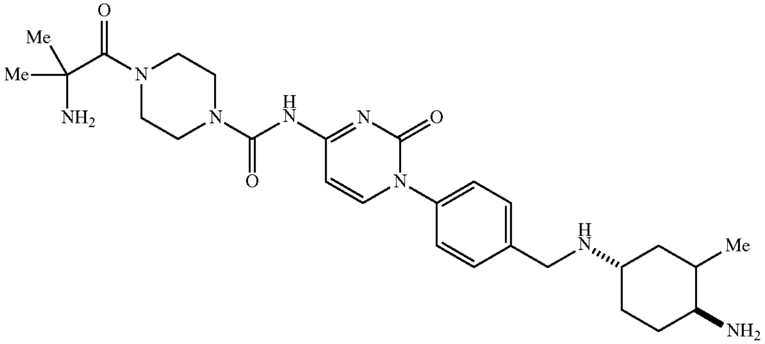 [SMILES: CC1C[C@@H](NCc2ccc(-n3ccc(NC(=O)N4CCN(C(=O)C(C)(C)N)CC4)nc3=O)cc2)CC[C@@H]1N] |

TABLE 11-continued
Compounds of Formula I Continued
| No. | Salt Structure | Free Base Structure |
| --- | --- | --- |
| 336 | 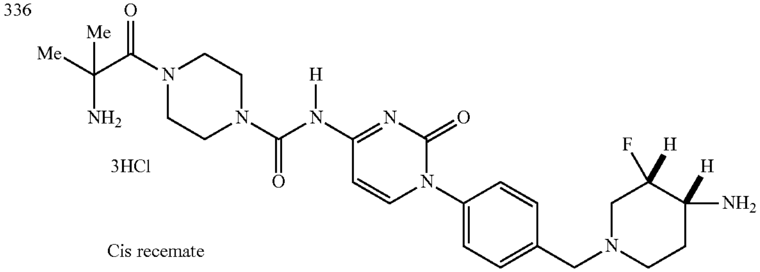 3HCl Cis recemate | 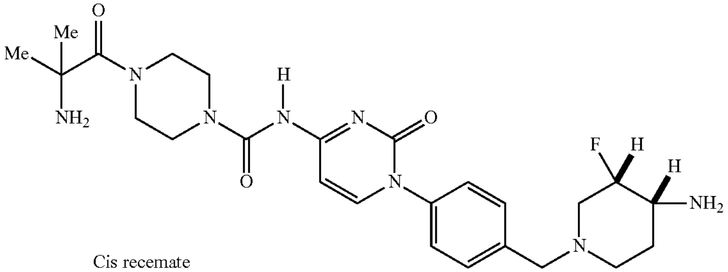 [SMILES: CC(C)(N)C(=O)N1CCN(C(=O)Nc2ccn(-c3ccc(CN4CC[C@@H](N)[C@@H](F)C4)cc3)c(=O)n2)CC1] Cis recemate |
| 337 | 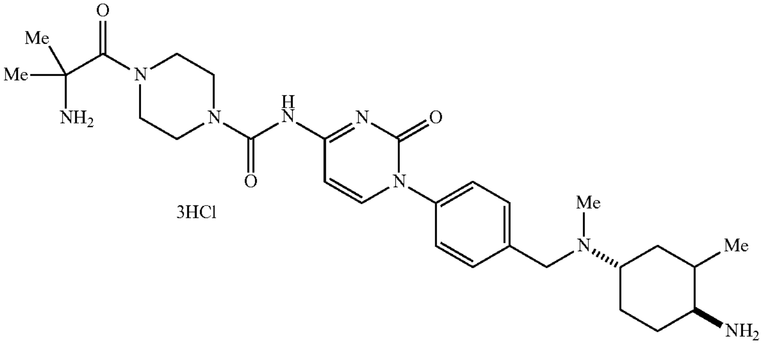 [SMILES: CC1C[C@@H](N(C)Cc2ccc(-n3ccc(NC(=O)N4CCN(C(=O)C(C)(C)N)CC4)nc3=O)cc2)CC[C@@H]1N] 3HCl | 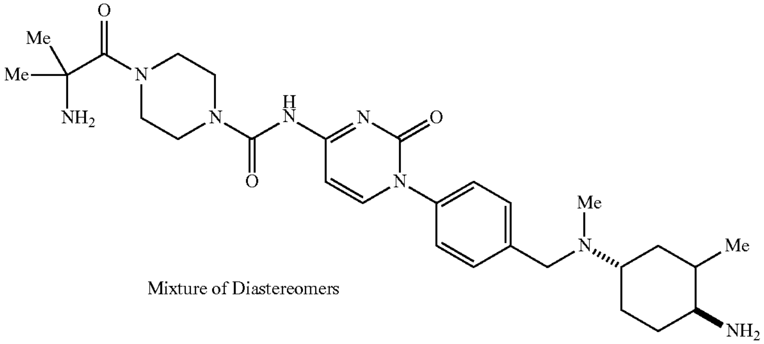 [SMILES: CC1C[C@@H](N(C)Cc2ccc(-n3ccc(NC(=O)N4CCN(C(=O)C(C)(C)N)CC4)nc3=O)cc2)CC[C@@H]1N] Mixture of Diastereomers |
| 338 | 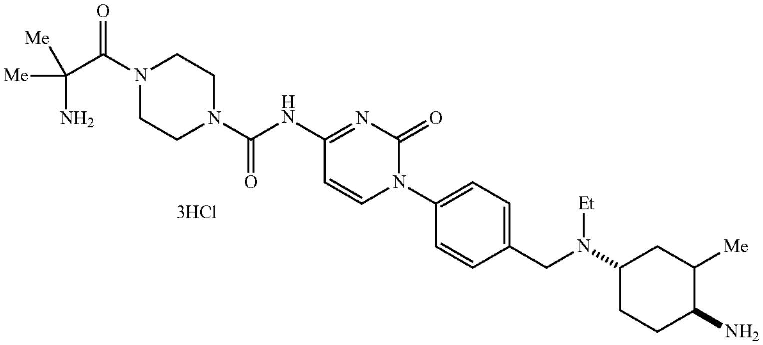 [SMILES: CCN(Cc1ccc(-n2ccc(NC(=O)N3CCN(C(=O)C(C)(C)N)CC3)nc2=O)cc1)[C@H]1CC[C@H](N)C(C)C1] 3HCl | 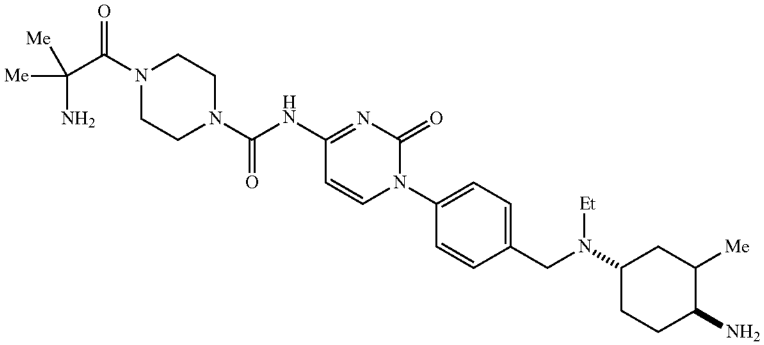 |

TABLE 11-continued
| Compounds of Formula I Continued | |
|---|---|
| No. Salt Structure | Free Base Structure |
| 339 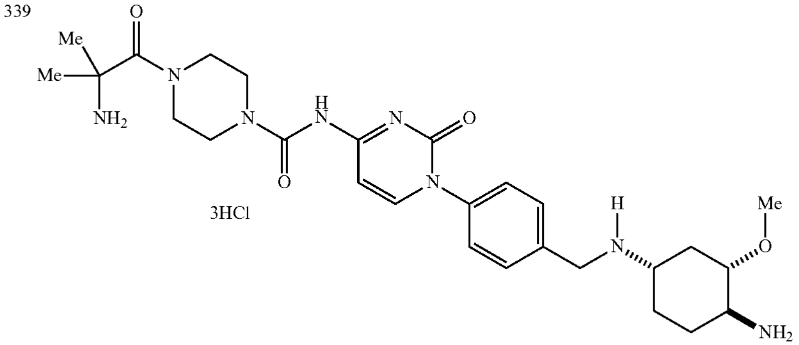 3HCl | 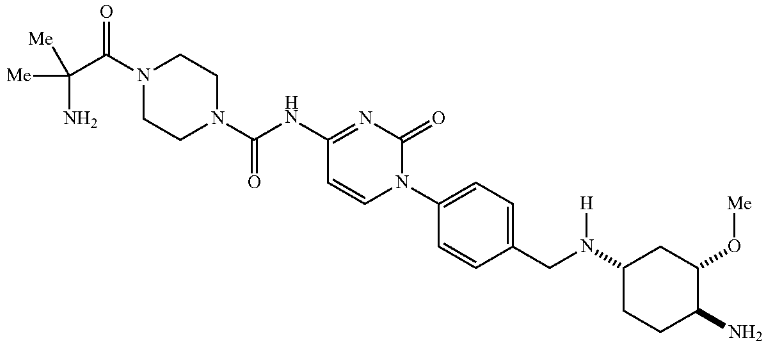 |
| 340 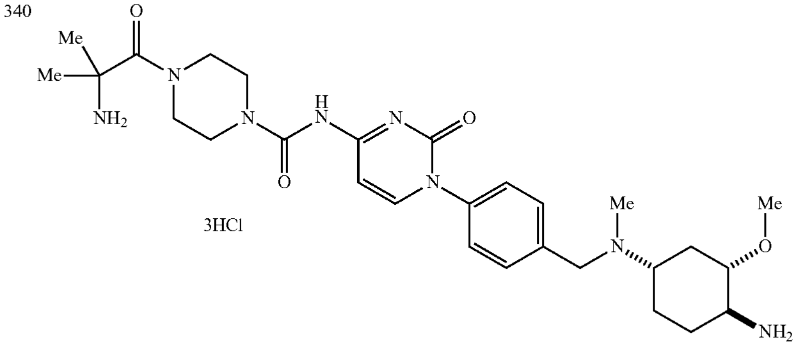 3HCl | 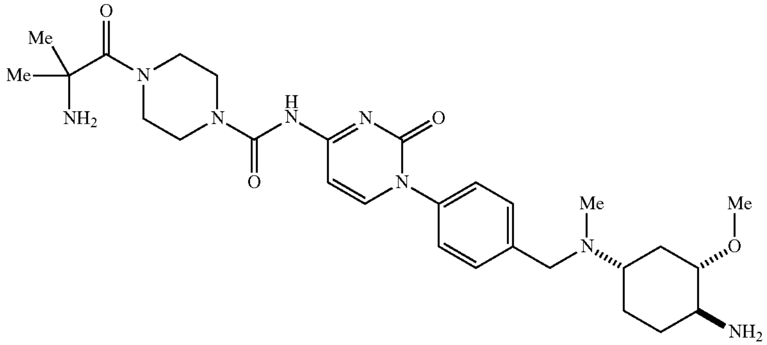 |

TABLE 11-continued
| Compounds of Formula I Continued | | |
|---|---|---|
| No. | Salt Structure | Free Base Structure |
| 341 | 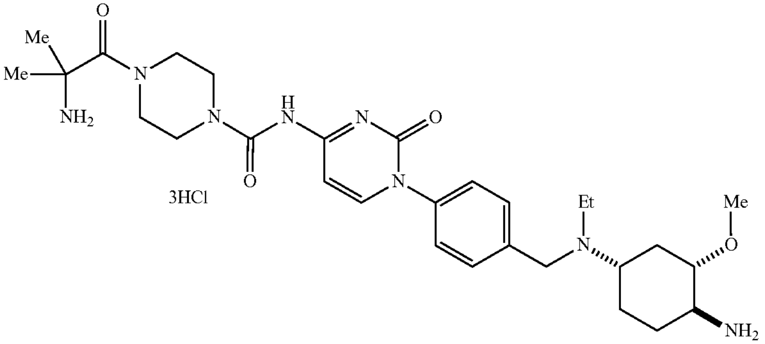 [SMILES: CCN(Cc1ccc(-n2ccc(NC(=O)N3CCN(C(=O)C(C)(C)N)CC3)nc2=O)cc1)[C@H]1CC[C@H](N)[C@@H](OC)C1] 3HCl | 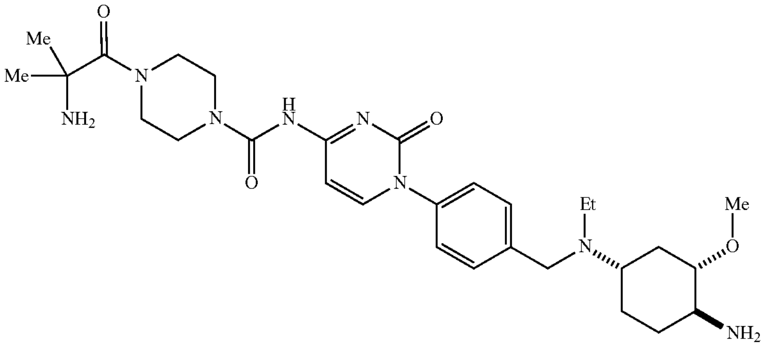 |
| 342 | 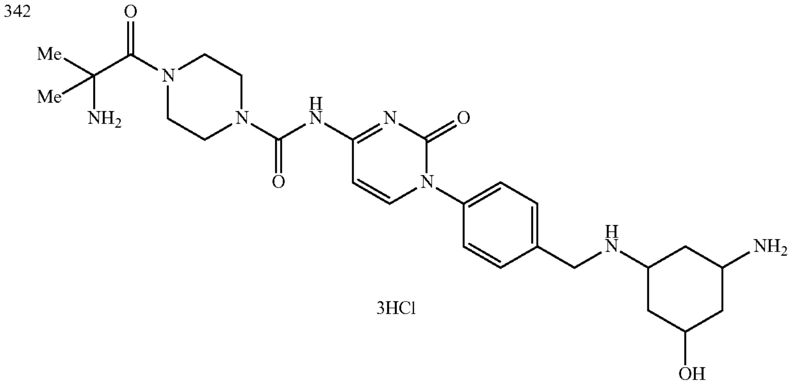 3HCl | 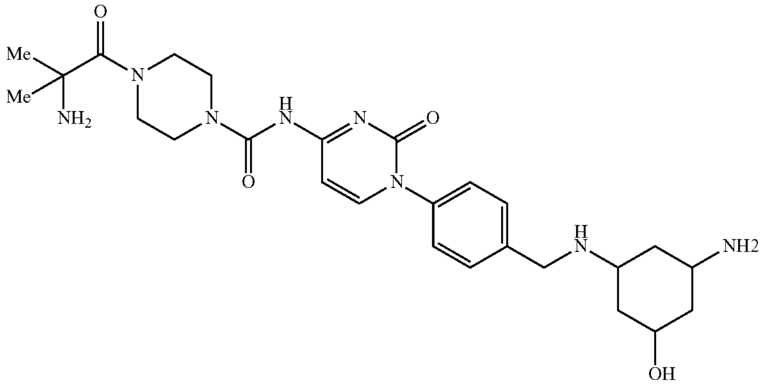 |

TABLE 11-continued
| Compounds of Formula I Continued | | |
|---|---|---|
| No. | Salt Structure | Free Base Structure |
| 343 | 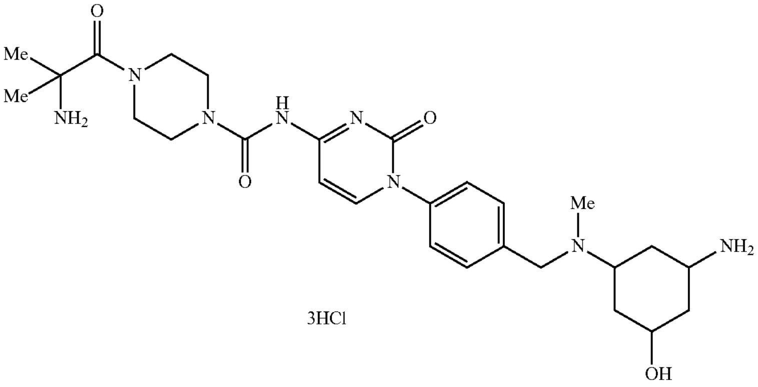 [SMILES: CN(Cc1ccc(-n2ccc(NC(=O)N3CCN(C(=O)C(C)(C)N)CC3)nc2=O)cc1)C1CC(N)CC(O)C1] 3HCl | 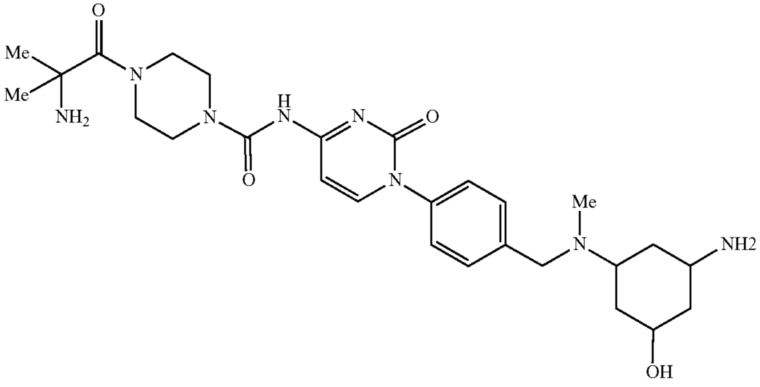 [SMILES: CN(Cc1ccc(-n2ccc(NC(=O)N3CCN(C(=O)C(C)(C)N)CC3)nc2=O)cc1)C1CC(N)CC(O)C1] |
| 344 | 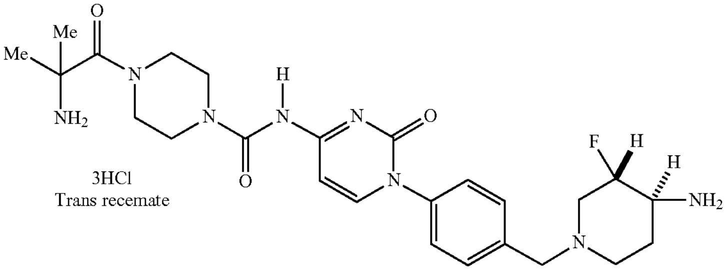 [SMILES: CC(C)(N)C(=O)N1CCN(C(=O)Nc2ccn(-c3ccc(CN4CC[C@H](N)[C@@H](F)C4)cc3)c(=O)n2)CC1] 3HCl Trans recemate | 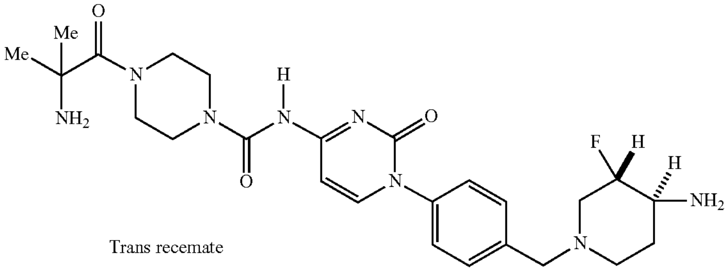 [SMILES: CC(C)(N)C(=O)N1CCN(C(=O)Nc2ccn(-c3ccc(CN4CC[C@H](N)[C@@H](F)C4)cc3)c(=O)n2)CC1] Trans recemate |
| 345 | 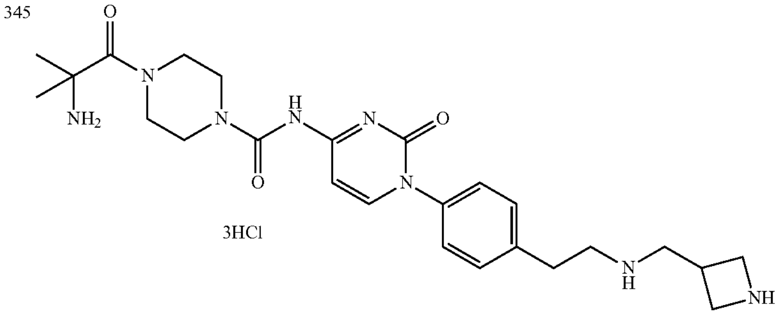 3HCl | 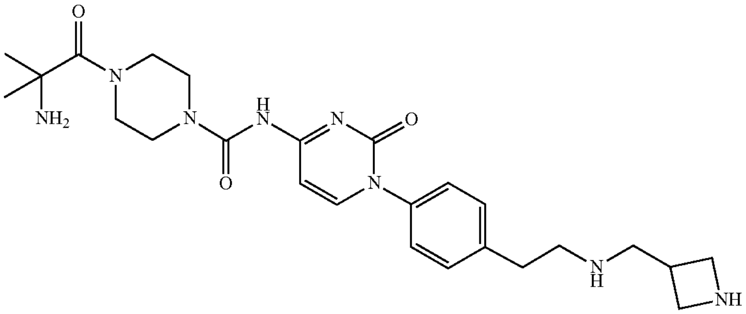 [SMILES: CC(C)(N)C(=O)N1CCN(C(=O)Nc2ccn(-c3ccc(CCNCC4CNC4)cc3)c(=O)n2)CC1] |

TABLE 11-continued
| Compounds of Formula I Continued | | |
|---|---|---|
| No. | Salt Structure | Free Base Structure |
| 346 | 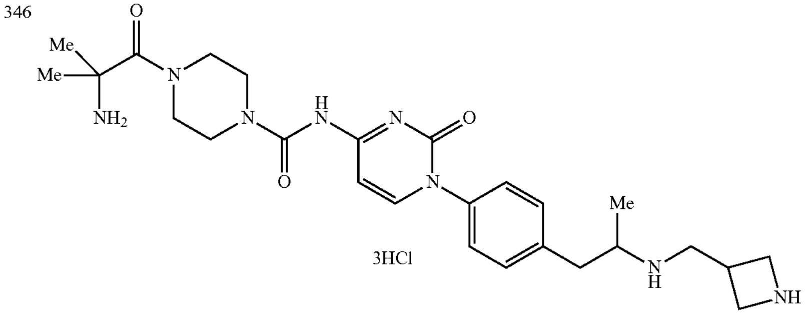 3HCl | 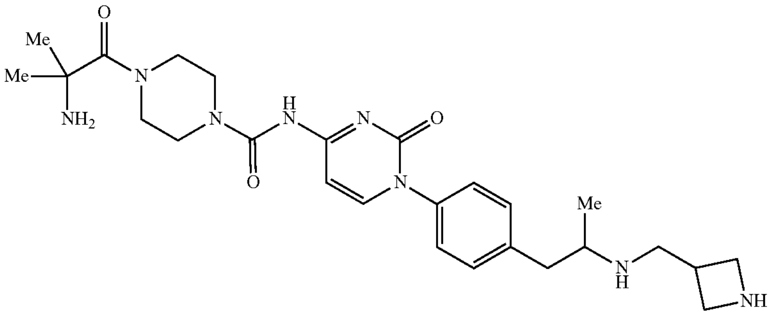 |
| 347 | 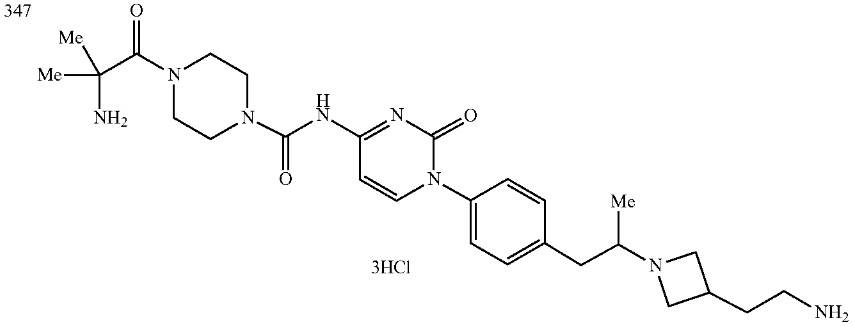 3HCl | 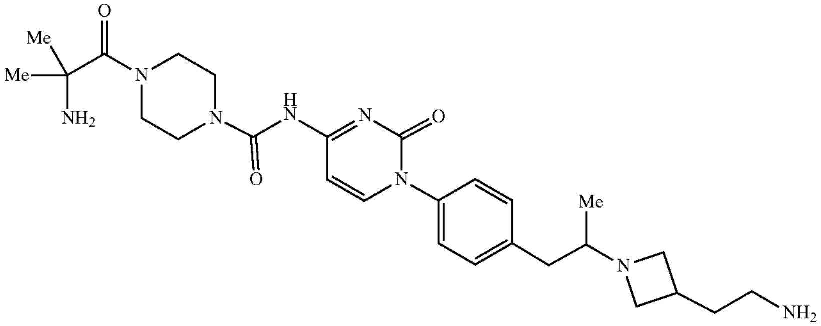 [SMILES: CC(Cc1ccc(-n2ccc(NC(=O)N3CCN(C(=O)C(C)(C)N)CC3)nc2=O)cc1)N1CC(CCN)C1] |
| 348 | 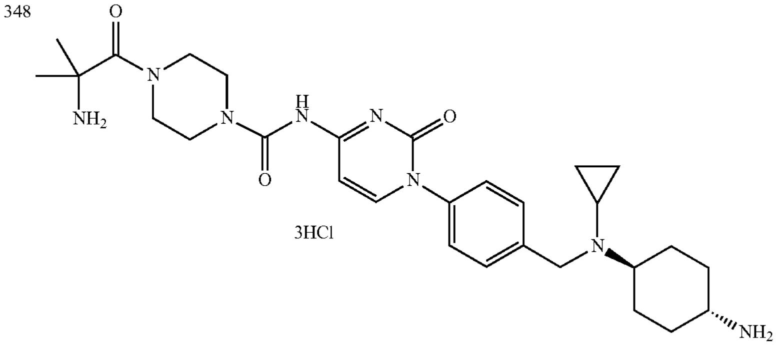 3HCl | 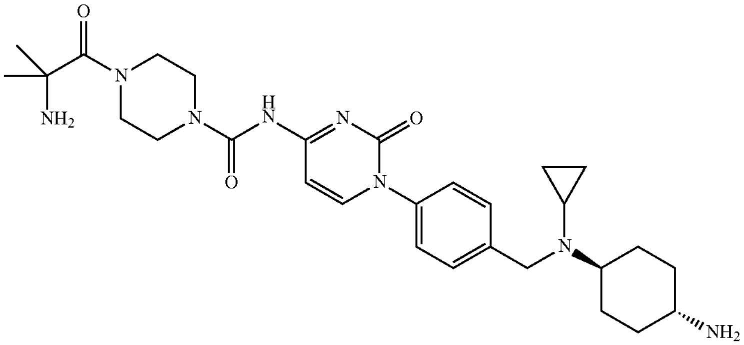 [SMILES: CC(C)(N)C(=O)N1CCN(C(=O)Nc2ccn(-c3ccc(CN(C4CC4)[C@H]4CC[C@H](N)CC4)cc3)c(=O)n2)CC1] |

TABLE 11-continued
| Compounds of Formula I Continued | | |
|---|---|---|
| No. | Salt Structure | Free Base Structure |
| 349 | 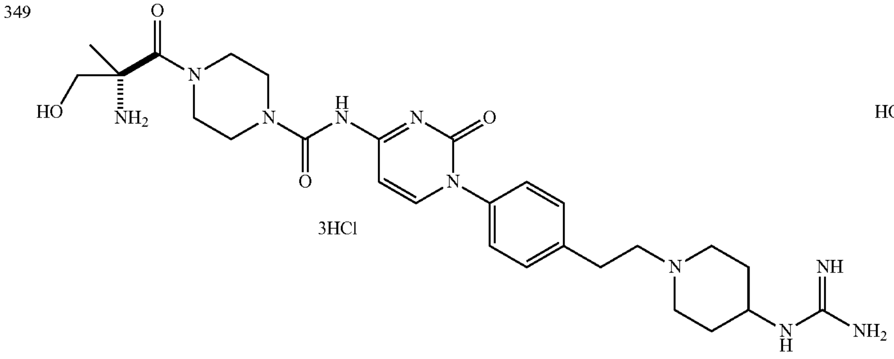 3HCl | 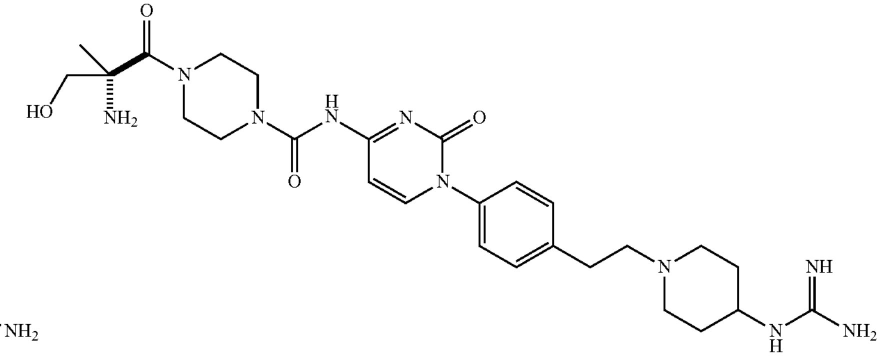 |
| 350 | 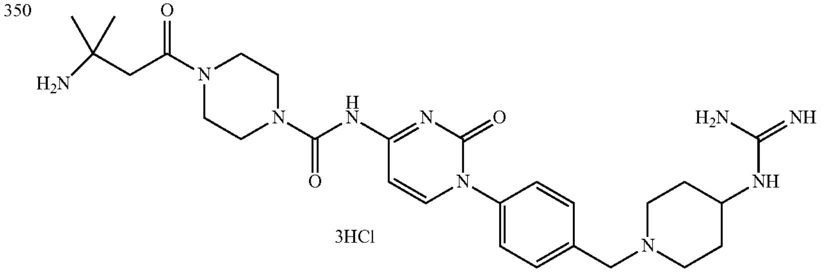 3HCl | 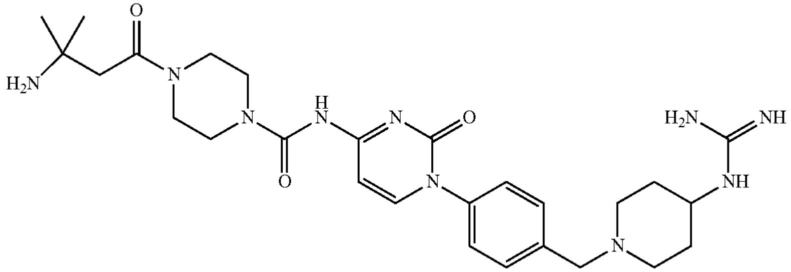 [SMILES: CC(C)(N)CC(=O)N1CCN(C(=O)Nc2ccn(-c3ccc(CN4CCC(NC(=N)N)CC4)cc3)c(=O)n2)CC1] |
| 351 | 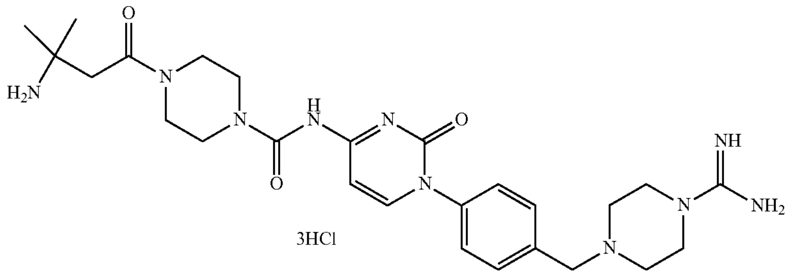 [SMILES: CC(C)(N)CC(=O)N1CCN(C(=O)Nc2ccn(-c3ccc(CN4CCN(C(=N)N)CC4)cc3)c(=O)n2)CC1] 3HCl | 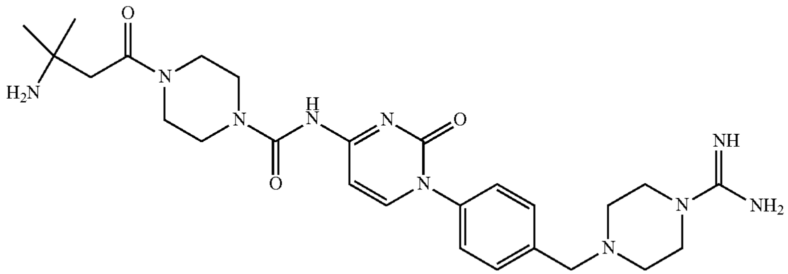 [SMILES: CC(C)(N)CC(=O)N1CCN(C(=O)Nc2ccn(-c3ccc(CN4CCN(C(=N)N)CC4)cc3)c(=O)n2)CC1] |

TABLE 11-continued
| Compounds of Formula I Continued | | |
|---|---|---|
| No. | Salt Structure | Free Base Structure |
| 352 | 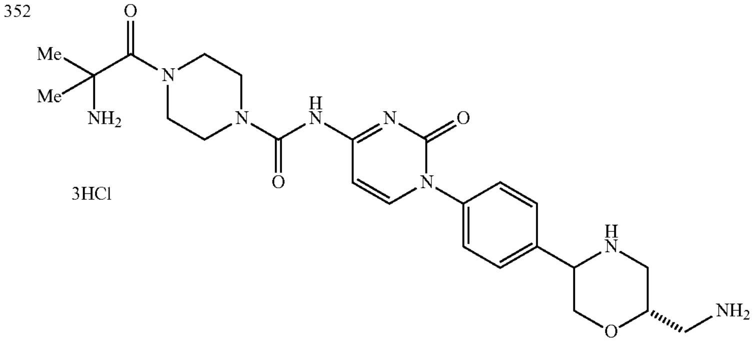 3HCl | 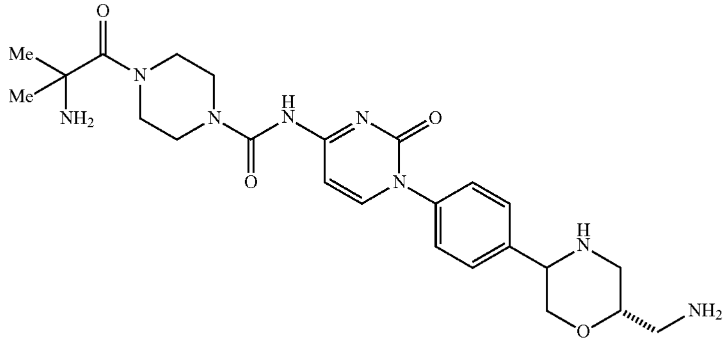 [SMILES: CC(C)(N)C(=O)N1CCN(C(=O)Nc2ccn(-c3ccc(C4CO[C@@H](CN)CN4)cc3)c(=O)n2)CC1] |
| 353 | 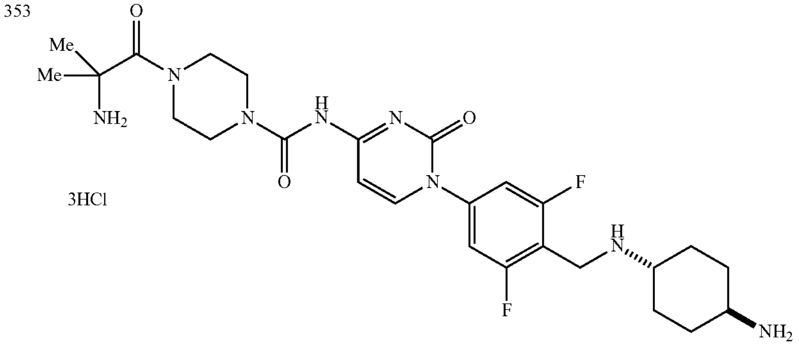 3HCl | 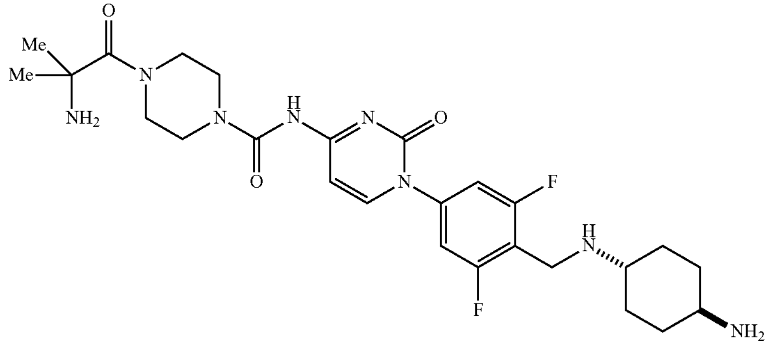 |

TABLE 11-continued
| Compounds of Formula I Continued | |
|---|---|
| No. Salt Structure | Free Base Structure |
| 354 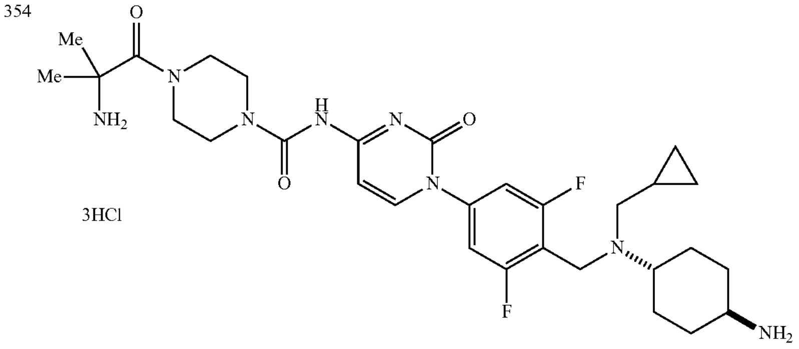 3HCl | 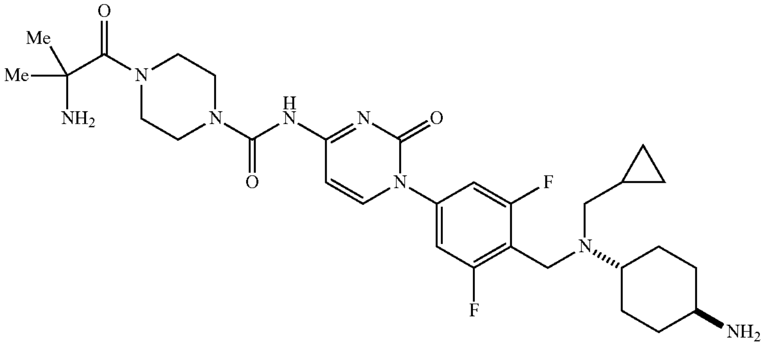 |
| 355 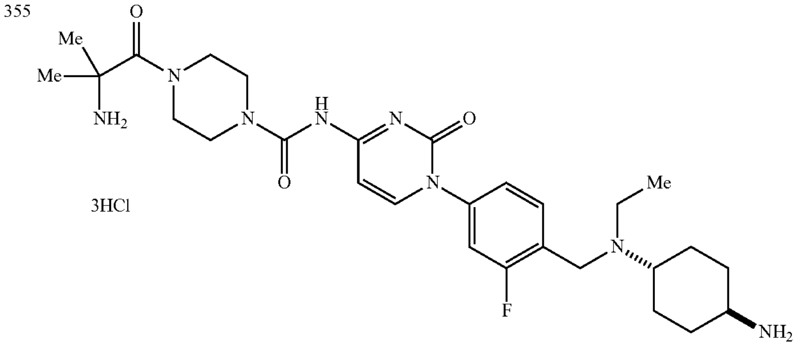 3HCl | 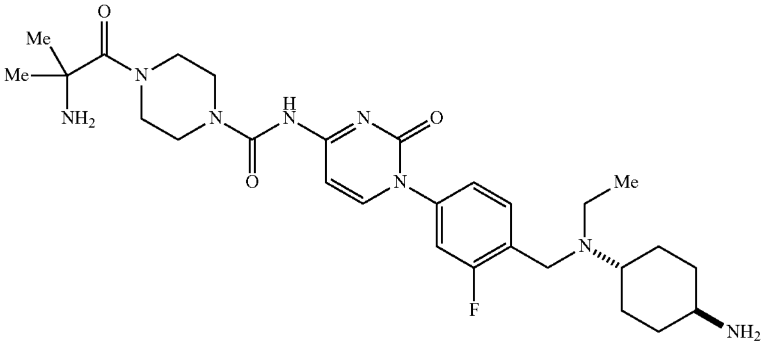 |

TABLE 11-continued
| Compounds of Formula I Continued | | |
|---|---|---|
| No. | Salt Structure | Free Base Structure |
| 356 | 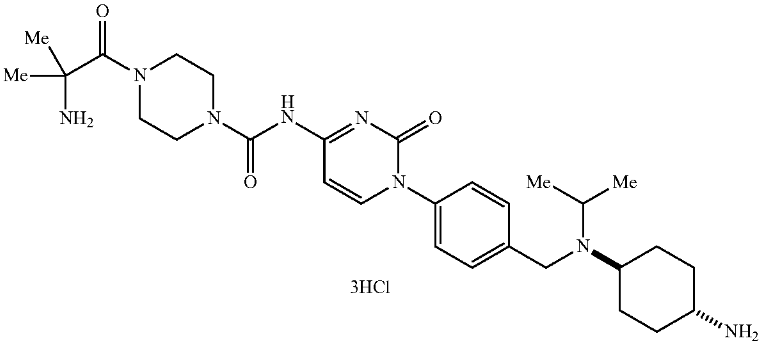 3HCl | 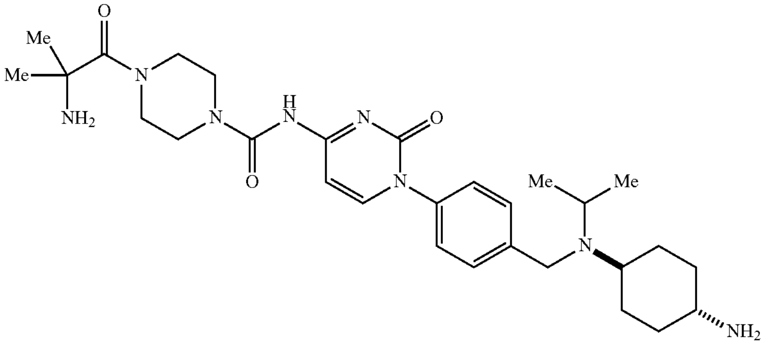 |
| 357 | 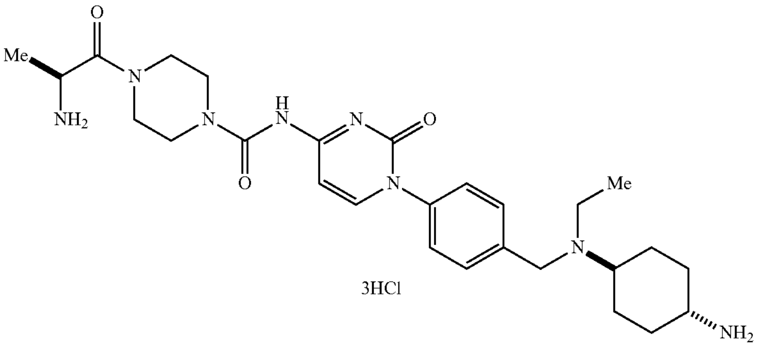 3HCl | 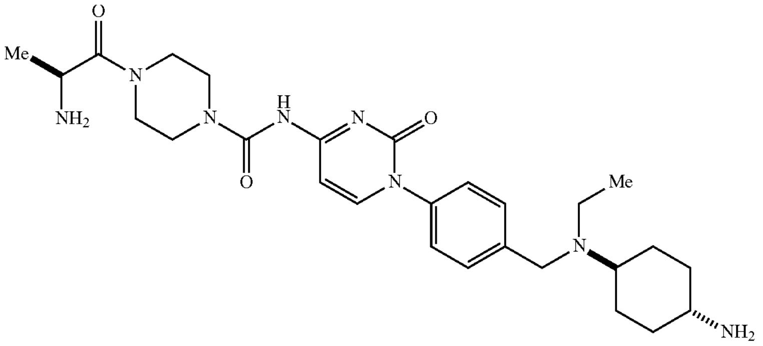 |

TABLE 11-continued
| Compounds of Formula I Continued | | |
|---|---|---|
| No. | Salt Structure | Free Base Structure |
| 358 | 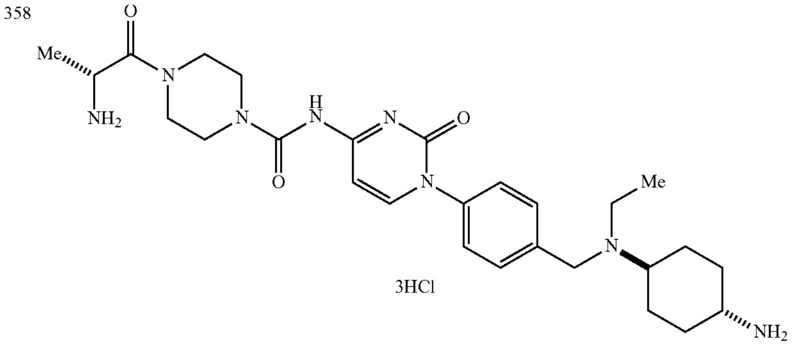 3HCl | 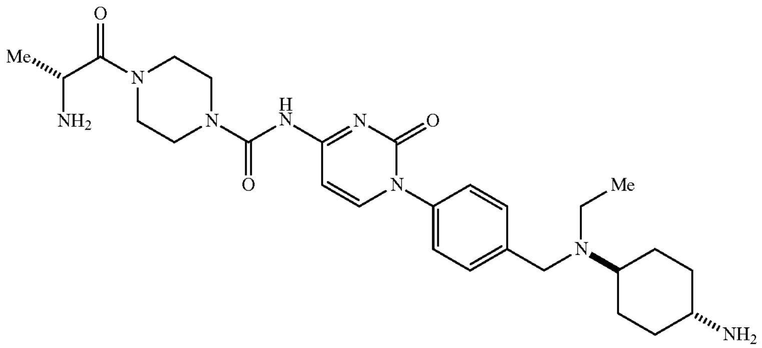 |
| 359 | 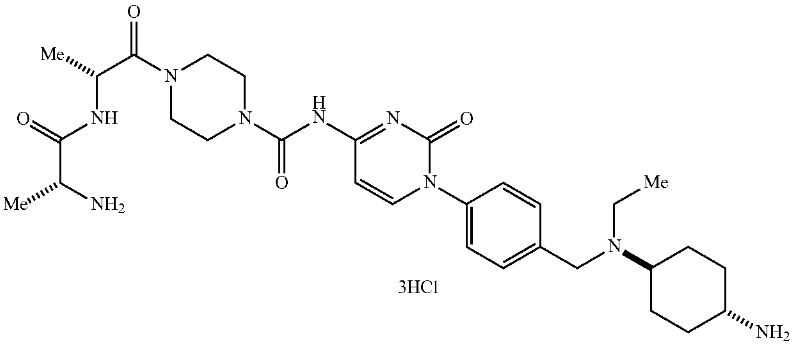 3HCl | 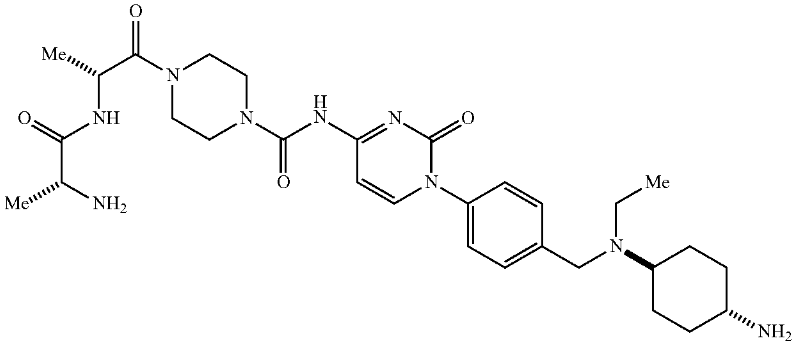 |
| 360 | 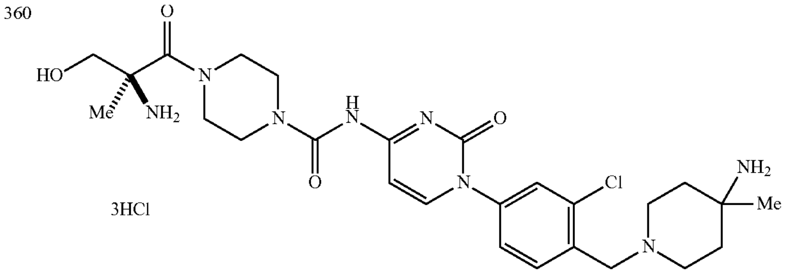 3HCl | 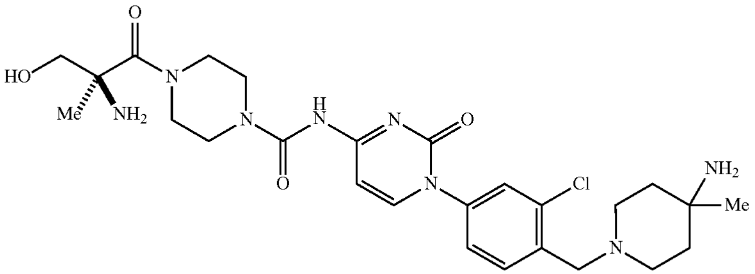 [SMILES: CC1(N)CCN(Cc2ccc(-n3ccc(NC(=O)N4CCN(C(=O)[C@@](C)(N)CO)CC4)nc3=O)cc2Cl)CC1] |

TABLE 11-continued
| Compounds of Formula I Continued | | |
|---|---|---|
| No. | Salt Structure | Free Base Structure |
| 361 | 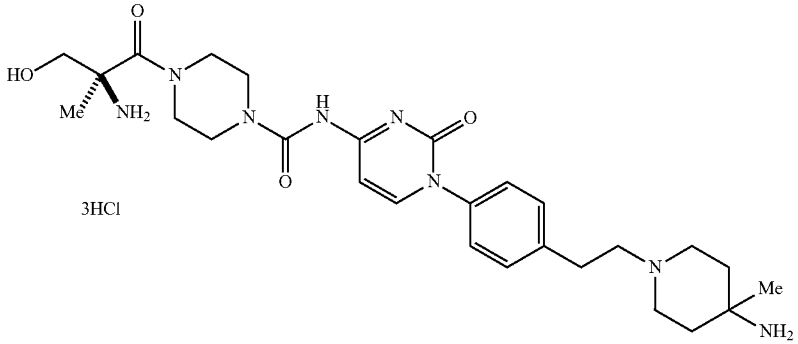 [SMILES: CC1(N)CCN(CCc2ccc(-n3ccc(NC(=O)N4CCN(C(=O)[C@@](C)(N)CO)CC4)nc3=O)cc2)CC1] 3HCl | 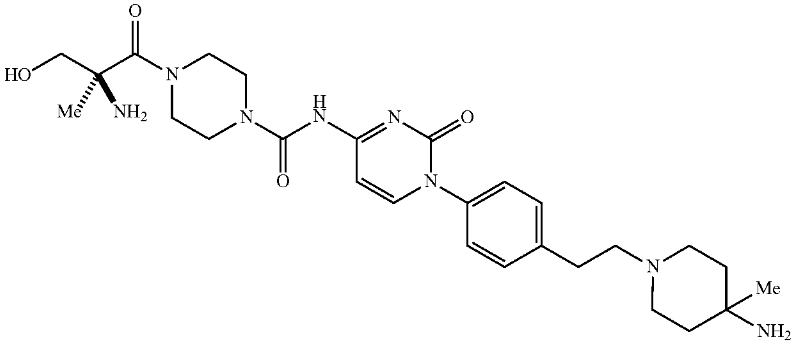 [SMILES: CC1(N)CCN(CCc2ccc(-n3ccc(NC(=O)N4CCN(C(=O)[C@@](C)(N)CO)CC4)nc3=O)cc2)CC1] |
| 362 | 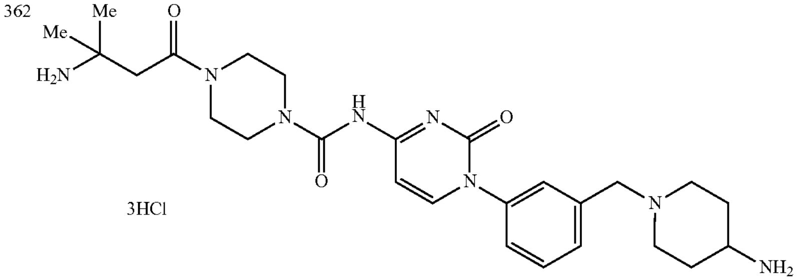 3HCl | 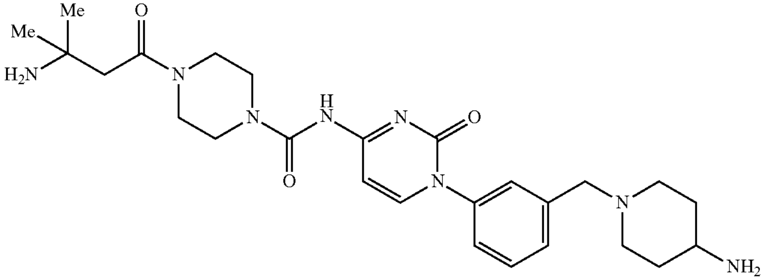 |
| 363 | 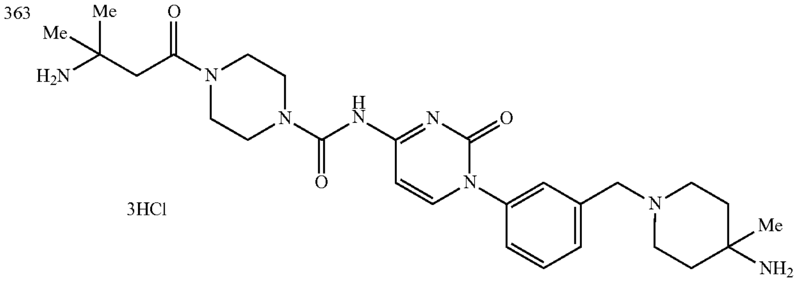 3HCl | 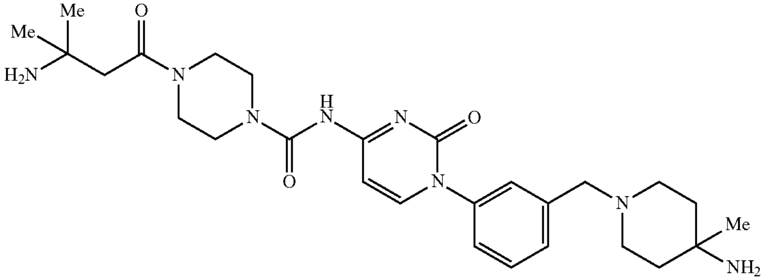 |

TABLE 11-continued
| Compounds of Formula I Continued | | |
|---|---|---|
| No. | Salt Structure | Free Base Structure |
| 364 | 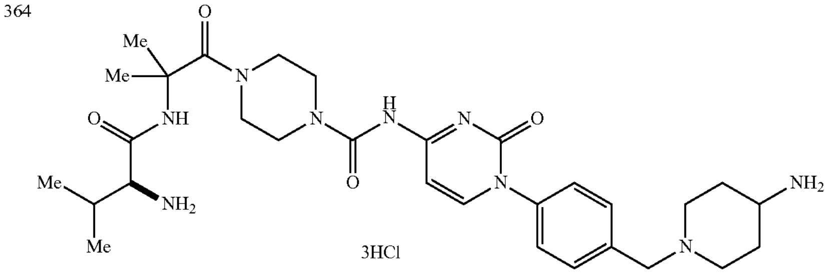 3HCl | 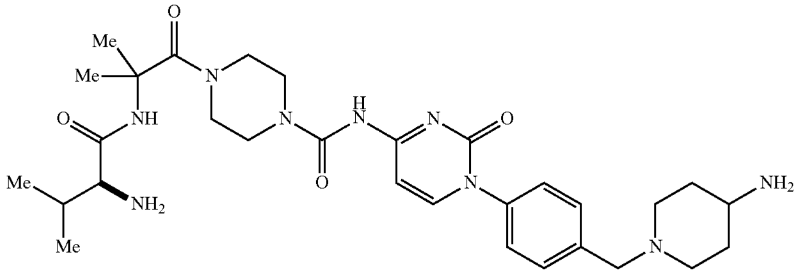 [SMILES: CC(C)[C@H](N)C(=O)NC(C)(C)C(=O)N1CCN(C(=O)Nc2ccn(-c3ccc(CN4CCC(N)CC4)cc3)c(=O)n2)CC1] |
| 365 | 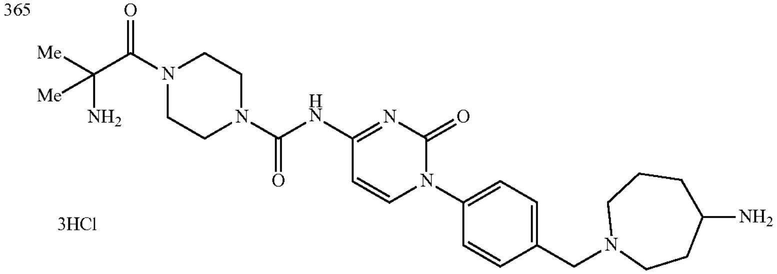 3HCl | 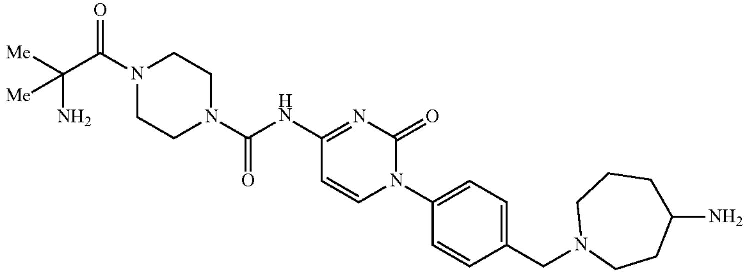 [SMILES: CC(C)(N)C(=O)N1CCN(C(=O)Nc2ccn(-c3ccc(CN4CCCC(N)CC4)cc3)c(=O)n2)CC1] |
| 366 | 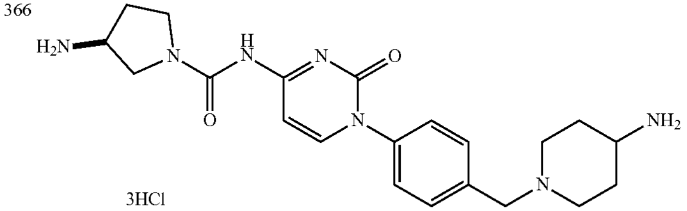 3HCl | 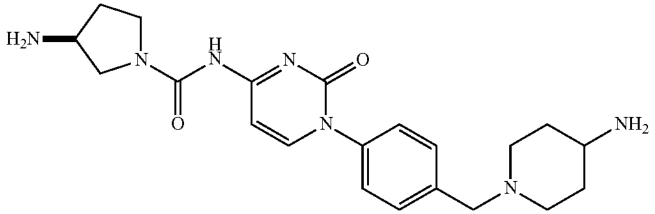 [SMILES: NC1CCN(Cc2ccc(-n3ccc(NC(=O)N4CC[C@H](N)C4)nc3=O)cc2)CC1] |
| 367 | 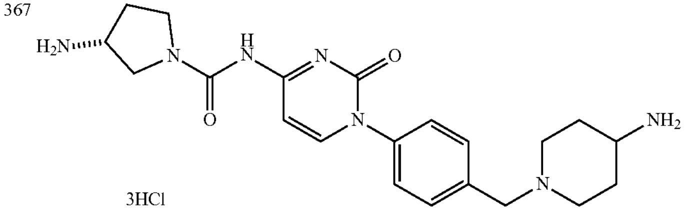 3HCl | 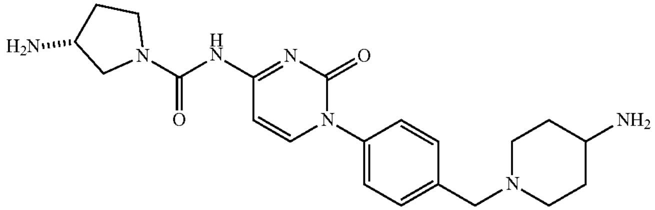 [SMILES: NC1CCN(Cc2ccc(-n3ccc(NC(=O)N4CC[C@@H](N)C4)nc3=O)cc2)CC1] |

TABLE 11-continued
| Compounds of Formula I Continued | | |
|---|---|---|
| No. | Salt Structure | Free Base Structure |
| 368 | 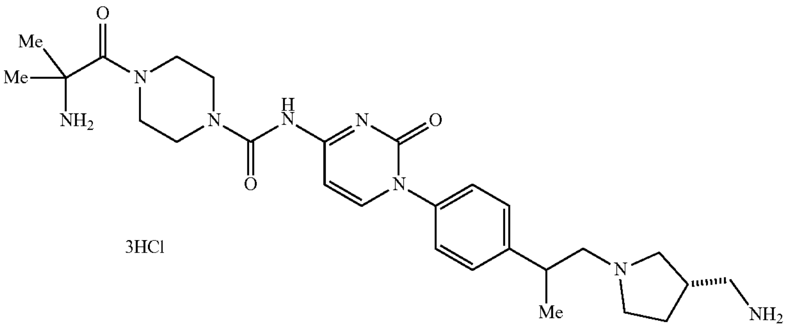 [SMILES: CC(CN1CC[C@@H](CN)C1)c1ccc(-n2ccc(NC(=O)N3CCN(C(=O)C(C)(C)N)CC3)nc2=O)cc1] 3HCl | 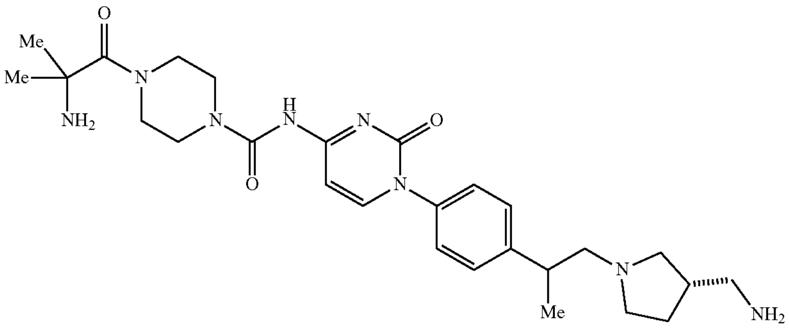 [SMILES: CC(CN1CC[C@@H](CN)C1)c1ccc(-n2ccc(NC(=O)N3CCN(C(=O)C(C)(C)N)CC3)nc2=O)cc1] |
| 369 | 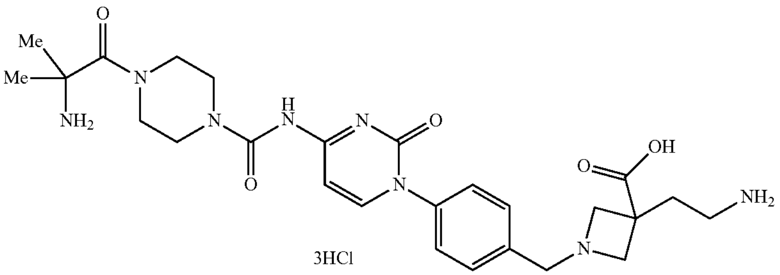 [SMILES: CC(C)(N)C(=O)N1CCN(C(=O)Nc2ccn(-c3ccc(CN4CC(CCN)(C(=O)O)C4)cc3)c(=O)n2)CC1] 3HCl | 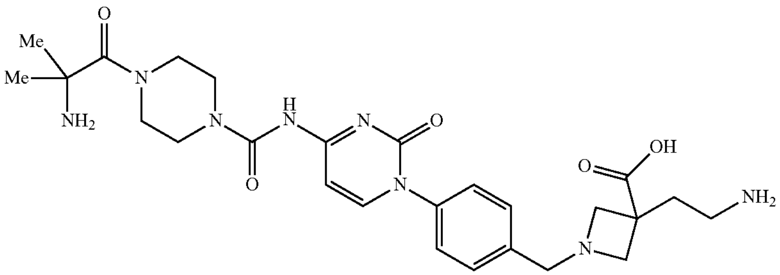 [SMILES: CC(C)(N)C(=O)N1CCN(C(=O)Nc2ccn(-c3ccc(CN4CC(CCN)(C(=O)O)C4)cc3)c(=O)n2)CC1] |
| 370 | 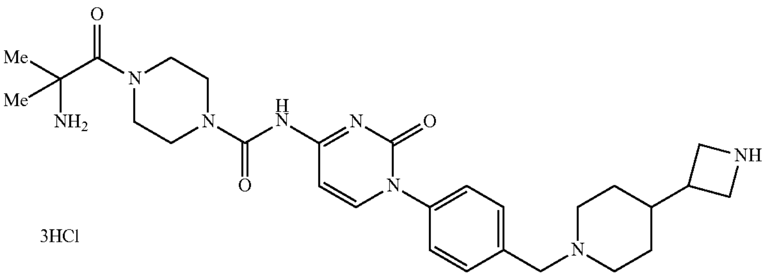 [SMILES: CC(C)(N)C(=O)N1CCN(C(=O)Nc2ccn(-c3ccc(CN4CCC(C5CNC5)CC4)cc3)c(=O)n2)CC1] 3HCl | 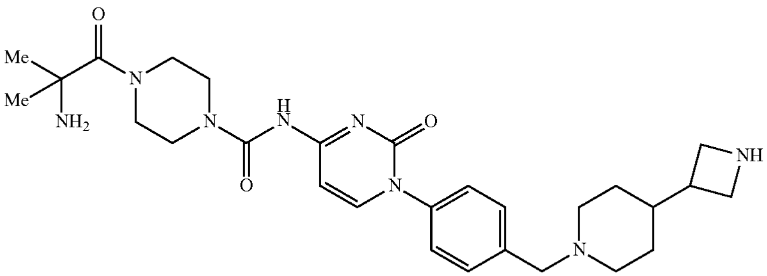 [SMILES: CC(C)(N)C(=O)N1CCN(C(=O)Nc2ccn(-c3ccc(CN4CCC(C5CNC5)CC4)cc3)c(=O)n2)CC1] |

TABLE 11-continued
| Compounds of Formula I Continued | |
|---|---|
| No. Salt Structure | Free Base Structure |
| 371 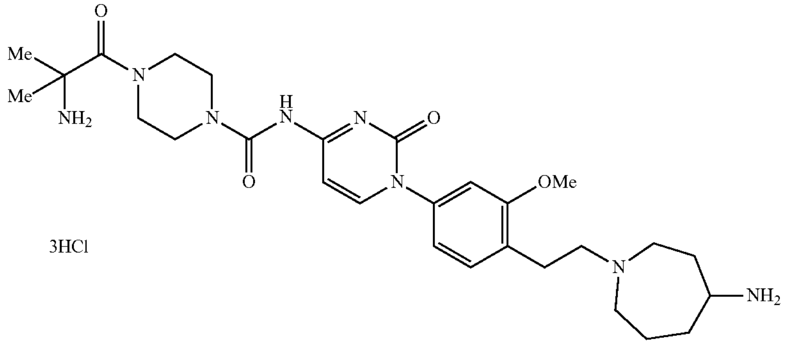 [SMILES: COc1cc(-n2ccc(NC(=O)N3CCN(C(=O)C(C)(C)N)CC3)nc2=O)ccc1CCN1CCCC(N)CC1] 3HCl | 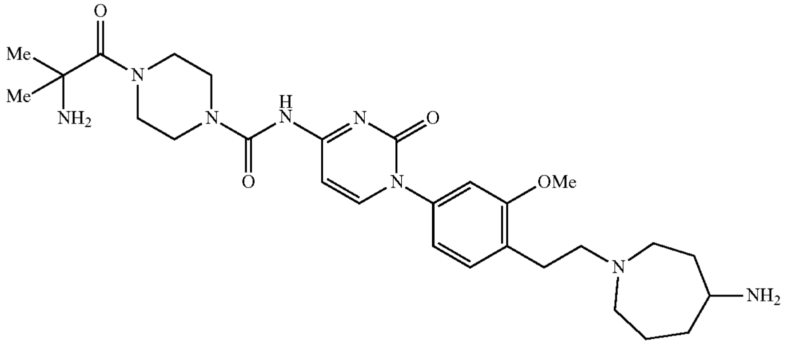 [SMILES: COc1cc(-n2ccc(NC(=O)N3CCN(C(=O)C(C)(C)N)CC3)nc2=O)ccc1CCN1CCCC(N)CC1] |
| 372 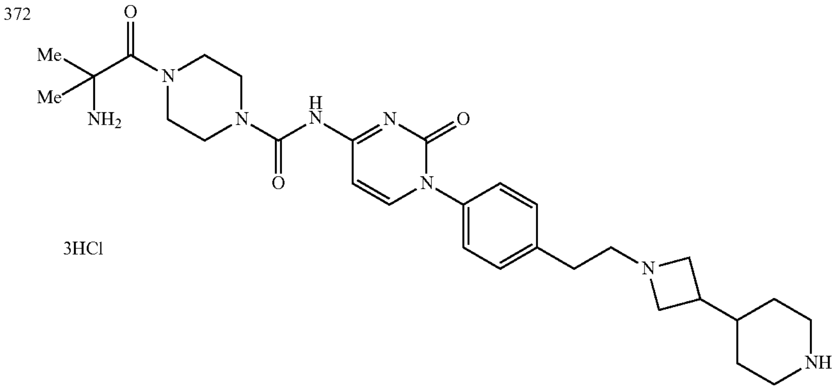 3HCl | 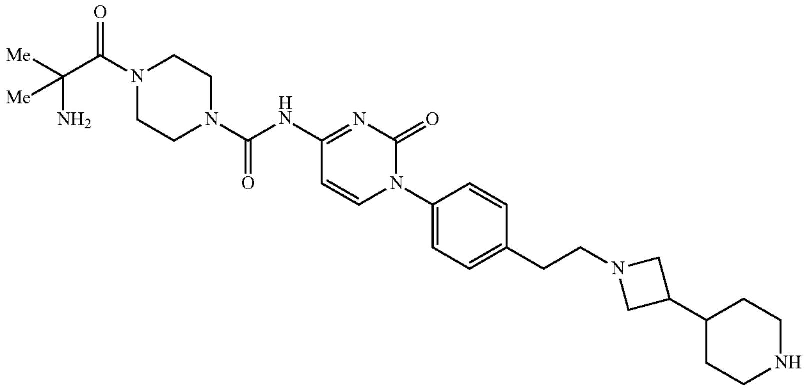 [SMILES: CC(C)(N)C(=O)N1CCN(C(=O)Nc2ccn(-c3ccc(CCN4CC(C5CCNCC5)C4)cc3)c(=O)n2)CC1] |

TABLE 11-continued
| Compounds of Formula I Continued | | |
|---|---|---|
| No. | Salt Structure | Free Base Structure |
| 373 | 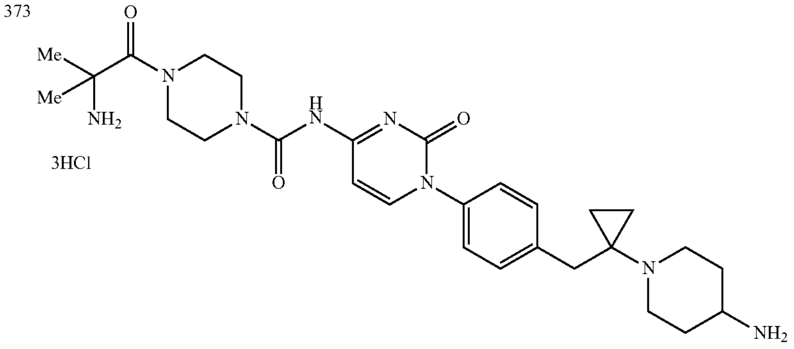 3HCl | 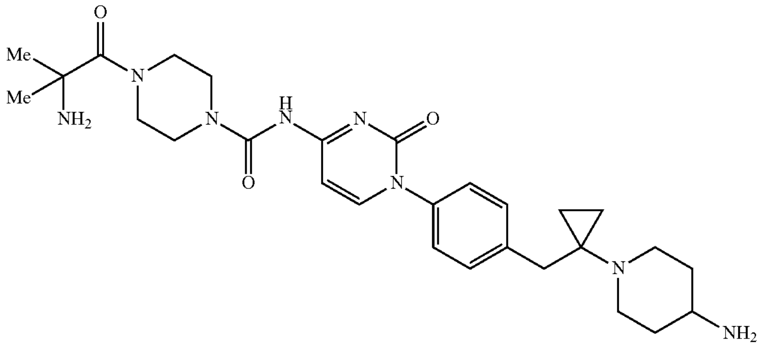 [SMILES: CC(C)(N)C(=O)N1CCN(C(=O)Nc2ccn(-c3ccc(CC4(N5CCC(N)CC5)CC4)cc3)c(=O)n2)CC1] |
| 374 | 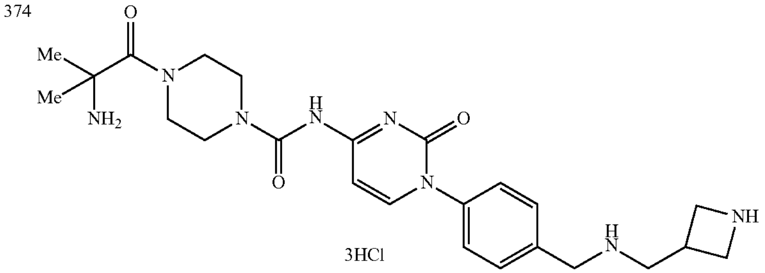 3HCl | 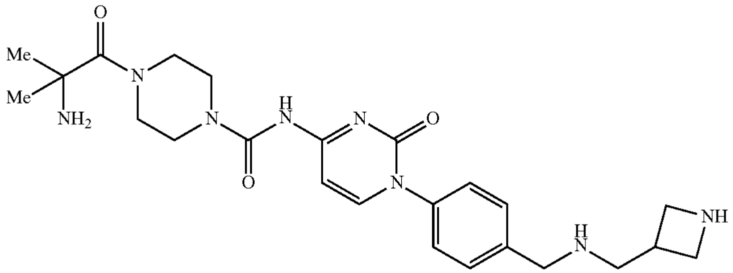 |
| 375 | 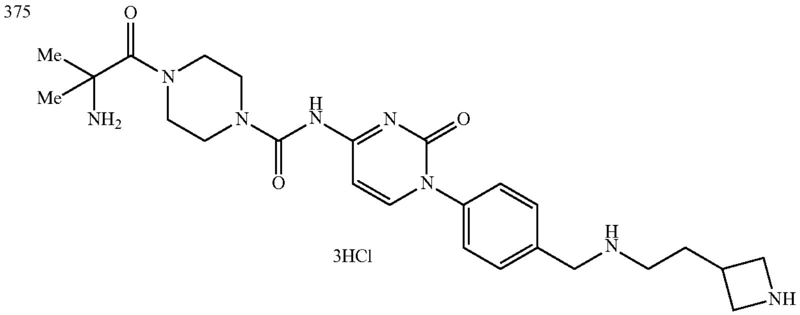 3HCl | 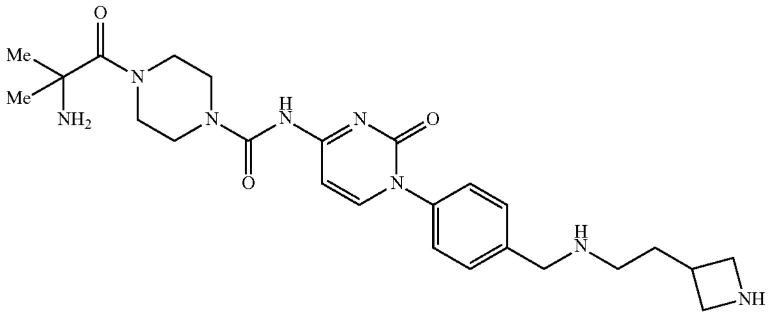 [SMILES: CC(C)(N)C(=O)N1CCN(C(=O)Nc2ccn(-c3ccc(CNCCC4CNC4)cc3)c(=O)n2)CC1] |

TABLE 11-continued
| Compounds of Formula I Continued | | |
|---|---|---|
| No. | Salt Structure | Free Base Structure |
| 376 | 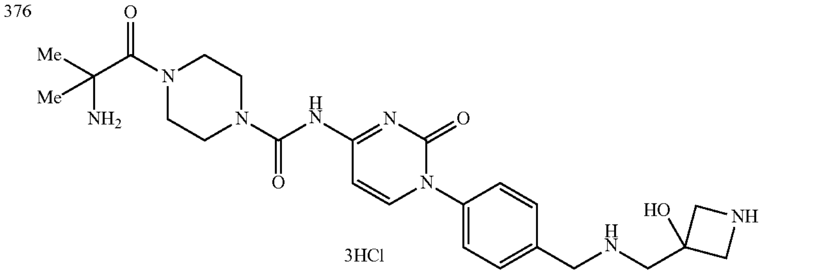 3HCl | 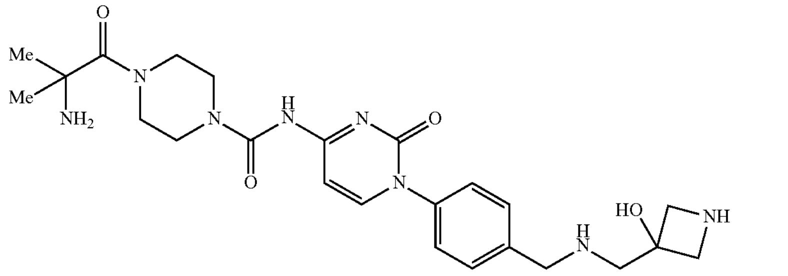 |
| 377 | 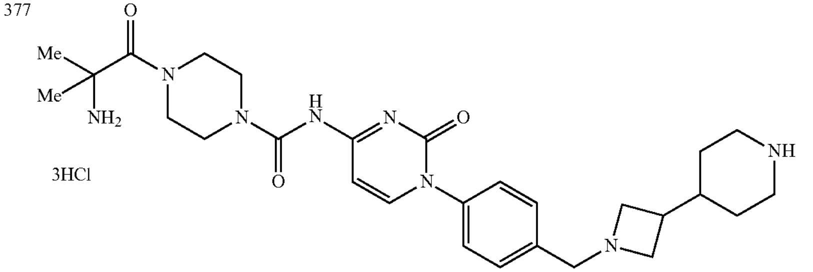 3HCl | 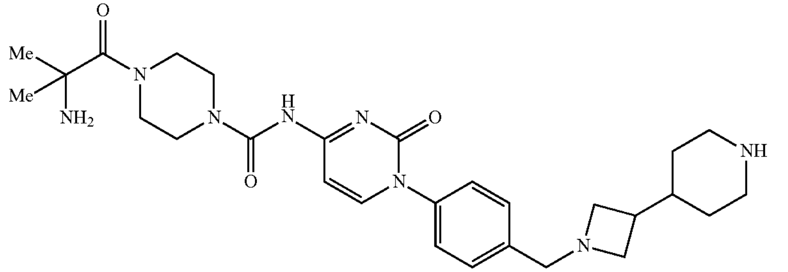 [SMILES: CC(C)(N)C(=O)N1CCN(C(=O)Nc2ccn(-c3ccc(CN4CC(C5CCNCC5)C4)cc3)c(=O)n2)CC1] |
| 378 | 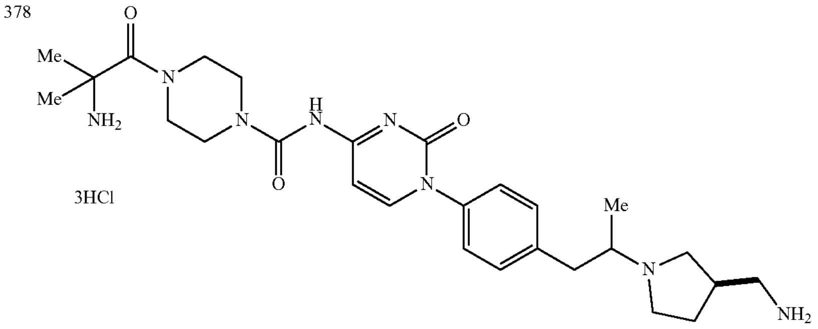 3HCl | 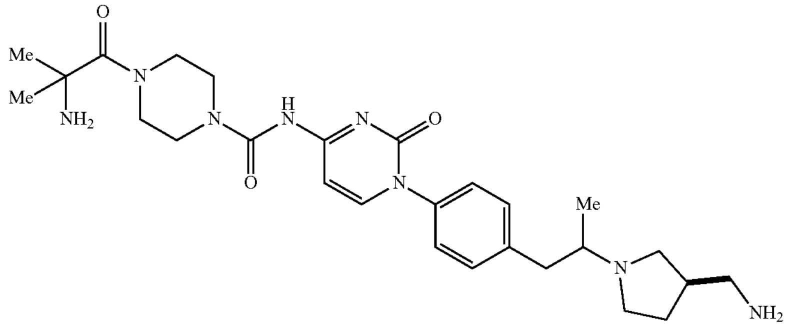 |

TABLE 11-continued
| Compounds of Formula I Continued | | |
|---|---|---|
| No. | Salt Structure | Free Base Structure |
| 379 | 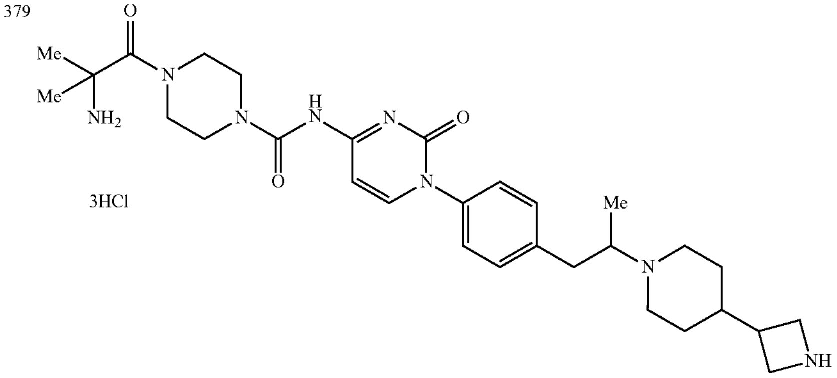 3HCl | 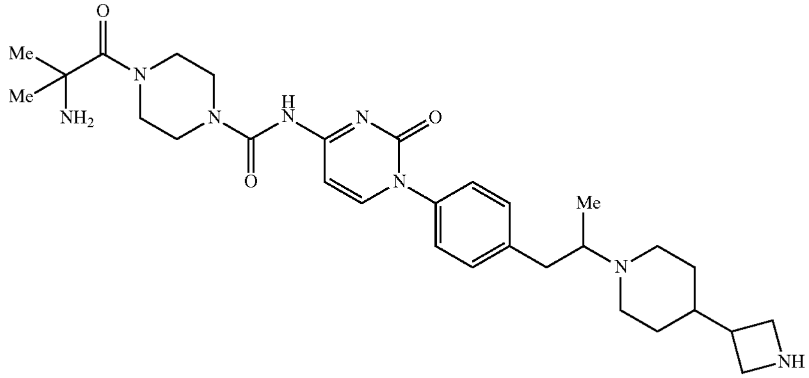 [SMILES: CC(Cc1ccc(-n2ccc(NC(=O)N3CCN(C(=O)C(C)(C)N)CC3)nc2=O)cc1)N1CCC(C2CNC2)CC1] |
| 380 | 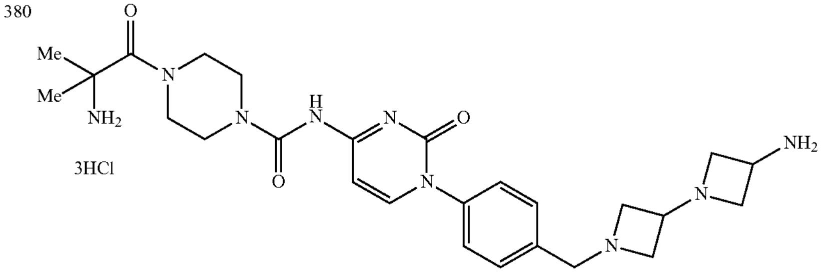 3HCl | 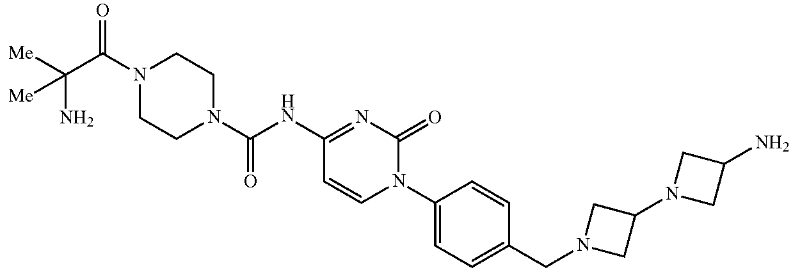 [SMILES: CC(C)(N)C(=O)N1CCN(C(=O)Nc2ccn(-c3ccc(CN4CC(N5CC(N)C5)C4)cc3)c(=O)n2)CC1] |
| 381 | 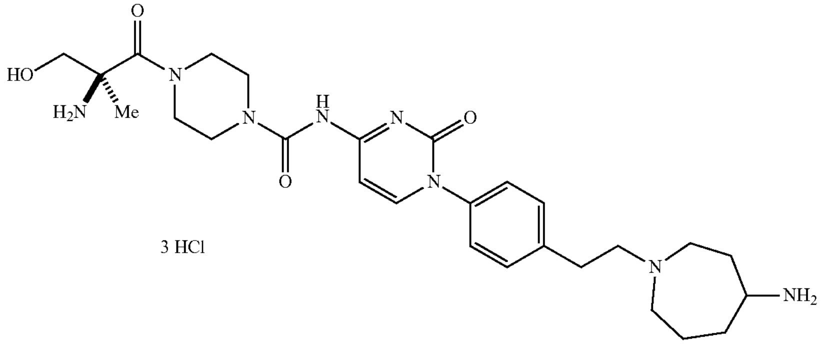 [SMILES: C[C@](N)(CO)C(=O)N1CCN(C(=O)Nc2ccn(-c3ccc(CCN4CCCC(N)CC4)cc3)c(=O)n2)CC1] 3 HCl | 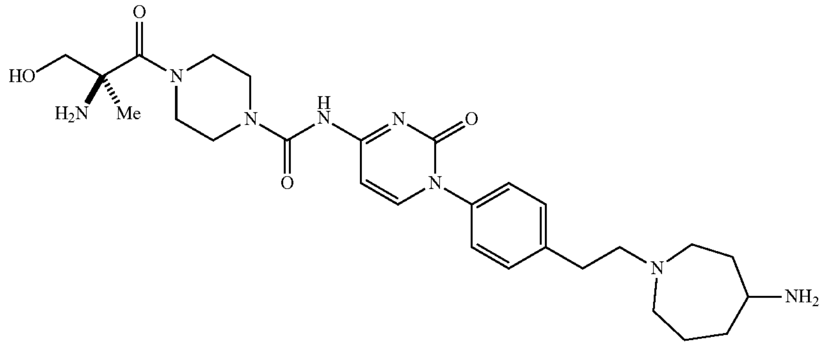 [SMILES: C[C@](N)(CO)C(=O)N1CCN(C(=O)Nc2ccn(-c3ccc(CCN4CCCC(N)CC4)cc3)c(=O)n2)CC1] |

TABLE 11-continued
| Compounds of Formula I Continued | |
|---|---|
| No. Salt Structure | Free Base Structure |
| 382 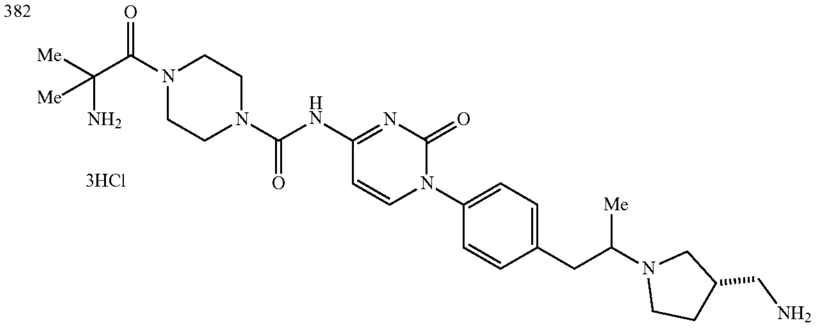 3HCl | 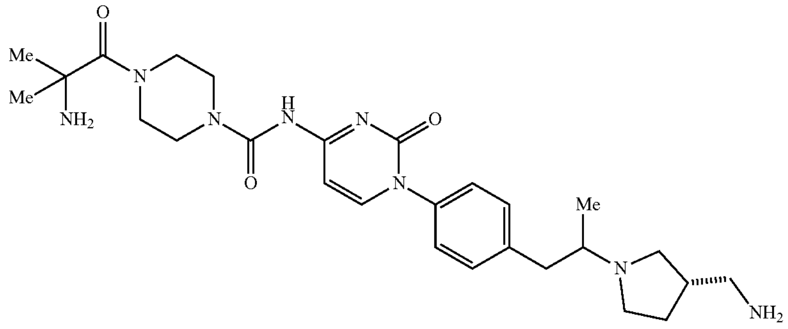 [SMILES: CC(Cc1ccc(-n2ccc(NC(=O)N3CCN(C(=O)C(C)(C)N)CC3)nc2=O)cc1)N1CC[C@@H](CN)C1] |
| 383 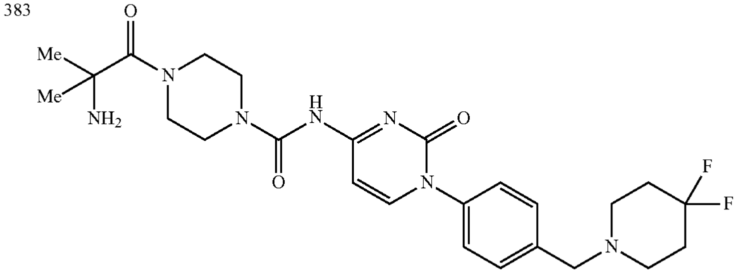 2 HCl | 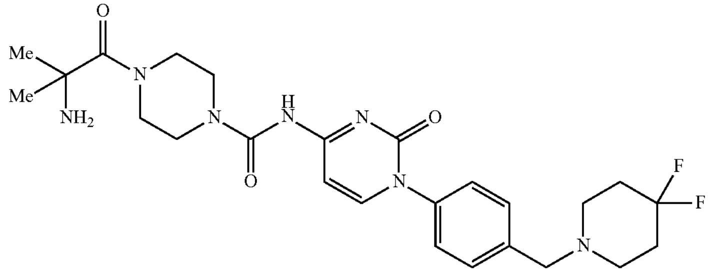 [SMILES: CC(C)(N)C(=O)N1CCN(C(=O)Nc2ccn(-c3ccc(CN4CCC(F)(F)CC4)cc3)c(=O)n2)CC1] |
| 384 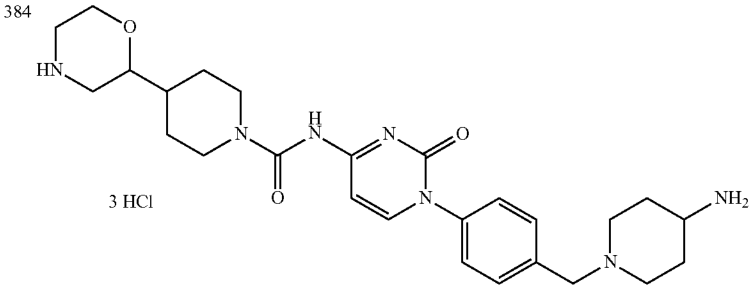 3 HCl | 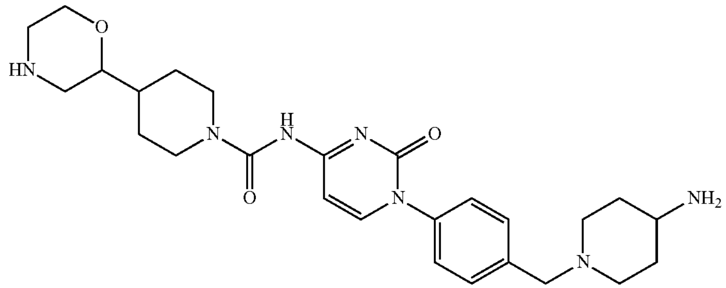 [SMILES: NC1CCN(Cc2ccc(-n3ccc(NC(=O)N4CCC(C5CNCCO5)CC4)nc3=O)cc2)CC1] |

TABLE 11-continued
| Compounds of Formula I Continued | | |
|---|---|---|
| No. | Salt Structure | Free Base Structure |
| 385 | 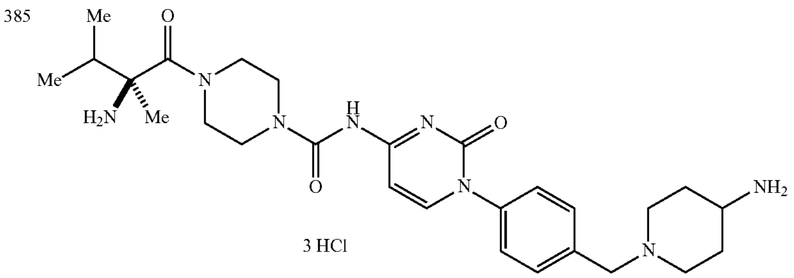 3 HCl | 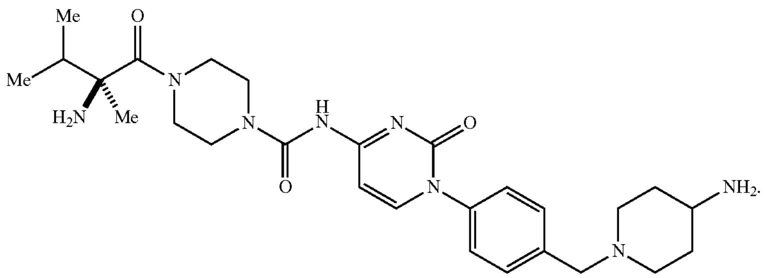 |

19. A compound of formula IV:
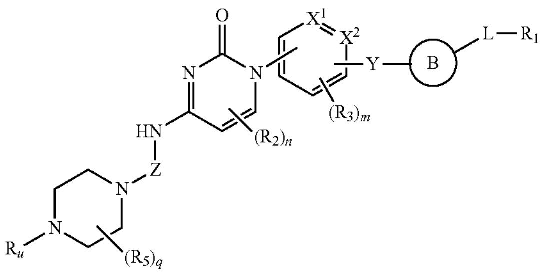
IV
or a pharmaceutically acceptable salt thereof, wherein the variables have the definitions as defined in claim 1, and $R_u$ is H or an amino protecting group.
20. A compound or a pharmaceutically acceptable salt thereof, wherein the compound is selected from the compounds listed in Table 12:
TABLE 12
| Compounds of Formula IV<br>Structure |
|---|
| 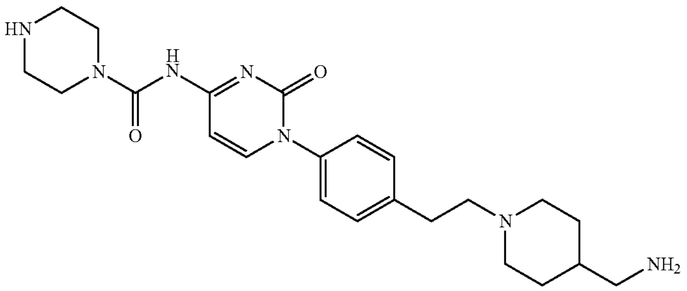 [SMILES: NCC1CCN(CCc2ccc(-n3ccc(NC(=O)N4CCNCC4)nc3=O)cc2)CC1] |
| 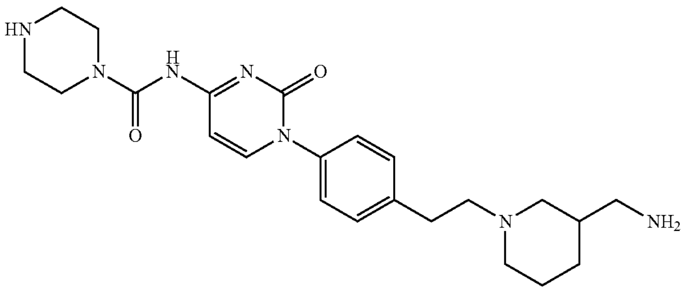 [SMILES: NCC1CCCN(CCc2ccc(-n3ccc(NC(=O)N4CCNCC4)nc3=O)cc2)C1] |
| 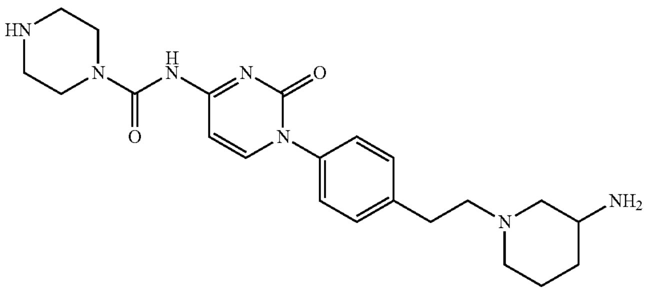 |

TABLE 12-continued
| Compounds of Formula IV Structure |
|---|
| 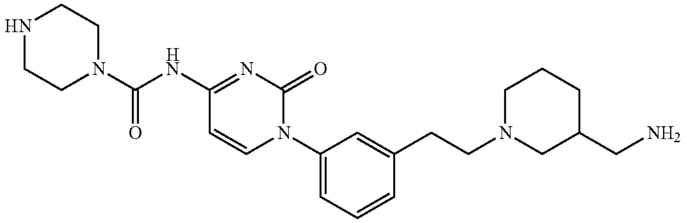 [SMILES: NCC1CCCN(CCc2cccc(-n3ccc(NC(=O)N4CCNCC4)nc3=O)c2)C1] |
| 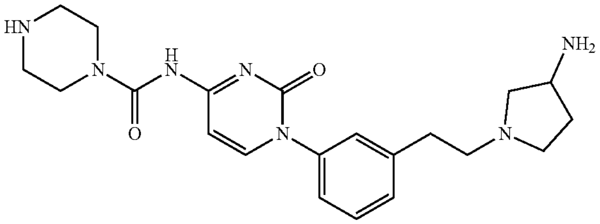 [SMILES: NC1CCN(CCc2cccc(-n3ccc(NC(=O)N4CCNCC4)nc3=O)c2)C1] |
| 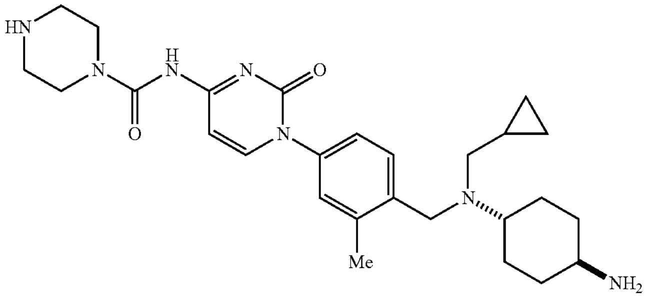 |
| 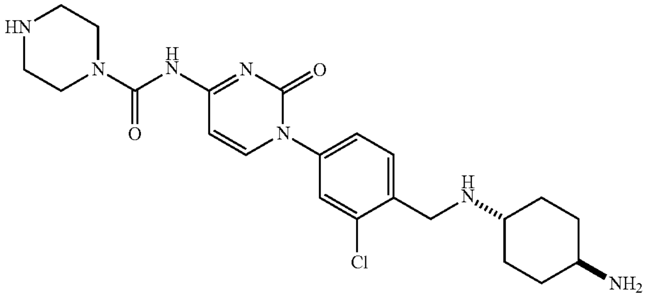 |
| 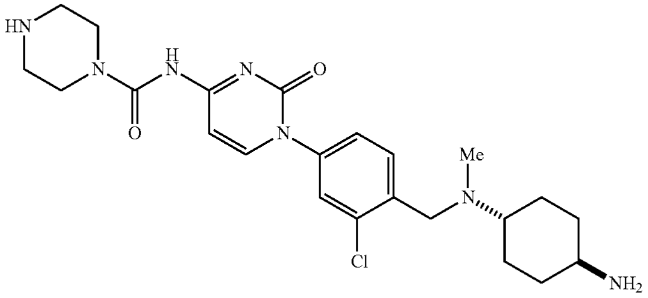 |

TABLE 12-continued
| Compounds of Formula IV<br>Structure |
|---|
| 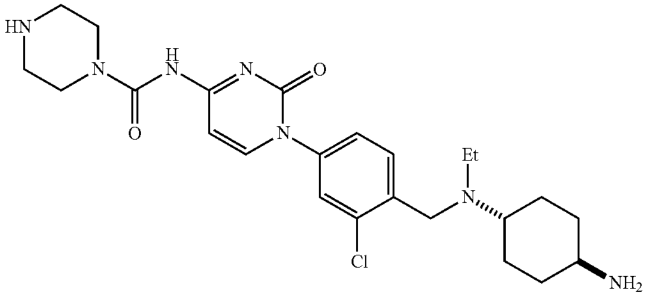 |
| 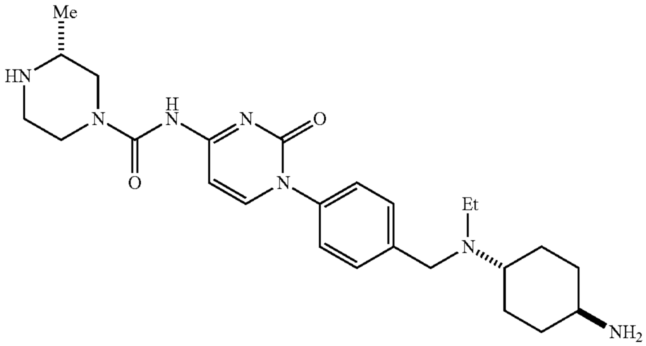 |
| 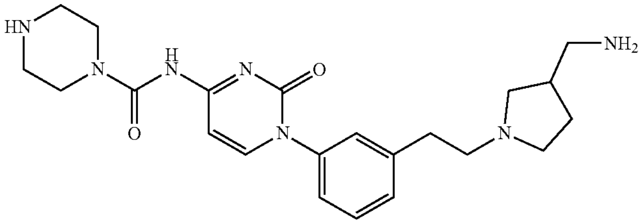 [SMILES: NCC1CCN(CCc2cccc(-n3ccc(NC(=O)N4CCNCC4)nc3=O)c2)C1] |
| 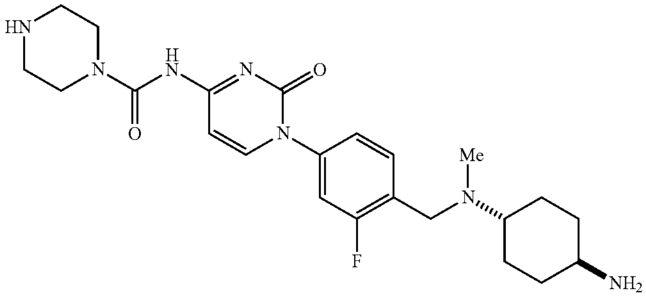 |
| 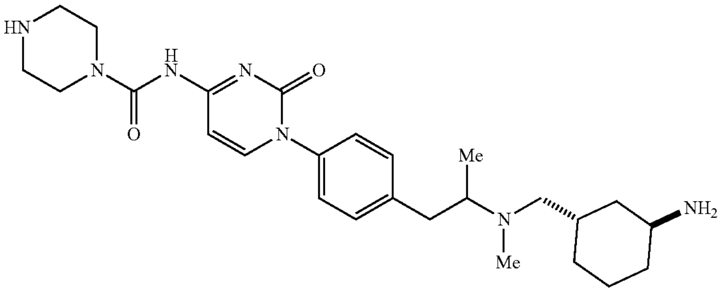 |

TABLE 12-continued
| Compounds of Formula IV Structure |
| --- |
| 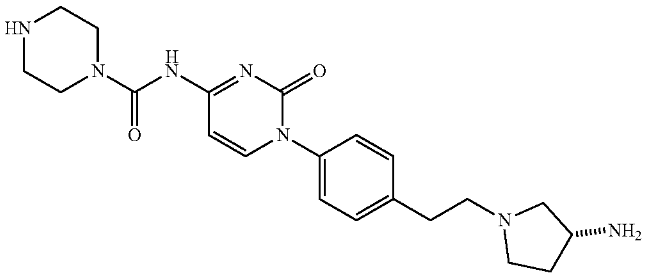 [SMILES: N[C@@H]1CCN(CCc2ccc(-n3ccc(NC(=O)N4CCNCC4)nc3=O)cc2)C1] |
| 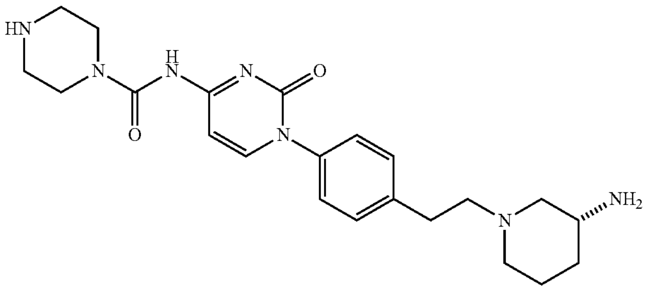 |
| 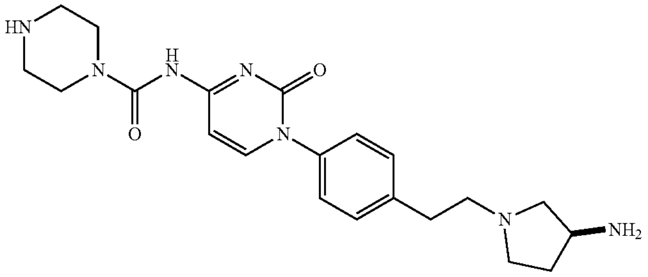 [SMILES: N[C@H]1CCN(CCc2ccc(-n3ccc(NC(=O)N4CCNCC4)nc3=O)cc2)C1] |
| 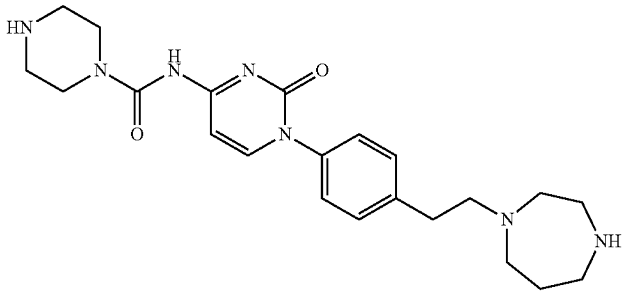 [SMILES: O=C(Nc1ccn(-c2ccc(CCN3CCCNCC3)cc2)c(=O)n1)N1CCNCC1] |
| 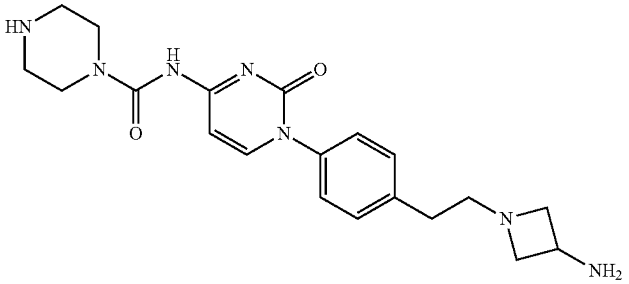 [SMILES: NC1CN(CCc2ccc(-n3ccc(NC(=O)N4CCNCC4)nc3=O)cc2)C1] |

TABLE 12-continued
| Compounds of Formula IV Structure |
|---|
| 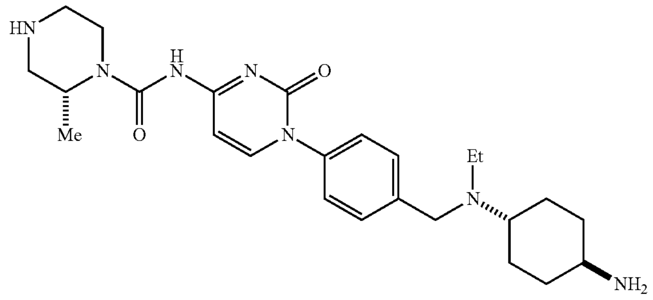 |
| 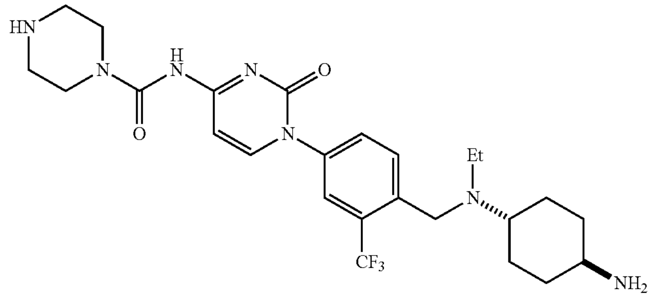 |
| 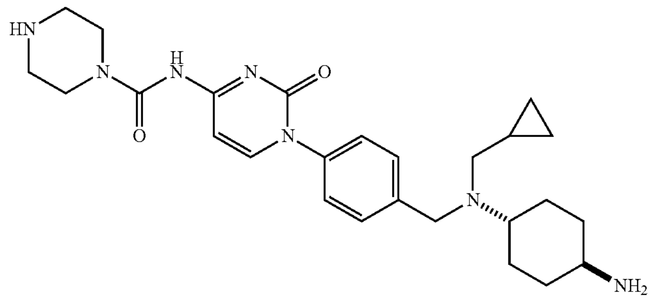 |
| 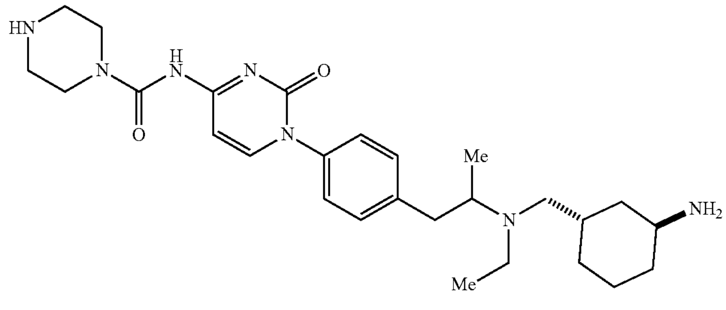 |
| 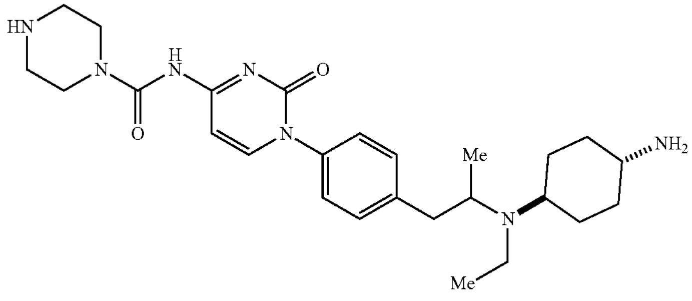 |

TABLE 12-continued
| Compounds of Formula IV<br>Structure |
| --- |
| 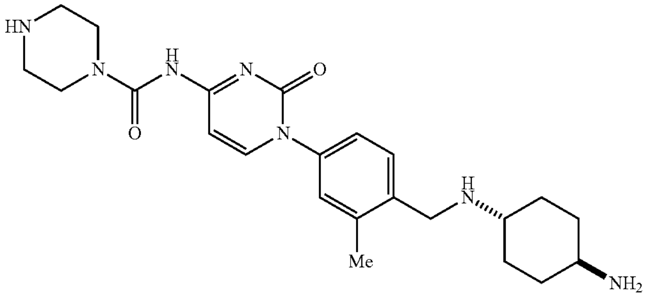 |
| 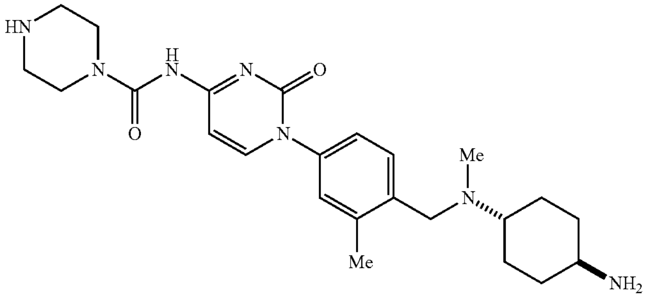 |
| 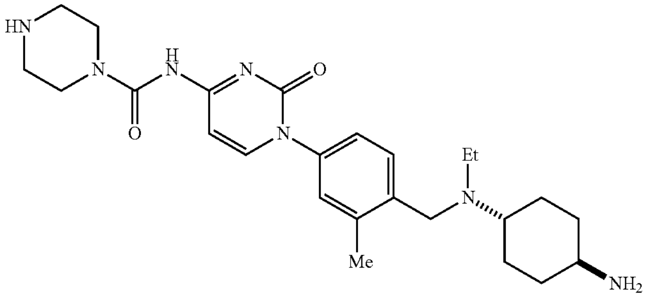 |
| 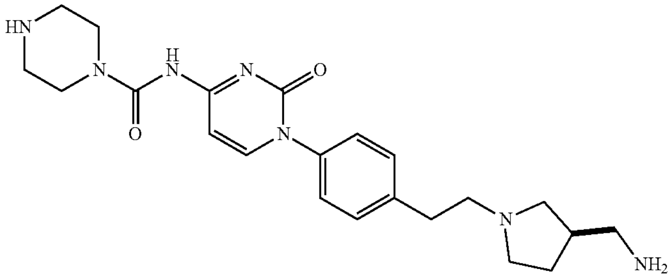 [SMILES: NC[C@H]1CCN(CCc2ccc(-n3ccc(NC(=O)N4CCNCC4)nc3=O)cc2)C1] |
| 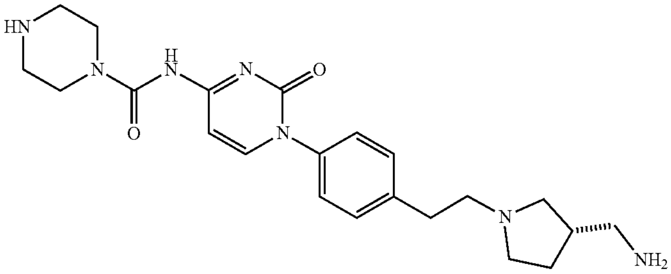 [SMILES: NC[C@@H]1CCN(CCc2ccc(-n3ccc(NC(=O)N4CCNCC4)nc3=O)cc2)C1] |

TABLE 12-continued
| Compounds of Formula IV Structure |
| --- |
| 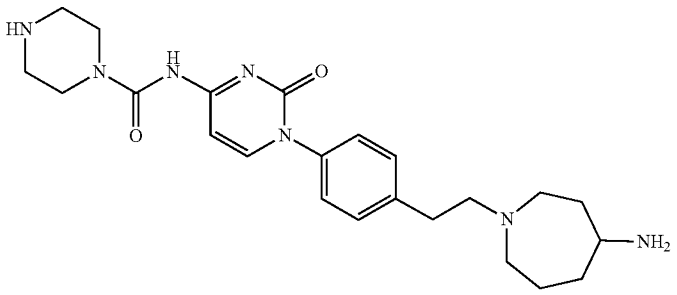 [SMILES: NC1CCCN(CCc2ccc(-n3ccc(NC(=O)N4CCNCC4)nc3=O)cc2)CC1] |
| 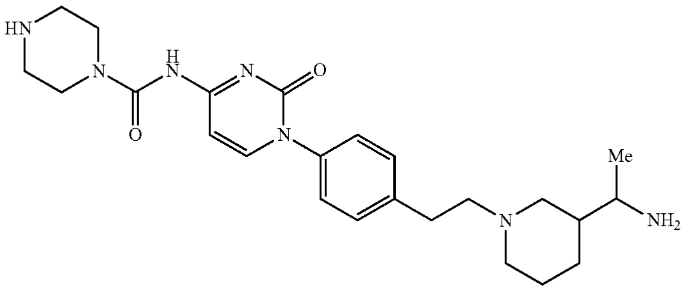 [SMILES: CC(N)C1CCCN(CCc2ccc(-n3ccc(NC(=O)N4CCNCC4)nc3=O)cc2)C1] |
| 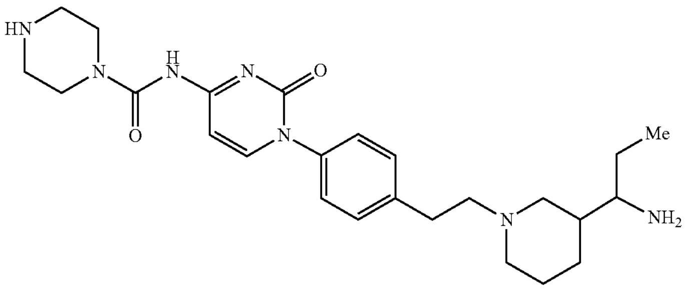 [SMILES: CCC(N)C1CCCN(CCc2ccc(-n3ccc(NC(=O)N4CCNCC4)nc3=O)cc2)C1] |
| 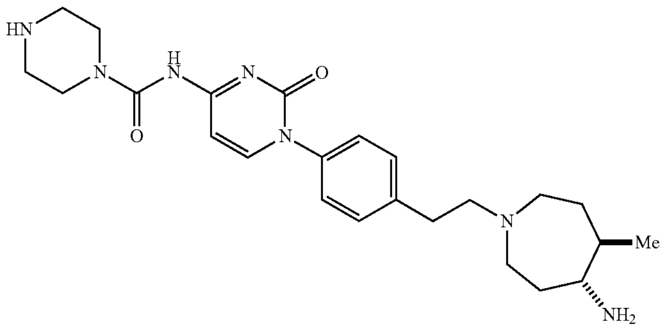 [SMILES: C[C@@H]1CCN(CCc2ccc(-n3ccc(NC(=O)N4CCNCC4)nc3=O)cc2)CC[C@H]1N] |
| 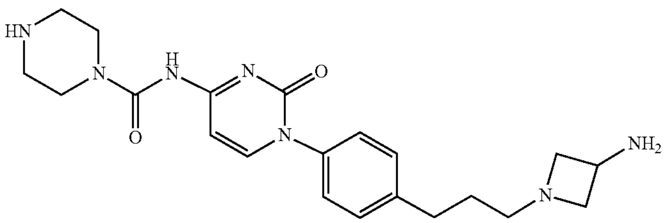 [SMILES: NC1CN(CCCc2ccc(-n3ccc(NC(=O)N4CCNCC4)nc3=O)cc2)C1] |

TABLE 12-continued
| Compounds of Formula IV Structure |
| --- |
| 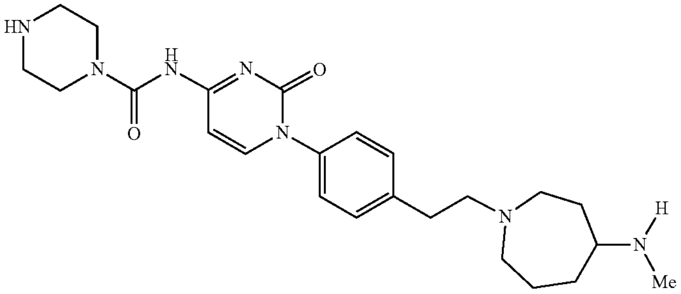 [SMILES: CNC1CCCN(CCc2ccc(-n3ccc(NC(=O)N4CCNCC4)nc3=O)cc2)CC1] |
| 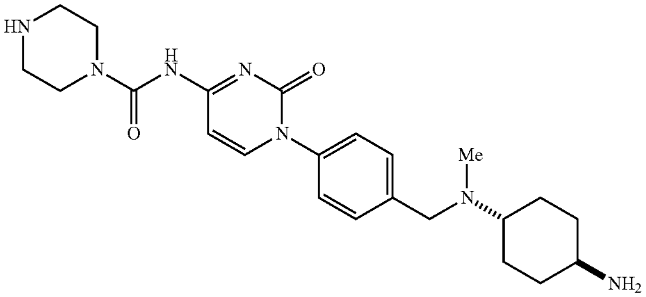 |
| 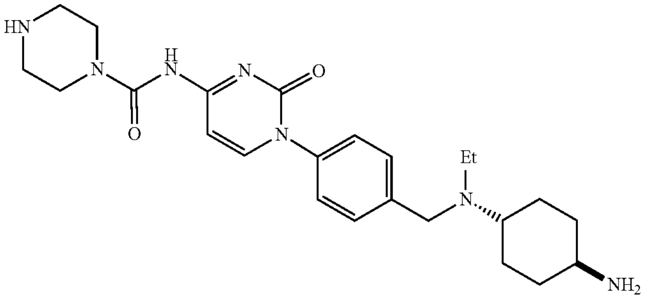 |
| 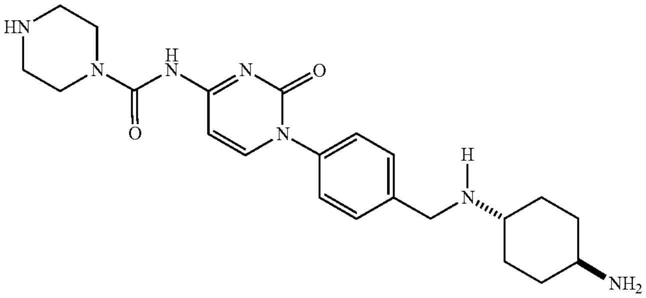 |
| 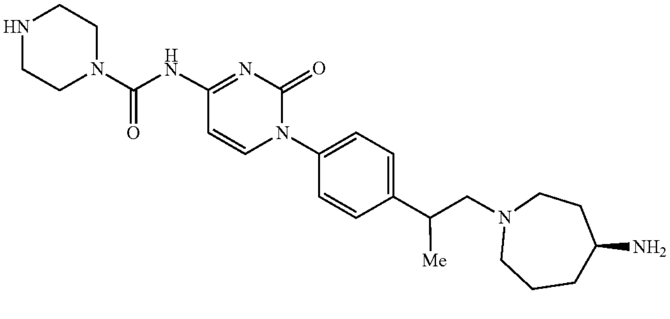 [SMILES: CC(CN1CCC[C@H](N)CC1)c1ccc(-n2ccc(NC(=O)N3CCNCC3)nc2=O)cc1] |

TABLE 12-continued
| Compounds of Formula IV Structure |
| --- |
| 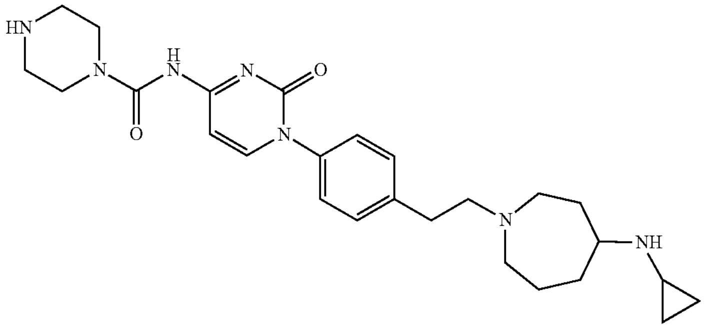 [SMILES: O=C(Nc1ccn(-c2ccc(CCN3CCCC(NC4CC4)CC3)cc2)c(=O)n1)N1CCNCC1] |
| 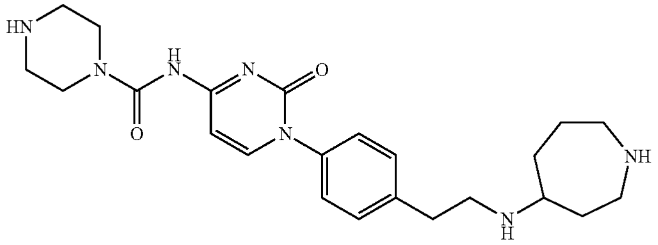 [SMILES: O=C(Nc1ccn(-c2ccc(CCNC3CCCNCC3)cc2)c(=O)n1)N1CCNCC1] |
| 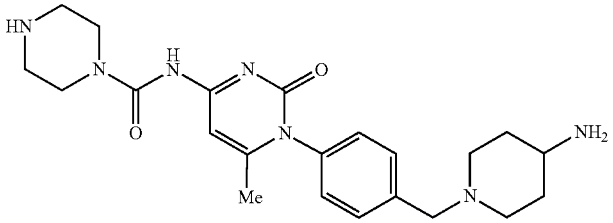 [SMILES: Cc1cc(NC(=O)N2CCNCC2)nc(=O)n1-c1ccc(CN2CCC(N)CC2)cc1] |
| 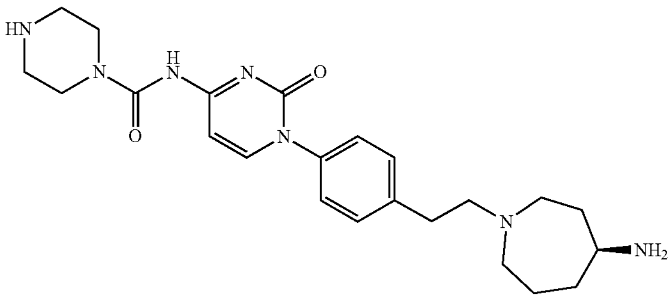 [SMILES: N[C@H]1CCCN(CCc2ccc(-n3ccc(NC(=O)N4CCNCC4)nc3=O)cc2)CC1] |
| 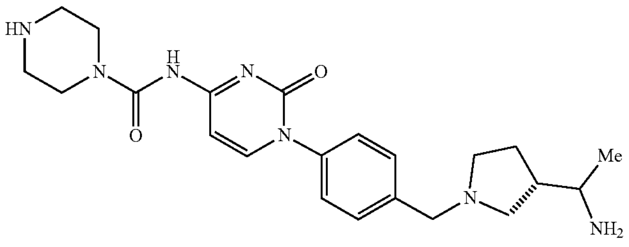 [SMILES: CC(N)[C@H]1CCN(Cc2ccc(-n3ccc(NC(=O)N4CCNCC4)nc3=O)cc2)C1] |

TABLE 12-continued
| Compounds of Formula IV Structure |
|---|
| 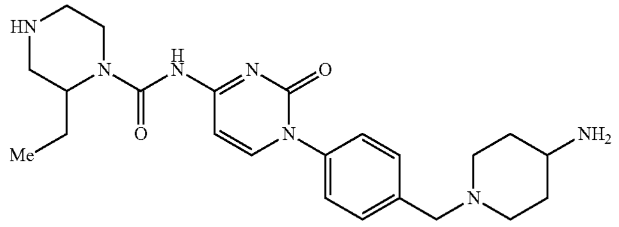 [SMILES: CCC1CNCCN1C(=O)Nc1ccn(-c2ccc(CN3CCC(N)CC3)cc2)c(=O)n1] |
| 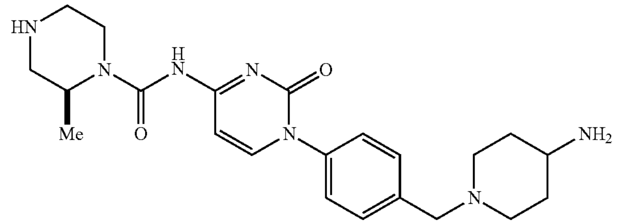 [SMILES: C[C@H]1CNCCN1C(=O)Nc1ccn(-c2ccc(CN3CCC(N)CC3)cc2)c(=O)n1] |
| 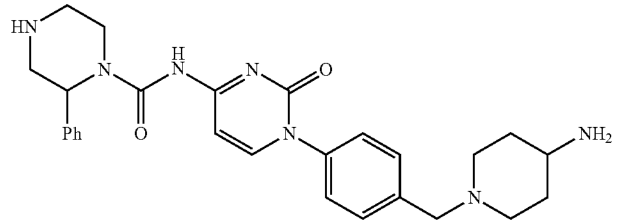 [SMILES: NC1CCN(Cc2ccc(-n3ccc(NC(=O)N4CCNCC4c4ccccc4)nc3=O)cc2)CC1] |
| 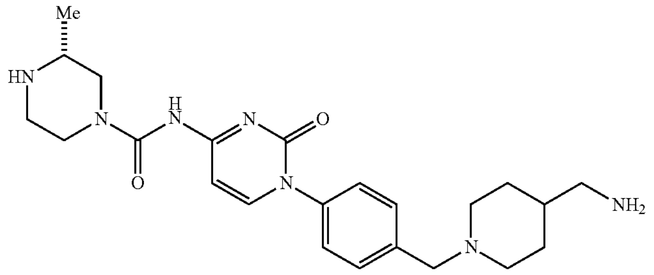 [SMILES: C[C@@H]1CN(C(=O)Nc2ccn(-c3ccc(CN4CCC(CN)CC4)cc3)c(=O)n2)CCN1] |
| 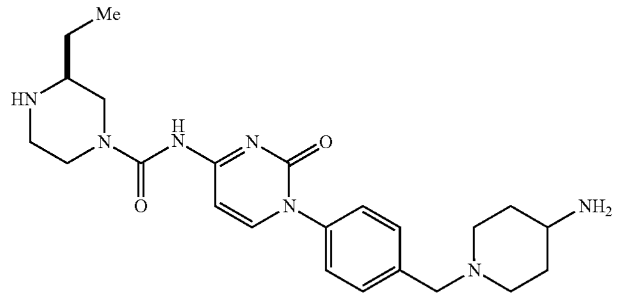 [SMILES: CC[C@H]1CN(C(=O)Nc2ccn(-c3ccc(CN4CCC(N)CC4)cc3)c(=O)n2)CCN1] |
| 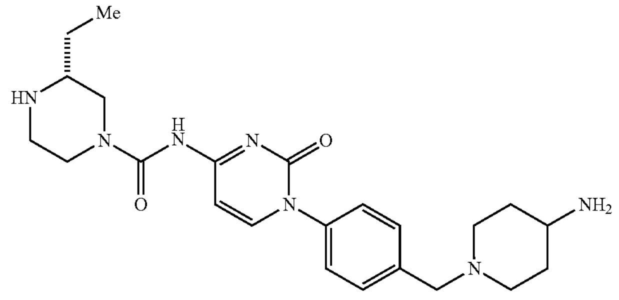 |

TABLE 12-continued
| Compounds of Formula IV Structure |
| --- |
| 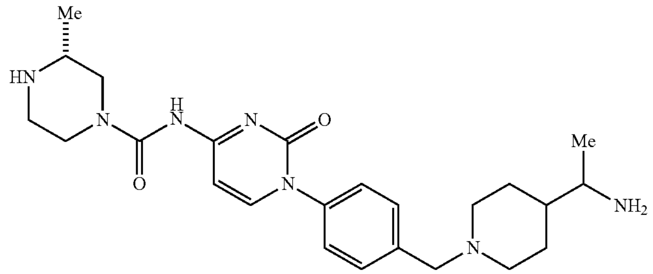 [SMILES: CC(N)C1CCN(Cc2ccc(-n3ccc(NC(=O)N4CCN[C@H](C)C4)nc3=O)cc2)CC1] |
| 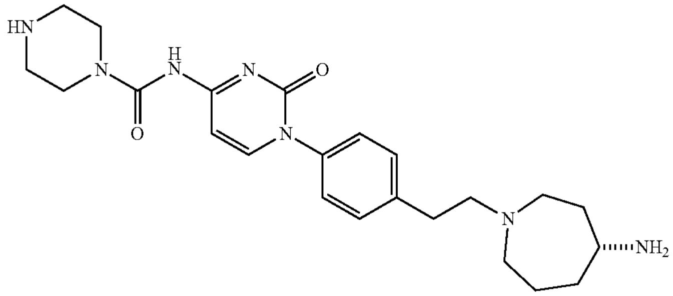 [SMILES: N[C@@H]1CCCN(CCc2ccc(-n3ccc(NC(=O)N4CCNCC4)nc3=O)cc2)CC1] |
| 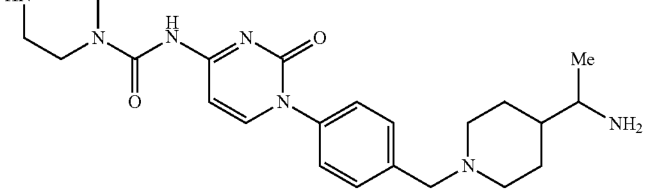 |
| 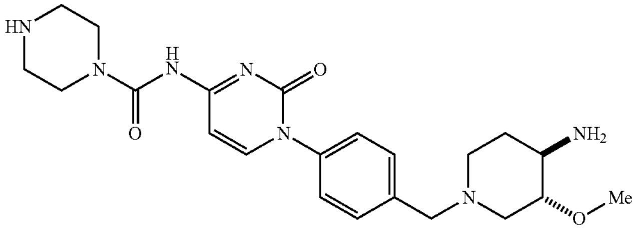 [SMILES: CO[C@@H]1CN(Cc2ccc(-n3ccc(NC(=O)N4CCNCC4)nc3=O)cc2)CC[C@H]1N] |
| 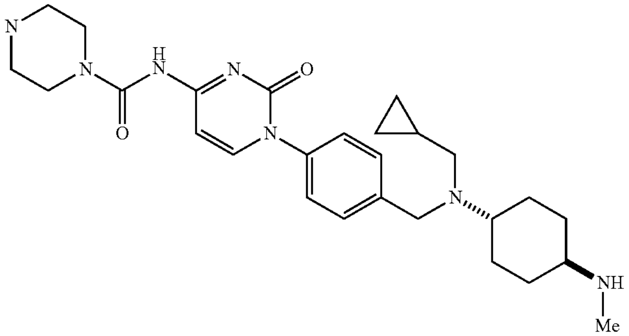 |

TABLE 12-continued
| Compounds of Formula IV Structure |
| --- |
| 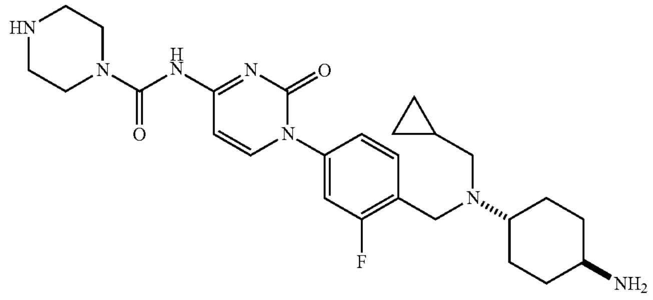 |
| 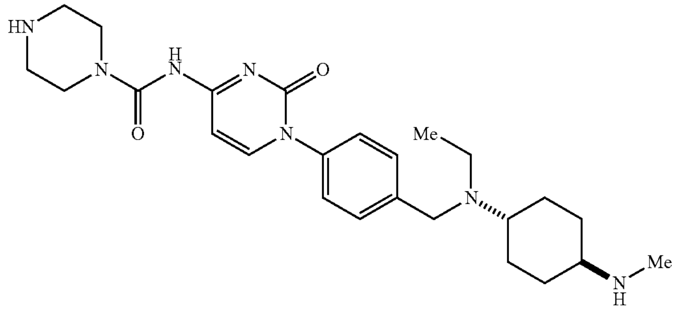 |
| 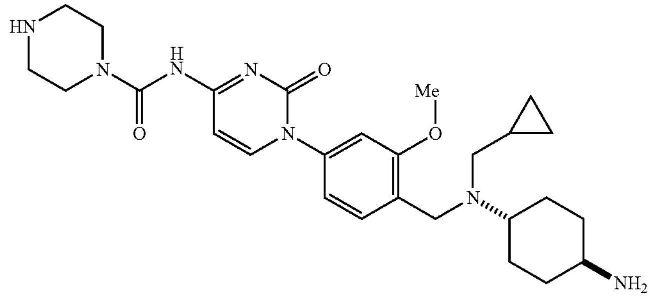 |
| 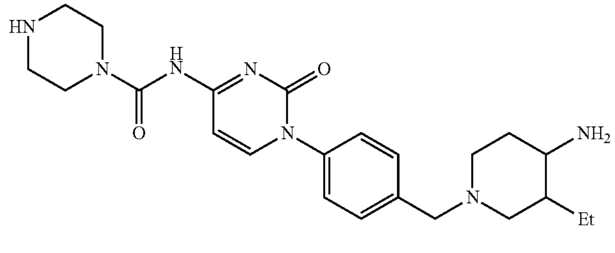 [SMILES: CCC1CN(Cc2ccc(-n3ccc(NC(=O)N4CCNCC4)nc3=O)cc2)CCC1N] |
| 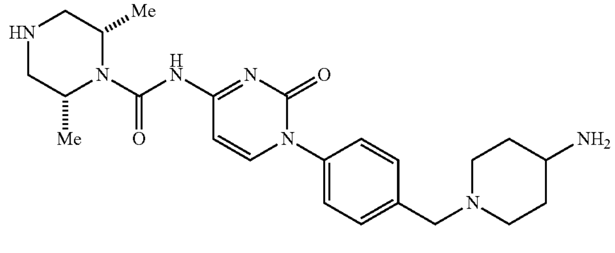 [SMILES: C[C@@H]1CNC[C@H](C)N1C(=O)Nc1ccn(-c2ccc(CN3CCC(N)CC3)cc2)c(=O)n1] |

TABLE 12-continued
| Compounds of Formula IV Structure |
|---|
| 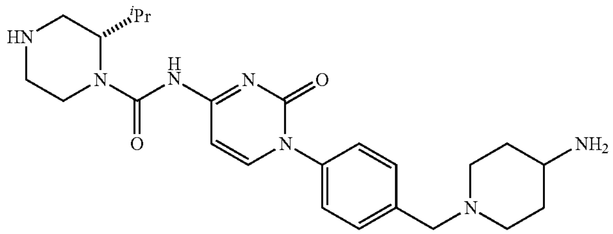 [SMILES: CC(C)[C@H]1CNCCN1C(=O)Nc1ccn(-c2ccc(CN3CCC(N)CC3)cc2)c(=O)n1] |
| 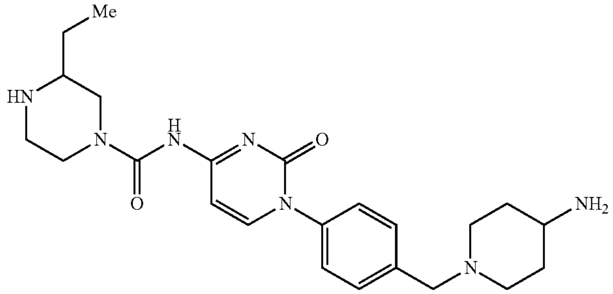 |
| 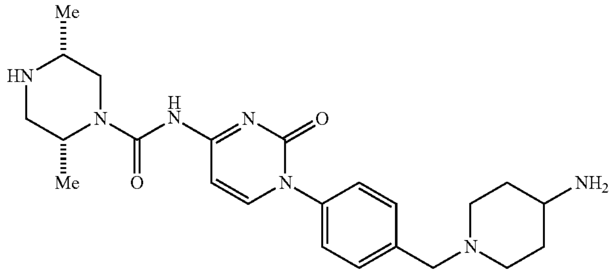 [SMILES: C[C@@H]1CN(C(=O)Nc2ccn(-c3ccc(CN4CCC(N)CC4)cc3)c(=O)n2)[C@H](C)CN1] |
| 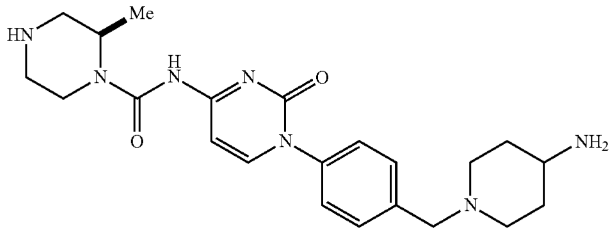 [SMILES: C[C@@H]1CNCCN1C(=O)Nc1ccn(-c2ccc(CN3CCC(N)CC3)cc2)c(=O)n1] |
| 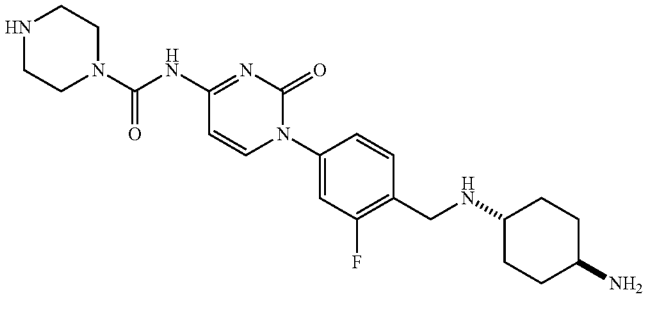 |

TABLE 12-continued
| Compounds of Formula IV Structure |
| --- |
| 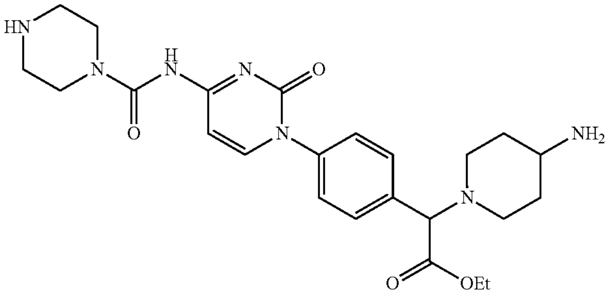 |
| 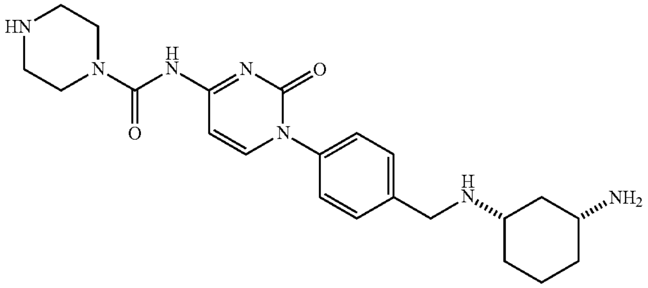 |
| 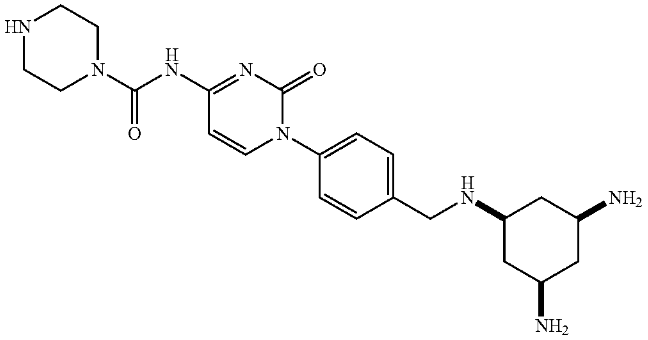 |
| 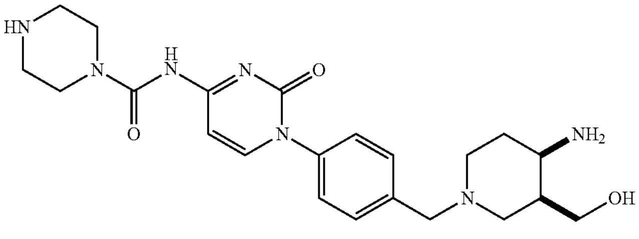 [SMILES: N[C@@H]1CCN(Cc2ccc(-n3ccc(NC(=O)N4CCNCC4)nc3=O)cc2)C[C@@H]1CO] |
| 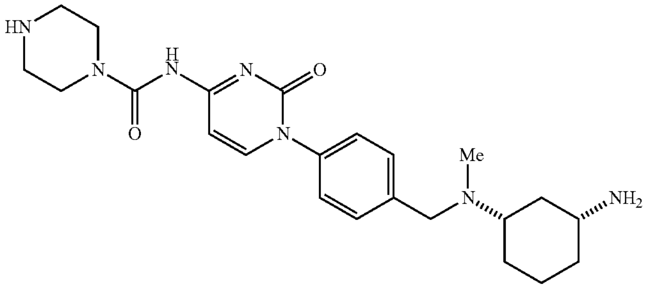 |

TABLE 12-continued
| Compounds of Formula IV Structure |
| --- |
| 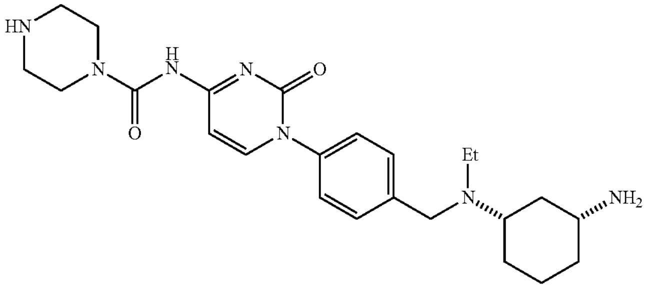 |
| 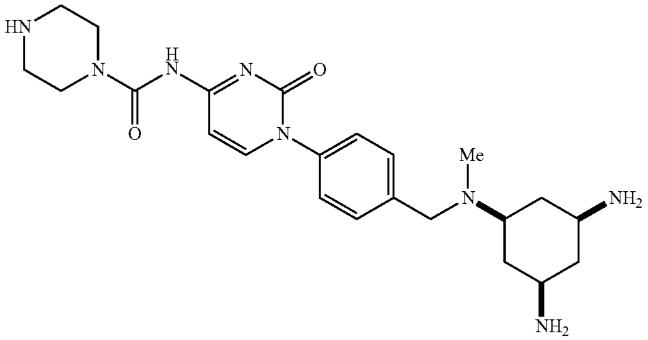 |
| 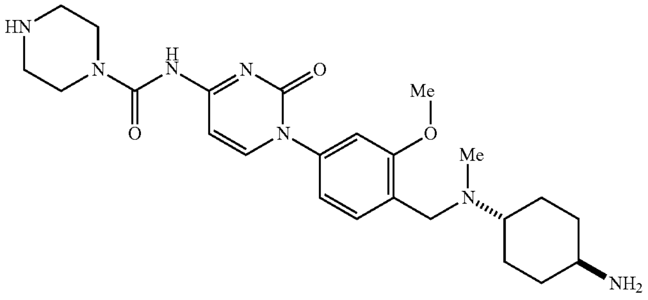 |
| 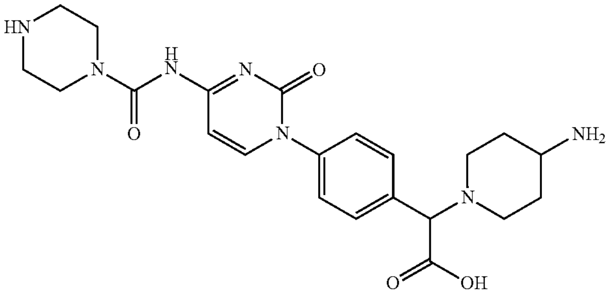 |
| 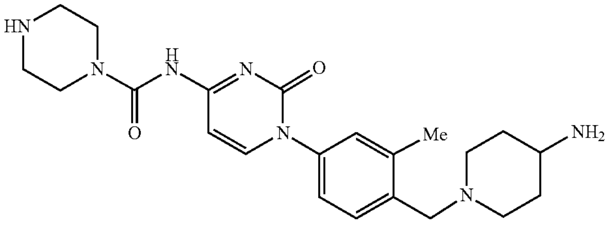 [SMILES: Cc1cc(-n2ccc(NC(=O)N3CCNCC3)nc2=O)ccc1CN1CCC(N)CC1] |

TABLE 12-continued
| Compounds of Formula IV<br>Structure |
| --- |
| 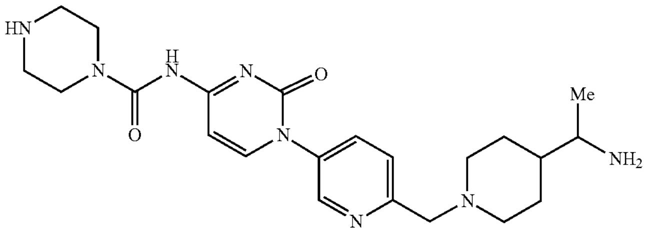 [SMILES: CC(N)C1CCN(Cc2ccc(-n3ccc(NC(=O)N4CCNCC4)nc3=O)cn2)CC1] |
| 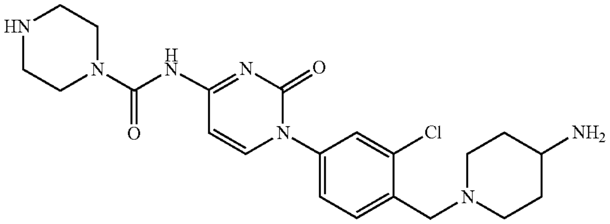 |
| 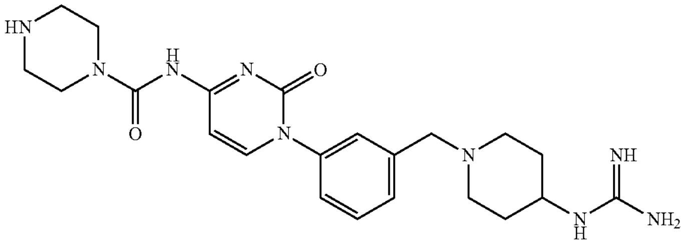 [SMILES: N=C(N)NC1CCN(Cc2cccc(-n3ccc(NC(=O)N4CCNCC4)nc3=O)c2)CC1] |
| 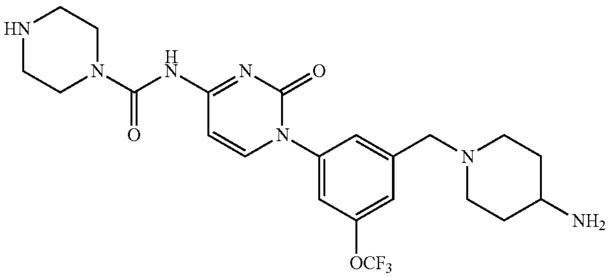 [SMILES: NC1CCN(Cc2cc(OC(F)(F)F)cc(-n3ccc(NC(=O)N4CCNCC4)nc3=O)c2)CC1] |
| 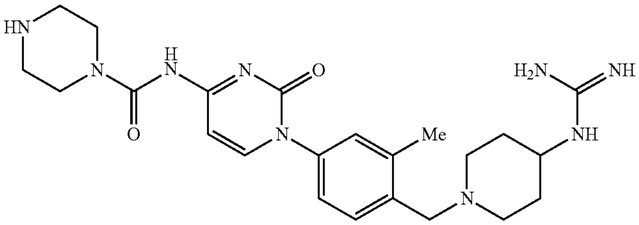 [SMILES: Cc1cc(-n2ccc(NC(=O)N3CCNCC3)nc2=O)ccc1CN1CCC(NC(=N)N)CC1] |
| 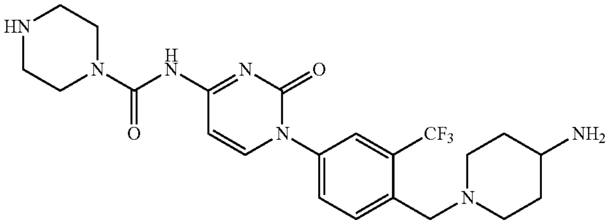 |

TABLE 12-continued
| Compounds of Formula IV Structure |
|---|
| 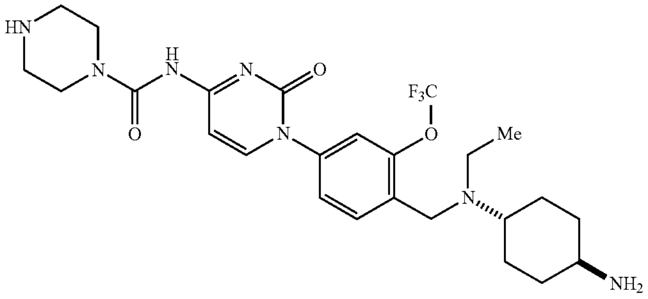 [SMILES: CCN(Cc1ccc(-n2ccc(NC(=O)N3CCNCC3)nc2=O)cc1OC(F)(F)F)[C@H]1CC[C@H](N)CC1] |
| 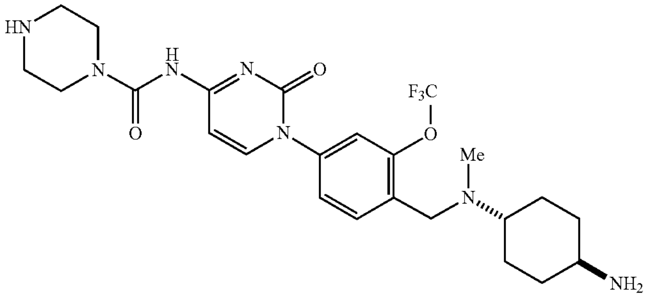 |
| 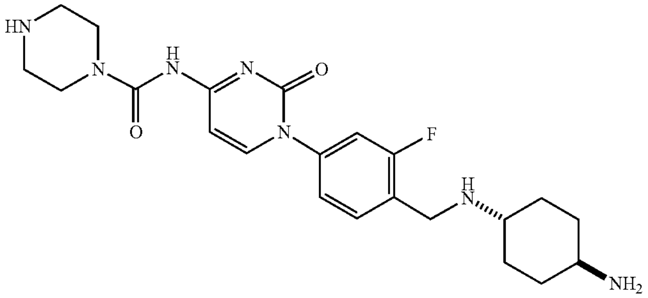 [SMILES: N[C@H]1CC[C@H](NCc2ccc(-n3ccc(NC(=O)N4CCNCC4)nc3=O)cc2F)CC1] |
| 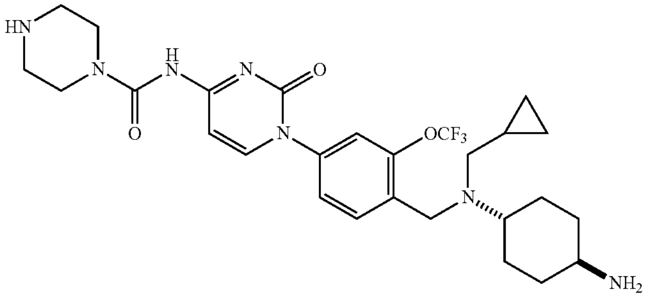 [SMILES: N[C@H]1CC[C@H](N(Cc2ccc(-n3ccc(NC(=O)N4CCNCC4)nc3=O)cc2OC(F)(F)F)CC2CC2)CC1] |
| 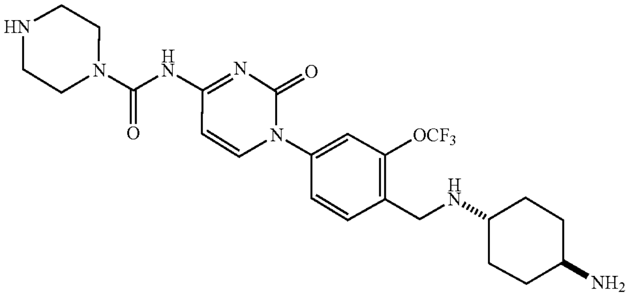 [SMILES: N[C@H]1CC[C@H](NCc2ccc(-n3ccc(NC(=O)N4CCNCC4)nc3=O)cc2OC(F)(F)F)CC1] |

TABLE 12-continued
| Compounds of Formula IV Structure |
| --- |
| 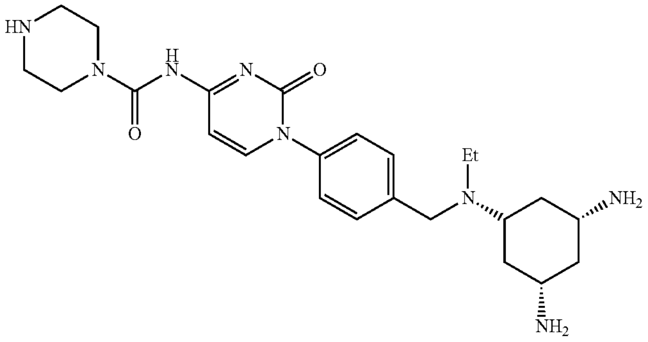 |
| 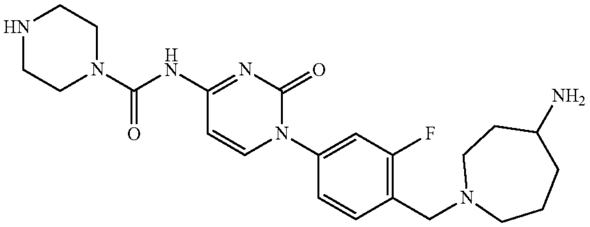 [SMILES: NC1CCCN(Cc2ccc(-n3ccc(NC(=O)N4CCNCC4)nc3=O)cc2F)CC1] |
| 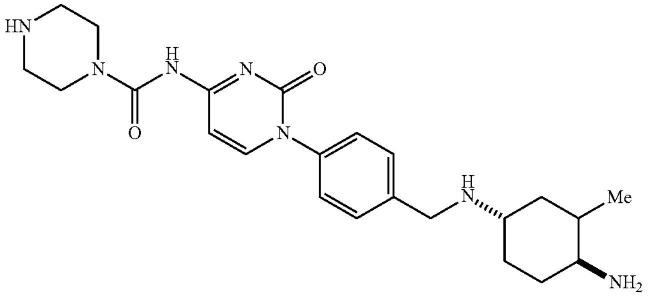 |
| 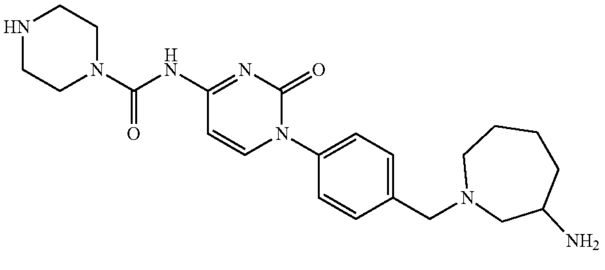 [SMILES: NC1CCCCN(Cc2ccc(-n3ccc(NC(=O)N4CCNCC4)nc3=O)cc2)C1] |
| 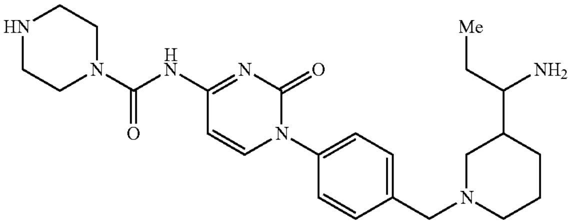 [SMILES: CCC(N)C1CCCN(Cc2ccc(-n3ccc(NC(=O)N4CCNCC4)nc3=O)cc2)C1] |

TABLE 12-continued
| Compounds of Formula IV<br>Structure |
|---|
| 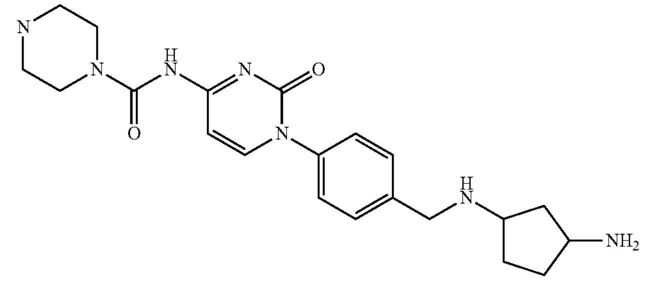 [SMILES: NC1CCC(NCc2ccc(-n3ccc(NC(=O)N4CCNCC4)nc3=O)cc2)C1] |
| 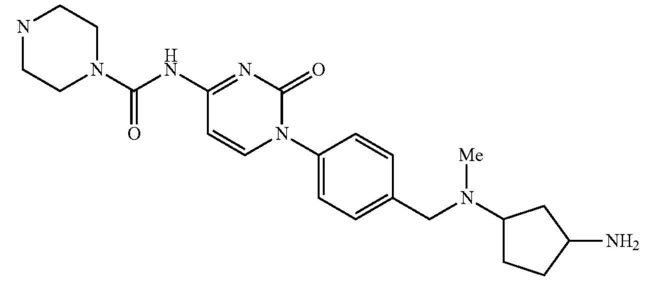 [SMILES: CN(Cc1ccc(-n2ccc(NC(=O)N3CCNCC3)nc2=O)cc1)C1CCC(N)C1] |
| 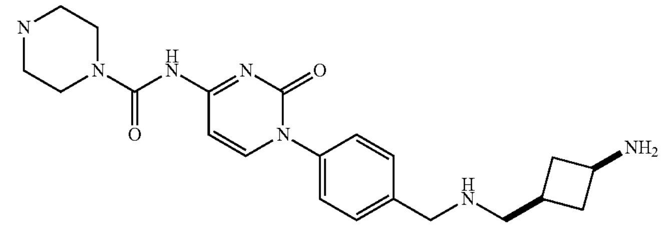 |
| 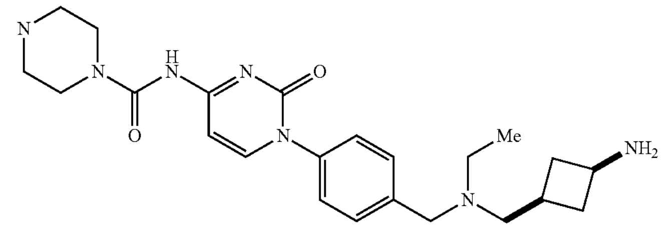 |
| 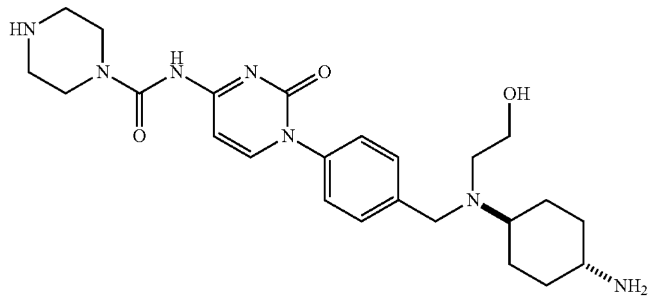 |
| 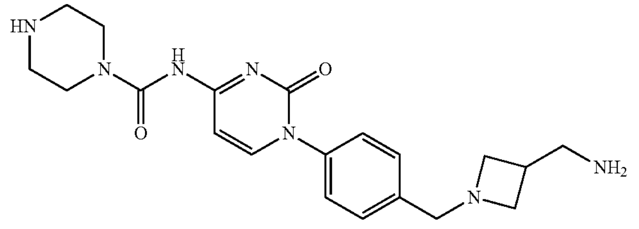 [SMILES: NCC1CN(Cc2ccc(-n3ccc(NC(=O)N4CCNCC4)nc3=O)cc2)C1] |

TABLE 12-continued
| Compounds of Formula IV Structure |
| --- |
| 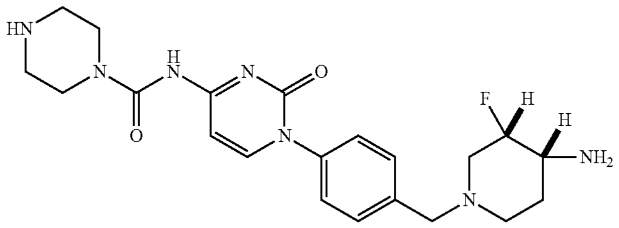 [SMILES: N[C@@H]1CCN(Cc2ccc(-n3ccc(NC(=O)N4CCNCC4)nc3=O)cc2)C[C@@H]1F] |
| 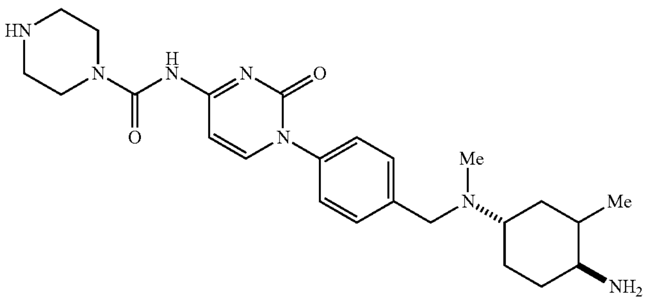 |
| 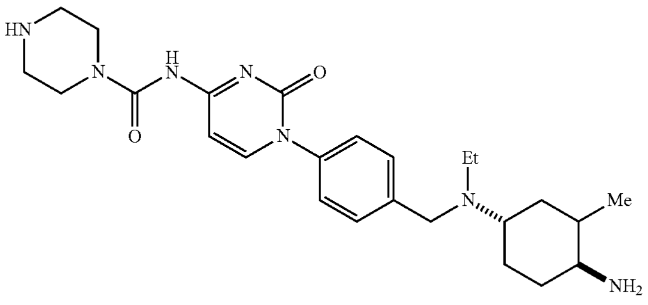 |
| 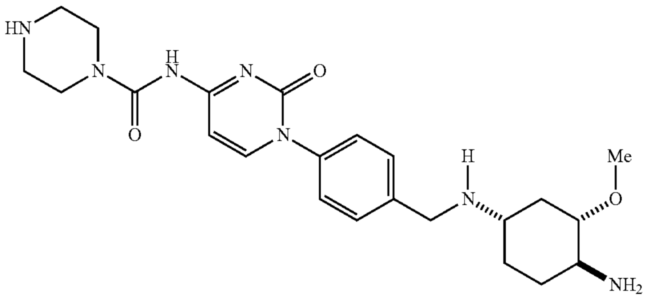 |
| 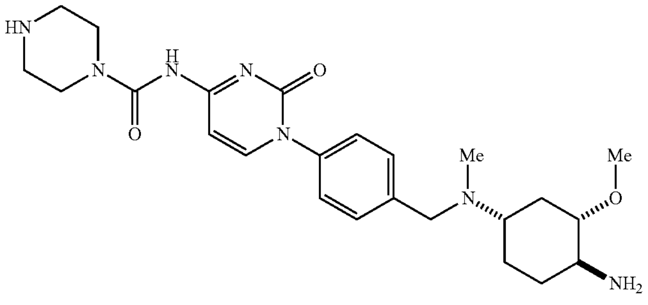 |

TABLE 12-continued
| Compounds of Formula IV<br>Structure |
| --- |
| 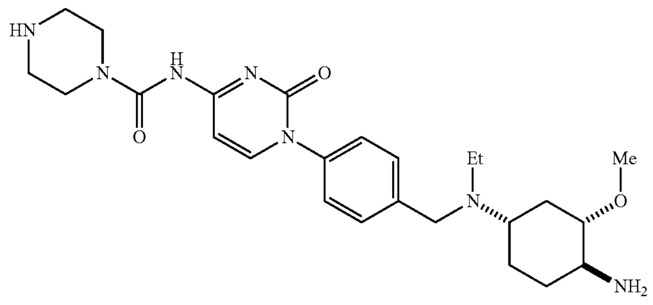 |
| 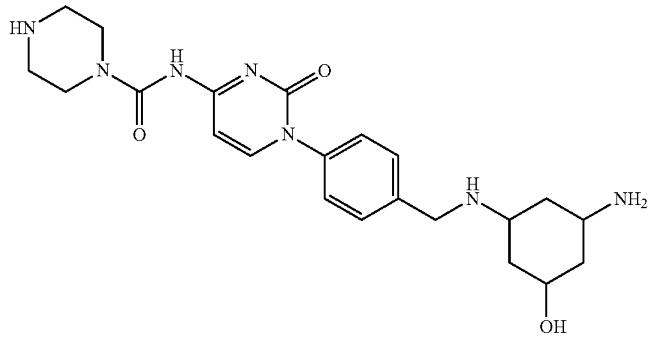 [SMILES: NC1CC(O)CC(NCc2ccc(-n3ccc(NC(=O)N4CCNCC4)nc3=O)cc2)C1] |
| 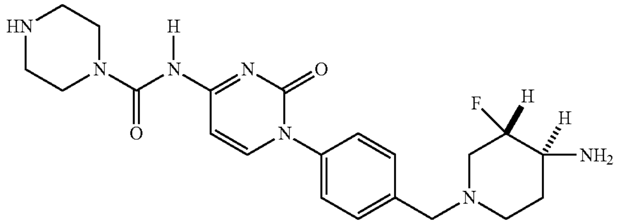 [SMILES: N[C@H]1CCN(Cc2ccc(-n3ccc(NC(=O)N4CCNCC4)nc3=O)cc2)C[C@@H]1F] |
| 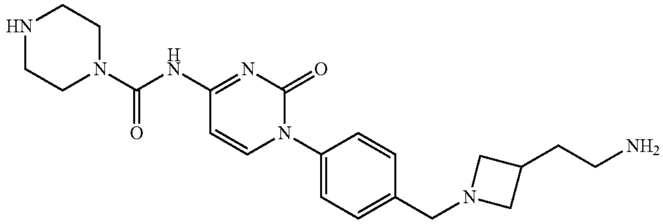 [SMILES: NCCC1CN(Cc2ccc(-n3ccc(NC(=O)N4CCNCC4)nc3=O)cc2)C1] |
| 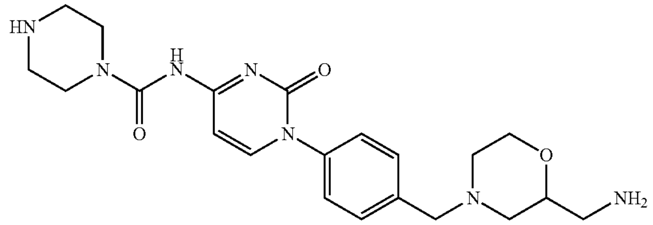 [SMILES: NCC1CN(Cc2ccc(-n3ccc(NC(=O)N4CCNCC4)nc3=O)cc2)CCO1] |
| 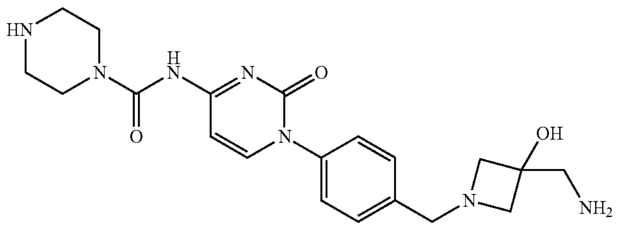 [SMILES: NCC1(O)CN(Cc2ccc(-n3ccc(NC(=O)N4CCNCC4)nc3=O)cc2)C1] |

TABLE 12-continued
| Compounds of Formula IV<br>Structure |
| --- |
| 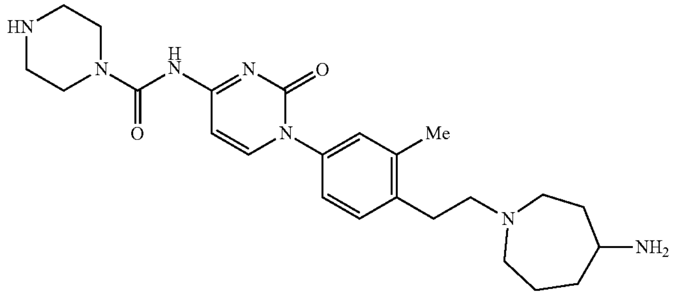 [SMILES: Cc1cc(-n2ccc(NC(=O)N3CCNCC3)nc2=O)ccc1CCN1CCCC(N)CC1] |
| 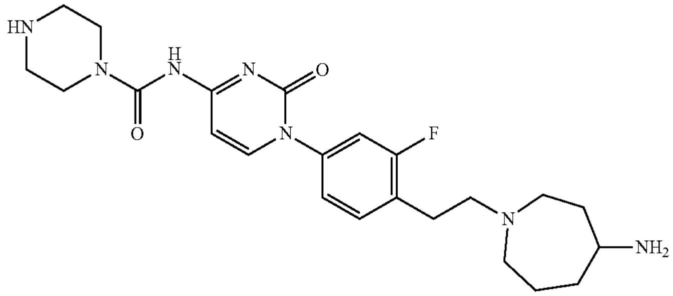 [SMILES: NC1CCCN(CCc2ccc(-n3ccc(NC(=O)N4CCNCC4)nc3=O)cc2F)CC1] |
| 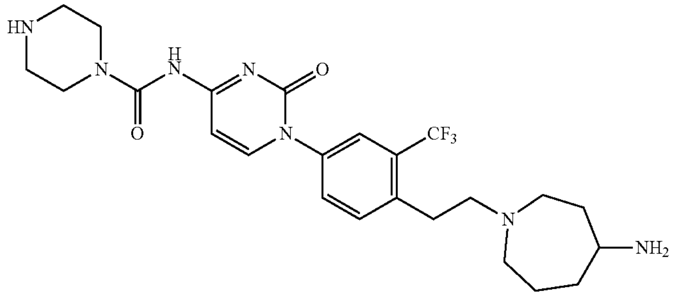 [SMILES: NC1CCCN(CCc2ccc(-n3ccc(NC(=O)N4CCNCC4)nc3=O)cc2C(F)(F)F)CC1] |
| 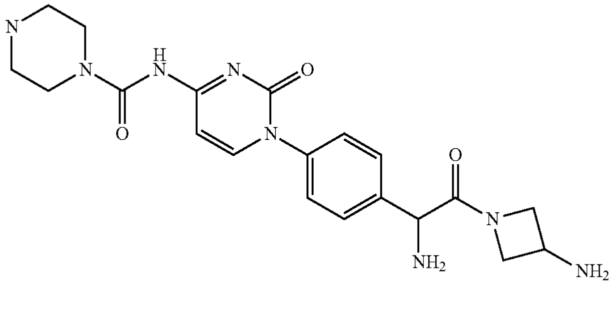 |
| 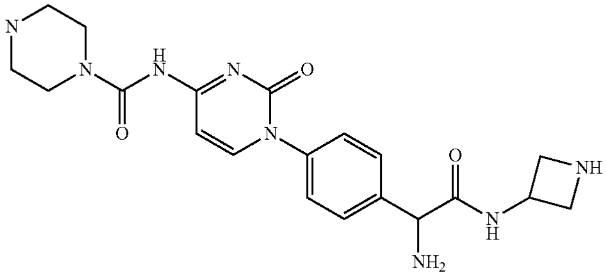 |

TABLE 12-continued
| Compounds of Formula IV Structure |
|---|
| 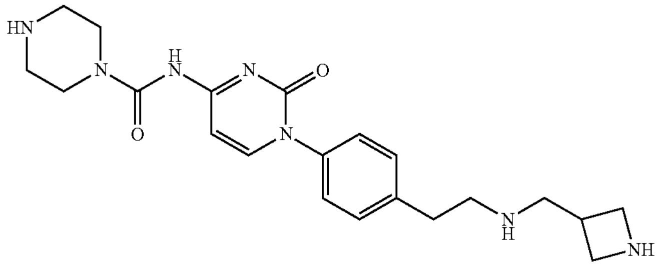 [SMILES: O=C(Nc1ccn(-c2ccc(CCNCC3CNC3)cc2)c(=O)n1)N1CCNCC1] |
| 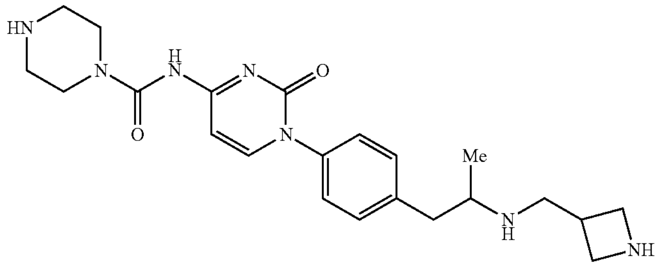 [SMILES: CC(Cc1ccc(-n2ccc(NC(=O)N3CCNCC3)nc2=O)cc1)NCC1CNC1] |
| 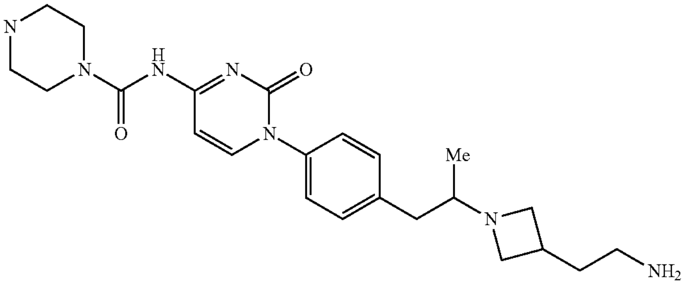 [SMILES: CC(Cc1ccc(-n2ccc(NC(=O)N3CCNCC3)nc2=O)cc1)N1CC(CCN)C1] |
| 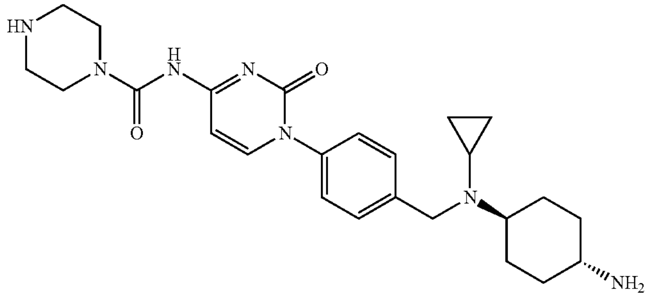 [SMILES: N[C@H]1CC[C@H](N(Cc2ccc(-n3ccc(NC(=O)N4CCNCC4)nc3=O)cc2)C2CC2)CC1] |
| 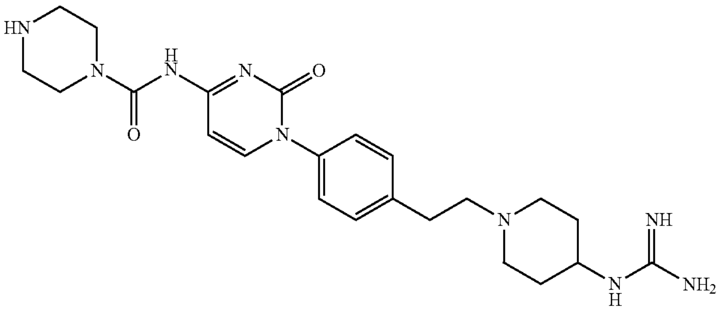 [SMILES: N=C(N)NC1CCN(CCc2ccc(-n3ccc(NC(=O)N4CCNCC4)nc3=O)cc2)CC1] |

TABLE 12-continued
| Compounds of Formula IV<br>Structure |
|---|
| 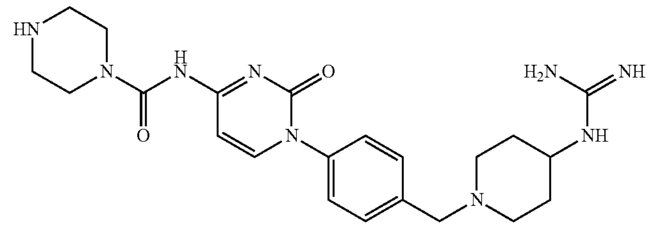 [SMILES: N=C(N)NC1CCN(Cc2ccc(-n3ccc(NC(=O)N4CCNCC4)nc3=O)cc2)CC1] |
| 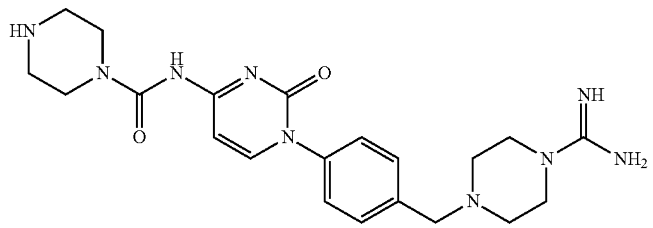 [SMILES: N=C(N)N1CCN(Cc2ccc(-n3ccc(NC(=O)N4CCNCC4)nc3=O)cc2)CC1] |
| 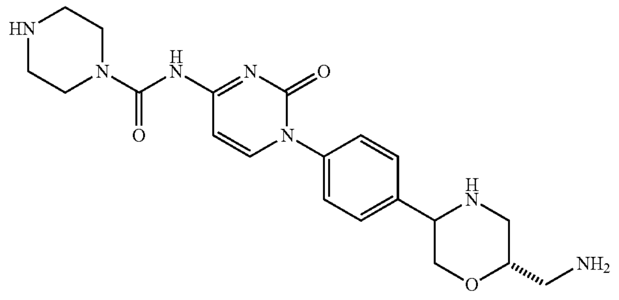 [SMILES: NC[C@H]1CNC(c2ccc(-n3ccc(NC(=O)N4CCNCC4)nc3=O)cc2)CO1] |
| 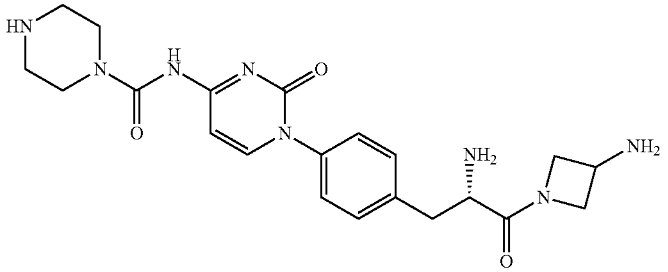 [SMILES: NC1CN(C(=O)[C@@H](N)Cc2ccc(-n3ccc(NC(=O)N4CCNCC4)nc3=O)cc2)C1] |
| 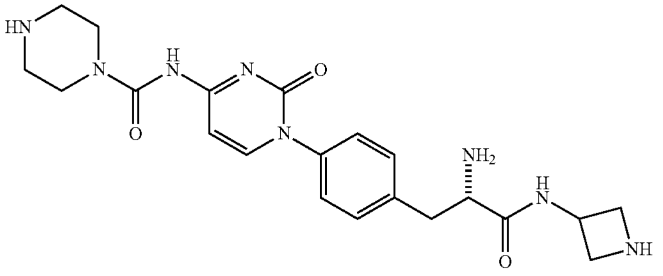 [SMILES: N[C@@H](Cc1ccc(-n2ccc(NC(=O)N3CCNCC3)nc2=O)cc1)C(=O)NC1CNC1] |

TABLE 12-continued
| Compounds of Formula IV Structure |
|---|
| 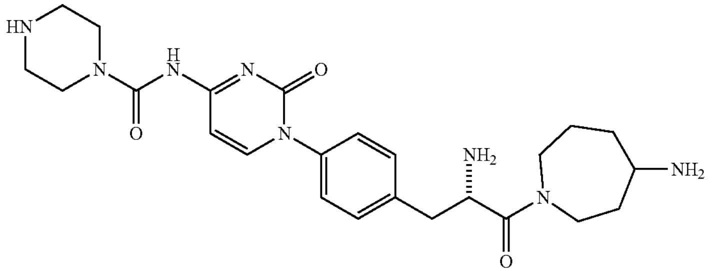 [SMILES: NC1CCCN(C(=O)[C@@H](N)Cc2ccc(-n3ccc(NC(=O)N4CCNCC4)nc3=O)cc2)CC1] |
| 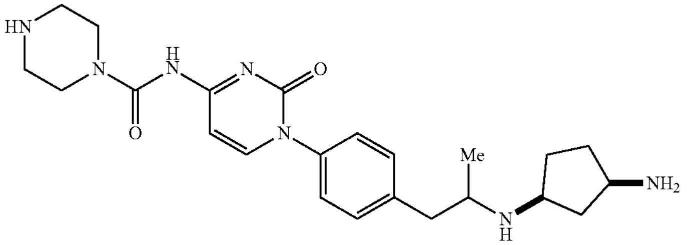 [SMILES: CC(Cc1ccc(-n2ccc(NC(=O)N3CCNCC3)nc2=O)cc1)N[C@H]1CC[C@@H](N)C1] |
| 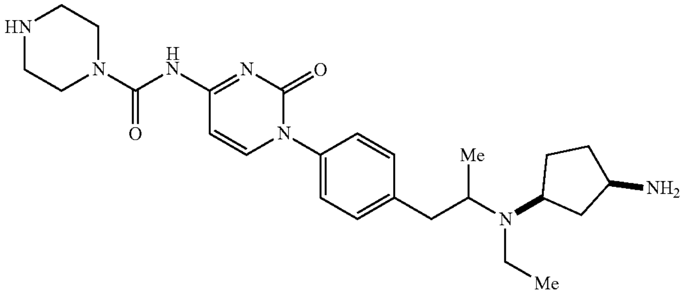 |
| 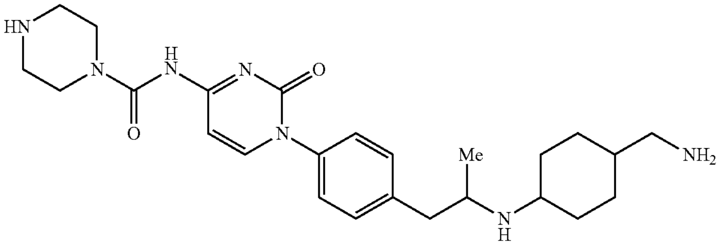 [SMILES: CC(Cc1ccc(-n2ccc(NC(=O)N3CCNCC3)nc2=O)cc1)NC1CCC(CN)CC1] |
| 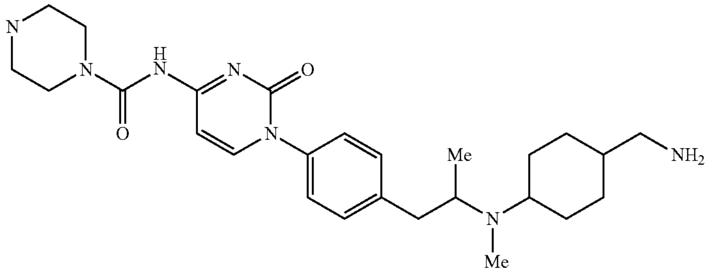 |

TABLE 12-continued
| Compounds of Formula IV Structure |
|---|
| 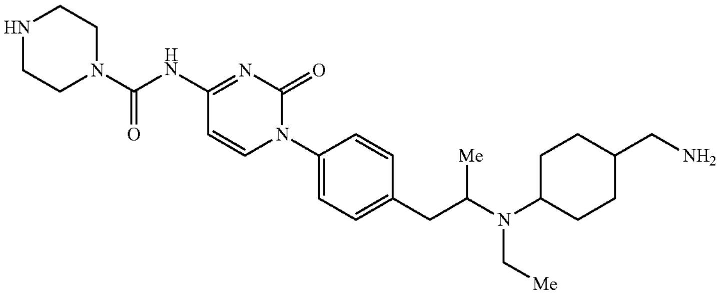 [SMILES: CCN(C(C)Cc1ccc(-n2ccc(NC(=O)N3CCNCC3)nc2=O)cc1)C1CCC(CN)CC1] |
| 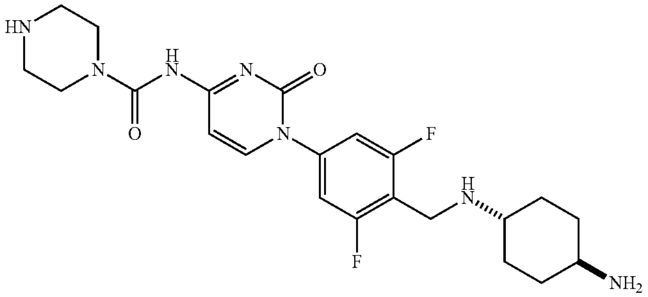 |
| 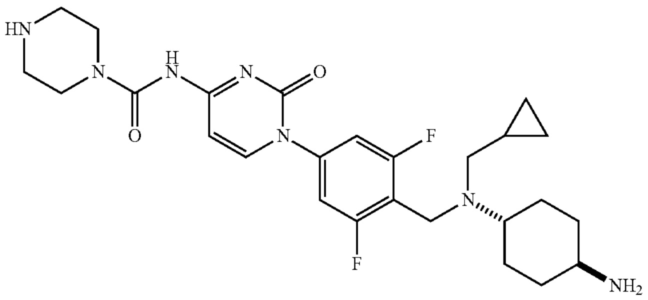 |
| 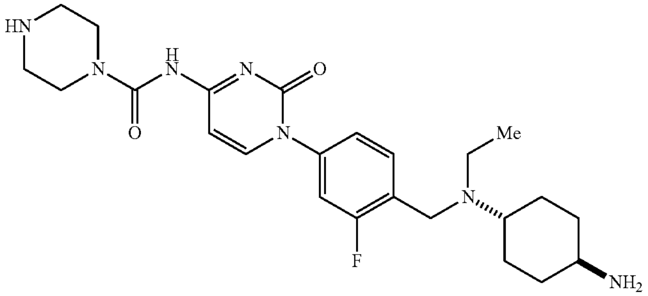 |
| 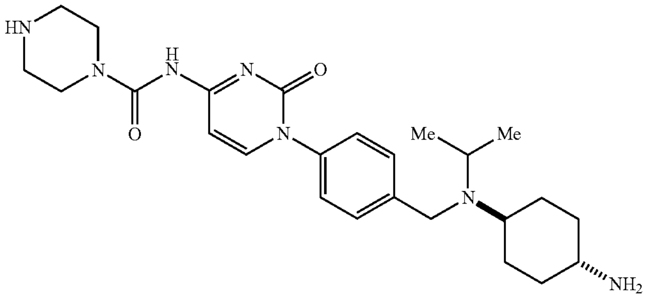 |

TABLE 12-continued
| Compounds of Formula IV Structure |
|---|
| 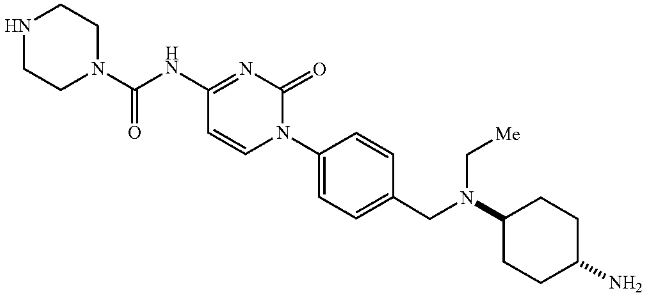 |
| 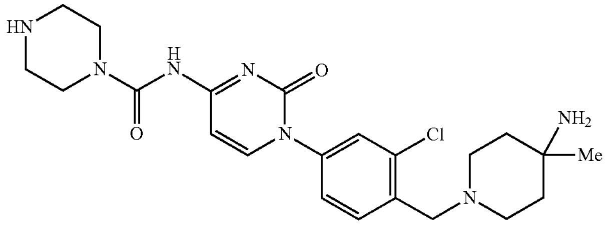 [SMILES: CC1(N)CCN(Cc2ccc(-n3ccc(NC(=O)N4CCNCC4)nc3=O)cc2Cl)CC1] |
| 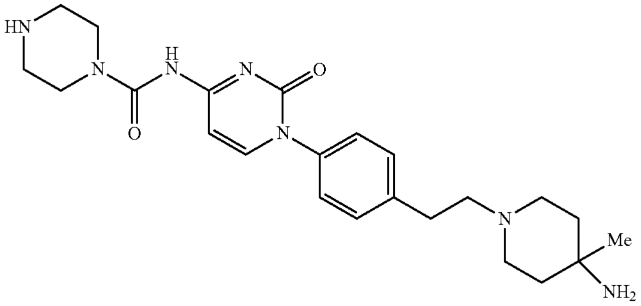 [SMILES: CC1(N)CCN(CCc2ccc(-n3ccc(NC(=O)N4CCNCC4)nc3=O)cc2)CC1] |
| 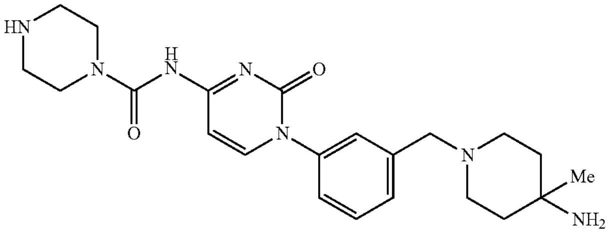 [SMILES: CC1(N)CCN(Cc2cccc(-n3ccc(NC(=O)N4CCNCC4)nc3=O)c2)CC1] |
| 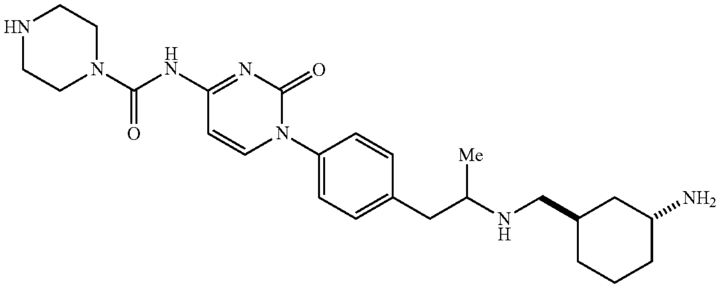 [SMILES: CC(Cc1ccc(-n2ccc(NC(=O)N3CCNCC3)nc2=O)cc1)NC[C@@H]1CCC[C@@H](N)C1] |

TABLE 12-continued
| Compounds of Formula IV Structure |
| --- |
| 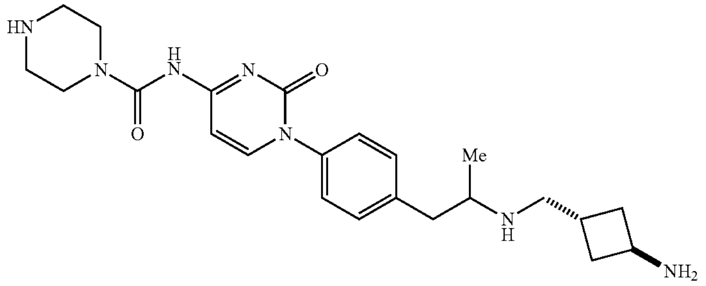 [SMILES: CC(Cc1ccc(-n2ccc(NC(=O)N3CCNCC3)nc2=O)cc1)NC[C@H]1C[C@H](N)C1] |
| 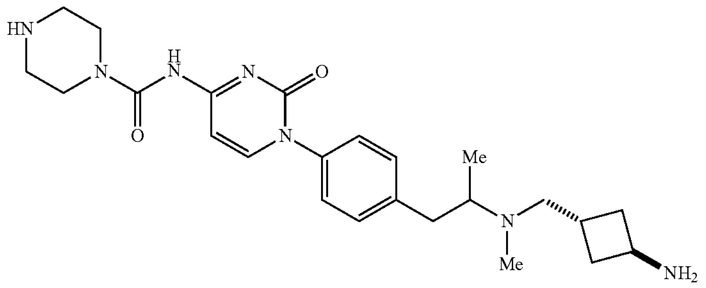 [SMILES: CC(Cc1ccc(-n2ccc(NC(=O)N3CCNCC3)nc2=O)cc1)N(C)C[C@H]1C[C@H](N)C1] |
| 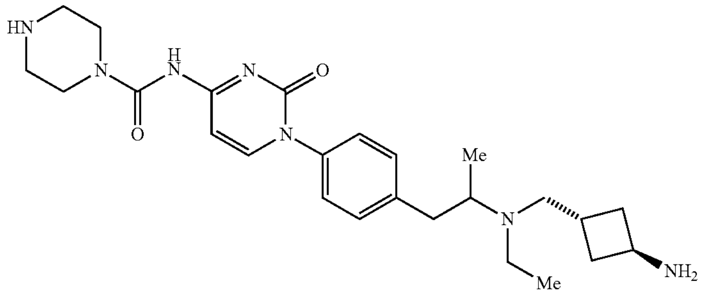 [SMILES: CCN(C[C@H]1C[C@H](N)C1)C(C)Cc1ccc(-n2ccc(NC(=O)N3CCNCC3)nc2=O)cc1] |
| 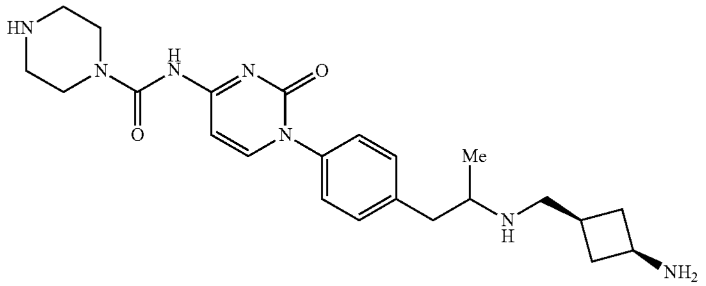 [SMILES: CC(Cc1ccc(-n2ccc(NC(=O)N3CCNCC3)nc2=O)cc1)NC[C@H]1C[C@@H](N)C1] |
| 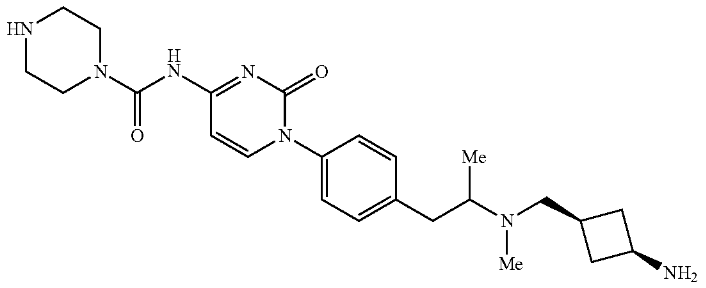 [SMILES: CC(Cc1ccc(-n2ccc(NC(=O)N3CCNCC3)nc2=O)cc1)N(C)C[C@H]1C[C@@H](N)C1] |

TABLE 12-continued
| Compounds of Formula IV Structure |
| --- |
| 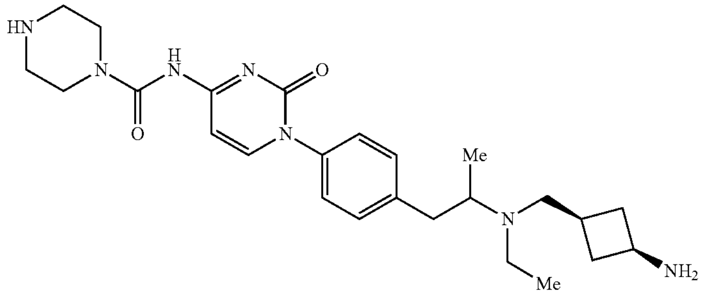 [SMILES: CCN(C[C@H]1C[C@@H](N)C1)C(C)Cc1ccc(-n2ccc(NC(=O)N3CCNCC3)nc2=O)cc1] |
| 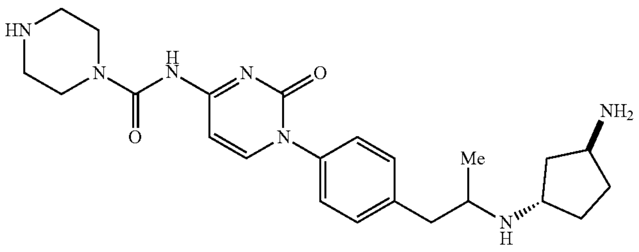 [SMILES: CC(Cc1ccc(-n2ccc(NC(=O)N3CCNCC3)nc2=O)cc1)N[C@H]1CC[C@H](N)C1] |
| 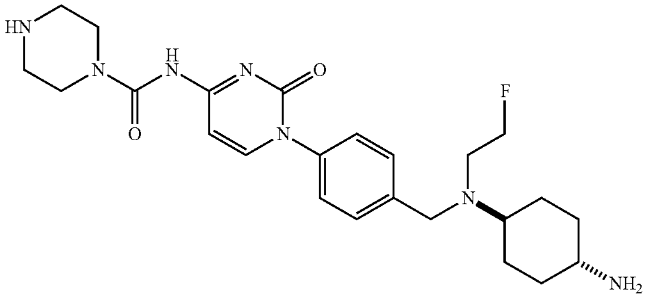 [SMILES: N[C@H]1CC[C@H](N(CCF)Cc2ccc(-n3ccc(NC(=O)N4CCNCC4)nc3=O)cc2)CC1] |
| 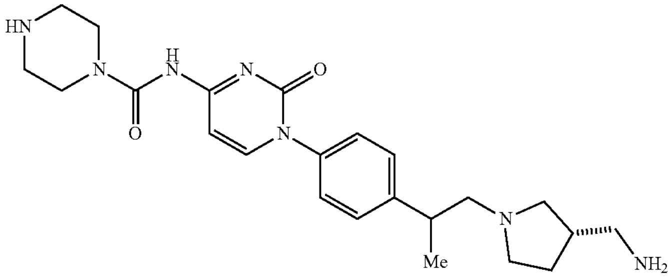 [SMILES: CC(CN1CC[C@@H](CN)C1)c1ccc(-n2ccc(NC(=O)N3CCNCC3)nc2=O)cc1] |
| 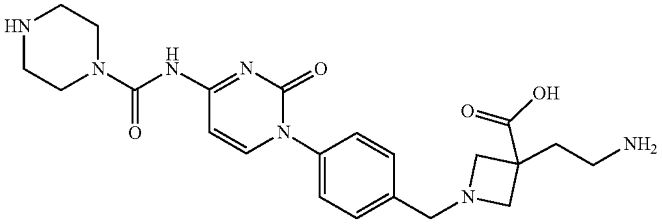 [SMILES: NCCC1(C(=O)O)CN(Cc2ccc(-n3ccc(NC(=O)N4CCNCC4)nc3=O)cc2)C1] |

TABLE 12-continued
| Compounds of Formula IV Structure |
| --- |
| 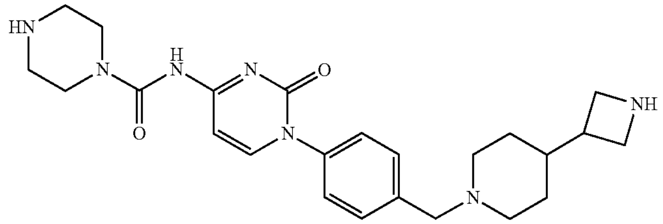 [SMILES: O=C(Nc1ccn(-c2ccc(CN3CCC(C4CNC4)CC3)cc2)c(=O)n1)N1CCNCC1] |
| 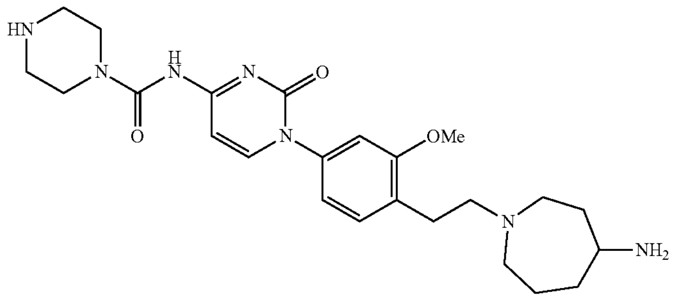 [SMILES: COc1cc(-n2ccc(NC(=O)N3CCNCC3)nc2=O)ccc1CCN1CCCC(N)CC1] |
| 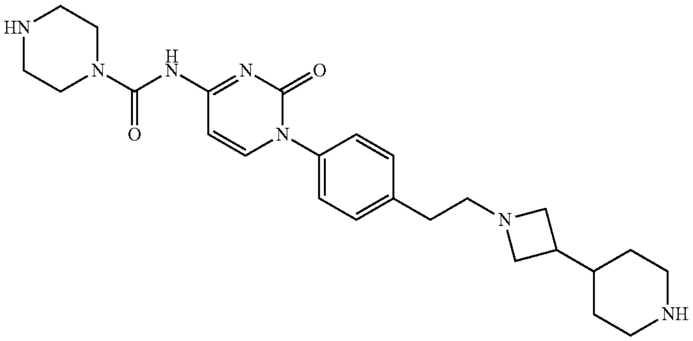 [SMILES: O=C(Nc1ccn(-c2ccc(CCN3CC(C4CCNCC4)C3)cc2)c(=O)n1)N1CCNCC1] |
| 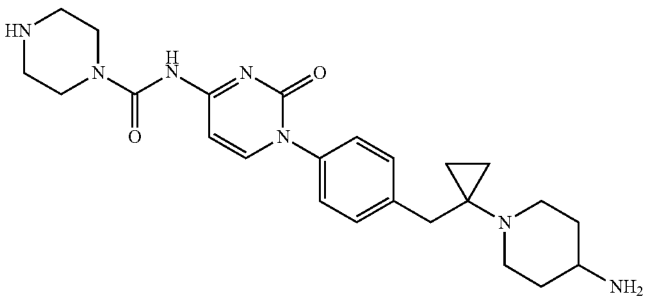 [SMILES: NC1CCN(C2(Cc3ccc(-n4ccc(NC(=O)N5CCNCC5)nc4=O)cc3)CC2)CC1] |
| 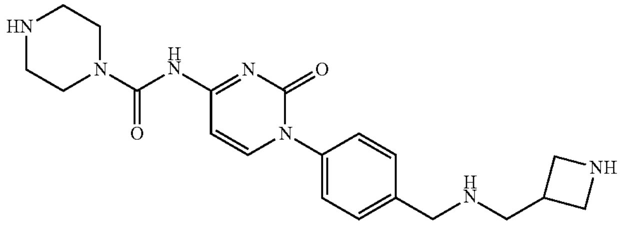 [SMILES: O=C(Nc1ccn(-c2ccc(CNCC3CNC3)cc2)c(=O)n1)N1CCNCC1] 3 HCl |

TABLE 12-continued
| Compounds of Formula IV<br>Structure |
| --- |
| 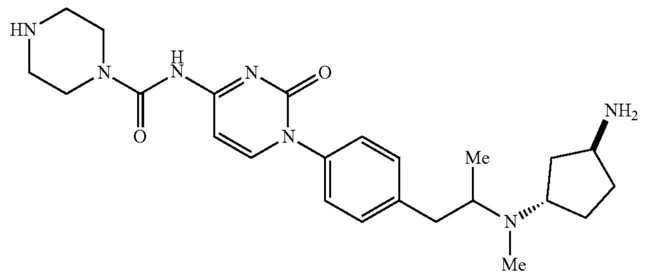 [SMILES: CC(Cc1ccc(-n2ccc(NC(=O)N3CCNCC3)nc2=O)cc1)N(C)[C@H]1CC[C@H](N)C1] |
| 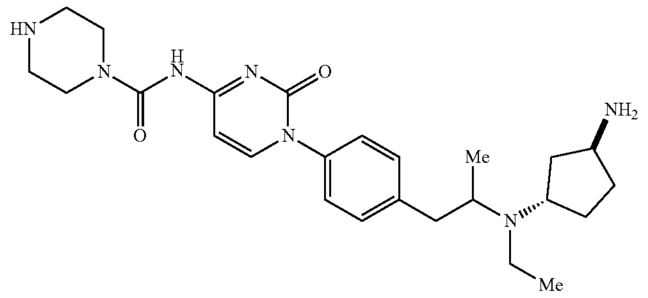 [SMILES: CCN(C(C)Cc1ccc(-n2ccc(NC(=O)N3CCNCC3)nc2=O)cc1)[C@H]1CC[C@H](N)C1] |
| 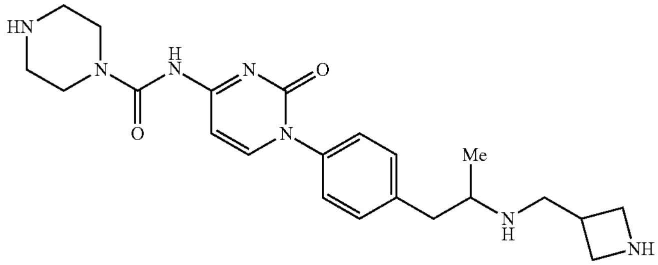 [SMILES: CC(Cc1ccc(-n2ccc(NC(=O)N3CCNCC3)nc2=O)cc1)NCC1CNC1] |
| 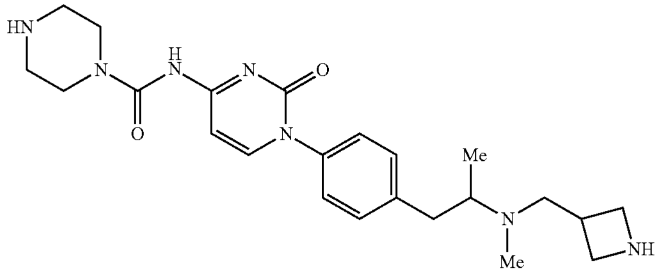 [SMILES: CCN(CC1CNC1)C(C)Cc1ccc(-n2ccc(NC(=O)N3CCNCC3)nc2=O)cc1] |
| 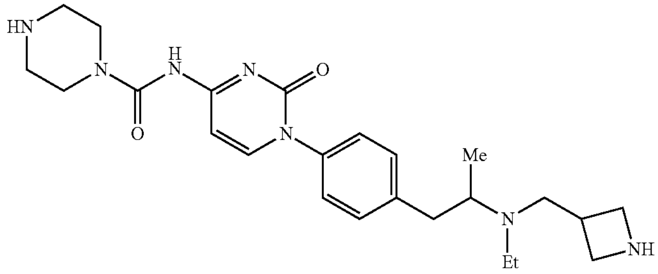 |

TABLE 12-continued
| Compounds of Formula IV Structure |
|---|
| 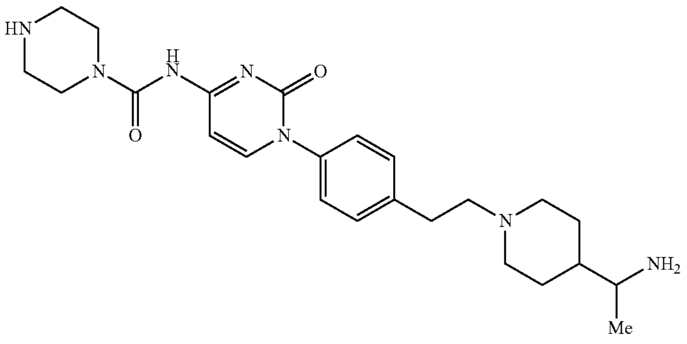 [SMILES: CC(N)C1CCN(CCc2ccc(-n3ccc(NC(=O)N4CCNCC4)nc3=O)cc2)CC1] |
| 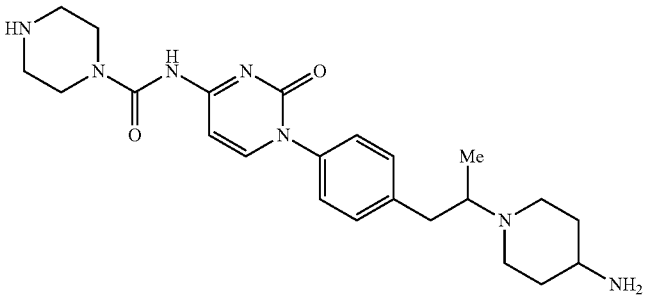 [SMILES: CC(Cc1ccc(-n2ccc(NC(=O)N3CCNCC3)nc2=O)cc1)N1CCC(N)CC1] |
| 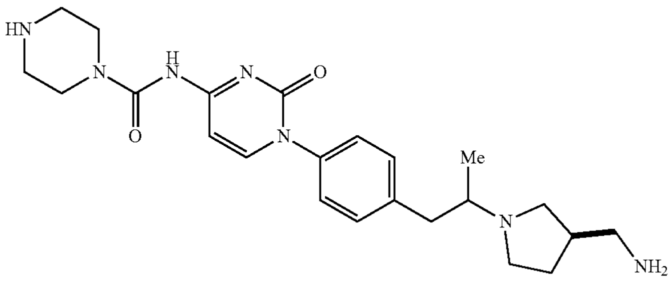 [SMILES: CC(Cc1ccc(-n2ccc(NC(=O)N3CCNCC3)nc2=O)cc1)N1CC[C@H](CN)C1] |
| 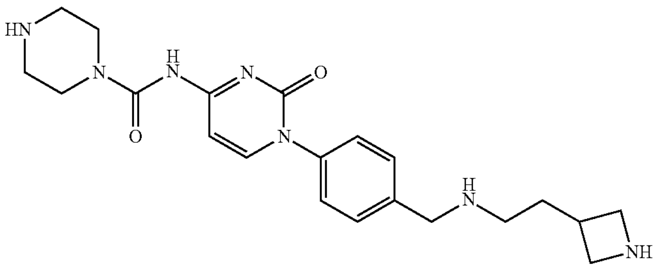 [SMILES: O=C(Nc1ccn(-c2ccc(CNCCC3CNC3)cc2)c(=O)n1)N1CCNCC1] |
| 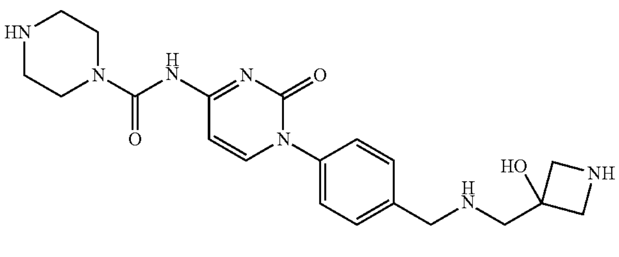 [SMILES: O=C(Nc1ccn(-c2ccc(CNCC3(O)CNC3)cc2)c(=O)n1)N1CCNCC1] |

TABLE 12-continued
| Compounds of Formula IV Structure |
| --- |
| 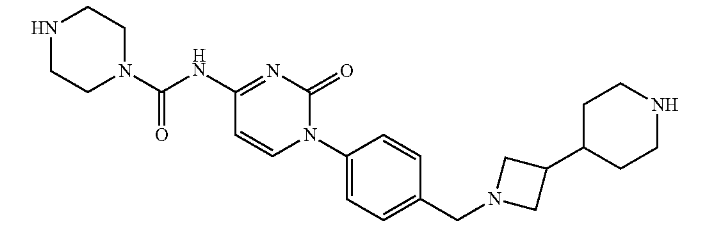 [SMILES: O=C(Nc1ccn(-c2ccc(CN3CC(C4CCNCC4)C3)cc2)c(=O)n1)N1CCNCC1] |
| 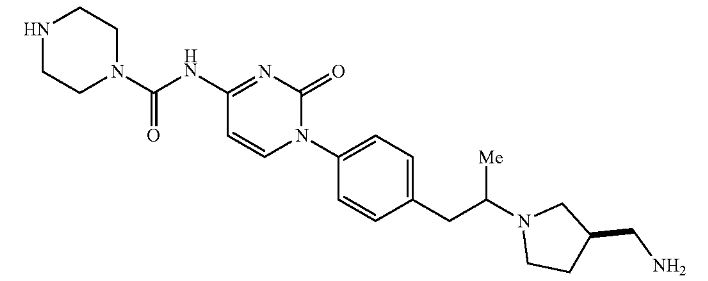 [SMILES: CC(Cc1ccc(-n2ccc(NC(=O)N3CCNCC3)nc2=O)cc1)N1CC[C@H](CN)C1] |
| 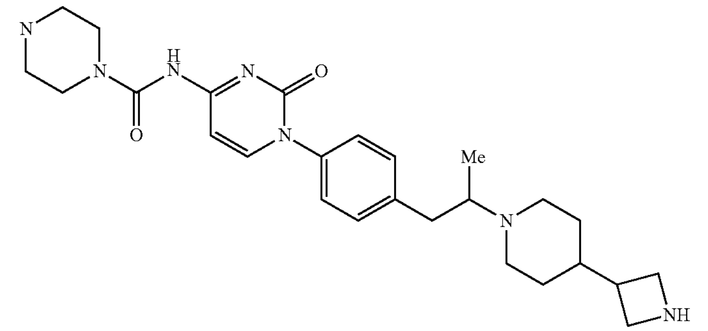 |
| 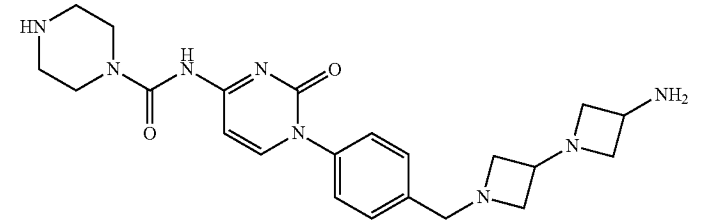 [SMILES: NC1CN(C2CN(Cc3ccc(-n4ccc(NC(=O)N5CCNCC5)nc4=O)cc3)C2)C1] |
| 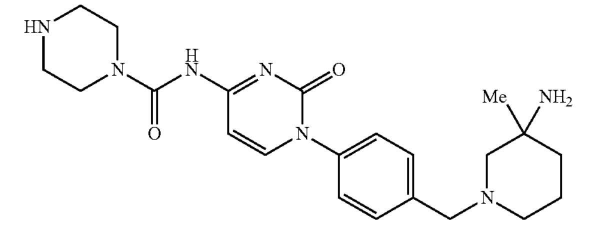 [SMILES: CC1(N)CCCN(Cc2ccc(-n3ccc(NC(=O)N4CCNCC4)nc3=O)cc2)C1] |
| 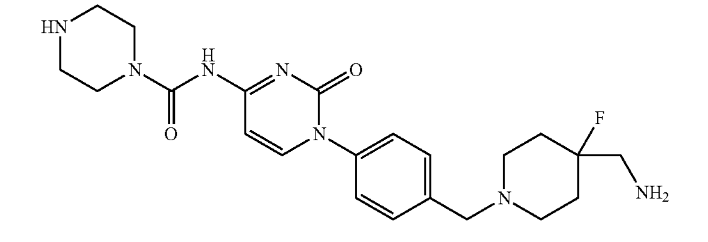 [SMILES: NCC1(F)CCN(Cc2ccc(-n3ccc(NC(=O)N4CCNCC4)nc3=O)cc2)CC1] |

TABLE 12-continued
| Compounds of Formula IV<br>Structure |
|---|
| 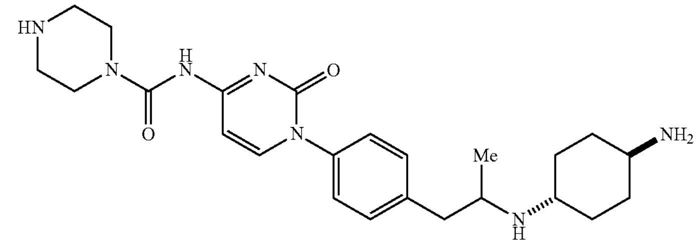 |
| 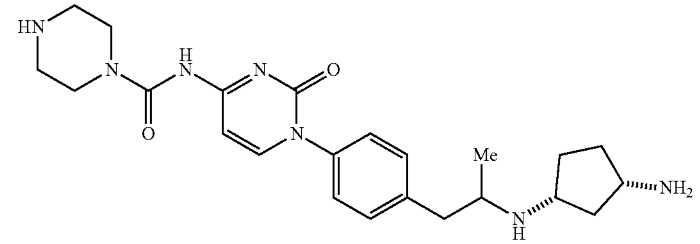 |
| 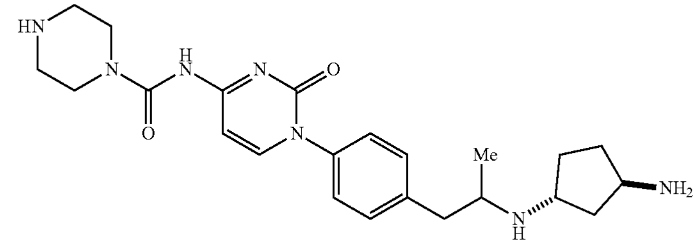 |
| 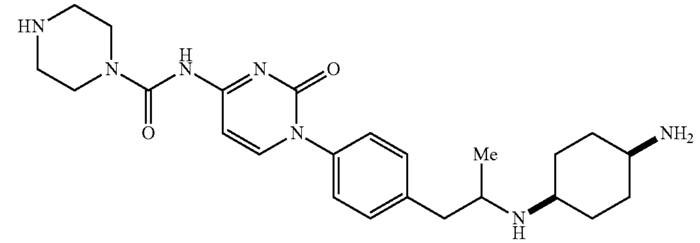 |
| 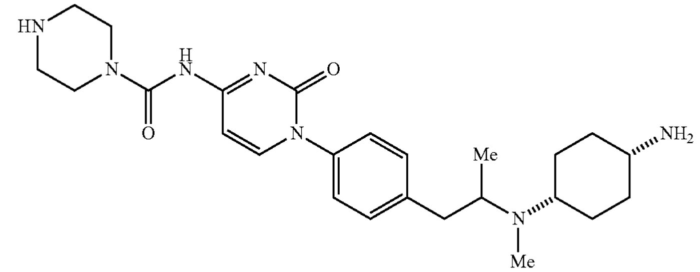 |
| 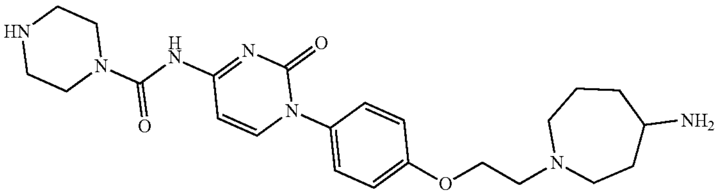 [SMILES: NC1CCCN(CCOc2ccc(-n3ccc(NC(=O)N4CCNCC4)nc3=O)cc2)CC1] |

TABLE 12-continued
| Compounds of Formula IV<br>Structure |
|---|
| 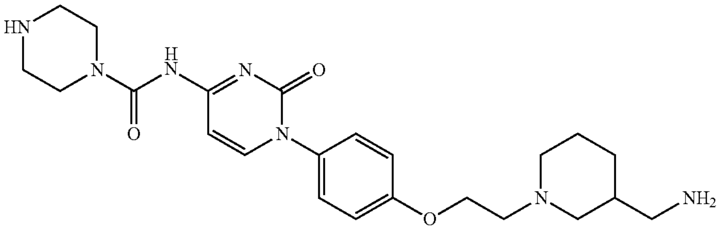 [SMILES: NCC1CCCN(CCOc2ccc(-n3ccc(NC(=O)N4CCNCC4)nc3=O)cc2)C1] |
| 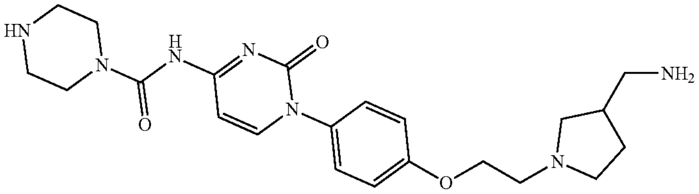 [SMILES: NCC1CCN(CCOc2ccc(-n3ccc(NC(=O)N4CCNCC4)nc3=O)cc2)C1] |
| 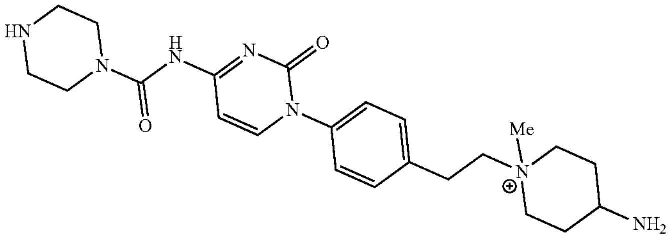 [SMILES: C[N+]1(CCc2ccc(-n3ccc(NC(=O)N4CCNCC4)nc3=O)cc2)CCC(N)CC1] |
| 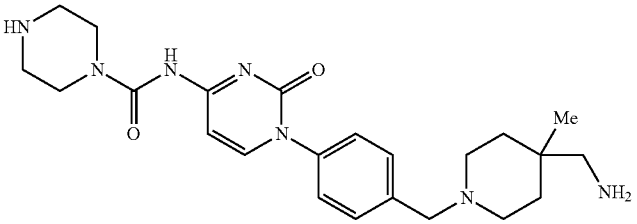 |
| 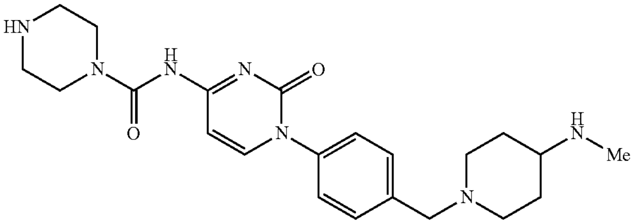 [SMILES: CNC1CCN(Cc2ccc(-n3ccc(NC(=O)N4CCNCC4)nc3=O)cc2)CC1] |
| 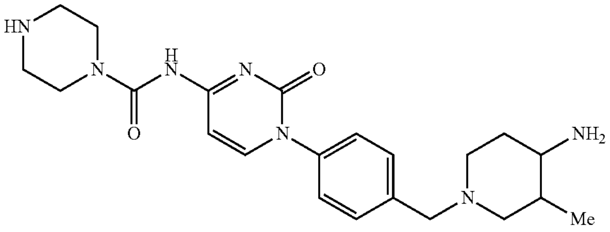 [SMILES: CC1CN(Cc2ccc(-n3ccc(NC(=O)N4CCNCC4)nc3=O)cc2)CCC1N] |

TABLE 12-continued
| Compounds of Formula IV Structure |
| --- |
| 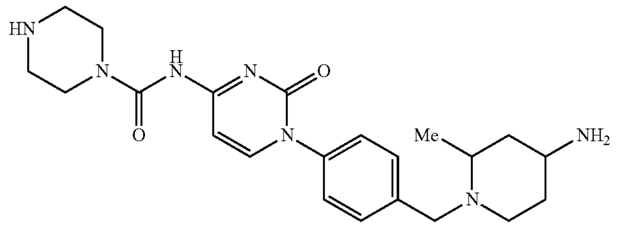 [SMILES: CC1CC(N)CCN1Cc1ccc(-n2ccc(NC(=O)N3CCNCC3)nc2=O)cc1] |
| 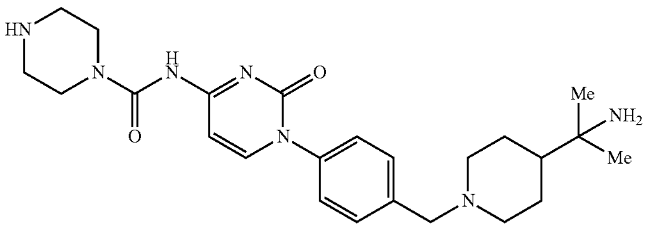 [SMILES: CC(C)(N)C1CCN(Cc2ccc(-n3ccc(NC(=O)N4CCNCC4)nc3=O)cc2)CC1] |
| 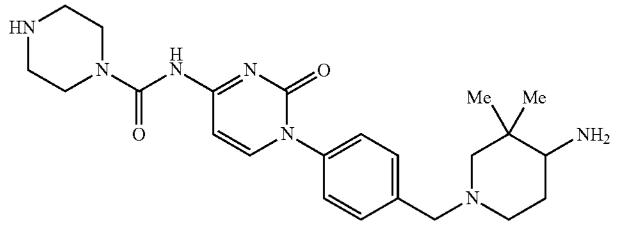 [SMILES: CC1(C)CN(Cc2ccc(-n3ccc(NC(=O)N4CCNCC4)nc3=O)cc2)CCC1N] |
| 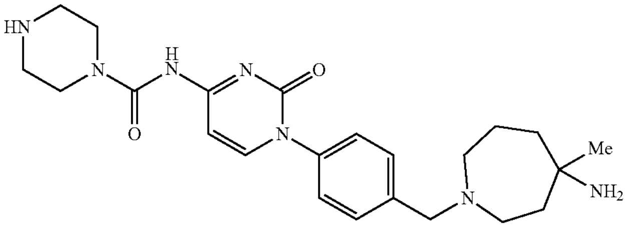 [SMILES: CC1(N)CCCN(Cc2ccc(-n3ccc(NC(=O)N4CCNCC4)nc3=O)cc2)CC1] |
| 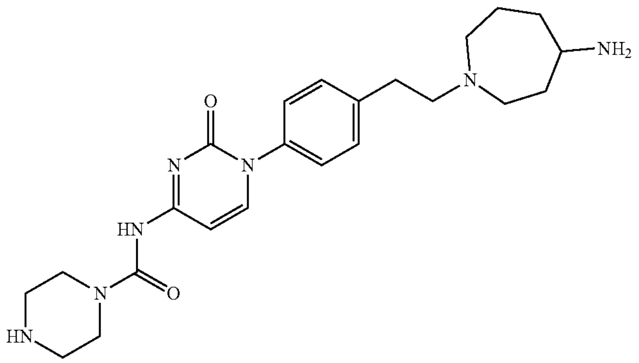 [SMILES: NC1CCCN(CCc2ccc(-n3ccc(NC(=O)N4CCNCC4)nc3=O)cc2)CC1] |
| 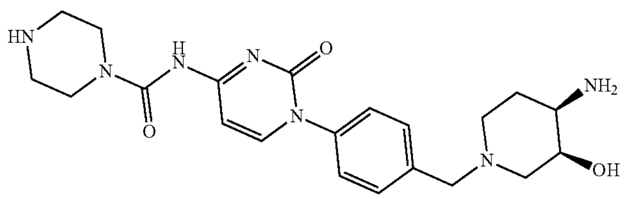 [SMILES: N[C@@H]1CCN(Cc2ccc(-n3ccc(NC(=O)N4CCNCC4)nc3=O)cc2)C[C@@H]1O] |

TABLE 12-continued
| Compounds of Formula IV Structure |
| --- |
| 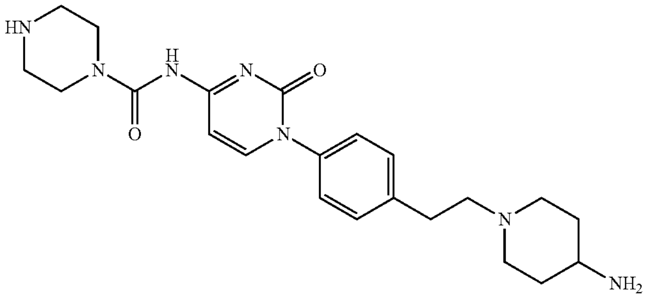 [SMILES: NC1CCN(CCc2ccc(-n3ccc(NC(=O)N4CCNCC4)nc3=O)cc2)CC1] |
| 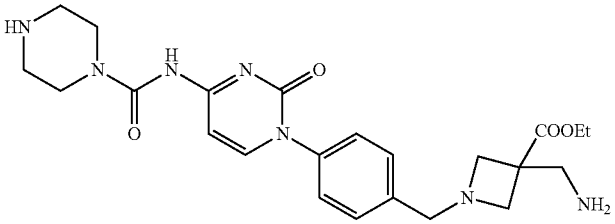 [SMILES: CCOC(=O)C1(CN)CN(Cc2ccc(-n3ccc(NC(=O)N4CCNCC4)nc3=O)cc2)C1] |
| 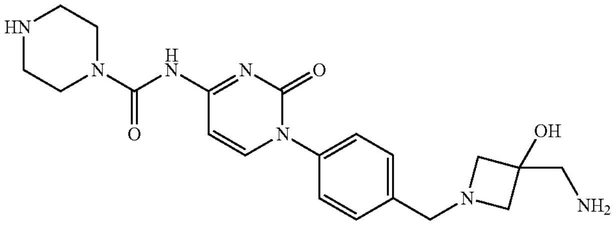 [SMILES: NCC1(O)CN(Cc2ccc(-n3ccc(NC(=O)N4CCNCC4)nc3=O)cc2)C1] |
| 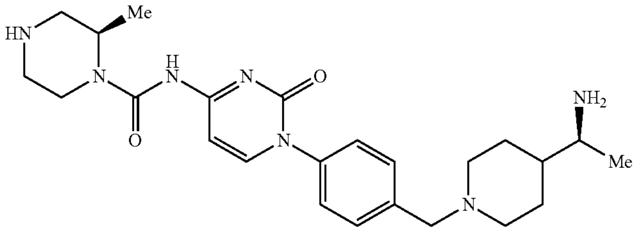 [SMILES: C[C@H](N)C1CCN(Cc2ccc(-n3ccc(NC(=O)N4CCNC[C@H]4C)nc3=O)cc2)CC1] |
| 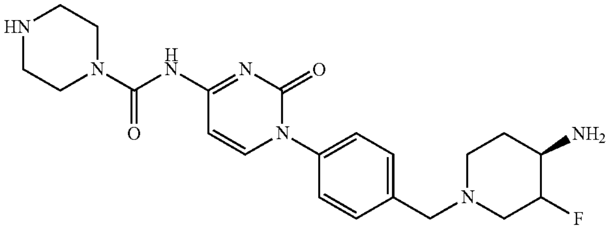 [SMILES: N[C@@H]1CCN(Cc2ccc(-n3ccc(NC(=O)N4CCNCC4)nc3=O)cc2)CC1F] |
| 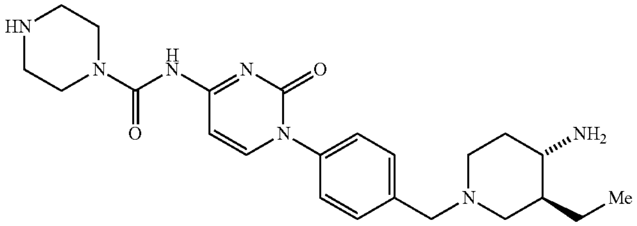 [SMILES: CC[C@H]1CN(Cc2ccc(-n3ccc(NC(=O)N4CCNCC4)nc3=O)cc2)CC[C@@H]1N] |

TABLE 12-continued
| Compounds of Formula IV Structure |
|---|
| 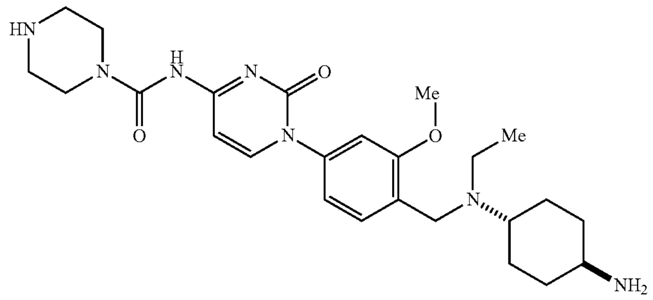 |
| 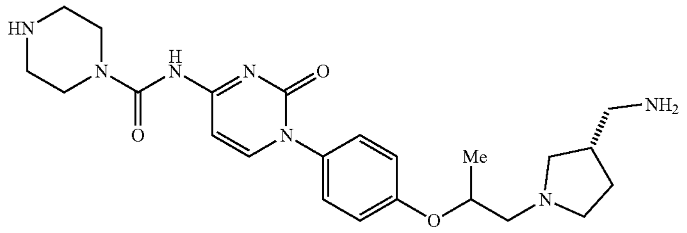 [SMILES: CC(CN1CC[C@@H](CN)C1)Oc1ccc(-n2ccc(NC(=O)N3CCNCC3)nc2=O)cc1] |
| 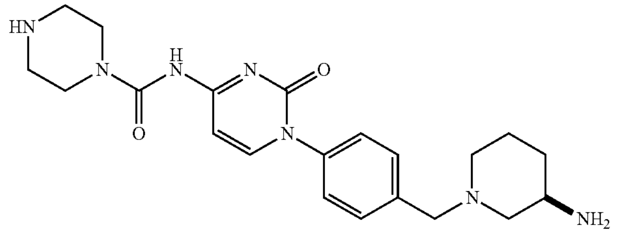 [SMILES: N[C@@H]1CCCN(Cc2ccc(-n3ccc(NC(=O)N4CCNCC4)nc3=O)cc2)C1] |
| 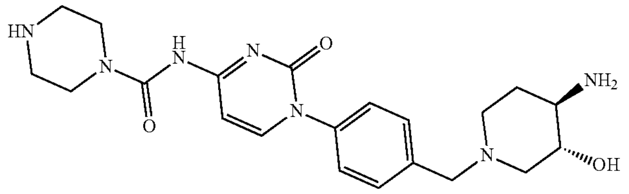 [SMILES: N[C@@H]1CCN(Cc2ccc(-n3ccc(NC(=O)N4CCNCC4)nc3=O)cc2)C[C@H]1O] |
| 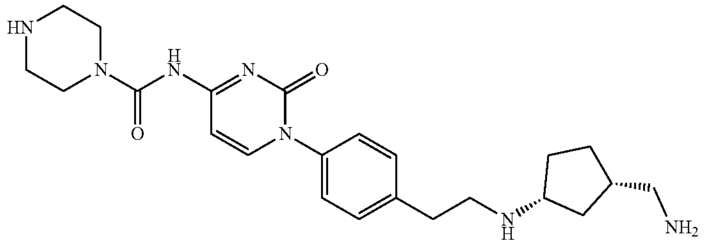 [SMILES: NC[C@H]1CC[C@@H](NCCc2ccc(-n3ccc(NC(=O)N4CCNCC4)nc3=O)cc2)C1] |
| 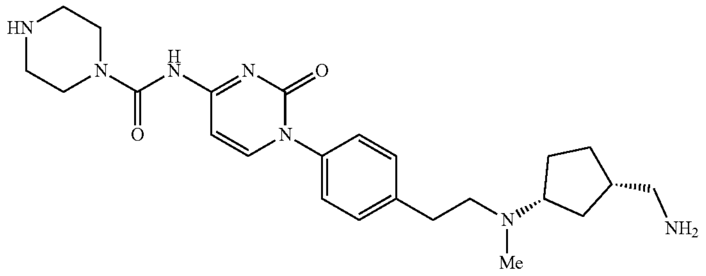 [SMILES: CN(CCc1ccc(-n2ccc(NC(=O)N3CCNCC3)nc2=O)cc1)[C@@H]1CC[C@H](CN)C1] |

TABLE 12-continued
| Compounds of Formula IV Structure |
|---|
| 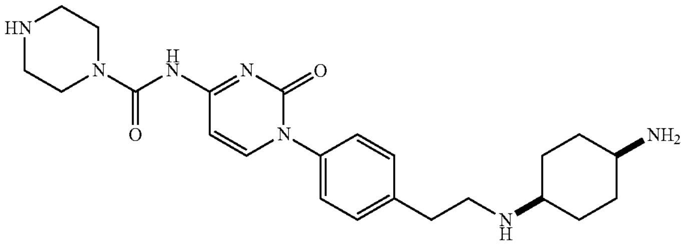 |
| 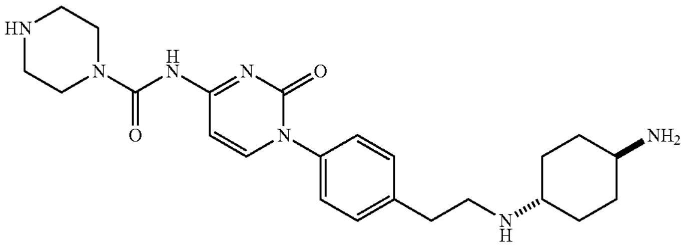 |
| 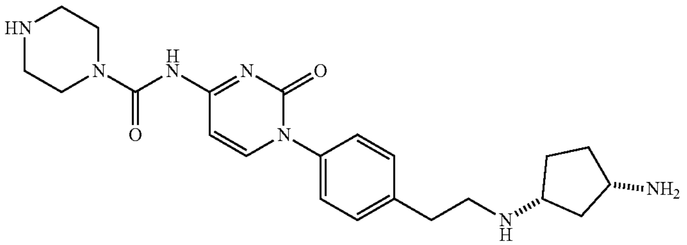 |
| 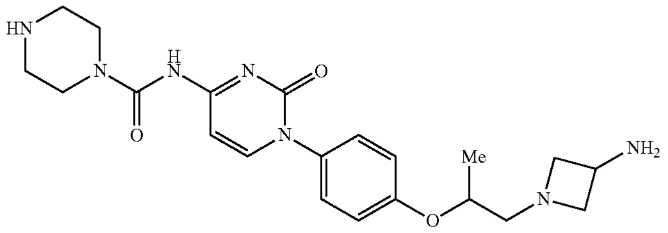 [SMILES: CC(CN1CC(N)C1)Oc1ccc(-n2ccc(NC(=O)N3CCNCC3)nc2=O)cc1] |
| 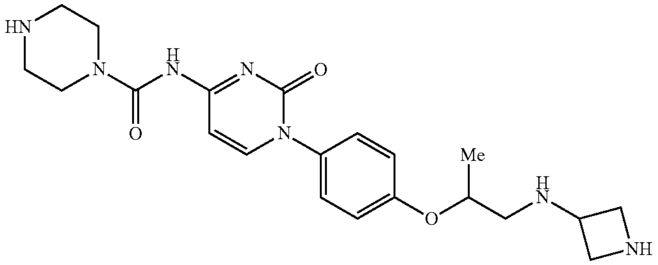 [SMILES: CC(CNC1CNC1)Oc1ccc(-n2ccc(NC(=O)N3CCNCC3)nc2=O)cc1] |
| 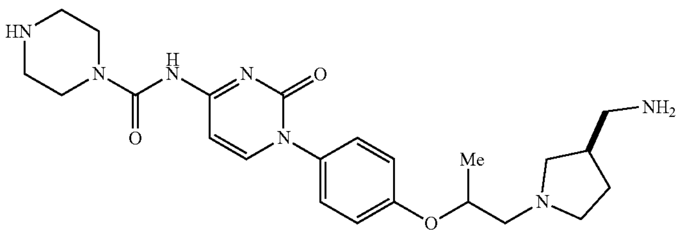 [SMILES: CC(CN1CC[C@H](CN)C1)Oc1ccc(-n2ccc(NC(=O)N3CCNCC3)nc2=O)cc1] |

TABLE 12-continued
| Compounds of Formula IV Structure |
| --- |
| 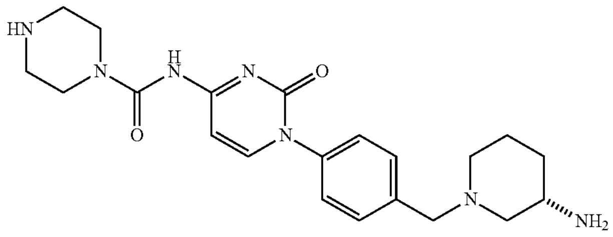 [SMILES: N[C@H]1CCCN(Cc2ccc(-n3ccc(NC(=O)N4CCNCC4)nc3=O)cc2)C1] |
| 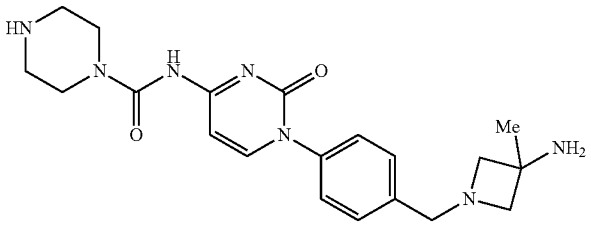 [SMILES: CC1(N)CN(Cc2ccc(-n3ccc(NC(=O)N4CCNCC4)nc3=O)cc2)C1] |
| 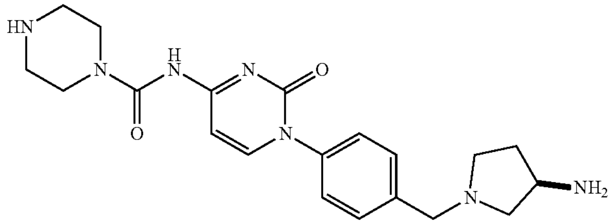 [SMILES: N[C@@H]1CCN(Cc2ccc(-n3ccc(NC(=O)N4CCNCC4)nc3=O)cc2)C1] |
| 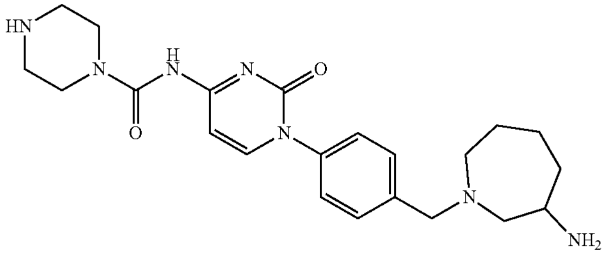 [SMILES: NC1CCCCN(Cc2ccc(-n3ccc(NC(=O)N4CCNCC4)nc3=O)cc2)C1] |
| 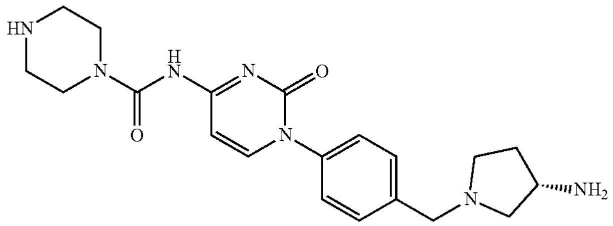 [SMILES: N[C@H]1CCN(Cc2ccc(-n3ccc(NC(=O)N4CCNCC4)nc3=O)cc2)C1] |
| 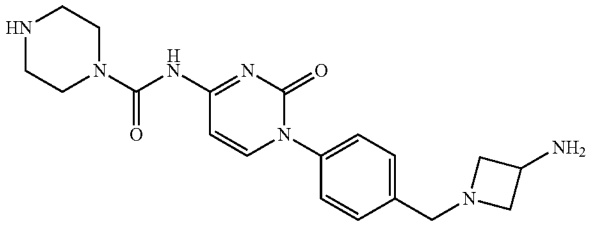 [SMILES: NC1CN(Cc2ccc(-n3ccc(NC(=O)N4CCNCC4)nc3=O)cc2)C1] |

TABLE 12-continued
| Compounds of Formula IV Structure |
| --- |
| 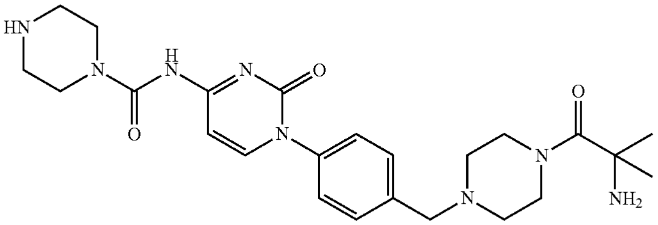 [SMILES: CC(C)(N)C(=O)N1CCN(Cc2ccc(-n3ccc(NC(=O)N4CCNCC4)nc3=O)cc2)CC1] |
| 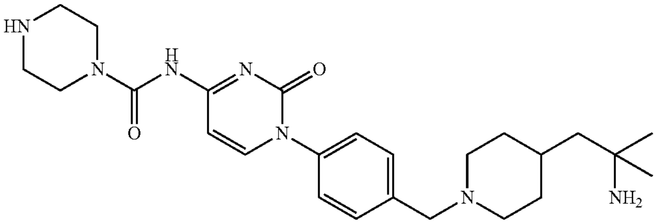 [SMILES: CC(C)(N)CC1CCN(Cc2ccc(-n3ccc(NC(=O)N4CCNCC4)nc3=O)cc2)CC1] |
| 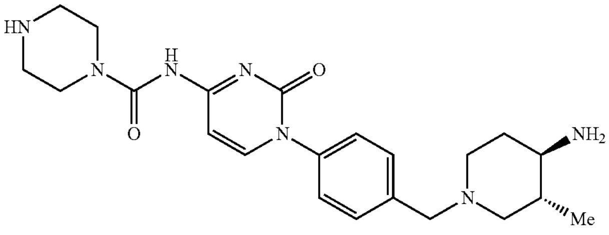 |
| 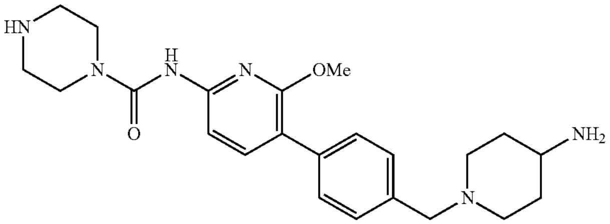 [SMILES: COc1nc(NC(=O)N2CCNCC2)ccc1-c1ccc(CN2CCC(N)CC2)cc1] |
| 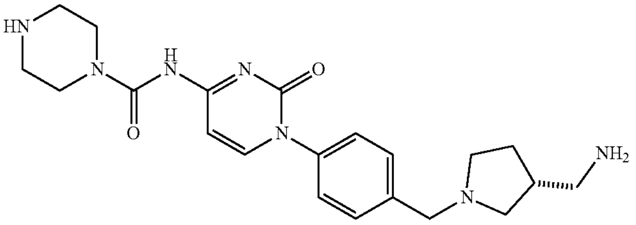 [SMILES: NC[C@H]1CCN(Cc2ccc(-n3ccc(NC(=O)N4CCNCC4)nc3=O)cc2)C1] |
| 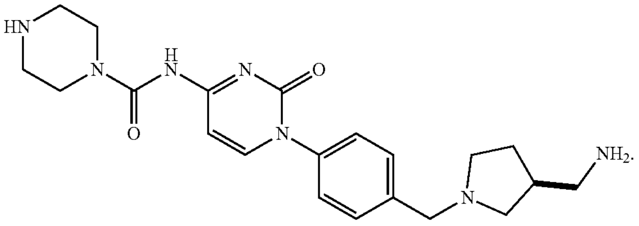 [SMILES: NC[C@@H]1CCN(Cc2ccc(-n3ccc(NC(=O)N4CCNCC4)nc3=O)cc2)C1] |

21. A compound of formula V:

V

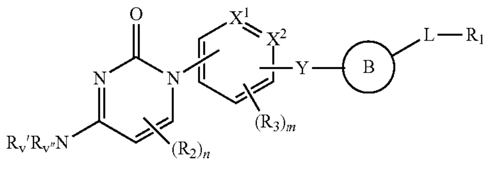

or a pharmaceutically acceptable salt thereof, wherein the variables have the definitions defined in claim 1, and one of $R_{v'}$ and $R_{v''}$ is H and the other of $R_{v'}$ and $R_{v''}$ is H or an amino protecting group.

22. A compound or a pharmaceutically acceptable salt thereof, wherein the compound is selected from the compounds listed in Table 13:

TABLE 13

| Compounds of Formula VI<br>Structure |
|---|
| 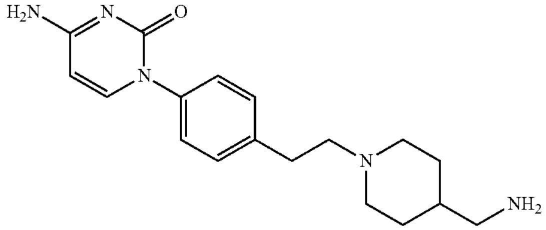 [SMILES: NCC1CCN(CCc2ccc(-n3ccc(N)nc3=O)cc2)CC1] |
| 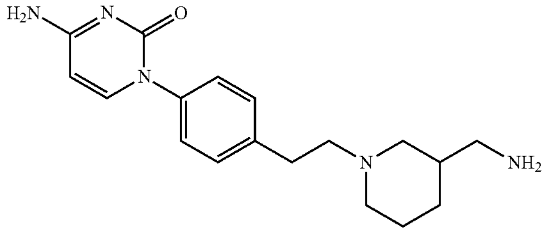 [SMILES: NCC1CCCN(CCc2ccc(-n3ccc(N)nc3=O)cc2)C1] |
| 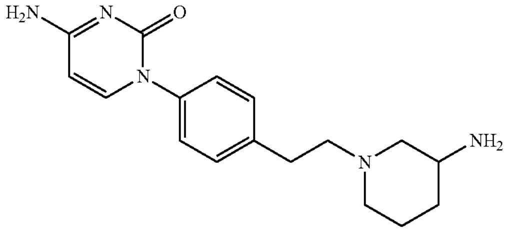 |
| 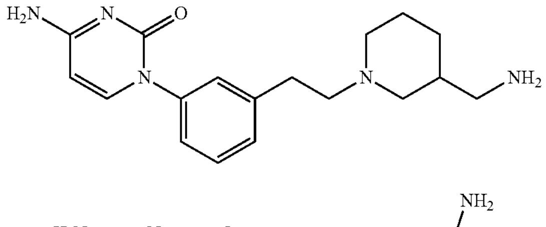 |
| 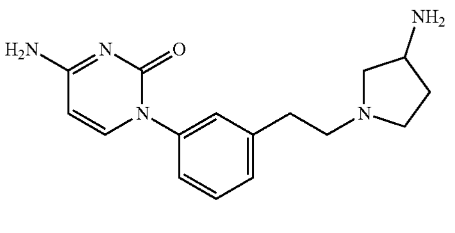 [SMILES: Nc1ccn(-c2cccc(CCN3CCC(N)C3)c2)c(=O)n1] |

TABLE 13-continued

| Compounds of Formula VI<br>Structure |
|---|
| 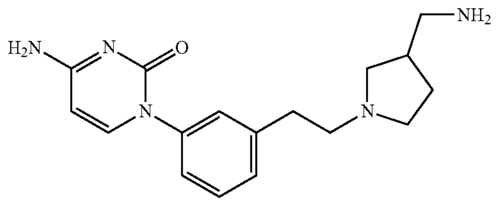 [SMILES: NCC1CCN(CCc2cccc(-n3ccc(N)nc3=O)c2)C1] |
| 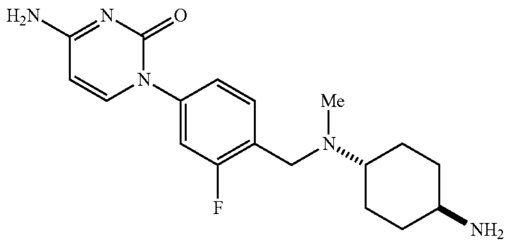 |
| 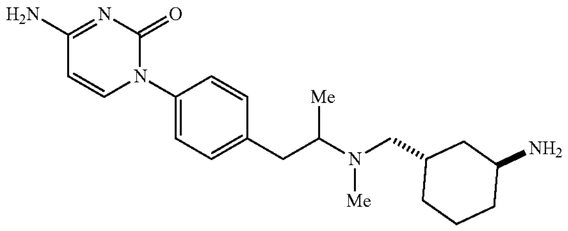 |
| 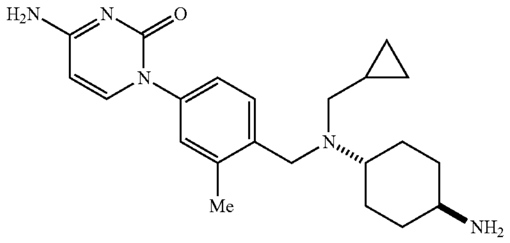 [SMILES: Cc1cc(-n2ccc(N)nc2=O)ccc1CN(CC1CC1)[C@H]1CC[C@H](N)CC1] |
| 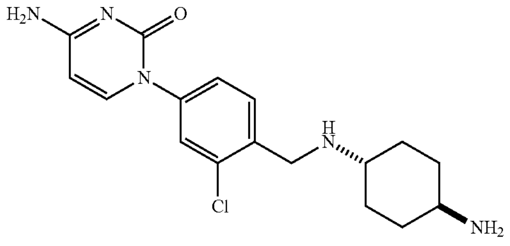 [SMILES: Nc1ccn(-c2ccc(CN[C@H]3CC[C@H](N)CC3)c(Cl)c2)c(=O)n1] |
| 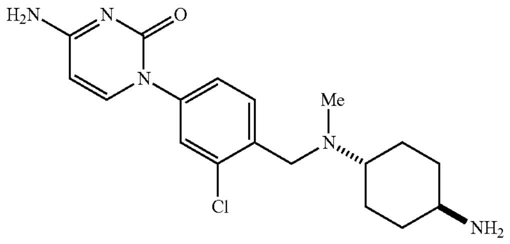 |

TABLE 13-continued
| Compounds of Formula VI Structure |
|---|
| 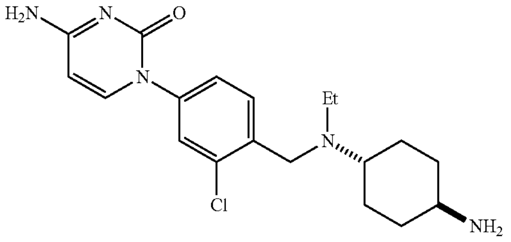 |
| 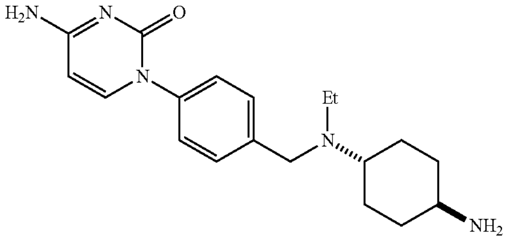 |
| 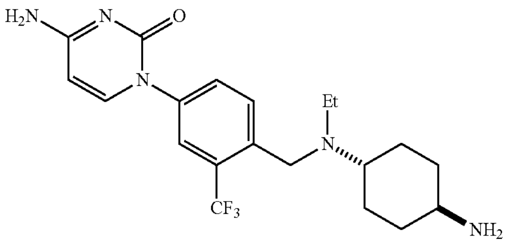 |
| 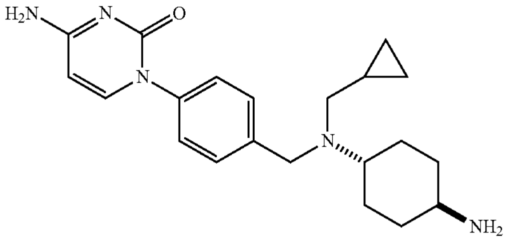 |
| 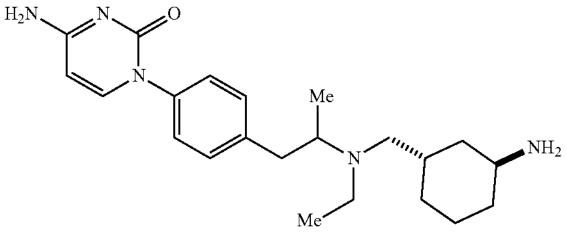 |
| 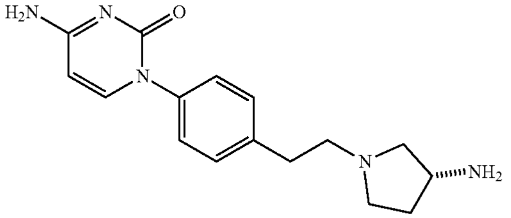 [SMILES: Nc1ccn(-c2ccc(CCN3CC[C@@H](N)C3)cc2)c(=O)n1] |
TABLE 13-continued
| Compounds of Formula VI Structure |
|---|
| 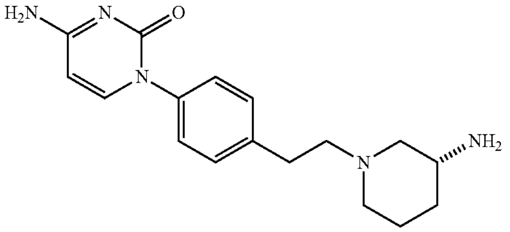 [SMILES: Nc1ccn(-c2ccc(CCN3CCC[C@@H](N)C3)cc2)c(=O)n1] |
| 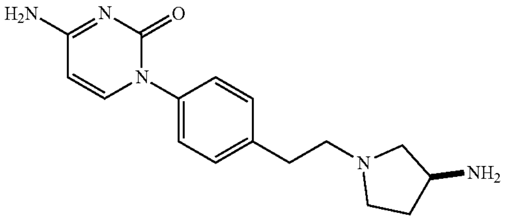 [SMILES: Nc1ccn(-c2ccc(CCN3CC[C@H](N)C3)cc2)c(=O)n1] |
| 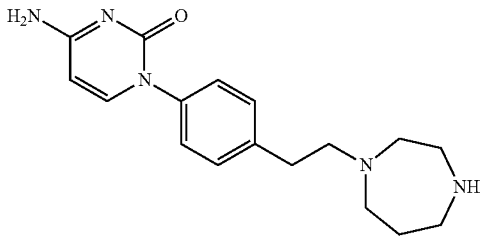 [SMILES: Nc1ccn(-c2ccc(CCN3CCCNCC3)cc2)c(=O)n1] |
| 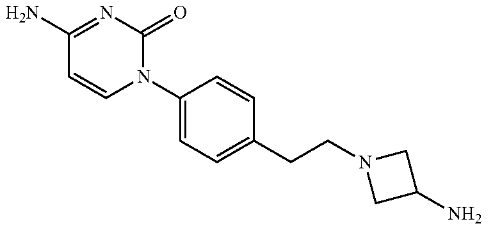 [SMILES: Nc1ccn(-c2ccc(CCN3CC(N)C3)cc2)c(=O)n1] |
| 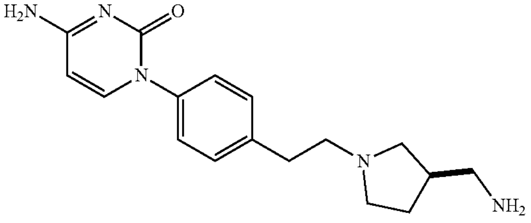 [SMILES: NC[C@H]1CCN(CCc2ccc(-n3ccc(N)nc3=O)cc2)C1] |
| 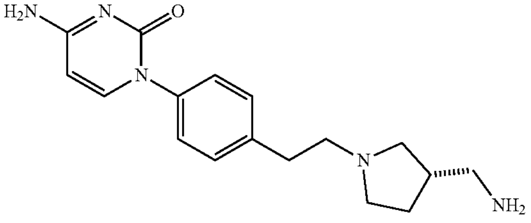 [SMILES: NC[C@@H]1CCN(CCc2ccc(-n3ccc(N)nc3=O)cc2)C1] |

TABLE 13-continued
| Compounds of Formula VI Structure |
| --- |
| 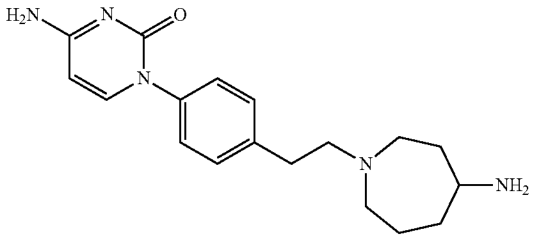 [SMILES: Nc1ccn(-c2ccc(CCN3CCCC(N)CC3)cc2)c(=O)n1] |
| 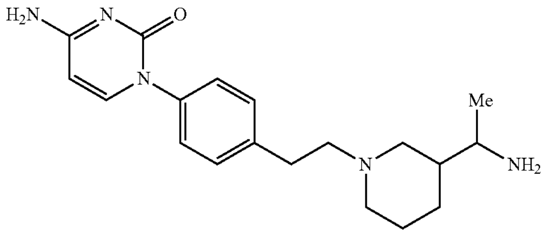 [SMILES: CC(N)C1CCCN(CCc2ccc(-n3ccc(N)nc3=O)cc2)C1] |
| 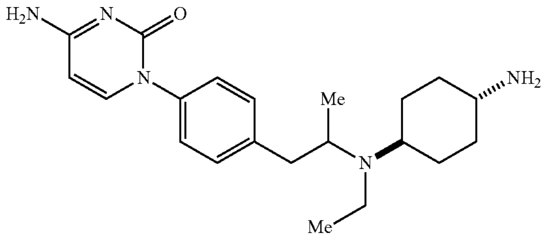 |
| 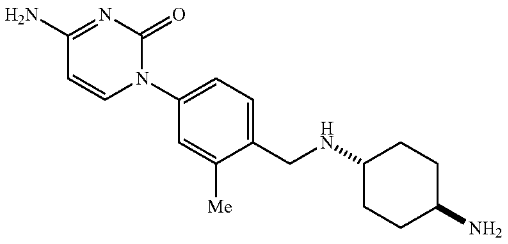 |
| 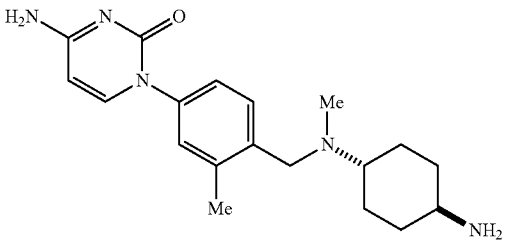 |
| 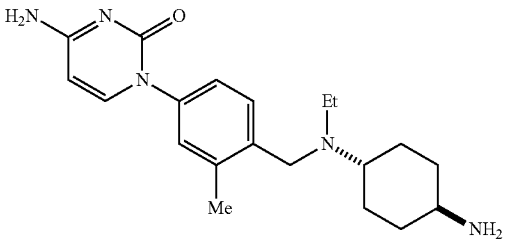 |
TABLE 13-continued
| Compounds of Formula VI Structure |
| --- |
| 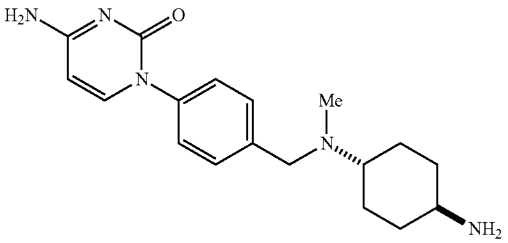 |
| 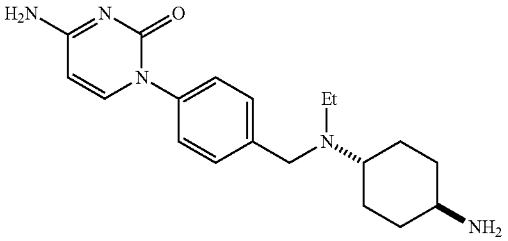 |
| 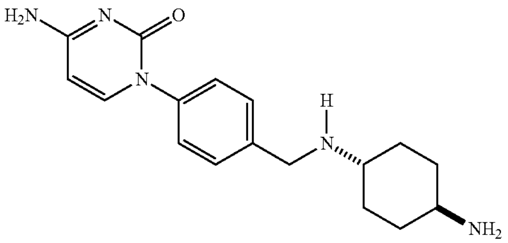 |
| 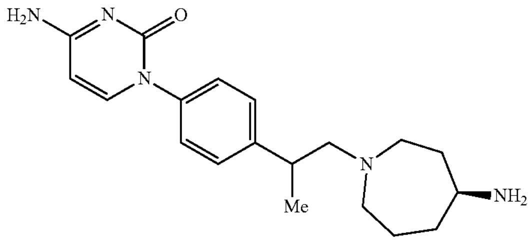 [SMILES: CC(CN1CCC[C@H](N)CC1)c1ccc(-n2ccc(N)nc2=O)cc1] |
| 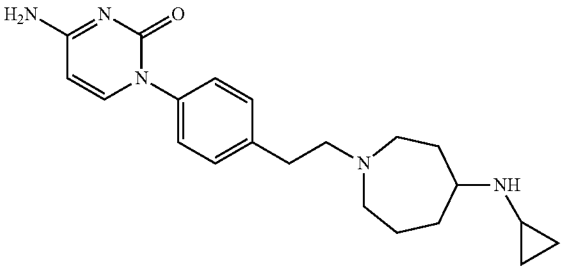 [SMILES: Nc1ccn(-c2ccc(CCN3CCCC(NC4CC4)CC3)cc2)c(=O)n1] |
| 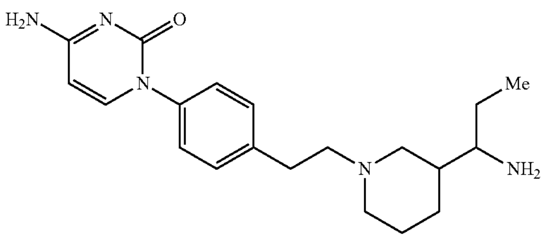 [SMILES: CCC(N)C1CCCN(CCc2ccc(-n3ccc(N)nc3=O)cc2)C1] |

TABLE 13-continued
| Compounds of Formula VI Structure |
|---|
| 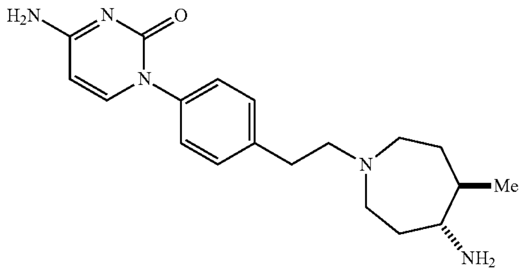 [SMILES: C[C@@H]1CCN(CCc2ccc(-n3ccc(N)nc3=O)cc2)CC[C@H]1N] |
| 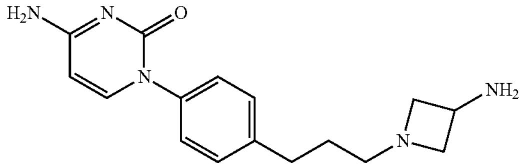 [SMILES: Nc1ccn(-c2ccc(CCCN3CC(N)C3)cc2)c(=O)n1] |
| 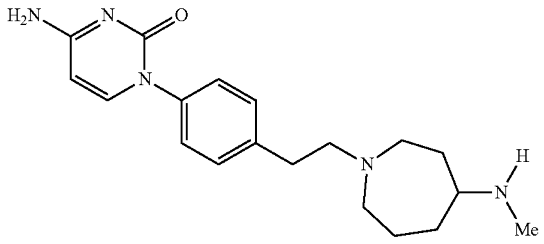 [SMILES: CNC1CCCN(CCc2ccc(-n3ccc(N)nc3=O)cc2)CC1] |
| 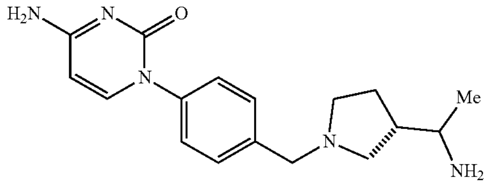 |
| 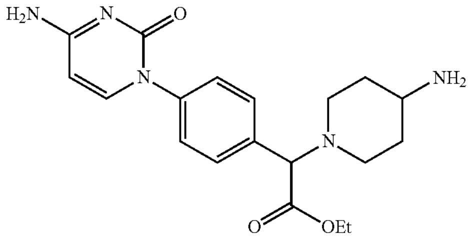 |
| 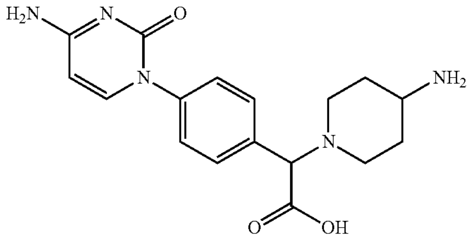 |
| 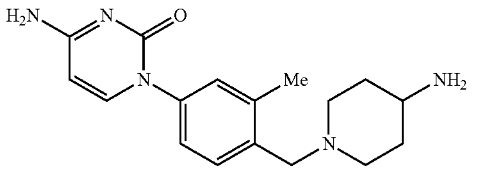 |
TABLE 13-continued
| Compounds of Formula VI Structure |
|---|
| 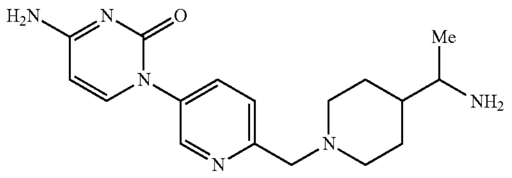 [SMILES: CC(N)C1CCN(Cc2ccc(-n3ccc(N)nc3=O)cn2)CC1] |
| 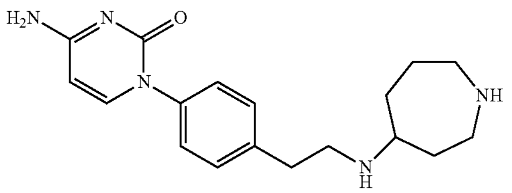 [SMILES: Nc1ccn(-c2ccc(CCNC3CCCNCC3)cc2)c(=O)n1] |
| 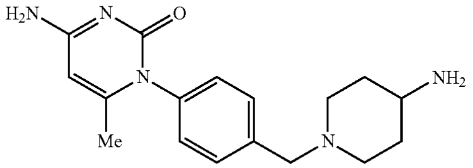 [SMILES: Cc1cc(N)nc(=O)n1-c1ccc(CN2CCC(N)CC2)cc1] |
| 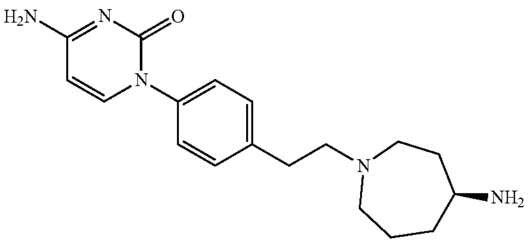 [SMILES: Nc1ccn(-c2ccc(CCN3CCC[C@H](N)CC3)cc2)c(=O)n1] |
| 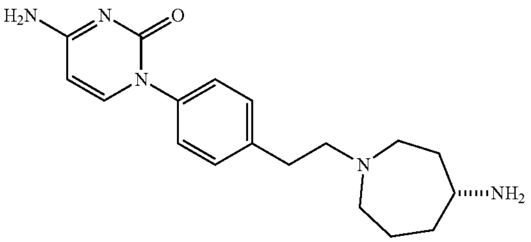 [SMILES: Nc1ccn(-c2ccc(CCN3CCC[C@@H](N)CC3)cc2)c(=O)n1] |
| 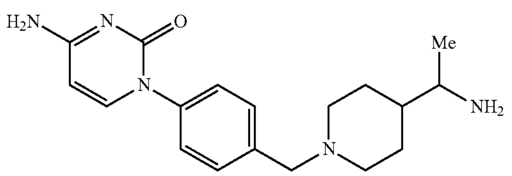 [SMILES: CC(N)C1CCN(Cc2ccc(-n3ccc(N)nc3=O)cc2)CC1] |
| 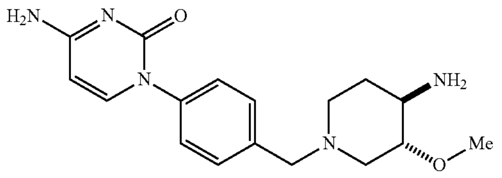 [SMILES: CO[C@@H]1CN(Cc2ccc(-n3ccc(N)nc3=O)cc2)CC[C@H]1N] |

TABLE 13-continued
| Compounds of Formula VI Structure |
| --- |
| 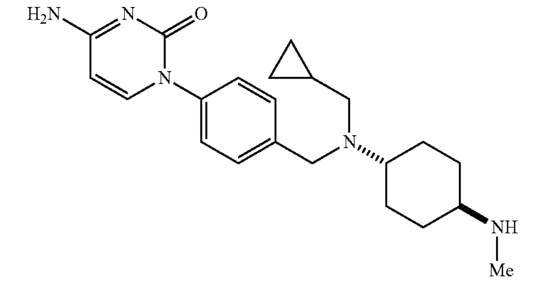 |
| 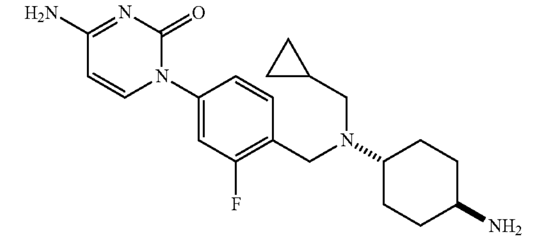 |
| 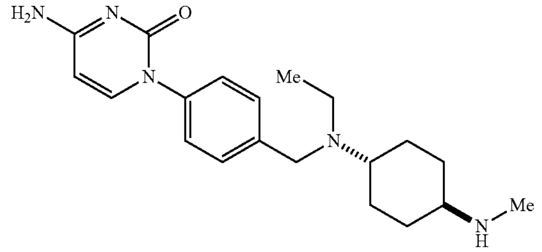 |
| 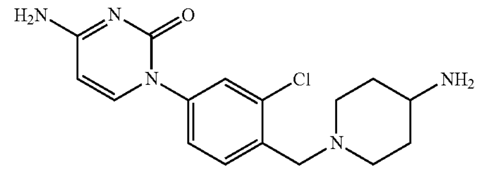 [SMILES: Nc1ccn(-c2ccc(CN3CCC(N)CC3)c(Cl)c2)c(=O)n1] |
| 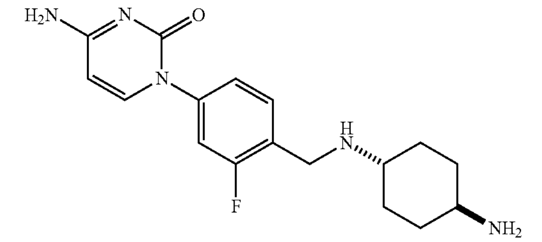 |
| 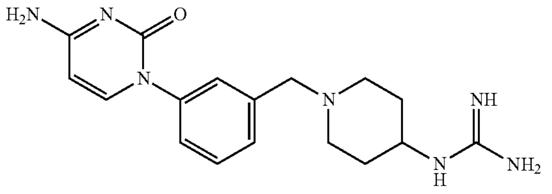 [SMILES: N=C(N)NC1CCN(Cc2cccc(-n3ccc(N)nc3=O)c2)CC1] |
TABLE 13-continued
| Compounds of Formula VI Structure |
| --- |
| 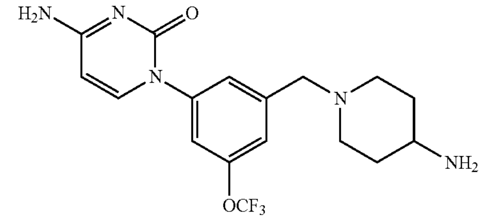 [SMILES: Nc1ccn(-c2cc(CN3CCC(N)CC3)cc(OC(F)(F)F)c2)c(=O)n1] |
| 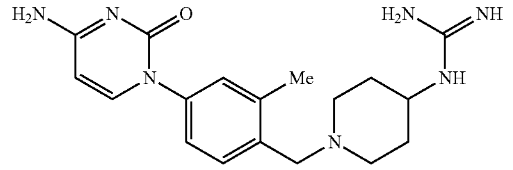 [SMILES: Cc1cc(-n2ccc(N)nc2=O)ccc1CN1CCC(NC(=N)N)CC1] |
| 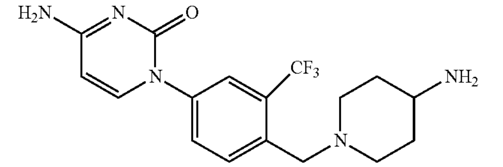 [SMILES: Nc1ccn(-c2ccc(CN3CCC(N)CC3)c(C(F)(F)F)c2)c(=O)n1] |
| 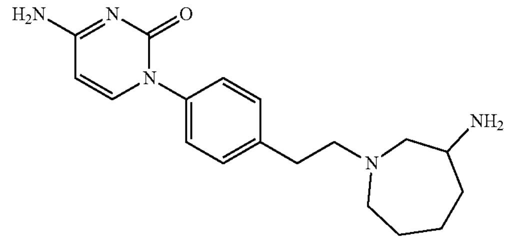 [SMILES: Nc1ccn(-c2ccc(CCN3CCCCC(N)C3)cc2)c(=O)n1] |
| 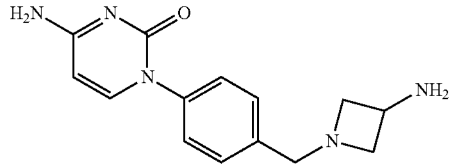 [SMILES: Nc1ccn(-c2ccc(CN3CC(N)C3)cc2)c(=O)n1] |
| 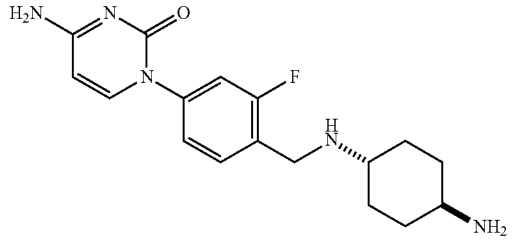 |
| 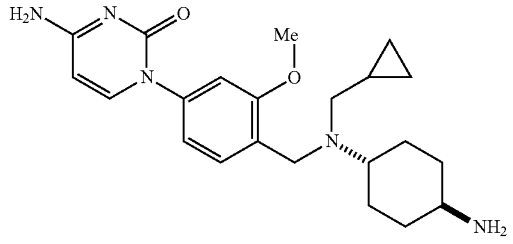 |

TABLE 13-continued
| Compounds of Formula VI Structure |
|---|
| 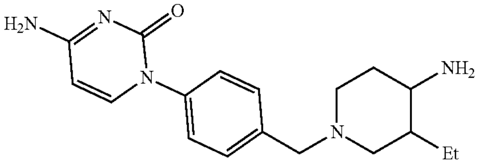 [SMILES: CCC1CN(Cc2ccc(-n3ccc(N)nc3=O)cc2)CCC1N] |
| 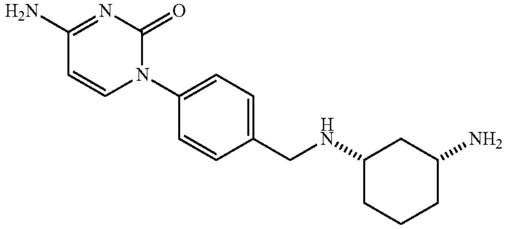 |
| 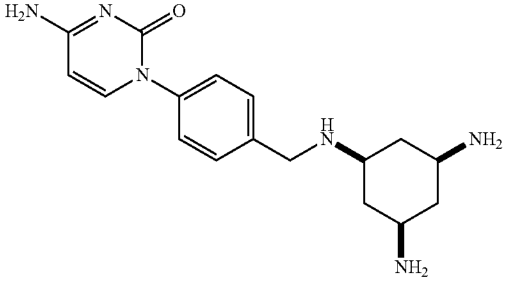 |
| 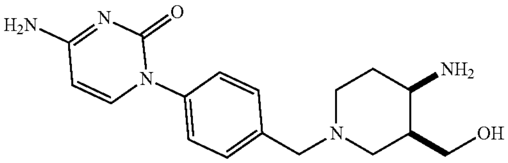 [SMILES: Nc1ccn(-c2ccc(CN3CC[C@@H](N)[C@@H](CO)C3)cc2)c(=O)n1] |
| 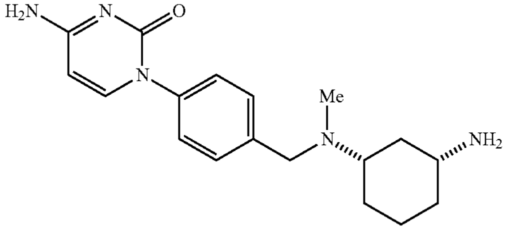 |
| 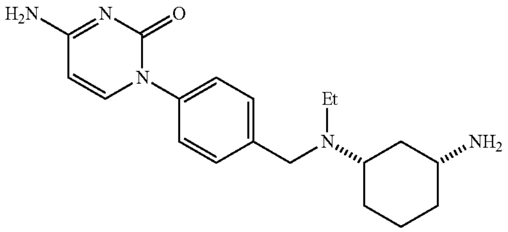 |
TABLE 13-continued
| Compounds of Formula VI Structure |
|---|
| 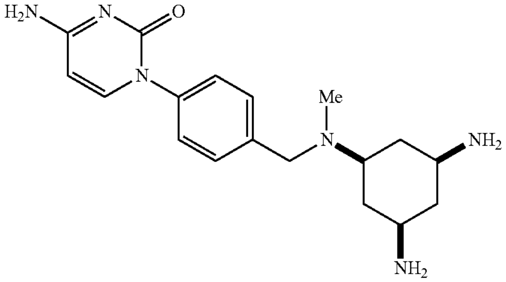 |
| 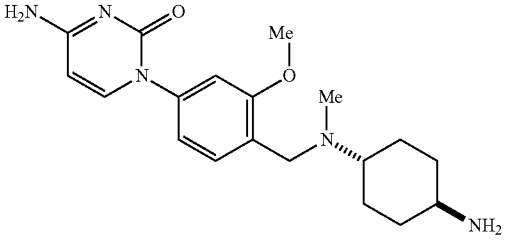 |
| 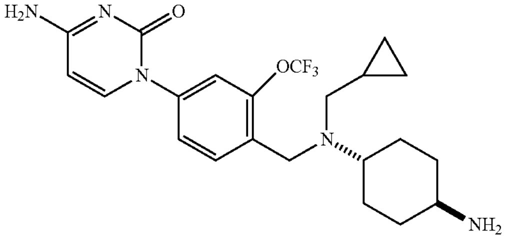 |
| 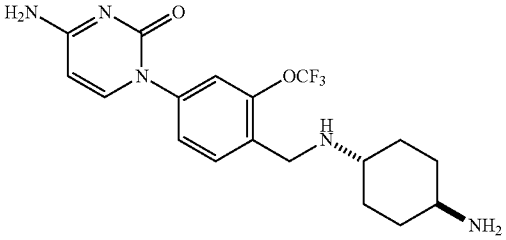 |
| 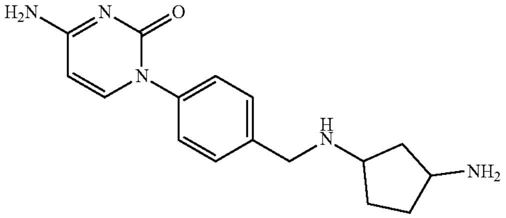 [SMILES: Nc1ccn(-c2ccc(CNC3CCC(N)C3)cc2)c(=O)n1] |
| 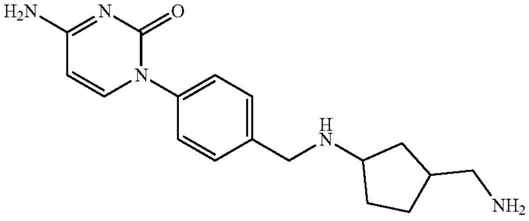 [SMILES: NCC1CCC(NCc2ccc(-n3ccc(N)nc3=O)cc2)C1] |

TABLE 13-continued
| Compounds of Formula VI Structure |
|---|
| 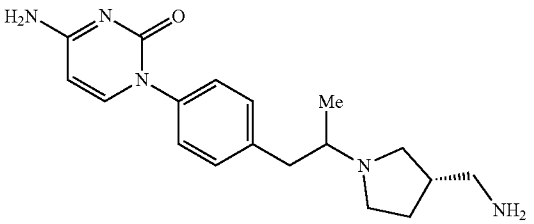 [SMILES: CC(Cc1ccc(-n2ccc(N)nc2=O)cc1)N1CC[C@@H](CN)C1] |
| 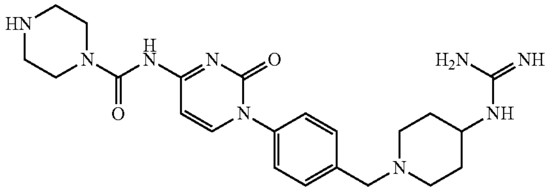 [SMILES: N=C(N)NC1CCN(Cc2ccc(-n3ccc(NC(=O)N4CCNCC4)nc3=O)cc2)CC1] |
| 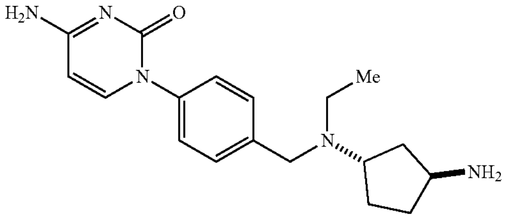 |
| 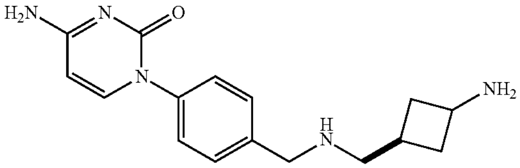 |
| 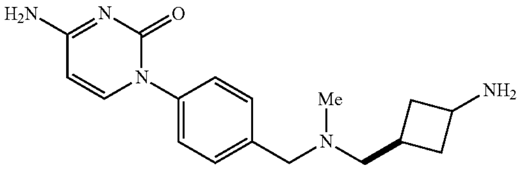 |
| 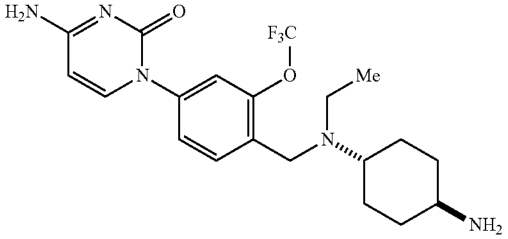 |
| 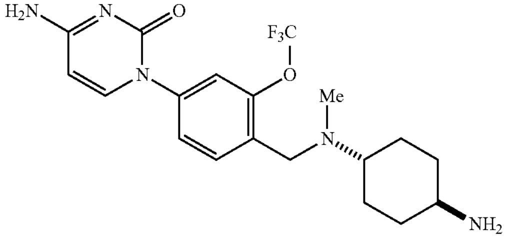 |
TABLE 13-continued
| Compounds of Formula VI Structure |
|---|
| 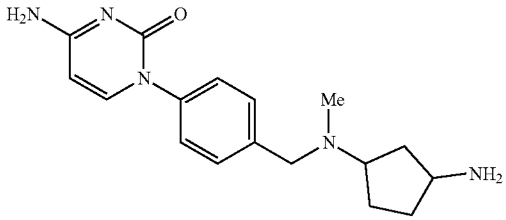 [SMILES: CN(Cc1ccc(-n2ccc(N)nc2=O)cc1)C1CCC(N)C1] |
| 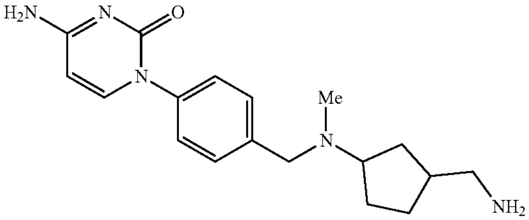 [SMILES: CN(Cc1ccc(-n2ccc(N)nc2=O)cc1)C1CCC(CN)C1] |
| 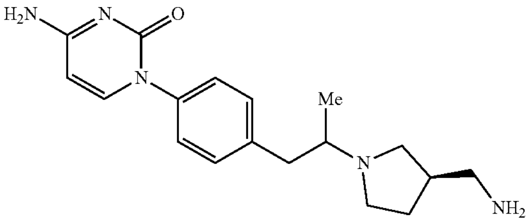 [SMILES: CC(Cc1ccc(-n2ccc(N)nc2=O)cc1)N1CC[C@H](CN)C1] |
| 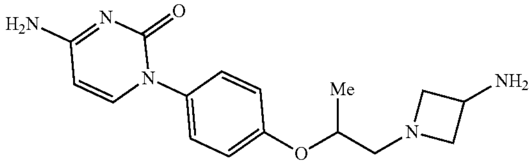 [SMILES: CC(CN1CC(N)C1)Oc1ccc(-n2ccc(N)nc2=O)cc1] |
| 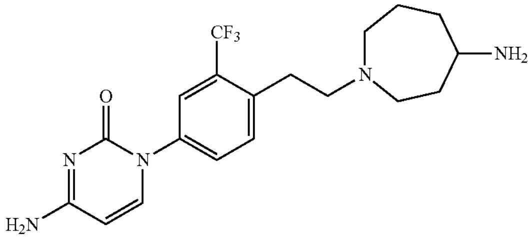 [SMILES: Nc1ccn(-c2ccc(CCN3CCCC(N)CC3)c(C(F)(F)F)c2)c(=O)n1] |
| 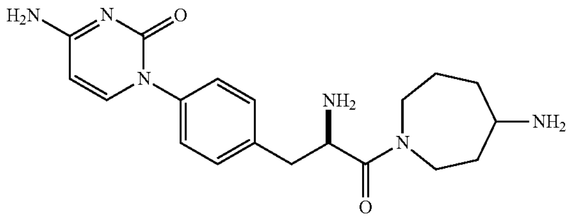 [SMILES: Nc1ccn(-c2ccc(C[C@@H](N)C(=O)N3CCCC(N)CC3)cc2)c(=O)n1] |
| 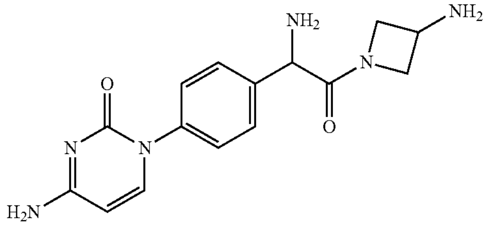 [SMILES: Nc1ccn(-c2ccc(C(N)C(=O)N3CC(N)C3)cc2)c(=O)n1] |

TABLE 13-continued
| Compounds of Formula VI Structure |
|---|
| 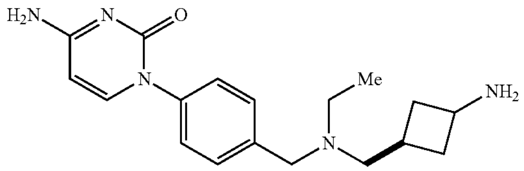 |
| 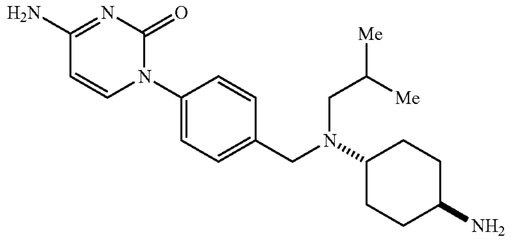 |
| 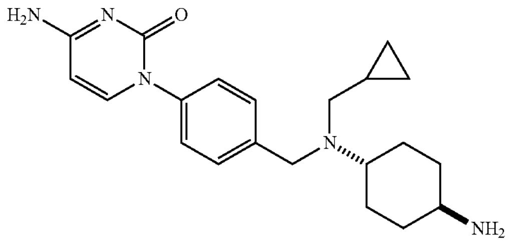 |
| 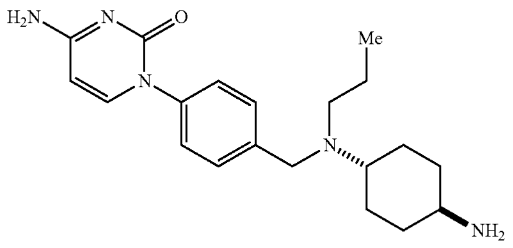 |
| 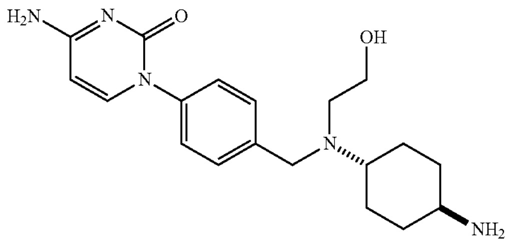 |
| 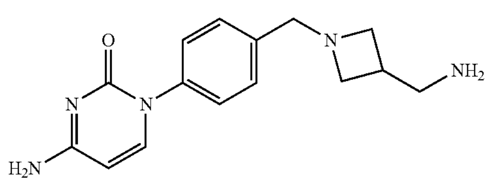 [SMILES: NCC1CN(Cc2ccc(-n3ccc(N)nc3=O)cc2)C1] |
| 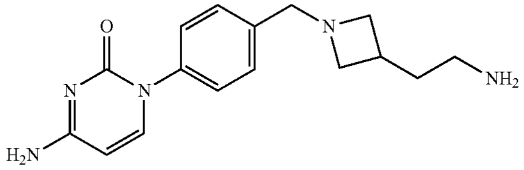 [SMILES: NCCC1CN(Cc2ccc(-n3ccc(N)nc3=O)cc2)C1] |
TABLE 13-continued
| Compounds of Formula VI Structure |
|---|
| 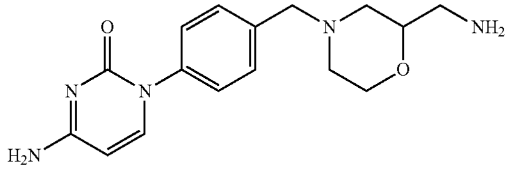 [SMILES: NCC1CN(Cc2ccc(-n3ccc(N)nc3=O)cc2)CCO1] |
| 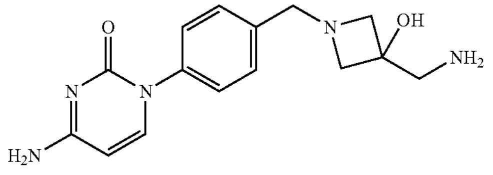 [SMILES: NCC1(O)CN(Cc2ccc(-n3ccc(N)nc3=O)cc2)C1] |
| 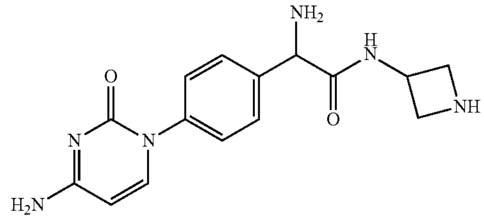 [SMILES: Nc1ccn(-c2ccc(C(N)C(=O)NC3CNC3)cc2)c(=O)n1] |
| 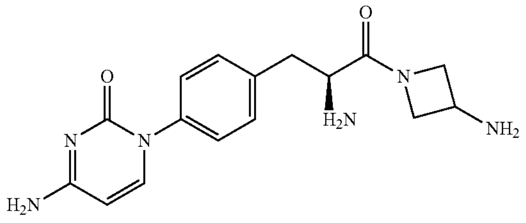 [SMILES: Nc1ccn(-c2ccc(C[C@H](N)C(=O)N3CC(N)C3)cc2)c(=O)n1] |
| 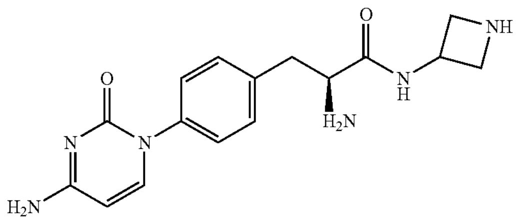 [SMILES: Nc1ccn(-c2ccc(C[C@H](N)C(=O)NC3CNC3)cc2)c(=O)n1] |
| 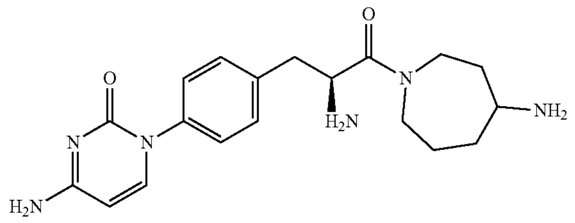 [SMILES: Nc1ccn(-c2ccc(C[C@H](N)C(=O)N3CCCC(N)CC3)cc2)c(=O)n1] |
| 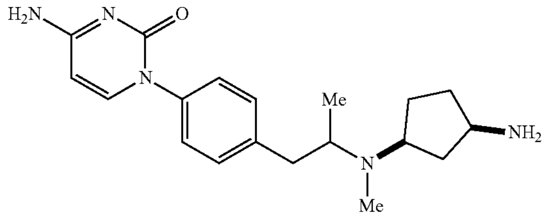 |

TABLE 13-continued
| Compounds of Formula VI<br>Structure |
|---|
| 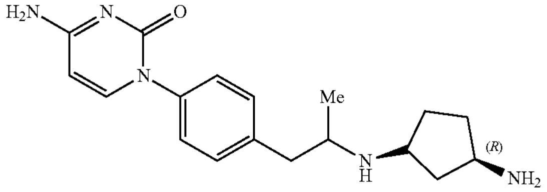 |
| 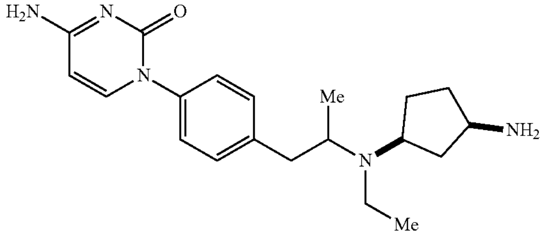 |
| 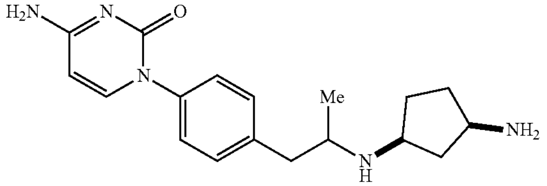 |
| 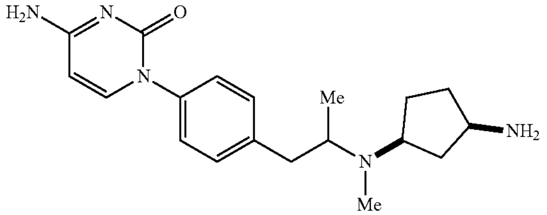 |
| 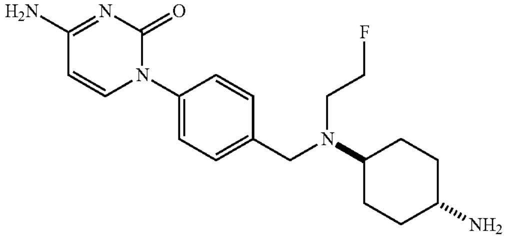 |
| 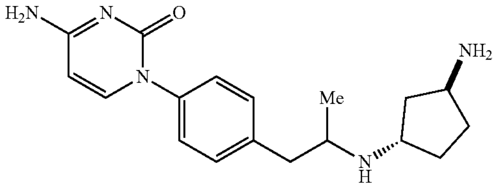 [SMILES: CC(Cc1ccc(-n2ccc(N)nc2=O)cc1)N[C@H]1CC[C@H](N)C1] |
| 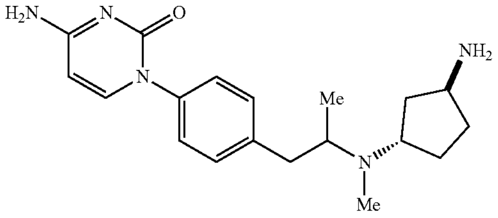 [SMILES: CC(Cc1ccc(-n2ccc(N)nc2=O)cc1)N(C)[C@H]1CC[C@H](N)C1] |
TABLE 13-continued
| Compounds of Formula VI<br>Structure |
|---|
| 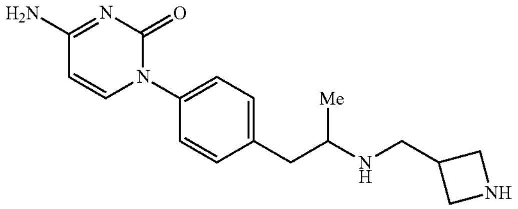 [SMILES: CC(Cc1ccc(-n2ccc(N)nc2=O)cc1)NCC1CNC1] |
| 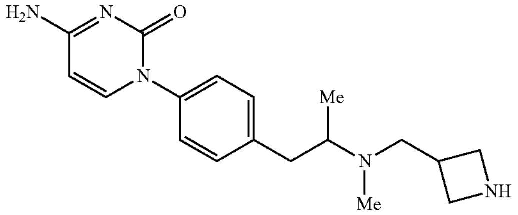 [SMILES: CC(Cc1ccc(-n2ccc(N)nc2=O)cc1)N(C)CC1CNC1] |
| 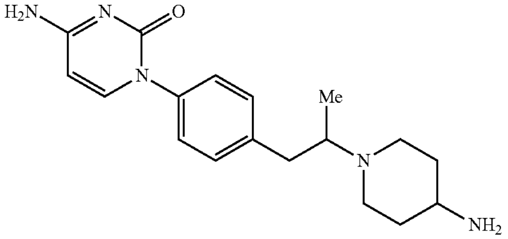 [SMILES: CC(Cc1ccc(-n2ccc(N)nc2=O)cc1)N1CCC(N)CC1] |
| 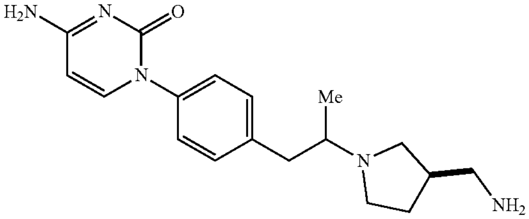 [SMILES: CC(Cc1ccc(-n2ccc(N)nc2=O)cc1)N1CC[C@H](CN)C1] |
| 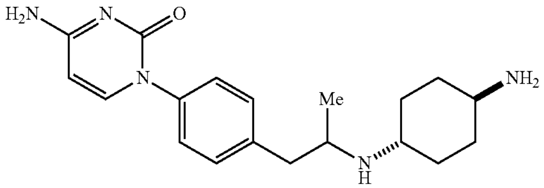 |
| 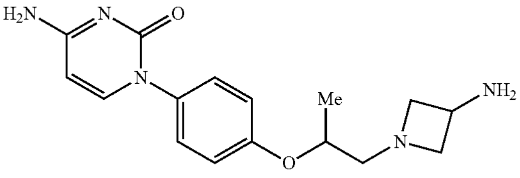 [SMILES: CC(CN1CC(N)C1)Oc1ccc(-n2ccc(N)nc2=O)cc1] |
| 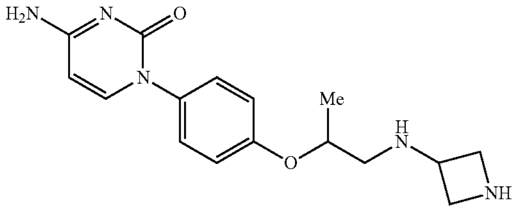 [SMILES: CC(CNC1CNC1)Oc1ccc(-n2ccc(N)nc2=O)cc1] |

TABLE 13-continued
Compounds of Formula VI
Structure
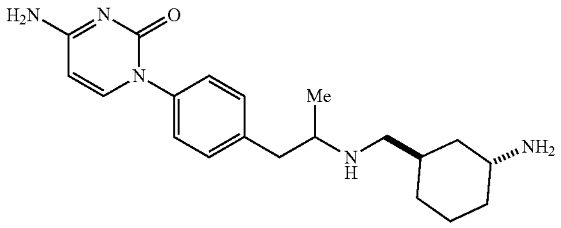
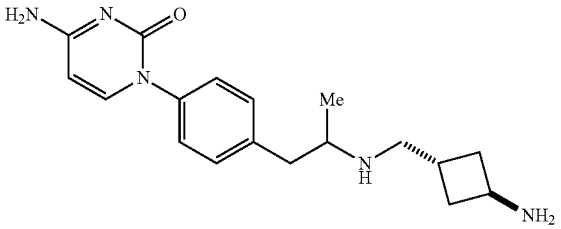
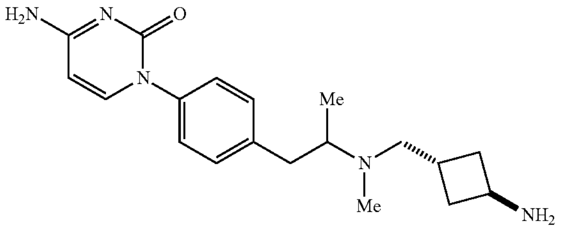
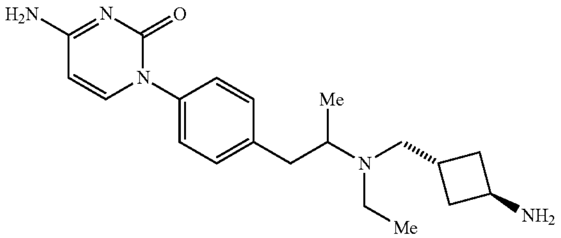
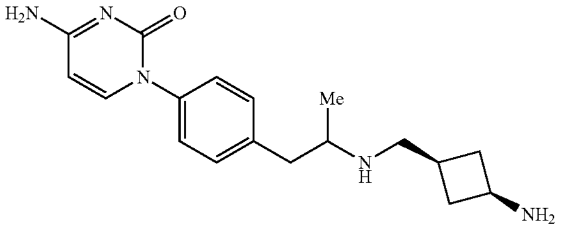 [SMILES: CC(Cc1ccc(-n2ccc(N)nc2=O)cc1)NC[C@H]1C[C@@H](N)C1]
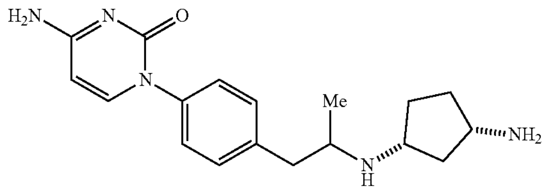
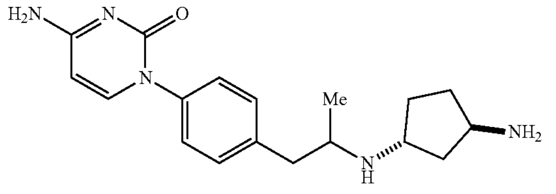
TABLE 13-continued
Compounds of Formula VI
Structure
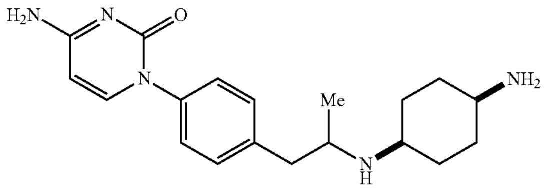
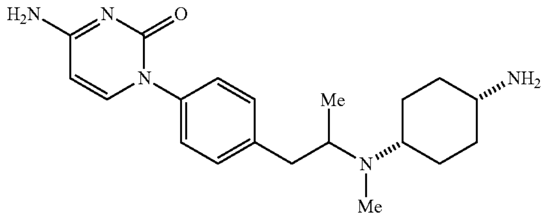
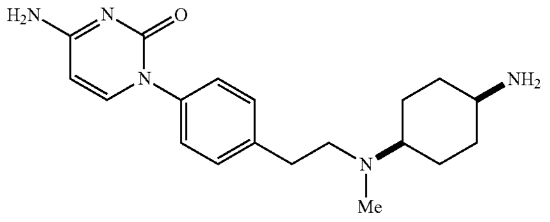
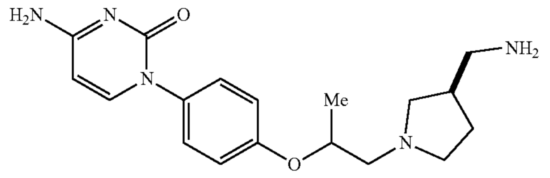 [SMILES: CC(CN1CC[C@H](CN)C1)Oc1ccc(-n2ccc(N)nc2=O)cc1]
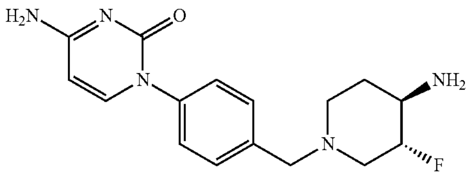 [SMILES: Nc1ccn(-c2ccc(CN3CC[C@@H](N)[C@H](F)C3)cc2)c(=O)n1]
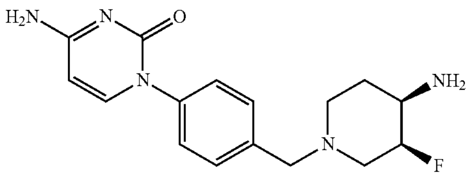
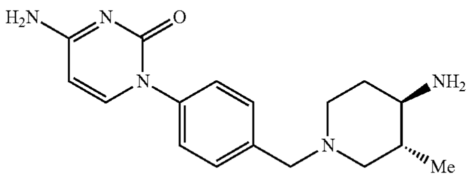 [SMILES: C[C@@H]1CN(Cc2ccc(-n3ccc(N)nc3=O)cc2)CC[C@H]1N]
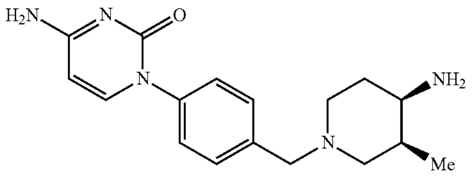

TABLE 13-continued
| Compounds of Formula VI Structure |
| --- |
| 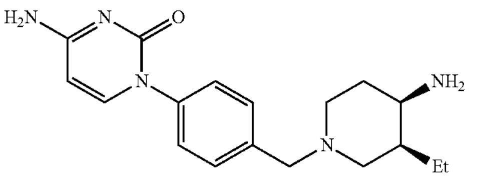 |
| 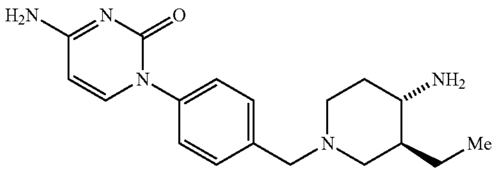 [SMILES: CC[C@H]1CN(Cc2ccc(-n3ccc(N)nc3=O)cc2)CC[C@@H]1N] |
| 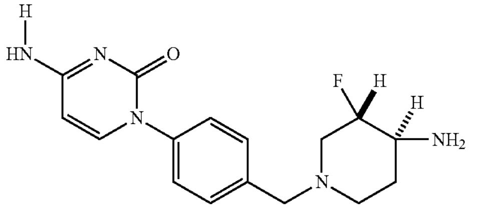 |
| 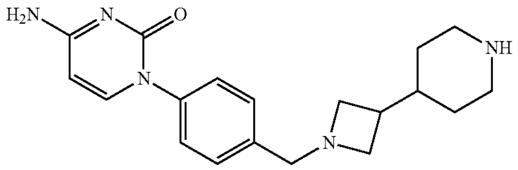 [SMILES: Nc1ccn(-c2ccc(CN3CC(C4CCNCC4)C3)cc2)c(=O)n1] |
| 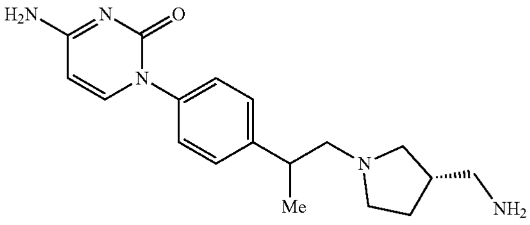 [SMILES: CC(CN1CC[C@@H](CN)C1)c1ccc(-n2ccc(N)nc2=O)cc1] |
| 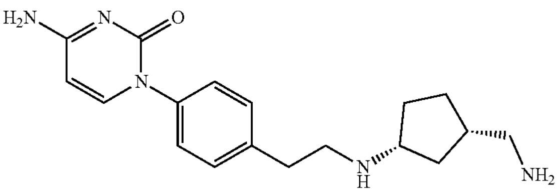 [SMILES: NC[C@H]1CC[C@@H](NCCc2ccc(-n3ccc(N)nc3=O)cc2)C1] |
| 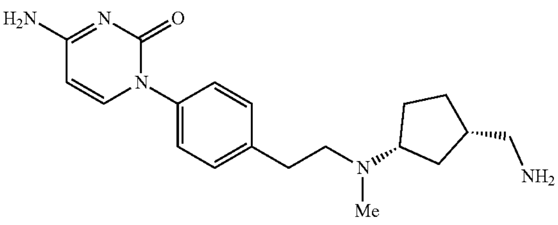 [SMILES: CN(CCc1ccc(-n2ccc(N)nc2=O)cc1)[C@@H]1CC[C@H](CN)C1] |
TABLE 13-continued
| Compounds of Formula VI Structure |
| --- |
| 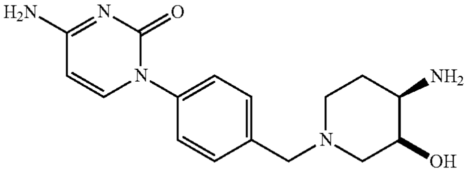 [SMILES: Nc1ccn(-c2ccc(CN3CC[C@@H](N)[C@@H](O)C3)cc2)c(=O)n1] |
| 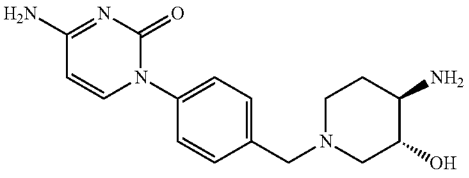 [SMILES: Nc1ccn(-c2ccc(CN3CC[C@@H](N)[C@H](O)C3)cc2)c(=O)n1] |
| 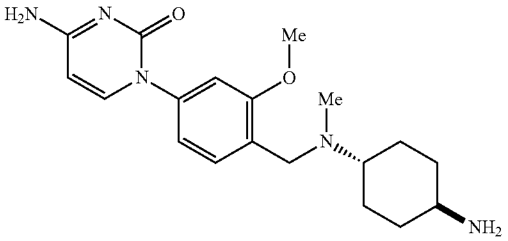 |
| 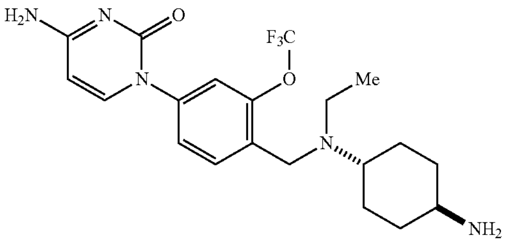 |
| 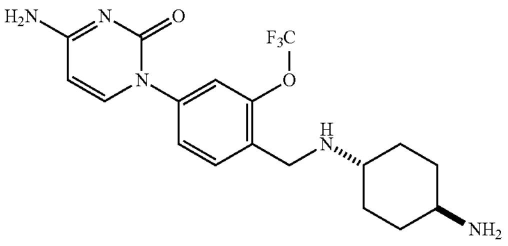 |
| 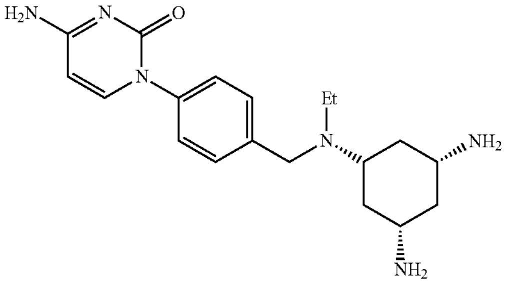 |

TABLE 13-continued

| Compounds of Formula VI Structure |
|---|
| 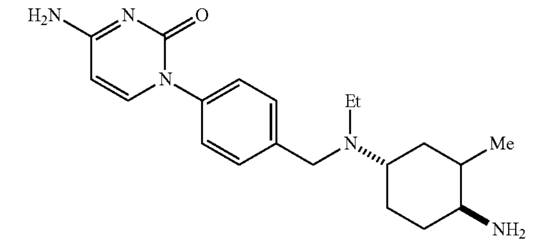 [SMILES: CCN(Cc1ccc(-n2ccc(N)nc2=O)cc1)[C@H]1CC[C@H](N)C(C)C1] |
| 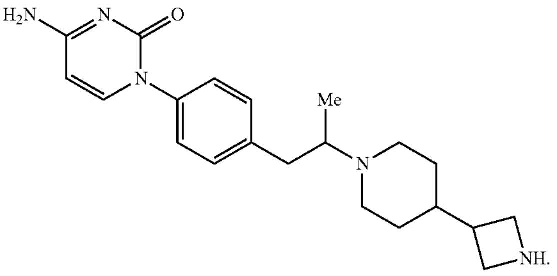 [SMILES: CC(Cc1ccc(-n2ccc(N)nc2=O)cc1)N1CCC(C2CNC2)CC1] |

23. A compound of formula E:

E

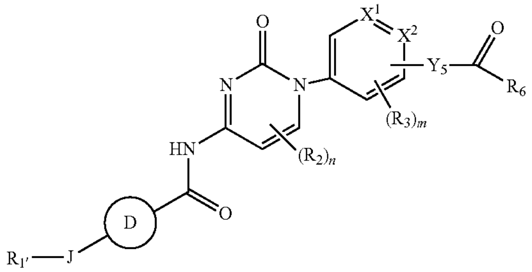

or a pharmaceutically acceptable salt thereof wherein:

ring A, ring B, J, $X^1$, $X^2$, $R_{1'}$, $R_2$, $R_3$, $R_6$, m, and n have the same definitions in claim 1;

$Y_5$ is a bond or is a linear $C_1$-$C_7$ alkylene, $C_2$-$C_7$ alkenylene, or $C_2$-$C_7$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, wherein up to two carbon atoms of the $C_2$-$C_7$ alkylene, $C_2$-$C_7$ alkenylene, or $C_2$-$C_7$ alkynylene may be independently replaced by O, (C═O), or

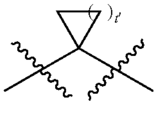

wherein t' is 1, 2, 3, or 4; and $R_6$ is H or $C_1$-$C_6$ alkyl.

24. A compound or a pharmaceutically acceptable salt thereof, wherein the compound is selected from the compounds listed in Table 14:

TABLE 14

| Compound of formula E |
|---|
| 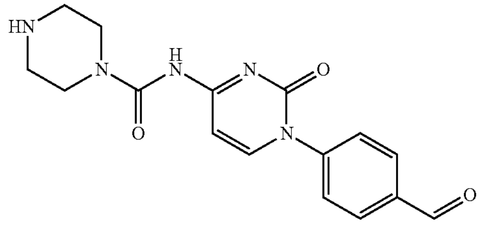 [SMILES: O=Cc1ccc(-n2ccc(NC(=O)N3CCNCC3)nc2=O)cc1] |
| 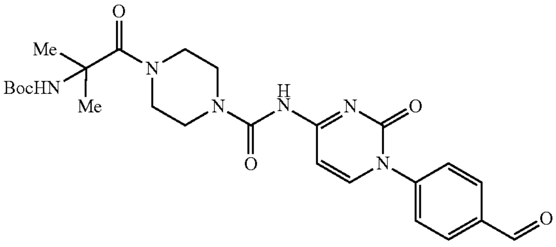 [SMILES: CC(C)(C)OC(=O)NC(C)(C)C(=O)N1CCN(C(=O)Nc2ccn(-c3ccc(C=O)cc3)c(=O)n2)CC1] |
| 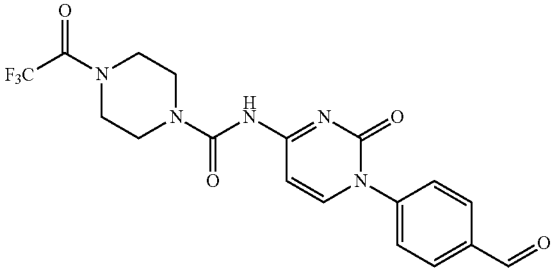 [SMILES: O=Cc1ccc(-n2ccc(NC(=O)N3CCN(C(=O)C(F)(F)F)CC3)nc2=O)cc1] |
| 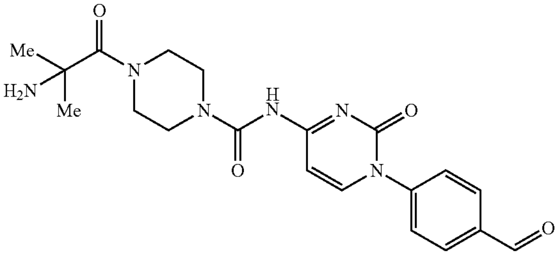 [SMILES: CC(C)(N)C(=O)N1CCN(C(=O)Nc2ccn(-c3ccc(C=O)cc3)c(=O)n2)CC1] |
| 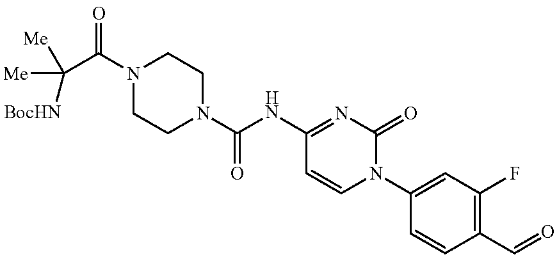 [SMILES: CC(C)(C)OC(=O)NC(C)(C)C(=O)N1CCN(C(=O)Nc2ccn(-c3ccc(C=O)c(F)c3)c(=O)n2)CC1] |
| 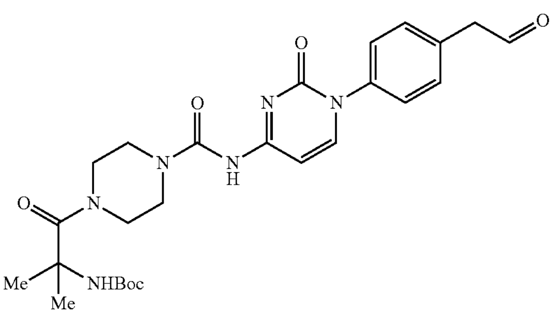 [SMILES: CC(C)(C)OC(=O)NC(C)(C)C(=O)N1CCN(C(=O)Nc2ccn(-c3ccc(CC=O)cc3)c(=O)n2)CC1] |

TABLE 14-continued
| Compound of formula E |
|---|
| 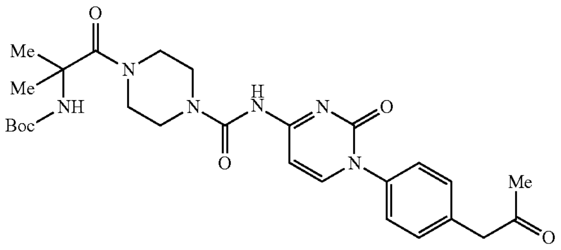 [SMILES: CC(=O)Cc1ccc(-n2ccc(NC(=O)N3CCN(C(=O)C(C)(C)NC(=O)OC(C)(C)C)CC3)nc2=O)cc1] |
| 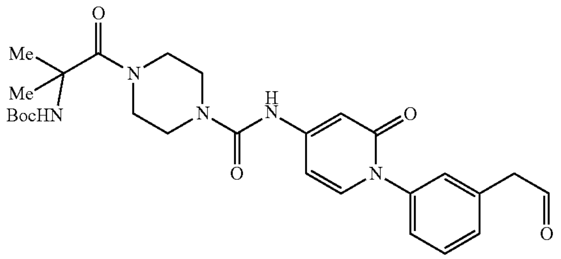 [SMILES: CC(C)(C)OC(=O)NC(C)(C)C(=O)N1CCN(C(=O)Nc2ccn(-c3cccc(CC=O)c3)c(=O)c2)CC1] |
| 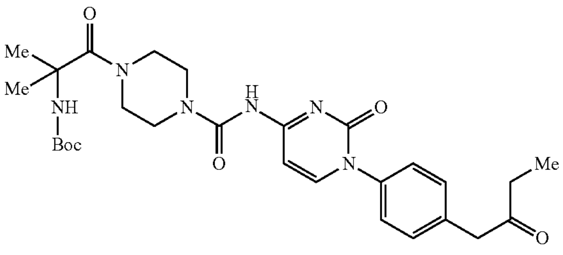 [SMILES: CCC(=O)Cc1ccc(-n2ccc(NC(=O)N3CCN(C(=O)C(C)(C)NC(=O)OC(C)(C)C)CC3)nc2=O)cc1] |
| 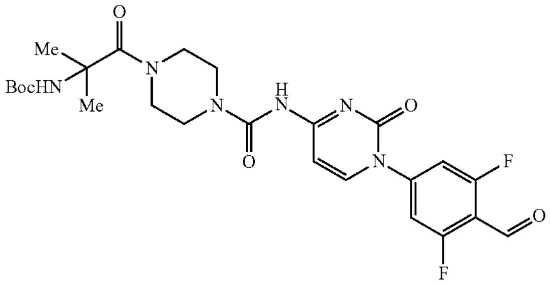 [SMILES: CC(C)(C)OC(=O)NC(C)(C)C(=O)N1CCN(C(=O)Nc2ccn(-c3cc(F)c(C=O)c(F)c3)c(=O)n2)CC1] |
| 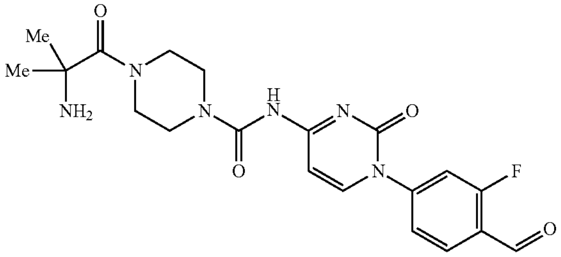 [SMILES: CC(C)(N)C(=O)N1CCN(C(=O)Nc2ccn(-c3ccc(C=O)c(F)c3)c(=O)n2)CC1] |
TABLE 14-continued
| Compound of formula E |
|---|
| 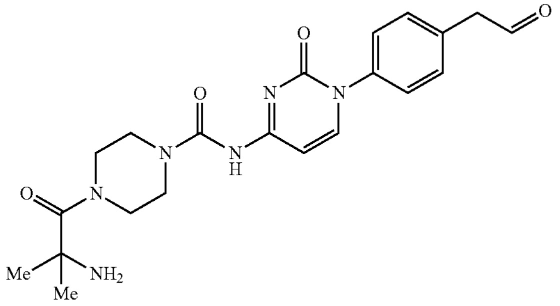 [SMILES: CC(C)(N)C(=O)N1CCN(C(=O)Nc2ccn(-c3ccc(CC=O)cc3)c(=O)n2)CC1] |
| 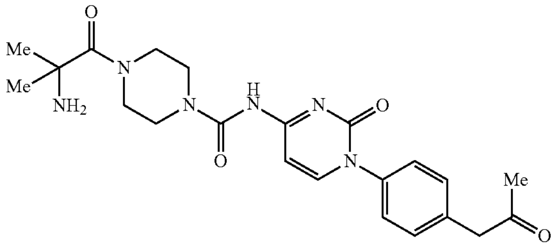 [SMILES: CC(=O)Cc1ccc(-n2ccc(NC(=O)N3CCN(C(=O)C(C)(C)N)CC3)nc2=O)cc1] |
| 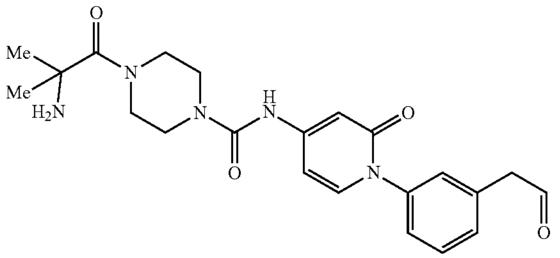 [SMILES: CC(C)(N)C(=O)N1CCN(C(=O)Nc2ccn(-c3cccc(CC=O)c3)c(=O)c2)CC1] |
| 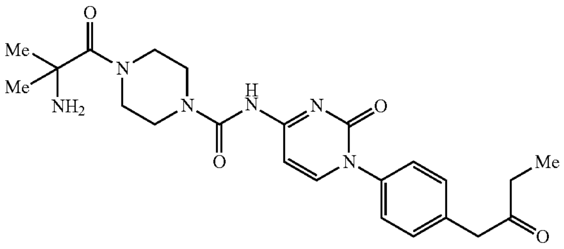 [SMILES: CCC(=O)Cc1ccc(-n2ccc(NC(=O)N3CCN(C(=O)C(C)(C)N)CC3)nc2=O)cc1] |
| 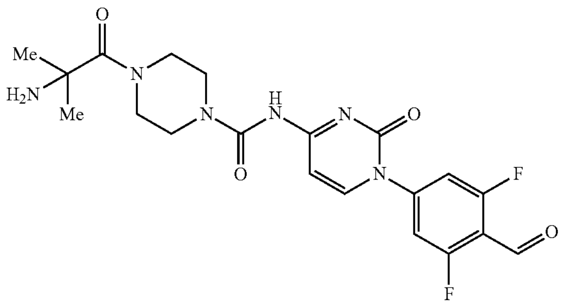 [SMILES: CC(C)(N)C(=O)N1CCN(C(=O)Nc2ccn(-c3cc(F)c(C=O)c(F)c3)c(=O)n2)CC1] |

TABLE 14-continued

| Compound of formula E |
|---|
| 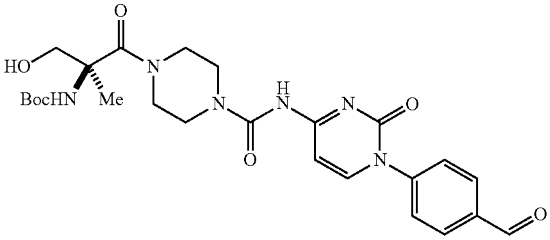 [SMILES: CC(C)(C)OC(=O)N[C@@](C)(CO)C(=O)N1CCN(C(=O)Nc2ccn(-c3ccc(C=O)cc3)c(=O)n2)CC1] |
| 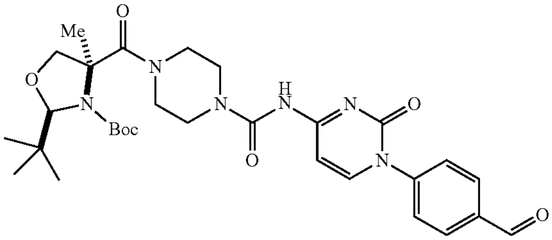 |
| 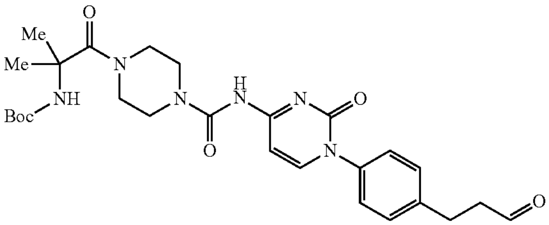 [SMILES: CC(C)(C)OC(=O)NC(C)(C)C(=O)N1CCN(C(=O)Nc2ccn(-c3ccc(CCC=O)cc3)c(=O)n2)CC1] |
| 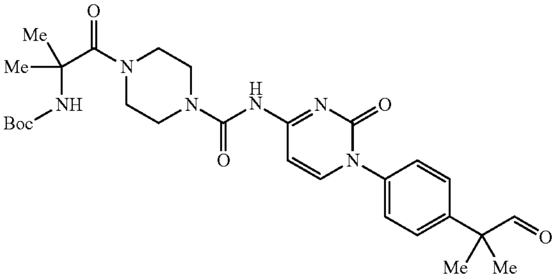 [SMILES: CC(C)(C)OC(=O)NC(C)(C)C(=O)N1CCN(C(=O)Nc2ccn(-c3ccc(C(C)(C)C=O)cc3)c(=O)n2)CC1] |
| 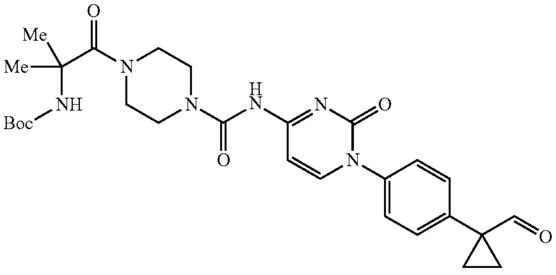 [SMILES: CC(C)(C)OC(=O)NC(C)(C)C(=O)N1CCN(C(=O)Nc2ccn(-c3ccc(C4(C=O)CC4)cc3)c(=O)n2)CC1] |
| 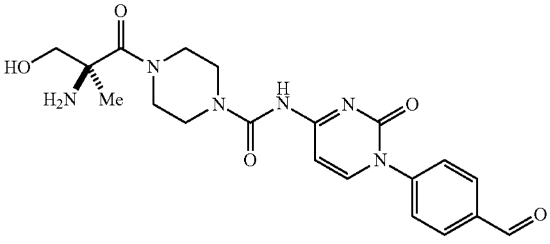 [SMILES: C[C@](N)(CO)C(=O)N1CCN(C(=O)Nc2ccn(-c3ccc(C=O)cc3)c(=O)n2)CC1] |

TABLE 14-continued

| Compound of formula E |
|---|
| 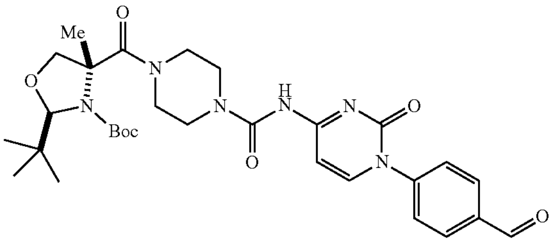 |
| 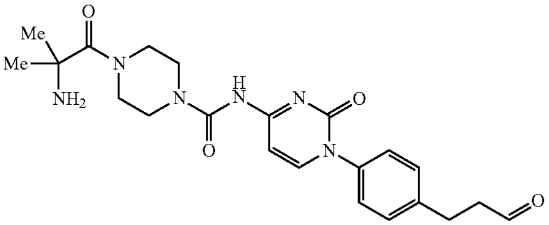 [SMILES: CC(C)(N)C(=O)N1CCN(C(=O)Nc2ccn(-c3ccc(CCC=O)cc3)c(=O)n2)CC1] |
| 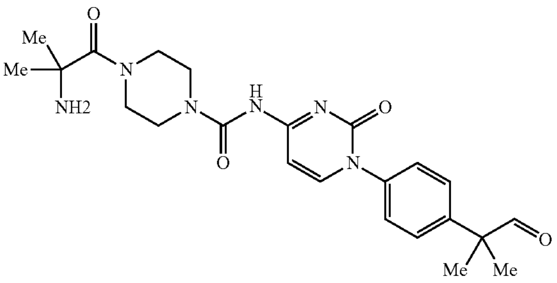 [SMILES: CC(C)(N)C(=O)N1CCN(C(=O)Nc2ccn(-c3ccc(C(C)(C)C=O)cc3)c(=O)n2)CC1] |
| 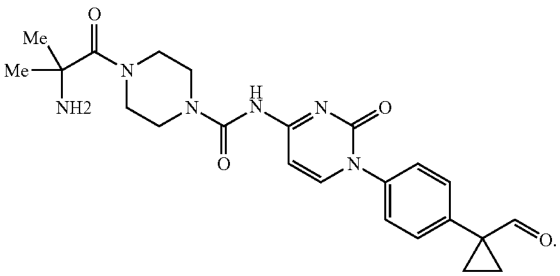 [SMILES: CC(C)(N)C(=O)N1CCN(C(=O)Nc2ccn(-c3ccc(C4(C=O)CC4)cc3)c(=O)n2)CC1] |

25. A pharmaceutical composition comprising a compound of claim 1, or a pharmaceutically acceptable salt thereof, and a pharmaceutically acceptable excipient.

26. A method of treating a bacterial infection in a patient in need of such treatment, comprising administering the compound of formula I, or a pharmaceutically acceptable salt thereof, or a pharmaceutical composition comprising a compound of formula 1 and a pharmaceutically acceptable excipient.

27. The method of claim 26, wherein the bacterial infection is caused by a bacterium including gram positive and gram negative bacteria selected from the group consisting of *Francisella tularensis, Burkholderia mallei, Burkholderia pseudomallei, Bacillus anthracis, Yersinia pestis, Salmonella, Clostridium difficile, Citrobacter, Enterobacter, Burkholderia* genus, *cepacia, Mycobacterium, Proteus, Streptococcus, Serratia, Enterobacteriaceae, Escherichia, Klebsiella, Pseudomonas*, and *Acinetobacter.*

28. A process for preparing a compound of formula I-2:

I-2

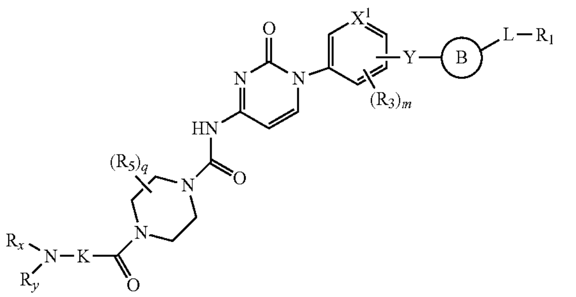

or a pharmaceutically acceptable salt thereof, the process comprising:

coupling a compound of formula A with a compound of formula B to provide a compound of formula I-2:

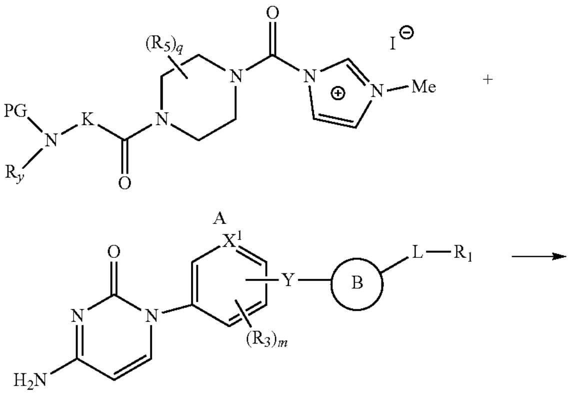

A

B

I-2 wherein ring B, K, L, Y, $R_1$, $R_x$, $R_y$, $R_5$, $X^1$, m, and q are as defined in claim 1, and wherein PG is an amino protecting group.

29. A process for preparing a compound of formula I-6:

I-6

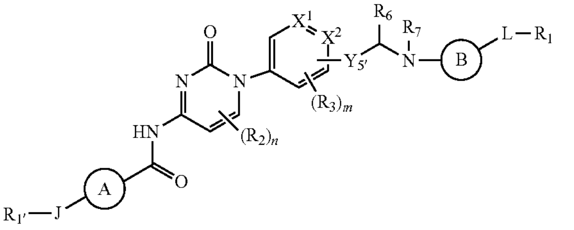

or a pharmaceutically acceptable salt thereof, the process comprising:

combining a compound of formula C with a compound of formula D under a reductive amination condition to provide a compound of formula I-6:

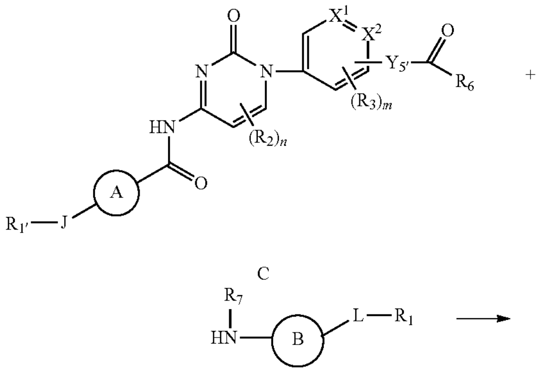

C

D

I-6, wherein ring A, ring B, J, L, $R_1$, Rr, $R_2$, $R_3$, $X^1$, $X^2$, m, and n are as defined in claim 1;

$Y_5$s is a bond or is a linear $C_1$-$C_6$ alkylene, $C_2$-$C_6$ alkenylene, or $C_2$-$C_6$ alkynylene, any of which are optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two carbon atoms of the $C_2$-$C_8$ alkylene, $C_2$-$C_8$ alkenylene, or $C_2$-$C_8$ alkynylene may be optionally and independently replaced by O, (C=O), or

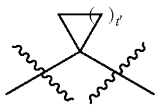

;

wherein t' is 1, 2, 3, or 4;

$R_6$ is H or $C_1$-$C_6$ alkyl; and $R_7$ is H, $C_1$-$C_6$ alkyl, $C_1$-$C_6$ hydroxyalkyl, $C_1$-$C_6$ haloalkyl, $C_3$-$C_8$ cycloalkyl, or $C_1$-$C_6$ alkylene-$C_3$-$C_8$ cycloalkyl.

30. A process for preparing a compound of formula I-7:

I-7

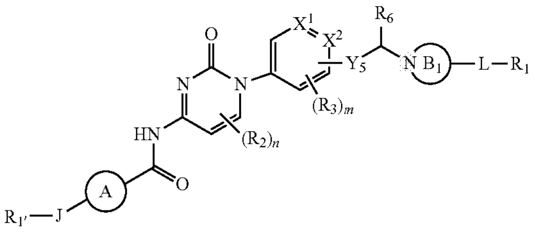

or a pharmaceutically acceptable salt thereof, the process comprising:

combining a compound of formula E with a compound of formula F under a reductive amination condition to provide a compound of formula I-7

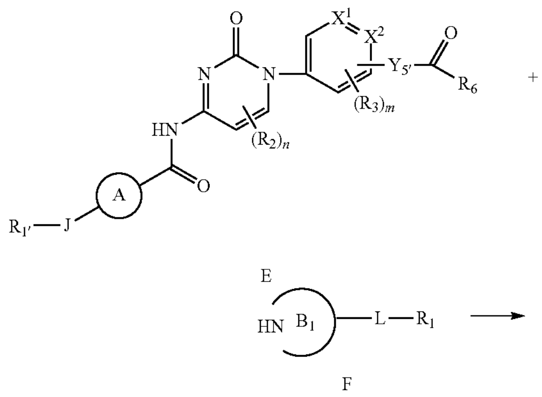

I-7 wherein ring A, ring B, J, L, $R_1$, $R_{1'}$, $R_2$, $R_3$, $X^1$, $X^2$, m, and n are as defined in claim 1;

ring $B_1$ is a nitrogen containing monocyclic heterocycloalkylene optionally substituted with up to three substituents independently selected from the group consisting of $C_1$-$C_6$ alkyl, $C_1$-$C_6$ alkoxy, halo, CN, $C_1$-$C_6$ haloalkyl, OH, COO($C_1$-$C_6$ alkyl), $CONH_2$, and $C_1$-$C_6$ hydroxyalkyl;

$Y_5$ is a bond or is a linear $C_1$-$C_7$ alkylene, $C_2$-$C_7$ alkenylene, or $C_2$-$C_7$ alkynylene, any of which are optionally substituted with OH, $NH_2$, halo, $C_1$-$C_6$ alkyl, or $C_1$-$C_6$ alkoxy; and $R_6$ is H or $C_1$-$C_6$ alkyl.

* * * * *